US00RE47221E

(19) United States
(12) Reissued Patent
Wishart et al.

(10) Patent Number: US RE47,221 E
(45) Date of Reissued Patent: Feb. 5, 2019

(54) TRICYCLIC COMPOUNDS

(71) Applicant: AbbVie Inc., North Chicago, IL (US)

(72) Inventors: Neil Wishart, Jefferson, MA (US); Kristine E. Frank, Grayslake, IL (US); Michael Friedman, Kennebunkport, ME (US); Dawn M. George, Charlton, MA (US); Kent D. Stewart, Charlotte, NC (US); Grier A. Wallace, Sterling, MA (US)

(73) Assignee: AbbVie Inc., North Chicago, IL (US)

(21) Appl. No.: 15/446,102

(22) Filed: Mar. 1, 2017

Related U.S. Patent Documents

Reissue of:
(64) Patent No.: 8,426,411
Issued: Apr. 23, 2013
Appl. No.: 12/958,115
Filed: Dec. 1, 2010

U.S. Applications:
(60) Provisional application No. 61/364,116, filed on Jul. 14, 2010, provisional application No. 61/265,563, filed on Dec. 1, 2009.

(51) Int. Cl.

| | |
|---|---|
| ***A61K 31/50*** | (2006.01) |
| ***C07D 487/14*** | (2006.01) |
| ***A61K 31/437*** | (2006.01) |
| ***C07D 498/14*** | (2006.01) |
| ***A61K 31/4985*** | (2006.01) |
| ***A61K 45/06*** | (2006.01) |
| ***C07D 513/14*** | (2006.01) |
| ***C07D 471/14*** | (2006.01) |

(52) U.S. Cl.
CPC ..... *C07D 487/14* (2013.01); *A61K 31/437* (2013.01); *A61K 31/4985* (2013.01); *A61K 45/06* (2013.01); *C07D 471/14* (2013.01); *C07D 498/14* (2013.01); *C07D 513/14* (2013.01)

(58) Field of Classification Search
CPC .. C07D 487/14; C07D 471/14; C07D 498/14; C07D 513/14; A61K 45/06; A61K 31/4985; A61K 31/437
USPC ..... 514/250
See application file for complete search history.

(56) References Cited

U.S. PATENT DOCUMENTS

| | | | |
|---|---|---|---|
| 3,663,559 | A | 5/1972 | Derijckere et al. |
| 3,929,992 | A | 12/1975 | Sehgal et al. |
| 4,053,474 | A | 10/1977 | Treuner et al. |
| 5,212,310 | A | 5/1993 | Thurkauf et al. |
| 5,266,698 | A | 11/1993 | Shaw et al. |
| 5,521,173 | A | 5/1996 | Venkatesan et al. |
| 5,605,690 | A | 2/1997 | Jacobs et al. |
| 5,693,801 | A | 12/1997 | Shaw et al. |
| 5,733,905 | A | 3/1998 | Albright et al. |
| 5,736,540 | A | 4/1998 | Albright et al. |
| 5,753,648 | A | 5/1998 | Albright et al. |
| 5,763,137 | A | 6/1998 | Deprez et al. |
| 5,840,888 | A | 11/1998 | Shaw et al. |
| 5,990,109 | A | 11/1999 | Chen et al. |
| 6,090,382 | A | 7/2000 | Salfeld et al. |
| 6,262,241 | B1 | 7/2001 | Cook et al. |
| 6,653,471 | B2 | 11/2003 | Yohannes et al. |
| 6,949,562 | B2 | 9/2005 | Yohannes et al. |
| 7,169,926 | B1 | 1/2007 | Burgess et al. |
| 7,593,820 | B2 | 9/2009 | Wilks et al. |
| 7,772,231 | B2 | 8/2010 | Sheppard et al. |
| 8,426,411 | B2 | 4/2013 | Wishart et al. |
| 8,637,529 | B2 | 1/2014 | Woller et al. |
| 8,785,639 | B2 | 7/2014 | Wishart et al. |
| 8,962,629 | B2 | 2/2015 | Wishart et al. |
| 9,365,579 | B2 | 6/2016 | Wishart et al. |
| 2003/0078277 | A1 | 4/2003 | Hibi et al. |
| 2004/0023992 | A1 | 2/2004 | Das et al. |
| 2005/0176796 | A1 | 8/2005 | D'Alessio et al. |
| 2006/0183758 | A1 | 8/2006 | Beard et al. |
| 2008/0070914 | A1 | 3/2008 | Freyne et al. |
| 2009/0215724 | A1 | 8/2009 | Dubois et al. |
| 2009/0215750 | A1 | 8/2009 | Bamberg et al. |
| 2009/0215788 | A1 | 8/2009 | Elworthy et al. |
| 2009/0264399 | A1 | 10/2009 | Inoue et al. |
| 2009/0312338 | A1 | 12/2009 | Wishart et al. |

(Continued)

FOREIGN PATENT DOCUMENTS

| | | | |
|---|---|---|---|
| CA | 2675288 | A1 | 7/2008 |
| EA | 007415 | B1 | 10/2006 |

(Continued)

OTHER PUBLICATIONS

Applicant's Amended Claims for U.S. Appl. No. 12/958,115.

(Continued)

*Primary Examiner* — Dwayne C. Jones
(74) *Attorney, Agent, or Firm* — Sterne, Kessler, Goldstein & Fox P.L.L.C.

(57) ABSTRACT

The invention provides compounds of Formula (I) and Formula (II)

Formula (I)

Formula (II)

pharmaceutically acceptable salts, pro-drugs, biologically active metabolites, stereoisomers and isomers thereof wherein the variable are defined herein. The compounds of the invention are useful for treating immunological and oncological conditions.

2 Claims, No Drawings

(56) References Cited

U.S. PATENT DOCUMENTS

| | | | |
|---|---|---|---|
| 2011/0021425 | A1 | 1/2011 | Billedeau |
| 2011/0190489 | A1 | 8/2011 | Wishart et al. |
| 2011/0311474 | A1 | 12/2011 | Wishart et al. |
| 2012/0034250 | A1 | 2/2012 | Shirakami et al. |
| 2012/0330012 | A1 | 12/2012 | Frank et al. |
| 2013/0072470 | A1 | 3/2013 | Wishart et al. |
| 2013/0216497 | A1 | 8/2013 | Wishart et al. |
| 2015/0118229 | A1 | 4/2015 | Voss et al. |
| 2015/0210708 | A1 | 7/2015 | Wishart et al. |
| 2016/0222020 | A1 | 8/2016 | Wishart et al. |
| 2016/0326181 | A1 | 11/2016 | Wishart et al. |
| 2017/0129902 | A1 | 5/2017 | Allian et al. |

FOREIGN PATENT DOCUMENTS

| | | | |
|---|---|---|---|
| EP | 0423805 | A2 | 4/1991 |
| EP | 0423805 | B1 | 8/2000 |
| EP | 1097709 | A2 | 5/2001 |
| EP | 2123651 | | 11/2009 |
| GB | 716327 | A | 10/1954 |
| RU | 2158127 | C2 | 10/2000 |
| RU | 2250904 | C2 | 4/2005 |
| WO | WO-1991/010671 | A1 | 7/1991 |
| WO | WO-1992/016553 | A1 | 10/1992 |
| WO | WO-1992/022552 | A1 | 12/1992 |
| WO | WO 1993/022314 | A1 | 11/1993 |
| WO | WO-1994/005665 | A1 | 3/1994 |
| WO | WO-1994/011026 | A2 | 5/1994 |
| WO | WO-1994/019351 | A1 | 9/1994 |
| WO | WO-1995/019970 | A1 | 7/1995 |
| WO | 92/09304 | A1 | 3/1996 |
| WO | WO-1996/009304 | A1 | 3/1996 |
| WO | WO-1999/045009 | A1 | 9/1999 |
| WO | WO-0015231 | A1 | 3/2000 |
| WO | WO-2003/000695 | A1 | 1/2003 |
| WO | WO-2003/031606 | A2 | 4/2003 |
| WO | WO-2004/065378 | A1 | 8/2004 |
| WO | WO 2004/106293 | A2 | 12/2004 |
| WO | WO-2005/110410 | A2 | 11/2005 |
| WO | WO-2006/002051 | A1 | 1/2006 |
| WO | WO-2006/010567 | A1 | 2/2006 |
| WO | WO-2006/074984 | A1 | 7/2006 |
| WO | WO-2006/074985 | A1 | 7/2006 |
| WO | WO-2006/107771 | A2 | 10/2006 |
| WO | WO-2006/122137 | A1 | 11/2006 |
| WO | WO-2007/007919 | A2 | 1/2007 |
| WO | WO-2007/022268 | A2 | 2/2007 |
| WO | WO-2007/035935 | A1 | 3/2007 |
| WO | WO-2007/061764 | A2 | 5/2007 |
| WO | WO-2007/077949 | A1 | 7/2007 |
| WO | WO-2007/079164 | A2 | 7/2007 |
| WO | WO-2007/143434 | A2 | 12/2007 |
| WO | WO-2008/021369 | A2 | 2/2008 |
| WO | WO-2008/063287 | A2 | 5/2008 |
| WO | WO-2008/084861 | A1 | 7/2008 |
| WO | WO-2008/094602 | A2 | 8/2008 |
| WO | WO-2008/112695 | A2 | 9/2008 |
| WO | WO-2008/121748 | A2 | 10/2008 |
| WO | WO-2009/005675 | A1 | 1/2009 |
| WO | WO-2009/108827 | A1 | 9/2009 |
| WO | WO-2009/152133 | A1 | 12/2009 |
| WO | WO-2010/003133 | A2 | 1/2010 |
| WO | WO-2011/068899 | A1 | 6/2011 |

OTHER PUBLICATIONS

Banker, et al., (1996), Modern Pharmaceuticals, p. 596.

Baslund, B. et al. "Targeting Interleukin-15 in Patients with Rheumatoid Arthritis," Arthritis & Rheumatism, vol. 52, No. 9 Sep. 2005 pp. 2686-2692.

Dorwal, F. Z., Side Reactions in Organic Synthesis : A Guide to Successful Sythesis Design, Weinheim: WILEY-VCH Verlag GmbH & Co. KGaA, 2005, Preface.

Hauser, et al., Journal of Organic Chemistry (1961), 26, 451-5.

Jain, Sanjay et al., A Novel Synthesis of Di(I-Methylazacycloalkeno)[2,3-b:2',3'-d]Pyridines Through Annulation on Lactam Acetals; Tetrahedron Letters,1990, pp. 131-134, vol. 31 No. 1.

Jordan, V. C., "Tamoxifen: A most Unlikely Pionering Medicine." Nature Reviews: Drug Discovery, 2003, 2: 205-213.

Kempson, J. et al., "Synthesis, initial SAR and biological evaluation of 1.6-dihydroimidazo[4, 5-d]pyrrolo[2,3-b]pyridin-4-amine derived inhibtors of IkB kinase", Bioorganic & Medicinal Chemistry Letters, 2009, vol. 19, pp. 2646-2649.

Metabolite. Merriam-Webster.com. Merriam-Webster, n.d. Web. Dec. 4, 2013. <http://www.merriam-webster.com/dictionary/metabolite.

Mikhaleva, et al., Khimiya Geterotsiklicheskikh Soedinenii (1972),(12), 1696-9.

Noble, M. et al., "Protein Kinase Inhibitors: Insights into Drug Design from Structure." Science, 2004, 303 (5665): p. 1800-1805.

Rochais et al., "Synthesis of New Dipyrrolo- and Furopyrrolopyazinones related to Tripentones and Their Biological Evaluation as Potential Kinases (CDKs1-5, GSK3) Inhibitors," Eur.J. Med.Chem(2009)44:708-716.

Schram et al. (Journal of Heterocyclic Chemistry (1975) 12:(5); pp. 1021-1023.

Stella et al., "Prodrugs: Challenges and Rewards, Part 1" Biotechnology: Pharmaceutical Aspects, 2007, p. 24.

Van Epps, S. et al., "Design and Synthesis of Tricyclic Cores for Kinase Inhibition." Bioorganic & Medicinal Chemistry Letters, 2013, vol. 23, p. 693-698.

Wermuth, Camille G., "The Practice of Medicinal Chemistry." Chapter 13: Molecular Variations Based on Isoteric Replacements. Academic Press, London, 1996, pp. 203-237.

Wolff et al., "Burger's Medicinal Chemistry and Drug Discovery," 5th Ed. Part 1, p. 975-977 (1995).

AbbVie Announces Positive Phase 2 Study Results for Upadacitinib (ABT-494), an Investigational Jak1—Selective Inhibitor, in Crohn's Disease (May 9, 2017), accessed at https://news.abbvie.com/news/press-releases/abbvie-announces-positive-phase-2-study-results-for-upadacitinib-abt-494-an-investigational-jak1-selective-inhibitor-in-crohns-disease.htm, accessed on Dec. 18, 2017, 3 pages.

AbbVie's Upadacitinib (ABT-494) Meets All Primary and Ranked Secondary Endpoint in Second Phase 3 Study in Rheumatoid Arthritis (Sep. 11, 2017), accessed at https://news.abbvie.com/alert-topics/immunology/abbvies-upadacitinib-abt-494-meets-all-primary-and-ranked-secondary-endpoints-in-second-phase-3-study-in-rheumatoid-arthritis.htm. accessed on Dec. 18, 2017, 4 pages.

AbbVie's Upadacitinib (ABT-494) Meets All Primary and Ranked Secondary Endpoint in Phase 3 Study in Rheumatoid Arthritis (Jun. 7, 2017), accessed at https://news.abbvie.com/news/abbvies-upadacitinib-abt-494-meets-all-primary-and-ranked-secondary-endpoints-in-phase-3-study-in-rheumatoid-arthritis.htm, accessed on Dec. 18, 2017, 4 pages.

AbbVie's Upadacitinib (ABT-494) meets Primary Endpoint in Phase 2b Study in Atopic Dermatitis (Sep. 7, 2017), accessed at https://news.abbvie.com/news/abbvies-upadacitinib-abt-494-meets-primary-endpoint-in-phase-2b-study-in-atopic-dermatitis.htm, accessed on Dec. 18, 2017, 3 pages.

Burmester, G., "A Phase 3 Randomized, Placebo-Controlled, Double-Blind Study of Upadacitinib (ABT-494), a Selective JAK-1 Inhibitor, in Patients with Active Rheumatoid Arthritis with Inadequate Response to Conventional Synthetic Dmards," 2017 ACR/ARHP Annual Meeting, Abstract No. 1904, United States, 4 pages.

Genovese, M., "Efficacy and Safety of ABT-494, a Selective JAK-1 Inhibitor, in a Phase IIb Study in Patients with Rheumatoid Arthritis and an Inadequate Response to Methotrexate," Arthritis & Rheumatology 68(12):2857-2866, American College of Rheumatology, United States (Dec. 2016).

Genovese, M., "Long-Term Safety and Efficacy of Upadacitinib (ABT-494), an Oral JAK-1 Inhibitor in Patients with Rheumatoid Arthritis in an Open Label Extension Study," 2017 ACR/ARHP Annual Meeting, Abstract No. 509, 5 pages.

(56) References Cited

OTHER PUBLICATIONS

Genovese, M., et al., "Safety and Efficacy of ABT-494, a Novel Selective JAK1 Inhibitor, in Patients with Active Rheumatoid Arthritis with an Inadequate Response to Methotrexate," Annual European Congress of Rheumatology, Abstract No. OP0223, Jun. 2016, 2 pages.
Goedken, E., et al., "Minimum Significant Ratio of Selectivity Ratios (MSRSR) and Confidence in Ratio of Selectivity Ratios (CRSR): Quantitative Measures for Selectivity Ratios Obtained by Screening Assays," Journal of Biomolecular Screening 17: 857-867, Society for Laboratory Automation and Screening, United States (Apr. 2012).
Graff, C., et al., "Characterization of ABT-494, a Second Generation JAK1 Selective Inhibitor," 2014 ACR/ARHP Annual Meeting, Abstract No. 1499, 3 pages.
Grebien, F., et al., "Stat5 activation enables erythropoiesis in the absence of EpoR and JAK2," Blood 111(9):4511-4522, American Society of Hematology, United States (May 2008).
Guschin, D., et al., "A major role for the protein tyrosine kinase JAK1 in the JAK/STAT signal transduction pathway in response to interleukin-6," The Embo Journal 14(7):1421-1429, Oxford University Press, United Kingdom (1995).
Klunder, B., et al., "Exposure—Response Analyses of the Effect of Upadacitinib on ACR Responses in th Phase 2b Rheumatoid Arthritis Trials in Patients with Inadequate Response to Methotrxate or to Anti-Tumor Necrosis Factor Therapy," 2017 ACR/ARHP Annual Meeting, Abstract No. 505 , 4 pages.
Kremer, J.M., et al., "A Phase IIb Study of ABT-494, a Selective JAK-1 Inhibitor, in Patients with Rheumatoid Arthritis and an Inadequate Response to Anti-Tumor Necrosis Factor Therapy," Arthritis & Rheumatology 68(12):2867-2877, Wiley, United States (Dec. 2016).
Kremer, J., et al., "Safety and Efficacy of ABT-494, a Novel Selective JAK1 Inhibitor, in Patients with Active Rheumatoid Arthritis and Inadequate Response or Intolerance to Anti-TNF Biologic Therapy," 2015 ACR/ARHP Annual Meeting, Abstract No. 14L, Oct. 2015, 5 pages.
Klünder. B, et al., "Population Pharmacokinetics of ABT-494 in Healthy Subjects and in Subjects With Rheumatoid Arthritis: Combined Analysis of Phase I and II Trials," Clinical Pharmacology & Therapeutics 101(S1):S79, Abstract PII-098, John Wiley & Sons, Inc., United States (Feb. 2017).
Mohamed, M.-E.F., "Exposure-Response Analysis to Assess the Effect of ABT-494 on QT Interval and Utilization of a Non-Pharmacological Approach to Demonstrate ECG Assay Sensitivity," Clinical Pharmacology & Therapeutics 101(S1):S39, Abstract PI-076, John Wiley & Sons, Inc., United States (Feb. 2017).
Mohamed, M.-E., et al., "Pharmacokinetics of ABT-494 with the Once-Daily Extended-Release Tablet Formulation Being Utilized in the Ongoing Rheumatoid Arthritis Phase 3 Trials," 2016 ACR/ARHP Annual Meeting, Abstract No. 1629, 2 pages.
Mohamed, M.-E.F., et al., "ABT-494 Has no Effect on the QT Interval at the Doses Being Evaluated in Rheumatoid Arthritis Phase 3 Trials," Annals of the Rheumatic Diseases, Abstract No. AB0432, Jun. 2017, 1 page.
Mohamed, M.-E.F., et al., "ABT-494 Pharmacokinetics Following Administration of the Once-Daily Extended-Release Tablet Formulation Being Utilized in the Ongoing Rheumatoid Arthritis Phase 3 Trials," Annals of the Rheumatic Diseases, Abstract No. THU0177, Jun. 2017, 2 pages.
Mohamed, M.-E., et al., "Assessment of the Effect of CYP3A Inhibition, CYP Induction, OATP1B Inhibition and Administration of High-Fat Meal on the Pharmacokinetics of the Potent and Selective JAK1 Inhibitor ABT-494," 2017 ACR/ARHP Annual Meeting, Abstract No. 2751, 2 pages.
Mohamed, M.-E.F., et al., "Pharmacokinetics, Safety and Tolerability of ABT-494, a Novel Selective JAK1 Inhibitor, in healthy volunteers and subjects with Rheumatoid Arthritis," Clinical Pharmacokinetics 55(12):1547-1558, Springer International, Switzerland (Jun. 2016).
Mohamed, M.-E., et al., "Pharmacokinetics, Safety and Tolerability of the Selective JAK1 Inhibitor; ABT-494, in Healthy Volunteers and Subjects with Rheumatoid Arthritis," Annals of the Rheumatic Diseases 74(2):258, Abstract THU0176, BMJ Publishing Group Ltd., (2015).
Mohamed, M.-E., et al., "Preferential Inhibition of IL-6 Relative to IL-7 Signaling Pathways by ABT-494: Exposure-Response Analysis of Ex-Vivo Data from two Phase 1 Clinical Trials and Comparison to Tofacitinib," Annals of the Rheumatic Diseases 75(2):256, Abstract THU0195, BMJ Publishing Group Ltd., England (Jun. 2016).
Mohamed, M., et al., "The Selective JAK1 Inhibitor Upadacitinib has no Effect on Pharmacokinetics of the Hormonal Contraceptives Levonorgesrel and Ethinylestradiol," 2017 ACR/ARHP Annual Meeting, Abstract No. 506, Sep. 2017, 4 pages.
Mohamed, M.-E.F., et al., "Use of Early Clinical Trial Data to Support Thorough QT Study Waiver for Upadacitinib and Utility of Food Effect to Demonstrate ECG Assay Sensitivity," Clinical Pharmacology & Therapeutics, accepted Jul. 24, 2017, 7 pages, John Wiley & Sons, Inc., United States.
Strand, V., et al., "Changes in Hemoglobin levels upon Treatment with ABT-494, a Selective JAK-1 Inhibitor, and relation to baseline levels of C-Reactive Protein," THU0210, 1 page.
Strand, V., et al., "Early Patient-Reported Outcomes and Clinical Outcomes with ABT-494 in Patients with Active Rheumatoid Arthritis who are Inadequate Responses to Methotrexate or Tumor Necrosis Factor Inhibitors: Post-Hoc Analysis of Phase 2 Randomized Controlled Trials," Annals of the Rheumatic Diseases, Abstract No. SAT0217, Jun. 2017, 1 page.
Strand, V., et al., "Economic Burden of Non-Responders to Biologic DMARD Treatments in Rheumatoid Arthritis," 2016 ACR/ARHP Annual Meeting, Abstract No. 2617, 2 pages.
Strand, V., et al., "Patient-Reported Outcomes of Long-Term Upadacitinib Use in Patients with Rheumatoid Arthritis: Interim Analysis Results of a Phase 2, Open-Label Extension Study," 2017 ACR/ARHP Annual Meeting, Abstract No. 501, 3 pages.
Voss, J., et al., Pharmacodynamics of a novel JAK1 Selective Inhibitor in Rat Arthritis and Anemia Models and in Healthy Human Subjects, 2013 ACR/ARHP Annual Meeting, Abstract No. 2374, 2 pages.
Neubauer, H., et al., "JAK2 Deficiency Defines an Essential Developmental Checkpoint in Definitive Hematopoiesis," Cell 93: 397-409, Cell Press, United States (May 1998).
Ortmann, R., et al., "Janus kinases and signal transducers and activators of transcription: their roles in cytokine signaling, development and immunoregulation," Arthritis Res., 2:16-32, 2000.
Weiss, F., et al., "Anemia of Chronic Disease," The New England Journal of Medicine 352: 1011-1123, Massachusetts Medical Society, United States (Mar. 2005).
*The Merck Index, An Encyclopedia of Chemicals, Drugs, and Biologicals*, Fourteenth Edition (2006), Adalimumab, entry 148, pp. 26-27; Etanercept, entry 3712, p. 637; Infliximab, entry 4972, p. 863; Rapamycin, entry 8114, p. 1397; Rituximab, entry 8239, p. 1422.
"Annex A—Relative IC50 Values for Compounds of Formula I(c)," submitted in European Application No. EP10835061.2-1462, dated Nov. 7, 2014, cited as Document TM3 in Opposition to European Patent EP 2 506 716 (submitted on Feb. 16, 2018), 10 pages.
Notice of Opposition to European Patent EP 2 506 716, submitted on Feb. 16, 2018, 5 pages.
Opposition Brief to European Patent EP 2 506 716, submitted on Feb. 16, 2018, 16 pages.
Response to Communication pursuant to Art. 94(3) EPC dated Jul. 12, 2016, submitted in European Application No. EP10835061.2-1462, cited as Document TM4 in Opposition to European Patent EP 2 506 716 (submitted on Feb. 16, 2018), 3 pages.
Statement of Case in Opposition to Israel Patent Application 248466, dated Nov. 23, 2017, 4 Pages.
Amended Pleadings on Behalf of the Opponent in Opposition to Israel Patent Application 248466, dated Mar. 26, 2018, 136 Pages.
Mohamed, M-E. F., et al., "Assessment of effect of CYP3A Inhibition, CYP induction, OATP1B inhibition, and high-fat meal on pharmacokinetics of the JAK1 inhibitor upadacitinib," British Journal of Clinical Pharmacology 83: 2242-2248, British Pharmacological Society, United Kingdom, 2017.

(56) References Cited

OTHER PUBLICATIONS

Hisham A. Abd El-Nabi, 1-Aryl-2-Chloro-5-Methoxy-1H-3-Pyrrolecarbaldehyde As Synthons for Fused Heterocycles: Synthesis of Pyrazolo[3,4-D] Pyridine Derivatives, Journal of Chemical Research, May 2004, pp. 325-327, vol. 5.
Shashi Nayana et al., COMFA and Docking Studies on Triazolopyridine Oxazole Derivatives as P38 Map Kinase Inhibitors, European Journal of Medicinal Chemistry 43, pp. 1261-1269, 2008, Abstract; p. 1263-1268.
U.S. Appl. No. 12/958,291, Dec. 1, 2010, Wishart et al.
Zaragoza, Side Reactions in Organic Synthesis: A Guide to Successful Synthesis Design, Weinheim: Wiley-VCH Verlag GmbH & Co. KGaA, 2005, Preface.

TRICYCLIC COMPOUNDS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATION

This application [incorporate] *is a reissue application of U.S. Pat. No. 8,426,411, which incorporates* by reference the entire [content] *contents* of U.S. Utility application Ser. No. 12/481,028 filed on Jun. 9, 2009, and its priority applications including U.S. Provisional Application Ser. No. 61/131,599 filed on Jun. 10, 2008, U.S. Provisional Application Ser. No. 61/131,602 filed on Jun. 10, 2008, U.S. Provisional Application Ser. No. 61/190,159 filed on Aug. 26, 2008, and U.S. Provisional Application Ser. No. 61/201,064 filed Dec. 5, 2008. [This application] *U.S. Pat. No. 8,426,411 issued on Apr. 23, 2013 from U.S. Utility application Ser. No. 12/958,115, which* claims priority to U.S. Provisional Application Ser. No. 61/265,563 filed on Dec. 1, 2009, and U.S. Provisional Application Ser. No. 61/364,116 filed *on* Jul. 14, 2010, the entire contents of which are incorporated by reference herein.

BACKGROUND OF THE INVENTION

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the Jak1, Jak2, Jak3, Tyk2, KDR, Flt-3, CDK2, CDK4, TANK, Trk, FAK, Abl, Bcr-Abl, cMet, b-RAF, FGFR3, c-kit, PDGF-R, Syk, BTK, CSF1R, PKC kinases or Aurora kinases.

The protein kinases represent a large family of proteins that play a central role in the regulation of a wide variety of cellular processes and maintenance of cellular function. A partial, non-limiting, list of these kinases include: non-receptor tyrosine kinases such as the Janus kinase family (Jak1, Jak2, Jak3 and Tyk2); the fusion kinases, such as BCR-Abl, focal adhesion kinase (FAK), Fes, Lck and Syk; receptor tyrosine kinases such as platelet-derived growth factor receptor kinase (PDGF-R), the receptor kinase for stem cell factor, c-kit, the hepatocyte growth factor receptor, c-Met, and the fibroblast growth factor receptor, FGFR3; and serine/threonine kinases such as b-RAF, mitogen-activated protein kinases (e.g., MKK6) and SAPK2β. Aberrant kinase activity has been observed in many disease states including benign and malignant proliferative disorders as well as diseases resulting from inappropriate activation of the immune and nervous systems. The novel compounds of this invention inhibit the activity of one or more protein kinases and are, therefore, expected to be useful in the treatment of kinase-mediated diseases.

SUMMARY OF THE INVENTION

In a first embodiment the invention provides a compound of Formula (I)

Formula (I)

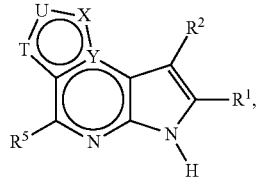

pharmaceutically acceptable salts, pro-drugs, biologically active metabolites, stereoisomers and isomers thereof wherein T is N, U is N, X is $CR^3$ and Y is N; or T is $CR^6$, U is N, X is $CR^3$ and Y is N; or T is N, U is $CR^4$, X is $CR^3$ and Y is N; or T is $CR^6$, U is $CR^4$, X is $CR^3$ and Y is N; or T is $CR^6$, U is N, X is $NR^3$ and Y is C; or T is O, U is N, X is $CR^3$ and Y is C; or T is $NR^6$, U is N, X is $CR^3$ and Y is C; or T is $CR^6$, U is $CR^4$, X is $NR^3$ and Y is C; or T is S, U is N, X is $CR^3$ and Y is C; or T is N, U is $CR^4$, X is $NR^3$ and Y is C; or T is N, U is N, X is $NR^3$ and Y is C;

$R^1$, $R^2$ and $R^5$ are each independently hydrogen, deuterium, —$N(R^a)(R^b)$, halogen, —$OR^a$, —$SR^a$, —$S(O)R^a$, —$S(O)_2R^a$, —$NO_2$, —$C(O)OR^a$, —CN, —$C(O)N(R^a)(R^b)$, —$N(R^a)C(O)(R^b)$, —$C(O)R^a$, —$C(OH)R^aR^b$, —$N(R^a)S(O)_2$—$R^b$, —$S(O)_2N(R^a)(R^b)$, —$CF_3$, —$OCF_3$, optionally substituted $(C_1$-$C_6)$alkyl, optionally substituted $(C_2$-$C_6)$alkenyl, optionally substituted $(C_2$-$C_6)$alkynyl, optionally substituted $(C_3$-$C_{10})$cycloalkyl, optionally substituted $(C_1$-$C_{10})$ heteroaryl, optionally substituted $(C_1$-$C_{10})$ heterocyclyl, or optionally substituted $(C_6$-$C_{10})$aryl;

wherein in a moiety containing —$N(R^a)(R^b)$, the nitrogen, $R^a$ and $R^b$ may form a ring such that —$N(R^a)(R^b)$ represents an optionally substituted $(C_2$-$C_{10})$heterocyclyl or optionally substituted $(C_1$-$C_{10})$heteroaryl linked through a nitrogen;

$R^3$ is hydrogen, an optionally substituted bridged $(C_5$-$C_{12})$ cycloalkyl, optionally substituted bridged $(C_2$-$C_{10})$heterocyclyl, optionally substituted $(C_1$-$C_8)$alkyl, optionally substituted $(C_3$-$C_{10})$cycloalkyl, optionally substituted $(C_3$-$C_8)$ cycloalkenyl, optionally substituted $(C_6$-$C_{10})$aryl, optionally substituted $(C_1$-$C_{10})$heteroaryl, optionally substituted $(C_2$-$C_{10})$heterocyclyl; or $R^3$ is -A-D-E-G, wherein:

A is a bond, —C(O)—, optionally substituted $(C_1$-$C_6)$ alkylene, optionally substituted $(C_2$-$C_6)$alkenylene, optionally substituted $(C_2$-$C_6)$alkynylene, optionally substituted $(C_3$-$C_{12})$cycloalkylene, optionally substituted $(C_2$-$C_6)$heterocyclylene, —$C(O)N(R^a)$—$R^e$—, —$N(R^a)C(O)$—$R^e$—, —O—$R^e$—, —$N(R^a)$—$R^e$—, —S—$R^e$—, —$S(O)_2$—$R^e$—, —$S(O)R^e$—, —$C(O$—$R^a)(R^b)$—$R^e$—, —$S(O)_2N(R^a)$—$R^e$—, —$N(R^a)S(O)_2$—$R^e$— or —$N(R^a)C(O)N(R^b)$—$R^e$—;

D is an optionally substituted $(C_1$-$C_8)$alkylene, optionally substituted bridged $(C_5$-$C_{12})$cycloalkylene, optionally substituted $(C_3$-$C_{10})$cycloalkylene, optionally substituted bridged $(C_5$-$C_{10})$cycloalkenylene, optionally substituted $(C_3$-$C_{10})$cycloalkenylene, optionally substituted $(C_6$-$C_{10})$ arylene, optionally substituted $(C_1$-$C_{10})$heteroarylene, optionally substituted bridged $(C_2$-$C_{10})$heterocyclylene or an optionally substituted $(C_2$-$C_{10})$heterocyclylene;

E is a bond, —$R^e$—, —$R^e$—C(=NCN)—$R^e$—, —$R^e$—C(O)—$R^e$—, —$R^e$—C(O)C(O)—$R^e$—, —$R^e$—C(O)O—$R^e$—, —$R^e$—C(O)C(O)$N(R^a)$—$R^e$—, —$R^e$—$N(R^a)$—C(O)

C(O)—$R^e$—, —$R^e$—O—$R^e$—, —$R^e$—$S(O)_2$—$R^e$—, —$R^e$—S(O)—$R^e$—, —$R^e$—S—$R^e$—, —$R^e$—N($R^a$)—$R^e$—, =N—$R^e$—, —$R^e$—N($R^a$)C(O)—$R^e$—, —$R^e$C(O)N($R^a$)$R^e$—, —$R^e$—OC(O)N($R^a$)—$R^e$—, —$R^e$—N($R^a$)C(O)O$R^e$—, —$R^e$—OC(O)—$R^e$, —$R^e$—OC(O)—O—$R^e$, —$R^e$—N($R^a$)C(O)N($R^b$)—$R^e$—, —$R^e$—N($R^a$)$S(O)_2$—$R^e$—, —$R^e$—$S(O)_2$N($R^a$)—$R^e$—, or —$R^e$—N($R^a$)$S(O)_2$N($R^a$)—$R^e$—; or

E is

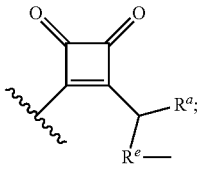

where in all cases, E is linked to either a carbon or a nitrogen atom in D;

G is hydrogen, deuterium, —N($R^a$)($R^b$), halogen, —O$R^a$, —S$R^a$, —S(O)$R^a$, —$S(O)_2R^a$, —$NO_2$, —C(O)O$R^a$, —CN, —C(O)N($R^a$)($R^b$), —N($R^a$)C(O)$R^b$, —N($R^a$)C(O)O$R^b$, —OC(O)N($R^a$), —N($R^a$)C(O)N$(R^b)_2$, —C(O—$R^a$)$(R^b)_2$, —C(O)$R^a$, —$CF_3$, —$OCF_3$, —N($R^a$)$S(O)_2R^b$, —$S(O)_2$N($R^a$)($R^b$), —$S(O)_2$N($R^a$)C(O)$R^b$, an optionally substituted —($C_1$-$C_6$)alkyl, an optionally substituted —($C_2$-$C_6$)alkenyl, an optionally substituted —($C_2$-$C_6$)alkynyl, an optionally substituted —($C_3$-$C_{10}$)cycloalkyl, an optionally substituted —($C_1$-$C_{10}$)heteroaryl, an optionally substituted —($C_1$-$C_{10}$) heterocyclyl, an optionally substituted —($C_6$-$C_{10}$)aryl;

wherein in a moiety containing —N($R^a$)($R^b$), the nitrogen, $R^a$ and $R^b$ may form a ring such that —N($R^a$)($R^b$) represents an optionally substituted ($C_2$-$C_{10}$)heterocyclyl or an optionally substituted ($C_1$-$C_{10}$) heteroaryl linked through a nitrogen;

$R^4$ and $R^6$ are each independently a hydrogen, halogen, deuterium, $CF_3$, $CHF_2$, $CH_2F$, $CH_2CF_3$, C(O)OH, C(O)$OCH_3$, CN, an optionally substituted bridged ($C_5$-$C_{12}$)cycloalkyl group, optionally substituted bridged ($C_2$-$C_{10}$)heterocyclyl group, optionally substituted ($C_1$-$C_8$)alkyl, optionally substituted ($C_3$-$C_{10}$)cycloalkyl, optionally substituted ($C_3$-$C_8$)cycloalkenyl, optionally substituted ($C_6$-$C_{10}$) aryl, optionally substituted ($C_1$-$C_{10}$)heteroaryl, optionally substituted ($C_2$-$C_{10}$)heterocyclyl or -J-L-M-Q;

wherein:

J is a bond, —C(O)—, optionally substituted ($C_1$-$C_6$) alkylene, optionally substituted ($C_2$-$C_6$)alkenylene, optionally substituted ($C_2$-$C_6$)alkynylene, optionally substituted ($C_3$-$C_{12}$)cycloalkylene, optionally substituted ($C_2$-$C_6$)heterocyclylene, —C(O)N($R^a$)—$R^e$—, —N($R^a$)C(O)—$R^e$—, —O—$R^e$—, —N($R^a$)—$R^e$—, —S—$R^e$—, —$S(O)_2$—$R^e$—, —S(O)$R^e$—, —C(O—$R^a$)($R^b$)—$R^e$—, —$S(O)_2$N($R^a$)—$R^e$—, —N($R^a$)$S(O)_2$—$R^e$— or —N($R^a$)C(O)N($R^b$)—$R^e$—;

L is a bond, an optionally substituted ($C_1$-$C_8$)alkylene, optionally substituted bridged ($C_5$-$C_{12}$)cycloalkylene, optionally substituted ($C_3$-$C_{10}$)cycloalkylene, optionally substituted bridged ($C_5$-$C_{10}$)cycloalkenylene, optionally substituted ($C_3$-$C_{10}$)cycloalkenylene, optionally substituted ($C_6$-$C_{10}$)arylene, optionally substituted ($C_1$-$C_{10}$)heteroarylene, optionally substituted bridged ($C_2$-$C_{10}$)heterocyclylene or an optionally substituted ($C_2$-$C_{10}$)heterocyclylene;

M is a bond, —$R^e$—, —$R^e$—C(O)—$R^e$—, —$R^e$—C(O)C(O)—$R^e$—, —$R^e$—C(O)O—$R^e$—, —$R^e$—OC(O)—$R^e$, —$R^e$— C(O)C(O)N($R^a$)—$R^e$—, —$R^e$—N($R^a$)—C(O)C(O)—$R^e$—, —$R^e$—O—$R^e$—, —$R^e$—$S(O)_2$—$R^e$—, —$R^e$—S(O)—$R^e$—, —$R^e$—S—$R^e$—, —$R^e$—N($R^a$)—$R^e$—, —$R^e$—N($R^a$)C(O)—$R^e$—, —$R^e$—C(O)N($R^a$)$R^e$—, —$R^e$—OC(O)N($R^a$)—$R^e$—, —$R^e$—N($R^a$)C(O)O$R^e$—, —$R^e$—N($R^a$)C(O)N($R^b$)—$R^e$—, —$R^e$—N($R^a$)$S(O)_2$—$R^e$—, or —$R^e$—$S(O)_2$N($R^a$)—$R^e$—; or M is

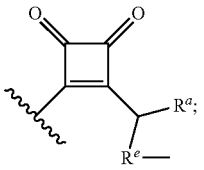

where in all cases, M is linked to either a carbon or a nitrogen atom in L;

Q is hydrogen, deuterium, —N($R^a$)($R^b$), halogen, —O$R^a$, —S$R^a$, —S(O)$R^a$, —$S(O)_2R^a$, —$NO_2$, —C(O)O$R^a$, —CN, —C(O)N($R^a$)($R^b$), —N($R^a$)C(O)$R^b$, —N($R^a$)C(O)O$R^b$, —N($R^a$)C(O)N$(R^b)_2$, —C(O—$R^a$)$(R^b)_2$, —C(O)$R^a$, —$CF_3$, —$OCF_3$, —N($R^a$)$S(O)_2R^b$, —$S(O)_2$N($R^a$)($R^b$), —$S(O)_2$N($R^a$)C(O)$R^b$, an optionally substituted ($C_1$-$C_6$)alkyl, an optionally substituted ($C_2$-$C_6$)alkenyl, an optionally substituted ($C_2$-$C_6$)alkynyl, an optionally substituted ($C_3$-$C_{10}$) cycloalkyl, an optionally substituted ($C_1$-$C_{10}$)heteroaryl, an optionally substituted ($C_1$-$C_{10}$) heterocyclyl, an optionally substituted ($C_6$-$C_{10}$)aryl;

wherein in a moiety containing —N($R^a$)($R^b$), the nitrogen, $R^a$ and $R^b$ may form a ring such that —N($R^a$)($R^b$) represents an optionally substituted ($C_2$-$C_{10}$)heterocyclyl or an optionally substituted ($C_1$-$C_{10}$) heteroaryl linked through a nitrogen;

$R^a$ and $R^b$ are each independently hydrogen, deuterium, CN, an optionally substituted ($C_1$-$C_{10}$)alkyl, an optionally substituted ($C_2$-$C_{10}$)alkenyl, an optionally substituted ($C_2$-$C_{10}$)alkynyl, an optionally substituted ($C_1$-$C_{10}$)alkyl-O—($C_1$-$C_{10}$)alkyl, an optionally substituted ($C_3$-$C_{10}$)cycloalkyl, an optionally substituted ($C_6$-$C_{10}$)aryl, an optionally substituted ($C_1$-$C_{10}$)heteroaryl, an optionally substituted ($C_1$-$C_{10}$) heterocyclyl, an optionally substituted —($C_1$-$C_6$)alkylene-($C_3$-$C_{10}$)cycloalkyl, an optionally substituted —($C_1$-$C_6$) alkylene-($C_6$-$C_{10}$)aryl, an optionally substituted —($C_1$-$C_6$) alkylene-($C_1$-$C_{10}$)heteroaryl, or an optionally substituted —($C_1$-$C_6$)alkylene-($C_1$-$C_{10}$)heterocyclyl; and $R^e$ for each occurrence is independently a bond, an optionally substituted ($C_1$-$C_{10}$)alkylene, an optionally substituted ($C_2$-$C_{10}$)alkenylene, an optionally substituted ($C_2$-$C_{10}$)alkynylene, an optionally substituted —($C_1$-$C_{10}$)alkylene-O—($C_1$-$C_{10}$)alkylene group, an optionally substituted ($C_3$-$C_{10}$)cycloalkylene, an optionally substituted ($C_6$-$C_{10}$) arylene, an optionally substituted ($C_1$-$C_{10}$)heteroarylene, or an optionally substituted ($C_1$-$C_{10}$)heterocyclylene;

provided that when T is N, U is $CR^4$, X is $NR^3$ and Y is C, $R^4$ is not OH;

provided that when T is N, U is $CR^4$, X is $NR^3$ and Y is C, $R^1$ is H;

provided that when the compound is

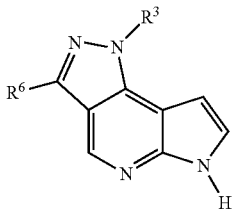

$R^3$ is defined as above and $R^6$ is not linked to the pyrazole ring by a nitrogen or oxygen atom; and provided that when the compound is

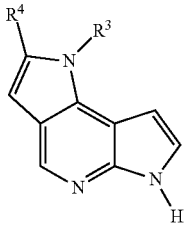

when $R^3$ is H, $CH_3$ or —C(O)OH then $R^4$ is not H, —C(O)$OCH_2CH_3$, —C(O)NH-optionally substituted phenyl, —NHC(O)-optionally substituted phenyl or —$S(O)_2$-phenyl.

In a second embodiment the invention provides a compound according to the first embodiment wherein $R^3$ is -A-D-E-G and A is a bond, optionally substituted ($C_1$-$C_6$)alkylene, optionally substituted ($C_3$-$C_{12}$)cycloalkylene or optionally substituted ($C_2$-$C_6$)heterocyclylene.

In a third embodiment the invention provides a compound according to the any of the foregoing embodiments wherein $R^3$ is -A-D-E-G and D is an optionally substituted ($C_1$-$C_8$)alkylene, optionally substituted ($C_3$-$C_{10}$)cycloalkylene, optionally substituted bridged ($C_5$-$C_{10}$)cycloalkenylene, optionally substituted ($C_3$-$C_{10}$)bridged heterocyclylene or optionally substituted ($C_2$-$C_{10}$)heterocyclylene.

In a fourth embodiment the invention provides a compound according to the any of the foregoing embodiments 3 wherein D is optionally substituted ($C_1$-$C_6$)alkylene, optionally substituted ($C_3$-$C_6$)cycloalkylene, optionally substituted bicyclo[2.2.2]octany-1-yl, optionally substituted 2,5-diazabicyclo[2.2.1]heptane, optionally substituted 2,6-diazabicyclo[3.2.1]octane, optionally substituted octahydropyrrolo[3,4-c]pyrrole, optionally substituted octahydropyrrolo[3,2-b]pyridine, optionally substituted 1,4-diazepane, optionally substituted cubane, optionally substituted 1,4-dioxane-spiro[4.4]nonane, optionally substituted 2,5-diazaspiro[3.5]nonane, optionally substituted piperidine, optionally substituted piperazine, optionally substituted pyrrolidine, optionally substituted tetrahydrofuran or optionally substituted tetrahydropyran.

In a fifth embodiment the invention provides a compound according to the any of the foregoing embodiments wherein $R^3$ is -A-D-E-G and E is a bond, —$R^e$—, —$R^3$—C(O)—$R^e$—, —$R^e$—O—$R^e$—, —$R^e$—$S(O)_2$—$R^e$—, —$R^e$—N($R^a$)—$R^e$—, =N—$R^e$—. —$R^e$—N($R^a$)C(O)—$R^e$—, —$R^e$—N($R^a$)C(O)O—$R^e$—, —$R^e$—N($R^a$)C(O)N($R^b$)—$R^e$—, —$R^e$C(O)N($R^a$)$R^e$—, —$R^e$—N($R^a$)$S(O)_2$—$R^e$—, —$R^e$—$S(O)_2$N($R^a$)—$R^e$—, —$R^e$— N($R^a$)$S(O)_2$N($R^a$)—$R^e$—, —$R^e$—OC(O)N($R^a$)—$R^e$, —$R^e$—C(O)O—$R^e$, —$R^e$—OC(O)—$R^e$; or

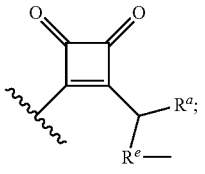

wherein $R^a$ for each occurrence is independently hydrogen, CN, an optionally substituted ($C_1$-$C_{10}$)alkyl or an optionally substituted —($C_1$-$C_6$)alkylene-($C_3$-$C_{10}$)cycloalkyl; and $R^e$ for each occurrence is independently a bond, an optionally substituted ($C_1$-$C_{10}$)alkylene, an optionally substituted ($C_3$-$C_{10}$)cycloalkylene, an optionally substituted ($C_6$-$C_{10}$)arylene, an optionally substituted ($C_1$-$C_{10}$)heteroarylene, or an optionally substituted ($C_1$-$C_{10}$)heterocyclylene.

In a sixth embodiment the invention provides a compound according to the any of the foregoing embodiments wherein $R^3$ is -A-D-E-G and G is hydrogen, deuterium, —N($R^a$)($R^b$), halogen, —O$R^a$, —$S(O)_2R^a$, —CN, —C(O)N($R^a$)($R^b$), —N($R^a$)C(O)$R^b$, —$CF_3$, —$S(O)_2$N($R^a$)($R^b$), an optionally substituted —($C_1$-$C_6$)alkyl, an optionally substituted —($C_3$-$C_{10}$)cycloalkyl, an optionally substituted —($C_1$-$C_{10}$)heteroaryl, an optionally substituted —($C_1$-$C_{10}$)heterocyclyl, or an optionally substituted —($C_6$-$C_{10}$)aryl;

wherein in a moiety containing —N($R^a$)($R^b$), the nitrogen, $R^a$ and $R^b$ may form a ring such that —N($R^a$)($R^b$) represents an optionally substituted ($C_2$-$C_{10}$)heterocyclyl or an optionally substituted ($C_1$-$C_{10}$)heteroaryl linked through a nitrogen;

$R^a$ is independently hydrogen, CN, an optionally substituted ($C_1$-$C_{10}$)alkyl, an optionally substituted ($C_3$-$C_{10}$)cycloalkyl, or an optionally substituted ($C_6$-$C_{10}$)aryl.

In a seventh embodiment the invention provides a compound according to the any of the foregoing embodiments wherein G is hydrogen, deuterium, —N($R^a$)($R^b$), halogen, —O$R^a$, —$S(O)_2R^a$, —CN, —C(O)N($R^a$)($R^b$), —N($R^a$)C(O)$R^b$, —$CF_3$, —$S(O)_2$N($R^a$)($R^b$), an optionally substituted —($C_1$-$C_4$)alkyl, an optionally substituted —($C_3$-$C_6$)cycloalkyl, optionally substituted azepanyl, optionally substituted azetidinyl, optionally substituted benzo[d]isoxazolyl, optionally substituted 4,5-dihydroisoxazolyl, optionally substituted isothiazolidinyl, optionally substituted isothiazolyl, optionally substituted isoxazolyl, optionally substituted morpholinyl, optionally substituted oxadiazolyl, optionally substituted oxazolyl, optionally substituted oxetanyl, optionally substitute phenyl, optionally substituted piperazinyl, optionally substituted piperidinyl, optionally substituted pyrazinyl, optionally substituted pyrazolyl, optionally substituted pyridazinyl, optionally substituted pyridinyl, optionally substituted pyrimidinyl, optionally substituted pyrrolidinyl, optionally substituted pyrrolyl, optionally substituted tetrahydrofuranyl, optionally substituted tetrahydropyranyl, optionally substituted tetrahydrothiopyranyl, optionally substituted thienyl, optionally substituted thiomorpholinyl, optionally substituted 1,1-dioxo-thiomorpholinyl, optionally substituted thiazolyl or optionally substituted triazolyl.

In eighth embodiment the invention provides a compound according to the any of the foregoing embodiments wherein $R^3$ is hydrogen, optionally substituted ($C_1$-$C_8$)alkyl, optionally substituted ($C_3$-$C_{10}$)cycloalkyl, or optionally substituted ($C_2$-$C_{10}$)heterocyclyl.

In a ninth embodiment the invention provides a compound according to the any of the foregoing embodiments wherein $R^6$ is -J-L-M-Q and J is a bond, optionally substituted ($C_1$-$C_6$)alkylene, or an optionally substituted ($C_2$-$C_6$)alkenylene.

In a tenth embodiment the invention provides a compound according to the any of the foregoing embodiments wherein $R^6$ is -J-L-M-Q and L is a bond, or an optionally substituted ($C_1$-$C_8$)alkylene.

In an eleventh embodiment the invention provides a compound according to the any of the foregoing embodiments wherein $R^6$ is -J-L-M-Q and M is a bond, —$R^e$—, —$R^e$—C(O)—$R^e$—, —$R^e$—O—$R^e$—, —$R^e$—$S(O)_2$—$R^e$—, —$R^e$—S(O)—$R^e$—, —$R^e$—S—$R^e$—, —$R^e$—N $(R^a)$—$R^e$—, —$R^e$—$N(R^a)C(O)$—$R^e$—, —$R^e$—$C(O)N(R^a)R^e$—, —$R^e$—$N(R^a)C(O)N(R^b)$—$R^e$—, —$R^e$—$N(R^a)S(O)_2$—$R^e$—, or —$R^e$—$S(O)_2N(R^a)$—$R^e$—; where in all cases, M is linked to either a carbon or a nitrogen atom in L.

In a twelfth embodiment the invention provides a compound according to the any of the foregoing embodiments wherein $R^6$ is -J-L-M-Q and Q is hydrogen, deuterium, —$N(R^a)(R^b)$, halogen, —$OR^a$, —$SR^a$, —$S(O)R^a$, —$S(O)_2R^a$, —$NO_2$, —$C(O)OR^a$, —CN, —$C(O)N(R^a)(R^b)$, —$N(R^a)C(O)R^b$, —$N(R^a)C(O)OR^b$, —$N(R^a)C(O)N(R^b)_2$, —$C(O—R^a)(R^b)_2$, —$C(O)R^a$, —$CF_3$, —$OCF_3$, —$N(R^a)S(O)_2R^b$, —$S(O)_2N(R^a)(R^b)$, —$S(O)_2N(R^a)C(O)R^b$, an optionally substituted $(C_1$-$C_6)$alkyl, an optionally substituted $(C_3$-$C_{10})$cycloalkyl, an optionally substituted $(C_1$-$C_{10})$ heteroaryl, an optionally substituted $(C_1$-$C_{10})$ heterocyclyl, an optionally substituted $(C_6$-$C_{10})$aryl;

wherein in a moiety containing —$N(R^a)(R^b)$, the nitrogen, $R^a$ and $R^b$ may form a ring such that —$N(R^a)(R^b)$ represents an optionally substituted $(C_2$-$C_{10})$heterocyclyl or an optionally substituted $(C_1$-$C_{10})$ heteroaryl linked through a nitrogen;

$R^a$ and $R^b$ are each independently hydrogen, deuterium, an optionally substituted $(C_1$-$C_6)$alkyl, an optionally substituted $(C_2$-$C_{10})$alkenyl, an optionally substituted $(C_3$-$C_6)$ cycloalkyl, an optionally substituted $(C_6$-$C_{10})$aryl, an optionally substituted $(C_1$-$C_{10})$heteroaryl, or an optionally substituted $(C_1$-$C_{10})$heterocyclyl.

In a thirteenth embodiment the invention provides a compound according to the any of the foregoing embodiments wherein T is N, U is N, X is $CR^3$ and Y is N and forms a compound of Formula (Ia)

Formula (Ia)

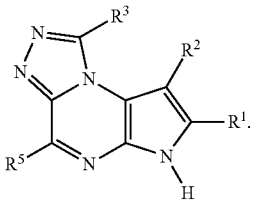

In a fourteenth embodiment the invention provides a compound according to the thirteenth embodiment wherein in the compound is N-(1-((6H-pyrrolo[2,3-e][1,2,4]triazolo[4,3-a]pyrazin-1-yl)methyl)cyclobutyl)cyclopropanesulfonamide;

N-(1-((6H-pyrrolo[2,3-e][1,2,4]triazolo[4,3-a]pyrazin-1-yl)methyl)cyclobutyl)-2-cyanoacetamide;

(S)-1-((1-(cyclopropylsulfonyl)pyrrolidin-3-yl)methyl)-6H-pyrrolo[2,3-e][1,2,4]triazolo[4,3-a]pyrazine;

N-((1S,3R,4R)-4-ethyl-3-fluoro-3-(6H-pyrrolo[2,3-e][1,2,4]triazolo[4,3-a]pyrazin-1-yl)cyclopentyl)cyclopropanesulfonamide;

N-((1R,3S,4S)-4-ethyl-3-fluoro-3-(6H-pyrrolo[2,3-e][1,2,4]triazolo[4,3-a]pyrazin-1-yl)cyclopentyl)cyclopropanesulfonamide;

N-((1R,3R,4S)-4-ethyl-3-fluoro-3-(6H-pyrrolo[2,3-e][1,2,4]triazolo[4,3-a]pyrazin-1-yl)cyclopentyl)cyclopropanesulfonamide;

N-((1S,3S,4R)-4-ethyl-3-fluoro-3-(6H-pyrrolo[2,3-e][1,2,4]triazolo[4,3-a]pyrazin-1-yl)cyclopentyl)cyclopropanesulfonamide;

(1S,3R)-1-[3-(6H-pyrrolo[2,3-e][1,2,4]triazolo[4,3-a]pyrazin-1-yl)-isothiazolidin-2-yl-1,1-dioxide]cyclopentane;

N-((1S,3R,4S)-3-ethyl-4-(6H-pyrrolo[2,3-e][1,2,4]triazolo[4,3-a]pyrazin-1-yl)cyclopentyl)-N-methylcyclopropanesulfonamide;

1-((1S,2R,4S)-2-ethyl-4-(4-methoxybenzyloxy)cyclopentyl)-6H-pyrrolo[2,3-e][1,2,4]triazolo[4,3-a]pyrazine;

(S)-5-(3-((6H-pyrrolo[2,3-e][1,2,4]triazolo[4,3-a]pyrazin-1-yl)methyl)pyrrolidin-1-yl)pyrazine-2-carbonitrile;

N-(cyclopropylmethyl)-N-((1S,3R,4S)-3-ethyl-4-(6H-pyrrolo[2,3-e][1,2,4]triazolo[4,3-a]pyrazin-1-yl)cyclopentyl)cyclopropanesulfonamide;

N-((1S,3R)-3-(6H-pyrrolo[2,3-e][1,2,4]triazolo[4,3-a]pyrazin-1-yl)cyclopentyl)-2-(4-cyanophenyl)acetamide;

N-((1S,3R)-3-(6H-pyrrolo[2,3-e][1,2,4]triazolo[4,3-a]pyrazin-1-yl)cyclopentyl)cyclopropanecarboxamide;

N-((1S,3R)-3-(6H-pyrrolo[2,3-e][1,2,4]triazolo[4,3-a]pyrazin-1-yl)cyclopentyl)-2-cyclopropylacetamide;

N-((1S,3R)-3-(6H-pyrrolo[2,3-e][1,2,4]triazolo[4,3-a]pyrazin-1-yl)cyclopentyl)-4-cyanobenzamide;

N,N-diethyl-1-(3-ethyl-4-(6H-pyrrolo[2,3-e][1,2,4]triazolo[4,3-a]pyrazin-1-yl)cyclopentyl)methanesulfonamide;

1-((1S,2S,4R)-4-((azetidin-1-ylsulfonyl)methyl)-2-ethylcyclopentyl)-6H-pyrrolo[2,3-e][1,2,4]triazolo[4,3-a]pyrazine;

1-((1R,2R,4S)-4-((azetidin-1-ylsulfonyl)methyl)-2-ethylcyclopentyl)-6H-pyrrolo[2,3-e][1,2,4]triazolo[4,3-a]pyrazine;

1-((1R,2S,4R)-4-((azetidin-1-ylsulfonyl)methyl)-2-ethylcyclopentyl)-6H-pyrrolo[2,3-e][1,2,4]triazolo[4,3-a]pyrazine;

1-((1S,2R,4S)-4-((azetidin-1-ylsulfonyl)methyl)-2-ethylcyclopentyl)-6H-pyrrolo[2,3-e][1,2,4]triazolo[4,3-a]pyrazine;

N-((1S,3R,4S)-3-ethyl-4-(7-methyl-6H-pyrrolo[2,3-e][1,2,4]triazolo[4,3-a]pyrazin-1-yl)cyclopentyl)cyclopropane sulfonamide;

N-((1S,3R,4S)-3-ethyl-4-(6H-pyrrolo[2,3-e][1,2,4]triazolo[4,3-a]pyrazin-1-yl)cyclopentyl)-N-(2-hydroxyethyl)cyclopropanesulfonamide;

5-((1R,3R)-3-(6H-pyrrolo[2,3-e][1,2,4]triazolo[4,3-a]pyrazin-1-yl)cyclopentylamino)pyrazine-2-carbonitrile N-((1R,3R)-3-(6H-pyrrolo[2,3-e][1,2,4]triazolo[4,3-a]pyrazin-1-yl)cyclopentyl)-4-methylaniline;

1-((1R,3S)-3-(1H-pyrrol-1-yl)cyclopentyl)-6H-pyrrolo[2,3-e][1,2,4]triazolo[4,3-a]pyrazine;

1-((1S,3R)-3-(6H-pyrrolo[2,3-e][1,2,4]triazolo[4,3-a]pyrazin-1-yl)cyclopentyl)-1H-pyrrole-3-carbonitrile;

N-((1R,3R)-3-(6H-pyrrolo[2,3-e][1,2,4]triazolo[4,3-a]pyrazin-1-yl)cyclopentyl)aniline;

N-((1-((6H-pyrrolo[2,3-e][1,2,4]triazolo[4,3-a]pyrazin-1-yl)methyl)cyclobutyl)methyl)-2-cyanoacetamide;

N-((1R,3R)-3-(6H-pyrrolo[2,3-e][1,2,4]triazolo[4,3-a]pyrazin-1-yl)cyclopentyl)-4-fluoroaniline;

N-((1R,3R)-3-(6H-pyrrolo[2,3-e][1,2,4]triazolo[4,3-a]pyrazin-1-yl)cyclopentyl)-4-chloroaniline;

N-((1R,3R)-3-(6H-pyrrolo[2,3-e][1,2,4]triazolo[4,3-a]pyrazin-1-yl)cyclopentyl)-3,4-dichloroaniline;

N-((1R,3R)-3-(6H-pyrrolo[2,3-e][1,2,4]triazolo[4,3-a]pyrazin-1-yl)cyclopentyl)-4-methoxyaniline;

N-((1R,3R)-3-(6H-pyrrolo[2,3-e][1,2,4]triazolo[4,3-a]pyrazin-1-yl)cyclopentyl)-4-methoxy-N-(4-methoxyphenyl)aniline;

3-((3R,4R)-4-methyl-3-(6H-pyrrolo[2,3-e][1,2,4]triazolo[4,3-a]pyrazin-1-yl)piperidin-1-yl)-3-oxopropanenitrile;

1-methyl-N-((1S,3R,4S)-3-methyl-4-(6H-pyrrolo[2,3-e][1,2,4]triazolo[4,3-a]pyrazin-1-yl)cyclopentyl)-1H-pyrazole-4-sulfonamide;

3-((1R,3R)-3-(6H-pyrrolo[2,3-e][1,2,4]triazolo[4,3-a]pyrazin-1-yl)cyclopentylamino)benzonitrile;

N-((1S,3R,4S)-3-methyl-4-(6H-pyrrolo[2,3-e][1,2,4]triazolo[4,3-a]pyrazin-1-yl)cyclopentyl)aniline;

4-((1S,2R,4S)-4-(benzyloxy)-2-ethylcyclopentyl)-6H-pyrrolo[2,3-e][1,2,4]triazolo[4,3-a]pyrazine;

4-((1R,2S,4R)-4-(benzyloxy)-2-ethylcyclopentyl)-6H-pyrrolo[2,3-e][1,2,4]triazolo[4,3-a]pyrazine;

5-methyl-N-((1S,3R,4S)-3-methyl-4-(6H-pyrrolo[2,3-e][1,2,4]triazolo[4,3-a]pyrazin-1-yl)cyclopentyl)isoxazole-4-sulfonamide;

N-(4-(6H-pyrrolo[2,3-e][1,2,4]triazolo[4,3-a]pyrazin-1-yl)bicyclo[2.2.2]octan-1-yl)cyclobutanesulfonamide;

6-((1R,3R,4S)-3-ethyl-4-(6H-pyrrolo[2,3-e][1,2,4]triazolo[4,3-a]pyrazin-1-yl)cyclopentyloxy)nicotinonitrile;

N-(4-(6H-pyrrolo[2,3-e][1,2,4]triazolo[4,3-a]pyrazin-1-yl)bicyclo[2.2.2]octan-1-yl)pyrrolidine-1-carboxamide;

4-((1R,3R,4S)-3-ethyl-4-(6H-pyrrolo[2,3-e][1,2,4]triazolo[4,3-a]pyrazin-1-yl)cyclopentyloxy)benzonitrile;

4-((1S,3S,4R)-3-ethyl-4-(6H-pyrrolo[2,3-e][1,2,4]triazolo[4,3-a]pyrazin-1-yl)cyclopentyloxy)benzonitrile;

4-methyl-N-((1S,3R,4S)-3-methyl-4-(6H-pyrrolo[2,3-e][1,2,4]triazolo[4,3-a]pyrazin-1-yl)cyclopentyl)aniline;

4-chloro-N-((1S,3R,4S)-3-methyl-4-(6H-pyrrolo[2,3-e][1,2,4]triazolo[4,3-a]pyrazin-1-yl)cyclopentyl)aniline;

3-((1S,3R,4S)-3-methyl-4-(6H-pyrrolo[2,3-e][1,2,4]triazolo[4,3-a]pyrazin-1-yl)cyclopentylamino)benzonitrile;

4-fluoro-N-((1S,3R,4S)-3-methyl-4-(6H-pyrrolo[2,3-e][1,2,4]triazolo[4,3-a]pyrazin-1-yl)cyclopentyl)aniline;

N-((1S,3S,4R)-3-methyl-4-(6H-pyrrolo[2,3-e][1,2,4]triazolo[4,3-a]pyrazin-1-yl)cyclopentyl)aniline;

N-((1R,3R,4S)-3-methyl-4-(6H-pyrrolo[2,3-e][1,2,4]triazolo[4,3-a]pyrazin-1-yl)cyclopentyl)aniline;

5-((1S,3R,4S)-3-methyl-4-(6H-pyrrolo[2,3-e][1,2,4]triazolo[4,3-a]pyrazin-1-yl)cyclopentylamino)pyrazine-2-carbonitrile;

6-((1S,3R,4S)-3-methyl-4-(6H-pyrrolo[2,3-e][1,2,4]triazolo[4,3-a]pyrazin-1-yl)cyclopentylamino)nicotinonitrile;

6-((1R,3R,4S)-3-ethyl-4-(6H-pyrrolo[2,3-e][1,2,4]triazolo[4,3-a]pyrazin-1-yl)cyclopentyloxy)nicotinonitrile;

6-((1S,3S,4R)-3-ethyl-4-(6H-pyrrolo[2,3-e][1,2,4]triazolo[4,3-a]pyrazin-1-yl)cyclopentyloxy)nicotinonitrile;

1-((1S,2S,4R)-2-ethyl-4-(4-methoxybenzyloxy)cyclopentyl)-6H-pyrrolo[2,3-e][1,2,4]triazolo[4,3-a]pyrazine;

1-((1R,2R,4S)-2-ethyl-4-(4-methoxybenzyloxy)cyclopentyl)-6H-pyrrolo[2,3-e][1,2,4]triazolo[4,3-a]pyrazine;

N-((1S,3R,4S)-3-ethyl-4-(6H-pyrrolo[2,3-e][1,2,4]triazolo[4,3-a]pyrazin-1-yl)cyclopentyl)-3,3,3-trifluoropropane-1-sulfonamide;

5-((1S,3R,4S)-3-ethyl-4-(6H-pyrrolo[2,3-e][1,2,4]triazolo[4,3-a]pyrazin-1-yl)cyclopentylamino)pyrazine-2-carbonitrile;

6-((1S,3R,4S)-3-ethyl-4-(6H-pyrrolo[2,3-e][1,2,4]triazolo[4,3-a]pyrazin-1-yl)cyclopentylamino)nicotinonitrile;

2-((1S,3R,4S)-3-methyl-4-(6H-pyrrolo[2,3-e][1,2,4]triazolo[4,3-a]pyrazin-1-yl)cyclopentylamino)thiazole-5-carbonitrile;

N-((1S,3R,4S)-3-ethyl-4-(6H-pyrrolo[2,3-e][1,2,4]triazolo[4,3-a]pyrazin-1-yl)cyclopentyl)azetidine-1-sulfonamide;

N-((1R,3R,4R)-3-ethyl-4-(6H-pyrrolo[2,3-e][1,2,4]triazolo[4,3-a]pyrazin-1-yl)cyclopentyl)cyclopropanesulfonamide;

N-((1S,3S,4S)-3-ethyl-4-(6H-pyrrolo[2,3-e][1,2,4]triazolo[4,3-a]pyrazin-1-yl)cyclopentyl)cyclopropanesulfonamide;

3-cyano-N-((1S,3R,4S)-3-ethyl-4-(6H-pyrrolo[2,3-e][1,2,4]triazolo[4,3-a]pyrazin-1-yl)cyclopentyl)azetidine-1-sulfonamide;

N-((1S,3R,4S)-3-ethyl-4-(6H-pyrrolo[2,3-e][1,2,4]triazolo[4,3-a]pyrazin-1-yl)cyclopentyl)-3,3-difluoroazetidine-1-sulfonamide;

5-((1R,3R,4S)-3-ethyl-4-(6H-pyrrolo[2,3-e][1,2,4]triazolo[4,3-a]pyrazin-1-yl)cyclopentyloxy)pyrazine-2-carbonitrile;

5-((1S,3S,4R)-3-ethyl-4-(6H-pyrrolo[2,3-e][1,2,4]triazolo[4,3-a]pyrazin-1-yl)cyclopentyloxy)pyrazine-2-carbonitrile;

6-((1S,3S,4S)-3-ethyl-4-(6H-pyrrolo[2,3-e][1,2,4]triazolo[4,3-a]pyrazin-1-yl)cyclopentyloxy)nicotinonitrile;

6-((1R,3R,4R)-3-ethyl-4-(6H-pyrrolo[2,3-e][1,2,4]triazolo[4,3-a]pyrazin-1-yl)cyclopentyloxy)nicotinonitrile;

2-((1S,3R,4S)-3-ethyl-4-(6H-pyrrolo[2,3-e][1,2,4]triazolo[4,3-a]pyrazin-1-yl)cyclopentylamino)thiazole-5-carbonitrile;

5-((1S,3R,4S)-3-ethyl-4-(6H-pyrrolo[2,3-e][1,2,4]triazolo[4,3-a]pyrazin-1-yl)cyclopentyloxy)pyrazine-2-carbonitrile;

5-((1R,3S,4R)-3-ethyl-4-(6H-pyrrolo[2,3-e][1,2,4]triazolo[4,3-a]pyrazin-1-yl)cyclopentyloxy)pyrazine-2-carbonitrile;

N-(4-(6H-pyrrolo[2,3-e][1,2,4]triazolo[4,3-a]pyrazin-1-yl)bicyclo[2.2.2]octan-1-yl)pyrrolidine-1-sulfonamide;

5-(((1S,3R)-3-(6H-pyrrolo[2,3-e][1,2,4]triazolo[4,3-a]pyrazin-1-yl)cyclopentyl)methylamino)pyrazine-2-carbonitrile;

(S)-N-((1S,3R,4S)-3-ethyl-4-(6H-pyrrolo[2,3-e][1,2,4]triazolo[4,3-a]pyrazin-1-yl)cyclopentyl)-2-(trifluoromethyl)pyrrolidine-1-sulfonamide;

N-((1S,3R,4S)-3-ethyl-4-(6H-pyrrolo[2,3-e][1,2,4]triazolo[4,3-a]pyrazin-1-yl)cyclopentyl)-3,3-difluoropyrrolidine-1-sulfonamide;

N-((1S,3R,4S)-3-ethyl-4-(6H-pyrrolo[2,3-e][1,2,4]triazolo[4,3-a]pyrazin-1-yl)cyclopentyl)-4,4-difluoropiperidine-1-sulfonamide;

N-((1S,3R,4S)-3-ethyl-4-(6H-pyrrolo[2,3-e][1,2,4]triazolo[4,3-a]pyrazin-1-yl)cyclopentyl)-1-methylcyclopropane-1-sulfonamide;

N-(4-(6H-pyrrolo[2,3-e][1,2,4]triazolo[4,3-a]pyrazin-1-yl)bicyclo[2.2.2]octan-1-yl)-1-methylcyclopropane-1-sulfonamide;

N-(4-(6H-pyrrolo[2,3-e][1,2,4]triazolo[4,3-a]pyrazin-1-yl)bicyclo[2.2.2]octan-1-yl)azetidine-1-sulfonamide;

6-((1S,3R,4S)-3-methyl-4-(6H-pyrrolo[2,3-e][1,2,4]triazolo[4,3-a]pyrazin-1-yl)cyclopentylamino)nicotinonitrile;

N-((1S,3R,4R)-3-ethyl-4-(6H-pyrrolo[2,3-e][1,2,4]triazolo[4,3-a]pyrazin-1-yl)cyclopentyl)cyclopentanesulfonamide;

5-(((1S,3R,4S)-3-ethyl-4-(6H-pyrrolo[2,3-e][1,2,4]triazolo[4,3-a]pyrazin-1-yl)cyclopentyl)methoxy)pyrazine-2-carboxamide;

((1S,3R,4S)-3-ethyl-4-(6H-pyrrolo[2,3-e][1,2,4]triazolo[4,3-a]pyrazin-1-yl)cyclopentyl)methanol;

((1R,3S,4R)-3-ethyl-4-(6H-pyrrolo[2,3-e][1,2,4]triazolo[4,3-a]pyrazin-1-yl)cyclopentyl)methanol;

5-(((1S,3R,4S)-3-ethyl-4-(6H-pyrrolo[2,3-e][1,2,4]triazolo[4,3-a]pyrazin-1-yl)cyclopentyl)methoxy)pyrazine-2-carbonitrile;

5-(((1R,3S,4R)-3-ethyl-4-(6H-pyrrolo[2,3-e][1,2,4]triazolo[4,3-a]pyrazin-1-yl)cyclopentyl)methoxy)pyrazine-2-carbonitrile;

N-(4-(6H-pyrrolo[2,3-e][1,2,4]triazolo[4,3-a]pyrazin-1-yl)bicyclo[2.2.2]octan-1-yl)-3,3-difluoroazetidine-1-sulfonamide;

N-(3-ethyl-4-(6H-pyrrolo[2,3-e][1,2,4]triazolo[4,3-a]pyrazin-1-yl)cyclopentyl)aniline;

1-((1S,2R,4R)-2-ethyl-4-(5-(trifluoromethyl)pyridin-2-yloxy)cyclopentyl)-6H-pyrrolo[2,3-e][1,2,4]triazolo[4,3-a]pyrazine;

1-((1R,2S,4S)-2-ethyl-4-(5-(trifluoromethyl)pyridin-2-yloxy)cyclopentyl)-6H-pyrrolo[2,3-e][1,2,4]triazolo[4,3-a]pyrazine;

5-((1R,3S,4S)-3-ethyl-4-(6H-pyrrolo[2,3-e][1,2,4]triazolo[4,3-a]pyrazin-1-yl)cyclopentyloxy)pyrazine-2-carbonitrile;

5-((1S,3R,4R)-3-ethyl-4-(6H-pyrrolo[2,3-e][1,2,4]triazolo[4,3-a]pyrazin-1-yl)cyclopentyloxy)pyrazine-2-carbonitrile;

N-((1S,3R,4S)-3-ethyl-4-(6H-pyrrolo[2,3-e][1,2,4]triazolo[4,3-a]pyrazin-1-yl)cyclopentyl)-2,2,2-trifluoroethanesulfonamide;

N-((1S,3R,4S)-3-ethyl-4-(6H-pyrrolo[2,3-e][1,2,4]triazolo[4,3-a]pyrazin-1-yl)cyclopentyl)-4-methylpiperazine-1-sulfonamide;

4-((1S,3S,4R)-3-methyl-4-(6H-pyrrolo[2,3-e][1,2,4]triazolo[4,3-a]pyrazin-1-yl)cyclopentyloxy)benzonitrile;

4-((1R,3R,4S)-3-methyl-4-(6H-pyrrolo[2,3-e][1,2,4]triazolo[4,3-a]pyrazin-1-yl)cyclopentyloxy)benzonitrile;

3-(((1R,3R,4S)-3-ethyl-4-(6H-pyrrolo[2,3-e][1,2,4]triazolo[4,3-a]pyrazin-1-yl)cyclopentyloxy)methyl)benzonitrile;

3-(((1S,3S,4R)-3-ethyl-4-(6H-pyrrolo[2,3-e][1,2,4]triazolo[4,3-a]pyrazin-1-yl)cyclopentyloxy)methyl)benzonitrile;

4-(((1R,3R,4S)-3-ethyl-4-(6H-pyrrolo[2,3-e][1,2,4]triazolo[4,3-a]pyrazin-1-yl)cyclopentyloxy)methyl)benzonitrile;

4-(((1S,3S,4R)-3-ethyl-4-(6H-pyrrolo[2,3-e][1,2,4]triazolo[4,3-a]pyrazin-1-yl)cyclopentyloxy)methyl)benzonitrile;

1-ethyl-N-((1S,3R,4S)-3-ethyl-4-(6H-pyrrolo[2,3-e][1,2,4]triazolo[4,3-a]pyrazin-1-yl)cyclopentyl)cyclopropane-1-sulfonamide;

N-(((1R,3S,4R)-3-ethyl-4-(6H-pyrrolo[2,3-e][1,2,4]triazolo[4,3-a]pyrazin-1-yl)cyclopentyl)methyl)cyclopropanesulfonamide;

N-(((1S,3R,4S)-3-ethyl-4-(6H-pyrrolo[2,3-e][1,2,4]triazolo[4,3-a]pyrazin-1-yl)cyclopentyl)methyl)cyclopropanesulfonamide;

4-((1R,3R,4S)-3-ethyl-4-(6H-pyrrolo[2,3-e][1,2,4]triazolo[4,3-a]pyrazin-1-yl)cyclopentyloxy)-2-fluorobenzonitrile;

4-((1R,3R,4S)-3-ethyl-4-(6H-pyrrolo[2,3-e][1,2,4]triazolo[4,3-a]pyrazin-1-yl)cyclopentyloxy)-3-fluorobenzonitrile;

3-((1R,3R,4S)-3-ethyl-4-(6H-pyrrolo[2,3-e][1,2,4]triazolo[4,3-a]pyrazin-1-yl)cyclopentyloxy)benzonitrile;

N-((1S,3R,4S)-3-ethyl-4-(6H-pyrrolo[2,3-e][1,2,4]triazolo[4,3-a]pyrazin-1-yl)cyclopentyl)-2-morpholinoethanesulfonamide;

1-butyl-N-((1S,3R,4S)-3-ethyl-4-(6H-pyrrolo[2,3-e][1,2,4]triazolo[4,3-a]pyrazin-1-yl)cyclopentyl)cyclopropane-1-sulfonamide;

2-(3,3-difluoropyrrolidin-1-yl)-N-((1S,3R,4S)-3-ethyl-4-(6H-pyrrolo[2,3-e][1,2,4]triazolo[4,3-a]pyrazin-1-yl)cyclopentyl)ethanesulfonamide;

2-(((1S,3R)-3-(6H-pyrrolo[2,3-e][1,2,4]triazolo[4,3-a]pyrazin-1-yl)cyclopentyl)methylamino)isonicotinonitrile;

N-((1S,3R,4S)-3-ethyl-4-(6H-pyrrolo[2,3-e][1,2,4]triazolo[4,3-a]pyrazin-1-yl)cyclopentyl)-2-methylpropane-2-sulfonamide;

N-((1S,3R,4S)-3-ethyl-4-(6H-pyrrolo[2,3-e][1,2,4]triazolo[4,3-a]pyrazin-1-yl)cyclopentyl)-2-(1H-1,2,4-triazol-1-yl)ethanesulfonamide;

2-(4,4-difluoropiperidin-1-yl)-N-((1S,3R,4S)-3-ethyl-4-(6H-pyrrolo[2,3-e][1,2,4]triazolo[4,3-a]pyrazin-1-yl)cyclopentyl)ethanesulfonamide;

N-((1S,3R,4S)-3-ethyl-4-(6H-pyrrolo[2,3-e][1,2,4]triazolo[4,3-a]pyrazin-1-yl)cyclopentyl)-2-(2H-1,2,3-triazol-2-yl)ethanesulfonamide;

N-((1S,3R,4S)-3-ethyl-4-(6H-pyrrolo[2,3-e][1,2,4]triazolo[4,3-a]pyrazin-1-yl)cyclopentyl)-2-(1H-1,2,3-triazol-1-yl)ethanesulfonamide;

(1R,3R,4S)-3-ethyl-4-(6H-pyrrolo[2,3-e][1,2,4]triazolo[4,3-a]pyrazin-1-yl)cyclopentanol;

1-((1S,2R,4R)-2-ethyl-4-(3,3,3-trifluoropropoxy)cyclopentyl)-6H-pyrrolo[2,3-e][1,2,4]triazolo[4,3-a]pyrazine;

N-((1S,3R,4S)-3-ethyl-4-(8-iodo-6H-pyrrolo[2,3-e][1,2,4]triazolo[4,3-a]pyrazin-1-yl)cyclopentyl)cyclopropane sulfonamide;

(1S,3R,4S)-N-(2-(3,3-difluoropyrrolidin-1-ylsulfonyl)ethyl)-3-ethyl-4-(6H-pyrrolo[2,3-e][1,2,4]triazolo[4,3-a]pyrazin-1-yl)cyclopentanamine;

N-cyano-N-((1S,3R,4S)-3-ethyl-4-(6H-pyrrolo[2,3-e][1,2,4]triazolo[4,3-a]pyrazin-1-yl)cyclopentyl)cyclopropane sulfonamide;

N-((1S,3R,4S)-3-ethyl-4-(methyl(7H-pyrrolo[2,3-d]pyrimidin-4-yl)amino)cyclopentyl)cyclopropanesulfonamide;

N-((1S,3R,4S)-3-ethyl-4-(8-methyl-6H-pyrrolo[2,3-e][1,2,4]triazolo[4,3-a]pyrazin-1-yl)cyclopentyl)-N-(hydroxymethyl)cyclopropanesulfonamide;

N-((1S,3S,4R)-3-(8-cyano-6H-pyrrolo[2,3-e][1,2,4]triazolo[4,3-a]pyrazin-1-yl)-4-ethylcyclopentyl)cyclopropane sulfonamide;

1-((1S,2R,4S)-4-(cyclopropylmethoxy)-2-ethylcyclopentyl)-6H-pyrrolo[2,3-e][1,2,4]triazolo[4,3-a]pyrazine;

1-((1S,2R,4S)-4-(cyclopropylmethoxy)-2-methylcyclopentyl)-6H-pyrrolo[2,3-e][1,2,4]triazolo[4,3-a]pyrazine;

1-((1S,2R,4S)-2-ethyl-4-(2,2,2-trifluoroethylsulfonyl)cyclopentyl)-6H-pyrrolo[2,3-e][1,2,4]triazolo[4,3-a]pyrazine;

1-((1S,2R,4S)-2-ethyl-4-(tetrahydro-2H-pyran-4-yloxy)cyclopentyl)-6H-pyrrolo[2,3-e][1,2,4]triazolo[4,3-a]pyrazine;

1-((1S,2R,4S)-2-ethyl-4-((tetrahydro-2H-pyran-4-yl)methoxy)cyclopentyl)-6H-pyrrolo[2,3-e][1,2,4]triazolo[4,3-a]pyrazine;

1-((1R,2R,4S)-2-ethyl-4-((tetrahydro-2H-pyran-4-yl)methoxy)cyclopentyl)-6H-pyrrolo[2,3-e][1,2,4]triazolo[4,3-a]pyrazine;

1-((1S,2R,4R)-4-(cyclopropylmethoxy)-2-ethylcyclopentyl)-6H-pyrrolo[2,3-e][1,2,4]triazolo[4,3-a]pyrazine;

1-((1S,2R,4R)-2-ethyl-4-(tetrahydro-2H-pyran-4-yloxy)cyclopentyl)-6H-pyrrolo[2,3-e][1,2,4]triazolo[4,3-a]pyrazine;

2-(4-cyano-1H-pyrazol-1-yl)-N-((1S,3R,4S)-3-ethyl-4-(6H-pyrrolo[2,3-e][1,2,4]triazolo[4,3-a]pyrazin-1-yl)cyclopentyl)ethanesulfonamide;

1-((1S,2R,4S)-2-ethyl-4-(2-(tetrahydro-2H-pyran-4-yl)ethoxy)cyclopentyl)-6H-pyrrolo[2,3-e][1,2,4]triazolo[4,3-a]pyrazine;

1-((1R,2R,4S)-2-ethyl-4-(2-(tetrahydro-2H-pyran-4-yl)ethoxy)cyclopentyl)-6H-pyrrolo[2,3-e][1,2,4]triazolo[4,3-a]pyrazine;

1-((1S,2R,4R)-2-ethyl-4-((tetrahydro-2H-pyran-4-yl) methoxy)cyclopentyl)-6H-pyrrolo[2,3-e][1,2,4]triazolo [4,3-a]pyrazine;

1-((1S,2R,4S)-2-ethyl-4-(2-methoxyethoxy)cyclopentyl)-6H-pyrrolo[2,3-e][1,2,4]triazolo[4,3-a]pyrazine;

1-((1R,2R,4S)-2-ethyl-4-(2-methoxyethoxy)cyclopentyl)-6H-pyrrolo[2,3-e][1,2,4]triazolo[4,3-a]pyrazine;

1-((1S,2R,4R)-2-ethyl-4-isopropoxycyclopentyl)-6H-pyrrolo[2,3-e][1,2,4]triazolo[4,3-a]pyrazine;

N-((3R,5R)-1-ethyl-5-(6H-pyrrolo[2,3-e][1,2,4]triazolo[4, 3-a]pyrazin-1-yl)pyrrolidin-3-yl)cyclopropanesulfonamide;

(3R,4S)-3-ethyl-4-(6H-pyrrolo[2,3-e][1,2,4]triazolo[4,3-a] pyrazin-1-yl)cyclopentanone;

1-((7S,8R)-8-ethyl-1,4-dioxaspiro[4.4]nonan-7-yl)-6H-pyrrolo[2,3-e][1,2,4]triazolo[4,3-a]pyrazine;

(1S,3R,4S)-3-ethyl-4-(6H-pyrrolo[2,3-e][1,2,4]triazolo[4,3-a]pyrazin-1-yl)-N-(2,2,2-trifluoroethyl)cyclopentanamine;

(3R,4S)-3-ethyl-4-(6H-pyrrolo[2,3-e][1,2,4]triazolo[4,3-a] pyrazin-1-yl)cyclopentanone O-cyclopropylmethyl oxime;

(3R,4S)-3-ethyl-4-(6H-pyrrolo[2,3-e][1,2,4]triazolo[4,3-a] pyrazin-1-yl)cyclopentanone O-2-(methylsulfonyl)ethyl oxime;

(3R,4S)-3-ethyl-4-(6H-pyrrolo[2,3-e][1,2,4]triazolo[4,3-a] pyrazin-1-yl)cyclopentanone O-cyclobutylmethyl oxime;

1-((1S,2R,4R)-4-(4,4-dimethylcyclohexyloxy)-2-ethylcyclopentyl)-6H-pyrrolo[2,3-e][1,2,4]triazolo[4,3-a]pyrazine;

N-((1S,3R,4S)-3-ethyl-4-(6H-pyrrolo[2,3-e][1,2,4]triazolo [4,3-a]pyrazin-1-yl)cyclopentyl)-2-methoxyethanesulfonamide;

N-((3R,5R)-1-acetyl-5-(6H-pyrrolo[2,3-e][1,2,4]triazolo[4, 3-a]pyrazin-1-yl)pyrrolidin-3-yl)cyclopropanesulfonamide;

1-((3S,4R)-1-(cyclopropylmethylsulfonyl)-4-ethylpyrrolidin-3-yl)-6H-pyrrolo[2,3-e][1,2,4]triazolo[4,3-a]pyrazine;

2-((1S,3R,4S)-3-ethyl-4-(6H-pyrrolo[2,3-e][1,2,4]triazolo [4,3-a]pyrazin-1-yl)cyclopentyl)acetic acid;

N-cyclopropyl-2-((1S,3R,4S)-3-ethyl-4-(6H-pyrrolo[2,3-e] [1,2,4]triazolo[4,3-a]pyrazin-1-yl)cyclopentyl)acetamide;

(3R,4S)-3-ethyl-4-(6H-pyrrolo[2,3-e][1,2,4]triazolo[4,3-a] pyrazin-1-yl)cyclopentanone O-tetrahydro-2H-pyran-4-yl oxime;

1-((1S,2R,4S)-4-(3,3-difluoroazetidin-1-yl)-2-ethylcyclopentyl)-6H-pyrrolo[2,3-e][1,2,4]triazolo[4,3-a]pyrazine;

1-((1S,2R,4S)-4-(3,3-difluoropyrrolidin-1-yl)-2-ethylcyclopentyl)-6H-pyrrolo[2,3-e][1,2,4]triazolo[4,3-a]pyrazine;

Dimethyl-carbamic acid (1S,3R,4S)-3-ethyl-4-(6H-pyrrolo [2,3-e][1,2,4]triazolo[4,3-a]pyrazin-1-yl)-cyclopentyl ester;

{3-[(1S,3R,4S)-3-Ethyl-4-(6H-pyrrolo[2,3-e][1,2,4]triazolo [4,3-a]pyrazin-1-yl)-cyclopentylamino]-oxetan-3-yl}-acetonitrile;

Cyclopropanesulfonic acid cyanomethyl-[(1S,3R,4S)-3-ethyl-4-(6H-pyrrolo[2,3-e][1,2,4]triazolo[4,3-a]pyrazin-1-yl)-cyclopentyl]-amide;

1-[(3R,4S)-4-Ethyl-1-(2-morpholin-4-yl-ethyl)-pyrrolidin-3-yl]-6H-pyrrolo[2,3-e][1,2,4]triazolo[4,3-a]pyrazin-1-yl;

Cyclopropanesulfonic acid [(3R,5R)-1-(2,2-difluoro-ethyl)-5-(6H-pyrrolo[2,3-e][1,2,4]triazolo[4,3-a]pyrazin-1-yl) pyrrolidin-3-yl]-amide;

1-[(3R,4S)-4-Ethyl-1-(3,3,3-trifluoro-propane-1-sulfonyl) pyrrolidin-3-yl]-6H-pyrrolo[2,3-e][1,2,4]triazolo[4,3-a] pyrazin-1-yl;

3-[(1R,3R,4S)-3-Ethyl-4-(6H-pyrrolo[2,3-e][1,2,4]triazolo [4,3-a]pyrazin-1-yl)-cyclopentyloxy]-propionitrile;

1-[(3R,4S)-4-Ethyl-1-(3,3,3-trifluoro-propyl)-pyrrolidin-3-yl]-6H-pyrrolo[2,3-e][1,2,4]triazolo[4,3-a]pyrazin-1-yl;

2-Cyclopropyl-1-[(3S,4R)-3-ethyl-4-(6H-pyrrolo[2,3-e][1, 2,4]triazolo[4,3-a]pyrazin-1-yl)-pyrrolidin-1-yl]-ethanone;

1-[(3S,4R)-3-Ethyl-4-(6H-pyrrolo[2,3-e][1,2,4]triazolo[4,3-a]pyrazin-1-yl)-pyrrolidin-1-yl]-2-(tetrahydro-pyran-4-yl)-ethanone;

(3S,4R)-3-Ethyl-4-(6H-pyrrolo[2,3-e][1,2,4]triazolo[4,3-a] pyrazin-1-yl)-pyrrolidine-1-carboxylic acid cyclopropylmethyl-amide;

Cyclopropanesulfonic acid [(3R,5R)-1-ethyl-5-(6H-pyrrolo [2,3-e][1,2,4]triazolo[4,3-a]pyrazin-1-yl)-pyrrolidin-3-yl]-methyl-amide;

(3S,4R)-3-Ethyl-4-(6H-pyrrolo[2,3-e][1,2,4]triazolo[4,3-a] pyrazin-1-yl)-pyrrolidine-1-carboxylic acid (tetrahydro-pyran-4-ylmethyl)-amide;

3,3-Difluoro-cyclobutanesulfonic acid [(1S,3R,4S)-3-ethyl-4-(6H-pyrrolo[2,3-e][1,2,4]triazolo[4,3-a]pyrazin-1-yl)-cyclopentyl]-amide;

Cyclopropanesulfonic acid [(1S,4S)-3,3-dimethyl-4-(6H-pyrrolo[2,3-e][1,2,4]triazolo[4,3-a]pyrazin-1-yl)-cyclopentyl]-amide;

Cyclopropanesulfonic acid [(1R,4R)-3,3-dimethyl-4-(6H-pyrrolo[2,3-e][1,2,4]triazolo[4,3-a]pyrazin-1-yl)-cyclopentyl]-amide;

1-[(1S,2R,4R)-4-(4,4-Difluoro-cyclohexyloxy)-2-ethyl-cyclopentyl]-6H-pyrrolo[2,3-e][1,2,4]triazolo[4,3-a] pyrazin-1-yl;

1-[(1R,2R,4R)-4-(4,4-Difluoro-cyclohexyloxy)-2-ethyl-cyclopentyl]-6H-pyrrolo[2,3-e][1,2,4]triazolo[4,3-a] pyrazin-1-yl;

6-[(3S,4R)-3-Ethyl-4-(6H-pyrrolo[2,3-e][1,2,4]triazolo[4,3-a]pyrazin-1-yl)-pyrrolidin-1-yl]-nicotinonitrile;

1-[(3R,4S)-1-(3,3-Difluoro-cyclobutanesulfonyl)-4-ethyl-pyrrolidin-3-yl]-6H-pyrrolo[2,3-e][1,2,4]triazolo[4,3-a] pyrazin-1-yl;

[(1S,3R,4S)-3-Ethyl-4-(6H-pyrrolo[2,3-e][1,2,4]triazolo[4, 3-a]pyrazin-1-yl)-cyclopentyl]-bis-(4,4,4-trifluoro-butyl)-amine;

1-[(1S,2R,4R)-2-Ethyl-4-(4-trifluoromethyl-cyclohexyloxy)-cyclopentyl]-6H-pyrrolo[2,3-e][1,2,4]triazolo[4,3-a]pyrazin-1-yl;

4-[(3S,4R)-3-Ethyl-4-(6H-pyrrolo[2,3-e][1,2,4]triazolo[4,3-a]pyrazin-1-yl)-pyrrolidin-1-ylmethyl]-benzonitrile;

3-[(3S,4R)-3-Ethyl-4-(6H-pyrrolo[2,3-e][1,2,4]triazolo[4,3-a]pyrazin-1-yl)-pyrrolidin-1-yl]-3-oxo-propionitrile;

1-[(1S,2R,4R)-2-Ethyl-4-(4-trifluoromethyl-cyclohexyloxy)-cyclopentyl]-6H-pyrrolo[2,3-e][1,2,4]triazolo[4,3-a]pyrazin-1-yl;

1-[(1R,2R,4R)-2-Ethyl-4-(4-trifluoromethyl-cyclohexyloxy)-cyclopentyl]-6H-pyrrolo[2,3-e][1,2,4]triazolo[4,3-a]pyrazin-1-yl;

1-[(1R,2R,4R)-2-Ethyl-4-(4-trifluoromethyl-cyclohexyloxy)-cyclopentyl]-6H-pyrrolo[2,3-e][1,2,4]triazolo[4,3-a]pyrazin-1-yl;

{3-[(3S,4R)-3-Ethyl-4-(6H-pyrrolo[2,3-e][1,2,4]triazolo[4, 3-a]pyrazin-1-yl)-pyrrolidin-1-yl]-oxetan-3-yl}-acetonitrile;

3-[(1S,3R,4R)-3-Ethyl-4-(6H-pyrrolo[2,3-e][1,2,4]triazolo [4,3-a]pyrazin-1-yl)-cyclopentyloxy]-propionitrile;

3-[(1S,3R,4S)-3-Ethyl-4-(6H-pyrrolo[2,3-e][1,2,4]triazolo[4,3-a]pyrazin-1-yl)-cyclopentyloxy]-propionitrile;

Cyclopropanesulfonic acid (2-cyano-ethyl)-[(1S,3R,4S)-3-ethyl-4-(6H-pyrrolo[2,3-e][1,2,4]triazolo[4,3-a]pyrazin-1-yl)-cyclopentyl]-amide;

4-[(1R,3R,4S)-3-Ethyl-4-(6H-pyrrolo[2,3-e][1,2,4]triazolo[4,3-a]pyrazin-1-yl)-cyclopentyloxy]-cyclohexanecarbonitrile;

4-[(1R,3R,4S)-3-Ethyl-4-(6H-pyrrolo[2,3-e][1,2,4]triazolo[4,3-a]pyrazin-1-yl)-cyclopentyloxy]-cyclohexanecarbonitrile;

1-((3R,4S)-1-Cyclopropanesulfonyl-4-ethyl-pyrrolidin-3-yl)-6H-pyrrolo[2,3-e][1,2,4]triazolo[4,3-a]pyrazin-1-yl;

N-[(1S,3R,4S)-3-Ethyl-4-(6H-pyrrolo[2,3-e][1,2,4]triazolo[4,3-a]pyrazin-1-yl)-cyclopentyl]-N-(4,4,4-trifluoro-butyl)-acetamide;

Cyclopropyl-carbamic acid (1R,3R,4S)-3-ethyl-4-(6H-pyrrolo[2,3-e][1,2,4]triazolo[4,3-a]pyrazin-1-yl)-cyclopentyl ester;

3,3-Difluoro-azetidine-1-carboxylic acid (1R,3R,4S)-3-ethyl-4-(6H-pyrrolo[2,3-e][1,2,4]triazolo[4,3-a]pyrazin-1-yl)-cyclopentyl ester;

Cyanomethyl-carbamic acid (1R,3R,4S)-3-ethyl-4-(6H-pyrrolo[2,3-e][1,2,4]triazolo[4,3-a]pyrazin-1-yl)-cyclopentyl ester;

N-[(1S,3R,4S)-3-Ethyl-4-(6H-pyrrolo[2,3-e][1,2,4]triazolo[4,3-a]pyrazin-1-yl)-cyclopentyl]-N-(tetrahydro-pyran-4-ylmethyl)-acetamide;

3-[(1S,3R,4S)-3-Ethyl-4-(6H-pyrrolo[2,3-e][1,2,4]triazolo[4,3-a]pyrazin-1-yl)-cyclopentyl]-1,1-dimethyl-urea;

Dimethyl-carbamic acid (1R,3R,4S)-3-ethyl-4-(6H-pyrrolo[2,3-e][1,2,4]triazolo[4,3-a]pyrazin-1-yl)-cyclopentyl ester;

(1S,3R,4S)-3-Ethyl-1-(morpholine-4-sulfonylmethyl)-4-(6H-pyrrolo[2,3-e][1,2,4]triazolo[4,3-a]pyrazin-1-yl)-cyclopentanol;

(1R,3R,4R)-3-Ethyl-1-(morpholine-4-sulfonylmethyl)-4-(6H-pyrrolo[2,3-e][1,2,4]triazolo[4,3-a]pyrazin-1-yl)-cyclopentanol;

(1S,3R,4R)-3-Ethyl-1-(morpholine-4-sulfonylmethyl)-4-(6H-pyrrolo[2,3-e][1,2,4]triazolo[4,3-a]pyrazin-1-yl)-cyclopentanol;

N-Cyclopropylmethyl-N-[(1S,3R,4S)-3-ethyl-4-(6H-pyrrolo[2,3-e][1,2,4]triazolo[4,3-a]pyrazin-1-yl)-cyclopentyl]-acetamide;

1-[(1S,3R,4R)-3-Ethyl-4-(6H-pyrrolo[2,3-e][1,2,4]triazolo[4,3-a]pyrazin-1-yl)-cyclopentyl]-2-methyl-propan-2-ol;

1-[(1R,3R,4S)-3-Ethyl-4-(6H-pyrrolo[2,3-e][1,2,4]triazolo[4,3-a]pyrazin-1-yl)-cyclopentyl]-2-methyl-propan-2-ol;

1-[(1S,3R,4S)-3-Ethyl-4-(6H-pyrrolo[2,3-e][1,2,4]triazolo[4,3-a]pyrazin-1-yl)-cyclopentyl]-2-methyl-propan-2-ol;

1-[(1R,2R,4S)-4-(3-Cyclopropyl-[1,2,4]oxadiazol-5-ylmethyl)-2-ethyl-cyclopentyl]-6H-pyrrolo[2,3-e][1,2,4]triazolo[4,3-a]pyrazin-1-yl;

1-[(1S,2R,4S)-4-(3-Cyclopropyl-[1,2,4]oxadiazol-5-ylmethyl)-2-ethyl-cyclopentyl]-6H-pyrrolo[2,3-e][1,2,4]triazolo[4,3-a]pyrazin-1-yl;

1-[(1S,2R,4R)-4-(3-Cyclopropyl-[1,2,4]oxadiazol-5-ylmethyl)-2-ethyl-cyclopentyl]-6H-pyrrolo[2,3-e][1,2,4]triazolo[4,3-a]pyrazin-1-yl;

1-[(1S,2R,4R)-2-Ethyl-4-(5-methyl-isoxazol-3-ylmethoxy)-cyclopentyl]-6H-pyrrolo[2,3-e][1,2,4]triazolo[4,3-a]pyrazin-1-yl;

Oxetan-3-yl-carbamic acid (1R,3R,4S)-3-ethyl-4-(6H-pyrrolo[2,3-e][1,2,4]triazolo[4,3-a]pyrazin-1-yl)-cyclopentyl ester;

Cyclobutyl-carbamic acid (1R,3R,4S)-3-ethyl-4-(6H-pyrrolo[2,3-e][1,2,4]triazolo[4,3-a]pyrazin-1-yl)-cyclopentyl ester;

Cyclopropanesulfonic acid [(1R,3R,4S)-3-ethyl-4-(6H-pyrrolo[2,3-e][1,2,4]triazolo[4,3-a]pyrazin-1-yl)-cyclopentyl]-amide;

{3-[(1R,3R,4S)-3-Ethyl-4-(6H-pyrrolo[2,3-e][1,2,4]triazolo[4,3-a]pyrazin-1-yl)-cyclopentylamino]-oxetan-3-yl}-acetonitrile;

[(1S,3R,4S)-3-Ethyl-4-(6H-pyrrolo[2,3-e][1,2,4]triazolo[4,3-a]pyrazin-1-yl)-cyclopentyl]-carbamic acid isopropyl ester;

[(1S,3R,4S)-3-Ethyl-4-(6H-pyrrolo[2,3-e][1,2,4]triazolo[4,3-a]pyrazin-1-yl)-cyclopentyl]-oxetan-3-yl-amine;

1-((3R,4S)-1-Benzyl-4-isopropyl-pyrrolidin-3-yl)-6H-pyrrolo[2,3-e][1,2,4]triazolo[4,3-a]pyrazin-1-yl;

3-Fluoro-propane-1-sulfonic acid [(1S,3R,4S)-3-ethyl-4-(6H-pyrrolo[2,3-e][1,2,4]triazolo[4,3-a]pyrazin-1-yl)-cyclopentyl]-amide;

[(1S,3R,4S)-3-Ethyl-4-(6H-pyrrolo[2,3-e][1,2,4]triazolo[4,3-a]pyrazin-1-yl)-cyclopentyl]-(3-methyl-oxetan-3-yl)-amine;

1-[(1S,2R,4R)-2-Ethyl-4-(2-morpholin-4-yl-ethoxy)-cyclopentyl]-6H-pyrrolo[2,3-e][1,2,4]triazolo[4,3-a]pyrazin-1-yl;

Carbamoylmethyl-carbamic acid (1R,3R,4S)-3-ethyl-4-(6H-pyrrolo[2,3-e][1,2,4]triazolo[4,3-a]pyrazin-1-yl)-cyclopentyl ester;

4-Hydroxy-piperidine-1-carboxylic acid (1R,3R,4S)-3-ethyl-4-(6H-pyrrolo[2,3-e][1,2,4]triazolo[4,3-a]pyrazin-1-yl)-cyclopentyl ester;

(2,2,2-Trifluoro-ethyl)-carbamic acid (1R,3R,4S)-3-ethyl-4-(6H-pyrrolo[2,3-e][1,2,4]triazolo[4,3-a]pyrazin-1-yl)-cyclopentyl ester;

Cyclopropylmethyl-[(1S,3R,4S)-3-ethyl-4-(6H-pyrrolo[2,3-e][1,2,4]triazolo[4,3-a]pyrazin-1-yl)-cyclopentyl]-oxetan-3-yl-amine;

Pentane-2-sulfonic acid [(1S,3R,4S)-3-ethyl-4-(6H-pyrrolo[2,3-e][1,2,4]triazolo[4,3-a]pyrazin-1-yl)-cyclopentyl]-amide;

3-Phenyl-propane-1-sulfonic acid [(1S,3R,4S)-3-ethyl-4-(6H-pyrrolo[2,3-e][1,2,4]triazolo[4,3-a]pyrazin-1-yl)-cyclopentyl]-amide;

4,4,4-Trifluoro-butane-1-sulfonic acid [(1S,3R,4S)-3-ethyl-4-(6H-pyrrolo[2,3-e][1,2,4]triazolo[4,3-a]pyrazin-1-yl)-cyclopentyl]-amide;

2-Ethyl-cyclopropanesulfonic acid [(1S,3R,4S)-3-ethyl-4-(6H-pyrrolo[2,3-e][1,2,4]triazolo[4,3-a]pyrazin-1-yl)-cyclopentyl]-amide;

2-Methyl-propane-1-sulfonic acid [(1S,3R,4S)-3-ethyl-4-(6H-pyrrolo[2,3-e][1,2,4]triazolo[4,3-a]pyrazin-1-yl)-cyclopentyl]-amide;

2-Phenyl-ethanesulfonic acid [(1S,3R,4S)-3-ethyl-4-(6H-pyrrolo[2,3-e][1,2,4]triazolo[4,3-a]pyrazin-1-yl)-cyclopentyl]-amide;

C-Cyclohexyl-N-[(1S,3R,4S)-3-ethyl-4-(6H-pyrrolo[2,3-e][1,2,4]triazolo[4,3-a]pyrazin-1-yl)-cyclopentyl]-methanesulfonamide;

Butane-1-sulfonic acid [(1S,3R,4S)-3-ethyl-4-(6H-pyrrolo[2,3-e][1,2,4]triazolo[4,3-a]pyrazin-1-yl)-cyclopentyl]-amide;

Propane-2-sulfonic acid [(1S,3R,4S)-3-ethyl-4-(6H-pyrrolo[2,3-e][1,2,4]triazolo[4,3-a]pyrazin-1-yl)-cyclopentyl]-amide;

N-[(1S,3R,4S)-3-Ethyl-4-(6H-pyrrolo[2,3-e][1,2,4]triazolo[4,3-a]pyrazin-1-yl)-cyclopentyl]-C-phenyl-methanesulfonamide;

Propane-1-sulfonic acid [(1S,3R,4S)-3-ethyl-4-(6H-pyrrolo[2,3-e][1,2,4]triazolo[4,3-a]pyrazin-1-yl)-cyclopentyl]-amide;

3-Methyl-butane-1-sulfonic acid [(1S,3R,4S)-3-ethyl-4-(6H-pyrrolo[2,3-e][1,2,4]triazolo[4,3-a]pyrazin-1-yl)-cyclopentyl]-amide;

N-[(1S,3R,4S)-3-Ethyl-4-(6H-pyrrolo[2,3-e][1,2,4]triazolo[4,3-a]pyrazin-1-yl)-cyclopentyl]-C,C-difluoro-methanesulfonamide;

4-Cyano-butane-1-sulfonic acid [(1S,3R,4S)-3-ethyl-4-(6H-pyrrolo[2,3-e][1,2,4]triazolo[4,3-a]pyrazin-1-yl)-cyclopentyl]-amide;

2-Ethoxy-ethanesulfonic acid [(1S,3R,4S)-3-ethyl-4-(6H-pyrrolo[2,3-e][1,2,4]triazolo[4,3-a]pyrazin-1-yl)-cyclopentyl]-amide;

N-[(1S,3R,4S)-3-Ethyl-4-(6H-pyrrolo[2,3-e][1,2,4]triazolo[4,3-a]pyrazin-1-yl)-cyclopentyl]-C-(tetrahydro-furan-2-yl)-methanesulfonamide;

Tetrahydro-pyran-4-sulfonic acid [(1S,3R,4S)-3-ethyl-4-(6H-pyrrolo[2,3-e][1,2,4]triazolo[4,3-a]pyrazin-1-yl)-cyclopentyl]-amide;

3-Cyano-propane-1-sulfonic acid [(1S,3R,4S)-3-ethyl-4-(6H-pyrrolo[2,3-e][1,2,4]triazolo[4,3-a]pyrazin-1-yl)-cyclopentyl]-amide;

N-[(1S,3R,4S)-3-Ethyl-4-(6H-pyrrolo[2,3-e][1,2,4]triazolo[4,3-a]pyrazin-1-yl)-cyclopentyl]-C-(5-methyl-isoxazol-3-yl)-methanesulfonamide;

N-[(1S,3R,4S)-3-Ethyl-4-(6H-pyrrolo[2,3-e][1,2,4]triazolo[4,3-a]pyrazin-1-yl)-cyclopentyl]-C-(tetrahydro-pyran-2-yl)-methanesulfonamide;

2-Pyridin-2-yl-ethanesulfonic acid [(1S,3R,4S)-3-ethyl-4-(6H-pyrrolo[2,3-e][1,2,4]triazolo[4,3-a]pyrazin-1-yl)-cyclopentyl]-amide;

C-(2,2-Dichloro-cyclopropyl)-N-[(1S,3R,4S)-3-ethyl-4-(6H-pyrrolo[2,3-e][1,2,4]triazolo[4,3-a]pyrazin-1-yl)-cyclopentyl]-methanesulfonamide;

(3S,4R)-3-Isopropyl-4-(6H-pyrrolo[2,3-e][1,2,4]triazolo[4,3-a]pyrazin-1-yl)-pyrrolidine-1-carboxylic acid cyclobutylamide;

(1S,3R,4S)-3-Ethyl-1-methyl-4-(6H-pyrrolo[2,3-e][1,2,4]triazolo[4,3-a]pyrazin-1-yl)-cyclopentanol;

Carbonic acid (1S,3R,4S)-3-ethyl-4-[6-(toluene-4-sulfonyl)-6H-pyrrolo[2,3-e][1,2,4]triazolo[4,3-a]pyrazin-1-yl]-cyclopentyl ester 4-nitro-phenyl ester;

Cyclobutyl-carbamic acid (1S,3R,4S)-3-ethyl-4-(6H-pyrrolo[2,3-e][1,2,4]triazolo[4,3-a]pyrazin-1-yl)-cyclopentyl ester;

4-Hydroxy-piperidine-1-carboxylic acid (1S,3R,4S)-3-ethyl-4-(6H-pyrrolo[2,3-e][1,2,4]triazolo[4,3-a]pyrazin-1-yl)-cyclopentyl ester;

3-(Cyclopropylmethyl-amino)-4-[(1S,3R,4S)-3-ethyl-4-(6H-pyrrolo[2,3-e][1,2,4]triazolo[4,3-a]pyrazin-1-yl)-cyclopentylamino]-cyclobut-3-ene-1,2-dione;

3-[(1S,3R,4S)-3-Ethyl-4-(6H-pyrrolo[2,3-e][1,2,4]triazolo[4,3-a]pyrazin-1-yl)-cyclopentylamino]-4-(oxetan-3-ylamino)-cyclobut-3-ene-1,2-dione;

3-[(1S,3R,4S)-3-Ethyl-4-(6H-pyrrolo[2,3-e][1,2,4]triazolo[4,3-a]pyrazin-1-yl)-cyclopentylamino]-4-(3,3,3-trifluoro-propylamino)-cyclobut-3-ene-1,2-dione;

[(1S,3R,4S)-3-Ethyl-4-(6H-pyrrolo[2,3-e][1,2,4]triazolo[4,3-a]pyrazin-1-yl)-cyclopentyl]-methyl-oxetan-3-yl-amine;

[(1S,3R,4S)-3-Ethyl-4-(6H-pyrrolo[2,3-e][1,2,4]triazolo[4,3-a]pyrazin-1-yl)-cyclopentyl]-(3-methyl-oxetan-3-ylmethyl)-amine;

3-Cyclopropylamino-4-[(1S,3R,4S)-3-ethyl-4-(6H-pyrrolo[2,3-e][1,2,4]triazolo[4,3-a]pyrazin-1-yl)-cyclopentylamino]-cyclobut-3-ene-1,2-dione;

Cyanomethyl-carbamic acid (1S,3R,4S)-3-ethyl-4-(6H-pyrrolo[2,3-e][1,2,4]triazolo[4,3-a]pyrazin-1-yl)-cyclopentyl ester;

Cyclopropyl-carbamic acid (1S,3R,4S)-3-ethyl-4-(6H-pyrrolo[2,3-e][1,2,4]triazolo[4,3-a]pyrazin-1-yl)-cyclopentyl ester;

(2,2,2-Trifluoro-ethyl)-carbamic acid (1S,3R,4S)-3-ethyl-4-(6H-pyrrolo[2,3-e][1,2,4]triazolo[4,3-a]pyrazin-1-yl)-cyclopentyl ester;

3,3-Difluoro-azetidine-1-carboxylic acid (1S,3R,4S)-3-ethyl-4-(6H-pyrrolo[2,3-e][1,2,4]triazolo[4,3-a]pyrazin-1-yl)-cyclopentyl ester;

4-Cyano-piperidine-1-carboxylic acid (1S,3R,4S)-3-ethyl-4-(6H-pyrrolo[2,3-e][1,2,4]triazolo[4,3-a]pyrazin-1-yl)-cyclopentyl ester;

(3S,4R)-3-Ethyl-4-(6H-pyrrolo[2,3-e][1,2,4]triazolo[4,3-a]pyrazin-1-yl)-pyrrolidine-1-carboxylic acid (1-cyano-cyclopropyl)-amide;

(3R,4S)-3-Ethyl-4-(6H-pyrrolo[2,3-e][1,2,4]triazolo[4,3-a]pyrazin-1-yl)-pyrrolidine-1-carboxylic acid (1-cyano-cyclopropyl)-amide;

(3R,4S)-3-Ethyl-4-(6H-pyrrolo[2,3-e][1,2,4]triazolo[4,3-a]pyrazin-1-yl)-pyrrolidine-1-carboxylic acid cyclobutyl-amide;

(3S,4R)-3-Ethyl-4-(6H-pyrrolo[2,3-e][1,2,4]triazolo[4,3-a]pyrazin-1-yl)-pyrrolidine-1-carboxylic acid cyclobutyl-amide;

(3S,4R)-3-Ethyl-4-(6H-pyrrolo[2,3-e][1,2,4]triazolo[4,3-a]pyrazin-1-yl)-pyrrolidine-1-carboxylic acid (3-methyl-isothiazol-5-yl)-amide;

(3R,4S)-3-Ethyl-4-(6H-pyrrolo[2,3-e][1,2,4]triazolo[4,3-a]pyrazin-1-yl)-pyrrolidine-1-carboxylic acid (3-methyl-isothiazol-5-yl)-amide;

(3S,4R)-3-Ethyl-4-(6H-pyrrolo[2,3-e][1,2,4]triazolo[4,3-a]pyrazin-1-yl)-pyrrolidine-1-carboxylic acid cyanomethyl-amide;

(3R,4S)-3-Ethyl-4-(6H-pyrrolo[2,3-e][1,2,4]triazolo[4,3-a]pyrazin-1-yl)-pyrrolidine-1-carboxylic acid cyanomethyl-amide;

(2-Cyclopropyl-ethyl)-[(1S,3R,4S)-3-ethyl-4-(6H-pyrrolo[2,3-e][1,2,4]triazolo[4,3-a]pyrazin-1-yl)-cyclopentyl]-oxetan-3-yl-amine;

Cyclopropylmethyl-[(1S,3R,4S)-3-ethyl-4-(6H-pyrrolo[2,3-e][1,2,4]triazolo[4,3-a]pyrazin-1-yl)-cyclopentyl]-(3-methyl-oxetan-3-yl)-amine;

(3S,4R)-3-Ethyl-4-(6H-pyrrolo[2,3-e][1,2,4]triazolo[4,3-a]pyrazin-1-yl)-pyrrolidine-1-carboxylic acid (oxazol-4-yl-methyl)-amide;

(3R,4S)-3-Ethyl-4-(6H-pyrrolo[2,3-e][1,2,4]triazolo[4,3-a]pyrazin-1-yl)-pyrrolidine-1-carboxylic acid (oxazol-4-yl-methyl)-amide;

(3S,4R)-3-Ethyl-4-(6H-pyrrolo[2,3-e][1,2,4]triazolo[4,3-a]pyrazin-1-yl)-pyrrolidine-1-carboxylic acid (2,2,2-trifluoro-ethyl)-amide;

(3R,4S)-3-Ethyl-4-(6H-pyrrolo[2,3-e][1,2,4]triazolo[4,3-a]pyrazin-1-yl)-pyrrolidine-1-carboxylic acid (2,2,2-trifluoro-ethyl)-amide;

(2-Cyclopropyl-ethyl)-[(1S,3R,4S)-3-ethyl-4-(6H-pyrrolo[2,3-e][1,2,4]triazolo[4,3-a]pyrazin-1-yl)-cyclopentyl]-(3-methyl-oxetan-3-yl)-amine;

3-Cyano-azetidine-1-carboxylic acid (1S,3R,4S)-3-ethyl-4-(6H-pyrrolo[2,3-e][1,2,4]triazolo[4,3-a]pyrazin-1-yl)-cyclopentyl ester;

Benzyl-carbamic acid (1S,3R,4S)-3-ethyl-4-(6H-pyrrolo[2,3-e][1,2,4]triazolo[4,3-a]pyrazin-1-yl)-cyclopentyl ester;

Oxetan-3-yl-carbamic acid (1S,3R,4S)-3-ethyl-4-(6H-pyrrolo[2,3-e][1,2,4]triazolo[4,3-a]pyrazin-1-yl)-cyclopentyl ester;

(1-Cyano-cyclopropyl)-carbamic acid (1S,3R,4S)-3-ethyl-4-(6H-pyrrolo[2,3-e][1,2,4]triazolo[4,3-a]pyrazin-1-yl)-cyclopentyl ester;

(3-Methyl-oxetan-3-yl)-carbamic acid (1S,3R,4S)-3-ethyl-4-(6H-pyrrolo[2,3-e][1,2,4]triazolo[4,3-a]pyrazin-1-yl)-cyclopentyl ester;

(R)-3-Hydroxy-pyrrolidine-1-carboxylic acid (1S,3R,4S)-3-ethyl-4-(6H-pyrrolo[2,3-e][1,2,4]triazolo[4,3-a]pyrazin-1-yl)-cyclopentyl ester;

(S)-3-Hydroxy-pyrrolidine-1-carboxylic acid (1S,3R,4S)-3-ethyl-4-(6H-pyrrolo[2,3-e][1,2,4]triazolo[4,3-a]pyrazin-1-yl)-cyclopentyl ester;

4-Fluoro-piperidine-1-carboxylic acid (1S,3R,4S)-3-ethyl-4-(6H-pyrrolo[2,3-e][1,2,4]triazolo[4,3-a]pyrazin-1-yl)-cyclopentyl ester;

(2,2-Difluoro-ethyl)-carbamic acid (1S,3R,4S)-3-ethyl-4-(6H-pyrrolo[2,3-e][1,2,4]triazolo[4,3-a]pyrazin-1-yl)-cyclopentyl ester;

(3,3-Difluoro-azetidin-1-yl)-[(3S,4R)-3-ethyl-4-(6H-pyrrolo[2,3-e][1,2,4]triazolo[4,3-a]pyrazin-1-yl)-pyrrolidin-1-yl]-methanone;

1-[(1S,2R,4R)-2-Ethyl-4-(pyrazol-1-yloxy)-cyclopentyl]-6H-pyrrolo[2,3-e][1,2,4]triazolo[4,3-a]pyrazin-1-yl;

(3,3-Difluoro-azetidin-1-yl)-[(3R,4S)-3-ethyl-4-(6H-pyrrolo[2,3-e][1,2,4]triazolo[4,3-a]pyrazin-1-yl)-pyrrolidin-1-yl]-methanone;

{2-[(3S,4R)-3-Ethyl-4-(6H-pyrrolo[2,3-e][1,2,4]triazolo[4,3-a]pyrazin-1-yl)-pyrrolidin-1-yl]-4,5-dihydro-oxazol-4-yl}-methanol;

(3S,4R)-3-Ethyl-4-(6H-pyrrolo[2,3-e][1,2,4]triazolo[4,3-a]pyrazin-1-yl)-pyrrolidine-1-carboxylic acid oxetan-3-yl-amide;

(3R,4S)-3-Ethyl-4-(6H-pyrrolo[2,3-e][1,2,4]triazolo[4,3-a]pyrazin-1-yl)-pyrrolidine-1-carboxylic acid oxetan-3-yl-amide;

3-Fluoro-azetidine-1-carboxylic acid (1S,3R,4S)-3-ethyl-4-(6H-pyrrolo[2,3-e][1,2,4]triazolo[4,3-a]pyrazin-1-yl)-cyclopentyl ester;

(1-Methyl-cyclobutyl)-carbamic acid (1S,3R,4S)-3-ethyl-4-(6H-pyrrolo[2,3-e][1,2,4]triazolo[4,3-a]pyrazin-1-yl)-cyclopentyl ester;

(1-Hydroxy-cyclopropylmethyl)-carbamic acid (1S,3R,4S)-3-ethyl-4-(6H-pyrrolo[2,3-e][1,2,4]triazolo[4,3-a]pyrazin-1-yl)-cyclopentyl ester;

Methyl-oxetan-3-yl-carbamic acid (1S,3R,4S)-3-ethyl-4-(6H-pyrrolo[2,3-e][1,2,4]triazolo[4,3-a]pyrazin-1-yl)-cyclopentyl ester;

(3-Methyl-oxetan-3-ylmethyl)-carbamic acid (1S,3R,4S)-3-ethyl-4-(6H-pyrrolo[2,3-e][1,2,4]triazolo[4,3-a]pyrazin-1-yl)-cyclopentyl ester;

Phenyl-carbamic acid (1S,3R,4S)-3-ethyl-4-(6H-pyrrolo[2,3-e][1,2,4]triazolo[4,3-a]pyrazin-1-yl)-cyclopentyl ester;

[(3S,4R)-3-Ethyl-4-(6H-pyrrolo[2,3-e][1,2,4]triazolo[4,3-a]pyrazin-1-yl)-pyrrolidin-1-yl]-((R)-3-hydroxy-pyrrolidin-1-yl)-methanone;

[(3R,4S)-3-Ethyl-4-(6H-pyrrolo[2,3-e][1,2,4]triazolo[4,3-a]pyrazin-1-yl)-pyrrolidin-1-yl]-((R)-3-hydroxy-pyrrolidin-1-yl)-methanone;

(1R,3R,4S)-3-Ethyl-4-(6H-pyrrolo[2,3-e][1,2,4]triazolo[4,3-a]pyrazin-1-yl)-cyclopentanecarbonitrile;

[(3S,4R)-3-Ethyl-4-(6H-pyrrolo[2,3-e][1,2,4]triazolo[4,3-a]pyrazin-1-yl)-pyrrolidin-1-yl]-((S)-3-hydroxy-pyrrolidin-1-yl)-methanone;

[(3R,4S)-3-Ethyl-4-(6H-pyrrolo[2,3-e][1,2,4]triazolo[4,3-a]pyrazin-1-yl)-pyrrolidin-1-yl]-((S)-3-hydroxy-pyrrolidin-1-yl)-methanone;

tert-Butyl-carbamic acid (1S,3R,4S)-3-ethyl-4-(6H-pyrrolo[2,3-e][1,2,4]triazolo[4,3-a]pyrazin-1-yl)-cyclopentyl ester;

(2,2-Dimethyl-propyl)-carbamic acid (1S,3R,4S)-3-ethyl-4-(6H-pyrrolo[2,3-e][1,2,4]triazolo[4,3-a]pyrazin-1-yl)-cyclopentyl ester;

(2-Methoxy-ethyl)-carbamic acid (1S,3R,4S)-3-ethyl-4-(6H-pyrrolo[2,3-e][1,2,4]triazolo[4,3-a]pyrazin-1-yl)-cyclopentyl ester;

(3,5-Bis-trifluoromethyl-benzyl)-carbamic acid (1S,3R,4S)-3-ethyl-4-(6H-pyrrolo[2,3-e][1,2,4]triazolo[4,3-a]pyrazin-1-yl)-cyclopentyl ester;

(2-Dimethylamino-ethyl)-methyl-carbamic acid (1S,3R,4S)-3-ethyl-4-(6H-pyrrolo[2,3-e][1,2,4]triazolo[4,3-a]pyrazin-1-yl)-cyclopentyl ester; compound with trifluoro-acetic acid;

(3-Dimethylamino-propyl)-methyl-carbamic acid (1S,3R,4S)-3-ethyl-4-(6H-pyrrolo[2,3-e][1,2,4]triazolo[4,3-a]pyrazin-1-yl)-cyclopentyl ester; compound with trifluoro-acetic acid;

Benzyl-isopropyl-carbamic acid (1S,3R,4S)-3-ethyl-4-(6H-pyrrolo[2,3-e][1,2,4]triazolo[4,3-a]pyrazin-1-yl)-cyclopentyl ester;

(R)-3-Hydroxy-piperidine-1-carboxylic acid (1S,3R,4S)-3-ethyl-4-(6H-pyrrolo[2,3-e][1,2,4]triazolo[4,3-a]pyrazin-1-yl)-cyclopentyl ester;

4-Methyl-piperazine-1-carboxylic acid (1S,3R,4S)-3-ethyl-4-(6H-pyrrolo[2,3-e][1,2,4]triazolo[4,3-a]pyrazin-1-yl)-cyclopentyl ester; compound with trifluoro-acetic acid;

4-Acetyl-piperazine-1-carboxylic acid (1S,3R,4S)-3-ethyl-4-(6H-pyrrolo[2,3-e][1,2,4]triazolo[4,3-a]pyrazin-1-yl)-cyclopentyl ester;

4-(2-Fluoro-phenyl)-piperazine-1-carboxylic acid (1S,3R,4S)-3-ethyl-4-(6H-pyrrolo[2,3-e][1,2,4]triazolo[4,3-a]pyrazin-1-yl)-cyclopentyl ester; compound with trifluoro-acetic acid;

Pyridin-2-ylmethyl-carbamic acid (1S,3R,4S)-3-ethyl-4-(6H-pyrrolo[2,3-e][1,2,4]triazolo[4,3-a]pyrazin-1-yl)-cyclopentyl ester; compound with trifluoro-acetic acid;

Pyridin-3-ylmethyl-carbamic acid (1S,3R,4S)-3-ethyl-4-(6H-pyrrolo[2,3-e][1,2,4]triazolo[4,3-a]pyrazin-1-yl)-cyclopentyl ester; compound with trifluoro-acetic acid;

Pyridin-4-ylmethyl-carbamic acid (1S,3R,4S)-3-ethyl-4-(6H-pyrrolo[2,3-e][1,2,4]triazolo[4,3-a]pyrazin-1-yl)-cyclopentyl ester; compound with trifluoro-acetic acid;

Isobutyl-carbamic acid (1S,3R,4S)-3-ethyl-4-(6H-pyrrolo[2,3-e][1,2,4]triazolo[4,3-a]pyrazin-1-yl)-cyclopentyl ester;

[(S)-1-(Tetrahydro-furan-2-yl)methyl]-carbamic acid (1S,3R,4S)-3-ethyl-4-(6H-pyrrolo[2,3-e][1,2,4]triazolo[4,3-a]pyrazin-1-yl)-cyclopentyl ester;

[(R)-1-(Tetrahydro-furan-2-yl)methyl]-carbamic acid (1S,3R,4S)-3-ethyl-4-(6H-pyrrolo[2,3-e][1,2,4]triazolo[4,3-a]pyrazin-1-yl)-cyclopentyl ester;

(2-Cyano-ethyl)-cyclopropyl-carbamic acid (1S,3R,4S)-3-ethyl-4-(6H-pyrrolo[2,3-e][1,2,4]triazolo[4,3-a]pyrazin-1-yl)-cyclopentyl ester;

Diisobutyl-carbamic acid (1S,3R,4S)-3-ethyl-4-(6H-pyrrolo[2,3-e][1,2,4]triazolo[4,3-a]pyrazin-1-yl)-cyclopentyl ester;

Azetidine-1-carboxylic acid (1S,3R,4S)-3-ethyl-4-(6H-pyrrolo[2,3-e][1,2,4]triazolo[4,3-a]pyrazin-1-yl)-cyclopentyl ester;

(2-Methoxy-ethyl)-methyl-carbamic acid (1S,3R,4S)-3-ethyl-4-(6H-pyrrolo[2,3-e][1,2,4]triazolo[4,3-a]pyrazin-1-yl)-cyclopentyl ester;

Morpholine-4-carboxylic acid (1S,3R,4S)-3-ethyl-4-(6H-pyrrolo[2,3-e][1,2,4]triazolo[4,3-a]pyrazin-1-yl)-cyclopentyl ester;

Thiomorpholine-4-carboxylic acid (1S,3R,4S)-3-ethyl-4-(6H-pyrrolo[2,3-e][1,2,4]triazolo[4,3-a]pyrazin-1-yl)-cyclopentyl ester;

(2-Dimethylamino-ethyl)-carbamic acid (1S,3R,4S)-3-ethyl-4-(6H-pyrrolo[2,3-e][1,2,4]triazolo[4,3-a]pyrazin-1-yl)-cyclopentyl ester; compound with trifluoro-acetic acid;

(3-Dimethylamino-propyl)-carbamic acid (1S,3R,4S)-3-ethyl-4-(6H-pyrrolo[2,3-e][1,2,4]triazolo[4,3-a]pyrazin-1-yl)-cyclopentyl ester; compound with trifluoro-acetic acid;

(2-Pyrrolidin-1-yl-ethyl)-carbamic acid (1S,3R,4S)-3-ethyl-4-(6H-pyrrolo[2,3-e][1,2,4]triazolo[4,3-a]pyrazin-1-yl)-cyclopentyl ester; compound with trifluoro-acetic acid;

(3-Pyrrolidin-1-yl-propyl)-carbamic acid (1S,3R,4S)-3-ethyl-4-(6H-pyrrolo[2,3-e][1,2,4]triazolo[4,3-a]pyrazin-1-yl)-cyclopentyl ester; compound with trifluoro-acetic acid;

(2-Piperidin-1-yl-ethyl)-carbamic acid (1S,3R,4S)-3-ethyl-4-(6H-pyrrolo[2,3-e][1,2,4]triazolo[4,3-a]pyrazin-1-yl)-cyclopentyl ester; compound with trifluoro-acetic acid;

(3-Piperidin-1-yl-propyl)-carbamic acid (1S,3R,4S)-3-ethyl-4-(6H-pyrrolo[2,3-e][1,2,4]triazolo[4,3-a]pyrazin-1-yl)-cyclopentyl ester; compound with trifluoro-acetic acid;

(2-Morpholin-4-yl-ethyl)-carbamic acid (1S,3R,4S)-3-ethyl-4-(6H-pyrrolo[2,3-e][1,2,4]triazolo[4,3-a]pyrazin-1-yl)-cyclopentyl ester; compound with trifluoro-acetic acid;

(3-Morpholin-4-yl-propyl)-carbamic acid (1S,3R,4S)-3-ethyl-4-(6H-pyrrolo[2,3-e][1,2,4]triazolo[4,3-a]pyrazin-1-yl)-cyclopentyl ester; compound with trifluoro-acetic acid;

1-[(1S,2R,4S)-4-(2,2-Difluoro-ethoxy)-2-ethyl-cyclopentyl]-6H-pyrrolo[2,3-e][1,2,4]triazolo[4,3-a]pyrazin-1-yl;

1-[(1S,3R,4S)-3-Ethyl-4-(6H-pyrrolo[2,3-e][1,2,4]triazolo[4,3-a]pyrazin-1-yl)-cyclopentyloxy]-2-methyl-propan-2-ol;

(2-Cyclopropyl-ethyl)-[(1S,3R,4S)-3-ethyl-4-(6H-pyrrolo[2,3-e][1,2,4]triazolo[4,3-a]pyrazin-1-yl)-cyclopentyl]-(2,2,2-trifluoro-ethyl)-amine;

Cyclopropylmethyl-[(1S,3R,4S)-3-ethyl-4-(6H-pyrrolo[2,3-e][1,2,4]triazolo[4,3-a]pyrazin-1-yl)-cyclopentyl]-(2,2,2-trifluoro-ethyl)-amine;

Cyclopropylmethyl-[(1S,3R,4S)-3-ethyl-4-(6H-pyrrolo[2,3-e][1,2,4]triazolo[4,3-a]pyrazin-1-yl)-cyclopentyl]-(2,2,2-trifluoro-ethyl)-amine;

1-((7S,8R)-8-Ethyl-1,4-dioxa-spiro[4.4]non-7-yl)-6-(toluene-4-sulfonyl)-6H-pyrrolo[2,3-e][1,2,4]triazolo[4,3-a]pyrazin-1-yl;

1-[(1R,3R,4R)-3-Ethyl-4-(6H-pyrrolo[2,3-e][1,2,4]triazolo[4,3-a]pyrazin-1-yl)-cyclopentyl]-2-methyl-propan-2-ol;

Acetic acid (1S,3R,4S)-3-ethyl-4-(6H-pyrrolo[2,3-e][1,2,4]triazolo[4,3-a]pyrazin-1-yl)-cyclopentyl ester;

(3R,4S)-3-Ethyl-4-(6H-pyrrolo[2,3-e][1,2,4]triazolo[4,3-a]pyrazin-1-yl)-pyrrolidine-1-sulfonic acid cyclopropylmethyl-amide;

(3S,4R)-3-Ethyl-4-(6H-pyrrolo[2,3-e][1,2,4]triazolo[4,3-a]pyrazin-1-yl)-pyrrolidine-1-sulfonic acid cyclopropylmethyl-amide;

(3R,4S)-3-Ethyl-4-(6H-pyrrolo[2,3-e][1,2,4]triazolo[4,3-a]pyrazin-1-yl)-pyrrolidine-1-carboxylic acid (2-cyclopropyl-ethyl)-amide;

(3S,4R)-3-Ethyl-4-(6H-pyrrolo[2,3-e][1,2,4]triazolo[4,3-a]pyrazin-1-yl)-pyrrolidine-1-carboxylic acid (2-cyclopropyl-ethyl)-amide;

(3R,4S)-3-Ethyl-4-(6H-pyrrolo[2,3-e][1,2,4]triazolo[4,3-a]pyrazin-1-yl)-pyrrolidine-1-sulfonic acid oxetan-3-ylamide;

(3S,4R)-3-Ethyl-4-(6H-pyrrolo[2,3-e][1,2,4]triazolo[4,3-a]pyrazin-1-yl)-pyrrolidine-1-sulfonic acid oxetan-3-ylamide;

[(1S,3R,4S)-3-Ethyl-4-(6H-pyrrolo[2,3-e][1,2,4]triazolo[4,3-a]pyrazin-1-yl)-cyclopentyl]-oxetan-3-yl-(4,4,4-trifluoro-butyl)-amine;

(3R,4S)-3-Ethyl-4-(6H-pyrrolo[2,3-e][1,2,4]triazolo[4,3-a]pyrazin-1-yl)-cyclopentanesulfonic acid cyclopropylamide;

2-[(1S,3R,4S)-3-Ethyl-4-(6H-pyrrolo[2,3-e][1,2,4]triazolo[4,3-a]pyrazin-1-yl)-cyclopentyl]-ethanol;

2-[(1R,3R,4S)-3-Ethyl-4-(6H-pyrrolo[2,3-e][1,2,4]triazolo[4,3-a]pyrazin-1-yl)-cyclopentyl]-ethanol;

(3R,4S)-3-Ethyl-4-(6H-pyrrolo[2,3-e][1,2,4]triazolo[4,3-a]pyrazin-1-yl)-pyrrolidine-1-sulfonic acid cyclobutylamide;

(3S,4R)-3-Ethyl-4-(6H-pyrrolo[2,3-e][1,2,4]triazolo[4,3-a]pyrazin-1-yl)-pyrrolidine-1-sulfonic acid cyclobutylamide;

1-[(1S,2R,4S)-2-Ethyl-4-(3-methoxymethyl-[1,2,4]oxadiazol-5-ylmethyl)-cyclopentyl]-6H-pyrrolo[2,3-e][1,2,4]triazolo[4,3-a]pyrazin-1-yl;

(3R,4S)-3-Ethyl-4-(6H-pyrrolo[2,3-e][1,2,4]triazolo[4,3-a]pyrazin-1-yl)-pyrrolidine-1-sulfonic acid amide;

(3S,4R)-3-Ethyl-4-(6H-pyrrolo[2,3-e][1,2,4]triazolo[4,3-a]pyrazin-1-yl)-pyrrolidine-1-sulfonic acid amide;

4-[(1S,3R,4S)-3-Ethyl-4-(6H-pyrrolo[2,3-e][1,2,4]triazolo[4,3-a]pyrazin-1-yl)-cyclopentyl]-butyronitrile;

4-[(1R,3R,4S)-3-Ethyl-4-(6H-pyrrolo[2,3-e][1,2,4]triazolo[4,3-a]pyrazin-1-yl)-cyclopentyl]-butyronitrile;

[(1R,3R,4S)-3-Ethyl-4-(6H-pyrrolo[2,3-e][1,2,4]triazolo[4,3-a]pyrazin-1-yl)-cyclopentyl]-acetonitrile;

[(1S,3R,4S)-3-Ethyl-4-(6H-pyrrolo[2,3-e][1,2,4]triazolo[4,3-a]pyrazin-1-yl)-cyclopentyl]-acetonitrile;

[(1S,3R,4S)-3-Ethyl-4-(6H-pyrrolo[2,3-e][1,2,4]triazolo[4,3-a]pyrazin-1-yl)-cyclopentyl]-(5-methyl-isoxazol-3-yl-methyl)-oxetan-3-yl-amine;

{5-[(1S,3R,4S)-3-Ethyl-4-(6H-pyrrolo[2,3-e][1,2,4]triazolo[4,3-a]pyrazin-1-yl)-cyclopentylmethyl]-[1,2,4]oxadiazol-3-yl}-methanol;

1-[(1S,2R,4S)-4-(3-Cyclopropyl-pyrazol-1-yl)-2-ethyl-cyclopentyl]-6H-pyrrolo[2,3-e][1,2,4]triazolo[4,3-a]pyrazin-1-yl;

1-[(1S,2R,4S)-4-(5-Cyclopropyl-pyrazol-1-yl)-2-ethyl-cyclopentyl]-6H-pyrrolo[2,3-e][1,2,4]triazolo[4,3-a]pyrazin-1-yl;

(3S,4R)-3-Ethyl-4-(6H-pyrrolo[2,3-e][1,2,4]triazolo[4,3-a]pyrazin-1-yl)-pyrrolidine-1-sulfonic acid (2,2,2-trifluoro-ethyl)-amide;

(3R,4S)-3-Ethyl-4-(6H-pyrrolo[2,3-e][1,2,4]triazolo[4,3-a]pyrazin-1-yl)-pyrrolidine-1-sulfonic acid (2,2,2-trifluoro-ethyl)-amide;

1-[(1S,2R,4S)-4-(3-Cyclopropyl-[1,2,4]triazol-1-yl)-2-ethyl-cyclopentyl]-6H-pyrrolo[2,3-e][1,2,4]triazolo[4,3-a]pyrazin-1-yl;

1-[(1S,2R,4S)-4-(5-Cyclopropyl-[1,2,4]triazol-1-yl)-2-ethyl-cyclopentyl]-6H-pyrrolo[2,3-e][1,2,4]triazolo[4,3-a]pyrazin-1-yl; or

[(1S,3R,4S)-3-Ethyl-4-(6H-pyrrolo[2,3-e][1,2,4]triazolo[4,3-a]pyrazin-1-yl)-cyclopentyl]-oxetan-3-yl-(3,3,3-trifluoro-propyl)-amine.

In a fifteenth embodiment the invention provides a compound according to the first through twelfth embodiments wherein T is $CR^6$, U is N, X is $CR^3$ and Y is N and forms a compound of Formula (Ib)

Formula (Ib)

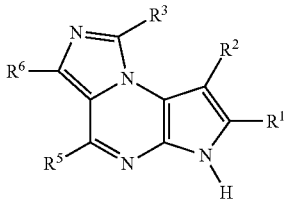

In a sixteenth embodiment the invention provides a compound according to the fifteenth embodiment wherein the compound is ((cis)-3-(6H-imidazo[1,5-a]pyrrolo[2,3-e]pyrazin-1-yl)-4-methylpiperidin-1-yl)(2,4-difluorophenyl)methanone;

((cis)-3-(6H-imidazo[1,5-a]pyrrolo[2,3-e]pyrazin-1-yl)-4-methylpiperidin-1-yl)(4-(trifluoromethyl)phenyl)methanone;

((cis)-3-(6H-imidazo[1,5-a]pyrrolo[2,3-e]pyrazin-1-yl)-4-methylpiperidin-1-yl)(pyridin-3-yl)methanone;

((cis)-3-(6H-imidazo[1,5-a]pyrrolo[2,3-e]pyrazin-1-yl)-4-methylpiperidin-1-yl)(3-(trifluoromethyl)phenyl)methanone;

((cis)-3-(6H-imidazo[1,5-a]pyrrolo[2,3-e]pyrazin-1-yl)-4-methylpiperidin-1-yl)(pyrazin-2-yl)methanone;

((cis)-3-(6H-imidazo[1,5-a]pyrrolo[2,3-e]pyrazin-1-yl)-4-methylpiperidin-1-yl)(pyrimidin-5-yl)methanone;

1-((cis)-3-(6H-imidazo[1,5-a]pyrrolo[2,3-e]pyrazin-1-yl)-4-methylpiperidin-1-yl)-2-cyclopropylethanone;

((cis)-3-(6H-imidazo[1,5-a]pyrrolo[2,3-e]pyrazin-1-yl)-4-methylpiperidin-1-yl)(phenyl)methanone;

1-((cis)-3-(6H-imidazo[1,5-a]pyrrolo[2,3-e]pyrazin-1-yl)-4-methylpiperidin-1-yl)-2-cyclobutylethanone;

1-((cis)-3-(6H-imidazo[1,5-a]pyrrolo[2,3-e]pyrazin-1-yl)-4-methylpiperidin-1-yl)-3-cyclobutylpropan-1-one;

((cis)-3-(6H-imidazo[1,5-a]pyrrolo[2,3-e]pyrazin-1-yl)-4-methylpiperidin-1-yl)(1H-pyrazol-4-yl)methanone;

((cis)-3-(6H-imidazo[1,5-a]pyrrolo[2,3-e]pyrazin-1-yl)-4-methylpiperidin-1-yl)(1H-pyrazol-3-yl)methanone;

1-((cis)-3-(6H-imidazo[1,5-a]pyrrolo[2,3-e]pyrazin-1-yl)-4-methylpiperidin-1-yl)propan-1-one;

N-((1S,3R,4S)-3-ethyl-4-(3-(3-hydroxypropyl)-6H-imidazo[1,5-a]pyrrolo[2,3-e]pyrazin-1-yl)cyclopentyl)cyclopropanesulfonamide;

1-((cis)-3-(6H-imidazo[1,5-a]pyrrolo[2,3-e]pyrazin-1-yl)-4-methylpiperidine-1-carbonyl)cyclopropanecarbonitrile;

3-((3S,4S)-4-ethyl-3-(6H-imidazo[1,5-a]pyrrolo[2,3-e]pyrazin-1-yl)piperidin-1-yl)-3-oxopropanenitrile;

3-((3R,4R)-4-ethyl-3-(6H-imidazo[1,5-a]pyrrolo[2,3-e]pyrazin-1-yl)piperidin-1-yl)-3-oxopropanenitrile;

N-((1S,3R,4S)-3-ethyl-4-(3-(hydroxymethyl)-6H-imidazo[1,5-a]pyrrolo[2,3-e]pyrazin-1-yl)cyclopentyl)cyclopropanesulfonamide;

N-((1S,3R,4S)-3-ethyl-4-(3-(2-hydroxyethyl)-6H-imidazo[1,5-a]pyrrolo[2,3-e]pyrazin-1-yl)cyclopentyl)cyclopropanesulfonamide;

((cis)-3-(6H-imidazo[1,5-a]pyrrolo[2,3-e]pyrazin-1-yl)-4-methylpiperidin-1-yl)(1-methyl-1H-pyrazol-4-yl)methanone;

((cis)-3-(6H-imidazo[1,5-a]pyrrolo[2,3-e]pyrazin-1-yl)-4-methylpiperidin-1-yl)(pyridin-4-yl)methanone;

1-((cis)-3-(6H-imidazo[1,5-a]pyrrolo[2,3-e]pyrazin-1-yl)-4-methylpiperidin-1-yl)-2-(3-methylisoxazol-5-yl)ethanone;

1-((cis)-3-(6H-imidazo[1,5-a]pyrrolo[2,3-e]pyrazin-1-yl)-4-methylpiperidin-1-yl)-2-(2,4-difluorophenyl)ethanone;

6-((cis)-3-(6H-imidazo[1,5-a]pyrrolo[2,3-e]pyrazin-1-yl)-4-methylpiperidin-1-yl)pyridazine-3-carbonitrile;

5-((cis)-3-(6H-imidazo[1,5-a]pyrrolo[2,3-e]pyrazin-1-yl)-4-methylpiperidin-1-yl)pyrazine-2-carbonitrile;

2-((cis)-3-(6H-imidazo[1,5-a]pyrrolo[2,3-e]pyrazin-1-yl)-4-methylpiperidin-1-yl)thiazole-5-carbonitrile;

6-((cis)-3-(6H-imidazo[1,5-a]pyrrolo[2,3-e]pyrazin-1-yl)-4-methylpiperidin-1-yl)nicotinonitrile;

((cis)-3-(6H-imidazo[1,5-a]pyrrolo[2,3-e]pyrazin-1-yl)-4-methylpiperidin-1-yl)(pyrrolidin-1-yl)methanone;

1-((cis)-3-(6H-imidazo[1,5-a]pyrrolo[2,3-e]pyrazin-1-yl)-4-methylpiperidine-1-carbonyl)azetidine-3-carbonitrile;

(cis)-3-(6H-imidazo[1,5-a]pyrrolo[2,3-e]pyrazin-1-yl)-N,N,4-trimethylpiperidine-1-carboxamide;

1-((cis)-1-(cyclopropylsulfonyl)-4-methylpiperidin-3-yl)-6H-imidazo[1,5-a]pyrrolo[2,3-e]pyrazine;

(cis)-N-(cyanomethyl)-3-(6H-imidazo[1,5-a]pyrrolo[2,3-e]pyrazin-1-yl)-4-methylpiperidine-1-carboxamide;

((cis)-3-(6H-imidazo[1,5-a]pyrrolo[2,3-e]pyrazin-1-yl)-4-methylpiperidin-1-yl)(isoxazol-5-yl)methanone;

1-((3R,4R)-3-(6H-imidazo[1,5-a]pyrrolo[2,3-e]pyrazin-1-yl)-4-methylpiperidin-1-yl)-3,3,3-trifluoropropan-1-one;

1-((3R,4R)-3-(6H-imidazo[1,5-a]pyrrolo[2,3-e]pyrazin-1-yl)-4-methylpiperidin-1-yl)-3-hydroxy-3-methylbutan-1-one;

1-((3R,4R)-3-(6H-imidazo[1,5-a]pyrrolo[2,3-e]pyrazin-1-yl)-4-methylpiperidin-1-yl)-2-methoxyethanone;

1-((3R,4R)-3-(6H-imidazo[1,5-a]pyrrolo[2,3-e]pyrazin-1-yl)-4-methylpiperidin-1-yl)-3-methoxypropan-1-one;

1-((3R,4R)-3-(6H-imidazo[1,5-a]pyrrolo[2,3-e]pyrazin-1-yl)-4-methylpiperidin-1-yl)pent-4-yn-1-one;

1-((3R,4R)-3-(6H-imidazo[1,5-a]pyrrolo[2,3-e]pyrazin-1-yl)-4-methylpiperidin-1-yl)-2-(4-chlorophenyl)ethanone;

1-((3R,4R)-3-(6H-imidazo[1,5-a]pyrrolo[2,3-e]pyrazin-1-yl)-4-methylpiperidin-1-yl)-2-(3-chlorophenyl)ethanone;

4-((3R,4R)-3-(6H-imidazo[1,5-a]pyrrolo[2,3-e]pyrazin-1-yl)-4-methylpiperidine-1-carbonyl)benzonitrile;

1-((3R,4R)-3-(6H-imidazo[1,5-a]pyrrolo[2,3-e]pyrazin-1-yl)-4-methylpiperidin-1-yl)-3-(3-chloroisoxazol-5-yl)propan-1-one;

3-(2-((3R,4R)-3-(6H-imidazo[1,5-a]pyrrolo[2,3-e]pyrazin-1-yl)-4-methylpiperidin-1-yl)-2-oxoethyl)benzonitrile;

4-(2-((3R,4R)-3-(6H-imidazo[1,5-a]pyrrolo[2,3-e]pyrazin-1-yl)-4-methylpiperidin-1-yl)-2-oxoethyl)benzonitrile;

1-((3R,4R)-3-(6H-imidazo[1,5-a]pyrrolo[2,3-e]pyrazin-1-yl)-4-methylpiperidin-1-yl)-2-(1H-pyrrol-2-yl)ethanone;

1-((3R,4R)-3-(6H-imidazo[1,5-a]pyrrolo[2,3-e]pyrazin-1-yl)-4-methylpiperidin-1-yl)-2-(pyrazin-2-yl)ethanone;

1-((3R,4R)-3-(6H-imidazo[1,5-a]pyrrolo[2,3-e]pyrazin-1-yl)-4-methylpiperidin-1-yl)-2-(tetrahydro-2H-pyran-4-yl)ethanone;

1-((3R,4R)-3-(6H-imidazo[1,5-a]pyrrolo[2,3-e]pyrazin-1-yl)-4-methylpiperidin-1-yl)-2-(pyrimidin-2-yl)ethanone;

5-((1S,3S,4R)-3-(6H-imidazo[1,5-a]pyrrolo[2,3-e]pyrazin-1-yl)-4-methylcyclopentylamino)pyrazine-2-carbonitrile;

N-(4-(3-allyl-6H-imidazo[1,5-a]pyrrolo[2,3-e]pyrazin-1-yl)bicyclo[2.2.2]octan-1-yl)cyclopropanesulfonamide;

N-(1-(6H-imidazo[1,5-a]pyrrolo[2,3-e]pyrazin-1-yl)pyrrolidin-3-yl)cyclopropanesulfonamide;

N-(4-(3-propyl-6H-imidazo[1,5-a]pyrrolo[2,3-e]pyrazin-1-yl)bicyclo[2.2.2]octan-1-yl)cyclopropanesulfonamide;

2-((3R,4R)-3-(6H-imidazo[1,5-a]pyrrolo[2,3-e]pyrazin-1-yl)-4-methylpiperidin-1-yl)thiazole-5-carbonitrile;

N-(4-(3-(2,3-dihydroxypropyl)-6H-imidazo[1,5-a]pyrrolo[2,3-e]pyrazin-1-yl)bicyclo[2.2.2]octan-1-yl)cyclopropanesulfonamide;

1-((3R,4R)-3-(6H-imidazo[1,5-a]pyrrolo[2,3-e]pyrazin-1-yl)-4-methylpiperidine-1-carbonyl)pyrrolidine-3-carbonitrile;

(3R,4R)-N-(4-(cyanomethyl)phenyl)-3-(6H-imidazo[1,5-a]pyrrolo[2,3-e]pyrazin-1-yl)-4-methylpiperidine-1-carboxamide;

((3R,4R)-3-(6H-imidazo[1,5-a]pyrrolo[2,3-e]pyrazin-1-yl)-4-methylpiperidin-1-yl)(morpholino)methanone;

((3R,4R)-3-(6H-imidazo[1,5-a]pyrrolo[2,3-e]pyrazin-1-yl)-4-methylpiperidin-1-yl)(4-methylpiperazin-1-yl)methanone;

((3R,4R)-3-(6H-imidazo[1,5-a]pyrrolo[2,3-e]pyrazin-1-yl)-4-methylpiperidin-1-yl)(piperidin-1-yl)methanone;

(3R,4R)-N-(2,4-difluorophenyl)-3-(6H-imidazo[1,5-a]pyrrolo[2,3-e]pyrazin-1-yl)-4-methylpiperidine-1-carboxamide;

(3R,4R)-N-(3-cyanophenyl)-3-(6H-imidazo[1,5-a]pyrrolo[2,3-e]pyrazin-1-yl)-4-methylpiperidine-1-carboxamide;

(R)-1-((3R,4R)-3-(6H-imidazo[1,5-a]pyrrolo[2,3-e]pyrazin-1-yl)-4-methylpiperidine-1-carbonyl)pyrrolidine-2-carbonitrile;

(S)-1-((3R,4R)-3-(6H-imidazo[1,5-a]pyrrolo[2,3-e]pyrazin-1-yl)-4-methylpiperidine-1-carbonyl)pyrrolidine-2-carbonitrile;

((3R,4R)-3-(6H-imidazo[1,5-a]pyrrolo[2,3-e]pyrazin-1-yl)-4-methylpiperidin-1-yl)((R)-2-(trifluoromethyl)pyrrolidin-1-yl)methanone;

((3R,4R)-3-(6H-imidazo[1,5-a]pyrrolo[2,3-e]pyrazin-1-yl)-4-methylpiperidin-1-yl)((S)-2-(trifluoromethyl)pyrrolidin-1-yl)methanone;

((3R,4R)-3-(6H-imidazo[1,5-a]pyrrolo[2,3-e]pyrazin-1-yl)-4-methylpiperidin-1-yl)(3,3-difluoroazetidin-1-yl)methanone;

2-((3R,4R)-3-(6H-imidazo[1,5-a]pyrrolo[2,3-e]pyrazin-1-yl)-4-methylpiperidin-1-yl)benzo[d]oxazole;

N-((1S,3R,4S)-3-ethyl-4-(3-(2-(methylsulfonyl)ethyl)-6H-imidazo[1,5-a]pyrrolo[2,3-e]pyrazin-1-yl)cyclopentyl)cyclopropanesulfonamide;

((3R,4R)-3-(6H-imidazo[1,5-a]pyrrolo[2,3-e]pyrazin-1-yl)-4-methylpiperidin-1-yl)(azetidin-1-yl)methanone;

(3R,4R)-N-(4-cyanophenyl)-3-(6H-imidazo[1,5-a]pyrrolo[2,3-e]pyrazin-1-yl)-4-methylpiperidine-1-carboxamide;

((3R,4R)-3-(6H-imidazo[1,5-a]pyrrolo[2,3-e]pyrazin-1-yl)-4-methylpiperidin-1-yl)((R)-3-fluoropyrrolidin-1-yl)methanone;

((3R,4R)-3-(6H-imidazo[1,5-a]pyrrolo[2,3-e]pyrazin-1-yl)-4-methylpiperidin-1-yl)(3,3-difluoropyrrolidin-1-yl)methanone;

1-((3R,4R)-4-methyl-1-(pyrrolidin-1-ylsulfonyl)piperidin-3-yl)-6H-imidazo[1,5-a]pyrrolo[2,3-e]pyrazine;

(R)-N-(1-(6H-imidazo[1,5-a]pyrrolo[2,3-e]pyrazin-1-yl)pyrrolidin-3-yl)cyclopropanesulfonamide;

(S)-N-(1-(6H-imidazo[1,5-a]pyrrolo[2,3-e]pyrazin-1-yl)pyrrolidin-3-yl)cyclopropanesulfonamide;

3-((3R,4R)-3-(6H-imidazo[1,5-a]pyrrolo[2,3-e]pyrazin-1-yl)-4-(trifluoromethyl)piperidin-1-yl)-3-oxopropanenitrile;

3-((3S,4S)-3-(6H-imidazo[1,5-a]pyrrolo[2,3-e]pyrazin-1-yl)-4-(trifluoromethyl)piperidin-1-yl)-3-oxopropanenitrile;

N-(3-((3R,4R)-3-(6H-imidazo[1,5-a]pyrrolo[2,3-e]pyrazin-1-yl)-4-methylpiperidin-1-yl)-3-oxopropyl)acetamide;

((3R,4R)-3-(6H-imidazo[1,5-a]pyrrolo[2,3-e]pyrazin-1-yl)-4-methylpiperidin-1-yl)(tetrahydrofuran-2-yl)methanone;

((3R,4R)-3-(6H-imidazo[1,5-a]pyrrolo[2,3-e]pyrazin-1-yl)-4-methylpiperidin-1-yl)(tetrahydrofuran-3-yl)methanone;

((3R,4R)-3-(6H-imidazo[1,5-a]pyrrolo[2,3-e]pyrazin-1-yl)-4-methylpiperidin-1-yl)(3-methoxycyclohexyl)methanone;

1-((3R,4R)-3-(6H-imidazo[1,5-a]pyrrolo[2,3-e]pyrazin-1-yl)-4-methylpiperidin-1-yl)-3-hydroxypropan-1-one;

1-((3R,4R)-1-benzyl-4-methylpiperidin-3-yl)-6H-imidazo[1,5-a]pyrrolo[2,3-e]pyrazine;

1-((3R,4R)-3-(6H-imidazo[1,5-a]pyrrolo[2,3-e]pyrazin-1-yl)-4-methylpiperidin-1-yl)-4,4,4-trifluorobutan-1-one;

((3R,4R)-3-(6H-imidazo[1,5-a]pyrrolo[2,3-e]pyrazin-1-yl)-4-methylpiperidin-1-yl)(tetrahydro-2H-pyran-4-yl)methanone;

((3R,4R)-3-(6H-imidazo[1,5-a]pyrrolo[2,3-e]pyrazin-1-yl)-4-methylpiperidin-1-yl)(tetrahydro-2H-pyran-3-yl)methanone;

4-((3R,4R)-3-(6H-imidazo[1,5-a]pyrrolo[2,3-e]pyrazin-1-yl)-4-methylpiperidin-1-yl)-4-oxobutanenitrile;

((3R,4R)-3-(6H-imidazo[1,5-a]pyrrolo[2,3-e]pyrazin-1-yl)-4-methylpiperidin-1-yl)(tetrahydro-2H-pyran-2-yl)methanone;

((3R,4R)-3-(6H-imidazo[1,5-a]pyrrolo[2,3-e]pyrazin-1-yl)-4-methylpiperidin-1-yl)((R)-2-(hydroxymethyl)pyrrolidin-1-yl)methanone;

((3R,4R)-3-(6H-imidazo[1,5-a]pyrrolo[2,3-e]pyrazin-1-yl)-4-methylpiperidin-1-yl)(3-methylpyrrolidin-1-yl)methanone;

((3R,4R)-3-(6H-imidazo[1,5-a]pyrrolo[2,3-e]pyrazin-1-yl)-4-methylpiperidin-1-yl)(3-fluoroazetidin-1-yl)methanone;

((3R,4R)-3-(6H-imidazo[1,5-a]pyrrolo[2,3-e]pyrazin-1-yl)-4-methylpiperidin-1-yl)((S)-3-fluoropyrrolidin-1-yl)methanone;

((3R,4R)-3-(6H-imidazo[1,5-a]pyrrolo[2,3-e]pyrazin-1-yl)-4-methylpiperidin-1-yl)((R)-2-methylpyrrolidin-1-yl)methanone;

((3R,4R)-3-(6H-imidazo[1,5-a]pyrrolo[2,3-e]pyrazin-1-yl)-4-methylpiperidin-1-yl)((R)-morpholin-3-yl)methanone;

1-((3R,4R)-3-(6H-imidazo[1,5-a]pyrrolo[2,3-e]pyrazin-1-yl)-4-methylpiperidin-1-yl)-3-(methylsulfonyl)propan-1-one;

((3R,4R)-3-(6H-imidazo[1,5-a]pyrrolo[2,3-e]pyrazin-1-yl)-4-methylpiperidin-1-yl)(1,4-dioxan-2-yl)methanone;

((3R,4R)-3-(6H-imidazo[1,5-a]pyrrolo[2,3-e]pyrazin-1-yl)-4-methylpiperidin-1-yl)(tetrahydrothiophen-3-yl-1,1-dioxide)methanone;

((3R,4R)-3-(6H-imidazo[1,5-a]pyrrolo[2,3-e]pyrazin-1-yl)-4-methylpiperidin-1-yl)(3,3-difluorocyclobutyl)methanone;

N-((1S,3R,4S)-3-(6H-imidazo[1,5-a]pyrrolo[2,3-e]pyrazin-1-yl)-4-methylcyclopentyl)aniline;

N-((1R,3S,4R)-3-(6H-imidazo[1,5-a]pyrrolo[2,3-e]pyrazin-1-yl)-4-methylcyclopentyl)aniline;

3-bromo-1-cyclohexyl-6H-imidazo[1,5-a]pyrrolo[2,3-e]pyrazine;

(R)-(3-(6H-imidazo[1,5-a]pyrrolo[2,3-e]pyrazin-1-yl)piperidin-1-yl)(3,3-difluoroazetidin-1-yl)methanone;

(R)-(3-(6H-imidazo[1,5-a]pyrrolo[2,3-e]pyrazin-1-yl)piperidin-1-yl)(3,3-difluoropyrrolidin-1-yl)methanone;

(R)-(3-(6H-imidazo[1,5-a]pyrrolo[2,3-e]pyrazin-1-yl)piperidin-1-yl)(4,4-difluoropiperidin-1-yl)methanone;

(R)-1-(3-(6H-imidazo[1,5-a]pyrrolo[2,3-e]pyrazin-1-yl)piperidine-1-carbonyl)azetidine-3-carbonitrile;

(3R,4R)-3-(6H-imidazo[1,5-a]pyrrolo[2,3-e]pyrazin-1-yl)-4-methyl-N-(pyrimidin-2-yl)piperidine-1-carboxamide;

(3R,4R)-3-(6H-imidazo[1,5-a]pyrrolo[2,3-e]pyrazin-1-yl)-4-methyl-N-(pyridin-2-yl)piperidine-1-carboxamide;

(3R,4R)-3-(6H-imidazo[1,5-a]pyrrolo[2,3-e]pyrazin-1-yl)-4-methyl-N-(pyrimidin-4-yl)piperidine-1-carboxamide;

(3R,4R)-3-(6H-imidazo[1,5-a]pyrrolo[2,3-e]pyrazin-1-yl)-4-methyl-N-(pyrazin-2-yl)piperidine-1-carboxamide;

1-cyclohexyl-3-phenyl-6H-imidazo[1,5-a]pyrrolo[2,3-e]pyrazine;

N-((3S,5R)-1-(6H-imidazo[1,5-a]pyrrolo[2,3-e]pyrazin-1-yl)-5-methylpyrrolidin-3-yl)cyclopropanesulfonamide;

((3R,4R)-3-(6H-imidazo[1 ,5-a]pyrrolo[2,3-e]pyrazin-1-yl)-4-methylpiperidin-1-yl)(1-methylpyrrolidin-3-yl)methanone;

((3R,4R)-3-(6H-imidazo[1,5-a]pyrrolo[2,3-e]pyrazin-1-yl)-4-methylpiperidin-1-yl)(1-methylpiperidin-4-yl)methanone;

(3R,4R)-phenyl 3-(6H-imidazo[1,5-a]pyrrolo[2,3-e]pyrazin-1-yl)-4-methylpiperidine-1-carboxylate;

((R)-3-(6H-imidazo[1,5-a]pyrrolo[2,3-e]pyrazin-1-yl)piperidin-1-yl)((R)-2-(trifluoromethyl)pyrrolidin-1-yl)methanone;

(R)-1-(1-(pyrrolidin-1-ylsulfonyl)piperidin-3-yl)-6H-imidazo[1,5-a]pyrrolo[2,3-e]pyrazine;

(R)-(3-(6H-imidazo[1,5-a]pyrrolo[2,3-e]pyrazin-1-yl)piperidin-1-yl)(pyrrolidin-1-yl)methanone;

3-(1-cyclohexyl-6H-imidazo[1,5-a]pyrrolo[2,3-e]pyrazin-3-yl)propanoic acid;

(S)-1-((R)-3-(6H-imidazo[1,5-a]pyrrolo[2,3-e]pyrazin-1-yl)piperidine-1-carbonyl)pyrrolidine-3-carbonitrile;

(R)-cyclopentyl 3-(6H-imidazo[1,5-a]pyrrolo[2,3-e]pyrazin-1-yl)piperidine-1-carboxylate;

(E)-N-(((3R,4R)-3-(6H-imidazo[1,5-a]pyrrolo[2,3-e]pyrazin-1-yl)-4-methylpiperidin-1-yl)(pyrrolidin-1-yl)methylene)cyanamide;

4-((1R,3R)-3-(6H-imidazo[1,5-a]pyrrolo[2,3-e]pyrazin-1-yl)cyclopentylamino)benzonitrile;

(R)-(3-(6H-imidazo[1,5-a]pyrrolo[2,3-e]pyrazin-1-yl)piperidin-1-yl)(3,3-difluorocyclobutyl)methanone;

5-((1S,3R,4S)-3-ethyl-4-(6H-imidazo[1,5-a]pyrrolo[2,3-e]pyrazin-1-yl)cyclopentylamino)pyrazine-2-carbonitrile;

N-((1S,3S,4R)-3-(3-bromo-6H-imidazo[1,5-a]pyrrolo[2,3-e]pyrazin-1-yl)-4-ethylcyclopentyl)cyclopropanesulfonamide;

((3R,4R)-3-(6H-imidazo[1,5-a]pyrrolo[2,3-e]pyrazin-1-yl)-4-methylpiperidin-1-yl)(4,4-difluorocyclohexyl)methanone;

(R)-(3-(6H-imidazo[1,5-a]pyrrolo[2,3-e]pyrazin-1-yl)pyrrolidin-1-yl)(3,3-dimethylpyrrolidin-1-yl)methanone;

(R)-(3-(6H-imidazo[1,5-a]pyrrolo[2,3-e]pyrazin-1-yl)piperidin-1-yl)(3,3-difluoropiperidin-1-yl)methanone;

(R)-1-(3-(6H-imidazo[1,5-a]pyrrolo[2,3-e]pyrazin-1-yl)piperidine-1-carbonyl)piperidine-4-carbonitrile;

(R)-(3-(6H-imidazo[1,5-a]pyrrolo[2,3-e]pyrazin-1-yl)piperidin-1-yl)(thiomorpholino-1,1-dioxide)methanone;

((3R,4R)-3-(6H-imidazo[1,5-a]pyrrolo[2,3-e]pyrazin-1-yl)-4-methylpiperidin-1-yl)(azepan-1-yl)methanone;

(R)-(3-(6H-imidazo[1,5-a]pyrrolo[2,3-e]pyrazin-1-yl)piperidin-1-yl)(4,4-dimethylpiperidin-1-yl)methanone;

(R)-(3-(6H-imidazo[1,5-a]pyrrolo[2,3-e]pyrazin-1-yl)piperidin-1-yl)(4-chloropiperidin-1-yl)methanone;

5-(((1S,3R)-3-(6H-imidazo[1,5-a]pyrrolo[2,3-e]pyrazin-1-yl)cyclopentyl)methylamino)pyrazine-2-carbonitrile;

5-(((1S,3S)-3-(6H-imidazo[1,5-a]pyrrolo[2,3-e]pyrazin-1-yl)cyclopentyl)methylamino)pyrazine-2-carbonitrile;

1-((R)-3-(6H-imidazo[1,5-a]pyrrolo[2,3-e]pyrazin-1-yl)piperidine-1-carbonyl)piperidine-3-carbonitrile;

N-((3S,5R)-5-ethyl-1-(6H-imidazo[1,5-a]pyrrolo[2,3-e]pyrazin-1-yl)pyrrolidin-3-yl)cyclopropanesulfonamide;

1-((3,3-difluoro cyclobutyl)-6H-imidazo[1,5-a]pyrrolo[2,3-e]pyrazine;

N-(1-(6H-imidazo[1,5-a]pyrrolo[2,3-e]pyrazin-1-yl)pyrrolidin-3-yl)cyclopropanesulfonamide;

(E)-3-(1-cyclohexyl-6H-imidazo[1,5-a]pyrrolo[2,3-e]pyrazin-3-yl)acrylic acid;

N-((1S,3S,4R)-3-(3-chloro-6H-imidazo[1,5-a]pyrrolo[2,3-e]pyrazin-1-yl)-4-ethylcyclopentyl)cyclopropanesulfonamide;

4-(((cis)-3-(6H-imidazo[1,5-a]pyrrolo[2,3-e]pyrazin-1-yl)cyclobutoxy)methyl)benzonitrile;

5-((3S,5R)-5-ethyl-1-(6H-imidazo[1,5-a]pyrrolo[2,3-e]pyrazin-1-yl)pyrrolidin-3-ylamino)pyrazine-2-carbonitrile;

N-((3S,5R)-5-ethyl-1-(6H-imidazo[1,5-a]pyrrolo[2,3-e]pyrazin-1-yl)pyrrolidin-3-yl)-3,3,3-trifluoropropane-1-sulfonamide;

4-((1R,3R,4S)-3-ethyl-4-(6H-imidazo[1,5-a]pyrrolo[2,3-e]pyrazin-1-yl)cyclopentyloxy)benzonitrile;

N-((1S,3S,4R)-3-(6H-imidazo[1,5-a]pyrrolo[2,3-e]pyrazin-1-yl)-4-methylcyclopentyl)-1-methylcyclopropane-1-sulfonamide;

1-((1S,4S)-5-(3,3,3-trifluoropropylsulfonyl)-2,5-diazabicyclo[2.2.1]heptan-2-yl)-6H-imidazo[1,5-a]pyrrolo[2,3-e]pyrazine;

N-((1S,3S,4R)-3-(6H-imidazo[1,5-a]pyrrolo[2,3-e]pyrazin-1-yl)-4-methylcyclopentyl)-3,3-difluoroazetidine-1-sulfonamide;

N-((1S,3S,4R)-3-(6H-imidazo[1,5-a]pyrrolo[2,3-e]pyrazin-1-yl)-4-methylcyclopentyl)-3,3,3-trifluoropropane-1-sulfonamide;

N-((1S,3S,4R)-3-(6H-imidazo[1,5-a]pyrrolo[2,3-e]pyrazin-1-yl)-4-methylcyclopentyl)-3,3-difluoropyrrolidine-1-sulfonamide;

(S)-N-((1S,3S,4R)-3-(6H-imidazo[1,5-a]pyrrolo[2,3-e]pyrazin-1-yl)-4-methylcyclopentyl)-2-(trifluoromethyl)pyrrolidine-1-sulfonamide;

N-(((1S,3S)-3-(6H-imidazo[1,5-a]pyrrolo[2,3-e]pyrazin-1-yl)cyclopentyl)methyl)cyclopropanesulfonamide;

N-(((1S,3R)-3-(6H-imidazo[1,5-a]pyrrolo[2,3-e]pyrazin-1-yl)cyclopentyl)methyl)-3,3,3-trifluoropropane-1-sulfonamide;

N-(((1S,3S)-3-(6H-imidazo[1,5-a]pyrrolo[2,3-e]pyrazin-1-yl)cyclopentyl)methyl)-3,3,3-trifluoropropane-1-sulfonamide;

N-((1S,3S,4R)-3-(6H-imidazo[1,5-a]pyrrolo[2,3-e]pyrazin-1-yl)-4-methylcyclopentyl)-1-ethylcyclopropane-1-sulfonamide;

1-((3aR,6aS)-5-(3,3,3-trifluoropropylsulfonyl)hexahydropyrrolo[3,4-c]pyrrol-2(1H)-yl)-6H-imidazo[1,5-a]pyrrolo[2,3-e]pyrazine;

1-(6-fluoro-4-(3,3,3-trifluoropropylsulfonyl)-1,4-diazepan-1-yl)-6H-imidazo[1,5-a]pyrrolo[2,3-e]pyrazine;

4-([4-(6H-imidazo[1,5-a]ppyrrolo[2,3-e]pyrazin-1-yl)cubanyl]methoxy)benzonitrile;

N-((3R,4S)-4-methyl-1-(3,3,3-trifluoropropylsulfonyl)piperidin-3-yl)-6H-imidazo[1,5-a]pyrrolo[2,3-e]pyrazin-1-amine;

1-(2-(3,3,3-trifluoropropylsulfonyl)-2,5-diazaspiro[3.5]nonan-5-yl)-6H-imidazo[1,5-a]pyrrolo[2,3-e]pyrazine;

1-((3aS,7aR)-4-(3,3,3-trifluoropropylsulfonyl)octahydro-1H-pyrrolo[3,2-b]pyridin-1-yl)-6H-imidazo[1,5-a]pyrrolo[2,3-e]pyrazine;

1-(7-methyl-4-(3,3,3-trifluoropropylsulfonyl)-1,4-diazepan-1-yl)-6H-imidazo[1,5-a]pyrrolo[2,3-e]pyrazine;

1-(5-(3,3,3-trifluoropropylsulfonyl)-2,5-diazaspiro[3.5]nonan-2-yl)-6H-imidazo[1,5-a]pyrrolo[2,3-e]pyrazine;

N-(1-(6H-imidazo[1,5-a]pyrrolo[2,3-e]pyrazin-1-yl)piperidin-3-yl)-3,3,3-trifluoropropane-1-sulfonamide;

1-((1R,5S)-2-(3,3,3-trifluoropropylsulfonyl)-2,6-diazabicyclo[3.2.1]octan-6-yl)-6H-imidazo[1,5-a]pyrrolo[2,3-e]pyrazine;

1-cyclohexyl-3-(4-(methylsulfonyl)phenyl)-6H-imidazo[1,5-a]pyrrolo[2,3-e]pyrazine;

N-(4-(1-cyclohexyl-6H-imidazo[1,5-a]pyrrolo[2,3-e]pyrazin-3-yl)phenyl)methanesulfonamide;

N-((1S,3S,4R)-3-(6H-imidazo[1,5-a]pyrrolo[2,3-e]pyrazin-1-yl)-4-methylcyclopentyl)-3-chlorobenzenesulfonamide;

Cyclopropanesulfonic acid [(1S,3R,4R)-3-ethyl-4-(3-trifluoromethyl-6H-2,5,6,8b-tetraaza-as-indacen-1-yl)-cyclopentyl]-amide;

Cyclopropanesulfonic acid [(1S,3R,4S)-3-ethyl-4-(3-trifluoromethyl-6H-2,5,6,8b-tetraaza-as-indacen-1-yl)-cyclopentyl]-amide;

1-((1S,2R,4S)-4-Cyclopropanesulfonylamino-2-ethyl-cyclopentyl)-6H-2,5,6,8b-tetraaza-as-indacene-3-carboxylic acid;

1-((1 R,2R,4S)-4-Cyclopropanesulfonylamino-2-ethyl-cyclopentyl)-6H-2,5,6,8b-tetraaza-as-indacene-3-carboxylic acid;

Cyclopropanesulfonic acid [(1S,3R,4S)-3-methyl-4-(3-trifluoromethyl-6H-2,5,6,8b-tetraaza-as-indacen-1-yl)-cyclopentyl]-amide;

1-[(1R,3R,4S)-3-Ethyl-4-(3-trifluoromethyl-6H-2,5,6,8b-tetraaza-as-indacen-1-yl)-cyclopentyl]-2-methyl-propan-2-ol;

Cyclopropanesulfonic acid {(1S,3R,4S)-3-ethyl-4-[3-(2,2,2-trifluoro-ethyl)-6H-2,5,6,8b-tetraaza-as-indacen-1-yl]-cyclopentyl}-amide;

[(1R,3R,4S)-3-Ethyl-4-(3-trifluoromethyl-6H-2,5,6,8b-tetraaza-as-indacen-1-yl)-cyclopentyl]-acetic acid ethyl ester or 1-[(1S,2R,4R)-2-Ethyl-4-(3-methoxymethyl-[1,2,4]oxadiazol-5-ylmethyl)-cyclopentyl]-3-trifluoromethyl-6H-2,5,6,8b-tetraaza-as-indacene.

In a seventeenth embodiment the invention provides a compound according to the first through twelfth embodiments wherein T is N, U is $CR^4$, X is $CR^3$and Y is N and forms a compound of Formula (Ic)

Formula (Ic)

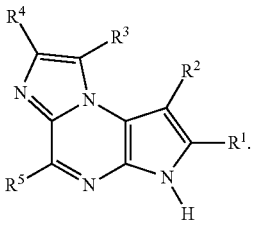

In an eighteenth embodiment the invention provides a compound according to the seventeenth embodiment wherein the compound is 3-((3S,4S)-3-(3H-imidazo[1,2-a]pyrrolo[2,3-e]pyrazin-8-yl)-4-methylpiperidin-1-yl)-3-oxopropanenitrile;

5-(3-(3H-imidazo[1,2-a]pyrrolo[2,3-e]pyrazin-8-yl)piperidin-1-yl)pyrazine-2-carbonitrile;

(S)-1-(3-(3H-imidazo[1,2-a]pyrrolo[2,3-e]pyrazin-8-yl)piperidine-1-carbonyl)cyclopropanecarbonitrile;

N-((1S,3R,4R)-3-ethyl-4-(3H-imidazo[1,2-a]pyrrolo[2,3-e]pyrazin-8-yl)cyclopentyl)cyclopropanesulfonamide;

N-((1R,3S,4S)-3-ethyl-4-(3H-imidazo[1,2-a]pyrrolo[2,3-e]pyrazin-8-yl)cyclopentyl)cyclopropanesulfonamide;

(S)-6-(3-(3H-imidazo[1,2-a]pyrrolo[2,3-e]pyrazin-8-yl)piperidin-1-yl)nicotinonitrile;

(R)-6-(3-(3H-imidazo[1,2-a]pyrrolo[2,3-e]pyrazin-8-yl)piperidin-1-yl)nicotinonitrile;

(S)-2-(3-(3H-imidazo[1,2-a]pyrrolo[2,3-e]pyrazin-8-yl)piperidin-1-yl)thiazole-5-carbonitrile;

(R)-2-(3-(3H-imidazo[1,2-a]pyrrolo[2,3-e]pyrazin-8-yl)piperidin-1-yl)thiazole-5-carbonitrile;

(R)-(3-(3H-imidazo[1,2-a]pyrrolo[2,3-e]pyrazin-8-yl)piperidin-1-yl)(3,3-difluoroazetidin-1-yl)methanone;

(S)-(3-(3H-imidazo[1,2-a]pyrrolo[2,3-e]pyrazin-8-yl)piperidin-1-yl)(3,3-difluoroazetidin-1-yl)methanone;

5-((1R,3S,4S)-3-(3H-imidazo[1,2-a]pyrrolo[2,3-e]pyrazin-8-yl)-4-methylcyclopentylamino)pyrazine-2-carbonitrile;

5-((1S,3R,4R)-3-(3H-imidazo[1,2-a]pyrrolo[2,3-e]pyrazin-8-yl)-4-methylcyclopentylamino)pyrazine-2-carbonitrile;

5-((1R,3R,4S)-3-(3H-imidazo[1,2-a]pyrrolo[2,3-e]pyrazin-8-yl)-4-methylcyclopentylamino)pyrazine-2-carbonitrile;

5-((1S,3S,4R)-3-(3H-imidazo[1,2-a]pyrrolo[2,3-e]pyrazin-8-yl)-4-methylcyclopentylamino)pyrazine-2-carbonitrile;

N-(4-(3H-imidazo[1,2-a]pyrrolo[2,3-e]pyrazin-8-yl)bicyclo[2.2.2]octan-1-yl)cyclopropanesulfonamide;

(R)-(3-(3H-imidazo[1,2-a]pyrrolo[2,3-e]pyrazin-8-yl)piperidin-1-yl)(3,3-difluorocyclobutyl)methanone;

(R)-(3-(3H-imidazo[1,2-a]pyrrolo[2,3-e]pyrazin-8-yl)piperidin-1-yl)(3,3-difluoropyrrolidin-1-yl)methanone;

(R)-(3-(3H-imidazo[1,2-a]pyrrolo[2,3-e]pyrazin-8-yl)piperidin-1-yl)(4,4-difluoropiperidin-1-yl)methanone;

N-((1S,3S,4R)-3-(3H-imidazo[1,2-a]pyrrolo[2,3-e]pyrazin-8-yl)-4-methylcyclopentyl)-3,3,3-trifluoropropane-1-sulfonamide;

N-((1R,3R,4S)-3-(3H-imidazo[1,2-a]pyrrolo[2,3-e]pyrazin-8-yl)-4-methylcyclopentyl)-3,3,3-trifluoropropane-1-sulfonamide;

N-((1R,3S,4S)-3-(3H-imidazo[1,2-a]pyrrolo[2,3-e]pyrazin-8-yl)-4-methylcyclopentyl)-3,3,3-trifluoropropane-1-sulfonamide;

N-((1S,3R,4R)-3-(3H-imidazo[1,2-a]pyrrolo[2,3-e]pyrazin-8-yl)-4-methylcyclopentyl)-3,3,3-trifluoropropane-1-sulfonamide;

((R)-3-(3H-imidazo[1,2-a]pyrrolo[2,3-e]pyrazin-8-yl)piperidin-1-yl)((R)-2-(trifluoromethyl)pyrrolidin-1-yl)methanone;

N-((3S,5R)-5-ethyl-1-(3H-imidazo[1,2-a]pyrrolo[2,3-e]pyrazin-8-yl)pyrrolidin-3-yl)cyclopropanesulfonamide;

1-cyclohexyl-1,6-dihydroimidazo[4,5-d]pyrrolo[2,3-b]pyridine;

N-((3S,5R)-5-ethyl-1-(3H-imidazo[1,2-a]pyrrolo[2,3-e]pyrazin-8-yl)pyrrolidin-3-yl)-3,3,3-trifluoropropane-1-sulfonamide;

3-(3H-imidazo[1,2-a]pyrrolo[2,3-e]pyrazin-8-yl)-4-methylcyclopentanamine;

N-((1R,3S,4R)-3-ethyl-4-(3H-imidazo[1,2-a]pyrrolo[2,3-e]pyrazin-8-yl)cyclopentyl)-3,3,3-trifluoropropane-1-sulfonamide;

N-((1S,3R,4S)-3-ethyl-4-(3H-imidazo[1,2-a]pyrrolo[2,3-e]pyrazin-8-yl)cyclopentyl)-3,3,3-trifluoropropane-1-sulfonamide;

N-((1S,3S,4R)-3-(3H-imidazo[1,2-a]pyrrolo[2,3-e]pyrazin-8-yl)-4-methylcyclopentyl)cyclopropanesulfonamide;

N-((1S,3R,4S)-3-ethyl-4-(3H-imidazo[1,2-a]pyrrolo[2,3-e]pyrazin-8-yl)cyclopentyl)cyclopropanesulfonamide;

N-((1S,3R,4S)-3-ethyl-4-(3H-imidazo[1,2-a]pyrrolo[2,3-e]pyrazin-8-yl)cyclopentyl)-3,3-difluoroazetidine-1-sulfonamide;

3-chloro-N-((1S,3R,4S)-3-ethyl-4-(3H-imidazo[1,2-a]pyrrolo[2,3-e]pyrazin-8-yl)cyclopentyl)-4-fluorobenzenesulfonamide;

N-((1S,3S,4R)-3-(3H-imidazo[1,2-a]pyrrolo[2,3-e]pyrazin-8-yl)-4-methylcyclopentyl)-3,3-difluoroazetidine-1-sulfonamide;

N-(((1S,3R,4S)-3-ethyl-4-(3H-imidazo[1,2-a]pyrrolo[2,3-e]pyrazin-8-yl)cyclopentyl)methyl)-3,3,3-trifluoropropane-1-sulfonamide;

N-((1R,3S,4R)-3-ethyl-4-(3H-imidazo[1,2-a]pyrrolo[2,3-e]pyrazin-8-yl)cyclopentyl)methyl)-3,3,3-trifluoropropane-1-sulfonamide;

N-(((1S,3S,4R)-3-ethyl-4-(3H-imidazo[1,2-a]pyrrolo[2,3-e]pyrazin-8-yl)cyclopentyl)methyl)-3,3,3-trifluoropropane-1-sulfonamide;

N-(((1R,3R,4S)-3-ethyl-4-(3H-imidazo[1,2-a]pyrrolo[2,3-e]pyrazin-8-yl)cyclopentyl)methyl)-3,3,3-trifluoropropane-1-sulfonamide;

N-((1S,3S,4R)-3-(3H-imidazo[1,2-a]pyrrolo[2,3-e]pyrazin-8-yl)-4-methylcyclopentyl)morpholine-4-sulfonamide;

3,3,3-Trifluoro-propane-1-sulfonic acid [(2S,4S,5R)-4-methyl-5-(3H-imidazo[1,2-a]pyrrolo[2,3-e]pyrazin-8-yl)-tetrahydro-furan-2-ylmethyl]-amide;

3,3,3-Trifluoro-propane-1-sulfonic acid [(2R,4R,5S)-4-methyl-5-(3H-imidazo[1,2-a]pyrrolo[2,3-e]pyrazin-8-yl)-tetrahydro-furan-2-ylmethyl]-amide;

3,3,3-Trifluoro-propane-1-sulfonic acid methyl-[(1S,3R,4S)-3-methyl-4-(3H-imidazo[1,2-a]pyrrolo[2,3-e]pyrazin-8-yl)-cyclopentyl]-amide;

Azetidine-1-sulfonic acid [(1S,3R,4S)-3-methyl-4-(3H-imidazo[1,2-a]pyrrolo[2,3-e]pyrazin-8-yl)-cyclopentyl]-amide;

{3-[(1S,3R,4S)-3-Methyl-4-(3H-imidazo[1,2-a]pyrrolo[2,3-e]pyrazin-8-yl)-cyclopentylamino]-oxetan-3-yl}-acetonitrile;

3,3-Difluoro-cyclobutanesulfonic acid [(1S,3R,4S)-3-methyl-4-(3H-imidazo[1,2-a]pyrrolo[2,3-e]pyrazin-8-yl)-cyclopentyl]-amide;

8-[(1S,2R,4S)-2-Methyl-4-(tetrahydro-pyran-4-yloxy)-cyclopentyl]-3H-3,4,6,8a-tetraaza-as-indacene;

8-[(1R,2R)-2-Methyl-4-(tetrahydro-pyran-4-yloxy)-cyclopentyl]-3H-3,4,6,8a-tetraaza-as-indacene;

3-Fluoro-azetidine-1-sulfonic acid [(1S,3R,4S)-3-methyl-4-(3H-imidazo[1,2-a]pyrrolo[2,3-e]pyrazin-8-yl)-cyclopentyl]-amide;

3-Fluoro-propane-1-sulfonic acid [(1S,3R,4S)-3-methyl-4-(3H-imidazo[1,2-a]pyrrolo[2,3-e]pyrazin-8-yl)-cyclopentyl]-amide;

Cyclopropanesulfonic acid [(1S,3R,4S)-3-methyl-4-(7-methyl-3H-imidazo[1,2-a]pyrrolo[2,3-e]pyrazin-8-yl)-cyclopentyl]-amide;

Cyclopropanesulfonic acid [(1R,3S,4R)-3-methyl-4-(7-methyl-3H-imidazo[1,2-a]pyrrolo[2,3-e]pyrazin-8-yl)-cyclopentyl]-amide;

2-Cyano-N-[(1S,3R,4S)-3-methyl-4-(3H-imidazo[1,2-a]pyrrolo[2,3-e]pyrazin-8-yl)-cyclopentyl]-acetamide;

8-[(1S,2R,4R)-2-Methyl-4-(tetrahydro-pyran-4-yloxy)-cyclopentyl]-3H-3,4,6,8a-tetraaza-as-indacene;

(2-Cyclopropyl-ethyl)-[(1S,3R,4S)-3-methyl-4-(3H-imidazo[1,2-a]pyrrolo[2,3-e]pyrazin-8-yl)-cyclopentyl]-oxetan-3-yl-amine;

Cyclopropylmethyl-[(1S,3R,4S)-3-methyl-4-(3H-imidazo[1,2-a]pyrrolo[2,3-e]pyrazin-8-yl)-cyclopentyl]-oxetan-3-yl-amine;

(3R,4S)-3-Ethyl-4-(3H-imidazo[1,2-a]pyrrolo[2,3-e]pyrazin-8-yl)-pyrrolidine-1-carboxylic acid (2,2,2-trifluoro-ethyl)-amide; or (3S,4R)-3-Ethyl-4-(3H-imidazo[1,2-a]pyrrolo[2,3-e]pyrazin-8-yl)-pyrrolidine-1-carboxylic acid (2,2,2-trifluoro-ethyl)-amide.

In a nineteenth embodiment the invention provides a compound according to the first through twelfth embodiments wherein T is $CR^6$, U is $CR^4$, X is $CR^3$ and Y is N and forms a compound of Formula (Id)

Formula (Id)

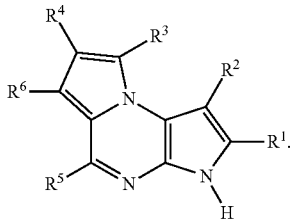

In a twentieth embodiment the invention provides a compound according to the nineteenth embodiment wherein the compound is N-(4-(3H-dipyrrolo[1,2-a:2',3'-e]pyrazin-8-yl)bicyclo[2.2.2]octan-1-yl)cyclopropanesulfonamide.

In a twenty-first embodiment the invention provides a compound according to the first through twelfth embodiments wherein T is $CR^6$, U is N, X is $NR^3$ and Y is C and forms a compound of Formula (Ie)

Formula (Ie)

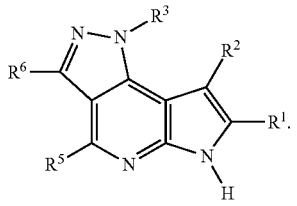

In a twenty-second embodiment the invention provides a compound according to the twenty-first embodiment wherein the compound is (R)-1-(3-(pyrazolo[3,4-d]pyrrolo[2,3-b]pyridin-[(61])-yl)piperidine-1-carbonyl)cyclopropanecarbonitrile; or (S)-1-(3-(pyrazolo[3,4-d]pyrrolo[2,3-b]pyridin-[(61])-yl)piperidine-1-carbonyl)cyclopropanecarbonitrile.

In a twenty-third embodiment the invention provides a compound according to the first through twelfth embodiments wherein T is O, U is N, X is $CR^3$ and Y is C and forms a compound of Formula (If)

Formula (If)

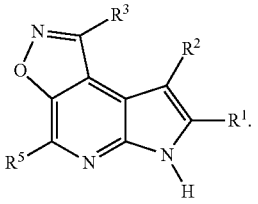

In a twenty-fourth embodiment the invention provides a compound according to the first through twelfth embodiments wherein T is $NR^6$, U is N, X is $CR^3$ and Y is C and forms a compound of Formula (Ig)

Formula (Ig)

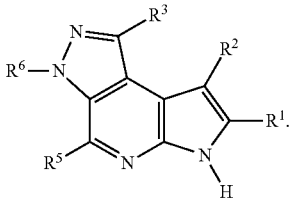

In a twenty-fifth embodiment the invention provides a compound according to the twenty-fourth embodiment wherein the compound is 1-((1R,2R,4S)-2-ethyl-4-(4-methoxybenzyloxy)cyclopentyl)-3,6-dihydropyrazolo[4,3-d]pyrrolo[2,3-b]pyridine;

1-((1S,2S,4R)-2-ethyl-4-(4-methoxybenzyloxy)cyclopentyl)-3,6-dihydropyrazolo[4,3-d]pyrrolo[2,3-b]pyridine; or N-(4-(3,6-dihydropyrazolo[4,3-d]pyrrolo[2,3-b]pyridin-1-yl)bicyclo[2.2.2]octan-1-yl)cyclopropanesulfonamide.

In a twenty-sixth embodiment the invention provides a compound according to the first through twelfth embodiments wherein T is $CR^6$, U is $CR^4$, X is $NR^3$ and Y is C and forms a compound of Formula (Ih)

Formula (Ih)

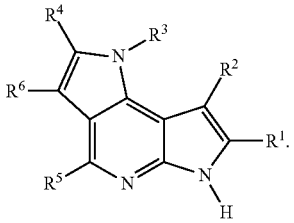

In a twenty-seventh embodiment the invention provides a compound according to the twenty-sixth embodiment wherein the compound is 1-cyclohexyl-1,6-dihydroimidazo[4,5-d]pyrrolo[2,3-b]pyridine;

1-cyclohexyl-2-methyl-1,6-dihydroimidazo[4,5-d]pyrrolo[2,3-b]pyridine; or 1-cyclohexyl-2-(trifluoromethyl)-1,6-dihydroimidazo[4,5-d]pyrrolo[2,3-b]pyridine.

In a twenty-eighth embodiment the invention provides a compound according to the first through twelfth embodiments wherein T is S, U is N, X is $CR^3$ and Y is C and forms a compound of Formula (Ii)

Formula (Ii)

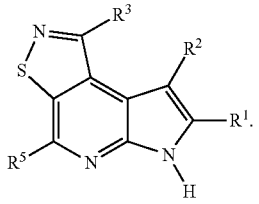

In a twenty-ninth embodiment the invention provides a compound according to the first through twelfth embodiments wherein T is N, U is $CR^4$, X is $NR^3$ and Y is C and forms a compound of formula (Ij)

Formula (Ij)

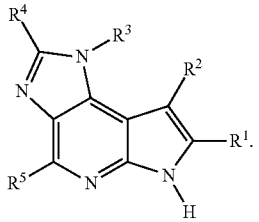

In a thirtieth embodiment the invention provides a compound according to the twenty-ninth embodiment wherein the compound is N-((1S,3R,4S)-3-ethyl-4-(imidazo[4,5-d]pyrrolo[2,3-b]pyridin-1(6H)-yl)cyclopentyl)cyclopropanesulfonamide;

N-((1S,3S,4R)-3-(imidazo[4,5-d]pyrrolo[2,3-b]pyridin-1(6H)-yl)-4-methylcyclopentyl)cyclopropanesulfonamide;

N-((1S,3S,4R)-3-(2-cyclopropylimidazo[4,5-d]pyrrolo[2,3-b]pyridin-1(6H)-yl)-4-methylcyclopentyl)cyclopropanesulfonamide;

N-((1S,3R,4S)-3-methyl-4-(2-methylimidazo[4,5-d]pyrrolo[2,3-b]pyridin-1(6H)-yl)cyclopentyl)cyclopropanesulfonamide;

Cyclopropanesulfonic acid [(1S,3R,4S)-3-methyl-4-(2-trifluoromethyl-imidazo[4,5-d]pyrrolo[2,3-b]pyridin-1(6H)-yl)-cyclopentyl]-amide;

Cyclopropanesulfonic acid [(1S,3R,4S)-3-ethyl-4-(2-trifluoromethyl-imidazo[4,5-d]pyrrolo[2,3-b]pyridin-1(6H)-yl)-cyclopentyl]-amide;

Cyclopropanesulfonic acid [(1S,3S,4R)-3-(2-difluoromethyl-imidazo[4,5-d]pyrrolo[2,3-b]pyridin-1(6H)-yl)-4-ethyl-cyclopentyl]-amide;

Cyclopropanesulfonic acid [(1S,3R,4S)-3-ethyl-4-(2-methyl-imidazo[4,5-d]pyrrolo[2,3-b]pyridin-1(6H)-yl)-cyclopentyl]-amide;

Cyclopropanesulfonic acid [(1S,3S,4R)-3-(2-amino-imidazo[4,5-d]pyrrolo[2,3-b]pyridin-1(6H)-yl)-4-ethyl-cyclopentyl]-amide.

according to the first through twelfth embodiments wherein is N, U is N, X is $NR^3$ and Y is C and forms a compound of Formula (Ik)

Formula (Ik)

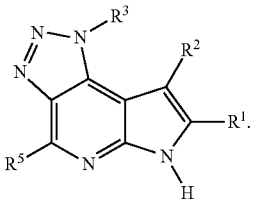

In a thirty-second embodiment the invention provides a compound according to the thirty-first embodiment wherein the compound is Cyclopropanesulfonic acid [(1S,3R,4S)-3-ethyl-4-(6H)-[1,2,3]triazolo[4,5-d]pyrrolo[2,3-b]pyridin-1-yl)-cyclopentyl]-amide.

In a thirty-third embodiment the invention provides a compound of Formula (II) wherein the compound is Formula (II)

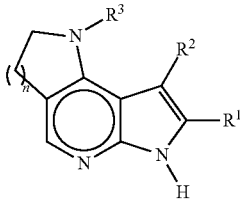

pharmaceutically acceptable salts, pro-drugs, biologically active metabolites, stereoisomers and isomers thereof wherein $R^1$, and $R^2$ are independently hydrogen, deuterium, —N($R^a$)($R^b$), halogen, —O$R^a$, —S$R^a$, —S(O)$R^a$, —S(O)$_2$$R^a$, —NO$_2$, —C(O)O$R^a$, —CN, —C(O)N($R^a$)($R^b$), —N($R^a$)C(O)($R^b$), —C(O)$R^a$, —C(OH)$R^a$$R^b$, —N($R^a$)S(O)$_2$—$R^b$, —S(O)$_2$N($R^a$)($R^b$), —CF$_3$, —OCF$_3$, optionally substituted ($C_1$-$C_6$)alkyl, optionally substituted ($C_2$-$C_6$)alkenyl, optionally substituted ($C_2$-$C_6$)alkynyl, optionally substituted ($C_3$-$C_{10}$)cycloalkyl, optionally substituted ($C_1$-$C_{10}$) heteroaryl, optionally substituted ($C_1$-$C_{10}$) heterocyclyl, or optionally substituted ($C_6$-$C_{10}$)aryl;

wherein in a moiety containing —N($R^a$)($R^b$), the nitrogen, $R^a$ and $R^b$ may form a ring such that —N($R^a$)($R^b$) represents an optionally substituted ($C_2$-$C_{10}$)heterocyclyl or optionally substituted ($C_1$-$C_{10}$)heteroaryl linked through a nitrogen;

$R^3$ is hydrogen, an optionally substituted bridged ($C_5$-$C_{12}$) cycloalkyl, optionally substituted bridged ($C_2$-$C_{10}$)heterocyclyl, optionally substituted ($C_1$-$C_8$)alkyl, optionally substituted ($C_3$-$C_{10}$)cycloalkyl, optionally substituted ($C_3$-$C_8$) cycloalkenyl, optionally substituted ($C_6$-$C_{10}$)aryl, optionally substituted ($C_1$-$C_{10}$)heteroaryl, optionally substituted ($C_2$-$C_{10}$)heterocyclyl; or $R^3$is -A-D-E-G, wherein:

A is a bond, —C(O)—, optionally substituted ($C_1$-$C_6$) alkylene, optionally substituted ($C_2$-$C_6$)alkenylene, optionally substituted ($C_2$-$C_6$)alkynylene, optionally substituted ($C_3$-$C_{12}$)cycloalkylene, optionally substituted ($C_2$-$C_6$)heterocyclylene, —C(O)N($R^a$)—$R^e$—, —N($R^a$)C(O)—$R^e$—, —O—$R^e$—, —N($R^a$)—$R^e$—, —S—$R^e$—, —S(O)$_2$—$R^e$—, —S(O)$R^e$—, —C(O—$R^a$)($R^b$)—$R^e$—, —S(O)$_2$N($R^a$)—$R^e$—, —N($R^a$)S(O)$_2$—$R^e$— or —N($R^a$)C(O)N($R^b$)—$R^e$—;

D is an optionally substituted ($C_1$-$C_8$)alkylene, optionally substituted bridged ($C_5$-$C_{12}$)cycloalkylene, optionally substituted ($C_3$-$C_{10}$)cycloalkylene, optionally substituted bridged ($C_5$-$C_{10}$)cycloalkenylene, optionally substituted ($C_3$-$C_{10}$)cycloalkenylene, optionally substituted ($C_6$-$C_{10}$) arylene, optionally substituted ($C_1$-$C_{10}$)heteroarylene, optionally substituted bridged ($C_2$-$C_{10}$)heterocyclylene or an optionally substituted ($C_2$-$C_{10}$)heterocyclylene;

E is a bond, —$R^e$—, —$R^e$—C(=NCN)—$R^e$—, —$R^e$—C(O)—$R^e$—, —$R^e$—C(O)C(O)—$R^e$—, —$R^e$—C(O)O—$R^e$—, —$R^e$—C(O)C(O)N($R^a$)—$R^e$—, —$R^e$—N($R^a$)—C(O)C(O)—$R^e$—, —$R^e$—O—$R^e$—, —$R^e$—S(O)$_2$—$R^e$—, —$R^e$—S(O)—$R^e$—, —$R^e$—S—$R^e$—, —$R^e$—N($R^a$)—$R^e$—, =N—$R^e$—, —$R^e$—N($R^a$)C(O)—$R^e$—, —$R^e$C(O)N($R^a$)$R^e$—, —$R^e$—OC(O)N($R^a$)—$R^e$—, —$R^e$—N($R^a$)C(O)O$R^e$—, —$R^e$—OC(O)—$R^e$, —$R^e$—OC(O)—O—$R^e$, —$R^e$—N($R^a$)C(O)N($R^b$)—$R^e$—, —$R^e$—N($R^a$)S(O)$_2$—$R^e$—, —$R^e$—S(O)$_2$N($R^a$)—$R^e$—, or —$R^e$—N($R^a$)S(O)$_2$N($R^a$)—$R^e$—; or E is

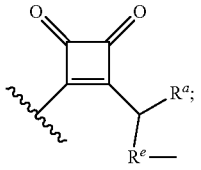

where in all cases, E is linked to either a carbon or a nitrogen atom in D;

G is hydrogen, deuterium, —N($R^a$)($R^b$), halogen, —O$R^a$, —S$R^a$, —S(O)$R^a$, —S(O)$_2$$R^a$, —NO$_2$, —C(O)O$R^a$, —CN, —C(O)N($R^a$)($R^b$), —N($R^a$)C(O)$R^b$, —N($R^a$)C(O)O$R^b$, —OC(O)N($R^a$), —N($R^a$)C(O)N($R^b$)$_2$, —C(O—$R^a$)($R^b$)$_2$, —C(O)$R^a$, —CF$_3$, —OCF$_3$, —N($R^a$)S(O)$_2$$R^b$, —S(O)$_2$N($R^a$)($R^b$), —S(O)$_2$N($R^a$)C(O)$R^b$, an optionally substituted —($C_1$-$C_6$)alkyl, an optionally substituted —($C_2$-$C_6$)alkenyl, an optionally substituted —($C_2$-$C_6$)alkynyl, an optionally substituted —($C_3$-$C_{10}$)cycloalkyl, an optionally substituted —($C_1$-$C_{10}$)heteroaryl, an optionally substituted —($C_1$-$C_{10}$) heterocyclyl, an optionally substituted —($C_6$-$C_{10}$)aryl;

wherein in a moiety containing —N($R^a$)($R^b$), the nitrogen, $R^a$ and $R^b$ may form a ring such that —N($R^a$)($R^b$) represents an optionally substituted ($C_2$-$C_{10}$)heterocyclyl or an optionally substituted ($C_1$-$C_{10}$) heteroaryl linked through a nitrogen;

$R^a$ and $R^b$ are each independently hydrogen, deuterium, CN, an optionally substituted ($C_1$-$C_{10}$)alkyl, an optionally substituted ($C_2$-$C_{10}$)alkenyl, an optionally substituted ($C_2$-$C_{10}$)alkynyl, an optionally substituted ($C_1$-$C_{10}$)alkyl-O—($C_1$-$C_{10}$)alkyl, an optionally substituted ($C_3$-$C_{10}$)cycloalkyl, an optionally substituted ($C_6$-$C_{10}$)aryl, an optionally substituted ($C_1$-$C_{10}$)heteroaryl, an optionally substituted ($C_1$-$C_{10}$) heterocyclyl, an optionally substituted —($C_1$-$C_6$)alkylene-($C_3$-$C_{10}$)cycloalkyl, an optionally substituted —($C_1$-$C_6$) alkylene-($C_6$-$C_{10}$)aryl, an optionally substituted —($C_1$-$C_6$) alkylene-($C_1$-$C_{10}$)heteroaryl, or an optionally substituted —($C_1$-$C_6$)alkylene-($C_1$-$C_{10}$)heterocyclyl; and $R^e$ for each occurrence is independently a bond, an optionally substituted ($C_1$-$C_{10}$)alkylene, an optionally substituted ($C_2$-$C_{10}$)alkenylene, an optionally substituted ($C_2$-$C_{10}$)alkynylene, an optionally substituted —($C_1$-$C_{10}$)alkylene-O—($C_1$-$C_{10}$)alkylene group, an optionally substituted ($C_3$-$C_{10}$)cycloalkylene, an optionally substituted ($C_6$-$C_{10}$) arylene, an optionally substituted ($C_1$-$C_{10}$)heteroarylene, or an optionally substituted ($C_1$-$C_{10}$)heterocyclylene.

In a thirty-fourth embodiment the invention provides a compound according to the thirty-third embodiment wherein the compound is 1-Cyclohexyl-2,3,4,7-tetrahydro-1H-pyrrolo[2,3-h][1,6]naphthyridine;

Cyclopropanesulfonic acid [(1S,3R,4S)-3-ethyl-4-(3,6,7,8-tetrahydro-3,4,9-triaza-cyclopenta[a]naphthalen-9-yl)-cyclopentyl]-amide; or Cyclopropanesulfonic acid [(1S,3S,4R)-3-(3,6-dihydro-2H-dipyrrolo[2,3-b;2',3'-d]pyridin-1-yl)-4-ethyl-cyclopentyl]-amide.

In a thirty-fifth embodiment the invention provides a pharmaceutical composition comprising a compound of Formula (I) or Formula (II) as defined in any of the foregoing embodiments Formula (I)

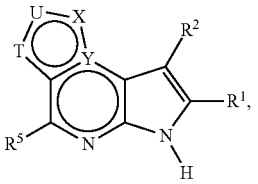

Formula (II)

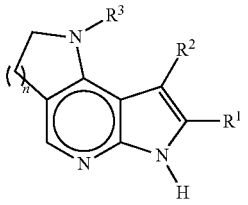

a pharmaceutically acceptable carrier and excipient and a second therapeutic agent selected from the group consisting of cytokine suppressive anti-inflammatory drugs, antibodies to or antagonists of other human cytokines or growth factors, IL-1, IL-2, IL-3, IL-4, IL-5, IL-6, IL-7, IL-8, IL-12, IL-15, IL-16, IL-21, IL-23, interferons, EMAP-II, GM-CSF, FGF, PDGF, CTLA or their ligands including CD154, HUMIRA™, REMICADE™, SIMPONI™(golimumab), CIMZIA™, ACTEMRA™, CDP 571, soluble p55 or p75 TNF receptors, ENBREL™, Lenercept, TNFα converting enzyme inhibitors, IL-1 inhibitors, Interleukin 11, IL-18 antagonists, IL-12 antagonists, IL-12 antibodies, soluble IL-12 receptors, IL-12 binding proteins, non-depleting anti-CD4 inhibitors FK506, rapamycin, mycophenolate mofetil, leflunomide, NSAIDs, ibuprofen, corticosteroids, phosphodiesterase inhibitors, adensosine agonists, antithrombotic agents, complement inhibitors, adrenergic agents, IL-1β converting enzyme inhibitors, T-cell signalling kinase inhibitors, metalloproteinase inhibitors, sulfasalazine, 6-mercaptopurines, derivatives p75TNFRIgG, sIL-1RI, sIL-1RII, sIL-6R, celecoxib, hydroxychloroquine sulfate, rofecoxib, influximab, naproxen, valdecoxib, sulfasalazine, meloxicam, acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, anti-IL15, VX-740, Roflumilast, IC-485, CDC-801, S1P1 agonists, FTY720, PKC family inhibitors, Ruboxistaurin, AEB-071, Mesopram, methotrexate, leflunomide, corticosteroids, budenoside, dexamethasone, sulfasalazine, 5-aminosalicylic acid, olsalazine, IL-1β converting enzyme inhibitors, IL-1ra, T cell signaling inhibitors, tyrosine kinase inhibitors, 6-mercaptopurines, IL-11, mesalamine, prednisone, azathioprine, mercaptopurine, infliximab, methylprednisolone sodium succinate, diphenoxylate/atrop sulfate, loperamide hydrochloride, omeprazole, folate, ciprofloxacin/dextrose-water, hydrocodone, bitartrate/apap, tetracycline hydrochloride, fluocinonide, metronidazole, thimerosal/boric acid, cholestyramine/sucrose, ciprofloxacin hydrochloride, hyoscyamine sulfate, meperidine hydrochloride, midazolam hydrochloride, oxycodone HCl/acetaminophen, promethazine hydrochloride, sodium phosphate, sulfamethoxazole/trimethoprim, polycarbophil, propoxyphene napsylate, hydrocortisone, multivitamins, balsalazide disodium, codeine phosphate/apap, colesevelam HCl, cyanocobalamin, folic acid, levofloxacin, natalizumab, interferon-gamma, methylprednisolone, azathioprine, cyclophosphamide, cyclosporine, methotrexate, 4-aminopyridine, tizanidine, interferon-β1a, AVONEX®, interferon-β1b, BETASERON®, interferon α-n3, interferon-α, interferon β1A-IF, Peginterferon α 2b, Copolymer 1, COPAXONE®, hyperbaric oxygen, intravenous immunoglobulin, cladribine, cyclosporine, FK506, mycophenolate mofetil, leflunomide, NSAIDs, corticosteroids, prednisolone, phosphodiesterase inhibitors, adensosine agonists, anti-thrombotic agents, complement inhibitors, adrenergic agents, antiinflammatory cytokines, interferon-β, IFNβ1a, IFNβ1b, copaxone, corticosteroids, caspase inhibitors, inhibitors of caspase-1, antibodies to CD40 ligand and CD80, alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, liposome encapsulated mitoxantrone, THC.CBD, cannabinoid agonists, MBP-8298, mesopram, MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists, interferon gamma antagonists, IL-4 agonists, diclofenac, misoprostol, naproxen, meloxicam, indomethacin, diclofenac, methotrexate, azathioprine, minocyclin, prednisone, etanercept, rofecoxib, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodon bitartrate/apap, risedronate sodium, sulfadiazine, thioguanine, valdecoxib, alefacept, and efalizumab, diclofenac, naproxen, ibuprofen, piroxicam, indomethacin, COX2 inhibitors, rofecoxib, valdecoxib, hydroxychloroquine, steroids, prednisolone, budenoside, dexamethasone, cytotoxics, azathioprine, cyclophosphamide, mycophenolate mofetil, inhibitors of PDE4, purine synthesis inhibitor, sulfasalazine, 5-aminosalicylic acid, olsalazine, Imuran®, CTLA-4-IgG, anti-B7 family antibodies, anti-PD-1 family antibodies, anti-cytokine antibodies, fonotolizumab, anti-IFNg antibody, anti-receptor receptor antibodies, anti-IL-6 receptor antibody, antibodies to B-cell surface molecules, LJP 394, Rituximab, anti-CD20 antibody and lymphostat-B.

DETAILED DESCRIPTION OF THE INVENTION

Protein kinases are a broad and diverse class, of over 500 enzymes, that include oncogenes, growth factors receptors, signal transduction intermediates, apoptosis related kinases and cyclin dependent kinases. They are responsible for the transfer of a phosphate group to specific tyrosine, serine or threonine amino acid residues, and are broadly classified as tyrosine and serine/threonine kinases as a result of their substrate specificity.

The Jak family kinases (Jak1, Jak2, Jak3 and Tyk2) are cytoplasmic tyrosine kinases that associate with membrane bound cytokine receptors. Cytokine binding to their receptor initiates Jak kinase activation via trans and autophosphorylation processes. The activated Jak kinases phosphorylate residues on the cytokine receptors creating phosphotyrosine binding sites for SH2 domain containing proteins such as Signal Transduction Activators of Transcript (STAT) factors and other signal regulators transduction such as suppressor of cytokine signaling (SOCS) proteins and SH2 domain-containing inositol 5'-phosphatases (SHIP). Activation of STAT factors via this process leads to their dimerization, nuclear translocation and new mRNA transcription resulting in expression of immunocyte proliferation and survival factors as well as additional cytokines, chemokines and molecules that facilitate cellular trafficking (see Journal of Immunology, 2007, 178, p. 2623). Jak kinases transduce signals for many different cytokine families and hence potentially play roles in diseases with widely different pathologies including but not limited to the following examples. Both Jak1 and Jak3 control signaling of the so-called common gamma chain cytokines (IL2, IL4, IL7, IL9, IL15 and IL21), hence simultaneous inhibition of either Jak1 or Jak3 could be predicted to impact Th1 mediated diseases such as rheumatoid arthritis via blockade of IL2, IL7 and IL15 signaling. On the other hand, IL2 signaling has recently been shown to be essential for development and homeostasis of T-regulatory cells (Malek T R et al., Immunity, 2002, 17(2), p. 167-78). Thus, based on genetic data, blockade of IL2 signaling alone is predicted to result in autoimmunity (Yamanouchi J et al., Nat Genet., 2007, 39(3), p. 329-37, and Willerford D M et al., Immunity, 1995, 3(4), p. 521-30). Th2 mediated diseases such as asthma or atopic dermatitis via IL4 and IL9 signaling blockade. Jak1 and Tyk2 mediate signaling of IL13 (see Int. Immunity, 2000, 12, p. 1499). Hence, blockade of these may also be predicted to have a therapeutic effect in asthma. These two kinases are also thought to mediate Type I interferon signaling; their blockade could therefore be predicted to reduce the severity of systemic lupus erythematosus (SLE). Tyk2 and Jak2 mediate signaling of IL12 and IL23. In fact, blockade of these cytokines using monoclonal antibodies has been effective in treating psoriasis. Therefore blockade of this pathway using inhibitors of these kinases could be predicted to be effective in psoriasis as well. In summary, this invention describes small-molecule compounds that inhibit, regulate and/or modulate Jak family kinase activity that is pivotal to several mechanisms thought critical to the progression of autoimmune diseases including, but not limited to, rheumatoid arthritis (RA), systemic lupus erythematosus (SLE), multiple sclerosis (MS), Crohn's disease, psoriasis and asthma.

Several pathologically significant cytokines signal via Jak1 alone (Guschin D, et al., EMBO J. 1995 Apr. 3; 14(7): 1421-9; Parganas E, et al., Cell. 1998 May 1; 93(3):385-95; Rodig S. J., et al., Cell. 1998 May 1; 93(3):373-83). Blockade of one of these, IL6, using an IL6R neutralizing antibody, has been shown to significantly improve disease scores in human rheumatoid arthritis patients (Nishimoto N. et al., Ann Rheum Dis., 2007, 66(9), p. 1162-7). Similarly, blockaded of GCSF signaling, which is also mediated by Jak1 alone, using neutralizing monoclonal antibodies or target gene deletion protects mice from experimental arthritis (Lawlor K. E. et al., Proc Natl Acad Sci U.S.A., 2004, 101(31), p. 11398-403). Accordingly, the identification of small-molecule compounds that inhibit, regulate and/or modulate the signal transduction of kinases, such as Jak1, is a desirable means to prevent or treat autoimmune diseases or other diseases related to abberant Jak1 function.

Jak2 is also activated in a wide variety of human cancers such as prostate, colon, ovarian and breast cancers, melanoma, leukemia and other haematopoietic malignancies. In addition, somatic point mutation of the Jak2 gene has been identified to be highly associated with classic myeloproliferative disorders (MPD) and infrequently in other myeloid disorders. Constitutive activation of Jak2 activity is also caused by chromosomal translocation in hematopoeitic malignancies. It has also been shown that inhibition of the Jak/STAT pathway, and in particular inhibition of Jak2 activity, results in anti-proliferative and pro-apoptotic effects largely due to inhibition of phosphorylation of STAT. Furthermore, pharmacological modulation or inhibition of Jak2 activity could effectively block tumor growth and induce apoptosis by reducing the STAT phosphorylation in cell culture and human tumor xenografts in vivo. Accordingly, the identification of small-molecule compounds that inhibit, regulate and/or modulate the signal transduction of kinases, particularly Jak2, is desirable as a means to treat or prevent diseases and conditions associated with cancers.

Jak kinases also transmit signals regulating essential physiological processes whose inhibition could be undesirable. For example Jak2 mediates the signaling of Erythropoetin (Epo) and Granulocyte/Monocyte-Colony Stimulating Factor (GM-CSF). Individuals with genetic, congenital or acquired defects in these signaling pathways can develop potentially life-threatening complications such as anemia and neutrophil dysfunction. Accordingly, one non-limiting aspect of this invention also relates to a method to identify compounds that may have a favorable safety profile as a result of them selectively avoiding inhibition of Jak2.

The protein kinase C family is a group of serine/threonine kinases that comprises twelve related isoenzymes. Its members are encoded by different genes and are sub-classified according to their requirements for activation. The classical enzymes (cPKC) require diacylglycerol (DAG), phosphatidylserine (PS) and calcium for activation. The novel PKC's (nPKC) require DAG and PS but are calcium independent. The atypical PKC's (aPKC) do not require calcium or DAG.

PKCtheta is a member of the nPKC sub-family (Baier, G., et al., J. Biol. Chem., 1993, 268, 4997). It has a restricted expression pattern, found predominantly in T cells and skeletal muscle (Mischak, H. et al., FEBS Lett., 1993, 326, p. 51), with some expression reported in mast cells (Liu, Y. et al., J. Leukoc. Biol., 2001, 69, p. 831) and endothelial cells (Mattila, P. et al., Life Sci., 1994, 55, p. 1253).

Upon T cell activation, a supramolecular activation complex (SMAC) forms at the site of contact between the T cell and the antigen presenting cell (APC). PKCtheta is the only PKC isoform found to localize at the SMAC (Monks, C. et al., Nature, 1997, 385, 83), placing it in proximity with other signaling enzymes that mediate T cell activation processes.

In another study (Baier-Bitterlich, G. et al., Mol. Cell. Biol., 1996, 16, 842) the role of PKCtheta in the activation of AP-1, a transcription factor important in the activation of the IL-2 gene, was confirmed. In unstimulated T cells, constitutively active PKCtheta stimulated AP-1 activity while in cells with dominant negative PKCtheta, AP-1 activity was not induced upon activation by PMA.

Other studies showed that PKCtheta, via activation of IκB kinase beta, mediates activation of NF-κB induced by T cell receptor/CD28 co-stimulation (N. Coudronniere et al., Proc.

Nat. Acad. Sci. U.S.A., 2000, 97, p. 3394; and Lin, X. et al., Mol. Cell. Biol., 2000, 20, p. 2933).

Proliferation of peripheral T cells from PKCtheta knockout mice, in response to T cell receptor (TCR)/CD28 stimulation was greatly diminished compared to T cells from wild type mice. In addition, the amount of IL-2 released from the T cells was also greatly reduced (Sun, Z. et al., Nature, 2000, 404, p. 402). It has also been shown that PKCtheta-deficient mice show impaired pulmonary inflammation and airway hyperresponsiveness (AHR) in a Th2-dependent murine asthma model, with no defects in viral clearance and Th1-dependent cytotoxic T cell function (Berg-Brown, N. N. et al., J. Exp. Med., 2004, 199, p. 743; Marsland, B. J. et al., J. Exp. Med., 2004, 200, p. 181). The impaired Th2 cell response results in reduced levels of IL-4 and immunoglobulin E (IgE), contributing to the AHR and inflammatory pathophysiology. Otherwise, the PKCtheta knockout mice seemed normal and fertile.

Evidence also exists that PKCtheta participates in the IgE receptor (Fc$\epsilon$RI)-mediated response of mast cells (Liu, Y. et al., J. Leukoc. Biol., 2001, 69, p. 831). In human-cultured mast cells (HCMC), it has been demonstrated that PKC kinase activity rapidly localizes to the membrane following Fc$\epsilon$RI cross-linking (Kimata, M. et al., Biochem. Biophys. Res. Commun., 1999, 257(3), p. 895). A recent study examining in vitro activity of bone marrow mast cells (BMMC) derived from wild-type and PKCtheta-deficient mice shows that upon FceRI cross linking, BMMCs from PKCtheta-deficient mice reduced levels of IL-6, tumor necrosis factor-alpha (TNF$\alpha$) and IL-13in comparison with BMMCs from wild-type mice, suggesting a potential role for PKCtheta in mast cell cytokine production in addition to T cell activation (Ciarletta, A. B. et al., poster presentation at the 2005 American Thoracic Society International Conference).

The studies cited above and others studies confirm the critical role of PKCtheta in T cells activation and in mast cell (MC) signaling. Thus an inhibitor of PKCtheta would be of therapeutic benefit in treating immunological disorders and other diseases mediated by the inappropriate activation of T cells and MC signaling.

Many of the kinases, whether a receptor or non-receptor tyrosine kinase or a S/T kinase have been found to be involved in cellular signaling pathways involved in numerous pathogenic conditions, including immunomodulation, inflammation, or proliferative disorders such as cancer.

Many autoimmune diseases and disease associated with chronic inflammation, as well as acute responses, have been linked to excessive or unregulated production or activity of one or more cytokines.

The compounds of the invention are also useful in the treatment of cardiovascular disorders, such as acute myocardial infarction, acute coronary syndrome, chronic heart failure, myocardial infarction, atherosclerosis, viral myocarditis, cardiac allograft rejection, and sepsis-associated cardiac dysfunction. Furthermore, the compounds of the present invention are also useful for the treatment of central nervous system disorders such as meningococcal meningitis, Alzheimer's disease and Parkinson's disease.

The compounds of the invention are also useful in the treatment of an ocular condition, a cancer, a solid tumor, a sarcoma, fibrosarcoma, osteoma, melanoma, retinoblastoma, a rhabdomyosarcoma, glioblastoma, neuroblastoma, teratocarcinoma, hypersensitivity reactions, hyperkinetic movement disorders, hypersensitivity pneumonitis, hypertension, hypokinetic movement disorders, aordic and peripheral aneuryisms, hypothalamic-pituitary-adrenal axis evaluation, aortic dissection, arterial hypertension, arteriosclerosis, arteriovenous fistula, ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, heart transplant rejection, hemachromatosis, hemodialysis, hemolytic uremic syndrome/thrombolytic thrombocytopenic purpura, hemorrhage, idiopathic pulmonary fibrosis, antibody mediated cytotoxicity, Asthenia, infantile spinal muscular atrophy, inflammation of the aorta, influenza A, ionizing radiation exposure, iridocyclitis/uveitis/optic neuritis, juvenile spinal muscular atrophy, lymphoma, myeloma, leukaemia, malignant ascites, hematopoietic cancers, a diabetic condition such as insulin-dependent diabetes mellitus glaucoma, diabetic retinopathy or microangiopathy, sickle cell anaemia, chronic inflammation, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, post perfusion syndrome, post pump syndrome, post-MI cardiotomy syndrome, preeclampsia, menometrorrhagia, endometriosis, pulmonary hypertension, infantile hemangioma, or infection by Herpes simplex, Herpes Zoster, human immunodeficiency virus, parapoxvirus, protozoa or toxoplasmosis, progressive supranucleo palsy, primary pulmonary hypertension, radiation therapy, Raynaud's phenomenon, Raynaud's disease, Refsum's disease, regular narrow QRS tachycardia, renovascular hypertension, restrictive cardiomyopathy, sarcoma, senile chorea, senile dementia of Lewy body type, shock, skin allograft, skin changes syndrome, ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy, macular degeneration, restenosis, ischemia/reperfusion injury, ischemic stroke, vascular occlusion, carotid obstructive disease, ulcerative colitis, inflammatory bowel disease, diabetes, diabetes mellitus, insulin dependent diabetes mellitus, allergic diseases, dermatitis scleroderma, graft versus host disease, organ transplant rejection (including but not limited to bone marrow and solid organ rejection), acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasculitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, idiopathic Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, chlamydia, yersinia and salmonella associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, peripheral vascular disorders, peritonitis, pernicious anemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis A, Hepatitis B, Hepatitis C, His bundle arrythmias, HIV infection/HIV neuropathy, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, pneumocystis carinii pneumonia, pneumonia, connective tissue disease associated interstitial lung disease, mixed connective tissue disease, associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthritis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, acute and chronic pain (different forms of pain), Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, toxicity, transplants, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer Helicobacter related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, or age-related macular degeneration. In addition, these compounds can be used as active agents against hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Compounds of Formula (I) or Formula (II) of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the compounds of this invention. Non-limiting examples of therapeutic agents for rheumatoid arthritis with which a compound of Formula (I) or Formula (II) of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. Compounds of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7 (U.S. Pat. No. 6,090,382, HUMIRA™), CA2 (REMICADE™), SIMPONI™ (golimumab), CIMZIA™, ACTEMRA™, CDP 571, and soluble p55 or p75 TNF receptors, derivatives, thereof, (p75TNFR1gG (ENBREL™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination is non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of Formula (I) or Formula (II) of the invention may also be combined with agents, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™) and p55TNFRIgG (Lenercept), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. Preferred combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of Formula (I) or Formula (II) of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinylimidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of Formula (I) or Formula (II) can be combined include the following: TNF antagonists, for example, anti-TNF antibodies, D2E7 (U.S. Pat. No. 6,090,382, HUMIRA™), CA2 (REMICADE™), CDP 571, TNFRIg constructs, (p75TNFRIgG (ENBREL™) and p55TNFRIgG (LENERCEPT™) inhibitors and PDE4 inhibitors. A compound of Formula (I) or Formula (II) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) or Formula (II) can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) or Formula (II) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) or Formula (II) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα, or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13and TGFβ).

Preferred examples of therapeutic agents for multiple sclerosis in which a compound of Formula (I) or Formula (II) can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

A compound of Formula (I) or Formula (II) may also be combined with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (BDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (I) or Formula (II) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™)

Non-limiting examples of therapeutic agents for asthma with which a compound of Formula (I) or Formula (II) can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of Formula (I) or Formula (II) can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for HCV with which a compound of Formula (I) or Formula (II) can be combined include the following: Interferon-alpha-2α, Interferon-alpha-2β, Interferon-alpha con1, Interferon-alpha-n1, pegylated interferon-alpha-2α, pegylated interferon-alpha-2β, ribavirin, peginterferon alfa-2b+ribavirin, ursodeoxy-cholic acid, glycyrrhizic acid, thymalfasin, Maxamine, VX-497 and any compounds that are used to treat HCV through intervention with the following targets: HCV polymerase, HCV protease, HCV helicase, and HCV IRES (internal ribosome entry site).

Non-limiting examples of therapeutic agents for Idiopathic Pulmonary Fibrosis with which a compound of Formula (I) or Formula (II) can be combined include the following: prednisone, azathioprine, albuterol, colchicine, albuterol sulfate, digoxin, gamma interferon, methylprednisolone sodium succinate, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-alpha, methotrexate, mycophenolate mofetil and interferon-gamma-1β.

Non-limiting examples of therapeutic agents for myocardial infarction with which a compound of Formula (I) or Formula (II) can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril hydrochloride/magnesium carbonate, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

Non-limiting examples of therapeutic agents for psoriasis with which a compound of Formula (I) or Formula (II) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) or Formula (II) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (U.S. Pat. No. 6,090,382, HUMIRA™), and efalizumab.

Non-limiting examples of therapeutic agents for restenosis with which a compound of Formula (I) or Formula (II) can be combined include the following: sirolimus, paclitaxel, everolimus, tacrolimus, ABT-578, and acetaminophen.

Non-limiting examples of therapeutic agents for sciatica with which a compound of Formula (I) or Formula (II) can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol hcl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene n-pap, asa/oxycod/oxycodone ter, ibuprofen/hydrocodone bit, tramadol HCl, etodolac, propoxyphene HCl, amitriptyline HCl, carisoprodol/codeine phos/asa, morphine sulfate, multivitamins, naproxen sodium, orphenadrine citrate, and temazepam.

Preferred examples of therapeutic agents for SLE (Lupus) with which a compound of Formula (I) or Formula (II) can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) or Formula (II) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) or Formula (II) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) or Formula (II) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) or Formula (II) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (U.S. Pat. No. 6,090,382; HUMIRA™), CA2 (REMICADE™), CDP 571, TNFRIg constructs, (p75TNFRIgG (ENBREL™) and p55TNFRIgG (LENERCEPT™).

In this invention, the following definitions are applicable:

A "therapeutically effective amount" is an amount of a compound of Formula (I) or Formula (II) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of Formula (I) or Formula (II) which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of Formula (I) or Formula (II) and their salts may exist in more than one crystal form and the present invention includes each crystal form and mixtures thereof.

Certain compounds of Formula (I) or Formula (II) and their salts may also exist in the form of solvates, for example hydrates, and the present invention includes each solvate and mixtures thereof.

Certain compounds of Formula (I) or Formula (II) may contain one or more chiral centers, and exist in different optically active forms. When compounds of Formula (I) or Formula (II) contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula (I) or Formula (II) contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of Formula (I) or Formula (II), and mixtures thereof.

Certain compounds of Formula (I) or Formula (II) may exist in different tautomeric forms or as different geometric isomers, and the present invention includes each tautomer and/or geometric isomer of compounds of Formula (I) or Formula (II) and mixtures thereof.

Certain compounds of Formula (I) or Formula (II) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula (I) or Formula (II) and mixtures thereof.

Certain compounds of Formula (I) or Formula (II) may exist in zwitterionic form and the present invention includes each zwitterionic form of compounds of Formula (I) or Formula (II) and mixtures thereof.

As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial.

Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents wherein the free hydrogen is replaced by $(C_1\text{-}C_4)$alkyl, $(C_1\text{-}C_{12})$alkanoyloxymethyl, $(C_4\text{-}C_9)$1-(alkanoyloxy)ethyl, 1-methyl-1-(alkanoyloxy)-ethyl having from 5 to 10 carbon atoms, alkoxycarbonyloxymethyl having from 3to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_1\text{-}C_2)$alkylamino$(C_2\text{-}C_3)$alkyl (such as β-dimethylamino ethyl), carbamoyl-$(C_1\text{-}C_2)$alkyl, N,N-di$(C_1\text{-}C_2)$-alkylcarbamoyl-$(C_1\text{-}C_2)$alkyl and piperidino-, pyrrolidino- or morpholino$(C_2\text{-}C_3)$alkyl.

Other exemplary pro-drugs release an alcohol of Formula (I) or Formula (II) wherein the free hydrogen of the hydroxyl substituent (e.g., R group contains hydroxyl) is replaced by $(C_1\text{-}C_6)$alkanoyloxymethyl, 1-($(C_1\text{-}C_6)$alkanoyloxy)ethyl, 1-methyl-1-($(C_1\text{-}C_6)$alkanoyloxy)ethyl, $(C_1\text{-}C_{12})$alkoxycarbonyloxymethyl, N—$(C_1\text{-}C_6)$alkoxycarbonylamino-methyl, succinoyl, $(C_1\text{-}C_6)$alkanoyl, α-amino$(C_1\text{-}C_4)$alkanoyl, arylactyl and α-aminoacyl, or α-aminoacyl-α-aminoacyl wherein said α-aminoacyl moieties are independently any of the naturally occurring L-amino acids found in proteins, $P(O)(OH)_2$, —$P(O)(O(C_1\text{-}C_6)\text{alkyl})_2$ or glycosyl (the radical resulting from detachment of the hydroxyl of the hemiacetal of a carbohydrate).

As used herein, the term "bridged $(C_5\text{-}C_{12})$cycloalkyl group" means a saturated or unsaturated, bicyclic or polycyclic bridged hydrocarbon group having two or three $C_3\text{-}C_{10}$ cycloalkyl rings. Non bridged cycloalkyls are excluded. Bridged cyclic hydrocarbon may include, such as bicyclo[2.1.1]hexyl, bicyclo[2.2.1]heptyl, bicyclo[2.2.2]octyl, bicyclo[3.2.1]octyl, bicyclo[4.3.1]decyl, bicyclo[3.3.1]nonyl, bornyl, bornenyl, norbornyl, norbornenyl, 6,6-dimethylbicyclo[3.1.1]heptyl, tricyclobutyl, and adamantyl.

As used herein the term "bridged $(C_2\text{-}C_{10})$ heterocyclyl" means bicyclic or polycyclic aza-bridged hydrocarbon groups and may include azanorbornyl, quinuclidinyl, isoquinuclidinyl, tropanyl, azabicyclo[3.2.1]octanyl, azabicyclo[2.2.1]heptanyl, 2-azabicyclo[3.2.1]octanyl, azabicyclo[3.2.1]octanyl, azabicyclo[3.2.2]nonanyl , azabicyclo[3.3.0]nonanyl, and azabicyclo[3.3.1]nonanyl.

The term "heterocyclic", "heterocyclyl" or "heterocyclylene", as used herein, include non-aromatic, ring systems, including, but not limited to, monocyclic, bicyclic, tricyclic and spirocyclic rings, which can be completely saturated or which can contain one or more units of unsaturation, for the avoidance of doubt, the degree of unsaturation does not result in an aromatic ring system) and have 5 to 12 atoms including at least one heteroatom, such as nitrogen, oxygen, or sulfur. For purposes of exemplification, which should not be construed as limiting the scope of this invention, the following are examples of heterocyclic rings: azepinyl, azetidinyl, indolinyl, isoindolinyl, morpholinyl, piperazinyl, piperidinyl, pyrrolidinyl, quinucludinyl, thiomorpholinyl, tetrahydropyranyl, tetrahydrofuranyl, tetrahydroindolyl, thiomorpholinyl and tropanyl.

The term "heteroaryl" or "heteroarylene" as used herein, include aromatic ring systems, including, but not limited to, monocyclic, bicyclic and tricyclic rings, and have 5 to 12 atoms including at least one heteroatom, such as nitrogen, oxygen, or sulfur. For purposes of exemplification, which should not be construed as limiting the scope of this invention: azaindolyl, benzo[b]thienyl, benzimidazolyl, benzofuranyl, benzoxazolyl, benzothiazolyl, benzothiadiazolyl, benzoxadiazolyl, furanyl, imidazolyl, imidazopyridinyl, indolyl, indazolyl, isoxazolyl, isothiazolyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrazolyl, thiadiazolyl, or thienyl.

An "heterocycloalkyl" group, as used herein, is a heterocyclic group that is linked to a compound by an aliphatic group having from one to about eight carbon atoms. For example, a heterocycloalkyl group is a morpholinomethyl group.

As used herein, "alkyl", "alkylene" or notations such as "($C_1$-$C_8$)" include straight chained or branched hydrocarbons which are completely saturated. Examples of alkyls are methyl, ethyl, propyl, isopropyl, butyl, pentyl, hexyl and isomers thereof. As used herein, "alkenyl", "alkenylene", "alkynylene" and "alkynyl" means $C_2$-$C_8$ and includes straight chained or branched hydrocarbons which contain one or more units of unsaturation, one or more double bonds for alkenyl and one or more triple bonds for alkynyl.

As used herein, "aromatic" groups (or "aryl" or "arylene" groups) include aromatic carbocyclic ring systems (e.g. phenyl) and fused polycyclic aromatic ring systems (e.g. naphthyl, biphenyl and 1,2,3,4-tetrahydronaphthyl).

As used herein, "cycloalkyl" or "cycloalkylene" means $C_3$-$C_{12}$ monocyclic or multicyclic (e.g., bicyclic, tricyclic, spirocyclic, etc.) hydrocarbons that is completely saturated or has one or more unsaturated bonds but does not amount to an aromatic group. Examples of a cycloalkyl group are cyclopropyl, cyclobutyl, cyclopentyl, cyclopentenyl, cyclohexyl and cyclohexenyl.

As used herein, many moieties or substituents are termed as being either "substituted" or "optionally substituted". When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: ($C_1$-$C_8$)alkyl groups, ($C_2$-$C_8$)alkenyl groups, ($C_2$-$C_8$)alkynyl groups, ($C_3$-$C_{10}$)cycloalkyl groups, halogen (F, Cl, Br or I), halogenated ($C_1$-$C_8$)alkyl groups (for example but not limited to —$CF_3$), —O—($C_1$-$C_8$)alkyl groups, —OH, —S—($C_1$-$C_8$)alkyl groups, —SH, —NH($C_1$-$C_8$)alkyl groups, —N(($C_1$-$C_8$)alkyl)$_2$ groups, —$NH_2$, —C(O)$NH_2$, —C(O)NH($C_1$-$C_8$)alkyl groups, —C(O)N(($C_1$-$C_8$)alkyl)$_2$, —NHC(O)H, —NHC(O)($C_1$-$C_8$)alkyl groups, —NHC(O)($C_3$-$C_8$)cycloalkyl groups, —N(($C_1$-$C_8$)alkyl)C(O)H, —N(($C_1$-$C_8$)alkyl)C(O)($C_1$-$C_8$)alkyl groups, —NHC(O)$NH_2$, —NHC(O)NH($C_1$-$C_8$)alkyl groups, —N(($C_1$-$C_8$)alkyl)C(O)$NH_2$ groups, —NHC(O)N(($C_1$-$C_8$)alkyl)$_2$ groups, —N(($C_1$-$C_8$)alkyl)C(O)N(($C_1$-$C_8$)alkyl)$_2$ groups, —N(($C_1$-$C_8$)alkyl)C(O)NH(($C_1$-$C_8$)alkyl), —C(O)H, —C(O)($C_1$-$C_8$)alkyl groups, —CN, —$NO_2$, —S(O)($C_1$-$C_8$)alkyl groups, —S(O)$_2$($C_1$-$C_8$)alkyl groups, —S(O)$_2$N(($C_1$-$C_8$)alkyl)$_2$ groups, —S(O)$_2$NH($C_1$-$C_8$)alkyl groups, —S(O)$_2$NH($C_3$-$C_8$)cycloalkyl groups, —S(O)$_2$$NH_2$ groups, —NHS(O)$_2$($C_1$-$C_8$)alkyl groups, —N(($C_1$-$C_8$)alkyl)S(O)$_2$($C_1$-$C_8$)alkyl groups, —($C_1$-$C_8$)alkyl-O—($C_1$-$C_8$)alkyl groups, —O—($C_1$-$C_8$)alkyl-O—($C_1$-$C_8$)alkyl groups, —C(O)OH, —C(O)O($C_1$-$C_8$)alkyl groups, NHOH, NHO($C_1$-$C_8$)alkyl groups, —O-halogenated ($C_1$-$C_8$)alkyl groups (for example but not limited to —$OCF_3$), —S(O)$_2$-halogenated ($C_1$-$C_8$)alkyl groups (for example but not limited to —S(O)$_2$$CF_3$), —S-halogenated ($C_1$-$C_8$)alkyl groups (for example but not limited to —$SCF_3$), —($C_1$-$C_6$) heterocycle (for example but not limited to pyrrolidine, tetrahydrofuran, pyran or morpholine), —($C_1$-$C_6$) heteroaryl (for example but not limited to tetrazole, imidazole, furan, pyrazine or pyrazole), -phenyl, —NHC(O)O—($C_1$-$C_6$)alkyl groups, —N(($C_1$-$C_6$)alkyl)C(O)O—($C_1$-$C_6$)alkyl groups, —C(═NH)$_4$$C_1$-$C_6$)alkyl groups, —C(═NOH)—($C_1$-$C_6$)alkyl groups, or —C(═N—O—($C_1$-$C_6$)alkyl)-($C_1$-$C_6$)alkyl groups.

"O" in Formula (I) represents an aromatic ring.

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few hours up to over several days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition (see e.g. Fingl et al., 1975, in "The Pharmacological Basis of Therapeutics", Ch. 1 p. 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the following Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

| | Parts by weight |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intra-cellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors, PI3kinase inhibitors, calcineurin inhibitors and immunosuppressants. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deletrious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

The present invention also comprises the use of a compound of Formula (I) or Formula (II) as a medicament.

A further aspect of the present invention provides the use of a compound of Formula (I) or Formula (II) or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of Formula (I) or Formula (II) to a mammal, particularly a human being, in need thereof.

ABBREVIATIONS

| | |
|---|---|
| aa | Amino acids |
| $Ac_2O$ | Acetic anhydride |
| AcOH | Glacial acetic acid |
| ATP | Adenosine triphosphate |

-continued

ABBREVIATIONS

| | |
|---|---|
| b.p. | Boiling point |
| BArF | tetrakis-[3,5-bis(trifluoromethyl)phenyl]borate |
| Bn | Benzyl |
| Boc | t-Butoxycarbonyl |
| BOP-Cl | Bis(2-oxo-3-oxazolidinyl)phosphonic chloride |
| BSA | Bovine serum albumin |
| BuOH | Butanol |
| CAN | Ceric ammonium nitrate |
| Cbz | Carboxybenzyl |
| CDI | 1,1'-Carbonyldiimidazole |
| COD | 1,5-Cyclooctadiene |
| concd | Concentrated |
| CT | Computed tomography |
| cym | p-cymene (4-isopropyltoluene) |
| CyPFt-Bu | 1-Dicyclohexylphosphino-2-di-tert-butylphosphinoethylferrocene |
| d | Doublet |
| DAST | Diethylaminosulfur trifluoride |
| dba | Dibenzylideneacetone |
| DBU | 1,8-Diazabicyclo[5.4.0]undec-7-ene |
| DCC | Dicyclohexylcarbodiimide |
| DCE | Dichloroethane |
| DCM | Dichloromethane (methylene chloride) |
| dd | Doublet of doublets |
| DEAD | Diethyl azodicarboxylate |
| DIBAL-H | Diisobutylaluminium hydride |
| DIAD | Diisopropyl azodicarboxylate |
| DIEA | N,N-Diisopropylethylamine |
| DMA | Dimethylacetamide |
| DMAP | N,N-Dimethylaminopyridine |
| DME | 1,2-Dimethoxyethane |
| DMEM | Dulbecco's Modified Eagle Medium |
| DMF | N,N-Dimethylformamide |
| DMS | Dimethylsulfide |
| DMSO | Dimethyl sulfoxide |
| DNP-HSA | Dinitrophenyl-human serum albumin |
| DPPA | Diphenyl phosphorazidate |
| dppf | 1,1'-Bis(diphenylphosphino)ferrocene |
| dr | Diastereomeric ratio |
| DTT | Dithiothreitol |
| EDC•HCl | N-(3-Dimethylaminopropy1)-N'-ethylcarbodiimide hydrochloride |
| EDTA | Ethylene diamine tetraacetic acid |
| EGTA | Ethylene glycol tetraacetic acid |
| equiv | Equivalent(s) |
| er | Enantiomeric ratio |
| $Et_2NH$ | Diethylamine |
| EtOAc | Ethyl acetate |
| $Et_2O$ | Diethyl ether |
| EtOH | Ethanol |
| FBS | Fetal bovine serum |
| FLAG | DYKDDDDK peptide sequence |
| g | Gram(s) |
| GST | Glutathione S-transferase |
| h | Hour(s) |
| $H_2SO_4$ | Sulfuric acid |
| HATU | O(7-Azabenzotriazol-1-yl)-N,N,N',N'-tetramethyluronium hexafluorophosphate |
| HEPES | N-2-Hydroxyethylpiperazine-N'-2-ethanesulfonic acid |
| HOBt | Hydroxybenzotriazole |
| HPLC | High-pressure liquid chromatography |
| Hz | Hertz |
| IBCF | Isobutylchloroformate |
| i.d. | Intradermal |
| IFA | Incomplete Freunds Adjuvant |
| IPA | Isopropyl alcohol |
| KHMDS | Potassium hexamethyldisilazane |
| LAH | Lithium aluminum hydride |
| LC | Liquid chromatography |
| LDA | Lithium diisopropylamide |
| LHMDS | Lithium bis(trimethylsilyl)amide |
| $LiBH_4$ | Lithium borohydride |
| LiOH | Lithium hydroxide |
| m | Multiplet |
| M | Molar |
| m-CPBA | meta-Chloroperbenzoic acid |
| MeCN | Acetonitrile |

-continued

| ABBREVIATIONS | |
|---|---|
| MeOH | Methyl alcohol |
| min | Minute(s) |
| mL | Milliliter(s) |
| mmHg | Millimeters of mercury |
| mmol | Millimole |
| MOPS | 3-(N-morpholino)-propanesulfonic acid |
| MOPSO | 3-(N-morpholino)-2-hydroxypropanesulfonic acid |
| MS | Mass spectrometry |
| MTBE | Methyl tert-butyl ether |
| n- | Normal (nonbranched) |
| n-BuLi | n-Butyl lithium |
| N | Normal |
| NaHMDS | Sodium bis(trimethylsilyl)amide |
| NaOAc | Sodium acetate |
| $Na(OAc)_3BH$ | Sodium triacetoxyborohydride |
| NaOt-Bu | Sodium tert-butoxide |
| NBS | N-Bromosuccinimide |
| NCS | N-Chlorosuccinimide |
| ND | Not determined |
| $NH_4OAc$ | Ammonium acetate |
| NIS | N-Iodosuccinimide |
| NMM | N-Methylmorpholine |
| NMP | N-Methylpyrrolidinone |
| NMR | Nuclear magnetic resonance |
| OD | Optical density |
| or | Optical rotation |
| OVA | Ovalbumin |
| p- | Para |
| PBS | Phosphate buffered saline |
| PFPAA | 2,2,3,3,3-Pentafluoropropanoic Anhydride |
| pH | $-\log[H^+]$ |
| PMB | p-Methoxybenzyl |
| pNAG | Nitrophenyl-N-acetyl-β-D-glucosaminide |
| $P(n\text{-}Bu)_3$ | tri-n-Butyl phosphine |
| $POCl_3$ | Phosphorus oxychloride |
| $PPh_3$ | Triphenylphosphine |
| ppm | Parts per million |
| PrOH | Propanol |
| psi | Pounds per square inch |
| rcf | Relative centrifugal force |
| RP-HPLC | Reverse-phase high-pressure liquid chromatography |
| $R_t$ | Retention time |
| rt | Room temperature |
| s | Singlet |
| SEM | 2-(Trimethylsilyl)ethoxymethyl |
| SEM-Cl | 2-(Trimethylsilyl)ethoxymethyl chloride |
| SFC | Supercritical Fluid Chromatography |
| SLM | Standard liters per minute |
| t | Triplet |
| t- | Tertiary |
| TBDMS | tert-Butyldimethylsilyl |
| TBDMSCl | tert-Butyldimethylsilyl chloride |
| TBAB | Tetra-n-butylammonium bromide |
| TBAF | Tetra-n-butylammonium fluoride |
| TBAI | Tetra-n-butylammonium iodide |
| TEA | Triethylamine |
| tert- | Tertiary |
| TFA | Trifluoroacetic acid |
| TFAA | Trifluoracetic anhydride |
| THF | Tetrahydrofuran |
| TIPS | Triisopropylsilyl |
| TLC | Thin layer chromatography |
| TMA | Trimethyl aluminium |
| TMAD | N,N,N',N'-Tetramethylazodicarbonamide or 1,1'-azobis (N,N-dimethylformamide) or diamide [Sigma ®] |
| TMOF | Trimethyl orthoformate |
| TMS | Trimethylsilyl |
| TPP | 2,4,6-Tripropyl-[1,3,5,2,4,6]trioxatriphosphinane 2,4,6-trioxide |
| TsCl | para-Toluenesulfonyl chloride |
| TsOH | para-Toluenesulfonic acid |
| USP | United States Pharmacopeia |
| UV | Ultraviolet |
| wt % | Weight percent |
| w/v | Weight/volume |

Assays

In Vitro Jak1 Kinase Activity Measured by Time-Resolved Fluorescence Resonance Energy Transfer (trFRET)

Varying concentrations of inhibitor were added to to an assay well containing: Jak1 enzyme (aa 845-1142; expressed in SF9 cells as a GST fusion and purified by glutathione affinity chromatography; 4 nM), peptide substrate (biotin-TYR2, Sequence: Biotin-(Ahx)-AEEEYFFLFA-amide; 2 μM), MOPSO pH 6.5 (50 mM), $MgCl_2$ (10 mM), $MnCl_2$ (2 mM), DTT (2.5 mM), BSA (0.01% w/v), $Na_3VO_4$ (0.1 mM) and ATP (0.001 mM). After about 60 min incubation at rt, the reaction was quenched by addition of EDTA (final concentration: 100 mM) and developed by addition of revelation reagents (final approximate concentrations: 30 mM HEPES pH 7.0, 0.06% BSA, 0.006% Tween-20, 0.24 M KF, 80 ng/mL PT66K (europium labeled anti-phosphotyrosine antibody cat #61T66KLB Cisbio, Bedford, Mass.) and 3.12 μg/mL SAXL (Phycolink streptavidin-allophycocyanin acceptor, cat #PJ52S, Prozyme, San Leandro, Calif.). The developed reaction was incubated in the dark either at about 4° C. for about 14 h or for about 60 min at rt, then read via a time-resolved fluorescence detector (Rubystar, BMG) using a 337 nm laser for excitation and emission wavelength of 665 nm. Within the linear range of the assay, the observed signal at 665 nm is directly related to phosphorylated product and used to calculate the $IC_{50}$ values.

In Vitro Jak3 Kinase Activity Measured by Time-Resolved Fluorescence Resonance Energy Transfer (trFRET)

Varying concentrations of inhibitor were added to to an assay well containing: Jak3 enzyme (aa 811-1103; expressed in SF9 cells as a GST fusion and purified by glutathione affinity chromatography; 3nM), peptide substrate (biotin-TYR2, Sequence: Biotin-(Ahx)-AEEEYFFLFA-amide; 2 μM), MOPSO pH 6.5 (50 mM), $MgCl_2$ (10 mM), $MnCl_2$ (2 mM), DTT (2.5 mM), BSA (0.01% w/v), $Na_3VO_4$ (0.1 mM) and ATP (0.001 mM). After about 60 min incubation at rt, the reaction was quenched by addition of EDTA (final concentration: 100 mM) and developed by addition of revelation reagents (final approximate concentrations: 30 mM HEPES pH 7.0, 0.06% BSA, 0.006% Tween-20, 0.24 M KF, 80 ng/mL PT66K (europium labeled anti-phosphotyrosine antibody cat #61T66KLB Cisbio, Bedford, Mass.) and 0.8 μg/mL SAXL (Phycolink streptavidin-allophycocyanin acceptor, cat #PJ52S, Prozyme, San Leandro, Calif.). The developed reaction was incubated in the dark either at about 4° C. for about 14 h or for about 60 min at rt, then read via a time-resolved fluorescence detector (Rubystar, BMG) using a 337 nm laser for excitation and emission wavelength of 665 nm. Within the linear range of the assay, the observed signal at 665 nm is directly related to phosphorylated product and used to calculate the $IC_{50}$ values.

In Vitro Syk Kinase Activity Measured by Time-Resolved Fluorescence Resonance Energy Transfer (trFRET)

0.3nM Syk catalytic domain (aa356-635, purified in-house at the Abbott Bioreseach Center) was mixed with 0.1 μM peptide substrate (biotin-TYR1, Sequence: Biotin-(Ahx)-GAEEEIYAAFFA-COOH) at varying concentrations of inhibitor in reaction buffer: 50 mM MOPSO pH 6.5, 10 mM $MgCl_2$, 2 mM $MnCl_2$, 2.5 mM DTT, 0.01% BSA, 0.1 mM $Na_3VO_4$ and 0.001 mM ATP. After about 60 min incubation at rt, the reaction was quenched by addition of EDTA (final concentration: 100 mM) and developed by addition of revelation reagents (final approximate concentrations: 30 mM HEPES pH 7.0, 0.06% BSA, 0.006% Tween-20, 0.24 M KF, 90 ng/mL PT66K (europium labeled anti-phosphotyrosine antibody cat #61T66KLB Cisbio, Bedford, Mass.) and 0.6 μg/mL SAXL (Phycolink streptavidin-allophycocyanin acceptor, cat #PJ52S, Prozyme, San Leandro, Calif.). The developed reaction was incubated in the dark either at about 4° C. for about 14 h or for about 60 min at rt, then read via a time-resolved fluorescence detector (Rubystar, BMG) using a 337 nm laser for excitation and emission wavelength of 665 nm. Within the linear range of the assay, the observed signal at 665 nm is directly related to phosphorylated product and used to calculate the $IC_{50}$ values.

Other In Vitro Kinase Assays Measured by Time-Resolved Fluorescence Resonance Energy Transfer (trFRET)

Other kinase assays were performed using a similar protocol. Additional purified enzymes Tyk2 (aa 880-1185 with an N-terminal histidine-tag and C-terminal FLAG tag; purified in-house by immobilized metal ion affinity chromatography), RET (aa 711-1072 with an N-terminal histidine-tag; purified by immobilized metal ion affinity chromatography), Syk (aa356-635 with a C-terminal histidine tag; purified by immobilized metal ion affinity chromatography), and KDR (aa 792-1354 with an N-terminal histidine-tag; purified in-house by immobilized metal ion affinity and ion-exchange chromatography) were expressed in SF9 cells and Aurora 1/B (aa1-344 with a N-terminal histidine-tag and purified by immobilized metal ion affinity chromatography) was expressed in E. coli. Other enzymes used are available from commercial sources. Enzymes were mixed with biotinylated substrates at varying concentrations of inhibitor in different reaction buffers (see Table A). After about 60 min incubation at rt, the reaction was quenched by addition of EDTA and developed by addition of revelation reagents (final approximate concentrations: 30 mM HEPES pH 7.0, 0.06% BSA, 0.006% Tween-20, 0.24 M KF, varying amounts of donor europium labeled antibodies and acceptor streptavidin labeled allophycocyanin (SAXL)). The developed reactions were incubated in the dark either at about 4° C. for about 14 h or for about 60 min at rt, then read in a time-resolved fluorescence detector (Rubystar, BMG Labtech) as described above.

TABLE A

Specific conditions (per 40 μL enzyme reaction) for the various enzymes are detailed below:

| Enzyme | Construct | Substrate | Assay Buffer | Enzyme Conc. (ng/well) | Substrate Conc. | ATP Conc. (mM) | DMSO Conc. (%) | Reaction Time (min) | Detection condition |
|---|---|---|---|---|---|---|---|---|---|
| Jak1 | aa 845-1142 | Biotin-TYR2 | MOPSO | 5 | 2 μM | 0.001 | 5 | 60 | 8 ng/well PT66K, 0.39 μg/well SAXL |
| Jak2 | Millipore cat# 14-640 | Biotin-TYR1 | MOPSO | 2.5 | 2 μM | 0.001 | 5 | 60 | 8 ng/well PT66K, 0.078 μg/well SAXL |
| Jak3 | aa 811-1103 | Biotin-TYR2 | MOPSO | 4.5 | 2 μM | 0.001 | 5 | 60 | 8 ng/well PT66K, 0.078 μg/well SAXL |
| Tyk2 | aa 880-1185 | Biotin-TYR1 | MOPSO | 9 | 2 μM | 0.001 | 5 | 60 | 8 ng/well PT66K, 0.078 μg/well SAXL |
| Aurora 1/B | aa 1-344 | KinEASE S2 | MOPS | 20 | 0.5 μM | 0.1 | 5 | 60 | 15 ng/well Eu-STK-Ab, 0.34 μg/wel SAXL |
| KDR | aa 789-1354 | Biotin-TYR2 | HEPES | 10 | 2 μM | 0.1 | 5 | 60 | 8 ng/well PT66K, 0.078 μg/well SAXL |
| JNK1 | Millipore cat# 14-327 | Biotin-ATF2-pep | MOPS | 10 | 1 μM | 0.01 | 5 | 60 | 2.58 ng/well Anti-pATF2-Eu, 0.6 μg/well SAXL |
| JNK2 | Millipore cat# 14-329 | Biotin-ATF2-pep | MOPS | 5 | 0.5 μM | 0.01 | 5 | 60 | 2.58 ng/well Anti-pATF2-Eu, 0.6 μg/well SAXL |
| RET | aa 711-1072 | Biotin-poly GluTyr | HEPES | 4 | 10 ng/well | 0.01 | 5 | 60 | 8 ng/well PT66K, 0.078 μg/well SAXL |
| P70 S6 Kinase | Millipore cat# 14-486 | KinEASE S3 | MOPS | 0.5 | 0.25 μM | 0.01 | 5 | 60 | 15 ng/well Eu-STK-Ab, 0.34 μg/well SAXL |

TABLE A-continued

Specific conditions (per 40 μL enzyme reaction) for the various enzymes are detailed below:

| Enzyme | Construct | Substrate | Assay Buffer | Enzyme Conc. (ng/well) | Substrate Conc. | ATP Conc. (mM) | DMSO Conc. (%) | Reaction Time (min) | Detection condition |
|---|---|---|---|---|---|---|---|---|---|
| PKN2 | Invitrogen cat# PV3879 | KinEASE S3 | MOPS | 0.7 | 0.5 μM | 0.001 | 5 | 60 | 15 ng/well Eu-STK-Ab, 0.34 μg/well SAXL |
| Syk | aa 356-635 | Biotin-TYR1 | MOPSO | 0.4 | 0.1 μM | 0.001 | 5 | 60 | 6.8 ng/well PT66K, 0.045 μg/well SAXL |
| CDK2/Cyclin A | Millipore cat# 14-448 | Biotin-MBP | MOPS | 50 | 2 μM | 0.1 | 5 | 60 | 15 ng/well Anti-pMBP-Eu; 0.34 μg/well SAXL |

Reaction Buffers:

MOPSO buffer contains: 50 mM MOPSO pH 6.5, 10 mM $MgCl_2$, 2 mM $MnCl_2$, 2.5 mM DTT, 0.01% BSA, and 0.1 mM $Na_3VO_4$ HEPES buffer contains: 50 mM HEPES pH 7.1, 2.5 mM DTT, 10 mM $MgCl_2$, 2 mM $MnCl_2$, 0.01% BSA, and 0.1 mM $Na_3VO_4$ MOPS buffer contains: 20 mM MOPS pH 7.2, 10 mM $MgCl_2$, 5 mM EGTA, 5 mM Beta-phosphoglycerol, 1 mM $Na_3VO_4$, 0.01% Triton-X-100 and 1 mM DTT Substrates:

Biotin-ATF2-peptide sequence: Biotin-(Ahx)-AGAGDQTPTPTRFLKRPR-amide

Biotin-TYR1-peptide sequence: Biotin-(Ahx)-GAEEEI-YAAFFA-COOH

Biotin-TYR2-peptide sequence: Biotin-(Ahx)-AEEEYF-FLFA-amide

Biotin-MBP-peptide sequence: Biotin-(Ahx)-VHFFKNIVTPRTPPPSQGKGAEGQR-amide

Biotin-polyGluTyr peptide was purchased from Cisbio (cat #61GT0BLA, Bedford, Mass.)

KinEASE S2 and S3peptides were purchased from Cisbio (cat #62ST0PEB, Bedford, Mass.)

Detection Reagents:

Anti-pATF2-Eu was custom-labeled by Cisbio (Bedford, Mass.)

Anti-pMBP-Eu was custom-labeled by Cisbio (Bedford, Mass.)

PT66K was purchased from Cisbio (cat #61T66KLB, Bedford, Mass.)

SAXL was purchased from Prozyme (cat #PJ25S, San Leandro, Calif.)

Human T-Blasts IL-2 pSTAT5 Cellular Assay

Materials:

Phytohemaglutinin T-blasts were prepared from Leukopacks purchased from Biological Specialty Corporation, Colmar, Pa. 18915, and cryopreserved in 5% DMSO/media prior to assay.

For this assay the cells were thawed in assay medium with the following composition: RPMI 1640 medium (Gibco 11875093) with 2 mM L-glutamine (Gibco 25030-081), 10 mM HEPES (Gibco 15630-080), 100 μg/mL Pen/Strep (Gibco 15140-122), and 10% heat inactivated FBS (Gibco 10438026). Other materials used in the assay: DMSO (Sigma D2650), 96-well dilution plates (polypropylene) (Corning 3365), 96-well assay plates (white, ½ area, 96 well) (Corning 3642), D-PBS (Gibco 14040133), IL-2 (R&D 202-IL-10 (10 μg)), Alphascreen pSTAT5 kit (Perkin Elmer TGRS5S10K) and Alphascreen protein A kit (Perkin Elmer 6760617M)

Methods:

T-Blasts were thawed and cultured for about 24 h without IL-2 prior to assay. Test compounds or controls are dissolved and serially diluted in 100% DMSO. DMSO stocks are subsequently diluted 1:50 in cell culture media to create the 4× compound stocks (containing 2% DMSO). Using a Corning white 96 well, ½ area plate, cells are plated at $2\times10^5$/10 μl/well in 10 μL media followed by addition of 5 μL of 4× test compound in duplicate. Cells are incubated with compound for about 0.5 h at about 37° C. Next, 5 μL of IL-2 stock is added at 20 ng/mL final concentration. IL-2 is stored as a 4 μg/mL stock solution, as specified by the manufacturer, at about −20° C. in aliquots and diluted 1:50 with assay media (to 80 ng/mL) just prior to use. The contents of the wells are mixed by carefully tapping sides of plate(s) several times followed by incubation at about 37° C. for about 15 min. The assay is terminated by adding 5 μL of 5× AlphaScreen lysis buffer and shaking on an orbital shaker for about 10 min at rt. Alphascreen acceptor bead mix is reconstituted following Perkin Elmer's protocol. 30 μL/well of reconstituted Alphascreen acceptor bead mix was added, covered with foil then shaken on orbital shaker for about 2 min on high then about 2 h on low. Donor bead mix is reconstituted following Perkin Elmer's AlphaScreen protocol; 12 μL/well are added, covered with foil then shaken for about 2 min on high, and about 2 h on low. Plates are read on an EnVision reader following Perkin Elmer's AlphaScreen protocol instructions.

TF-1 IL-6 pSTAT3Cellular Assay

Materials:

TF-1 cells (ATCC #CRL-2003). Culture medium: DMEM medium (Gibco 11960-044) with 2 mM L-glutamine (Gibco 25030-081), 10 mM HEPES (Gibco 15630-080), 100 μg/mL Pen/Strep (Gibco 15140-122), 1.5 g/L sodium bicarbonate (Gibco 25080-094), 1 mM sodium pyruvate (Gibco 11360-070), 10% heat inactivated FBS (Gibco 10437-028), and 2 ng/mL GM-CSF (R&D 215-GM-010). Other materials used in this assay: DMSO (Sigma D2650), 96-well dilution plates (polypropylene) (Corning 3365), 96-well assay plates (white, ½ area, 96 well) (Corning 3642), D-PBS (Gibco 14040133), IL-6 (R&D 206-IL/CF-050 (50 μg)), Alphascreen pSTAT3 kit (Perkin Elmer TGRS3S10K) and Alphascreen protein A kit (Perkin Elmer 6760617M).

Methods:

Prior to the assay, cells are cultured for about 18 h in the culture medium without GM-CSF. Test compounds or controls are dissolved and serially diluted in 100% DMSO. DMSO stocks are subsequently diluted 1:50 in cell culture media to create the 4× compound stocks (containing 2% DMSO). Using a Corning white 96 well, ½ area plate, cells are plated at $2\times10^7$/10 μL/well in 10 μL media followed by addition of 5 μL of the 4× test compound stock in duplicate. Cells are incubated with compound for about 0.5 h at about 37° C. followed by addition of 5 μL of 400 ng/mL IL-6. IL-6 is stored in 10 μg/mL aliquots using endotoxin free D-PBS (0.1% BSA) at about −20° C. Prior to assay IL-6 is diluted to 400 ng/mL in culture media and applied (5 μL/well) to all wells, except to negative control wells where 5 μL/well of media is added. The contents of the wells are mixed carefully by tapping the side of the plate several times. Plates are incubated at about 37° C. for about 30 min. Cells are lysed by adding 5 μL of 5× AlphaScreen cell lysis buffer to all wells, shaken for about 10 min at rt then assayed. Alternatively, assay plates may be frozen at about −80° C. and thawed later at P. Using the pSTAT3 SureFire Assay kit (Perkin Elmer #TGRS3S10K) acceptor bead mix is reconstituted following Perkin Elmer's AlphaScreen protocol instructions. 30 μL are added per well then the plate is covered with foil and shaken on an orbital shaker for about 2 min on high, then about 2 h on low at rt. Donor bead mix is reconstituted following Perkin Elmer's AlphaScreen protocol instructions. 12 μL are added per well, then covered with foil and shaken on orbital shaker for about 2 min on high, then about 2 h on low at about 37° C. Plates are read on an EnVision reader following Perkin Elmer's AlphaScreen protocol instructions at rt.

UT7/EPO pSTAT5 Cellular Assay

Materials:

UT7/EPO cells are passaged with erythropoietin (EPO), split twice per week and fresh culture medium is thawed and added at time of split. Culture Medium: DMEM medium (Gibco 11960-044) with 2 mM L-glutamine (Gibco 25030-081), 10 mM HEPES (Gibco 15630-080), 100 U/mL Pen/Strep (Gibco 15140-122), 10% heat inactivated FBS (Gibco 10437-028), EPO (5 μL/mL=7.4 μL of a 7 μg/mL stock per mL of medium). Assay media: DMEM, 2 mM L-glutamine, 5% FBS, 10 mM HEPES. Other materials used in the assay: DMSO (Sigma D2650), 96-well dilution plates (polypropylene) (Corning 3365), 96-well assay plates (white, ½ area, 96 well) (Corning 3642), D-PBS (Gibco 14040133), IL-2 (R&D 202-IL-10 (10 ng)), Alphascreen pSTAT5 kit (Perkin Elmer TGRS5S10K) and Alphascreen protein A kit (Perkin Elmer 6760617M).

Methods:

Culture cells for about 16 h without EPO prior to running assay. Test compounds or controls are dissolved and serially diluted in 100% DMSO. DMSO stocks are subsequently diluted 1:50 in cell culture media to create the 4× compound stocks (containing 2% DMSO). Using a Corning white 96 well, ½ area plate, cells are plated at $2\times10^5$/10 μL/well in 10 μL media followed by addition of 5 μL, of 4× test compound stock in duplicate. Cells are incubated with compound for about 0.5 h at about 37° C. After incubation, 5 μL of EPO is added to afford a final concentration of 1 nM EPO. The contents of the wells are mixed by carefully tapping sides of the plate several times followed by incubation at about 37° C. for about 20 min. 5 μL of 5× AlphaScreen lysis buffer are added followed by shaking on an orbital shaker for about 10 min at rt. 30 μL/well of acceptor beads are added after reconstitution following Perkin Elmer's AlphaScreen protocol, covered with foil and shaken on orbital shaker for about 2 min on high, then about 2 h on low. Donor beads are reconstituted following Perkin Elmer's AlphaScreen protocol instructions followed by addition of 12 μL/well, covered with foil and shaken on an orbital shaker for about 2 min on high, about 2 h on low. Plates are read on an EnVision reader following Perkin Elmer's AlphaScreen protocol instructions.

Antigen-Induced Degranulation of RBL-2H$_3$Cells:

RBL-2H3 cells are maintained in T75 flasks at about 37° C. and 5% $CO_2$, and passaged every 3-4 days. To harvest cells, 20 mL of PBS is used to rinse the flask once, and then 3 mL of Trypsin-EDTA is added and incubated at about 37° C. for about 2 min. Cells are transferred to a tube with 20 mL medium, spun down at 1000 RPM at rt for about 5 min and resuspended at $1\times10^6$ cells/mL. Cells are sensitized by adding DNP-specific mouse IgE to a final concentration of 0.1 μg/mL. 50 pt of cells are added to each well of a 96 well flat bottom plate ($50\times10^3$ cells/well) and incubated overnight at about 37° C. in 5% $CO_2$. The next day, compounds are prepared in 100% DMSO at 10 mM. Each compound is then serially diluted 1:4 six times in 100% DMSO. Each compound dilution is then diluted 1:20 and then 1:25, both dilutions in Tyrode's buffer. Media is aspirated from the cell plates and the cells are rinsed twice with 100 μL of Tyrode's buffer (prewarmed to about 37° C.). 50 pt of compounds diluted in Tyrode's buffer are added to each well and the plates are incubated for about 15 min at about 37° C. in 5% $CO_2$. 50 μL of 0.2 μg/mL DNP-HSA in Tyrode's buffer is then added to each well and the plates are incubated for about 30 min at about 37° C. in 5% $CO_2$. The final concentration of the various components in the incubation mix are 0.002-10 μM compounds, 0.1% DMSO, and 0.1 μg/mL DNP-HSA. As one control, 0.2% DMSO (no compound) in Tyrode's buffer is added to a set of wells to determine maximum stimulated release. As a second control, Tyrode's buffer without DNP-HSA is added to a set of wells with containing 0.2% DMSO without compounds to determine unstimulated release. Each condition (compounds and controls) is set up in triplicate wells. At the end of the 30 min incubation, 50 μL of supernate is transferred to a new 96 well plate. The remaining supernate in the cell plates is aspirated and replaced with 50 μL of 0.1% Triton X-100 in Tyrode's buffer to lyse the cells. 50 μL of freshly prepared 1.8 mM 4-Nitrophenyl N-acetyl-β-D-glucosaminide (pNAG) is then added to each well of supernate and cell lysate and the plates are incubated for about 60 min at about 37° C. in 5% $CO_2$. 100 μL of 7.5 mg/mL sodium bicarbonate is added to each well to stop the reaction. The plates are then read at 405 nm on a Molecular Devices SpectraMax 250 plate reader.

Calculation of Results

1) The plate background $OD_{405}$ obtained from wells containing Tyrode's buffer and pNAG (no supernate or lysate) is subtracted from the $OD_{405}$ reading for each well containing supernate or lysate.

2) The release for each well is expressed as the percentage of the total release for that well, where the total release is twice the release in the supernate plus the release in the cell lysate. This calculation corrects for variable cell number in each well.

3) The maximum response is the mean response of wells containing DNP-HSA but no compound.

4) The minimum response is the mean response of wells containing no DNP-HSA and no compound.

5) The response in each compound well is calculated as a percentage of the maximum response (expressed as % control) where the maximum response is 100% and the minimum response is 0%.

6) A dose response curve is generated for each compound and the $IC_{50}$ of the curve is calculated using Prism GraphPad software and nonlinear least squares regression analysis.

Acute in vivo measurement of JAK inhibition by compounds is measured using the:

Concanavalin A (Con A)-Induced Cytokine Production in Lewis Rats

The test compound is formulated in an inert vehicle (for example but not limited to 0.5% hydroxypropylmethyl cellulose (Sigma, cat #H3785)/0.02% Tween 80 (Sigma, cat #4780) in water) at the desired concentration to achieve doses in the range of 0.01-100 mg/kg. Six-week-old male Lewis rats (125 g-150 g) (Charles River Laboratories) are dosed with the compound orally, at time zero (0 min). After about 30 min the rats are injected intravenously (i.v.) with 10 mg/kg Concanavalin A (Con A, AmershamBioscience, cat #17-0450-01) dissolved in PBS (Invitrogen, cat #14190). About 4 h later, the rats are cardiac bled and their plasma is analyzed for levels of IL-2 (ELISA kit: R&D Systems cat #R2000) and IFN-γ (ELISA kit: R&D Systems cat #RIF00).

Acute in vivo measurement of Fcγ receptor signaling inhibition of the compounds is measured using the:

Reverse Passive Arthus Model

On day 0, OVA was made up at a concentration of 17.5 mg/mL, in PBS by rocking gently until a solution was formed. 2% Evans Blue solution (Sigma Aldrich, cat #E2129) was then added to double the volume for a final concentration of 8.75 mg/mL of OVA and 1% Evans Blue dye. Anti-OVA antibody (Abazyme), stock concentration 10 mg/mL, was thawed and a 400 μg/100 μL solution was made with PBS. Compounds were made up by adding the vehicle, 0.5% HPMC with 0.02% Tween80, and vortexing for about 15 seconds followed by homogenizing for a minimum of about 2 min at 28,000 rpm until there was a fine particulate suspension with no clumps of compound. Rats were weighed and dosed with compound at a pre-determined t-max based on pharmacokinetic studies. Animals were then placed under general anesthesia with a 5% isoflourane and oxygen mixture and shaved. Using a ½ mL insulin syringe two sites were injected i.d., 1 site with 100 μL of 400 μg/100 μL of anti-OVA antibody, and 1 site with 100 μL of sterile PBS. Each site was then circled with permanent marker for explant later. Right after i.d. injections animals were injected with 2004, of the OVA (10 mg/kg)/Evans Blue mixture i.v., using a ½ mL insulin syringe. About four hours post injection animals were euthanized, bled via cardiac puncture and blood was collected using a plasma separating tube. Blood samples were stored on ice until centrifugation (within about 2 h of collection). Each injection site was removed with a disposable biopsy punch (Acuderm Acu-Punch Disposable 12 mm), cut into four pieces and placed in a pre-labeled 2 mL eppendorf tube. One mL of DMF was added to each biopsy tube and placed in a heat block for about 24 h at about 50° C. About 24 h after incubation 100 μL of each sample was added to a 96 well flat bottom plate. The samples were read at 620 nm on a plate reader using the Softmax software in order to measure the levels of Evan's Blue dye. Background was removed by subtracting the OD from the PBS injected site from the OD of the anti-OVA injected site for each individual animal. Plasma samples were spun down in a microcentrifuge for about 5 min at 16.1 rcf. 200 μL of plasma was placed in a 1.7 mL eppendorf tube for drug level measurement and tubes were stored at −80° C. until evaluation.

Chronic in vivo effects of the compounds on anc arthritis disease model is measured using the:

Adjuvant Induced Arthritis (AIA) in a Lewis Rat

Female Lewis rats, (6 weeks of age, 125 g-150 g in weight from Charles River Laboratories) are immunized intradermally (i.d.) in the right hind-footpad with 100 μL of a suspension of mineral oil (Sigma, cat #M5905) and containing 200 μg M. tuberculosis, H37RA (Difco, cat #231141). The inflammation appears in the contra-lateral (left) hind paw seven days after the initial immunization. Seven days post immunization, the compound is formulated in an inert vehicle (for example but not limited to 0.5% hydroxypropylmethyl cellulose (Sigma, cat #H3785)/0.02% Tween 80 (Sigma, cat #4780) in water) and dosed orally once or twice a day for at least 10 days. Baseline paw volume is taken on day 0 using a water displacement pleythsmograph (Vgo Basile North America Inc. PA 19473, Model #7140). Rats are lightly anesthetized with an inhalant anesthetic (isoflurane) and the contra-lateral (left) hind paw is dipped into the plethysmograph and the paw volume is recorded. The rats are scored every other day up to day 17 after immunization. On day 17 after immunization, all rats are exsanguinated by cardiac puncture under isoflurane anesthesia, and the left hind paw is collected to assess the impact on bone erosion using micro-CT scans (SCANCO Medical, Southeastern, Pa., Model #μCT 40) at a voxel size of 18 μm, a threshold of 400, sigma-gauss 0.8, support-gauss 1.0. Bone volume and density is determined for a 360 μm (200 slice) vertical section encompassing the tarsal section of the paw. The 360 nm section is analyzed from the base of the metatarsals to the top of the tibia, with the lower reference point fixed at the tibiotalar junction. Drug exposure is determined in the plasma using LC/MS. or the:

Collagen Induced Arthritis (CIA) in a Lewis Rat

On day −1 Collagen Type II (CII), soluble from bovine nasal septum (Elastin Products, Cat #CN276) was weighed out for a dose of 600 μg/rat, 0.01M acetic acid (150 μL HOAc USP grade. J. T. Baker, order#9522-03, and 250 mL Milli Q Water) was added for a concentration of 4 mg/mL. The vial was covered with aluminum foil and placed on a rocker at about 4° C. overnight. On day 0 collagen stock solution was diluted 1:1 with Incomplete Freunds adjuvant (IFA) (Difco labs, cat #263910) using a glass Hamilton luer lock syringe (SGE Syringe Perfection VWR cat #007230), final concentration 2 mg/mL. Female Lewis rats (Charles River Laboratories) acclimated for 7 days at the time of immunization weighing approximately 150 g were anesthetized in an anesthesia chamber using isoflurane (5%) and oxygen. Once the rats were completely anesthetized, they were transferred to a nose cone to maintain anesthesia during the injections. Rats were shaved at the base of the tail, 300 μL of collagen was injected i.d. on the rump of the rat, n=9 per group. 100 μL at three sites with a 500 μL leur lock syringe and a 27 g needle. IFA control rats are injected in the same manner (n=6). The IFA is a 1:1 emulsion with the 0.01M acetic acid. Boost was done on day 6 of the study. Shaving was not done on this day and injections were done in the same manner as the immunization. The inflammation appears in both hind paws 10 days after the initial immunization. 10 days post immunization, the compound was formulated in an inert vehicle (for example but not limited to 0.5% hydroxypropylmethyl cellulose (Sigma, cat

#H3785)/0.02% Tween 80 (Sigma, cat #4780) in water) and dosed orally once or twice a day for at least 9 days. Baseline paw volume was taken on day 7 using a water displacement pleythsmograph (Vgo Basile North America Inc. PA 19473, Model #7140). Rats were lightly anesthetized with an inhalant anesthetic (isoflurane) and both hind paws were dipped into the plethysmograph and the paw volume was recorded. The rats were scored 2 to 3 times a week up to day 18 after immunization. On day 18 after immunization, all rats were exsanguinated by cardiac puncture under isoflurane anesthesia, and the hind paws were collected to assess the impact on bone erosion using micro-CT scans (SCANCO Medical, Southeastern, Pa., Model # μCT 40) at a voxel size of 18 μm, a threshold of 400, sigma-gauss 0.8, support-gauss 1.0. Bone volume and density was determined for a 360 μm (200 slice) vertical section encompassing the tarsal section of the paw. The 360 μm section was analyzed from the base of the metatarsals to the top of the tibia, with the lower reference point fixed at the tibiotalar junction. Drug exposure was determined from plasma using LC/MS.

Chronic in vivo effects of the compounds on an asthma disease model is measured using the:

OVA Induced Rat Asthma Model

Female Brown Norway rats (7-9 weeks of age) were sensitized on day 0 and 7 with 40 μg ovalbumin (OVA) (Sigma-Aldrich, St. Louis, Mo.) in a 20 mg/ml solution of Alum Imject (Pierce, Rockford, Ill.). The rats were subsequently challenged intratracheally on day 19 and 20 with 1.5 μg OVA in 50 μL PBS. Dosing of inhibitor began on day 18 and continues through day 22. On day 22, 48 h after the second challenge, rats were subjected to an anesthetized and restrained pulmonary function test. Airway hyperresponsiveness (AHR) was assessed using whole body plethysmography. Briefly, a surgical plane of anesthesia was induced with an intraperitoneal injection of 60 mg/kg ketamine and 5 mg/kg xylazine (Henry Schein, Inc., Melville, N.Y.). A tracheal cannula was surgically inserted between the 3rd and 4th tracheal rings. Spontaneous breathing was prevented by jugular vein injection of 0.12 mg/kg pancuronium bromide (Sigma-Aldrich, St Louis, Mo.). Animals were placed in a whole body plethysmograph (Buxco Electronics, Inc., Wilmington, N.C.) and mechanically ventilated with 0.2 mL room air at 150 breaths per minute with a volume controlled ventilator (Harvard Apparatus, Framingham, Mass.). Pressure in the lung and flow within the plethysmograph were measured using transducers and lung resistance was calculated as pressure/flow using Biosystem Xa software (Buxco Electronics). Airway resistance was measured at baseline and following challenge with 3, 10, and 30 mg/mL methacholine (Sigma Aldrich, St. Louis, Mo.) delivered with an inline ultrasonic nebulizer. Upon completion of pulmonary function testing, the lungs were lavaged 3 times with 1 mL sterile PBS. The volume from the first wash was centrifuged at 2000 rpm for 5 min, and the supernatant is stored for subsequent analysis. The volume of washes 2 through 3 are added to the pellet derived from the first wash and subsequently processed for evaluation of cellular infiltrate by flow cytometry. Plasma was collected from blood drawn from the vena cava and was used for evaluation of drug concentrations.

The teachings of all references, including journal articles, patents and published patent applications, are incorporated herein by reference in their entirety.

The following examples are for illustrative purposes and are not to be construed as limiting the scope of the present invention.

General Synthetic Schemes

Compounds of the invention may be prepared using the synthetic transformations illustrated in Schemes I-XXVIII. Starting materials are commercially available, may be prepared by the procedures described herein, by literature procedures, or by procedures that would be well known to one skilled in the art of organic chemistry. Methods for preparing pyrrolo[2,3-e][1,2,4]triazolo[4,3-a]pyrazine compounds of the invention are illustrated in Scheme I. In Scheme I, step a, commercially available 3,5-dibromopyrazin-2-amine 1 is reacted with a (trimethylsilyl)acetylene via a Sonogashira cross coupling using methods known to one skilled in the art (for example Example #1 or WO2006058120A1) to give alkyne 2. Alkyne 2 can be cyclized (Scheme I, step b) to provide protected pyrrolo[2,3-b]pyrazine 3using methods known to one skilled in the art (for example Example #1 or WO2006058120A1). In Scheme I, step c, a substituted hydrazine is introduced by reaction with pyrrolopyrazines 3under Buchwald-Hartwig amination conditions (for example Example #1 or Advanced Synthesis & Catalysis 2004, 346, 1599-1626) to give pyrrolopyrazines 4. If R" is such that pyrrolopyrazines 4 contain a hydrazide (R"=—C(O)R'''), the material may be directly cyclized to pyrrolotriazolopyrazines 7 (Scheme I, step h) using conditions such as those described in General Procedures B or ZZZZ or by methods known to one skilled in the art (for example Bioorganic & Medicinal Chemistry Letters 2007, 17(12), 3373-3377 or Journal of Medicinal Chemistry 1990, 33(9), 2326-2334). If R" is a protecting group, deprotection of compounds 4 (Scheme I, step d) to yield hydrazinylpyrrolopyrazines 5 can be performed using conditions such as those described in General Procedures E, E.1, F, F.1, Y or BB; or Greene, T. W. and Wuts, P. G. M. "Protective Groups in Organic Synthesis, 3rd Edition", 1999, Wiley-Interscience. For example, a protecting group such as a t-butoxycarbonyl (Boc) group can be removed with acid using conditions such as those described in Example #1, General Procedures E and E.1, or by methods known to one skilled in the art (for example, the books from Larock, R. C. "Comprehensive Organic Transformations: A Guide to Functional Group Preparations, 2nd edition", 1999, Wiley-VCH or Greene, T. W. and Wuts, P. G. M. referenced above). The formation of hydrazides 6 from hydrazinylpyrrolopyrazines 5 (Scheme I, step e) may be accomplished by a variety of methods known to one skilled in the art including in situ conditions such as those described in Example #1, General Procedure A, or standard peptide coupling methods such as those found in Larock, R. C. referenced above. The hydrazides 6 may be cyclized to pyrrolotriazolopyrazines 7 using conditions such as those described in Example #1, General Procedures B, OO, OO.1, or ZZZZ, or by methods known to one skilled in the art (for example, Bioorganic & Medicinal Chemistry Letters 2007, 17(12), 3373-3377 or Journal of Medicinal Chemistry 1990, 33(9), 2326-34). Further functionalization of hydrazides 6 or pyrrolotriazolopyrazines 7 can be performed, if desired, using reactions known to one skilled in the art (for example, Larock, R. C. referenced above). For example, formation of amides, ureas, sulfonamides, aryl amines, heteroaryl amines, sulfonyl ureas, substituted amines, squaramides, or guanidines can be prepared from pyrrolotriazolopyrazines 7 containing a primary or secondary amine (for example General Procedures G, H, I, J, J.1, XXX, EEEE, K, K.1, L, DD, QQ, RR, YY, ZZ followed by AAA, CCC, YYY, X, X.1, TTTT, or EEEEE). Also, deprotection of hydrazides 6 or pyrrolotriazolopyrazines 7 containing a protected primary or secondary amine can be performed using conditions such as those described in Greene, T. W. and Wuts, P. G. M. referenced above or in General Procedures E, E.1, F, F.1, or BB. For example, for R''' containing a protecting group such as a benzyloxycarbonyl (Cbz) group, the protecting group can be removed to yield the unprotected amine (for example General Procedures F, F.1, and DDDDD) and the deprotected compounds 7 may then be reacted further as described above. In some cases, additional reactions may also occur without isolation of initial pyrrolotriazolopyrazines 7 as seen in General Procedure C. Alternatively, hydrazinylpyrrolopyrazines 5 may be directly cyclized to pyrrolotriazolopyrazines 7 (Scheme I, step i) using conditions such as those described in General Procedure BBBBB. Removal of the sulfonamide protecting group of pyrrolotriazolopyrazines 7 may be accomplished using conditions such as those described in Example #1, General Procedures D, XXX, AAAA, BBBB, or CCCC or by methods known to one skilled in the art (for example, the books from Larock, R. C. or Greene, T. W. and Wuts, P. G. M. referenced above) to give pyrrolotriazolopyrazines 8 (Scheme I, step g). Further functionalization of the R''' group in pyrrolotriazolopyrazines 8 can be performed, if desired, using reactions known to one skilled in the art (for example, Larock, R. C. referenced above). For example, amides, ureas, sulfonamides, aryl amines, heteroaryl amines, sulfonyl ureas, substituted amines, squaramides, or guanidines can be prepared from pyrrolotriazolopyrazines 8 with an R''' containing a primary or secondary amine (for example Examples #8-9 or General Procedures G, H, I, J, J.1, XXX, EEEE, K, K.1, L, DD, QQ, RR, YY, ZZ followed by AAA, CCC, YYY, X, X.1, TTTT, or EEEEE). Also, deprotection of the R''' group in pyrrolotriazolopyrazines 8 to yield an unprotected compound can be performed using conditions such as those described in Greene, T. W. and Wuts, P. G. M. referenced above or in General Procedures E, E.1, F, F.1, Y, or BB. For example, a protecting group such as a benzyloxycarbonyl (Cbz) group can be removed from a protected amine to yield the unprotected amine (for example General Procedures F, F.1, and DDDDD) and the deprotected compounds 8 may then be reacted further as described above.

Methods for preparing imidazo[1,2-a]pyrrolo[2,3-e]pyrazines compounds of the invention are illustrated in Scheme II. In step a, Pd-mediated carbonylation of pyrrolopyrazines 3 gives esters 9 using methods known to one skilled in the art such as those described in Example #3; U.S. Pat. Appl. Publ., US 2007293509; or U.S. Pat. Appl. Publ., US 2008248537. Hydrolysis of esters 9 gives acids 10 (Scheme II, step b) using well known conditions such as those described in Example #3 or General Procedure Z. A Curtius rearrangement is used to prepare carbamates 11 as shown in Scheme II, step c using conditions such as those described in Example #3or referenced in Li, J. J. "Name Reactions. A Collection of Detailed Reaction Mechanisms, 2$^{nd}$ edition", 2003, Springer: New York. Alkylation of pyrrolopyrazin-2-ylcarbamates 11 with appropriately substituted 2-halomethyl ketones (which may be prepared via procedures such as those described in General Procedures R and LLLL; Tetrahedron Letters, 1992, (33), 309-312) by methods known to one skilled in the art (for example General Procedures S or S.1; Tetrahedron Letters, 2006, 47(34), 6113-6115; or Journal of Medicinal Chemistry, 2005, 48(14), 4535-4546) yields pyrrolopyrazines 12 (Scheme II, step d). The deprotection of pyrrolopyrazines 12 to pyrrolopyrazines 13 (Scheme II, step e) is accomplished using conditions such as those described in General Procedures E and E.1, or in Greene, T. W. and Wuts, P. G. M. referenced above. As shown in Scheme II, step f, cyclization of pyrrolopyrazines 13 to imidazopyrrolopyrazines 14 can be accomplished by methods known to one skilled in the art (for example, General Procedures T or KKKK; Example #3, European Journal of Medicinal Chemistry, 2001, 36(3), 255-264; or Bioorganic and Medicinal Chemistry Letters, 2007, 17(5), 1233-1237). Further functionalization of the R''' group in imidazopyrrolopyrazines 14 can be performed, Scheme I

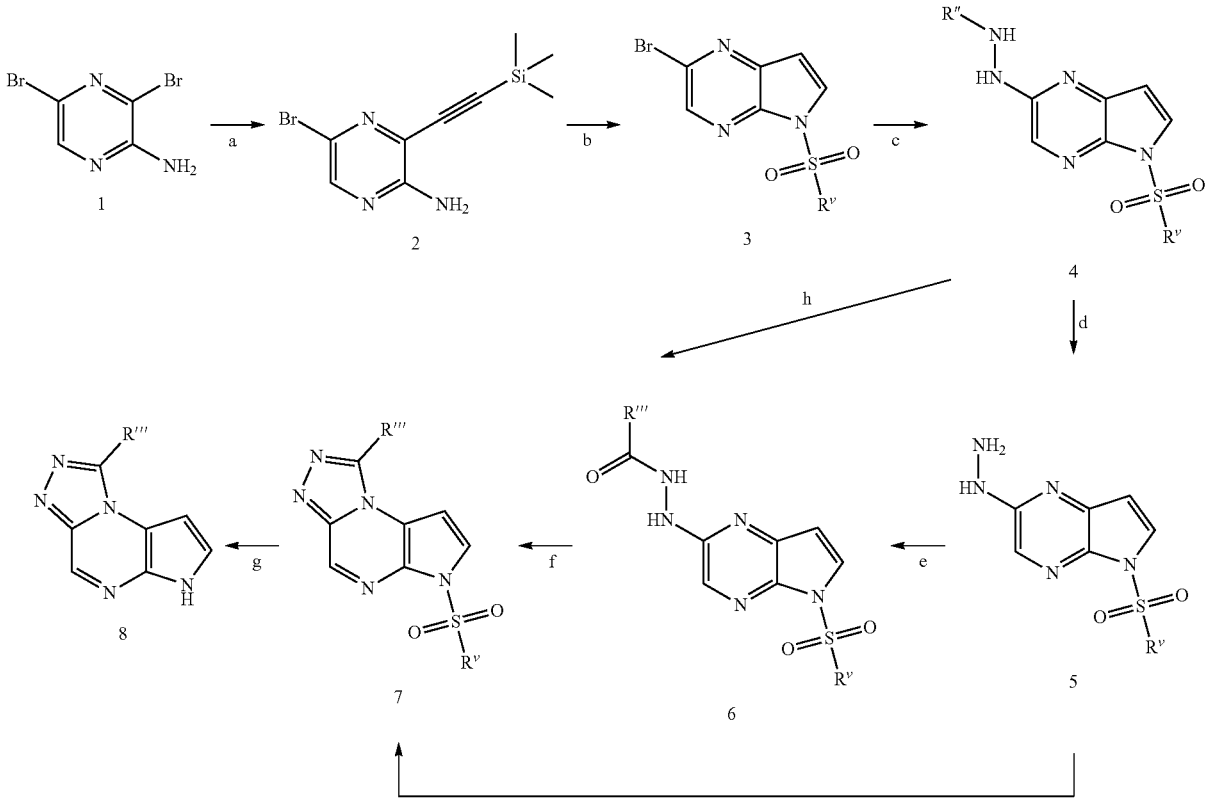

if desired, using reactions known to one skilled in the art (for example, Larock, R. C. referenced above). For example, amides, ureas, sulfonamides, aryl amines, heteroaryl amines, sulfonyl ureas, substituted amines, squaramides, or guanidines can be prepared from imidazopyrrolopyrazines 14 with an R''' group containing a primary or secondary amine (for example, Example #3, Example #7, or General Procedures G, H, I, J, J.1, XXX, EEEE, K, K.1, L, DD, QQ, RR, YY, ZZ followed by AAA, CCC, YYY, X, X.1, TTTT, or EEEEE). Also, deprotection of the R''' group in imidazopyrrolopyrazines 14 to yield deprotected compounds 14 can be performed using conditions such as those described in Greene, T. W. and Wuts, P. G. M. referenced above or in General Procedures E, E.1, F, F.1, Y, or BB and the deprotected compounds 14 may then be reacted further as described above. Removal of the sulfonamide protecting group of imidazopyrrolopyrazines 14 may be accomplished using conditions such as those described in Example #3, General Procedures D, XXX, AAAA, BBBB, or CCCC or by methods known to one skilled in the art (for example, the books from Larock, R. C. or Greene, T. W. and Wuts, P. G. M. referenced above) to give imidazopyrrolopyrazines 15 (Scheme II, step g).

Scheme II

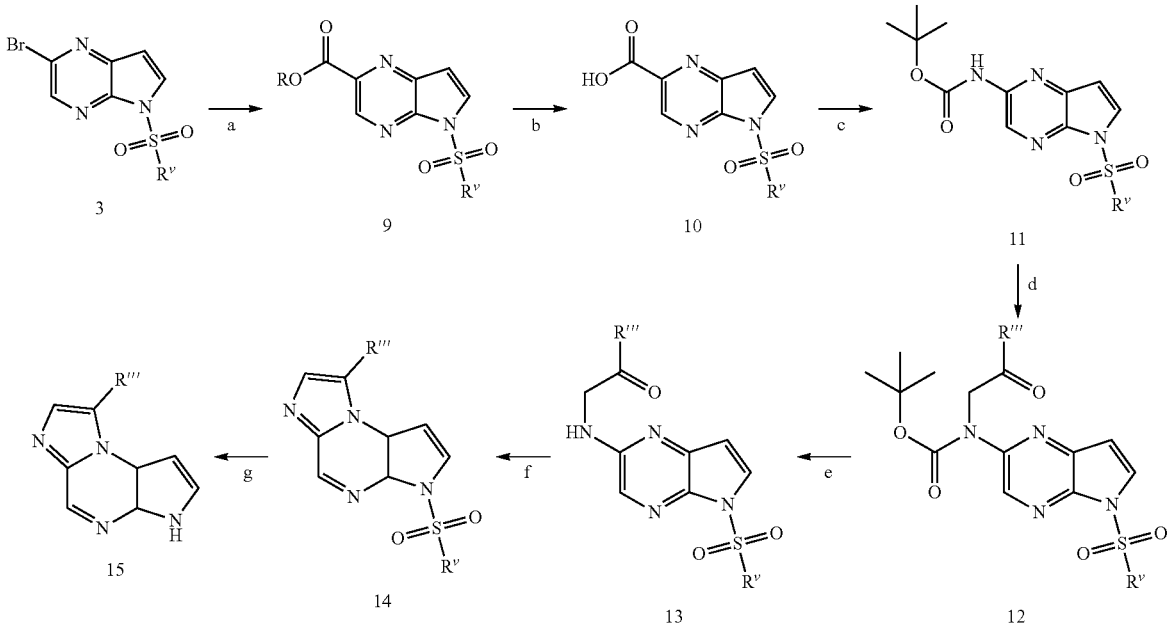

Methods for preparing imidazo[1,5-a]pyrrolo[2,3-e]pyrazines compounds of the invention are illustrated in Scheme III. In step a, Pd-mediated cyanation of bromides 3 gives the corresponding nitriles 16 (for example Example #5 or Tetrahedron Letters 1999, 40(47), 8193-8195). Subsequent reduction of nitriles 16 gives amines 17 (Scheme III, step b) using methods known to one skilled in the art (for example Example #5 or Journal of Medicinal Chemistry 2003, 46(4), 461-473). The coupling of amines 17 with acids provides amides 18 (Scheme III, step c) using well known conditions such as those given in Example #5 or General Procedure H. As shown in Scheme III, step d, the cyclization of amides 18 can be accomplished by conversion to the thioamide followed by treatment with an activating agent (such as a mercury salt, a silver salt or a copper salt) providing the imidazo[1,5-a]pyrrolo[2,3-e]pyrazines 19 (for example Example #5 or General Procedure Q). Alternatively, if R''' contains a nitrogen such that the compounds 18 are ureas instead of amides, then cyclization to imidazo[1,5-a]pyrrolo[2,3-e]pyrazines 19 may be accomplished using $POCl_3$ as described in General Procedure OO or OO.1. Deprotection of the sulfonamide of compounds 19 to yield imidazo[1,5-a]pyrrolo[2,3-e]pyrazines 20 (Scheme III, step e) can be performed using conditions such as those described in Greene, T. W. and Wuts, P. G. M. "Protective Groups in Organic Synthesis, 3rd Edition", 1999, Wiley-Interscience, General Procedures D, XXX, AAAA, BBBB, or CCCC, or Example #5. Further functionalization of the R''' group in imidazo[1,5-a]pyrrolo[2,3-e]pyrazines 19 or imidazo[1,5-a]pyrrolo[2,3-e]pyrazines 20 can be performed, if desired, using reactions known to one skilled in the art (for example, Larock, R. C. referenced above). For example, formation of amides, ureas, sulfonamides, aryl amines, heteroaryl amines, sulfonyl ureas, substituted amines, squaramides, or guanidines can be prepared from compounds 19 or 20 with an R''' group containing a primary or secondary amine (for example, Example #6, or General Procedures G, H, I, J, J.1, XXX, EEEE, K, K.1, L, DD, QQ, RR, YY, ZZ followed by AAA, CCC, YYY, X, X.1, TTTT, or EEEEE). Also, deprotection of the R''' group in compounds 19 or 20 to yield an unprotected compound can be performed using conditions such as those described in Greene, T. W. and Wuts, P. G. M. referenced above or in General Procedures E, E.1, F or F.1 and the deprotected compounds may then be reacted further as described above.

Scheme III

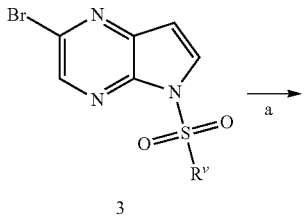

-continued

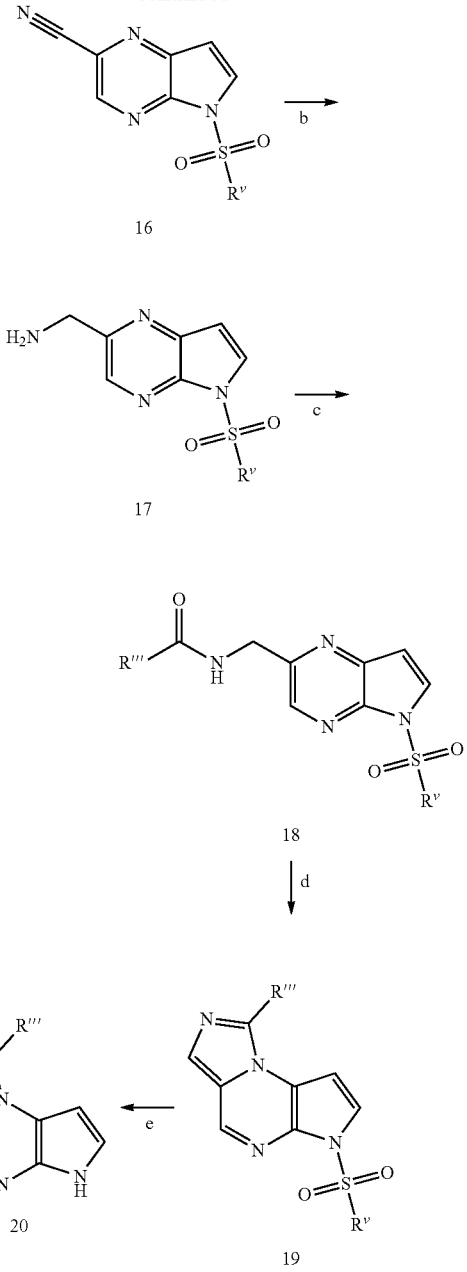

Methods for preparing 4-substituted piperidine-3-carboxylic acid compounds of the invention are illustrated in Scheme IV. In step a, 4-substituted nicotinic acids 21 may be fully saturated using methods that are known to one skilled in the art (for example, General Procedure O or Bioorganic and Medicinal Chemistry Letters 2004, 14(17), 4453-4459). The resulting piperidines 22 may be protected with a suitable amine protecting group (Scheme IV, step b) such as those described in Greene, T. W. and Wuts, P. G. M. "Protective Groups in Organic Synthesis, 3rd Edition", 1999, Wiley-Interscience; Larock, R. C. "Comprehensive Organic Transformations: A Guide to Functional Group Preparations, 2$^{nd}$ edition", 1999, Wiley-VCH or General Procedures M, M.1, or N to give protected piperidines 23.

Scheme IV

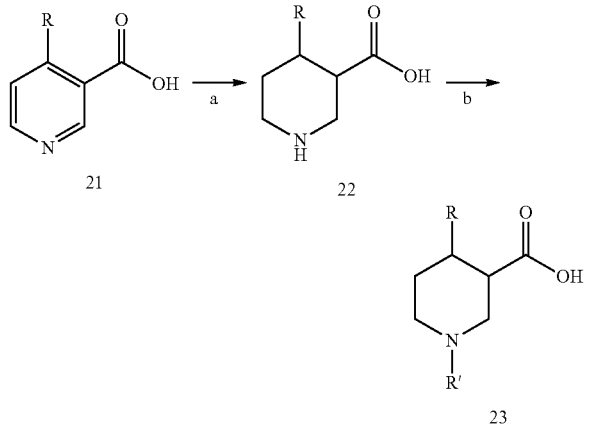

Methods for preparing amino-substituted cyclopentyl carboxylic acids 32 for use in the preparation of compounds of the invention are illustrated in Scheme V. In step a, β-ketoesters 24 may be condensed with an alkyl 4-chloroacetoacetate 25 to give cyclic β-ketoester enolate salts 26 (for example, General Procedure U). Decarboxylation of compounds 26 to give α,β-unsaturated ketones 27 (Scheme V, step b) is accomplished by standard methods known to one skilled in the art (for example, General Procedure V). As shown in step c, hydrogenation of α,β-unsaturated ketones 27 provides the saturated ketones 28 (for example, General Procedures W or W.1). Reductive amination of ketones 28 with dibenzylamine yields compounds 29 (Scheme V, step d) using conditions such as those described in General Procedures X or X.1. The debenzylation of compounds 29 may be accomplished via hydrogenation as described in General Procedure Y to give amines 30 (Scheme V, step e). Alternate conditions may be used to access amines 30 from ketones 28, for example, as described in Larock, R. C. "Comprehensive Organic Transformations: A Guide to Functional Group Preparations, 2$^{nd}$ edition", 1999, Wiley-VCH (Scheme V, step h). Amines 30 may undergo further functionalization using reactions known to one skilled in the art (for example, Larock, R. C. referenced above). For example, amides, ureas, sulfonamides, aryl amines, heteroaryl amines, sulfonyl ureas, substituted amines, squaramides, or guanidines can be prepared from amines 30 (for example, General Procedures G, H, I, J, J.1, XXX, EEEE, K, K.1, L, DD, QQ, RR, YY, ZZ followed by AAA, CCC, YYY, X, X.1, TTTT, or EEEEE) to give compounds 31 (Scheme V, step f). The ester of compounds 31 may be hydrolyzed under aqueous base or acid conditions to give the desired carboxylic acids 32 (Scheme V, step g) using conditions such as those described in General Procedures Z or TT or Larock, R. C. referenced above). Alternatively, the ester of compounds 29 may be hydrolyzed to give intermediate carboxylic acids 32' as shown in Scheme V, step i, using aqueous base or acid conditions (for example, Preparation #TT.1).

Scheme V

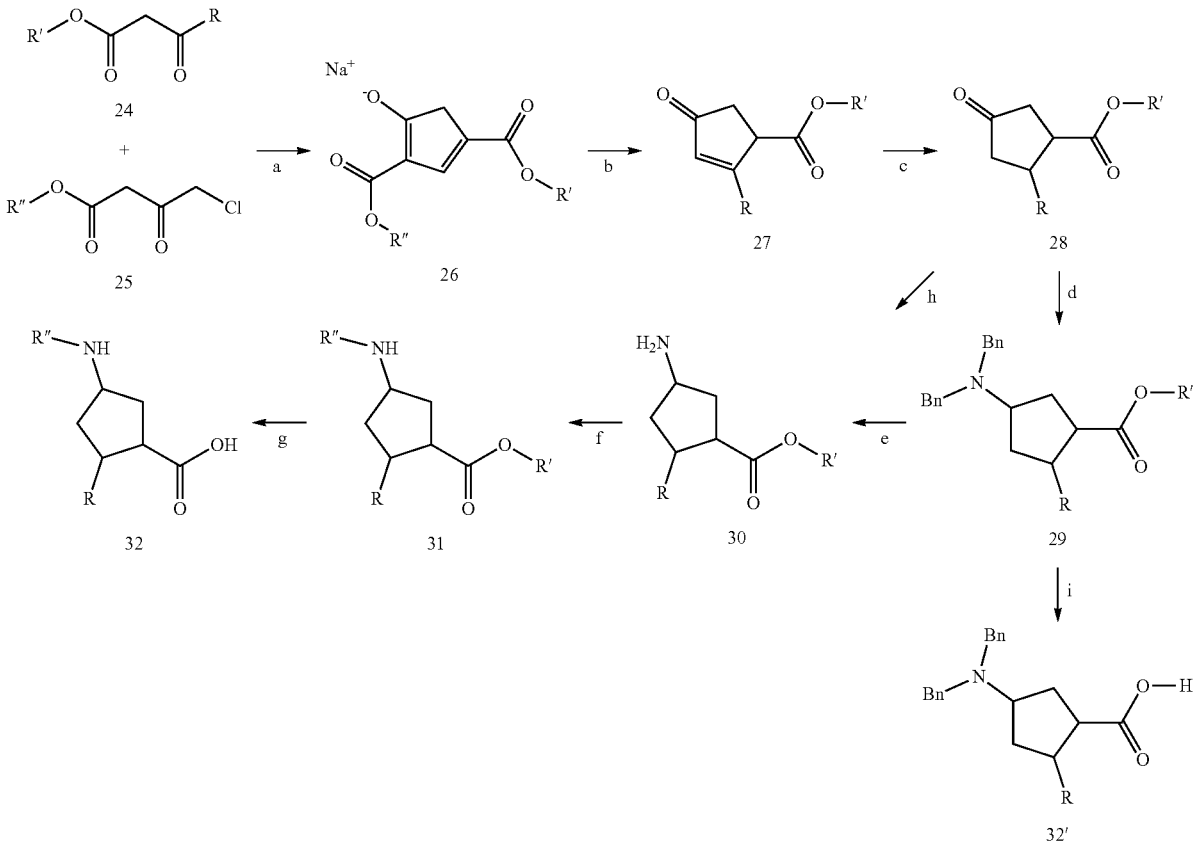

Methods for preparing ether-substituted 1-cyclopentyl-6H-pyrrolo[2,3-e][1,2,4]triazolo[4,3-a]pyrazine compounds of the invention are illustrated in Scheme VI. As shown in step a, reduction of α,β-unsaturated ketones 27 with concomitant reduction of the ketone provides the saturated alcohols 33 (for example, the chiral reduction conditions described in Example #4). Alternate conditions may be used to access alcohols 33 from ketones 28 via reduction (Scheme VI, step b) as described in General Procedure P or in Larock, R. C. "Comprehensive Organic Transformations: A Guide to Functional Group Preparations, 2$^{nd}$ edition", 1999, Wiley-VCH. The alcohols 33 may be reacted to give ethers 34 (Scheme VI, step c) using conditions such as those described in General Procedure EE (which may require first making the 2,2,2-trichloroimidate as described in General Procedure UU), II, JJ, or VV followed by General Procedure FFF or by methods known to one skilled in the art (for example, Tet. Lett. 1983, 24(48), 5363 or Greene, T. W. and Wuts, P. G. M. "Protective Groups in Organic Synthesis, 3$^{rd}$ Edition", 1999, Wiley-Interscience). The ester of compounds 34 may be hydrolyzed under aqueous base or acid conditions to give the desired carboxylic acids 35 (Scheme VI, step d), using conditions such as those described in General Procedure Z or TT or Larock, R. C. referenced above. The formation of hydrazides 36 from hydrazinylpyrrolopyrazines 5 and carboxylic acids 35 (Scheme VI, step e) may be accomplished by a variety of methods known to one skilled in the art such as those described in General Procedure A or standard peptide coupling methods such as those found in Larock, R. C. referenced above. The hydrazides 36 may be cyclized to pyrrolotriazolopyrazines 37 (Scheme VI, step f) using conditions such as those described in General Procedures B or ZZZZ or by methods known to one skilled in the art (for example, Bioorganic & Medicinal Chemistry Letters 2007, 17(12), 3373-3377 or Journal of Medicinal Chemistry 1990, 33(9), 2326-2334). Removal of the sulfonamide protecting group of pyrrolotriazolopyrazines 37 may be accomplished using conditions such as those described in General Procedures D, AAAA, BBBB, or CCCC or by methods known to one skilled in the art (for example, the books from Larock, R. C. or Greene, T. W. and Wuts, P. G. M. referenced above) to give pyrrolotriazolopyrazines 38 as final products or intermediates (Scheme VI, step g). The pyrrolotriazolopyrazines 38 may be SEM protected (Scheme VI, step h) using conditions such as those described in General Procedure KK, or as described in Greene, T. W. and Wuts, P. G. M. referenced above. If the R" group in pyrrolotriazolopyrazines 37 or 39 is a protecting group, it may be deprotected to yield alcohols 40 (Scheme VI, step k) or 43 (Scheme VI, step i), respectively, using conditions such as those described in Greene, T. W. and Wuts, P. G. M. referenced above. For example, a protecting group such as a p-methoxybenzyl (PMB) group can be removed from a PMB-ether to yield the unprotected alcohol (for example General Procedure FF) and the deprotected compounds 40 or 43 may then be reacted further. Mitsunobu reaction of alcohols 40 or 43 may be used to prepare ethers or esters 41 (Scheme VI, step 1), 44 (Scheme VI, step j), or 45 (Scheme VI, step n) with inversion at the reacting center using conditions such as those described in General Procedure II or by methods known to one skilled in the art such as those found in Larock, R. C. referenced above. Additionally, ethers 44 may be prepared from alcohols 43 via alkylation using conditions such as those described in General Procedure HHHH Alternatively, alcohols 40 or 43 may be converted to carbamates 41 or 44 using well-known conditions such as those described in General Procedures OOO, WWW and PPPP. Removal of the sulfonamide protecting group of pyrrolotriazolopyrazines 41 may be accomplished using conditions such as those described in General Procedures D, AAAA, BBBB, CCCC or PPPP, or by methods known to one skilled in the art (for example, the books from Larock, R. C. or Greene, T. W. and Wuts, P. G. M. referenced above) to give pyrrolotriazolopyrazines 42 (Scheme VI, step m). The ester group of esters 45 may by cleaved to yield the unprotected alcohols 46 (Scheme VI, step o) using conditions such as those described in General Procedure SS. The alcohols 46 can be reacted further to form ethers 44 (Scheme VI, step p) via Mitsunobu chemistry (in a manner as described for Scheme VI, step j) or by conditions such as those described in General Procedure EE (which may require first making the 2,2,2-trichloroimidate as described in General Procedure UU) or JJ or by methods known to one skilled in the art (for example, the book from Larock, R. C. referenced above). The SEM protecting group of pyrrolotriazolopyrazines 44 may be removed by methods such as those described in General Procedures LL and LL.1, or using conditions such as described in Greene, T. W. and Wuts, P. G. M. referenced above to give pyrrolotriazolopyrazines 42 (Scheme VI, step q).

Scheme VI

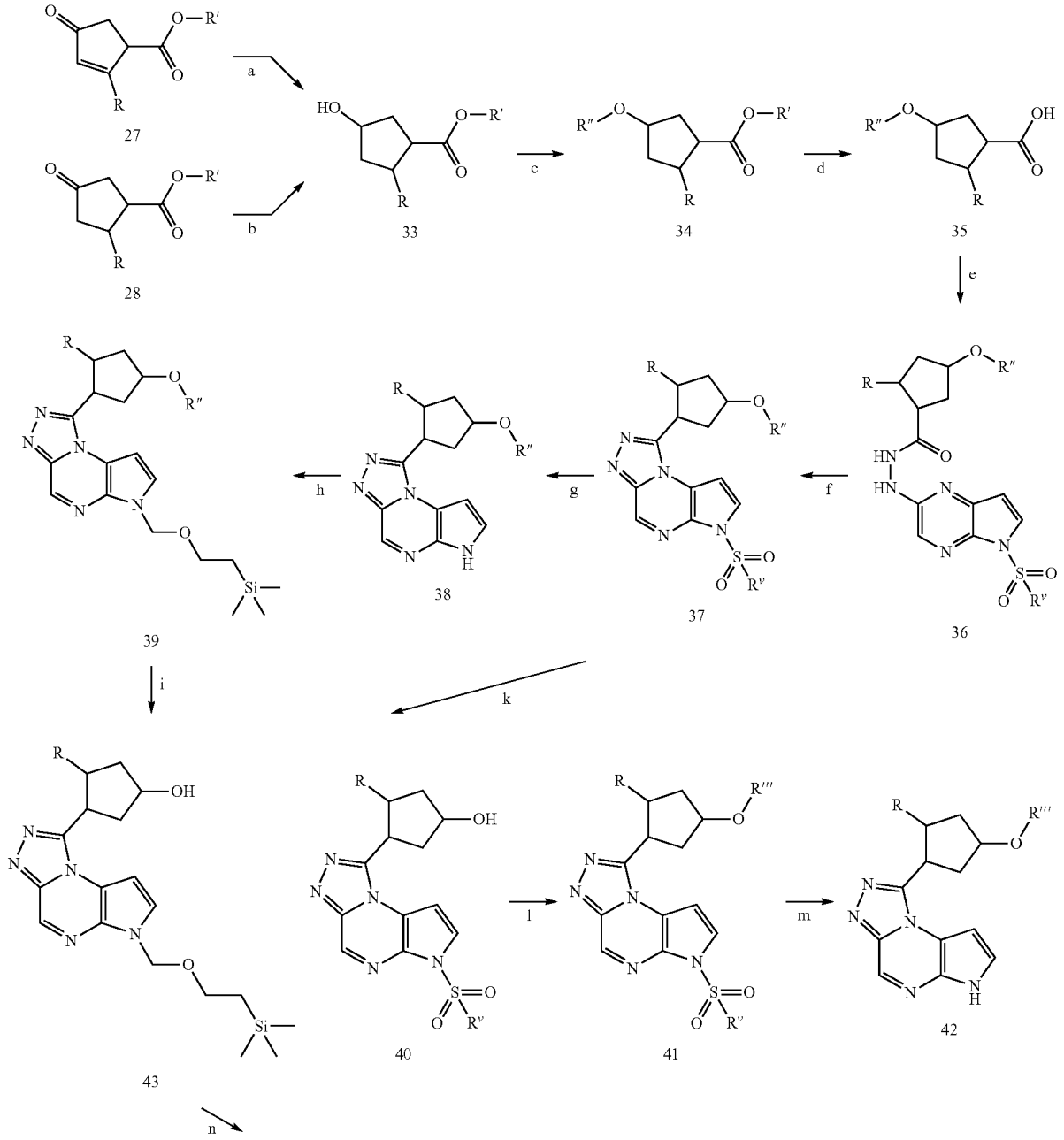

-continued

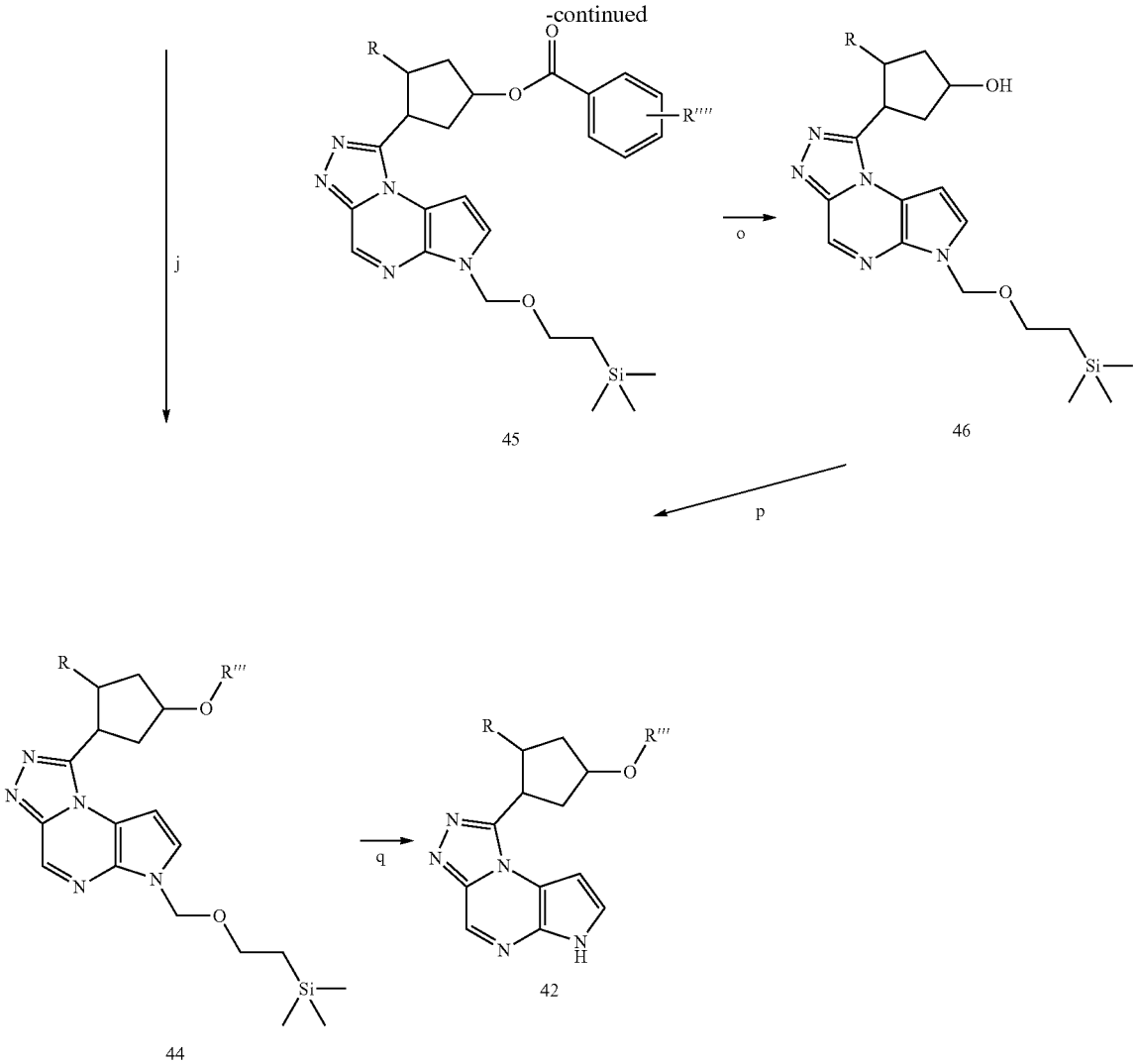

An alternate method for preparing ether-substituted 1-cyclopentyl-6H-pyrrolo[2,3-e][1,2,4]triazolo[4,3-a]pyrazine compounds of the invention is illustrated in Scheme VII. As shown in step a, the ester of compounds 33 may be hydrolyzed under aqueous base or acid conditions to give the desired carboxylic acids 47, using conditions such as those described in General Procedures Z or TT or Larock, R. C. referenced above. The formation of lactones 48 from carboxylic acids 47 (Scheme VII, step b) may be accomplished by methods such as those described in Example #4, General Procedure GG, or by methods known to one skilled in the art such as those found in Larock, R. C. referenced above. The formation of hydrazides 49 from hydrazinylpyrrolopyrazines 5 and lactones 48 (Scheme VII, step c) may be accomplished by a variety of methods known to one skilled in the art such as those described in Example #4 or General Procedure HH. The alcohols 49 may be reacted to form ethers 50 (Scheme VII, step d) using conditions such as those described in General Procedures VV (which may require first making the 2,2,2-trichloroimidate as described in General Procedure UU) or JJ, or by methods known to one skilled in the art (for example, Tet. Lett. 1983, 24(48), 5363). Mitsunobu reaction of alcohols 49 may be used to prepare ethers 51 (Scheme VII, step f) with inversion at the reacting center using conditions such as those described in Example #4, General Procedure II, or by methods known to one skilled in the art such as those found in Larock, R. C. referenced above. The hydrazides 50 or 51 may be cyclized to pyrrolotriazolopyrazines 37 (Scheme VII, step e) or 41 (Scheme VII, step g) using conditions such as those described in Example #4, General Procedures B or ZZZZ, or by methods known to one skilled in the art (for example, Bioorganic & Medicinal Chemistry Letters 2007, 17(12), 3373-3377 or Journal of Medicinal Chemistry 1990, 33(9), 2326-2334). Further elaboration of 37 or 41 may be performed as described in Scheme VI.

Scheme VII

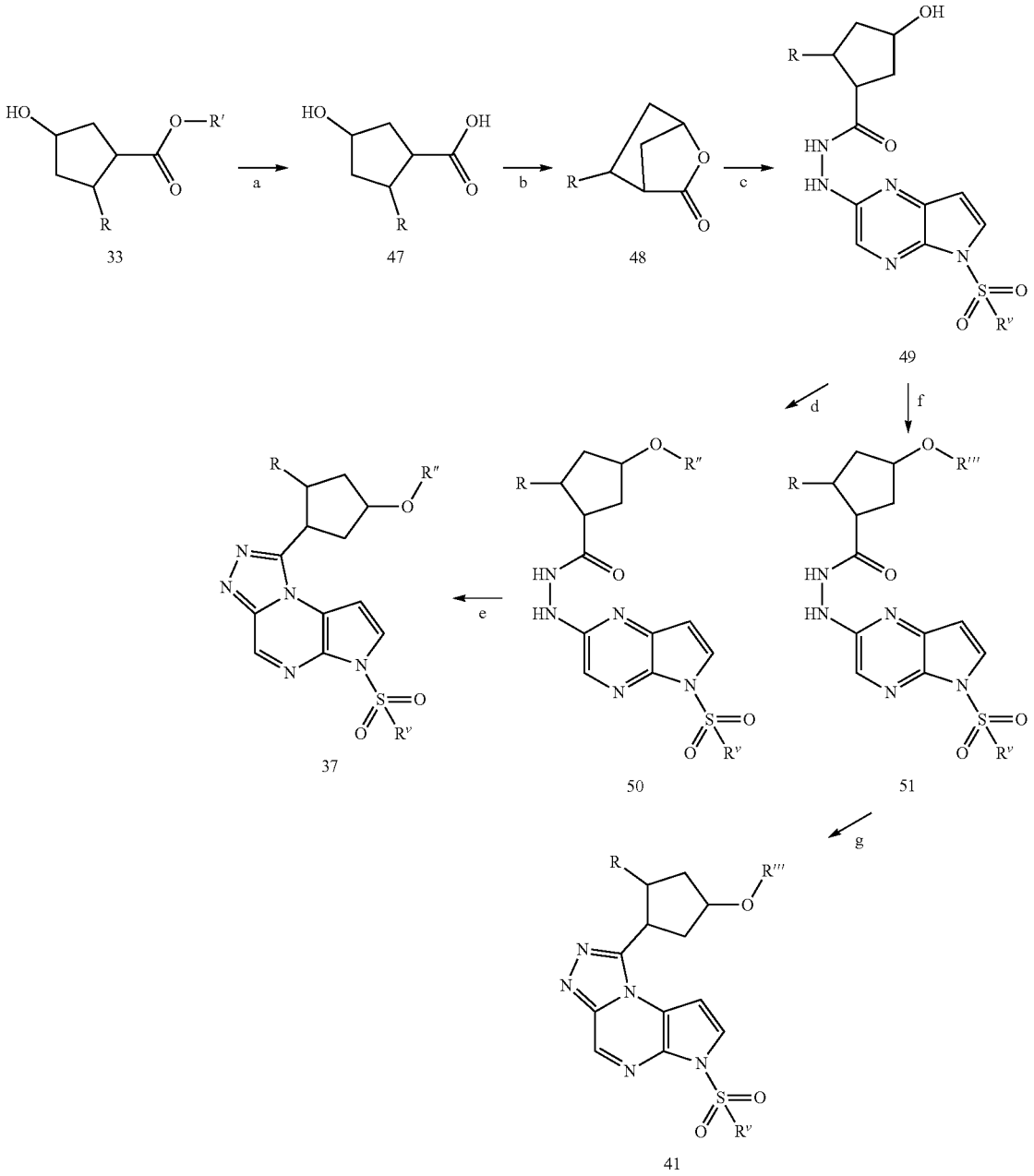

Methods for preparing 1,6-dihydroimidazo[4,5-d]pyrrolo[2,3-b]pyridine compounds of the invention are illustrated in Scheme VIII. As shown in step a, 4-chloro-3-iodopyridin-2-amine 52 may be nitrated to give 4-chloro-3-iodo-5-nitropyridin-2-amine 53as described in Example #21 or in Larock, R. C. "Comprehensive Organic Transformations: A Guide to Functional Group Preparations, 2$^{nd}$ edition", 1999, Wiley-VCH. 4-Chloro-3-iodo-5-nitropyridin-2-amine 53is reacted with a (trimethylsilyl)acetylene via a Sonogashira cross coupling using methods known to one skilled in the art (for example Example #21 or WO2006058120A1) to give 4-chloro-5-nitro-3-((trimethylsilyl)ethynyl)pyridin-2-amine 54 (Scheme VIII, step b). As shown in step c, 4-chloro-5-nitro-3-((trimethylsilyl)ethynyl)pyridin-2-amine 54 is deprotected to give the 4-chloro-3-ethynyl-5-nitropyridin-2-amine 55 as described in Example #21 or using methods known to one skilled in the art (for example, the books from Greene, T. W. and Wuts, P. G. M. "Protective Groups in Organic Synthesis, 3$^{rd}$ Edition", 1999, Wiley-Interscience or Larock, R. C. referenced above). 4-Chloro-3-ethynyl-5-nitropyridin-2-amine 55 is cyclized, as shown in step d, to give 4-chloro-5-nitro-1H-pyrrolo[2,3-b]pyridine 56 as described in Example #21, or by methods known to one skilled in the art (for example, as described in WO2008004117). As shown in step e, amino-substituted 1H-pyrrolo[2,3-b]pyridines 57 are prepared using methods known to one skilled in the art (for example, Example #21 or Larock, R. C. referenced above). Diamino-substituted 1H-pyrrolo[2,3-b]pyridines 58 (Scheme VIII, step f) are prepared from the reduction of nitro-containing 1H-pyrrolo[2,3-b]pyridines 57 using methods known to one skilled in the art (for example, Example #21, General Procedure BBB, or Larock, R. C. referenced above). As shown in step g, diamino-substituted 1H-pyrrolo[2,3-b]pyridines 58 can be cyclized as described in Example #21 or General Procedure DDD to give 1,6-dihydroimidazo[4,5-d]pyrrolo[2,3-b]pyridines 59. Further functionalization of the R group in 1,6-dihydroimidazo[4,5-d]pyrrolo[2,3-b]pyridines 59 can be performed, if desired, using reactions known to one skilled in the art (for example, Larock, R. C. referenced above). For example, amides, ureas, sulfonamides, aryl amines, heteroaryl amines, sulfonyl ureas, substituted amines, squaramides, or guanidines can be prepared from 1,6-dihydroimidazo[4,5-d]pyrrolo[2,3-b]pyridine 59 with an R group containing a primary or secondary amine (for example General Procedures G, H, I, J, J.1, XXX, EEEE, K, K.1, L, DD, QQ, RR, YY, ZZ followed by AAA, CCC, YYY, X, X.1, TTTT, or EEEEE). Also, deprotection of the R group in 1,6-dihydroimidazo[4,5-d]pyrrolo[2,3-b]pyridines 59 to yield an unprotected compound can be performed using conditions such as those described in Greene, T. W. and Wuts, P. G. M. referenced above or in General Procedures E, E.1, F, F.1, Y, or BB. For example, a protecting group such as a benzyloxycarbonyl (Cbz) group can be removed from a protected amine to yield the unprotected amine (for example General Procedures F, F.1, or Y) and the deprotected compounds 59 may then be reacted further as described above. Alternatively, intermediates 56 or 57 may be sulfonamide protected using reactions known to one skilled in the art (for example, Greene, T. W. and Wuts, P. G. M. referenced above or General Procedure K.1) to give sulfonamides 134 and 135 respectively (Scheme VII, steps h and m). As shown in step i, amino-substituted 1H-pyrrolo[2,3-b]pyridines 135 may also be prepared from chloro-substituted 1H-pyrrolo[2,3-b]pyridines 134 using methods known to one skilled in the art (for example, Example #23 or Larock, R. C. referenced above). Diamino-substituted 1H-pyrrolo[2,3-b]pyridines 136 are prepared from the reduction of nitro-containing 1H-pyrrolo[2,3-b]pyridines 135 using methods known to one skilled in the art (for example, Example #23, General Procedure BBB, or Larock, R. C. referenced above). As shown in step k, diamino-substituted 1H-pyrrolo[2,3-b]pyridines 136 can be cyclized as described in Example #23 or General Procedure DDD to give sulfonamide-protected 1,6-dihydroimidazo[4,5-d]pyrrolo[2,3-b]pyridines 137. Deprotection of the sulfonamide of compounds 137 to yield 1,6-dihydroimidazo[4,5-d]pyrrolo[2,3-b]pyridines 59 (Scheme VIII, step 1) can be performed using conditions such as those described in Greene, T. W. and Wuts, P. G. M. "Protective Groups in Organic Synthesis, 3rd Edition", 1999, Wiley-Interscience, General Procedures D, XXX, AAAA, BBBB, or CCCC or Example #23.

Scheme VIII

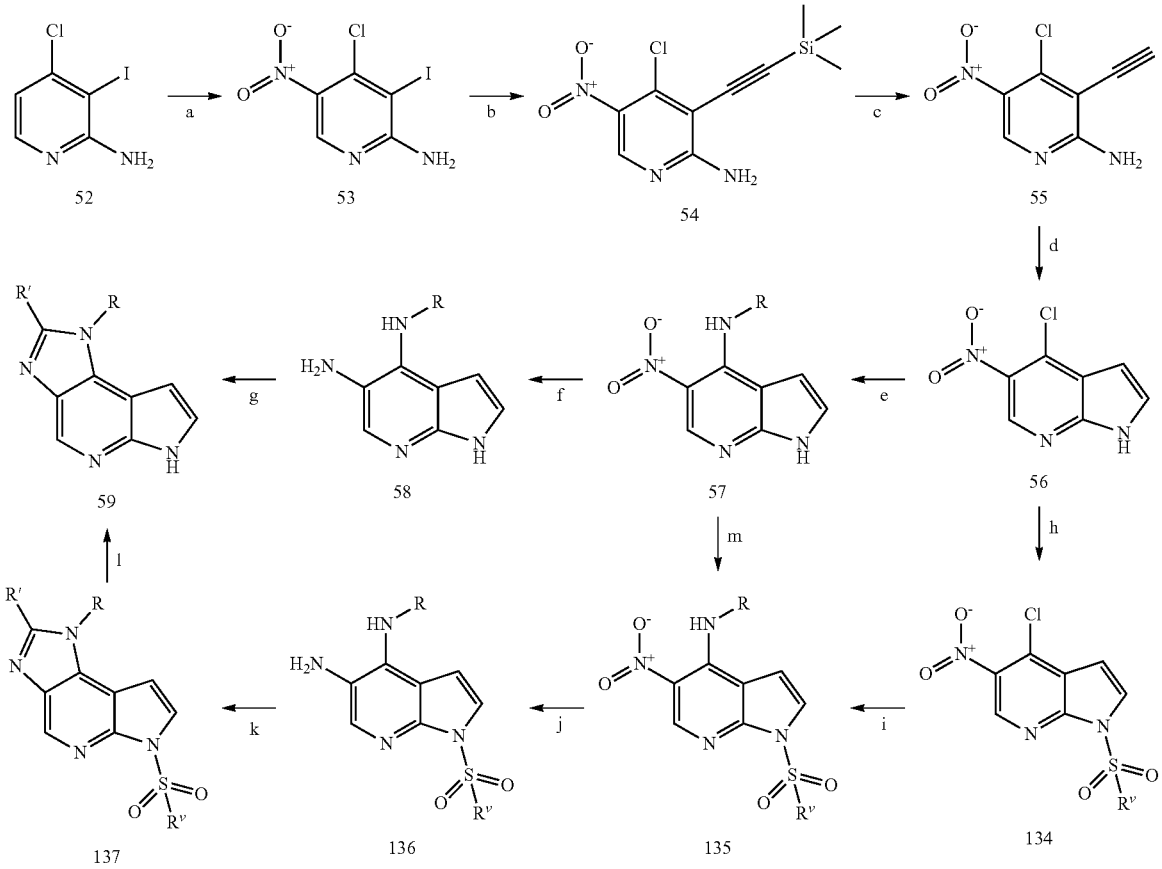

Methods for preparing substituted cyclopentyl amines 61 for use in the preparation of compounds of the invention are illustrated in Scheme IX. In step a, carboxylic acids 32 are subjected to a Curtius rearrangement as described in General Procedure NNN to form isocyanates 60. The hydrolysis of isocyanates 60 yields amines 61 (for example, General Procedure OOO).

Scheme IX

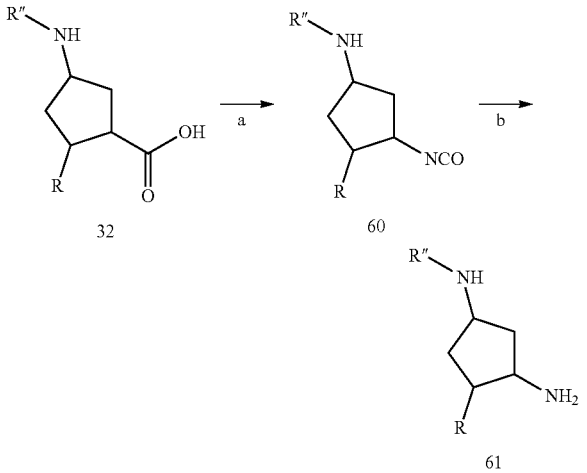

Methods for preparing 4-(6H-pyrrolo[2,3-e][1,2,4]triazolo[4,3-a]pyrazin-1-yl)cyclo-pentanones and their derivatives as compounds of the invention are illustrated in Scheme X. In step a, ketones 28 are protected as ketals 62 using conditions as described in General Procedure WW or as those described in Greene, T. W. and Wuts, P. G. M. referenced above. The ester of compounds 62 may be hydrolyzed under aqueous base conditions to give the desired carboxylic acids 63 (Scheme X, step b), using conditions such as those described in General Procedure Z or Larock, R. C. referenced above. The formation of hydrazides 64 from hydrazinylpyrrolopyrazines 5 and carboxylic acids 63 (Scheme X, step c) may be accomplished by a variety of methods known to one skilled in the art such as those described in General Procedure A or standard peptide coupling methods such as those found in Larock, R. C. referenced above. The hydrazides 64 may be cyclized to pyrrolotriazolopyrazines 65 (Scheme X, step d) using conditions such as those described in General Procedures B or ZZZZ or by methods known to one skilled in the art (for example, Bioorganic & Medicinal Chemistry Letters 2007, 17(12), 3373-3377 or Journal of Medicinal Chemistry 1990, 33(9), 2326-2334). Ketals 65 may be deprotected to yield ketones 66 as described in Preparation #25 or Greene, T. W. and Wuts, P. G. M. referenced above. Deprotection of the sulfonamide protecting group of pyrrolotriazolopyrazines 66 may be accomplished using conditions such as those described in General Procedures D, AAAA, BBBB, or CCCC or by methods known to one skilled in the art (for example, Greene, T. W. and Wuts, P. G. M. referenced above) to give pyrrolotriazolopyrazines 67 as final products or intermediates (Scheme X, step f). For example, step g illustrates the formation of oxime ethers 68 from ketones 67 which may be accomplished using conditions such as those described in General Procedure PPP or Larock, R. C. referenced above.

Scheme X

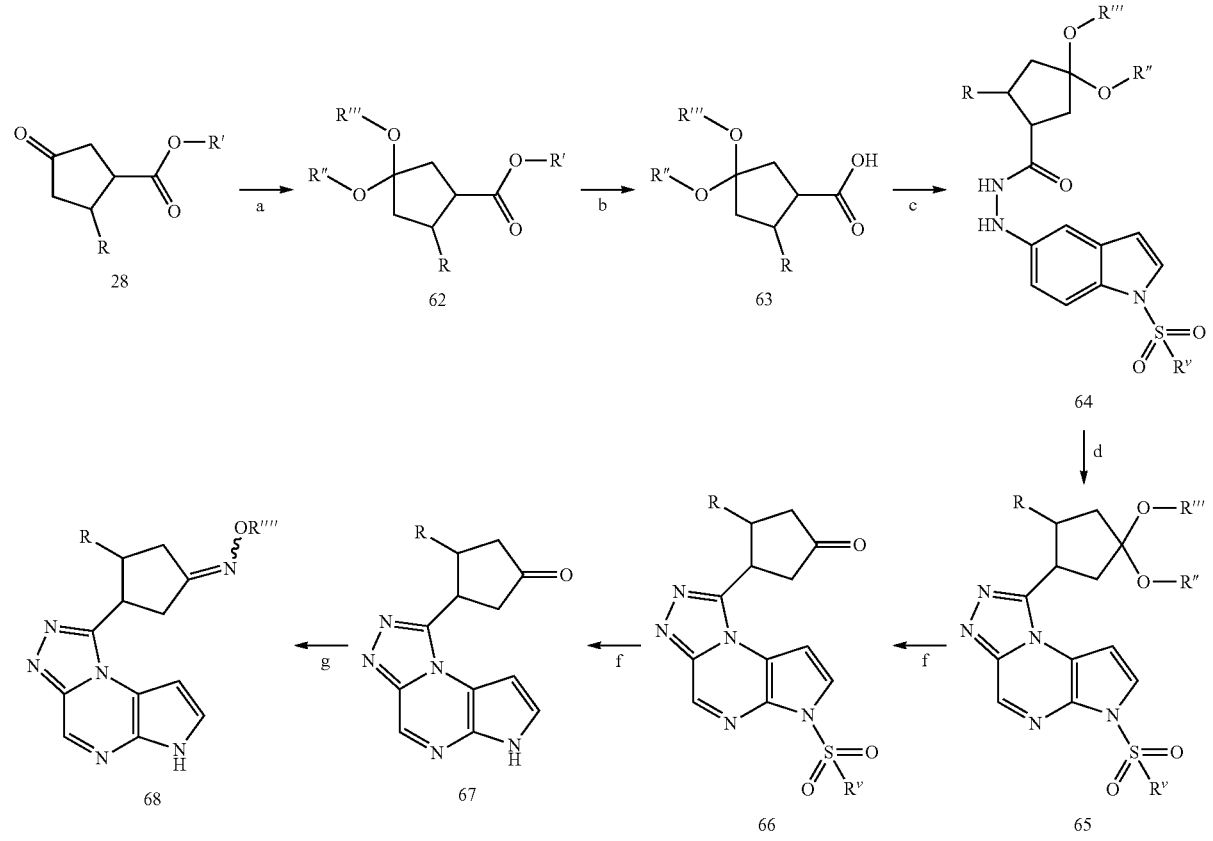

Methods for preparing acetic acid and acetamide derivatives from 4-(6H-pyrrolo[2,3-e][1,2,4]triazolo[4,3-a]pyrazin-1-yl)cyclopentanones as compounds of the invention are illustrated in Scheme XI. As shown in step a, Horner-Wadsworth-Emmons reaction of ketones 66 to give alkenes 69 may be accomplished using procedures known to one skilled in the art such as those described in General Procedure III. Deprotection of the sulfonamide protecting group of pyrrolotriazolopyrazines 69 may be accomplished using conditions such as those described in General Procedures D, AAAA, BBBB, or CCCC or by methods known to one skilled in the art (for example, Greene, T. W. and Wuts, P. G. M. referenced above) to give pyrrolotriazolopyrazines 70 (Scheme XI, step b). Hydrogenation of alkenes 70 as described in General Procedures W or W.1 yields pyrrolotriazolopyrazines 71 (Scheme XI, step c). Hydrolysis of esters 71 gives acids 72 (Scheme XI, step d) using well known conditions such as those described in General Procedure Z. The acids 72 may be further reacted to give amides 73 as shown in step e using conditions such as those described in General Procedure H.

Scheme XI

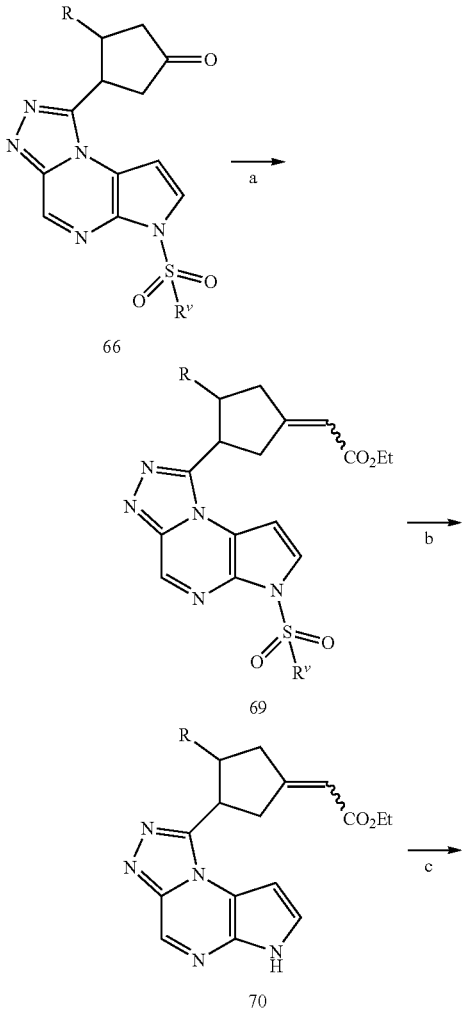

-continued

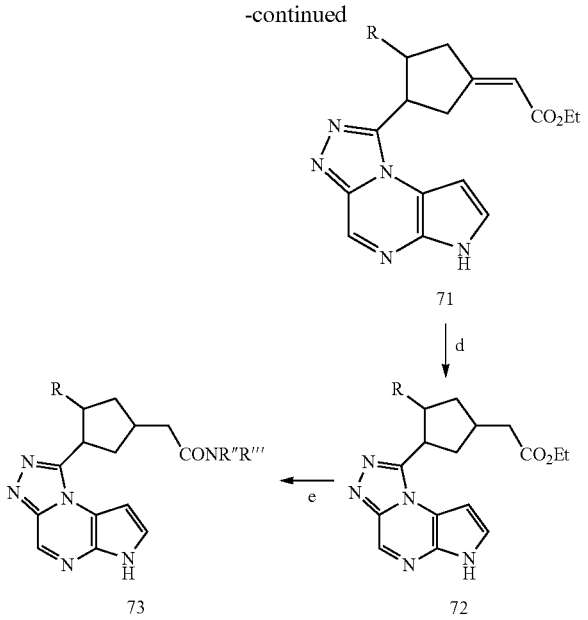

Methods for preparing 4-(6H-pyrrolo[2,3-e][1,2,4]triazolo[4,3-a]pyrazin-1-yl)cyclo-pentylamines as compounds of the invention are illustrated in Scheme XII. As shown in step a, reductive amination of ketones 66 to give amines 74 may be accomplished using well known conditions such as those described in General Procedures X or X.1. Deprotection of the sulfonamide protecting group of pyrrolotriazolopyrazines 74 may be accomplished using conditions such as those described in General Procedures D, AAAA, BBBB, or CCCC or by methods known to one skilled in the art (for example, Greene, T. W. and Wuts, P. G. M. referenced above) to give pyrrolotriazolopyrazines 75 (Scheme XII, step b).

Scheme XII

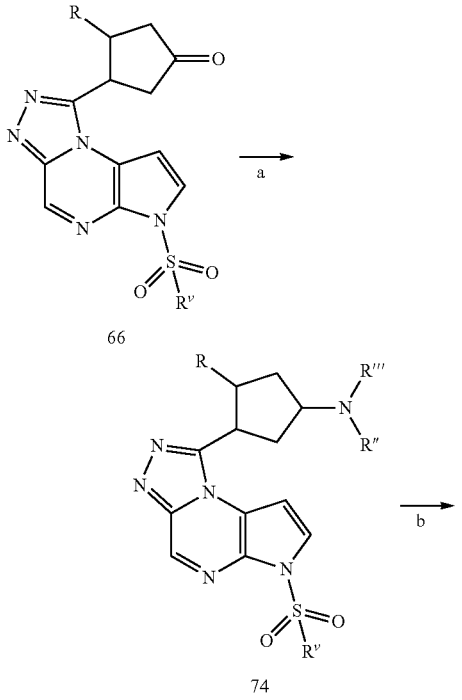

-continued

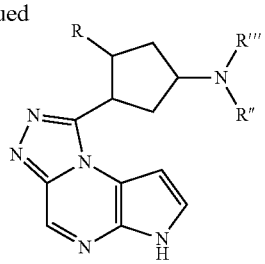

75

Methods for preparing dihydropyrazolo[4,3-d]pyrrolo[2,3-b]pyridine compounds of the invention are illustrated in Scheme XIII. In step a, reaction of 5-chloro-4-iodo-1-(triisopropylsilyl)-1H-pyrrolo[2,3-b]pyridine 76 with a substituted aldehyde provides alcohols 77 using procedures such as those described in Example #29, Example #30, or in WO2009152133. Preparation of ketones 78 (step b) can be accomplished by treatment of alcohols 77 with an oxidizing agent by methods known to one skilled in the art (for example, Example #29, Example #30, or Larock, R. C. referenced above). Ketones 78 can then be converted to hydrazones 79 with the loss of the TIPS protecting group through reaction with hydrazine using conditions such as those described in Example #29, Example #30 or General Procedure XXXX. Cyclization of hydrazones 79 to provide dihydropyrazolo[4,3-a]pyrrolo[2,3-b]pyridines 80 can be accomplished via an intramolecular Buchwald-Hartwig cyclization (for example, General Procedure XX or Organic Letters, 2008, 10(18), 4109-4112). Further functionalization of the R''' group in dihydropyrazolo[4,3-a]pyrrolo[2,3-b]pyridines 80 can be performed, if desired, using reactions known to one skilled in the art (for example, Larock, R. C. referenced above). For example, amides, ureas, sulfonamides, aryl amines, heteroaryl amines, sulfonyl ureas, substituted amines, squaramides, or guanidines can be prepared from dihydropyrazolo[4,3-a]pyrrolo[2,3-b]pyridines 80 with an R''' group containing a primary or secondary amine (for example, General Procedures G, H, I, J, J.1, XXX, EEEE, K, K.1, L, DD, QQ, RR, YY, ZZ followed by AAA, CCC, YYY, X, X.1, TTTT, or EEEEE). Also, deprotection of the R''' group in dihydropyrazolo[4,3-d]pyrrolo[2,3-b]pyridines 80 to yield deprotected compounds 80 can be performed using conditions such as those described in Greene, T. W. and Wuts, P. G. M. referenced above or in General Procedures E, E.1, F, F.1, Y, or BB and the deprotected compounds 80 may then be reacted further as described above.

Scheme XIII

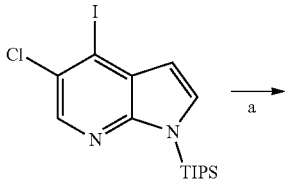

76

-continued

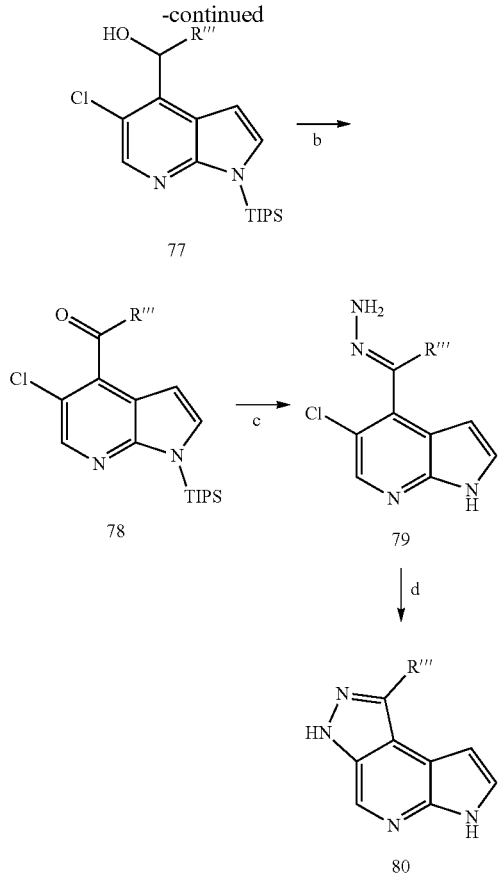

77 78 79 80

Methods for preparing 2,3,4,7-tetrahydro-1H-pyrrolo[2,3-h][1,6]naphthyridine compounds of the invention are illustrated in Scheme XIV. In step a, o-lithiation of 4-chloro-1-(triisopropylsilyl)-1H-pyrrolo[2,3-b]pyridine 81 followed by trapping of the anion with ethyl chloro formate yields ethyl 4-chloro-1-(triisopropylsilyl)-1H-pyrrolo[2,3-b]pyridine-5-carboxylate 82 using conditions described in Example #28. The removal of the TIPS group of 82 may be accomplished as shown in step b to give ethyl 4-chloro-1H-pyrrolo[2,3-b]pyridine-5-carboxylate 83 using conditions well known in the literature (for example, Greene, T. W. and Wuts, P. G. M. referenced above or Example #28). In step c, sulfonamide protected compounds 84 are prepared using reactions known to one skilled in the art (for example, Greene, T. W. and Wuts, P. G. M. referenced above or Example #28). As shown in step d, amino-substituted 1H-pyrrolo[2,3-b]pyridines 85 are prepared using methods known to one skilled in the art (for example, Example #28 or Larock, R. C. referenced above). The reduction of esters 85 to alcohols 86 (Scheme XIV, step e) may be accomplished using conditions well known in the literature (for example, Example #28 or Larock, R. C. referenced above). In step f, alcohols 86 are oxidized to aldehydes 87 using methods known to one skilled in the art (for example, Example #28 or Larock, R. C. referenced above). The Wittig reaction of aldehydes 87 with ((1,3-dioxolan-2-yl)methyl) triphenylphosphonium bromide (Scheme XIV, step g) yields alkenes 88 using conditions such as those described in Example #28. Reduction of alkenes 88 may be accomplished using conditions such as those described in Example #28 or General Procedures W or W.1 (Scheme XIV, step h).

The cyclization of aminoacetals 89 to give protected 2,3,4,7-tetrahydro-1H-pyrrolo[2,3-h][1,6]naphthyridines 90 is accomplished using conditions described in Example #28 (scheme XIV, step i). Deprotection of the sulfonamide protecting group of 2,3,4,7-tetrahydro-1H-pyrrolo[2,3-h][1,6]naphthyridines 90 may be accomplished using conditions tetrahydro-1H-pyrrolo[2,3-h][1,6]naphthyridines 91 to yield deprotected compounds 91 can be performed using conditions such as those described in Greene, T. W. and Wuts, P. G. M. referenced above or in General Procedures E, E.1, F, F.1, Y, or BB and the deprotected compounds 91 may then be reacted further as described above.

Scheme XIV

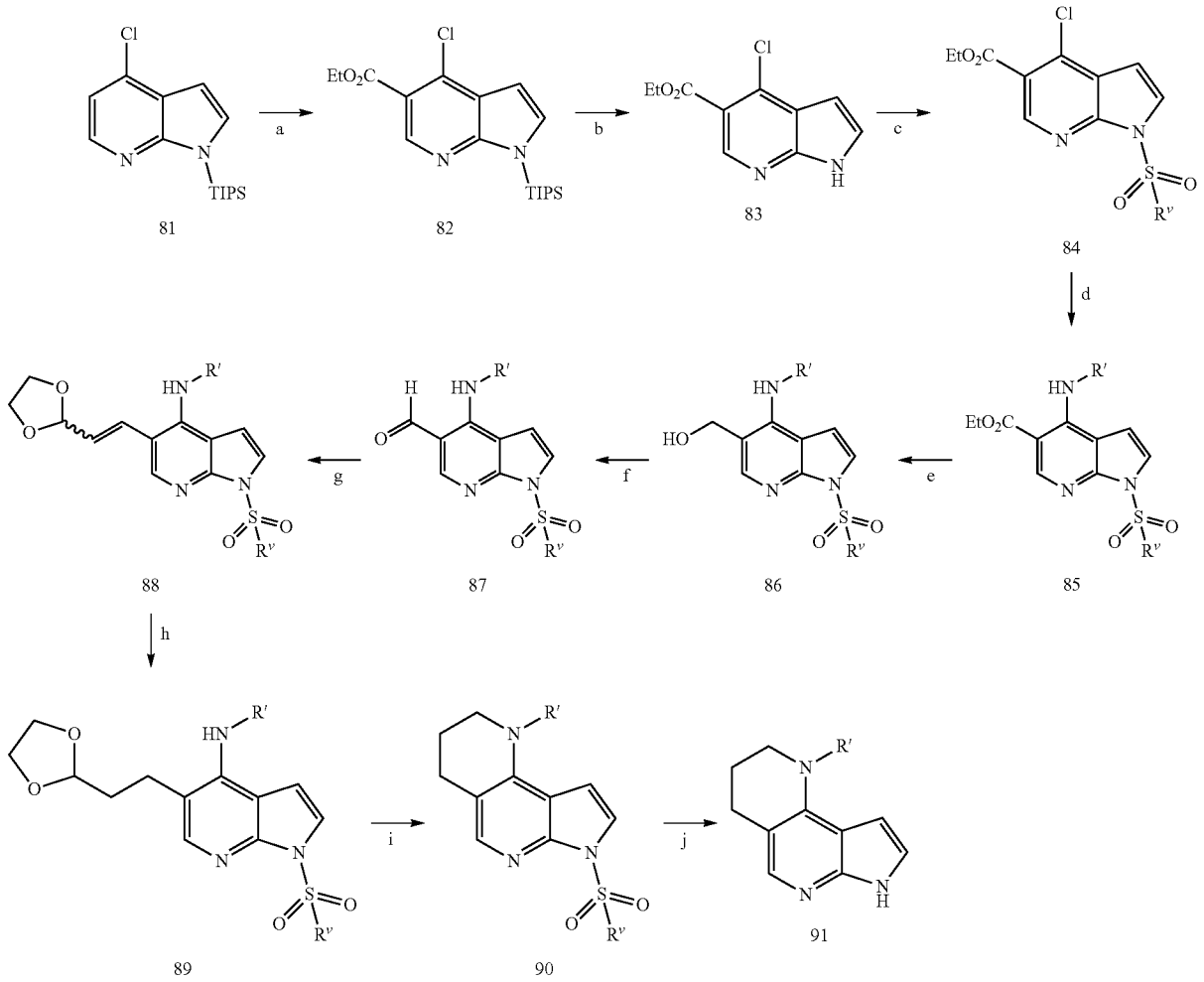

such as those described in General Procedures D, AAAA, BBBB, or CCCC or by methods known to one skilled in the art (for example, Greene, T. W. and Wuts, P. G. M. referenced above) to give 2,3,4,7-tetrahydro-1H-pyrrolo[2,3-h][1,6]naphthyridines 91 (Scheme XIV, step j). Further functionalization of the R' group in 2,3,4,7-tetrahydro-1H-pyrrolo[2,3-h][1,6]naphthyridines 91 can be performed, if desired, using reactions known to one skilled in the art (for example, Larock, R. C. referenced above). For example, amides, ureas, sulfonamides, aryl amines, heteroaryl amines, sulfonyl ureas, substituted amines, squaramides, or guanidines can be prepared from 2,3,4,7-tetrahydro-1H-pyrrolo[2,3-h][1,6]naphthyridines 91 with an R' group containing a primary or secondary amine (for example, General Procedures G, H, I, J, J.1, XXX, EEEE, K, K.1, L, DD, QQ, RR, YY, ZZ followed by AAA, CCC, YYY, X, X.1, TTTT, or EEEEE). Also, deprotection of the R' group in 2,3,4,7-

Methods for preparing substituted imidazo[1,5-a]pyrrolo[2,3-e]pyrazines compounds of the invention are illustrated in Scheme XV. As shown in step a, imidazo[1,5-a]pyrrolo[2,3-e]pyrazines 19 may be halogenated using conditions such as those described in General Procedure MM to give 3-halo-imidazo[1,5-a]pyrrolo[2,3-e]pyrazines 92. The 3-halo-imidazo[1,5-a]pyrrolo-[2,3-e]pyrazines 92 may undergo a variety of reactions known to one skilled in the art (for example, Larock, R. C. referenced above) including, but not limited to, io cyanation as described in General Procedure HHH (Scheme XVI, step c) or Suzuki coupling reactions such as those described in General Procedures UUU or VVV (Scheme XV, step b). Deprotection of the sulfonamide protecting group of imidazo[1,5-a]pyrrolo[2,3-e]pyrazines 93 may be accomplished using conditions such as those described in General Procedures D, UUU, AAAA, BBBB, or CCCC, or by methods known to one skilled in the art (for example, Greene, T. W. and Wuts, P. G. M. referenced above) to give imidazo[1,5-a]pyrrolo[2,3-e]pyrazines 94 (Scheme XV, step c).

Scheme XV

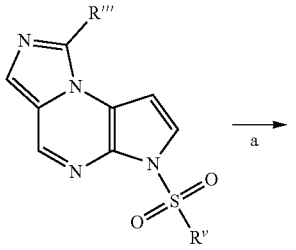

19

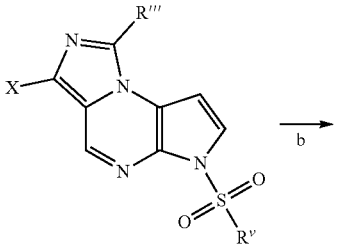

92

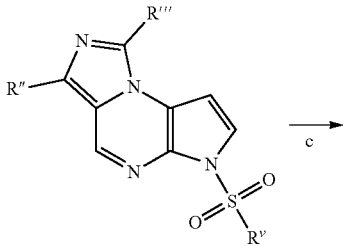

93

-continued

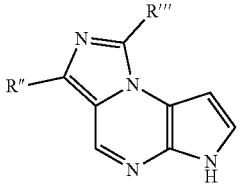

94

Methods for preparing pyrrolo[2,3-e][1,2,4]triazolo[4,3-a]pyrazine compounds of the invention are illustrated in Scheme XVI. Pyrrolotriazolopyrazines 8 may be halogenated using conditions such as those described in General Procedures GGG or GGG.1 to give 8-halopyrrolotriazolopyrazines 95 (Scheme XVI, step a). In step b, 8-halopyrrolotriazolopyrazines 95 may be protected with a SEM group using conditions known in the literature such as those found in Greene, T. W. and Wuts, P. G. M. referenced above or as in General Procedure KK. The resulting SEM-protected 8-halopyrrolotriazolopyrazines 96 may undergo a variety of reactions known to one skilled in the art (for example, Larock, R. C. referenced above) including, but not limited to, cyanation as described in General Procedure HHH (Scheme XVI, step c), Suzuki coupling reactions as described in Preparation #23, formation of a carboxylic ester as described in General Procedure AAAAA, or Stille coupling reactions as described in General Procedure CCCCC (Scheme XVI, step e). The resulting products 97 or 99 may be deprotected using conditions such as those described in General Procedure LL, LL.1, or by methods known to one skilled in the art (for example, Greene, T. W. and Wuts, P. G. M. referenced above) to give pyrrolo[2,3-e][1,2,4]triazolo[4,3-a]pyrazines 98 or 100 (Scheme XV, steps d and f, respectively). Additionally, compounds 99 and 100 may undergo further functionalzation, if desired, using reactions known to one skilled in the art (for example, Larock, R. C. referenced above). For example, for R═$CO_2$Et, the compound may be hydrolyzed using conditions such as those described in General Procedure D and then undergo amide bond formation as described in General Procedure H.

Scheme XVI

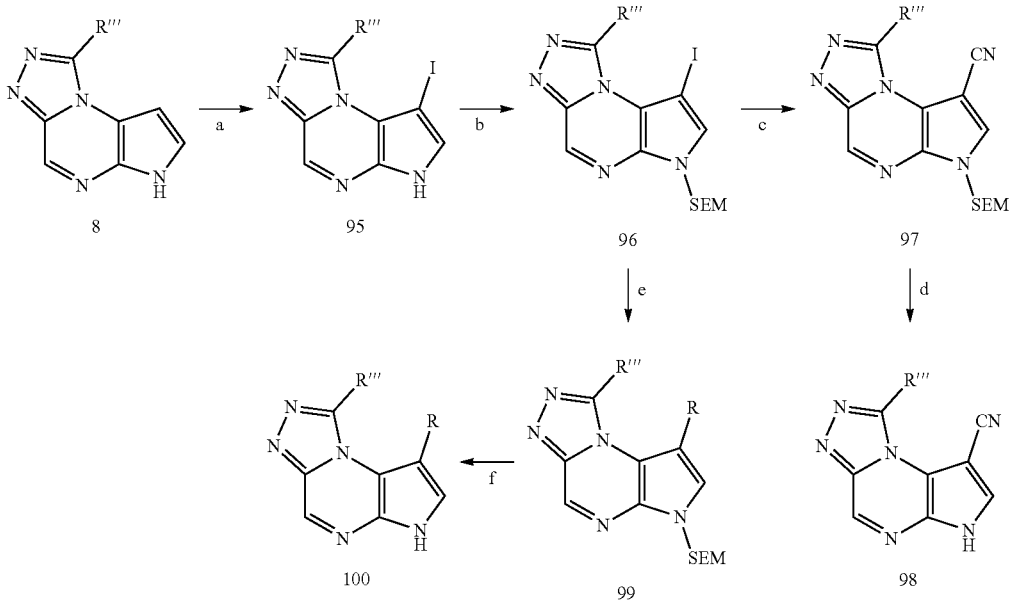

Methods for preparing substituted 4-(sulfonamidomethyl) cyclopentanecarboxylic acids 110 for use in the preparation of compounds of the invention are illustrated in Scheme XVII. In step a, 5-substituted-bicyclo[2.2.1]hept-2-enes 101 are oxidized to dicarboxylic acids 102 using known conditions such as those described in Preparation #11, Bioorganic & Medicinal Chemistry, 2007, 15, 7581, or Journal of Organic Chemistry, 1993, 58, 4745. Formation of the monoesters 103 are achieved through the cyclic anhydride as described in Preparation #11 (Scheme XVII, step b). The t-butyl esters 104 are prepared in step c using standard condition such as those described in Preparation #11 or Larock, R. C. referenced above. Reduction of the methyl ester of compounds 104 to alcohols 105 is achieved using well known conditions such as those found in Preparation #21 (Scheme XVII, step d). The mesylates 106 are prepared as described in Preparation #21 or by methods known to one skilled in the art (Scheme XVII, step e). As shown in step f, the mesylates 106 may be used to form azides 107 using well known conditions such as those described in Preparation #21 or Larock, R. C. referenced above (Scheme XVII, step f). The reduction of azides 107 to amines 108 is a standard transformation that may be accomplished as described in Preparation #21 or using conditions such as those described in General Procedure TTT or in Larock, R. C. referenced above (Scheme XVII, step g). Step h shows the formation of sulfonamides 109 from amines 108 which is achieved as described in General Procedures K or K.1 or by methods known to one skilled in the art (for example, Greene, T. W. and Wuts, P. G. M. referenced above). The acidic cleavage of t-butyl esters 109 to give 4-(sulfonamidomethyl)cyclopentanecarboxylic acids 110 (Scheme XVII, step i) may be done with the conditions described in General Procedure QQQ or with methods known to one skilled in the art (for example, the books from Larock, R. C. or Greene, T. W. and Wuts, P. G. M. referenced above).

Scheme XVII

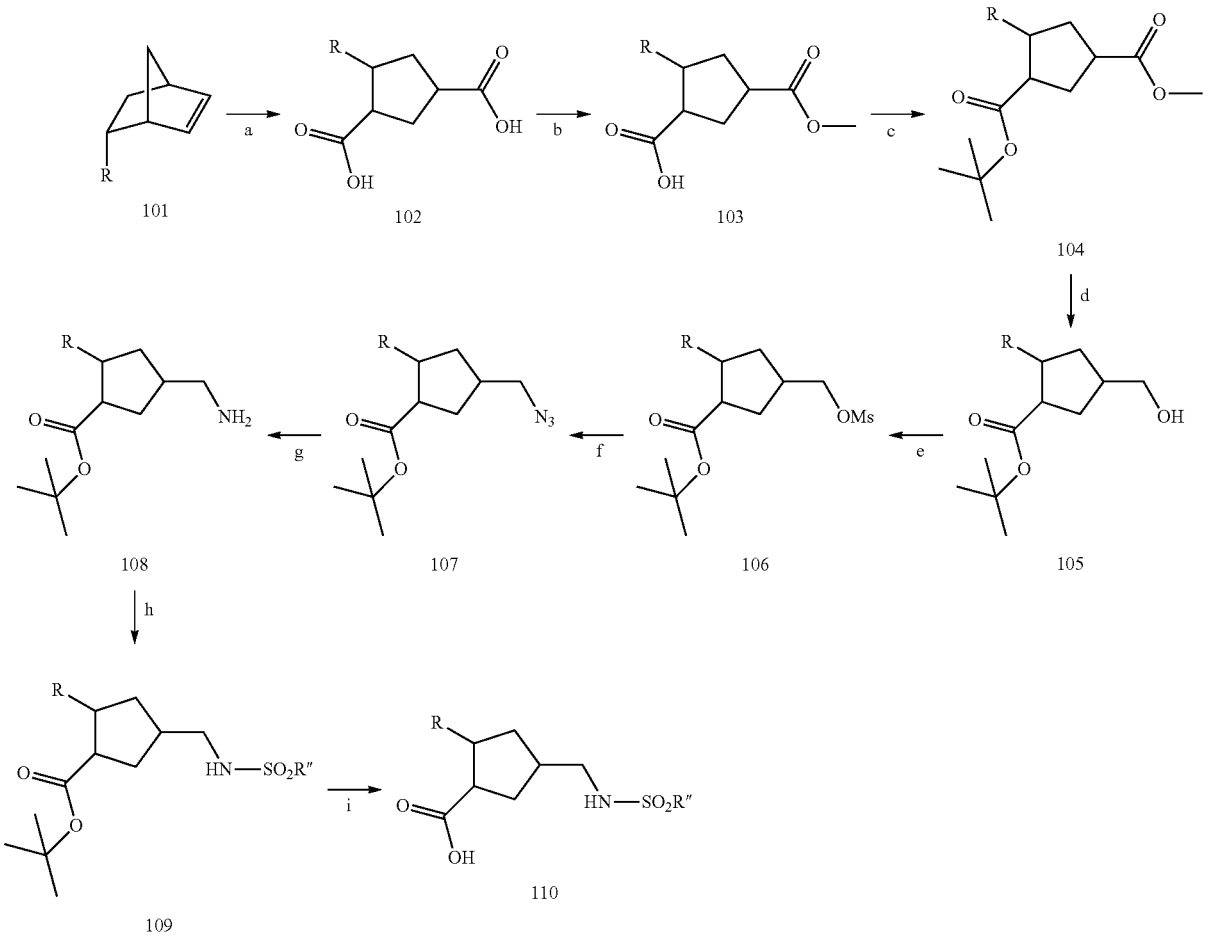

Methods for preparing 4-((dibenzylamino)methyl)-2-substituted-cyclopentanecarboxylic acids 115 for use in the preparation of compounds of the invention are illustrated in Scheme XVIII. Reduction of the methyl ester of compounds 103 to alcohols 111 is achieved using well known conditions such as those found in Preparation #22 or Larock, R. C. referenced above (Scheme XVIII, step a). Step b illustrates the formation of esters 112 which is achieved as described in Preparation #22 or Larock, R. C. referenced above. In step c, alcohols 112 are oxidized to aldehydes 113 using known conditions such as those described in Preparation #22 or Larock, R. C. referenced above. The reductive amination of aldehydes 113 using conditions such as those described in General Procedures X or X.1 gives amines 114 (Scheme XVIII, step d). In step e, esters 114 are hydrolyzed to give 4-((dibenzylamino)methyl)-2-substituted-cyclopentane-carboxylic acids 115 using conditions such as those described in General Procedures Z or TT or known to one skilled in the art (for example, the books from Larock, R. C. or Greene, T. W. and Wuts, P. G. M. referenced above).

Scheme XVIII

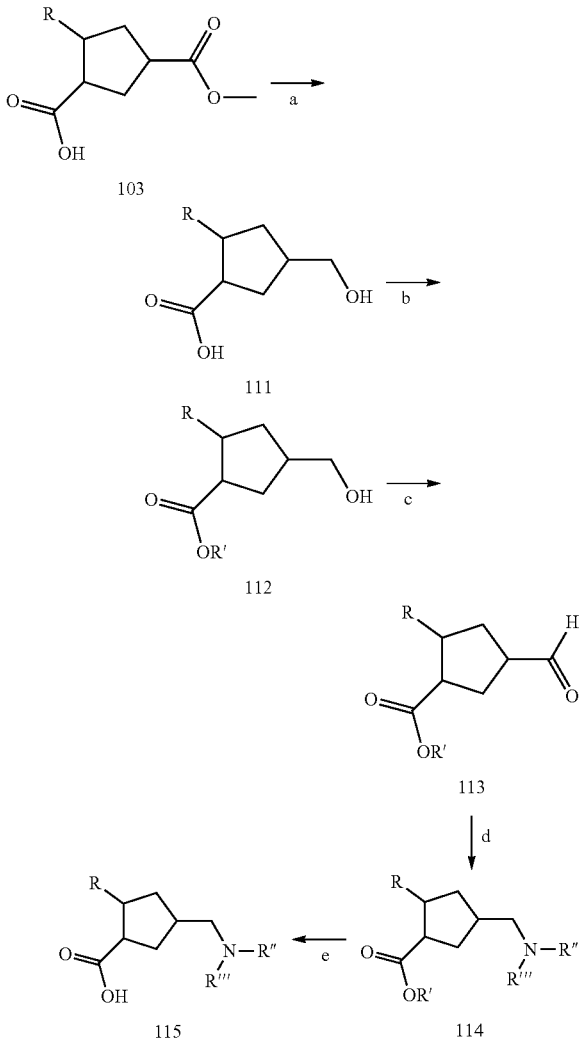

Methods for preparing 3H-imidazo[1,2-a]pyrrolo[2,3-e] pyrazin-8-amine compounds of the invention are illustrated in Scheme XIX. Alkylation of pyrrolopyrazin-2-ylcarbamates 11 with t-butyl 2-bromoacetate, by methods known to one skilled in the art (for example, General Procedures S or S.1), gives pyrrolopyrazines 116 (Scheme XIX, step a). The double deprotection of pyrrolopyrazines 116 to aminoacetic acids 117 may be accomplished using conditions such as those described in General Procedures E, E.1, or QQQ (Scheme XIX, step b). The coupling of acids 117 with amines provides amides 118 (Scheme XIX, step c) using well known conditions such as those given in General Procedure H or Larock, R. C. referenced above. As shown in step d, the cyclization of amides 118 to imidazopyrrolopyrazin-8-amines 119 may be accomplished using conditions such as those described in General Procedures OO or OO.1. Further functionalization of the R' or R" group in imidazopyrrolopyrazin-8-amines 119 can be performed, if desired, using reactions known to one skilled in the art (for example, Larock, R. C. referenced above). For example, amides, ureas, sulfonamides, aryl amines, heteroaryl amines, sulfonyl ureas, substituted amines, squaramides, or guanidines can be prepared from imidazopyrrolopyrazin-8-amines 119 with an R' or R" group containing a primary or secondary amine (for example, General Procedures G, H, I, J, J.1, XXX, EEEE, K, K.1, L, DD, QQ, RR, YY, ZZ followed by AAA, CCC, YYY, X, X.1, TTTT, or EEEEE). Also, deprotection of the of the R' or R" group in imidazopyrrolopyrazin-8-amines 119 to yield deprotected compounds 119 can be performed using conditions such as those described in Greene, T. W. and Wuts, P. G. M. referenced above or in General Procedures E, E.1, F, F.1, Y, or BB and the deprotected compounds 119 may then be reacted further as described above. Removal of the sulfonamide protecting group of imidazopyrrolopyrazin-8-amines 119 may be accomplished using conditions such as those described in General Procedures D, XXX, AAAA, BBBB, or CCCC or by methods known to one skilled in the art (for example, the books from Larock, R. C. or Greene, T. W. and Wuts, P. G. M. referenced above) to give imidazopyrrolopyrazin-8-amines 120 (Scheme XIX, step e).

Scheme XIX

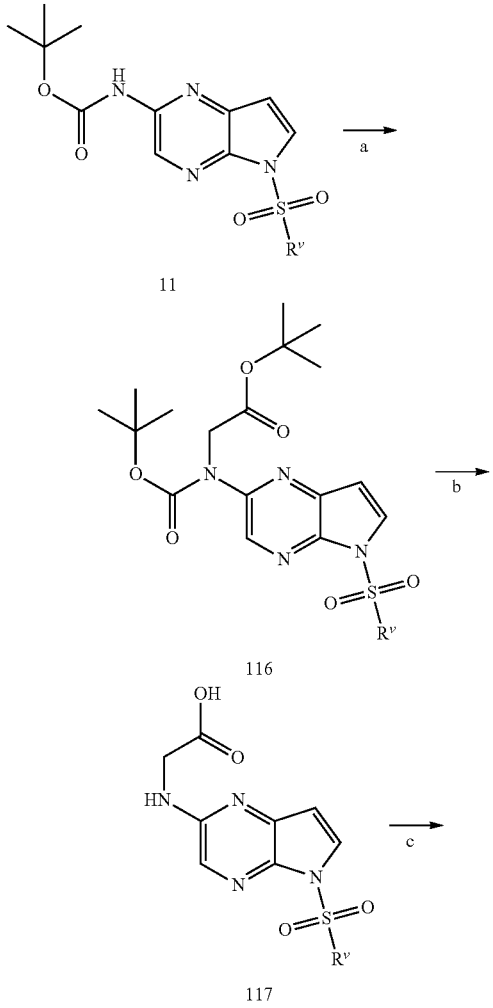

-continued

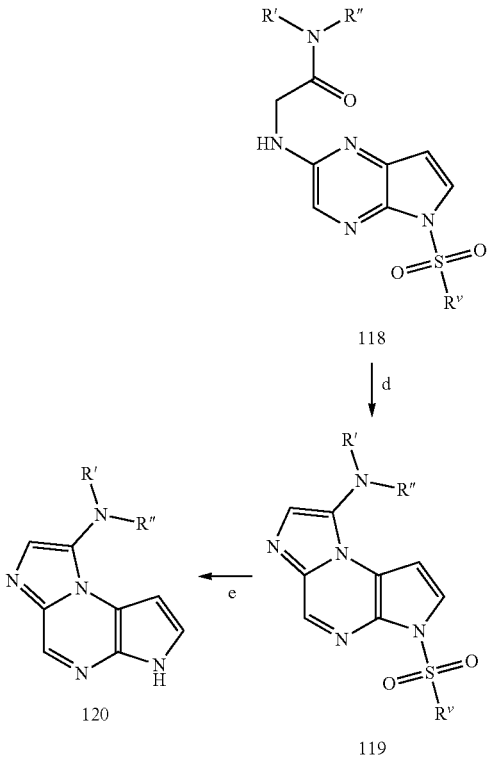

Methods for preparing pyrrolidine-3-carboxylic acids 125 for use in the preparation of compounds of the invention are illustrated in Scheme XX. In step a, alkynes 121 are reduced to alkenes 122 as described in General Procedure RRR or using methods known to one skilled in the art (for example, Larock, R. C. referenced above). The 1,3-dipolar cycloaddition of alkenes 122 and N-substituted-1-methoxy-N-((trimethylsilyl)methyl)methanamine 123 to give pyrrolidines 124 (Scheme XX, step b) can be accomplished by methods known to one skilled in the art (for example, General Procedure SSS or Journal of Medicinal Chemistry, 2009, 52(24), 7946-7949). The ester of compounds 124 may be hydrolyzed under aqueous base or acid conditions to give carboxylic acids 125 (Scheme XX, step c) using conditions such as those described in General Procedures Z or TT or Larock, R. C. referenced above.

Scheme XX

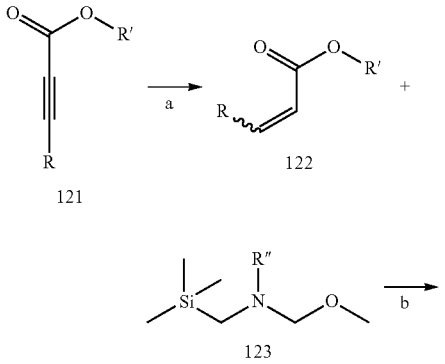

-continued

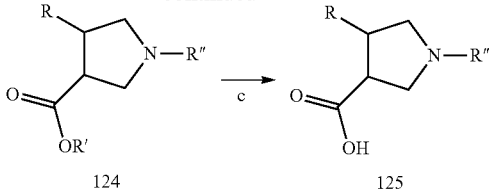

Methods for preparing sulfone-substituted 1-cyclopentyl-6H-pyrrolo[2,3-e][1,2,4]triazolo[4,3-a]pyrazine compounds of the invention are illustrated in Scheme XXI. As shown in step a, Mitsunobu reaction of alcohols 46 with appropriate thiols gives sulfides 126 using conditions such as those described in General Procedure MMM or by methods known to one skilled in the art (for example, Larock, R. C. referenced above). The oxidation of sulfides 126 to sulfones 127 (Scheme XXI, step b) is accomplished as described in General Procedure LLL or by methods known to one skilled in the art (for example, Larock, R. C. referenced above). The SEM protecting group of pyrrolotriazolopyrazines 127 may be removed by methods such as those described in General Procedures LL and LL.1, or using conditions such as described in Greene, T. W. and Wuts, P. G. M. referenced above to give pyrrolotriazolopyrazines 128 (Scheme XXI, step c).

Scheme XXI

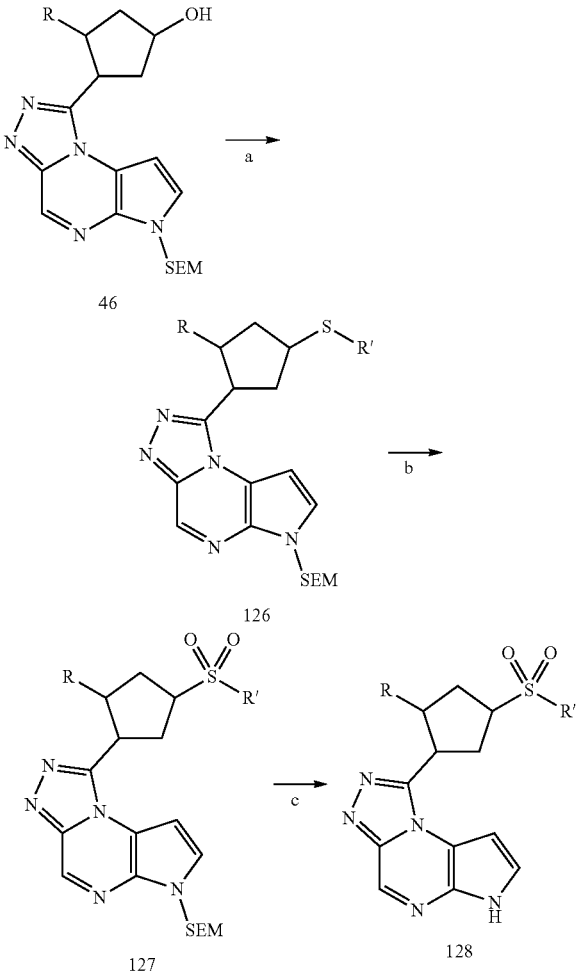

Methods for preparing sulfonyl chlorides 133 for use in the preparation of compounds of the invention are illustrated in Scheme XXII. In step a, sulfonates 130 are prepared from sulfonyl chlorides 129 using known reaction conditions such as those described in Preparation #6 Step A, WO2007014011, or WO2009018238. An additional substitutent is added to sulfonates 130 to give sulfonates 131 via alkylation as described in General Procedure KKK, WO2007014011, or WO2009018238 (Scheme XXII, step b). In step c, potassium sulfonates 132 are prepared from sulfonates 131 with aqueous potassium cyanate using conditions such as those in General Procedure JJJ, WO2007014011, or WO2009018238. Potassium sulfonates 132 are converted to sulfonyl chlorides 133 (Scheme XXII, step d) using thionyl chloride as described in General Procedure EEE, WO2007014011, or WO2009018238.

Scheme XXII

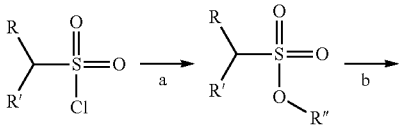

129 130

-continued

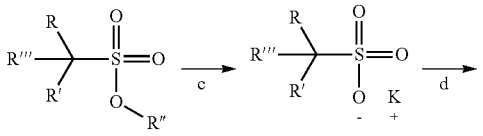

131 132

-continued

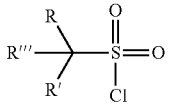

133

Methods for preparing imidazopyrrolo[2,3-e]pyrazines compounds of the invention are illustrated in Scheme XXIII. Imidazopyrrolopyrazines 15 [T=N, U=CH] or 20 [T=CH, U=N] may be halogenated using conditions such as those described in General Procedures GGG or GGG.1 to give 8-haloimidazopyrrolopyrazines 138 (Scheme XXIII, step a). In step b, 8-haloimidazopyrrolopyrazines 138 may be protected with a SEM group using conditions known in the literature such as those found in Greene, T. W. and Wuts, P. G. M. referenced above or as in General Procedure KK. The resulting SEM-protected 8-haloimidazopyrrolopyrazines 139 may undergo a variety of reactions known to one skilled in the art (for example, Larock, R. C. referenced above) including, but not limited to, cyanation as described in General Procedure HHH (Scheme XXIII, step c) or Suzuki coupling reactions as described in General Procedure VVV or Stille coupling reactions as described in General Procedure CCCCC (Scheme XXIII, step e). The resulting products 140 or 142 may be deprotected using conditions such as those described in General Procedures LL and LL.1, or by methods known to one skilled in the art (for example, Greene, T. W. and Wuts, P. G. M. referenced above) to give imidazopyrrolo[2,3-e]pyrazines 141 or 143 (Scheme XXIII, steps d and f, respectively).

Scheme XXIII

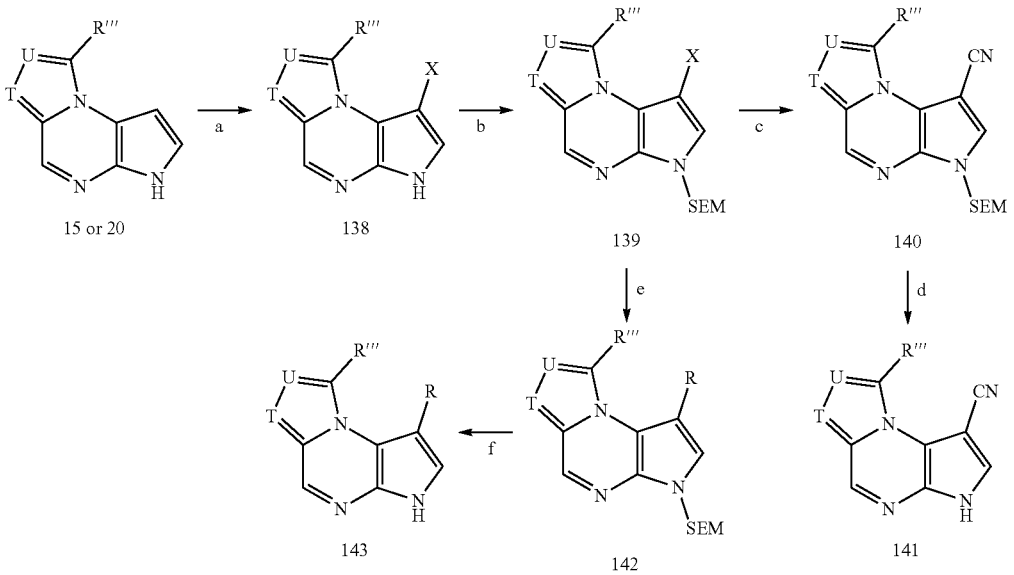

15 or 20 138 139 140 141 142 143

Methods for preparing compounds of the invention from a common ketone intermediate are illustrated in Scheme XXIV. As shown in scheme XXIV, step a, ketones 144 may be reacted with an alkyl lithium or a Grignard reagent to give alcohols 145 using conditions known to one skilled in the art (for example, Larock, R. C. referenced above or General Procedure ZZZ). Alternatively, ketones 144 may undergo a Horner-Wadsworth-Emmons reaction with a reagent such as ethyl 2-(diethoxyphosphoryl)acetate (R'''=$CO_2Et$) or diethyl cyanomethylphosphonate (R'''=CN) as described in General Procedure III to give alkenes 146 (Scheme XXIV, step b). Alkenes 146 may be hydrogenated to alkanes 147 using well-known conditions such as those described in General Procedure W and W.1 (Scheme XXIV, step c). The R''' group may be further functionalized using a variety of reactions such as those described in Larock, R. C. referenced above. For example, for R'''=$CO_2Et$, alcohols 148 can be prepared as described in General Procedure ZZZ (Scheme XXIV, step d) or oxadiazoles 149 may be prepared as described in General Procedure DDDD (Scheme XXIV, step e). As shown in scheme XXIV, step f, ketones 144 may also be reduced to alcohols 150 as described in General Procedure P or in Larock, R. C. referenced above. Mesylates 151 are formed from alcohols 150 using conditions known to one skilled in the art such as those described in General Procedure IIII (Scheme XXIV, step g) and can be reacted with a variety of nucleophiles (Nu) as described in General Procedure JJJJ (Scheme XXIV, step h) to give compounds 152. Depending on the nucleophile used, further functionalization can be done to give compounds 153 (Scheme XXIV, step i). These functionalizations may be accomplished using methods such as those described in Larock, R. C. referenced above or General Procedures QQQQ or UUUU.

Scheme XXIV

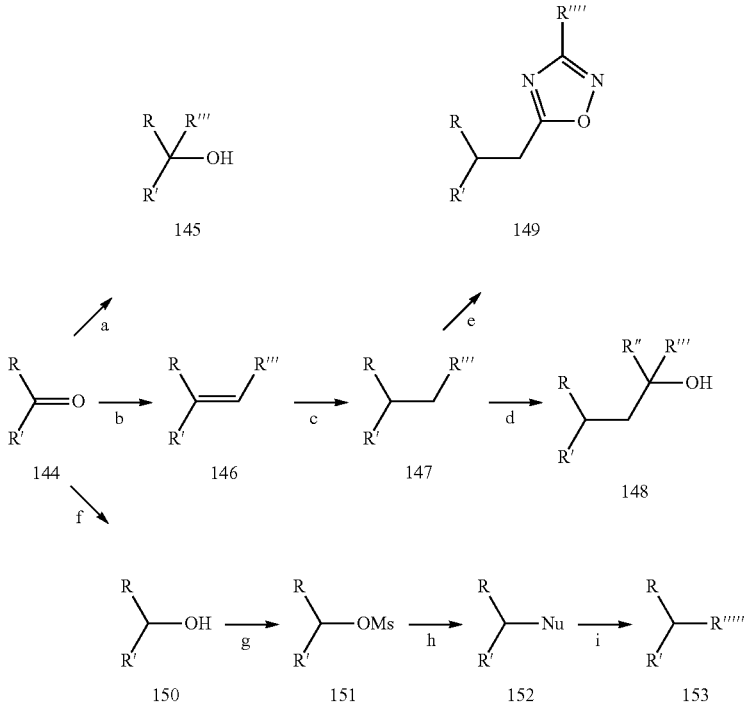

Methods for preparing 1,6-dihydroimidazo[4,5-d]pyrrolo[2,3-b]pyridin-2-amine compounds of the invention are illustrated in Scheme XXV. Diamines 136 (Scheme XVIII) may be reacted with cyanogen bromide as described in General Procedure RRRR (Scheme XXV, step a). The resulting 1,6-dihydroimidazo[4,5-d]pyrrolo[2,3-b]pyridin-2-amines 154 may be further further functionalized, if desired, using reactions known to one skilled in the art (see, for example, Larock, R. C. above) to give 1,6-dihydroimidazo[4,5-d]pyrrolo[2,3-b]pyridin-2-amines 155 (Scheme XXV, step b). Removal of the sulfonamide protecting group of 1,6-dihydroimidazo[4,5-d]pyrrolo[2,3-b]pyridin-2-amines 155 or 154 may be accomplished using conditions such as those described in General Procedures D, AAAA, BBBB, or CCCC or by methods known to one skilled in the art (for example, the books from Larock, R. C. or Greene, T. W. and Wuts, P. G. M. referenced above) to give 1,6-dihydroimidazo[4,5-d]pyrrolo[2,3-b]pyridin-2-amines 156 or 157, respectively (Scheme XXV, steps c and d).

Scheme XXV

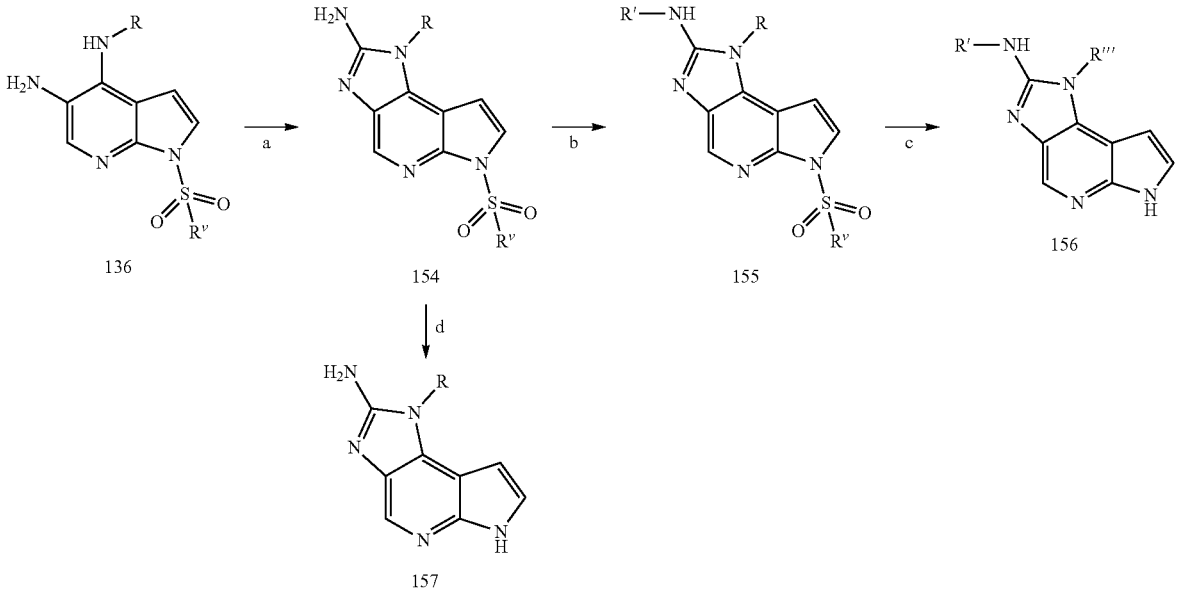

Methods for preparing 1,6-dihydropyrrolo[2,3-b][1,2,3]triazolo[4,5-d]pyridine compounds of the invention are illustrated in Scheme XXV. Diamines 136 (Scheme XVIII) may be reacted with sodium nitrite as described in General Procedure SSSS to give 1,6-dihydropyrrolo[2,3-b][1,2,3]triazolo[4,5-d]pyridines 158 (Scheme XXVI, step a). Removal of the sulfonamide protecting group of 1,6-dihydroimidazo[4,5-d]pyrrolo[2,3-b]pyridin-2-amines 158 may be accomplished using conditions such as those described in General Procedures D, AAAA, BBBB, or CCCC or by methods known to one skilled in the art (for example, the books from Larock, R. C. or Greene, T. W. and Wuts, P. G. M. referenced above) to give 1,6-dihydropyrrolo[2,3-b][1,2,3]triazolo[4,5-d]pyridines 159 (Scheme XXV, step b).

Scheme XXVI

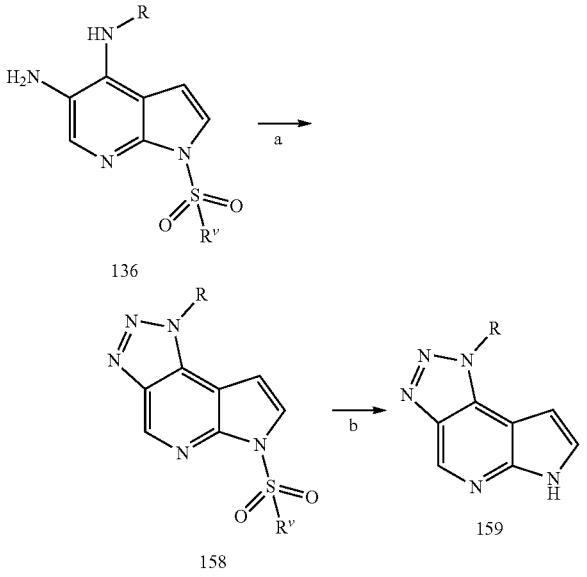

Alternate methods for preparing the ketone intermediate used to make dihydropyrazolo[4,3-d]pyrrolo[2,3-b]pyridine compounds of the invention are illustrated in Scheme XXVII. In step a, carboxylic acids 160 are converted to the corresponding acid chlorides 161 using conditions widely known to one skilled in the art such as those described in General Procedure WWWW. Acid chlorides 161 are reacted with 5-chloro-1-(triisopropylsilyl)-1H-pyrrolo[2,3-b]pyridine 162 as described in General Procedure VVVV (Scheme XXVII, step b) to give ketones 78 which may be further reacted as described in Scheme XIII.

Scheme XXVII

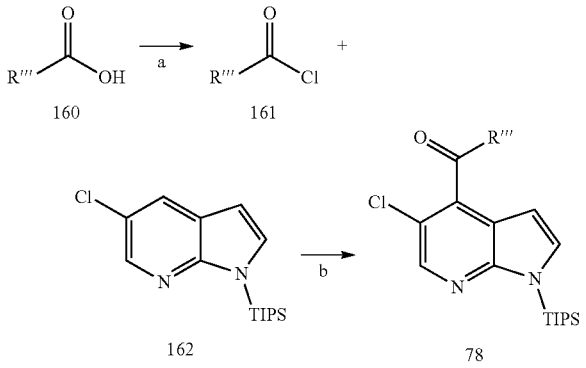

Alternate methods for preparing imidazo[1,2-a]pyrrolo[2,3-e]pyrazines compounds of the invention are illustrated in Scheme XXVIII. In step a, carboxylic acids 160 are converted to the corresponding sulfoxonium ylides 163 using conditions such as those described in General Procedure FFFFF or J. Org. Chem. 2004, 69, 1629. Pyrrolopyrazin-2-amines 164 may be prepared from pyrrolopyrazin-2-ylcarbamates 11 (Scheme II) using conditions known to one skilled in the art such as those described in General Procedure E or Greene, T. W. and Wuts, P. G. M. referenced above (Scheme XXVIII, step b). Sulfoxonium ylides 163 are reacted with pyrrolopyrazin-2-amines 164 using conditions such as those described in General Procedure GGGGG or Org. Lett. 2009, 11, 3566 to give pyrrolopyrazines 13 which may be further reacted as described in Scheme II (Scheme XXVIII, step c). Alternatively, as shown in step d, pyrrolopyrazin-2-amines 164 may be reacted with an α-haloaldehyde using conditions such as those given in General Procedure YYYY to give imidazopyrrolopyrazines 14 which may be further reacted as described in Scheme II.

Scheme XXVIII

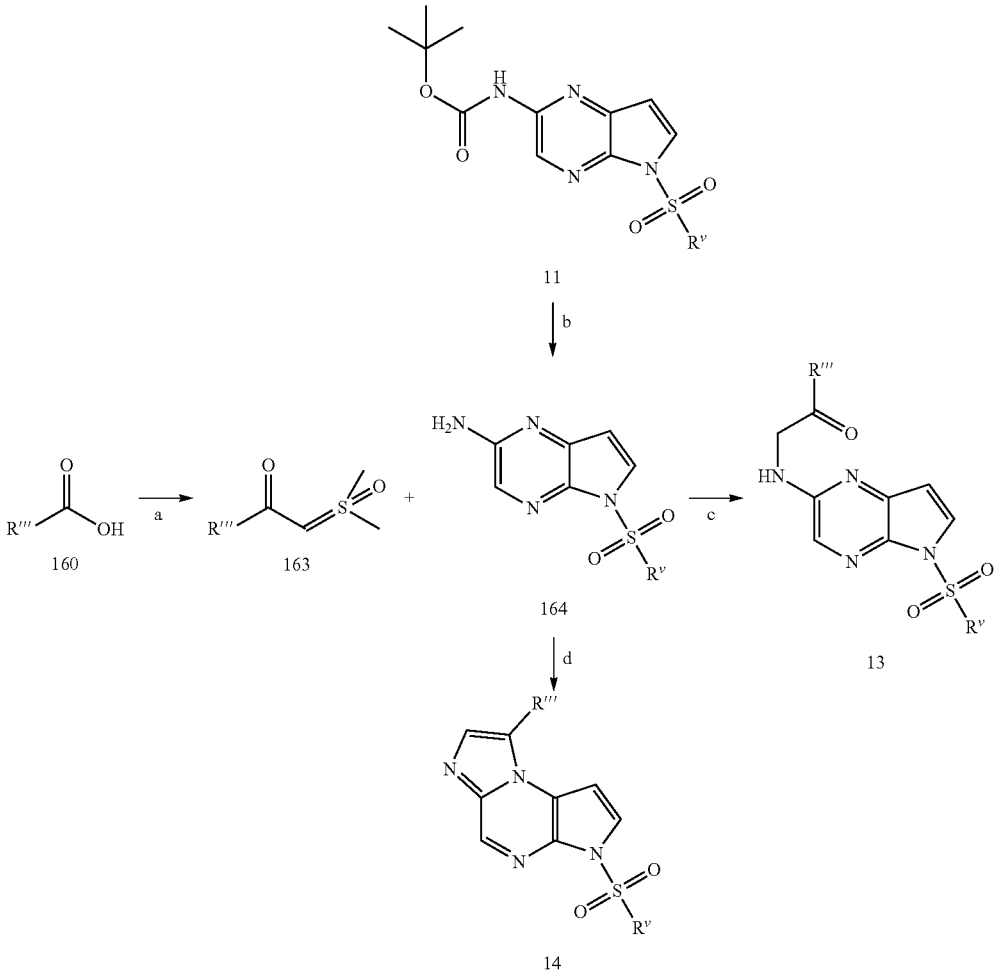

If desired, chiral separation of any of the chiral compounds in Schemes I-XXVIII may be done using methods known to one skilled in the art such as chiral preparative HPLC or chiral SFC (for example, General Procedure AA) or crystallization of diastereomeric salts as described in Example #5. Further functionalization of any of the R groups above (e.g. R, R", R'''', R'''', and R''''') can be performed, if desired, using reactions known to one skilled in the art (for example, Larock, R. C. referenced above). For example, formation of amides, ureas, sulfonamides, aryl amines, heteroaryl amines, sulfonyl ureas, substituted amines, squaramides, or guanidines can be prepared with an R group containing a primary or secondary amine (for example, General Procedures G, H, I, J, J.1, XXX, EEEE, K, K.1, L, DD, QQ, RR, YY, ZZ followed by AAA, CCC, YYY, X, X.1, TTTT, or EEEEE). Also, deprotection of an R group to yield deprotected compounds may be performed using conditions such as those described in Greene, T. W. and Wuts, P. G. M. referenced above or in General Procedures E, E.1, F, F.1, Y, or BB and the deprotected compounds may then be reacted further as described above.

GENERAL PROCEDURES AND EXAMPLES

The general synthetic schemes that were utilized to construct the majority of compounds disclosed in this application are described below in Schemes 1-111. These schemes are provided for illustrative purposes only and are not to be construed as limiting the scope of the invention.

Scheme 1. Formation of a hydrazide from a carboxylic acid (General Procedure A)

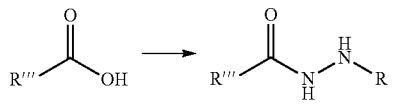

Scheme 2. Cyclization of a hydrazide (General Procedure B)

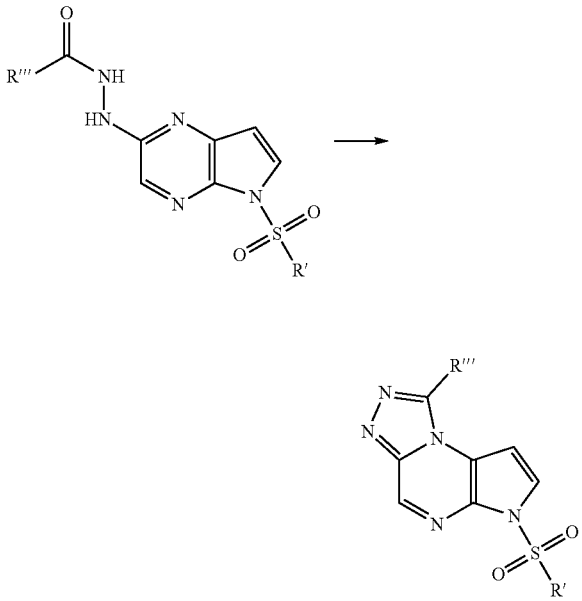

Scheme 3. Cyclization of a hydrazide with loss of Boc-protecting group (General Procedure C)

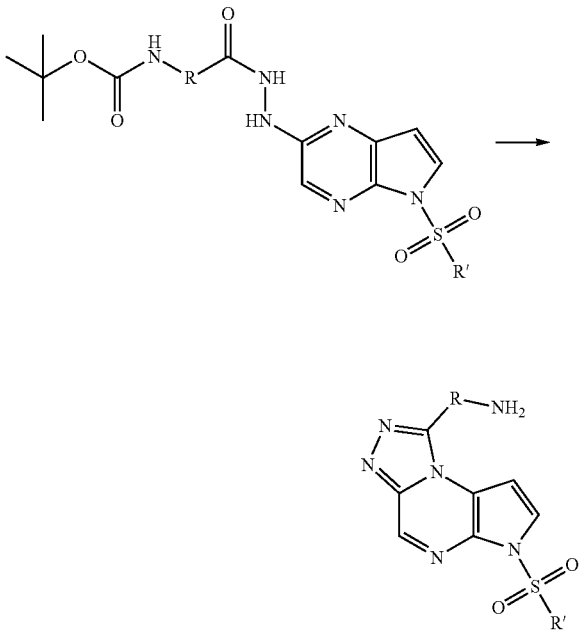

Scheme 4. Hydrolysis of a sulfonamide (General Procedure D)

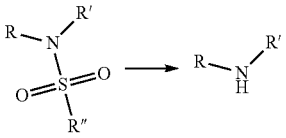

Scheme 5. Acidic cleavage of a Boc-protected amine (General Procedure E and E.1)

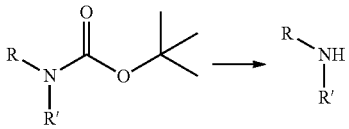

Scheme 6. Deprotection of a Cbz-protected amine using HBr in AcOH (General Procedure F and F.1)

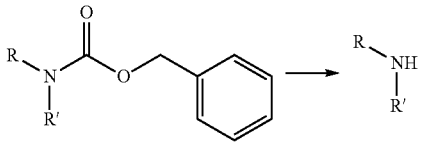

Scheme 7. Formation of an acetamide (General Procedure G)

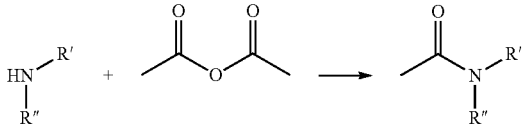

Scheme 8. Formation of an amide from a carboxylic acid and an amine (General Procedure H)

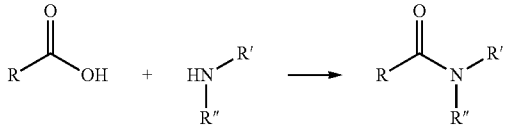

Scheme 9. Formation of a urea from an amine and a carbamoyl chloride (General Procedure I)

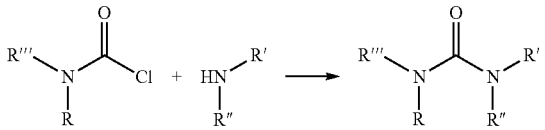

Scheme 10. Formation of a urea (X = O) or thiourea (X = S) using CDI or thiocarbonyl diimidazole, respectively (General Procedures J and J.1)

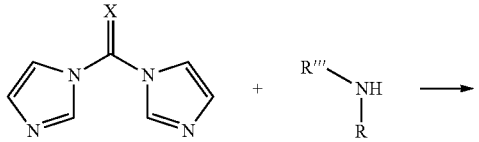

-continued

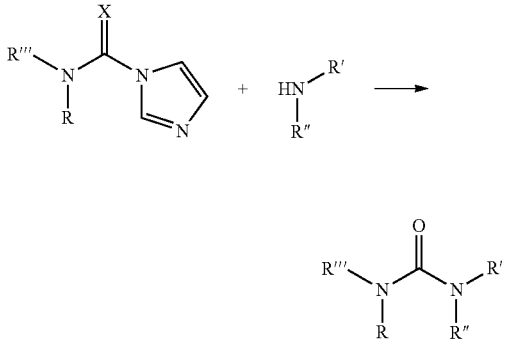

Scheme 11. Formation of a sulfonamide from an amine (General Procedure K and K.1)

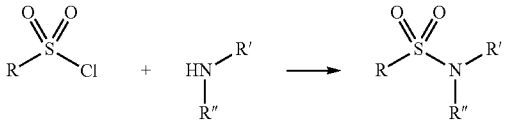

Scheme 12. Displacement of an aryl or heteroaryl halide with an amine (General Procedure L)

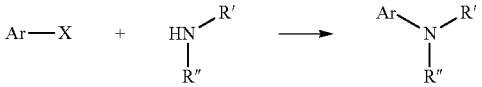

Scheme 13. Boc-protection of an amine (General Procedures M and M.1)

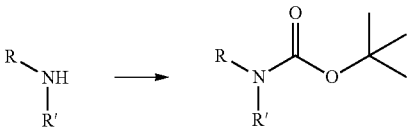

Scheme 14. Cbz-protection of an amine (General Procedure N)

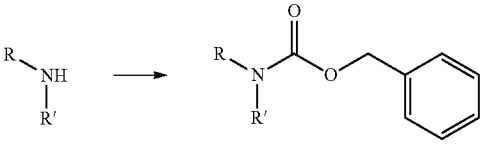

Scheme 15. Reduction of a pyridine (General Procedure O)

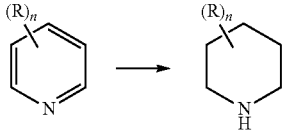

Scheme 16. Reduction of a carbonyl to an alcohol (General Procedure P)

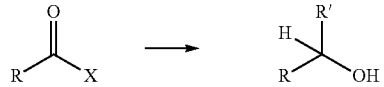

X = H, R′, OR″ for X = H or OR″, R′ = H

Scheme 17. Cyclization of an amide using a dithiaphosphetane reagent (General Procedure Q)

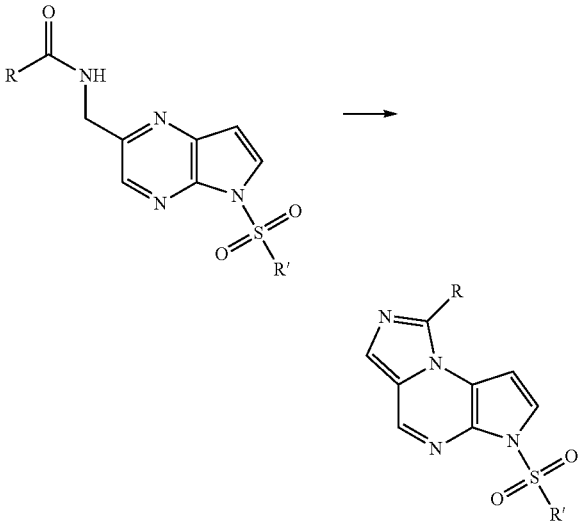

Scheme 18. Formation of a bromomethyl ketone from an acid (General Procedure R)

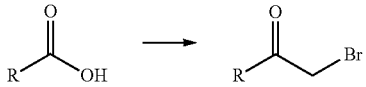

Scheme 19. N-Alkylation using an alkyl halide, α-haloketone, or α-haloamide (General Procedures S and S.1)

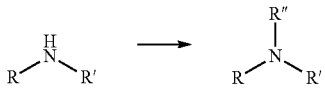

Scheme 20. Cyclization of a ketone using a dithiaphosphetane reagent (General Procedure T)

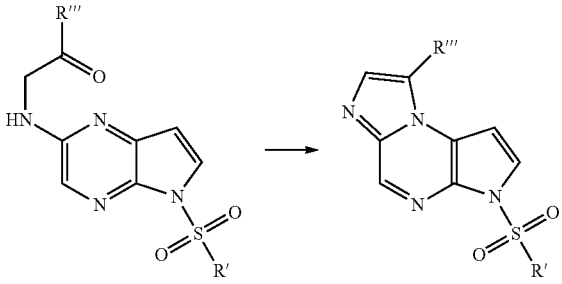

Scheme 21. Knoevenagel condensation to form a substituted cyclopentadiene (General Procedure U)

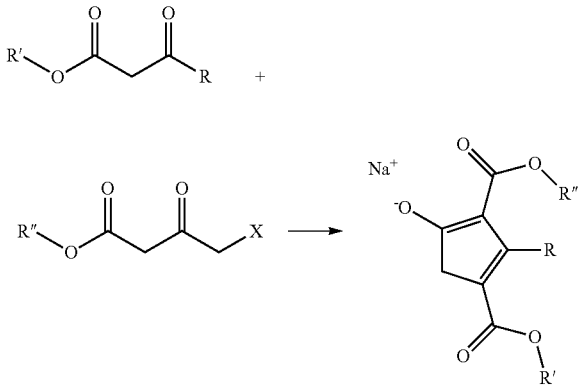

Scheme 22. Decarboxylation of a β-ketoester enolate (General Procedure V)

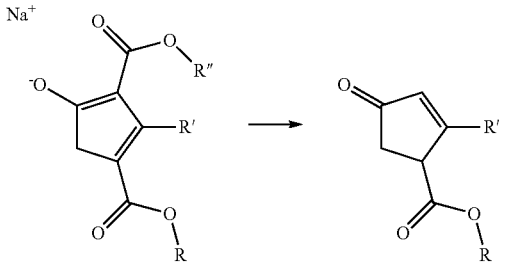

Scheme 23. Hydrogenation of an alkene (General Procedures W and W.1)

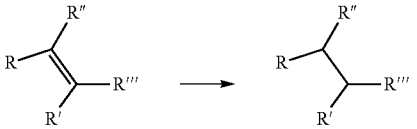

Scheme 24. Reductive amination of a ketone or aldehyde (R′ = H) (General Procedures X and X.1)

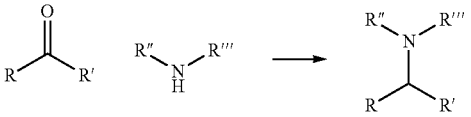

Scheme 25. Hydrogenation of a benzyl- or Cbz-protected amine (General Procedure Y)

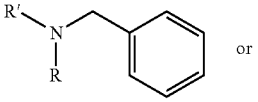

-continued

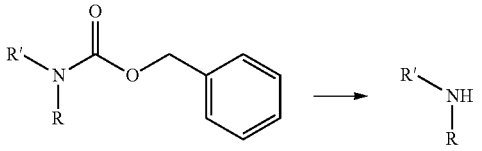

Scheme 26. Basic hydrolysis of an ester to a carboxylic acid (General Procedure Z)

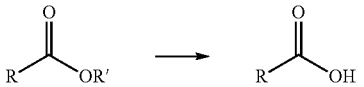

Scheme 27: Chiral preparative HPLC separation of stereoisomers (General Procedure AA)

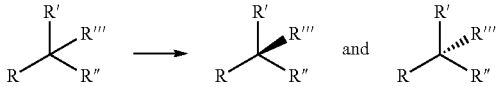

Scheme 28: Acidic hydrolysis of an acetyl protected amine (General Procedure BB)

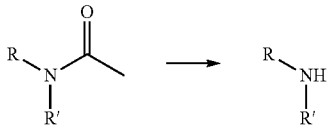

Scheme 29: Formation of a sulfamoyl chloride (General Procedure CC)

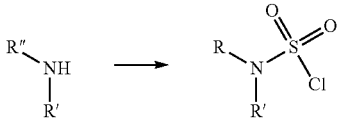

Scheme 30: Formation of a sulfonylurea (General Procedure DD)

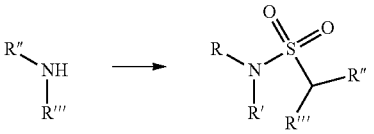

Scheme 31: Ether formation from a trichloroacetimidate derivative (General Procedure EE)

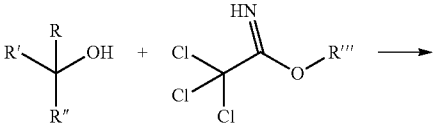

-continued

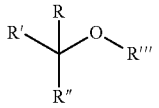

Scheme 32: Deprotection of a PMB-protected alcohol (General Procedure FF)

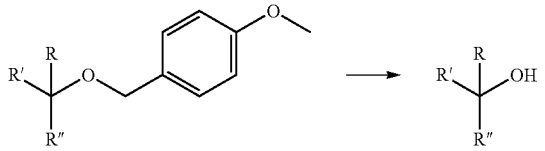

Scheme 33: Formation of a lactone (General Procedure GG)

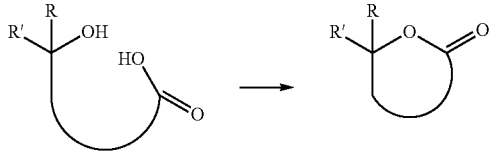

Scheme 34: Opening of a lactone with an amine or hydrazine (General Procedure HH)

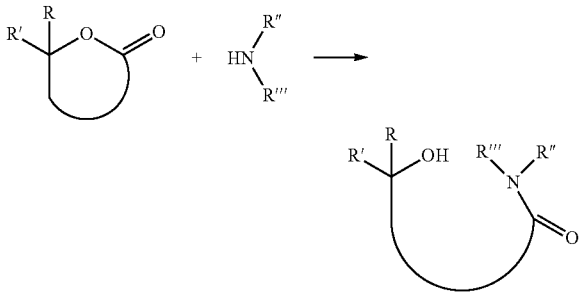

Scheme 35: Mitsunobu reaction of an alcohol (General Procedure II)

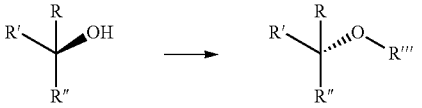

Scheme 36: Displacement of a halide with an alcohol (General Procedure JJ)

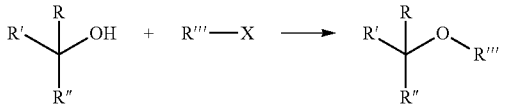

Scheme 37: SEM protection of a nitrogen (General Procedure KK)

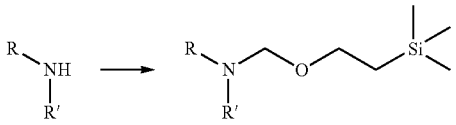

Scheme 38: SEM deprotection of a nitrogen (General Procedure LL and LL.1)

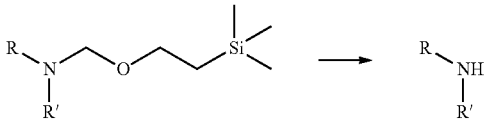

Scheme 39: Halogenation of an imidazole (General Procedure MM)

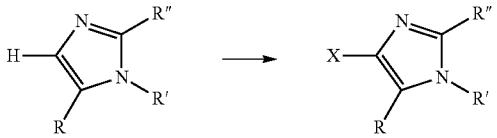

Scheme 40: Formation of an amide from a carboxylic acid and an amine with loss of a sulfonamide protecting group (General Procedure NN)

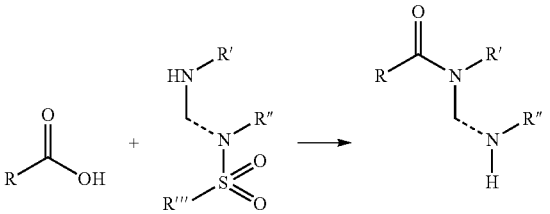

Scheme 41: Cyclization with $POCl_3$ (General Procedures OO and OO.1)

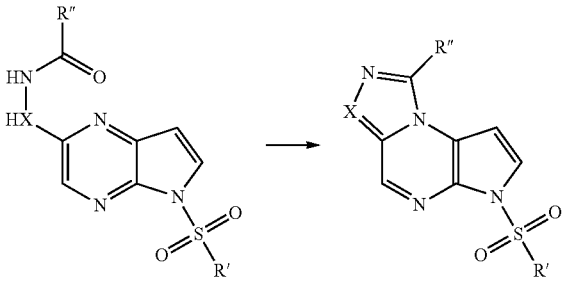

X = CR or N
R″ = R‴ or NR‴R⁗ or

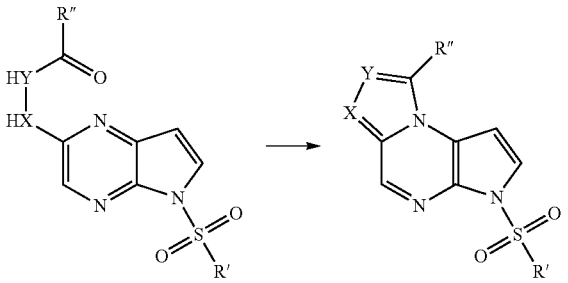

X = CR or N
Y = CR or N
R″ = R‴ or NR‴R⁗

Scheme 42: Reaction of an amine with an aryl boronic acid (General Procedure PP)

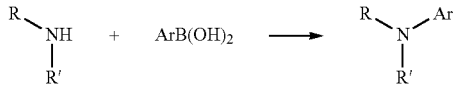

Scheme 43: Formation of a urea from an amine and an isocyanate (General Procedure QQ)

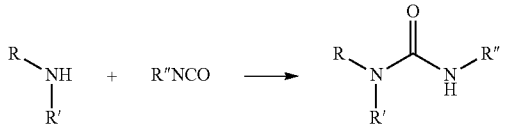

Scheme 44: Formation of a urea from an amine, a heteroaryl amine and phenyl chloroformate (General Procedure RR)

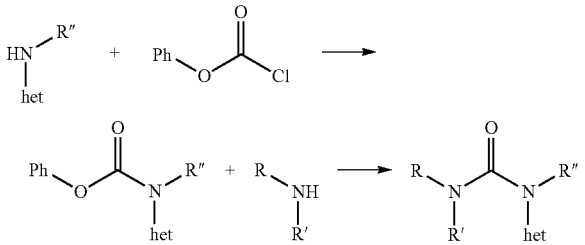

Scheme 45: Hydrolysis of an ester to an alcohol (General Procedure SS)

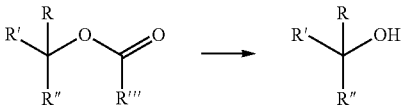

Scheme 46: Acid-meditated conversion of an ester to a carboxylic acid (General Procedure TT)

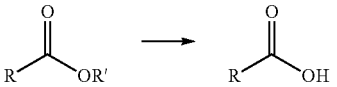

Scheme 47: Formation of a 2,2,2-trichloroacetimidate (General Procedure UU)

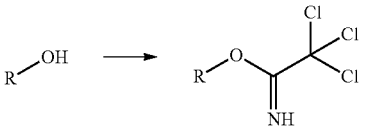

Scheme 48: Formation of a TBDMS-protected alcohol (General Procedure VV)

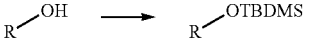

Scheme 49: Formation of a ketal (General Procedure WW)

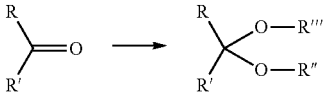

Scheme 50: Palladium catalyzed coupling of a hydrazone (General Procedure XX)

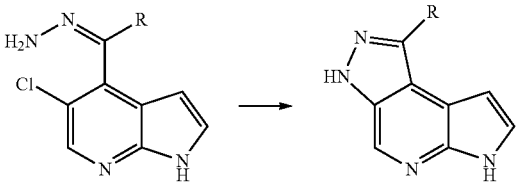

Scheme 51: Michael addition of an amine to an α,β-unsaturated sulfonamide (General Procedure YY)

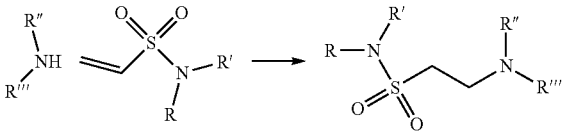

Scheme 52: Formation of an oxazolidinone sulfonourea (General Procedure ZZ)

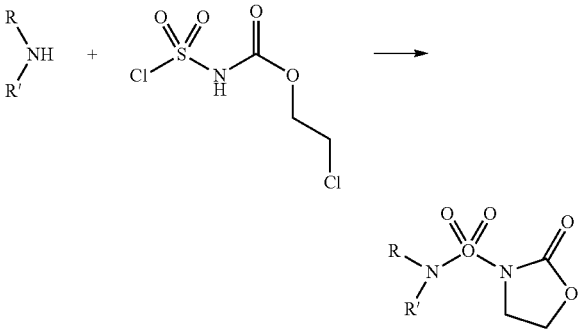

Scheme 53: Formation of a sulfonylurea from an oxazolidinone sulfonourea (General Procedure AAA)

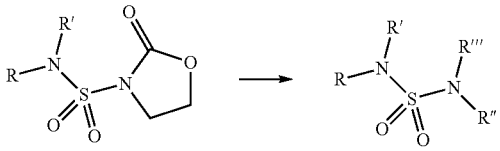

Scheme 54: Reduction of a nitro group (General Procedure BBB)

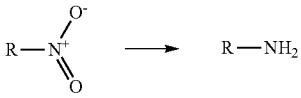

Scheme 55: Formation of an amide (General Procedure CCC)

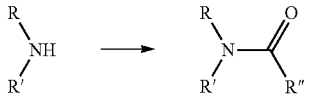

Scheme 56: Cyclization to form a fused imidazole (General Procedure DDD)

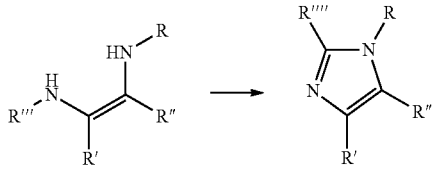

R''' = H or R''''CO—

Scheme 57: Formation of a sulfonyl chloride (General Procedure EEE)

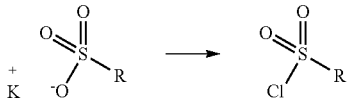

Scheme 58: Generation of an ether under reductive conditions ((General Procedure FFF)

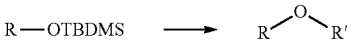

Scheme 59: Iodination, chlorination or bromination of a heterocycle or halogenation of a heterocycle (General Procedures GGG and GGG.1)

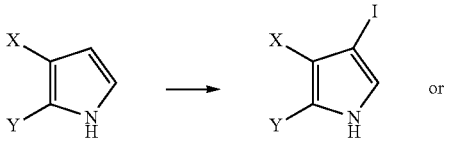

or

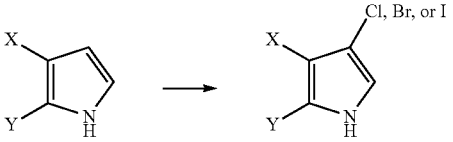

Scheme 60: Cyanation of a heterocycle (General Procedure HHH)

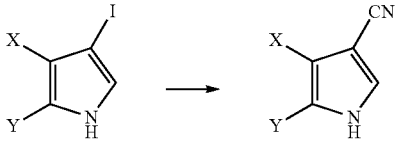

Scheme 61: Horner-Wadsworth-Emmons reaction of a ketone (General Procedure III)

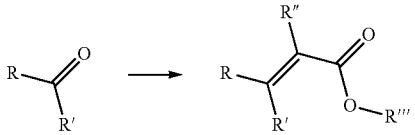

Scheme 62: Formation of a potassium sulfonate (General Procedure JJJ)

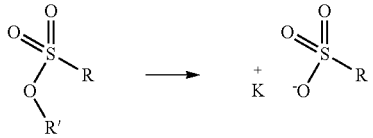

Scheme 63: Alkylation of a sulfonate (General Procedure KKK)

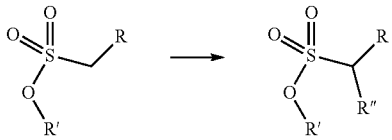

Scheme 64: Oxidation of a thioether to a sulfone (General Procedure LLL)

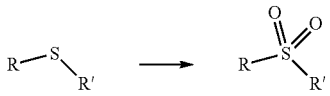

Scheme 65: Mitsunobu reaction using thiol (General Procedure MMM)

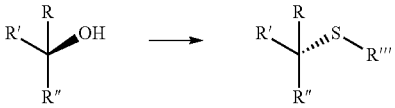

Scheme 66: Curtius reaction to form an isocyanate (General Procedure NNN)

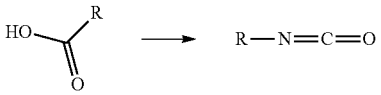

Scheme 67: Hydrolysis of an isocyanate (General Procedure OOO)

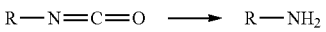

Scheme 68: Formation of an oxime ether from a ketone (General Procedure PPP)

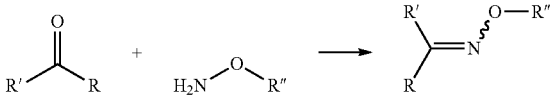

Scheme 69: TFA-mediated conversion of an ester to a carboxylic acid (General Procedure QQQ)

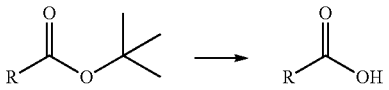

Scheme 70: Reduction of an alkyne to an alkene (General Procedure RRR)

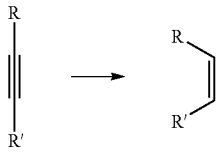

Scheme 71: 1,3-dipolar cycloaddition to form a pyrrolidine (General Procedure SSS)

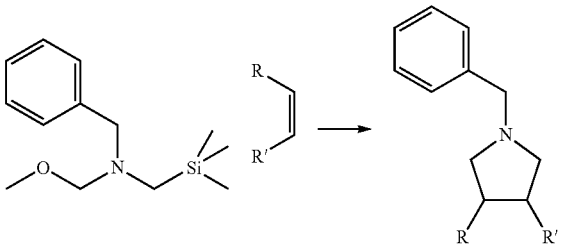

Scheme 72: Hydrogenation of an azide to an amine (General Procedure TTT)

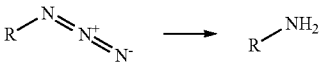

Scheme 73: Reaction of an aryl or heteroaryl halide with a boronic acid or boronic ester followed by tosyl deprotection (General Procedure UUU)

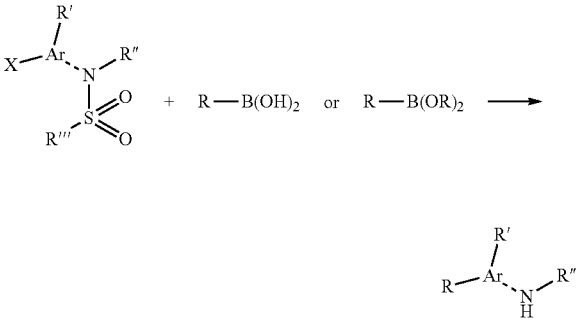

Scheme 74: Reaction of an aryl or heteroaryl halide with a boronic acid or boronate ester (General Procedure VVV)

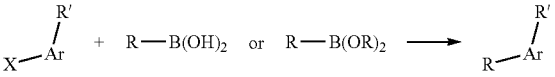

Scheme 75: Formation of a carbamate (General Procedure WWW)

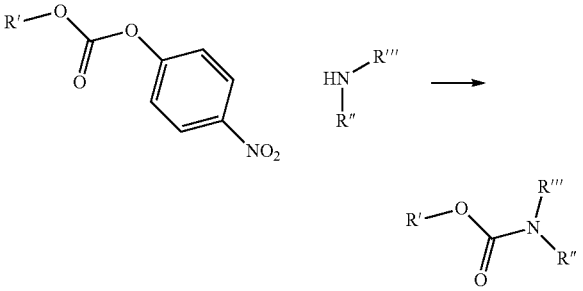

Scheme 76: Urea formation with loss of protecting group (General Procedure XXX)

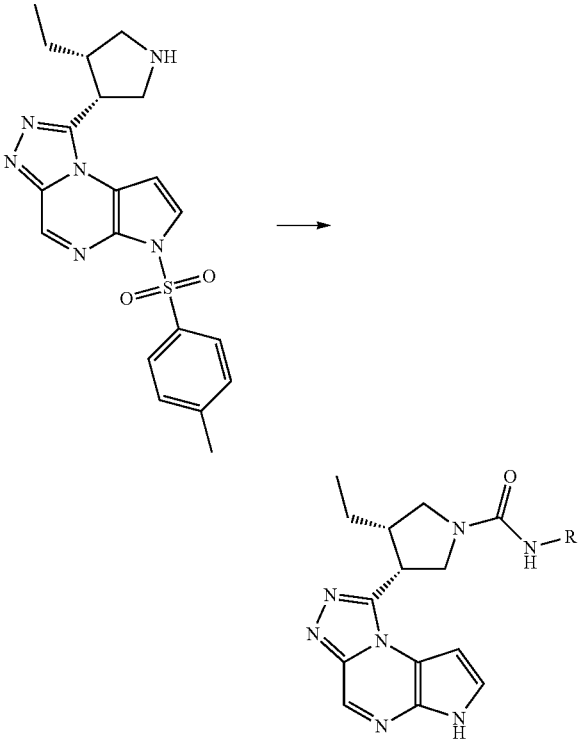

Scheme 77: Michael addtion (General Procedure YYY)

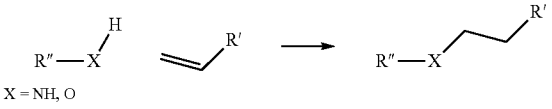

Scheme 78: Grignard or alkyl lithium addition to a carbonyl-containing compound (General Procedure ZZZ)

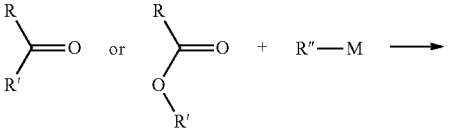

-continued

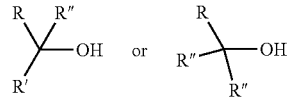

M = Li, MgX (X = Cl, Br, I)

Scheme 79: Deprotection of a sulfonamide with DBU (General Procedure AAAA)

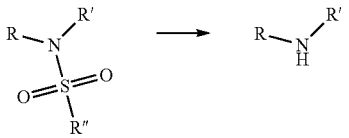

Scheme 80: Deprotection of a sulfonamide with TBAF (General Procedure BBBB)

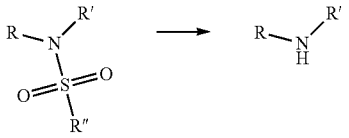

Scheme 81: Deprotection of a sulfonamide with KCN (General Procedure CCCC)

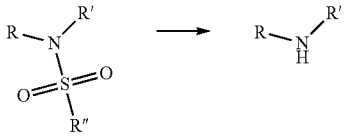

Scheme 82: Formation of oxadiazole (General Procedure DDDD)

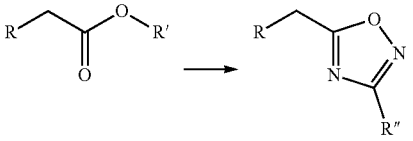

Scheme 83: Formation of a urea using phosgene (General Procedure EEEE)

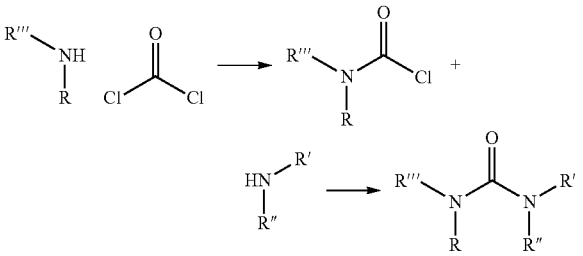

Scheme 84: Formation of an amide from an ester (General Procedure FFFF)

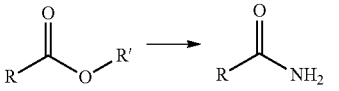

Scheme 85: Formation of a nitrile from a primary amide (General Procedure GGGG)

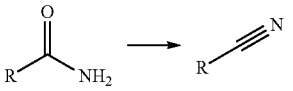

Scheme 86: O-alkylation with KOH or NaOH and TBAB (General Procedure HHHH)

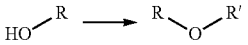

Scheme 87: Formation of mesylate (General Procedure IIII)

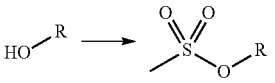

Scheme 88: Displacement of an alkyl mesylate, tosylate, or halide with a nucleophile (General Procedure JJJJ)

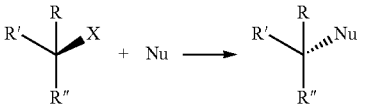

Scheme 89: Cyclization of a ketone using TFAA or PFPAA (General Procedure KKKK)

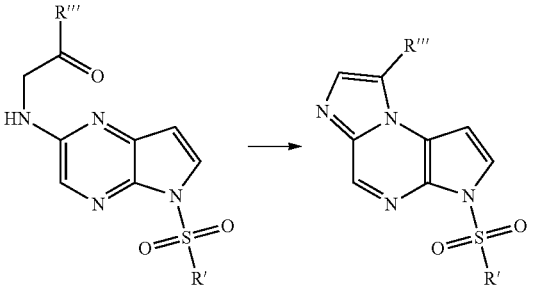

Scheme 90: Formation of a bromoketone (General Procedure LLLL)

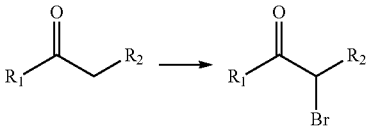

Scheme 91: Formation of a ketone from a Weinreb amide (General Procedure MMMM)

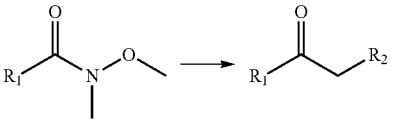

Scheme 92: Formation of β-hydroxysulfonamide from a ketone (General Procedure NNNN)

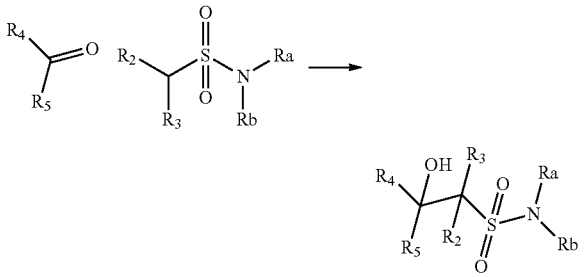

Scheme 93: Formation of a phenyl carbonate (General Procedure OOOO)

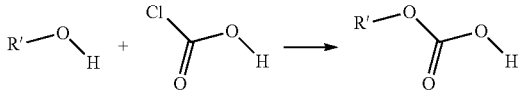

Scheme 94: Formation of a carbamate followed by sulfonamide hydrolysis (General Procedure PPPP)

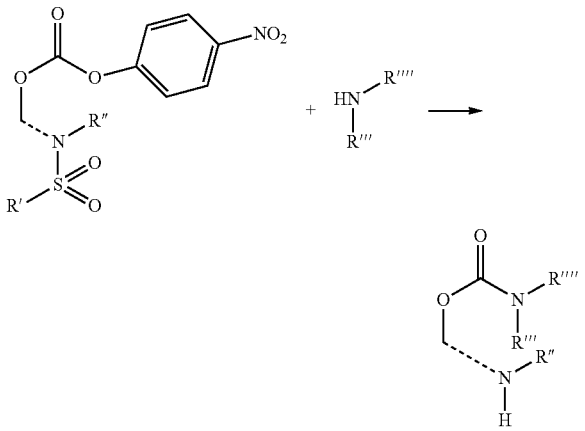

Scheme 95: Oxidation of an alkyl thioacetate to an alkyl sulfonic acid (General Procedure QQQQ)

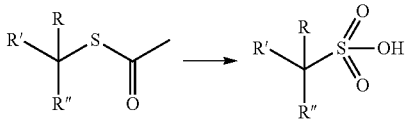

Scheme 96: Cyclization of a diamine with cynaogen bromide (General Procedure RRRR)

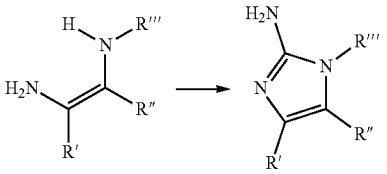

Scheme 97:
Cyclization of a diamine with $NaNO_2$ (General Procedure SSSS)

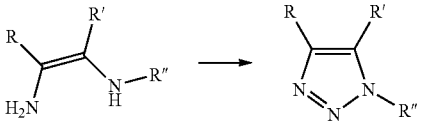

Scheme 98: Formation of a squaramide (General Procedure TTTT)

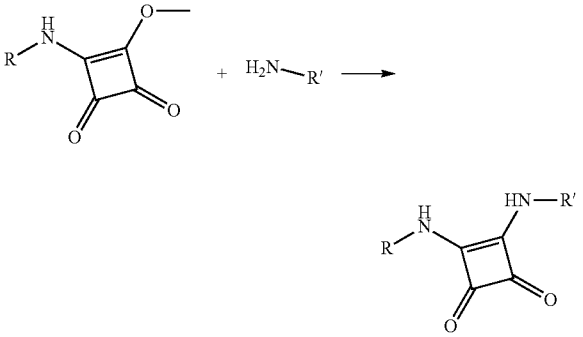

Scheme 99: Reduction of an azide to an amine (General Procedure UUUU)

$$R-N_3 \longrightarrow R-NH_2$$

Scheme 100:
Formation of a ketone from a heteroaryl halide (General Procedure VVVV)

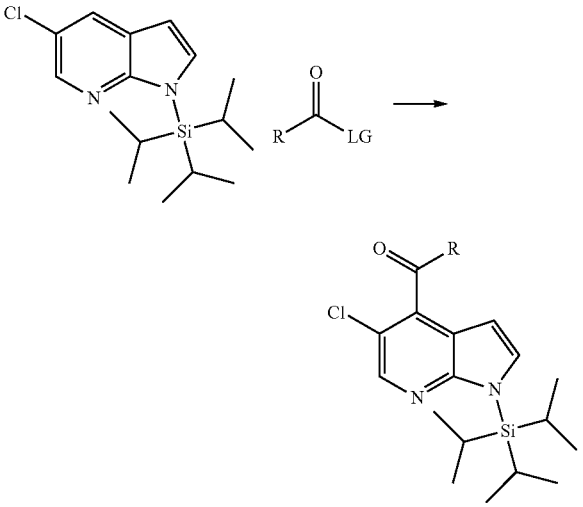

Scheme 101: Formation of an acid chloride (General Procedure WWWW)

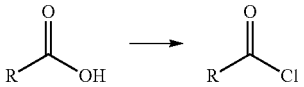

Scheme 102: Formation of a hydrazone (General Procedure XXXX)

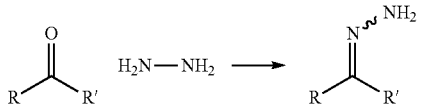

Scheme 103:
Cyclization with an α-haloaldehyde (General Procedure YYYY)

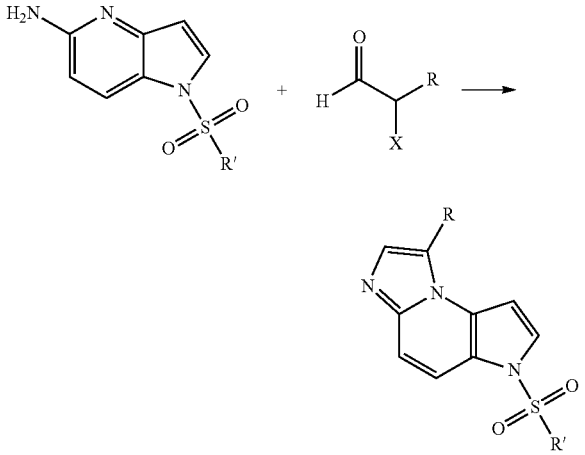

Scheme 104: Cyclization of a hydrazide
followed by hydrolysis of a sulfonamide (General Procedure YYYY)

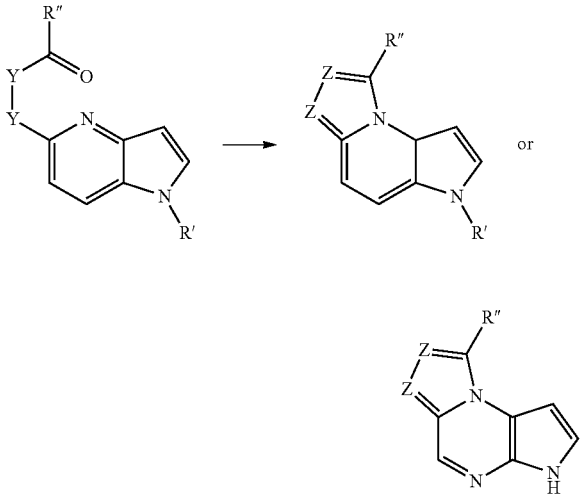

Y = CHR or NH
Z = CR or N

Scheme 105: Formation of a
carboxylic acid or ester from an aryl halide (General Procedure AAAAA)

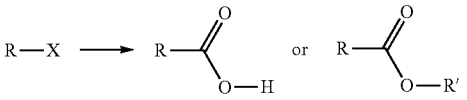

Scheme 106:
Cyclization with an orthosformate (General Procedure BBBBB)

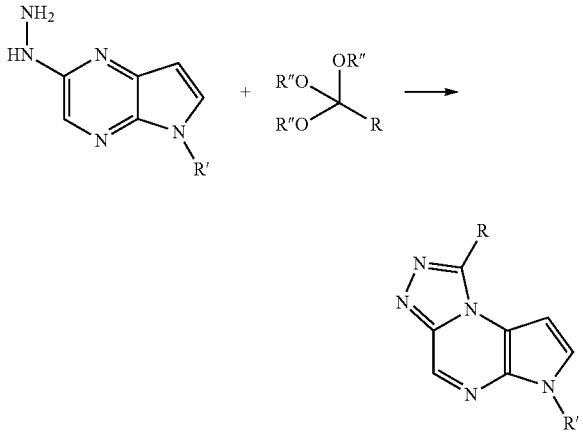

Scheme 107:
Stille coupling of an aryl or heteroaryl halide (General Procedure CCCCC)

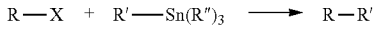

Scheme 108: Deprotection
of a Cbz-protected amine using triethylsilane (General Procedure DDDDD)

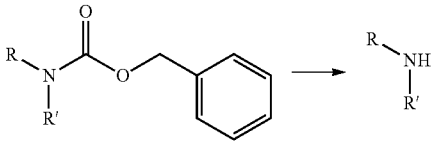

Scheme 109: Formation of guanidine (General Procedure EEEEE)

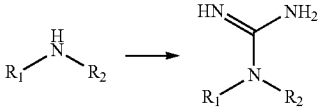

Scheme 110: Formation of a sulfoxonium ylide (General Procedure FFFFF)

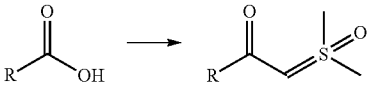

Scheme 111: Reaction
of a sulfoxonium ylide with an amine (General Procedure GGGGG)

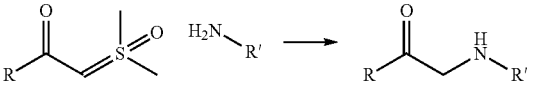

| List of General Procedures | |
|---|---|
| General Procedure A | Formation of a hydrazide from a carboxylic acid |
| General Procedure B | Cyclization of a hydrazide |
| General Procedure C | Cyclization of a hydrazide with loss of Boc-protecting group |
| General Procedure D | Hydrolysis of a sulfonamide |
| General Procedure E | Acidic cleavage of a Boc-protected amine |
| General Procedure E.1 | Acidic cleavage of a Boc-protected amine |
| General Procedure F | Deprotection of a Cbz-protected amine using HBr in AcOH |
| General Procedure G | Formation of an acetamide |
| General Procedure H | Formation of an amide from a carboxylic acid and an amine |
| General Procedure I | Formation of a urea from an amine and a carbamoyl chloride |
| General Procedure J | Formation of a urea or thiourea using CDI or thiocarbonyl diimidazole, respectively |
| General Procedure K | Formation of a sulfonamide from an amine |
| General Procedure K.1 | Formation of a sulfonamide from an amine or nitrogen containing heterocycle |
| General Procedure L | Displacement of an aryl or heteroaryl halide with an amine |
| General Procedure M | Boc-protection of an amine |
| General Procedure M.1 | Boc-protection of a nitrogen-containing compound |
| General Procedure N | Cbz-protection of an amine |
| General Procedure O | Reduction of a pyridine |
| General Procedure P | Reduction of carbonyl to an alcohol |
| General Procedure Q | Cyclization of an amide using a dithiaphosphetane reagent |
| General Procedure R | Formation of a bromomethyl ketone from an acid |
| General Procedure S | N-Alkylation using an alkyl halide or α-haloketone |
| General Procedure T | Cyclization of a ketone using a dithiaphosphetane reagent |
| General Procedure U | Knoevenagel condensation to form a substituted cyclopentadiene |
| General Procedure V | Decarboxylation of a β-ketoester enolate |
| General Procedure W | Hydrogenation of an alkene |
| General Procedure W.1 | Hydrogenation of an alkene |
| General Procedure X | Reductive amination of a ketone or aldehyde |
| General Procedure X.1 | Reductive amination of a ketone or aldehyde |
| General Procedure Y | Hydrogenation of a benzyl- or Cbz-protected amine |
| General Procedure Z | Basic hydrolysis of an ester to a carboxylic acid |
| General Procedure AA | Chiral preparative HPLC separation of stereoisomers |
| General Procedure BB | Acidic hydrolysis of an acetyl protected amine |
| General Procedure CC | Formation of a sulfamoyl chloride |
| General Procedure DD | Formation of a sulfonylurea |
| General Procedure EE | Ether formation from a trichloroacetimidate derivative |
| General Procedure FF | Deprotection of a PMB-protected alcohol |
| General Procedure GG | Formation of a lactone |
| General Procedure HH | Opening of a lactone with an amine or hydrazine |
| General Procedure II | Mitsunobu reaction of an alcohol |
| General Procedure JJ | Displacement of a halide with an alcohol |
| General Procedure KK | SEM protection of a nitrogen |
| General Procedure LL | SEM deprotection of a nitrogen |
| General Procedure MM | Halogenation of an imidazole |
| General Procedure NN | Formation of an amide from a carboxylic acid and an amine with loss of a sulfonamide protecting group |
| General Procedure OO | Cyclization with $POCl_3$ |
| General Procedure OO.1 | Cyclization with $POCl_3$ |
| General Procedure PP | Reaction of an amine with an aryl boronic acid |
| General Procedure QQ | Formation of a urea from an amine and an isocyanate |
| General Procedure RR | Formation of a urea from an amine, a heteroaryl amine and phenyl chloroformate |
| General Procedure SS | Hydrolysis of an ester to an alcohol |
| General Procedure TT | Acid-mediated conversion of an ester to a carboxylic acid |
| General Procedure UU | Formation of a 2,2,2-trichloroacetimidate |
| General Procedure VV | Formation of a TBDMS-protected alcohol |
| General Procedure WW | Formation of a ketal |
| General Procedure XX | Palladium catalyzed coupling of a hydrazone |
| General Procedure YY | Michael addition of an amine to an α,β-unsaturated sulfonamide |
| General Procedure ZZ | Formation of an oxazolidinone sulfonourea |
| General Procedure AAA | Formation of a sulfonylurea from an oxazolidinone sulfonourea |
| General Procedure BBB | Reduction of a nitro group |
| General Procedure CCC | Formation of an amide |
| General Procedure DDD | Cyclization to form a fused imidazole |
| General Procedure EEE | Formation of a sulfonyl chloride |
| General Procedure FFF | Generation of an ether under reductive conditions |
| General Procedure GGG | Iodination, chlorination or bromination of a heterocycle or halogenation of a heterocycle |
| General Procedure GGG.1 | Iodination of a heterocycle or halogenation of a heterocycle |

-continued

| List of General Procedures | |
|---|---|
| General Procedure HHH | Cyanation of a heterocycle |
| General Procedure III | Horner-Wadsworth-Emmons reaction of a ketone |
| General Procedure JJJ | Formation of a potassium sulfonate |
| General Procedure KKK | Alkylation of a sulfonate |
| General Procedure LLL | Oxidation of a thioether to a sulfone |
| General Procedure MMM | Mitsunobu reaction using a thiol |
| General Procedure NNN | Curtius reaction to form an isocyanate |
| General Procedure OOO | Hydrolysis of an isocyanate |
| General Procedure PPP | Formation of an oxime ether from a ketone |
| General Procedure QQQ | TFA-mediated conversion of a t-butyl ester to a carboxylic acid |
| General Procedure RRR | Reduction of an alkyne to an alkene |
| General Procedure SSS | 1,3-Dipolar cycloaddition to form a pyrrolidine |
| General Procedure TTT | Hydrogenation of an azide to an amine |
| General Procedure UUU | Reaction of an aryl or heteroaryl halide with a boronic acid or boronate ester followed by tosyl deprotection |
| General Procedure VVV | Reaction of an aryl or heteroaryl halide with a boronic acid or boronate ester |
| General Procedure WWW | Formation of a carbamate |
| General Procedure XXX | Urea formation with loss of protecting group |
| General Procedure YYY | Michael addition |
| General Procedure ZZZ | Grignard or alkyl lithium addition to a carbonyl-containing compound |
| General Procedure AAAA | Deprotection of a sulfonamide with DBU |
| General Procedure BBBB | Deprotection of a sulfonamide with TBAF |
| General Procedure CCCC | Deprotection of a sulfonamide with KCN |
| General Procedure DDDD | Formation of an oxadiazole |
| General Procedure EEEE | Formation of a urea using phosgene |
| General Procedure FFFF | Formation of an amide from an ester |
| General Procedure GGGG | Formation of a nitrile from a primary amide |
| General Procedure HHHH | O-alkylation with KOH or NaOH and TBAB |
| General Procedure IIII | Formation of a mesylate |
| General Procedure JJJJ | Displacement of an alkyl mesylate, tosylate, or halide with a nucleophile |
| General Procedure KKKK | Cyclization of a ketone using TFAA or PFPAA |
| General Procedure LLLL | Formation of a bromoketone from a ketone or an aldehyde |
| General Procedure MMMM | Formation of a ketone from a Weinreb amide |
| General Procedure NNNN | Formation of β-hydroxysulfonamide from a ketone |
| General Procedure OOOO | Formation of a phenyl carbonate |
| General Procedure PPPP | Formation of a carbamate followed by sulfonamide hydrolysis |
| General Procedure QQQQ | Oxidation of an alkyl thioacetate to an alkyl sulfonic acid |
| General Procedure RRRR | Cyclization of a diamine with cyanogen bromide |
| General Procedure SSSS | Cyclization of a diamine with $NaNO_2$ |
| General Procedure TTTT | Formation of a squaramide |
| General Procedure UUUU | Reduction of an azide to an amine |
| General Procedure VVVV | Formation of a ketone from a heteroaryl halide |
| General Procedure WWWW | Formation of an acid chloride |
| General Procedure XXXX | Formation of a hydrazone |
| General Procedure YYYY | Cyclization with an α-haloaldehyde. |
| General Procedure ZZZZ | Cyclization of a hydrazide followed by hydrolysis of a sulfonamide |
| General Procedure AAAAA | Formation of a carboxylic acid or ester from an aryl halide |
| General Procedure BBBBB | Cyclization with an orthoformate |
| General Procedure CCCCC | Stille coupling of an aryl or heteroaryl halide |
| General Procedure DDDDD | Deprotection of a Cbz-protected amine using triethylsilane |
| General Procedure EEEEE | Formation of a guanidine |
| General Procedure FFFFF | Formation of a sulfoxonium ylide |
| General Procedure GGGGG | Reaction of a sulfoxonium ylide with an amine |

The following examples are ordered according to the final general procedure used in their preparation. The synthetic routes to any novel intermediates are detailed by sequentially listing the general procedure (letter codes) in parentheses after their name with additional reactants or reagents as appropriate. A worked example of this protocol is given below using Preparation #Z.1 as a non-limiting illustration. Preparation #Z.1 is (1S,2R,4S)-4-(cyclopropanesulfonamido)-2-ethylcyclopentane-carboxylic acid, which was prepared from (1S,2R,4S)-ethyl 4-(cyclopropanesulfonamido)-2-ethylcyclopentane carboxylate using General Procedure Z as represented in Scheme A.

Scheme A

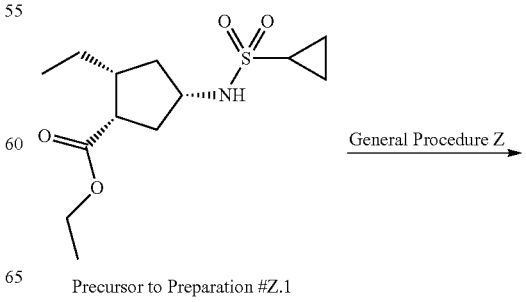

Precursor to Preparation #Z.1

-continued

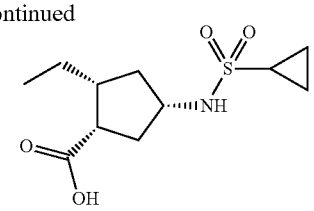

Preparation #Z.1

The precursor to Preparation #Z.1, (1S,2R,4S)-ethyl 4-(cyclopropanesulfonamido)-2-ethylcyclopentane-carboxylate, was prepared (as shown in Scheme B) by initially reacting ethyl 4-amino-2-ethylcyclopentanecarboxylate (Preparation #Y.1) with the commercially available cyclopropanesulfonyl chloride, following the conditions given in General Procedure K, to give ethyl 4-(cyclopropanesulfonamido)-2-ethyl-cyclopentane-carboxylate as a mixture of stereoisomers. This mixture of stereoisomers is separated as described in General Procedure AA, using the conditions from Method 1 in Table 2, to give the precursor to Preparation #Z.1, (1S,2R,4S)-ethyl 4-(cyclopropanesulfonamido)-2-ethylcyclopentane-carboxylate as a single enantiomer with a retention time of 9.5 minutes and a negative optical rotation. The reaction sequence to synthesize the precursor to Preparation #Z.1, (1S,2R,4S)-ethyl 4-(cyclopropanesulfonamido)-2-ethylcyclopentane-carboxylate, (detailed above) is consequently translated in the preparations and examples section to: (1S,2R,4S)-ethyl 4-(cyclopropanesulfonamido)-2-ethylcyclopentane-carboxylate (prepared using K from Preparation #Y.1 and cyclopropanesulfonyl chloride, AA [Table 2, Method 1, $R_t$=9.5 min, or =negative]). Hence the Preparation #Z.1 would be written as: Preparation #Z.1 was prepared from (1S,2R,4S)-ethyl 4-(cyclopropanesulfonamido)-2-ethylcyclopentane carboxylate (prepared using K from Preparation #Y.1 and cyclopropanesulfonyl chloride, AA [Table 2, Method 1, $R_t$=9.5 min, or =negative]) using General Procedure Z.

Scheme B

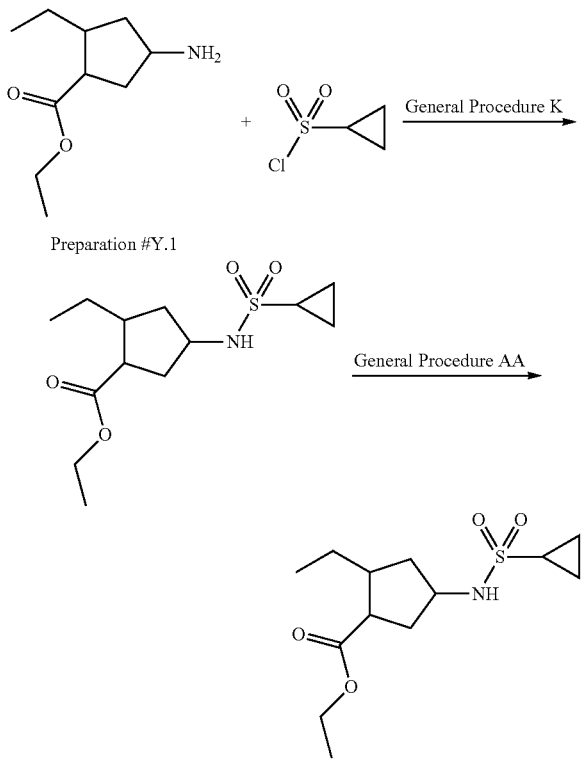

Preparation #Y.1

Precursor to Preparation #Z.1

Analytical Methods

Analytical data was included within the procedures below, in the illustrations of the general procedures, or in the tables of examples. Unless otherwise stated, all $^1$H NMR data were collected on a Varian Mercury Plus 400 MHz or a Varian Inova 600 MHz instrument and chemical shifts are quoted in parts per million (ppm). LC/MS and HPLC data are referenced to the table of LC/MS and HPLC conditions using the lower case method letter provided in Table 1.

TABLE 1

LC/MS and HPLC methods

| Method | Conditions |
|---|---|
| a | LC/MS: The gradient was 5-60% B in 1.5 min then 60-95% B to 2.5 min with a hold at 95% B for 1.2 min (1.3 mL/min flow rate). Mobile phase A was 10 mM $NH_4OAc$, mobile phase B was HPLC grade MeCN. The column used for the chromatography is a 4.6 × 50 mm MAC-MOD Halo C18 column (2.7 μm particles). Detection methods are diode array (DAD) and evaporative light scattering (ELSD) detection as well as positive/negative electrospray ionization. |
| b | LC/MS: The gradient was 5-60% B in 1.5 min then 60-95% B to 2.5 min with a hold at 95% B for 1.2 min (1.3 mL/min flow rate). Mobile phase A was 10 mM $NH_4OAc$, mobile phase B was HPLC grade MeCN. The column used for the chromatography is a 4.6 × 50 mm MAC-MOD Halo C8 column (2.7 μm particles). Detection methods are diode array (DAD) and evaporative light scattering (ELSD) detection as well as positive/negative electrospray ionization. |
| c | LC/MS: The gradient was 5-60% B in 0.75 min then 60-95% B to 1.15 min with a hold at 95% B for 0.75 min (1.3 mL/min flow rate). Mobile phase A was 10 mM $NH_4OAc$, mobile phase B was HPLC grade MeCN. The column used for the chromatography was a 4.6 × 50 mm MAC-MOD Halo C8 column (2.7 μm particles). Detection methods are diode array (DAD) and evaporative light scattering (ELSD) detection as well as positive/negative electrospray ionization. |

TABLE 1-continued

LC/MS and HPLC methods

| Method | Conditions |
|---|---|
| d | HPLC: The gradient was 5-100% B over 40 min, hold at 100% for 5 min, 2 min back to 5% B, hold at 5% B for 4 min (21 mL/min flow rate). Mobile phase A was 50 mM $NH_4OAc$ (pH 4.5) and mobile phase B was HPLC grade MeCN. The column used for the chromatography was a 21.2 × 250 mm Hypersil C18 HS column (8 μm particles). Detection method was UV. |
| e | HPLC: The gradient was 1-5% B over 3 min then 5-55% B over 6 min with a hold at 55% B for 0.10 min then 55-95% B over 1.5 min (22.5 mL/min flow rate). Mobile phase A was 50 mM $NH_4OAc$ (pH 4.5) and mobile phase B was HPLC grade MeCN, the column used for the chromatography was a 19 × 50 mm Waters Atlantis T3 OBD C18 column (5 μm particles), detection methods are Photodiode array DAD and Waters ZQ 2000 mass spectrometer. |
| f | HPLC: The gradient was 10-75% B over 9 min with a hold at 75% for 0.10 min then 75%-100% B over 1.5 min (22.5 mL/min flow rate). Mobile phase A was 50 mM NH4OAc (pH 4.5) and mobile phase B was HPLC grade MeCN, the column used for the chromatography was a 19 × 50 mm Waters Atlantis T3 OBD C18 column (5 μm particles), detection methods were Photodiode array DAD and Waters ZQ 2000 mass spectrometer. |
| g | HPLC: The gradient was 10% B over 2.5 min then 10-15% B over 0.50 min then 15-75% B over 3 min then 75-85% B over 3.10 min then 85%-100% B over 1.5 min (22.5 mL/min flow rate). Mobile phase A was 50 mM $NH_4OAc$ (pH 4.5) and mobile phase B was HPLC grade MeCN, the column used for the chromatography was a 19 × 50 mm Waters Atlantis T3 OBD C18 column (5 μm particles), detection methods were Waters 2996 photodiode array DAD and Waters ZQ 2000 mass spectrometer. |
| h | HPLC: The gradient was 10-85% B over 9.00 min then 85-95% B over 0.10 min then held at 95% B for 1.50 min (25.0 mL/min flow rate). Mobile phase A was 50 mM $NH_4OAc$ (pH 4.5) and mobile phase B was HPLC grade MeCN, the column used for the chromatography was a 19 × 50 mm Waters Atlantis T3 OBD C18 column (5 μm particles), detection methods were Waters 2996 photodiode array DAD and Waters ZQ 2000 mass spectrometer. |
| i | HPLC: The gradient was 10-35% B over 45 min (25 mL/min flow rate). Mobile phase A was 50 mM $NH_4OAc$ (pH 4.5) and mobile phase B was HPLC grade MeCN. The column used for the chromatography was a 21.2 × 250 mm Hypersil C18 HS column (8 μm particles). Detection method was UV. |
| j | HPLC: The gradient was 5-75% B over 25 min (21 mL/min flow rate). Mobile phase A was 50 mM $NH_4OAc$ (pH 4.5) and mobile phase B was HPLC grade MeCN. The column used for the chromatography was a 21.2 × 250 mm Hypersil C18 HS column (8 μm particles). Detection method was UV. |
| k | HPLC: The gradient was 20-40% B over 30 min (21 mL/min flow rate). Mobile phase A was 50 mM $NH_4OAc$ (pH 4.5) and mobile phase B was HPLC grade MeCN. The column used for the chromatography was a 21.2 × 250 mm Hypersil C18 HS column (8 μm particles). Detection method was UV. |
| l | HPLC: The gradient was 0-100% B over 30 min (21 mL/min flow rate). Mobile phase A was 50 mM $NH_4OAc$ (pH 4.5) and mobile phase B was HPLC grade MeCN. The column used for the chromatography was a 21.2 × 250 mm Hypersil C18 HS column (8 μm particles). Detection method was UV. |
| m | HPLC: The gradient was 5% B, hold for 5 min, 5-100% B over 40 min, hold at 100% for 5 min, 2 min back to 5% B, hold at 5% B for 4 min, (21 mL/min flow rate). Mobile phase A was 50 mM $NH_4OAc$ (pH 4.5) and mobile phase B was HPLC grade MeCN. The column used for the chromatography was a 21.2 × 250 mm Hypersil C18 HS column (8 μm particles). Detection method was UV. |
| n | LC/MS: The gradient was 5-60% B in 0.60 min then 60-95% B to 1.0 min with a hold at 95% B for 0.30 min (1.25 mL/min flow rate). Mobile phase A was 10 mM $NH_4OAc$, mobile phase B was HPLC grade MeCN. The column used for the chromatography is 2.1 × 30 mm Acquity UPLC HSS T3 column (1.8 μm particles). Detection methods are diode array (DAD) and evaporative light scattering (ELSD) detection as well as positive/negative electrospray ionization. |
| o | LC/MS: The gradient was 60-95% B in 1.15 min with a hold at 95% B for 3 min (1.3 mL/min flow rate). Mobile phase A was 10 mM $NH_4OAc$, mobile phase B was HPLC grade MeCN. The column used for the chromatography is a 4.6 × 50 mm MAC-MOD Halo C8 column (2.7 μm particles). Detection methods are diode array (DAD) and evaporative light scattering (ELSD) detection as well as positive/negative electrospray ionization. |
| p | LC/MS: The gradient was 5% B, hold for 0.2 min, 5-95% B over 1.7 min, hold at 95% for 1.3 min, back to 5% B within 0.01 min, (2.3 mL/min flow rate). Mobile phase A was water (0.05% TFA) and mobile phase B was HPLC grade MeCN (0.05% TFA). The column used for the chromatography was a 4.6 × 50 mm XBridge C18 column (3.5 μm particles). Temperature 50° C. Detection method was UV. |
| q | HPLC: The gradient was 10-75% B over 10 min (22.5 mL/min flow rate). Mobile phase A was 50 mM $NH_4OAc$ (pH 4.5) and mobile phase B was HPLC grade MeCN, the column used for the chromatography was a 19 × 50 mm Waters Atlantis T3 OBD C18 column (5 μm particles), detection methods were Photodiode array DAD and Waters ZQ 2000 mass spectrometer. |

TABLE 1-continued

| LC/MS and HPLC methods | |
|---|---|
| Method | Conditions |
| r | LC/MS: The gradient was 80-65% B in 1.80 min then 65-40% B to 2.80 min with a hold at 40% for another 1.20 min (1.3 mL/min flow rate). The column used for the chromatography is a 4.6 × 50 mm X-bridge hilic column (3.5 μm particles). Mobile phase A was 10 mM ammonium acetate, mobile phase B was HPLC grade acetonitrile. Detection methods are diode array (DAD) and evaporative light scattering (ELSD) detection as well as positive/negative electrospray ionization. |
| s | HPLC: The gradient was 0-100% B over 15 min, hold at 100% for 15 min (21 mL/min flow rate). Mobile phase A was 50 mM $NH_4OAc$ (pH 4.5) and mobile phase B was HPLC grade MeCN. The column used for the chromatography was a 21.2 × 250 mm Hypersil C18 HS column (8 μm particles). Detection method was UV. |
| t | HPLC: The gradient was 24% B over 2 min then 24-55% B over 7.6 min then 55-98% B over 1 min (25 mL/min flow rate). Mobile phase A was 50 mM $NH_4OAc$ (pH 4.5) and mobile phase B was HPLC grade MeCN, the column used for the chromatography was a 19 × 50 mm Waters Atlantis T3 OBD C18 column (5 μm particles), detection methods were Waters 2996 photodiode array DAD and Waters ZQ 2000 mass spectrometer. |
| u | LC/MS: The gradient was 0-0.1 min 10% A, 0.1-1.1 min 10-100% A, 1.1-1.3 min 100% A, then 1.3-1.4 min 100-10% A. Flow rate was 1 mL/min. Mobile phase A was HPLC grade acetonitrile and mobile phase B was 0.1% trifluoroacetic acid in water. The column used was a Waters BEH C8, 1.7 μm (2.1 mm × 30 mm) at a temperature of 55° C. Detection methods were diode array (DAD) and evaporative light scattering (ELSD) detection as well as positive APCI ionization. |
| v | The gradient was 0-0.1 min 10% A, 0.1-2.6 min 10-100% A, 2.6-2.9 min 100% A, 2.9-3.0 min 100-10% A then 0.5 min post-run delay. Flow rate was 2 mL/min. Mobile phase A was HPLC grade acetonitrile and mobile phase B was 0.1% trifluoroacetic acid in water. The column used for the chromatography was a Phenomenex Luna Combi-HTS C8(2) 5 μm 100 Å (2.1 mm × 50 mm), at a temperature of 55° C. Detection methods were diode array (DAD) and evaporative light scattering (ELSD) detection as well as positive APCI ionization. |
| w | HPLC: The gradient was 15% B over 3.5 min then 15-46% B over 6.1 min then 46-98% B over 1.2 min (25 mL/min flow rate). Mobile phase A was 50 mM $NH_4OAc$ (pH 4.5) and mobile phase B was HPLC grade MeCN, the column used for the chromatography was a 19 × 50 mm Waters Atlantis T3 OBD C18 column (5 micron particles), detection methods were Waters 2996 photodiode array DAD and Waters ZQ 2000 mass spectrometer. |
| x | HPLC: The gradient was 0-80% B over 5 min, hold at 80% for 4 min, 0.1 min at 90% B, then 90 to 0% B for 2.9 min, hold at 0% B for 2 min (1 mL/min flow rate). Mobile phase A was 0.1% $H_3PO_4$ in water and mobile phase B was HPLC grade MeCN. The column used for the chromatography was a 4.6 × 150 mm Ascentis Express column (2.8 μm particles). Detection method was UV. |
| y | HPLC: The gradient was 0-50% B over 45 min (25 mL/min flow rate). Mobile phase A was 50 mM $NH_4OAc$ (pH 4.5) and mobile phase B was HPLC grade MeCN. The column used for the chromatography was a 21.2 × 250 mm Hypersil C18 HS column (8 μm particles). Detection method was UV. |

TABLE 2

| Chiral HPLC methods | |
|---|---|
| Method | Conditions |
| 1 | Isocratic 50% A for 25 min (20 mL/min flow rate). Mobile phase A was a 50:50 mixture of HPLC grade MeOH and EtOH (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 2 | Isocratic 100% EtOH (200 proof) for 13 min (10 mL/min flow rate). The column used for the chromatography was a Daicel IC, 20 × 250 mm column (5 μm particles). Detection methods were evaporative light scattering (ELSD) detection as well as optical rotation. |
| 3 | Isocratic 20% A for 10-23 min (20 mL/min flow rate). Mobile phase A was EtOH (200 proof), mobile phase B was HPLC grade heptane with 0.12% diethylamine added. The column used for the chromatography was a Daicel IC, 20 × 250 mm column (5 μm particles). Detection methods were evaporative light scattering (ELSD) detection as well as optical rotation. |
| 4 | Isocratic 70% A for 25 min (20 mL/min flow rate). Mobile phase A was EtOH (200 proof), mobile phase B was HPLC grade heptane with 0.12% diethylamine added. The column used for the chromatography was a Daicel IA, 20 × 250 mm column (5 μm particles). Detection methods were evaporative light scattering (ELSD) detection as well as optical rotation. |

TABLE 2-continued

Chiral HPLC methods

| Method | Conditions |
|---|---|
| 5 | Isocratic 50% A for 20 min (20 mL/min flow rate). Mobile phase A was EtOH (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 6 | Isocratic 25% A for 18 min (20 mL/min flow rate). Mobile phase A was a 50:50 mixture of HPLC grade MeOH and EtOH (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 7 | Isocratic 30% A for 18 min (20 mL/min flow rate). Mobile phase A was a 50:50 mixture of HPLC grade MeOH and EtOH (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 8 | The gradient was 15-54% A in 16 min then step to 90% A in 0.5 min, with a hold at 90% for 4.3 min (20 mL/min flow rate). Mobile phase A was a 50:50 mixture of HPLC grade MeOH and EtOH (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 9 | The gradient was 10-70% A in 16 min then re-equilibrated at 10% A for 9 min (20 mL/min flow rate). Mobile phase A was EtOH (200 proof), mobile phase B was HPLC grade heptane with 0.1% diethylamine added. The column used for the chromatography was a Daicel IA, 20 × 250 mm column (5 μm particles). Detection methods were UV, λ = 315 nm. |
| 10 | The gradient was 10-50% A in 19 min with a hold at 50% for 2 min (20 mL/min flow rate). Mobile phase A was EtOH (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 11 | Isocratic 60% A for 20 min (20 mL/min flow rate). Mobile phase A was EtOH (200 proof), mobile phase B was HPLC grade heptane with 0.1% diethylamine added. The column used for the chromatography was a Daicel IA, 20 × 250 mm column (5 μm particles). Detection methods were UV, λ = 300 nm. |
| 12 | Isocratic 30% A for 25 min (20 mL/min flow rate). Mobile phase A was HPLC grade IPA, mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 13 | Isocratic 20% A for 20 min (20 mL/min flow rate). Mobile phase A was HPLC grade IPA, mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 14 | Isocratic 100% EtOH (200 proof) for 20 min (13 mL/min flow rate). The column used for the chromatography was a Daicel IC, 20 × 250 mm column (5 μm particles). Detection methods were evaporative light scattering (ELSD) detection as well as optical rotation. |
| 15 | Isocratic 50% A for 20 min (20 mL/min flow rate). Mobile phase A was HPLC grade IPA, mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 16 | Isocratic 30% A for 18 min (20 mL/min flow rate). Mobile phase A was a 50:50 mixture of HPLC grade MeOH and EtOH (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 17 | The gradient was 10-50% A in 19 min with a hold at 50% for 2 min then re-equilibrated at 10% A for 11 min (20 mL/min flow rate). Mobile phase A was EtOH (200 proof), mobile phase B was HPLC grade heptane with 0.1% diethylamine added. The column used for the chromatography was a Daicel IC, 20 × 250 mm column (5 μm particles). Detection methods were evaporative light scattering (ELSD) detection as well as optical rotation. |
| 18 | The gradient was 10-50% A in 19 min with a hold at 50% for 1.5 min (20 mL/min flow rate). Mobile phase A was HPLC grade IPA, mobile phase B was HPLC grade heptane with 0.1% diethylamine added. The column used for the chromatography was a Daicel IA, 20 × 250 mm column (5 μm particles). Detection methods were evaporative light scattering (ELSD) detection, and/or UV (variable wavelength) as well as optical rotation. |

TABLE 2-continued

| Chiral HPLC methods | |
|---|---|
| Method | Conditions |
| 19 | The gradient was 10-50% A in 19 min then re-equilibrated at 10% A for 6 min (20 mL/min flow rate). Mobile phase A was HPLC grade IPA, mobile phase B was HPLC grade heptane with 0.1% diethylamine added. The column used for the chromatography was a Daicel IC, 20 × 250 mm column (5 μm particles). Detection methods were evaporative light scattering (ELSD) detection as well as optical rotation. |
| 20 | Isocratic 40% A for 16 min (20 mL/min flow rate). Mobile phase A was HPLC grade IPA, mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 21 | Isocratic 40% A for 15-25 min (20 mL/min flow rate). Mobile phase A was EtOH (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection, and/or UV (variable wavelength) as well as optical rotation. |
| 22 | The gradient was 10-40% A in 19 min (20 mL/min flow rate). Mobile phase A was EtOH (200 proof), mobile phase B was HPLC grade heptane with 0.1% diethylamine added. The column used for the chromatography was a Daicel IB, 20 × 250 mm column (5 μm particles). Detection methods were evaporative light scattering (ELSD) detection as well as optical rotation. |
| 23 | The gradient was 15-70% A in 19 min (20 mL/min flow rate). Mobile phase A was EtOH (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 24 | Isocratic 15% A for 14 min (20 mL/min flow rate). Mobile phase A was EtOH (200 proof), mobile phase B was HPLC grade heptane with 0.12% diethylamine added. The column used for the chromatography was a Daicel IC, 20 × 250 mm column (5 μm particles). Detection methods were evaporative light scattering (ELSD) detection as well as optical rotation. |
| 25 | Isocratic 30% A for 10 min (20 mL/min flow rate). Mobile phase A was HPLC grade IPA, mobile phase B was HPLC grade heptane with 0.1% diethylamine added. The column used for the chromatography was a Daicel IB, 20 × 250 mm column (5 μm particles). Detection methods were evaporative light scattering (ELSD) detection as well as optical rotation. |
| 26 | Isocratic 40% A for 5 min then gradient 40 to 95% A in 2 min, with a hold at 95% for 11 min (20 mL/min flow rate). Mobile phase A was a 50:50 mixture of HPLC grade MeOH and EtOH (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 27 | The gradient was 10-50% A in 19 min (20 mL/min flow rate). Mobile phase A was EtOH (200 proof), mobile phase B was HPLC grade heptane with 0.1% diethylamine added. The column used for the chromatography was a Daicel IB, 20 × 250 mm column (5 μm particles). Detection methods were evaporative light scattering (ELSD) detection as well as optical rotation. |
| 28 | Isocratic 15% A for 35 min (20 mL/min flow rate). Mobile phase A was EtOH (200 proof), mobile phase B was HPLC grade heptane with 0.12% diethylamine added. The column used for the chromatography was a Daicel IA, 20 × 250 mm column (5 μm particles). Detection methods were evaporative light scattering (ELSD) detection as well as optical rotation. |
| 29 | The gradient was 10-50% A in 19 min with a hold at 50% for 3 min then re-equilibrate at 10% A for 13 min (1 mL/min flow rate). Mobile phase A was IPA, mobile phase B was HPLC grade heptane with 0.1% diethylamine added. The column used for the chromatography was a Daicel IC, 4.6 × 250 mm column (5 μm particles). Detection methods were evaporative light scattering (ELSD) detection as well as optical rotation. |
| 30 | Isocratic 20% A for 20 min (1 mL/min flow rate). Mobile phase A was IPA, mobile phase B was HPLC grade heptane with 0.1% diethylamine added. The column used for the chromatography was a Daicel IC, 4.6 × 250 mm column (5 μm particles). Detection methods were UV, $\lambda$ = 230 nm as well as positive electrospray ionization. |
| 31 | Isocratic 20% A for 10 min (20 mL/min flow rate). Mobile phase A was ethanol (200 proof), mobile phase B was HPLC grade heptane with 0.12% diethylamine added. The column used for the chromatography was a Daicel IA, 20 × 250 mm column (5 μm particles). Detection methods were evaporative light scattering (ELSD) detection as well as optical rotation. |
| 32 | The gradient was 10-70% A in 19 min then re-equilibrate at 10% A for 11 min (20 mL/min flow rate). Mobile phase A was ethanol (200 proof), mobile phase B was HPLC grade heptane with 0.1% diethylamine added. The column used for the chromatography was a Daicel IA, 20 × 250 mm column (5 μm particles). Detection methods were ELSD and optical rotation. |

TABLE 2-continued

Chiral HPLC methods

| Method | Conditions |
|---|---|
| 33 | Isocratic 30% A for 20-30 min (20 mL/min flow rate). Mobile phase A was ethanol (200 proof), mobile phase B was HPLC grade heptane with 0.12% diethylamine added. The column used for the chromatography was a Daicel IA, 20 × 250 mm column (5 μm particles). Detection methods were evaporative light scattering (ELSD) detection, and/or UV (variable wavelength) as well as optical rotation. |
| 34 | Isocratic 40% A for 10-30 min (20 mL/min flow rate). Mobile phase A was ethanol (200 proof), mobile phase B was HPLC grade heptane with 0.12% diethylamine added. The column used for the chromatography was a Daicel IC, 20 × 250 mm column (5 μm particles). Detection methods were evaporative light scattering (ELSD) detection as well as optical rotation. |
| 35 | Isocratic 15% A for 22.5 min then step to 60% A and hold for 5 min (20 mL/min flow rate). Mobile phase A was HPLC grade IPA, mobile phase B was HPLC grade heptane with 0.12% diethylamine added. The column used for the chromatography was a Daicel IA, 20 × 250 mm column (5 μm particles). Detection method was UV, λ = 325 nm |
| 36 | Isocratic 40% A for 20 min (20 mL/min flow rate). Mobile phase A was a 50:50 mixture of HPLC grade MeOH and EtOH (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 37 | The gradient was 10-70% A in 19 min (20 mL/min flow rate). Mobile phase A was EtOH (200 proof), mobile phase B was HPLC grade heptane with 0.1% diethylamine added. The column used for the chromatography was a Daicel IC, 20 × 250 mm column (5 μm particles). Detection methods were evaporative light scattering (ELSD) detection as well as optical rotation. |
| 38 | Isocratic 35% A for 25 min (20 mL/min flow rate). Mobile phase A was HPLC grade IPA, mobile phase B was HPLC grade heptane with 0.1% diethylamine added. The column used for the chromatography was a Daicel IC, 20 × 250 mm column (5 μm particles). Detection methods were evaporative light scattering (ELSD) detection as well as optical rotation. |
| 39 | Isocratic 70% A for 7 min then gradient 70-95% A in 3 min and hold at 95% A for 12 min (20 mL/min flow rate). Mobile phase A was EtOH (200 proof), mobile phase B was HPLC grade heptane with 0.12% diethylamine added. The column used for the chromatography was a Daicel IA, 20 × 250 mm column (5 μm particles). Detection methods were evaporative light scattering (ELSD) detection, and/or UV (variable wavelength) as well as optical rotation. |
| 40 | Isocratic 25% A for 25 min (20 mL/min flow rate). Mobile phase A was HPLC grade IPA, mobile phase B was HPLC grade heptane with 0.12% diethylamine added. The column used for the chromatography was a Daicel IA, 20 × 250 mm column (5 μm particles). Detection method was UV, λ = 325 nm |
| 41 | Isocratic 10% A for 25 min (20 mL/min flow rate). Mobile phase A was EtOH (200 proof), mobile phase B was HPLC grade heptane with 0.12% diethylamine added. The column used for the chromatography was a Daicel IA, 20 × 250 mm column (5 μm particles). Detection method was UV, λ = 320 nm |
| 42 | Isocratic 20% A for 20 min (20 mL/min flow rate). Mobile phase A was EtOH (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 43 | Isocratic 15% A for 30 min (20 mL/min flow rate). Mobile phase A was EtOH (200 proof), mobile phase B was HPLC grade heptane with 0.1% diethylamine added. The column used for the chromatography was a Daicel IB, 20 × 250 mm column (5 μm particles). Detection methods were evaporative light scattering (ELSD) detection as well as optical rotation. |
| 44 | Isocratic 25% A for 25 min (20 mL/min flow rate). Mobile phase A was EtOH (200 proof), mobile phase B was HPLC grade heptane with 0.12% diethylamine added. The column used for the chromatography was a Daicel IA, 20 × 250 mm column (5 μm particles). Detection methods were evaporative light scattering (ELSD) detection as well as optical rotation. |
| 45 | The gradient was 10-60% A in 20 min (20 mL/min flow rate). Mobile phase A was EtOH (200 proof), mobile phase B was HPLC grade heptane with 0.1% diethylamine added. The column used for the chromatography was a Daicel IC, 20 × 250 mm column (5 μm particles). Detection methods were evaporative light scattering (ELSD) detection, and/or UV (variable wavelength) as well as optical rotation. |
| 46 | The gradient was 10-50% A in 13 min (20 mL/min flow rate). Mobile phase A was EtOH (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection, and/or UV (variable wavelength) as well as optical rotation. |

TABLE 2-continued

| Chiral HPLC methods | |
|---|---|
| Method | Conditions |
| 47 | The gradient was 10-50% A in 17 min (20 mL/min flow rate). Mobile phase A was EtOH (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection, and/or UV (variable wavelength) as well as optical rotation. |
| 48 | The gradient was 15-60% A in 17 min (20 mL/min flow rate). Mobile phase A was a 50:50 mixture of HPLC grade MeOH and EtOH (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection, and/or UV (variable wavelength) as well as optical rotation. |
| 49 | Isocratic 25% A for 17 min then step to 60% A and hold for 10 min (20 mL/min flow rate). Mobile phase A was HPLC grade IPA, mobile phase B was HPLC grade heptane with 0.12% diethylamine added. The column used for the chromatography was a Daicel IC, 20 × 250 mm column (5 μm particles). Detection method was UV, $\lambda$ = 340 nm |
| 50 | Isocratic 20% A for 20 min (20 mL/min flow rate). Mobile phase A was EtOH (200 proof), mobile phase B was HPLC grade heptane with 0.1% diethylamine added. The column used for the chromatography was a Daicel IB, 20 × 250 mm column (5 μm particles). Detection methods were evaporative light scattering (ELSD) detection, and/or UV (variable wavelength) as well as optical rotation. |
| 51 | Isocratic 10% A for 60 min (20 mL/min flow rate). Mobile phase A was a 50:50 mixture of HPLC grade MeOH and EtOH (200 proof), mobile phase B was HPLC grade heptane with 0.12% diethylamine added. The column used for the chromatography was a Daicel IA, 20 × 250 mm column (5 μm particles). Detection methods were evaporative light scattering (ELSD) detection as well as optical rotation. |
| 52 | Isocratic 50% A for 20 min (20 mL/min flow rate). Mobile phase A was a 50:50 mixture of HPLC grade MeOH and EtOH (200 proof), mobile phase B was HPLC grade heptane with 0.12% diethylamine added. The column used for the chromatography was a Daicel IC, 20 × 250 mm column (5 μm particles). Detection methods were evaporative light scattering (ELSD) detection as well as optical rotation. |
| 53 | The gradient was 30-70% A in 18 min with a hold at 70% for 4 min then re-equilibrate at 30% A for 13 min (20 mL/min flow rate). Mobile phase A was IPA, mobile phase B was HPLC grade heptane with 0.12% diethylamine added. The column used for the chromatography was a Daicel IC, 20 × 250 mm column (5 μm particles). Detection methods were evaporative light scattering (ELSD) detection as well as optical rotation. |
| 54 | Isocratic 30% A for 30 min (20 mL/min flow rate). Mobile phase A was ethanol (200 proof), mobile phase B was HPLC grade heptane with 0.12% diethylamine added. The column used for the chromatography was a Daicel IC, 20 × 250 mm column (5 μm particles). Detection methods were evaporative light scattering (ELSD) detection, and/or UV (variable wavelength) as well as optical rotation. |
| 55 | Isocratic 30% A for 30 min (20 mL/min flow rate). Mobile phase A was ethanol (200 proof), mobile phase B was HPLC grade heptane with 0.12% diethylamine added. The column used for the chromatography was a (R,R) Whelk-O1, 21 × 250 mm column (5 μm particles). Detection methods were evaporative light scattering (ELSD) detection, and/or UV (variable wavelength) as well as optical rotation. |
| 56 | Isocratic 35% A for 30 min (20 mL/min flow rate). Mobile phase A was ethanol (200 proof), mobile phase B was HPLC grade heptane with 0.12% diethylamine added. The column used for the chromatography was a Daicel IC, 20 × 250 mm column (5 μm particles). Detection methods were evaporative light scattering (ELSD) detection, and/or UV (variable wavelength) as well as optical rotation. |
| 57 | Isocratic 30% A for 30 min (20 mL/min flow rate). Mobile phase A was a 50:50 mixture of HPLC grade MeOH and EtOH (200 proof), mobile phase B was HPLC grade heptane with 0.12% diethylamine added. The column used for the chromatography was a Daicel IC, 20 × 250 mm column (5 μm particles). Detection methods were evaporative light scattering (ELSD) detection, and/or UV (variable wavelength) as well as optical rotation. |
| 58 | Isocratic 15% A for 11 min then step to 50% A in 0.5 min and hold for 4.5 min (20 mL/min flow rate). Mobile phase A was HPLC grade ethanol (200 proof), mobile phase B was HPLC grade heptane with 0.12% diethylamine added. The column used for the chromatography was a Daicel IA, 20 × 250 mm column (5 μm particles). Detection methods were evaporative light scattering (ELSD) detection, and/or UV (variable wavelength) as well as optical rotation. |
| 59 | The gradient was 10-95% A in 17 min with a hold at 95% for 2 min (20 mL/min flow rate). Mobile phase A was EtOH (200 proof), mobile phase B was HPLC grade heptane with 0.12% diethylamine added. The column used for the chromatography was a Daicel IA, 20 × 250 mm column (5 μm particles). Detection methods were evaporative light scattering (ELSD) detection, and/or UV (variable wavelength) as well as optical rotation. |

TABLE 2-continued

| Chiral HPLC methods | |
|---|---|
| Method | Conditions |
| 60 | Isocratic 20% A for 10 min then step to 60% A in 0.5 min and hold at 60% for 5.5 min (20 mL/min flow rate). Mobile phase A was HPLC grade IPA, mobile phase B was HPLC grade heptane with 0.12% diethylamine added. The column used for the chromatography was a Daicel IA, 20 × 250 mm column (5 μm particles). Detection methods were evaporative light scattering (ELSD) detection, and/or UV (variable wavelength) as well as optical rotation. |
| 61 | The gradient was 10-20% A in 28 min, hold at 20% for 2 min then 20-70% A in 5 min (20 mL/min flow rate). Mobile phase A was EtOH (200 proof), mobile phase B was HPLC grade heptane with 0.12% diethylamine added. The column used for the chromatography was a Daicel IC, 20 × 250 mm column (5 μm particles). Detection methods were evaporative light scattering (ELSD) detection, and/or UV (variable wavelength) as well as optical rotation. |
| 62 | Isocratic 22% A for 30 min (20 mL/min flow rate). Mobile phase A was EtOH (200 proof), mobile phase B was HPLC grade heptane with 0.12% diethylamine added. The column used for the chromatography was a Daicel IB, 20 × 250 mm column (5 μm particles). Detection methods were evaporative light scattering (ELSD) detection, and/or UV (variable wavelength) as well as optical rotation. |
| 63 | Isocratic 25% A for 30 min (20 mL/min flow rate). Mobile phase A was EtOH (200 proof), mobile phase B was HPLC grade heptane with 0.12% diethylamine added. The column used for the chromatography was a Daicel IB, 20 × 250 mm column (5 μm particles). Detection methods were evaporative light scattering (ELSD) detection, and/or UV (variable wavelength) as well as optical rotation. |
| 64 | Isocratic 65% A for 30 min (20 mL/min flow rate). Mobile phase A was ethanol (200 proof), mobile phase B was HPLC grade heptane with 0.12% diethylamine added. The column used for the chromatography was a (R,R) Whelk-O1, 21 × 250 mm column (5 μm particles). Detection methods were evaporative light scattering (ELSD) detection, and/or UV (variable wavelength) as well as optical rotation. |
| 65 | Isocratic 65% A for 6 min then step to 90% A in 0.5 min and hold at 90% for 6.5 min (20 mL/min flow rate). Mobile phase A was ethanol (200 proof), mobile phase B was HPLC grade heptane with 0.12% diethylamine added. The column used for the chromatography was a (R,R) Whelk-O1, 21 × 250 mm column (5 μm particles). Detection methods were evaporative light scattering (ELSD) detection, and/or UV (variable wavelength) as well as optical rotation. |
| 66 | Isocratic 30% A for 30 min (20 mL/min flow rate). Mobile phase A was HPLC grade IPA, mobile phase B was HPLC grade heptane with 0.12% diethylamine added. The column used for the chromatography was a Daicel IC, 20 × 250 mm column (5 μm particles). Detection methods were evaporative light scattering (ELSD) detection, and/or UV (variable wavelength) as well as optical rotation. |
| 67 | Isocratic 55% A for 8 min then step to 90% A in 1 min and hold at 90 for 7 min (20 mL/min flow rate). Mobile phase A was EtOH (200 proof), mobile phase B was HPLC grade heptane with 0.12% diethylamine added. The column used for the chromatography was a Daicel IC, 20 × 250 mm column (5 μm particles). Detection methods were evaporative light scattering (ELSD) detection, and/or UV (variable wavelength) as well as optical rotation. |
| 68 | The gradient was 60-90% A in 4 min with a hold at 90% for 6 min (20 mL/min flow rate). Mobile phase A was EtOH (200 proof), mobile phase B was HPLC grade heptane with 0.12% diethylamine added. The column used for the chromatography was a Daicel IA, 20 × 250 mm column (5 μm particles). Detection methods were evaporative light scattering (ELSD) detection, and/or UV (variable wavelength) as well as optical rotation. |
| 69 | Isocratic 20% A for 12 min then step to 50% A in 0.5 min and hold at 50% for 3.5 min (20 mL/min flow rate). Mobile phase A was EtOH (200 proof), mobile phase B was HPLC grade heptane with 0.12% diethylamine added. The column used for the chromatography was a Daicel IA, 20 × 250 mm column (5 μm particles). Detection methods were evaporative light scattering (ELSD) detection, and/or UV (variable wavelength) as well as optical rotation. |
| 70 | The gradient was 20-50% B over 10 min (0.6 mL/min flow rate). Mobile phase A was 10 mM $KH_2PO_4$ buffer (pH = 6.9) and mobile phase B was HPLC grade MeCN. The column used for the chromatography was a 4.6 × 150 mm Chiralpak AS-RH, Diacel col. Detection method was UV. |
| 71 | The gradient was 15-85% A in 37 min with a hold at 85% A for 0.5 min (20 mL/min flow rate). Mobile phase A was HPLC grade IPA, mobile phase B was HPLC grade heptane with 0.12% diethylamine added. The column used for the chromatography was a Daicel IC, 20 × 250 mm column (5 μm particles). Detection methods were evaporative light scattering (ELSD) detection, and/or UV (variable wavelength) as well as optical rotation. |

Purification Methods

For the general procedures, the intermediates and final compounds may be purified by any technique or combination of techniques known to one skilled in the art. Some examples that are not limiting include flash chromatography with a solid phase (e.g. silica gel, alumina, etc.) and a solvent (or combination of solvents) that elutes the desired compounds (e.g. heptane, EtOAc, DCM, MeOH, MeCN, water, etc.); preparatory TLC with a solid phase (e.g. silica gel, alumina etc.) and a solvent (or combination of solvents) that elutes the desired compounds (e.g. heptane, EtOAc, DCM, MeOH, MeCN, water, etc.); reverse phase HPLC (see Table 1 for some non-limiting conditions); recrystallization from an appropriate solvent or combination of solvents (e.g.

MeOH, EtOH, IPA, EtOAc, toluene, etc.) or combination of solvents (e.g. EtOAc/heptane, EtOAc/MeOH, etc.); chiral LC with a solid phase and an appropriate solvent (see Table 2 for some non-limiting conditions) to elute the desired compound; chiral SFC with a solid phase and $CO_2$ with an appropriate modifier (e.g. MeOH, EtOH, IPA with or without additional modifier such as diethylamine, TFA, etc.); precipitation from a combination of solvents (e.g. DMF/water, DMSO/DCM, EtOAc/heptane, etc.); trituration with an appropriate solvent (e.g. EtOAc, DCM, MeCN, MeOH, EtOH, IPA, n-IPA, etc.); extractions by dissolving a compound in a liquid and washing with an appropriately immiscible liquid (e.g. DCM/water, EtOAc/water, DCM/saturated aqueous $NaHCO_3$, EtOAc/saturated aqueous $NaHCO_3$, DCM/10% aqueous HCl, EtOAc/10% aqueous HCl, etc.); distillation (e.g. simple, fractional, Kugelrohr, etc.); gas chromatography using an appropriate temperature, carrier gas and flow rate; sublimation at an appropriate temperature and pressure; filtration through a media (e.g. Florosil®, alumina, Celite®, silica gel, etc.) with a solvent (e.g. heptane, hexanes, EtOAc, DCM, MeOH, etc.) or combination of solvents; salt formation with solid support (resin based, e.g. ion exchange) or without. Compounds of interest may be isolated as a salt without the use of a specific salt formation purification method. For example, on occasions where purification is accomplished with reverse phase HPLC with an aqueous TFA buffer, the TFA salt may be isolated. Some descriptions of these techniques can be found in the following references: Gordon, A. J. and Ford, R. A. "The Chemist's Companion", 1972; Palleros, D. R. "Experimental Organic Chemistry", 2000; Still, W. C., Kahn and M. Mitra, A. J. Org. Chem. 1978, 43, 2923; Yan, B. "Analysis and Purification Methods in Combinatorial Chemistry", 2003; Harwood, L. M., Moody, C. J. and Percy, J. M. "Experimental Organic Chemistry: Standard and Microscale, 2$^{nd}$ Edition", 1999; Stichlmair, J. G. and Fair, J. R. "Distillation; Principles and Practices", 1998; Beesley, T. E. and Scott, R. P. W. "Chiral Chromatography", 1999; Landgrebe, J. A. "Theory and Practice in the Organic Laboratory, 4$^{th}$ Ed.", 1993; Skoog, D. A. and Leary, J. J. "Principles of Instrumental Analysis, 4$^{th}$ Ed.", 1992; G. Subramanian, "Chiral Separation Techniques, 3$^{rd}$ Edition", 2007; Y. Kazakevich, R. Lobrutto, "HPLC for Pharmaceutical Scientists", 2007.

PREPARATIONS AND EXAMPLES

The general synthetic methods used in each General Procedure follow and include an illustration of a compound that was synthesized using the designated General Procedure. None of the specific conditions and reagents noted herein are to be construed as limiting the scope of the invention and are provided for illustrative purposes only. All starting materials are commercially available from Sigma-Aldrich (including Fluka and Discovery CPR) unless otherwise noted after the chemical name. Reagent/reactant names given are as named on the commercial bottle or as generated by IUPAC conventions, CambridgeSoft® ChemDraw Ultra 9.0.7, CambridgeSoft® Chemistry E-Notebook 9.0.127, or AutoNom 2000. Compounds designated as salts (e.g. hydrochloride, acetate) may contain more than one molar equivalent of the salt. Compounds of the invention where the absolute stereochemistry has been determined by the use of a commercially available enantiomerically pure starting material or a stereochemically defined intermediate, or by X-ray diffraction are denoted by an asterisk after the example number.

Preparation #1:
cis-3-(4-cyanobenzyloxy)cyclobutanecarboxylic acid

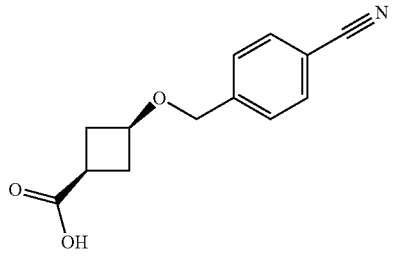

Step A: cis-ethyl 3-hydroxycyclobutanecarboxylate

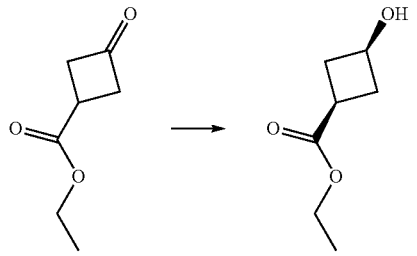

A solution of ethyl 3-oxocyclobutanecarboxylate (2.90 g, 20.4 mmol, Parkway) in EtOH (30 mL) at ambient temperature was treated with $NaBH_4$ (0.77 g, 20 mmol). The reaction was stirred for about 1 h and then 2 N aqueous HCl was added to adjust the pH to about 2. The reaction was concd in vacuo. The reaction was partitioned with DCM (50 mL) and brine (50 mL). The organic layer was separated, dried over anhydrous $Na_2SO_4$, filtered then concd in vacuo. The resulting residue was purified on silica gel (80 g) using 20-40% EtOAc in DCM to give cis-ethyl 3-hydroxycyclobutanecarboxylate (2.75 g, 66%) as a clear oil: $^1$H NMR (DMSO-$d_6$) δ 5.17 (d, 1H), 4.09-3.99 (m, 2H), 3.99-3.90 (m, 1H), 2.57-2.47 (m, 1H), 2.42-2.29 (m, 2H), 1.98-1.89 (m, 2H), 1.17 (m, 3H).

Step B: cis-ethyl 3-(4-cyanobenzyloxy)cyclobutanecarboxylate

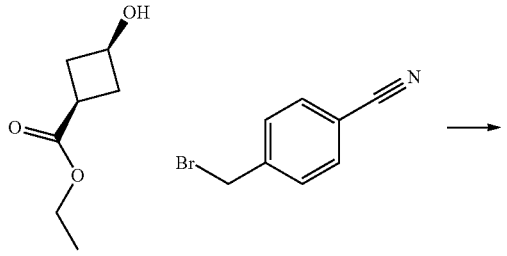

-continued

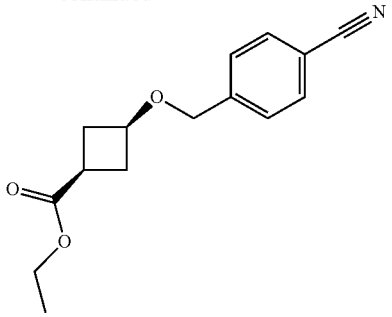

To a solution of cis-ethyl 3-hydroxycyclobutanecarboxylate (0.17 g, 1.2 mmol) in DMF (4 mL) was added $K_2CO_3$ (0.24 g, 1.8 mmol) followed by 4-(bromomethyl)benzonitrile (0.28 g, 1.4 mmol). The reaction was stirred at about 25° C. for about 16 h. The reaction was partitioned between EtOAc (50 mL) and brine (50 mL). The layers were separated and the organic layer was washed with additional brine (50 mL). The organic layer was then dried over anhydrous $Na_2SO_4$, filtered, and concd in vacuo to give cis-ethyl 3-(4-cyanobenzyloxy)cyclobutanecarboxylate (0.29 g, 95%) as an oil: $^1$H NMR (DMSO-$d_6$) δ 7.82 (d, J=8.5 Hz, 2H), 7.63 (d, J=8.4 Hz, 2H), 4.75 (s, 2H), 4.02 (q, J=7.1 Hz, 2H), 3.93 (m, 1H), 2.58-2.45 (m, 1H), 2.41-2.28 (m, 2H), 1.98-1.85 (m, 2H), 1.20-1.08 (t, J=7.1 Hz, 3H).

Step C:
cis-3-(4-cyanobenzyloxy)cyclobutanecarboxylic acid

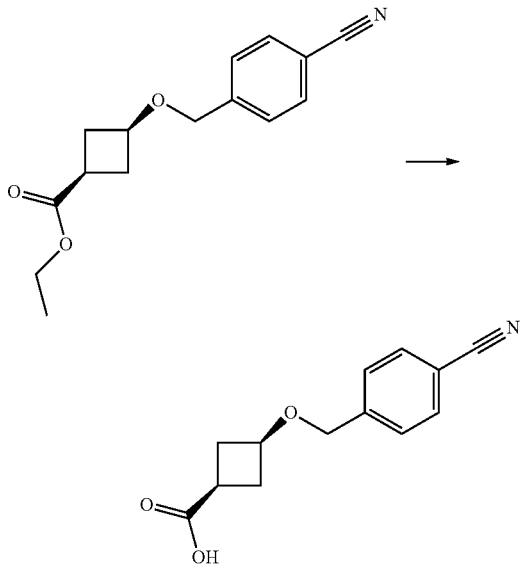

To a solution of cis-ethyl 3-(4-cyanobenzyloxy)cyclobutanecarboxylate (0.44 g, 1.70 mmol) in 1,4-dioxane (10 mL) was added aqueous NaOH (1 N, 2.0 mL). The reaction was stirred at about 25° C. for about 16 h. The reaction was partitioned between 10% aqueous AcOH (20 mL) and EtOAc (25 mL). The layers were separated and the aqueous layer was extracted with additional EtOAc (25 mL). The combined organic extracts were washed with brine (20 mL), dried over anhydrous $Na_2SO_4$, filtered then concd in vacuo to give cis-3-(4-cyanobenzyloxy)-cyclobutanecarboxylic acid (0.24 g, 60%): LC/MS (Table 1, Method b) $R_t$=1.67 min; MS m/z: 232 $(M+H)^+$.

Preparation #2*: (1S,3R)-1-[3-(6-tosyl-6H-pyrrolo[2,3-e][1,2,4]triazolo[4,3-a]pyrazin-1-yl)-isothiazolidin-2-yl-1,1-dioxide]cyclopentane

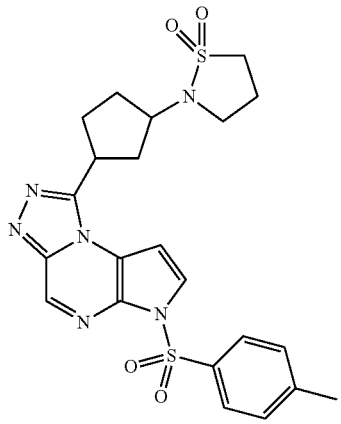

Step A: 3-chloro-N-((1S,3R)-3-(6-tosyl-6H-pyrrolo[2,3-e][1,2,4]triazolo[4,3-a]pyrazin-1-yl)cyclopentyl)propane-1-sulfonamide

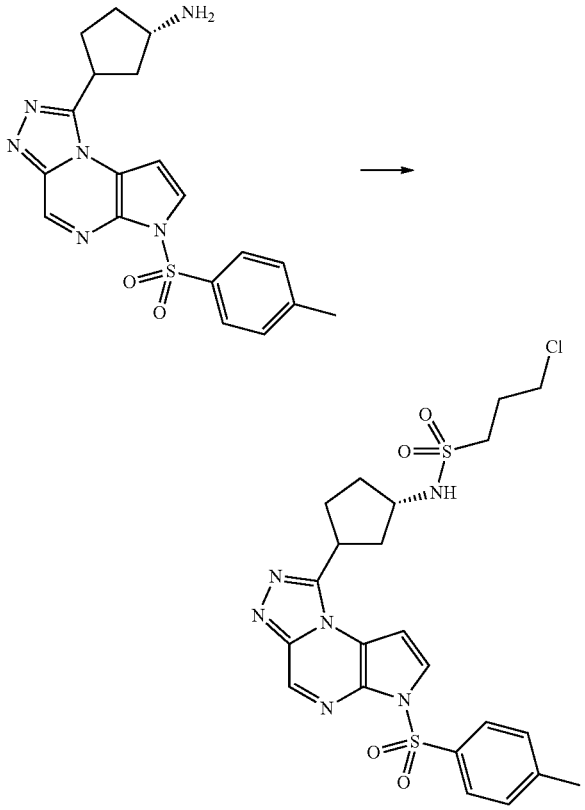

To a suspension of (1S,3R)-3-(6-tosyl-6H-pyrrolo[2,3-e][1,2,4]triazolo[4,3-a]pyrazin-1-yl)cyclopentanamine hydrochloride (0.05 g, 0.11 mmol, prepared using E from Preparation #B.1 and HCl) and TEA (0.03 mL, 0.21 mmol) in DCM (5 mL) at about 0° C. was added 3-chloropropane-1-sulfonyl chloride (0.02 g, 0.11 mmol) dropwise. The reaction mixture was stirred at about 0° C. for about 1.5 h. The reaction mixture was diluted with 5% aqueous citric acid (10 mL), and the layers were separated. The organic layer was washed with saturated aqueous $NaHCO_3$ (10 mL), water (10 mL), brine (10 mL), dried over anhydrous $MgSO_4$, filtered, and concd under reduced pressure to give 3-chloro-N-((1S,3R)-3-(6-tosyl-6H-pyrrolo[2,3-e][1,2,4]triazolo[4,3-a]pyrazin-1-yl)cyclopentyl)propane-1-sulfonamide (0.052 g, 91%) as a brown residue: LC/MS (Table 1, Method a) $R_t$=2.18 min; MS m/z: 537 $(M+H)^+$.

Step B: (1S,3R)-1-[3-(6-tosyl-6H-pyrrolo[2,3-e][1,2,4]triazolo[4,3-a]pyrazin-1-yl)-isothiazolidin-2-yl-1,1-dioxide]cyclopentane

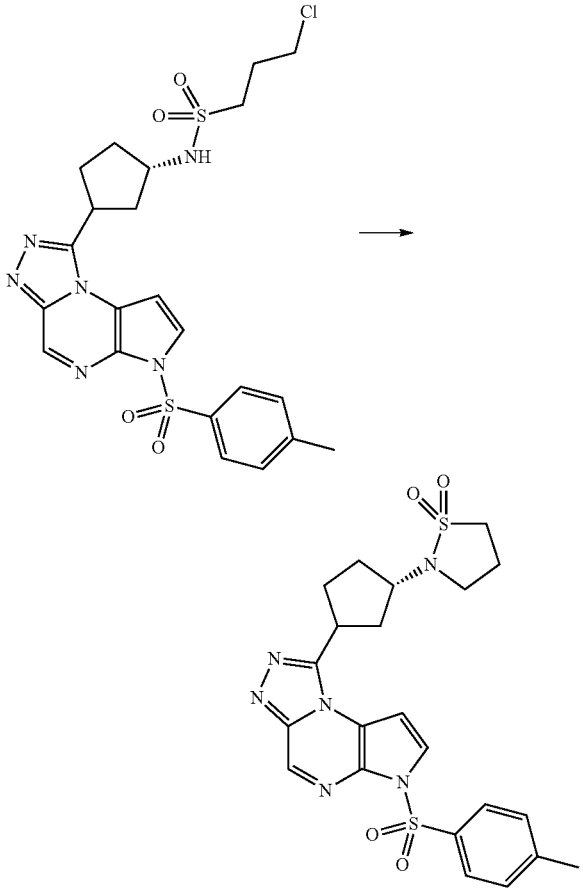

To a solution of 3-chloro-N-((1S,3R)-3-(6-tosyl-6H-pyrrolo[2,3-e][1,2,4]triazolo[4,3-a]pyrazin-1-yl)cyclopentyl)propane-1-sulfonamide (0.11 g, 0.21 mmol) in DMF (5 mL) was added 1,8-diazabicyclo[5.4.0]undec-7-ene (0.04 mL, 0.27 mmol crude). The reaction mixture was stirred at ambient temperature for about 16 h. The solvent was removed under reduced pressure to give (1S,3R)-1-[3-(6-tosyl-6H-pyrrolo[2,3-e][1,2,4]triazolo[4,3-a]pyrazin-1-yl)-isothiazolidin-2-yl-1,1-dioxide]cyclopentane (0.106 g, 99%): LC/MS (Table 1, Method a) $R_t$=2.04 min; MS m/z: 501 $(M+H)^+$.

Preparation #3*: 1-((1R,3S)-3-(1H-pyrrol-1-yl)cyclopentyl)-6-tosyl-6H-pyrrolo[2,3-e][1,2,4]triazolo[4,3-a]pyrazine

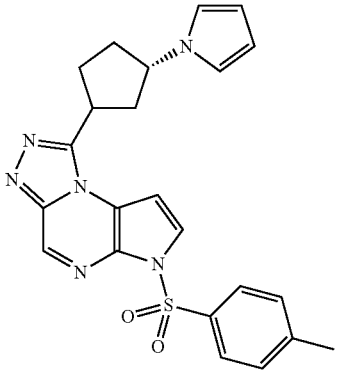

A solution of 2,5-dimethoxytetrahydrofuran (0.14 g, 1.1 mmol) in water (3 mL) was heated at about 100° C. for about 1.5 h. The solution was cooled to ambient temperature. A suspension of (1S,3R)-3-(6-tosyl-6H-pyrrolo[2,3-e][1,2,4]triazolo[4,3-a]pyrazin-1-yl)cyclo-pentanamine hydro-chloride (0.10 g, 0.21 mmol, prepared using E from Preparation #B.1 and HCl) and NaOAc (0.05 g, 0.61 mmol) in DCM (5 mL) was added to the aqueous solution. The reaction mixture was stirred at ambient temperature for about 1 h followed by addition of additional 2,5-dimethoxytetrahydrofuran (0.14 g, 1.1 mmol). The reaction mixture was heated to about 40° C. for about 15 h. Additional 2,5-dimethoxytetrahydrofuran (0.14 g, 1.1 mmol) was added and the reaction mixture was stirred at about 40° C. for about 8 h then at about 35° C. for about 48 h. The reaction was diluted with DCM (10 mL) and water (10 mL). The layers were separated and the organic layer was washed with water (2×10 mL) and brine (10 mL), dried over anhydrous $MgSO_4$, filtered, and the solvent was removed under reduced pressure to give 1-((1R,3S)-3-(1H-pyrrol-1-yl)cyclopentyl)-6-tosyl-6H-pyrrolo[2,3-e][1,2,4]triazolo[4,3-a]pyrazine (0.095 g, 99%) as a yellow residue: LC/MS (Table 1, Method a) $R_t$=2.42 min; MS m/z: 447 $(M+H)^+$.

Preparation #4*: 1-((1S,3R)-3-(6-tosyl-6H-pyrrolo[2,3-e][1,2,4]triazolo[4,3-a]pyrazin-1-yl)cyclopentyl)-1H-pyrrole-3-carbonitrile

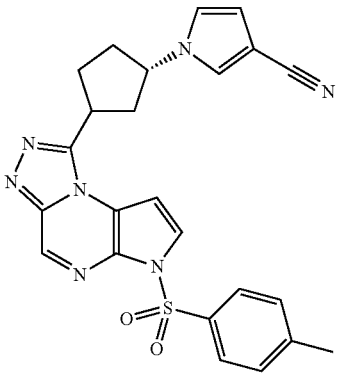

Step A: 1-((1S,3R)-3-(6-tosyl-6H-pyrrolo[2,3-e][1,2,4]triazolo[4,3-a]pyrazin-1-yl)cyclopentyl)-1H-pyrrole-3-carbaldehyde

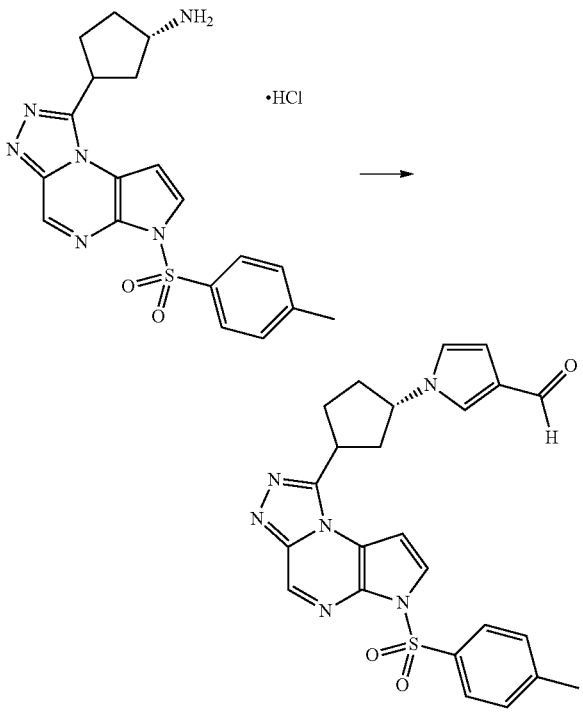

To a suspension of (1S,3R)-3-(6-tosyl-6H-pyrrolo[2,3-e][1,2,4]triazolo[4,3-a]pyrazin-1-yl)cyclopentanamine hydrochloride (0.175 g, 0.373 mmol, prepared using E from Preparation #B.1 and HCl) and NaOAc (0.100 g, 1.22 mmol) in DCM (3 mL) and water (2 mL) was added 2,5-dimethoxytetrahydrofuran-3-carbaldehyde (0.600 g, 3.37 mmol). The reaction was heated to about 40° C. for about 24 h. The reaction mixture was diluted with DCM (30 mL) and washed with water (4×20 mL). The organic layer was dried over anhydrous $MgSO_4$, filtered, and the solvent was removed under reduced pressure to give a brown residue. The crude material was purified by flash chromatography on silica gel eluting with a gradient of 20-100% EtOAc in DCM to give 1-((1S,3R)-3-(6-tosyl-6H-pyrrolo[2,3-e][1,2,4]triazolo[4,3-a]pyrazin-1-yl)cyclopentyl)-1H-pyrrole-3-carbaldehyde (0.059 g, 33%) as a yellow amorphous solid: LC/MS (Table 1, Method a) $R_t$=2.10 min; MS m/z: 475 $(M+H)^+$.

Step B: 1-((1S,3R)-3-(6-tosyl-6H-pyrrolo[2,3-e][1,2,4]triazolo[4,3-a]pyrazin-1-yl)cyclopentyl)-1H-pyrrole-3-carbonitrile

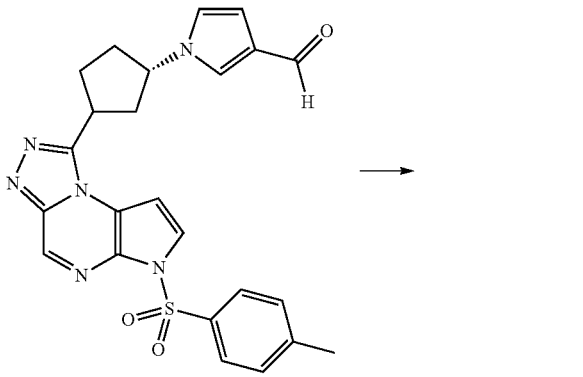

-continued

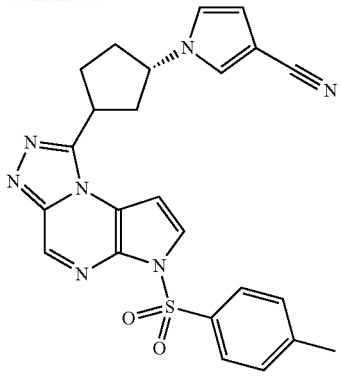

To a solution of 1-((1S,3R)-3-(6-tosyl-6H-pyrrolo[2,3-e][1,2,4]triazolo[4,3-a]pyrazin-1-yl)cyclopentyl)-1H-pyrrole-3-carbaldehyde (0.050 g, 0.105 mmol) in THF (2 mL) was added iodine (0.083 g, 0.327 mmol) and aqueous $NH_4OH$ (28-30% w/v, 0.733 mL, 5.27 mmol). The reaction mixture was stirred at ambient temperature for about 24 h. The reaction mixture was diluted with saturated aqueous $Na_2SO_3$ (30 mL) and EtOAc (30 mL). The layers were partitioned and the organic layer was dried over anhydrous $MgSO_4$, filtered, and the solvent was removed under reduced pressure to give 1-((1S,3R)-3-(6-tosyl-6H-pyrrolo[2,3-e][1,2,4]triazolo[4,3-a]pyrazin-1-yl)cyclopentyl)-1H-pyrrole-3-carbonitrile (0.05 g, 100%): LC/MS (Table 1, Method a) $R_t$=2.33 min; MS m/z: 472 $(M+H)^+$.

Preparation #5: 3,3-difluoro-N-(4-(6-tosyl-6H-pyrrolo[2,3-e][1,2,4]triazolo[4,3-a]pyrazin-1-yl)bicyclo[2.2.2]octan-1-yl)azetidine-1-sulfonamide

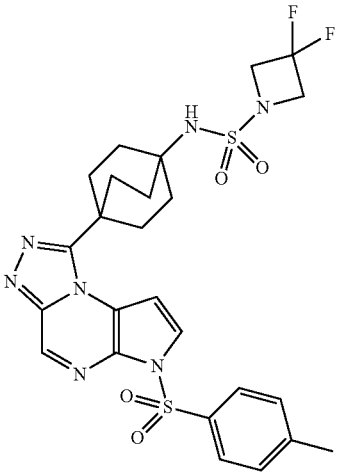

Step A: 1-(1H-imidazol-1-ylsulfonyl)-3-methyl-1H-imidazol-3-ium trifluoromethanesulfonate

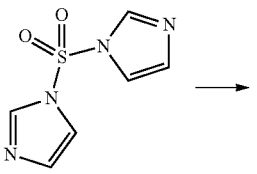

-continued

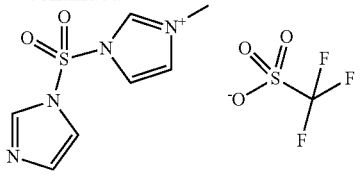

To a solution of 1,1'-sulfonyldiimidazole (3.50 g, 17.7 mmol) in DCM (75 mL) at about 0° C. was added methyl trifluoromethanesulfonate (1.94 mL, 17.7 mmol). The reaction mixture was stirred at about 0° C. for about 1 h, then warmed to ambient temperature and stirred for about 5 h. The solid was collected by vacuum filtration and washed with DCM (10 mL) to give 1-(1H-imidazol-1-ylsulfonyl)-3-methyl-1H-imidazol-3-ium trifluoromethanesulfonate (6.35 g, 98%) as a white solid: LC/MS (Table 1, Method a) $R_t$=0.082 min; MS m/z 213 $(M+H)^+$.

Step B: 1-(3,3-difluoroazetidin-1-ylsulfonyl)-1H-imidazole

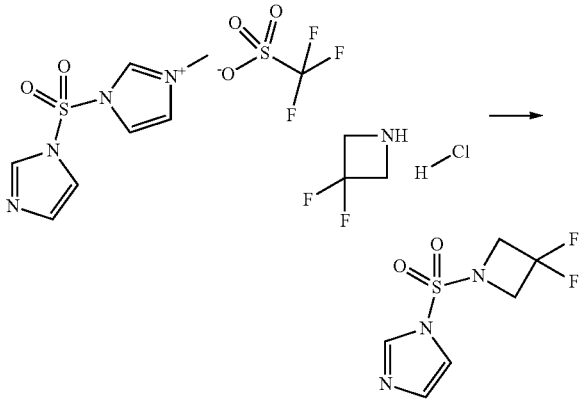

A solution of 3,3-difluoroazetidine hydrochloride (1.00 g, 7.72 mmol) and DIEA (1.5 mL, 8.6 mmol) in MeCN (5 mL) was stirred for about 5 min and then was added to a solution of 1-(1H-imidazol-1-ylsulfonyl)-3-methyl-1H-imidazol-3-ium trifluoromethanesulfonate (4.20 g, 11.6 mmol) in MeCN (10 mL) at about 0° C. The reaction mixture was stirred at about 0° C. for about 1 h, and then warmed to ambient temperature and stirred for about 16 h. The reaction mixture was then concd under reduced pressure. The crude material was purified by flash chromatography on silica gel eluting with a gradient of 5-100% EtOAc in DCM to give 1-(3,3-difluoroazetidin-1-ylsulfonyl)-1H-imidazole (0.95 g, 55%) as a yellow solid: LC/MS (Table 1, Method c) $R_t$=1.16 min; MS m/z 224 $(M+H)^+$.

Step C: 1-(3,3-difluoroazetidin-1-ylsulfonyl)-3-methyl-1H-imidazol-3-ium trifluoromethanesulfonate

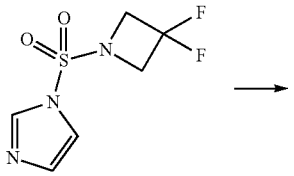

-continued

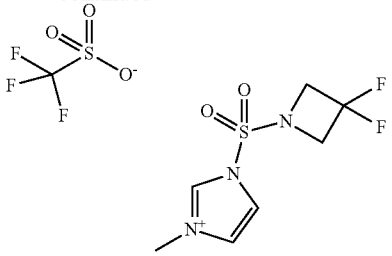

To a solution of 1-(3,3-difluoroazetidin-1-ylsulfonyl)-1H-imidazole (0.500 g, 2.24 mmol) in DCM (5 mL) at about 0° C. was added methyl trifluoromethanesulfonate (0.27 mL, 2.46 mmol) dropwise over about 3 min. The reaction mixture was stirred at about 0° C. for about 2 h. The solid was collected by vacuum filtration, washed with DCM (10 mL), and dried under vacuum to give 1-(3,3-difluoroazetidin-1-ylsulfonyl)-3-methyl-1H-imidazol-3-ium trifluoromethanesulfonate (0.79 g, 90%) as a white solid: LC/MS (Table 1, Method c) $R_t$=1.12 min; MS m/z 238 $(M+H)^+$.

Step D: 3,3-difluoro-N-(4-(6-tosyl-6H-pyrrolo[2,3-e][1,2,4]triazolo[4,3-a]pyrazin-1-yl)bicyclo[2.2.2]octan-1-yl)azetidine-1-sulfonamide

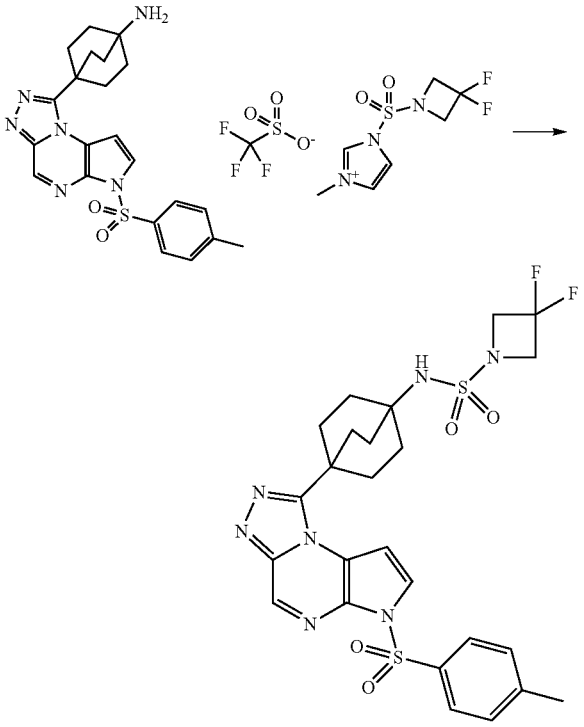

To a solution of 4-(6-tosyl-6H-pyrrolo[2,3-e][1,2,4]triazolo[4,3-a]pyrazin-1-yl)bicyclo[2.2.2]-octan-1-amine (0.20 g, 0.46 mmol, Example #9, Step F) in MeCN (5 mL) was added 1-(3,3-difluoroazetidin-1-ylsulfonyl)-3-methyl-1H-imidazol-3-ium trifluoromethanesulfonate (0.19 g, 0.50 mmol). The reaction mixture was heated to about 70° C. for about 24 h. The solvent was removed under reduced pressure. The residue was partitioned between EtOAc (30 mL) and water (10 mL). The layers were separated and the organic layer was washed with water (10 mL) and brine (2×10 mL), dried over anhydrous $MgSO_4$, filtered, and the solvent was removed under reduced pressure. The crude material was purified by flash chromatography on silica gel eluting with a gradient of 0-10% MeOH in DCM to give 3,3-difluoro-N-(4-(6-tosyl-6H-pyrrolo[2,3-e][1,2,4]triazolo[4,3-a]pyrazin-1-yl)bicyclo[2.2.2]octan-1-yl)azetidine-1-sulfonamide (0.119 g, 38%): LC/MS (Table 1, Method a) $R_t$=2.32 min; MS m/z 592 $(M+H)^+$.

Preparation #6: 1-methylcyclopropane-1-sulfonyl chloride

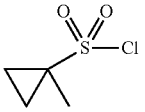

Step A: butyl cyclopropanesulfonate

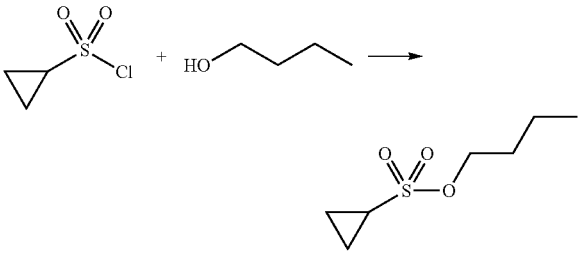

To a solution of cyclopropanesulfonyl chloride (5.00 g, 35.6 mmol) in n-BuOH (20 mL) at −20° C., pyridine (5.75 mL, 71.1 mmol) was added dropwise. The resulting mixture was stirred for about 16 h while warming slowly to ambient temperature. The solvents were removed under reduced pressure and the residue was partitioned between DCM and water (50 mL each). The organic phase was further washed with brine (40 mL), dried over anhydrous $MgSO_4$ and concd under reduced pressure to yield butyl cyclopropanesulfonate (4.7 g, 74%) as a yellow oil. $^1$H NMR (DMSO-$d_6$) δ 4.2 (t, 2H), 2.82 (m, 1H), 1.64 (m, 2H), 1.35 (m, 2H), 1.08 (m, 2H), 1.01 (m, 2H), 0.89 (t, 3H).

Step B: butyl 1-methylcyclopropane-1-sulfonate

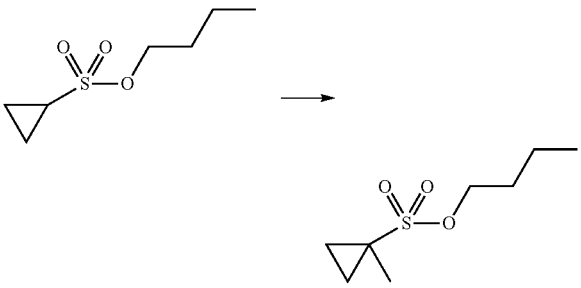

To a solution of butyl cyclopropanesulfonate (1.5 g, 8.4 mmol) in THF (8 mL) at about −78° C., n-BuLi (1.6 M in hexanes, 5.26 mL, 8.42 mmol) and iodomethane (0.684 mL, 10.9 mmol) were added simultaneously and the resulting mixture was stirred at about −78° C. for about 2 h and then at ambient temperature for about 2 h. The reaction was quenched by the addition of saturated aqueous $NH_4Cl$ (7 mL) and the layers were separated. The aqueous layer was back extracted with EtOAc (15 mL) and the combined organic extracts were dried over anhydrous $MgSO_4$ and concd under reduced pressure. The residue was subjected to silica gel column chromatography (5 to 25% EtOAc in heptane over 30 min) to yield butyl 1-methylcyclopropane-1-sulfonate (0.8 g, 49%) as a colorless oil. $^1$H NMR (DMSO-$d_6$) δ 4.17 (t, 2H), 1.62 (m, 2H), 1.43 (s, 3H), 1.35 (m, 2H), 1.22 (m, 2H), 0.94 (m, 2H), 0.88 (t, 3H).

Step C: 1-methylcyclopropane-1-sulfonyl chloride

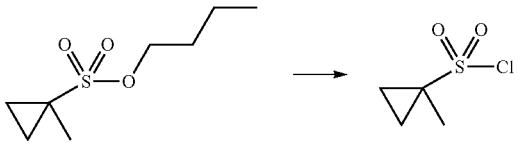

A mixture of butyl 1-methylcyclopropane-1-sulfonate (0.80 g, 4.2 mmol) and potassium thiocyanate (0.404 g, 4.16 mmol) in 1,4-dioxane/water (1:1, 10 mL) was heated at reflux for about 8 h. The reaction was cooled to ambient temperature and the solvents were concd under reduced pressure to yield crude potassium 1-methylcyclopropane-1-sulfonate which was suspended in thionyl chloride (7 mL). DMF (0.05 mL) was added and the mixture was heated at reflux for about 8 h and then cooled. The volatiles were removed under reduced pressure and the residue was dissolved in DCM (20 mL), washed with water (15 mL), dried over anhydrous $MgSO_4$ and concd under reduced pressure to yield 1-methylcyclopropane-1-sulfonyl chloride (0.56 g, 86%) as a yellow oil. $^1$H NMR (DMSO-$d_6$) δ 1.82 (br s, 2H), 1.79 (s, 3H), 1.15 (m, 2H).

Preparation #7: ethyl 4-(cyclopropanesulfonamido)-2-ethyl-1-fluorocyclopentanecarboxylate

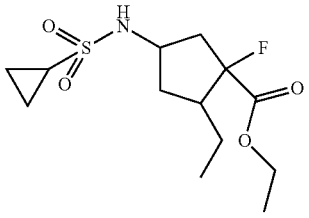

A solution of ethyl 4-(cyclopropanesulfonamido)-2-ethylcyclopentanecarboxylate (0.630 g, 2.18 mmol, prepared using K from Preparation #Y.1 and cyclopropanesulfonyl chloride) in THF (14.5 mL) was cooled to about −78° C. and then LDA (1.8 M in THF/hexane, 3.63 mL, 6.53 mmol) was added dropwise to the reaction mixture over about 30 min. The reaction mixture was stirred at about −78° C. for about 50 min before a solution of N-fluoro-N-(phenylsulfonyl) benzenesulfonamide (2.06 g, 6.53 mmol) in THF (7.3 mL) was added dropwise over about 30 min. The reaction mixture was stirred at about −78° C. for about 1 h and then was warmed to ambient temperature and stirred for about 16 h. Saturated aqueous $NH_4Cl$ (100 mL) was added. The reaction mixture was partitioned with EtOAc (50 mL). The aqueous layer was further extracted with EtOAc (2×50 mL). The combined organic layers were concd under reduced pressure. The residue was purified by silica gel chromatography eluting with a gradient of 0-60% EtOAc in heptane to yield ethyl 4-(cyclopropanesulfonamido)-2-ethyl-1-fluorocyclopentanecarboxylate (0.41 g, 46%) as clear oil: LC/MS (Table 1, Method b) $R_t$=2.12 min; MS m/z: 306 $(M-H)^-$.

Preparation #8: (1S,2R,4R)-ethyl 2-methyl-4-(phenylamino)cyclopentanecarboxylate and (1R,2S,4S)-ethyl 2-methyl-4-(phenylamino)cyclopentanecarboxylate

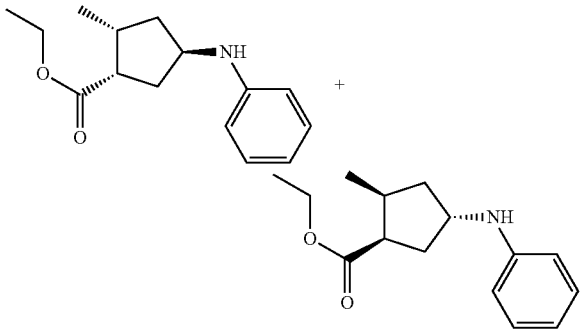

A solution of ethyl 4-hydroxy-2-methylcyclopentanecarboxylate (1.81 g, 10.5 mmol, prepared using P from Example #7, step G and $NaBH_4$) and pyridine (1.28 mL, 15.8 mmol) in THF (52.5 mL) was cooled to about 0° C. Methanesulfonyl chloride (0.90 mL, 12 mmol) was added dropwise. The reaction mixture was stirred at ambient temperature for about 16 h then partitioned between water (50 mL) and DCM (30 mL). The layers were separated and the aqueous layer was extracted with DCM (2×30 mL). The combined organic layers were dried over anhydrous $Na_2SO_4$ and concd under reduced pressure to give a white solid. The resulting solid was mixed with aniline (78.0 g, 841 mmol) and heated at about 90° C. for about 16 h. The reaction mixture was concd under reduced pressure and purified by silica gel chromatography eluting with a gradient of 20-100% EtOAc in DCM to yield (1S,2R,4R)-ethyl 2-methyl-4-(phenylamino)cyclopentanecarboxylate and (1R,2S,4S)-ethyl 2-methyl-4-(phenylamino)cyclo-pentanecarboxylate with 29 mol % aniline as an excipient (2.73 g, 75%) as a dark oil: LC/MS (Table 1, Method b) $R_t$=2.67 min; MS m/z: 248 $(M+H)^+$.

Preparation #9: 1-tert-butyl 3-ethyl 4-ethyl-5,6-dihydropyridine-1,3(2H)-dicarboxylate

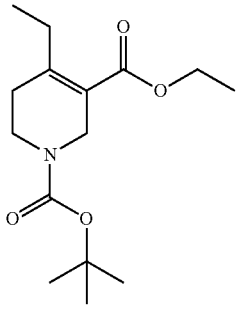

Step A: 1-tert-butyl 3-ethyl 4-(diethoxyphosphoryloxy)-5,6-dihydropyridine-1,3(2H)-dicarboxylate

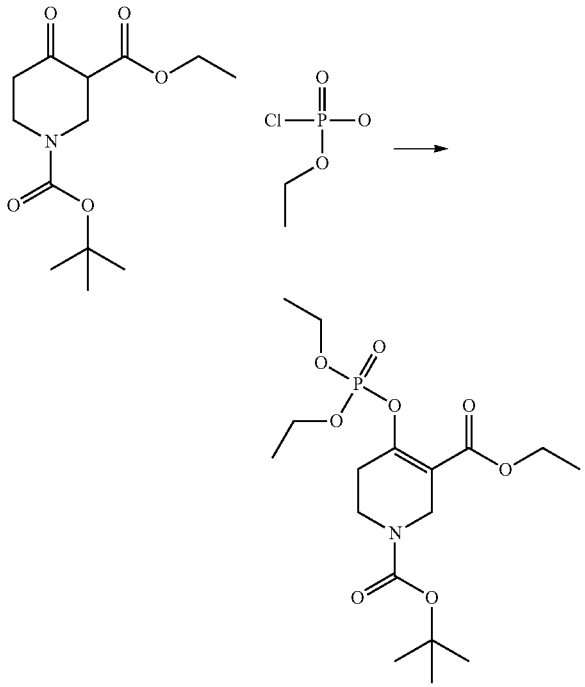

To a solution of 1-tert-butyl 3-ethyl 4-oxopiperidine-1,3-dicarboxylate (11.50 g, 42.4 mmol, ASDI) in MTBE (500 mL) at about −78° C. was added NaHMDS (1 M in THF, 53.0 mL, 53.0 mmol). After about 1 h, diethyl phosphorochloridate (7.62 mL, 53.0 mmol) was added to the reaction mixture. After about 30 min, the reaction mixture was allowed to warm to ambient temperature and stirred for about 16 h. The reaction mixture was partitioned between saturated aqueous $NH_4Cl$ (100 mL) and EtOAc (50 mL). The layers were separated. The aqueous layer was further extracted with EtOAc (2×50 mL). The combined organic layers were dried over anhydrous $Na_2SO_4$, filtered, and concd under reduced pressure. The crude material was purified by silica gel chromatography eluting with a gradient of 0-100% EtOAc in heptane to yield 1-tert-butyl 3-ethyl 4-(diethoxyphosphoryloxy)-5,6-dihydropyridine-1,3(2H)-dicarboxylate (8.55 g, 49%) as a yellow oil: LC/MS (Table 1, Method b) $R_t$=2.35 min; MS m/z: 408 $(M+H)^+$.

Step B: 1-tert-butyl 3-ethyl 4-ethyl-5,6-dihydropyridine-1,3(2H)-dicarboxylate

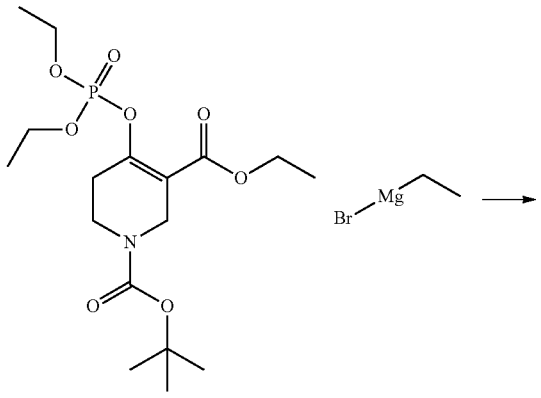

-continued

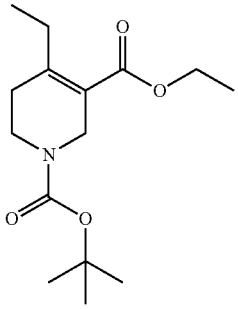

To a slurry of CuI (4.21 g, 22.12 mmol) in THF (61.4 mL) at about 0° C. was added ethylmagnesium bromide (1.0 M in THF, 44.2 mL, 44.2 mmol) dropwise. After about 30 min, the reaction mixture was cooled to about −78° C. and a solution of 1-tert-butyl 3-ethyl 4-(diethoxyphosphoryloxy)-5,6-dihydropyridine-1,3(2H)-dicarboxylate (7.51 g, 18.43 mmol) in THF (61 mL) was added slowly. The reaction mixture was stirred at about −78° C. for about 1 h then warmed to about 0° C. The reaction mixture was stirred at about 0° C. for about 1.5 h, then warmed to ambient temperature and stirred for about 1 h. The reaction mixture was cooled to about −78° C. and saturated aqueous $NH_4Cl$ (100 mL) was slowly added. The reaction mixture was allowed to warm to ambient temperature and stirred for about 16 h. The mixture was extracted with $Et_2O$ (100 mL). The aqueous layer was further extracted with $Et_2O$ (2×50 mL). The organic layers were combined, washed with saturated aqueous $NH_4Cl$ (50 mL), dried over anhydrous $Na_2SO_4$, filtered, concd under reduced pressure and purified by silica gel chromatography eluting with a gradient of 0-30% EtOAc in heptane to yield 1-tert-butyl 3-ethyl 4-ethyl-5,6-dihydropyridine-1,3(2H)-dicarboxylate (0.785 g, 15%) as a clear oil: $^1$H NMR ($CDCl_3$) δ 4.23 (d, J=7.1 Hz, 2H), 4.12 (s, 2H), 3.48 (t, J=5.8 Hz, 2H), 2.52 (q, J=7.5 Hz, 2H), 2.28 (t, J=5.8 Hz, 2H), 1.51 (s, 9H), 1.32 (t, J=7.1 Hz, 3H), 1.09 (t, J=7.5 Hz, 3H).

Preparation #10:1-(1-benzylpiperidin-3-yl)-1,6-dihydropyrazolo[3,4-d]pyrrolo[2,3-b]pyridine

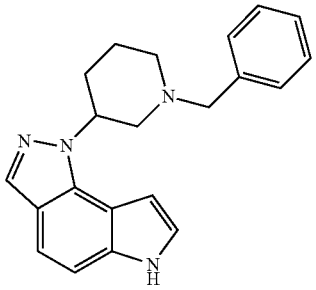

Step A: tert-butyl 2-(1-benzylpiperidin-3-yl)hydrazinecarboxylate

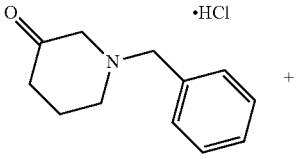

-continued

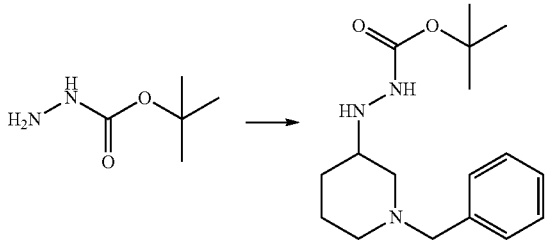

A mixture of 1-benzylpiperidin-3-one hydrochloride (1.00 g, 4.10 mmol), tert-butyl hydrazinecarboxylate (0.596 g, 4.51 mmol), and AcOH (0.470 mL, 8.21 mmol) in DCE (20 mL) was stirred at ambient temperature for about 1 h then $NaCNBH_3$ (0.258 g, 4.10 mmol) was added. The reaction mixture was stirred at ambient temperature for about 16 h. The reaction mixture was quenched by the addition of saturated aqueous $NaHCO_3$ (50 mL). The organic layer was separated, concd under reduced pressure and purified by RP-HPLC (Table 1, Method h) to afford tert-butyl 2-(1-benzylpiperidin-3-yl)hydrazinecarboxylate (1.25 g, 100%) as a clear oil: LC/MS (Table 1, Method b) $R_t$=1.66 min; MS m/z: 306 $(M+H)^+$.

Step B: 1-benzyl-3-hydrazinylpiperidine hydrochloride

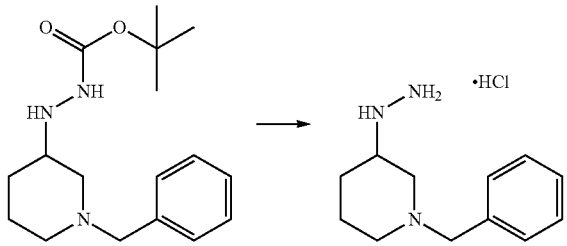

A solution of tert-butyl 2-(1-benzylpiperidin-3-yl)hydrazinecarboxylate (1.25 g, 4.10 mmol) in aqueous HCl (6 N, 6.83 mL, 41.0 mmol) was stirred at ambient temperature for about 8 h. The solvent was removed under reduced pressure to give crude 1-benzyl-3-hydrazinylpiperidine hydrochloride (1.45 g, 112%) as a white solid which was used without further purification: LC/MS (Table 1, Method b) $R_t$=0.66 min; MS m/z: 206 $(M+H)^+$.

Step C: 1-(1-benzylpiperidin-3-yl)-1,6-dihydropyrazolo[3,4-d]pyrrolo[2,3-b]pyridine

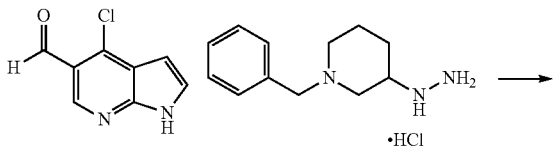

-continued

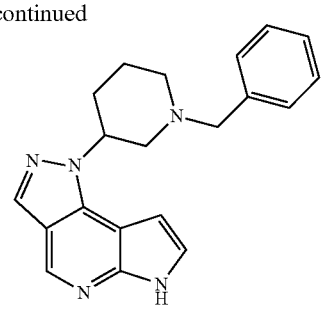

4-Chloro-1H-pyrrolo[2,3-b]pyridine-5-carbaldehyde (0.40 g, 2.21 mmol, Adesis) and 1-benzyl-3-hydrazinylpiperidine hydrochloride (1.39 g, 4.43 mmol) were suspended in n-BuOH (11.1 mL). The mixture was heated at about 90° C. for about 3 h and then heated at about 120° C. for about 5 h. The reaction mixture was cooled to ambient temperature and the solvent was removed under reduced pressure. The residue was purified by silica gel chromatography eluting with a gradient of 0-5% MeOH in DCM to yield 1-(1-benzylpiperidin-3-yl)-1,6-dihydropyrazolo[3,4-d]pyrrolo[2,3-b]pyridine (0.105 g, 14%) as a brown oil: LC/MS (Table 1, Method b) $R_t$=1.53 min; MS m/z: 332 $(M+H)^+$.

Preparation #11: cis-3-tert-butyl 1-methyl 4-ethylcyclopentane-1,3-dicarboxylate

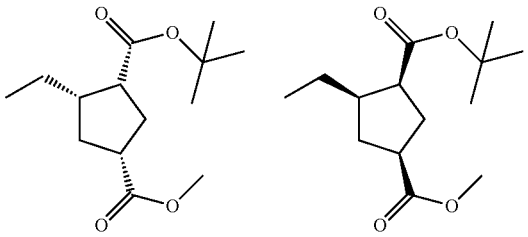

Step A: cis-2-ethyl-4-(methoxycarbonyl)cyclopentanecarboxylic acid

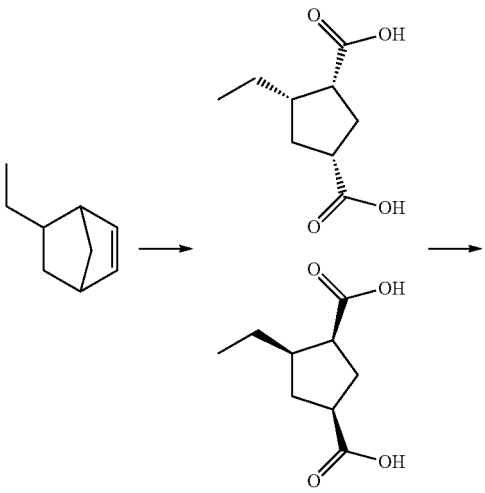

-continued

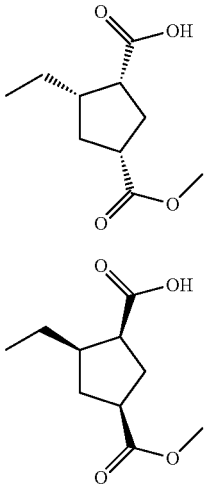

Ruthenium (III) chloride hydrate (0.203 g, 0.900 mmol) was added to a mixture of 5-ethylbicyclo[2.2.1]hept-2-ene (5.00 g, 40.9 mmol, ChemSampCo) and sodium periodate (35.0 g, 164 mmol) in water (117 mL), MeCN (78 mL) and EtOAc (78 mL). The reaction mixture was stirred at ambient temperature for about 16 h. The reaction mixture was filtered, extracted with $Et_2O$ (2×100 mL). The aqueous layer was further extracted with $Et_2O$ (3×100 mL). The organic layers were combined, washed with brine (100 mL), dried over anhydrous $MgSO_4$, filtered, and concd under reduced pressure. The residue was dissolved in $Ac_2O$ (20 mL, 24 mmol) and heated at reflux for about 4 h. The reaction mixture was cooled to ambient temperature and the solvent was removed under reduced pressure. MeOH (40 mL) was added and the reaction mixture was heated at reflux for about 6 h. The solvent was removed under reduced pressure to yield cis-2-ethyl-4-(methoxycarbonyl)cyclopentanecarboxylic acid (4.84 g, 59%) as a brown oil: LC/MS (Table 1, Method b) $R_t$=1.91 min; MS m/z: 201 $(M+H)^+$.

Step B: cis-3-tert-butyl 1-methyl 4-ethylcyclopentane-1,3-dicarboxylate

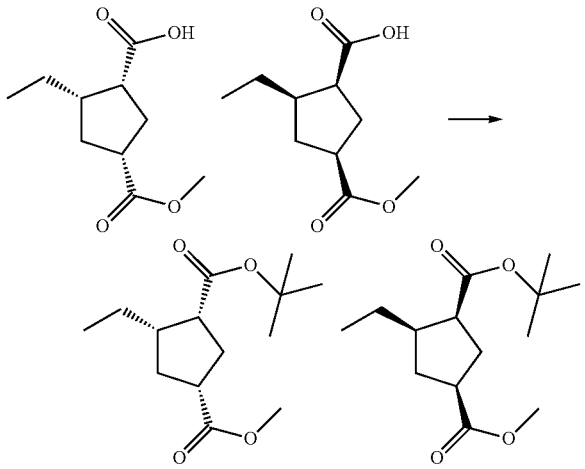

A mixture of cis-2-ethyl-4-(methoxycarbonyl)cyclopentanecarboxylic acid (4.50 g, 22.47 mmol) in $SOCl_2$ (8.20 mL, 112 mmol) was stirred at ambient temperature for about 16 h. The solvent was removed under reduced pressure. The resulting residue was dissolved in t-BuOH (22.5 mL). The reaction mixture was stirred at ambient temperature for about 16 h. The solvent was removed under reduced pressure. The residue was dissolved in water (50 mL) and DCM (100 mL). The organic layer was separated, washed with saturated aqueous $NaHCO_3$ (50 mL), dried over anhydrous $Na_2SO_4$, filtered, and concd under reduced pressure to give cis-3-tert-butyl 1-methyl 4-ethylcyclopentane-1,3-dicarboxylate (3.94 g, 68%) as a dark brown oil: LC/MS (Table 1, Method b) $R_t$=2.86 min; MS m/z: 257 $(M+H)^+$.

Preparation #12: 1-(5-tosyl-5H-pyrrolo[2,3-b]pyrazin-2-yl)but-3-en-1-amine hydrochloride

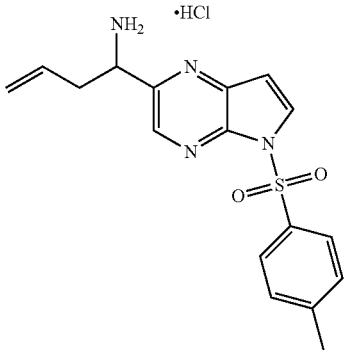

Step A: (E)-2-styryl-5-tosyl-5H-pyrrolo[2,3-b]pyrazine

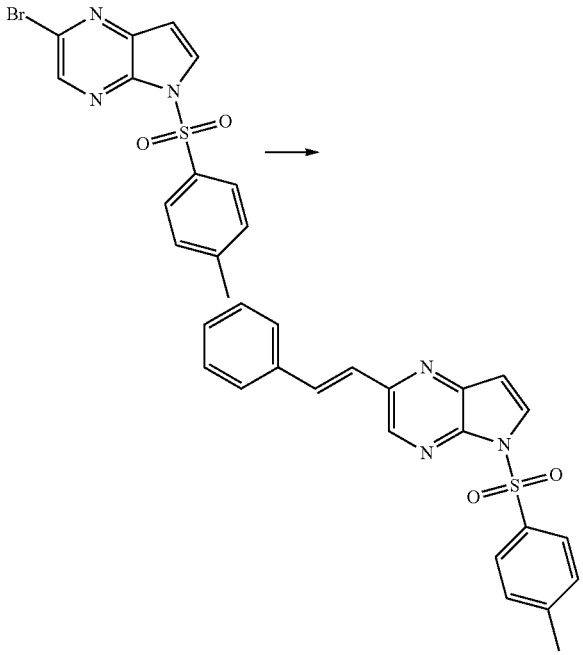

To a solution of 2-bromo-5-tosyl-5H-pyrrolo[2,3-b]pyrazine (3.1 g, 8.8 mmol, Example #1, Step B), $PdCl_2$ (dppf)•DCM (0.719 g, 0.880 mmol) and (E)-styrylboronic acid (2.60 g, 17.6 mmol) in THF (3 mL) and water (2 mL) was added $Na_2CO_3$ (2.33 g, 22.0 mmol). The reaction mixture was degassed with argon for about 5 min. The reaction mixture was heated at about 50° C. After about 24 h, additional $PdCl_2$ (dppf)•DCM (0.719 g, 0.880 mmol), (E)-styrylboronic acid (2.60 g, 17.6 mmol) and $Na_2CO_3$ (2.33 g, 22.0 mmol) were added to the reaction mixture. After heating at about 50° C. for about 48 h, the reaction mixture was cooled to ambient temperature and diluted with DCM (200 mL) and water (200 mL). The organic layer was separated, dried over anhydrous $Na_2SO_4$, filtered, and coned under reduced pressure. Purification by chromatography over silica gel eluting with a gradient of 20-60% EtOAc in heptane containing 5% DCM provided (E)-2-styryl-5-tosyl-5H-pyrrolo[2,3-b]pyrazine as a yellow solid (1.2 g, 36%): LC/MS (Table 1, Method a) $R_t$=2.99 min; MS m/z: 376 $(M+H)^+$.

Step B: 5-tosyl-5H-pyrrolo[2,3-b]pyrazine-2-carbaldehyde

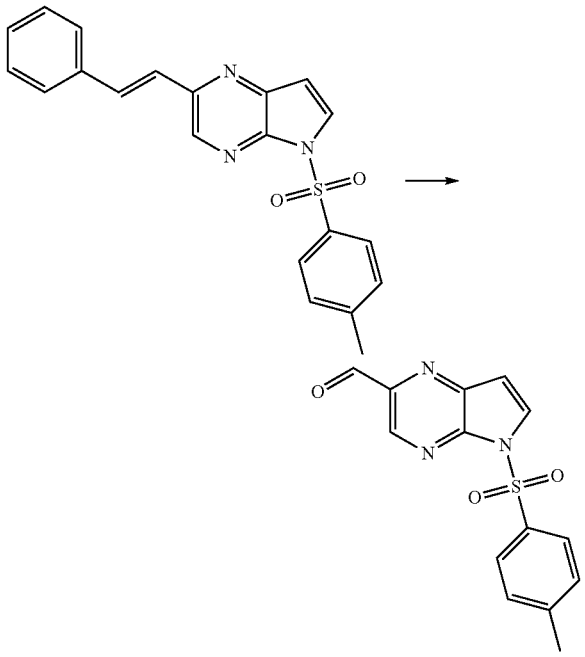

To a solution of (E)-2-styryl-5-tosyl-5H-pyrrolo[2,3-b]pyrazine (1.2 g, 3.2 mmol) in 1,4-dioxane (20 mL) and water (2.0 mL) was added sodium periodate (2.73 g, 12.8 mmol) followed by osmium tetroxide (2.5 wt % in t-BuOH, 4.01 mL, 0.320 mmol). The reaction mixture was stirred for about 1 day at ambient temperature and then additional sodium periodate (2.73 g, 12.78 mmol) and osmium tetroxide (2.5 wt % in t-BuOH, 4.01 mL, 0.320 mmol) were added. After stirring for about 2 days, a solution of 10% aqueous $Na_2S_2O_3$ (100 mL) and EtOAc (100 mL) was added. The organic layer was separated, dried over anhydrous $Na_2SO_4$, filtered, and coned under reduced pressure to give a solid, which was triturated with heptane to remove benzaldehyde. The resulting solid was dried in vacuo to provide 5-tosyl-5H-pyrrolo[2,3-b]pyrazine-2-carbaldehyde as a brown solid (0.77 g, 80%): LC/MS (Table 1, Method a) $R_t$=2.01 min; MS m/z: 334 $(M+H)^+$.

Step C: 1-(5-tosyl-5H-pyrrolo[2,3-b]pyrazin-2-yl) but-3-en-1-ol

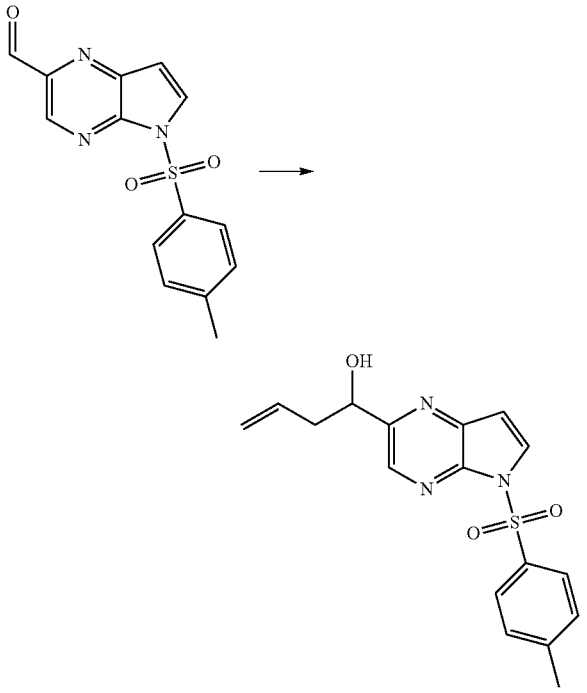

To a solution of 5-tosyl-5H-pyrrolo[2,3-b]pyrazine-2-carbaldehyde (5.1 g, 17 mmol) in THF (100 mL) and water (33.3 mL) was added 3-bromoprop-1-ene (2.86 mL, 33.9 mmol) followed by indium (3.89 g, 33.9 mmol). The reaction mixture was stirred for about 15 h at ambient temperature and then aqueous HCl (1 N, 150 mL) and EtOAc (150 mL) were added. The organic layer was separated, dried over anhydrous $Na_2SO_4$, filtered, coned in vacuo and purified by chromatography on silica gel eluting with 20-60% EtOAc in heptane to provide 1-(5-tosyl-5H-pyrrolo[2,3-b] pyrazin-2-yl)but-3-en-1-ol (4 g, 69%) as a thick oil: LC/MS (Table 1, Method a) $R_t$=2.30 min; MS m/z: 344 $(M+H)^+$.

Step D: 2-(1-azidobut-3-enyl)-5-tosyl-5H-pyrrolo[2, 3-b]pyrazine

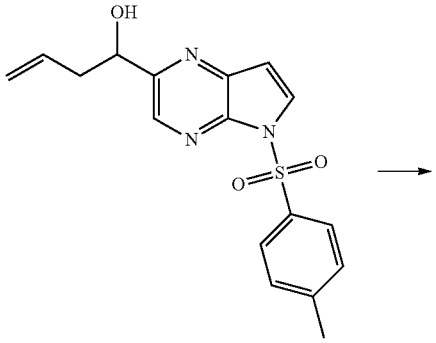

-continued

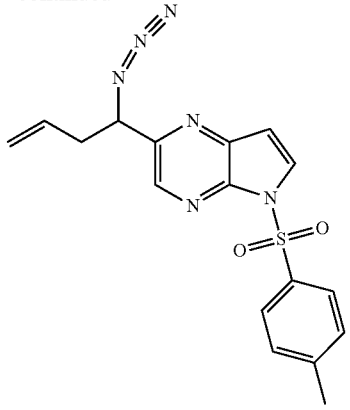

To a solution of 1-(5-tosyl-5H-pyrrolo[2,3-b]pyrazin-2-yl)but-3-en-1-ol (0.14 g, 0.41 mmol) in DCM (10 mL) was added thionyl chloride (0.045 mL, 0.61 mmol). The reaction mixture was stirred for about 8 h at ambient temperature and then EtOAc and saturated aqueous $NaHCO_3$ (10 mL each) were added. The organic layer was separated, dried over anhydrous $Na_2SO_4$, filtered and concd in vacuo. The crude chloride was dissolved in DMF (10 mL) and sodium azide (0.159 g, 2.45 mmol) was added to the reaction mixture. The reaction mixture was stirred for about 15 h at ambient temperature and then EtOAc and saturated aqueous $NaHCO_3$ (10 mL each) were added to the reaction mixture. The organic layer was separated, concd in vacuo, and purified by chromatography on silica gel eluting with 10-60% EtOAc in heptane to provide 2-(1-azidobut-3-enyl)-5-tosyl-5H-pyrrolo[2,3-b]pyrazine (0.153 g, 87%) as an oil: LC/MS (Table 1, Method a) $R_t$=2.84 min; MS m/z: 369 $(M+H)^+$.

Step E: 1-(5-tosyl-5H-pyrrolo[2,3-b]pyrazin-2-yl) but-3-en-1-amine hydrochloride

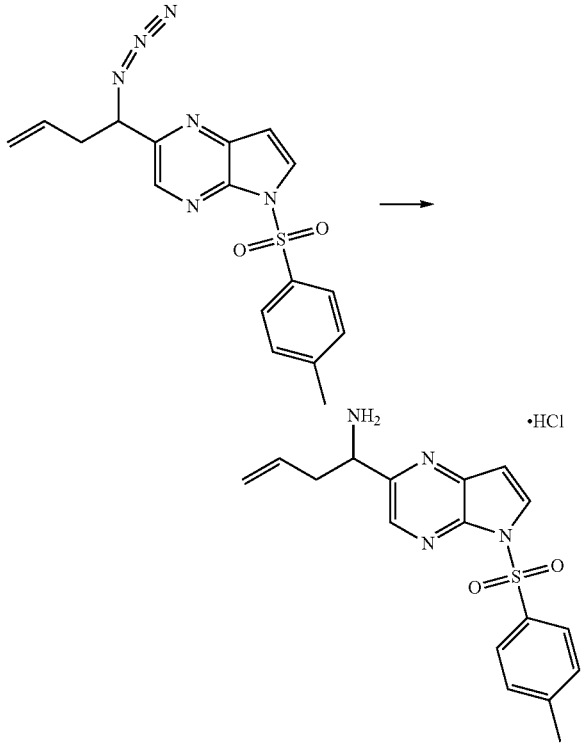

To a solution of 2-(1-azidobut-3-enyl)-5-tosyl-5H-pyrrolo[2,3-b]pyrazine (3.90 g, 10.6 mmol) in THF (60 mL) and water (30 mL) was added triphenylphosphine (3.33 g, 12.7 mmol). The reaction mixture was heated to about 50° C. for about 15 h. The reaction mixture was cooled to ambient temperature and concd in vacuo. The residue was dissolved in EtOAc (30 mL) and HCl (gas) was added until a pH of about 1 was maintained followed by the addition of $Et_2O$ to induce precipitate formation. After stirring for about 15 h, the precipitate was collected by filtration to provide 1-(5-tosyl-5H-pyrrolo[2,3-b]pyrazin-2-yl)but-3-en-1-amine hydrochloride (2.5 g, 62%) as a tan solid: LC/MS (Table 1, Method a) $R_t$=1.80 min; MS m/z: 343 $(M+H)^+$.

Preparation #13: N-((5-tosyl-5H-pyrrolo[2,3-b]pyrazin-2-yl)methyl)cyclohexanecarboxamide

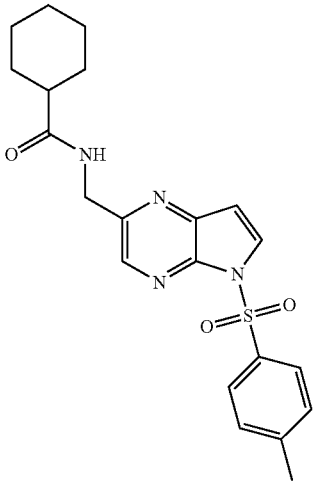

To a slurry of (5-tosyl-5H-pyrrolo[2,3-b]pyrazin-2-yl)methanamine hydrochloride (0.50 g, 1.476 mmol, Example #5, Step C) in DCM (10 mL) was added cyclohexanecarbonyl chloride (0.221 mL, 1.623 mmol) followed by DIEA (0.644 mL, 3.69 mmol). The reaction mixture was stirred for about 4 h at ambient temperature and then saturated aqueous $NaHCO_3$ (20 mL) and DCM (20 mL) were added to the reaction mixture. The organic layer was separated, concd in vacuo, and purified by chromatography on silica gel (40 g) eluting with 20-80% EtOAc in DCM to provide N-((5-tosyl-5H-pyrrolo[2,3-b]pyrazin-2-yl)methyl)cyclohexanecarboxamide (0.49 g, 80%) as a colorless solid: LC/MS (Table 1, Method a) $R_t$=2.40 min; MS m/z: 413 $(M+H)^+$.

Preparation #14*: (2R,4S)-tert-butyl 4-(cyclopropanesulfonamido)-2-methylpyrrolidine-1-carboxylate

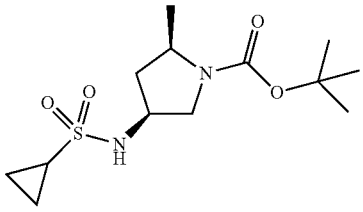

To a slurry of 20 wt % $Pd(OH)_2$ on C (0.605 g, 0.862 mmol) in EtOH (75 mL) was added a solution of (2R,4S)-tert-butyl 4-azido-2-methylpyrrolidine-1-carboxylate (3.9 g, 17 mmol, synthesized as described in Rosen, T.; Chu, D. T. W.; Lico, I. M.; Fernandes, P. B.; Marsh, K.; Shen, L.; Cepa, V. G.; Pernet, A. G. J. Med. Chem. 1988, 31, 1598-1611) in EtOH (25 mL). The reaction mixture was sparged with hydrogen and an atmosphere of hydrogen was maintained via balloon. The reaction mixture was stirred for about 2 h at ambient temperature and then was filtered and concd in vacuo. The residue was dissolved in DCM (100 mL), cooled to about 0° C. and TEA (6.01 mL, 43.1 mmol) was added followed by cyclopropanesulfonyl chloride (2.67 g, 19.0 mmol). The reaction mixture was stirred at ambient temperature for about 15 h, saturated aqueous $NaHCO_3$ (50 mL) was added to the reaction mixture and the organic layer was separated, concd in vacuo, and purified by chromatography on silica gel (80 g) eluting with 20-80% EtOAc in heptane to provide (2R,4S)-tert-butyl 4-(cyclopropanesulfonamido)-2-methylpyrrolidine-1-carboxylate (2.55 g, 48%) as an oil: LC/MS (Table 1, Method a) $R_t$=1.98 min (ELSD); MS m/z: 305 $(M+H)^+$.

Preparation #15*: (2R,4S)-tert-butyl 4-(cyclopropanesulfonamido)-2-ethylpyrrolidine-1-carboxylate

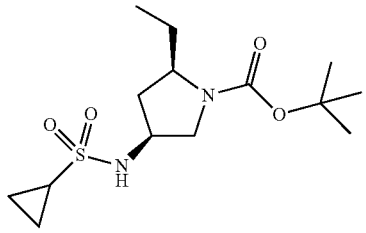

To a slurry of 20 wt % $Pd(OH)_2$ on C (0.044 g, 0.062 mmol) in EtOH (30 mL) was added a solution of (2R,4S)-tert-butyl 4-azido-2-ethylpyrrolidine-1-carboxylate (1.5 g, 6.2 mmol, synthesized as described in Rosen, T.; Chu, D. T. W.; Lico, I. M.; Fernandes, P. B.; Marsh, K.; Shen, L.; Cepa, V. G.; Pernet, A. G. J. Med. Chem. 1988, 31, 1598-1611) in EtOH (10 mL). The reaction mixture was sparged with hydrogen and an atmosphere of hydrogen was maintained via balloon. The reaction mixture was stirred for about 4 h at ambient temperature and then was filtered and concd in vacuo. The residue was dissolved in pyridine (30 mL) and cyclopropanesulfonyl chloride (1.05 g, 7.49 mmol) was added. The reaction mixture was stirred for about 15 h at ambient temperature and then was partitioned between EtOAc (50 mL) and saturated aqueous $CuSO_4$ (50 mL). The organic layer was separated, washed with brine (30 mL), dried over anhydrous $Na_2SO_4$, filtered, concd in vacuo, and purified by chromatography on silica gel (80 g) eluting with 20-80% EtOAc in heptane to provide (2R,4S)-tert-butyl 4-(cyclopropanesulfonamido)-2-ethylpyrrolidine-1-carboxylate (0.95 g, 48%) as an oil: LC/MS (Table 1, Method a) $R_t$=2.12 min (ELSD); MS m/z: 319 $(M+H)^+$.

Preparation #16: tert-butyl 1-(6-tosyl-6H-imidazo[1,5-a]pyrrolo[2,3-e]pyrazin-1-yl)pyrrolidin-3-ylcarbamate

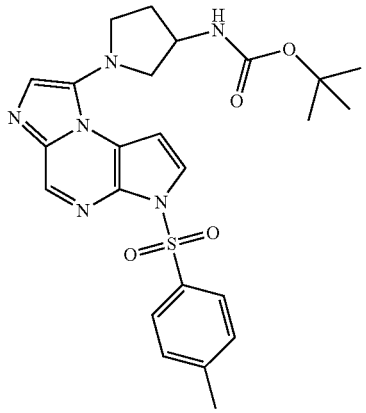

To a solution of tert-butyl 1-((5-tosyl-5H-pyrrolo[2,3-b]pyrazin-2-yl)methylcarbamothioyl)-pyrrolidin-3-ylcarbamate (0.54 g, 1.0 mmol, Preparation #J.1) in THF (15 mL) was added DIEA (0.444 mL, 2.54 mmol) followed by mercury (II) trifluoroacetate (0.478 g, 1.12 mmol). The reaction mixture was stirred at ambient temperature for about 2 h and then saturated aqueous $NaHCO_3$ (30 mL) and EtOAc (30 mL) were added. The organic layer was separated, dried over anhydrous $Na_2SO_4$, filtered, and concd in vacuo. The crude material was purified by chromatography on silica gel (40 g) eluting with 10-40% EtOAc in DCM to provide tert-butyl 1-(6-tosyl-6H-imidazo[1,5-a]pyrrolo[2,3-e]pyrazin-1-yl)pyrrolidin-3-ylcarbamate (0.411 g, 81%) as a yellow glass: LC/MS (Table 1, Method a) $R_t$=2.50 min; MS m/z: 497 $(M+H)^+$.

Preparation #17: N-(4-(3-(2,3-dihydroxypropyl)-6-tosyl-6H-imidazo[1,5-a]pyrrolo[2,3-e]pyrazin-1-yl)bicyclo[2.2.2]octan-1-yl)cyclopropanesulfonamide

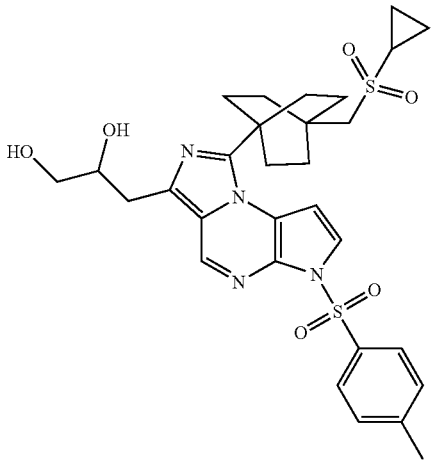

To a solution of N-(4-(3-allyl-6-tosyl-6H-imidazo[1,5-a]pyrrolo[2,3-e]pyrazin-1-yl)bicyclo-[2.2.2]octan-1-yl)cyclopropanesulfonamide (0.27 g, 0.47 mmol, prepared using E with 4-(tert-butoxycarbonylamino)bicyclo[2.2.2]octane-1-carboxylic acid [Prime Organics], K with cyclopropylsulfonyl chloride, H from Preparation #12, HATU and DIEA, Q with Lawesson's reagent and mercury (II) trifluoroacetate) in 1,4-dioxane (10 mL) and water (1 mL) was added N-methyl-morpholine-N-oxide (0.22 g, 1.8 mmol) followed by osmium tetroxide (4 wt % in water, 0.36 mL, 0.047 mmol). The reaction mixture was stirred for about 15 h and then DCM (20 mL) and water (10 mL) were added to the reaction mixture. The organic layer was separated, concd in vacuo, and purified by chromatography on silica gel eluting with 10-50% MeCN in DCM, to provide N-(4-(3-(2,3-dihydroxypropyl)-6-tosyl-6H-imidazo[1,5-a]pyrrolo[2,3-e]pyrazin-1-yl)bicyclo[2.2.2]octan-1-yl)cyclopropanesulfonamide (0.009 g, 3%): LC/MS (Table 1, Method a) $R_t$=1.90 min; MS m/z: 612 $(M-H)^-$.

Preparation #18: 2-hydrazinyl-6-methyl-5-tosyl-5H-pyrrolo[2,3-b]pyrazine

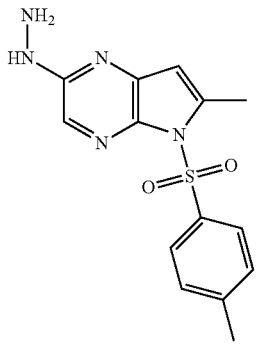

Step A: 5-bromo-3-(prop-1-ynyl)pyrazin-2-amine

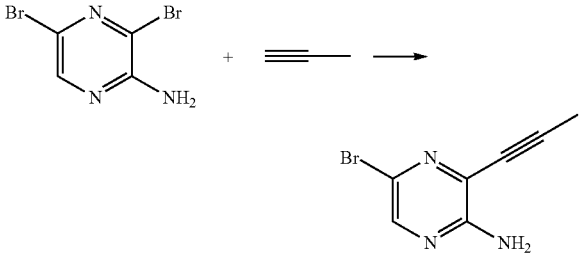

To a solution of 3,5-dibromopyrazin-2-amine (10.0 g, 39.5 mmol) in THF (200 mL) was added copper (I) iodide (0.377 g, 1.98 mmol), bis(triphenylphosphine)palladium (II) dichloride (1.39 g, 1.98 mmol) and TEA (16.5 mL, 119 mmol). The reaction mixture was cooled to about 0° C. and degassed with Ar. The reaction mixture was stirred for about 5 min and then the reaction mixture was sparged with propyne and a propyne atmosphere was maintained via balloon. The reaction mixture was stirred for about 30 min at about 0° C. and then was allowed to warm to ambient temperature. The reaction mixture was stirred for about 2 h and then EtOAc (100 mL) and water (100 mL) were added to the reaction mixture. The organic layer was separated, dried over anhydrous $Na_2SO_4$, filtered, and concd in vacuo. The crude mixture was purified by chromatography on silica gel (120 g) eluting with 10-60% EtOAc in DCM (dry loaded) to provide 5-bromo-3-(prop-1-ynyl)pyrazin-2-amine (7.05 g, 84%) as a yellow solid: LC/MS (Table 1, Method a) $R_t$=1.79 min; MS m/z: 212, 214 (1:1) $(M+H)^+$.

Step B: 2-bromo-6-methyl-5-tosyl-5H-pyrrolo[2,3-b]pyrazine

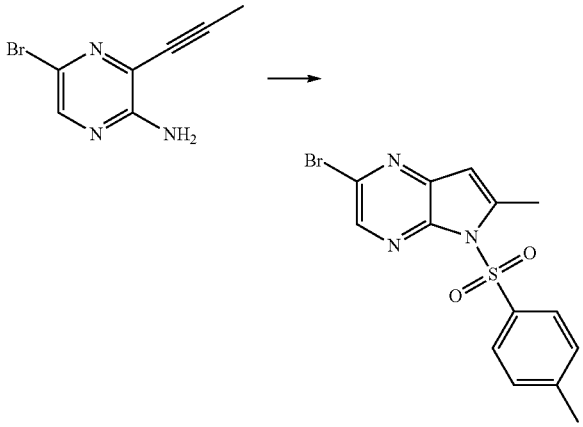

To a slurry of NaH (60% dispersion in mineral oil, 2.00 g, 49.9 mmol) in NMP (100 mL) was slowly added a solution of 5-bromo-3-(prop-1-ynyl)pyrazin-2-amine (7.05 g, 33.2 mmol) in NMP (20 mL). The reaction mixture was stirred at ambient temperature for about 20 min and then a solution of p-toluenesulfonyl chloride (6.97 g, 36.6 mmol) in NMP (20 mL) was added. The reaction mixture was stirred at ambient temperature for about 20 h and then aqueous HCl (1 N, 100 mL) was added to the reaction mixture. The resulting solids were collected by filtration. The brown solid was triturated with DCM/EtOAc (1:1, 30 mL) and collected by filtration to provide 2-bromo-6-methyl-5-tosyl-5H-pyrrolo[2,3-b]pyrazine (9.0 g, 74%) as a brown solid: LC/MS (Table 1, Method a) $R_t$=2.68 min; MS m/z: 366, 368 (1:1) $(M+H)^+$.

Step C: tert-butyl 2-(6-methyl-5-tosyl-5H-pyrrolo[2,3-b]pyrazin-2-yl)hydrazinecarboxylate

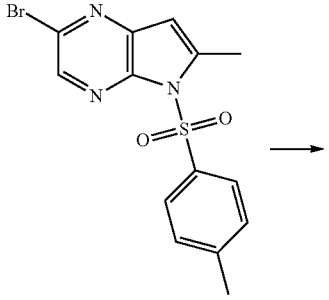

-continued

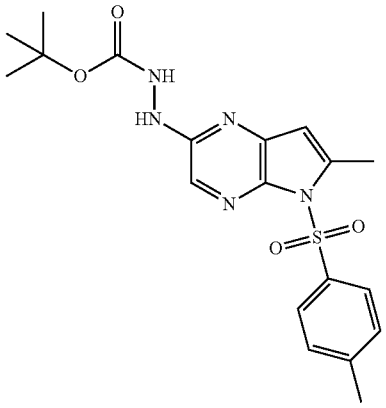

Tris(dibenzylideneacetone)dipalladium(0) (0.250 g, 0.273 mmol) and 2-di-tert-butylphosphino-2',4',6'-triisopropylbiphenyl (0.232 g, 0.546 mmol) were combined in 1,4-dioxane (15 mL). The flask was evacuated with some bubbling of solvent and then carefully refilled with nitrogen (3 times). Nitrogen was then bubbled directly into the reaction mixture. The mixture was then heated at about 80° C. for about 10 min and then removed from the heating source. 2-Bromo-6-methyl-5-tosyl-5H-pyrrolo[2,3-b]pyrazine (1.0 g, 2.73 mmol), tert-butyl hydrazinecarboxylate (0.541 g, 4.10 mmol) and NaOt-Bu (0.501 mL, 4.10 mmol) were added and the reaction was heated at about 80° C. for about 1 h. The reaction was cooled to ambient temperature and the solvents removed under reduced pressure. The black residue was then taken up in EtOAc (50 mL) and filtered. The filtrate was washed with saturated aqueous $NH_4Cl$ (50 mL), EDTA (1.0 M aqueous, 50 mL) and saturated aqueous $NaHCO_3$ (50 mL). The solution was dried over anhydrous $Na_2SO_4$, filtered, and concd under reduced pressure. The material was purified by chromatography on silica gel (80 g) eluting with 25-100% EtOAc in heptane to provide tert-butyl 2-(6-methyl-5-tosyl-5H-pyrrolo[2,3-b]pyrazin-2-yl) hydrazinecarboxylate (0.160 g, 14%) as a brown oil: LCMS (Table 1, Method a) $R_t$=2.51 min; MS m/z: 418 $(M+H)^+$.

Step D: 2-hydrazinyl-6-methyl-5-tosyl-5H-pyrrolo[2,3-b]pyrazine

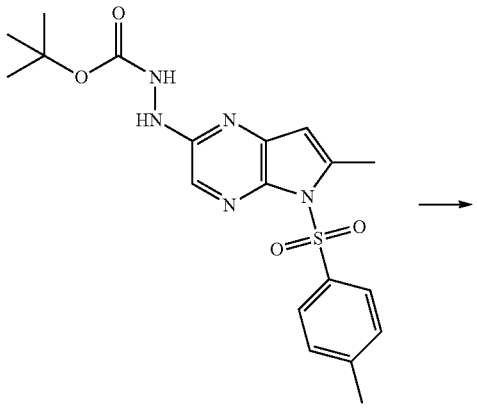

-continued

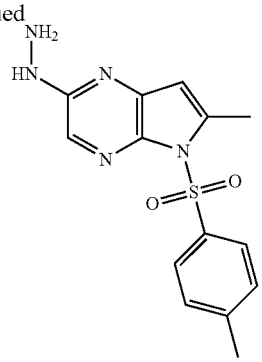

tert-Butyl 2-(6-methyl-5-tosyl-5H-pyrrolo[2,3-b]pyrazin-2-yl)hydrazine carboxylate (0.16 g, 0.38 mmol) was stirred in 1,4-dioxane (1.9 mL) in a sealed vial to give a brown solution. HCl (4 M in 1,4-dioxane, 0.958 mL, 3.83 mmol) was added and the reaction stirred at ambient temperature for about 20 h. The solvents were removed under reduced pressure. The residue was partitioned between saturated aqueous $NaHCO_3$ (10 mL) and EtOAc (10 mL). The layers were separated and the aqueous layer was extracted with EtOAc (2×10 mL). The combined organic extracts were washed with brine (20 mL), dried over anhydrous $Na_2SO_4$, filtered, and concd in vacuo to provide 2-hydrazinyl-6-methyl-5-tosyl-5H-pyrrolo[2,3-b]pyrazine (0.089 g, 73%): LC/MS (Table 1, Method a) $R_t$=1.92 min; MS m/z: 318 $(M+H)^+$.

Preparation #19

Preparation #19.1: (1S,3R,4S)-3-methyl-4-(6H-pyrrolo[2,3-e][1,2,4]triazolo[4,3-a]pyrazin-1-yl)cyclopentanamine Preparation #19.2: (1S,3R,4S)-3-methyl-4-(6-tosyl-6H-pyrrolo[2,3-e][1,2,4]triazolo[4,3-a]pyrazin-1-yl) cyclopentanamine

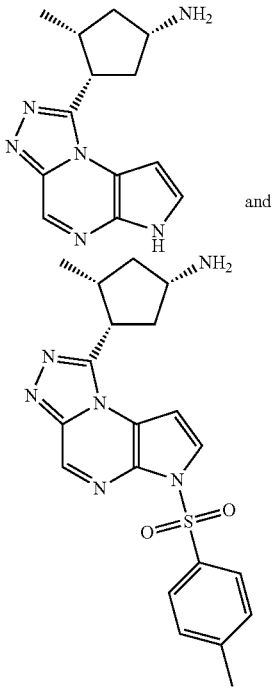

and

To a mixture of N-((1S,3R,4S)-3-methyl-4-(6-tosyl-6H-pyrrolo[2,3-e][1,2,4]triazolo[4,3-a]pyrazin-1-yl)cyclopentyl)acetamide (1.52 g, 3.36 mmol, prepared using Y from Example #7, step H and Pd/C, G, AA [Table 2, Method 3, $R_t$=6.1 min, or =ND], Z with NaOH, A with Example #1 Step D, HATU, and TEA, and B with TEA) and 1,4-dioxane (25 mL) was added aqueous HCl (6 N, 25 mL, 150 mmol). The reaction was heated at about 100° C. for about 14 h and then was cooled to ambient temperature and concd under reduced pressure. To the resulting brown residue was added MeOH (30 mL) and the solution was concd under reduced pressure. To the resulting residue was added MeOH (5 mL) followed by slow addition of $Et_2O$ (20 mL). Initially a cloudy solution formed and then a dark oil/gum formed and the mixture was concd under reduced pressure. To the resulting brown residue was added MeOH (30 mL), (1S,3R,4S)-3-methyl-4-(6-tosyl-6H-pyrrolo[2,3-e][1,2,4]triazolo[4,3-a]pyrazin-1-yl)cyclopentan-amine (1.35 g, 2.50 mmol, UV purity 75%) from a separate reaction, and silica gel (7 g). The mixture was concd under reduced pressure and purified by silica gel chromatography eluting with a gradient of 0-100% (DCM/[2 M $NH_3$ in MeOH] (9:1)) in DCM, the column was further flushed with MeOH then MeOH/aqueous $NH_4OH$ (9:1), to give (1S,3R,4S)-3-methyl-4-(6H-pyrrolo[2,3-e][1,2,4]triazolo[4,3-a]pyrazin-1-yl)cyclopentan-amine [Preparation #19.1] (0.092 g, 5%) as a dark brown solid: LC/MS (Table 1, Method a) $R_t$=1.35 min; MS m/z: 257 $(M+H)^+$ and 2.9 g of brown residue that was partitioned between DCM and saturated aqueous $NaHCO_3$ (50 mL each). The layers were separated and the aqueous layer was extracted with additional DCM (2×50 mL). The combined organic layers were washed with brine, dried over anhydrous MgSO4, filtered, and concd under reduced pressure to give (1S,3R,4S)-3-methyl-4-(6-tosyl-6H-pyrrolo[2,3-e][1,2,4] triazolo[4,3-a]pyrazin-1-yl)cyclopentanamine [Preparation #19.2](1.94 g, 78%) as a taupe foam: LC/MS (Table 1, Method a) $R_t$=1.80 min; MS m/z: 411 $(M+H)^+$.

Preparation #20: 3-ethyl-4-(6H-pyrrolo[2,3-e][1,2,4] triazolo[4,3-a]pyrazin-1-yl)cyclopentyl benzoate

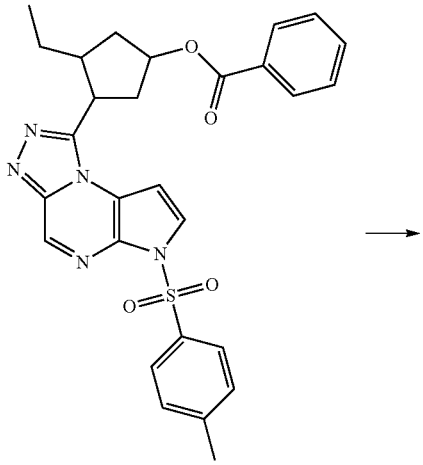

-continued

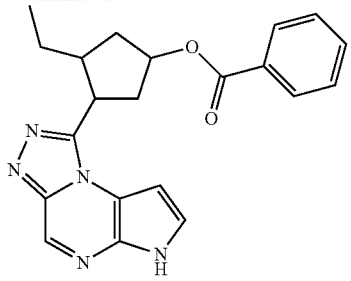

To a mixture of 3-ethyl-4-(6-tosyl-6H-pyrrolo[2,3-e][1,2,4]triazolo[4,3-a]pyrazin-1-yl)cyclopentyl benzoate (5.00 g, 7.84 mmol, prepared from Example #4 Step J using II with benzoic acid, and B) in MeOH (16 mL) was added a solution of potassium cyanide (0.74 mL, 17.2 mmol) in MeOH (16 mL). The reaction was stirred at ambient temperature for about 16 h. The reaction mixture was concd under reduced pressure to afford a residue. The residue was partitioned between water (20 mL) and DCM (20 mL). The layers were separated and the aqueous layer was extracted with DCM (3×10 mL). The extract was then washed with saturated aqueous $NaHCO_3$, dried over anhydrous $MgSO_4$, filtered, and concd under reduced pressure to afford a crude oil. The crude material was purified by silica gel chromatography eluting with a gradient of 0-10% MeOH in DCM to 3-ethyl-4-(6H-pyrrolo[2,3-e][1,2,4]triazolo[4,3-a]pyrazin-1-yl)cyclopentyl benzoate (2.30 g, 78%) as a red tinted solid. LC/MS (Table 1, Method a) $R_t$=2.08 min; MS m/z: 376 $(M+H)^+$.

Preparation #21: tert-butyl 4-(aminomethyl)-2-ethylcyclopentanecarboxylate

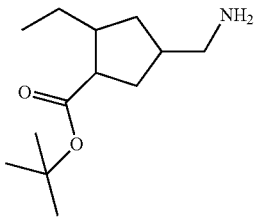

Step A: tert-butyl 2-ethyl-4-(hydroxymethyl)cyclopentanecarboxylate

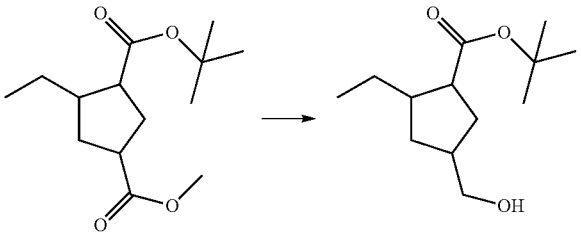

A solution of 3-tert-butyl 1-methyl 4-ethylcyclopentane-1,3-dicarboxylate (3.88 g, 15.1 mmol, Preparation #11, Step B) in $Et_2O$ (150 mL) was cooled to about −40° C. LAH (2 N in THF, 8.32 mL, 16.6 mmol) was added dropwise. The reaction mixture was stirred at about −40° C. for about 1 hour. The reaction mixture was partitioned between saturated aqueous $NaHCO_3$ (50 mL) and EtOAc (3×50 mL). The combined organic extracts were concd under reduced pressure. The crude material was purified by silica gel chromatography eluting with a gradient of 0-100% EtOAc/heptane to give tert-butyl 2-ethyl-4-(hydroxymethyl)cyclopentanecarboxylate (1.00 g, 29%) as a brown oil: LC/MS (Table 1, Method a) $R_t$=2.37 min; MS m/z: 229 $(M+H)^+$.

Step B: tert-butyl 2-ethyl-4-((methylsulfonyloxy)methyl)cyclopentanecarboxylate

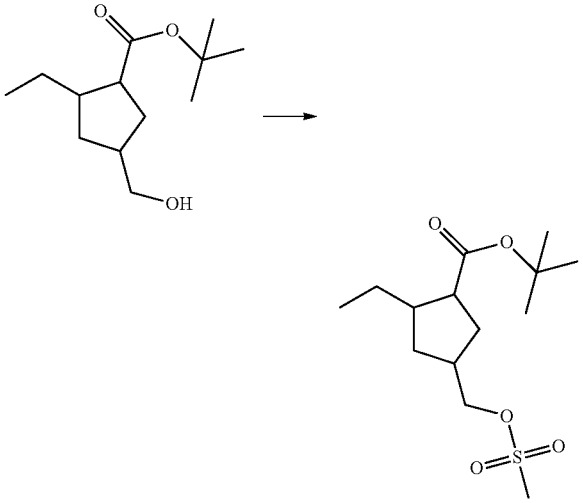

To a solution of tert-butyl 2-ethyl-4-(hydroxymethyl)cyclopentanecarboxylate (0.220 g, 0.964 mmol) in DCM (5 mL) was added TEA (0.16 mL, 1.15 mmol) and methanesulfonyl chloride (0.083 mL, 1.06 mmol) at about 0° C. The reaction mixture was allowed to warm to about 25° C. and stirred at about 25° C. for about 16 h. The reaction mixture was partitioned between water (20 mL) and DCM (20 mL). The aqueous solution was washed with DCM (2×20 mL). The combined organic extracts were dried over anhydrous $MgSO_4$, filtered, and concd under reduced pressure to give tert-butyl 2-ethyl-4-((methylsulfonyloxy)methyl)cyclopentanecarboxylate (0.295 g, 100%): LC/MS (Table 1, Method b) $R_t$=2.55 min; MS m/z: 307 $(M+H)^+$.

Step C: tert-butyl 4-(aminomethyl)-2-ethylcyclopentanecarboxylate

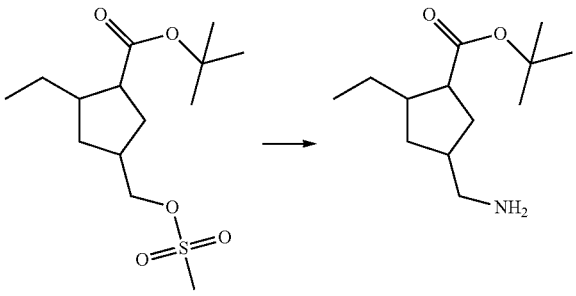

To a solution of tert-butyl 2-ethyl-4-((methylsulfonyloxy)methyl)cyclopentanecarboxylate (0.295 g, 0.964 mmol) in DMF (5 mL) was added sodium azide (0.313 g, 4.82 mmol). The reaction was heated at about 50° C. for about 16 h and then cooled to about 15-20° C. Water (40 mL) was added to the reaction mixture. The aqueous solution was extracted with DCM (3×30 mL). The combined organic extracts were dried over anhydrous $MgSO_4$, filtered, and concd under reduced pressure to give a dark brown oil. The brown oil was dissolved in THF (6.5 mL) and water (3.5 mL). Triphenylphosphine (0.316 g, 1.205 mmol) was added. The reaction mixture was stirred at about 25° C. for about 15 h. The organic solvent was removed under reduced pressure and the residue partitioned between saturated aqueous $NaHCO_3$ (20 mL) and DCM (20 mL). The organic phase was concd under reduced pressure. The resulting residue was purified using silica gel chromatography eluting with a gradient of 0-20% (20% (7 N ammonium in MeOH) in MeOH)) in DCM to give tert-butyl 4-(aminomethyl)-2-ethylcyclopentanecarboxylate (0.102 g, 46%) as a brown oil: LC/MS (Table 1, Method b) $R_t$=1.72 min; MS m/z: 228 $(M+H)^+$.

Preparation #22: ethyl 2-ethyl-4-formylcyclopentanecarboxylate

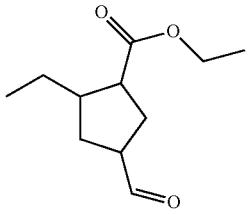

Step A: 2-ethyl-4-(hydroxymethyl)cyclopentanecarboxylic acid

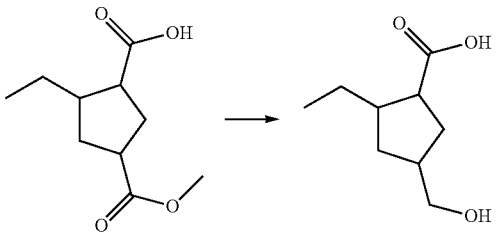

To a solution of 2-ethyl-4-(methoxycarbonyl)cyclopentanecarboxylic acid (8.34 g, 41.7 mmol, Preparation #11, Step A) in THF (208 mL) was added $LiBH_4$ (0.907 g, 41.7 mmol) at about −20° C. The reaction mixture was stirred at about −20° C. for about 1 h. The reaction mixture was allowed to warm to about 25° C. then was stirred at about 25° C. for about 16 h. Additional $LiBH_4$ (0.907 g, 41.7 mmol) was added. The reaction mixture was stirred at about 25° C. for about 4 h. Water (10 mL) was added slowly to quench the reaction. The solid was removed by vacuum filtration. The filtrate was concd under reduced pressure. The resulting residue was partitioned between water (50 mL) and DCM (3×50 mL). The combined organic extracts were dried over anhydrous $MgSO_4$, filtered, and concd under reduced pressure to give 2-ethyl-4-(hydroxymethyl)cyclopentanecarboxylic acid (7.29 g, 100%): LC/MS (Table 1, Method n) $R_t$=0.44 min; MS m/z: 173 $(M-H)^+$.

Step B: ethyl 2-ethyl-4-(hydroxymethyl)cyclopentanecarboxylate

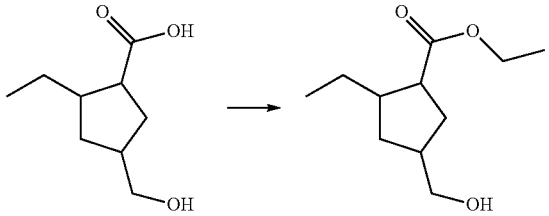

HCl gas was bubbled through a solution of 2-ethyl-4-(hydroxymethyl)cyclopentanecarboxylic acid (7.29 g, 42.3 mmol) in EtOH (60 mL) at about 25° C. for about 10 min. The reaction mixture was stirred at about 25° C. for about 72 h. The solvent was removed under reduced pressure. The crude residue was partitioned between water (30 mL) and DCM (3×30 mL). The combined organic extracts were concd under reduced pressure. The crude material was purified by silica gel chromatography eluting with a gradient of 0-100% EtOAc/heptane to give ethyl 2-ethyl-4-(hydroxymethyl)cyclopentanecarboxylate (4.89 g, 58%) as a yellow oil: $^1H$ NMR ($CDCl_3$) δ 4.23-4.02 (m, 2H), 3.74-3.47 (m, 2H), 2.96-2.83 (m, 1H), 2.31-2.17 (m, 1H), 2.15-1.98 (m, 2H), 1.97-1.84 (m, 1H), 1.79-1.66 (m, 1H), 1.65-1.50 (m, 1H), 1.49-1.37 (m, 1H), 1.30-1.21 (m, 5H), 1.04-0.82 (m, 3H).

Step C: ethyl 2-ethyl-4-formylcyclopentanecarboxylate

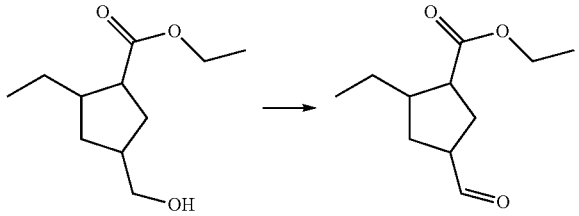

To a solution of ethyl 2-ethyl-4-(hydroxymethyl)cyclopentanecarboxylate (4.84 g, 24.2 mmol) in DCM (100 mL) was added pyridinium chlorochromate (10.42 g, 48.3 mmol). The reaction mixture was stirred at about 25° C. for about 3 h. Silica gel (1 g) was added. The mixture was stirred at about 25° C. for about 30 min. The solid was removed by vacuum filtration, while rinsing with DCM (100 mL). The filtrate was concd under reduced pressure. The resulting residue was purified using silica gel chromatography eluting with a gradient of 0-40% EtOAc/Heptane to give ethyl 2-ethyl-4-formylcyclopentanecarboxylate (3.03 g, 63%) as a clear oil: $^1H$ NMR (DMSO-$d_6$) δ 9.66-9.47 (m, 1H), 4.12-3.94 (m, 2H), 2.94-2.73 (m, 2H), 2.19-1.90 (m, 4H), 1.55-1.65 (m, 1H), 1.37-1.23 (m, 1H), 1.23-1.06 (m, 4H), 0.96-0.82 (m, 3H).

Preparation #23: N-((1S,3R,4S)-3-ethyl-4-(8-methyl-6-((2-(trimethylsilyl)ethoxy)methyl)-6H-pyrrolo[2,3-e][1,2,4]triazolo[4,3-a]pyrazin-1-yl)cyclopentyl)-N-((2-(trimethylsilyl)ethoxy)methyl) cyclopropanesulfonamide

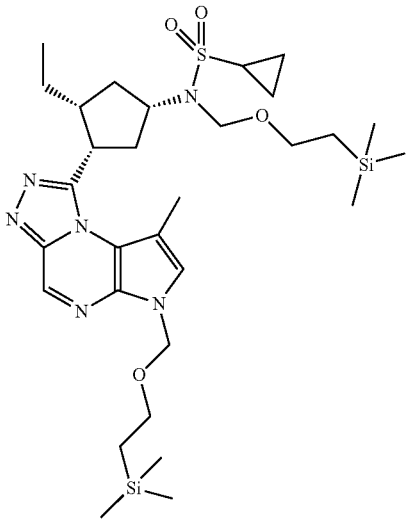

Cesium carbonate (0.274 g, 0.841 mmol), tricyclohexylphosphine (20 wt % solution in toluene, 0.094 g, 0.067 mmol), $Pd_2(dba)_3$ (0.039 g, 0.042 mmol) and trimethylborate (0.069 g, 0.547 mmol) were added to a solution of N-((1S,3R,4S)-3-ethyl-4-(8-iodo-6-((2-(trimethylsilyl) ethoxy)methyl)-6H-pyrrolo[2,3-e][1,2,4]triazolo[4,3-a] pyrazin-1-yl)cyclopentyl)-N-((2-(trimethylsilyl)ethoxy) methyl)cyclopropanesulfonamide (0.32 g, 0.421 mmol, prepared using KK from Preparation #GGG.1) in 1,4-dioxane (8 mL). The mixture was degassed and heated at about 85° C. for about 2 h. The solvent was removed and the residue was partitioned between EtOAc and water (20 mL each). The organic phase was washed with brine (15 mL), dried over anhydrous $MgSO_4$, filtered and concd. The resulting mixture was purified by silica gel flash chromatography (40 to 100% of EtOAc in heptane) to yield N-((1S,3R,4S)-3-ethyl-4-(8-methyl-6-((2-(trimethylsilyl)ethoxy)methyl)-6H-pyrrolo[2,3-e][1,2,4]triazolo[4,3-a]pyrazin-1-yl)cyclopentyl)-N-((2-(trimethylsilyl)ethoxy)methyl) cyclopropanesulfonamide (0.21 g, 77%) as a yellow amorphous solid. LC/MS (Table 1, Method a) $R_t$=3.39 min; MS m/z: 650 $(M+H)^+$.

Preparation #24: diethyl 2-(4-(cyclopropanesulfonamido)bicyclo[2.2.2]octan-1-yl)-2-oxoethylphosphonate

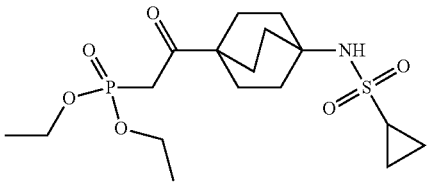

Step A: methyl 4-(cyclopropanesulfonamido)bicyclo[2.2.2]octane-1-carboxylate

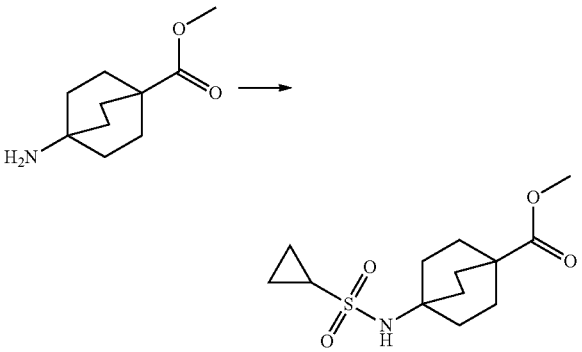

To a solution of methyl 4-aminobicyclo[2.2.2]octane-1-carboxylate (500 mg, 2.73 mmol) (Yeh, V. S. C.; Kurukulasuriya, R.; Madar, D.; Patel, J. R.; Fung, S.; Monzon, K.; Chiou, W.; Wang, J.; Jacobson, P.; Sham, H. L.; Link, J. T. Bioorg. and Med. Chem. Let, 2006, vol. 16, #20 p. 5408-5413) in DCM (10 mL) at rt was added TEA (0.76 mL, 5.46 mmol) and DMAP (50 mg, 0.41 mmol). Cyclopropanesulfonyl chloride (764 mg, 5.46 mmol, Matrix) was added dropwise by syringe. The reaction mixture was stirred for about 15 h at rt. The mixture was washed with water (10 mL), and the aqueous layer was extracted with DCM (2×10 mL), the organic layers were combined and dried over anhydrous $Na_2SO_4$, filtered and concd in vacuo. The crude materials was purified by silica gel chromatography eluting with a gradient of 20-35% EtOAc in hexanes to afford methyl 4-(cyclopropanesulfonamido)bicyclo[2.2.2]octane-1-carboxylate (410 mg, 52% yield). LC/MS (Table 1, Method p) $R_t$=1.68 min; MS m/z: 288 $(M+H)^+$.

Step B: diethyl (4-(cyclopropanesulfonamido)bicyclo[2.2.2]octan-1-yl)methylphosphonate

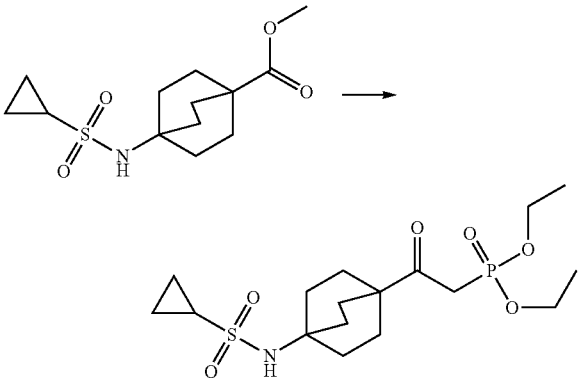

A solution of diethyl methylphosphonate (1.27 g, 8.36 mmol) was dissolved in THF (20 mL) and cooled to about −78° C. in a dry ice-acetone bath under nitrogen. Then n-BuLi (9.77 mmol, 3.9 mL, 2.5M in hexane) was added dropwise over about 5 min. The reaction mixture was stirred for about 3 h, keeping the temperature below about −70° C. Then a solution of methyl 4-(cyclopropanesulfonamido)

bicyclo[2.2.2]octane-1-carboxylate (800 mg, 2.79 mmol) in THF (10 mL) was added, keeping the temperature at about −78° C. The solution was stirred for about 15 h, allowing the temperature to rise slowly to rt. To the reaction mixture was added saturated aqueous $NH_4Cl$ (30 mL) and extracted with EtOAc (3×30 mL). The organic layers were combined and washed with brine, dried over anhydrous $Na_2SO_4$ and concd to provide diethyl(4-(cyclopropanesulfonamido)bicyclo[2.2.2]octan-1-yl)methylphosphonate (1.30 g, 100% yield). The crude product was used in next step without further purification. LC/MS (Table 1, Method p) $R_t$=1.62 min; MS m/z: 408 $(M+H)^+$.

Preparation #25: 3-ethyl-4-(6-tosyl-6H-pyrrolo[2,3-e][1,2,4]triazolo[4,3-a]pyrazin-1-yl)cyclopentanone

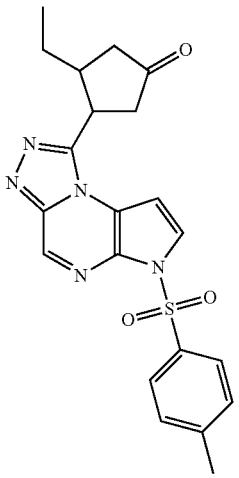

Step A: ethyl 2-ethyl-4-oxocyclopentanecarboxylate

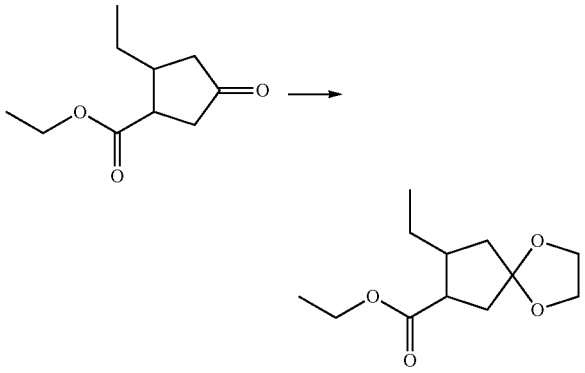

A round bottom flask was charged with ethyl 2-ethyl-4-oxocyclopentanecarboxylate (1.5 g, 8.1 mmol, Example #22, Step B) in DCM (22 mL). To the flask were added ethylene glycol (0.91 mL, 16 mmol), triethylorthoformate (2.0 mL, 12 mmol), and p-toluenesulfonic acid monohydrate (0.31 g, 1.6 mmol). The reaction mixture was stirred at rt for about 24 h. The solution was concd under reduced pressure to give a brown oil that was dissolved in EtOAc and purified by flash silica gel chromatography (Silicycle 25 g column) eluting with a gradient of 0-50% EtOAc in heptane. The product containing fractions were combined and concd to dryness under reduced pressure to give ethyl 2-ethyl-4-oxocyclopentanecarboxylate as a light yellow oil (1.6 g, 83%): LC/MS (Table 1, Method c) MS m/z 229 $(M+H)^+$; $^1H$ NMR (CDCl) δ 4.14 (q, 2H), 3.90 (m, 4H), 2.99 (q, 1H), 2.32-2.27 (m, 1H), 2.26-2.11 (m, 1H), 2.05-1.99 (m, 1H), 1.96-1.91 (m, 1H), 1.83-1.78 (m, 1H), 1.46-1.39 (m, 1H), 1.31-1.24 (m, 1H), 1.26 (t, 3H), 0.90 (t, 3H).

Step B: 8-ethyl-1,4-dioxaspiro[4.4]nonane-7-carboxylic acid

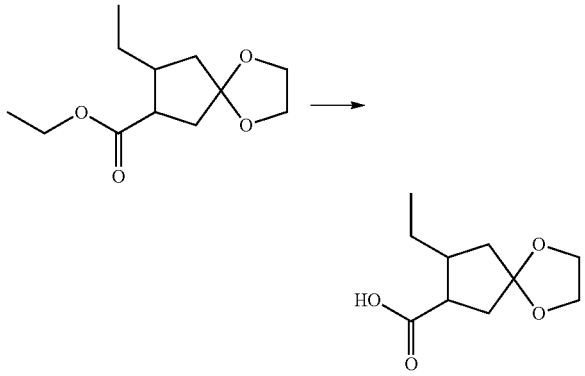

A round bottom flask was charged with ethyl 8-ethyl-1,4-dioxaspiro[4.4]nonane-7-carboxylate (0.32 g, 1.4 mmol) and aqueous 1 N sodium hydroxide (14.0 mL, 14.0 mmol). The solution was stirred overnight at rt. To the solution was added DCM (30 mL) followed by the addition of 20% aqueous citric acid (about 20 mL) to reach pH of about 2. The layers were separated and the aqueous solution was extracted with DCM (2×30 mL) and DCM/EtOAc (1:1, 30 mL). The combined extracts were dried over anhydrous $MgSO_4$, filtered, and concd under reduced pressure to give 8-ethyl-1,4-dioxaspiro[4.4]nonane-7-carboxylic acid as a clear, colorless oil (0.27 g, 96%): LC/MS (Table 1, Method c) $R_t$=1.20 min; MS m/z: 201 $(M+H)^+$.

Step C: 8-ethyl-N'-(5-tosyl-5H-pyrrolo[2,3-b]pyrazin-2-yl)-1,4-dioxaspiro[4.4]nonane-7-carbohydrazide

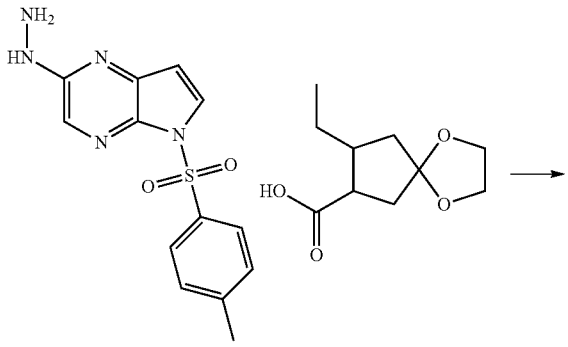

-continued

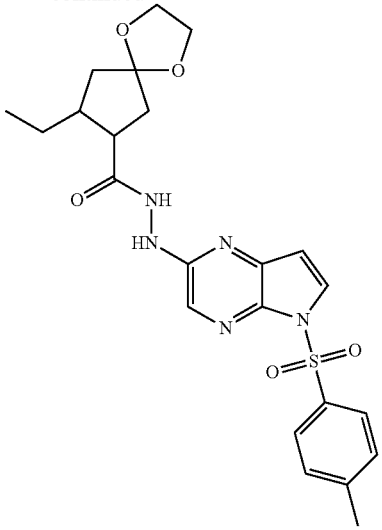

A 50 mL round bottom flask was charged with 2-hydrazinyl-5-tosyl-5H-pyrrolo[2,3-b]pyrazine (0.350 g, 1.16 mmol, Example #1, Step D), 8-ethyl-1,4-dioxaspiro[4.4]nonane-7-carboxylic acid (0.250 g, 1.25 mmol), and DCM (6.0 mL). To the reaction mixture was added HATU (0.483 g, 1.27 mmol) and TEA (0.64 mL, 4.6 mmol) and the resulting yellow suspension was stirred at rt for about 3 h. To the reaction solution was added DCM (25 mL) and the solution was washed with water and brine (20 mL each). The organic layer was dried over anhydrous $MgSO_4$, filtered, and concd under reduced pressure to give a brown oil. The crude product was purified by flash silica gel chromatography (25 g Silicycle column) eluting with a gradient of: 0-10% MeOH in DCM over 25 min. The product containing fractions were concd under reduced pressure to give 8-ethyl-N'-(5-tosyl-5H-pyrrolo[2,3-b]pyrazin-2-yl)-1,4-dioxaspiro[4.4]nonane-7-carbohydrazide as a foam (0.50 g, 89%): LC/MS (Table 1, Method c) $R_t$=1.49 min; MS m/z: 486 $(M+H)^+$.

Step D: 1-(8-ethyl-1,4-dioxaspiro[4.4]nonan-7-yl)-6-tosyl-6H-pyrrolo[2,3-e][1,2,4]triazolo[4,3-a]pyrazine

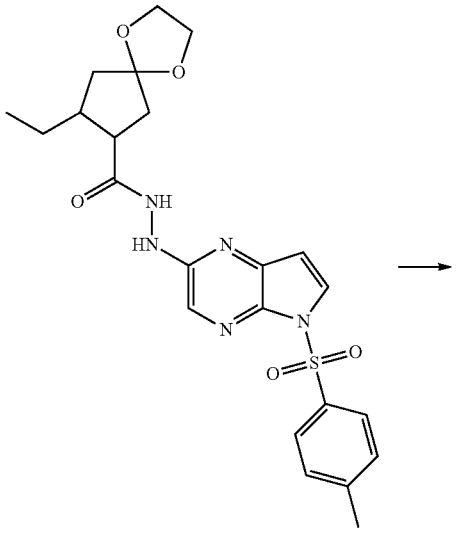

-continued

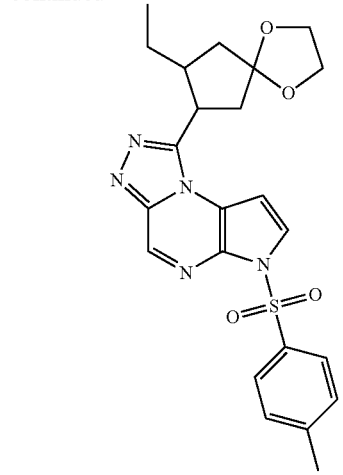

A round bottom flask was charged with 8-ethyl-N-(5-tosyl-5H-pyrrolo[2,3-b]pyrazin-2-yl)-1,4-dioxaspiro[4.4]nonane-7-carbohydrazide (4.90 g, 10.1 mmol) and 1,4-dioxane (50 mL). To the flask was added DIEA (8.81 mL, 50.5 mmol) followed by the addition of thionyl chloride (0.770 mL, 10.6 mmol). The mixture was heated to about 75° C. for about 90 min. Additional thionyl chloride (0.074 mL, 1.0 mmol) was added and heating was continued for about 1 h. The reaction was cooled to rt and stirred overnight. The solution was diluted with DCM (75 mL) and washed with water (50 mL). The layers were separated and the organic layer was dried over anhydrous $MgSO_4$, filtered, and concd under reduced pressure to give a dark brown oil. The crude product was purified via flash silica gel chromatography eluting with a gradient of 0-60% acetone in heptane with a hold at 60% acetone in heptane. The product containing fractions were combined and concd to give material that was loaded onto a second column (Silicycle, 40 g column), eluting with a gradient of 0-60% acetone in heptane. The product containing fractions were combined and concd under reduced pressure to give 1-(8-ethyl-1,4-dioxaspiro[4.4]nonan-7-yl)-6-tosyl-6H-pyrrolo[2,3-e][1,2,4]triazolo[4,3-a]pyrazine as a tan powder (3.0 g, 64%): LC/MS (Table 1, Method c) $R_t$=1.44 min; MS m/z: 468 $(M+H)^+$.

Step E: 3-ethyl-4-(6-tosyl-6H-pyrrolo[2,3-e][1,2,4]triazolo[4,3-a]pyrazin-1-yl)cyclopentanone

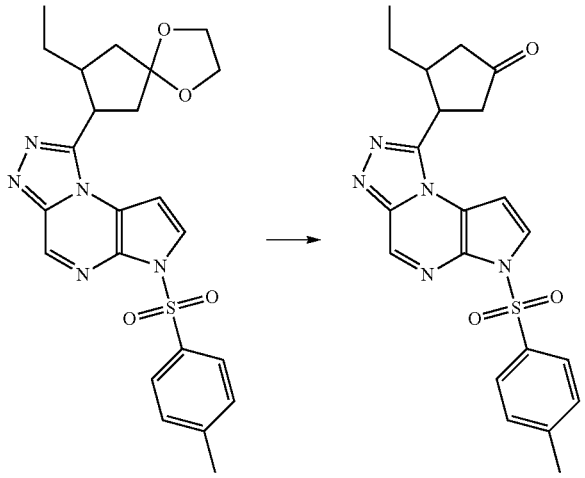

A round bottom flask was charged with 1-((7S,8R)-8-ethyl-1,4-dioxaspiro[4.4]nonan-7-yl)-6-tosyl-6H-pyrrolo[2,3-e][1,2,4]triazolo[4,3-a]pyrazine (3.56 g, 7.61 mmol) and THF (20 mL). To the solution was added aqueous HCl (6N, 3.81 mL, 22.8 mmol) and the mixture was stirred at rt for about 2 h. The solvent was removed under reduced pressure and DCM (75 mL) and water (50 mL) were added. The layers were separated and the organic solution was dried over anhydrous $MgSO_4$, filtered, and concd under reduced pressure to give 3-ethyl-4-(6-tosyl-6H-pyrrolo[2,3-e][1,2,4]triazolo[4,3-a]pyrazin-1-yl)cyclopentanone as a brown foam (2.99 g, 93%): LC/MS (Table 1, Method c) $R_t$=1.40 min; MS m/z: 424 $(M+H)^+$.

Preparation #26: 3,3-difluoro-1-(vinylsulfonyl)pyrrolidine

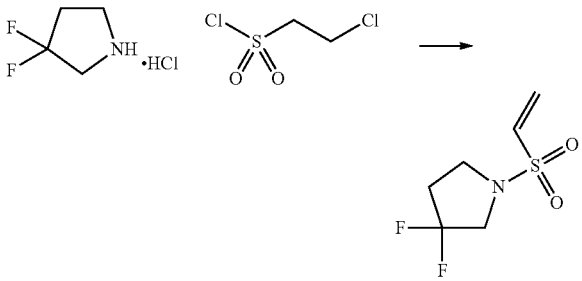

A solution of 3,3-difluoropyrrolidine hydrochloride (0.3 g, 2.1 mmol, Matrix) and DIEA (0.37 mL, 2.1 mmol) in MeCN (5 mL) was stirred at about 50° C. for about 30 min. The reaction was cooled to ambient temperature and concd under reduced pressure. The solid was dissolved in MeCN (2 mL) and a solution of 2-chloroethanesulfonyl chloride (0.22 mL, 2.1 mmol) in $Et_2O$ (3 mL) was added at about −78° C. and stirred for about 2 h. To the reaction mixture was added DIEA (0.6 mL, 3.4 mmol) and stirred for about 1 h. The reaction was warmed to ambient temperature and the solvent was removed under reduced pressure. The residue was partitioned between DCM (5 mL) and water (2×2 mL). The combined organic layers were dried over anhydrous $MgSO_4$, filtered and concd under reduced pressure to give crude 3,3-difluoro-1-(vinylsulfonyl)pyrrolidine (0.11 g, 27%) which was used without further purification: LC/MS (Table 1, Method b) $R_t$=2.04 min; MS m/z: 198 $(M+H)^+$.

Preparation #27: 4-chloro-5-nitro-1H-pyrrolo[2,3-b]pyridine

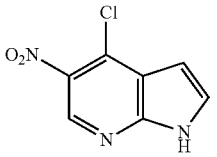

Step A: 4-chloro-3-iodo-5-nitropyridin-2-amine

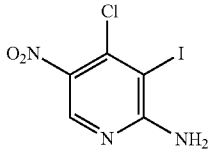

A solution of 4-chloro-3-iodopyridin-2-amine (0.25 g, 0.982 mmol, Boa Pharma) in concd $H_2SO_4$ (1.95 mL) was cooled to about 0° C. before the portion wise addition of potassium nitrate (0.21 g, 2.2 mmol) over 10 min. The reaction was stirred for about 4 h at about 0° C. The reaction mixture was slowly pipetted over a solution of ammonium hydroxide and crushed ice (10 mL) in an ice bath. The pH of the reaction was maintained above 9 by the incremental addition of ammonium hydroxide. The resulting precipitate was filtered and dried to afford 4-chloro-3-iodo-5-nitropyridin-2-amine (0.085 g, 29%) as a green-tinted solid LC/MS (Table 1, Method n) $R_t$=0.64 min; MS m/z: 298 $(M-H)^-$.

Step B: 4-chloro-5-nitro-3-((trimethylsilyl)ethynyl)pyridin-2-amine

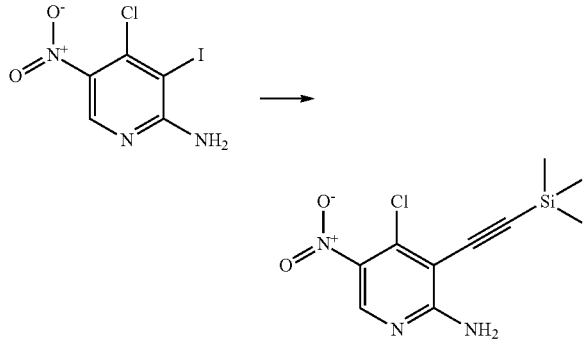

To a solution of 4-chloro-3-iodo-5-nitropyridin-2-amine (5.30 g, 17.7 mmol) in THF (90 mL) was added TEA (15.0 mL, 108 mmol). The reaction mixture was degassed and purged with nitrogen 3 times. Bis(triphenylphosphine)-palladium(II) dichloride (0.62 g, 0.88 mmol, Strem), copper(I) iodide (0.17 g, 0.89 mmol), and trimethylsilylacetylene (5.4 mL, 39 mmol) were added to the reaction mixture. The mixture was degassed and purged 3 times with nitrogen. The reaction was heated at about 60° C. for about 16 h. The reaction mixture was cooled to ambient temperature. The reaction mixture was filtered and washed with THF (200 mL). The filtrate was concd under reduced pressure. DCM (100 mL) was added to the residue and the precipitate that formed was filtered and collected to give 4-chloro-5-nitro-3-((trimethylsilyl)ethynyl)pyridin-2-amine (0.77 g). The remaining filtrate was concd under reduced pressure and the crude material was purified by flash chromatography on silica gel eluting with a gradient of 0-100% EtOAc in DCM. The purified material was combined with the 0.77 g of precipitate to afford 4-chloro-5-nitro-3-((trimethylsilyl)ethynyl)pyridin-2-amine (2.22 g, 47%) as a yellow solid: LC/MS (Table 1, Method c) $R_t$=1.62 min; MS m/z 268 $(M-H)^-$.

Step C: 4-chloro-3-ethynyl-5-nitropyridin-2-amine

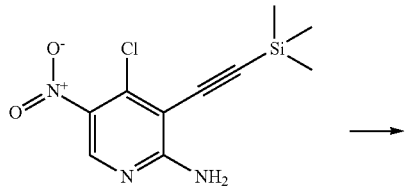

-continued

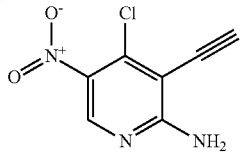

To a solution of 4-chloro-5-nitro-3-((trimethylsilyl)ethynyl)pyridin-2-amine (1.98 g, 7.34 mmol) in DMF (25 mL) was added potassium fluoride on alumina (40 wt %, 2.67 g, 18.35 mmol). The suspension was stirred at ambient temperature for about 1 h. Activated charcoal (0.3 g) was added and the suspension was filtered through Celite®, washing with DMF (150 mL). The solvent was removed under reduced pressure and the crude material was purified by silica gel chromatography eluting with a gradient of 0-10% MeOH in DCM to afford 4-chloro-3-ethynyl-5-nitropyridin-2-amine (1.03 g, 71%) as a yellow solid: LC/MS (Table 1, Method n) $R_t$=0.59 min; MS m/z: 196 $(M-H)^-$.

Step D: 4-chloro-5-nitro-1H-pyrrolo[2,3-b]pyridine

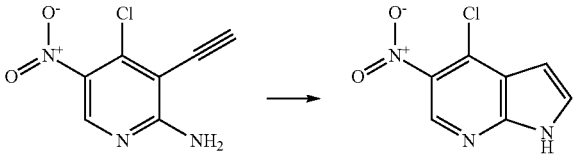

To a solution of 4-chloro-3-ethynyl-5-nitropyridin-2-amine (0.16 g, 0.81 mmol) in DMF (3 mL) was added chloro(1,5-cyclooctadiene) rhodium (I) dimer (0.02 g, 0.04 mmol) and tris(4-fluorophenyl)phosphine (0.128 g, 0.405 mmol). The reaction mixture was degassed by bubbling argon for 15 min. The reaction mixture was heated at about 80° C. for about 45 min. The reaction was cooled to ambient temperature and the solvent was removed under reduced pressure and the residue was suspended in ether (10 mL). The precipitate was collected by filtration and dried to give 4-chloro-5-nitro-1H-pyrrolo[2,3-b]pyridine (0.132 g, 83%, contains approximately 6% mol of DMF and approximately 3% mol of tris(4-fluorophenyl)phosphine) as a brown solid: LC/MS (Table 1, Method a) $R_t$=2.05 min; MS m/z 198 $(M+H)^+$.

Preparation #28*: N-((1S,3R,4S)-3-ethyl-4-(6-tosyl-6H-pyrrolo[2,3-e][1,2,4]triazolo[4,3-a]pyrazin-1-yl)cyclopentyl)-2-methylpropane-2-sulfonamide

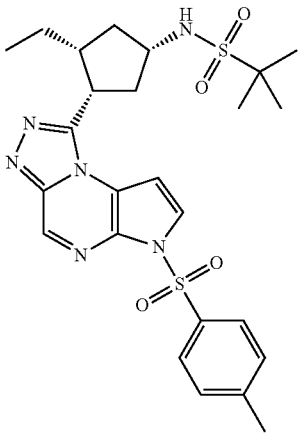

To a solution of (1S,3R,4S)-3-ethyl-4-(6-tosyl-6H-pyrrolo[2,3-e][1,2,4]triazolo[4,3-a]pyrazin-1-yl)cyclopentanamine (115 mg, 0.271 mmol, Preparation #BB.1*) in DCM (1.5 mL) was added DIEA (0.071 mL, 0.406 mmol) followed by 2-methylpropane-2-sulfinic chloride (0.037 mL, 0.298 mmol). After about 4 h the reaction mixture was diluted with EtOAc (10 mL) and aqueous saturated $NaHCO_3$ (10 mL). The organic layer was separated, dried over anhydrous $Na_2SO_4$, filtered and concd in vacuo. The crude residue was dissolved in DCM (1.5 mL) and a freshly prepared solution of m-chloroperbenzoic acid (0.271 mL, 0.271 mmol, 1M in DCM) was added. After about 2 h the reaction mixture was diluted with EtOAc (10 mL) and saturated aqueous $NaHCO_3$ (10 mL). The organic layer was separated, dried over anhydrous $Na_2SO_4$, filtered and concd in vacuo. The crude residue was purified by chromatography on silica gel eluting with EtOAc to provide N-((1S,3R,4S)-3-ethyl-4-(6-tosyl-6H-pyrrolo[2,3-e][1,2,4]triazolo[4,3-a]pyrazin-1-yl)cyclopentyl)-2-methylpropane-2-sulfonamide (95 mg, 64% yield) as an oil. LC/MS (Table 1, Method a) $R_t$=2.40 min; MS m/z: 545 $(M+H)^+$.

Preparation #29*: 3-((1S,3R,4S)-3-ethyl-4-(6-tosyl-6H-pyrrolo[2,3-e][1,2,4]triazolo[4,3-a]pyrazin-1-yl)cyclopentylamino)-4-methoxycyclobut-3-ene-1,2-dione

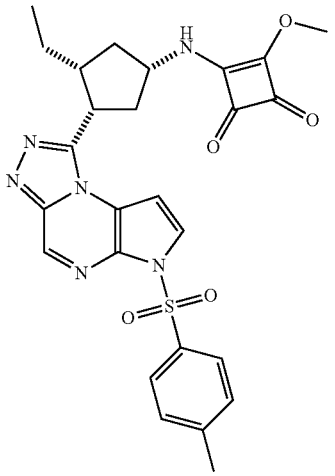

To a solution of (1S,3R,4S)-3-ethyl-4-(6-tosyl-6H-pyrrolo[2,3-e][1,2,4]triazolo[4,3-a]pyrazin-1-yl)cyclopentanamine (0.40 g, 0.942 mmol, Example #8 Step M) in MeOH (3 mL) was added 3,4-dimethoxycyclobut-3-ene-1,2-dione (0.14 g, 0.98 mmol) and DIEA (0.18 mL, 1.0 mmol). The reaction was stirred at rt for about 16.5 h. Then the solid from the reaction mixture was collected via vacuum filtration, while washing with cold MeOH (about 4° C., 10 mL), and dried in a vacuum oven at about 60° C. to give crude 3-((1S,3R,4S)-3-ethyl-4-(6-tosyl-6H-pyrrolo[2,3-e][1,2,4]triazolo[4,3-a]pyrazin-1-yl)cyclopentylamino)-4-methoxycyclobut-3-ene-1,2-dione (0.36 g, 73%, 90% purity): LC/MS (Table 1, Method a) $R_t$=2.13 min; MS m/z: 535 $(M+H)^+$.

Preparation #30: 3,3,3-trifluoro-1-(5-tosyl-5H-pyrrolo[2,3-b]pyrazin-2-yl)propan-1-amine hydrochloride

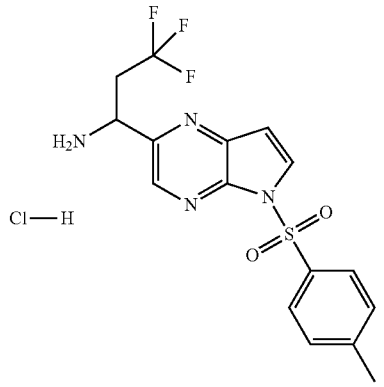

Step A: N-(diphenylmethylene)-1-(5-tosyl-5H-pyrrolo[2,3-b]pyrazin-2-yl)methanamine

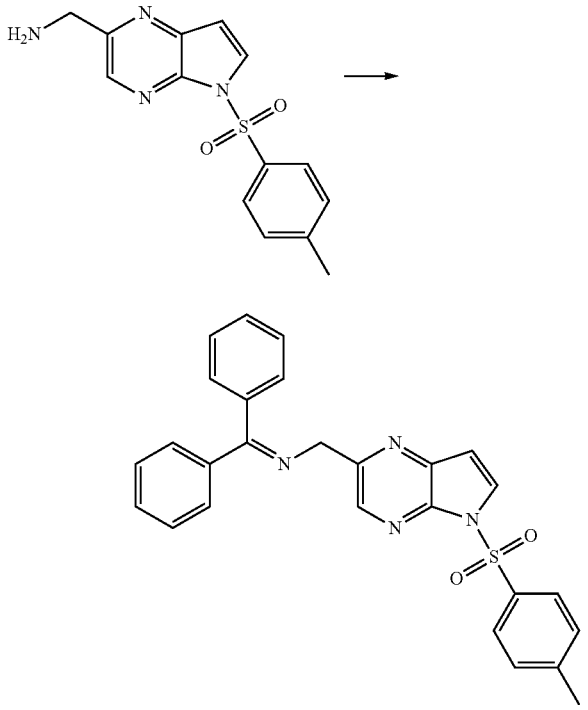

To a solution of (5-tosyl-5H-pyrrolo[2,3-b]pyrazin-2-yl) methanamine (2.00 g, 6.61 mmol, Example #5 Step C) in DCM (30 mL) was added diphenylmethanimine (1.16 mL, 6.61 mmol). After about 2 d, the reaction mixture was concd in vacuo to provide N-(diphenylmethylene)-1-(5-tosyl-5H-pyrrolo[2,3-b]pyrazin-2-yl)methanamine (2.75 g, 89%) as a foam and used without further purification. LC/MS (Table 1, Method a) $R_t$=3.02 min; MS m/z: 467 $(M+H)^+$.

Step B: 3,3,3-trifluoro-1-(5-tosyl-5H-pyrrolo[2,3-b]pyrazin-2-yl)propan-1-amine, hydrochloride

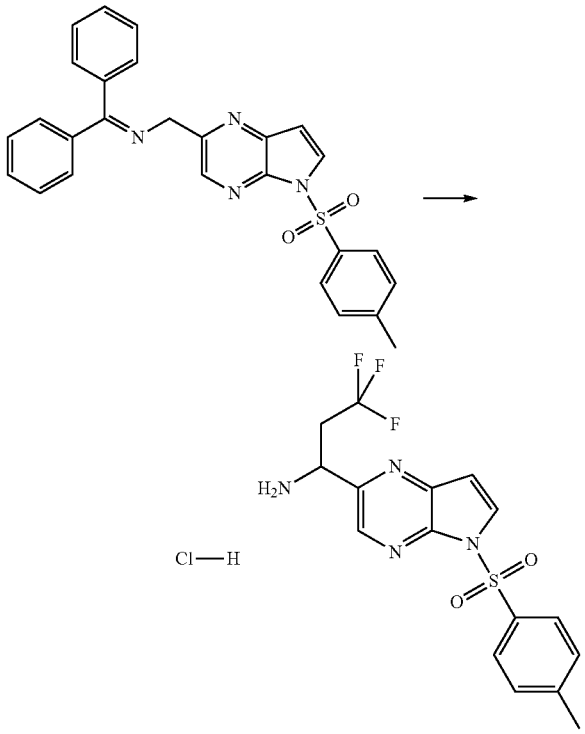

To a solution of N-(diphenylmethylene)-1-(5-tosyl-5H-pyrrolo[2,3-b]pyrazin-2-yl)methanamine (0.722 g, 1.55 mmol) in THF (3 mL) at about −78° C. was added NaHMDS (0.5 M in THF, 1.55 mL, 1.55 mmol). After about 30 min, 1,1,1-trifluoro-2-iodoethane (1.51 mL, 15.5 mmol) was added to the reaction mixture. After about 4 h, the reaction mixture was allowed to warm to rt slowly over night. After about 15 h, EtOAc (30 mL) and saturated aqueous $NaHCO_3$ (30 mL) were added. The organic layer was separated, concd in vacuo and purified by chromatography on silica gel eluting with EtOAc/heptane (20-50%) to provide the crude alkylated imine. The imine was dissolved in isopropyl acetate (30 mL) and concd HCl (0.50 mL) was added. The reaction mixture was spun on a rotory evaporator for 1 h prior to partial concentration to approx 10 mL. Additional isopropyl acetate (30 mL) was added and the solvent was partially removed in vacuo until approx. 10 mL remained. $Et_2O$ (30 mL) was added and the solution was allowed to age for about 30 min. The resulting solids were collected by filtration and dried in vacuo to provide 3,3,3-trifluoro-1-(5-tosyl-5H-pyrrolo[2,3-b]pyrazin-2-yl)propan-1-amine hydrochloride (0.150 g, 23%) as a colorless solid. LC/MS (Table 1, Method a) $R_t$=1.88 min; MS m/z 385 $(M+H)^+$.

Preparation #31: (1S,2R,4R)-4-(2-ethoxy-2-oxoethyl)-2-ethylcyclopentanecarboxylic acid

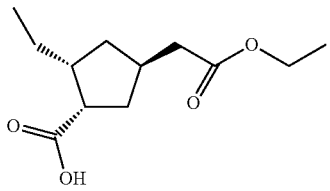

Step A:
(3R,4S)-3-ethyl-4-(hydroxymethyl)cyclopentanol

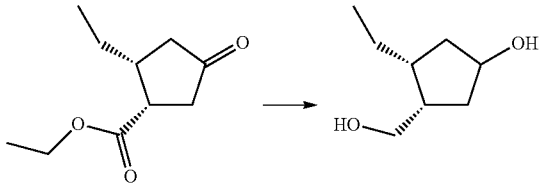

To a solution of (1S,2R)-ethyl 2-ethyl-4-oxocyclopentanecarboxylate (5 g, 27.1 mmol, Example #22 step B) in THF (100 mL) at about −78° C. was added LAH (2 M in THF, 54.3 mL, 109 mmol). After about 1 h, the reaction mixture was allowed to warm to rt slowly. After about 4 h, water (4.8 mL) followed by aqueous NaOH (15% w/v, 4.8 mL) followed by water (9.6 mL) was added to the reaction mixture. After about 15 h, anhydrous $Na_2SO_4$ was added and the slurry was filtered and concd in vacuo to provide crude (3R,4S)-3-ethyl-4-(hydroxymethyl)cyclopentanol (3.9 g, 100%) as an oil which was used without further purification. LC/MS (Table 1, Method a) $R_t$=2.40 min; MS m/z: 145 $(M+H)^+$.

Step B:
(3R,4S)-3-ethyl-4-(hydroxymethyl)cyclopentanone

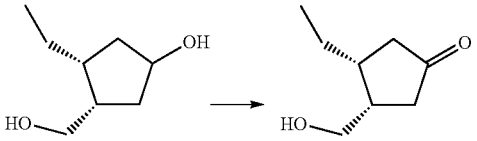

To a solution of (3R,4S)-3-ethyl-4-(hydroxymethyl)cyclopentanol (4.00 g, 27.7 mmol) in MeCN (70 mL) and water (30.0 mL) was added potassium bromate (1.487 mL, 29.1 mmol) and CAN (0.760 g, 1.387 mmol). The reaction mixture was heated to about 80° C. After about 2 h, the reaction mixture was cooled to rt and $Et_2O$ (100 mL) was added. The organic layer was separated, washed with brine (30 mL), concd in vacuo and purified by chromatography on silica gel eluting with EtOAc/heptane (20-60%) to provide (3R,4S)-3-ethyl-4-(hydroxymethyl)cyclopentanone (2.4 g, 61%) as an oil. $^1$H NMR (400 MHz, $CDCl_3$) δ 3.79 (dd, J=10.5, 5.3 Hz, 1H), 3.70 (dd, J=10.5, 6.5 Hz, 1H), 2.55-2.44 (m, 1H), 2.41-2.25 (m, 4H), 2.15-2.05 (m, 1H), 1.55-1.65 (m, 2H), 1.43-1.30 (m, 1H), 0.97 (t, J=7.3 Hz, 3H).

Step C: (3S,4R)-3-((tert-butyldimethylsilyloxy)methyl)-4-ethylcyclopentanone

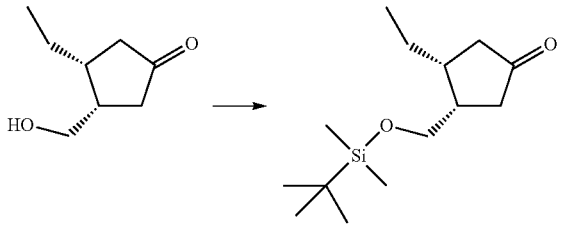

To a solution of (3R,4S)-3-ethyl-4-(hydroxymethyl)cyclopentanone (2.60 g, 18.3 mmol) in DMF (30 mL) was added imidazole (1.87 g, 27.4 mmol) followed by tert-butylchlorodimethylsilane (3.03 g, 20.1 mmol). After about 4 h, heptane (50 mL) was added. The heptane layer was removed and washed with brine. The brine layer was combined with the DMF layer and extracted with EtOAc/heptane (1:1, 30 mL). The heptane and EtOAc layers were combined, concd in vacuo and purified by chromatography on silica gel eluting with EtOAc/heptane (0-30%) to provide (3S,4R)-3-((tert-butyldimethylsilyloxy)methyl)-4-ethylcyclopentanone (3.5 g, 75%) as a colorless oil. $^1$H NMR (400 MHz, $CDCl_3$) δ 3.77 (dd, J=10.5, 4.3 Hz, 1H), 3.64 (dd, J=10.5, 4.0 Hz, 1H), 2.40-2.20 (m, 5H), 2.18-2.02 (m, 1H), 1.65-1.55 (m, 1H), 1.52-1.37 (m, 1H), 0.97 (t, J=7.4 Hz, 3H), 0.87 (s, 9H), 0.43 (s, 3H), 0.03 (s, 3H).

Step D: ethyl 2-((3S,4R)-3-((tert-butyldimethylsilyloxy)methyl)-4-ethylcyclopentylidene)acetate

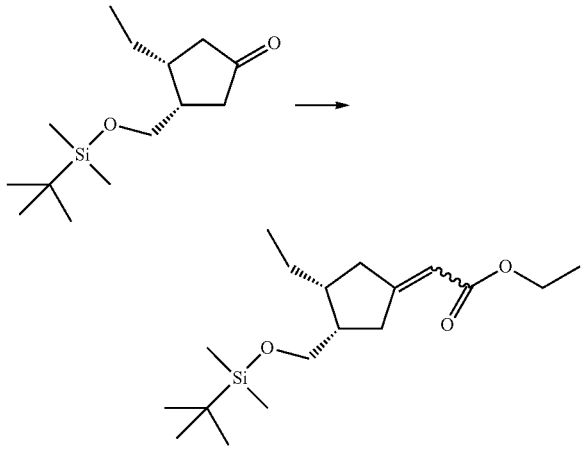

To a slurry of NaH (60% dispersion in mineral oil, 0.608 g, 15.2 mmol) in THF (50 mL) was added ethyl 2-(diethoxyphosphoryl)acetate (3.25 mL, 16.2 mmol). After about 30 min, the phosphonate solution was added to a flask charged with (3S,4R)-3-((tert-butyldimethylsilyloxy)methyl)-4-ethylcyclopentanone (2.6 g, 10.14 mmol). After about 20 h, EtOAc (20 mL) and saturated aqueous $NH_4Cl$ (20 mL) were added. The organic layer was removed concd in vacuo and purified by chromatography on silica gel eluting with EtOAc/heptane (20-60%) to provide ethyl 2-((3S,4R)-3-((tert-butyldimethylsilyloxy)methyl)-4-ethylcyclopentylidene)acetate (3.3 g, 100%) as an oil. LC/MS (Table 1, Method a) $R_t$=3.91, 3.96 min; MS m/z: 327 $(M+H)^+$.

Step E: ethyl 2-((3R,4S)-3-ethyl-4-(hydroxymethyl)cyclopentylidene)acetate

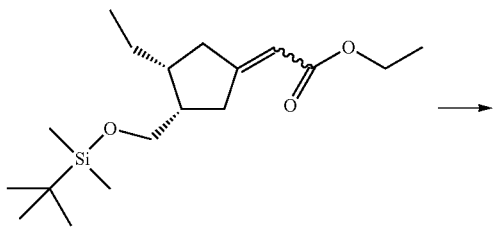

-continued

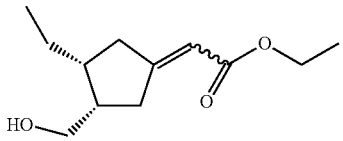

To a solution of ethyl 2-((3S,4R)-3-((tert-butyldimethylsilyloxy)methyl)-4-ethylcyclopentylidene)acetate (1.00 g, 3.06 mmol) in THF (20 mL) was added TBAF (1M in THF, 4.59 mL, 4.59 mmol). After 6 h, EtOAc and water were added. The organic layer was separated, concd in vacuo and purified by chromatography on silica gel eluting with EtOAc/heptane to provide ethyl 2-((3R,4S)-3-ethyl-4-(hydroxymethyl)cyclopentylidene)acetate (0.620 g, 95%) as an oil. LC/MS (Table 1, Method a) $R_t$=1.96, 2.08 min; MS m/z: 213 $(M+H)^+$.

Step F: ethyl 2-01R,3R,4S)-3-ethyl-4-(hydroxymethyl)cyclopentyl)acetate

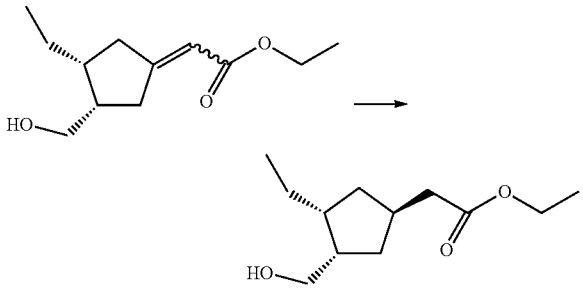

To a solution of ethyl 2-((3R,4S)-3-ethyl-4-(hydroxymethyl)cyclopentylidene)acetate (0.160 g, 0.754 mmol) in DCM (3 mL) was added Crabtree's catalyst (0.030 g, 0.038 mmol). The reaction mixture was sparged with hydrogen for about 5 min and an atmosphere of hydrogen was maintained via balloon. After about 24 h, the reaction mixture was concd in vacuo and purified by chromatography on silica gel eluting with EtOAc/heptane (30-80%) to provide ethyl 2-((1R,3R,4S)-3-ethyl-4-(hydroxymethyl)cyclopentyl)acetate (0.140 g, 87%) as an oil. $^1$H NMR (400 MHz, $CDCl_3$) δ 4.12 (q, J=7.1 Hz, 2H), 3.71-3.64 (dd, J=10.5, 8.0 Hz, 1H), 3.47 (dd, J=10.5, 8.0 Hz, 1H), 2.55-2.41 (m, 1H), 2.32 (d, J=6.7 Hz, 2H), 2.02-1.89 (m, 1H), 1.88-1.76 (m, 1H), 1.70-1.60 (m, 1H), 1.48-1.33 (m, 4H), 1.26 (t, J=7.1 Hz, 3H), 1.22-1.07 (m, 1H), 0.90 (t, J=7.4 Hz, 3H).

Step G: (1S,2R,4R)-4-(2-ethoxy-2-oxoethyl)-2-ethylcyclopentanecarboxylic acid

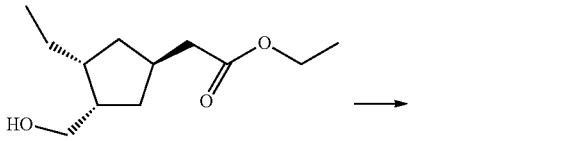

-continued

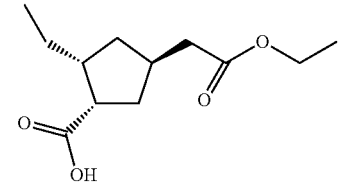

To a solution of ethyl 2-((1R,3R,4S)-3-ethyl-4-(hydroxymethyl)cyclopentyl)acetate (0.140 g, 0.653 mmol) in MeCN (2 mL), water (4 mL) and EtOAc (2 mL) was added sodium periodate (0.349 g, 1.633 mmol) followed by ruthenium(III) chloride hydrate (0.0015 g, 0.0065 mmol). After about 2 h, the reaction mixture was diluted with EtOAc (20 mL) and water (10 mL). The organic layer was separated and extracted with aqueous NaOH (1 N, 10 mL). The pH of the aqueous layer was adjusted to about 1 with concd HCl and extracted with EtOAc (20 mL). The organic layer was dried over anhydrous $MgSO_4$, filtered, and concd in vacuo to provide (1S,2R,4R)-4-(2-ethoxy-2-oxoethyl)-2-ethylcyclopentanecarboxylic acid (0.150 g, 101%) as an oil which was used without further purification. $^1$H NMR (600 MHz, $CDCl_3$) δ 10.68 (bs, 1H), 4.13 (q, J=7.1 hz, 2H), 2.99-2.95 (m, 1H), 2.76-2.64 (m, 1H), 2.31 (d, J=7.6 Hz, 2H), 2.24 (ddd, J=13.5, 8.7, 4.8 Hz, 1H), 2.18-2.11 (m, 1H), 1.81 (dt, J=13.0, 8.4 Hz, 1H), 1.55-1.45 (m, 3H), 1.31-1.27 (m, 1H), 1.25 (t, J=7.0 Hz, 3H), (t, J=7.4 Hz, 3H).

Preparation #32: 2,2,2-trifluoro-1-(5-tosyl-5H-pyrrolo[2,3-b]pyrazin-2-yl)ethanamine, hydrochloride

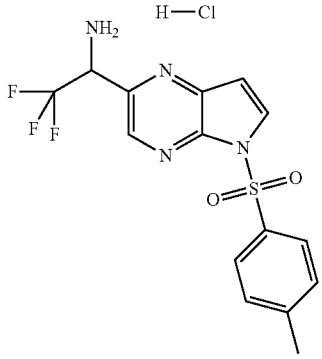

Step A: (S,E)-2-methyl-N-((5-tosyl-5H-pyrrolo[2,3-b]pyrazin-2-yl)methylene)propane-2-sulfinamide

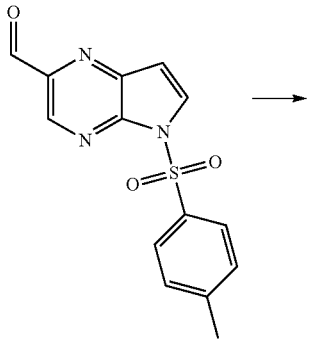

-continued

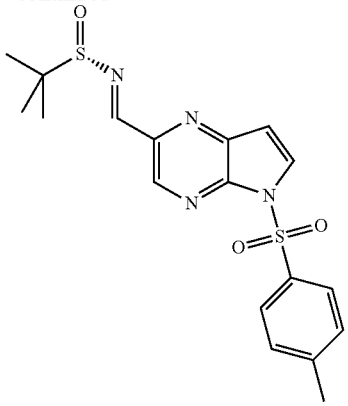

To a solution of 5-tosyl-5H-pyrrolo[2,3-b]pyrazine-2-carbaldehyde (8.66 g, 28.7 mmol, Preparation #12 Step B) and (S)-2-methylpropane-2-sulfinamide (4.18 g, 34.5 mmol) in DCM (20 mL) at ambient temperature was added anhydrous powdered copper(II) sulfate (13.8 g, 86 mmol). After about 20 h, the reaction mixture was filtered and partially concd in vacuo. Heptane was added to the solution and the resulting solids were collected by filtration and dried in vacuo to provide (S,E)-2-methyl-N-((5-tosyl-5H-pyrrolo[2,3-b]pyrazin-2-yl)methylene)propane-2-sulfinamide (11.5 g, 99%) as a solid. LC/MS (Table 1, Method a) $R_t$=2.50 min; MS m/z: 405 $(M+H)^+$.

Step B: (S)-2-methyl-N-(2,2,2-trifluoro-1-(5-tosyl-5H-pyrrolo[2,3-b]pyrazin-2-yl)ethyl)propane-2-sulfinamide

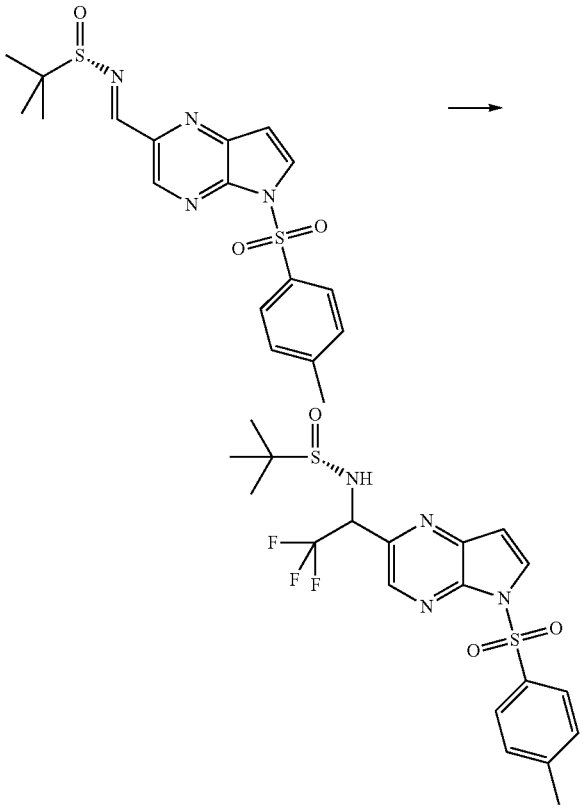

To a dry flask charged with 4 Å molecular sieves (5 g) and tetramethyl-ammonium fluoride (0.553 g, 5.93 mmol) was added THF (20 mL). The reaction mixture was stirred for about 30 min after which it was cooled to about −78° C. and a solution of (S,E)-2-methyl-N-((5-tosyl-5H-pyrrolo[2,3-b]pyrazin-2-yl)methylene)propane-2-sulfinamide (1.20 g, 2.97 mmol) in THF (10 mL) was added. After about 15 min trimethyl(trifluoromethyl)silane (0.877 mL, 5.93 mmol) was added to the reaction mixture. The mixture was allowed to warm to −35 to −45° C. After about 3 h, the reaction mixture was cooled to −78° C. and aqueous $NH_4Cl$ was added. The reaction mixture was allowed to warm to rt. EtOAc (30 mL) and brine (30 mL) were added. The organic layer was separated, dried over anhydrous $Na_2SO_4$, filtered and concd in vacuo to provide crude (S)-2-methyl-N-(2,2,2-trifluoro-1-(5-tosyl-5H-pyrrolo[2,3-b]pyrazin-2-yl)ethyl)propane-2-sulfinamide (1.4 g, 99%) as a foamsulfonamide which was used without further purification. LC/MS (Table 1, Method a) $R_t$=2.49 min; MS m/z 475 $(M+H)^+$.

Step C: 2,2,2-trifluoro-1-(5-tosyl-5H-pyrrolo[2,3-b]pyrazin-2-yl)ethanamine hydrochloride

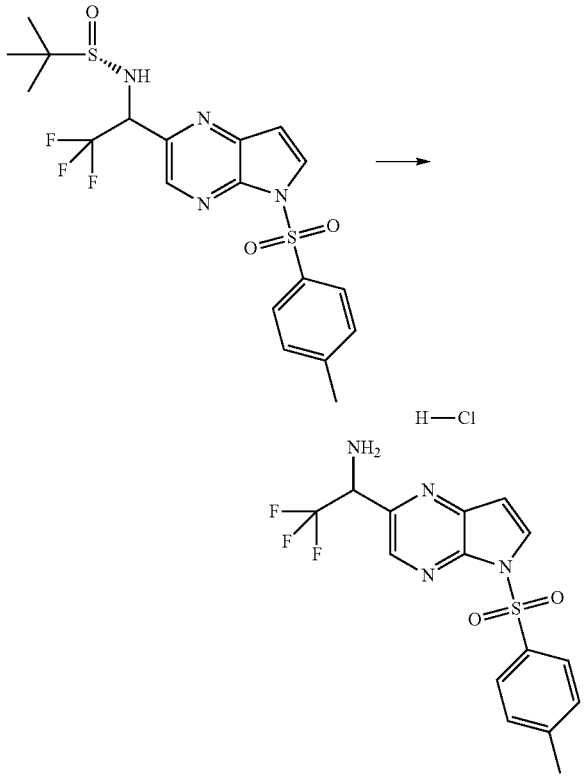

To a solution of (S)-2-methyl-N-(2,2,2-trifluoro-1-(5-tosyl-5H-pyrrolo[2,3-b]pyrazin-2-yl)ethyl)propane-2-sulfinamide (1.40 g, 2.95 mmol) in MeOH (20 mL) was added HCl (4 N in 1,4-dioxane, 7.38 mL, 29.5 mmol). After about 2 h, the reaction mixture was partially concd in vacuo and diluted with $Et_2O$ until solids began to form. After about 30 min, the resulting solids were collected by filtration and dried in vacuo to provide 2,2,2-trifluoro-1-(5-tosyl-5H-pyrrolo[2,3-b]pyrazin-2-yl)ethanamine hydrochloride (0.840 g, 70%) as a solid. LC/MS (Table 1, Method a) $R_t$=2.16 min; MS m/z 371 $(M+H)^+$.

Preparation #33: (1S,2R,4S)-4-(dibenzylamino)-2-methylcyclopentanecarboxylic acid

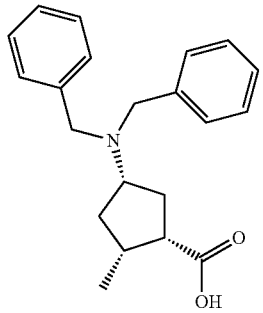

Step A: (1S,2R,4S)-4-(dibenzylamino)-2-methylcyclopentanecarboxylate•(R)-1-phenylethanamine

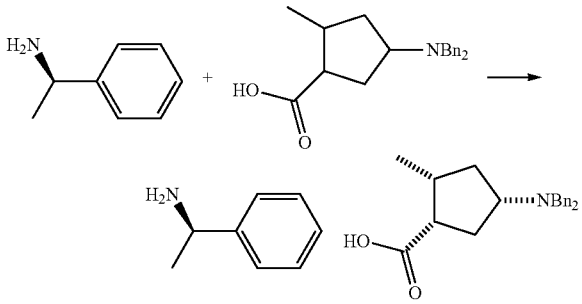

To a solution of 4-(dibenzylamino)-2-methylcyclopentanecarboxylic acid (1240 g, 1499 mmol, prepared using X with Example #24 Step H and dibenzylamine and TT) in THF (8.0 L) was added (R)-(+)-1-phenylethylamine (0.193L, 1499 mmol). The mixture was warmed to reflux to dissolve the solids, and was then cooled to ambient temperature. After about 15 h, the reaction mixture was filtered, washed THF (800 mL) and dried in a vacuum oven to afford (1S,2R,4S)-4-(dibenzylamino)-2-methylcyclopentanecarboxylate•(R)-1-phenylethanamine (565 g, 85%, 97.5% ee): LC/MS (Table 2, Method 70) $R_t$=8.49 min. The mother liquor was concd. The residue was dissolved in THF (1 L), heated to dissolve the solids, and cooled to ambient temperature. After about 15 h, the reaction mixture was filtered, washed THF (800 mL) and dried in a vacuum oven to afford additional (1S,2R,4S)-4-(dibenzylamino)-2-methylcyclopentanecarboxylate•(R)-1-phenylethanamine (78.5 g, 12%, 95.2% ee): HPLC (Table 2, Method 70) $R_t$=8.57 min Step B: (1S,2R,4S)-4-(dibenzylamino)-2-methylcyclopentanecarboxylic acid

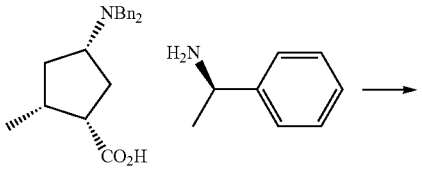

-continued

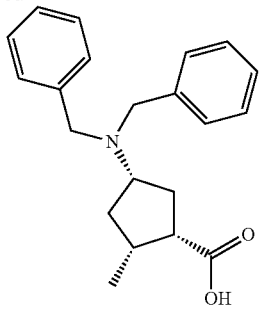

Phosphoric acid (11.40 mL, 196 mmol) was added to a flask containing water (500 mL). The solution was stirred for about 5 min. (1S,2R,4S)-4-(dibenzylamino)-2-methylcyclopentanecarboxylate•(R)-1-phenylethanamine (83 g, 187 mmol) was added to the solution in small portions. MTBE (500 mL) was added and the contents were mixed well, dissolving the solid. The phases were settled and separated. The aqueous layer was back extracted with MTBE (150 mL). The combined organic phases were dried over anhydrous sodium sulfate, filtered, and concentrated in vacuo to afford (1S,2R,4S)-4-(dibenzylamino)-2-methylcyclopentanecarboxylic acid (60 g, 99%) as an oil: HPLC (Table 1, Method x) $R_t$=4.57 min.

Preparation #34: 3,3-difluorocyclobutane-1-sulfonyl chloride

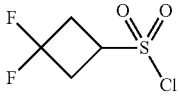

Step A: 3-bromo-1,1-difluorocyclobutane

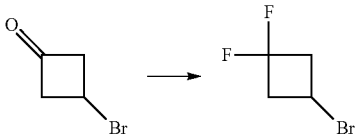

To a vigorously stirred solution of 3-bromocyclobutanone (18.0 g, 121 mmol, prepared as described in J. Am. Chem. Soc., 1971, 93, 2481) in DCM (375 mL) at about 0° C. was added dropwise via an addition funnel DAST (36.9 mL, 279 mmol) over about 1 h. The reaction mixture continued stirring at about 0° C. for about 2 h and at ambient temperature for about 14 h. The reaction was cooled to about −5° C. in an ice/acetone bath and a saturated aqueous solution of $NaHCO_3$ (400 mL) was added dropwise via addition funnel. The bilayers remained vigorously stirring for about 1 h. The layers were partitioned and the aqueous layer was extracted with DCM (4×200 mL). The combined organic layers were dried over anhydrous $MgSO_4$, filtered, and solvent removed under reduced pressure (180 mm Hg maximum, 30° C. water bath) to afford 3-bromo-1,1-difluorocyclobutane (15.3 g, 59%) as a light brown oil as product: $^1$H NMR (400 MHz, $CDCl_3$) δ 4.28-4.14 (m, 1H), 3.35-3.16 (m, 2H), 3.06-2.87 (m, 2H).

Step B: S-3,3-difluorocyclobutyl ethanethioate

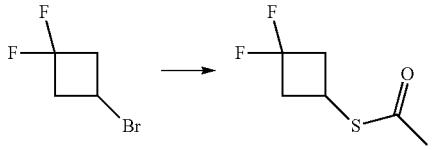

To a solution of 3-bromo-1,1-difluorocyclobutane (13.8 g, 64.7 mmol) in DMSO (24.6 mL) was added potassium thioacetate (22.2 g, 194 mmol). The solution was heated at about 45° C. for about 16 h. Water (20 mL) and $Et_2O$ (50 mL) were added. The layers were partitioned and the aqueous layer was extracted with $Et_2O$ (7×50 mL). The combined organic layers were dried over anhydrous $MgSO_4$, filtered, and solvent removed under reduced pressure (60 mm Hg maximum, 30° C. water bath) to afford crude S-3,3-difluorocyclobutyl ethanethioate (13.09 g, 78%) as an oil: $^1$H NMR (400 MHz, $d_6$-DMSO) δ 3.84-3.69 (m, 1H), 3.14 (ddd, J=13.0, 7.5, 3.9 Hz, 2H), 2.66-2.55 (m, 2H), 2.33 (s, 3H).

Step C: potassium 3,3-difluorocyclobutane-1-sulfonate

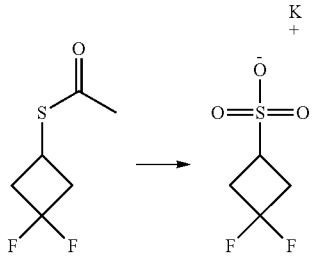

To a solution of crude S-3,3-difluorocyclobutyl ethanethioate (13.0 g, 39.1 mmol) in acetic acid (100 mL) was added $H_2O_2$ (24.0 mL, 235 mmol, 30% in water). After about 4 h, an exotherm was noted which generated enough heat to reflux the reaction mixture. After about 20 h, the reaction mixture was diluted with toluene (500 mL) and partially concd in vacuo. This process was repeated (5×). The solution was diluted with EtOH (about 500 mL) and KOH (4.4 g, 78 mmol) was added to the reaction mixture. The precipitate was collected by filtration and discarded. Additional KOH (4.4 g, 78 mmol) was added to the filtrate and the precipitate was collected by filtration. The solution was partially concd in vacuo. The solution was diluted with EtOH (approx. 500 mL) and partially concd again (3×). The precipitate was collected by filtration. The last 2 collected solids were dried in vacuo and combined to provide potassium 3,3-difluorocyclobutane-1-sulfonate (3.5 g, 42.6%). Additional KOH (4.39 g, 78 mmol) and the solution was partially concd in vacuo. The solution was diluted with EtOH (approx. 500 mL) and concd again (3×). The resulting solids were collected by filtration to provide potassium 3,3-difluorocyclobutane-1-sulfonate (1.6 g, 19%): $^1$H NMR (400 MHz, $d_6$-DMSO) δ 3.01 (ddd, J=13.5, 6.3, 2.5 Hz, 1H), 2.72-2.59 (m, 4H).

Step D: 3,3-difluorocyclobutane-1-sulfonyl chloride

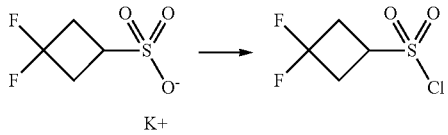

To a suspension of potassium 3,3-difluorocyclobutane-1-sulfonate (0.250 g, 1.189 mmol) in thionyl chloride (2.60 mL, 35.7 mmol) was added DMF (3 drops). The reaction was heated to about 60° C. for about 21 h. The solvent was removed under reduced pressure and the residue was used in the next reaction without further workup or purification to afford crude 3,3-difluorocyclobutane-1-sulfonyl chloride (0.227 g, 100%) as product. $^1$H NMR (400 MHz, $CDCl_3$) δ 4.33-4.17 (m, 1H), 3.28 (dd, J=11.1, 7.6 Hz, 2H), 3.21-3.05 (m, 2H).

Preparation #35: isopropyl (1S,3R,4S)-3-ethyl-4-(6-tosyl-6H-pyrrolo[2,3-e][1,2,4]triazolo[4,3-a]pyrazin-1-yl)cyclopentylcarbamate

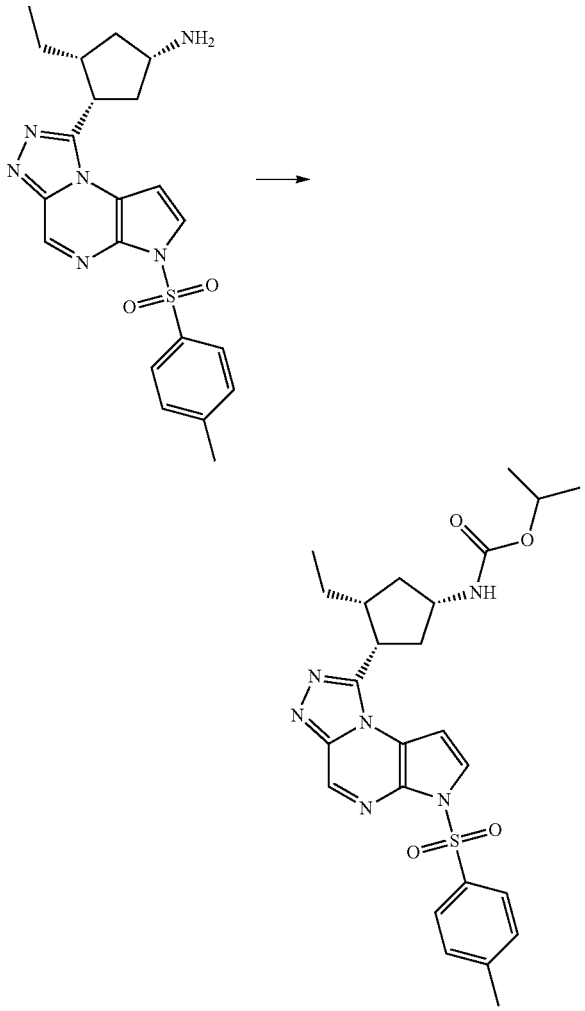

To a solution of (1S,3R,4S)-3-ethyl-4-(6-tosyl-6H-pyrrolo[2,3-e][1,2,4]triazolo[4,3-a]pyrazin-1-yl)cyclopentanamine (0.080 g, 0.19 mmol, Preparation #BB.1*) in THF (2 mL) was added TEA (0.079 mL, 0.565 mmol) and the solution was stirred at ambient temperature for about 10 min. To the reaction was added isopropyl chloroformate (1 M in toluene, 0.18 mL, 0.18 mmol) and the reaction mixture was stirred for about 1 h. The solvent was removed under reduced pressure and DCM (5 mL) and saturated aqueous $NaHCO_3$ (2 mL) were added. The layers were separated and the organic layer was washed with brine (2 mL), dried over $MgSO_4$, filtered and concentrated under reduced pressure to give crude isopropyl (1S,3R,4S)-3-ethyl-4-(6-tosyl-6H-pyrrolo[2,3-e][1,2,4]triazolo[4,3-a]pyrazin-1-yl)cyclopentylcarbamate (0.080 g, 60%) which was used without further purification: LC/MS (Table 1, Method b) $R_t$=2.33 min; MS m/z: 511 $(M+H)^+$.

Preparation #36:
3-(aminomethyl)cyclobutanecarboxylic acid

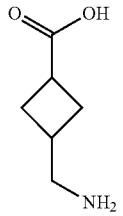

To a flask charged with 10% palladium on carbon (0.20 g, 0.19 mmol) was added a solution of benzyl 3-(azidomethyl)cyclobutanecarboxylate (2.00 g, 8.15 mmol, prepared using IIII from benzyl 3-(hydroxymethyl)cyclobutanecarboxylate (Parkway Scientific), JJJJ with sodium azide) in MeOH (100 mL). The reaction mixture was sparged with hydrogen and an atmosphere of hydrogen was maintained via a balloon. The reaction mixture was stirred for about 4 h at ambient temperature and then was filtered through a pad of Celite®, washed with MeOH and concentrated in vacuo to give the crude 3-(aminomethyl)cyclobutanecarboxylic acid (1.08 g, 100%) which was used without further purification: LC/MS (Table 1, Method r) $R_t$=2.41 min (ELSD); MS m/z: 130 $(M+H)^+$.

Preparation #37: ethyl 3-tosyl-3H-imidazo[1,2-a]pyrrolo[2,3-e]pyrazine-7-carboxylate

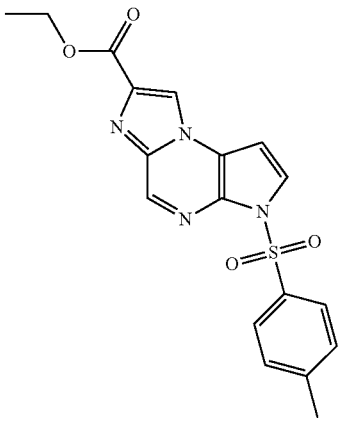

3-Bromo-2-oxo-propionic acid ethyl ester (0.090 mL, 0.72 mmol) was added to a mixture of 5-tosyl-5H-pyrrolo[3,2-b]pyrazin-2-amine (0.180 g, 0.624 mmol, prepared using E from Example #3 Step E and HCl) and 1,4-dioxane (3.5 mL) under nitrogen. After about 3 days, the volatiles were removed under reduced pressure. The residue was slurried in $Et_2O$ (5 mL) and then filtered to afford a tan powder. The solid was slurried in MeCN (3.50 mL) under nitrogen. PFPAA (0.40 mL, 2.1 mmol) was added. After about 30 min, the volatiles were removed under reduced pressure. The residue was dissolved in DCM (20 mL) and washed with saturated aqueous $NaHCO_3$/water (2:1, 20 mL). The aqueous layer was extracted with DCM (20 mL). The combined organics were dried over anhydrous $Na_2SO_4$, filtered, and concentrated under reduced pressure. The residue was purified by silica gel chromatography eluting with a gradient of 20-100% EtOAc/heptane to afford ethyl 3-tosyl-3H-imidazo[1,2-a]pyrrolo[2,3-e]pyrazine-7-carboxylate (0.181 g, 75%): LC/MS (Table 1, Method n) $R_t$=0.70 min; MS m/z: 385 $(M+H)^+$.

Preparation #38: 6H-pyrrolo[2,3-e][1,2,4]triazolo[4,3-a]pyrazine-8-carbaldehyde

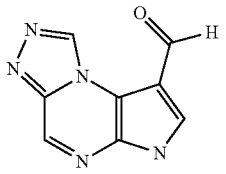

Water (1.0 mL) was added to a mixture of 6H-pyrrolo[2,3-e][1,2,4]triazolo[4,3-a]pyrazine (0.200 g, 1.26 mmol, prepared using D from Preparation #BBBBB.1 and NaOH) and hexamethylenetetramine (0.264 g, 1.89 mmol). Acetic acid (0.5 mL) was added. The reaction vessel was sealed and the mixture was warmed to about 100° C. After about 8 h, the solution was allowed to cool to ambient temperature. After sitting for about 13 h, the mixture was cooled to about 0° C. The resulting mixture was diluted with water (1 mL) and then filtered rinsing with water. The solid was dried to afford 6H-pyrrolo[2,3-e][1,2,4]triazolo[4,3-a]pyrazine-8-carbaldehyde (0.041 g, 18%): LC/MS (Table 1, Method n) $R_t$=0.23 min; MS m/z 188 $(M+H)^+$.

Preparation #39: 2-(4-methylpiperazin-1-yl)-4-(tributylstannyl)pyrimidine

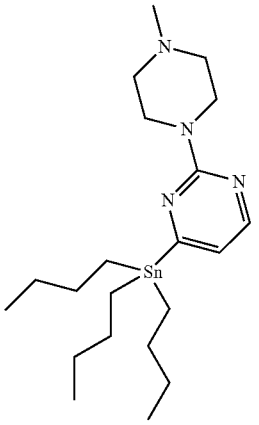

1-Methylpiperazine (0.160 mL, 1.44 mmol) was added to a solution of 2-(methylsulfonyl)-4-(tributylstannyl)pyrimidine (0.250 g, 0.481 mmol, synthesized as described in Majeed, A. J., et al. Tetrahedron 1989, 45, 993-1006) and 1,4-dioxane (1.0 mL) under nitrogen. After about 2 h, the solution was warmed to about 50° C. After about 30 min, the solution was warmed to about 80° C. After about 30 min, a reflux condenser was attached and the solution was warmed to about 100° C. After about 16 h, the brown solution was allowed to cool to ambient temperature. Water (5 mL) was added. The mixture was extracted with EtOAc (2×5 mL). The combined organics were dried over anhydrous $Na_2SO_4$, filtered, and concentrated. The residue was purified by silica gel chromatography eluting with a gradient of 2-10% MeOH/DCM to afford 2-(4-methylpiperazin-1-yl)-4-(tributylstannyl)pyrimidine (0.127 g, 56%): $^1$H NMR (400 MHz, $CDCl_3$) δ 8.07 (d, J=4.6 Hz, 1H), 6.63 (d, J=4.6 Hz, 1H), 3.98-3.82 (m, 4H), 2.63-2.48 (m, 4H), 2.40 (s, 3H), 1.70-1.43 (m, 6H), 1.42-1.20 (m, 6H), 1.18-0.97 (m, 6H), 0.88 (t, J=7.3Hz, 9H).

Preparation #40: 2-(4-methylpiperazin-1-yl)-4-(tributylstannyl)quinazoline

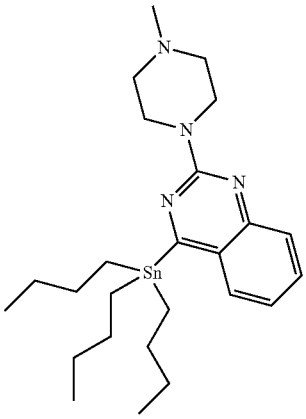

Step A:
4-chloro-2-(4-methylpiperazin-1-yl)quinazoline

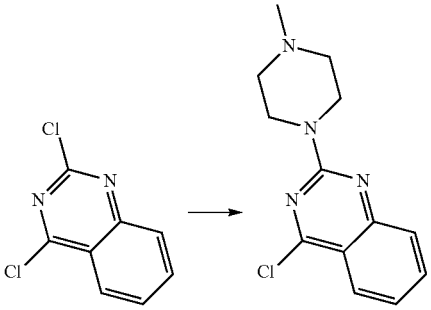

2,4-Dichloroquinazoline (2.00 g, 10.1 mmol, prepared as described in Prasad, M., et al. Org. Process Res. Dev. 2004, 8, 330-340) was slurried in 1,4-dioxane (20.0 mL). 1,4-Dimethylpiperazine (1.44 mL, 10.6 mmol) was added. The mixture was heated in a CEM microwave at about 150° C. for about 5 min. The material was poured into saturated aqueous $NaHCO_3$/water (1:1, 150 mL). The mixture was extracted with EtOAc (5×100 mL). 20 g of silica gel was added to the combined organics and the volatiles were removed under reduced pressure. The resulting solid was purified by silica gel chromatography eluting with a gradient of 2-10% MeOH/DCM to afford 4-chloro-2-(4-methylpiperazin-1-yl)quinazoline (1.36 g, 52%): LC/MS (Table 1, Method n) $R_t$=0.51 min; MS m/z 263 $(M+H)^+$.

Step B:
4-iodo-2-(4-methylpiperazin-1-yl)quinazoline

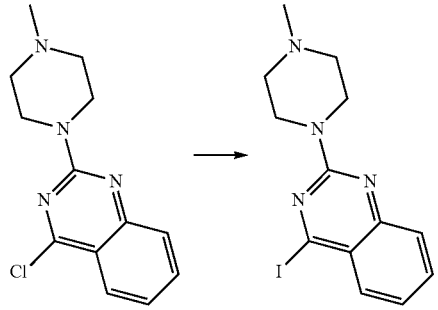

Hydrogen iodide (55% aqueous solution, 4.00 mL, 29.3 mmol) was slowly added to 4-chloro-2-(4-methylpiperazin-1-yl)quinazoline (1.36 g, 5.18 mmol) under air while cooling in an ambient temperature water bath. After about 5 min, the bath was removed, the reaction vessel was wrapped in aluminum foil, and the mixture was stirred at ambient temperature for about 5 h. DCM (4.0 mL) was added and the mixture was stirred for about 39 h. Hydrogen iodide (55% aqueous solution, 8.0 mL, 110 mmol) was added and the mixture was stirred for about 71 h. The mixture was slowly added to saturated aqueous $NaHCO_3$ (200 mL) and EtOAc (200 mL). After completion of the quench, the layers were separated. The organics were washed with saturated aqueous $NaHCO_3$/water (1:1, 200 mL). The organics were dried over anhydrous $Na_2SO_4$, filtered, and concentrated under reduced pressure. The residue was purified by silica gel chromatography eluting with a gradient of 2-5% MeOH/DCM to afford (1.18 g, 69%) as a 3:1 mixture of 4-iodo-2-(4-methylpiperazin-1-yl)quinazoline to 4-chloro-2-(4-methylpiperazin-1-yl)quinazoline. 4-iodo-2-(4-methylpiperazin-1-yl)quinazoline: LC/MS (Table 1, Method n) $R_t$=0.55 min; MS m/z 355 $(M+H)^+$.

Step C: 2-(4-methylpiperazin-1-yl)-4-(tributylstannyl)quinazoline

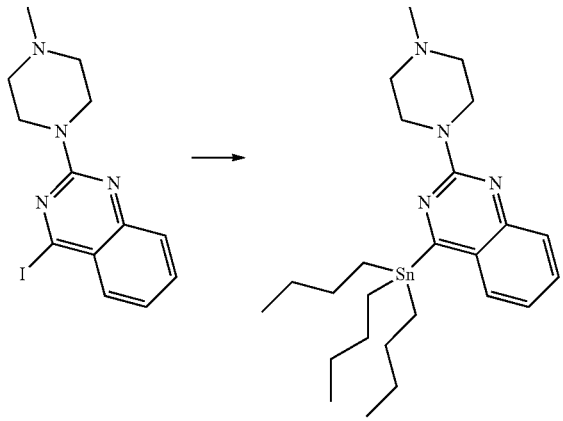

Bis(triphenylphosphine)palladium(II) acetate (0.063 g, 0.085 mmol) was added to 3:1 mixture of 4-iodo-2-(4-methylpiperazin-1-yl)quinazoline:4-chloro-2-(4-methylpiperazin-1-yl)quinazoline (0.300 g) under nitrogen. Bis(tributyltin) (0.855 mL, 1.69 mmol) was added. TBAF (1.0 M solution in THF, 2.54 mL, 2.54 mmol) was added. The mixture was purged with nitrogen for about 20 min and then stirred under nitrogen at ambient temperature for about 7 h. Saturated aqueous $NaHCO_3$/water (1:1, 20 mL) and EtOAc (50 mL) were added. The mixture was filtered through a syringe filter, the layers were separated and the organics were washed with water (2×10 mL). The organics were dried over anhydrous $Na_2SO_4$, filtered, and concentrated under reduced pressure. The residue was purified by silica gel chromatography eluting with a gradient of 5-10% MeOH/DCM to afford a sticky brown solid. The material was dissolved in EtOAc (10 mL) and washed with water (2×5 mL). The organics were dried over anhydrous $Na_2SO_4$, filtered, and concentrated to afford a 1:1 mix of 2-(4-methylpiperazin-1-yl)-4-(tributylstannyl)quinazoline: 4-chloro-2-(4-methylpiperazin-1-yl)quinazoline (0.058 g, 17%). 2-(4-methylpiperazin-1-yl)-4-(tributylstannyl)quinazoline: $^1$H NMR (400 MHz, DMSO-$d_6$) δ 7.69-7.64 (m, 1H), 7.61-7.57 (m, 1H), 7.49-7.44 (m, 1H), 7.31-7.26 (m, 1H), 3.95-3.83 (m, 4H), 2.44-2.35 (m, 4H), 2.22 (s, 3H), 1.66-1.48 (m, 6H), 1.37-1.18 (m, 12H), 0.82 (t, J=7.3 Hz, 9H).

Preparation #41: 4-(methylsulfonyl)morpholine

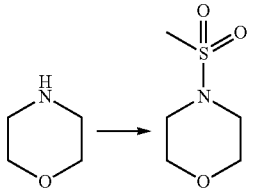

To a solution of morpholine (2.00 mL, 22.96 mmol) in DCM (40 mL) was added TEA (3.20 mL, 22.96 mmol) at about −20° C., then methanesulfonyl chloride (2.68 mL, 34.4 mmol) was added dropwise at about −20° C. The reaction mixture was stirred at about −20° C. for about 2 h, then warmed to rt. The mixture was partitioned with saturated aqueous $NH_4Cl$ (100 mL) and DCM (3×50 mL). The combined organic layers were concentrated and purified by silica gel chromatography eluting with a gradient of 0-100% EtOAc/heptane to give 4-(methylsulfonyl)morpholine (3.95 g, 100%) as a white solid: $^1$H NMR (DMSO-$d_6$) δ 3.70-3.60 (m, 4H), 3.12-3.04 (m, 4H), 2.89 (s, 3H).

Preparation #42: methyl 5-(chloromethyl)-3-methylfuran-2-carboxylate

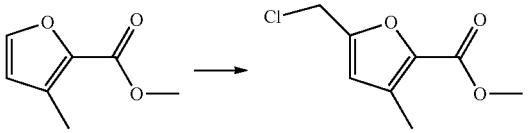

To a solution of methyl 3-methylfuran-2-carboxylate (8.00 g, 57.1 mmol) in DCM (285 mL) was added zinc chloride (2.14 g, 15.7 mmol) and paraformaldehyde (2.2 mL, 82 mmol). The solution was warmed to about 35° C. HCl gas was bubbled through the reaction mixture for about 20 min.

The mixture was partitioned with water (50 mL) and DCM (3×30 mL). The combined organic layers were concentrated and purified by silica gel chromatography eluting with a gradient of 0-50% EtOAc/heptane to give methyl 5-(chloromethyl)-3-methylfuran-2-carboxylate (8.24 g, 77%) as a white solid: LC/MS (Table 1, Method n) $R_t$=0.69 min; MS m/z: 189 $(M+H)^+$.

Preparation #43: cis-methyl 5-((t-butoxycarbonylamino)methyl)-3-methyltetrahydrofuran-2-carboxylate

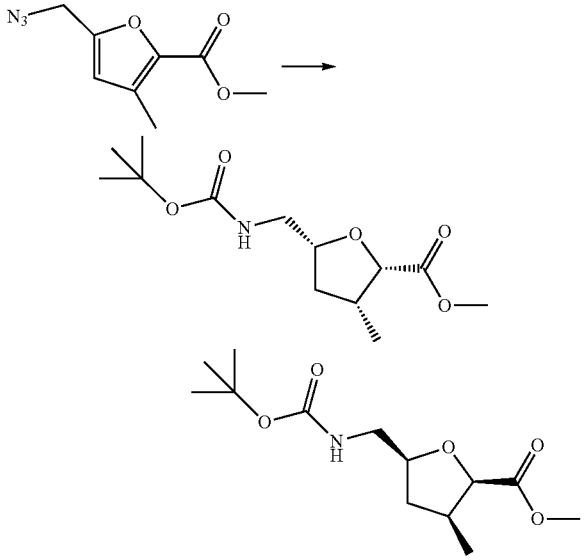

A solution of methyl 5-(azidomethyl)-3-methylfuran-2-carboxylate (3.10 g, 15.88 mmol, prepared using General Procedure JJJJ from Preparation #42 and sodium azide) in MeOH (50 mL) was added to a suspension of 5% Rh/C (0.31 g, 3.01 mmol) and di-tert-butyl dicarbonate (4.16 g, 19.06 mmol) in a 50 mL pressure bottle. The reaction mixture was stirred under 40 psi of hydrogen at about 50° C. for about 3.5 days. The mixture was filtered through a nylon membrane. The organic solvent was concentrated under reduced pressure to give cis-methyl 5-((t-butoxycarbonylamino)methyl)-3-methyltetrahydrofuran-2-carboxylate (4.19 g, 81%) as a brown oil: $^1$H NMR ($CDCl_3$) δ 5.70 (s, 1H), 4.43-4.46 (d, 1H), 4.28-4.12 (m, 1H), 3.75 (s, 3H), 3.50-3.30 (m, 2H), 2.75-2.55 (m, 1H), 1.95-2.05 (m, 1H), 1.65-1.48 (m, 1H), 1.45 (s, 9H), 1.03-0.97 (d, 3H).

Preparation #44: (1S,3R,4S)-3-ethyl-4-(6H-pyrrolo[2,3-e][1,2,4]triazolo[4,3-a]pyrazin-1-yl)cyclopentanamine and (1S,3R,4S)-3-ethyl-4-(6-tosyl-6H-pyrrolo[2,3-e][1,2,4]triazolo[4,3-a]pyrazin-1-yl)cyclopentanamine

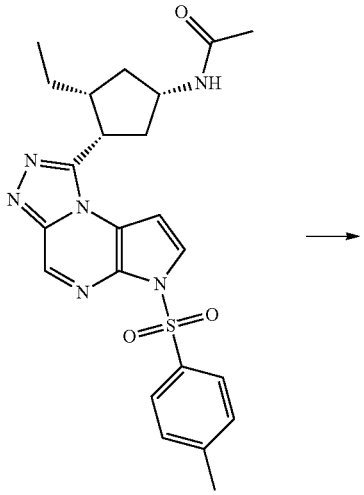

-continued

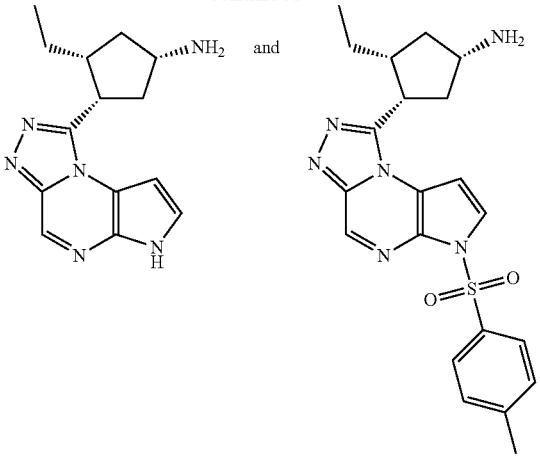

To a mixture of N-((1S,3R,4S)-3-ethyl-4-(6-tosyl-6H-pyrrolo[2,3-e][1,2,4]triazolo[4,3-a]pyrazin-1-yl)cyclopentyl)acetamide (5.0 g, 10.7 mmol, Example #8 Step L) and THF (110 mL) was added aqueous HCl (6 N, 63 mL, 375 mmol). The reaction was heated at about 95° C. for about 20 h and then cooled to ambient temperature and concd under reduced pressure. To the resulting brown residue was added DCM (100 mL) and the solution was washed with saturated $NaHCO_3$ (3×50 mL). The aqueous portion was extracted with DCM (3×50 mL). The combined organic layers were washed with brine (100 mL), dried over anhydrous $MgSO_4$, filtered, and concd under reduced pressure. The material was purified by chromatography on silica gel eluting with 0-100% DCM/MeOH/$NH_4OH$ (950:45:5) to give a mixture of (1S,3R,4S)-3-ethyl-4-(6H-pyrrolo[2,3-e][1,2,4]triazolo[4,3-a]pyrazin-1-yl)cyclopentanamine and (1S,3R,4S)-3-ethyl-4-(6-tosyl-6H-pyrrolo[2,3-e][1,2,4]triazolo[4,3-a]pyrazin-1-yl)cyclopentanamine (3.2 g, 70%) in a 1:10 ratio based on H-NMR as an off-white solid: LC/MS (Table 1, Method a) $R_t$=1.75 min; MS m/z: 425 $(M+H)^+$.

Preparation #45: Methyl 5-tosyl-5H-pyrrolo[2,3-b]pyrazine-2-carboxylate

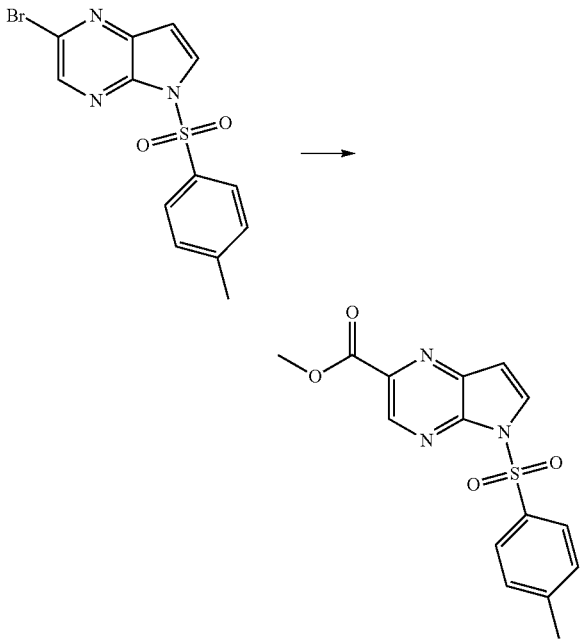

CO was bubbled into an orange solution of 2-bromo-5-tosyl-5H-pyrrolo[2,3-b]pyrazine (50.0 g, 142 mmol, Example #7, step B) in DMF (2.50 L) within a 5 L round bottom flask for about 2 min. Bis(triphenylphosphine)-palladium(II) dichloride (9.96 g, 14.2 mmol), TEA (59 mL, 423 mmol) and MeOH (173.0 mL, 4259 mmol) were added and the flask was fitted with a balloon of CO. The mixture was heated at about 95° C. under an atmosphere of CO (1 atmosphere). After stirring overnight, the reaction mixture was cooled to ambient temperature overnight and poured into ice water (3.2 L). The mixture was stirred for about 10 min and the precipitate was collected by filtration, while washing with water, and dried for 1 h. The crude material was dissolved in DCM, separated from residual water, dried over anhydrous $MgSO_4$, filtered, added silica gel, and concd under reduced pressure to prepare for chromatography. The crude material was purified by silica gel column chromatography eluting with 0-5% MeOH in DCM to yield methyl 5-tosyl-5H-pyrrolo[2,3-b]pyrazine-2-carboxylate with 5 mol % DCM as an excipient (40.7 g, 86%, 93% purity): LC/MS (Table 1, Method a) $R_t$=2.35 min; MS m/z 332 $(M+H)^+$.

Preparation #46: 5-Tosyl-5H-pyrrolo[2,3-b]pyrazine-2-carboxylic acid

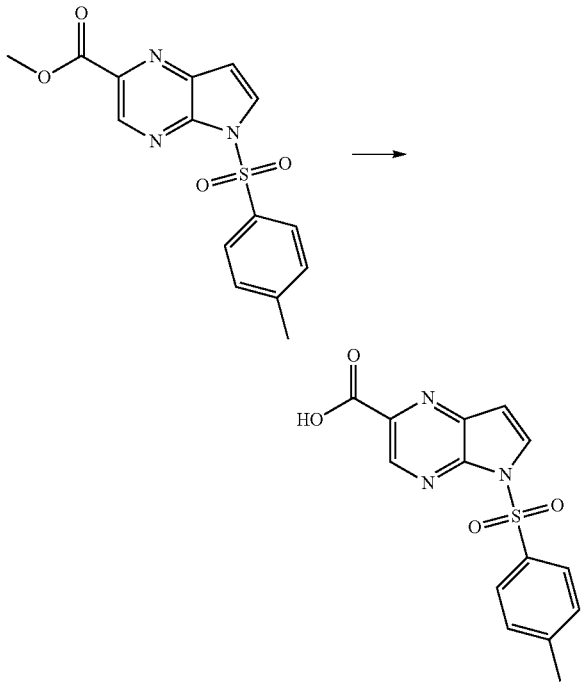

HCl (6 N aqueous, 714 mL) was added to a yellow solution of methyl 5-tosyl-5H-pyrrolo[2,3-b]pyrazine-2-carboxylate (17.8 g, 53.6 mmol, Preparation #45) in 1,4-dioxane (715 mL) within a 2 L round bottom flask, and the mixture was heated at about 60° C. for about 16 h. The reaction mixture was cooled to ambient temperature. The organic solvent was removed under reduced pressure and the precipitate was collected, washed with water, and dried to yield 5-tosyl-5H-pyrrolo[2,3-b]pyrazine-2-carboxylic acid (14.4 g, 85%) as a yellow solid: LC/MS (Table 1, Method a) $R_t$=1.63 min; MS m/z 316 $(M-H)^-$.

Preparation #47: tert-Butyl 5-tosyl-5H-pyrrolo[2,3-b]pyrazin-2-ylcarbamate

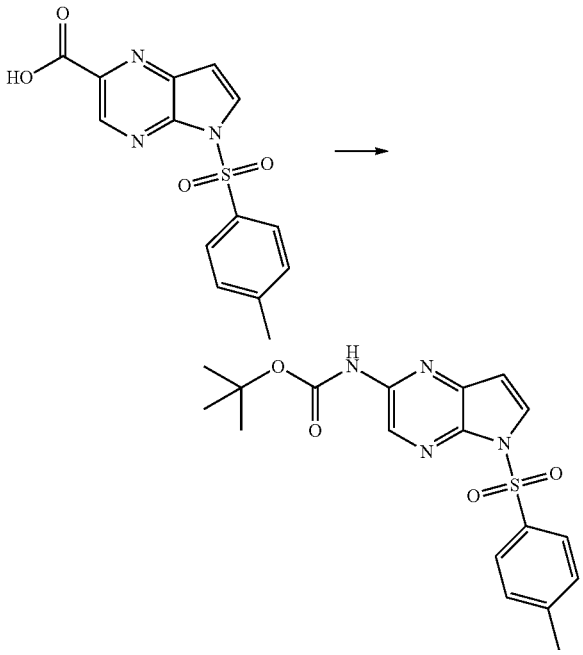

In a 500 mL round bottom flask, 5-tosyl-5H-pyrrolo[2,3-b]pyrazine-2-carboxylic acid (14.4 g, 45.3 mmol, Preparation #46), diphenylphosphoryl azide (9.78 mL, 45.3 mmol) and TEA (13.9 mL, 100 mmol) in t-BuOH (200 mL) were added to give an orange suspension. The mixture was heated at about 70° C. for about 16 h, cooled to ambient temperature and the insoluble material was filtered off. The solvent was removed under reduced pressure and the crude material was purified by silica gel column chromatography eluting with 25-60% EtOAc in heptane over 30 min to yield tert-butyl 5-tosyl-5H-pyrrolo[2,3-b]pyrazin-2-ylcarbamate (9.75 g, 54%) as an off-white solid: LC/MS (Table 1, Method a) $R_t$=2.79 min; MS m/z 389 $(M+H)^+$.

Preparation #48: 2-bromo-1-(4-(dibenzylamino)-2-methylcyclopentyl)ethanone

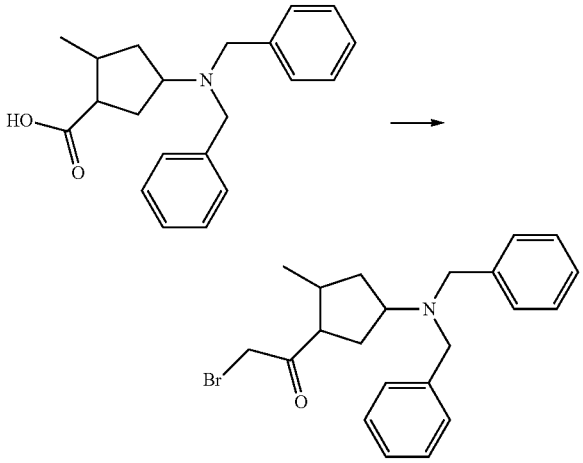

Oxalyl chloride (4.37 mL, 49.9 mmol) was slowly added to a solution of 4-(dibenzylamino)-2-methylcyclopentanecarboxylic acid (7.34 g, 22.7 mmol, Example #7, step I) in DCM (100 mL), (note: mild gas evolution) followed by a dropwise addition of DMF (0.26 mL, 3.41 mmol). The mixture was stirred at ambient temperature for about 14 h. The solvent was removed under reduced pressure to yield a beige amorphous solid, which was dissolved in THF and MeCN (1:1, 100 mL) and added to a solution of trimethylsilyldiazomethane (2 M in $Et_2O$, 39.7 mL, 79 mmol) in THF and MeCN (1:1, 100 mL) at about 0° C. The resulting mixture was stirred at about 0° C. for about 3h and then was quenched by a dropwise addition of HBr (48% aqueous, 25 mL, 221 mmol). The resulting mixture was neutralized by a dropwise addition of saturated aqueous $NaHCO_3$ (300 mL) and the layers were separated. The organic layer was dried over anhydrous $MgSO_4$ and concd under reduced pressure. The residue was purified by silica gel flash chromatography eluting with 5% to 45% of EtOAc in heptane to yield 2-bromo-1-(4-(dibenzylamino)-2-methylcyclopentyl)ethanone (6.3 g, 69%) as a yellow oil: LC/MS (Table 1, Method a) $R_t$=2.90 min; MS m/z 400, 402 $(M+H)^+$.

Preparation #49: tert-Butyl 2-(4-(dibenzylamino)-2-methylcyclopentyl)-2-oxoethyl(5-tosyl-5H-pyrrolo[2,3-b]pyrazin-2-yl)carbamate

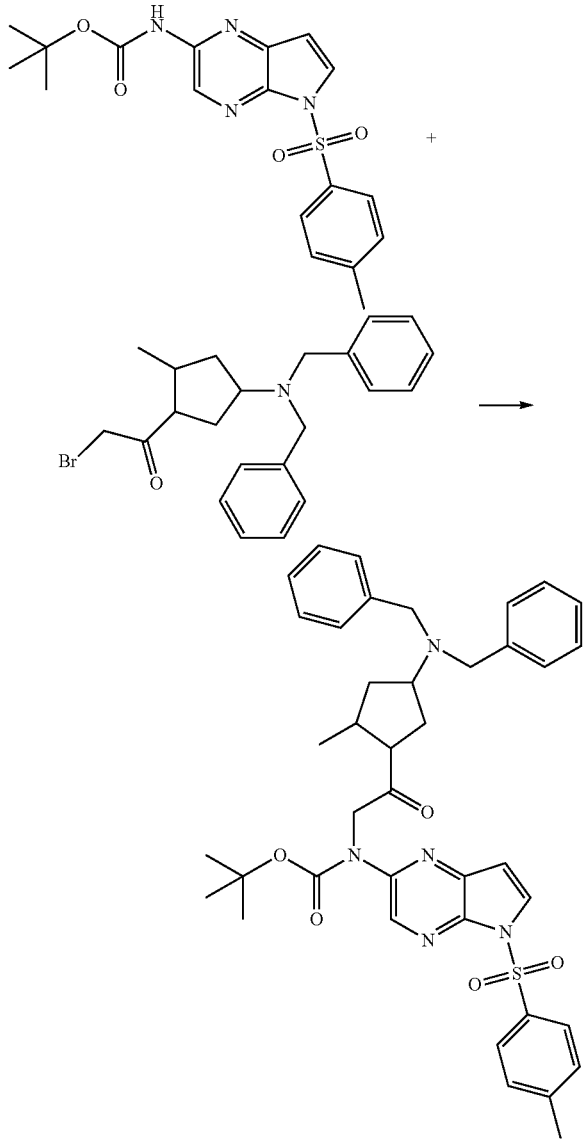

A solution of tert-butyl 5-tosyl-5H-pyrrolo[2,3-b]pyrazin-2-ylcarbamate (0.59 g, 1.519 mmol, Example #7, Step C) in DMF (5 mL) was added dropwise to a suspension of NaH (60% dispersion in mineral oil, 0.058 g, 1.45 mmol) in DMF (5 mL), at about 0° C. The resulting mixture was stirred at about 0° C. for about 30 min and then added dropwise to a solution of 2-bromo-1-(4-(dibenzylamino)-2-methylcyclopentyl)ethanone (0.73 g, 1.8 mmol) in DMF (10 mL) at about 0° C. The resulting mixture was stirred at about 0° C. for about 1 h and the solvent was removed under reduced pressure. The residue was partitioned between saturated aqueous $NaHCO_3$ and EtOAc (100 mL each). The organic phase was separated, dried over anhydrous $MgSO_4$ and concd under reduced pressure to yield tert-butyl 2-(4-(dibenzylamino)-2-methylcyclopentyl)-2-oxoethyl(5-tosyl-5H-pyrrolo[2,3-b]pyrazin-2-yl)carbamate (1.04 g, 97%) as a yellow amorphous solid: LC/MS (Table 1, Method a) $R_t$=3.30 min; MS m/z 708 $(M+H)^+$.

Preparation #50:1-(4-(dibenzylamino)-2-methylcyclopentyl)-2-(5-tosyl-5H-pyrrolo[2,3-b]pyrazin-2-ylamino)ethanone

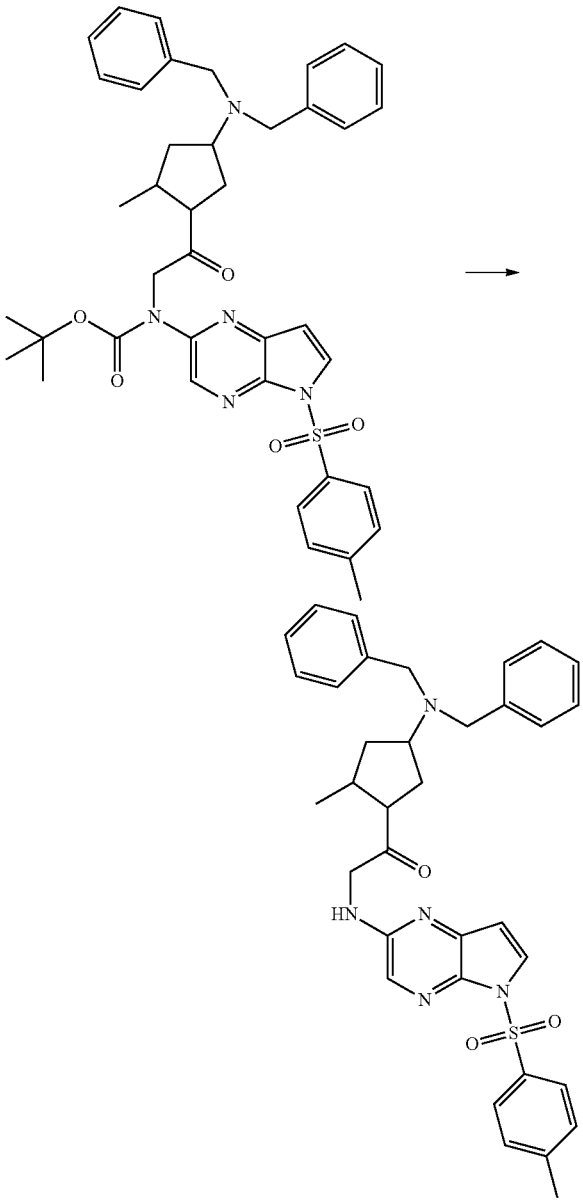

tert-Butyl 2-(4-(dibenzylamino)-2-methylcyclopentyl)-2-oxo ethyl(5-tosyl-5H-pyrrolo[2,3-b]pyrazin-2-yl)carbamate (6.19 g, 8.75 mmol, Preparation #49) was dissolved in HCl (4 N in 1,4-dioxane, 25 mL). The reaction mixture was stirred at ambient temperature for about 2 h. The solvent was removed under reduced pressure and the residue partitioned between saturated aqueous $NaHCO_3$ and EtOAc (100 mL each). The organic phase was washed with brine (80 mL), dried over anhydrous $MgSO_4$ and concd under reduced pressure to yield 1-(4-(dibenzylamino)-2-methylcyclopentyl)-2-(5-tosyl-5H-pyrrolo[2,3-b]pyrazin-2-ylamino)ethanone (5.2 g, 98%) as a brown amorphous solid: LC/MS (Table 1, Method a) $R_t$=3.00 min; MS m/z 608 $(M+H)^+$.

Preparation #51: N,N-dibenzyl-3-methyl-4-(3-tosyl-3H-imidazo[1,2-a]pyrrolo[2,3-e]pyrazin-8-yl)cyclopentanamine

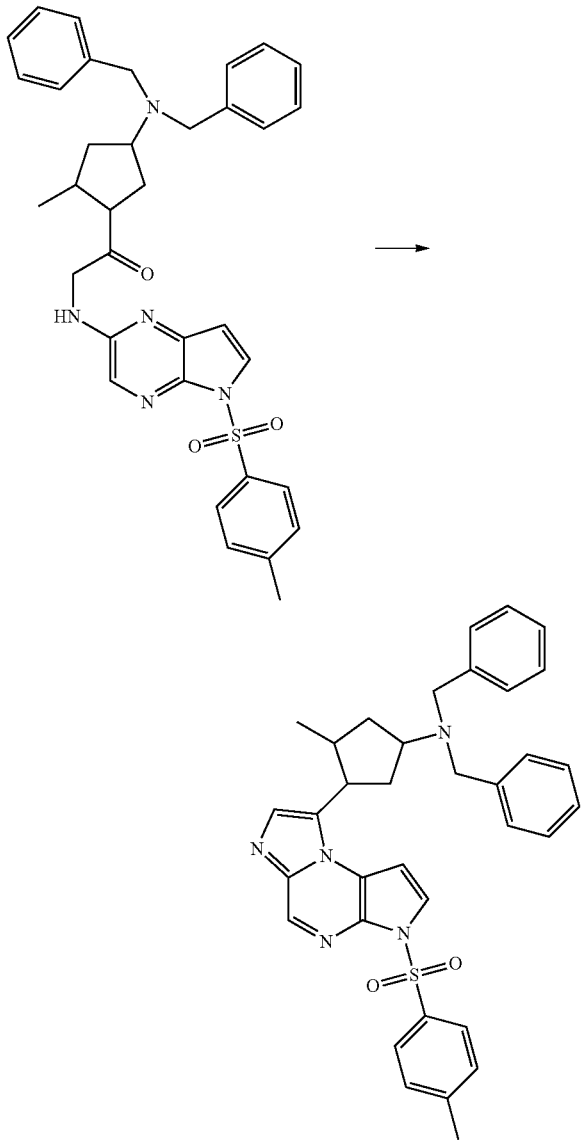

A mixture of 1-(4-dibenzylamino)-2-methylcyclopentyl)-2-(5-tosyl-5H-pyrrolo[2,3-b]pyrazin-2-ylamino)ethanone (5.32 g, 8.75 mmol, Preparation #50) and Lawesson's reagent (1.88 g, 4.64 mmol) was heated at about 60° C. for about 2 h. Lawesson's reagent (1.88 g, 4.64 mmol) was added. The reaction mixture was stirred at about 60° C. for about 1 h. The solvent was removed under reduced pressure and the residue purified by silica gel flash chromatography eluting with a gradient of 0-8% MeOH in DCM to yield N,N-dibenzyl-3-methyl-4-(3-tosyl-3H-imidazo[1,2-a]pyrrolo[2,3-e]pyrazin-8-yl)cyclopentanamine (4.47 g, 87%) as a brown amorphous solid: LC/MS (Table 1, Method a) $R_t$=2.99 min; MS m/z 590 $(M+H)^+$.

Preparation #52: N,N-dibenzyl-3-(3H-imidazo[1,2-a]pyrrolo[2,3-e]pyrazin-8-yl)-4-methylcyclopentanamine

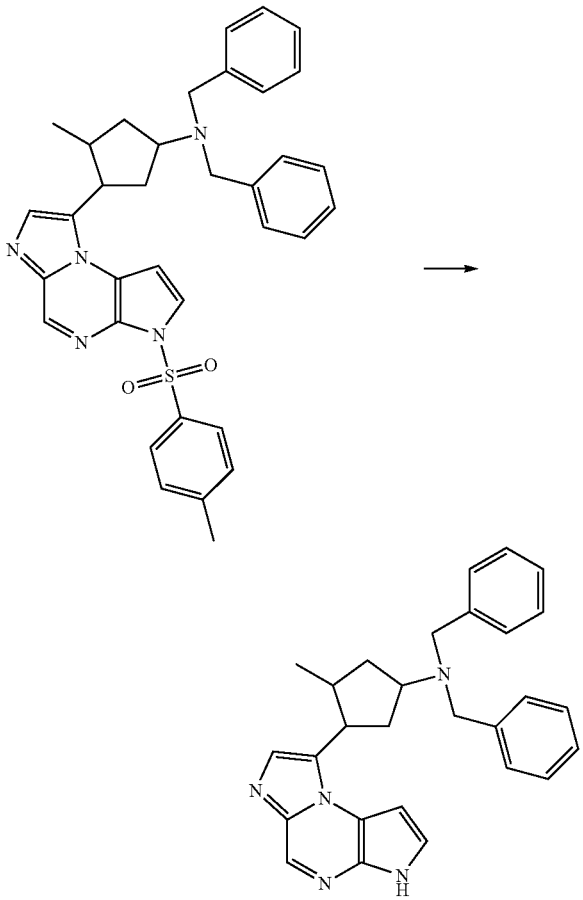

N,N-Dibenzyl-3-methyl-4-(3-tosyl-3H-imidazo[1,2-a]pyrrolo[2,3-e]pyrazin-8-yl)cyclopentan-amine (4.47 g, 7.58 mmol, Preparation #51) was dissolved in 1,4-dioxane (40 mL). NaOH (2 N aqueous, 4 mL) was added and the reaction mixture was heated at about 90° C. for about 80 min. The organic solvent was removed under reduced pressure and the residue was treated with saturated aqueous $NH_4Cl$ (70 mL) and extracted with DCM (2×60 mL). The combined organic extracts were washed with brine (70 mL), dried over anhydrous $MgSO_4$ and concd under reduced pressure. Purification by silica gel flash chromatography eluting with a gradient of 0-8% MeOH in DCM yielded N,N-dibenzyl-3-(3H-imidazo[1,2-a]pyrrolo[2,3-e]pyrazin-8-yl)-4-methylcyclopentanamine (1.84 g, 56%) as a yellow oil: LC/MS (Table 1, Method a) $R_t$=2.31 min; MS m/z 436 $(M+H)^+$.

Preparation #53: 3-(3H-Imidazo[1,2-a]pyrrolo[2,3-e]pyrazin-8-yl)-4-methylcyclopentanamine

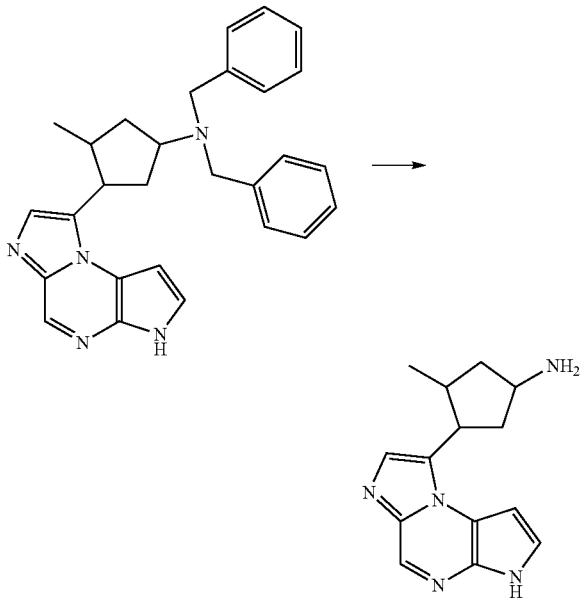

To a mixture of N,N-dibenzyl-3-(3H-imidazo[1,2-a]pyrrolo[2,3-e]pyrazin-8-yl)-4-methylcyclo-pentanamine (1.84 g, 4.22 mmol, Preparation #52) in EtOH (50 mL) was added 20 wt % $Pd(OH)_2$ on C (0.43 g, 0.61 mmol) and the resulting mixture was shaken under hydrogen pressure of about 50 psi on a Parr shaker at about 50° C. for about 2 h. The catalyst was filtered off using a pad of Celite®, 20 wt % $Pd(OH)_2$ on C (0.43 g, 0.61 mmol) was added, and the mixture was shaken under hydrogen pressure of about 50 psi on a Parr shaker at about 50° C. for about 16 h. The catalyst was filtered off using a pad of Celite®, 20 wt % $Pd(OH)_2$ on C (0.43 g, 0.61 mmol) was added, and the mixture was shaken under hydrogen pressure of about 50 psi on a Parr shaker at about 50° C. for about 4 h. The catalyst was filtered off using a pad of Celite® and the filtrate was concd under reduced pressure to yield 3-(3H-imidazo[1,2-a]pyrrolo[2,3-e]pyrazin-8-yl)-4-methylcyclopentanamine (0.88 g, 82%) as an off-white amorphous solid: LC/MS (Table 1, Method a) $R_t$=0.75 min and 0.87 min; MS m/z 256 $(M+H)^+$.

General Procedure A: Formation of a Hydrazide from a Carboxylic Acid

To a mixture of a 2-hydrazinylpyrrolo[2,3-b]pyrazine (preferably 1 equiv) and a carboxylic acid (1-2 equiv, preferably 1.1-1.3 equiv) in an organic solvent (such as DCM, DMF or THF, preferably DMF) is added a coupling agent such as EDC•HCl or HATU (1.0-2.0 equiv, preferably 1.2-1.6 equiv) with or without an organic base (such as TEA or DIEA, 2-5 equiv, preferably 3-4 equiv). After about 1-72 h (preferably 2-16 h) at about 20-60° C. (preferably about ambient temperature), the reaction is worked up using one of the following methods. If DMF is the solvent, the reaction is first concd under reduced pressure. Method 1: Water is added and the layers are separated. Optionally, the mixture may be filtered through Celite® prior to the separation of the layers. The aqueous layer is then extracted with an organic solvent such as EtOAc or DCM. The combined organic layers are optionally washed with brine, dried over anhydrous $Na_2SO_4$ or $MgSO_4$, filtered or decanted, and concd under reduced pressure. Method 2: The reaction is diluted with an organic solvent such as EtOAc or DCM and is washed with either water or brine or both. The aqueous layer is optionally further extracted with an organic solvent such as EtOAc or DCM. Then the organic layer or combined organic layers are optionally washed with brine, dried over anhydrous $Na_2SO_4$ or $MgSO_4$, filtered or decanted, and concd under reduced pressure. Method 3: The reaction is diluted with an organic solvent such as EtOAc or DCM and water is added. The layers are separated and the organic layer is concd under reduced pressure and directly purified by chromatography.

Illustration of General Procedure A

Preparation #A.1*: (S)-tert-butyl 3-(2-oxo-2-(2-(5-tosyl-5H-pyrrolo[2,3-b]pyrazin-2-yl)hydrazinyl)ethyl)pyrrolidine-1-carboxylate

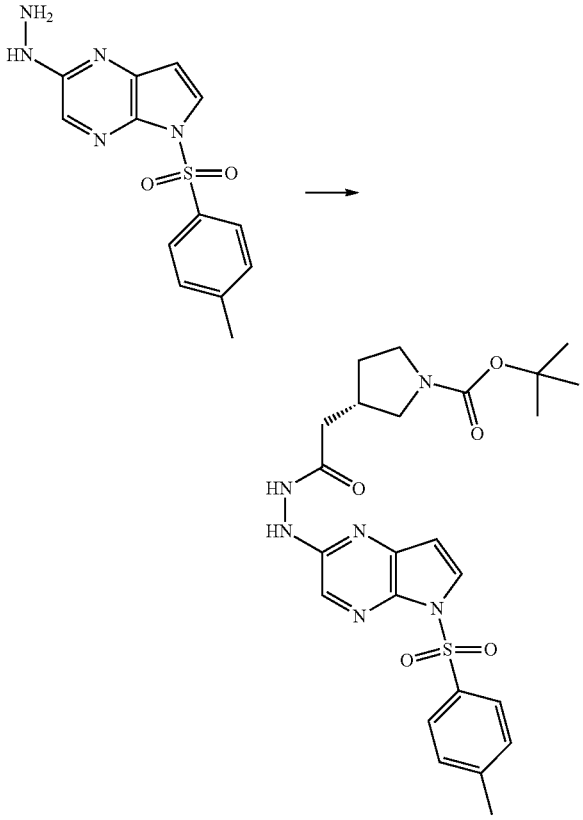

To a solution of (S)-3-carboxymethyl-pyrrolidine-1-carboxylic acid tert-butyl ester (0.756 g, 3.30 mmol, Asta Tech) and 2-hydrazinyl-5-tosyl-5H-pyrrolo[2,3-b]pyrazine (1.0 g, 3.3 mmol, Example #1, Step D) in DMF (33 mL) was added TEA (1.38 mL, 9.89 mmol) followed by the addition of HATU (1.25 g, 3.30 mmol). The resulting mixture was stirred at ambient temperature for about 15 h then concd under reduced pressure. The residue was taken up in EtOAc (100 mL) and washed with water (100 mL). The organic portion was separated, washed with brine (100 mL), dried over anhydrous $Na_2SO_4$, filtered, and concd under reduced pressure to give (S)-tert-butyl 3-(2-oxo-2-(2-(5-tosyl-5H-pyrrolo[2,3-b]pyrazin-2-yl)hydrazinyl)ethyl)pyrrolidine-1-carboxylate as a sticky brown solid (1.90 g, 100%). This material was used without further purification: LC/MS (Table 1, Method c) $R_t$=1.38 min; MS m/z: 515 $(M+H)^+$.

General Procedure B: Cyclization of a Hydrazide

To a solution of a 2-hydrazidyl-5H-pyrrolo[2,3-b]pyrazine (preferably 1 equiv) in an organic solvent (for example 1,4-dioxane) is added a base (such as TEA or DIEA, 1-5 equiv, preferably 2-4 equiv) and $SOCl_2$ (1-5 equiv, preferably 1-2 equiv). The mixture is heated at about 60-100° C. (preferably about 80° C.) for about 1-16 h (preferably about 1-2 h). The reaction mixture is cooled to ambient temperature and worked up using one of the following methods. Method 1: An organic solvent (such as EtOAc or DCM) and water are added. The layers are separated and the aqueous layer is optionally extracted with additional organic solvent. The combined organic layers may be optionally washed with aqueous base (such as $NaHCO_3$) and/or brine, dried over anhydrous $Na_2SO_4$ or $MgSO_4$, then decanted or filtered prior to concentrating under reduced pressure. Method 2: An organic solvent (such as EtOAc or DCM) is added and the organic layer is optionally washed with brine or water, dried over anhydrous $MgSO_4$ or $Na_2SO_4$, filtered or decanted, and concd under reduced pressure. Method 3: The reaction mixture is partitioned between an organic solvent (such as EtOAc or DCM) and saturated aqueous $NaHCO_3$ or brine, dried over anhydrous $Na_2SO_4$ or $MgSO_4$, then decanted or filtered prior to concentrating under reduced pressure.

Illustration of General Procedure B

Preparation #B.1*: tert-butyl (1S,3R)-3-(6-tosyl-6H-pyrrolo[2,3-e][1,2,4]triazolo[4,3-a]pyrazin-1-yl)cyclopentylcarbamate

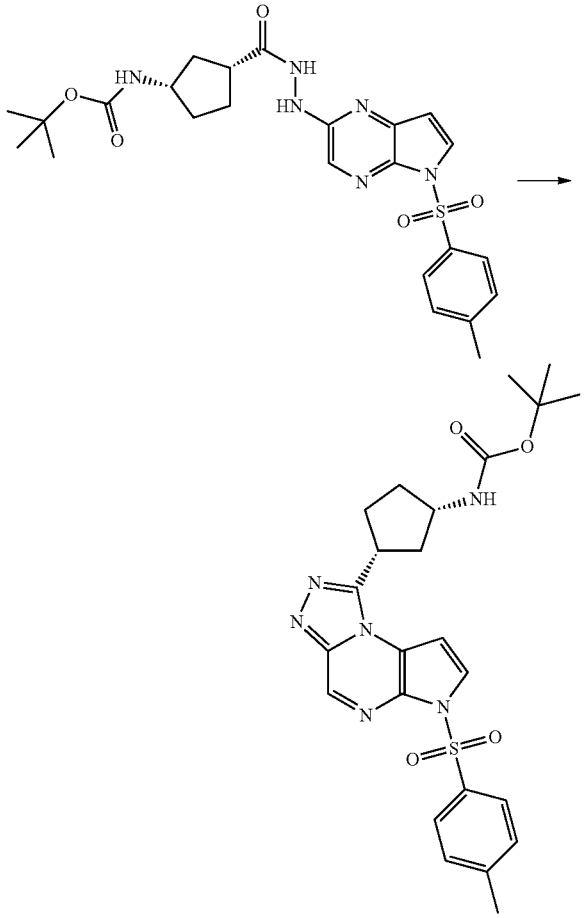

To a solution of tert-butyl (1S,3R)-3-(2-(5-tosyl-5H-pyrrolo[2,3-b]pyrazin-2-yl)hydrazinecarbonyl)cyclopentylcarbamate (9.30 g, 18.1 mmol, prepared using A from Example

#1 Step D, and (1R,3S)-3-tert-butoxycarbonylamino)cyclopentanecarboxylic acid [Peptech]) in 1,4-dioxane (100 mL) was added TEA (10.0 mL, 72.3 mmol) and $SOCl_2$ (2.11 mL, 28.9 mmol). The mixture was heated at about 80° C. for about 1.5 h. The reaction mixture was cooled to ambient temperature, EtOAc (200 mL) and water (200 mL) were added, and the layers were separated. The aqueous portion was extracted with EtOAc (2×100 mL) and the combined organic extracts were washed with saturated aqueous $NaHCO_3$ (100 mL) and brine (100 mL), dried over anhydrous $Na_2SO_4$, filtered, and concd under reduced pressure. The crude material was purified by silica gel chromatography eluting with a gradient of 25-100% EtOAc in DCM to give tert-butyl-(1S,3R)-3-(6-tosyl-6H-pyrrolo[2,3-e][1,2,4]triazolo[4,3-a]pyrazin-1-yl)cyclopentylcarbamate (7.65 g, 85%): LC/MS (Table 1, Method a) $R_t$=2.37 min; MS m/z: 497 $(M+H)^+$.

General Procedure C: Cyclization of a Hydrazide with Loss of Boc-Protecting Group To a solution of an appropriately substituted 2-hydrazidyl-5H-pyrrolo[2,3-b]pyrazine containing a Boc protecting group (preferably 1 equiv) and TEA or DIEA (0-6 equiv, preferably 4 equiv) in an organic solvent (such as 1,4-dioxane or DCM, preferably 1,4-dioxane) is added $SOCl_2$ (2.0-6.0 equiv, preferably 2.5 equiv). The reaction is heated at about 60-120° C. (preferably about 80-90° C.) for about 1-8 h (preferably about 2-4 h) and then worked up using one of the following methods. Method 1: The reaction mixture is filtered and washed with a suitable organic solvent (such as EtOAc or DCM) to give the target compound with no further purification. Method 2: The crude material is diluted with a suitable organic solvent (such as EtOAc or DCM) and saturated aqueous $NaHCO_3$ is added, the layers are separated and the organic portion is dried over anhydrous $Na_2SO_4$ or $MgSO_4$, filtered, and concd under reduced pressure. Method 3: The reaction mixture is washed with a basic aqueous solution (preferably saturated aqueous $NaHCO_3$) and filtered to give the Boc-deprotected target compound with no further purification. If partial Boc-deprotection occurs, the filtrate is extracted with a suitable organic solvent (such as EtOAc or DCM), the layers are separated and the organic portion is dried over anhydrous $Na_2SO_4$ or $MgSO_4$, filtered, and concd under reduced pressure to give the remaining Boc-protected compound. The crude Boc-protected material or partially Boc-protected material obtained above is dissolved in 1,4-dioxane or DCM (preferably 1,4-dioxane) and added to a solution of HCl in an organic solvent (1-6 N, preferably 4 N HCl in 1,4-dioxane) and heated to about 30-60° C. (preferably about 50° C.) for about 1-5 h (preferably about 3h). If a precipitate forms, it is collected and then dissolved in a suitable organic solvent (such as EtOAc or DCM) and washed with a basic aqueous solution (preferably saturated aqueous $NaHCO_3$). If no precipitate forms, the reaction mixture is washed with a basic aqueous solution (preferably saturated aqueous $NaHCO_3$). In either case, the layers are separated and the organic portion is dried over anhydrous $Na_2SO_4$ or $MgSO_4$, filtered, and concd under reduced pressure.

Illustration of General Procedure C

Preparation #C.1 4-(6-tosyl-6H-pyrrolo[2,3-e][1,2,4]triazolo[4,3-a]pyrazin-1-yl)bicyclo[2.2.2]octan-1-amine

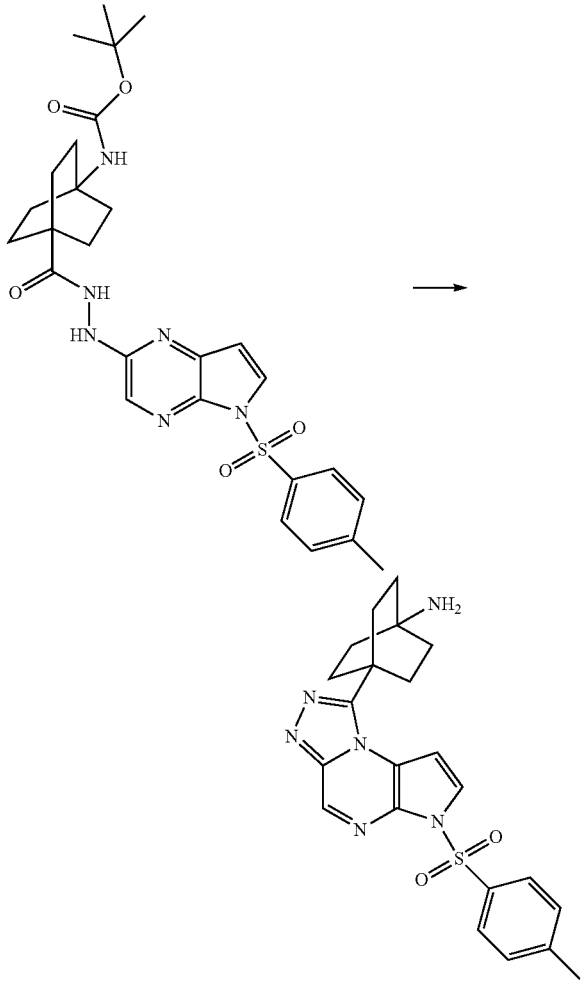

To a solution of tert-butyl 4-(2-(5-tosyl-5H-pyrrolo[2,3-b]pyrazin-2-yl)hydrazinecarbonyl)-bicyclo[2.2.2]octan-1-yl-carbamate (6.1 g, 11.0 mmol, Example #9, Step E), and TEA (6.1 mL, 44.0 mmol) in 1,4-dioxane (110 mL) was added $SOCl_2$ (2.0 mL, 27.5 mmol). The reaction mixture was heated at about 80° C. for about 2 h then cooled to ambient temperature. The reaction mixture was washed with saturated aqueous $NaHCO_3$ (3×50 mL). The layers were separated and the aqueous portion was filtered to give 4-(6-tosyl-6H-pyrrolo[2,3-e][1,2,4]triazolo[4,3-a]pyrazin-1-yl)bicyclo[2.2.2]-octan-1-amine as a brown solid (1.17 g, 24%): LC/MS (Table 1, Method a) $R_t$=1.28 min; MS m/z: 437 $(M+H)^+$. The remaining filtrate was extracted with EtOAc (10 mL). The combined organic layer was dried over anhydrous $MgSO_4$, filtered, and concd under reduced pressure to afford crude tert-butyl 4-(6-tosyl-6H-pyrrolo[2,3-e][1,2,4]triazolo[4,3-a]pyrazin-1-yl)bicyclo[2.2.2]octan-1-yl-carbamate (3.5 g). The crude Boc-protected material was dissolved in 1,4-dioxane (38 mL) and HCl (4 N in 1,4-dioxane, 8 mL) was added. The reaction mixture was heated to about 50° C. for about 3h. The precipitate formed was collected by filtration. The solid was dissolved in DCM (50 mL), and washed with saturated aqueous $NaHCO_3$ (3×20 mL). The layers were separated and the organic portion was dried over anhydrous $MgSO_4$, filtered, and concd under reduced pressure to give additional 4-(6-tosyl-6H-pyrrolo[2,3-e][1,2,4]triazolo[4,3-a]pyrazin-1-yl)bicyclo[2.2.2]octan-1-amine as a brown solid (2.3 g, 50% over 2 steps): LC/MS (Table 1, Method a) $R_t$=1.28 min; MS m/z: 437 $(M+H)^+$.

General Procedure D: Hydrolysis of a Sulfonamide

To a flask containing a sulfonamide, for example, a sulfonyl-protected pyrrole, (preferably 1 equiv) in an organic solvent (such as 1,4-dioxane, MeOH, or THF/MeOH, preferably 1,4-dioxane) is added an aqueous base (such as aqueous $Na_2CO_3$ or aqueous NaOH, 1-30 equiv, preferably 2-3 equiv for aqueous NaOH, preferably 15-20 equiv for aqueous $Na_2CO_3$). The mixture is stirred at about 25-100° C. (preferably about 60° C.) for about 1-72 h (preferably about 1-16 h). In cases where the reaction does not proceed to completion as monitored by TLC, LC/MS, or HPLC, additional aqueous base (such as aqueous $Na_2CO_3$, 10-20 equiv, preferably 10 equiv or aqueous NaOH, 1-5 equiv, preferably 1-2 equiv) and/or a cosolvent (such as EtOH) is added. The reaction is continued at about 25-100° C. (preferably about 60° C.) for about 0.25-3 h (preferably about 1-2 h). In any case where an additional base labile group is present (for example, an ester a trifluoromethyl, or a cyano group), this group may also be hydrolyzed. The reaction is worked up using one of the following methods. Method 1. The organic solvent is optionally removed under reduced pressure and the aqueous solution is neutralized with the addition of a suitable aqueous acid (such as aqueous HCl). A suitable organic solvent (such as EtOAc or DCM) and water are added, the layers are separated, and the organic solution is dried over anhydrous $Na_2SO_4$ or $MgSO_4$, filtered, and concd to dryness under reduced pressure to give the target compound. Method 2. The organic solvent is optionally removed under reduced pressure, a suitable organic solvent (such as EtOAc or DCM) and water are added, the layers are separated, and the organic solution is dried over anhydrous $Na_2SO_4$ or $MgSO_4$, filtered, and concd to dryness under reduced pressure to give the target compound. Method 3. The reaction mixture is concd under reduced pressure and directly purified by one of the subsequent methods.

Illustration of General Procedure D

Preparation #D.1*: (3R,4R)-tert-butyl-3-(6H-imidazo[1,5-a]pyrrolo[2,3-e]pyrazin-1-yl)-4-methylpiperidine-1-carboxylate

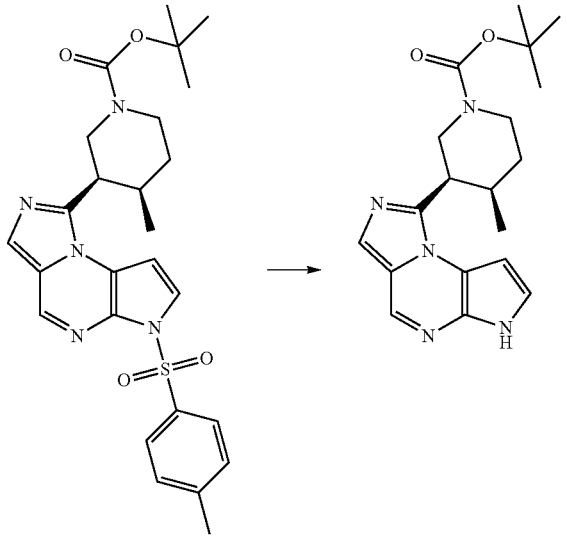

To a solution of (3R,4R)-tert-butyl 4-methyl-3-(6-tosyl-6H-imidazo[1,5-a]pyrrolo[2,3-e]pyrazin-1-yl)piperidine-1-carboxylate (40 g, 78 mmol, Example #5 Step H) in 1,4-dioxane (160 mL) was added NaOH (1 N aqueous, 157 mL). The reaction was heated at about 60° C. for about 1 h. The reaction was allowed to cool to ambient temperature. The reaction was neutralized with aqueous HCl (4 N, 50 mL). The layers and extracted with DCM (2×300 mL). The combined organic extracts were washed with brine (400 mL), dried over anhydrous $Na_2SO_4$, filtered then concd in vacuo. The product was purified by chromatography on silica gel (330 g) using 1-5% MeOH in DCM to give (3R,4R)-tert-butyl 3-(6H-imidazo[1,5-a]pyrrolo[2,3-e]pyrazin-1-yl)-4-methylpiperidine-1-carboxylate (30 g, 99%): LC/MS (Table 1, Method b) $R_t$=2.00 min; MS m/z: 356 $(M+H)^+$.

TABLE D.1

Examples prepared using General Procedure D with NaOH

| Sulfonamide | Product | Ex # | $R_t$ min (Table 1, Method) | m/z ESI+ $(M + H)^+$ |
|---|---|---|---|---|
| (S)-1-((1-(cyclopropylsulfonyl) pyrrolidin-3-yl)methyl)-6-tosyl-6H-pyrrolo[2,3-e][1,2,4]triazolo [4,3-a]pyrazine (prepared using C from Preparation #A.1, and K with cyclopropanesulfonyl chloride and TEA) | 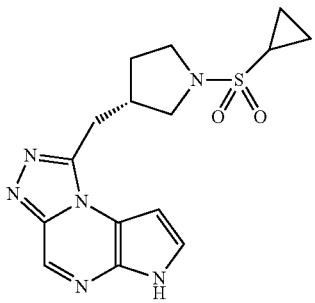 | D. 1. 1* | 1.34 (a) | 347 |

TABLE D.1-continued

| Examples prepared using General Procedure D with NaOH | | | | |
|---|---|---|---|---|
| Sulfonamide | Product | Ex # | $R_t$ min (Table 1, Method) | m/z ESI+ $(M + H)^+$ |
| N-(1-((6-tosyl-6H-pyrrolo[2,3-e][1,2,4]triazolo[4,3-a]pyrazin-1-yl)methyl)cyclobutyl)-cyclopropanesulfonamide (prepared using A fromExample #1 Step D and 2-(1-(tert-butoxycarbonyl-amino)cyclobutyl)acetic acid [prepared as described in Eur. J. Med.Chem, 1999, 34, 363] with EDC•HCl, B with TEA, E with HCl, K with cyclopropanesulfonyl chloride and DIEA) | 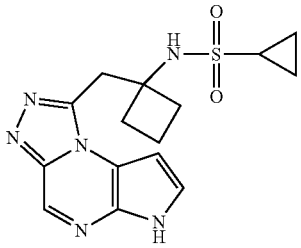 | D.1.2 | 1.60 (a) | 347 |
| N-((1S,3R)-3-(6-tosyl-6H-pyrrolo[2,3-e][1,2,4]triazolo[4,3-a]pyrazin-1-yl)cyclopentyl)cyclo-propanecarboxamide (prepared using E from Preparation #B.1 with HCl, H with cyclopropanecarboxylic acid, EDC, and DIEA) | 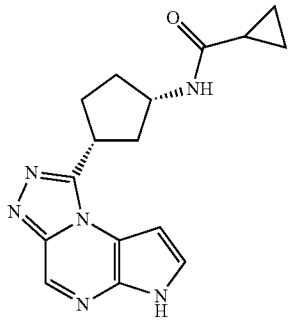 | D.1.3* | 1.15 (c) | 311 |
| 2-cyclopropyl-N-((1S,3R)-3-(6-tosyl-6H-pyrrolo[2,3-e][1,2,4]triazolo[4,3-a]pyrazin-1-yl)cyclopentyl)acetamide (prepared using using E from Preparation #B.1 with HCl, H with cyclopropylacetic acid [Lancaster], EDC, and DIEA) | 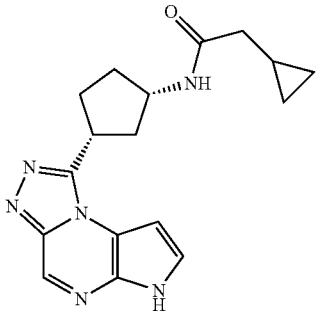 | D.1.4* | 1.17 (c) | 325 |
| 4-fluoro-N-((1R,3R)-3-(6-tosyl-6H-pyrrolo[2,3-e][1,2,4]triazolo[4,3-a]pyrazin-1-yl)cyclopentyl)aniline (prepared using PP with Example #2 Step F, 4-fluorophenyl boronic acid, and DIEA) | 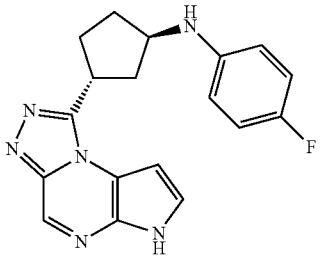 | D.1.5* | 1.91 (a) | 337 |
| 4-chloro-N-((1R,3R)-3-(6-tosyl-6H-pyrrolo[2,3-e][1,2,4]triazolo[4,3-a]pyrazin-1-yl)cyclopentyl)aniline (prepared using PP with Example #2 Step F, 4-chlorophenylboronic acid and DIEA) | 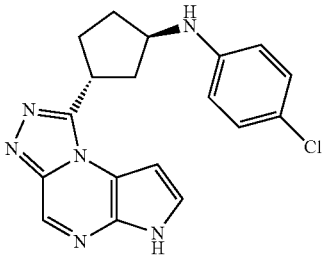 | D.1.6* | 2.07 (a) | 353 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| 3,4-dichloro-N-((1R,3R)-3-(6-tosyl-6H-pyrrolo[2,3-e][1,2,4]triazolo[4,3-a]pyrazin-1-yl)cyclopentyl)aniline (prepared using PP with Example #2 Step F, 3,4-dichlorophenylboronic acid and DIEA) | 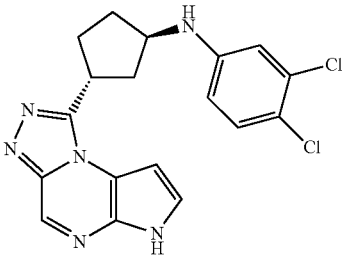 | D.1.7* | 2.24 (a) | 387 |
| 4-methoxy-N-((1R,3R)-3-(6-tosyl-6H-pyrrolo[2,3-e][1,2,4]triazolo[4,3-a]pyrazin-1-yl)cyclopentyl)aniline (prepared using PP with Example #2 Step F, 4-methoxyphenyl boronic acid and DIEA) | 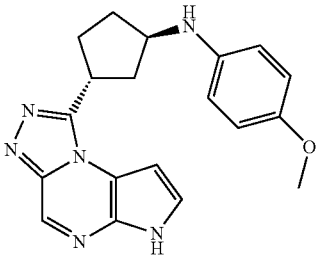 | D.1.8* | 1.74 (a) | 349 |
| 4-methoxy-N-(4-methoxyphenyl)-N-((1R,3R)-3-(6-tosyl-6H-pyrrolo[2,3-e][1,2,4]triazolo[4,3-a]pyrazin-1-yl)cyclopentyl)aniline (prepared using PP with Example #2 Step F, 4-methoxyphenyl boronic acid and DIEA) | 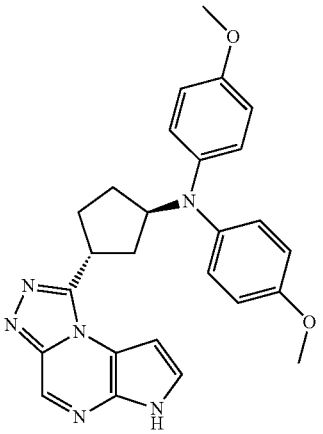 | D.1.9* | 2.30 (a) | 455 |
| N-((1S,3R,4S)-3-ethyl-4-(6-tosyl-6H-pyrrolo[2,3-e][1,2,4]triazolo[4,3-a]pyrazin-1-yl)cyclopentyl)azetidine-1-sulfonamide (Preparation #DD. 1) | 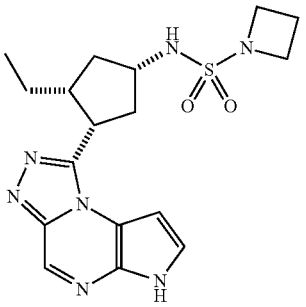 | D.1.10* | 1.81 (a) | 390 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| N-((1S,3R,4S)-3-ethyl-4-(6-tosyl-6H-pyrrolo[2,3-e][1,2,4]triazolo[4,3-a]pyrazin-1-yl)cyclopentyl)-3,3-difluoroazetidine-1-sulfonamide (prepared using DD with Example #8 Step M, 3,3-difluoroazetidine-1-sulfonyl chloride [prepared from CC with 3,3-difluoroazetidine hydrochloride [Matrix] and DIEA] and TEA) | 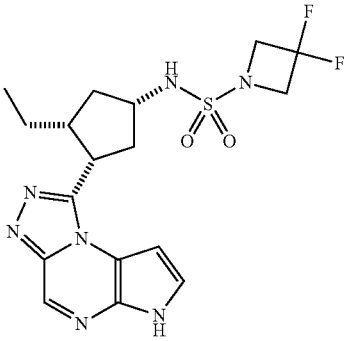 | D.1.11* | 1.97 (a) | 426 |
| (S)-N-((1S,3R,4S)-3-ethyl-4-(6-tosyl-6H-pyrrolo[2,3-e][1,2,4]triazolo[4,3-a]pyrazin-1-yl)cyclopentyl)-2-(trifluoromethyl)pyrrolidine-1-sulfonamide (prepared using DD with Example #8 Step M, (S)-2-(trifluoromethyl)pyrrolidine-1-sulfonyl chloride [prepared from CC with (S)-(-)-2-(trifluoromethyl)pyrrolidine and DIEA] and TEA) | 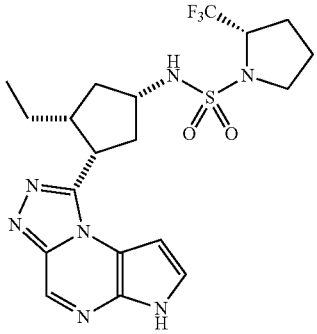 | D.1.12* | 2.13 (a) | 472 |
| N-((1S,3R,4S)-3-ethyl-4-(6-tosyl-6H-pyrrolo[2,3-e][1,2,4]triazolo[4,3-a]pyrazin-1-yl)cyclopentyl)-3,3-difluoropyrrolidine-1-sulfonamide (prepared using DD with Example #8 Step M, 3,3-difluoropyrrolidine-1-sulfonyl chloride [prepared from CC with 3,3-difluoropyrrolidine hydrochloride and DIEA] and TEA) | 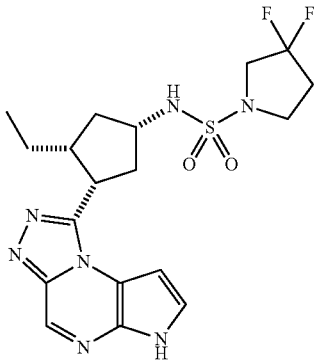 | D.1.13* | 1.98 (a) | 440 |
| N-((1S,3R,4S)-3-ethyl-4-(6-tosyl-6H-pyrrolo[2,3-e][1,2,4]triazolo[4,3-a]pyrazin-1-yl)cyclopentyl)-4,4-difluoropiperidine-1-sulfonamide (prepared using DD with Example #8 Step M, 4,4-difluoropiperidine-1-sulfonyl chloride [prepared from CC with 4,4-difluoropiperidine hydrochloride and DIEA] and TEA) | 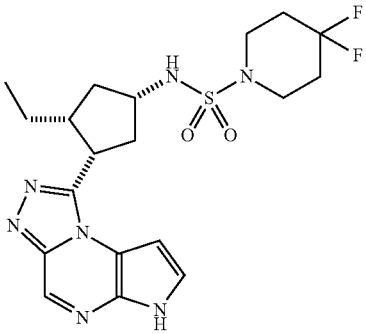 | D.1.14* | 2.01 (a) | 454 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| N-((1S,3R,4S)-3-methyl-4-(6-tosy;-6H-pyrrolo[2,3-e][1,2,4]triazolo[4,3-a]pyrazin-1-yl)cyclopentyl)aniline (prepared using PP from Preparation #19.2, phenylboronic acid, and DIEA) | 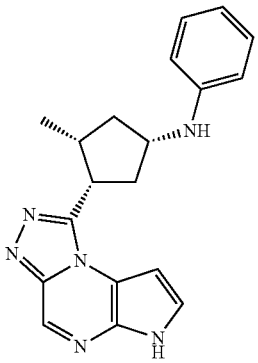 | D.1.15* | 2.01 (a) | 333 |
| 4-methyl-N-((1S,3R,4S)-3-methyl-4-(6-tosyl-6H-pyrrolo[2,3-e][1,2,4]triazolo[4,3-a]pyrazin-1-yl)cyclopentyl)aniline (prepared using PP from Preparation #19.2, p-tolylboronic acid and DIEA) | 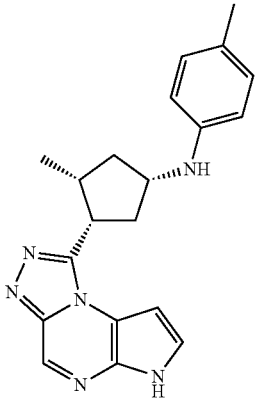 | D.1.16* | 2.08 (a) | 347 |
| 4-chloro-N-((1S,3R,4S)-3-methyl-4-(6-tosyl-6H-pyrrolo[2,3-e][1,2,4]triazolo[4,3-a]pyrazin-1-yl)cyclopentyl)aniline (prepared using PP from Preparation #19.2, 4-chlorophenylboronic acid, and DIEA) | 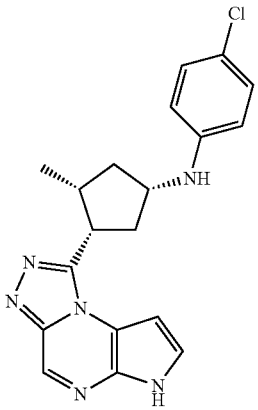 | D.1.17* | 2.25 (a) | 367 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| 4-fluoro-N-((1S,3R,4S)-3-methyl-4-(6-tosyl-6H-pyrrolo[2,3-e][1,2,4]triazolo[4,3-a]pyrazin-1-yl)cyclopentyl)aniline (prepared using PP from Preparation #19.2, 4-fluorophenylboronic acid, and DIEA) | 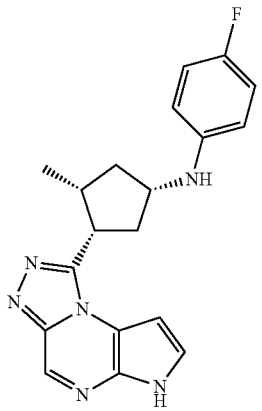 | D.1.18* | 2.05 (a) | 351 |
| 1-(3,3-difluorocyclobutyl)-6-tosyl-6H-imidazo[1,5-a]pyrrolo[2,3-e]pyrazine (prepared using H from Example #5 Step C and 3,3-difluorocyclobutanecarboxylic acid [Waterstone], HATU, and DIEA; Q with Lawesson's reagent and mercury (II) trifluoroacetate) | 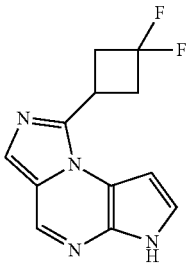 | D.1.19 | 1.63 (b) | 249 |
| 4-((cis-3-(6-tosyl-6H-imidazo[1,5-a]pyrrolo[2,3-e]pyrazin-1-yl)cyclobutoxy)methyl)benzonitrile (prepared using H from Example #5 Step C and Preparation #1 with HATU and DIEA; Q with Lawesson's reagent and mercury (II) trifluoroacetate) | 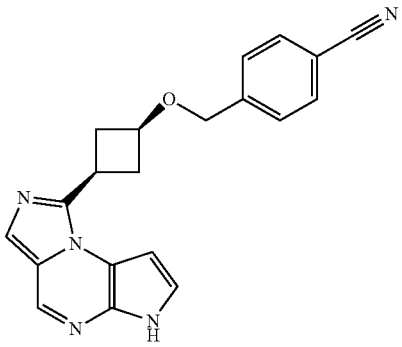 | D.1.20 | 1.81 (b) | 344 |
| N-((1S,3R,4S)-3-ethyl-4-(6-tosyl-6H-pyrrolo[2,3-e][1,2,4]triazolo[4,3-a]pyrazin-1-yl)cyclopentyl)-N-methylcyclopropanesulfonamide (prepared using A from Example #1 Step D and Preparation #Z.1 with HATU and TEA, B with TEA, S with iodomethane and NaH) | 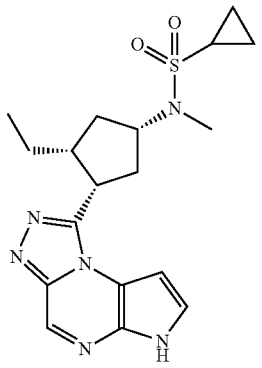 | D.1.21* | 1.75 (a) | 389 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| N-(cyclopropylmethyl)-N-((1S,3R,4S)-3-ethyl-4-(6-tosyl-6H-pyrrolo[2,3e][1,2,4]triazolo[4,3-a]pyrazin-1-yl)cyclopentyl)cyclopropanesulfonamide (prepared using A from Example #1 Step D and Preparation #Z.1 with HATU and TEA, B with TEA, S with (bromomethyl)-cyclopropane and NaH) | 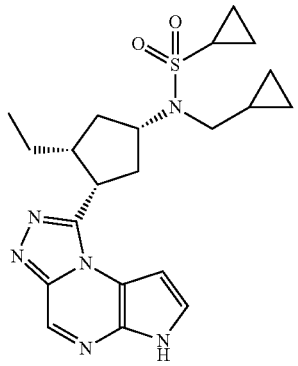 | D.1.22* | 1.98 (a) | 429 |
| 1-methyl-N-((1S,3R,4S)-3-methyl-4-(6-tosyl-6H-pyrrolo[2,3-e][1,2,4]triazolo[4,3-a]pyrazin-1-yl)cyclopentyl)-1H-pyrazole-4-sulfonamide (prepared using K from Preparation #19.2, 1-methyl-1H-pyrazole-4-sulfonyl chloride [Oakwood] and DIEA) | 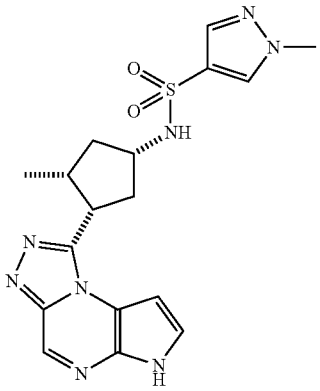 | D.1.23* | 1.60 (a) | 401 |
| N-((1S,3R,4S)-3-ethyl-4-(6-tosyl-6H-pyrrolo[2,3-e][1,2,4]triazolo[4,3-a]pyrazin-1-yl)cyclopentyl)-3,3,3-trifluoropropane-1-sulfonamide (prepared using K from Example #8 Step M and 3,3,3-trifluoropropane-1-sulfonyl chloride [Matrix] and DIEA) | 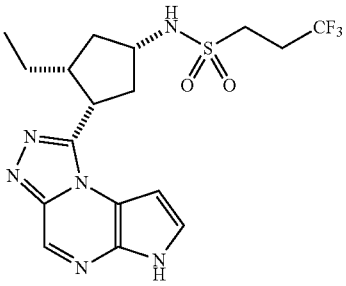 | D.1.24* | 2.05 (a) | 431 |
| N-((3S,5R)-5-ethyl-1-(3-tosyl-3H-imidazo[1,2-a]pyrrolo[2,3-e]pyrazin-8-yl)pyrrolidin-3-yl)cyclopropanesulfonamide (prepared using S from Example #3 Step E and tert-butyl bromoacetate, E with HCl, H with Preparation #E.1, OO) | 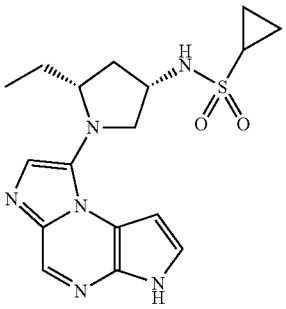 | D.1.25* | 1.60 (a) | 375 |

TABLE D.1-continued

| Examples prepared using General Procedure D with NaOH | | | | |
|---|---|---|---|---|
| Sulfonamide | Product | Ex # | $R_t$ min (Table 1, Method) | m/z ESI+ $(M + H)^+$ |
| N-((1R,3S,4R)-3-ethyl-4-(6-tosyl-6H-pyrrolo[2,3-e][1,2,4]triazolo[4,3-a]pyrazin-1-yl)cyclopentyl)cyclopentane-sulfonamide and N-((1S,3R,4S)-3-ethyl-4-(6-tosyl-6H-pyrrolo[2,3-e][1,2,4]triazolo[4,3-a]pyrazin-1-yl)cyclopentyl)cyclo-pentanesulfonamide (prepared using K from Preparation #Y.1 and cyclopentanesulfonyl chloride, Z with NaOH, A with Example #1 Step D, HATU, and TEA, B with TEA) | 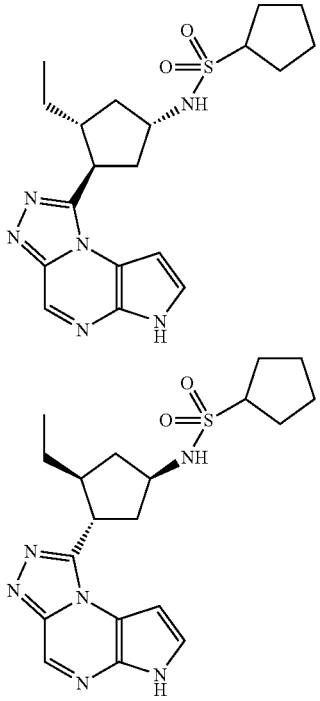 | D.1.26 | 1.77 (a) | 403 |
| (1S,3R)-1-[3-(6-tosyl-6H-pyrrolo[2,3-e][1,2,4]triazolo[4,3-a]pyrazin-1-yl)-isothiazolidin-2-yl-1,1-dioxide]cyclopentane (Preparation #2) | 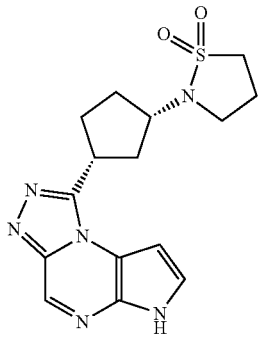 | D.1.27* | 1.47 (a) | 347 |
| 1-((1R,3S)-3-(1H-pyrrol-1-yl)cyclopentyl)-6-tosyl-6H-pyrrolo[2,3-e][1,2,4]triazolo[4,3-a]pyrazine (Preparation #3) | 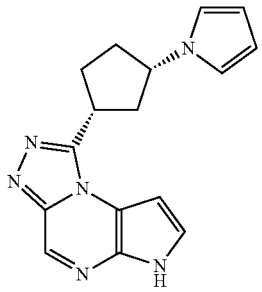 | D.1.28* | 1.82 (a) | 293 |

TABLE D.1-continued

| Examples prepared using General Procedure D with NaOH | | | | |
|---|---|---|---|---|
| Sulfonamide | Product | Ex # | $R_t$ min (Table 1, Method) | m/z ESI+ $(M + H)^+$ |
| N-(4-(6-tosyl-6H-pyrrolo[2,3-e][1,2,4]triazolo[4,3-a]pyrazin-1-yl)bicyclo[2.2.2]octan-1-yl)azetidine-1-sulfonamide (prepared using DD with Example #9, Step F and Preparation #CC.1) | 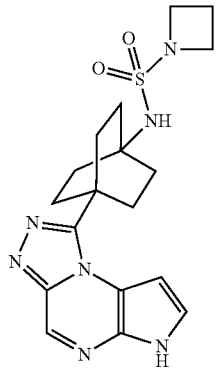 | D.1.29 | 1.44 (a) | 402 |
| 3,3-difluoro-N-(4-(6-tosyl-6H-pyrrolo[2,3-e][1,2,4]triazolo[4,3-a]pyrazin-1-yl)bicyclo[2.2.2]octan-1-yl)azetidine-1-sulfonamide (Preparation #5) | 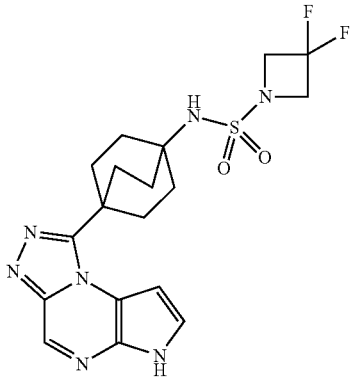 | D.1.30 | 1.61 (a) | 438 |
| 2-(N-((1S,3R,4S)-3-ethyl-4-(6-tosyl-6H-pyrrolo[2,3-e][1,2,4]triazolo[4,3-a]pyrazin-1-yl)cyclopentyl)cyclopropanesulfonamido)ethyl acetate (prepared using A from Preparation #Z.1, Example #1, Step D, HATU, and TEA, B with TEA, S with 2-bromoethyl acetate) | 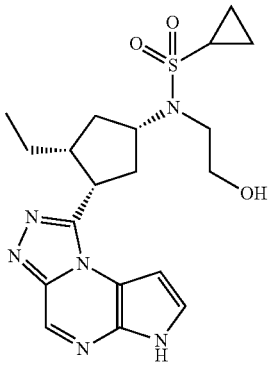 | D.1.31* | 1.54 (a) | 419 |
| 1-((1S,2R,4S)-2-ethyl-4-(4-methoxybenzyloxy)cyclopentyl)-6-tosyl-6H-pyrrolo[2,3-e][1,2,4]triazolo[4,3-a]pyrazine and 1-((1R,2S,4R)-2-ethyl-4-(4-methoxybenzyloxy)cyclopentyl)-6-tosyl-6H-pyrrolo[2,3-e][1,2,4]triazolo[4,3-a]pyrazine (prepared using Z from Preparation #EE.1, A from Example #1, Step D, HATU, and TEA, B with DIEA) | 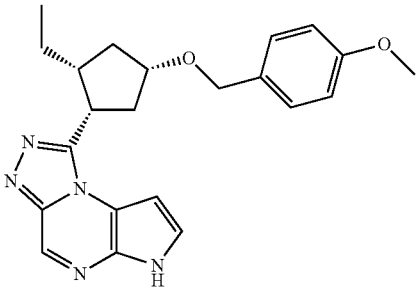 | D.1.32 | 2.02 (b) | 392 |

TABLE D.1-continued

| Examples prepared using General Procedure D with NaOH | | | | |
|---|---|---|---|---|
| Sulfonamide | Product | Ex # | $R_t$ min (Table 1, Method) | m/z ESI+ $(M + H)^+$ |
| | 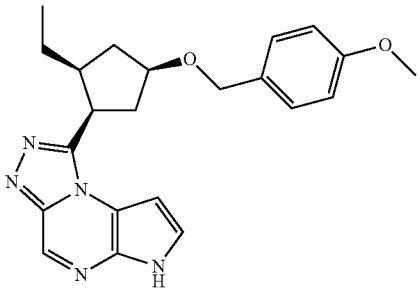 | | | |
| 1-methyl-N-(4-(6-tosyl-6H-pyrrolo[2,3-e][1,2,4]triazolo[4,3-a]pyrazin-1-yl)bicyclo[2.2.2]octan-1-yl)cyclopropane-1-sulfonamide (prepared using K from Preparation #C.1 and Preparation #6) | 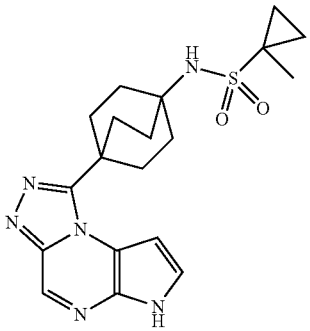 | D.1.33 | 1.48 (a) | 401 |
| 4-methyl-N-((1R,3R)-3-(6-tosyl-6H-pyrrolo[2,3-e][1,2,4]triazolo[4,3-a]pyrazin-1-yl)cyclopentyl)aniline (prepared using PP from Example #2, Step F and p-tolylboronic acid) | 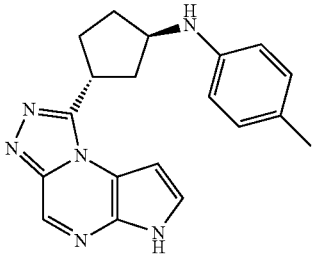 | D.1.34* | 1.89 (b) | 333 |
| N-((1S,3R,4S)-3-ethyl-4-(6-tosyl-6H-pyrrolo[2,3-e][1,2,4]triazolo[4,3-a]pyrazin-1-yl)cyclopentyl)-1-methylcyclopropane-1-sulfonamide (prepared using K from Example #8, Step M and Preparation #6) | 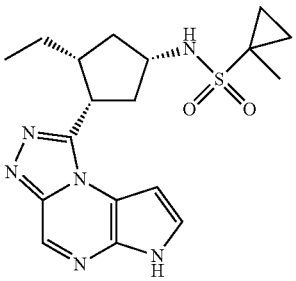 | D.1.35* | 1.66 (a) | 389 |
| 1-((1S,2R,4S)-4-(benzyloxy)-2-ethylcyclopentyl)-6-tosyl-6H-pyrrolo[2,3-e][1,2,4]triazolo[4,3-a]pyrazine and 1-((1R,2S,4R)-4-(benzyloxy)-2-ethylcyclopentyl)-6-tosyl-6H-pyrrolo[2,3-e][1,2,4]triazolo[4,3-a]pyrazine (prepared using EE from benzyl 2,2,2-trichloroacetimidate and Preparation #FF.1) | 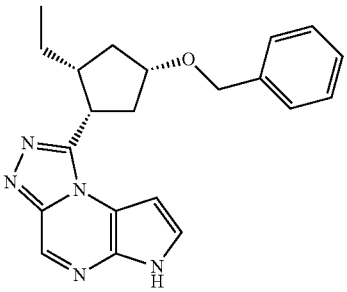 | D.1.36 | 2.15 (b) | 362 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| | 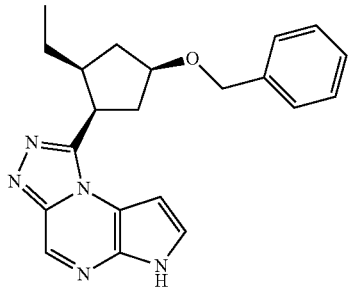 | | | |
| N-(4-(6-tosyl-6H-pyrrolo[2,3-e][1,2,4]triazolo[4,3-a]pyrazin-1-yl)bicyclo[2.2.2]octan-1-yl)pyrrolidine-1-carboxamide (prepared using I from methyl 4-aminobicyclo[2.2.2]octane-1-carboxylate hydrochloride [Prime Organics], pyrrolidine-1-carbonyl chloride and TEA, Z with NaOH, A from Example #1, Step D, HATU and TEA, B with TEA)) | 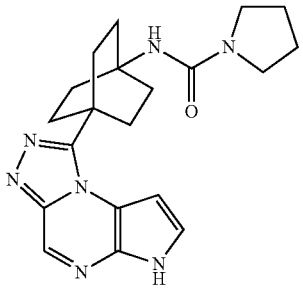 | D.1.37 | 1.65 (a) | 380 |
| 1-((1R,2R,4S)-2-ethyl-4-(4-methoxybenzyloxy)cyclopentyl)-6-tosyl-6H-pyrrolo[2,3-e][1,2,4]triazolo[4,3-a]pyrazine and 1-((1S,2S,4R)-2-ethyl-4-(4-methoxybenzyloxy)cyclopentyl)-6-tosyl-6H-pyrrolo[2,3-e][1,2,4]triazolo[4,3-a]pyrazine (prepared using Z from Preparation #EE.1, A from Example #1, Step D, HATU, and TEA, B with DIEA) | 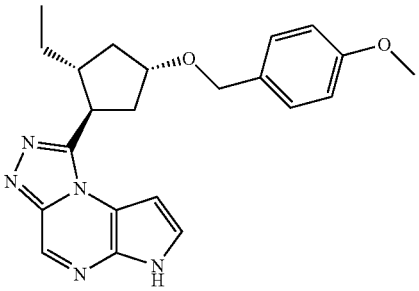 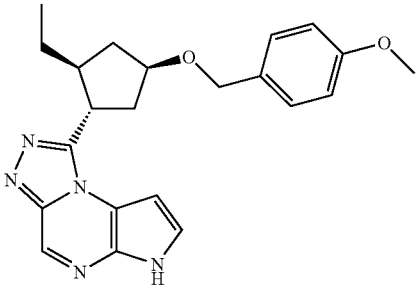 | D.1.38 | 2.14 (b) | 392 |
| N-(4-(6-tosyl-6H-pyrrolo[2,3-e][1,2,4]triazolo[4,3-a]pyrazin-1-yl)bicyclo[2.2.2]octan-1-yl)cyclobutanesulfonamide (prepared using K from methyl 4-aminobicyclo[2.2.2]octane-1-carboxylate hydrobromide [Prime Organics], cyclobutanesulfonyl chloride [Hande] and TEA, Z with NaOH, A from Example #1, Step D, HATU and TEA, B with TEA)) | 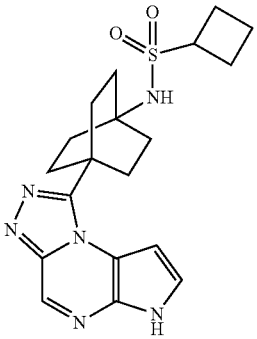 | D.1.39 | 1.71 (a) | 401 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| N-(4-(3-allyl-6-tosyl-6H-imidazo[1,5,-a]pyrrolo[2,3,-e]pyrazin-1-yl)bicyclo[2.2.2]octan-1-yl)cyclopropane-sulfonamide(prepared using E with 4-(tert-butoxycarbonylamino)-bicyclo[2.2.2]octane-1-carboxylic acid [Prime Organics], K with cyclopropyl-sulfonyl chloride, H from Preparation #12, HATU and DIEA, Q with Lawesson's reagent and mercury (II) trifluoroacetate) | 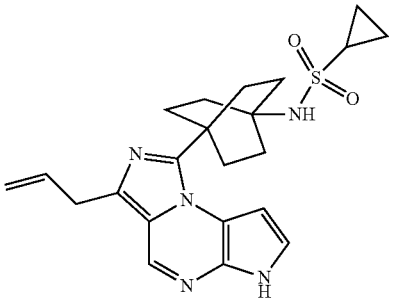 | D.1.40 | 1.89 (a) | 426 |
| N-(4-(3-(2,3-dihydroxypropyl)-6-tosyl-6H-imidazo[1,5-a]pyrrolo[2,3-e]pyrazin-1-yl)bicyclo[2.2.2]octan-1-yl)cyclopropanesulfonamide (Preparation #17) | 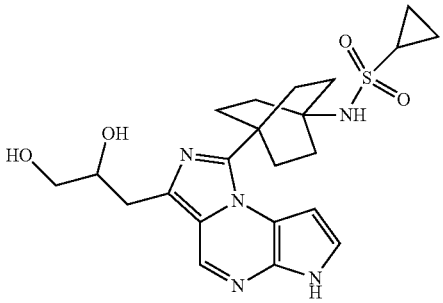 | D.1.41 | 1.37 (a) | 460 |
| tert-butyl 1-(6-tosyl-6H-imidazo[1,5-a]pyrrolo[2,3-e]pyrazin-1-yl)pyrrolidin-3-ylcarbamate (Preparation #16) | 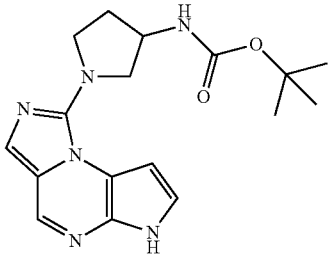 | D.1.42 | 1.78 (a) | 343 |
| 3-bromo-1-cyclohexyl-6-tosyl-6H-imidazo[1,5-a]pyrrolo[2,3-e]pyrazine (Preparation #MM.1) | 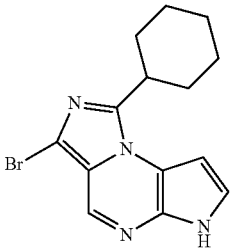 | D.1.43 | 2.38 (a) | 319, 321 (1:1) |
| N-((1S,3S,4R)-3-(3-chloro-6-tosyl-6H-imidazo[1,5-a]pyrrolo[2,3-e]pyrazin-1-yl)-4-ethylcyclopentyl)-cyclopropanesulfonamide (prepared using H from Example #5, Step C and Preparation #Z.1, HATU and DIEA, Q with Lawesson's reagent and mercury (II) trifluroacetate, MM with NCS) | 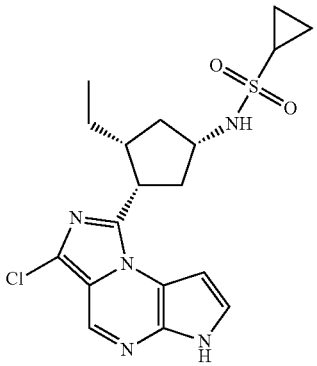 | D.1.44* | 2.01 (a) | 408 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| N-((1S,3S,4R)-3-(3-bromo-6-tosyl-6H-imidazo[1,5-a]pyrrolo[2,3-e]pyrazin-1-yl)-4-ethylcyclopentyl)-cyclopropanesulfonamide (prepared using H from Example #5, Step C and Preparation #Z.1, HATU and DIEA, Q with Lawesson's reagent and mercury (II) trifluroacetate, MM with NBS | 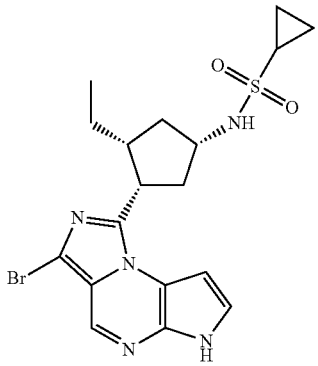 | D.1.45* | 2.05 (a) | 452, 454 (1:1) |
| N-((3S,5R)-5-ethyl-1-(6-tosyl-6H-imidazo[1,5-a]pyrrolo[2,3-e]pyrazin-1-yl)pyrrolidin-3-yl)cyclopropanesulfonamide, (prepared using E from Preparation #15, J from Example #5, Step C with CDI, OO) | 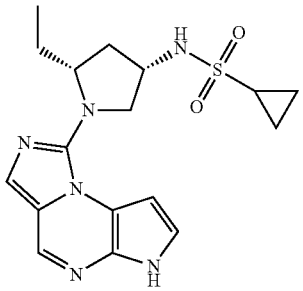 | D.1.46* | 1.63 (a) | 375 |
| N-((3S,5R)-5-methyl-1-(6-tosyl-6H-imidazo[1,5-a]pyrrolo[2,3-e]pyrazin-1-yl)pyrrolidin-3-yl)cyclopropanesulfonamide, (prepared using E from Preparation #14, J from Example #5, Step C with CDI, OO) | 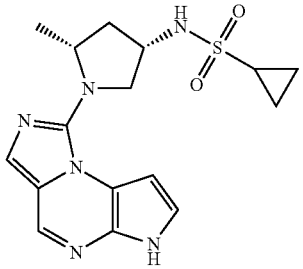 | D.1.47* | 1.31 (a) | 359 |
| N-((1S,3R,4S)-3-ethyl-4-(7-methyl-6-tosyl-6H-pyrrolo[2,3-e][1,2,4]triazolo[4,3-a]pyrazin-1-yl)cyclopentyl) cyclo-propanesulfonamide (prepared using A with Preparation #18 and Preparation #Z.1, B with thionyl chloride and TEA) | 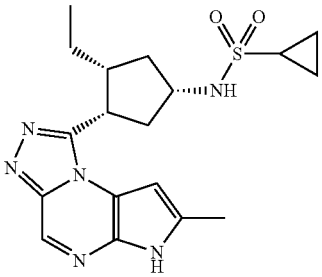 | D.1.48* | 1.74 (a) | 389 |
| 4-((4-(6-tosyl-6H-imidazo[1,5-a]pyrrolo[2,3-e]pyrazin-1-yl)cubanyl)methoxy)-benzonitrile (prepared using H from (5-tosyl-5H-pyrrolo[2,3-b]pyrazin-2-yl)methanamine hydrochloride (Example #5, Step C) and 4-methoxycarbonylcubanecarboxylic acid [Boron Molecular]with EDC•HCl and DIEA; P with DIBAL-H; II with 4-hydroxybenzonitrile, triphenylphosphine and DIAD; Q with Lawesson's reagent and mercury (II) trifluoroacetate) | 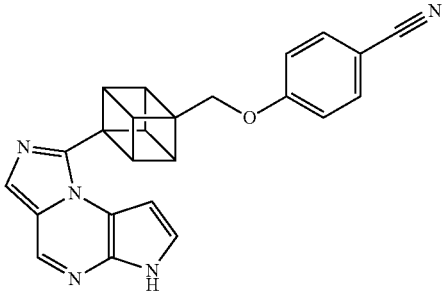 | D.1.49 | 2.05 (b) | 392 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| N-((1S,3R,4S)-3-ethyl-4-(6-tosyl-6H-pyrrolo[2,3-e][1,2,4]triazolo[4,3-a]pyrazin-1-yl)cyclopentyl)-4-methylpiperazine-1-sulfonamide (prepared using ZZ from Preparation BB.1, AAA with 1-methylpiperazine) | 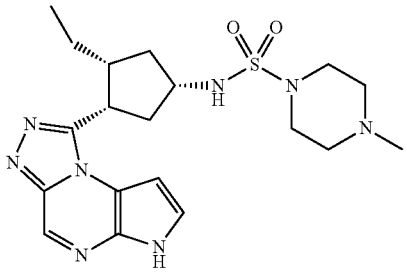 | D.1.50* | 1.32 (a) | 433 |
| 1-cyclohexyl-2-methyl-6-tosyl-1,6-dihydroimidazo[4,5-d]pyrrolo[2,3-b]pyridine (prepared using K.1 from Example #21, Step E with 4-methylbenzene-1-sulfonyl chloride, L with cyclohexylamine, BBB, G with acetic anhydride and OO) | 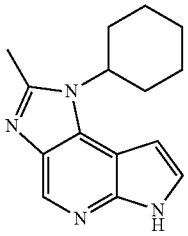 | D.1.51 | 1.86 (a) | 255 |
| 1-cyclohexyl-6-tosyl-2-(trifluoromethyl)-1,6-dihydroimidazo[4,5-d]pyrrolo[2,3-b]pyridine (prepared using prepared using K.1 from Example #21, Step E with 4-methylbenzene-1-sulfonyl chloride, L with cyclo-hexylamine, BBB, G with trifluoroacetic anhydride, DDD with 2,4,6-tripropyl-[1,3,5,2,4,6]trioxatriphosphinane 2,4,6-trioxide) | 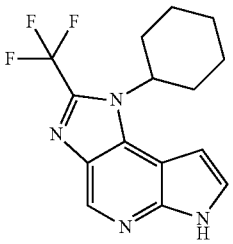 | D.1.52 | 2.37 (a) | 309 |
| N-((1S,3R,4S)-3-methyl-4-(2-methyl-6-tosylimidazo[4,5-d]pyrrolo[2,3-b]pyridin-1(6H)-yl)cyclopentyl)cyclo-propanesulfonamide (prepared from Preparation #27 and Preparation #OOO.1 using L and DIEA, K.1 with TsCl and NaH, BBB, H with acetic anhydride, and DDD with $POCl_3$) | 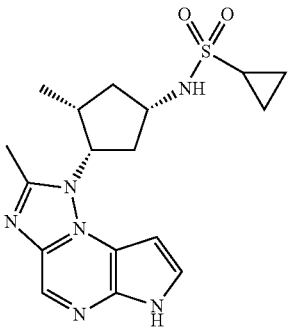 | D.1.53* | 1.59 (a) | 374 |
| 1-((1S,2R,4S)-4-(cyclopropylmethoxy)-2-methylcyclopentyl)-6-tosyl-6H-pyrrolo[2,3-e][1,2,4]triazolo[4,3-a]pyrazine (prepared using P from Example #24 Step H and $NaBH_4$, VV, FFF with 2-cyclopropylacetaldehyde, Z with NaOH, A with Example #1 Step D, HATU and TEA, B with $SOCl_2$ and DIEA) | 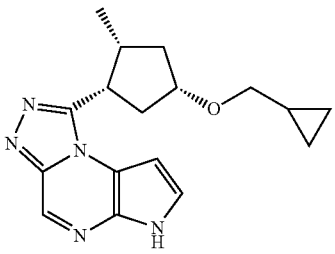 | D.1.54 | 1.73 (a) | 312 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| 1-methyl-N-((1S,3R,4S)-3-methyl-4-(6-tosyl-6H-imidazo[1,5-a]pyrrolo[2,3-e]pyrazin-1-yl)cyclopentyl)-cyclopropane-1-sulfonamide (prepared from 5-tosyl-5H-pyrrolo[2,3-b]pyrazin-2-yl)methanamine hydrochloride (WO2009152133) and (1S,2R,4S)-4-acetamido-2-methylcyclopentane-carboxylic acid [prepared from ethyl 4-amino-2-methyl-cyclopentanecarboxylate (WO2009152133) using G, AA [Table 2, Method 3, $R_t$ = 6.1 min, or = ND], and Z using H, OO, BB, and K with 3-chlorophenysulfonyl chloride) | 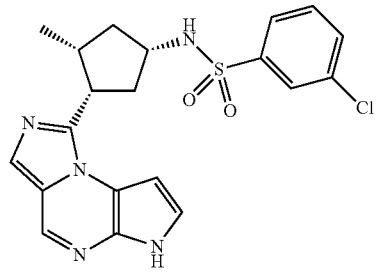 | D.1.55* | 2.17 (a) | 430 |
| N-((1S,3R,4S)-3-ethyl-4-(6H-pyrrolo[2,3-e][1,2,4]triazolo [4,3-a]pyrazin-1-yl) cyclopentyl)-2-hydroxyethylamino-1-sulfonamide (Preparation #ZZ.1) | 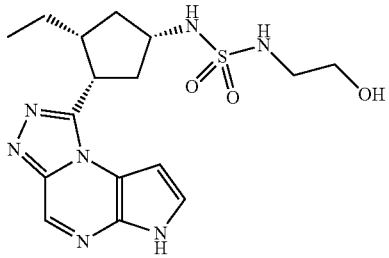 | D.1.56* | 1.33 (a) | 394 |
| N-((1S,3R,4S)-3-ethyl-4-(6H-pyrrolo[2,3-e][1,2,4]triazolo[4,3-a]pyrazin-1-yl)cyclopentyl)-2-methoxyethanesulfonamide (prepared using K from Example #8 Step M and 2-methoxyethane-1-sulfonyl chloride [Focus Synthesis] with TEA) | 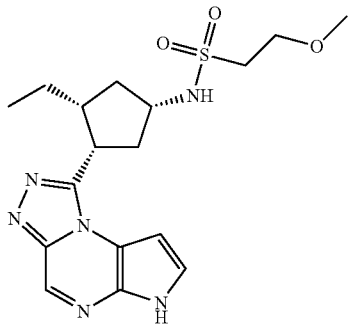 | D.1.57* | 1.53 (b) | 393 |
| N-((1S,3R,4S)-3-ethyl-4-(6H-pyrrolo[2,3-e][1,2,4]triazolo[4,3-a]pyrazin-1-yl)cyclopentyl)-2-(1H-1,2,3-triazol-1-yl)ethanesulfonamide (prepared using K.1 from Example #8 Step M and 2-chloroethanesulfonyl chloride with TEA, YY with 1H-1,2,3-triazole and DIEA) | 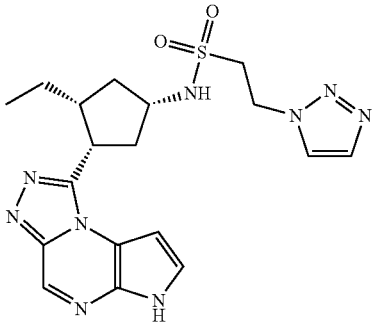 | D.1.58* | 1.45 (b) | 430 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| N-((1S,3R,4S)-3-ethyl-4-(6H-pyrrolo[2,3-e][1,2,4]triazolo[4,3-a]pyrazin-1-yl)cyclopentyl)-2-(2H-1,2,3-triazol-2-yl)ethanesulfonamide (prepared using K.1 from Example #8 Step M and 2-chloro-ethanesulfonyl chloride with TEA, YY with 1H-1,2,3-triazole and DIEA) | 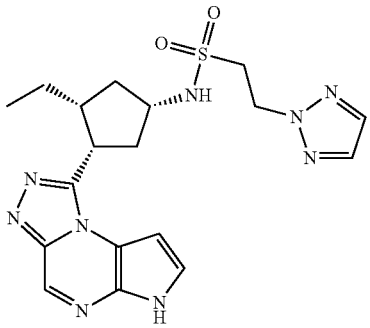 | D.1.59* | 1.58 (b) | 430 |
| 2-(4,4-difluoropiperidin-1-yl)-N-((1S,3R,4S)-3-ethyl-4-(6H-pyrrolo[2,3-e][1,2,4]triazolo[4,3-a]pyrazin-1-yl)cyclopentyl)ethanesulfonamide (prepared using K.1 from Example #8 Step M and 2-chloroethanesulfonyl chloride with TEA, YY with 4,4-difluoropiperidine hydrochloride and DIEA) | 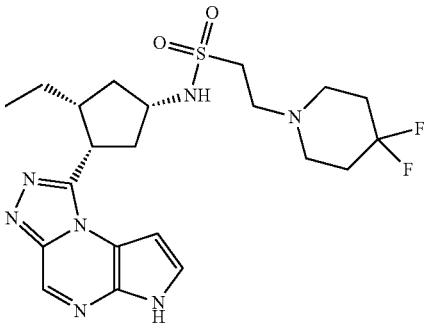 | D.1.60* | 1.76 (b) | 482 |
| N-((1S,3R,4S)-3-ethyl-4-(6H-pyrrolo[2,3-e][1,2,4]triazolo[4,3-a]pyrazin-1-yl)cyclopentyl)-2-morpholinoethanesulfonamide (prepared using K.1 from Example #8 Step M and 2-chloroethanesulfonyl chloride with TEA, YY with morpholine) | 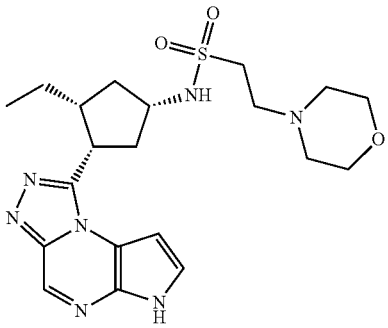 | D.1.61* | 1.35 (b) | 448 |
| (1S,3R,4S)-N-(2-(3,3-difluoropyrrolidin-1-ylsulfonyl)ethyl)-3-ethyl-4-(6H-pyrrolo[2,3-e][1,2,4]triazolo[4,3-a]pyrazin-1-yl)cyclopentanamine (prepared using YY from Preparation #26 and Example #8 Step M with DIEA) | 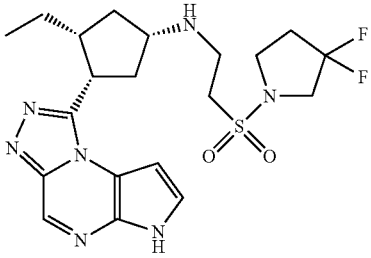 | D.1.62* | 1.53 (b) | 468 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| (cis)-6-tosyl-1-(5-(3,3,3-trifluoropropylsulfonyl)-2,5-diazabicyclo[2.2.1]heptan-2-yl)-6H-imidazo[1,5-a]pyrrolo[2,3-e]pyrazine (prepared using K from (cis)-tert-butyl 2,5-diazabicyclo[2.2.1]heptane-2-carboxylate (US2003/225268) and 3,3,3-trifluoropropane-1-sulfonyl chloride (Matrix), E with HCl, J with CDI and (5-tosyl-5H-pyrrolo[2,3-b]pyrazin-2-yl)methanamine hydrochloride (Example #5, Step C) with DIEA, OO). | 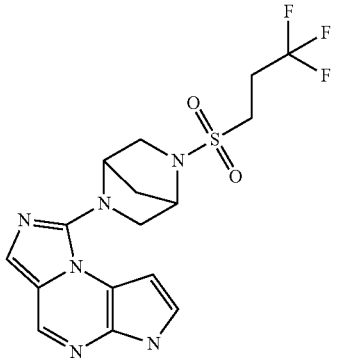 | D.1.63 | 1.85 | 415 |
| (cis)-6-tosyl-1-(5-(3,3,3-trifluoropropylsulfonyl)hexa-hydropyrrolo[3,4-c]pyrrol-2(1H)-yl)-6H-imidazo[1,5-a]pyrrolo[2,3-e]pyrazine (prepared using K from (cis)-tert-butyl hexahydropyrrolo [3,4-c]pyrrole-2(1H)-carboxylate and 3,3,3-trifluoropropane-1-sulfonyl chloride (Matrix), E with HCl, J with CDI and (5-tosyl-5H-pyrrolo[2,3-b]pyrazin-2-yl)methanamine hydrochloride (Example #5, Step C) with DIEA, OO). | 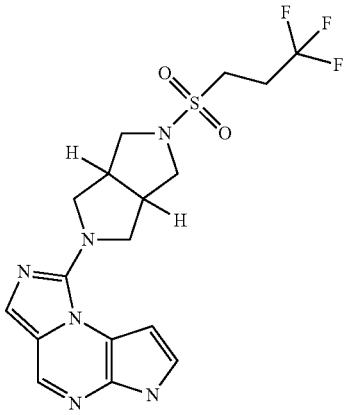 | D.1.64 | 1.80 | 429 |
| 1-(6-fluoro-4-(3,3,3-trifluoro-propylsulfonyl)-1,4-diazepan-1-yl)-6-tosyl-6H-imidazo[1,5-a]pyrrolo[2,3-e]pyrazine (prepared using K from tert-butyl 6-fluoro-1,4-diazepane-1-carboxylate (WO2007/126935) and 3,3,3-trifluoropropane-1-sulfonyl chloride (Matrix), E with HCl, J with CDI and (5-tosyl-5H-pyrrolo[2,3-b]pyrazin-2-yl)methanamine hydrochloride (Example #5, Step C) with DIEA, OO). | 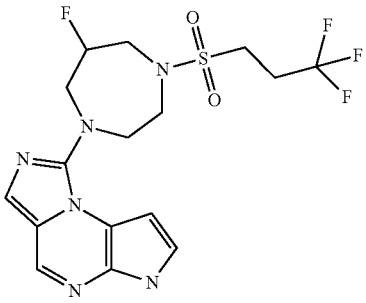 | D.1.65 | 1.86 | 435 |
| trans-N-(4-methyl-1-(3,3,3-trifluoropropylsulfonyl)piper-idin-3-yl)-6-tosyl-6H-imidazo[1,5-a]pyrrolo[2,3-e]pyrazin-1-amine (prepared using K from trans-tert-butyl 4-methylpiperidin-3-ylcarbamate (WO2009/140320) and 3,3,3-trifluoropropane-1-sulfonyl chloride (Matrix), E with HCl, J with CDI and (5-tosyl-5H-pyrrolo[2,3-b]pyrazin-2-yl)methanamine hydrochloride (Example #5, Step C) with DIEA, OO). | 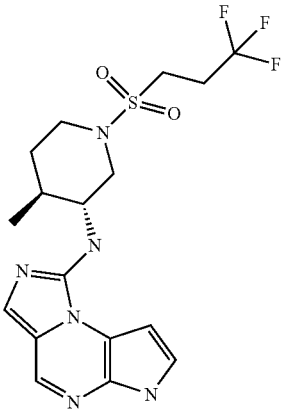 | D.1.66 | 1.89 | 431 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| | 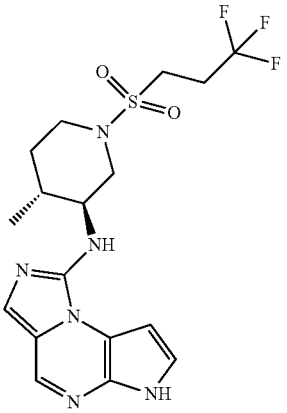 | | | |
| N-((1S,3R,4S)-3-ethyl-4-(6-tosyl-6H-pyrrolo[2,3-e][1,2,4] triazolo[4,3-a]pyrazin-1-yl)cyclopentyl)-2-methylpropane-2-sulfonamide (Preparation #28) | 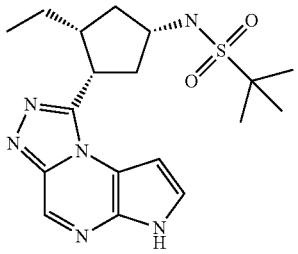 | D.1.67* | 1.76 | 391 |
| 6-tosyl-1-(2-(3,3,3-trifluoropropylsulfonyl)-2,5-diazaspiro[3.5]nonan-5-yl)-6H-imidazo[1,5-a]pyrrolo[2,3-e]pyrazine (prepared using K from 5-benzyl-2,5-diazaspiro[3.5] nonane (WO2008/60767) and 3,3,3-trifluoropropane-1-sulfonyl chloride (Matrix), Y with $Pd(OH)_2$, J with CDI and (5-tosyl-5H-pyrrolo[2,3-b]pyrazin-2-yl)methanamine hydrochloride (Example #5, Step C) with DIEA, OO). | 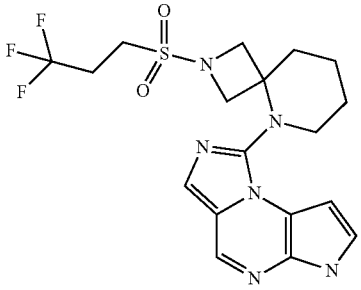 | D.1.68 | 2.07 | 443 |
| 6-tosyl-1-((trans)-4-(3,3,3-trifluoropropylsulfonyl)octahydro-1H-pyrrolo[3,2-b]pyridin-1-yl)-6H-imidazo[1,5-a]pyrrolo[2,3-e]pyrazine (prepared using K from (trans)-tert-butyl octahydro-1H-pyrrolo[3,2-b]pyridine-1-carboxylate (WO2009/140320) and 3,3,3-trifluoropropane-1-sulfonyl chloride (Matrix), E with HCl, J with CDI and (5-tosyl-5H-pyrrolo[2,3-b]pyrazin-2-yl)methanamine hydrochloride (Example #5, Step C) with DIEA, OO). | 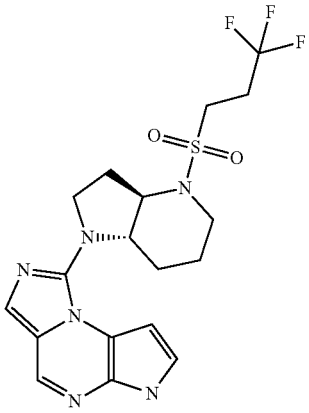 | D.1.69 | 1.94 | 443 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| | 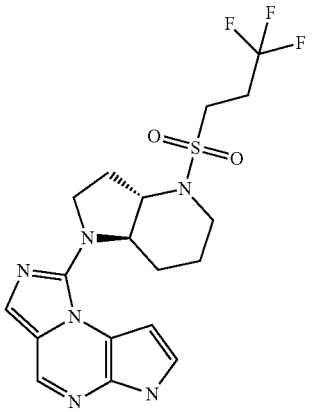 | | | |
| 1-(7-methyl-4-(3,3,3-trifluoropropyl-sulfonyl)-1,4-diazepan-1-yl)-6-tosyl-6H-imidazo[1,5-a]pyrrolo[2,3-e]pyrazine (prepared using K from benzyl 7-methyl-1,4-diazepane-1-carboxylate, Hydrochloric Acid (Wlodarczyk, N.; Gilleron, P.; Millet, R.; Houssin, R.; Henichart, J.-P. Tet. Let., 2007, vol. 48, #14 p. 2583-2586) and 3,3,3-trifluoropropane-1-sulfonyl chloride (Matrix), Y with $Pd(OH)_2$, J with CDI and (5-tosyl-5H-pyrrolo[2,3-b]pyrazin-2-yl)methanamine hydrochloride (Example #5, Step C) with DIEA, OO). | 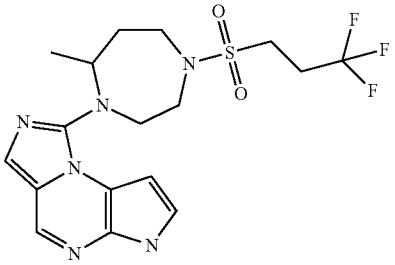 | D.1.70 | 1.97 | 431 |
| 6-tosyl-1-(5-(3,3,3-trifluoropropylsulfonyl)-2,5-diazaspiro[3.5]nonan-2-yl)-6H-imidazo[1,5-a]pyrrolo[2,3-e]pyrazine (prepared using K from tert-butyl 2,5-diazaspiro[3.5]nonane-2-carboxylate (WO2008/60767) and 3,3,3-trifluoropropane-1-sulfonyl chloride (Matrix), E with HCl, J with CDI and (5 tosyl-5H-pyrrolo[2,3-b]pyrazin-2-yl)methanamine hydrochloride (Example #5, Step C) with DIEA, OO). | 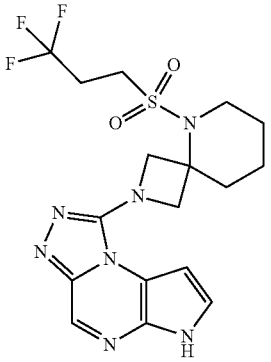 | D.1.71 | 2.03 | 443 |
| 3,3,3-trifluoro-N-(1-(6-tosyl-6H-imidazo[1,5-a]pyrrolo[2,3-e]pyrazin-1-yl)piperidin-3-yl)propane-1-sulfonamide (prepared using K tert-butyl 3-aminopiperidine-1-carboxylate (3B-Scientific Corp.) and 3,3,3-trifluoropropane-1-sulfonyl chloride (Matrix), E with HCl, J with CDI and (5-tosyl-5H-pyrrolo[2,3-b]pyrazin-2-yl)methanamine hydrochloride (Example #5, Step C) with DIEA, OO). | 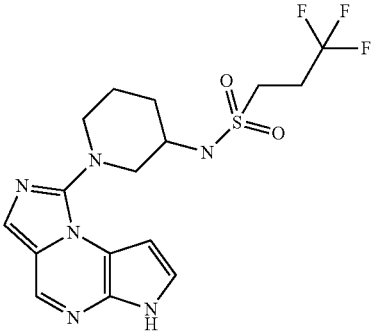 | D.1.72 | 1.76 | 417 |

TABLE D.1-continued

| Examples prepared using General Procedure D with NaOH | | | | |
|---|---|---|---|---|
| Sulfonamide | Product | Ex # | $R_t$ min (Table 1, Method) | m/z ESI+ $(M + H)^+$ |
| 6-tosyl-1-(2-(3,3,3-trifluoropropylsulfonyl)-2,6-diazabicyclo[3.2.1]octan-6-yl)-6H-imidazo[1,5-a]pyrrolo[2,3-e]pyrazine (prepared using K from benzyl 2,6-diazabicyclo[3.2.1]octane-6-carboxylate (Pharmabridge) and 3,3,3-trifluoropropane-1-sulfonyl chloride (Matrix), Y with $Pd(OH)_2$, J with CDI and (5-tosyl-5H-pyrrolo[2,3-b]pyrazin-2-yl)methanamine hydrochloride (Example #5, Step C) with DIEA, OO). | 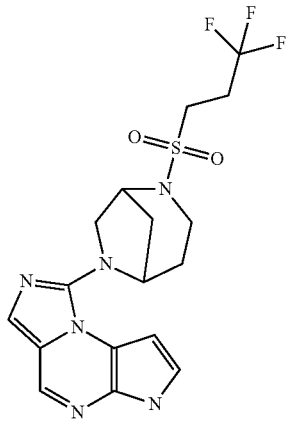 | D.1.73 | 1.91 | 429 |
| N-((3R,5R)-1-ethyl-5-(6-tosyl-6H-pyrrolo[2,3-e][1,2,4]triazolo[4,3-a]pyrazin-1-yl)pyrrolidin-3-yl)cyclopropanesulfonamide (prepared using K with (2R,4R)-1-tert-butyl 2-methyl 4-aminopyrrolidine-1,2-dicarboxylate Hydrochloric Acid (Acesys Pharmatech Corp) and cylcopropylsulfonylchloride and TEA, Z with NaOH, A with Example #8 Step M, B, E with HCl, X with acetaldehyde. | 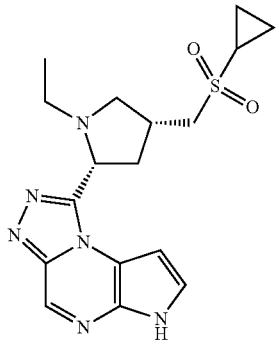 | D.1.74* | 1.32 | 376 |
| (cis)-tert-butyl 3-ethyl-4-(6-tosyl-6H-pyrrolo[2,3-e][1,2,4]triazolo[4,3-a]pyrazin-1-yl)pyrrolidine-1-carboxylate (prepared using SSS from N-benzyl-1-methoxy-N-((trimethylsilyl)methyl)methanamine and (Z)-ethyl pent-2-enoate (Lee, R. D.; Kassahun, K.; Abbott, F. S. J. of Pharm. Sci., 1989, vol. 78, #8 p. 667-671), TT, Y, M, A, B, E and K with cyclopropylmethanesulfonyl chloride and TEA | 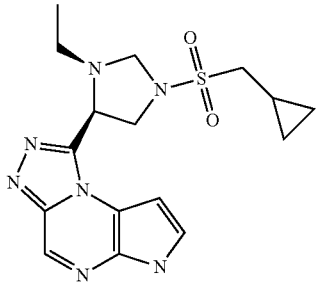 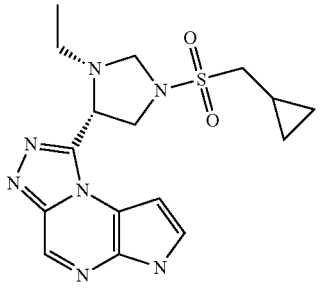 | D.1.75 | 1.66 | 375 |

TABLE D.1-continued

| Examples prepared using General Procedure D with NaOH | | | | |
|---|---|---|---|---|
| Sulfonamide | Product | Ex # | $R_t$ min (Table 1, Method) | m/z ESI+ $(M + H)^+$ |
| N-(4-(3-tosyl-3H-dipyrrolo[1,2-a:2',3'-e]pyrazin-8-yl)bicyclo[2.2.2]octan-1-yl)cyclopropanesulfonamide (prepared using III from 5-tosyl-5H-pyrrolo[2,3-b]pyrazine-2-carbaldehyde (Preparation #12: step B) and diethyl 2-(4-(cyclopropanesulfonamido)bicyclo[2.2.2]octan-1-yl)-2-oxoethylphosphonate (Preparation #24), W, T with Lawesson's reagent). | 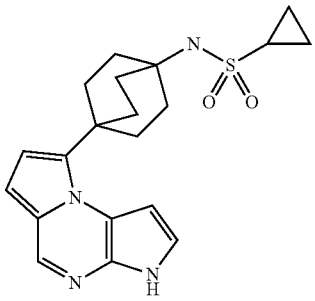 | D.1.76 | 1.97 | 385 |
| 1-methyl-N-((1S,3R,4S)-3-methyl-4-(6-tosyl-6H-imidazo[1,5-a]pyrrolo[2,3-e]pyrazin-1-yl)cyclopentyl)cyclopropane-1-sulfonamide (prepared from 5-tosyl-5H-pyrrolo[2,3-b]pyrazin-2-yl)methanamine hydrochloride (WO2009152133) and (1S,2R,4S)-4-acetamido-2-methylcyclopentanecarboxylic acid [prepared from ethyl 4-amino-2-methyl-cyclopentanecarboxylate (WO2009152133) using G, AA [Table 2, Method 3, $R_t$ = 6.1 min, or = ND], and Z] using H, OO, BB, and K from Preparation #6 and TEA) | 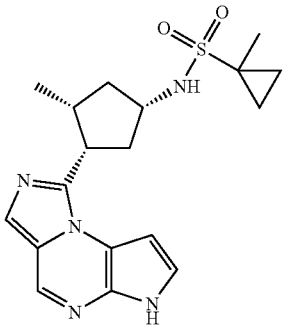 | D.1.77* | 1.87 (a) | 374 |
| 3,3-difluoro-N-((1S,3R,4S)-3-methyl-4-(6-tosyl-6H-imidazo[1,5-a]pyrrolo[2,3-e]pyrazin-1-yl)cyclopentyl)azetidine-1-sulfonamide (prepared from 5-tosyl-5H-pyrrolo[2,3-b]pyrazin-2-yl)methanamine hydrochloride (WO2009152133) and (1S,2R,4S)-4-acetamido-2-methylcyclopentanecarboxylic acid [prepared from ethyl 4-amino-2-methyl-cyclopentanecarboxylate (WO2009152133) using G, AA[Table 2, Method 3, $R_t$ = 6.1 min, or = ND], and Z using H, OO, BB, ZZ and AAA with 3,3- difluoroazetidine hydrochloride and TEA) | 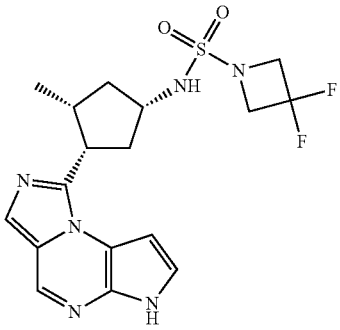 | D.1.78* | 1.99 (a) | 411 |
| 3,3,3-trifluoro-N-((1S,3R,4S)-3-methyl-4-(6-tosyl-6H-imidazo[1,5-a]pyrrolo[2,3-e]pyrazin-1-yl)cyclopentyl)propane-1-sulfonamide (prepared from 5-tosyl-5H-pyrrolo[2,3-b]pyrazin-2-yl)methanamine hydrochloride (WO2009152133) and (1S,2R,4S)-4-acetamido-2-methylcyclopentanecarboxylic acid [prepared from ethyl 4-amino-2-methyl-cyclopentanecarboxylate (WO2009152133) using G, AA [Table 2, Method 3, $R_t$ = 6.1 min, or = ND], and Z using H, OO, BB, and K from 3,3,3-trifluoro-propane-1-sulfonyl chloride [Matrix]and TEA) | 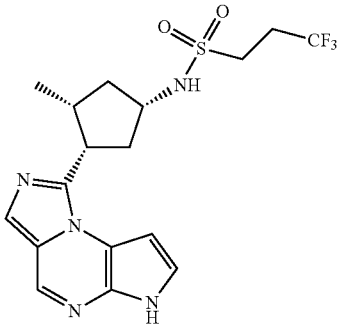 | D.1.79* | 2.00 (a) | 416 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| 3,3-difluoro-N-((1S,3R,4S)-3-methyl-4-(6-tosyl-6H-imidazo[1,5-a]pyrrolo[2,3-e]pyrazin-1-yl)cyclopentyl)pyrrolidine-1-sulfonamide (prepared from 5-tosyl-5H-pyrrolo[2,3-b]pyrazin-2-yl)methanamine hydrochloride(WO2009152133) and (1S,2R,4S)-4-acetamido-2-methylcyclopentanecarboxylic acid [prepared from ethyl 4-amino-2-methyl-cyclopentanecarboxylate (WO2009152133) using G, AA [Table 2, Method 3, $R_t$ = 6.1 min, or = ND], and Z] using H, OO, BB, ZZ and AAA with 3,3-difluoropyrrolidine hydrochloride and TEA) | 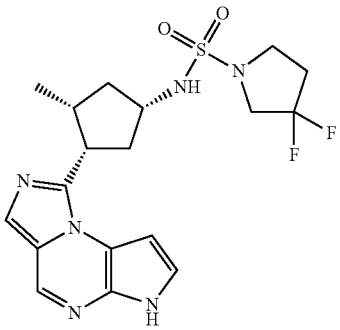 | D.1.80* | 2.01 (a) | 425 |
| (R)-N-((1S,3R,4S)-3-methyl-4-(6-tosyl-6H-imidazo[1,5-a]pyrrolo[2,3-e]pyrazin-1-yl)cyclopentyl)-2-(trifluoromethyl)pyrrolidine-1-sulfonamide sulfonamide (Preparation #AAA.1) | 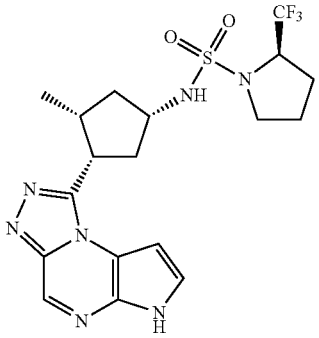 | D.1.81* | 2.16 (a) | 457 |
| 1-ethyl-N-((1S,3R,4S)-3-ethyl-4-(6-tosyl-6H-pyrrolo[2,3-e][1,2,4]triazolo[4,3-a]pyrazin-1-yl)cyclopentyl) cyclopropane-1-sulfonamide (prepared from Example #8 Step M and Preparation #EEE.1 using K and TEA) | 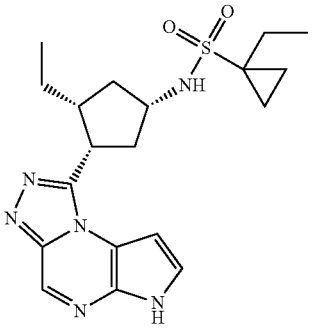 | D.1.82* | 1.90 (a) | 403 |
| 1-ethyl-N-((1S,3R,4S)-3-methyl-4-(6-tosyl-6H-imidazo[1,5-a]pyrrolo[2,3-e]pyrazin-1-yl)cyclopentyl)cyclopropane-1-sulfonamide (prepared from5-tosyl-5H-pyrrolo[2,3-b]pyrazin-2-yl)methanamine hydrochloride (WO2009152133) and (1S,2R,4S)-4-acetamido-2-methylcyclo-pentanecarboxylic acid [prepared from ethyl 4-amino-2-methyl-cyclopentanecarboxylate (WO2009152133) using G, AA [Table 2, Method 3, $R_t$ = 6.1 min, or = ND], and Z] using H, OO, BB, and K using Preparation #EEE.1 and TEA) | 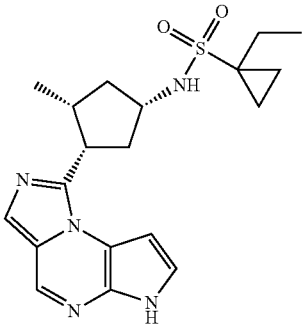 | D.1.83* | 1.96 (a) | 388 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| 1-butyl-N-((1S,3R,4S)-3-ethyl-4-(6-tosyl-6H-pyrrolo[2,3-e][1,2,4]triazolo[4,3-a]pyrazin-1-yl)cyclopentyl)cyclopropane-1-sulfonamide (prepared from Example #8 Step M and 1-butylcyclopropane-1-sulfonyl chloride [prepared from Preparation #6 Step A and 1,1,1-trifluoro-2-iodoethane, KHMDS using KKK, JJJ, and EEE with TEA] using K and TEA) | 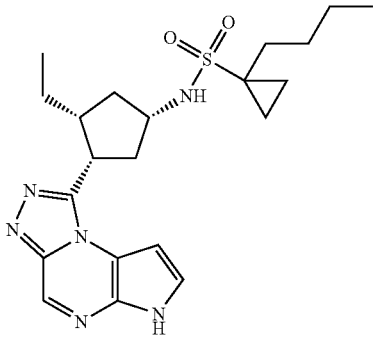 | D.1.84* | 2.13 (a) | 431 |
| N-((1S,3R,4S)-3-methyl-4-(6-tosylimidazo[4,5-d]pyrrolo[2,3-b]pyridin-1(6H)-yl)cyclopentyl)cyclopropane-sulfonamide (Preparation #DDD.1) | 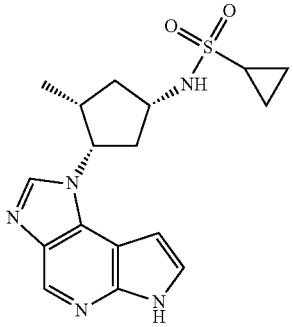 | D.1.85* | 1.65 (a) | 360 |
| N-((1S,3S,4R)-3-(2-cyclopropyl-6-tosylimidazo[4,5-d]pyrrolo[2,3-b]pyridin-1(6H)-yl)-4-methylcyclopentyl)cyclo-propanesulfonamide (prepared from Preparation #27 and Preparation #OOO.1 using L and DIEA, K.1 with TsCl and NaH, BBB, H with cyclopropanecarboxylic acid, HATU, and TEA, and DDD with $POCl_3$) | 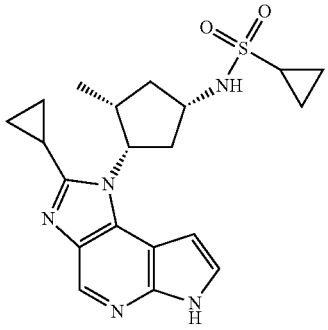 | D.1.86* | 1.74 (a) | 400 |
| N-((1S,3R,4S)-3-ethyl-4-(6-tosylpyrrolo[2,3-b][1,2,3]triazolo[4,5-d]pyridin-1(6H)-yl)cyclopentyl)cyclo-propanesulfonamide (Preparation #SSSS.1) | 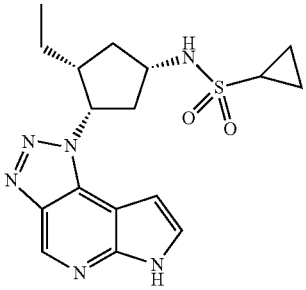 | D.1.87* | 1.82 (a) | 375 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| N-((1S,3R,4S)-3-ethyl-4-(6-tosyl-6H-pyrrolo[2,3-e][1,2,4]triazolo[4,3-a]pyrazin-1-yl)cyclopentyl)pentane-2-sulfonamide (prepared using K from Example #8 Step M and pentane-2-sulfonyl chloride) | 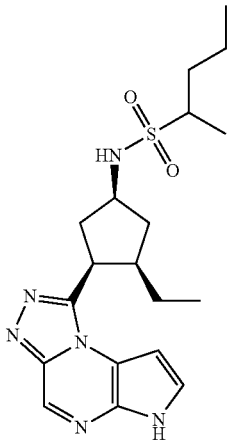 | D.1.88 | 1.88 (b) | 405 |
| N-((1S,3R,4S)-3-ethyl-4-(6-tosyl-6H-pyrrolo[2,3-e][1,2,4]triazolo[4,3-a]pyrazin-1-yl)cyclopentyl)-3-phenylpropane-1-sulfonamide (prepared using K from Example #8 Step M and 3-phenylpropane-1-sulfonyl chloride) | 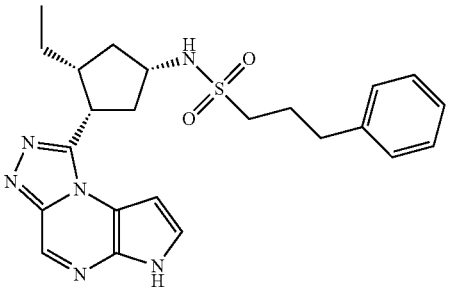 | D.1.89* | 1.98 (b) | 453 |
| N-((1S,3R,4S)-3-ethyl-4-(6-tosyl-6H-pyrrolo[2,3-e][1,2,4]triazolo[4,3-a]pyrazin-1-yl)cyclopentyl)-4,4,4-trifluorobutane-1-sulfonamide (prepared using K from Example #8 Step M and 4,4,4-trifluorobutane-1-sulfonyl chloride) | 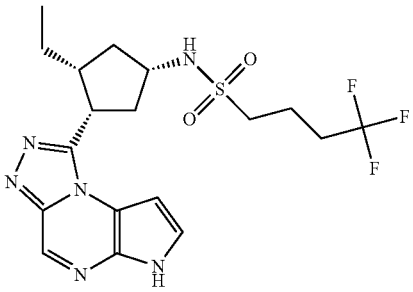 | D.1.90* | 1.85 (b) | 445 |
| 2-ethyl-N-((1S,3R,4S)-3-ethyl-4-(6-tosyl-6H-pyrrolo[2,3-e][1,2,4]triazolo[4,3-a]pyrazin-1-yl)cyclopentyl)cyclopropane-1-sulfonamide (prepared using K from Example #8 Step M and 2-ethylcyclopropane-1-sulfonyl chloride) | 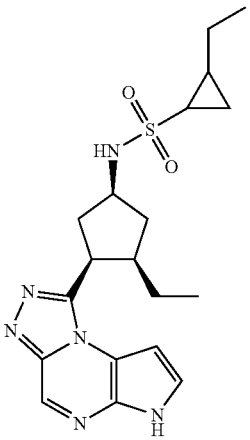 | D.1.91 | 1.81 (b) | 403 |

TABLE D.1-continued

| Examples prepared using General Procedure D with NaOH | | | | |
|---|---|---|---|---|
| Sulfonamide | Product | Ex # | $R_t$ min (Table 1, Method) | m/z ESI+ $(M + H)^+$ |
| N-((1S,3R,4S)-3-ethyl-4-(6-tosyl-6H-pyrrolo[2,3-e][1,2,4]triazolo[4,3-a]pyrazin-1-yl)cyclopentyl)-2-methylpropane-1-sulfonamide (prepared using K from Example #8 Step M and 2-methylpropane-1-sulfonyl chloride) | 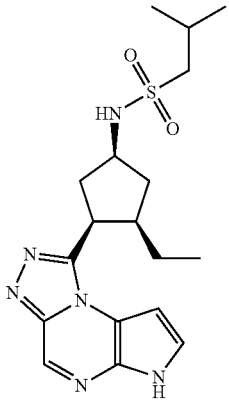 | D.1.92* | 1.77 (b) | 391 |
| N-((1S,3R,4S)-3-ethyl-4-(6-tosyl-6H-pyrrolo[2,3-e][1,2,4]triazolo[4,3-a]pyrazin-1-yl)cyclopentyl)-2-phenylethanesulfonamide (prepared using K from Example #8 Step M and 2-phenylethanesulfonyl chloride) | 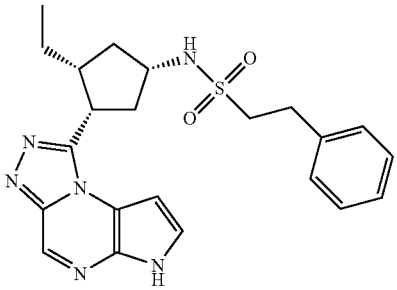 | D.1.93* | 1.92 (b) | 439 |
| 1-cyclohexyl-N-((1S,3R,4S)-3-ethyl-4-(6-tosyl-6H-pyrrolo[2,3-e][1,2,4]triazolo[4,3-a]pyrazin-1-yl)cyclopentyl)methanesulfonamide (prepared using K from Example #8 Step M and cyclohexylmethanesulfonyl chloride) | 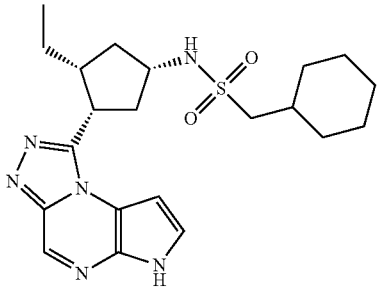 | D.1.94* | 2.04 (b) | 431 |
| N-((1S,3R,4S)-3-ethyl-4-(6-tosyl-6H-pyrrolo[2,3-e][1,2,4]triazolo[4,3-a]pyrazin-1-yl)cyclopentyl)butane-1-sulfonamide (prepared using K from Example #8 Step M and butane-1-sulfonyl chloride) | 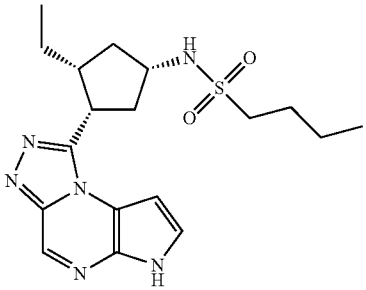 | D.1.95* | 1.78 (b) | 391 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| N-((1S,3R,4S)-3-ethyl-4-(6-tosyl-6H-pyrrolo[2,3-e][1,2,4]triazolo[4,3-a]pyrazin-1-yl)cyclopentyl)propane-2-sulfonamide (prepared using K from Example #8 Step M and propane-2-sulfonyl chloride) | 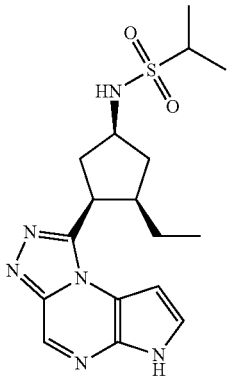 | D.1.96* | 1.61 (b) | 377 |
| N-((1S,3R,4S)-3-ethyl-4-(6-tosyl-6H-pyrrolo[2,3-e][1,2,4]triazolo[4,3-a]pyrazin-1-yl)cyclopentyl)-1-phenylmethanesulfonamide (prepared using K from Example #8 Step M and phenylmethanesulfonyl chloride) | 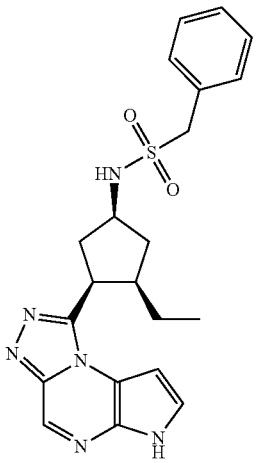 | D.1.97* | 1.82 (b) | 425 |
| N-((1S,3R,4S)-3-ethyl-4-(6-tosyl-6H-pyrrolo[2,3-e][1,2,4]triazolo[4,3-a]pyrazin-1-yl)cyclopentyl)propane-1-sulfonamide (prepared using K from Example #8 Step M and propane-1-sulfonyl chloride) | 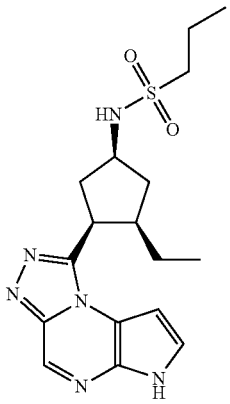 | D.1.98* | 1.64 (b) | 377 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| N-((1S,3R,4S)-3-ethyl-4-(6-tosyl-6H-pyrrolo[2,3-e][1,2,4]triazolo[4,3-a]pyrazin-1-yl)cyclopentyl)-3-methylbutane-1-sulfonamide (prepared using K from Example #8 Step M and 3-methylbutane-1-sulfonyl chloride) | 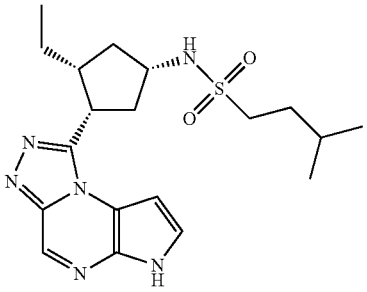 | D.1.99* | 1.90 (b) | 405 |
| N-((1S,3R,4S)-3-ethyl-4-(6-tosyl-6H-pyrrolo[2,3-e][1,2,4]triazolo[4,3-a]pyrazin-1-yl)cyclopentyl)-1,1-difluoromethanesulfonamide (prepared using K from Example #8 Step M and difluoromethanesulfonyl chloride) | 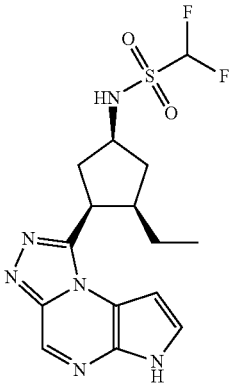 | D.1.100* | 1.75 (b) | 385 |
| 4-cyano-N-((1S,3R,4S)-3-ethyl-4-(6-tosyl-6H-pyrrolo[2,3-e][1,2,4]triazolo[4,3-a]pyrazin-1-yl)cyclopentyl)butane-1-sulfonamide (prepared using K from Example #8 Step M and 4-cyanobutane-1-sulfonyl chloride) | 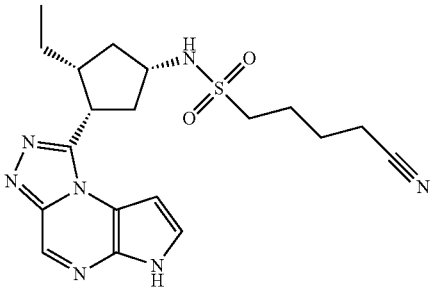 | D.1.101* | 1.56 (b) | 416 |
| 2-ethoxy-N-((1S,3R,4S)-3-ethyl-4-(6-tosyl-6H-pyrrolo[2,3-e][1,2,4]triazolo[4,3-a]pyrazin-1-yl)cyclopentyl)ethanesulfonamide (prepared using K from Example #8 Step M and 2-ethoxyethanesulfonyl chloride) | 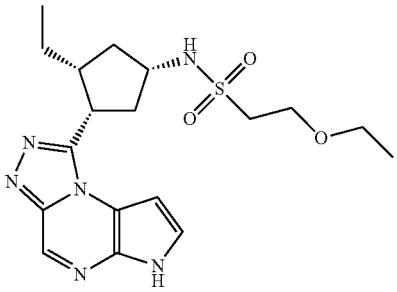 | D.1.102* | 1.62 (b) | 407 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| N-((1S,3R,4S)-3-ethyl-4-(6-tosyl-6H-pyrrolo[2,3-e][1,2,4]triazolo[4,3-a]pyrazin-1-yl)cyclopentyl)-1-(tetrahydro-furan-2-yl)methanesulfonamide (prepared using K from Example #8 Step M and (tetrahydrofuran-2-yl)methanesulfonyl chloride) | 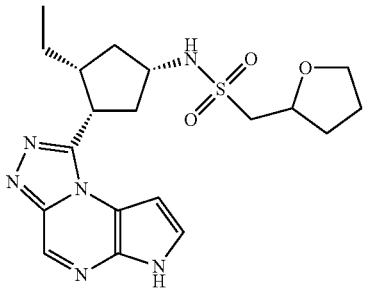 | D.1.103 | 1.58 (b) | 419 |
| N-((1S,3R,4S)-3-ethyl-4-(6-tosyl-6H-pyrrolo[2,3-e][1,2,4]triazolo[4,3-a]pyrazin-1-yl)cyclopentyl)tetrahydro-2H-pyran-4-sulfonamide (prepared using K from Example #8 Step M and tetrahydro-2H-pyran-4-sulfonyl chloride) | 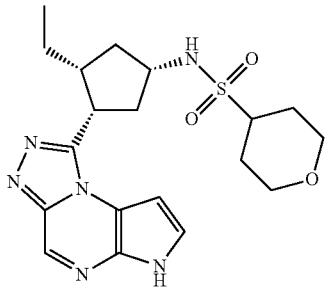 | D.1.104* | 1.50 (b) | 419 |
| 3-cyano-N-((1S,3R,4S)-3-ethyl-4-(6-tosyl-6H-pyrrolo[2,3-e][1,2,4]triazolo[4,3-a]pyrazin-1-yl)cyclopentyl)propane-1-sulfonamide (prepared using K from Example #8 Step M and 3-cyanopropane-1-sulfonyl chloride) | 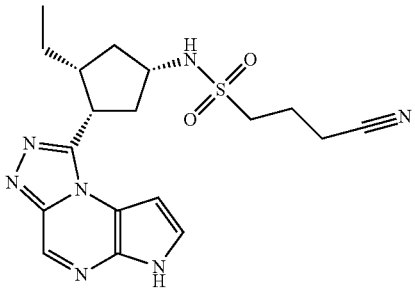 | D.1.105* | 1.51 (b) | 402 |
| N-((1S,3R,4S)-3-ethyl-4-(6-tosyl-6H-pyrrolo[2,3-e][1,2,4]triazolo[4,3-a]pyrazin-1-yl)cyclopentyl)-1-(5-methylisoxazol-3-yl)methanesulfonamide (prepared using K from Example #8 Step M and (5-methylisoxazol-3-yl)methanesulfonyl chloride) | 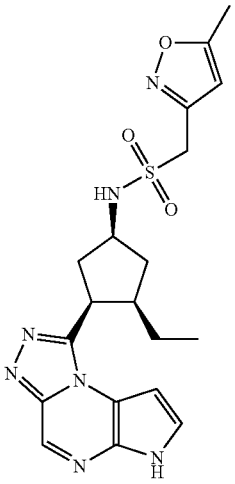 | D.1.106* | 1.66 (b) | 430 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| N-((1S,3R,4S)-3-ethyl-4-(6-tosyl-6H-pyrrolo[2,3-e][1,2,4]triazolo[4,3-a]pyrazin-1-yl)cyclopentyl)-1-(tetrahydro-2H-pyran-2-yl)methanesulfonamide (prepared using K from Example #8 Step M and (tetrahydro-2H-pyran-2-yl)methanesulfonyl chloride) | 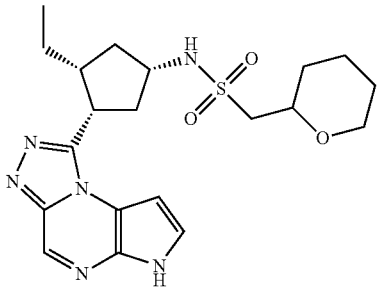 | D.1.107 | 1.73 (b) | 433 |
| N-((1S,3R,4S)-3-ethyl-4-(6-tosyl-6H-pyrrolo[2,3-e][1,2,4]triazolo[4,3-a]pyrazin-1-yl)cyclopentyl)-2-(pyridin-2-yl)ethanesulfonamide (prepared using K from Example #8 Step M and 2-(pyridin-2-yl)ethanesulfonyl chloride) | 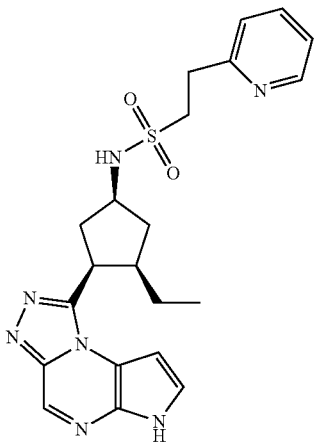 | D.1.108* | 1.58 (b) | 440 |
| 1-(2,2-dichlorocyclopropyl)-N-((1S,3R,4S)-3-ethyl-4-(6-tosyl-6H-pyrrolo[2,3-e][1,2,4]triazolo[4,3-a]pyrazin-1-yl)cyclopentyl)methane-sulfonamide (prepared using K from Example #8 Step M and (2,2-dichlorocyclopropyl)methane sulfonyl chloride) | 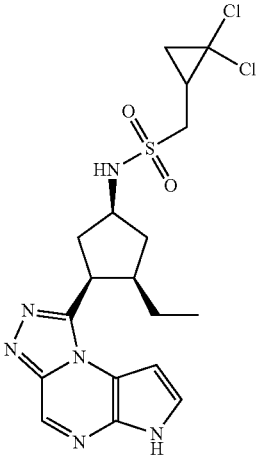 | D.1.109 | 1.91 (b) | 457 |
| N-((1S,3R,4S)-3-methyl-4-(6-tosyl-6H-pyrrolo[2,3-e][1,2,4]triazolo[4,3-a]pyrazin-1-yl)cyclopentyl)-3-phenylpropane-1-sulfonamide (prepared using K from Preparation #19.2 and 3-phenylpropane-1-sulfonyl chloride) | 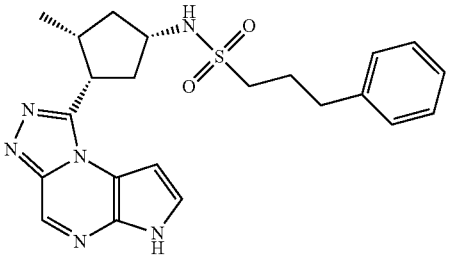 | D.1.110* | 1.90 (b) | 439 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| 4,4,4-trifluoro-N-((1S,3R,4S)-3-methyl-4-(6-tosyl-6H-pyrrolo[2,3-e][1,2,4]triazolo[4,3-a]pyrazin-1-yl)cyclopentyl)butane-1-sulfonamide (prepared using K from Preparation #19.2 and 4,4,4-trifluorobutane-1-sulfonyl chloride) | 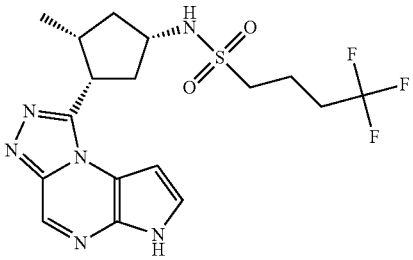 | D.1.111* | 1.76 (b) | 431 |
| 2-ethyl-N-((1S,3R,4S)-3-methyl-4-(6-tosyl-6H-pyrrolo[2,3-e][1,2,4]triazolo[4,3-a]pyrazin-1-yl)cyclopentyl)cyclopropane-1-sulfonamide (prepared using K from Preparation #19.2 and 2-ethylcyclopropane-1-sulfonyl chloride) | 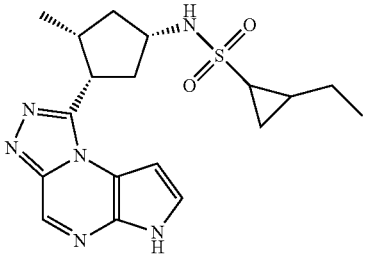 | D.1.112 | 1.70 (b) | 389 |
| 2-methyl-N-((1S,3R,4S)-3-methyl-4-(6-tosyl-6H-pyrrolo[2,3-e][1,2,4]triazolo[4,3-a]pyrazin-1-yl)cyclopentyl)propane-1-sulfonamide (prepared using K from Preparation #19.2 and 2-methylpropane-1-sulfonyl chloride) | 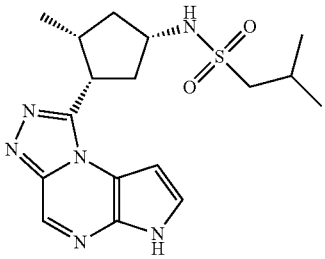 | D.1.113* | 1.67 (b) | 377 |
| N-((1S,3R,4S)-3-methyl-4-(6-tosyl-6H-pyrrolo[2,3-e][1,2,4]triazolo[4,3-a]pyrazin-1-yl)cyclopentyl)-2-phenylethanesulfonamide (prepared using K from Preparation #19.2 and 2-phenylethanesulfonyl chloride) | 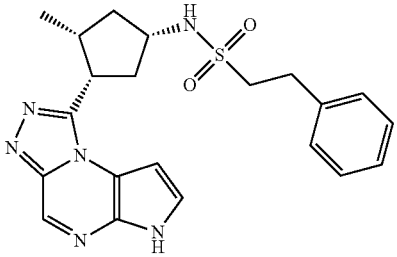 | D.1.114* | 1.83 (b) | 425 |
| N-((1S,3R,4S)-3-methyl-4-(6-tosyl-6H-pyrrolo[2,3-e][1,2,4]triazolo[4,3-a]pyrazin-1-yl)cyclopentyl)butane-2-sulfonamide (prepared using K from Preparation #19.2 and 2-(methylsulfonyl)butane) | 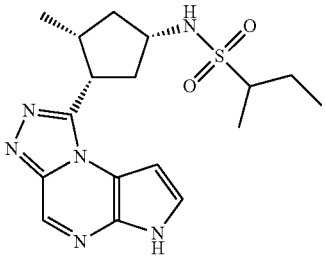 | D.1.115 | 1.63 (b) | 377 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| 1-cyclohexyl-N-((1S,3R,4S)-3-methyl-4-(6-tosyl-6H-pyrrolo[2,3-e][1,2,4]triazolo[4,3-a]pyrazin-1-yl)cyclopentyl) methane-sulfonamide (prepared using K from Preparation #19.2 and cyclohexylmethanesulfonyl chloride) | 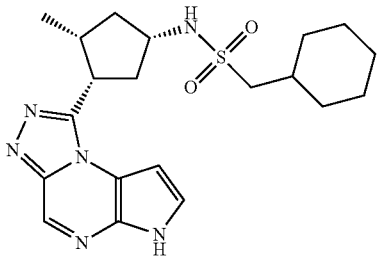 | D.1.116* | 1.94 (b) | 417 |
| N-((1S,3R,4S)-3-methyl-4-(6-tosyl-6H-pyrrolo[2,3-e][1,2,4]triazolo[4,3-a]pyrazin-1-yl)cyclopentyl)butane-1-sulfonamide (prepared using K from Preparation #19.2 and butane-1-sulfonyl chloride) | 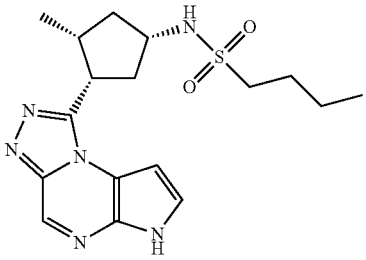 | D.1.117* | 1.67 (b) | 377 |
| 2-methoxy-N-((1S,3R,4S)-3-methyl-4-(6-tosyl-6H-pyrrolo[2,3-e][1,2,4]triazolo[4,3-a]pyrazin-1-yl)cyclopentyl)ethanesulfonamide (prepared using K from Preparation #19.2 and 2-methoxyethanesulfonyl chloride) | 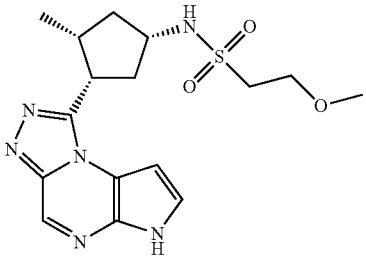 | D.1.118* | 1.38 (b) | 379 |
| N-((1S,3R,4S)-3-methyl-4-(6-tosyl-6H-pyrrolo[2,3-e][1,2,4]triazolo[4,3-a]pyrazin-1-yl)cyclopentyl)propane-2-sulfonamide (prepared using K from Preparation #19.2 and propane-2-sulfonyl chloride) | 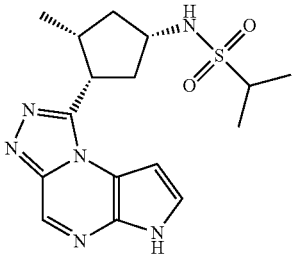 | D.1.119* | 1.50 (b) | 363 |
| N-((1S,3R,4S)-3-methyl-4-(6-tosyl-6H-pyrrolo[2,3-e][1,2,4]triazolo[4,3-a]pyrazin-1-yl)cyclopentyl)-1-phenylmethanesulfonamide (prepared using K from Preparation #19.2 and phenylmethanesulfonyl chloride) | 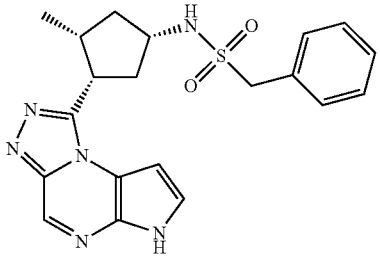 | D.1.120* | 1.72 (b) | 411 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| N-((1S,3R,4S)-3-methyl-4-(6-tosyl-6H-pyrrolo[2,3-e][1,2,4]triazolo[4,3-a]pyrazin-1-yl)cyclopentyl)propane-1-sulfonamide (prepared using K from Preparation #19.2 and propane-1-sulfonyl chloride) | 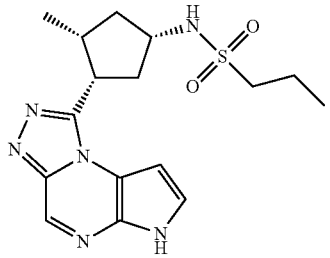 | D.1.121* | 1.53 (b) | 363 |
| N-((1S,3R,4S)-3-methyl-4-(6-tosyl-6H-pyrrolo[2,3-e][1,2,4]triazolo[4,3-a]pyrazin-1-yl)cyclopentyl)-3-methylbutane-1-sulfonamide (prepared using K from Preparation #19.2 and 3-methylbutane-1-sulfonyl chloride) | 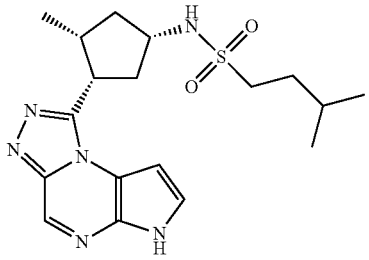 | D.1.122* | 1.80 (b) | 391 |
| N-((1S,3R,4S)-3-methyl-4-(6-tosyl-6H-pyrrolo[2,3-e][1,2,4]triazolo[4,3-a]pyrazin-1-yl)cyclopentyl)-1,1-difluoromethanesulfonamide (prepared using K from Preparation #19.2 and difluoromethanesulfonyl chloride) | 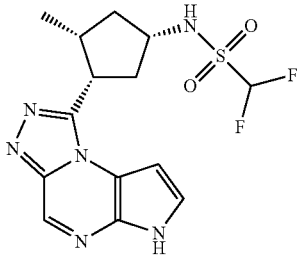 | D.1.123* | 1.64 (b) | 371 |
| 4-cyano-N-((1S,3R,4S)-3-methyl-4-(6-tosyl-6H-pyrrolo[2,3-e][1,2,4]triazolo[4,3-a]pyrazin-1-yl)cyclopentyl)butane-1-sulfonamide (prepared using K from Preparation #19.2 and 4-cyanobutane-1-sulfonyl chloride) | 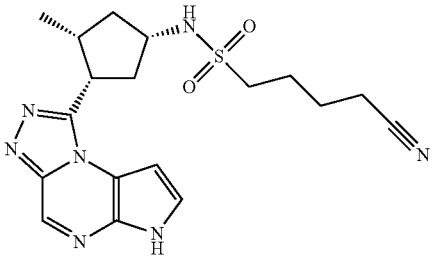 | D.1.124* | 1.45 (b) | 402 |
| 2-ethoxy-N-((1S,3R,4S)-3-methyl-4-(6-tosyl-6H-pyrrolo[2,3-e][1,2,4]triazolo[4,3-a]pyrazin-1-yl)cyclopentyl) ethanesulfonamide (prepared using K from Preparation #19.2 and 2-ethoxyethanesulfonyl chloride) | 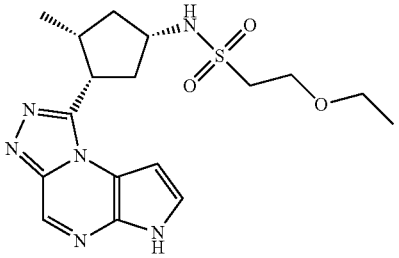 | D.1.125* | 1.50 (b) | 393 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| N-((1S,3R,4S)-3-methyl-4-(6-tosyl-6H-pyrrolo[2,3-e][1,2,4]triazolo[4,3-a]pyrazin-1-yl)cyclopentyl)-1-(tetrahydrofuran-2-yl)methanesulfonamide (prepared using K from Preparation #19.2 and (tetrahydrofuran-2-yl)methanesulfonyl chloride) | 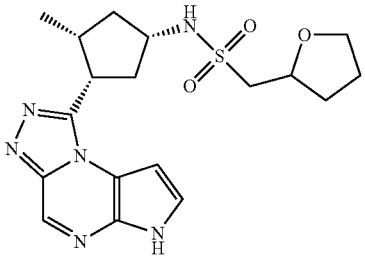 | D.1.126 | 1.46 (b) | 405 |
| N-((1S,3R,4S)-3-methyl-4-(6-tosyl-6H-pyrrolo[2,3-e][1,2,4]triazolo[4,3-a]pyrazin-1-yl)cyclopentyl)tetrahydro-2H-pyran-4-sulfonamide (prepared using K from Preparation #19.2 and tetrahydro-2H-pyran-4-sulfonyl chloride) | 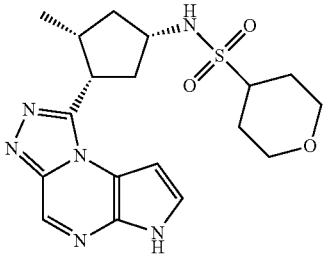 | D.1.127* | 1.39 (b) | 405 |
| 3-fluoro-N-((1S,3R,4S)-3-methyl-4-(6-tosyl-6H-pyrrolo[2,3-e][1,2,4]triazolo[4,3-a]pyrazin-1-yl)cyclopentyl)propane-1-sulfonamide (prepared using K from Preparation #19.2 and 3-fluoropropane-1-sulfonyl chloride) | 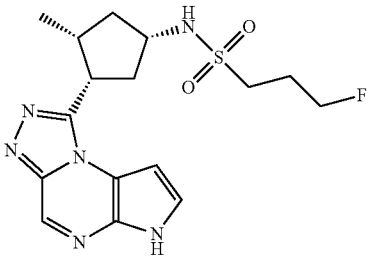 | D.1.128* | 1.48 (b) | 381 |
| 3-cyano-N-((1S,3R,4S)-3-methyl-4-(6-tosyl-6H-pyrrolo[2,3-e][1,2,4]triazolo[4,3-a]pyrazin-1-yl)cyclopentyl)propane-1-sulfonamide (prepared using K from Preparation #19.2 and 3-cyanopropane-1-sulfonyl chloride) | 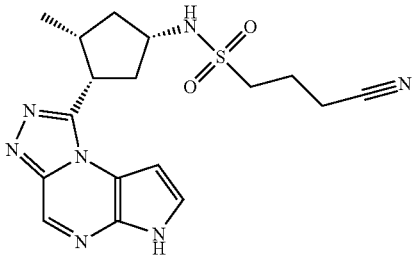 | D.1.129* | 1.39 (b) | 388 |
| N-((1S,3R,4S)-3-methyl-4-(6-tosyl-6H-pyrrolo[2,3-e][1,2,4]triazolo[4,3-a]pyrazin-1-yl)cyclopentyl)-1-(5-methylisoxazol-3-yl)methanesulfonamide (prepared using K from Preparation #19.2 and (5-methylisoxazol-3-yl)methanesulfonyl chloride) | 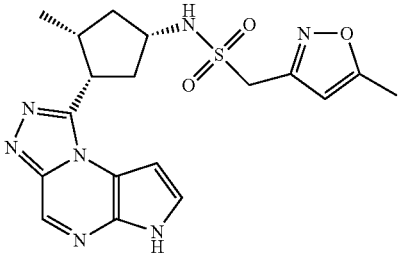 | D.1.130* | 1.55 (b) | 416 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| N-((1S,3R,4S)-3-methyl-4-(6-tosyl-6H-pyrrolo[2,3-e][1,2,4]triazolo[4,3-a]pyrazin-1-yl)cyclopentyl)-1-(tetrahydro-2H-pyran-2-yl)methanesulfonamide (prepared using K from Preparation #19.2 and (tetrahydro-2H-pyran-2-yl)methanesulfonyl chloride) | 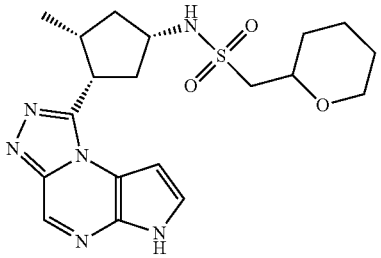 | D.1.131 | 1.63 (b) | 419 |
| N-((1S,3R,4S)-3-methyl-4-(6-tosyl-6H-pyrrolo[2,3-e][1,2,4]triazolo[4,3-a]pyrazin-1-yl)cyclopentyl)-2-(pyridin-2-yl)ethanesulfonamide (prepared using K from Preparation #19.2 and 2-(pyridin-2-yl)ethanesulfonyl chloride) | 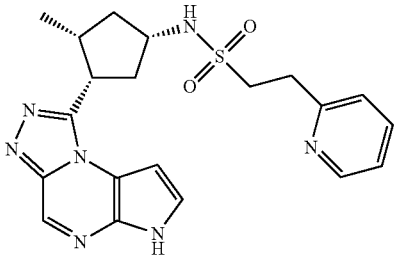 | D.1.132* | 1.47 (b) | 426 |
| 1-(benzo[d]isoxazol-3-yl)-N-((1S,3R,4S)-3-methyl-4-(6-tosyl-6H-pyrrolo[2,3-e][1,2,4]triazolo[4,3-a]pyrazin-1-yl)cyclopentyl)methane-sulfonamide (prepared using K from Preparation #19.2 and benzo[d]isoxazol-3-ylmethanesulfonyl chloride) | 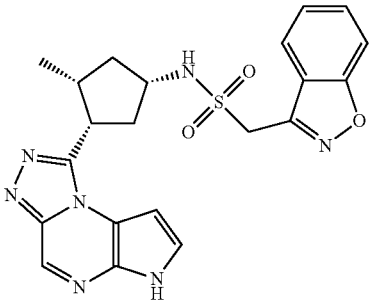 | D.1.133* | 1.77 (b) | 452 |
| 1-(2,2-dichlorocyclopropyl)-N-((1S,3R,4S)-3-methyl-4-(6-tosyl-6H-pyrrolo[2,3-e][1,2,4]triazolo[4,3-a]pyrazin-1-yl)cyclopentyl)methane-sulfonamide (prepared using K from Preparation #19.2 and (2,2-dichlorocyclopropyl)methane sulfonyl chloride) | 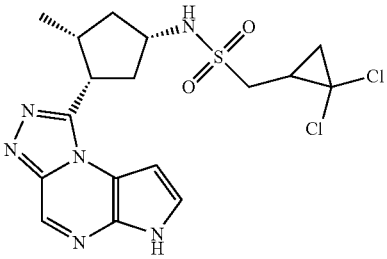 | D.1.134 | 1.81 (b) | 443 |
| tert-butyl 3-(N-((1S,3R,4S)-3-methyl-4-(6-tosyl-6H-pyrrolo[2,3-e][1,2,4]triazolo[4,3-a]pyrazin-1-yl)cyclopentyl) sulfamoyl)azetidine-1-carboxylate (prepared using K from Preparation #19.2 and tert-butyl 3-(chlorosulfonyl)azetidine-1-carboxylate) | 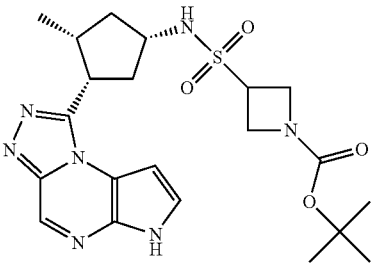 | D.1.135* | 1.78 (b) | 476 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| N-((1S,3R,4S)-3-ethyl-4-(6-tosyl-6H-pyrrolo[2,3-e][1,2,4]triazolo[4,3-a]pyrazin-1-yl)cyclopentyl)-N-(4,4,4-trifluorobutyl)oxetan-3-amine (prepared using X from Example #8 Step M with oxetan-3-one [PharmaBlock R&D], X with 4,4,4-trifluorobutanal [Matrix]) | 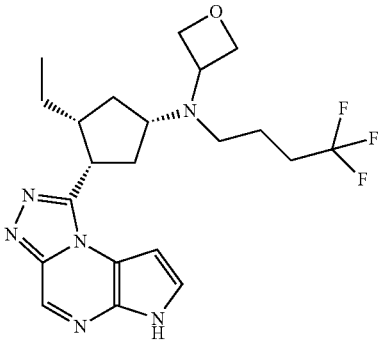 | D.1.136* | 1.75 (a) | 437 |
| N-((1S,3S,4R)-3-(2-amino-6-tosylimidazo[4,5-d]pyrrolo[2,3-b]pyridin-1(6H)-yl)-4-ethylcyclopentyl) cyclopropanesulfonamide (Preparation #RRRR.1) | 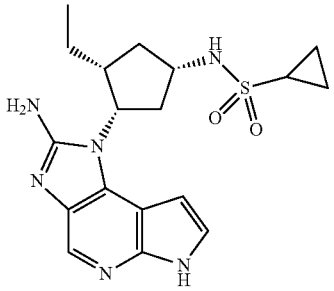 | D.1.137* | 1.30 (a) | 389 |
| N-((1S,3R,4S)-3-ethyl-4-(6-tosyl-6H-pyrrolo[2,3-e][1,2,4]triazolo[4,3-a]pyrazin-1-yl)cyclopentyl)-N-(3,3,3-trifluoropropyl)oxetan-3-amine (prepared using X from Example #8 Step M with oxetan-3-one [PharmaBlock], and X with 3,3,3-trifluoropropanal [Apollo Sci]) | 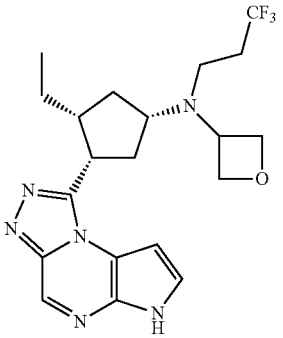 | D.1.138* | 1.91 (b) | 423 |
| (3R,4S)-N-cyclopropyl-3-ethyl-4-(6H-pyrrolo[2,3-e][1,2,4]triazolo[4,3-a]pyrazin-1-yl)cyclopentane-1-sulfonamide (prepared using EEE from Preparation #QQQQ.1; K with cyclopropylamine) | 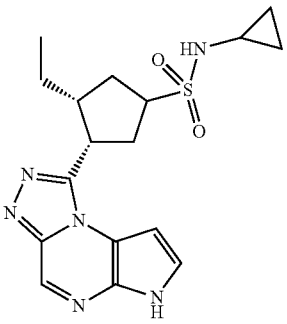 | D.1.139 | 1.53 (b) | 375 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| N-((3R,5R)-1-(2,2-difluoroethyl)-5-(6-tosyl-6H-pyrrolo[2,3-e][1,2,4]triazolo[4,3-a]pyrazin-1-yl)pyrrolidin-3-yl)cyclopropanesulfonamide (prepared using K from (2R,4R)-1-tert-butyl-4-aminopyrrolidine-1,2-dicarboxylate hydrochloric acid (Acesys Pharmatech Corp) and cylcopropylsulfonylchloride, TEA, Z with NaOH, A with Example #1 Step D, HATU and TEA, B with $SOCl_2$ and TEA, E with HCl, S with 1,1-difluoro-2-iodoethane) | 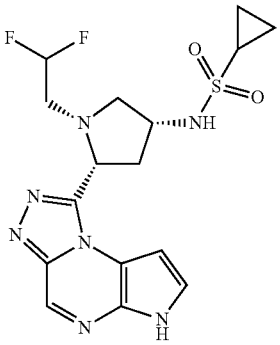 | D.1.140* | 1.46 (a) | 412 |
| N-((3R,5R)-1-ethyl-5-(6-tosyl-6H-pyrrolo[2,3-e][1,2,4]triazolo[4,3-a]pyrazin-1-yl)pyrrolidin-3-yl)-N-methylcyclopropanesulfonamide (prepared using K with (2R,4R)-1-tert-butyl-4-aminopyrrolidine-1,2-dicarboxylate Hydrochloric Acid (Acesys Pharmatech Corp), d cylcopropylsulfonylchloride and TEA, Z with NaOH, A with Example #1 Step D, HATU and TEA, B, E with HCl, X with acetaldehyde, S with iodomethane) | 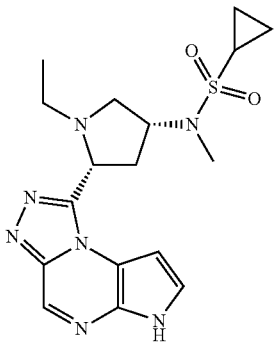 | D.1.141* | 1.44 (a) | 390 |
| 1-((cis)-1-(cyclopropylsulfonyl)-4-ethylpyrrolidin-3-yl)-6-tosyl-6H-pyrrolo[2,3-e][1,2,4]triazolo[4,3-a]pyrazine (prepared using K with Example #36 Step F and cylcopropylsulfonylchloride (Matrix) and TEA) | 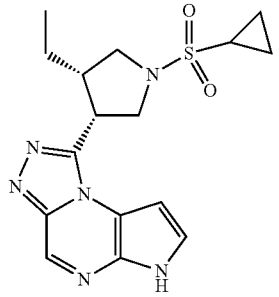 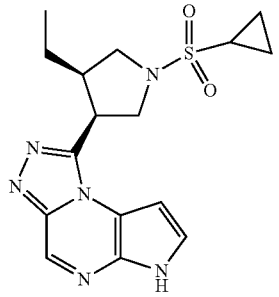 | D.1.142 | 1.50 (a) | 361 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| 1-(( cis)-1-benzyl-4-isopropylpyrrolidin-3-yl)-6-tosyl-6H-pyrrolo[2,3-e][1,2,4]triazolo[4,3-a]pyrazine (prepared using A with (Example #1, Step D) and (cis)-1-benzyl-4-isopropylpyrrolidine-3-carboxylic acid hydrochloride (prepared using SSS with (Z)-ethyl 4-methylpent-2-enoate and N-benzyl-1-methoxy-N-((trimethylsilyl)methyl)methan-amine (Aldrich)), B with TEA) | 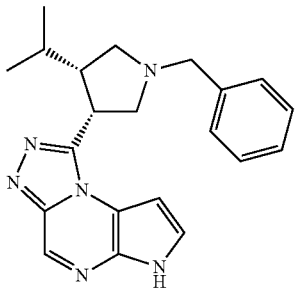 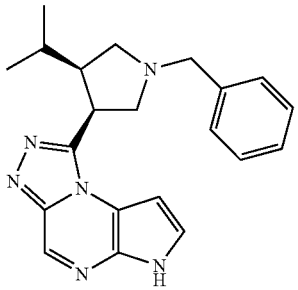 | D.1.143 | 0.47 (a) | 361 |
| N-((1S,3R,4R)-3-ethyl-4-(6-tosyl-3-(trifluoromethyl)-6H-imidazo[1,5-a]pyrrolo[2,3-e]pyrazin-1-yl)cyclopentyl)cyclo-propanesulfonamide (prepared using H with Preparation #32 and Preparation #Z.1, OO) | 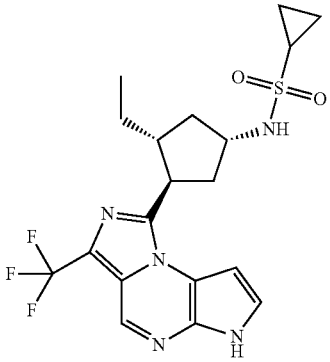 | D.1.144* | 2.12 (a) | 442 |
| N-((1S,3R,4R)-3-ethyl-4-(6-tosyl-3-(trifluoromethyl)-6H-imidazo[1,5-a]pyrrolo[2,3-e]pyrazin-1-yl)cyclopentyl)cyclo-propanesulfonamide (prepared using H with Preparation #32 and Preparation #Z.1, OO | 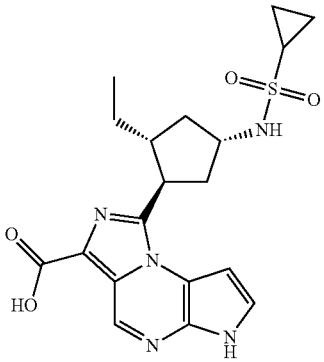 | D.1.145* | 1.59 (a) | 418 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| N-((1S,3R,4S)-3-ethyl-4-(6-tosyl-3-(trifluoromethyl)-6H-imidazo[1,5-a]pyrrolo[2,3-e]pyrazin-1-yl)cyclopentyl)cyclopropanesulfonamide (prepared using H with Preparation #32 and Preparation #Z.1, OO | 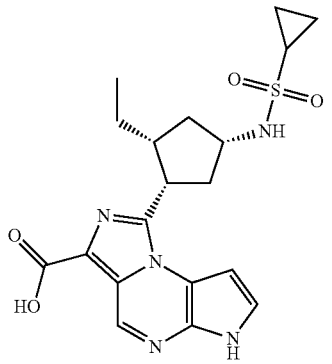 | D.1.146* | 1.45 (a) | 418 |
| N-((1S,3R,4S)-3-methyl-4-(6-tosyl-3-(trifluoromethyl)-6H-imidazo[1,5-a]pyrrolo[2,3-e]pyrazin-1-yl)cyclopentyl)cyclopropanesulfonamide (prepared using Y from Example #24 Step J, K with cyclopropylsulfonyl chloride (Matrix), H from Preparation #32 and OO) | 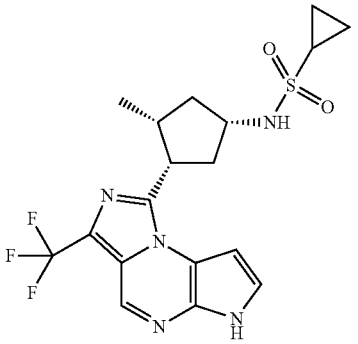 | D.1.147* | 2.03 (a) | 428 |
| 1-((cis)-4-ethylpyrrolidin-3-yl)-6-tosyl-6H-pyrrolo[2,3-e][1,2,4]triazolo[4,3-a]pyrazine•hydrochloride (prepared using K from Example #36, Step F, 3,3,3-trifluoropropane-1-sulfonyl chloride [Matrix] and TEA) | 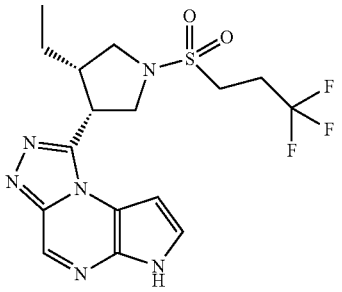 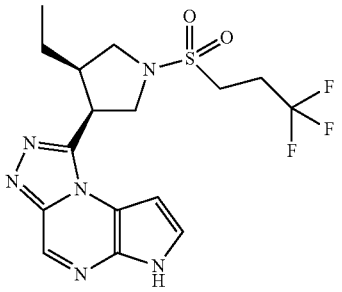 | D.1.148 | 1.86 (a) | 417 |

TABLE D.1-continued

| Examples prepared using General Procedure D with NaOH | | | | |
|---|---|---|---|---|
| Sulfonamide | Product | Ex # | $R_t$ min (Table 1, Method) | m/z ESI+ $(M + H)^+$ |
| 1-((cis)-4-ethyl-1-(3,3,3-trifluoropropyl)pyrrolidin-3-yl)-6-tosyl-6H-pyrrolo[2,3-e][1,2,4]triazolo[4,3-a]pyrazine (prepared using X from Example #36, Step F, 3,3,3-trifluoropropanal [Alfa Aesar], sodium triacetoxyborohydride and DIEA) | 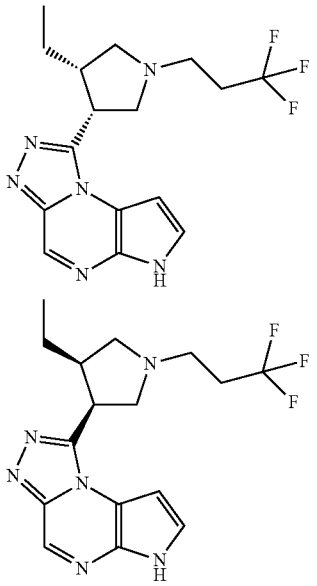 | D.1.149 | 1.54 (a) | 353 |
| 4-(2-((cis)-3-ethyl-4-(6-tosyl-6H-pyrrolo[2,3-e][1,2,4]triazolo[4,3-a]pyrazin-1-yl)pyrrolidin-1-yl)ethyl)morpholine (prepared using X from Example #36, Step F, 2-morpholinoacetaldehyde [Matrix], sodium triacetoxyborohydride and DIEA) | 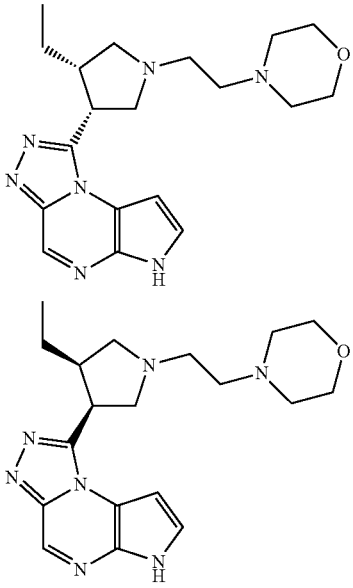 | D.1.150 | 1.35 (a) | 370 |
| 2-cyclopropyl-1-((cis)-3-ethyl-4-(6-tosyl-6H-pyrrolo[2,3-e][1,2,4]triazolo[4,3-a]pyrazin-1-yl)pyrrolidin-1-yl)ethanone (prepared using H from Example #36, Step F, 2-cyclopropylacetic acid, HATU [Novabiochem] and DIEA) | 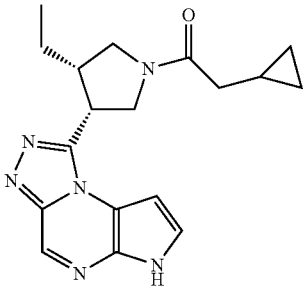 | D.1.151 | 1.54 (a) | 339 |

TABLE D.1-continued

| Examples prepared using General Procedure D with NaOH | | | | |
|---|---|---|---|---|
| Sulfonamide | Product | Ex # | $R_t$ min (Table 1, Method) | m/z ESI+ $(M + H)^+$ |
| | 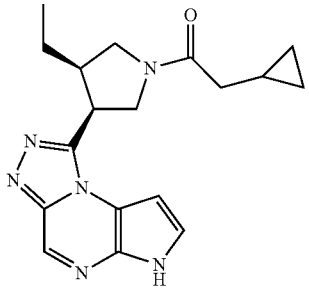 | | | |
| 1-((cis)-4-ethylpyrrolidin-3-yl)-6-tosyl-6H-pyrrolo[2,3-e][1,2,4]triazolo[4,3-a]pyrazine•hydrochloride (prepared using H from Example #36, Step F, 2-(tetrahydro-2H-pyran-4-yl)acetic acid [Astatech], HATU [Novabiochem] and DIEA) | 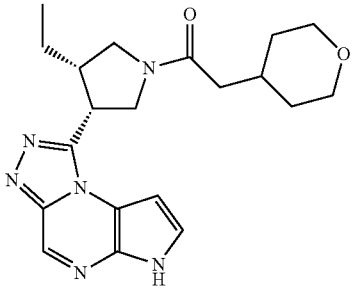 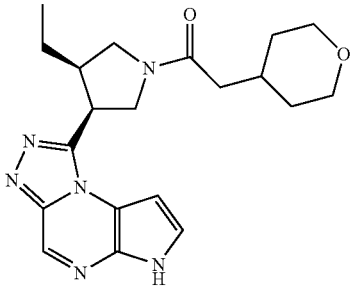 | D.1.152 | 1.54 (a) | 383 |
| N-((1S,3R,4S)-3-ethyl-4-(6-tosyl-6H-pyrrolo[2,3-e][1,2,4]triazolo[4,3-a]pyrazin-1-yl)cyclopentyl)-3,3-difluorocyclobutane-1-sulfonamide (prepared using K from Example 8, Step M, Preparation #34, and DIEA) | 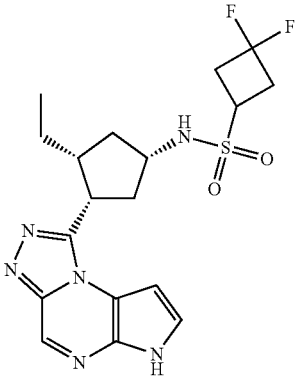 | D.1.153 | 1.75 (a) | 425 |

TABLE D.1-continued

| Examples prepared using General Procedure D with NaOH | | | | |
|---|---|---|---|---|
| Sulfonamide | Product | Ex # | $R_t$ min (Table 1, Method) | m/z ESI+ $(M + H)^+$ |
| 1-((cis)-4-ethylpyrrolidin-3-yl)-6-tosyl-6H-pyrrolo[2,3-e][1,2,4]triazolo[4,3-a]pyrazine•hydrochloride (prepared using K from Example #36, Step F, Preparation #34, and DIEA) | 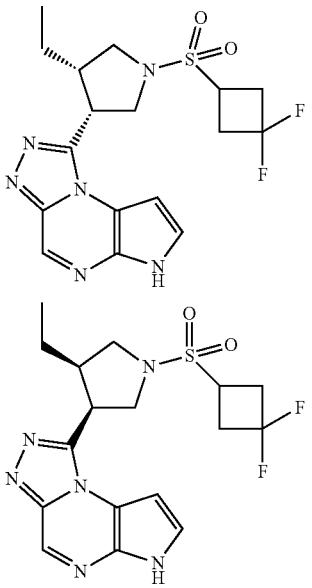 | D.1.154 | 1.90 (a) | 411 |
| isopropyl (1S,3R,4S)-3-ethyl-4-(6-tosyl-6H-pyrrolo[2,3-e][1,2,4]triazolo[4,3-a]pyrazin-1-yl)cyclopentylcarbamate sulfonamide (Preparation #35) | 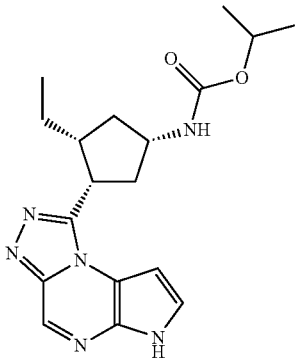 | D.1.155* | 1.74 (b) | 357 |
| 3-tosyl-8-(2-tosyl-2-azaspiro[3.3]heptan-6-yl)-3H-imidazo[1,2-a]pyrrolo[2,3-e]pyrazine (Preparation #KKKK.1) | 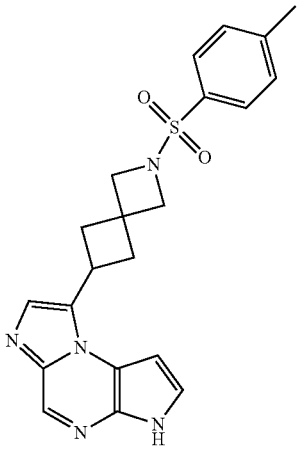 | D.1.156 | 1.99 (a) | 294 (M − H) |

TABLE D.1-continued

| Examples prepared using General Procedure D with NaOH | | | | |
|---|---|---|---|---|
| Sulfonamide | Product | Ex # | $R_t$ min (Table 1, Method) | m/z ESI+ $(M + H)^+$ |
| 4-(6-tosyl-6H-pyrrolo[2,3-e][1,2,4]triazolo[4,3-a]pyrazin-1-yl)bicyclo[2.2.2]octan-1-amine (Example #9 Step F) | 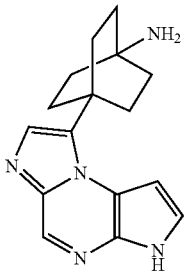 | D.1.157 | 2.72 (r) | 283 |
| 8-(piperidin-1-yl)-3-tosyl-3H-imidazo[1,2-a]pyrrolo[2,3-e]pyrazine (prepared using S from Example #3, Step E and 1-(bromoacetyl)piperidine [ChemBridge], E with HCl, OO.1) | 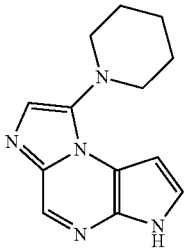 | D.1.158 | 1.78 (a) | 242 |
| 8-(2-(4-methylpiperazin-1-yl)pyrimidin-4-yl)-6-tosyl-6H-pyrrolo[2,3-e][1,2,4]triazolo[4,3-a]pyrazine (Preparation #CCCCC.1) | 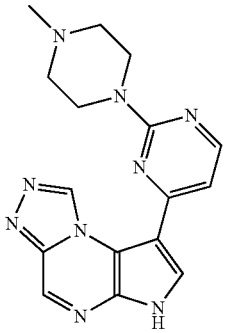 | D.1.159 | 1.00 (a) | 336 |
| 8-(2-(4-methylpiperazin-1-yl)quinazolin-4-yl)-6-tosyl-6H-pyrrolo[2,3-e][1,2,4]triazolo[4,3-a]pyrazine (prepared using D from Preparation #BBBBB.1 and NaOH, GGG.1 with NBS, K.1 with TsCl and NaH, CCCCC with Preparation #40, tetrakis(triphenylphosphine)palladium(0), LiCl, CsF, and CuI | 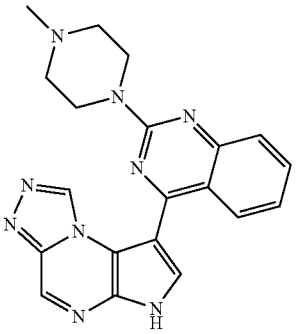 | D.1.160 | 1.16 (a) | 386 |
| 8-(2-methoxypyridin-4-yl)-6-tosyl-6H-pyrrolo[2,3-e][1,2,4]triazolo[4,3-a]pyrazine (prepared using D from Preparation #BBBBB.1 and NaOH, GGG.1 with NBS, K.1 with TsCl and NaH, CCCCC with 2-methoxy-4-(tributylstannyl)pyridine [Synthonix], tetrakis(triphenylphosphine)palladium(0), LiCl, CsF, and CuI | 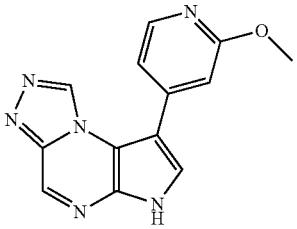 | D.1.161 | 1.28 (a) | 267 |

TABLE D.1-continued

Examples prepared using General Procedure D with NaOH

| Sulfonamide | Product | Ex # | $R_t$ min (Table 1, Method) | m/z ESI+ $(M + H)^+$ |
|---|---|---|---|---|
| 8-(1-benzylpyrrolidin-3-yl)-3-tosyl-3H-imidazo[1,2-a]pyrrolo[2,3-e]pyrazine (prepared using R from 1-benzylpyrrolidine-3-carboxylic acid, S from Example #3 Step E, E with TFA, KKKK with PFPAA) | 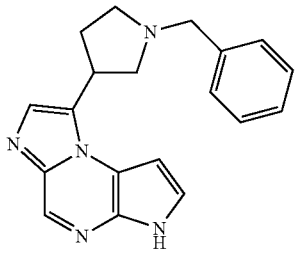 | D.1.162 | 1.40 (b) | 317 |
| 2-(3-((1S,3R,4S)-3-ethyl-4-(6-tosyl-6H-pyrrolo[2,3-e][1,2,4]triazolo[4,3-a]pyrazin-1-yl)cyclopentylamino)oxetan-3-yl)acetonitrile (prepared using YYY from Preparation #BB.1* and 2-(oxetan-3-yliden)acetonitrile (J. Med. Chem, 2010, 53(8) 3227-3246) with Hunig's base) | 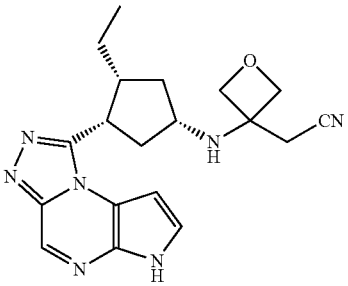 | D.1.163* | 1.35 (a) | 366 |
| N-((1S,3R,4S)-3-methyl-4-(6-tosyl-2-(trifluoromethyl)imidazo[4,5-d]pyrrolo[2,3-b]pyridin-1(6H)-yl)cyclopentyl) cyclopropanesulfonamide (prepared using L from Preparation #27 and Preparation #OOO.1 and DIEA, K with TsCl and NaH, BBB, CCC with TFAA, DDD with HCl) | 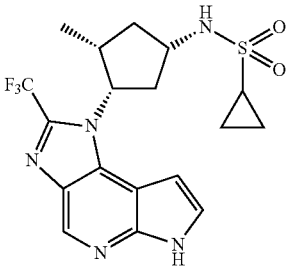 | D.1.164 | 1.95 (a) | 428 |
| N-(3-ethyl-4-(6-tosyl-6H-pyrrolo[2,3-e][1,2,4]triazolo[4,3-a]pyrazin-1-yl)cyclopentyl)-N-(4,4,4-trifluorobutyl)acetamide (prepared using X from Example #8 Step M and 4,4,4-trifluorobutanal [Matrix], CCC with $Ac_2O$) | 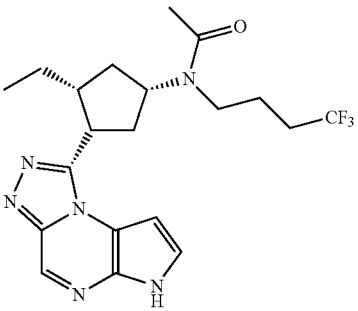 | D.1.165* | 1.85 (a) | 423 |
| N-((1S,3R,4S)-3-ethyl-4-(6-tosyl-6H-pyrrolo[2,3-e][1,2,4]triazolo[4,3-a]pyrazin-1-yl)cyclopentyl)-N-((tetrahydro-2H-pyran-4-yl)methyl)acetamide (prepared using X from Example #8 Step M and tetrahydro-2H-pyran-4-carbaldehyde [Pharmacore], CCC with $Ac_2O$) | 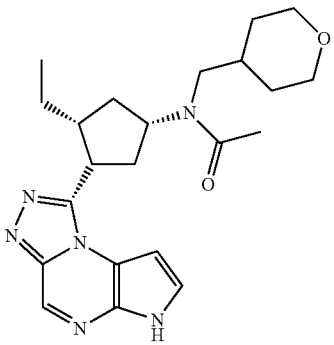 | D.1.166* | 1.61 (a) | 411 |

TABLE D.1-continued

| Examples prepared using General Procedure D with NaOH | | | | |
|---|---|---|---|---|
| Sulfonamide | Product | Ex # | $R_t$ min (Table 1, Method) | m/z ESI+ $(M + H)^+$ |
| N-(cyclopropylmethyl)-N-((1S,3R,4S)-3-ethyl-4-(6-tosyl-6H-pyrrolo[2,3-e][1,2,4]triazolo[4,3-a]pyrazin-1-yl)cyclopentyl)acetamide (prepared using X from Example #8 Step M and cyclopropanecarbaldehyde, CCC with $Ac_2O$) | 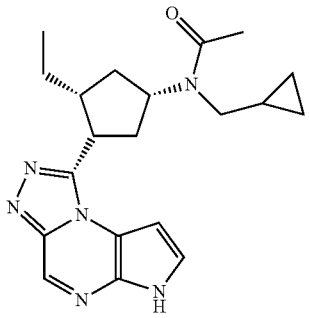 | D.1.167* | 1.73 (a) | 367 |
| N-((1S,3S,4R)-3-(2- (difluoromethyl)-6-tosylimidazo[4,5-d]pyrrolo[2,3-b]pyridin-1(6H)-yl)-4-ethylcyclopentyl)cyclopropane-sulfonamide (prepared using H from Example #23 Step I, difluoroacetic acid, HATU, and TEA, DDD with TPP) | 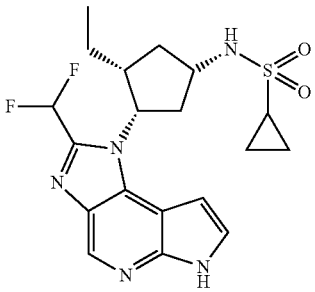 | D.1.168 | 1.76 (a) | 424 |
| N-((1S,3R,4S)-3-ethyl-4-(6-tosyl-6H-pyrrolo[2,3-e][1,2,4]triazolo[4,3-a]pyrazin-1-yl)cyclopentyl)-N-methyloxetan-3-amine (prepared using X from Preparation #25 and N-methyloxetan-3-amine [Synthonix]) | 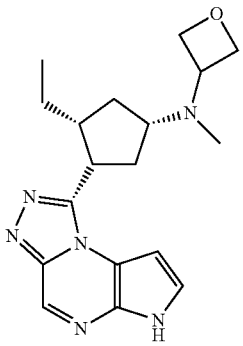 | D.1.169 | 1.02 (a) | 341 |
| (1S,3R,4S)-3-ethyl-N-((3-methyloxetan-3-yl)methyl)-4-(6-tosyl-6H-pyrrolo[2,3-e][1,2,4]triazolo[4,3-a]pyrazin-1-yl)cyclopentanamine (prepared using X from Preparation #25 and (3-methyloxetan-3-yl)methanamine [Synthonix]) | 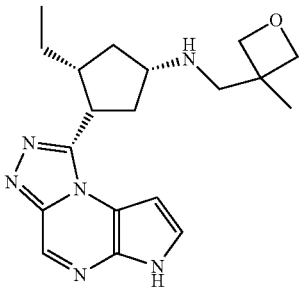 | D.1.170 | 1.11 (a) | 355 |

TABLE D.1-continued

| Examples prepared using General Procedure D with NaOH | | | | |
|---|---|---|---|---|
| Sulfonamide | Product | Ex # | $R_t$ min (Table 1, Method) | m/z ESI+ $(M + H)^+$ |
| N-((1S,3R,4S)-3-ethyl-4-(2-methyl-6-tosylimidazo[4,5-d]pyrrolo[2,3-b]pyridin-1(6H)-yl)cyclopentyl)cyclopropane-sulfonamide (prepared using CCC from Example #23 Step I and $Ac_2O$, DDD with TPP) | 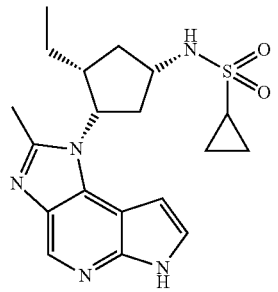 | D.1.171 | 1.53 (a) | 358 |
| N-(cyclopropylmethyl)-N-((1S,3R,4S)-3-ethyl-4-(6-tosyl-6H-pyrrolo[2,3-e][1,2,4]triazolo[4,3-a]pyrazin-1-yl)cyclopentyl)-3-methyloxetan-3-amine (prepared using X from Preparation #25 and 3-methyloxetan-3-amine [Synthonix], X using cyclopropanecarbaldehyde) | 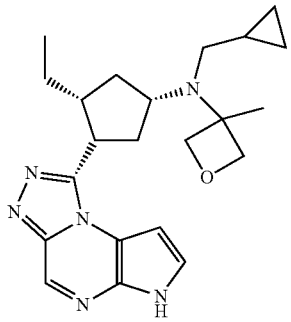 | D.1.172 | 1.23 (a) | 395 |
| N-(2-cyclopropylethyl)-N-((1S,3R,4S)-3-ethyl-4-(6-tosyl-6H-pyrrolo[2,3-e][1,2,4]triazolo[4,3-a]pyrazin-1-yl)cyclopentyl)-3-methyloxetan-3-amine (prepared using X from Preparation #25 and 3-methyloxetan-3-amine [Synthonix], X using 2-cyclopropylacetaldehyde [Anichem]) | 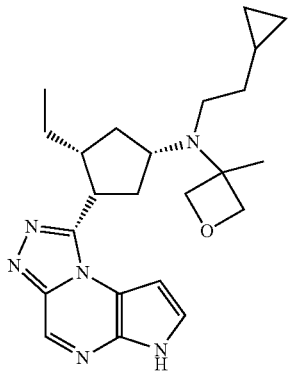 | D.1.173 | 1.40 (a) | 409 |
| N-((1S,3R,4S)-3-ethyl-4-(6-tosyl-2-(trifluoromethyl)imidazo[4,5-d]pyrrolo[2,3-b]pyridin-1(6H)-yl)cyclopentyl)cyclopropane-sulfonamide (prepared using CCC from Example #23 Step I and TFAA, DDD with HCl) | 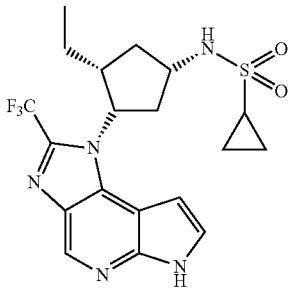 | D.1.174 | 1.95 (a) | 442 |

TABLE D.1-continued

| Examples prepared using General Procedure D with NaOH | | | | |
|---|---|---|---|---|
| Sulfonamide | Product | Ex # | $R_t$ min (Table 1, Method) | m/z ESI+ $(M + H)^+$ |
| 3-((1R,3R,4S)-3-ethyl-4-(6-tosyl-6H-pyrrolo[2,3-e][1,2,4]triazolo[4,3-a]pyrazin-1-yl)cyclo-pentyloxy)propanenitrile (prepared using YYY from Example #41 Step I and acrylonitrile, Z with NaOH, A with Example #1 Step D, HATU and TEA, B with thionyl chloride and TEA) | 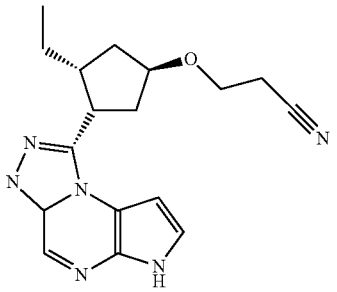 | D.1.175 | 1.72 (b) | 325 |

TABLE D.2

| Examples prepared using General Procedure D with $Na_2CO_3$ | | | | |
|---|---|---|---|---|
| Sulfonamide | Product | Example # | $R_t$ min (Table 1, Method) | m/z ESI+ $(M + H)^+$ |
| (S)-5-(3-((6-tosyl-6H-pyrrolo[2,3-e][1,2,4]triazolo[4,3-a]pyrazin-1-yl)methyl)pyrrolidin-1-yl)pyrazine-2-carbonitrile (Preparation #L.1) | 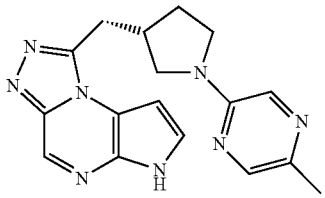 | D.2.1* | 1.46 (a) | 346 |
| 2-(4-cyanophenyl)-N-((1S,3R)-3-(6-tosyl-6H-pyrrolo[2,3-e][1,2,4]triazolo[4,3-a]pyrazin-1-yl)cyclopentyl)acetamide (prepared using E from Preparation #B.1 with HCl, and H with 4-cyanophenylacetic acid, EDC and DIEA) | 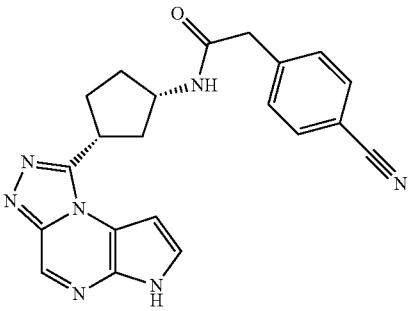 | D.2.2* | 1.20 (c) | 386 |
| 4-cyano-N-((1S,3R)-3-(6-tosyl-6H-pyrrolo[2,3-e][1,2,4]triazolo[4,3-a]pyrazin-1-yl)cyclopentyl)benzamide (prepared using E from Preparation #B.1 with HCl, H with 4-cyanobenzoic acid, EDC, and DIEA) | 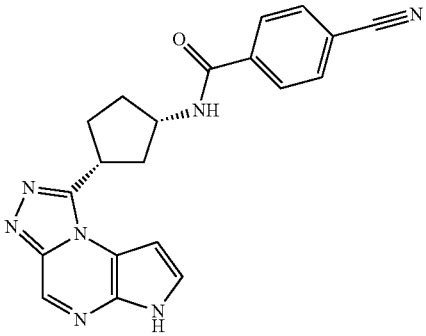 | D.2.3* | 1.16 (c) | 372 |

TABLE D.2-continued

Examples prepared using General Procedure D with $Na_2CO_3$

| Sulfonamide | Product | Example # | $R_t$ min (Table 1, Method) | m/z ESI+ $(M + H)^+$ |
|---|---|---|---|---|
| 3-((1R,3R)-3-(6-tosyl-6H-pyrrolo[2,3-e][1,2,4]triazolo[4,3-a]pyrazin-1-yl)cyclopentylamino)benzonitrile (prepared using PP with Example #2, Step F, 3-cyanophenylboronic acid and DIEA) | 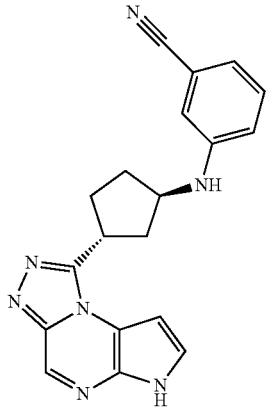 | D.2.4* | 1.91 (a) | 344 |
| 3-cyano-N-((1S,3R,4S)-3-ethyl-4-(6-tosyl-6H-pyrrolo[2,3-e][1,2,4]triazolo[4,3-a]pyrazin-1-yl)cyclopentyl)azetidine-1-sulfonamide (prepared using DD with Example #8, Step M, 3-cyanoazetidine-1-sulfonyl chloride [prepared from CC with azetidine-3-carbonitrile hydrochloride (Astatech) and DIEA] and TEA) | 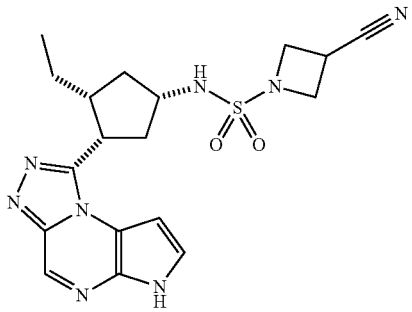 | D.2.5* | 1.82 (a) | 415 |
| 3-((1S,3R,4S)-3-methyl-4-(6-tosyl-6H-pyrrolo[2,3-e][1,2,4]triazolo[4,3-a]pyrazin-1-yl)cyclopentylamino)-benzonitrile (prepared using PP from Preparation #19.2, 3-cyanophenyl boronic acid, and DIEA) | 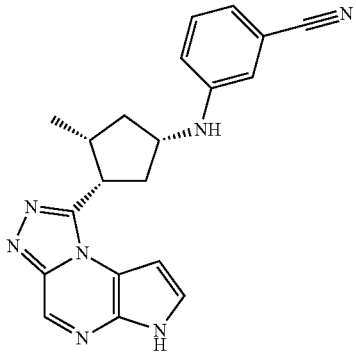 | D.2.6* | 2.04 (a) | 358 |
| 5-((1S,3R,4S)-3-methyl-4-(6-tosyl-6H-pyrrolo[2,3-e][1,2,4]triazolo[4,3-a]pyrazin-1-yl)cyclopentylamino)-pyrazine-2-carbonitrile (prepared using L from Preparation #19.2, 2-chloro-5-cyanopyrazine [ArkPharm], and DIEA) | 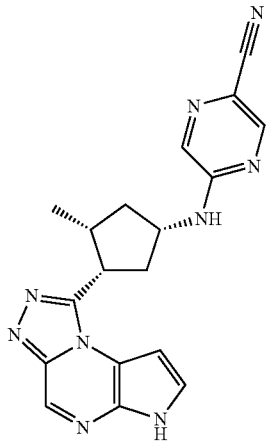 | D.2.7* | 1.89 (a) | 360 |

TABLE D.2-continued

Examples prepared using General Procedure D with $Na_2CO_3$

| Sulfonamide | Product | Example # | $R_t$ min (Table 1, Method) | m/z ESI+ $(M + H)^+$ |
|---|---|---|---|---|
| 6-((1S,3R,4S)-3-methyl-4-(6-tosyl-6H-pyrrolo[2,3-e][1,2,4]triazolo[4,3-a]pyrazin-1-yl)cyclopentylamino)-nicotinonitrile (prepared using L from Preparation #19.2, 5-cyano-2-fluoropyridine [Matrix] and DIEA) | 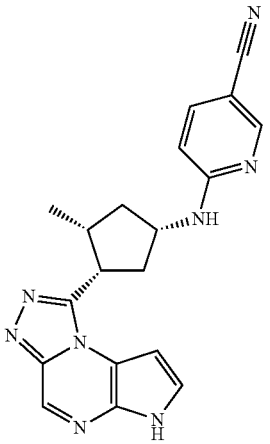 | D.2.8* | 1.81 (a) | 359 |
| 2-((1S,3R,4S)-3-methyl-4-(6-tosyl-6H-pyrrolo[2,3-e][1,2,4]triazolo[4,3-a]pyrazin-1-yl)cyclopentylamino)-thiazole-5-carbonitrile (prepared using L from Preparation #19.2, 2-chlorothiazole-5-carbonitrile [ArkPharm] and DIEA) | 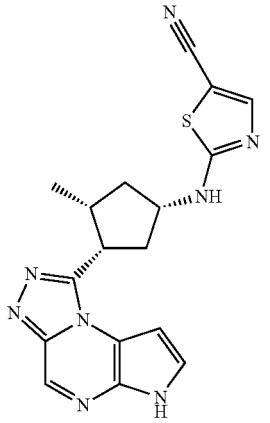 | D.2.9* | 1.89 (a) | 365 |
| 6-((1R,3R,4R)-3-ethyl-4-(6-tosyl-6H-pyrrolo[2,3-e][1,2,4]triazolo[4,3-a]pyrazin-1-yl)cyclopentyloxy)nicotino nitrile and 6-((1S,3S,4S)-3-ethyl-4-(6-tosyl-6H-pyrrolo[2,3-e][1,2,4]triazolo[4,3-a]pyrazin-1-yl)cyclopentyloxy)-nicotinonitrile (prepared using II from 6-hydroxynicotinonitrile [Asta Tech], Preparation #FF.1 and DEAD) | 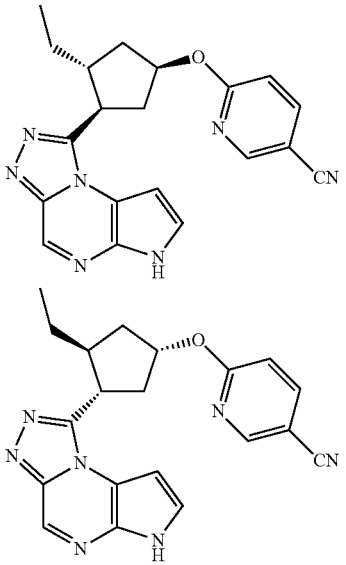 | D.2.10 | 2.01 (b) | 374 |

TABLE D.2-continued

Examples prepared using General Procedure D with $Na_2CO_3$

| Sulfonamide | Product | Example # | $R_t$ min (Table 1, Method) | m/z ESI+ $(M + H)^+$ |
|---|---|---|---|---|
| 5-((1S,3R,4S)-3-ethyl-4-(6-tosyl-6H-pyrrolo[2,3-e][1,2,4]triazolo[4,3-a]pyrazin-1-yl)cyclopentylamino)-pyrazin-2-carbonitrile (prepared using L from Example #8, Step M and 2-chloro-5-cyanopyrazine [ArkPharm] and DIEA) | 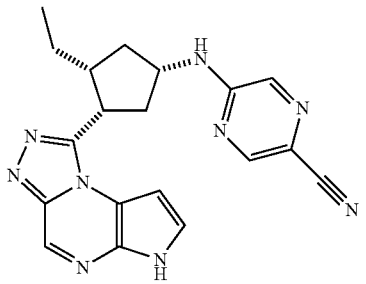 | D.2.11* | 1.94 (a) | 374 |
| 1-((1S,3R)-3-(6-tosyl-6H-pyrrolo[2,3-e][1,2,4]triazolo[4,3-a]pyrazin-1-yl)cyclopentyl)-1H-pyrroloe-3-carbonitrile (Preparation #4) | 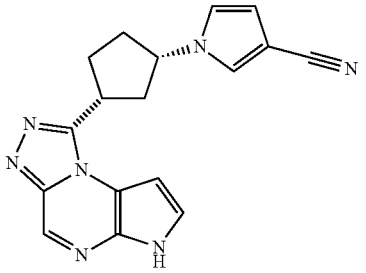 | D.2.12* | 1.92 (a) | 318 |
| 5-((1S,3R,4S)-3-ethyl-4-(6-tosyl-6H-imidazo[1,5-a]pyrrolo[2,3-e]pyrazin-1-yl)cyclopentylamino)pyrazine-2-carbonitrile (prepared using H from Example #8, Step K, Example #5, Step C, HATU and TEA, Q with Lawesson's reagent and mercury (II) trifluoroacetate, BB with HCl, L with 2-chloro-5-cyanopyrazine [ArkPharm] and DIEA) | 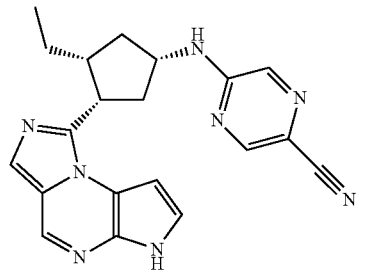 | D.2.13* | 2.10 (a) | 373 |
| 5-(((1S,3R)-3-(6-tosyl-6H-pyrrolo[2,3-e][1,2,4]triazolo[4,3-a]pyrazin-1-yl)cyclopentyl)methyl-amino)pyrazine-2-carbonitrile (prepared using M from (1R,3S)-3-(aminomethyl)cyclo-pentanecarboxylic acid (AFID), A from Example #1, Step D, HATU and TEA, C with TEA, L with 2-chloro-5-cyanopyrazine [ArkPharm] and DIEA) | 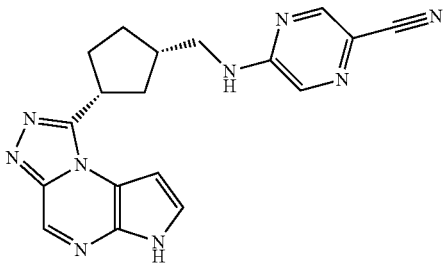 | D.2.14* | 1.79 (a) | 360 |

TABLE D.2-continued

Examples prepared using General Procedure D with $Na_2CO_3$

| Sulfonamide | Product | Example # | $R_t$ min (Table 1, Method) | m/z ESI+ $(M + H)^+$ |
|---|---|---|---|---|
| 5-(((1S,3S)-3-(6-tosyl-6H-pyrrolo[2,3-e][1,2,4]triazolo[4,3-a]pyrazin-1-yl)cyclopentyl)methyl-amino)pyrazine-2-carbonitrile and 5-(((1S,3R)-3-(6-tosyl-6H-pyrrolo[2,3-e][1,2,4]triazolo[4,3-a]pyrazin-1-yl)cyclopentyl)methyl-amino)pyrazine-2-carbonitrile (prepared using M from (1R,3S)-3-(aminomethyl)cyclo-pentanecarboxylic acid (AFID), H from Example #5, Step C, HATU and TEA, Q with Lawesson's reagent and mercury(II) trifluoroacetate, E with HCl, L with 5-chloropyrazine-2-carbonitrile [ArkPharm] and DIEA) | 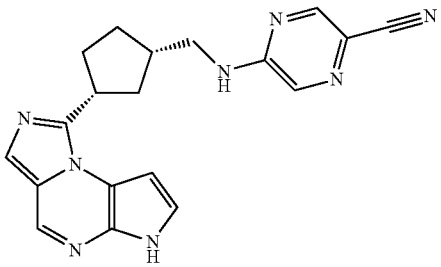 | D.2.15* | 1.84 (a) | 359 |
| 5-(((1S,3S)-3-(6-tosyl-6H-pyrrolo[2,3-e][1,2,4]triazolo[4,3-a]pyrazin-1-yl)cyclopentyl)methyl-amino)pyrazine-2-carbonitrile and 5-(((1S,3R)-3-(6-tosyl-6H-pyrrolo[2,3-e][1,2,4]triazolo[4,3-a]pyrazin-1-yl)cyclopentyl)methyl-amino)pyrazine-2-carbonitrile (prepared using M from (1R,3S)-3-(aminomethyl)cyclo-pentanecarboxylic acid (AFID), H from Example #5, Step C, HATU and TEA, Q with Lawesson's reagent and mercury(II) trifluoroacetate, L with 5-chloropyraine-2-carbonitrile [ArkPharm] and DIEA) | 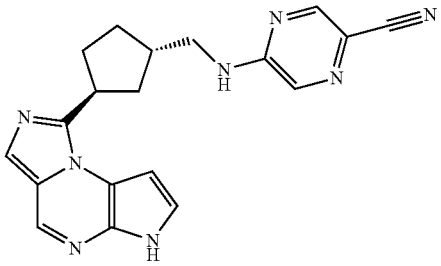 | D.2.16* | 1.73 (a) | 359 |

TABLE D.2-continued

Examples prepared using General Procedure D with $Na_2CO_3$

| Sulfonamide | Product | Example # | $R_t$ min (Table 1, Method) | m/z ESI+ $(M + H)^+$ |
|---|---|---|---|---|
| 6-(cis-3-methyl-4-(6-tosyl-6H-pyrrolo[2,3-e][1,2,4]triazolo[4,3-a]pyrazin-1-yl)cyclopentylamino)-nicotinonitrile (prepared using Y from Preparation #46 with $Pd(OH)_2$ in C, Z with NaOH, M, A from Example #1, Step D, HATU, and TEA, C with TEA, L with 6-fluoronicotinonitrile [Matrix] and DIEA) | 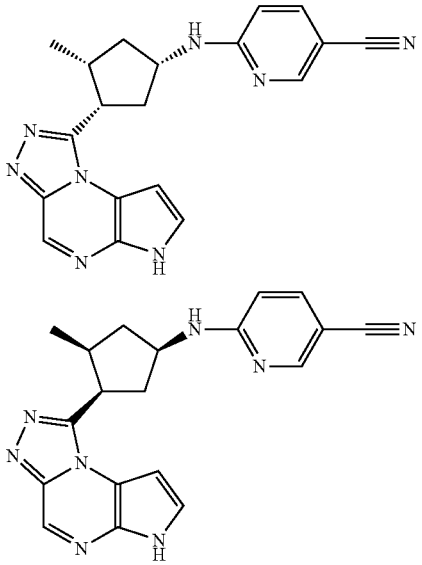 | D.2.17 | 1.74 (a) | 359 |
| 5-((cis-3-ethyl-4-(6-tosyl-6H-pyrrolo[2,3-e][1,2,4]triazolo[4,3-a]pyrazin-1-yl)cyclopentyl)methoxy)-pyrazine-2-carbonitrile (prepared using P from Preparation #11 with LAH, JJ with 2-chloro-5-cyanopyrazine [ArkPharm], TT with HCl, A from Example #1, Step D with HATU and TEA, B with TEA) | 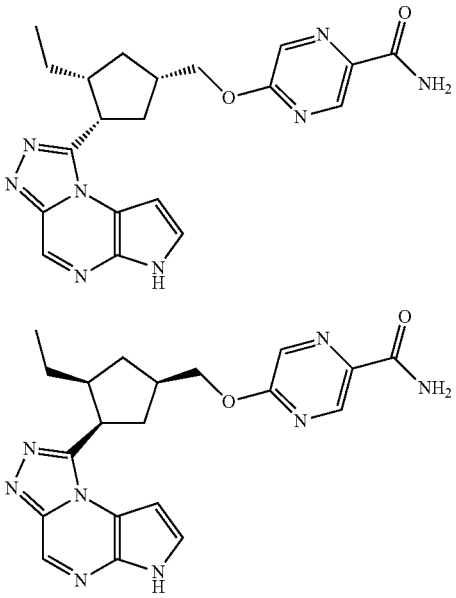 | D.2.18 | 1.81 (a) | 407 |
| 6-((1S,3R,4S)-3-ethyl-4-(6-tosyl-6H-pyrrolo[2,3-e][1,2,4]triazolo[4,3-a]pyrazin-1-yl)cyclopentylamino)-nicotinonitrile (prepared using L from Example #8, Step M and 6-fluoronicotinonitrile [Matrix] and DIEA) | 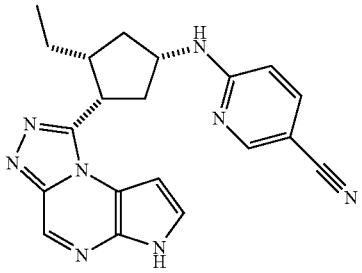 | D.2.19* | 2.02 (a) | 373 |

TABLE D.2-continued

Examples prepared using General Procedure D with $Na_2CO_3$

| Sulfonamide | Product | Example # | $R_t$ min (Table 1, Method) | m/z ESI+ $(M + H)^+$ |
|---|---|---|---|---|
| 5-((1R,3R)-3-(6-tosyl-6H-pyrrolo[2,3-e][1,2,4]triazolo[4,3-a]pyrazin-1-yl)cyclopentylamino)-pyrazine-2-carbonitrile (prepared using L from Example #2, Step F, 5-chloropyrazine-2-carbonitrile [Ark Pharm] and DIEA) | 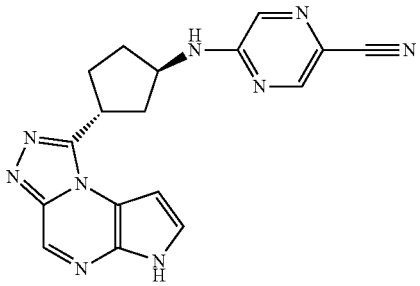 | D.2.20* | 1.57 (b) | 346 |
| 5-((1S,3R,4S)-3-methyl-4-(6-tosyl-6H-imidazo[1,5-a]pyrrolo[2,3-e]pyrazin-1-yl)cyclopentylamino)pyrazine-2-carbonitrile (prepared using L from Preparation #19.2, 2-chloropyrazine-2-carbonitrile [Ark Pharm] and DIEA) | 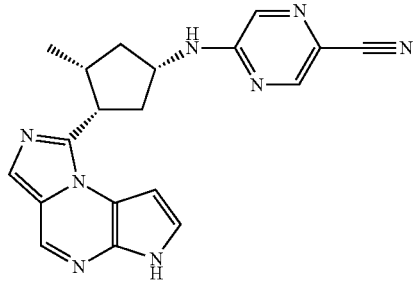 | D.2.21* | 1.97 (b) | 359 |
| 6-((1R,3R,4S)-3-ethyl-4-(6-tosyl-6H-pyrrolo[2,3-e][1,2,4]triazolo[2,3-e][1,2,4]triazolo[4,3-a]pyrazin-1-yl)cyclopentyloxy)-nicotinonitrile and 6-((1S,3S,4R)-3-ethyl-4-(6-tosyl-6H-pyrrolo[2,3-e][1,2,4]triazolo[4,3-a]pyrazin-1-yl)cyclopentyloxy)-nicotinonitrile (prepared using II from 6-hydroxynicotino-nitrile [Asta Tech], Preparation #FF.1 and DEAD) | 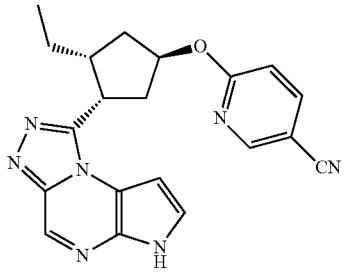 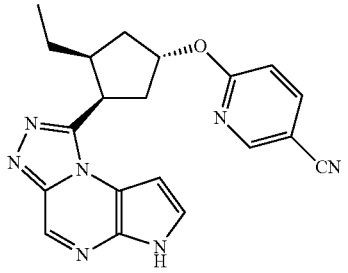 | D.2.22 | 1.99 (b) | 374 |
| 2-(((1S,3R)-3-(6-tosyl-6H-pyrrolo[2,3-e][1,2,4]triazolo[4,3-a]pyrazin-1-yl)cyclopentyl)methylamino) isonicotinonitrile (prepared using A from Example #1, Step D, Preparation #M.1, HATU and TEA, B with TEA; L with 2-fluoroisonicotinonitrile) | 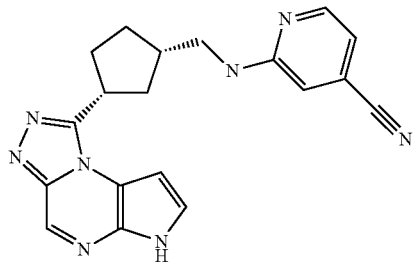 | D.2.23* | 1.69 (a) | 359 |

TABLE D.2-continued

Examples prepared using General Procedure D with $Na_2CO_3$

| Sulfonamide | Product | Example # | $R_t$ min (Table 1, Method) | m/z ESI+ $(M + H)^+$ |
|---|---|---|---|---|
| 4-((1R,3R,4S)-3-ethyl-4-(6-tosyl-6H-imidazo[1,5-a]pyrrolo[2,3-e]pyrazin-1-yl)cyclopentyloxy)benzonitrile (prepared from prepared from 5-tosyl-5H-pyrrolo[2,3-b]pyrazin-2-yl)methanamine hydrochloride (WO2009152133) and Preparation #GG.1 using HH with TMA and DIEA, II with 4-cyanophenol, DEAD, $PPh_3$, and TEA, and Q with Lawesson's reagent and and mercury (II) trifluoroacetate) | 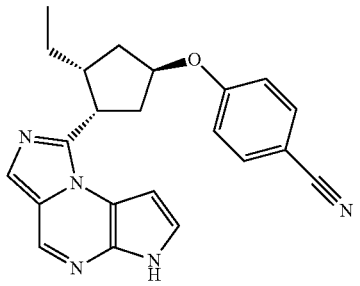 | D.2.24 | 2.28 (a) | 372 |
| N-(cyanomethyl)-N-((1S,3R,4S)-3-ethyl-4-(6-tosyl-6H-pyrrolo[2,3-e][1,2,4]triazolo[4,3-a]pyrazin-1-yl)cyclopentyl)cyclopropane-sulfonamide (prepared using S.1 from N-((1S,3R,4S)-3-ethyl-4-(6-tosyl-6H-pyrrolo[2,3-e][1,2,4]triazolo[4,3-a]pyrazin-1-yl)cyclopentyl)cyclo-propanesulfonamide [WO2009152133A1] and 2-iodoacetonitrile) | 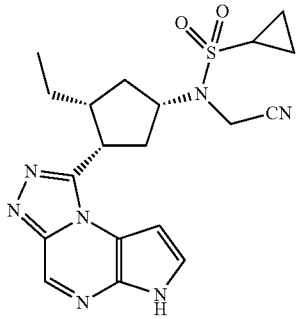 | D.2.25* | 1.74 (a) | 414 |
| (1S,3R,4S)-N-(2-cyclopropylethyl)-3-ethyl-4-(6-tosyl-6H-pyrrolo[2,3-e][1,2,4]triazolo[4,3-a]pyrazin-1-yl)-N-(2,2,2-trifluoroethyl)cyclopentanamine (prepared using X from Preparation #25 with 2,2,2-trifluoroethanamine, X with 2-cyclopropylacetaldehyde [Anichem]) | 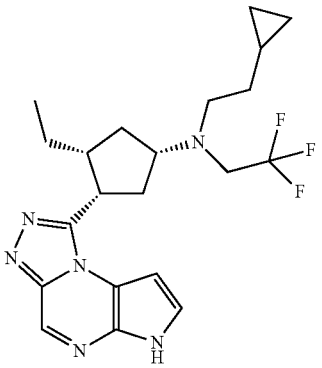 | D.2.26* | 2.49 (a) | 421 |
| (1S,3R,4S)-N-(cyclopropylmethyl)-3-ethyl-4-(6-tosyl-6H-pyrrolo[2,3-e][1,2,4]triazolo[4,3-a]pyrazin-1-yl)-N-(2,2,2-trifluoroethyl)cyclopentanamine (prepared using X from Preparation #25 with 2,2,2-trifluoroethanamine, X with cyclopropanecarbaldehyde) | 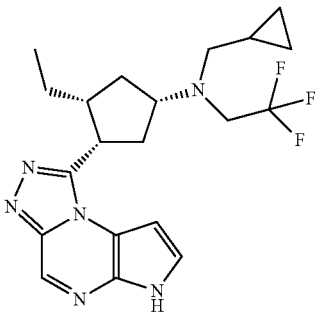 | D.2.27* | 2.31 (a) | 407 |

TABLE D.2-continued

Examples prepared using General Procedure D with $Na_2CO_3$

| Sulfonamide | Product | Example # | $R_t$ min (Table 1, Method) | m/z ESI+ $(M + H)^+$ |
|---|---|---|---|---|
| N-((1S,3R,4S)-3-ethyl-4-(6-tosyl-6H-pyrrolo[2,3-e][1,2,4]triazolo[4,3-a]pyrazin-1-yl)cyclopentyl)cyclopropane-sulfonamide (prepared using K from Example #8, Step M and cyclopropanesulfonyl chloride; YYY from acrylonitrile with DBU) | 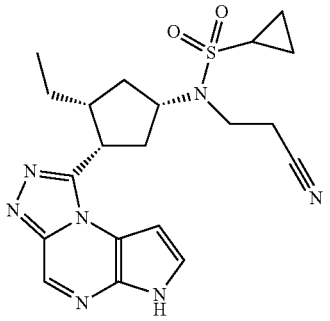 | D.2.28* | 1.70 (b) | 428 |
| (1S,3R,4S)-3-ethyl-4-(6-tosyl-6H-pyrrolo[2,3-e][1,2,4]triazolo[4,3-a]pyrazin-1-yl)cyclopentanamine (prepared using K from Example #8, Step M and 3-fluoropropane-1-sulfonyl chloride [Hande]) | 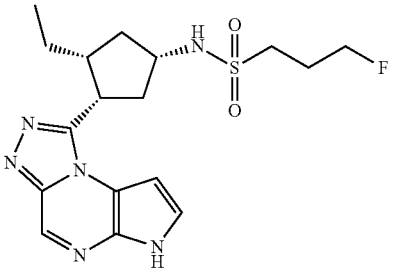 | D.2.29* | 1.59 (b) | 395 |
| 1-((cis)-4-ethylpyrrolidin-3-yl)-6-tosyl-6H-pyrrolo[2,3-e][1,2,4]triazolo[4,3-a]pyrazine • hydrochloride (prepared using L from Example #36, Step F, 6-fluoronicotinonitrile [Matrix], and TEA) | 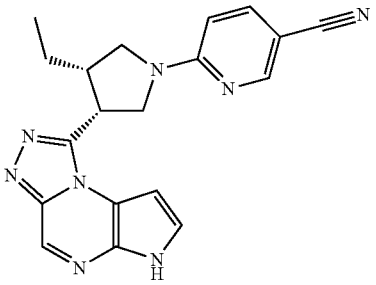 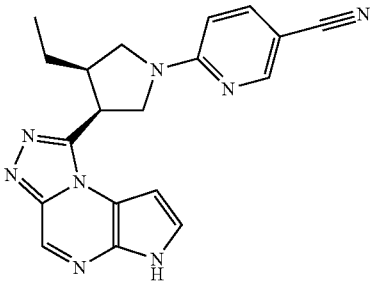 | D.2.30 | 1.81 (a) | 359 |
| 1-((cis)-4-ethylpyrrolidin-3-yl)-6-tosyl-6H-pyrrolo[2,3-e][1,2,4]triazolo[4,3-a]pyrazine • hydrochloride (prepared using X from Example #36, Step F, 4-formylbenzonitrile, sodium triacetoxyborohydride and DIEA) | 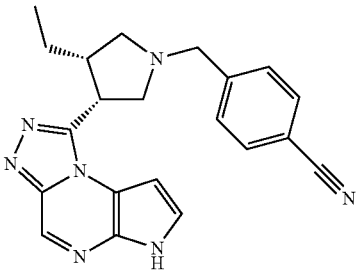 | D.2.31 | 1.53 (a) | 372 |

TABLE D.2-continued

Examples prepared using General Procedure D with $Na_2CO_3$

| Sulfonamide | Product | Example # | $R_t$ min (Table 1, Method) | m/z ESI+ $(M + H)^+$ |
|---|---|---|---|---|
| | 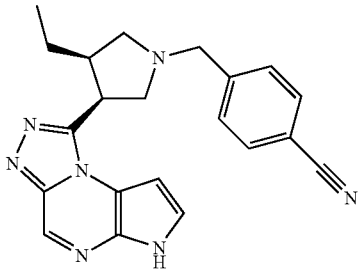 | | | |
| 1-((cis)-4-ethylpyrrolidin-3-yl)-6-tosyl-6H-pyrrolo[2,3-e][1,2,4]triazolo[4,3-a]pyrazine • hydrochloride (prepared using H from Example #36, Step F, 2-cyanoacetic acid, HATU [Novabiochem] and DIEA) | 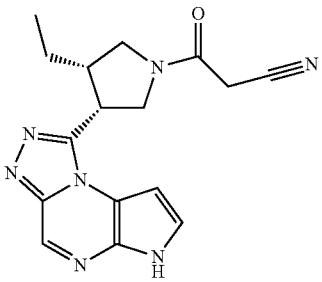 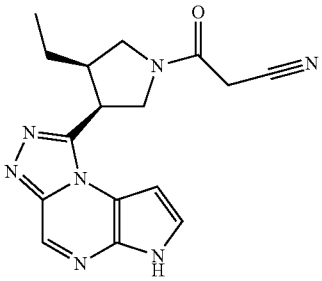 | D.2.32 | 1.49 (a) | 324 |
| 1-((cis)-4-ethylpyrrolidin-3-yl)-6-tosyl-6H-pyrrolo[2,3-e][1,2,4]triazolo[4,3-a]pyrazine • hydrochloride (prepared using YYY from Example #36, Step F, 2-(ocetan-3-ylidene)acetonitrile [J. Med. Chem, 2010, 53, 3227-3246], and DIEA) | 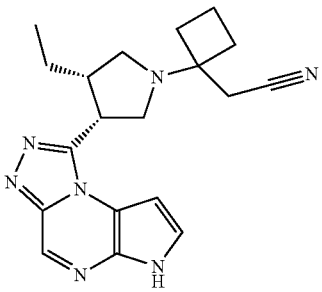 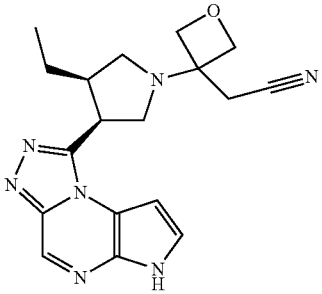 | D.2.33 | 1.55 (a) | 352 |

TABLE D.2-continued

| Examples prepared using General Procedure D with $Na_2CO_3$ | | | | |
|---|---|---|---|---|
| Sulfonamide | Product | Example # | $R_t$ min (Table 1, Method) | m/z ESI+ $(M + H)^+$ |
| (1S,3R,4S)-3-ethyl-4-(6H-pyrrolo[2,3-e][1,2,4]triazolo[4,3-a]pyrazin-1-yl)cyclopentyl phenylcarbamate (prepared using WWW from Example #42 Step N and phenylamine) | 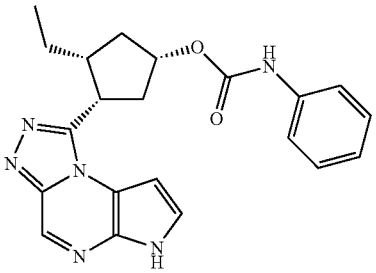 | D.2.34* | 2.04 (b) | 391 |

TABLE D.3

| Examples prepared using General Procedure D with $Na_2CO_3$ followed by NaOH | | | | |
|---|---|---|---|---|
| Sulfonamide | Product | Ex # | $R_t$ min (Table 1, Method) | m/z ESI+ $(M + H)^+$ |
| 3-(cyclopropylmethylamino)-4-((1S,3R,4S)-3-ethyl-4-(6-tosyl-6H-pyrrolo[2,3-e][1,2,4]triazolo[4,3-a]pyrazin-1-yl)cyclopentylamino)-cyclobut-3-ene-1,2-dione (prepared using TTTT from Preparation #29 and cyclopropylmethanamine) | 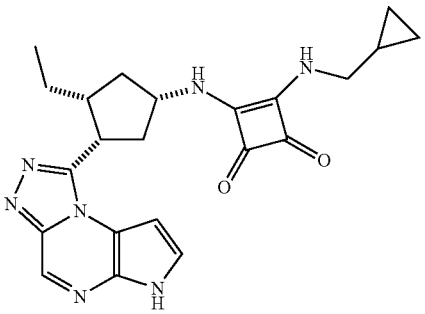 | D.3.1* | 1.71 (a) | 420 |
| 3-((1S,3R,4S)-3-erthyl-4-(6-tosyl-6H-pyrrolo[2,3-e][1,2,4]triazolo[4,3-a]pyrazin-1-yl)cyclopentylamino)-4-(oxetan-3-ylamino)cyclobut-3-ene-1,2-dione (prepared using TTTT from Preparation #29 and oxetan-3-amine [Synthonix]) | 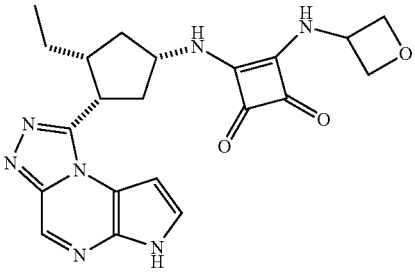 | D.3.2* | 1.55 (a) | 422 |

TABLE D.3-continued

Examples prepared using General Procedure D with $Na_2CO_3$ followed by NaOH

| Sulfonamide | Product | Ex # | $R_t$ min (Table 1, Method) | m/z ESI+ $(M + H)^+$ |
|---|---|---|---|---|
| 3-((1S,3R,4S)-3-ethyl-4-(6-tosyl-6H-pyrrolo[2,3-e][1,2,4]triazolo[4,3-a]pyrazin-1-yl)cyclopentylamino)-4-(3,3,3-trifluoropropylamino)cyclobut-3-ene-1,2-dione (Preparation #TTTT.1) | 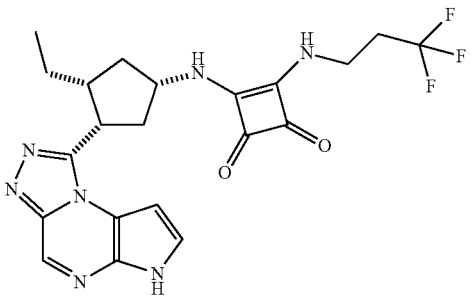 | D.3.3* | 1.58 (a) | 462 |
| 3-(cyclopropylamino)-4-((1S,3R,4S)-3-ethyl-4-(6-tosyl-6H-pyrrolo[2,3-e][1,2,4]triazolo[4,3-a]pyrazin-1-yl)cyclopentylamino)cyclobut-3-ene-1,2-dione (prepared using TTTT from Preparation #29 and cyclopropylamine) | 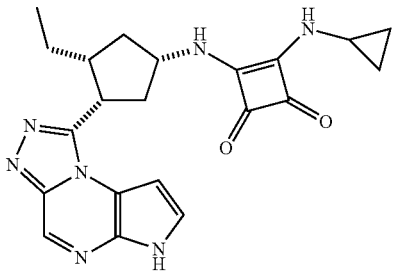 | D.3.4* | 1.65 (a) | 406 |

General Procedure E: Acidic Cleavage of a Boc-Protected Amine

To a solution of a Boc-protected amine (preferably 1 equiv) in an organic solvent (such as DCM, 1,4-dioxane, or MeOH) is added TFA or HCl (preferably 4 N HCl in 1,4-dioxane, 2-35 equiv, preferably 2-15 equiv). The reaction is stirred at about 20-100° C. (preferably ambient temperature to about 60° C.) for about 1-24 h (preferably about 1-6 h). In any case where an additional acid labile group is present (for example, a t-butyl ester), this group may also be cleaved during the reaction. Optionally, additional TFA or HCl (preferably 4 N HCl in 1,4-dioxane solution, 2-35 equiv, preferably 2-15 equiv) may be added to the reaction mixture in cases where the reaction does not proceed to completion as monitored by TLC, LC/MS, or HPLC. Once the reaction has proceeded to an acceptable level, the reaction mixture can be concd in vacuo to provide the amine as a salt. Alternatively, the reaction may be partitioned between an organic solvent (such as EtOAc, DCM or 1,4-dioxane) and an aqueous base (such as saturated aqueous $NaHCO_3$ or saturated aqueous $Na_2CO_3$, preferably saturated aqueous $NaHCO_3$). The aqueous layer can be optionally extracted with additional organic solvent such as EtOAc or DCM. The combined organic layers may optionally be washed with brine, dried over anhydrous $Na_2SO_4$ or $MgSO_4$, then decanted or filtered, prior to concentrating under reduced pressure to give the target compound.

Preparation #E.1: N-((3S,5R)-5-ethylpyrrolidin-3-yl)cyclopropanesulfonamide hydrochloride

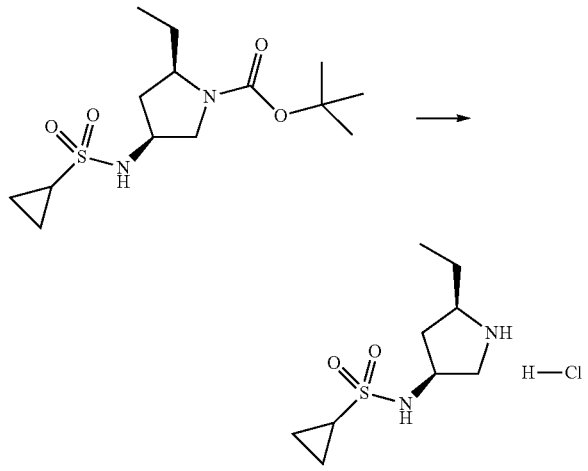

To a solution of (2R,4S)-tert-butyl 4-(cyclopropanesulfonamido)-2-ethylpyrrolidine-1-carboxylate (0.95 g, 2.98 mmol, Preparation #15) in 1,4-dioxane (7.5 mL) was added HCl (4 N in 1,4-dioxane, 7.46 mL, 29.8 mmol). The reaction mixture was heated to about 60° C. After about 4 h, the reaction mixture was cooled to ambient temperature and concd in vacuo to provide crude N-((3S,5R)-5-ethylpyrrolidin-3-yl)cyclopropanesulfonamide hydrochloride (0.38 g, 50%) as a brown residue: LC/MS (Table 1, Method a) $R_t$=0.63 min; MS m/z: 219 $(M+H)^+$.

TABLE E.1

Examples prepared using General Procedure E with HCl

| Boc-protected Amine | Product | Ex # | $R_t$ min (Table 1, Method) | m/z ESI+ $(M + H)^+$ |
|---|---|---|---|---|
| (R)-tert-butyl 3-((3R,4R)-3-(6H-imidazo[1,5-a]pyrrolo[2,3-e]pyrazin-1-yl)-4-methylpiperidine-1-carbonyl)morpholine-4-carboxylate (prepared using H from Example #5, Step J and (R)-4-(tert-butoxycarbonyl)morpholine-3-carboxylic acid [Tyger] with EDC•HCl and DIEA) | 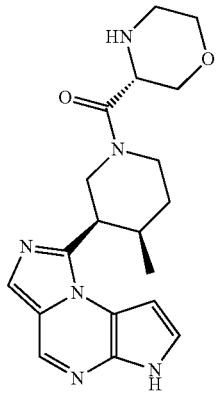 | E.1.1* | 1.16 (b) | 369 |
| tert-butyl 2-(3H-imidazo[1,2-a]pyrrolo[2,3-e]pyrazin-8-ylamino)-2-oxoethylcarbamate (prepared using H from Preparation #OO.1.1, tert-butoxycarbonylaminoacetic acid [TCI], HATU and TEA, D with NaOH) | 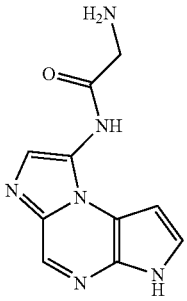 | E.1.2 | 1.72 (r) | 231 |
| tert-butyl 3-(3H-imidazo[1,2-a]pyrrolo[2,3-e]pyrazin-8-ylamino)-3-oxopropylcarbamate (prepared using H from Preparation #OO.1.1, 3-tert-butoxycarbonylaminopropionic acid, HATU and TEA, D with NaOH) | 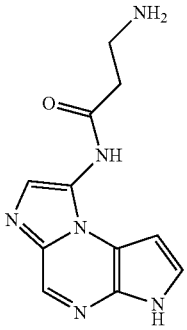 | E.1.3 | 2.09 (r) | 245 |
| tert-butyl 4-(3H-imidazol[1,2-a]pyrrolo[2,3-e]pyrazine-8-carbonyl)piperazine-1-carboxylate (prepared using D from Preparation #YYYY.1 and NaOH, H with piperidin-4-yl-carbamic acid tert-butyl ester [Tyger], EDC, HOBt, and TEA) | 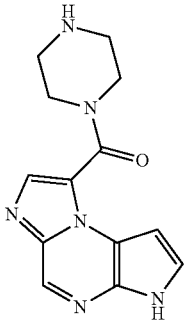 | E.1.4 | 2.75 (r) | 271 |

TABLE E.1-continued

| Examples prepared using General Procedure E with HCl | | | | |
|---|---|---|---|---|
| Boc-protected Amine | Product | Ex # | $R_t$ min (Table 1, Method) | m/z ESI+ $(M + H)^+$ |
| tert-butyl 1-(3H-imidazo[1,2-a]pyrrolo[2,3-e]pyrazine-8-carbonyl)piperidin-4-ylcarbamate (prepared using D from Preparation #YYYY.1 and NaOH, H with piperazine-1-carboxylic acid tert-butyl ester, EDC, HOBt, and TEA) | 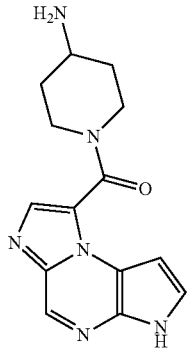 | E.1.5 | 2.81 (r) | 285 |
| tert-butyl 4-(3H-imidazo[1,2-a]pyrrolo[2,3-e]pyrazine-7-carbonyl)piperazine-1-carboxylate (prepared using D from Preparation #37 and NaOH, H with piperazine-1-carboxylic acid tert-butyl ester, EDC, HOBt, and TEA) | 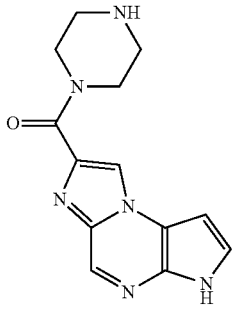 | E.1.6 | 2.68 (r) | 271 |
| tert-butyl (trans-4-(6H-pyrrolo[2,3-e][1,2,4]triazolo[4,3-a]pyrazine-8-carboxamido)cyclohexyl)methylcarbamate (Preparation #LL.1.1) | 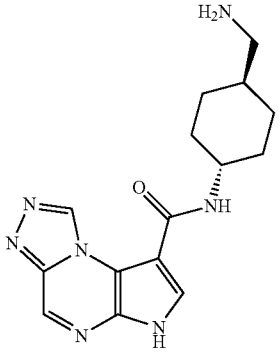 | E.1.7 | 0.74 (a) | 314 |
| tert-butyl (trans-4-((6H-pyrrolo[2,3-e][1,2,4]triazolo[4,3-a]pyrazin-8-yl)methylamino)cyclohexyl)methylcarbamate (Preparation #X.1.1) | 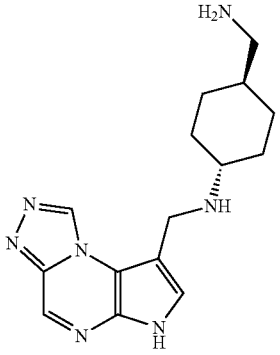 | E.1.8 | 2.66 (r) | 300 |

TABLE E.1-continued

| Examples prepared using General Procedure E with HCl | | | | |
|---|---|---|---|---|
| Boc-protected Amine | Product | Ex # | $R_t$ min (Table 1, Method) | m/z ESI+ $(M + H)^+$ |
| tert-butyl (trans-4-((6H-pyrrolo[2,3-e][1,2,4]triazolo[4,3-a]pyrazin-1-yl)methyl)cyclohexyl)methylcarbamate (Preparation #ZZZZ.1) | 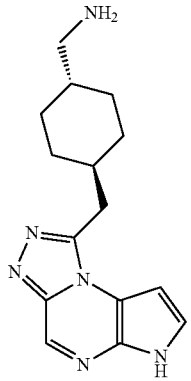 | E.1.9 | 1.01 (a) | 285 |
| t-butyl 2-(4-(3H-imidazo[1,2-a]pyrrolo[2,3-e]pyrazin-8-yl)piperidin-1-yl)ethylcarbamate (prepared using R from 1-(benzyloxycarbonyl)piperidine-4-carboxylic acid (Matrix), S from Example #3 Step E, E with TFA, KKKK with PFPAA, D with NaOH, F, X with t-butyl 2-oxoethylcarbamate) | 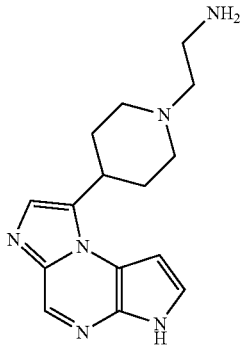 | E.1.10 | 2.28 (r) | 285 |
| tert-butyl 4-((3,6-dihydropyrazolo[4,3-d]pyrrolo[2,3-b]pyridin-1-yl)methyl)piperidine-1-carboxylate (prepared using XX from Preparation #XXXX.1) | 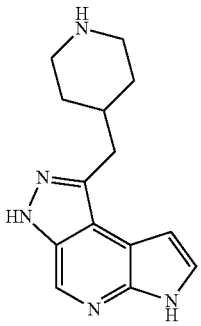 | E.1.11 | 1.30 (a) | 256 |

General Procedure E.1: Acidic Cleavage of a Boc-Protected Amine

To a solution of a Boc-protected amine (preferably 1 equiv) in an organic solvent (such as DCM, 1,4-dioxane, MeOH, or THF) is added an acid (such as TFA, HCl, or $H_3PO_4$ (preferably $H_3PO_4$, 1-50 equiv, preferably 5-10 equiv). The reaction is stirred at about 20-100° C. (preferably ambient temperature to about 65° C.) for about 1-24 h (preferably about 1-6 h). In any case where an additional acid labile group is present (for example, a t-butyl ester), this group may also be cleaved during the reaction. Optionally, additional TFA, HCl, or $H_3PO_4$ may be added to the reaction mixture in cases where the reaction does not proceed to completion as monitored by TLC, LC/MS, or HPLC. Once the reaction has proceeded to an acceptable level, the reaction mixture can be concd in vacuo to provide the amine as a salt. Alternatively, the reaction may be cooled to about −10-25° C. before the addition of an aqueous base (such as saturated aqueous $NaHCO_3$, saturated aqueous $Na_2CO_3$, or aqueous $K_3PO_4$, preferably aqueous $K_3PO_4$) and optionally partitioned between an organic solvent (such as EtOAc, DCM, THF, or 1,4-dioxane). The aqueous layer can be optionally extracted with additional organic solvent such as EtOAc or DCM. The combined organic layers may optionally be washed with brine, dried over anhydrous $Na_2SO_4$ or $MgSO_4$, then decanted or filtered, prior to concentrating under reduced pressure to give the target compound.

Preparation #E.1.1 5-tosyl-5H-pyrrolo[2,3-b] pyrazin-2-amine

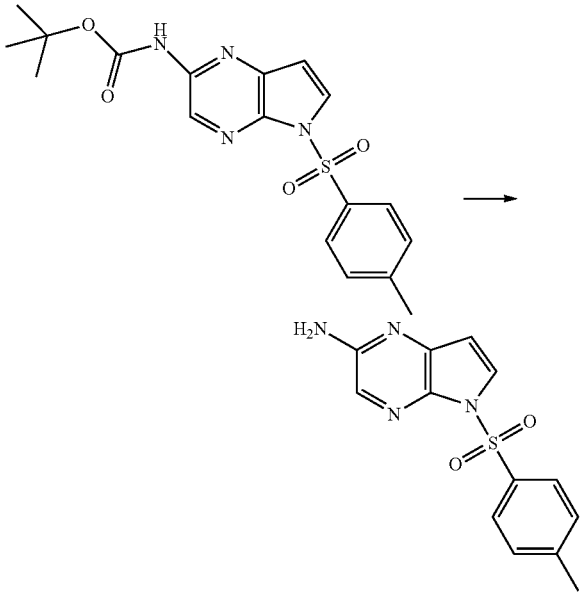

To a solution of tert-butyl 5-tosyl-5H-pyrrolo[2,3-b] pyrazin-2-ylcarbamate (12.35 g, 31.8 mmol, Example #3 Step E) in THF (35 mL) was added $H_3PO_4$ (20.16 mL, 350 mmol). The reaction mixture was heated to about 65° C. After about 90 min, the reaction mixture was cooled to about 0° C. and a solution of $K_3PO_4$ (29.0 mL, 350 mmol) in water (100 mL) was added. A white precipitate was removed by filtration. The organic layer was separated, dried over anhydrous $MgSO_4$, and concd in vacuo to provide crude 5-tosyl-5H-pyrrolo[2,3-b]pyrazin-2-amine (8.58 g, 94%) as a tan solid: LC/MS (Table 1, Method a) $R_t$=1.85 min; MS m/z: 289 $(M+H)^+$.

General Procedure F: Deprotection of a Cbz Protected Amine Using HBr in AcOH

To a Cbz protected amine (preferably 1 equiv) is added HBr in AcOH (40-400 equiv, preferably 70-90 equiv of 33% HBr in AcOH) at about 0° C. to 40° C. (preferably at ambient temperature) and the mixture is stirred at this temperature for about 5-45 min (preferably about 10 min). The precipitate is collected by filtration and extensively washed with an organic solvent such as $Et_2O$, EtOAc, 1,4-dioxane, THF or MeCN (preferably EtOAc or MeCN) to yield the target compound.

Illustration of General Procedure F

Preparation #F.1: 4-(3H-imidazo[1,2-a]pyrrolo[2,3-e]pyrazin-8-yl)bicyclo[2.2.2]octan-1-amine hydrobromide

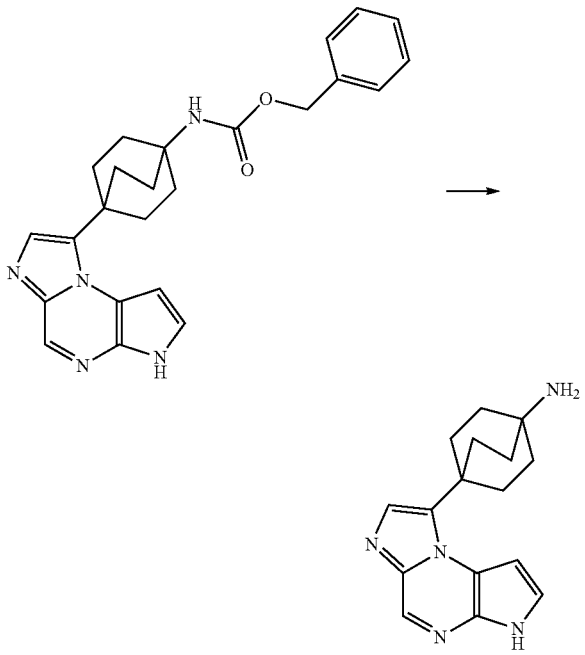

Benzyl 4-(3H-imidazo[1,2-a]pyrrolo[2,3-e]pyrazin-8-yl) bicyclo[2.2.2]octan-1-ylcarbamate (0.22 g, 0.529 mmol, prepared using Z from Preparation #N.1 and NaOH, R with diazomethane, S from Example #3, Step E, T with Lawesson's reagent and D with NaOH) was dissolved in HBr (33% in AcOH, 10 mL) and the mixture was stirred for about 10 min at ambient temperature. The reaction was then diluted with EtOAc (30 mL) and the precipitate was collected by filtration, extensively washed with MeCN and dried to yield 4-(3H-imidazo[1,2-a]pyrrolo[2,3-e]pyrazin-8-yl)bicyclo [2.2.2]octan-1-amine hydrobromide (0.16 g, 83%) as a yellow solid: LC/MS (Table 1, Method a) $R_t$=1.67 min; MS m/z 282 $(M+H)^+$.

TABLE F.1

Examples prepared using General Procedure F with HBr in AcOH

| Cbz-protected Amine | Product | Ex # | $R_t$ min (Table 1, Method) | m/z ESI+ $(M + H)^+$ |
|---|---|---|---|---|
| benzyl-4-(3H-imidazo[1,2-a]pyrrolo[2,3-e]pyrazin-8-yl)cyclohexylcarbamate (prepared using N from (cis)-4-aminocyclohexanecarboxylic acid with benzyl 2,5-dioxopyrrolidin-1-yl carbonate and $Na_2CO_3$, R with (trimethylsilyl)diazomethane, S with Example#3 Step E, E with HCl, T with Lawesson's reagent, D with NaOH) | 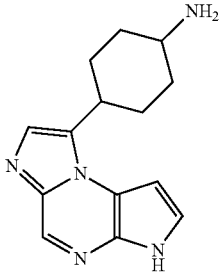 | F.1.1 | 0.48 and 0.69 (a) | 256 |

TABLE F.1-continued

| Examples prepared using General Procedure F with HBr in AcOH | | | | |
|---|---|---|---|---|
| Cbz-protected Amine | Product | Ex # | $R_t$ min (Table 1, Method) | m/z ESI+ $(M + H)^+$ |
| benzyl-4-(3H-imidazo[1,2-a]pyrrolo[2,3-e]pyrazin-8-yl)cyclohexylcarbamate (prepared using N from (cis)-4-aminocyclohexanecarboxylic acid with benzyl 2,5-dioxopyrrolidin-1-yl carbonate and $Na_2CO_3$, R with (trimethylsilyl)diazomethane, S with Example#3 Step E, E with HCl, T with Lawesson's reagent, D with NaOH) | 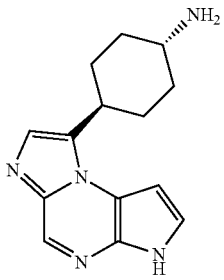 | F.1.2 | 2.77 (r) | 256 |
| benzyl 3-(3H-imidazo[1,2-a]pyrrolo[2,3-e]pyrazin-8-yl)pyrrolidine-1-carboxylate (prepared using R from 1-(benzyloxycarbonyl)pyrrolidine-3-carboxylic acid (Astatech), S from Example #3 Step E, E with TFA, KKKK with PFPAA) | 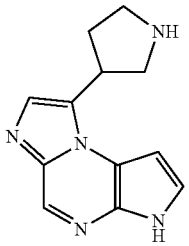 | F.1.3 | 2.83 (r) | 228 |
| benzyl 4-(3H-imidazo[1,2-a]pyrrolo[2,3-e]pyrazin-8-yl)piperidine-1-carboxylate (prepared using R from 1-(benzyloxycarbonyl)piperidine-4-carboxylic acid (Matrix), S from Example #3 Step E, E with TFA, KKKK with PFPAA) | 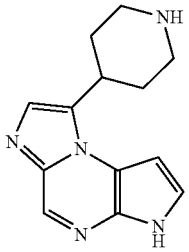 | F.1.4 | 2.82 (r) | 242 |

General Procedure F.1: Deprotection of a Cbz Protected Amine Using HBr in AcOH To a Cbz protected amine (preferably 1 equiv) is added HBr in acetic acid (5-400 equiv, 33% HBr in AcOH) at about 0° C. to 40° C. (preferably at ambient temperature) and the mixture is stirred at this temperature for about 0.5-5 h (preferably about 1 h). The reaction is worked up using one of the following methods. Method 1: The precipitate is collected by filtration and extensively washed with an organic solvent such as $Et_2O$, EtOAc, 1,4-dioxane, THF or MeCN (preferably EtOAc or MeCN) to yield the target compound. Method 2: The reaction mixture is diluted with water and a suitable organic solvent (such as $Et_2O$). The layers are stirred for short period and the organic layer is decanted. This is repeated (3-10×) and the organic layer is discarded. The aqueous layer is basified with an aqueous base (such as saturated aqueous $NaHCO_3$ or saturated aqueous $Na_2CO_3$, preferably saturated aqueous $NaHCO_3$) and extracted with a suitable organic solvent (such as EtOAc, DCM or $Et_2O$). The combined organic layers may optionally be washed with brine and concd in vacuo or dried over anhydrous $Na_2SO_4$ or $MgSO_4$ and then decanted or filtered prior to concentrating under reduced pressure to give the target compound.

Illustration of General Procedure F.1

Preparation #F.1.1: 8-((cis)-4-ethylpyrrolidin-3-yl)-3-tosyl-3H-imidazo[1,2-a]pyrrolo[2,3-e]pyrazine

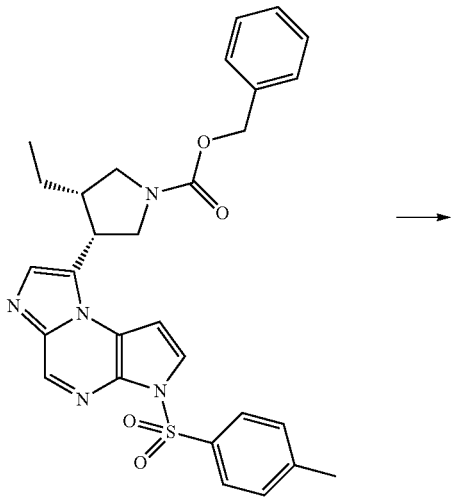

-continued

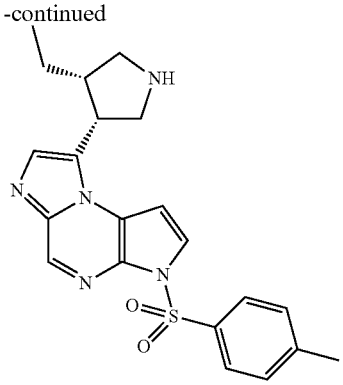

To a solution of (cis)-benzyl 3-ethyl-4-(3-tosyl-3H-imidazo[1,2-a]pyrrolo[2,3-e]pyrazin-8-yl)pyrrolidine-1-carboxylate (0.838 g, 1.541 mmol, prepared using E from Example #36 Step D with TFA, N, R, S.1 with Example #3 Step E, and T with Lawesson's reagent) was added a solution of HBr (2.50 mL, 15.19 mmol, 33% in acetic acid). The reaction mixture was stirred at ambient temperature for about 1 h. The reaction was diluted with $Et_2O$ (50 mL) and water (20 mL). The layers were stirred for about 3 min and the organic layer was decanted then the procedure was repeated 5 times. The aqueous layer was cooled to about 0° C. was basified with saturated aqueous $NaHCO_3$ solution (10 mL) to about pH 7. The aqueous layer was extracted with EtOAc (3×50 mL), combined, and dried over anhydrous $Na_2SO_4$, filtered and concd to give a brown solid. The solid was dissolved in DCM (50 mL) and washed with water (3×20 mL), dried over anhydrous $Na_2SO_4$, filtered and coned to afford 8-((cis)-4-ethylpyrrolidin-3-yl)-3-tosyl-3H-imidazo[1,2-a]pyrrolo[2,3-e]pyrazine (0.453, 61%) as a brown residue: LC/MS (Table 1, Method a) $R_t$=1.73 min; MS m/z: 410 $(M+H)^+$.

General Procedure G: Formation of an Acetamide

To a solution of amine (preferably 1 equiv) in pyridine (5-25 equiv, preferably 10 equiv) at about 0-25° C. (preferably about 0° C.) is added $Ac_2O$ (2-10 equiv, preferably 5 equiv). If the reaction is cooled, stirring is continued at the lower temperature for about 5-30 min (preferably 10-15 min) and then warmed to ambient temperature. After about 1-24 h (preferably 2-16 h), the reaction is concd under reduced pressure and partitioned between an organic solvent such as EtOAc or DCM (preferably EtOAc) and aqueous acid such as aqueous HCl (1-6 N, preferably 1 N). The layers are separated and the organic layer is optionally washed with aqueous acid such as aqueous HCl (1-6 N, preferably 1 N), aqueous base such as aqueous $NaHCO_3$ or aqueous $Na_2CO_3$ (preferably saturated aqueous $NaHCO_3$), and brine. The organic layer is then dried over anhydrous $MgSO_4$, filtered through a pad of Florisil® while washing with additional organic solvent such as EtOAc or DCM (preferably EtOAc), and concd under reduced pressure.

Illustration of General Procedure G

Preparation #G.1*: (1S,2R,4S)-ethyl 4-acetamido-2-ethylcyclopentanecarboxylate

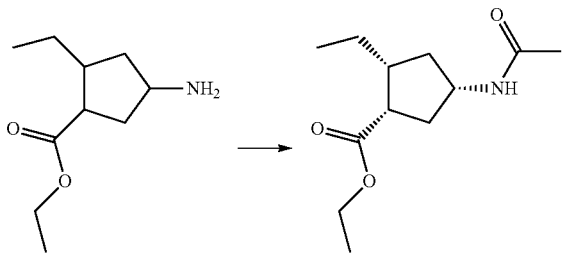

A solution of ethyl 4-amino-2-ethylcyclopentanecarboxylate (49.0 g, 264 mmol, Example #8, Step I) in pyridine (214 mL, 2645 mmol) was cooled to about 0° C. $Ac_2O$ (125 mL, 1322 mmol) was added and stirring was continued at about 0° C. for about 15 min. The resulting solution was warmed to ambient temperature and stirred for about 12 h. The reaction was concd under reduced pressure and EtOAc (500 mL) and aqueous HCl (1 N, 200 mL) were added. The layers were separated and the organic layer was washed with aqueous HCl (1 N, 200 mL), saturated aqueous $NaHCO_3$ (2×200 mL) and brine (150 mL), dried over anhydrous $MgSO_4$, filtered through a pad of Florisil® while washing with EtOAc (600 mL), and concd under reduced pressure to give an off-white solid (52 g) that was purified by using General Procedure AA (Table 2, Method 24, $R_t$=8.2 min, or =positive) to give (1S,2R,4S)-ethyl 4-acetamido-2-ethylcyclopentanecarboxylate (20.3 g, 34%): LC/MS (Table 1, Method a) $R_t$=1.82 min; MS m/z: 228 $(M+H)^+$.

TABLE G.1

Examples prepared using General Procedure G

| Amine | Product | Ex. # | $R_t$ min (Table 1, Method) | m/z ESI+ $(M + H)^+$ |
|---|---|---|---|---|
| N-((3R,5R)-5-(6H-pyrrolo[2,3-e][1,2,4]triazolo[4,3-a]pyrazin-1-yl)pyrrolidin-3-yl)cyclopropanesulfonamide (prepared using K from (2R,4R)-1-tert-butyl-4-aminopyrrolidine-1,2-dicarboxylate hydrochloric acid (Acesys Pharmatech Corp) and cylcopropylsulfonylchloride, TEA, Z with NaOH, A with HATU and TEA, B with $SOCl_2$ and TEA, E with HCl. | 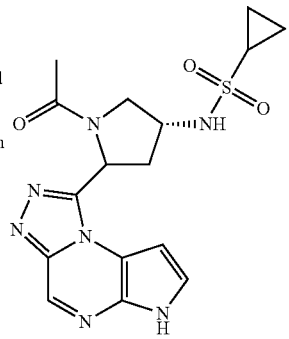 | G.1.1* | 1.13 | 390 |

General Procedure H: Formation of an Amide from a Carboxylic Acid and an Amine

To a solution or suspension of a carboxylic acid (1-5 equiv, preferably 1.0 equiv) and an amine or an amine salt (1-5 equiv, preferably 1 equiv) in an organic solvent (such as DCM, DCE, THF, or 1,4-dioxane, preferably DCM) is added a peptide coupling reagent (such as BOP-Cl, IBCF, HATU, or EDC•HCl, preferably HATU, 1-10 equiv, preferably 1-1.5 equiv), a base (such as TEA, DIEA, or pyridine, preferably DIEA, 0-20 equiv, preferably 3equiv). The reaction mixture is then stirred at ambient temperature for about 15 min to 24 h (preferably about 45 min-16 h). The reaction mixture is then worked up using one of the following methods. Method 1: The reaction mixture is diluted with water or saturated aqueous $NaHCO_3$. The layers are separated. The aqueous layer is optionally extracted with additional organic solvent such as EtOAc or DCM. The organic layer is (or combined layers are) optionally washed with water, saturated aqueous $NaHCO_3$ and/or brine, dried over anhydrous $MgSO_4$ or $Na_2SO_4$, filtered or decanted, and concd under reduced pressure. Method 2: The crude reaction mixture is filtered through a pad of silica gel, washing with a suitable solvent (such as EtOAc, MeOH, or DCM, preferably MeOH), and concd under reduced pressure. Method 3: The crude reaction mixture is directly purified by chromatography without a work up.

Illustration of General Procedure H

Preparation #H.1*: (3R,4R)-tert-butyl 4-methyl-3-((5-tosyl-5H-pyrrolo[2,3-b]pyrazin-2-yl)methylcarbamoyl)piperidine-1-carboxylate

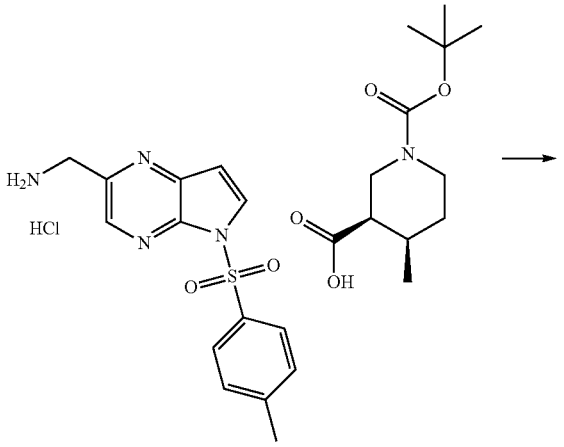

-continued

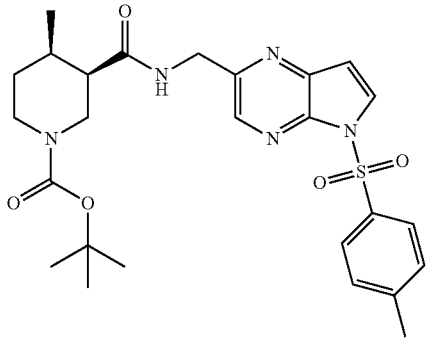

To a slurry of (5-tosyl-5H-pyrrolo[2,3-b]pyrazin-2-yl) methanamine hydrochloride (34.0 g, 100 mmol, Example #5, Step C), (3R,4R)-1-(tert-butoxycarbonyl)-4-methylpiperidine-3-carboxylic acid (24.43 g, 100 mmol, Example #5, Step F) and HATU (38.2 g, 100 mmol) in DCM (700 mL) was added DIEA (52.6 mL, 301 mmol). The reaction was stirred at ambient temperature for about 45 min. The reaction was washed with saturated aqueous $NaHCO_3$ (300 mL). The organic layer was separated, dried over anhydrous $Na_2SO_4$, filtered, and concd in vacuo. The resulting residue was purified by chromatography on silica gel (330 g) using 33-100% EtOAc in heptanes to give (3R,4R)-tert-butyl-4-methyl-3-O-tosyl-5H-pyrrolo[2,3-b]pyrazin-2-yl)methylcarbamoyl)-piperidine-1-carboxylate (53 g, 96%) as a pale-yellow foam: LC/MS (Table 1, Method b) $R_t$=2.40 min; MS m/z: 528 $(M+H)^+$.

TABLE H.1
Examples prepared from 1-((3R,4R)-4-methylpiperidin-3-yl)-6H-imidazo[1,5-a]pyrrolo[2,3-e]pyrazinehydrochloride (Example #5, Step J) using General Procedure H with EDC•HCl and DIEA
| Carboxylic Acid | Product | Example # | $R_t$ min (Table 1, Method) | m/z ESI+ $(M + H)^+$ |
|---|---|---|---|---|
| 4,4-difluorocyclohexane-carboxylic acid | 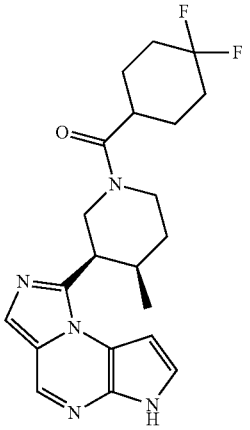 | H.1.1* | 1.82 (b) | 402 |
| 3,3,3-trifluoropropanoic acid | 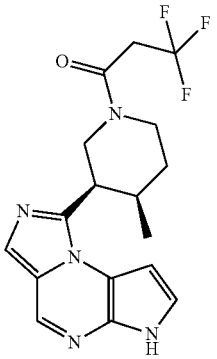 | H.1.2* | 1.68 (b) | 366 |
| 3-hydroxy-3-methylbutanoic acid (Fluka) | 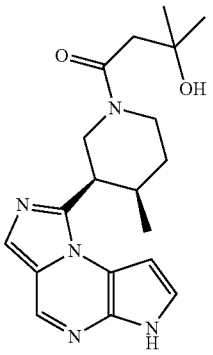 | H.1.3* | 1.49 (b) | 356 |

TABLE H.1-continued
Examples prepared from 1-((3R,4R)-4-methylpiperidin-3-yl)-6H-imidazo[1,5-a]pyrrolo[2,3-e]pyrazinehydrochloride (Example #5, Step J) using General Procedure H with EDC•HCl and DIEA
| Carboxylic Acid | Product | Example # | $R_t$ min (Table 1, Method) | m/z ESI+ $(M + H)^+$ |
|---|---|---|---|---|
| 2-methoxyacetic acid | 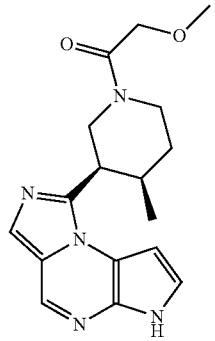 | H.1.4* | 1.39 (b) | 328 |
| 3-methoxypropanoic acid | 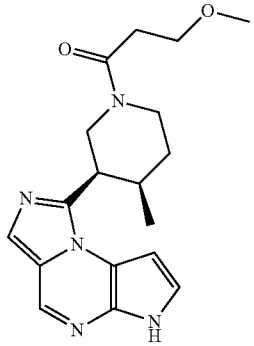 | H.1.5* | 1.44 (b) | 342 |
| pent-4-ynoic acid (Fluka) | 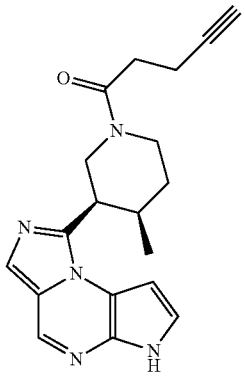 | H.1.6* | 1.59 (b) | 336 |
| 2-(4-chlorophenyl)acetic acid | 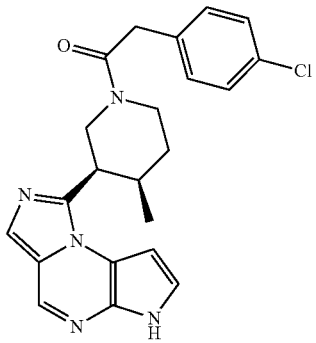 | H.1.7* | 1.90 (b) | 408 |

TABLE H.1-continued
Examples prepared from 1-((3R,4R)-4-methylpiperidin-3-yl)-6H-imidazo[1,5-a]pyrrolo[2,3-e]pyrazinehydrochloride (Example #5, Step J) using General Procedure H with EDC•HCl and DIEA
| Carboxylic Acid | Product | Example # | $R_t$ min (Table 1, Method) | m/z ESI+ $(M + H)^+$ |
|---|---|---|---|---|
| 2-(3-chlorophenyl)acetic acid | 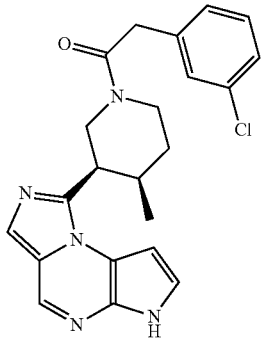 | H.1.8* | 1.91 (b) | 408 |
| 4-cyanobenzoic acid | 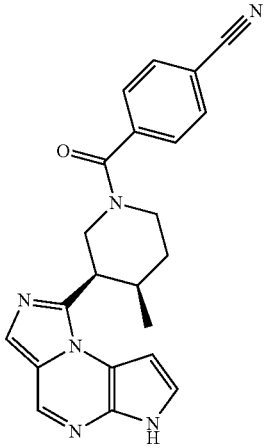 | H.1.9* | 1.68 (b) | 385 |
| 3-(3-chloroisoxazol-5-yl)propanoic acid (Matrix) | 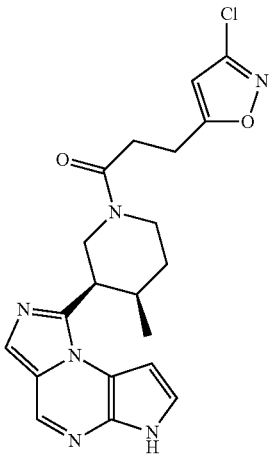 | H.1.10* | 1.78 (b) | 413 |

TABLE H.1-continued

Examples prepared from 1-((3R,4R)-4-methylpiperidin-3-yl)-6H-imidazo[1,5-a]pyrrolo[2,3-e]pyrazinehydrochloride (Example #5, Step J) using General Procedure H with EDC•HCl and DIEA

| Carboxylic Acid | Product | Example # | $R_t$ min (Table 1, Method) | m/z ESI+ $(M + H)^+$ |
|---|---|---|---|---|
| 2-(3-cyanophenyl)acetic acid | 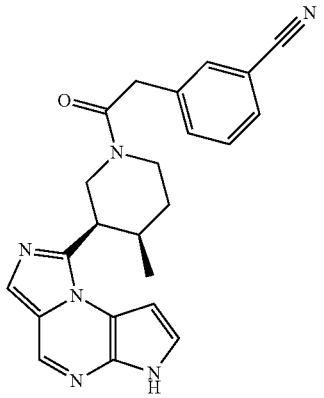 | H.1.11* | 1.71 (b) | 399 |
| 2-(4-cyanophenyl)acetic acid | 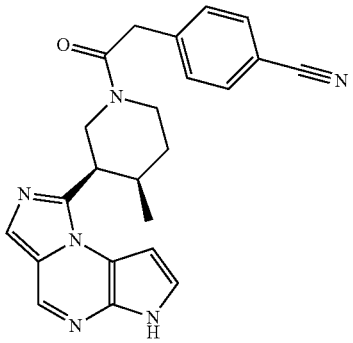 | H.1.12* | 1.70 (b) | 399 |
| 2-(1H-pyrrol-2-yl)acetic acid (Tyger) | 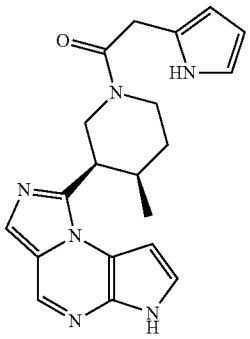 | H.1.13* | 1.62 (b) | 363 |
| 2-(pyrazin-2-yl)acetic acid (Astatech) | 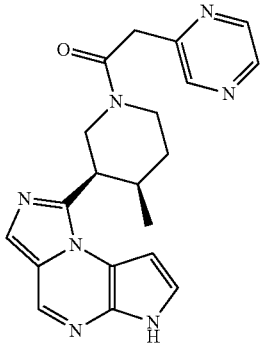 | H.1.14* | 1.37 (b) | 376 |

TABLE H.1-continued

Examples prepared from 1-((3R,4R)-4-methylpiperidin-3-yl)-6H-imidazo[1,5-a]pyrrolo[2,3-e]pyrazinehydrochloride (Example #5, Step J) using General Procedure H with EDC•HCl and DIEA

| Carboxylic Acid | Product | Example # | $R_t$ min (Table 1, Method) | m/z ESI+ $(M + H)^+$ |
|---|---|---|---|---|
| 2-(tetrahydro-2H-pyran-4-yl)acetic acid (Astatech) | 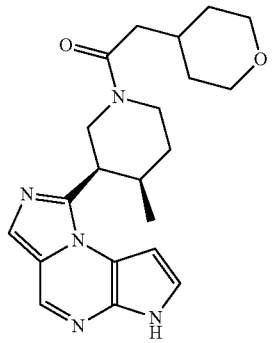 | H.1.15 * | 1.49 (b) | 382 |
| 2-(pyrimidin-2-yl)acetic acid (Caymen Chemical) | 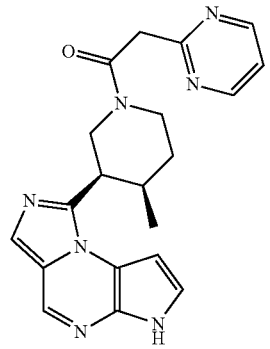 | H.1.16* | 1.56 (b) | 376 |
| 3-acetamidopropanoic acid | 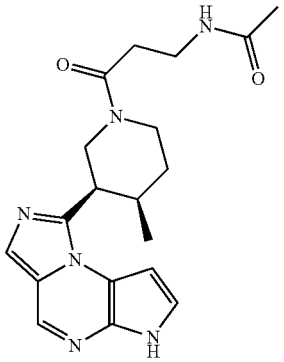 | H.1.17* | 1.29 (b) | 369 |

TABLE H.1-continued
Examples prepared from 1-((3R,4R)-4-methylpiperidin-3-yl)-6H-imidazo[1,5-a]pyrrolo[2,3-e]pyrazinehydrochloride (Example #5, Step J) using General Procedure H with EDC•HCl and DIEA
| Carboxylic Acid | Product | Example # | $R_t$ min (Table 1, Method) | m/z ESI+ $(M + H)^+$ |
|---|---|---|---|---|
| tetrahydrofuran-2-carboxylic acid | 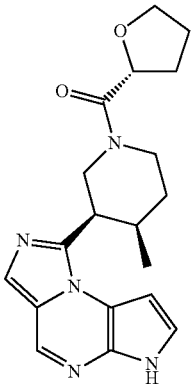 | H.1.18* | 1.45 (b) | 354 |
| | 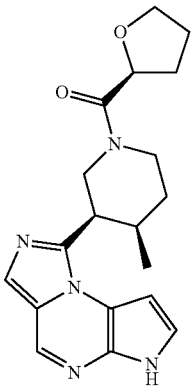 | | | |
| tetrahydrofuran-3-carboxylic acid | 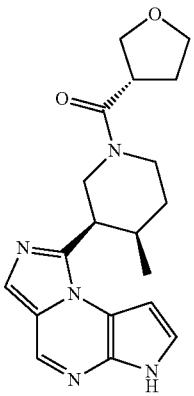 | H.1.19* | 1.43 (b) | 354 |

TABLE H.1-continued
Examples prepared from 1-((3R,4R)-4-methylpiperidin-3-yl)-6H-imidazo[1,5-a]pyrrolo[2,3-e]pyrazinehydrochloride (Example #5, Step J) using General Procedure H with EDC•HCl and DIEA
| Carboxylic Acid | Product | Example # | $R_t$ min (Table 1, Method) | m/z ESI+ $(M + H)^+$ |
|---|---|---|---|---|
| | 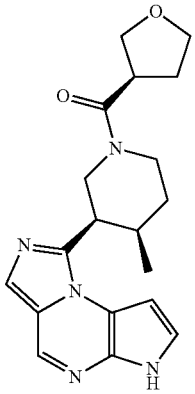 | | | |
| 3-methoxycyclohexane-carboxylic acid | 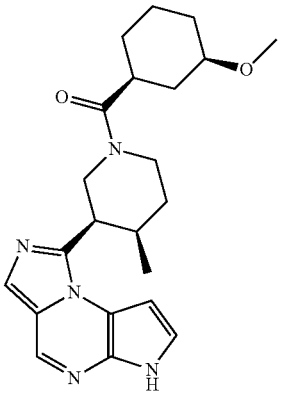 | H.1.20* | 1.62, 1.69 (b) | 396 |
| | 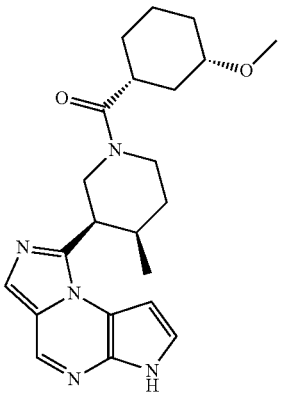 | | | |

TABLE H.1-continued
Examples prepared from 1-((3R,4R)-4-methylpiperidin-3-yl)-6H-imidazo[1,5-a]pyrrolo[2,3-e]pyrazinehydrochloride (Example #5, Step J) using General Procedure H with EDC•HCl and DIEA
| Carboxylic Acid | Product | Example # | $R_t$ min (Table 1, Method) | m/z ESI+ $(M + H)^+$ |
|---|---|---|---|---|
| | 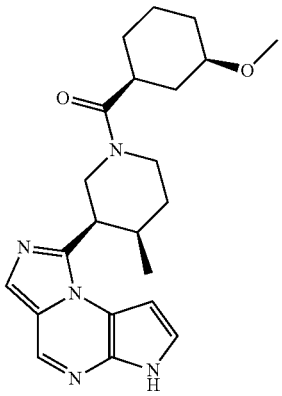 | | | |
| | 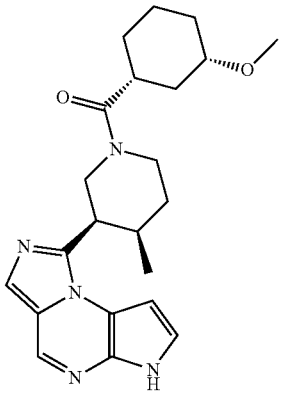 | | | |
| 3,3-difluorocyclobutane-carboxylic acid (Waterstone) | 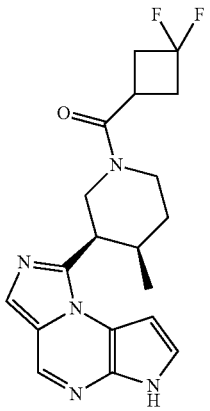 | H.1.21* | 1.75 (b) | 374 |

TABLE H.1-continued

Examples prepared from 1-((3R,4R)-4-methylpiperidin-3-yl)-6H-imidazo[1,5-a]pyrrolo[2,3-e]pyrazinehydrochloride (Example #5, Step J) using General Procedure H with EDC•HCl and DIEA

| Carboxylic Acid | Product | Example # | $R_t$ min (Table 1, Method) | m/z ESI+ $(M + H)^+$ |
|---|---|---|---|---|
| 4,4,4-trifluoro-butanoic acid (Matrix) | 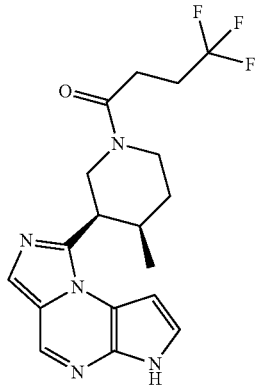 | H.1.22* | 1.78 (b) | 380 |
| tetrahydro-2H-pyran-4-carboxylic acid (Matrix) | 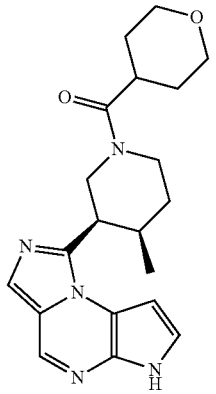 | H.1.23* | 1.75 (b) | 368 |
| tetrahydro-2H-pyran-3-carboxylic acid (Chem Impex) | 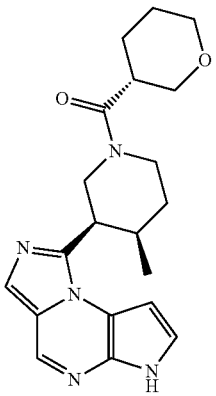 | H.1.24* | 1.74 (b) | 368 |

TABLE H.1-continued
Examples prepared from 1-((3R,4R)-4-methylpiperidin-3-yl)-6H-imidazo[1,5-a]pyrrolo[2,3-e]pyrazinehydrochloride (Example #5, Step J) using General Procedure H with EDC•HCl and DIEA
| Carboxylic Acid | Product | Example # | $R_t$ min (Table 1, Method) | m/z ESI+ $(M + H)^+$ |
|---|---|---|---|---|
| | 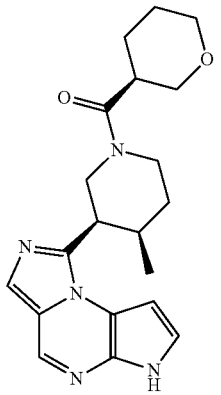 | | | |
| 3-cyanopropanoic acid (Tyger) | 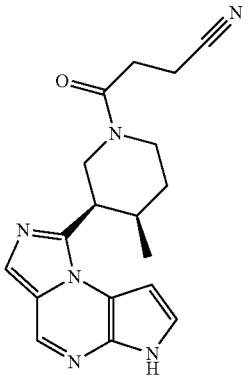 | H.1.25* | 1.65 (b) | 337 |
| tetrahydro-2H-pyran-2-carboxylic acid (Acella Chembio Co.) | 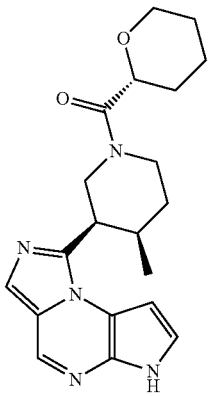 | H.1.26* | 1.76 (b) | 368 |

TABLE H.1-continued
Examples prepared from 1-((3R,4R)-4-methylpiperidin-3-yl)-6H-imidazo[1,5-a]pyrrolo[2,3-e]pyrazinehydrochloride (Example #5, Step J) using General Procedure H with EDC•HCl and DIEA
| Carboxylic Acid | Product | Example # | $R_t$ min (Table 1, Method) | m/z ESI+ $(M + H)^+$ |
|---|---|---|---|---|
| | 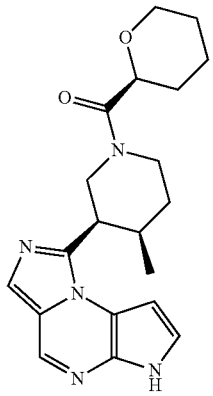 | | | |
| 3-(methylsulfonyl) propanoic acid (Enamine) | 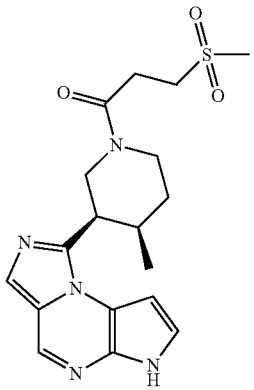 | H.1.27* | 1.36 (b) | 390 |
| 1,4-dioxane-2-carboxylic acid (Enamine) | 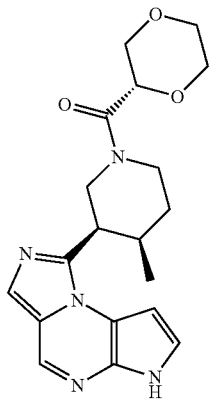 | H.1.28* | 1.41 (b) | 370 |

TABLE H.1-continued
Examples prepared from 1-((3R,4R)-4-methylpiperidin-3-yl)-6H-imidazo[1,5-a]pyrrolo[2,3-e]pyrazinehydrochloride (Example #5, Step J) using General Procedure H with EDC•HCl and DIEA
| Carboxylic Acid | Product | Example # | $R_t$ min (Table 1, Method) | m/z ESI+ $(M + H)^+$ |
|---|---|---|---|---|
| | 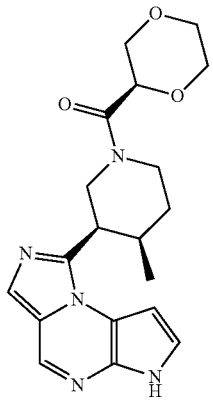 | | | |
| tetrahydrothiophene-3-carboxylic acid-1,1-dioxide | 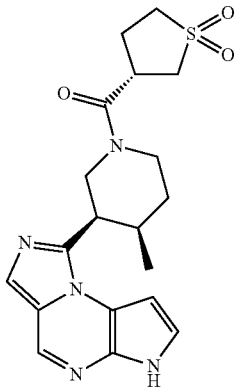 | H.1.29* | 1.41 (b) | 402 |
| | 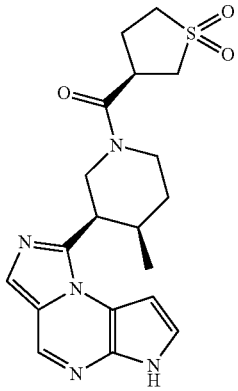 | | | |

TABLE H.1-continued
Examples prepared from 1-((3R,4R)-4-methylpiperidin-3-yl)-6H-imidazo[1,5-a]pyrrolo[2,3-e]pyrazinehydrochloride (Example #5, Step J) using General Procedure H with EDC•HCl and DIEA
| Carboxylic Acid | Product | Example # | $R_t$ min (Table 1, Method) | m/z ESI+ $(M + H)^+$ |
|---|---|---|---|---|
| 1-methylpyrrolidine-3-carboxylic acid (Chembridge) | 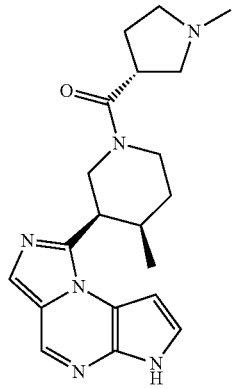 | H.1.30* | 1.18 (b) | 367 |
| | 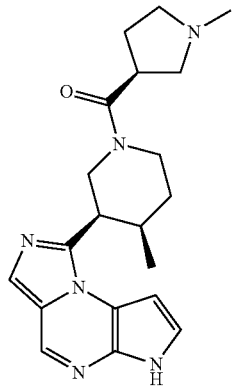 | | | |
| 1-methylpiperidine-4-carboxylic acid (Astatech) | 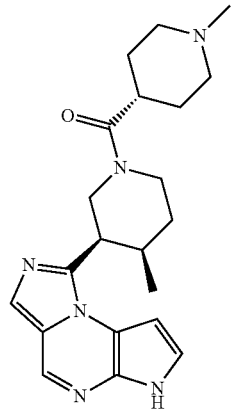 | H.1.31* | 1.19 (b) | 381 |

TABLE H.2

| Examples prepared from 1-((3R,4R)-4-methylpiperidin-3-yl)-6H-pyrrolo[2,3-e][1,2,4]triazolo[4,3-a]pyrazine hydrochloride (prepared using A from Example #1, Step D and Example #5, Step F, HATU and DIEA; B with DIEA; D with NaOH; E with HCl) using General Procedure H with EDC•HCl and DIEA | | | | |
|---|---|---|---|---|
| Carboxylic Acid | Product | Example # | $R_t$ min (Table 1, Method) | m/z ESI+ $(M + H)^+$ |
| 2-cyano-acetic acid | 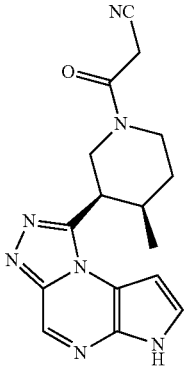 | H.2.1* | 1.23 (b) | 324 |

TABLE H.3

| Examples prepared from 1-(cis)-4-methylpiperidin-3-yl)-6H-imidazo[1,5-a]pyrrolo[2,3-e]pyrazine hydrochloride (prepared using D from Preparation #Q.1 with NaOH, and E with 4N HCl in 1,4-dioxane) using General Procedure H with HATU and DIEA | | | | |
|---|---|---|---|---|
| Carboxylic Acid | Product | Example # | $R_t$ min (Table 1, Method) | m/z ESI+ $(M + H)^+$ |
| 2,4-difluoro-benzoic acid | 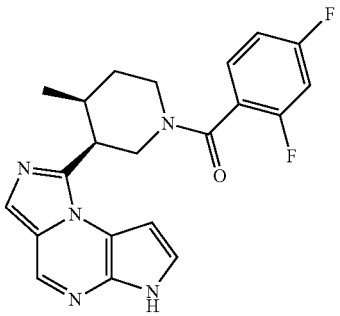 | H.3.1 | 1.79 (b) | 396 |
| | 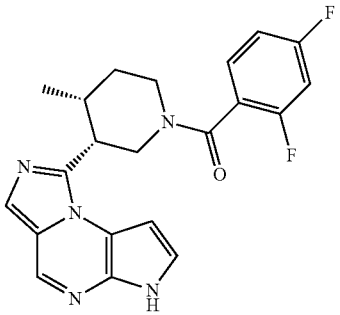 | | | |

TABLE H.3-continued
Examples prepared from 1-(cis)-4-methylpiperidin-3-yl)-6H-imidazo[1,5-a]pyrrolo[2,3-e]pyrazine hydrochloride (prepared using D from Preparation #Q.1 with NaOH, and E with 4N HCl in 1,4-dioxane) using General Procedure H with HATU and DIEA
| Carboxylic Acid | Product | Example # | $R_t$ min (Table 1, Method) | m/z ESI+ $(M + H)^+$ |
|---|---|---|---|---|
| 4-(trifluoro-methyl) benzoic acid | 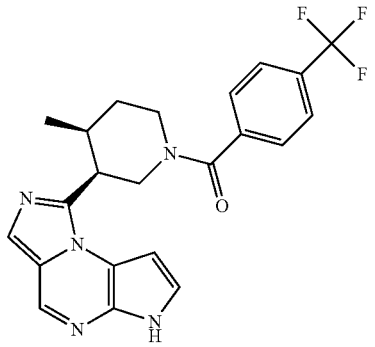 | H.3.2 | 1.96 (b) | 428 |
| | 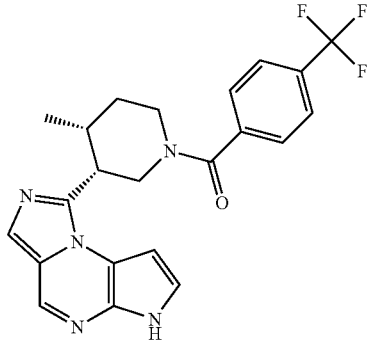 | | | |
| nicotinic acid | 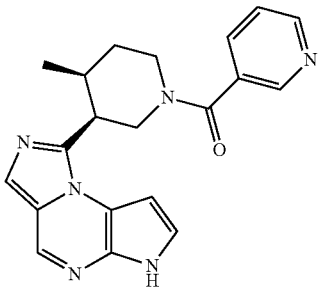 | H.3.3 | 1.41 (b) | 361 |
| | 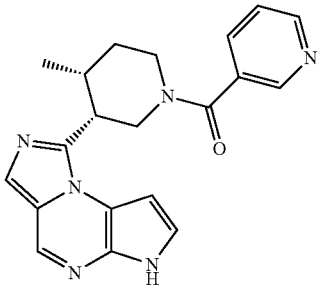 | | | |

TABLE H.3-continued

Examples prepared from 1-(cis)-4-methylpiperidin-3-yl)-6H-imidazo[1,5-a]pyrrolo[2,3-e]pyrazine hydrochloride (prepared using D from Preparation #Q.1 with NaOH, and E with 4N HCl in 1,4-dioxane) using General Procedure H with HATU and DIEA

| Carboxylic Acid | Product | Example # | $R_t$, min (Table 1, Method) | m/z ESI+ $(M + H)^+$ |
|---|---|---|---|---|
| 3-(trifluoromethyl) benzoic acid | 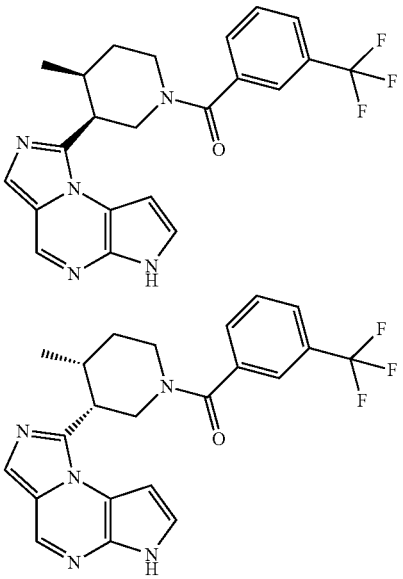 | H.3.4 | 1.97 (b) | 428 |
| pyrazine-2-carboxylic acid | 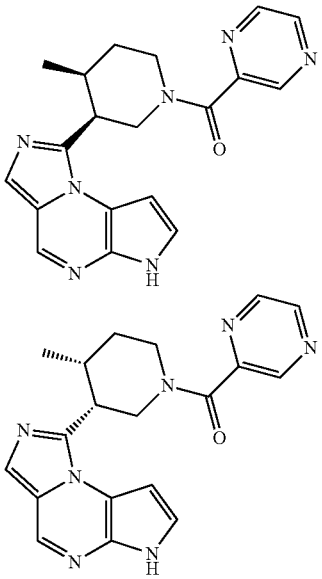 | H.3.5 | 1.40 (b) | 362 |
| pyrimidine-5-carboxylic acid [Frontier Scientific] | 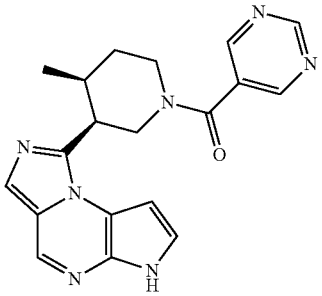 | H.3.6 | 1.37 (b) | 362 |

TABLE H.3-continued
Examples prepared from 1-(cis)-4-methylpiperidin-3-yl)-6H-imidazo[1,5-a]pyrrolo[2,3-e]pyrazine hydrochloride (prepared using D from Preparation #Q.1 with NaOH, and E with 4N HCl in 1,4-dioxane) using General Procedure H with HATU and DIEA
| Carboxylic Acid | Product | Example # | $R_t$ min (Table 1, Method) | m/z ESI+ $(M + H)^+$ |
|---|---|---|---|---|
| | 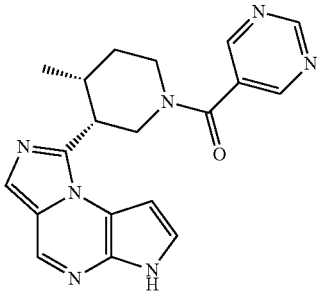 | | | |
| 2-cyclo-propyl-acetic acid [Lancaster] | 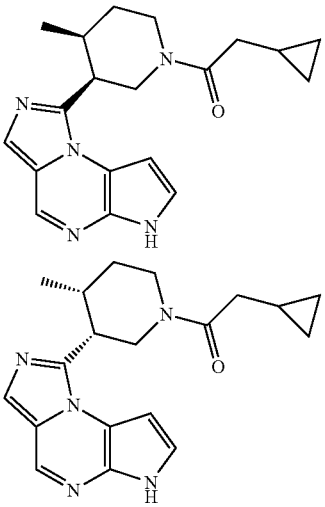 | H.3.7 | 1.62 (b) | 338 |
| benzoic acid | 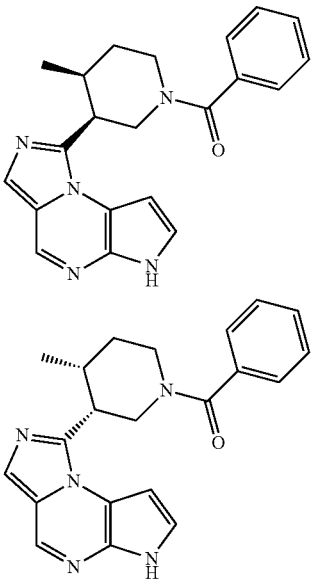 | H.3.8 | 1.69 (b) | 360 |

TABLE H.3-continued

Examples prepared from 1-(cis)-4-methylpiperidin-3-yl)-6H-imidazo[1,5-a]pyrrolo[2,3-e]pyrazine hydrochloride (prepared using D from Preparation #Q.1 with NaOH, and E with 4N HCl in 1,4-dioxane) using General Procedure H with HATU and DIEA

| Carboxylic Acid | Product | Example # | $R_t$ min (Table 1, Method) | m/z ESI+ $(M + H)^+$ |
|---|---|---|---|---|
| 2-cyclobutylacetic acid [Beta Pharmaceuticals] | 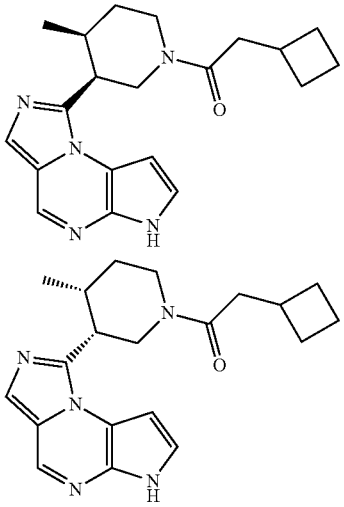 | H.3.9 | 1.78 (b) | 352 |
| 3-cyclobutylpropanoic acid [ChemBridge] | 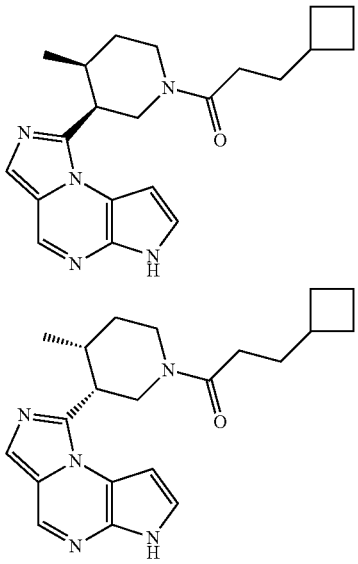 | H.3.10 | 1.91 (b) | 366 |
| 1H-pyrazole-4-carboxylic acid | 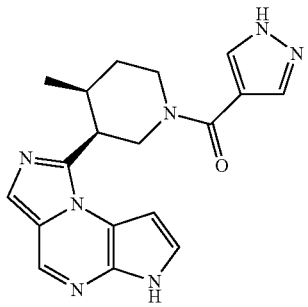 | H.3.11 | 1.32 (b) | 350 |

TABLE H.3-continued
Examples prepared from 1-(cis)-4-methylpiperidin-3-yl)-6H-imidazo[1,5-a]pyrrolo[2,3-e]pyrazine hydrochloride (prepared using D from Preparation #Q.1 with NaOH, and E with 4N HCl in 1,4-dioxane) using General Procedure H with HATU and DIEA
| Carboxylic Acid | Product | Example # | $R_t$ min (Table 1, Method) | m/z ESI+ $(M + H)^+$ |
|---|---|---|---|---|
| | 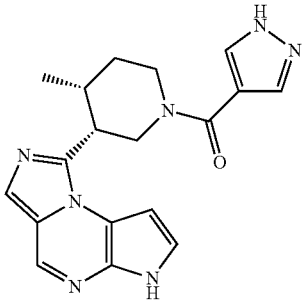 | | | |
| 1H-pyrazole-3-carboxylic acid [Oakwood] | 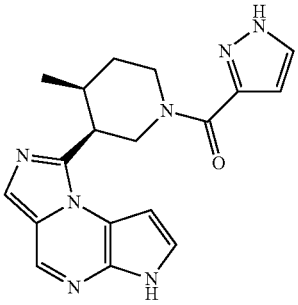 | H.3.12 | 1.34 (b) | 350 |
| | 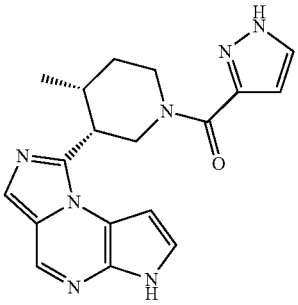 | | | |
| propionic acid | 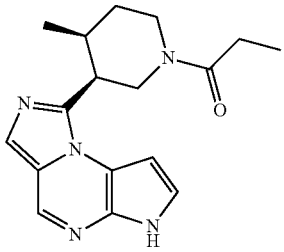 | H.3.13 | 1.49 (b) | 312 |
| | 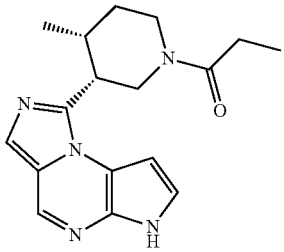 | | | |

TABLE H.3-continued

Examples prepared from 1-(cis)-4-methylpiperidin-3-yl)-6H-imidazo[1,5-a]pyrrolo[2,3-e]pyrazine hydrochloride (prepared using D from Preparation #Q.1 with NaOH, and E with 4N HCl in 1,4-dioxane) using General Procedure H with HATU and DIEA

| Carboxylic Acid | Product | Example # | $R_t$, min (Table 1, Method) | m/z ESI+ $(M + H)^+$ |
|---|---|---|---|---|
| 1-cyano-cyclo-propane carboxylic acid | 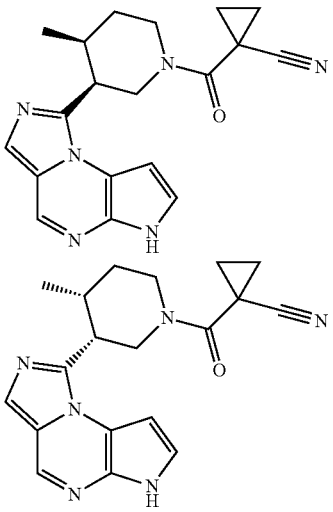 | H.3.14 | 1.60 (b) | 349 |
| 1-methyl-1H-pyrazole-4-carboxylic acid | 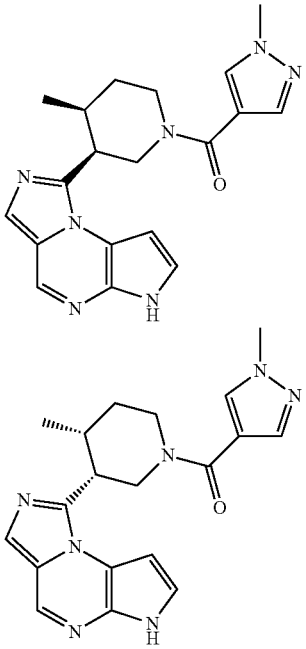 | H.3.15 | 1.37 (b) | 364 |
| isonicotinic acid | 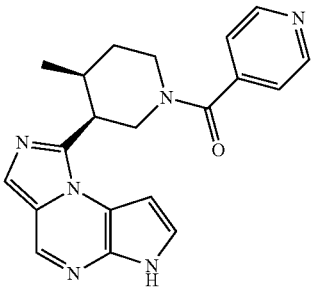 | H.3.16 | 1.44 (b) | 361 |

TABLE H.3-continued

Examples prepared from 1-(cis)-4-methylpiperidin-3-yl)-6H-imidazo[1,5-a]pyrrolo[2,3-e]pyrazine hydrochloride (prepared using D from Preparation #Q.1 with NaOH, and E with 4N HCl in 1,4-dioxane) using General Procedure H with HATU and DIEA

| Carboxylic Acid | Product | Example # | $R_t$ min (Table 1, Method) | m/z ESI+ $(M + H)^+$ |
|---|---|---|---|---|
| | 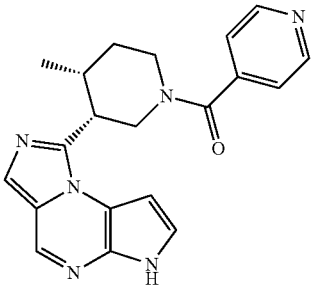 | | | |
| 2-(3-methyl-isoxazol-5-yl)acetic acid | 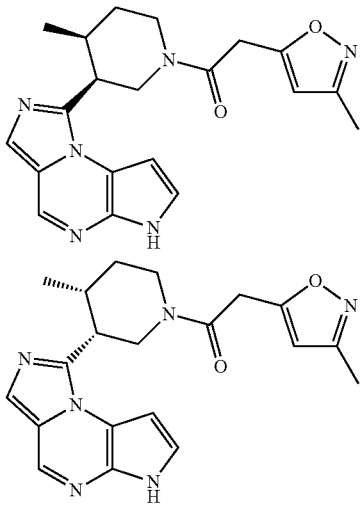 | H.3.17 | 1.52 (b) | 379 |
| 2-(2,4-difluoro-phenyl) acetic acid | 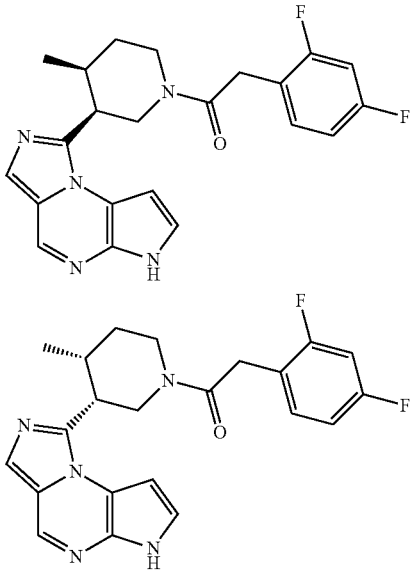 | H.3.18 | 1.84 (b) | 410 |

TABLE H.3-continued

| Examples prepared from 1-(cis)-4-methylpiperidin-3-yl)-6H-imidazo[1,5-a]pyrrolo[2,3-e]pyrazine hydrochloride (prepared using D from Preparation #Q.1 with NaOH, and E with 4N HCl in 1,4-dioxane) using General Procedure H with HATU and DIEA | | | | |
|---|---|---|---|---|
| Carboxylic Acid | Product | Example # | $R_t$ min (Table 1, Method) | m/z ESI+ $(M + H)^+$ |
| isoxazole-5-carboxylic acid | 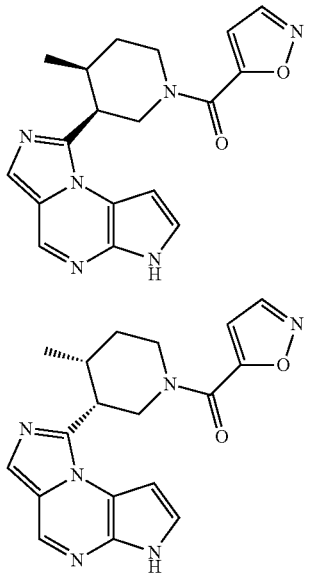 | H.3.19 | 1.52 (b) | 351 |

TABLE H.4

| Examples prepared from (R)-1-(piperidin-3-yl)-6H-imidazo[1,5-a]pyrrolo[2,3-e]pyrazine hydrochloride (Example #6, Step H) using General Procedure H with EDC•HCl and DIEA | | | | |
|---|---|---|---|---|
| Carboxylic Acid | Product | Example # | $R_t$ min (Table 1, Method) | m/z ESI+ $(M + H)^+$ |
| 3,3-difluorocyclobutanecarboxylic acid (Waterstone) | 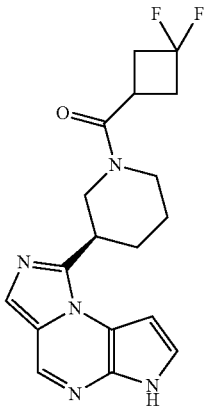 | H.4.1* | 1.86 (b) | 360 |

TABLE H.5

Examples prepared from cyclopropanamine (Aldrich) using General Procedure H with HATU and TEA

| Carboxylic Acid | Product | Example # | $R_t$ min (Table 2, Method a) | m/z ESI+ $(M + H)^+$ |
|---|---|---|---|---|
| 2-((1S,3R,4S)-3-ethyl-4-(6H-pyrrolo[2,3-e][1,2,4]triazolo[4,3-a]pyrazin-1-yl)cyclopentyl)acetic acid (Example W.1.2) | 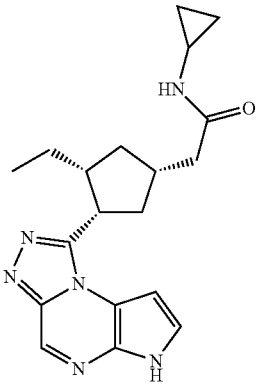 | H.5.1 | 1.45 | 353 |

General Procedure I: Formation of a Urea from an Amine and a Carbamoyl Chloride

To a flask containing an amine or an amine salt (1 equiv) in an organic solvent (such as THF or 1,4-dioxane, preferably THF) is added a base (such as DIEA or TEA, preferably TEA [3-5 equiv, preferably 4 equiv]) and stirred at ambient temperature for about 0-30 min (preferably about 5 min) then added a carbamoyl chloride (0.5-2 equiv, preferably 0.75 equiv). The mixture is stirred at about 0-90° C. (preferably about 45° C.) for about 2-24 h (preferably about 18 h). The reaction mixture is allowed to reach ambient temperature. The organic solvent is optionally removed under reduced pressure. The crude material can be partitioned between an organic solvent (such as EtOAc or DCM) and water, an aqueous base (such as saturated aqueous $NaHCO_3$) or brine. The layers are separated and the organic layer is optionally washed with water, an aqueous base (such as saturated aqueous $NaHCO_3$) or brine, dried over anhydrous $Na_2SO_4$ or $MgSO_4$, filtered, and concd under reduced pressure to give the target compound.

Illustration of General Procedure I

Example I.1.1*

((3R,4R)-3-(6H-imidazo[1,5-a]pyrrolo[2,3-e]pyrazin-1-yl)-4-methylpiperidin-1-yl)(piperidin-1-yl)methanone

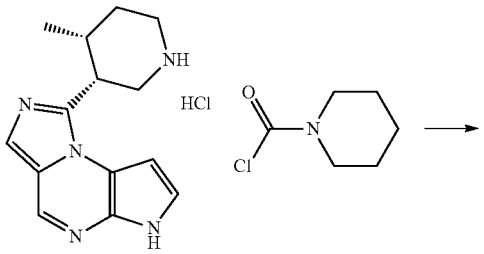

-continued

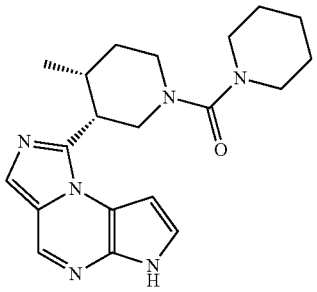

A round bottom flask was charged with 1-((3R,4R)-4-methylpiperidin-3-yl)-6H-imidazo[1,5-a]pyrrolo[2,3-e]pyrazine hydrochloride (0.050 g, 0.17 mmol, Example #5, Step J), TEA (0.10 mL, 0.69 mmol) in THF (1.6 mL). The reaction mixture was stirred for about 5 min at ambient temperature and then piperidine-1-carbonyl chloride (0.019 g, 0.13 mmol) was added. The reaction was heated at about 45° C. for about 18 h, cooled to ambient temperature, and concd under reduced pressure. The crude product was dissolved in DCM (5 mL) and washed with water (3 mL), dried over anhydrous $MgSO_4$, filtered, and concd under reduced pressure. The material was purified by RP-HPLC (Table 1, Method f) to give ((3R,4R)-3-(6H-imidazo[1,5-a]pyrrolo[2,3-e]pyrazin-1-yl)-4-methylpiperidin-1-yl)(piperidin-1-yl)methanone (0.018 g, 8%): LC/MS (Table 1, Method b) $R_t$=1.80 min; MS m/z 367 $(M+H)^+$.

TABLE I.1

Examples prepared from 1-((3R,4R)-4-methylpiperidin-3-yl)-6H-imidazo[1,5-a]pyrrolo[2,3-e]pyrazine hydrochloride (Example #5, Step J) using General Procedure I with TEA

| Carbamoyl chloride | Product | Example # | $R_t$ min (Table 1, Method) | m/z ESI+ $(M + H)^+$ |
|---|---|---|---|---|
| morpholine-4-carbonyl chloride | 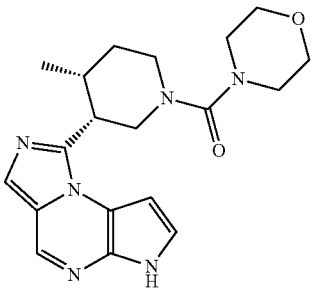 | I.1.2* | 1.48 (b) | 369 |
| 4-methyl-1-piperazinecarbonyl chloride hydrochloride | 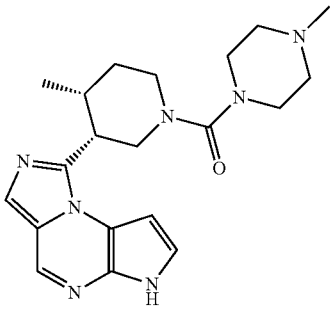 | I.1.3* | 1.22 (b) | 382 |

TABLE I.2

Examples prepared from 1-(cis-4-methylpiperidin-3-yl)-6H-imidazo[1,5-a]pyrrolo[2,3-e]pyrazine hydrochloride (prepared using D from Preparation #Q.1 with NaOH, and E with 4N HCl in 1,4-dioxane) using General Procedure I with TEA

| Carbamoyl chloride | Product | Example # | $R_t$ min (Table 1, Method) | m/z ESI+ $(M + H)^+$ |
|---|---|---|---|---|
| 1-pyrrolidinecarbonyl chloride | 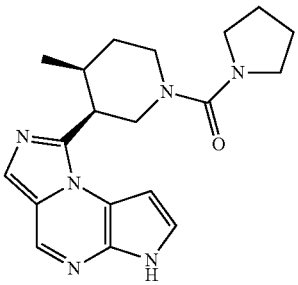 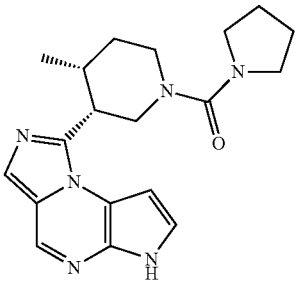 | I.2.1 | 1.63 (b) | 353 |

TABLE I.2-continued

Examples prepared from 1-(cis-4-methylpiperidin-3-yl)-6H-imidazo[1,5-a]pyrrolo[2,3-e]pyrazine hydrochloride (prepared using D from Preparation #Q.1 with NaOH, and E with 4N HCl in 1,4-dioxane) using General Procedure I with TEA

| Carbamoyl chloride | Product | Example # | $R_t$ min (Table 1, Method) | m/z ESI+ $(M + H)^+$ |
|---|---|---|---|---|
| dimethylcarbamoyl chloride | 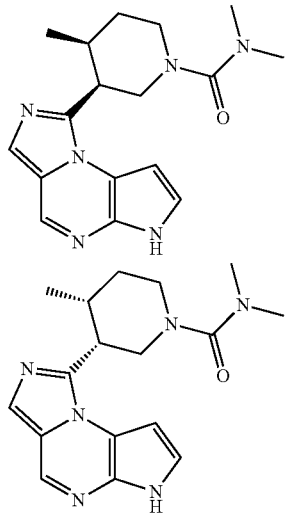 | I.2.2 | 1.52 (b) | 327 |

TABLE I.3

Example prepared from (R)-1-(piperidin-3-yl)-6H-imidazo[1,5-a]pyrrolo[2,3-e]pyrazine hydrochloride (Example #6, Step H) using General Procedure I with TEA

| Carbamoyl chloride | Product | Example # | $R_t$ min (Table 1, Method) | m/z ESI+ $(M + H)^+$ |
|---|---|---|---|---|
| 1-pyrrolidinecarbonyl chloride | 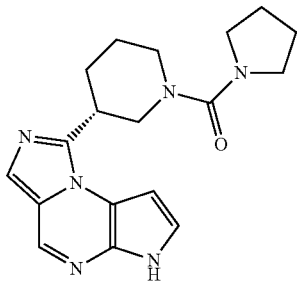 | I.3.1* | 1.53 (b) | 339 |

General Procedure J: Formation of a Urea or a Thiourea Using CDI or Thiocarbonyldiimidazole, Respectively To a solution or slurry of an amine or amine salt (1-3 equiv, preferably 1 equiv) in an organic solvent such as DCM, THF, or DMF (preferably DCM) at about −20-40° C. (preferably about 0° C.) is added an organic base, such as TEA, DIEA, pyridine (preferably TEA) (1-10 equiv, preferably 1-3 equiv) followed by CDI or 1,1'-thiocarbonyldiimidazole (0.5-2 equiv, preferably 1 equiv). After about 0.5-24 h (preferably about 0.5-1 h), a second amine or amine salt (1-10 equiv, preferably 3 equiv) is added neat or as a solution or slurry in an organic solvent such as DCM, THF, or DMF (preferably DCM). The reaction is held at about 0° C. for about 10-60 min (preferably about 15-30 min) and then the reaction is allowed to warm to ambient temperature. After about 1-48 h (preferably about 12-16 h), the reaction mixture is partitioned between an organic solvent (such as EtOAc, DCM or 1,4-dioxane) and an aqueous base (such as saturated aqueous $NaHCO_3$ or saturated aqueous $Na_2CO_3$, preferably saturated aqueous $NaHCO_3$). Optionally, the reaction mixture is concd under reduced pressure and the residue is partitioned as above. In either case, the aqueous layer is then optionally extracted with additional organic solvent such as EtOAc or DCM. The combined organic layers may optionally be washed with brine and concd in vacuo or dried over anhydrous $Na_2SO_4$ or $MgSO_4$ and then decanted or filtered prior to concentrating under reduced pressure to give the target compound. Intermediates and final compounds prepared via this General Procedure can be optionally purified using one or more of the Purification Methods described above.

Preparation #J.1: tert-butyl 1-((5-tosyl-5H-pyrrolo[2,3-b]pyrazin-2-yl)methylcarbamothioyl)pyrrolidin-3-ylcarbamate

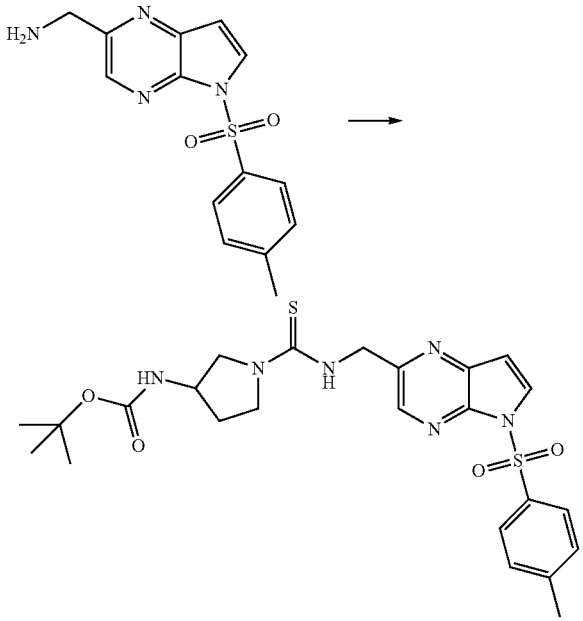

To a slurry of (5-tosyl-5H-pyrrolo[2,3-b]pyrazin-2-yl) methanamine hydrochloride (0.50 g, 1.5 mmol, Example #5, Step C) in DCM (10 mL) at about 0° C. was added TEA (0.226 mL, 1.62 mmol). To the homogeneous reaction mixture was added a solution of 1,1'-thiocarbonyldiimidazole (0.29 g, 1.6 mmol) in DCM (10 mL). After about 30 min, a slurry of tert-butyl pyrrolidin-3-ylcarbamate (0.83 g, 4.4 mmol, TCI) in DCM (10 mL) was added to the reaction mixture. After stirring for about 20 min, the reaction mixture was allowed to warm to ambient temperature. After stirring for about 15 h, saturated aqueous $NaHCO_3$ (30 mL) was added to the reaction mixture. The organic layer was separated, concd in vacuo, and purified by chromatography on silica gel eluting with 20-40% EtOAc in DCM to provide tert-butyl 1-((5-tosyl-5H-pyrrolo[2,3-b]pyrazin-2-yl)methylcarbamothioyl)pyrrolidin-3-ylcarbamate (0.54 g, 69%) as a yellow glass: LC/MS (Table 1, Method a) $R_t$=2.37 min; MS m/z: 531 $(M+H)^+$.

General Procedure J.1: Formation of a Urea or a Thiourea Using CDI or Thiocarbonyldiimidazole, Respectively To a solution or slurry of an amine or amine salt (1-3 equiv, preferably 1-2 equiv) in an organic solvent such as DCM, THF, or DMF (preferably DMF) at about 20-80° C. (preferably about 65° C.) is optionally added an organic base, such as TEA, DIEA, pyridine (preferably TEA) (1-10 equiv, preferably 1-5 equiv) followed by CDI or 1,1'-thiocarbonyldiimidazole (0.5-2 equiv, preferably 1 equiv). After about 0.5-24 h (preferably about 1-3 h), a second amine or amine salt (1-10 equiv, preferably 1-3 equiv) is added neat or as a solution or slurry in an organic solvent such as DCM, THF, or DMF (preferably DMF). The reaction is held at about 20-80° C. (preferably about 65° C.). for about 2-24 h (preferably about 3 h). If the reaction mixture is heated, it is cooled to ambient temperature. The reaction mixture is partitioned between an organic solvent (such as EtOAc, DCM or 1,4-dioxane) and an aqueous base (such as saturated aqueous $NaHCO_3$ or saturated aqueous $Na_2CO_3$, preferably saturated aqueous $NaHCO_3$). Optionally, the reaction mixture is concd under reduced pressure and the residue is partitioned as above. In either case, the aqueous layer is then optionally extracted with additional organic solvent such as EtOAc or DCM. The combined organic layers may optionally be washed with brine and concd in vacuo or dried over anhydrous $Na_2SO_4$ or $MgSO_4$ and then decanted or filtered prior to concentrating under reduced pressure to give the target compound. Optionally, the reaction mixture is concd under reduced pressure and the residue is directly purified.

Illustration of General Procedure J.1

Preparation #J.1.1: (cis)-N-(2-cyclopropylethyl)-3-ethyl-4-(6-tosyl-6H-pyrrolo[2,3-e][1,2,4]triazolo[4,3-a]pyrazin-1-yl)pyrrolidine-1-carboxamide

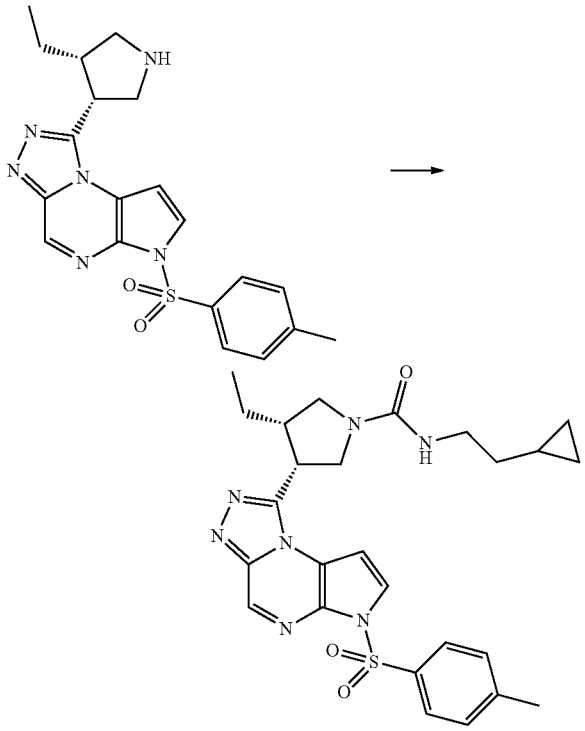

To a solution of 2-cyclopropylethanamine (0.068 g, 0.804 mmol, Oakwood) in DMF (3 mL) was added CDI (0.150 g, 0.926 mmol). The solution was stirred at about 65° C. for about 2 h. 1-((cis)-4-ethylpyrrolidin-3-yl)-6-tosyl-6H-pyrrolo[2,3-e][1,2,4]triazolo[4,3-a]pyrazine (0.250 g, 0.609 mmol, Example #36, step F) was added and the reaction mixture continued heating at about 65° C. After about 2 h, the reaction mixture was cooled to ambient temperature. The solvent was removed under reduced pressure. The crude material was purified by chromatography on silica gel eluting with a gradient of 0-10% MeOH in DCM to give (cis)-N-(2-cyclopropylethyl)-3-ethyl-4-(6-tosyl-6H-pyrrolo[2,3-e][1,2,4]triazolo[4,3-a]pyrazin-1-yl)pyrrolidine-1-carboxamide (0.238 g, 64%) as product: LC/MS (Table 1, Method a) $R_t$=2.17 min; MS m/z: 522 $(M+H)^+$.

TABLE J.1

Examples prepared from 1-(cis)-4-methylpiperidin-3-yl)-6H-imidazo[1,5-a]pyrrolo[2,3-e]pyrazine hydrochloride (prepared using D from Preparation #Q.1 with NaOH, and E with 4N HCl in 1,4-dioxane) using General Procedure J with CDI

| Amine or Amine hydrochloride | Product | Example # | $R_t$ min (Table 1, Method) | m/z ESI+ $(M + H)^+$ |
|---|---|---|---|---|
| azetidine-3-carbonitrile hydrochloride [AstaTech Inc] | 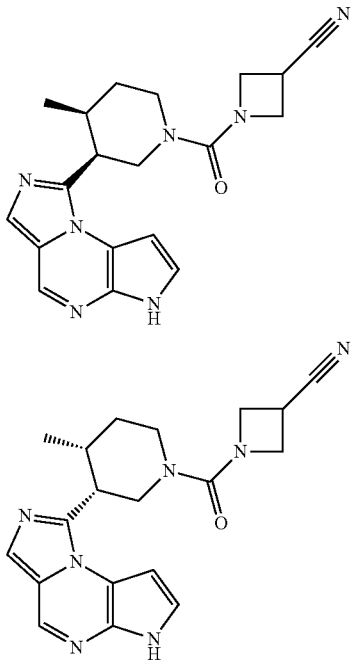 | J.1.1 | 1.48 (b) | 364 |
| 2-amino-acetonitrile | 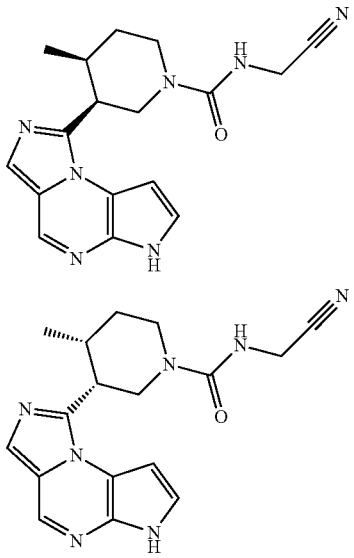 | J.1.2 | 1.37 (b) | 338 |

TABLE J.2

Examples prepared from 1-((3R,4R)-4-methylpiperidin-3-yl)-6H-imidazo[1,5-a]pyrrolo[2,3-e]pyrazine hydrochloride (Example #5, Step J) using General Procedure J with CDI

| Amine or Amine hydro-chloride | Product | Example # | R, min (Table 1, Method) | m/z ESI+ $(M + H)^+$ |
|---|---|---|---|---|
| pyrrolidine-3-carbonitrile hydro-chloride [Tyger] | 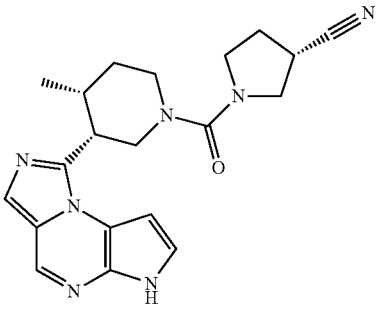 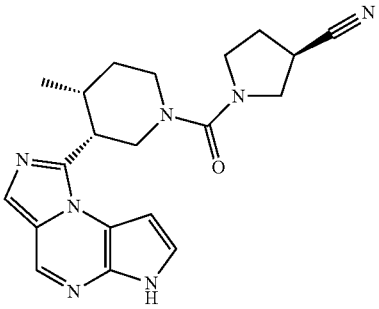 | J.2.1* | 1.51 (b) | 378 |
| (R)-pyrrolidine-2-carbonitrile hydro-chloride [AstaTech Inc] | 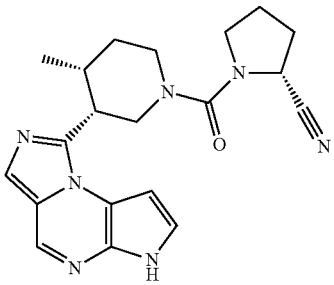 | J.2.2* | 1.61 (b) | 378 |
| (S)-pyrrolidine-2-carbonitrile hydro-chloride [AstaTech Inc] | 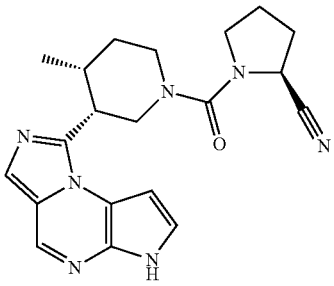 | J.2.3* | 1.63 (b) | 378 |

TABLE J.2-continued

Examples prepared from 1-((3R,4R)-4-methylpiperidin-3-yl)-6H-imidazo[1,5-a]pyrrolo[2,3-e]pyrazine hydrochloride (Example #5, Step J) using General Procedure J with CDI

| Amine or Amine hydro-chloride | Product | Example # | $R_t$ min (Table 1, Method) | m/z ESI+ $(M + H)^+$ |
|---|---|---|---|---|
| (S)-2-(trifluoro-methyl) pyrrolidine | 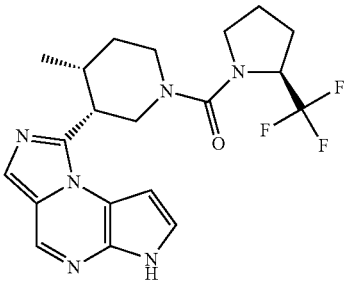 | J.2.4* | 1.99 (b) | 421 |
| 3,3-difluoro-azetidine hydro-chloride | 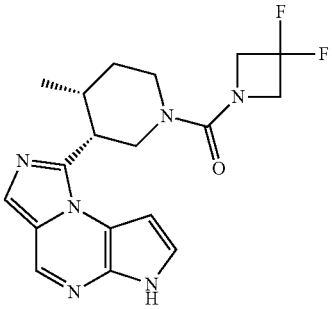 | J.2.5* | 1.71 (b) | 375 |
| azetidine | 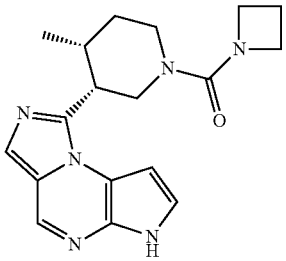 | J.2.6* | 1.51 (b) | 339 |
| (R)-3-fluoro-pyrrolidine hydro-chloride | 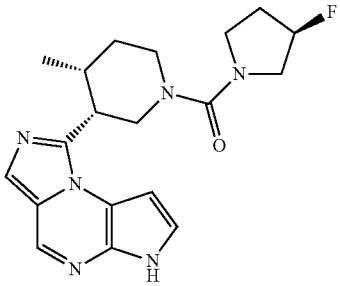 | J.2.7* | 1.59 (b) | 371 |
| 3,3-difluoro-pyrrolidine hydro-chloride | 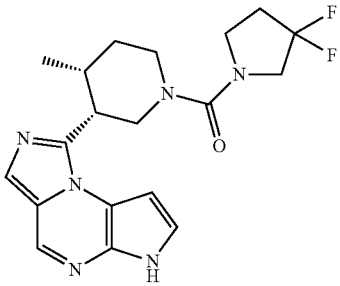 | J.2.8* | 1.71 (b) | 389 |

TABLE J.2-continued

Examples prepared from 1-((3R,4R)-4-methylpiperidin-3-yl)-6H-imidazo[1,5-a]pyrrolo[2,3-e]pyrazine hydrochloride (Example #5, Step J) using General Procedure J with CDI

| Amine or Amine hydro-chloride | Product | Example # | $R_t$ min (Table 1, Method) | m/z ESI+ $(M + H)^+$ |
|---|---|---|---|---|
| (R)-pyrrolidin-2-ylmethanol | 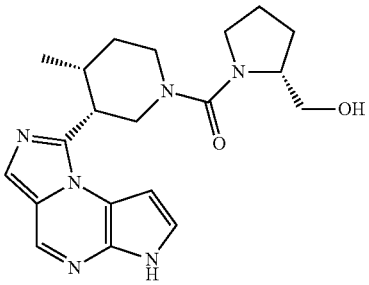 | J.2.9* | 1.45 (b) | 383 |
| 3-methyl-pyrrolidine [Tyger] | 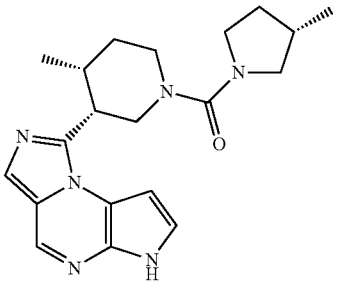 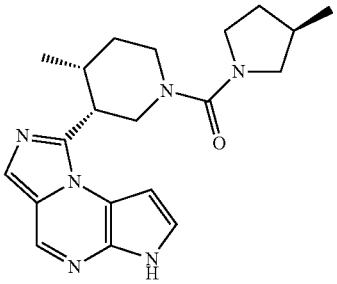 | J.2.10* | 1.75 (b) | 367 |
| 3-fluoro-azetidine hydro-chloride [Parkway Scientific] | 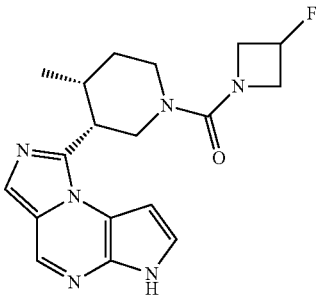 | J.2.11* | 1.53 (b) | 357 |
| (S)-3-fluoro-pyrrolidine hydro-chloride | 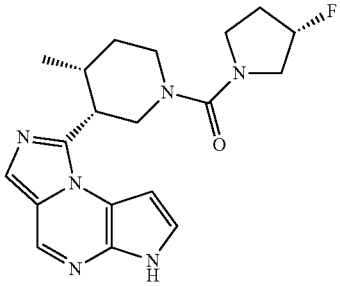 | J.2.12* | 1.56 (b) | 371 |

TABLE J.2-continued

Examples prepared from 1-((3R,4R)-4-methylpiperidin-3-yl)-6H-imidazo[1,5-a]pyrrolo[2,3-e]pyrazine hydrochloride (Example #5, Step J) using General Procedure J with CDI

| Amine or Amine hydrochloride | Product | Example # | $R_t$ min (Table 1, Method) | m/z ESI+ $(M + H)^+$ |
|---|---|---|---|---|
| (R)-2-methyl-pyrrolidine | 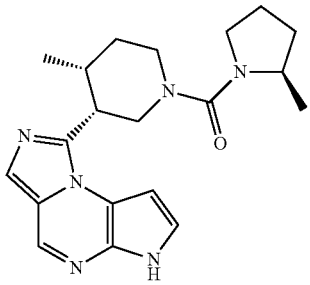 | J.2.13* | 1.74 (b) | 367 |
| hexamethyl-eneimine | 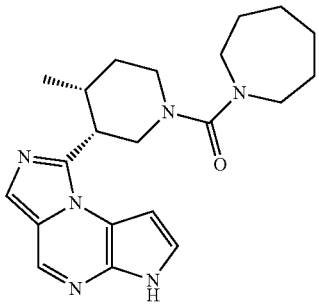 | J.2.14* | 1.87 (b) | 381 |
| (R)-2-(trifluoro-methyl) pyrrolidine | 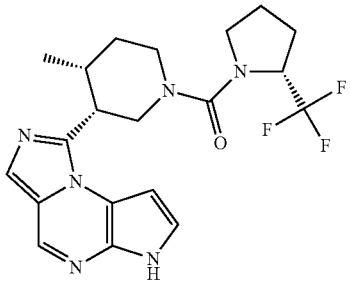 | J.2.15* | 2.03 (b) | 421 |

TABLE J.3

Examples prepared from (R)-1-(piperidin-3-yl)-6H-imidazo[1,5-a]pyrrolo[2,3-e]pyrazine hydrochloride (Example #6, Step H) using General Procedure J with CDI and pyridine

| Amine or Amine hydrochloride | Product | Example # | $R_t$ min (Table 1, Method) | m/z ESI+ $(M + H)^+$ |
|---|---|---|---|---|
| 3,3-difluoro-azetidine hydrochloride | 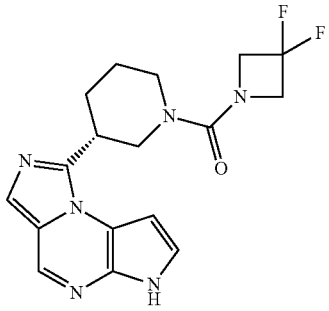 | J.3.1* | 1.56 (b) | 361 |

TABLE J.3-continued

Examples prepared from (R)-1-(piperidin-3-yl)-6H-imidazo[1,5-a]pyrrolo[2,3-e]pyrazine hydrochloride (Example #6, Step H) using General Procedure J with CDI and pyridine

| Amine or Amine hydrochloride | Product | Example # | $R_t$ min (Table 1, Method) | m/z ESI+ $(M + H)^+$ |
|---|---|---|---|---|
| 3,3-difluoro-pyrrolidine hydrochloride | 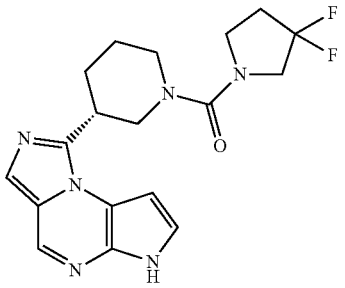 | J.3.2* | 1.60 (b) | 375 |
| piperidine-3-carbonitrile [ChemBridge-BB] | 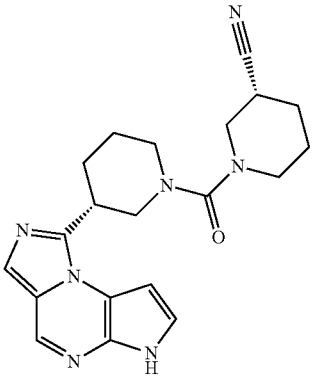 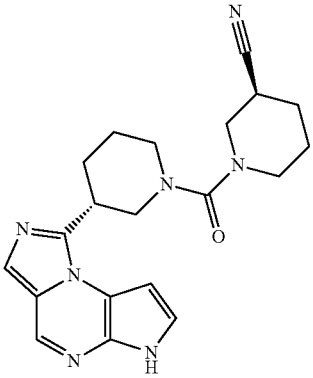 | J.3.3* | 1.55 (b) | 378 |
| azetidine-3-carbonitrile hydrochloride [AstaTech Inc] | 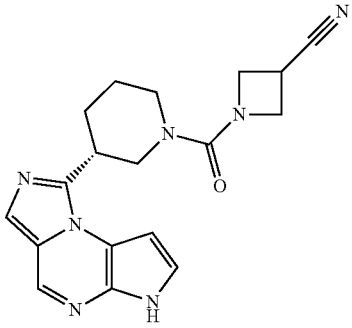 | J.3.4* | 1.36 (b) | 350 |

TABLE J.3-continued

Examples prepared from (R)-1-(piperidin-3-yl)-6H-imidazo[1,5-a]pyrrolo[2,3-e]pyrazine hydrochloride (Example #6, Step H) using General Procedure J with CDI and pyridine

| Amine or Amine hydrochloride | Product | Example # | $R_t$ min (Table 1, Method) | m/z ESI+ $(M + H)^+$ |
|---|---|---|---|---|
| (R)-2-(trifluoromethyl) pyrrolidine | 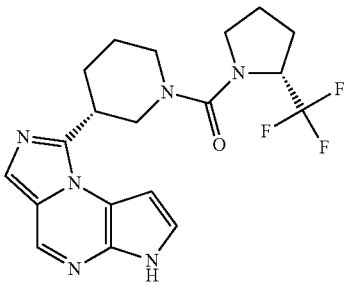 | J.3.5* | 1.76 (b) | 407 |
| 3,3-dimethyl-pyrrolidine hydrochloride [Matrix Scientific] | 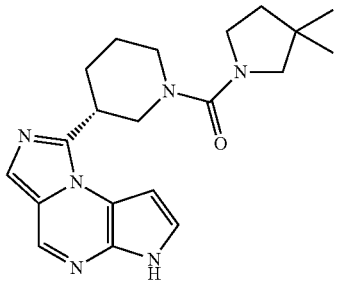 | J.3.6* | 1.75 (b) | 367 |
| 3,3-difluoro-piperidine hydrochloride | 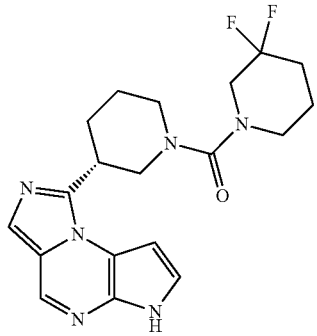 | J.3.7* | 1.71 (b) | 389 |
| piperidine-4-carbonitrile [Oakwood] | 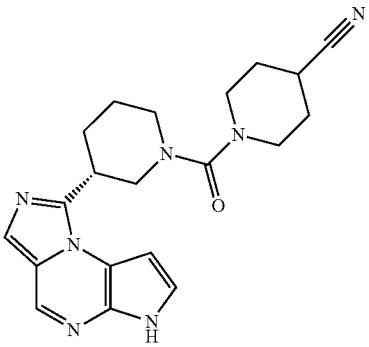 | J.3.8* | 1.48 (b) | 378 |

TABLE J.3-continued

Examples prepared from (R)-1-(piperidin-3-yl)-6H-imidazo[1,5-a]pyrrolo[2,3-e]pyrazine hydrochloride (Example #6, Step H) using General Procedure J with CDI and pyridine

| Amine or Amine hydrochloride | Product | Example # | $R_t$ min (Table 1, Method) | m/z ESI+ $(M + H)^+$ |
|---|---|---|---|---|
| thiomorpholine 1,1-dioxide [TCI-Europe] | 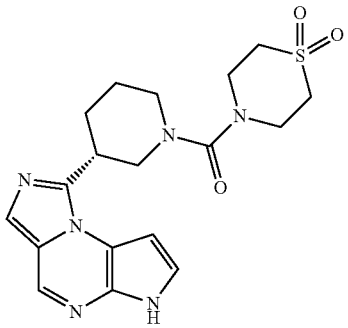 | J.3.9 * | 1.31 (b) | 403 |
| 4,4-dimethyl-piperidine hydrochloride [Matrix Scientific] | 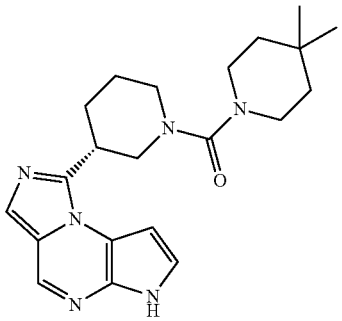 | J.3.10* | 1.93 (b) | 381 |
| 4-chloropiperidine hydrochloride [AstaTech Inc] | 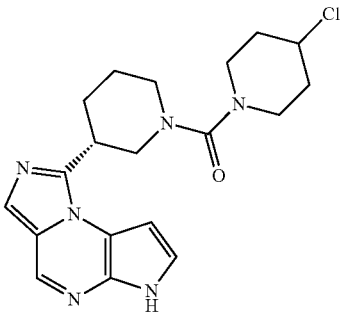 | J.3.11* | 1.72 (b) | 387 |

TABLE J.4

Examples prepared from 1-((3R,4S)-4-isopropylpyrrolidin-3-yl)-6H-pyrrolo[2,3-e][1,2,4]triazolo[4,3-a]pyrazine (prepared using Y from Example #D.1.143) using General Procedure J with CDI

| Amine or Amine hydrochloride | Product | Example # | $R_t$ min (Table 1, Method) | m/z ESI+ $(M + H)^+$ |
|---|---|---|---|---|
| Cyclobutanamine (Aldrich) | 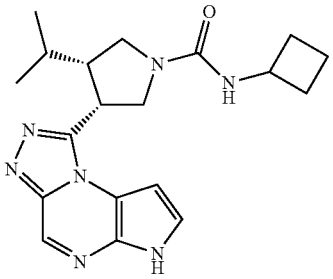 | J.4.1 | 1.58 (a) | 368 |

General Procedure K: Formation of a Sulfonamide from an Amine

To a mixture of an amine or an amine salt (preferably 1 equiv) in an organic solvent such as THF, DMA, DCM or DMF (preferably DMF) is added an organic base such as TEA or DIEA (1-10 equiv, preferably 2-4 equiv) or an aqueous base such as saturated aqueous $NaHCO_3$ (5-20 equiv, preferably 5-10 equiv) (preferably an organic base) and a sulfonyl chloride (0.9-3 equiv, preferably 1-1.5 equiv). The reaction mixture is stirred at about −10-25° C. (preferably at ambient temperature) for about 0.5-150 h (preferably about 144 h). Optionally, additional base (1-10 equiv) and/or sulfonyl chloride (0.4-2 equiv) may be added at any point during the reaction time. The reaction is worked up using one of the following methods. Method 1: The reaction is diluted with water and extracted with an organic solvent such as DCM or EtOAc. The combined organic layers are optionally washed with brine, dried over anhydrous $Na_2SO_4$ or $MgSO_4$, filtered or decanted, and concd under reduced pressure. Method 2: The crude reaction mixture is purified by preparative HPLC directly or after the addition of organic solvent such as MeOH or DMF or an aqueous buffer such as 50 mM $NH_4OAc$ with or without concentrating the mixture under reduced pressure first. Method 3: The solvent is removed under reduced pressure and the residue is partitioned between an organic solvent such as DCM or EtOAc (preferably EtOAc) and water. The layers are separated and the organic layer is optionally washed with brine, dried over anhydrous $Na_2SO_4$ or $MgSO_4$, filtered or decanted, and concd under reduced pressure. Method 4: The reaction is diluted with water and the resulting solid is collected by vacuum filtration.

Illustration of General Procedure K

Example #K.1

N-((1S,3S,4R)-3-(3H-imidazo[1,2-a]pyrrolo[2,3-e]pyrazin-8-yl)-4-methylcyclopentyl)-3,3,3-trifluoropropane-1-sulfonamide

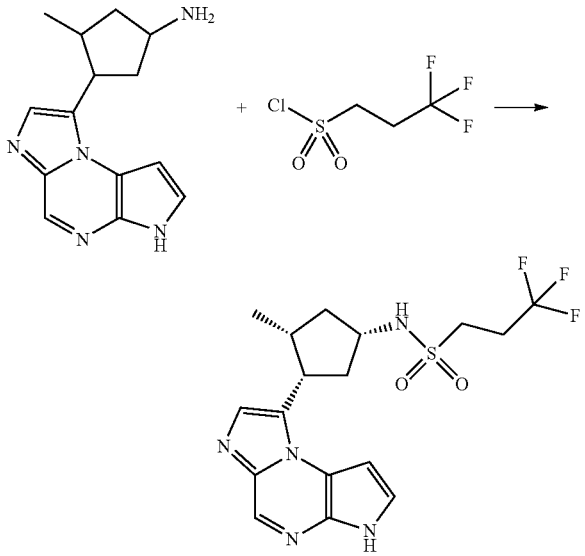

3,3,3-Trifluoropropane-1-sulfonyl chloride (0.194 g, 0.987 mmol, Matrix) was added dropwise to a solution of TEA (0.31 mL, 2.2 mmol) and 3-(3H-imidazo[1,2-a]pyrrolo

[2,3-e]pyrazin-8-yl)-4-methylcyclopentanamine (0.28 g, 1.1 mmol, Preparation #53) in DMF (10 mL). The resulting mixture was stirred at ambient temperature for about 144 h. The solvent was removed under reduced pressure and the residue was partitioned between EtOAc and water (20 mL each). The layers are separated and the organic layer was washed with brine (30 mL), dried over anhydrous $MgSO_4$, filtered, and concd under reduced pressure. The residue was purified by using General Procedure AA (Table 2, Method 9, $R_t$=17.7 min, or =negative) to give N-((1S,3S,4R)-3-(3H-imidazo[1,2-a]pyrrolo[2,3-e]pyrazin-8-yl)-4-methylcyclopentyl)-3,3,3-trifluoropropane-1-sulfonamide (0.021 g, 4.6%) as a white solid: LC/MS (Table 1, Method a) $R_t$=1.79 min; MS m/z 416 $(M+H)^+$.

TABLE K.1

Examples prepared from (1S,3R,4S)-3-methyl-4-(6H-pyrrolo[2,3-e][1,2,4]triazolo[4,3-a]pyrazin-1-yl)cyclopentanamine (Preparation #19.1) using General Procedure K

| Sulfonyl chloride | Product | Example # | $R_t$ min (Table 1, Method) | m/z ESI+ $(M + H)^+$ |
|---|---|---|---|---|
| 5-methylisoxazole-4-sulfonyl chloride [Maybridge] | 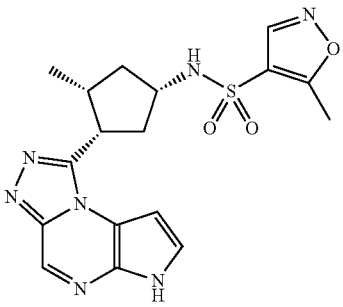 | K.1.1* | 1.91 (a) | 402 |

TABLE K.2

Example prepared from 1-(cis)-4-methylpiperidin-3-yl)-6H-imidazo[1,5-a]pyrrolo[2,3-e]pyrazine hydrochloride (prepared using D from Preparation #Q.1 with NaOH, and E with 4N HCl in 1,4-dioxane) using General Procedure K

| Sulfonyl chloride | Product | Example # | $R_t$ min (Table 1, Method) | m/z ESI+ $(M + H)^+$ |
|---|---|---|---|---|
| cyclopropanesulfonyl chloride | 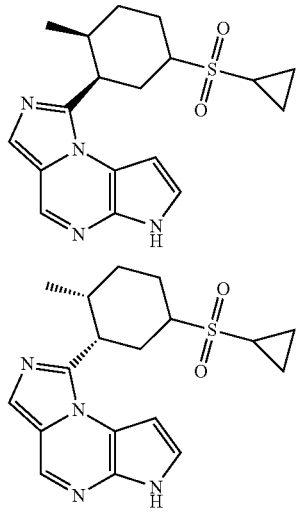 | K.2.1 | 1.66 (b) | 360 |

TABLE K.3

Examples prepared from 4-(3H-imidazo[1,2-a]pyrrolo[2,3-e]pyrazin-8-yl)bicyclo[2.2.2]octan-1-amine hydrobromide (Preparation #F.1) using General Procedure K

| Sulfonyl chloride | Product | Example # | $R_t$ min (Table 1, Method) | m/z ESI+ $(M + H)^+$ |
|---|---|---|---|---|
| Cyclopropanesulfonyl chloride | 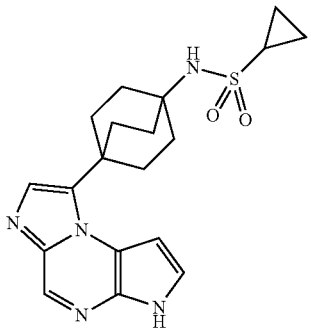 | K.3.1 | 1.59 (a) | 386 |

TABLE K.4

Examples prepared from (3S,5R)-5-ethyl-1-(3H-imidazo[1,2-a]pyrrolo[2,3-e]pyrazin-8-yl)pyrrolidin-3-amine (Preparation #TTT.1) using General Procedure K

| Sulfonyl chloride | Product | Example # | $R_t$ min (Table 1, Method) | m/z ESI+ $(M + H)^+$ |
|---|---|---|---|---|
| 3,3,3-trifluoropropane-1-sulfonyl chloride (Matrix) | 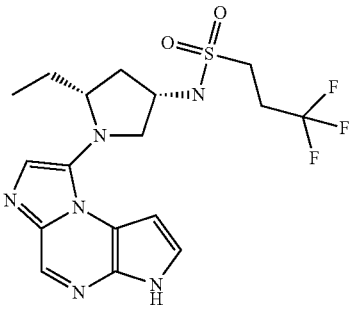 | K.4.1* | 1.86 (a) | 431 |

TABLE K.5

Examples prepared from (1S,3R,4S)-3-ethyl-4-(6H-pyrrolo[2,3-e][1,2,4]triazolo[4,3-a]pyrazin-1-yl)cyclopentanamine (Prepared from Example #8 Step M using D) using General Procedure K

| Sulfonyl chloride | Product | Example # | $R_t$ min (Table 1, Method) | m/z ESI+ $(M + H)^+$ |
|---|---|---|---|---|
| 2,2,2-trifluoroethane-1-sulfonyl chloride | 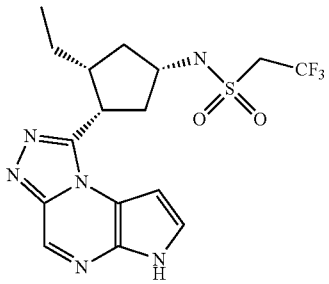 | K.5.1 | 1.89 (a) | 417 |

General Procedure K.1: Formation of a Sulfonamide from an Amine or Nitrogen Containing Heterocycle (Additional Conditions)

To a mixture of an amine, an amine salt or a nitrogen containing heterocycle (preferably 1 equiv) in an organic solvent such as THF, DMA, DCM or DMF (preferably DMF) is added an organic base such as TEA or DIEA (1-10 equiv, preferably 2-4 equiv) or an aqueous base such as saturated aqueous $NaHCO_3$ (5-20 equiv, preferably 5-10 equiv) or an inorganic base such as NaH (1-10 equiv, preferably 1-3equiv) and a sulfonyl chloride (0.9-3 equiv, preferably 1-1.5 equiv). The reaction mixture is stirred at about −10-25° C. (preferably at about 0° C.) for about 5 min-150 h (preferably about 90 min). Optionally, additional base (1-10 equiv) and/or sulfonyl chloride (0.4-2 equiv) may be added at any point during the reaction time. In cases where a halogen is present, the halogen may eliminate and the alkene may be obtained. The reaction is worked up using one of the following methods. Method 1: The reaction is diluted with water and extracted with an organic solvent such as DCM or EtOAc. The combined organic layers are optionally washed with saturated aqueous base and brine, dried over anhydrous $Na_2SO_4$ or $MgSO_4$, filtered or decanted, and concd under reduced pressure. Method 2: The crude reaction mixture is purified by preparative HPLC directly or after the addition of organic solvent such as MeOH or DMF or an aqueous buffer such as 50 mM $NH_4OAc$ with or without concentrating the mixture under reduced pressure first. Method 3: The solvent is removed under reduced pressure and the residue is partitioned between an organic solvent such as DCM or EtOAc (preferably EtOAc) and water. The layers are separated and the organic layer is optionally washed with brine, dried over anhydrous $Na_2SO_4$ or $MgSO_4$, filtered or decanted, and concd under reduced pressure. Method 4: The reaction is diluted with water and the resulting solid is collected by vacuum filtration.

Illustration of General Procedure K.1

Preparation #K.1: N-((1S,3R,4S)-3-ethyl-4-(5-nitro-1-tosyl-1H-pyrrolo[2,3-b]pyridin-4-ylamino)cyclopentyl)cyclopropanesulfonamide

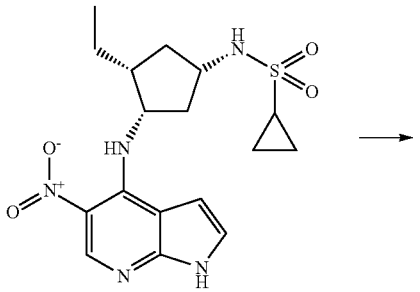

-continued

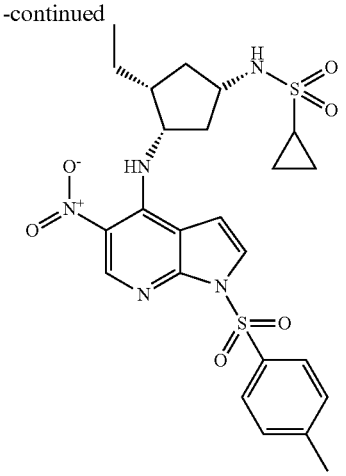

To a solution of N-((1S,3R,4S)-3-ethyl-4-(5-nitro-1H-pyrrolo[2,3-1)]pyridin-4-ylamino)cyclopentyl)cyclopropanesulfonamide (Example #23, Step G) (0.123 g, 0.314 mmol) in DMF (3.0 mL) at about 0° C. was added NaH (60% in mineral oil, 0.015 g, 0.37 mmol). The reaction mixture was stirred for about 5 min. 4-Methylbenzene-1-sulfonyl chloride (0.060 g, 0.314 mmol) was added and the reaction mixture was stirred for about 30 min. NaH (60% in mineral oil, 0.007 g, 0.18 mmol) was added and the reaction mixture was stirred for about 10 min. NaH (60% in mineral oil, 0.005 g, 0.12 mmol) was added and the reaction mixture was stirred for about 15 min. 4-Methylbenzene-1-sulfonyl chloride (0.012 g, 0.063 mmol) was added and the reaction mixture was stirred for about 40 min. The reaction mixture was concd under reduced pressure. The residue was dissolved in EtOAc (25 mL) and washed with water (15 mL). The organic layer was separated, dried over anhydrous $MgSO_4$, filtered and concd under reduced pressure to give N-((1S,3R,4S)-3-ethyl-4-(5-nitro-1-tosyl-1H-pyrrolo[2,3-b)]pyridin-4-ylamino)cyclopentyl)cyclopropanesulfonamide (0.218 g) as a red-orange oil containing 40 mol % DMF and 1 equiv EtOAc: LC/MS (Table 1, Method n) $R_t$=0.88 min; MS m/z 548 $(M+H)^+$.

General Procedure L: Displacement of an Aryl or Heteroaryl Halide with an Amine

To a microwave vessel or a round bottom flask is added an amine or an amine salt (preferably 1 equiv), an aryl or heteroaryl halide (1-10 equiv, preferably 1.5 equiv), a solvent (such as MeCN, n-PrOH, n-BuOH, toluene, DMSO, DMF, or EtOH, preferably n-PrOH[microwave] or DMF [thermal heating]), and a base (such as $K_2CO_3$, $Na_2CO_3$, TEA or DIEA, preferably TEA, DIEA, or $K_2CO_3$, 1-5 equiv, preferably 2-4 equiv). The reaction mixture is heated at about 40-220° C. thermally (preferably about 65° C.) for about 0.5-16 h (preferably about 8.5 h) or is subjected to microwave heating at about 100-200° C. (preferably about 130-150° C.) for about 0.5-8 h (preferably about 0.5-2 h). In cases where the reaction does not proceed to completion as monitored by TLC, LC/MS, or HPLC, the reaction may be resubjected to thermal heating at about 40-220° C. (preferably about 65° C.) for about 0.5-8 h (preferably about 1-2 h) or microwave heating at about 120-200° C. (preferably about 130-150° C.) for an additional about 1-8 h (preferably about 0.5-2 h) with the optional addition of more aryl or heteroaryl halide (1-10 equiv, preferably 1.5 equiv) and/or base (such as $K_2CO_3$, $Na_2CO_3$, TEA or DIEA, preferably TEA, DIEA or $K_2CO_3$, 1-5 equiv, preferably 2-4 equiv). This process is repeated until the reaction proceeds no further. After cooling to ambient temperature, the reaction is worked up using one of the following methods. Method 1: The reaction is concd under reduced pressure. Method 2: A reaction mixture containing a precipitate may be filtered to collect the target compound, while optionally washing with organic solvent or solvents such as $Et_2O$, DCM and/or petroleum ether. Method 3: The reaction mixture is diluted with an organic solvent such as MeOH, silica gel is added, and the mixture is concd under reduced pressure to prepare for separation by chromatography with solid loading. Method 4: The reaction mixture is concd under reduced pressure prior to the addition of an organic solvent such as EtOAc or DCM and is then optionally washed with water and/or brine, dried over anhydrous $Na_2SO_4$ or $MgSO_4$, filtered or decanted, and concd under reduced pressure. Method 5: An organic solvent such as EtOAc or DCM is added with the optional addition of water or brine and the layers are separated. The aqueous layer is then optionally extracted with additional organic solvent such as EtOAc or DCM. The combined organic layers are optionally washed with brine or water, dried over anhydrous $MgSO_4$ or $Na_2SO_4$, filtered or decanted, and concd under reduced pressure.

Illustration of General Procedure L

Preparation #L.1: (S)-5-(3-((6-tosyl-6H-pyrrolo[2,3-e][1,2,4]triazolo[4,3-a]pyrazin-1-yl)methyl)pyrrolidin-1-yl)pyrazine-2-carbonitrile

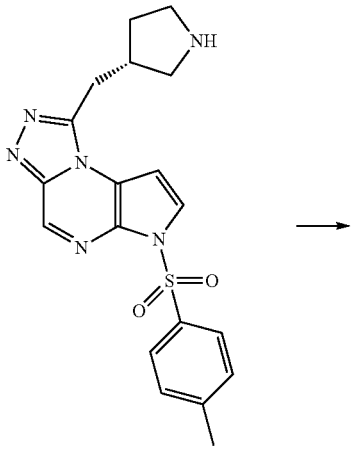

-continued

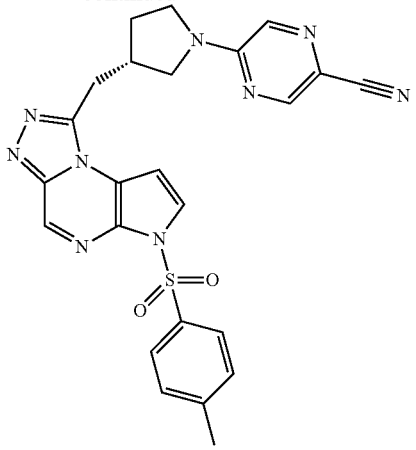

A mixture of (S)-1-(pyrrolidin-3-ylmethyl)-6-tosyl-6H-pyrrolo[2,3-e][1,2,4]triazolo[4,3-a]pyrazine (0.160 g, 0.404 mmol, prepared using B from Preparation #A.1 and E with HCl), 2-chloro-5-cyanopyrazine (0.084 g, 0.60 mmol, ArkPharm) and DIEA (0.28 mL, 1.6 mmol) in n-PrOH (2.0 mL) was heated in a CEM microwave at about 150° C. for about 30 min (250 psi maximum pressure, 10 min maximum ramp, 200 maximum watts). The reaction mixture was cooled to ambient temperature and DCM (20 mL) was added. The solution was washed with water (20 mL) and brine (20 mL). The organic layer was separated, dried over anhydrous $MgSO_4$, filtered, and concd under reduced pressure. The residue was taken up in DCM (10 mL), adsorbed onto silica gel (1 g), and purified by silica gel chromatography eluting with 100% EtOAc to give a pink solid. The material was triturated with a mixture of EtOAc (10 mL) and 10% MeOH in DCM (10 mL). The insoluble material was collected by filtration to give (S)-5-(3-(6-tosyl-6H-pyrrolo[2,3-e][1,2,4]triazolo[4,3-a]pyrazin-1-yl)methyl)pyrrolidin-1-yl)pyrazine-2-carbonitrile as an off-white solid (0.056 g, 27%): LC/MS (Table 1, Method c) $R_t$=1.34 min; MS m/z: 500 $(M+H)^+$.

TABLE L.1

Examples prepared from 1-(cis)-4-methylpiperidin-3-yl)-6H-imidazo[1,5-a]pyrrolo[2,3-e]pyrazine hydrochloride (prepared using D from Preparation #Q.1 with NaOH, and E with 4N HCl in 1,4-dioxane) using General Procedure L

| Heteroaryl Halide | Product | Example # | $R_t$ min (Table 1, Method) | m/z ESI+ $(M+H)^+$ |
|---|---|---|---|---|
| 6-chloropyridazine-3-carbonitrile [ArkPharm] | 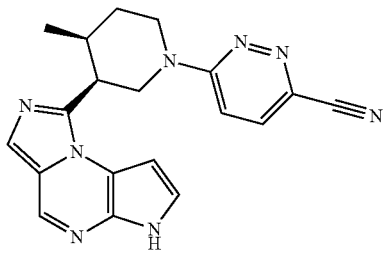 | L.1.1 | 1.68 (b) | 359 |

TABLE L.1-continued
Examples prepared from 1-(cis)-4-methylpiperidin-3-yl)-6H-imidazo[1,5-a]pyrrolo[2,3-e]pyrazine hydrochloride (prepared using D from Preparation #Q.1 with NaOH, and E with 4N HCl in 1,4-dioxane) using General Procedure L
| Heteroaryl Halide | Product | Example # | $R_t$ min (Table 1 , Method) | m/z ESI+ $(M+H)^+$ |
|---|---|---|---|---|
| | 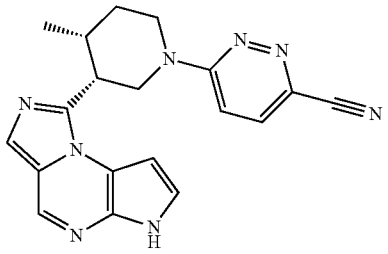 | | | |
| 2-chloro-5-cyanopyrazine [ArkPharm] | 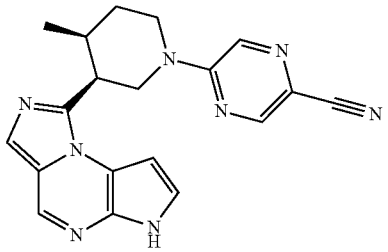 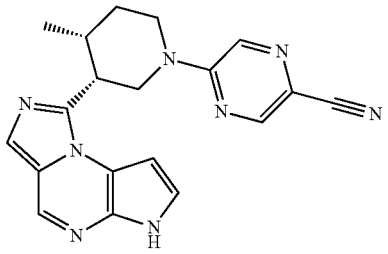 | L.1.2 | 1.81 (b) | 359 |
| 6-chloronicotinonitrile | 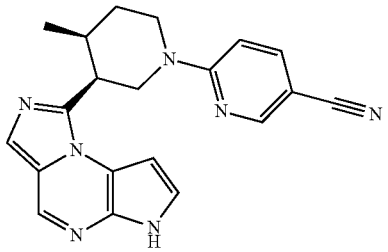 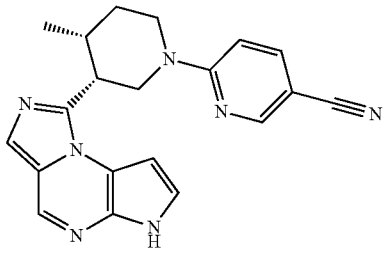 | L.1.3 | 1.88 (b) | 358 |

TABLE L.1-continued

Examples prepared from 1-(cis)-4-methylpiperidin-3-yl)-6H-imidazo[1,5-a]pyrrolo[2,3-e]pyrazine hydrochloride (prepared using D from Preparation #Q.1 with NaOH, and E with 4N HCl in 1,4-dioxane) using General Procedure L

| Heteroaryl Halide | Product | Example # | $R_t$ min (Table 1 , Method) | m/z ESI+ $(M+H)^+$ |
|---|---|---|---|---|
| 2-chlorothiazole-5-carbonitrile [ArkPharm] | 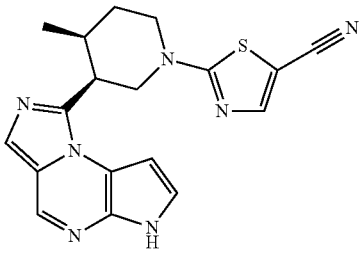 | L.1.4 | 1.84 (b) | 364 |
| | 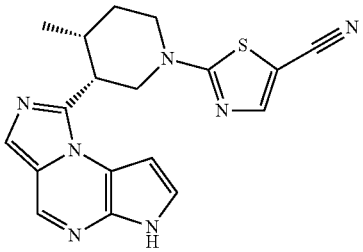 | | | |

TABLE L.2

Example prepared from 1-((3R,4R)-4-methylpiperidin-3-yl)-6H-imidazo[1,5-a]pyrrolo[2,3-e]pyrazine hydrochloride (Example #5, Step J) using General Procedure L

| Heteroaryl Halide | Product | Example # | $R_t$ min (Table 1, Method) | m/z ESI+ $(M+H)^+$ |
|---|---|---|---|---|
| 2-chlorobenzoxazole [TCI America] | 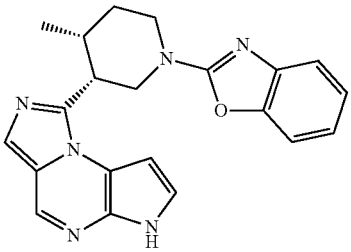 | L.2.1* | 1.94 (b) | 373 |

TABLE L.3

Examples prepared from (R)-8-(piperidin-3-yl)-3H-imidazo[1,2-a]pyrrolo[2,3-e]pyrazine hydrobromide and (S)-8-(piperidin-3-yl)-3H-imidazo[1,2-a]pyrrolo[2,3-e]pyrazine hydrobromide (Example #3, Step G) using General Procedure L

| Aryl chloride | Product | Example # | $R_t$ min (Table 1, Method) | m/z ESI+ $(M + H)^+$ |
|---|---|---|---|---|
| 2-chloro-5-cyanopyrazine [ArkPharm] | 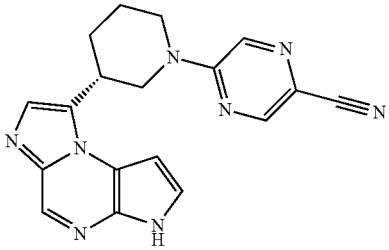 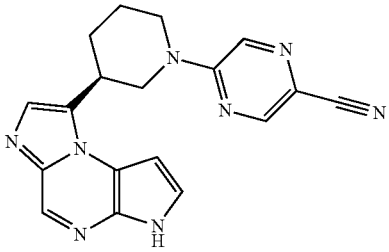 | L.3.1 | 1.71 (a) | 345 |

General Procedure M: Boc-Protection of an Amine

To a solution of an amine or amine salt (preferably 1 equiv) in an organic solvent (for example MeCN, 1,4-dioxane or THF, preferably THF) is added an aqueous base such as $Na_2CO_3$, NaOH, $K_2CO_3$ or $NaHCO_3$ (2-20 equiv, preferably 2-10 equiv of $Na_2CO_3$) or an organic base such as TEA or DIEA (1-5 equiv, preferably 1-2 equiv of TEA) followed by addition of di-tert-butyl dicarbonate (1-3.0 equiv, preferably 1.2 equiv). The addition of base is optional if an amine salt is not used. The reaction is stirred at about 10-40° C. (preferably ambient temperature) for about 2-24 h (preferably about 2-6 h) and worked up using one of the following methods. Method 1: An organic solvent (such as $Et_2O$, EtOAc or DCM) and water are added and the layers are separated. The aqueous layer is extracted with additional organic solvent and the combined organic layers may be optionally washed with brine, dried over anhydrous $Na_2SO_4$ or $MgSO_4$, and then decanted or filtered prior to concentrating under reduced pressure. Method 2: The reaction mixture is partitioned between an organic solvent (such as $Et_2O$, EtOAc or DCM) and aqueous acid (such as HCl). The acidic layer is extracted with additional organic solvent and the combined organic layers may be optionally washed with brine. The organic layer is optionally dried over anhydrous $Na_2SO_4$ or $MgSO_4$, and then decanted or filtered prior to concentrating under reduced pressure.

Illustration of General Procedure M

Preparation #M.1*: (1R,3S)-3-((tert-butoxycarbonylamino)methyl)cyclopentanecarboxylic acid

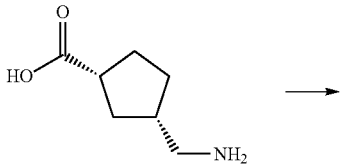

-continued

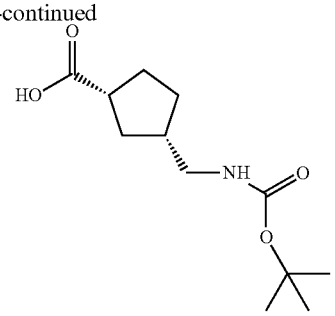

To a solution of (1R,3S)-3-(aminomethyl)cyclopentanecarboxylic acid (0.500 g, 3.49 mmol, AFID) in THF (4 mL) and water (4 mL) was added $Na_2CO_3$ (1.11 g, 10.5 mmol) and di-tert-butyl dicarbonate (0.915 g, 4.19 mmol). The reaction was stirred at ambient temperature for about 4 h. EtOAc (15 mL) and aqueous HCl (1 N, 15 mL) were added and the layers were separated. The aqueous layer was extracted with EtOAc (2×10 mL) and the combined organic layers were washed with brine (10 mL). The organic layer was dried over anhydrous $Na_2SO_4$, filtered, and concd under reduced pressure to give (1R,3S)-3-((tert-butoxycarbonylamino)methyl)cyclopentanecarboxylic acid (0.300 g, 35%). $^1H$ NMR (DMSO-$d_6$) δ 11.97 (s, 1H), 6.83 (s, 1H), 2.89-2.86 (t, J=8.0 Hz, 2H), 2.73-2.58 (m, 1H), 2.04-1.87 (m, 2H), 1.82-1.68 (m, 2H), 1.68-1.58 (m, 1H), 1.37 (s, 9H), 1.34-1.19 (m, 2H).

General Procedure M.1: Boc-Protection of a Nitrogen-Containing Compound

To a nitrogen-containing compound (preferably 1 equiv) in an organic solvent (for example DCM, MeCN, 1,4-dioxane or THF, preferably DCM) is added an aqueous base such as $Na_2CO_3$, NaOH, $K_2CO_3$ or $NaHCO_3$ (preferably $Na_2CO_3$, 2-20 equiv, preferably 2-10 equiv) or an organic base such as TEA or DIEA (preferably TEA, 1-5 equiv, preferably 1-2 equiv) followed by addition of di-tert-butyl dicarbonate (1-3 equiv, preferably 1.2 equiv). DMAP (0.1-2 equiv, preferably 0.1 equiv) is optionally added to the reaction mixture. The reaction is stirred at about 10-40° C. (preferably rt) for about 0.5-24 h (preferably about 1 h) and worked up using one of the following methods. Method 1: An organic solvent (such as $Et_2O$, EtOAc or DCM) and water are added and the layers are separated. The aqueous layer is optionally extracted with additional organic solvent and the combined organic layers may be optionally washed with brine, dried over anhydrous $Na_2SO_4$ or $MgSO_4$, and then decanted or filtered prior to concentrating under reduced pressure. Method 2: The reaction mixture is partitioned between an organic solvent (such as $Et_2O$, EtOAc or DCM) and aqueous acid (such as HCl). The acidic layer is extracted with additional organic solvent and the combined organic layers may be optionally washed with brine. The organic layer is optionally dried over anhydrous $Na_2SO_4$ or $MgSO_4$, and then decanted or filtered prior to concentrating under reduced pressure. Method 3: Water or an aqueous solution (such as brine) is added and the layers are separated. The aqueous layer is optionally extracted with additional organic solvent (such as $Et_2O$, EtOAc or DCM) and the combined organic layers may be optionally washed with brine, dried over anhydrous $Na_2SO_4$ or $MgSO_4$, and then decanted or filtered prior to concentrating under reduced pressure.

Illustration of General Procedure M.1

Preparation #M.1.1: t-butyl cyclopropylsulfonyl(cis-3-methyl-4-propionylcyclopentyl)carbamate

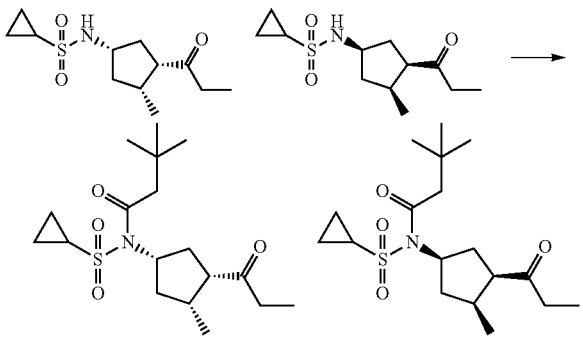

To a solution of N-(cis-3-methyl-4-propionylcyclopentyl) cyclopropanesulfonamide (2.70 g, 10.4 mmol, prepared using H from cis-4-(cyclopropanesulfonamido)-2-methylcyclopentanecarboxylic acid (WO2009152133) with N,O-dimethylhydroxylamine hydrochloric acid, MMMM with ethylmagnesium chloride) in DCM (52 mL) was added TEA (1.60 mL, 11.5 mmol), di-tert-butyl dicarbonate (2.90 mL, 12.5 mmol), and DMAP (0.127 g, 1.04 mmol). The reaction was stirred at rt for about 1 h. Water (50 mL) was added and the layers were separated. The aqueous layer was extracted with DCM (3×30 mL) and the combined organic layer was concd under reduced pressure. The product was purified by silica gel chromatography eluting with a gradient of 0-50% EtOAc in heptane to give t-butyl cyclopropylsulfonyl(cis-3-methyl-4-propionylcyclopentyl)carbamate (3.71 g, 99%) as a white solid: LC/MS (Table 1, Method b) $R_t$=2.62 min; MS m/z: 360 $(M+H)^+$.

General Procedure N: Cbz-Protection of an Amine

A solution of an amine or an amine salt (preferably 1 equiv) and a base (for example, $Na_2CO_3$ or NaOH, 1-3equiv, preferably $Na_2CO_3$, 1.6 equiv) in water or aqueous organic solvent (for example, water/1,4-dioxane or water/MeCN, preferably water/1,4-dioxane) is stirred at ambient temperature for about 1-10 min (preferably 5 min). A solution of benzyl 2,5-dioxopyrrolidin-1-yl carbonate (1-2 equiv, preferably 1.0 equiv) in an organic solvent such as 1,4-dioxane or MeCN is added to the reaction. The reaction is stirred at ambient temperature for about 8-144 h (preferably about 72 h). Optionally, the reaction mixture is concd under reduced pressure. The resulting aqueous solution is diluted with an organic solvent (such as EtOAc or DCM). The organic extracts are optionally washed with water and/or brine, dried over anhydrous $Na_2SO_4$ or $MgSO_4$, filtered or decanted, and concd under reduced pressure. Alternatively, the resulting aqueous solution is acidified by adding an acid such as aqueous $NH_4Cl$ or HCl and is then extracted with an organic solvent (such as EtOAc or DCM).

Illustration of General Procedure N

Preparation #N.1: methyl 4-(benzyloxycarbonylamino)bicyclo[2.2.2]octane-1-carboxylate

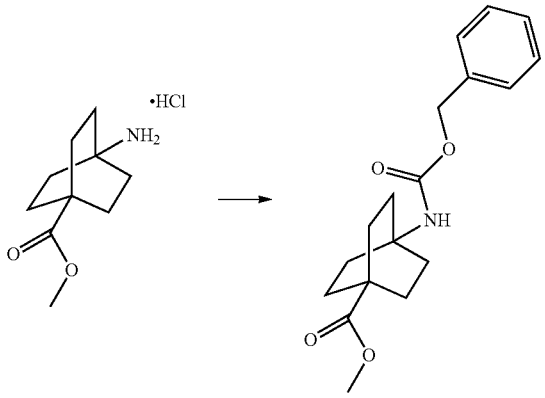

To a solution of methyl 4-aminobicyclo[2.2.2]octane-1-carboxylate hydrochloride (1.16 g, 5.29 mmol, Prime Organics) in 1,4-dioxane (15 mL) was added a solution of $Na_2CO_3$ (0.90 g, 8.49 mmol) in water (15 mL). The reaction mixture was stirred for about 5 min at ambient temperature. Benzyl 2,5-dioxopyrrolidin-1-yl carbonate (1.32 g, 5.29 mmol) was added and the reaction mixture was stirred at ambient temperature for about 72 h. The reaction mixture was diluted with EtOAc (50 mL). The layers were separated and the aqueous layer was extracted with EtOAc (2×20 mL). The combined organic layers were dried over anhydrous $MgSO_4$, filtered, and concd under reduced pressure to give methyl 4-(benzyloxycarbonylamino)bicyclo[2.2.2]octane-1-carboxylate (1.68 g, 95%): LC/MS (Table 1, Method a) $R_t$=2.44 min; MS m/z: 318 $(M+H)^+$.

General Procedure O: Reduction of a Pyridine

A substituted pyridine (preferably 1 equiv) is dissolved in an organic solvent (such as AcOH, EtOH, or MeOH; preferably AcOH if using a Parr Shaker or EtOH if using an H-cube™). A suitable catalyst such as platinum (IV) oxide or Pd/C (0.05-0.20 equiv, preferably 0.05-0.10 equiv platinum (IV) oxide for a Parr Shaker reaction or ThalesNano CatCart® 10 wt % Pd/C catalyst cartridges for an H-Cube™) is used for the reduction under an atmosphere of hydrogen at about 15-1450 psi (preferably about 220 psi for a Parr Shaker or preferably 1305 psi for an H-Cube™). The reaction is run for about 1-10 d (preferably about 3-5 d) at about 20-100° C. (preferably about 25° C.) for the Parr Shaker or at about 1-3 mL/min (preferably 1 mL/min) at about 25-100° C. (preferably about 80° C.) for about 1-10 h (preferably about 3 h) for an H-Cube™. The reaction mixture is filtered through Celite® if run in a Parr shaker and concd under reduced pressure in either case.

Illustration of General Procedure O

Preparation #O.1:
cis-4-(trifluoromethyl)piperidine-3-carboxylic acid

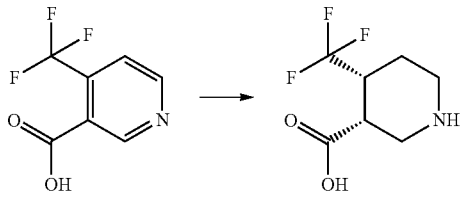

A solution of 4-(trifluoromethyl)nicotinic acid (1.50 g, 7.85 mmol) in EtOH (78 mL) was passed through an H-cube™ equipped with a ThalesNano CatCart® 10 wt % Pd/C catalyst cartridge at about 1.0 mL/min, at about 80° C., under about 1305 psi of hydrogen. After about 3 h, the solvent was removed under reduced pressure to afford cis-4-(trifluoromethyl)piperidine-3-carboxylic acid (1.55 g, 100% crude): LC/MS (Table 1, Method b) $R_t$=0.54 min; MS m/z: 198 $(M+H)^+$.

General Procedure P: Reduction of a Carbonyl to an Alcohol

A reducing agent (1.0-3.0 equiv, preferably 1.25 equiv), such as LAH, DIBAL-H, $NaBH_4$ or $LiBH_4$ (preferably DIBAL-H), is added either portionwise as a solid or dropwise as a solution in an organic solvent (such as THF, $Et_2O$, EtOH or MeOH, preferably THF) to a solution of a carbonyl compound (preferably 1 equiv) in an organic solvent (such as THF, $Et_2O$, EtOH or MeOH, preferably MeOH) at about −40-50° C. (preferably ambient temperature). The reaction mixture is stirred for about 1-20 h (preferably about 16 h) before quenching with an aqueous solution (such as $NH_4Cl$ or $NaHCO_3$, preferably saturated aqueous $NH_4Cl$). The reaction is stirred for about 10 min-3 h (preferably about 20-30 min) and then the solution is partitioned with an organic solvent (such as EtOAc, $Et_2O$ or DCM, preferably $Et_2O$). The organic layer is washed with brine, dried over anhydrous $Na_2SO_4$ or $MgSO_4$, filtered, and concd under reduced pressure.

Illustration of General Procedure P

Preparation #P.1: ethyl
2-ethyl-4-hydroxycyclopentanecarboxylate

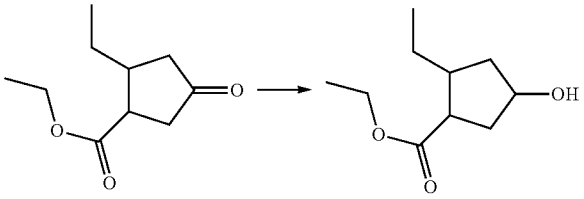

To ethyl 2-ethyl-4-oxocyclopentanecarboxylate (10 g, 54.3 mmol, Example #8, Step G) in MeOH (143 mL) was added $NaBH_4$ (2.57 g, 67.8 mmol) portionwise. The resulting suspension was stirred for about 16 h at ambient temperature then saturated aqueous $NH_4Cl$ (240 mL) was added. The reaction mixture was stirred for about 20 min then the solution was partitioned with $Et_2O$ (300 mL). The organic layer was separated and the aqueous layer was washed with $Et_2O$ (2×150 mL). The combined organic layers were washed with brine (100 mL), dried over anhydrous $MgSO_4$, filtered, and concd under reduced pressure. The product was purified by silica gel chromatography (220 g) eluting with a gradient of 30-70% EtOAc in heptane to give ethyl 2-ethyl-4-hydroxycyclopentanecarboxylate (8.51 g, 84%, predominantly (1S,2R,4S)-ethyl 2-ethyl-4-hydroxycyclopentanecarboxylate and (1R,2S,4R)-ethyl 2-ethyl-4-hydroxycyclopentanecarboxylate) as a clear oil: LC/MS (Table 1, Method b) $R_t$=2.02 min; MS m/z: 187 $(M+H)^+$.

TABLE P.1

Examples prepared using General Procedure P with DIBAL-H

| Carbonyl compound | Product | Example # | $R_t$ min (Table 1, Method) | m/z ESI+ $(M + H)^+$ |
|---|---|---|---|---|
| ethyl 2-((1S,3R,4S)-3-ethyl-4-(6H-pyrrolo[2,3-e][1,2,4]triazolo[4,3-a]pyrazin-1-yl)cyclopentyl)acetate (Preparation #W.1.2) | 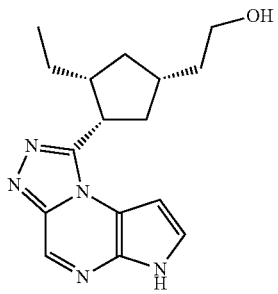 | P.1.1 | 1.47 (b) | 300 |

TABLE P.1-continued

| Examples prepared using General Procedure P with DIBAL-H | | | | |
|---|---|---|---|---|
| Carbonyl compound | Product | Example # | $R_t$ min (Table 1, Method) | m/z ESI+ $(M + H)^+$ |
| ethyl 2-((1R,3R,4S)-3-ethyl-4-(6H-pyrrolo[2,3-e][1,2,4]triazolo[4,3-a]pyrazin-1-yl)cyclopentyl)acetate (Preparation #W.1.1) | 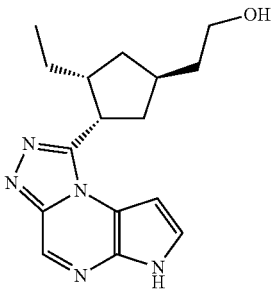 | P.1.2 | 1.47 (b) | 300 |

General Procedure Q: Cyclization of an Amide Using a Dithiadiphosphetane Reagent To a solution of an amide (preferably 1 equiv) in an organic solvent (preferably 1,4-dioxane) is added a dithiadiphosphetane reagent such as Lawesson's reagent or Belleau's reagent (2,4-bis(4-phenoxyphenyl)-1,3-dithia-2,4-diphosphetane-2,4-disulfide) (preferably Lawesson's reagent) (0.5-2.0 equiv, preferably 0.6 equiv). The reaction is heated at about 25-120° C. (preferably about 80° C.) for about 0.5-10 h (preferably about 1 h). The reaction mixture is cooled to ambient temperature and is optionally concd under reduced pressure to give a residue. The reaction mixture or residue is partitioned between an organic solvent (such as DCM or EtOAc, preferably EtOAc) and water, an aqueous base (such as saturated aqueous $NaHCO_3$) or brine. The layers are separated and the organic layer is optionally washed with water, an aqueous base (such as saturated aqueous $NaHCO_3$) and/or brine, dried over anhydrous $Na_2SO_4$ or $MgSO_4$, filtered, and concd under reduced pressure to give a thioamide. To a solution of thioamide (preferably 1 equiv) in an organic solvent (preferably 1,4-dioxane) is added a Lewis acid, such as diacetoxymercury, mercury dichloride, mercury (II) trifluoroacetate, silver trifluoroacetate, silver nitrate, copper bromide (preferably diacetoxymercury or mercury (II) trifluoroacetate) (1-3 equiv, preferably 1 equiv). The reaction mixture is stirred at about 20-60° C. (preferably ambient temperature) for about 0.5-4 h (preferably about 1 h). Optionally, additional Lewis acid (preferably diacetoxymercury or mercury (II) trifluoroacetate) (0.2-1.0 equiv, preferably 0.6 equiv) is added and the reaction is continued for about 10 min-3 h (preferably about 15 min). The reaction mixture is optionally diluted with saturated sodium thiosulfate, water, and/or an organic solvent (preferably EtOAc) and is filtered, preferably through a pad of Celite®. The pad of Celite® can be rinsed with additional organic solvent (preferably EtOAc or DCM). The filtrate is concd under reduced pressure. The crude material is optionally partitioned between an organic solvent (such as EtOAc or DCM) and washed with saturated sodium thiosulfate and/or water, an aqueous base (such as saturated aqueous $NaHCO_3$) and/or brine, dried over anhydrous $Na_2SO_4$ or $MgSO_4$, filtered, and concd under reduced pressure.

Illustration of General Procedure Q

Preparation #Q.1: cis-tert-butyl 4-methyl-3-(6-tosyl-6H-imidazo[1,5-a]pyrrolo[2,3-e]pyrazin-1-yl)piperidine-1-carboxylate

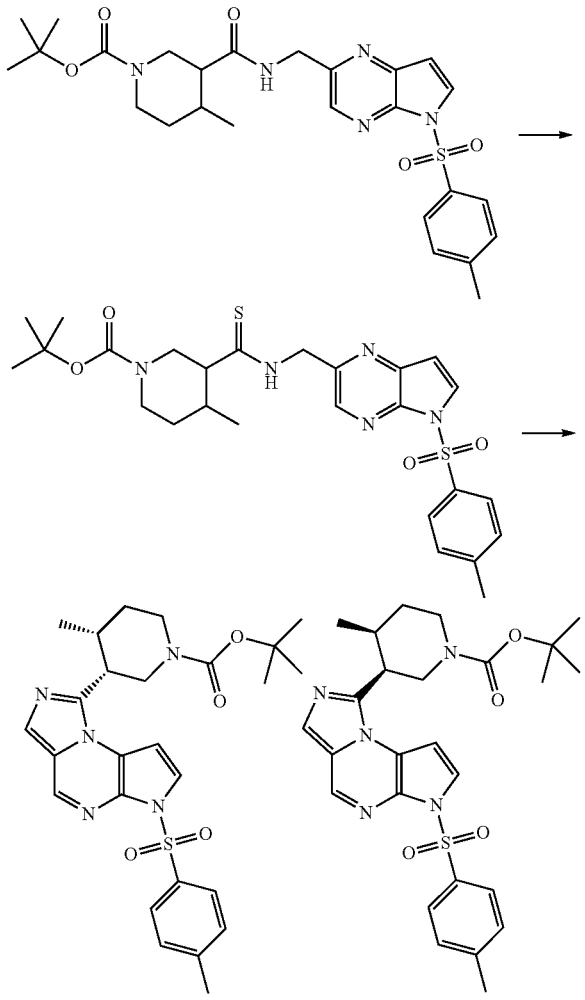

A round bottom flask was charged with cis-tert-butyl 4-methyl-3-((5-tosyl-5H-pyrrolo[2,3-b]pyrazin-2-yl)methylcarbamoyl)piperidine-1-carboxylate (5.62 g, 10.6 mmol, prepared using O from 4-methylnicotonic acid, M, H from Example #5, Step C, HATU and DIEA) and Lawesson's reagent (3.0 g, 7.4 mmol) in 1,4-dioxane (100 mL). The reaction was heated at about 80° C. for about 1 h, cooled to ambient temperature, and concd under reduced pressure. The crude product was dissolved in EtOAc (200 mL) and washed with saturated aqueous $NaHCO_3$ (3×100 mL). The organic layer was separated, dried over anhydrous $MgSO_4$, filtered, and concd under reduced pressure. The material was purified by silica gel chromatography eluting with a gradient of 0-5% MeOH in DCM to afford cis-tert-butyl 4-methyl-3-((5-tosyl-5H-pyrrolo[2,3-b]pyrazin-2-yl)methylcarbamothioyl)piperidine-1-carboxylate (5.2 g, 90%): LC/MS (Table 1, Method b) $R_t$=2.65 min; MS m/z: 544 $(M+H)^+$. A round bottom flask was charged with cis-tert-butyl 4-methyl-3-((5-tosyl-5H-pyrrolo[2,3-b]pyrazin-2-yl)methylcarbamothioyl) piperidine-1-carboxylate (2.6 g, 4.8 mmol) and mercury (II) trifluoroacetate (2.1 g, 4.8 mmol) in 1,4-dioxane (72 mL) and stirred at ambient temperature for about 1 h. The reaction mixture was filtered through a pad of Celite®. The Celite® pad was rinsed with DCM (30 mL) and EtOAc (30 mL). The filtrate was concd under reduced pressure. The residue was dissolved in DCM (50 mL) and washed with saturated aqueous sodium thiosulfate (10 mL), and saturated aqueous $NaHCO_3$ (25 mL), dried over anhydrous $MgSO_4$, filtered, and concd under reduced pressure. The material was purified by silica gel chromatography eluting with a gradient of 0-5% MeOH in DCM to afford cis-tert-butyl-4-methyl-3-(6-tosyl-6H-imidazo[1,5-a]pyrrolo[2,3-e]pyrazin-1-yl)piperidine-1-carboxylate (2.2 g, 90%): LC/MS (Table 1, Method b) $R_t$=2.57 min; MS m/z: 510 $(M+H)^+$.

General Procedure R: Formation of a Bromomethyl Ketone from an Acid

To a solution of a carboxylic acid (preferably 1 equiv) in an organic solvent (DCM or DCE, preferably DCM) is slowly added oxalyl chloride (1.2-3.0 equiv, preferably 2.2 equiv) followed by dropwise addition of DMF (0.01-0.20 equiv, preferably about 0.15 equiv). The reaction is stirred at about 0-40° C. (preferably ambient temperature) for about 3-24 h (preferably about 14 h) before it is concd under reduced pressure to a constant weight to give the crude acid chloride. A solution of a crude acid chloride (preferably 1 equiv) in an organic solvent (such as THF, MeCN, $Et_2O$, or THF/MeCN, preferably THF/MeCN) is added to trimethylsilyldiazomethane (2.0 M in $Et_2O$) or diazomethane solution in $Et_2O$ (prepared from Diazald® according to Aldrich protocol or J. Chromatogr. Sci. 1991, 29, 8) (2-10 equiv, preferably 3.5 equiv of trimethylsilyldiazomethane) at about −20-20° C. (preferably about 0° C.) in a suitable organic solvent such as THF, MeCN, $Et_2O$, or THF/MeCN (preferably THF/MeCN). The reaction mixture is stirred for about 0.5-5 h (preferably about 3 h) at about −20-20° C. (preferably about 0° C.) before the dropwise addition of 48% aqueous HBr (5-40 equiv, preferably about 10 equiv). After about 0-30 min, (preferably about 5 min) the reaction mixture can be concd to dryness to give the desired product, neutralized by a dropwise addition of saturated aqueous $NaHCO_3$ or is optionally washed with brine after optional addition of an organic solvent (such as EtOAc or DCM, preferably EtOAc). In cases where the reaction mixture is subjected to an aqueous work-up, the organic layer is dried over anhydrous $Na_2SO_4$ or $MgSO_4$ (preferably $MgSO_4$), filtered, and concd under reduced pressure.

Illustration of General Procedure R

Preparation #R.1: 2-bromo-1-(4-(dibenzylamino)-2-methylcyclopentyl)ethanone

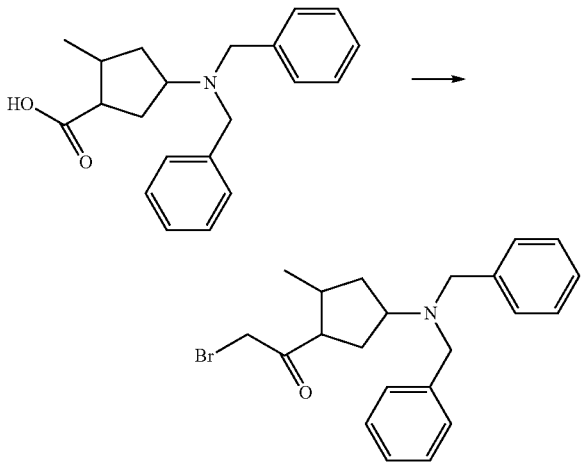

To a solution of 4-(dibenzylamino)-2-methylcyclopentanecarboxylic acid (7.34 g, 22.7 mmol, Preparation #TT.1) in DCM (100 mL), oxalyl chloride (4.37 mL, 49.9 mmol) was slowly added followed by a dropwise addition of DMF (0.26 mL, 3.4 mmol). The mixture was stirred at ambient temperature for about 14 h and the solvent was removed under reduced pressure to yield 4-(dibenzylamino)-2-methylcyclopentanecarbonyl chloride as a beige solid. The solid was dissolved in THF and MeCN (1:1, 100 mL) and added to a solution of trimethylsilyldiazomethane (2 M in $Et_2O$, 39.7 mL, 79.4 mmol) in 1:1 mixture of THF and MeCN (100 mL) at about 0° C. The resulting mixture was stirred at about 0° C. for about 3 h and then was quenched by dropwise addition of 48% aqueous HBr (25 mL, 221 mmol). The resulting mixture was neutralized by dropwise addition of saturated aqueous $NaHCO_3$ (300 mL) and the layers were separated. The organic layer was dried over anhydrous $MgSO_4$, filtered, and concd under reduced pressure. The residue was purified by silica gel flash chromatography eluting with a gradient of 5-45% EtOAc in heptane to yield 2-bromo-1-(4-(dibenzylamino)-2-methylcyclopentyl)ethanone (6.3 g, 69%) as a yellow oil: LC/MS (Table 1, Method a) $R_t$=2.90 min; MS m/z 400, 402 (1:1) $(M+H)^+$.

General Procedure S: N-Alkylation Using Alkyl Halide or α-Haloketone

A round bottom flask is charged with a base such as NaH (60% dispersion in mineral oil), $K_2CO_3$, or $Cs_2CO_3$ (preferably NaH (60% dispersion in mineral oil), 0.9-1.5 equiv, preferably 0.95 equiv) and an organic solvent (such as DMF or NMP, preferably DMF). The mixture is cooled to about −10° C. to 10° C. (preferably about 0° C.) and a solution of an appropriately substituted amine (preferably 1 equiv) in an organic solvent (such as DMF) is added. The reaction mixture is stirred for about 5-90 min (preferably about 15-30 min) at about −10° C. to ambient temperature (preferably about 0° C.) followed by the addition of an alkyl halide or α-haloketone (1-2 equiv, preferably 1.2 equiv). Alternatively, a solution of an amine and a base in an organic solvent may be added to a solution of an alkyl halide or α-haloketone in an organic solvent at about 0° C. The reaction mixture is stirred at about −10° C. to ambient temperature (preferably ambient temperature) for about 0.5-2 h (preferably about 1 h). The organic solvent is removed under reduced pressure. Optionally, the crude mixture may be diluted with water and an organic solvent (for example, EtOAc or DCM). The layers are separated and the aqueous layer is extracted further with organic solvent (such as EtOAc and/or DCM). The combined organic layers are optionally washed with brine, dried over anhydrous $MgSO_4$, filtered, and concd to dryness under reduced pressure.

Illustration of General Procedure S

Preparation #S.1: tert-butyl 2-(4-(dibenzylamino)-2-methylcyclopentyl)-2-oxoethyl(5-tosyl-5H-pyrrolo[2,3-b]pyrazin-2-yl)carbamate

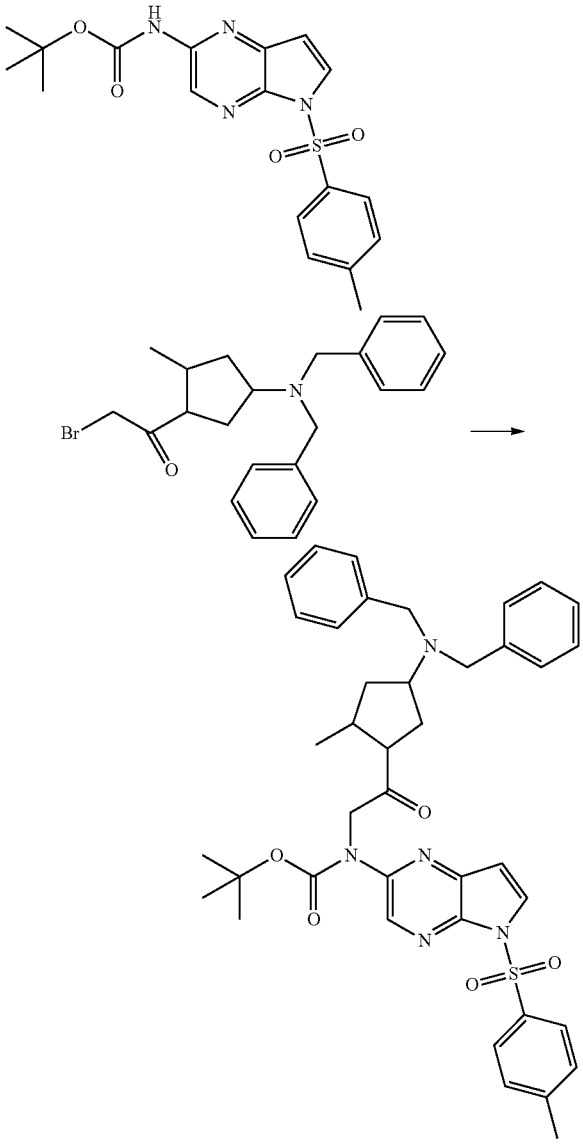

To a suspension of NaH (60% dispersion in mineral oil, 0.058 g, 1.45 mmol) in DMF (5 mL) was added a solution of tert-butyl 5-tosyl-5H-pyrrolo[2,3-b]pyrazin-2-ylcarbamate (0.59 g, 1.519 mmol, Example #3, Step E) in DMF (5 mL) dropwise at about 0° C. The resulting mixture was stirred at this temperature for about 30 min and then added dropwise to a solution of 2-bromo-1-(4-(dibenzylamino)-2-methylcyclopentyl)ethanone (0.73 g, 1.823 mmol, Preparation #R.1) in DMF (10 mL). The resulting mixture was stirred at about 0° C. for about 1 h and the solvent was removed under reduced pressure. The residue was partitioned between saturated aqueous $NaHCO_3$ and EtOAc (100 mL each). The organic phase was dried over anhydrous $MgSO_4$ and concd under reduced pressure to yield tert-butyl 2-(4-(dibenzylamino)-2-methylcyclopentyl)-2-oxoethyl(5-tosyl-5H-pyrrolo[2,3-b]pyrazin-2-yl)carbamate (1.04 g, 97%) as a yellow amorphous solid: LC/MS (Table 1, Method a) $R_t$=3.30 min; MS m/z 708 $(M+H)^+$.

General Procedure S.1: N-Alkylation using alkyl halide, α-haloketone or α-haloamide A round bottom flask is charged with a base such as NaH (60% dispersion in mineral oil), $K_2CO_3$, or $Cs_2CO_3$ (preferably NaH (60% dispersion in mineral oil), 0.9-1.5 equiv, preferably 0.95 equiv) and an organic solvent (such as DMF, DCM, 1,4-dioxane, or NMP, preferably DMF). The mixture is cooled to about −10° C. to ambient temperature (preferably about 0° C.) and a solution of an appropriately substituted amine (preferably 1 equiv) in an organic solvent (such as DMF) is added. Alternatively, the base may be added portionwise to a solution of the amine and an organic solvent at about 0° C. to ambient temperature. The reaction mixture is stirred for about 5-90 min (preferably about 15-30 min) at about −10° C. to ambient temperature (preferably about 0° C.) followed by the addition of an alkyl halide, α-haloketone, or α-haloamide (1-2 equiv, preferably 1.2 equiv). Alternatively, a solution of an amine and a base in an organic solvent may be added to a solution of an alkyl halide, α-haloketone, or α-haloamide in an organic solvent at about 0° C. The reaction mixture is stirred at about −10° C. to ambient temperature (preferably ambient temperature) for about 0.5-24 h (preferably about 1 h). Optionally, the organic solvent may be removed under reduced pressure. Optionally, the reaction mixture or residue may be diluted with water, aqueous $NH_4Cl$, or aqueous $NaHCO_3$. If a precipitate forms the solid may be optionally collected via vacuum filtration to give the target compound. Alternatively, an organic solvent (such as EtOAc or DCM) is added to the aqueous mixture and the layers are separated. The aqueous layer may optionally be extracted further with an organic solvent (such as EtOAc and/or DCM). The combined organic layers are optionally washed with additional aqueous solutions such as brine, dried over anhydrous $Na_2SO_4$ or $MgSO_4$, filtered, and concentrated to dryness under reduced pressure.

Illustration of General Procedure S.1

Preparation #S.1.1: tert-butyl 2-amino-2-oxoethyl(5-tosyl-5H-pyrrolo[3,2-b]pyrazin-2-yl)carbamate

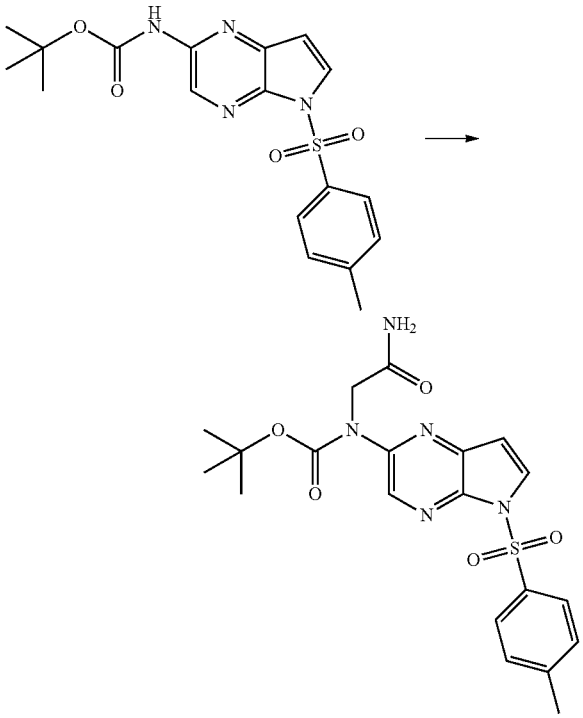

To a solution of tert-butyl 5-tosyl-5H-pyrrolo[3,2-b]pyrazin-2-ylcarbamate (1.00 g, 2.57 mmol, Example #3 Step E) and DMF (13 mL) under nitrogen at about 0° C. was added NaH (60% dispersion in mineral oil, 0.113 g, 2.83 mmol) in one portion. After about 30 min, 2-bromoacetamide (0.391 g, 2.83 mmol) was added in one portion. After about 30 min, the ice bath was removed and the solution was stirred at ambient temperature for about 2 h. Saturated aqueous $NH_4Cl$/water (1:1, 100 mL) was added. After stirring for about 10 min, the mixture was filtered using water to wash the filter cake. The aqueous phase was extracted with EtOAc (50 mL). The filter cake was dissolved in EtOAc and added to the organic layer. The organic layer was dried over $Na_2SO_4$, filtered, and concentrated under reduced pressure. The material was purified by silica gel chromatography eluting with a gradient of 20-100% EtOAc/heptane to give tert-butyl 2-amino-2-oxoethyl(5-tosyl-5H-pyrrolo[3,2-b]pyrazin-2-yl)carbamate (0.980 g, 82%): LC/MS (Table 1, Method n) $R_t$=0.70 min; MS m/z 446 $(M+H)^+$.

General Procedure T: Cyclization of a Ketone Using a Dithiaphosphetane Reagent

To a solution of a ketone (preferably 1 equiv) in an organic solvent such as THF or 1,4-dioxane (preferably 1,4-dioxane) is added a thiolating reagent such as Lawesson's reagent or Belleau's reagent (2,4-bis(4-phenoxyphenyl)-1,3-dithia-2,4-diphosphetane-2,4-disulfide) (0.5-2.0 equiv, preferably Lawesson's reagent, 0.5-0.6 equiv). The reaction is heated at about 30° C. to 120° C. (preferably about 60-70° C.) for about 0.5-10 h (preferably about 1-2 h). Optionally, additional thiolating reagent (0.5-2.0 equiv, preferably 0.5-0.6 equiv) can be added to the reaction mixture and heating can be continued for about 0.5-10 h (preferably about 1-2 h). The reaction mixture is concd under reduced pressure.

Illustration of General Procedure T

Preparation #T.1: N,N-dibenzyl-3-methyl-4-(3-tosyl-3H-imidazo[1,2-a]pyrrolo[2,3-e]pyrazin-8-yl)cyclopentanamine

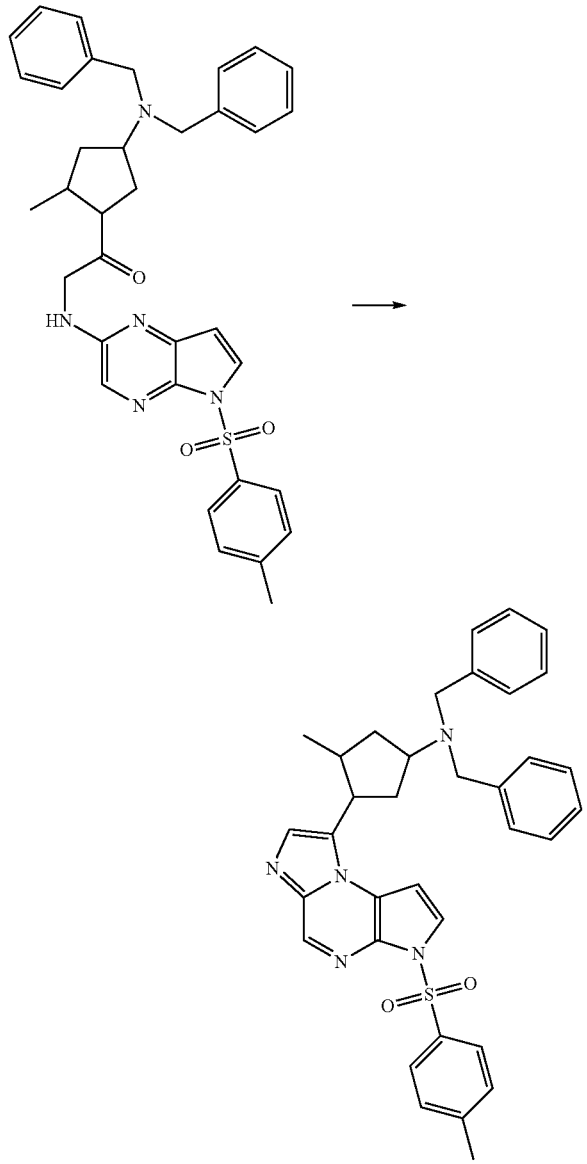

A mixture of 1-(4-(dibenzylamino)-2-methylcyclopentyl)-2-(5-tosyl-5H-pyrrolo[2,3-b]pyrazin-2-ylamino)ethanone (5.32 g, 8.75 mmol, Preparation #50) and Lawesson's reagent (1.88 g, 4.64 mmol) in 1,4-dioxane (60 mL) was heated at about 60° C. for about 2 h. Lawesson's reagent (1.88 g, 4.64 mmol) was added and stirring at about 60° C. was continued for about 1 h. The solvent was removed and the residue subjected to silica gel flash chromatography eluting with a gradient of 0-8% MeOH in DCM to yield N,N-dibenzyl-3-methyl-4-(3-tosyl-3H-imidazo[1,2-a]pyrrolo[2,3-e]pyrazin-8-yl)cyclopentanamine (4.47 g, 87%) as a brown amorphous solid: LC/MS (Table 1, Method a) $R_t$=2.99 min; MS m/z 590 $(M+H)^+$.

General Procedure U: Knoevenagel Condensation to Form a Substituted Cyclopentadiene A round bottom flask is charged with an organic solvent (for example THF or diethylene glycol dimethyl ether; preferably THF), followed by the portionwise addition of NaH (60% dispersion in mineral oil, preferably 1 equiv). An organic solvent can optionally be added. The reaction mixture is cooled to about −15-5° C. (preferably about −10-0° C.). A β-keto ester (preferably 1 equiv) is added dropwise at a rate to keep the internal temperature below about 10° C. The resulting mixture is stirred at about 0-60° C. (preferably about 25° C.) for about 0.1-2 h (preferably about 0.5 h), followed by dropwise addition of an appropriately substituted α-haloketone (preferably 0.45-0.55 equiv). The resulting mixture is heated to about 40-80° C. (preferably about 50° C.) for about 3-24 h (preferably about 19 h). The organic solvent is removed under reduced pressure and the resulting crude material is stirred with water while cooling in an ice bath. The resulting suspension is filtered after about 0.5-3 h (preferably about 2 h) and the filter cake is washed with water and dried under vacuum for about 1-3 h (preferably about 1 h). The resulting solid is suspended in an organic solvent (preferably $Et_2O$), collected by vacuum filtration, washed with an organic solvent (preferably $Et_2O$), and dried under vacuum to give the desired product as a sodium salt of the enolate. Optionally, toluene is added and the water is azetroped. The resulting solid is re-suspended in an organic solvent (preferably $Et_2O$), collected by vacuum filtration, washed with an organic solvent (preferably $Et_2O$), and then dried under vacuum.

Illustration of General Procedure U

Preparation #U.1: sodium 4-(ethoxycarbonyl)-3-ethyl-2-(methoxycarbonyl)cyclopenta-1,3-dienolate

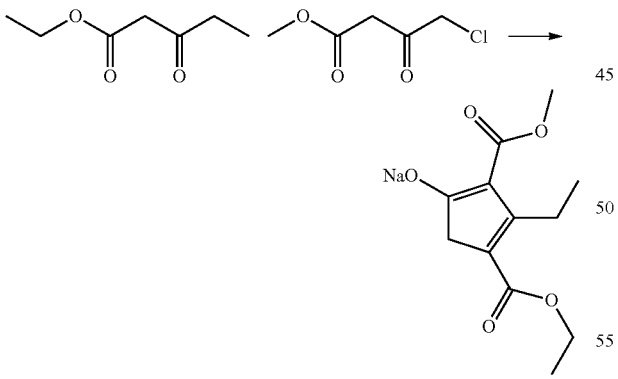

A round bottom flask was charged with THF (1.5 L) followed by the portionwise addition of NaH (60% dispersion in mineral oil, 70.0 g, 1.75 mol). Additional THF (500 mL) was added and the resulting mixture was cooled to about −10° C. Ethyl propionylacetate (250 mL, 1.80 mol) was added dropwise over about 1 h in order to keep internal temperature below about 10° C. The resulting mixture was stirred at ambient temperature for about 0.5 h to give a clear yellow solution and then methyl 4-chloroacetoacetate (100 mL, 0.88 mol) was added dropwise over about 5 min. The resulting mixture was heated at about 50° C. for about 19 h to give a reddish orange suspension. The reaction mixture was cooled to ambient temperature, concd under reduced pressure and the resulting liquid was transferred to a beaker and diluted with water (350 mL). The mixture was stirred in an ice bath for about 2 h. The solid was collected by vacuum filtration and the filter cake was rinsed with water (150 mL) and dried under vacuum for about 1 h. The solid was suspended in $Et_2O$ (1.5 L), filtered, washed with $Et_2O$ (1.5 L), and dried under vacuum. The resulting solid was azeotroped with toluene (1 L) to give a solid that was re-suspended in $Et_2O$ (1 L) and collected by vacuum filtration. The filter cake was washed with $Et_2O$ (500 mL) and dried under vacuum to give sodium 4-(ethoxycarbonyl)-3-ethyl-2-(methoxycarbonyl)cyclopenta-1,3-dienolate (204.2 g, 89%) as beige solid: $^1H$ NMR (DMSO-$d_6$) δ 3.94 (q, J=7.1 Hz, 2H), 3.46 (s, 3H), 3.04 (q, J=7.2 Hz, 2H), 2.66 (s, 2H), 1.13 (t, J=7.1 Hz, 3H), 0.99 (t, J=7.3Hz, 3H).

General Procedure V: Decarboxylation of a β-Ketoester Enolate

A round bottom flask is charged with an appropriate β-keto ester or its sodium enolate (preferably 1 equiv), an organic solvent (for example diethylene glycol dimethyl ether or toluene, preferably toluene), AcOH (2-5 equiv, preferably 3.5 equiv), NaI or KCl (1-5 equiv, preferably 1.4-1.5 equiv of KCl) with or without water (preferably with water). The reaction is heated to reflux for about 1-10 h (preferably about 3-6 h). The reaction is cooled to ambient temperature and is added dropwise into aqueous $NaHCO_3$ (preferably 8-10% $NaHCO_3$). The resulting mixture is extracted with an organic solvent such as $Et_2O$ or MTBE (preferably MTBE). The combined organic layers are dried over anhydrous $Na_2SO_4$ or $MgSO_4$, filtered, and concd to dryness under reduced pressure.

Illustration of General Procedure V

Preparation #V.1: ethyl 2-ethyl-4-oxocyclopent-2-enecarboxylate

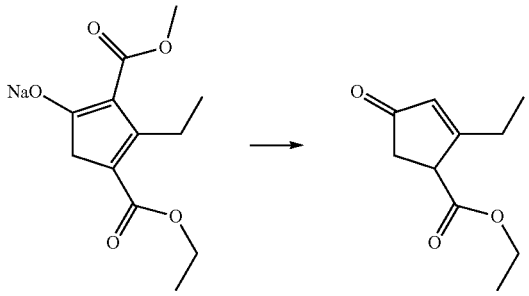

A 5 liter round bottom flask was charged with sodium 4-(ethoxycarbonyl)-3-ethyl-2-(methoxycarbonyl)cyclopenta-1,3-dienolate (316 g, 1205 mmol, Preparation #U.1), KCl (126 g, 1687 mmol, JT-Baker), AcOH (241 mL, 4218 mmol, JT-Baker), toluene (1850 mL) and water (130 mL). The reaction was heated at reflux for about 6 h then cooled to ambient temperature and added dropwise to 8% aqueous $NaHCO_3$ (3.5 L). The resulting biphasic mixture was extracted with MTBE (2×1.5 L). The combined organic layers were washed with brine (1 L), dried over anhydrous $MgSO_4$ and concd under reduced pressure to give 191 g of crude material that was purified by vacuum distillation (97-99° C., 0.600 mm Hg) to give ethyl 2-ethyl-4-oxocyclopent-2-enecarboxylate (160 g, 69%): $^1$H NMR ($CDCl_3$) δ 6.04 (m, 1H), 4.26-4.15 (m, 2H), 3.76-3.69 (m, 1H), 2.75-2.57 (m, 2H), 2.56-2.44 (m, 2H), 1.32-1.26 (m, 3H), 1.23-1.18 (m, 3H).

General Procedure W: Hydrogenation of an Alkene

A round bottom flask is charged with 10 wt % Pd/C (about 0.005-0.05 equiv, preferably 0.02 equiv). The flask is evacuated then flushed with nitrogen 2-5 times (preferably 3 times), then is optionally cooled to about −10-10° C. (preferably about 0° C.) prior to addition of an organic solvent or mixture of solvents (such as EtOAc, MeOH, EtOH or MeOH/AcOH, preferably EtOAc or MeOH) under a nitrogen atmosphere. The cooling bath is removed and to the mixture is added an alkene (preferably 1 equiv) neat or optionally as a solution in an organic solvent or mixture of solvents (such as EtOAc, MeOH, EtOH or MeOH/AcOH, preferably EtOAc or MeOH). Hydrogen gas is bubbled through the reaction mixture for about 1-20 min (preferably about 5 min) and the mixture is stirred under a hydrogen atmosphere for about 12-60 h (preferably about 48 h). In cases where the reaction does not proceed to completion as monitored by TLC, LC/MS, or HPLC, the hydrogen source is removed, the reaction mixture is bubbled with nitrogen for about 1-20 min (preferably about 5 min) and then filtered through a pad of Celite®, and the filtrate is concd under reduced pressure. The crude material is resubjected to the previously described reaction conditions for about 2-20 h (preferably about 5 h). The hydrogen source is removed and the mixture is bubbled with nitrogen for about 1-20 min (preferably about 5 min) and then filtered through a pad of Celite®. The filter cake is rinsed with an organic solvent (such as EtOAc, MeOH or EtOH, preferably the reaction solvent) and the filtrate is concd under reduced pressure to give the crude product.

Illustration of General Procedure W

Preparation #W.1: ethyl 2-ethyl-4-oxocyclopentanecarboxylate

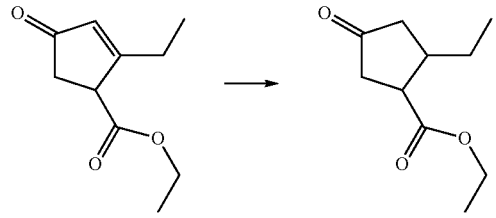

A round bottom flask was charged with 10 wt % Pd/C (10 g, 9.4 mmol). The flask was cooled to about 0° C. and EtOAc (400 mL) was added under a nitrogen atmosphere. The cooling bath was removed and ethyl 2-ethyl-4-oxocyclopent-2-enecarboxylate (47.8 g, 263 mmol, Preparation #V.1) was added. Hydrogen gas was bubbled through the mixture for about 5 min and the mixture was then stirred under a hydrogen atmosphere for about 48 h. The hydrogen source was removed and the mixture was bubbled with nitrogen for about 5 min and was filtered through a pad of Celite®. The filter cake was rinsed with EtOAc (400 mL). The filtrate was concd under reduced pressure to give ethyl 2-ethyl-4-oxocyclopentanecarboxylate (about 9:1 mixture cis:trans) (48.0 g, 99%) as a yellow liquid: $^1$H NMR ($CDCl_3$) δ 4.23-4.10 (m, 2H), 3.22 (m, 1H), 2.59-2.50 (m, 1H), 2.44-2.28 (m, 3H), 2.26-2.16 (m, 1H), 1.58-1.46 (m, 1H), 1.41-1.30 (m, 1H), 1.30-1.23 (m, 3H), 1.02-0.91 (m, 3H).

TABLE W.1

Examples prepared with General Procedure W

| Alkene | Product | Ex. # | $R_t$ min (Table 1, Method) | m/z ESI+ $(M + H)^+$ |
|---|---|---|---|---|
| N-(4-(3-allyl-6H-imidazo[1,5-a]pyrrolo[2,3-e]pyrazin-1-yl)bicyclo[2.2.2]octan-1-yl)cyclopropanesulfonamide (Example #D.1.40) | 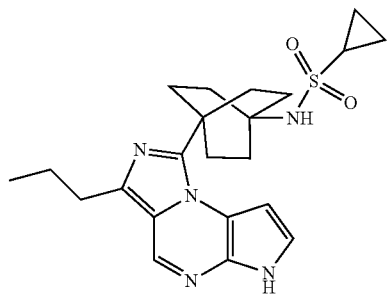 | W.1.1 | 1.95 (a) | 428 |
| 2-((3R,4S)-3-ethyl-4-(6H-pyrrolo[2,3-e][1,2,4]triazolo[4,3-a]pyrazin-1-yl)cyclopentylidene)acetic acid (prepared from Preparation #25 using III with triethyl phosphonoacetate, Z with NaOH, D with NaOH) | 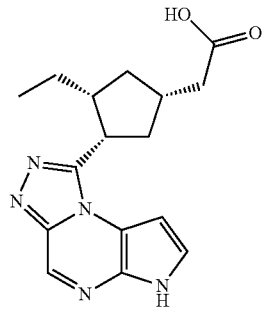 | W.1.2 | 1.47 | 314 |

General Procedure W.1: Hydrogenation of an Alkene

A round bottom flask is charged with a slurry of $Pd(OH)_2$ on carbon or Pd/C (about 0.005-0.10 equiv, preferably 0.05 equiv) in an organic solvent or mixture of solvents (such as THF, EtOAc, MeOH, EtOH or MeOH/AcOH, preferably THF) under a nitrogen atmosphere. The mixture is added to an alkene (preferably 1 equiv) neat or optionally as a solution in an organic solvent or mixture of solvents (such as THF, EtOAc, MeOH, EtOH or MeOH/AcOH, preferably THF) or optionally the alkene is added to the Pd mixture. The reaction mixture is sparged with hydrogen. The mixture is stirred or shaken (preferably stirred when atmospheric hydrogen is used or shaken when higher pressures of hydrogen is used) under hydrogen at about atmospheric pressure −60 psi (preferably atmospheric pressure) at about 20-60° C. (preferably ambient temperature) for about 0.5-5 days (preferably about 3 days). The reaction mixture is filtered through a pad of Celite®. The filter cake is rinsed with an organic solvent (such as THF, EtOAc, DCM, MeOH, or EtOH, preferably the reaction solvent) and the filtrate is concd under reduced pressure to give the crude product.

Illustration of General Procedure W.1

Preparation #W.1.1 and W.1.2: ethyl 2-((1R,3R,4S)-3-ethyl-4-(6H-pyrrolo[2,3-e][1,2,4]triazolo[4,3-a]pyrazin-1-yl)cyclopentyl)acetate and 2-((1S,3R,4S)-3-ethyl-4-(6H-pyrrolo[2,3-e][1,2,4]triazolo[4,3-a]pyrazin-1-yl)cyclopentyl)acetate

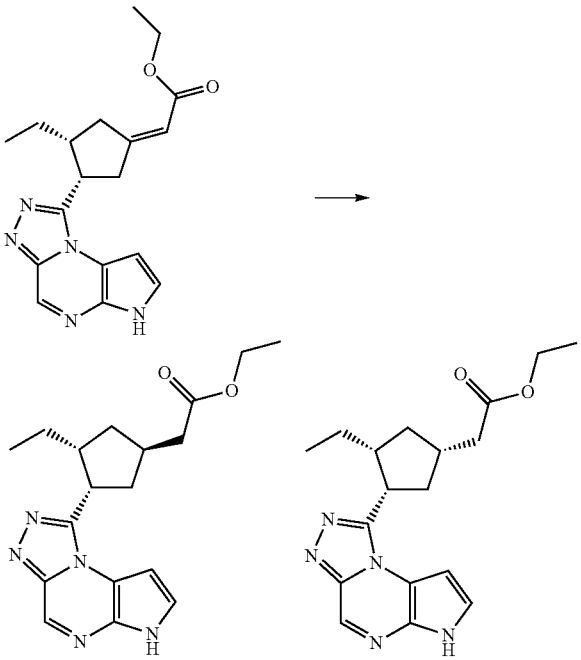

To a slurry of 20 wt % $Pd(OH)_2$ on carbon (0.134 g, 0.192 mmol) in THF (20 mL) was added a solution of (E)-ethyl 2-((cis)-3-ethyl-4-(6H-pyrrolo[2,3-e][1,2,4]triazolo[4,3-a]pyrazin-1-yl)cyclopentylidene)acetate (1.3 g, 3.83 mmol, Example #38, Step G) in THF (5 mL). The reaction mixture was sparged with hydrogen and an atmosphere of hydrogen was maintained via balloon. After about 3days, the reaction mixture was filtered through Celite®, concd under reduced pressure and purified by flash chromatography on silica gel eluting with EtOAc to afford a dark brown/black solid. The compound was further by purified by chiral chromatography (Table 2, Method 47) to afford ethyl 2-((1R,3R,4S)-3-ethyl-4-(6H-pyrrolo[2,3-e][1,2,4]triazolo[4,3-a]pyrazin-1-yl)cyclopentyl)acetate [W.1.1]($R_t$=12.0 min, or =negative) (0.400 g, 31%): LC/MS (Table 1, Method a) $R_t$=1.85 min; MS m/z: 342 $(M+H)^+$ and ethyl 2-((1S,3R,4S)-3-ethyl-4-(6H-pyrrolo[2,3-e][1,2,4]triazolo[4,3-a]pyrazin-1-yl)cyclopentyl)acetate [W.1.2]($R_t$=13.7 min, or =negative) (0.420 g, 32%) as a white solid: LC/MS (Table 1, Method a) $R_t$=1.85 min; MS m/z: 342 $(M+H)^+$.

General Procedure X: Reductive Amination of a Ketone or Aldehyde

A round bottom flask is charged with a ketone or an aldehyde (1-40 equiv; preferably 1 equiv) in an organic solvent (such as DCE, MeCN, MeOH, or MeCN/MeOH; preferably DCE). The mixture is optionally cooled to about −10-10° C. (preferably about 0° C.) and AcOH (1-3 equiv; preferably 1.5 equiv) and an amine (1-3 equiv, preferably 1 equiv) are added dropwise, followed by the portionwise addition of a suitable reducing agent such as $NaBH(OAc)_3$, $Na(CN)BH_3$, $NaBH_4$, preferably $NaBH(OAc)_3$ (1-6 equiv, preferably 1.5 equiv). Alternatively, to a solution of an amine (1-3 equiv, preferably 1 equiv) in an organic solvent (such as DCE, MeCN, or MeOH; preferably DCE) is added a ketone or an aldehyde (1-40 equiv; preferably 1 equiv) followed by subsequent portionwise addition of an appropriate reducing agent such as $NaBH(OAc)_3$, $Na(CN)BH_3$, $NaBH_4$, preferably NaBH $(OAc)_3$ (1-6 equiv, preferably 1.5 equiv). The mixture is stirred for about 5-20 min (preferably about 15 min) followed by the dropwise addition of AcOH (1-3 equiv; preferably 1.5 equiv). If the reaction mixture becomes too viscous to stir freely, additional organic solvent (such as DCE, MeCN, MeOH, or MeCN/MeOH mixture; preferably DCE) is optionally added to aid stirring. The reaction mixture is stirred at ambient temperature for about 1-48 h (preferably about 20 h). The reaction mixture is slowly poured into a solution of aqueous base (such as saturated aqueous $NaHCO_3$) followed by optional addition of solid $NaHCO_3$ and stirred for about 0.5-3 h (preferably about 2 h). The layers are separated and the organic solution is dried over anhydrous $Na_2SO_4$ or $MgSO_4$, filtered, and concd to dryness under reduced pressure.

Illustration of General Procedure X

Preparation #X.1: ethyl 4-(dibenzylamino)-2-ethylcyclopentanecarboxylate

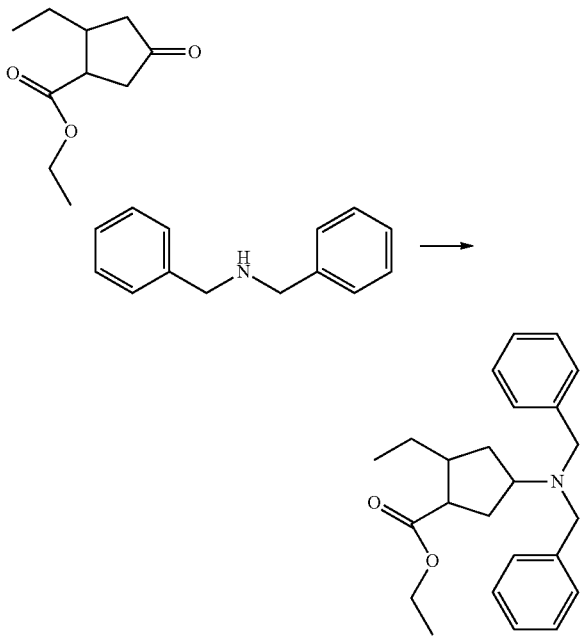

A round bottom flask was charged with ethyl 2-ethyl-4-oxocyclopentanecarboxylate (95.9 g, 521 mmol, Preparation #W.1) and DCE (1.8 L). The solution was cooled to about 0° C. and AcOH (45 mL, 780 mmol) and dibenzylamine (120 mL, 625 mmol) were added dropwise, resulting in formation of a thick suspension. The reaction mixture was warmed to about 10° C. and additional DCE (500 mL) was added. $NaBH(OAc)_3$ (166 g, 781 mmol) was added portionwise and the reaction mixture was stirred at ambient temperature for about 20 h. The reaction mixture was slowly poured into stirred saturated aqueous $NaHCO_3$ (1.5 L), followed by the portionwise addition of solid $NaHCO_3$ (175 g). The mixture was stirred for about 2 h and the organic layer was separated, dried over anhydrous $Na_2SO_4$, and concd to dryness under reduced pressure. The crude yellow oil was purified by silica gel chromatography eluting with 0-20% EtOAc in heptane to yield ethyl 4-(dibenzylamino)-2-ethylcyclopentanecarboxylate (136.6 g, 72%) as a white solid: LC/MS (Table 1, Method a) $R_t$=3.26 min; MS m/z: 366 $(M+H)^+$

TABLE X.1

Examples prepared from 1-((3R,4R)-4-methylpiperidin-3-yl)-6H-imidazo[1,5-a]pyrrolo[2,3-e]pyrazine hydrochloride (Example #5, Step J) using General Procedure X with $NaBH_3CN$

| Aldehyde | Product | Example # | $R_t$ min (Table 1, Method) | m/z ESI+ $(M + H)^+$ |
|---|---|---|---|---|
| Benzaldehyde | 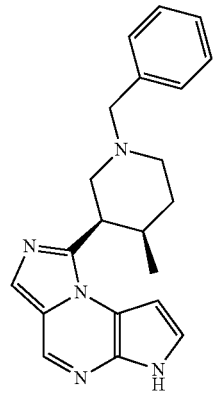 | X.1.1* | 1.51 (b) | 346 |

TABLE X.2

Examples prepared from acetaldehyde using General Procedure X with $NaBH_3CN$

| Amine | Product | Example # | $R_t$ min (Table 1, Method) | m/z ESI+ $(M + H)^+$ |
|---|---|---|---|---|
| (trans)-4-(3H-imidazo[1,2-a]pyrrolo[2,3-e]pyrazin-8-yl)cyclohexanamine (Example #F.1.2) | 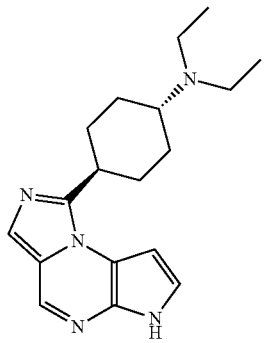 | X.2.1 | 0.97 (a) | 312 |

TABLE X.3

Examples prepared from 4,4,4-trifluorobutyraldehyde [Matrix] using General Procedure X with $Na(OAc)_3BH$

| Amine | Product | Example # | $R_t$ min (Table 1, Method) | m/z ESI+ $(M + H)^+$ |
|---|---|---|---|---|
| (1S,3R,4S)-3-ethyl-4-(6H-pyrrolo[2,3-e][1,2,4]triazolo[4,3-a]pyrazin-1-yl)cyclopentanamine (Preparation #44) | 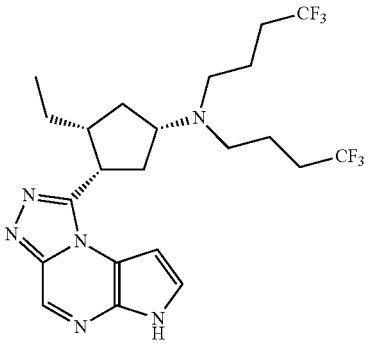 | X.3.1 | 1.90 (a) | 491 |

TABLE X.4

Examples prepared from (3R,4S)-3-ethyl-4-(6H-pyrrolo[2,3-e][1,2,4]triazolo[4,3-a]pyrazin-1-yl)cyclopentanone (prepared using D from Preparation #25 using D), and General Procedure X with $Na(OAc)_3BH$

| Amine | Product | Example # | $R_t$ min (Table 1, Method) | m/z ESI+ $(M + H)^+$ |
|---|---|---|---|---|
| oxetan-3-amine [Synthonix] | 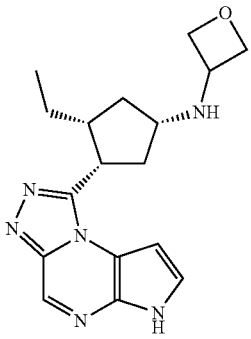 | X.4.1 | 1.01 (a) | 327 |
| 3-methyloxetan-3-amine [Synthonix] | 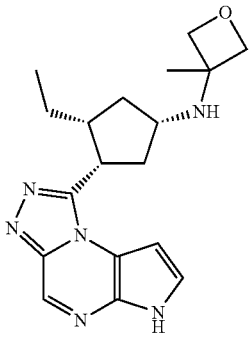 | X.4.2 | 1.06 (a) | 341 |

General Procedure X.1: Reductive Amination of a Ketone or Aldehyde

A ketone or an aldehyde (1-40 equiv; preferably 1 equiv) is optionally dissolved or slurried in an organic solvent or solvents such as DCE, MeCN, MeOH, MeCN/MeOH, EtOH, THF, DMF, AcOH, or DCM (preferably DCE). The mixture is optionally cooled to about −10-10° C. (preferably about 0° C.). Optionally, AcOH (1-3equiv; preferably 1.5 equiv) is added. An amine (1-3equiv, preferably 1 equiv) is added neat or as a solution in an organic solvent or solvents such as DCE, MeCN, MeOH, EtOH, THF, DMF, AcOH, or DCM (preferably DCE). Alternatively, a ketone or aldehyde or solution of ketone or aldehyde may be added to an amine or amine solution. A dehydrating reagent such as molecular sieves or titanium(IV) tetraisopropoxide may optionally be added or water may be removed using a Dean-Stark trap. The solvent is optionally removed under reduced pressure and an organic solvent or solvents such as DCE, MeCN, MeOH, EtOH, THF, DMF, AcOH, or DCM may be added. After stirring for about 5 min-24 h (preferably 15 min) at 0° C. to 100° C. (preferably ambient temperature), a suitable reducing agent such as $NaBH(OAc)_3$, $Na(CN)BH_3$, $NaBH_4$, preferably $NaBH(OAc)_3$ (1-10 equiv, preferably 1.5 equiv) is added portionwise. If the reaction mixture becomes too viscous to stir freely, additional organic solvent is optionally added to aid stirring. The reaction mixture is stirred at ambient temperature for about 1-72 h (preferably about 20 h). Optionally, the reaction mixture may be treated with water and then filtered or the volatiles may be removed under reduced pressure. The reaction mixture is slowly poured into a solution of aqueous base, water, or aqueous acid (preferably saturated aqueous $NaHCO_3$) or alternatively the aqueous solution is slowly added to the reaction mixture. Optionally, additional solid $NaHCO_3$ may be added. The mixture is vigorously stirred for about 0.5-20 h (preferably about 2 h). The layers are separated and the organic solution is dried over anhydrous $Na_2SO_4$ or $MgSO_4$, filtered, and concentrated to dryness under reduced pressure.

Illustration of General Procedure X.1

Preparation #X.1.1: tert-butyl(trans-4-((6H-pyrrolo[2,3-e][1,2,4]triazolo[4,3-a]pyrazin-8-yl)methylamino)cyclohexyl)methylcarbamate

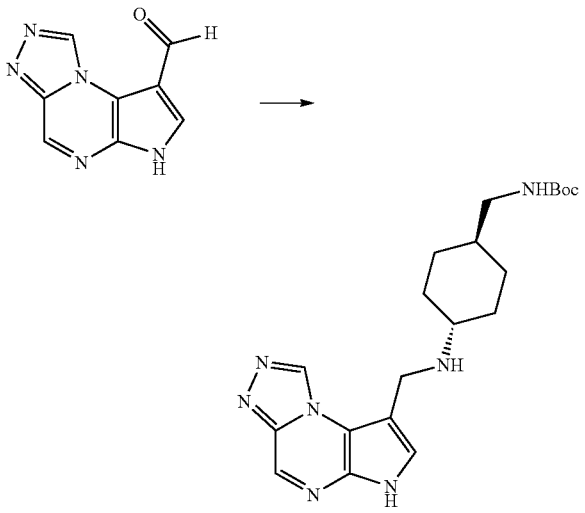

tert-Butyl trans-4-aminocyclohexylmethylcarbamate (0.059 g, 0.258 mmol, AMRI) was added to a mixture of 6H-pyrrolo[2,3-e][1,2,4]triazolo[4,3-a]pyrazine-8-carbaldehyde (0.0403 g, 0.215 mmol, Preparation #38) and THF (1.0 mL). The mixture was stirred at ambient temperature for about 90 min. Sodium triacetoxyborohydride (0.068 g, 0.32 mmol) was added. After about 3 h, DMF (0.500 mL) was added. After about 15 h, $Na(OAc)_3BH$ (0.091 g, 0.43 mmol) was added. After about 24 h, $Na(OAc)_3BH$ (0.091 g, 0.43 mmol) was added. The mixture was warmed to about 40° C. After about 22 h, the mixture was allowed to cool to ambient temperature. Saturated aqueous $NaHCO_3$/water (1:1, 2 mL) was added. After vigorously stirring for about 1 h, the solution was diluted with water (3 mL) and then extracted with EtOAc (6×10 mL). The combined organics were dried over $Na_2SO_4$, filtered, and concentrated under reduced pressure. The residue was purified silica gel chromatography eluting with a gradient of 10-100% [(1% 7 N $NH_3$ in MeOH) in 10% MeOH/DCM]/DCM to give tert-butyl(trans-4-((6H-pyrrolo[2,3-e][1,2,4]triazolo[4,3-a]pyrazin-8-yl)methylamino)cyclohexyl)methylcarbamate (0.0476 g, 53%): LC/MS (Table 1, Method a) $R_t$=1.24 min; MS m/z 400 $(M+H)^+$.

General Procedure Y: Hydrogenation of a Benzyl- or Cbz-Protected Amine

To a vessel charged with a benzyl- or Cbz-protected amine (preferably 1 equiv) was added a palladium catalyst (for example $Pd(OH)_2$ on C or Pd/C; preferably $Pd(OH)_2$ on C) (0.01-0.2 equiv, preferably 0.02-0.15 equiv) and an organic solvent (such as MeOH or EtOH, preferably EtOH). The mixture is shaken or stirred at about 25-60° C. (preferably about 50° C.) for about 1-96 h (preferably about 1.5-3 h) at about 15-60 psi hydrogen (preferably about 30-50 psi hydrogen). In cases where the reaction does not proceed to completion as monitored by TLC, LC/MS, or HPLC, the hydrogen source is removed, the reaction mixture is bubbled with nitrogen for about 5-20 min (preferably about 5 min) and then filtered through a pad of Celite®, and the filtrate is concd under reduced pressure. The crude material is resubjected to the previously described reaction conditions for about 2-20 h (preferably about 3-5 h). When the reaction is complete as monitored by TLC, LC/MS, or HPLC, the hydrogen source is removed, a nitrogen atmosphere is introduced, and the reaction mixture is filtered through a pad of Celite®. The filtrate is concd under reduced pressure to give the desired product.

Illustration of General Procedure Y

Preparation #Y1: ethyl 4-amino-2-ethylcyclopentanecarboxylate

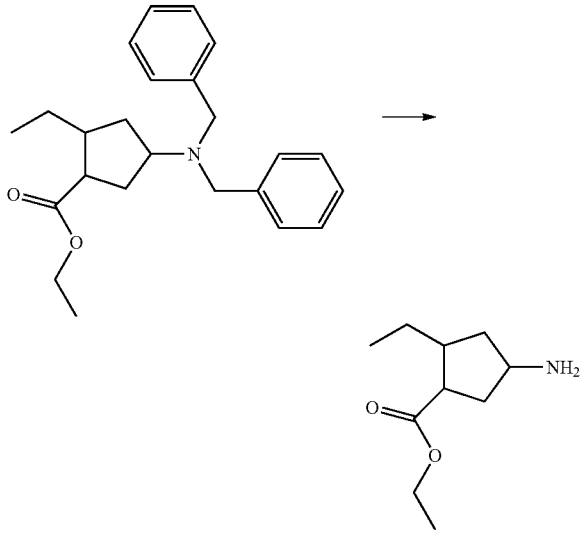

To a vessel containing a slurry of 20 wt % $Pd(OH)_2$ on C (12.9 g, 18.4 mmol) in EtOH (1.0 L) was added ethyl 4-(dibenzylamino)-2-ethylcyclopentanecarboxylate (129 g, 352 mmol, Preparation #X.1). The reaction was shaken for about 90 min at about 50° C. under about 30 psi of hydrogen. After removal of the hydrogen source and introduction of a nitrogen atmosphere, the resulting mixture was filtered through a pad of Celite® and the filtrate was concd under reduced pressure to give ethyl 4-amino-2-ethylcyclopentanecarboxylate (64.5 g, 99%) as a yellow syrup: $^1$H NMR ($CDCl_3$) δ 4.03-3.88 (m, 2H), 3.17 (m, 1H), 2.68 (m, 1H), 2.09-2.02 (m, 2H), 2.02-1.94 (m, 2H), 1.84 (m, 1H), 1.58-1.48 (m, 1H), 1.32-1.18 (m, 1H), 1.09 (m, 3H), 1.03 (m, 2H), 0.78-0.69 (m, 3H).

TABLE Y.1

Examples prepared using General Procedure Y

| Dibenzyl amine | Product | Ex # | $R_t$ min (Table 1, Method) | m/z ESI+ $(M + H)^+$ |
|---|---|---|---|---|
| trans-1-(4-(3H-imidazo[1,2-a]pyrrolo[2,3-e]pyrazin-8-yl)cyclohexyl)-N,N-dibenzylmethanamine (prepared using S from methyl 4-(aminomethyl)cyclohexanecarboxylate [prepared as described in Molecules 2008, 13, 1111-1119] and benzyl bromide, Z with NaOH, R, S with Example #3 Step E, E with TFA, KKKK with PFPAA, D with NaOH) | 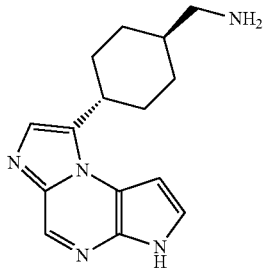 | Y.1.x | 1.27 (a) | 270 |

General Procedure Z: Basic Hydrolysis of an Ester to a Carboxylic Acid

To a flask containing an ester (preferably 1 equiv) either neat or in an organic solvent (such as 1,4-dioxane, MeOH, or THF/MeOH, preferably 1,4-dioxane) is added an aqueous base (such as aqueous NaOH or LiOH, 1-10 equiv, preferably 2-6 equiv). The mixture is stirred at about 0-100° C. (preferably ambient temperature) for about 1-48 h (preferably about 4-8 h). The reaction mixture is then acidified by the addition of a suitable aqueous acid (such as aqueous HCl). The layers are separated and the aqueous layer is optionally extracted with additional organic solvent (such as EtOAc or DCM, preferably DCM). The organic layer or layers are optionally dried over anhydrous $Na_2SO_4$ or $MgSO_4$, filtered, and concd to dryness under reduced pressure to give crude target compound. Alternatively, the reaction mixture is concd under reduced pressure to give crude target compound as a carboxylate salt.

Illustration of General Procedure Z

Preparation #Z.1*: (1S,2R,4S)-4-(cyclopropanesulfonamido)-2-ethylcyclopentanecarboxylic acid

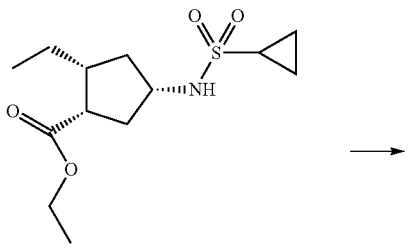

-continued

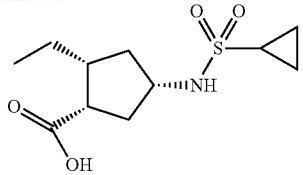

To a flask containing (1S,2R,4S)-ethyl 4-(cyclopropanesulfonamido)-2-ethylcyclopentane-carboxylate (11.1 g, 38.4 mmol, prepared using K from Preparation #Y.1, cyclopropanesulfonyl chloride and TEA, AA [Table 2, Method 1, $R_t$=9.5 min, or =negative]) was added aqueous NaOH (1 N, 210 mL, 210 mmol). After stirring at ambient temperature for about 8 h, the reaction was acidified to about pH 1 using 6 N aqueous HCl and extracted with DCM (3×150 mL). The combined organic layers were washed with brine, dried over anhydrous $MgSO_4$, filtered, and concd under reduced pressure to give (1S,2R,4S)-4-(cyclopropanesulfonamido)-2-ethylcyclopentanecarboxylic acid with 25 mol % DCM as an excipient (10.7 g, 99%): LC/MS (Table 1, Method a) $R_t$=1.71 min; MS m/z: 260 $(M-H)^-$.

General Procedure AA: Chiral Preparative HPLC Purification

Chiral purification is performed using Varian 218 LC pumps, a Varian CVM 500 with switching valves and heaters for automatic solvent, column and temperature control and a Varian 701 Fraction collector. Detection methods include a Varian 210 variable wavelength detector, an in-line polarimeter (PDR-chiral advanced laser polarimeter, model ALP2002) used to measure qualitative optical rotation (+/−) and an evaporative light scattering detector (ELSD) (a PSELS 2100 (Polymer Laboratories)) using a 100:1 split flow. ELSD settings are as follows: evaporator: 46° C., nebulizer: 24° C. and gas flow: 1.1 SLM. The absolute stereochemistry of the purified compounds was assigned arbitrarily and is drawn as such. Compounds of the invention where the absolute stereochemistry has been determined by the use of a commercially available enantiomerically pure starting material, or a stereochemically defined intermediate, or X-ray diffraction are denoted by an asterisk after the example number.

Illustration of General Procedure AA

Examples #AA.1.1 and AA.1.2

3-((3R,4R)-3-(6H-imidazo[1,5-a]pyrrolo[2,3-e]pyrazin-1-yl)-4-(trifluoromethyl)piperidin-1-yl)-3-oxopropanenitrile and 3-((3S,4S)-3-(6H-imidazo[1,5-a]pyrrolo[2,3-e]pyrazin-1-yl)-4-(trifluoromethyl)piperidin-1-yl)-3-oxopropanenitrile

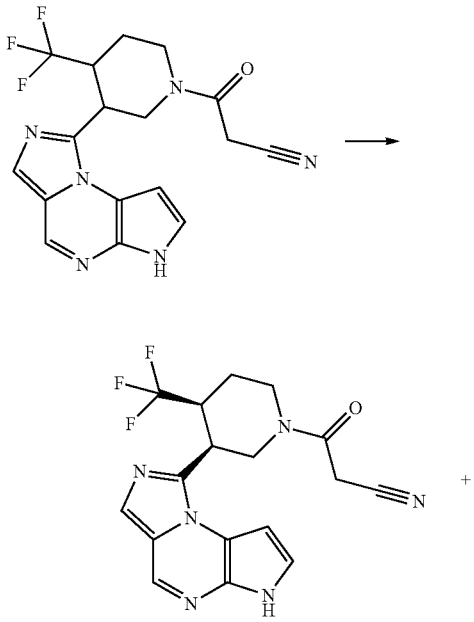

-continued

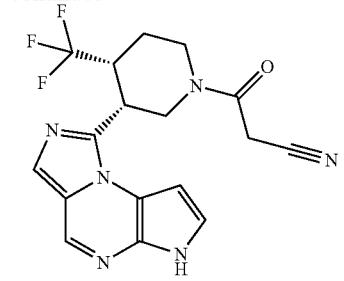

A mixture of 3-(6H-imidazo[1,5-a]pyrrolo[2,3-e]pyrazin-1-yl)-4-(trifluoromethyl)piperidin-1-yl)-3-oxopropanenitrile (0.067 g, 0.18 mmol, prepared using O from 4-(trifluoromethyl)nicotinic acid, N, H with Example #5, Step C, HATU and DIEA, Q with Lawesson's reagent and mercury (II) trifluoroacetate, D with NaOH, F, H with 2-cyanoacetic acid, HATU, and DIEA) was dissolved in DMSO:MeOH (2:1, 3 mL). The mixture was separated using Varian 218 LC pumps, a Varian CVM 500 with switching valves and heaters for automatic solvent, column and temperature control and a Varian 701 Fraction collector using Method 4 (Table 2) to give 3-((3R,4R)-3-(6H-imidazo[1,5-a]pyrrolo[2,3-e]pyrazin-1-yl)-4-(trifluoromethyl)piperidin-1-yl)-3-oxopropanenitrile ($R_t$=12.2 min, or =positive) (0.0284 g, 15%) [AA.1.1] and 3-((3S,4S)-3-(6H-imidazo[1,5-a]pyrrolo[2,3-e]pyrazin-1-yl)-4-(trifluoromethyl)piperidin-1-yl)-3-oxopropanenitrde ($R_t$=5.3 min, or =negative) (0.0282 g, 15%) [AA.1.2]: LC/MS (Table 1, Method b) $R_t$=1.55 min; MS m/z: 377 $(M+H)^+$.

TABLE AA.1

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| 4-((1R,3R)-3-(6H-imidazo[1,5-a]pyrrolo[2,3-e]pyrazin-1-yl)cyclopentylamino)benzonitrile and 4-((1R,35)-3-(6H-imidazo[1,5-a]pyrrolo[2,3-e]pyrazin-1-yl)cyclopentylamino)benzonitrile (prepared using H from Example #5, Step C and (1R,3R)-3-(tert-butoxycarbonylamino)cyclopentane carboxylic acid [Acros], HATU and DIEA; Q with Lawesson's reagent and mercury (II) trifluoroacetate; E with HCl; PP from 4-cyanophenylboronic acid; D with NaOH) [Table 2, Method 18, $R_t$ = 14.5 min, or = ND] | 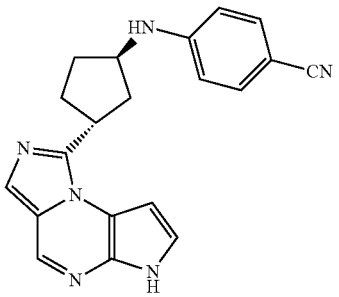 | AA.1.3* | 1.84 (b) | 343 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| N-3-ethyl-4-(6H-pyrrolo[2,3-e][1,2,4]triazolo[4,3-a]pyrazin-1-yl)-(cyclopentyl)cyclopropane-sulfonamide (prepared using A from Example #1, Step D and Preparation #Z.1 with HATU and TEA, B with TEA, D with NaOH) [Table 2, Method 2, $R_t$ = 10.4 min, or = negative] | 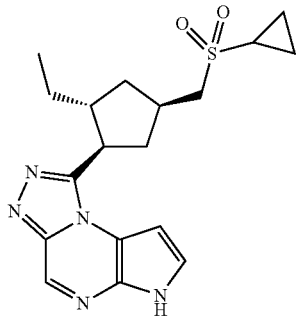 | AA.1.4* | 1.76 (a) | 375 |
| N-3-ethyl-4-(6H-pyrrolo[2,3-e][1,2,4]triazolo[4,3-a]pyrazin-1-yl)-cyclopentyl)cyclopropanesulfonamide (prepared using A from Example #1, Step D and Preparation #Z.1 with HATU and TEA, B with TEA, D with NaOH) [Table 2, Method 2, $R_t$ = 11.3 min, or = positive] | 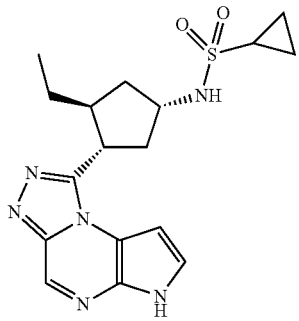 | AA.1.5* | 1.86 (a) | 375 |
| (3-(3H-imidazo[1,2-a]pyrrolo[2,3-e]pyrazin-8-yl)piperidin-1-yl)(3,3-difluoroazetidin-1-yl)methanone (prepared using J from Example #3, Step G and 3,3-difluoroazetidine hydrochloride with CDI) [Table 2, Method 12, $R_t$ = 11.4 min, or = positive] | 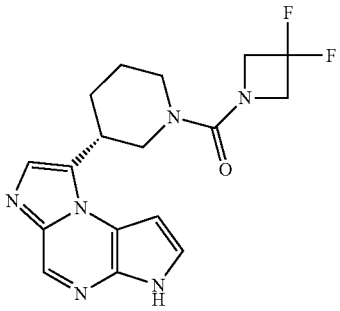 | AA.1.6* | 1.58(b) | 361 |
| (3-(3H-imidazo[1,2-a]pyrrolo[2,3-e]pyrazin-8-yl)piperidin-1-yl)(3,3-difluoroazetidin-1-yl)methanone (prepared using J from Example #3, Step G and 3,3-difluoroazetidine hydrochloride with CDI) [Table 2, Method 12, $R_t$ = 7.4 min, or = negative] | 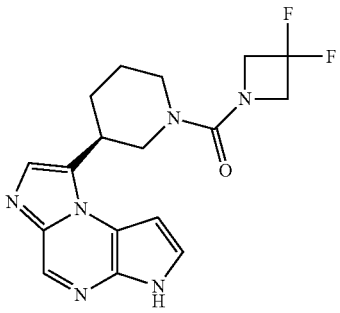 | AA.1.7* | 1.58 (b) | 361 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| (3-(3H-imidazo[1,2-a]pyrrolo[2,3-e]pyrazin-8-yl)piperidin-1-yl)(3,3-difluoropyrrolidin-1-yl)methanone (prepared using J from Example #3, Step G and 3,3-difluoropyrrolidine hydrochloride with CDI) [Table 2, Method 8, $R_t$ = 11.5 min, or = positive] | 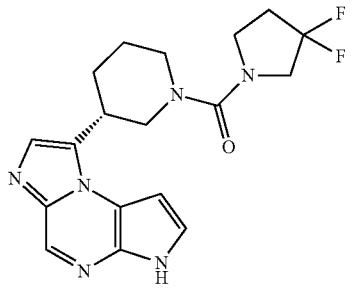 | AA.1.8* | 1.64 (b) | 375 |
| (3-(3H-imidazo[1,2-a]pyrrolo[2,3-e]pyrazin-8-yl)piperidin-1-yl)(4,4-difluoropiperidin-1-yl)methanone (prepared using J from Example #3, Step G and 4,4-difluoropiperidine hydrochloride with CDI) [Table 2, Method 13, $R_t$ = 15.6 min, or = positive] | 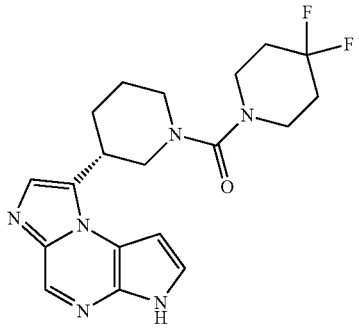 | AA.1.9* | 1.72 (b) | 389 |
| (3-(3H-imidazo[1,2-a]pyrrolo[2,3-e]pyrazin-8-yl)piperidin-1-yl)((R)-2-(trifluoromethyl)pyrrolidin-1-yl)methanone (prepared using J from Example #3, Step G and (R)-2-(trifluoromethyl)pyrrolidine with CDI) [Table 2, Method 9, $R_t$ = 10.4 min, or = positive] | 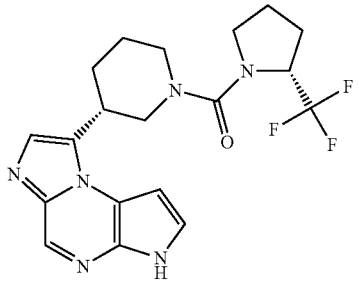 | AA.1.10* | 1.87 (b) | 407 |
| 2-(-3-(6H-imidazo[1,5-a] pyrrolo[2,3-e]pyrazin-1-yl)-4-methylpiperidin-1-yl)thiazole-5-carbonitrile (prepared using L from Example #5, Step J and 2-chlorothiazole-5-carbonitrile [ArkPharm]) [Table 2, Method 15, $R_t$ = 13.4 min, or = positive] | 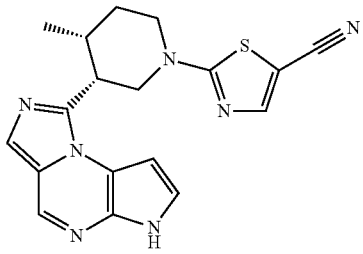 | AA.1.11* | 1.89 (b) | 364 |
| 1-((R)-3-(6H-imidazo[1,5-a]pyrrolo[2,3-e]pyrazin-1-yl)piperidine-1-carbonyl)pyrrolidine-3-carbonitrile (prepared using J from Example #6, Step H and pyrrolidine-3-carbonitrile [Tyger] with CDI) [Table 2, Method 14, $R_t$ = 16.9 min, or = positive] | 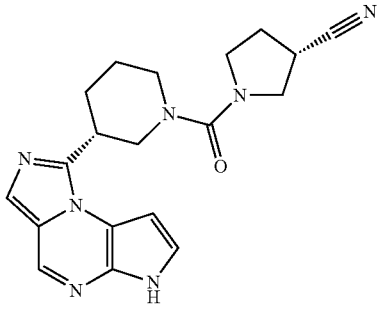 | AA.1.12* | 1.41 (b) | 364 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| N-(3-(3H-imidazo[1,2-a] pyrrolo[2,3-e]pyrazin-8-yl)-4-methylcyclopentyl)-3,3,3-trifluoropropane-1-sulfonamide (prepared using K from Preparation #53 and 3,3,3-trifluoropropylsulfonyl chloride [Matrix]) [Table 2, Method 9, $R_t$ = 14.3 min, or = positive] | 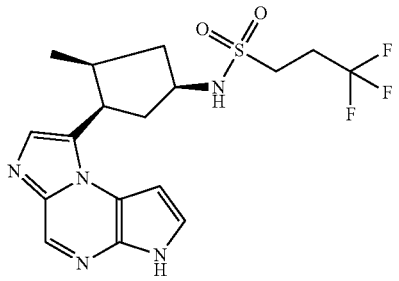 | AA.1.13 | 1.79 (a) | 416 |
| N-(3-(3H-imidazo[1,2-a] pyrrolo[2,3-e]pyrazin-8-yl)-4-methylcyclopentyl)-3,3,3-trifluoropropane-1-sulfonamide (prepared using K from Preparation #53 and 3,3,3-trifluoropropylsulfonyl chloride [Matrix]) [Table 2, Method 9, $R_t$ = 12.4 min, or = positive] | 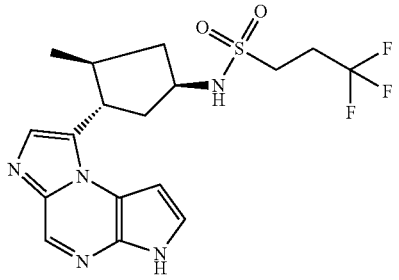 | AA.1.14 | 1.79 (a) | 416 |
| N-(3-(3H-imidazo[1,2-a]pyrrolo[2,3-e]pyrazin-8-yl)-4-methylcyclopentyl)-3,3,3-trifluoropropane-1-sulfonamide (prepared using K from Preparation #51 and 3,3,3-trifluoropropylsulfonyl chloride [Matrix]) [Table 2, Method 9, $R_t$ = 11.9 min, or = negative] | 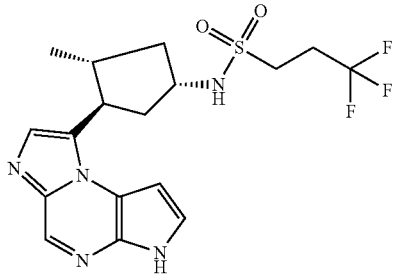 | AA.1.15 | 1.79 (a) | 416 |
| 5-(3-(3H-imidazo[1,2-a]pyrrolo[2,3,-e]pyrazin-8-yl)-4-methylcyclopentylamino)pyrazine-2-carbonitrile (prepared using L from Preparation #53 and 2-chloro-5-cyanopyrazine [ArkPharm]) [Table 2, Method 8, $R_t$ =18.6 min, or = negative] | 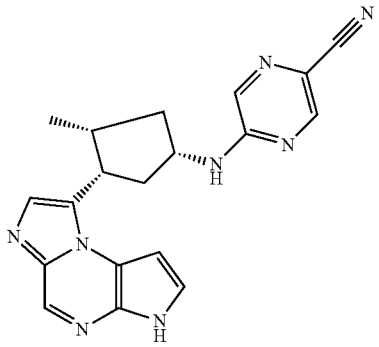 | AA.1.16 | 1.69 (a) | 359 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| 5-(3-(3H-imidazo[1,2-a]pyrrolo[2,3,-e]pyrazin-8-yl)-4-methylcyclopentylamino)pyrazine-2-carbonitrile (prepared using L from Preparation #51 and 2-chloro-5-cyanopyrazine [ArkPharm]) [Table 2, Method 8, $R_t$ = 14.8 min, or = positive] | 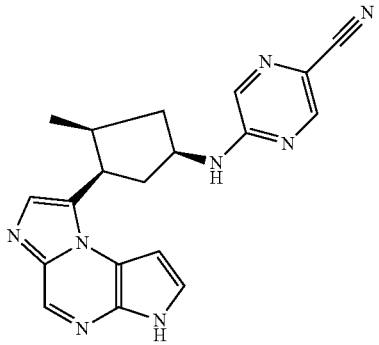 | AA.1.17 | 1.69 (a) | 359 |
| 5-(3-(3H-imidazo[1,2-a]pyrrolo[2,3,-e]pyrazin-8-yl)-4-methylcyclopentylamino)pyrazine-2-carbonitrile (prepared using L from Preparation #53 and 2-chloro-5-cyanopyrazine [ArkPharm]) 2, Method 8, Rt =11.5 min, or = positive] | 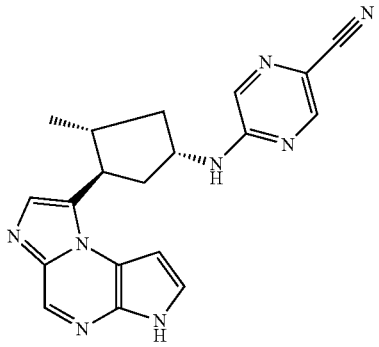 | AA.1.18 | 1.69 (a) | 359 |
| 5-(3-(3H-imidazo[1,2-a]pyrrolo[2,3,-e]pyrazin-8-yl)-4-methylcyclopentylamino)pyrazine-2-carbonitrile (prepared using L from Preparation #51 and 2-chloro-5-cyanopyrazine [ArkPharm]) [Table 2, Method 8, $R_t$ = 9.5 min, or = negative] | 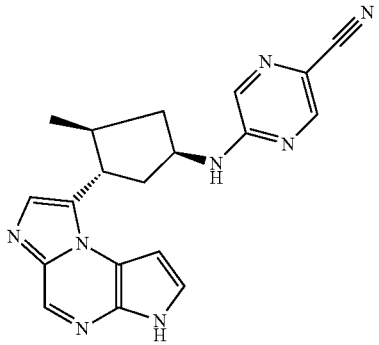 | AA.1.19 | 1.69 (a) | 359 |
| 6-(3-(3H-imidazo[1,2-a]pyrrolo[2,3,-e]pyrazin-8-yl)piperidin-1-yl)nicotinonitrile (prepared using L from Example #3, Step G and 2-chloro-5-cyanopyridine) [Table 2, Method 7, $R_t$ = 14.9 min, or = positive] | 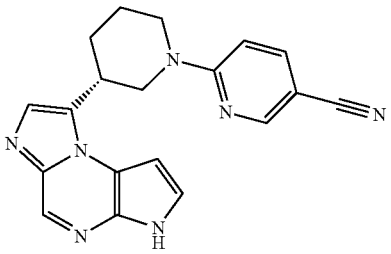 | AA.1.20* | 1.81 (a) | 344 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| 6-(3-(3H-imidazo[1,2-a]pyrrolo [2,3,-e] pyrazin-8-yl)piperidin-1-yl)nicotinonitrile (prepared using L from Example #3, Step G and 2-chloro-5-cyanopyridine) [Table 2, Method 7, $R_t$ = 11.9 min, or = negative] | 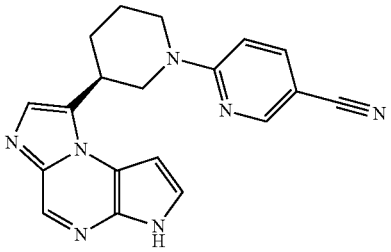 | AA.1.21 * | 1.81 (a) | 344 |
| 2-(3-(3H-imidazo[1,2-a]pyrrolo[2,3,-e]pyrazin-8-yl)piperidin-1-yl)thiazole-5-carbonitrile (prepared using L from Example #3, Step G and 2-chloro-5-cyanothiazole [ArkPharm]) [Table 2, Method 5, $R_t$ = 12.5 min, or = positive] | 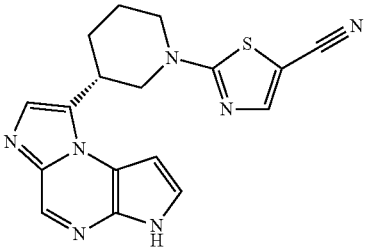 | AA.1.22* | 1.74 (a) | 350 |
| 2-(3-(3H-imidazo[1,2-a]pyrrolo[2,3,-e]pyrazin-8-yl)piperidin-1-yl)thiazole-5-carbonitrile (prepared using L from Example #3, Step G and 2-chloro-5-cyanothiazole [ArkPharm]) [Table 2, Method 5, $R_t$ = 9.4 min, or = negative] | 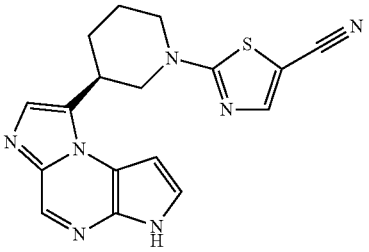 | AA.1.23* | 1.74 (a) | 350 |
| N-(3-ethyl-4-(3H-imidazo[1,2-a] pyrrolo[2,3-e]pyrazin-8-yl) cyclopentyl)cyclopropanesulfonamide (prepared using TT from Preparation #X.1 with HCl, R with trimethylsilyl diazomethane, S with Example #3, Step E, E with 4N HCl in 1,4-dioxane, T using Lawesson's reagent, D with NaOH, Y with $Pd(OH)_2$ on C, and K from cyclopropylsulfonyl chloride) [Table 2, Method 6, $R_t$ = 8.2 min, or = negative] | 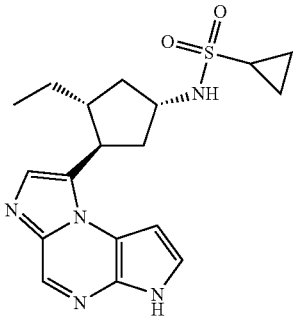 | AA.1.24 | 1.64 (a) | 374 |
| N-(3-ethyl-4-(3H-imidazo[1,2-a] pyrrolo[2,3-e]pyrazin-8-yl)cyclopentyl)cyclopropanesulfonamide (prepared using TT from Preparation #X.1 with HCl, R with trimethylsilyl diazomethane, S with Example #3, Step E, E with 4N HCl in 1,4-dioxane, T using Lawesson's reagent, D with NaOH, Y with $Pd(OH)_2$ on C, and K from cyclopropylsulfonyl chloride) [Table 2, Method 6, $R_t$ = 13.0 min, or = positive] | 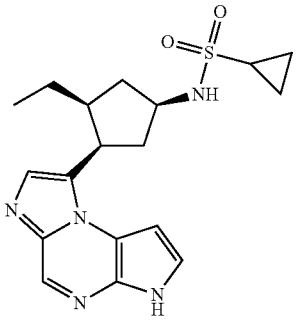 | AA.1.25 | 1.64 (a) | 374 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| 1-(3-(3H-imidazo[1,2-a]pyrrolo[2,3,-e]pyrazin-8-yl)piperidine-1-carbonyl)cyclopropanecarbonitrile (prepared using H from Example #3, Step G and 1-cyano-1-cyclopropane-carboxylic acid) [Table 2, Method 5, $R_t$ = 7.3 min, or = negative] | 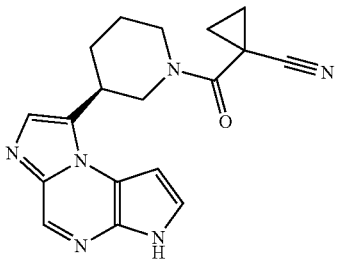 | AA.1.26* | 1.46 (a) | 335 |
| 3-(3-(3H-imidazo[1,2-a]pyrrolo[2,3-e]pyrazin-8-yl)-4-methylpiperidin-1-yl)-3-oxopropanenitrile (prepared using N from Example #5, Step D with N-(benzyloxycarbonyloxy) succinimide, R with trimethylsilyl diazomethane, S with Example #3, Step E, E with 4N HCl in 1,4-dioxane, T using Lawesson's reagent, D with NaOH, Y with Pd/C, and H from cyanoacetic acid, EDC, and DIEA) [Table 2, Method 4, $R_t$ = 15.9 min, or = negative] | 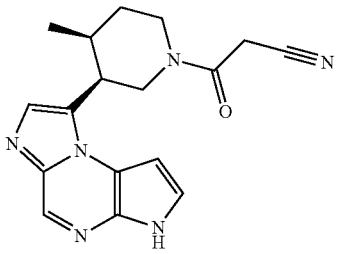 | AA.1.27 | 1.36 (a) | 323 |
| 4-(3-ethyl-4-(6H-pyrrolo[2,3-e][1,2,4]triazolo[4,3-a]pyrazin-1-yl)cyclopentyloxy)-benzonitrile (prepared using II from 4-hydroxybenzonitrile and Preparation #FF.1, D with $Na_2CO_3$) [Table 2, Method 17, $R_t$ 20.8 min, or = positive] | 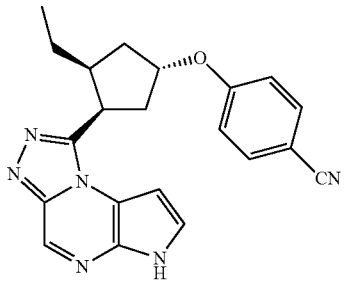 | AA.1.28 | 2.12 (b) | 373 |
| 6-(3-ethyl-4-(6H-pyrrolo[2,3-e][1,2,4]triazolo[4,3-a]pyrazin-1-yl)cyclopentyloxy)-nicotinonitrile (prepared using II from 6-hydroxynicotino-nitrile and Preparation #FF.1, D with $Na_2CO_3$) [Table 2, Method 18, Rt 14.6 min, or = positive] | 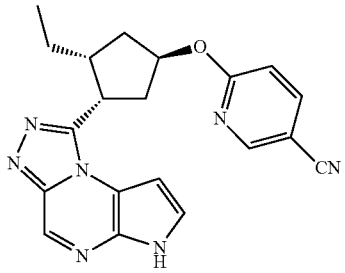 | AA.1.29 | 2.07 (b) | 374 |
| 6-(3-ethyl-4-(6H-pyrrolo[2,3-e][1,2,4]triazolo[4,3-a]pyrazin-1-yl)cyclopentyloxy)-nicotinonitrile (prepared using II from 6-hydroxynicotino-nitrile and Preparation #FF.1, D with $Na_2CO_3$) [Table 2, Method 18, Rt 16.9 min, or = positive] | 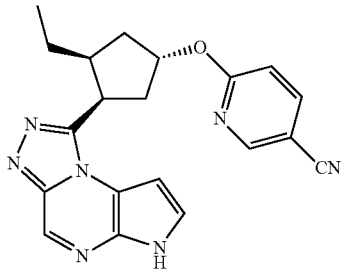 | AA.1.30 | 2.04 (b) | 374 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| 1-(2-ethyl-4-(4-methoxybenzyloxy)cyclopentyl)-6H-pyrrolo[2,3-e][1,2,4]triazolo[4,3-a]pyrazine (prepared using Z from Preparation #EE.1, A from Example #1, Step D, HATU, and TEA, B with DIEA, D with $Na_2CO_3$) [Table 2, Method 19, $R_t$ 17.1 min, or = negative] | 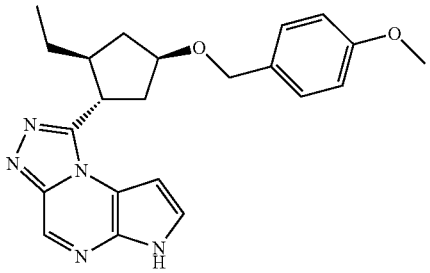 | AA.1.31 | 2.23 (b) | 392 |
| 1-(2-ethyl-4-(4-methoxybenzyloxy) cyclopentyl)-6H-pyrrolo[2,3-e][1,2,4]triazolo [4,3-a]pyrazine (prepared using Z from Preparation #EE.1, A from Example #1, Step D, HATU, and TEA, B with DIEA, D with $Na_2CO_3$) [Table 2, Method 19, $R_t$ 19.1 min, or = positive] | 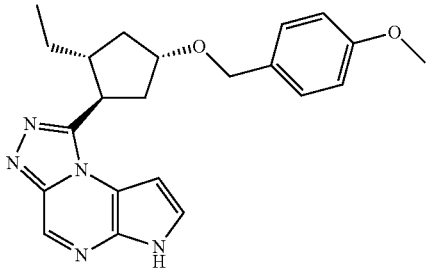 | AA.1.32 | 2.22 (b) | 392 |
| 5-(3-ethyl-4-(6H-pyrrolo[2,3-e][1,2,4]triazolo[4,3-a]pyrazin-1-yl)cyclopentyloxy)pyrazine-2-carbonitrile (Preparation #LL.1) [Table 2, Method 20, $R_t$ 8.1 min, or = negative] | 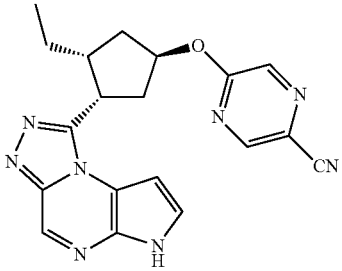 | AA.1.33 | 2.04 (b) | 375 |
| 5-(3-ethyl-4-(6H-pyrrolo[2,3-e][1,2,4]triazolo[4,3-a]pyrazin-1-yl)cyclopentyloxy)pyrazine-2-carbonitrile (Preparation #LL.1) [Table 2, Method 20, $R_t$ 13.9 min, or = positive] | 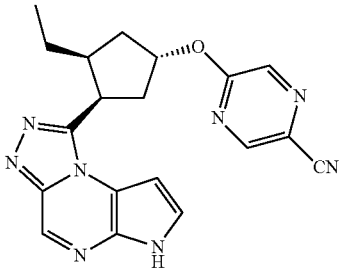 | AA.1.34 | 2.04 (b) | 375 |
| 6-(3-ethyl-4-(6H-pyrrolo[2,3-e][1,2,4]triazolo[4,3-a]pyrazin-1-yl)cyclopentyloxy)nicotino-nitrile carbonitrile (prepared using II from 6-hydroxynicotinonitrile and Preparation #FF.1, D with $Na_2CO_3$) [Table 2, Method 21, $R_t$ 10.9 min, or = negative] | 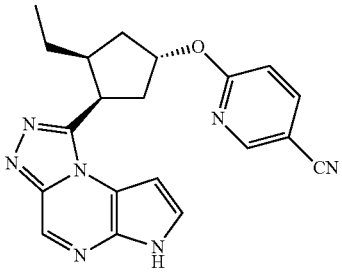 | AA.1.35 | 2.03 (b) | 374 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| 6-(3-ethyl-4-(6H-pyrrolo[2,3-e][1,2,4]triazolo[4,3-a]pyrazin-1-yl)cyclopentyloxy)nicotino-nitrile carbonitrile (prepared using II from 6-hydroxynicotinonitrile and Preparation #FF.1, D with $Na_2CO_3$) [Table 2, Method 21, $R_t$ 7.4 min, or = positive] | 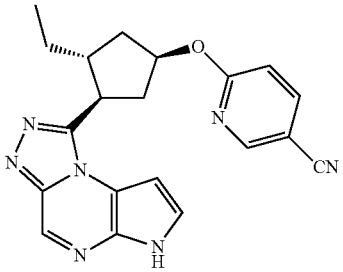 | AA.1.36 | 2.02 (b) | 374 |
| 5-(3-ethyl-4-(6H-pyrrolo[2,3-e][1,2,4]triazolo[4,3-a]pyrazin-1-yl)cyclopentyloxy)pyrazine-2-carbonitrile (prepared using LL from Preparation #JJ.1) [Table 2, Method 22, $R_t$ 15.5 min, or = negative] | 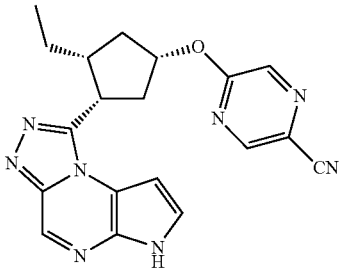 | AA.1.37 | 1.99 (b) | 375 |
| 5-(3-ethyl-4-(6H-pyrrolo[2,3-e][1,2,4]triazolo[4,3-a]pyrazin-1-yl)cyclopentyloxy)pyrazine-2-carbonitrile (prepared using LL from Preparation #JJ.1) [Table 2, Method 22, $R_t$ 16.4 min, or = positive] | 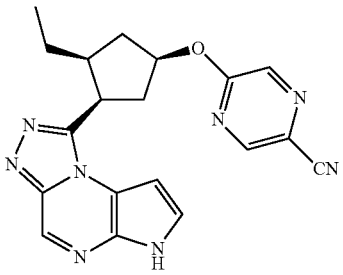 | AA.1.38 | 1.97 (b) | 375 |
| N-(1 -(6H-imidazo[1,5-a]pyrrolo[2,3-e]pyrazin-1-yl)pyrrolidin-3-yl)cyclopropanesulfonamide (Example #15) [Table 2, Method 16, $R_t$ = 15.3 min, or = negative] | 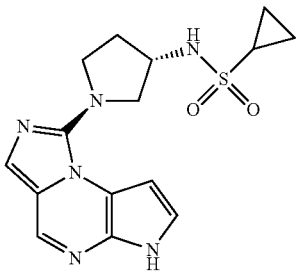 | AA.1.39 | 1.42 (a) | 347 |
| N-(1-(6H-imidazo[1,5-a]pyrrolo[2,3-e]pyrazin-1-yl)pyrrolidin-3-yl)cyclopropanesulfonamide (Example #15) [Table 2, Method 16, $R_t$ =12.5 min, or = positive] | 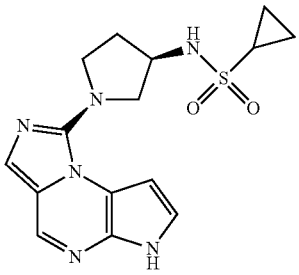 | AA.1.40 | 1.42 (a) | 347 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| 5-((cis-3-ethyl-4-(6H-pyrrolo[2,3-e][1,2,4]triazolo[4,3-a]pyrazin-1-yl)cyclopentyl)methoxy)-pyrazine-2-carbonitrile (prepared using P from Preparation #11 with LAH, JJ with 2-chloro-5-cyanopyrazine [ArkPharm], TT with HCl, A from Example #1, Step D, HATU and TEA, B with TEA, D with $Na_2CO_3$) [Table 2, Method 11, $R_t$ = 7.5 min, or = ND] | 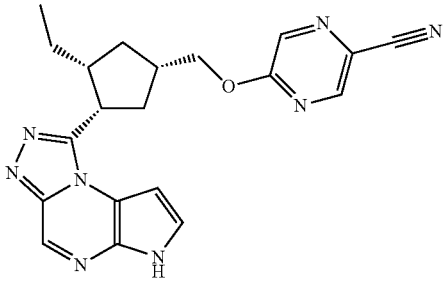 | AA.1.41 | 1.99 (a) | 389 |
| 5-((cis-3-ethyl-4-(6H-pyrrolo[2,3-e][1,2,4]triazolo[4,3-a]pyrazin-1-yl)cyclopentyl)methoxy)-pyrazine-2-carbonitrile (prepared using P from Preparation #11 with LAH, JJ with 2-chloro-5-cyanopyrazine [ArkPharm], TT with HCl, A from Example #1, Step D, HATU and TEA, B with TEA, D with $Na_2CO_3$) [Table 2, Method 11, $R_t$ = 16.1 min, or = ND] | 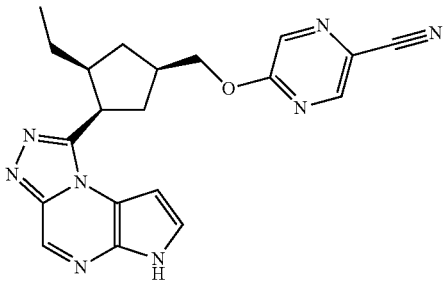 | AA.1.42 | 1.99 (a) | 389 |
| N-(cis-4-ethyl-3-fluoro-3-(6H-pyrrolo[2,3-e][1,2,4]triazolo[4,3-a] pyrazin-1-yl)cyclopentyl)cyclo-propanesulfonamide (prepared using Z from Preparation #7 with NaOH, A from Example #1, Step D, HATU and TEA, B with TEA, D with $Na_2CO_3$) [Table 2, Method 10, $R_t$ =18.3 min, or = negative] | 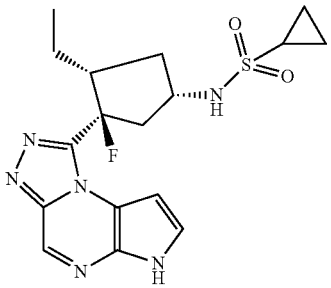 | AA.1.43 | 1.71 (a) | 393 |
| N-(cis-4-ethyl-3-fluoro-3-(6H-pyrrolo[2,3-e][1,2,4]triazolo[4,3-a]pyrazin-1-yl)cyclopentyl)cyclo-propanesulfonamide (prepared using Z from Preparation #7 with NaOH, A from Example #1, Step D, HATU and TEA, B with TEA, D with $Na_2CO_3$) [Table 2, Method 10, $R_t$ = 14.9 min, or = positive] | 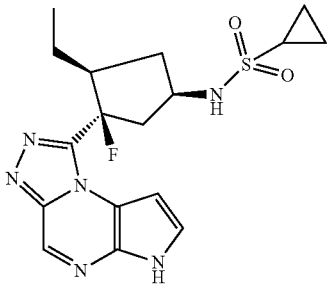 | AA.1.44 | 1.74 (a) | 393 |
| N-(cis-4-ethyl-3-fluoro-3-(6H-pyrrolo[2,3-e][1,2,4]triazolo[4,3-a]pyrazin-1-yl)cyclopentyl)cyclo-propanesulfonamide (prepared using Z from Preparation #7 with NaOH, A from Example #1, Step D, HATU and TEA, B with TEA, D with $Na_2CO_3$) [Table 2, Method 10, $R_t$ = 15.5 min, or = positive] | 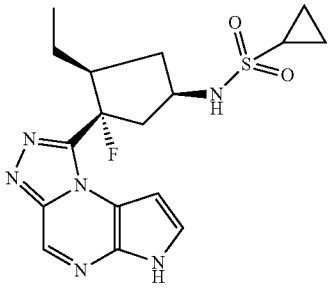 | AA.1.45 | 1.73 (a) | 393 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| N-(cis-4-ethyl-3-fluoro-3-(6H-pyrrolo[2,3-e][1,2,4]triazolo[4,3-a]pyrazin-1-yl)cyclopentyl)cyclo-propanesulfonamide (prepared using Z from Preparation #7 with NaOH, A from Example #1, Step D, HATU and TEA, B with TEA, D with $Na_2CO_3$) [Table 2, Method 10, $R_t$ =16.5 min, or = negative] | 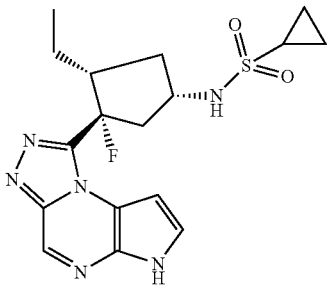 | AA.1.46 | 1.75 (a) | 393 |
| 1-(cis-4-((azetidin-1-ylsulfonyl)methyl)-2-ethylcyclopentyl)-6H-pyrrolo[2,3-e][1,2,4]triazolo[4,3-a]pyrazine (prepared using the conditions described in Example #1, Step K substituting azetidine for diethylamine, Z with NaOH, A from Example #1, Step D, HATU and TEA, B with TEA, D with NaOH) [Table 2, Method 27, $R_t$ = 14.3 min, racemic] | 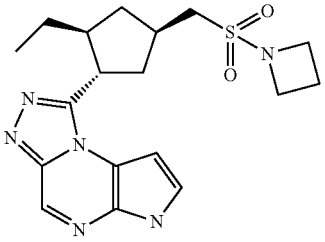 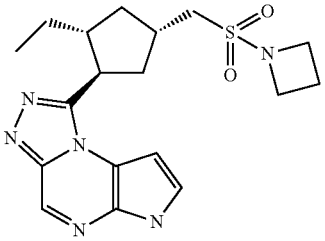 | AA.1.47 | 1.70 (a) | 389 |
| 1-(cis-4-((azetidin-1-ylsulfonyl)methyl)-2-ethylcyclopentyl)-6H-pyrrolo[2,3-e][1,2,4]triazolo[4,3-a]pyrazine (prepared using the conditions described in Example #1, Step K substituting azetidine for diethylamine, Step, Z with NaOH, A from Example #1, Step D, HATU and TEA, B with TEA, D with NaOH) [Table 2, Method 27, $R_t$ = 15.5 min, or = positive] | 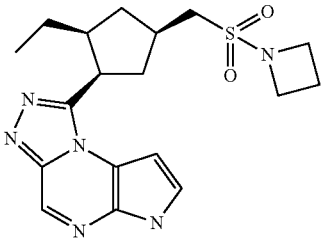 | AA.1.48 | 1.70 (a) | 389 |
| N-(3-(6H-imidazo[1,5-a]pyrrolo[2,3-e]pyrazin-1-yl)-4-methylcyclopentyl)aniline (prepared using TT from Preparation #8 with HCl, H from Example #5, Step C, HATU and TEA, Q with Lawesson's reagent and mercury (II) trifluoroacetate, D with NaOH) [Table 2, Method 25, $R_t$ = 8.0 min, or = negative] | 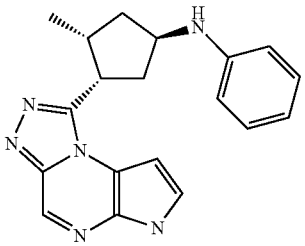 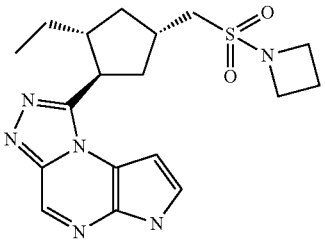 | AA.1.49 | 2.27 (a) | 332 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| N-(3-(6H-imidazo[1,5-a]pyrrolo[2,3-e]pyrazin-1-yl)-4-methylcyclopentyl)aniline (prepared using TT from Preparation #8 with HCl, H from Example #5, Step C, HATU and TEA, Q with Lawesson's reagent and mercury (II) trifluoroacetate, D with NaOH) [Table 2, Method 25, $R_t$ = 7.1 min, or = positive] | 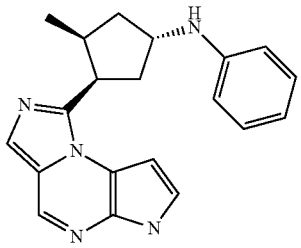 | AA.1.50 | 2.24 (a) | 332 |
| N-(3 -methyl-4-(6H-pyrrolo[2,3-e][1,2,4]triazolo[4,3-a]pyrazin-1-yl)cyclopentyl)aniline (prepared using TT from Preparation #8 with HCl, A from Example #1, Step D, HATU and TEA, B with TEA, D with NaOH) [Table 2, Method 19, $R_t$ = 17.1 min, or = negative] | 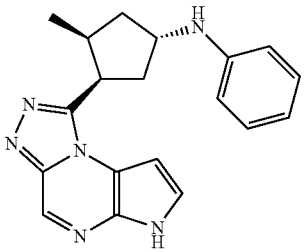 | AA.1.51 | 1.99 (a) | 333 |
| N-(3-methyl-4-(6H-pyrrolo[2,3-e][1,2,4]triazolo[4,3-a]pyrazin-1-yl)cyclopentyl)aniline (prepared using TT from Preparation #8 with HCl, A from Example #1, Step D, HATU and TEA, B with TEA, D with NaOH) [Table 2, Method 19, $R_t$ = 18.7 min, or = positive] | 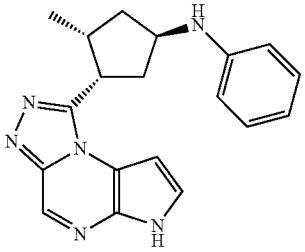 | AA.1.52 | 2.02 (a) | 333 |
| 3-(cis-4-ethyl-3-(6H-imidazo[1,5-a]pyrrolo[2,3-e]pyrazin-1-yl)piperidin-1-yl)-3-oxopropanenitrile (prepared using W from Preparation #9 with $Pd(OH)_2$ on C, TT with HCl, M, H from Example #5, Step C, HATU and DIEA, Q with Lawesson's reagent and mercury (II) trifluoroacetate, D with NaOH, E with HCl, H from cyanoacetic acid, EDC, and DIEA) [Table 2, Method 26, $R_t$ = 8.9 min, or = negative] | 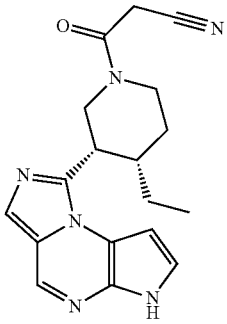 | AA.1.53 | 1.73 (a) | 337 |
| 3-(cis-4-ethyl-3-(6H-imidazo[1,5-a]pyrrolo[2,3-e]pyrazin-1-yl)piperidin-1-yl)-3-oxopropanenitrile (prepared using W from Preparation #W with $Pd(OH)_2$ on C, TT with HCl, M, H from Example #5, Step C, HATU and DIEA, Q with Lawesson's reagent and mercury (II) trifluoroacetate, D with NaOH, E with HCl, H from cyanoacetic acid, EDC, and DIEA) [Table 2, Method 26, $R_t$ = 16.1 min, or = positive] | 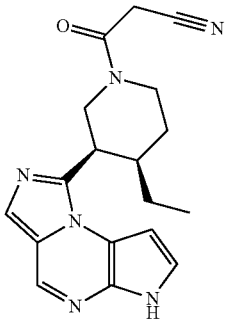 | AA.1.54 | 1.73 (a) | 337 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| 1-(3-(pyrazolo[3,4-d]pyrrolo[2,3-b]pyridin-1(6H)-yl)piperidine-1-carbonyl)cyclopropanecarbonitrile (prepared using Y from Preparation #10 with $Pd(OH)_2$ on C, H from 1-cyanocyclopropanecarboxylic acid, HATU, and DIEA) [Table 2, Method 10, $R_t$ = 18.6 min, or = negative] | 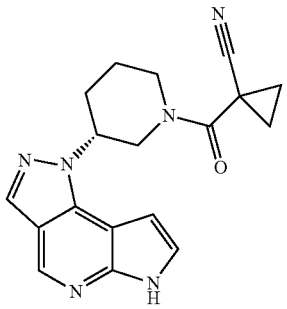 | AA.1.55 | 1.81 (a) | 335 |
| 1-(3-(pyrazolo[3,4-d]pyrrolo[2,3-b]pyridin-1(6H)-yl)piperidine-1-carbonyl)cyclopropanecarbonitrile (prepared using Y from Preparation #10 with $Pd(OH)_2$ on C, H from 1-cyanocyclopropanecarboxylic acid, HATU, and DIEA) [Table 2, Method 10, $R_t$ = 21.6 min, or = positive] | 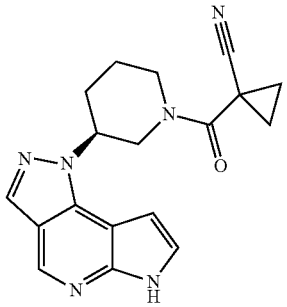 | AA.1.56 | 1.83 (a) | 335 |
| 1-(-2-ethyl-4-(2-(tetrahydro-2H-pyran-4-yl)ethoxy)cyclopentyl)-6H-pyrrolo[2,3-e][1,2,4]triazolo[4,3-a]pyrazine prepared using FFF from Example #22 Step D with 2-(tetrahydro-2H-pyran-4-yl)acetaldehyde (Biofine), Z, A with Example #1, Step D, HATU, and TEA, B with TEA, D with NaOH [Table 2, Method 33, $R_t$ = 11.2 min, or = negative] | 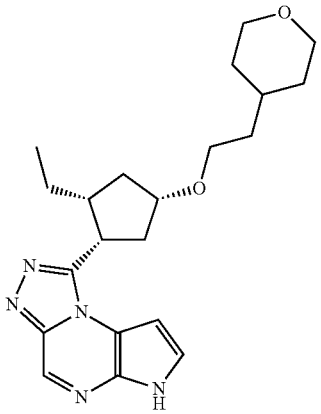 | AA.1.57 | 185 (a) | 384 |
| 1-(-2-ethyl-4-(2-(tetrahydro-2H-pyran-4-yl)ethoxy)cyclopentyl)-6H-pyrrolo[2,3-e][1,2,4]triazolo[4,3-a]pyrazine prepared using FFF from Example #22 Step D with 2-(tetrahydro-2H-pyran-4-yl)acetaldehyde (Biofine), Z, A with Example #1, Step D, HATU, and TEA, B with TEA, D with NaOH [Table 2, Method 33, $R_t$ = 5.2 min, or = negative] | 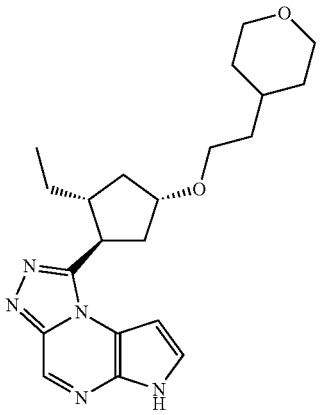 | AA.1.58 | 1.90 (a) | 384 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| 3-Ethyl-4-(6H-pyrrolo[2,3-e][1,2,4]triazolo[4,3-a]pyrazin-1-yl)cyclopentanone prepared using D with Preparation #25 and NaOH [Table 2, Method 34, $R_t$ = 9.7 min, or = negative] | 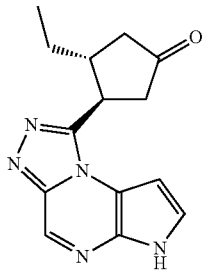 | AA.1.59 | 1.34 (a) | 270 |
| N-(((1S,3S)-3-(6H-imidazo[1,5-a]pyrrolo[2,3-e]pyrazin-1-yl)cyclopentyl)methyl)cyclopropane sulfonamide and N-(((1S,3R)-3-(6H-imidazo[1,5-a]pyrrolo[2,3-e]pyrazin-1-yl)cyclopentyl)methyl)cyclopropane sulfonamide (prepared using H from Example #5 Step C and Preparation #M.1, HATU and DIEA; Q with Lawesson's reagent and mercury (II) trifluoroacetate; K with cyclopropanesulfonyl chloride [Matrix]; D with NaOH) [Table 2, Method 21, $R_t$ = 9.3 min, or = ND] | 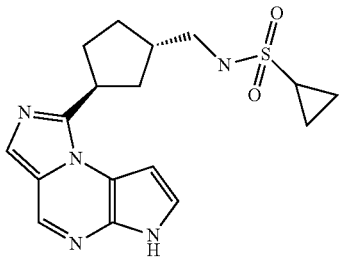 | AA.1.60* | 1.67 (a) | 360 |
| N-(((1S,3S)-3-(6H-imidazo [1,5-a]pyrrolo[2,3-e]pyrazin-1-yl)cyclopentyl)methyl)cyclopropane sulfonamide and N-(((1S,3R)-3-(6H-imidazo[1,5-a]pyrrolo[2,3-e]pyrazin-1-yl)cyclopentyl)methyl)cyclopropane sulfonamide (prepared using H from Example #5 Step C and Preparation #M.1, HATU and DIEA; Q with Lawesson's reagent and mercury (II) trifluoroacetate; K with cyclopropanesulfonyl chloride [Matrix]; D with NaOH) [Table 2, Method 21, $R_t$ = 11.6 min, or = ND] | 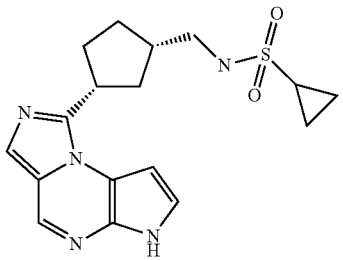 | AA.1.61* | 1.70 (a) | 360 |
| N-(((1S,3R)-3-(6H-imidazo[1,5-a]pyrrolo[2,3-e]pyrazin-1-yl)cyclopentyl)methyl)-3,3,3-trifluoropropane-1-sulfonamide and N-(((1S,3S)-3-(6H-imidazo [1,5-a]pyrrolo[2,3-e]pyrazin-1-yl)cyclopentyl)methyl)-3,3,3-trifluoropropane-1-sulfonamide (prepared using H from Example #5 Step C and Preparation #M.1, HATU and DIEA; Q with Lawesson's reagent and mercury (II) trifluoroacetate; K with 3,3,3-trifluoropropylsulfonyl chloride [Matrix]; D with NaOH) [Table 2, Method 33, $R_t$ = 11.8 min, or = negative] | 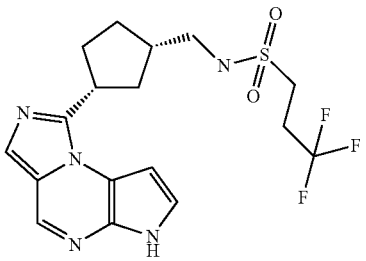 | AA.1.62 * | 1.90 (a) | 416 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| N-(((1S,3R)-3-(6H-imidazo[1,5-a]pyrrolo[2,3-e]pyrazin-1-yl)cyclopentyl)methyl)-3,3,3-trifluoropropane-1-sulfonamide and N-(((1S,3S)-3-(6H-imidazo[1,5-a]pyrrolo[2,3-e]pyrazin-1-yl)cyclopentyl)methyl)-3,3,3-trifluoropropane-1-sulfonamide (prepared using H from Example #5 Step C and Preparation #M.1, HATU and DIEA; Q with Lawesson's reagent and mercury (II) trifluoroacetate; K with 3,3,3-trifluoropropylsulfonyl chloride [Matrix]; D with NaOH) [Table 2, Method 33, $R_t$ = 9 min, or = negative] | 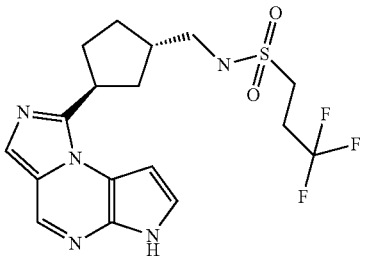 | AA.1.63* | 1.93 (a) | 416 |
| N-((3-ethyl-4-(6H-pyrrolo[2,3-e][1,2,4]triazolo[4,3-a]pyrazin-1-yl)cyclopentyl)methyl)cyclopropane sulfonamide (prepared using K with Preparation #21 Step C and cyclopropanesulfonyl chloride [Matrix]; QQQ with TFA; A from Example #1 Step D, HATU and TEA; B with TEA; D with NaOH [Table 2, Method 5, $R_t$ = 5.8 min, or = positive] | 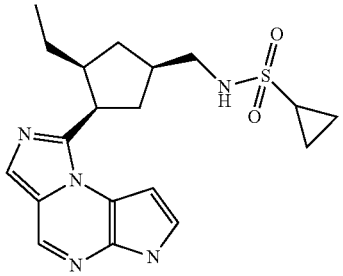 or 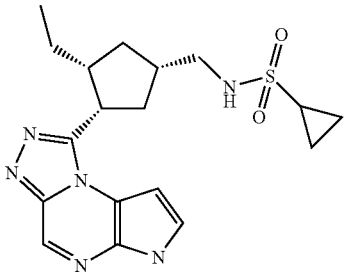 | AA.1.64 | 1.61 (a) | 389 |
| N-((3-ethyl-4-(6H-pyrrolo[2,3-e][1,2,4]triazolo[4,3-a]pyrazin-1-yl)cyclopentyl)methyl)cyclopropane sulfonamide (prepared using K with Preparation #21 Step C and cyclopropanesulfonyl chloride [Matrix]; QQQ with TFA; A from Example #1 Step D, HATU and TEA; B with TEA; D with NaOH) [Table 2, Method 5, $R_t$ = 11.4 min, or = negative] | 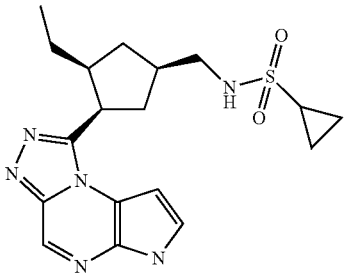 or 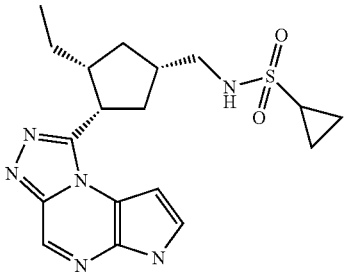 | AA.1.65 | 1.61 (a) | 389 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| 1-(2-ethyl-4-((tetrahydro-2H-pyran-4-yl)methoxy)cyclopentyl)-6H-pyrrolo[2,3-e][1,2,4]triazolo[4,3-a]pyrazine (prepared using FFF from Example 22 Step D and tetrahydro-2H-pyran-4-carbaldehyde [J & W PharmLab]; Z with NaOH; A from Example #1 Step D, HATU and TEA; B with TEA; D with NaOH) [Table 2, Method 47, $R_t$ = 8.7 min, or = negative] | 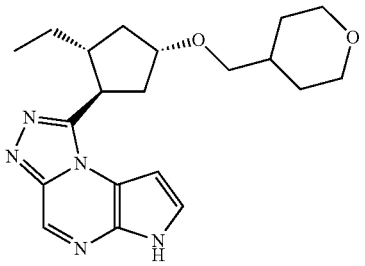 | AA.1.66 | 1.83 (a) | 370 |
| 1-(2-ethyl-4-((tetrahydro-2H-pyran-4-yl)methoxy)cyclopentyl)-6H-pyrrolo[2,3-e][1,2,4]triazolo[4,3-a]pyrazine (prepared using FFF from Example #22 Step D and tetrahydro-2H-pyran-4-carbaldehyde [J & W PharmLab]; Z with NaOH; A from Example #1 Step D, HATU and TEA; B with TEA; D with NaOH) [Table 2, Method 47, Rt = 13.8 min, or = negative] | 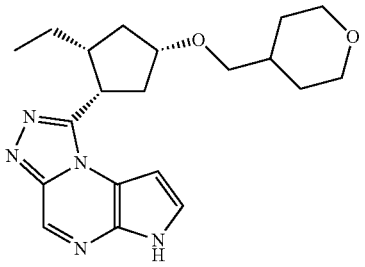 | AA.1.67 | 1.79 (a) | 370 |
| 1-(2-ethyl-4-(tetrahydro-2H-thiopyran 1,1-dioxide-4-yloxy)cyclopentyl)-6H-pyrrolo[2,3-e][1,2,4]triazolo[4,3-a]pyrazine (prepared using FFF from Example #22 Step D and dihydro-2H-thiopyran-4(3H)-one; LLL with mCPBA; Z with NaOH; A from Example #1 Step D, HATU and TEA; B with DIEA; D with NaOH) [Table 2, Method 48, Rt = 17.1 min, or = negative] | 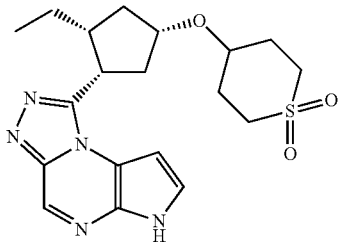 | AA.1.68 | 1.67 (a) | 404 |
| 1-(2-ethyl-4-(tetrahydro-2H-thiopyran 1,1-dioxide-4-yloxy)cyclopentyl)-6H-pyrrolo[2,3-e][1,2,4]triazolo[4,3-a]pyrazine (prepared using FFF from Example #22 Step D and dihydro-2H-thiopyran-4(3H)-one; LLL with mCPBA; Z with NaOH; A from Example #1 Step D, HATU and TEA; B with DIEA; D with NaOH) [Table 2, Method 48, $R_t$ = 11.6 min, or = negative] | 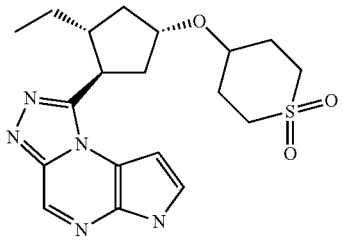 | AA.1.69 | 1.69 (a) | 404 |
| 1-(2-ethyl-4-(tetrahydro-2H-thiopyran 1,1-dioxide-4-yloxy)cyclopentyl)-6H-pyrrolo[2,3-e][1,2,4]triazolo[4,3-a]pyrazine (prepared using II from Example 22 Step C with 4-nitrobenzoic acid; SS; VV; FFF with dihydro-2H-thiopyran-4(3H)-one; LLL with mCPBA; Z with NaOH; A from Example #1 Step D, HATU and TEA; B with DIEA; D with NaOH) [Table 2, Method 32, $R_t$ = 17.3 min, or = negative] | 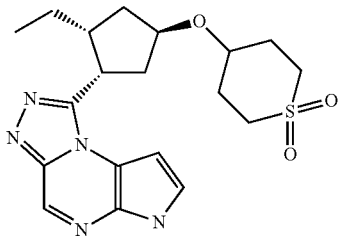 | AA.1.70 | 1.66 (a) | 404 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| 1-(2-ethyl-4-isopropoxycyclopentyl)-6H-pyrrolo[2,3-e][1,2,4]triazolo[4,3-a]pyrazine (prepared using II from Example 22 Step C with 4-nitrobenzoic acid; SS; VV; FFF with acetone; Z with NaOH; A from Example #1 Step D, HATU and TEA; B with DIEA; D with NaOH) 2, Method 28, $R_t$ = 7.1 min, or = negative] | 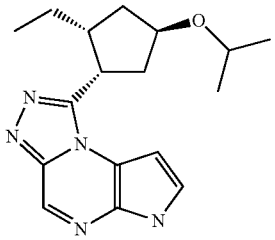 | AA.1.71 | 1.85 (a) | 314 |
| N-((3-ethyl-4-(3H-imidazo[1,2-a]pyrrolo[2,3-e]pyrazin-8-yl)cyclopentyl)methyl)-3,3,3-trifluoropropane-1-sulfonamide (prepared using X from Preparation #22 Step C with dibenzylamine and $NaBH(OAc)_3$; TT with HCl; R with trimethylsilyl diazomethane, S with Example #3 Step E; E with TFA; T using Lawesson's reagent; D with NaOH; KK; Y with $Pd(OH)_2$ on C; K with 3,3,3-trifluoropropylsulfonyl chloride [Matrix]; LL with $NH_4OH$) [Table 2, Method 49 $R_t$ = 24.9 min then 50, $R_t$ = 8.6 min, or = negative] | 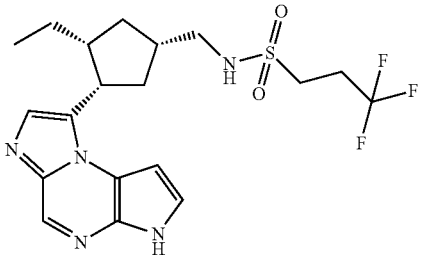 or 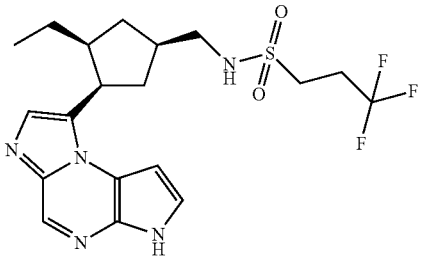 | AA.1.72 | 1.96 (a) | 444 |
| N-((3-ethyl-4-(3H-imidazo[1,2-a]pyrrolo[2,3-e]pyrazin-8-yl)cyclopentyl)methyl)-3,3,3-trifluoropropane-1-sulfonamide(prepared using X from Preparation #22 Step C with dibenzylamine and $NaBH(OAc)_3$; TT with HCl; R with trimethylsilyl diazomethane, S with Example #3 Step E; E with TFA; T using Lawesson's reagent; D with NaOH; KK; Y with $Pd(OH)_2$ on C; K with 3,3,3-trifluoropropylsulfonyl chloride [Matrix]; LL with $NH_4OH$) [Table 2, Method 49 $R_t$ = 15 min then 50 $R_t$ = 8.7 min, or = positive] | 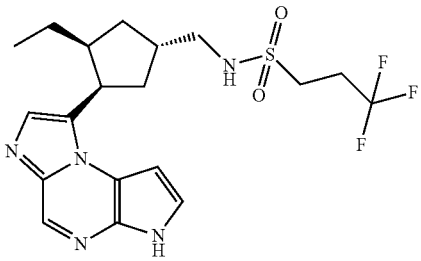 or 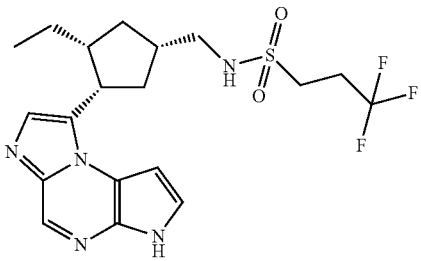 | AA.1.73 | 1.96 (a) | 444 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| N-((3-ethyl-4-(3H-imidazo[1,2-a]pyrrolo[2,3-e]pyrazin-8-yl)cyclopentyl)methyl)-3,3,3-trifluoropropane-1-sulfonamide (prepared using X from Preparation #22 Step C with dibenzylamine and $NaBH(OAc)_3$; TT with HCl; R with trimethylsilyl diazomethane, S with Example #3 Step E; E with TFA; T using Lawesson's reagent; D with NaOH; KK; Y with $Pd(OH)_2$ on C; K with 3,3,3-trifluoropropylsulfonyl chloride [Matrix]; LL with $NH_4OH$) [Table 2, Method 49 $R_t$ = 20.7 min then 50 $R_t$ = 9.5 min, or = positive] | 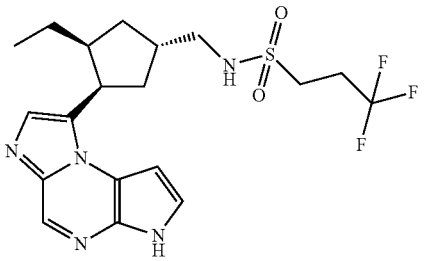 or 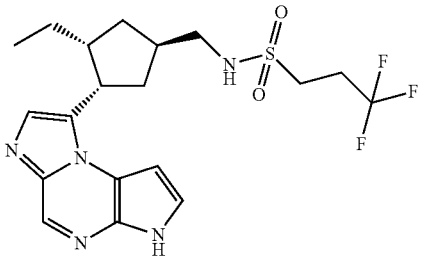 | AA.1.74 | 1.96 (a) | 444 |
| N-((3-ethyl-4-(3H-imidazo[1,2-a]pyrrolo[2,3-e]pyrazin-8-yl)cyclopentyl)methyl)-3,3,3-trifluoropropane-1-sulfonamide (prepared using X from Preparation #22 Step C with dibenzylamine and $NaBH(OAc)_3$; TT with HCl; R with trimethylsilyl diazomethane, S with Example #3 Step E; E with TFA; T using Lawesson's reagent; D with NaOH; KK; Y with $Pd(OH)_2$ on C; K with 3,3,3-trifluoropropylsulfonyl chloride [Matrix]; LL with $NH_4OH$) [Table 2, Method 49 $R_t$ =26.5 min then 50 $R_t$ = 9 min, or = negative] | 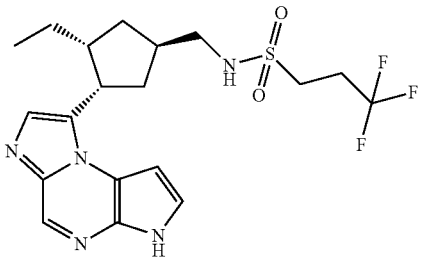 or 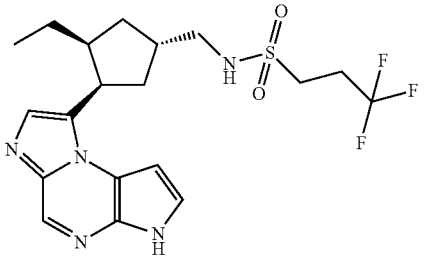 | AA.1.75 | 1.97 (a) | 444 |
| N-(3-ethyl-4-(3H-imidazo[1,2-a]pyrrolo[2,3-e]pyrazin-8-yl)cyclopentyl)-3,3,3-trifluoropropane-1-sulfonamide (prepared using X from Example #22 Step B with dibenzylamine, TT with HCl, R with trimethylsilyl diazomethane, S with Example #3 Step E, E with TFA, T with Lawesson's reagent, D with NaOH, Y, K with 3,3,3-trifluoropropane-1-sulfonyl chloride (Matrix) and DIEA) [Table 2, Method 31, $R_t$ = 16.9 min, or = postive] | 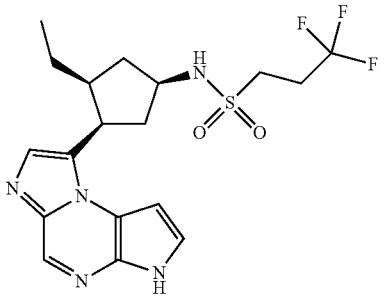 | AA.1.76 | 1.94 (a) | 430 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| N-(3-ethyl-4-(3H-imidazo[1,2-a]pyrrolo[2,3-e]pyrazin-8-yl)cyclopentyl)-3,3,3-trifluoropropane-1-sulfonamide (prepared using X from Example #22 Step B with dibenzylamine, TT with HCl ,R with trimethylsilyl diazomethane, S with Example #3 Step E, E with TFA, T with Lawesson's reagent, D with NaOH, Y, K with 3,3,3-trifluoropropane-1-sulfonyl chloride (Matrix) and DIEA) [Table 2, Method 31, $R_t$ = 24 min, or = negative] | | AA.1.77 | 1.94 (a) | 430 |
| N-(3-ethyl-4-(3H-imidazo[1,2-a]pyrrolo[2,3-e]pyrazin-8-yl)cyclopentyl)cyclopropane-sulfonamide (prepared using X from Example #22 Step B with dibenzylamine, TT with HCl ,R with trimethylsilyl diazomethane, S with Example #3 Step E, E with TFA, T with Lawesson's reagent, D with NaOH, Y, K with cyclopropanesulfonyl chloride (Matrix) and DIEA) [Table 2, Method 12, $R_t$ = 15 min, or = negative] | | AA.1.78 | 1.73 (a) | 374 |
| N-(3-ethyl-4-(3H-imidazo[1,2-a]pyrrolo[2,3-e]pyrazin-8-yl)cyclopentyl)-3,3-difluoroazetidine-1-sulfonamide (prepared from prepared using X from Example #22 Step B with dibenzylamine, TT with HCl ,R with trimethylsilyl diazomethane, S with Example #3 Step E, E with TFA, T with Lawesson's reagent, D with NaOH, Y, ZZ, AAA with 3,3-difluoroazetidine hydrochloride and TEA) [Table 2, Method 40, $R_t$ = 15.8 min, or = negative] | | AA.1.79 | 1.84 (a) | 425 |
| 1-(4-(cyclopropylmethoxy)-2-ethylcyclopentyl)-6H-pyrrolo[2,3-e][1,2,4]triazolo[4,3-a]pyrazine (prepared using FFF from Example #22 Step D and cyclopropanecarboxaldehyde, Z with NaOH, A with Example #1 Step D, HATU and TEA, B with DIEA, D with NaOH) [Table 2, Method 38, $R_t$ = 13.1 min, or = negative] | | AA.1.80 | 1.90 (a) | 326 |
| N-3-(3H-imidazo[1,2-a]pyrrolo[2,3-e]pyrazin-8-yl)-4-methylcyclopentyl)-2-hydroxyethylamino-1-sulfonamide (prepared using D from Example #25 Step R with NaOH, LL) [Table 2, Method 32, $R_t$ = 20.2 min, or = negative] | | AA.1.81 | 1.21 | 379 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| N-3-(3H-imidazo[1,2-a]pyrrolo[2,3-e]pyrazin-8-yl)-4-methylcyclopentyl)-2-methyl-2-hydroxypropylamino-1-sulfonamide (prepared using AAA from Example #25 Step R and 2-methyl-2-hydroxypropyl amine, D with NaOH, LL) [Table 2, Method 36, $R_t$ = 12.4 min, or = negative] | 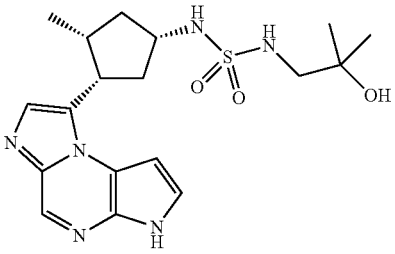 | AA.1.82 | 1.38 | 407 |
| N-(3-(3H-imidazo[1,2-a]pyrrolo[2,3-e]pyrazin-8-yl)-4-methylcyclopentyl)morpholine-4-sulfonamide (prepared using AAA from Example #25 Step R and morpholine, LL) [Table 2, Method 37, $R_t$ = 16.4 min, or = negative] | 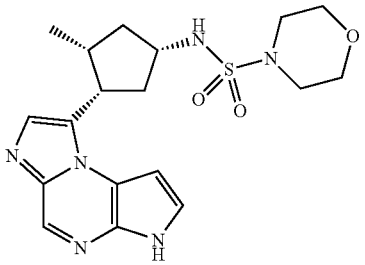 | AA.1.83 | 1.53 | 405 |
| N-3-(3H-imidazo[1,2-a]pyrrolo[2,3-e]pyrazin-8-yl)-4-methylcyclopentyl)-3-amino-1-N-methyazetidine-1-sulfonourea (prepared using AAA from Example #25 Step R and 3-amino-1-N-methyl azetidine, LL) [Table 2, Method 37, $R_t$ = 16.9 min, or = negative] | 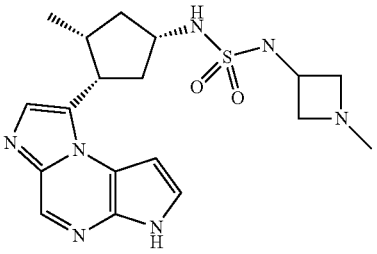 | AA.1.84 | 1.14 | 404 |
| 1-(8-ethyl-1,4-dioxaspiro[4.4]nonan-7-yl)-6H-pyrrolo[2,3-e][1,2,4]4,3-a]pyrazine (prepared using D from Preparation #25 Step D and NaOH) [Table 2, Method 12, $R_t$ = 9.9 min, or = negative] | 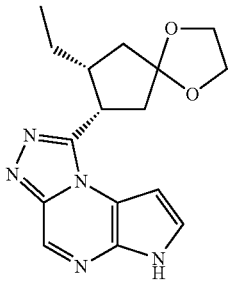 | AA.1.85 | 1.52 (a) | 314 |
| 3-ethyl-4-(6H-pyrrolo[2,3-e][1,2,4]triazolo[4,3-a]pyrazin-1-yl)-N-(2,2,2-trifluoroethyl)cyclopentanamine (prepared using X from Preparation #25 and 2,2,2-trifluoroethanamine, D with NaOH) [Table 2, Method 31, $R_t$ = 16.9 min, or = negative] | 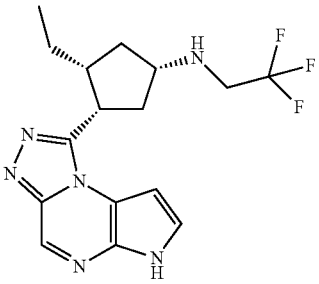 | AA.1.86 | 1.62 (a) | 353 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| 1-(4-(3,3-difluoroazetidin-1-yl)-2-ethylcyclopentyl)-6H-pyrrolo[2,3-e][1,2,4]triazolo[4,3-a]pyrazine (prepared using X from Preparation #25 and 3,3-difluoroazetidine hydrochloride [Matrix], D with NaOH) [Table 2, Method 21, $R_t$ = 9.4 min, or = negative] | 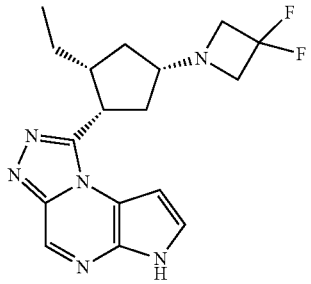 | AA.1.87 | 1.57 (a) | 347 |
| 1-(4-(3,3-difluoropyrrolidin-1-yl)-2-ethylcyclopentyl)-6H-pyrrolo[2,3-e][1,2,4]triazolo[4,3-a]pyrazine (prepared using X from Preparation #25 and 3,3-difluoropyrrolidine hydrochloride, D with NaOH) [Table 2, Method 20, $R_t$ = 9.5 min, or = negative] | 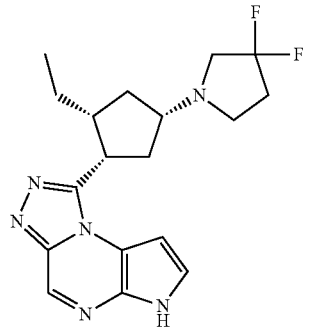 | AA.1.88 | 1.60 (a) | 361 |
| 1-(4-(4,4-dimethylcyclohexyloxy)-2-ethylcyclopentyl)-6H-pyrrolo[2,3-e][1,2,4]triazolo[4,3-a]pyrazine (prepared using II from Example #22 Step C with 4-nitrobenzoic acid, SS with NaOH, VV, FFF with 4,4-dimethylcyclohexanone, Z with NaOH, A with Example #1 Step D, HATU and TEA, B with DIEA, D with NaOH) [Table 2, Method 41, Rt = 10.5 min or = negative] | 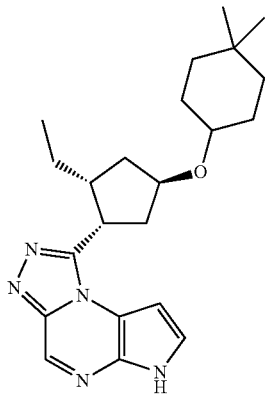 | AA.1.89 | 2.45 (b) | 382 |
| 1-(4-(cyclopropylmethoxy)-2-ethylcyclopentyl)-6H-pyrrolo[2,3-e][1,2,4]triazolo[4,3-a]pyrazine (prepared using II from Example #22 Step C with 4-nitrobenzoic acid, SS with NaOH, VV, FFF with cyclopropanecarboxaldehyde, Z with NaOH, A with Example #1 Step D, HATU and TEA, B with DIEA, D with NaOH) [Table 2, Method 42, $R_t$ = 6.8 min, or = negative] | 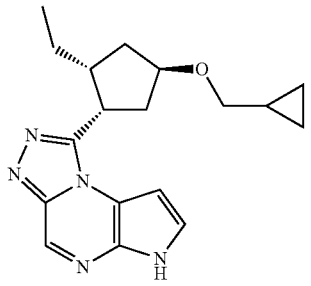 | AA.1.90 | 1.89 (b) | 326 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| 1-(2-ethyl-4-(tetrahydro-2H-pyran-4-yloxy)cyclopentyl)-6H-pyrrolo[2,3-e][1,2,4]triazolo[4,3-a]pyrazine (prepared using II from Example #22 Step C with 4-nitrobenzoic acid, SS with NaOH, VV, FFF with tetrahydro-4H-pyran-4-one, Z with NaOH, A from Example #1 Step D, HATU and TEA, B with DIEA, D with NaOH) [Table 2, Method 33, $R_t$ = 7.6 min, or = negative] | 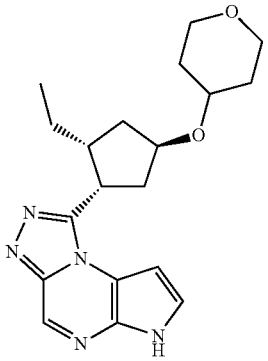 | AA.1.91 | 1.63 (b) | 356 |
| 3-chloro-N-(3-ethyl-4-(3H-imidazo[1,2-a]pyrrolo[2,3-e]pyrazin-8-yl)cyclopentyl)-4-fluorobenzenesulfonamide (prepared using X from Example #22 Step B with dibenzylamine, TT with HCl, R with trimethylsilyl diazomethane, S with Example #3 Step E, E with TFA, T with Lawesson's reagent, D with NaOH, Y, K with 3-chloro-4-fluorobenzenesulfonyl chloride [Lancaster] and DIEA [Table 2, Method 19, $R_t$ = 24.2 min, or = negative] | 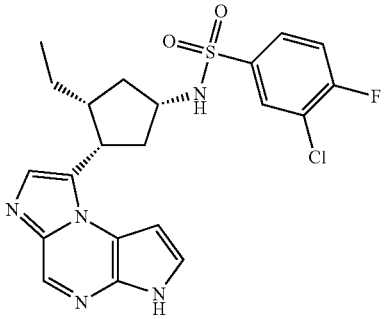 | AA.1.92 | 2.11 (a) | 462 |
| 4-(3-methyl-4-(6H-pyrrolo[2,3-e][1,2,4]triazolo[4,3-a]pyrazin-1-yl)cyclopentyloxy)benzonitril (prepared using P from Example #7, step G, EE with 4-methoxybenzyl-2,2,2-trichloroacetimidate, Z with NaOH,, A with Example #1 Step D, HATU, and TEA, B with DIEA, FF with 2,3-dichloro-5,6-dicyano-p-benzoquinone, II with hydroxybenzonitrile, D with $Na_2CO_3$) [Table 2, Method 17, $R_t$ = 25.7 min, or = positive] | 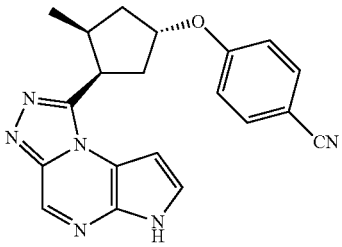 | AA.1.93 | 1.94 (b) | 430 |
| 4-(3-methyl-4-(6H-pyrrolo[2,3-e][1,2,4]triazolo[4,3-a]pyrazin-1-yl)cyclopentyloxy)benzonitrile (prepared using P from Example #7, step G, EE with 4-methoxybenzyl-2,2,2-tchloroacetimidate, Z with NaOH, A with Example #1 Step D, HATU, and TEA, B with DIEA, FF with 2,3-dichloro-5,6-dicyano-p-benzoquinone, II with hydroxybenzonitrile, D with $Na_2CO_3$) [Table 2, Method 17, $R_t$ = 14.7 min, or = negative] | 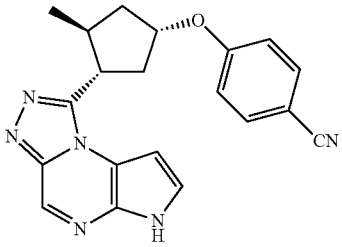 | AA.1.94 | 1.94 (b) | 430 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| 1-(2-ethyl-4-(5-(trifluoromethyl)pyridin-2-yloxy)cyclopentyl)-6H-pyrrolo[2,3-e][1,2,4]triazolo[4,3-a]pyrazine (prepared using II from 5-(trifluoromethyl)pyridin-2-ol and Preparation #FF.1, D with NaOH) [Table 2, Method 21, $R_t$ = 8 min, or = negative] | 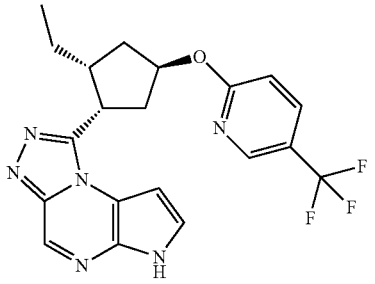 | AA.1.95 | 2.33 (b) | 417 |
| 1-(2-ethyl-4-(5-(trifluoromethyl)pyridin-2-yloxy)cyclopentyl)-6H-pyrrolo[2,3-e][1,2,4]triazolo[4,3-a]pyrazine (prepared using II from 5-(trifluoromethyl)pyridin-2-ol and Preparation #FF.1, D with NaOH) [Table 2, Method 21, $R_t$ = 5.3 min, or = positive] | 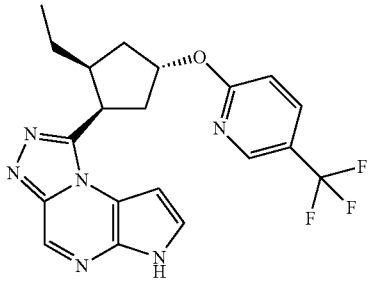 | AA.1.96 | 2.33 (b) | 417 |
| 5-(3-ethyl-4-(6H-pyrrolo[2,3-e][1,2,4]triazolo[4,3-a]pyrazin-1-yl)cyclopentyloxy)pyrazine-2-carbonitrile (prepared using LL from Preparation #JJ.1) [Table 2, Method 43, $R_t$ = 19.9 min, or = negative] | 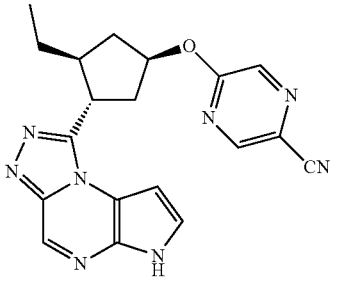 | AA.1.97 | 1.99 (b) | 375 |
| 5-(3-ethyl-4-(6H-pyrrolo[2,3-e][1,2,4]triazolo[4,3-a]pyrazin-1-yl)cyclopentyloxy)pyrazine-2-carbonitrile (prepared using LL from Preparation #JJ.1) [Table 2, Method 43, $R_t$ = 18.3 min, or = positive] | 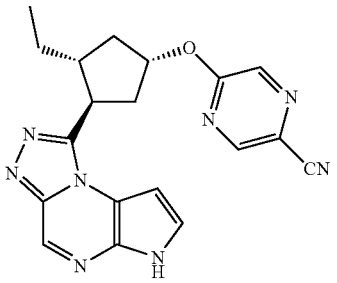 | AA.1.98 | 2.01 (b) | 375 |
| 3-((3-ethyl-4-(6H-pyrrolo[2,3-e][1,2,4]triazolo[4,3-a]pyrazin-1-yl)cyclopentyloxy)methyl)benzonitrile (prepared using JJ from 3-(bromomethyl)benzonitrile and Preparation #SS.1, LL with TFA and ammonium hydroxide) [Table 2, Method 34, $R_t$ = 11.9 min, or = negative] | 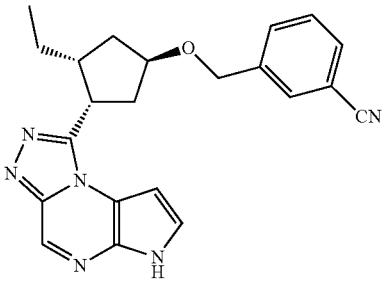 | AA.1.99 | 2.05 (b) | 387 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| 3-((3-ethyl-4-(6H-pyrrolo[2,3-e][1,2,4]triazolo[4,3-a]pyrazin-1-yl)cyclopentyloxy)methyl)benzonitrile (prepared using JJ from 3-(bromomethyl)benzonitrile and Preparation #SS.1, LL with TFA and ammonium hydroxide) [Table 2, Method 34, $R_t$ = 15.1 min, or = positive] | 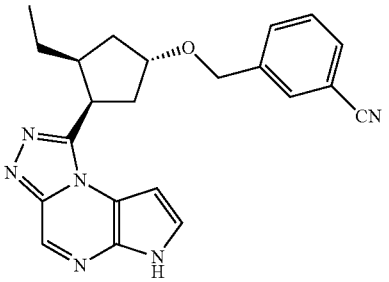 | AA.1.100 | 2.05 (b) | 387 |
| 4-((3-ethyl-4-(6H-pyrrolo[2,3-e][1,2,4]triazolo[4,3-a]pyrazin-1-yl)cyclopentyloxy)methyl)benzonitrile (prepared using JJ from 4-(bromomethyl)benzonitrile and Preparation #SS.1, LL with TFA and ammonium hydroxide) [Table 2, Method 34, $R_t$ = 13.4 min, or = negative] | 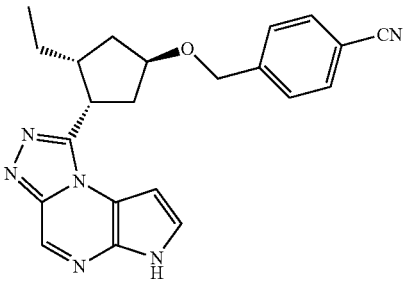 | AA.1.101 | 2.04 (b) | 387 |
| 4-((3-ethyl-4-(6H-pyrrolo[2,3-e][1,2,4]triazolo[4,3-a]pyrazin-1-yl)cyclopentyloxy)methyl)benzonitrile (prepared using JJ from 4-(bromomethyl)benzonitrile and Preparation #SS.1, LL with TFA and ammonium hydroxide) [Table 2, Method 34, $R_t$ = 16.9 min, or = positive] | 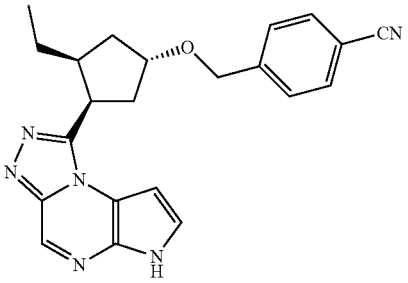 | AA.1.102 | 2.04 (b) | 387 |
| 4-(3-ethyl-4-(6H-pyrrolo[2,3-e][1,2,4]triazolo[4,3-a]pyrazin-1-yl)cyclopentyloxy)-2-fluorobenzonitrile (prepared using II from 2-fluoro-4-hydroxybenzonitrile and Example # 4 Step J, B with DIEA, D with $Na_2CO_3$) [Table 2, Method 5, $R_t$ = 7.7 min, or = negative] | 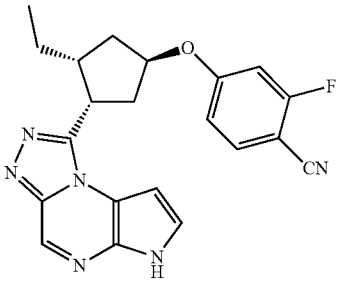 | AA.1.103 | 2.08 (b) | 391 |
| 4-(3-ethyl-4-(6H-pyrrolo[2,3-e][1,2,4]triazolo[4,3-a]pyrazin-1-yl)cyclopentyloxy)-3-fluorobenzonitrile (prepared using II from 3-fluoro-4-hydroxybenzonitrile and Example #4 Step J, B with DIEA, D with $Na_2CO_3$) [Table 2, Method 44, $R_t$ = 12.5 min, or = negative] | 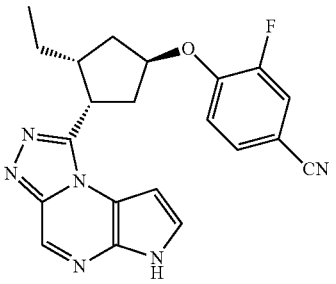 | AA.1.104 | 2.12 (b) | 391 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| 3-(3-ethyl-4-(6H-pyrrolo[2,3-e][1,2,4]triazolo[4,3-a]pyrazin-1-yl)cyclopentyloxy)benzonitrile (prepared using II from 3-hydroxybenzonitrile and Example #4 Step J, B with DIEA, D with $Na_2CO_3$) [Table 2, Method 33, $R_t$ = 12.1 min, or = negative] | 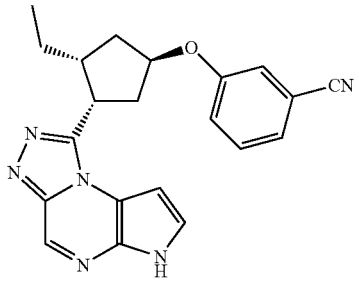 | AA.1.105 | 2.09 (b) | 373 |
| 3-ethyl-4-(6H-pyrrolo[2,3-e][1,2,4]triazolo[4,3-a]pyrazin-1-yl)cyclopentanol (prepared using II from benzoic acid and Example #4 Step J, B with DIEA, D with $Na_2CO_3$) [Table 2, Method 45, $R_t$ = 9.1 min, or = negative] | 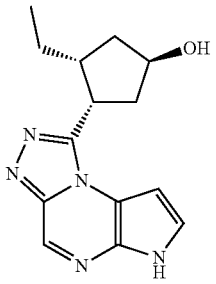 | AA.1.106 | 1.46 (b) | 272 |
| 1-(2-ethyl-4-(3,3,3-trifluoropropoxy)cyclopentyl)-6H-pyrrolo[2,3-e][1,2,4]triazolo[4,3-a]pyrazine (prepared using EE from Preparation #UU.1 with 3,3,3-trifluoropropanol, Z with NaOH, A from Example #1 Step D, HATU, and TEA, B with DIEA, D with NaOH) [Table 2, Method 46, $R_t$ = 8.1 min] | 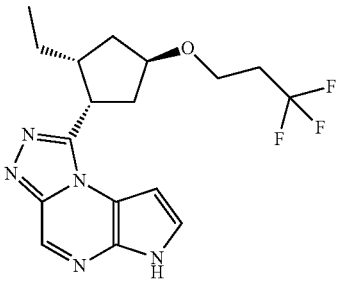 | AA.1.107 | 2.04 (b) | 368 |
| 1-(2-ethyl-4-((tetrahydro-2H-pyran-4-yl)methoxy)cyclopentyl)-6H-pyrrolo[2,3-e][1,2,4]triazolo[4,3-a]pyrazine (prepared using FFF from Example #22 Step D and tetrahydro-2H-pyran-4-carbaldehyde [Pharmacore], Z with NaOH, A from Example #1 Step D, HATU, and TEA, B with DIEA, D with NaOH) [Table 2, Method 47, $R_t$ = 10 min, or = negative] | 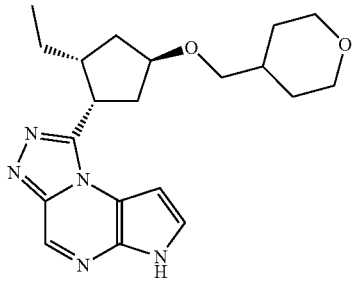 | AA.1.108 | 1.79 (b) | 370 |
| 1-(2-ethyl-4-(2-methoxyethoxy)cyclopentyl)-6H-pyrrolo[2,3-e][1,2,4]triazolo[4,3-a]pyrazine (prepared using FFF from Example #22 Step D and 2-methoxyacetaldehyde [BBB Scientific], Z with NaOH, A from Example #1 Step D, HATU, and TEA, B with DIEA, D with NaOH) [Table 2, Method 44, $R_t$ = 11.7 min, or = negative] | 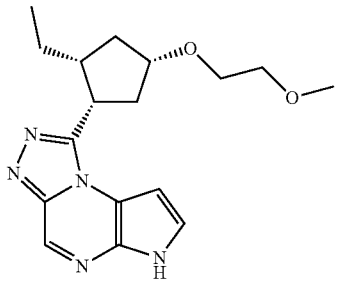 | AA.1.109 | 1.67 (b) | 330 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| 1-(2-ethyl-4-(2-methoxyethoxy)cyclopentyl)-6H-pyrrolo[2,3-e][1,2,4]triazolo[4,3-a]pyrazine pyrazine (prepared using FFF from Example #22 Step D and 2-methoxyacetaldehyde [BBB Scientific], Z with NaOH, A from Example #1 Step D, HATU, and TEA, B with DIEA, D with NaOH) [Table 2, Method 44, $R_t$ = 5.6 min, or = negative] | 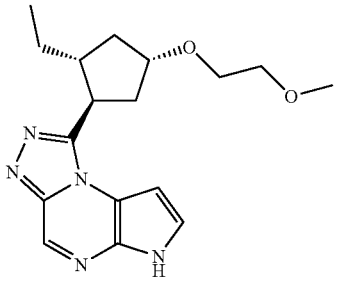 | AA.1.110 | 1.70 (b) | 330 |
| N-((1R,4R)-3,3-dimethyl-4-(6H-pyrrolo[2,3-e][1,2,4]triazolo[4,3-a]pyrazin-1-yl)cyclopentyl)cyclopropane-sulfonamide and N-((1S,4S)-3,3-dimethyl-4-(6H-pyrrolo[2,3-e][1,2,4]triazolo[4,3-a]pyrazin-1-yl)cyclopentyl)cyclopropane-sulfonamide (prepared as in WO2009152133A1) [Table 2, Method 54, $R_t$ = 12.4 min, or = negative] | 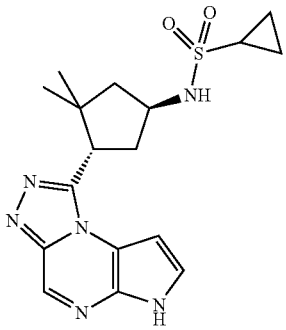 | AA.1.111 | 1.59 (b) | 375 |
| N -((1R,4R)-3,3-dimethyl-4-(6H-pyrrolo[2,3-e][1,2,4]triazolo[4,3-a]pyrazin-1-yl)cyclopentyl)cyclopropane-sulfonamide and N-((1S,4S)-3,3-dimethyl-4-(6H-pyrrolo[2,3-e][1,2,4]triazolo[4,3-a]pyrazin-1-yl)cyclopentyl)cyclopropane-sulfonamide (prepared as in WO2009152133A1) [Table 2, Method 54, $R_t$ = 16.9 min, or = positive] | 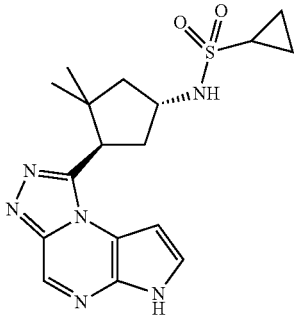 | AA.1.112 | 1.59 (b) | 375 |
| 2-(3-ethyl-4-(6H-pyrrolo[2,3-e][1,2,4]triazolo[4,3-a]pyrazin-1-yl)cyclopentyl)acetonitrile (prepared using III from Preparation #25, Step E and diethyl cyanomethylphosphonate; BBBB; W.1) [Table 2, Method 33, $R_t$ = 9.6 min, or = negative] | 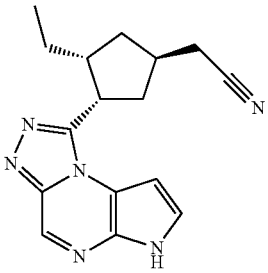 | AA.1.113 | 1.58 (b) | 295 |
| 2-(3-ethyl-4-(6H-pyrrolo[2,3-e][1,2,4]triazolo[4,3-a]pyrazin-1-yl)cyclopentyl)acetonitrile (prepared using III from Preparation #25, Step E and diethyl cyanomethylphosphonate; BBBB; W.1) [Table 2, Method 33, $R_t$ = 11.8 min, or = negative] | 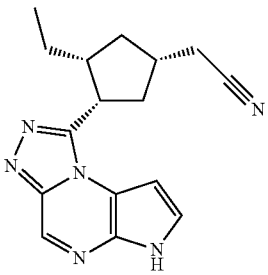 | AA.1.114 | 1.58 (a) | 295 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| N-(3-ethyl-4-(6H-pyrrolo[2,3-e][1,2,4]triazolo[4,3-a]pyrazin-1-yl)cyclopentyl)cyclopropane-sulfonamide (prepared using D from Preparation #25 and NaOH, KK, P with $NaBH_4$, IIII, JJJJ with $NaN_3$, UUUU, K with cyclopropylsulfonyl chloride [Matrix], LL) [Table 2, Method 56, $R_t$ = 12.2 min, or = negative] | 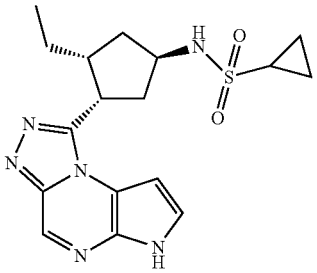 | AA.1.115 | 1.43 (a) | 375 |
| 2-(3-(3-ethyl-4-(6H-pyrrolo[2,3-e][1,2,4]triazolo[4,3-a]pyrazin-1-yl)cyclopentylamino)oxetan-3-yl)acetonitrile (prepared using D from Preparation #25 and NaOH, KK, P with $NaBH_4$, IIII, JJJJ with $NaN_3$, UUUU, YYY with 2-(oxetan-3-ylidene)acetonitrile [prepared as described in J. Med. Chem, 2010, 53(8) 3227-3246], LL) [Table 2, Method 5, $R_t$ = 17.2 min, or = negative] | 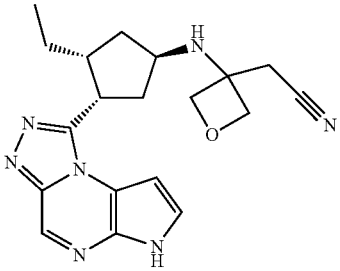 | AA.1.116 | 1.27 (a) | 366 |
| 3-ethyl-1-methyl-4-(6H-pyrrolo[2,3-e][1,2,4]triazolo[4,3-a]pyrazin-1-yl)cyclopentanol (prepared using ZZZ from Example #35, Step G and MeLi, LL) [Table 2, Method 33, $R_t$ = 7.6 min, or = negative] | 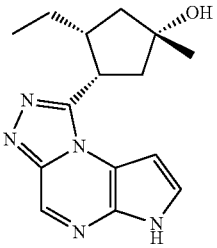 | AA.1.117 | 1.59 (a) | 286 |
| 3-(3-ethyl-4-(6-tosyl-6H-pyrrolo[2,3-e][1,2,4]triazolo[4,3-a]pyrazin-1-yl)cyclopentyloxy)propanenitrile (prepared using YYY from Example #22, Step C, acrylonitrile and DBU, Z with NaOH, A with Example #1, Step D, B with $SOCl_2$ and TEA, and D with NaOH) [Table 2, Method 60, $R_t$ = 10.9 min, or = negative] | 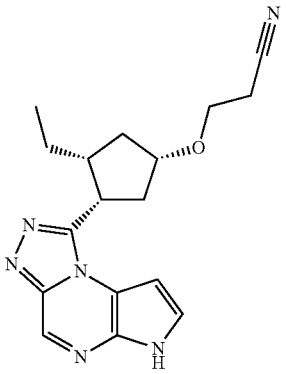 | AA.1.118 | 1.70 (a) | 325 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| 3-(3-ethyl-4-(6-tosyl-6H-pyrrolo[2,3-e][1,2,4]triazolo[4,3-a]pyrazin-1-yl)cyclopentyloxy)propanenitrile (prepared using YYY from Example #22, Step C, acrylonitrile and DBU, Z with NaOH, A with Example #1, Step D, B with $SOCl_2$ and TEA, and D with NaOH) [Table 2, Method 60, $R_t$ = 15.0 min, or = negative] | 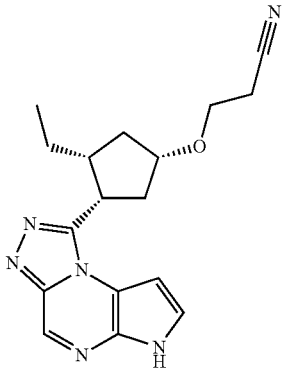 | AA.1.119 | 1.69 (a) | 325 |
| Ethyl 2-(3-ethyl-4-(6H-pyrrolo[2,3-e][1,2,4]triazolo[4,3-a]pyrazin-1-yl)cyclopentyl)acetate (prepared using W from Preparation #AAAA.1 and $PdOH_2$ on C, and ZZZ with $CH_3MgCl_2$) [Table 2, Method 40, $R_t$ = 6.0 min, or = negative] | 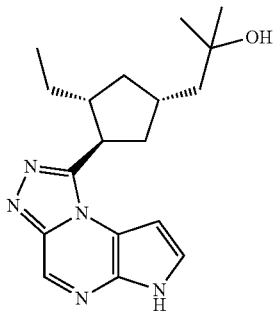 | AA.1.120 | 1.75 (a) | 328 |
| Ethyl 2-(3-ethyl-4-(6H-pyrrolo[2,3-e][1,2,4]triazolo[4,3-a]pyrazin-1-yl)cyclopentyl)acetate (prepared using W from Preparation #AAAA.1 and $PdOH_2$ on C, and ZZZ with $CH_3MgCl_2$) [Table 2, Method 40, $R_t$ = 10.3 min, or = negative] | 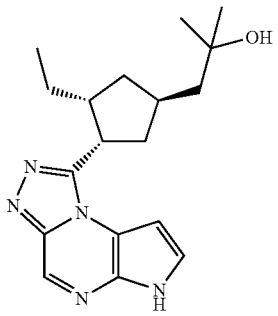 | AA.1.121 | 1.72 (a) | 328 |
| Ethyl 2-(3-ethyl-4-(6H-pyrrolo[2,3-e][1,2,4]triazolo[4,3-a]pyrazin-1-yl)cyclopentyl)acetate (prepared using W from Preparation #AAAA.1 and $PdOH_2$ on C, and ZZZ with $CH_3MgCl_2$) [Table 2, Method 40, $R_t$ = 14.8 min, or = negative] | 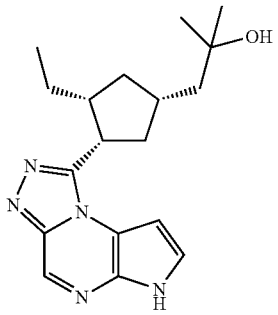 | AA.1.122 | 1.72 (a) | 328 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| Ethyl 2-(3-ethyl-4-(6H-pyrrolo[2,3-e][1,2,4]triazolo[4,3-a]pyrazin-1-yl)cyclopentyl)acetate (prepared using W from Preparation #AAAA.1 and $PdOH_2$ on C, and DDDD with (Z)-N'-hydroxycyclopropane-carboximidamide [Tyger Scientific]) [Table 2, Method 61, $R_t$ = 27.5 min, or = nd] | 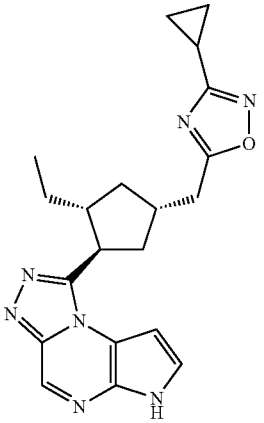 | AA.1.123 | 1.95 (a) | 378 |
| Ethyl 2-(3-ethyl-4-(6H-pyrrolo[2,3-e][1,2,4]triazolo[4,3-a]pyrazin-1-yl)cyclopentyl)acetate (prepared using W from Preparation #AAAA.1 and $PdOH_2$ on Carbon, and DDDD with (Z)-N'-hydroxycyclopropane-carboximidamide [Tyger Scientific]) [Table 2, Method 61, $R_t$ = 29.4 min, or = nd] | 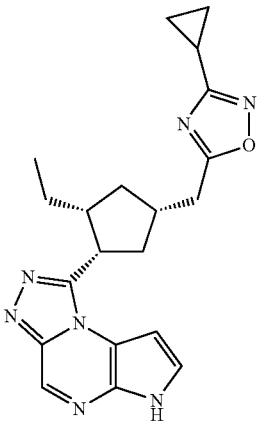 | AA.1.124 | 1.95 (a) | 378 |
| Ethyl 2-(3-ethyl-4-(6H-pyrrolo[2,3-e][1,2,4]triazolo[4,3-a]pyrazin-1-yl)cyclopentyl)acetate (prepared using W from Preparation #AAAA.1 and $PdOH_2$ on C, and DDDD with (Z)-N'-hydroxycyclopropane-carboximidamide [Tyger Scientific]) [Table 2, Method 61, $R_t$ = 32.8 min, or = nd] | 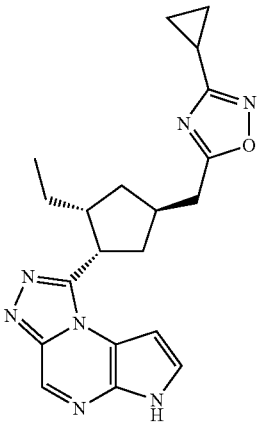 | AA.1.125 | 1.95 (a) | 378 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| (cis)-N-(1-cyanocyclopropyl)-3-ethyl-4-(6H-pyrrolo[2,3-e][1,2,4]triazolo[4,3-a]pyrazin-1-yl)pyrrolidine-1-carboxamide (prepared using J.1 from Example #36, step F, CDI and 1-aminocyclopropane-carbonitrile•hydrochloride [Astatech], and D with $Na_2CO_3$) [Table 2, Method 62, $R_t$ = 11.2 min, or = negative] | 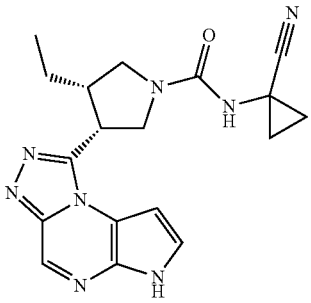 | AA.1.126 | 1.47 (a) | 365 |
| (cis)-N-(1-cyanocyclopropyl)-3-ethyl-4-(6H-pyrrolo[2,3-e][1,2,4]triazolo[4,3-a]pyrazin-1-yl)pyrrolidine-1-carboxamide (prepared using J.1 from Example #36, step F, CDI and 1-aminocyclopropane-carbonitrile•hydrochloride [Astatech], and D with $Na_2CO_3$) [Table 2, Method 62, $R_t$ = 13.7 min, or = positive] | 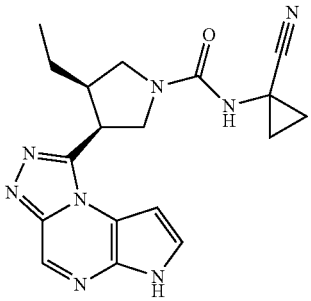 | AA.1.127 | 1.45 (a) | 365 |
| (cis)-N-cyclobutyl-3-ethyl-4-(6H-pyrrolo[2,3-e][1,2,4]triazolo[4,3-a]pyrazin-1-yl)pyrrolidine-1-carboxamide (prepared using J.1 from Example #36, step F, CDI and cyclobutanamine, and D with NaOH) [Table 2, Method 34, $R_t$ = 8.6 min, or = positive] | 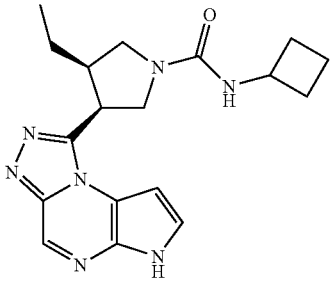 | AA.1.128 | 1.58 (a) | 354 |
| (cis)-N-cyclobutyl-3-ethyl-4-(6H-pyrrolo[2,3-e][1,2,4]triazolo[4,3-a]pyrazin-1-yl)pyrrolidine-1-carboxamide (prepared using J.1 from Example #36, step F, CDI and cyclobutanamine, and D with NaOH) [Table 2, Method 34, $R_t$ = 11.2 min, or = negative] | 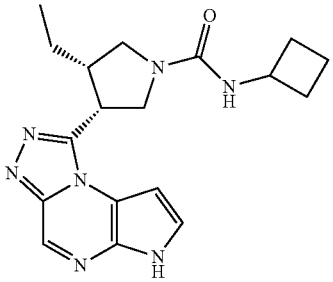 | AA.1.129 | 1.60 (a) | 354 |
| (cis)-3-ethyl-N-(3-methylisothiazol-5-yl)-4-(6H-pyrrolo[2,3-e][1,2,4]triazolo[4,3-a]pyrazin-1-yl)pyrrolidine-1-carboxamide (prepared using J.1 from Example #36, Step F, CDI and 3-methylisothiazol-5-amine•hydrochloride, and D with NaOH) [Table 2, Method 63, $R_t$ = 10.5 min, or = negative] | 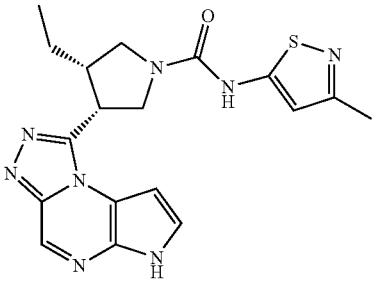 | AA.1.130 | 1.56 (a) | 397 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| (cis)-3-ethyl-N-(3-methylisothiazol-5-yl)-4-(6H-pyrrolo[2,3-e][1,2,4]triazolo[4,3-a]pyrazin-1-yl)pyrrolidine-1-carboxamide (prepared using J.1 from Example #36, Step F, CDI and 3-methylisothiazol-5-amine•hydrochloride, and D with NaOH) [Table 2, Method 63, $R_t$ = 13.4 min, or = positive] | 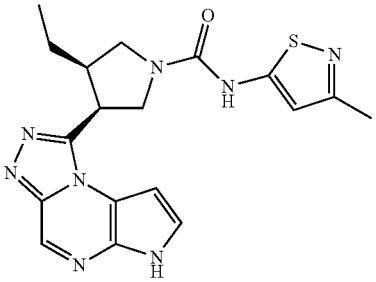 | AA.1.131 | 1.56 (a) | 397 |
| (cis)-N-(cyanomethyl)-3-ethyl-4-(6H-pyrrolo[2,3-e][1,2,4]triazolo[4,3-a]pyrazin-1-yl)pyrrolidine-1-carboxamide (prepared using J.1 from Example #36, Step F, CDI and 2-aminoacetonitrile, and D.2 with $Na_2CO_3$) [Table 2, Method 64, $R_t$ = 11.0 min, or = negative] | 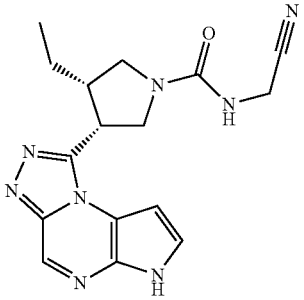 | AA.1.132 | 1.42 (a) | 339 |
| (cis)-N-(cyanomethyl)-3-ethyl-4-(6H-pyrrolo[2,3-e][1,2,4]triazolo[4,3-a]pyrazin-1-yl)pyrrolidine-1-carboxamide (prepared using J.1 from Example #36, Step F, CDI and 2-aminoacetonitrile, and D.2 with $Na_2CO_3$) [Table 2, Method 64, $R_t$ = 13.3 min, or = positive] | 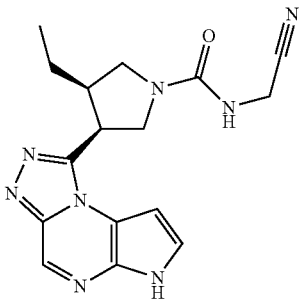 | AA.1.133 | 1.42 (a) | 339 |
| (cis)-3-ethyl-N-(oxazol-4-ylmethyl)-4-(6H-pyrrolo[2,3-e][1,2,4]triazolo[4,3-a]pyrazin-1-yl)pyrrolidine-1-carboxamide (prepared using J.1 from Example #36, Step F, CDI and oxazol-4-ylmethanamine•hydrochloride [J & W Pharmlab], and D with NaOH) [Table 2, Method 65, $R_t$ = 10.6 min, or = negative] | 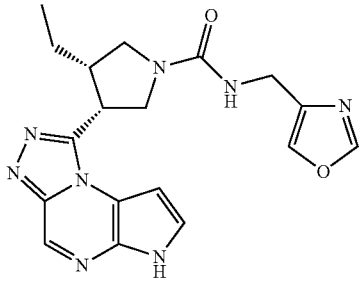 | AA.1.134 | 1.44 (a) | 381 |
| (cis)-3-ethyl-N-(oxazol-4-ylmethyl)-4-(6H-pyrrolo[2,3-e][1,2,4]triazolo[4,3-a]pyrazin-1-yl)pyrrolidine-1-carboxamide (prepared using J.1 from Example #36, Step F, CDI and oxazol-4-ylmethanamine•hydrochloride hydrochloride [J & W Pharmlab], and D with NaOH) [Table 2, Method 65, $R_t$ = 11.8 min, or = positive] | 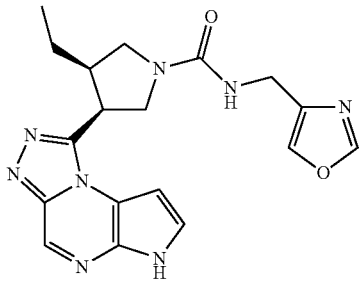 | AA.1.135 | 1.44 (a) | 381 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| (cis)-3-ethyl-4-(6H-pyrrolo[2,3-e][1,2,4]triazolo[4,3-a]pyrazin-1-yl)-N-(2,2,2-trifluoroethyl)pyrrolidine-1-carboxamide (prepared using J.1 from Example #36, Step F, CDI and 2,2,2-trifluoroethanamine, and D with NaOH) [Table 2, Method 55, $R_t$ = 14.5 min, or = negative] | 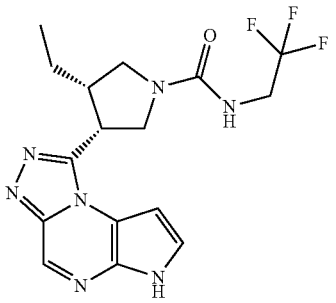 | AA.1.136 | 1.62 (a) | 382 |
| (cis)-3-ethyl-4-(6H-pyrrolo[2,3-e][1,2,4]triazolo[4,3-a]pyrazin-1-yl)-N-(2,2,2-trifluoroethyl)pyrrolidine-1-carboxamide (prepared using J.1 from Example #36, Step F, CDI and 2,2,2-trifluoroethanamine, and D with NaOH) [Table 2, Method 55, $R_t$ = 17.3 min, or = positive] | 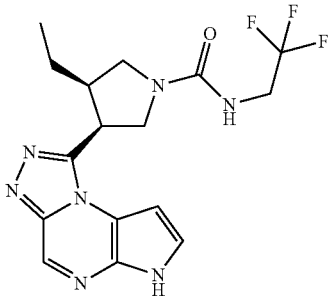 | AA.1.137 | 1.62 (a) | 382 |
| (3,3-difluoroazetidin-1-yl)((cis)-3-ethyl-4-(6H-pyrrolo[2,3-e][1,2,4]triazolo[4,3-a]pyrazin-1-yl)pyrrolidin-1-yl)methanone (prepared using D with Preparation #EEEE.1 and NaOH) [Table 2, Method 64, $R_t$ = 11.4 min, or = negative] | 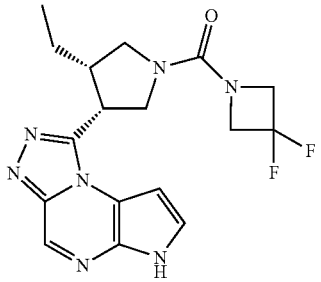 | AA.1.138 | 1.65 (a) | 376 |
| (3,3-difluoroazetidin-1-yl)((cis)-3-ethyl-4-(6H-pyrrolo[2,3-e][1,2,4]triazolo[4,3-a]pyrazin-1-yl)pyrrolidin-1-yl)methanone (prepared using D with Preparation #EEEE.1 and NaOH) [Table 2, Method 64, $R_t$ = 12.9 min, or = positive] | 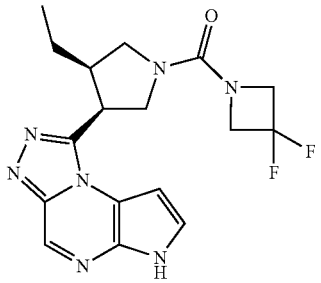 | AA.1.139 | 1.65 (a) | 376 |
| (cis)-3-ethyl-N-(oxetan-3-yl)-4-(6H-pyrrolo[2,3-e][1,2,4]triazolo[4,3-a]pyrazin-1-yl)pyrrolidine-1-carboxamide (prepared using J.1 from Example #36, Step F, CDI and oxetan-3-amine [Synthonix], and D with NaOH) [Table 2, Method 65, $R_t$ = 7.1 min, or = racemic] | 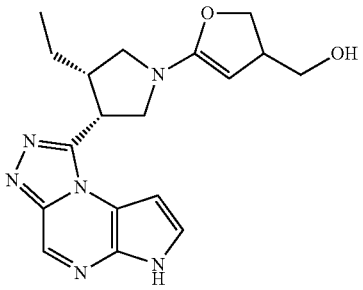 | AA.1.140 | 1.34 (a) | 356 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| (cis)-3-ethyl-N-(oxetan-3-yl)-4-(6H-pyrrolo[2,3-e][1,2,4]triazolo[4,3-a]pyrazin-1-yl)pyrrolidine-1-carboxamide (prepared using J.1 from Example #36, Step F, CDI and oxetan-3-amine [Synthonix], and D with NaOH) [Table 2, Method 65, $R_t$ = 11.7 min, or = negative] | 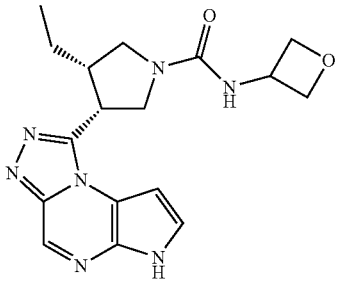 | AA.1.141 | 1.43 (a) | 356 |
| (cis)-3-ethyl-N-(oxetan-3-yl)-4-(6H-pyrrolo[2,3-e][1,2,4]triazolo[4,3-a]pyrazin-1-yl)pyrrolidine-1-carboxamide (prepared using J.1 from Example #36, Step F, CDI and oxetan-3-amine [Synthonix], and D with NaOH) [Table 2, Method 65, $R_t$ = 13.3 min, or = positive] | 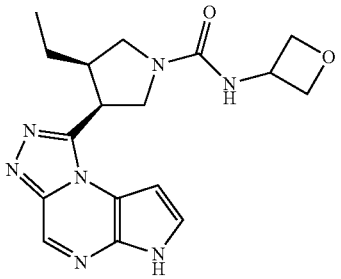 | AA.1.142 | 1.42 (a) | 356 |
| ((cis)-3-ethyl-4-(6H-pyrrolo[2,3-e][1,2,4]triazolo[4,3-a]pyrazin-1-yl)pyrrolidin-1-yl)((R)-3-hydroxypyrrolidin-1-yl)methanone (prepared using EEEE from Example #36, Step F, with (R)-pyrrolidin-3-ol, and D with NaOH) [Table 2, Method 64, $R_t$ = 10.1 min, or = negative] | 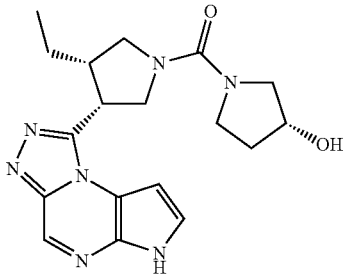 | AA.1.143 | 1.44 (a) | 370 |
| ((cis)-3-ethyl-4-(6H-pyrrolo[2,3-e][1,2,4]triazolo[4,3-a]pyrazin-1-yl)pyrrolidin-1-yl)((R)-3-hydroxypyrrolidin-1-yl)methanone (prepared using EEEE from Example #36, Step F, (R)-pyrrolidin-3-ol, and D with NaOH) [Table 2, Method 64, $R_t$ = 11.8 min, or = positive] | 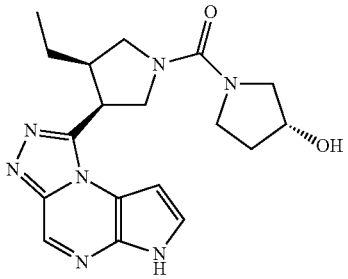 | AA.1.144 | 1.42 (a) | 370 |
| ((cis)-3-ethyl-4-(6H-pyrrolo[2,3-e][1,2,4]triazolo[4,3-a]pyrazin-1-yl)pyrrolidin-1-yl)((S)-3-hydroxypyrrolidin-1-yl)methanone (prepared using EEEE from Example #36, Step F, with (S)-pyrrolidin-3-ol, and D with NaOH) [Table 2, Method 67, $R_t$ = 11.9 min, or = negative] | 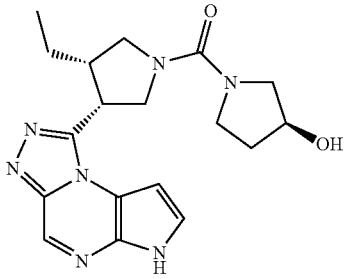 | AA.1.145 | 1.40 (a) | 370 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| ((cis)-3-ethyl-4-(6H-pyrrolo[2,3-e][1,2,4]triazolo[4,3-a]pyrazin-1-yl)pyrrolidin-1-yl)((S)-3-hydroxypyrrolidin-1-yl)methanone (prepared using EEEE from Example #36, Step F, (S)-pyrrolidin-3-ol, and D with NaOH) [Table 2, Method 67, $R_t$ = 13.9 min, or = positive] | 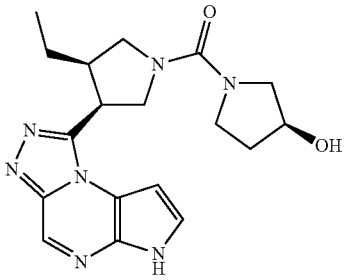 | AA.1.146 | 1.42 (a) | 370 |
| (cis)-N-(cyclopropylmethyl)-3-ethyl-4-(6H-pyrrolo[2,3-e][1,2,4]triazolo[4,3-a]pyrazin-1-yl)pyrrolidine-1-sulfonamide (prepared using ZZ from cyclopropylmethanamine and TEA, AAA with Example #36, Step F, and D with NaOH). [Table 2, Method 33, Rt = 10.0 min, or = positive] | 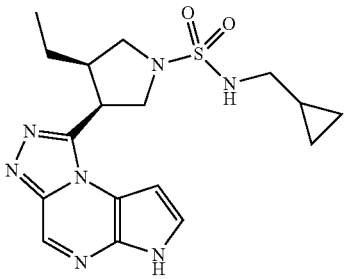 | AA.1.147 | 1.80 (a) | 390 |
| (cis)-N-(cyclopropylmethyl)-3-ethyl-4-(6H-pyrrolo[2,3-e][1,2,4]triazolo[4,3-a]pyrazin-1-yl)pyrrolidine-1-sulfonamide (prepared using ZZ from cyclopropylmethanamine and TEA, AAA with Example #36, Step F, and D with NaOH). [Table 2, Method 33, $R_t$ = 14.0 min, or = negative] | 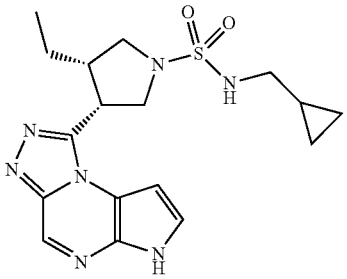 | AA.1.148 | 1.78 (a) | 390 |
| (cis)-N-(2-cyclopropylethyl)-3-ethyl-4-(6H-pyrrolo[2,3-e][1,2,4]triazolo[4,3-a]pyrazin-1-yl)pyrrolidine-1-carboxamide (prepared using J.1 from Example #36, Step F, CDI and 2-cyclopropylethanamine [Oakwood], and D with NaOH). [Table 2, Method 33, $R_t$ = 6.8 min, or = positive] | 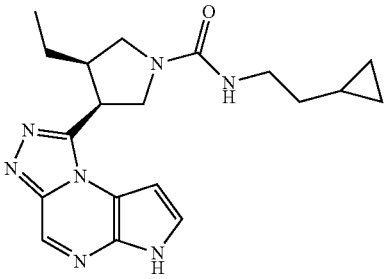 | AA.1.149 | 1.69 (a) | 368 |
| (cis)-N-(2-cyclopropylethyl)-3-ethyl-4-(6H-pyrrolo[2,3-e][1,2,4]triazolo[4,3-a]pyrazin-1-yl)pyrrolidine-1-carboxamide (prepared using J.1 from Example #36, Step F, CDI and 2-cyclopropylethanamine [Oakwood], and D with NaOH). [Table 2, Method 33, $R_t$ = 9.3 min, or = negative] | 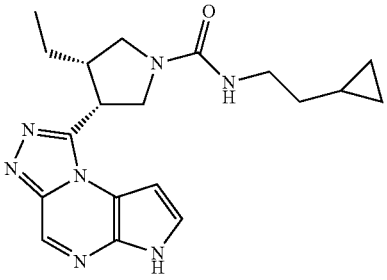 | AA.1.150 | 1.70 (a) | 368 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| (cis)-3-ethyl-N-(oxetan-3-yl)-4-(6H-pyrrolo[2,3-e][1,2,4]triazolo[4,3-a]pyrazin-1-yl)pyrrolidine-1-sulfonamide (prepared using ZZ from oxetan-3-amine [Synthonix] and TEA, AAA with Example #36, Step F, and D with NaOH). [Table 2, Method 11, $R_t$ = 6.6 min, or = positive] | 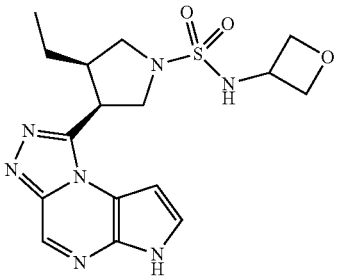 | AA.1.151 | 1.58 (a) | 392 |
| (cis)-3-ethyl-N-(oxetan-3-yl)-4-(6H-pyrrolo[2,3-e][1,2,4]triazolo[4,3-a]pyrazin-1-yl)pyrrolidine-1-sulfonamide (prepared using ZZ from oxetan-3-amine [Synthonix] and TEA, AAA with Example #36, Step F, and D with NaOH). [Table 2, Method 11, $R_t$ = 10.8 min, or = negative] | 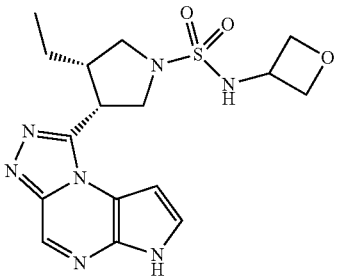 | AA.1.152 | 1.58(a) | 392 |
| (cis)-N-cyclobutyl-3-ethyl-4-(6H-pyrrolo[2,3-e][1,2,4]triazolo[4,3-a]pyrazin-1-yl)pyrrolidine-1-sulfonamide (prepared using ZZ from cyclobutanamine and TEA, AAA with Example #36, Step F, and D with NaOH). [Table 2, Method 33, $R_t$ = 9.5 min, or = positive] | 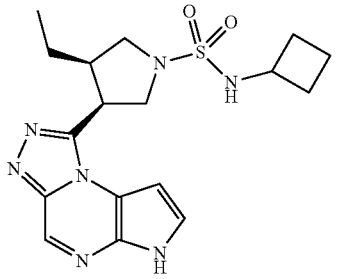 | AA.1.153 | 1.79 (a) | 390 |
| (cis)-N-cyclobutyl-3-ethyl-4-(6H-pyrrolo[2,3-e][1,2,4]triazolo[4,3-a]pyrazin-1-yl)pyrrolidine-1-sulfonamide (prepared using ZZ from cyclobutanamine and TEA, AAA with Example #36, Step F, and D with NaOH). [Table 2, Method 33, $R_t$ = 12.7 min, or = negative] | 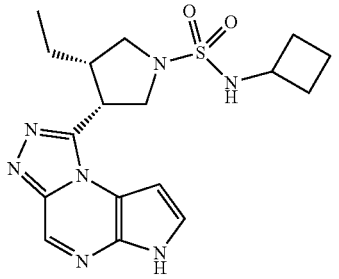 | AA.1.154 | 1.79 (a) | 390 |
| (cis)-3-ethyl-4-(6H-pyrrolo[2,3-e][1,2,4]triazolo[4,3-a]pyrazin-1-yl)pyrrolidine-1-sulfonamide(prepared using ZZ from 2-aminoacetonitrile and TEA, AAA with Example #36, Step F, and D with NaOH). [Table 2, Method 68, $R_t$ = 4.9 min, or = positive] | 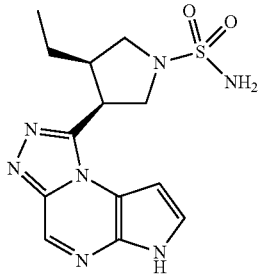 | AA.1.155 | 1.48 (a) | 336 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| (cis)-3-ethyl-4-(6H-pyrrolo[2,3-e][1,2,4]triazolo[4,3-a]pyrazin-1-yl)pyrrolidine-1-sulfonamide(prepared using ZZ from 2-aminoacetonitrile and TEA, AAA with Example #36, Step F, and D with NaOH). [Table 2, Method 68, $R_t$ = 10.4 min, or = negative] | 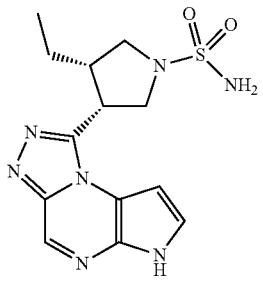 | AA.1.156 | 1.48 (a) | 336 |
| (cis)-3-ethyl-4-(6H-pyrrolo[2,3-e][1,2,4]triazolo[4,3-a]pyrazin-1-yl)-N-(2,2,2-trifluoroethyl)pyrrolidine-1-sulfonamide (prepared using ZZ from 2,2,2-trifluoroethanamine and TEA, AAA with Example #36, Step F, and D with NaOH). [Table 2, Method 66, $R_t$ = 12.9 min, or = negative] | 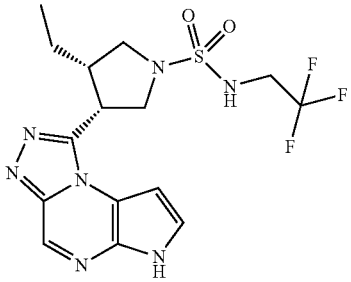 | AA.1.157 | 1.85 (a) | 418 |
| (cis)-3-ethyl-4-(6H-pyrrolo[2,3-e][1,2,4]triazolo[4,3-a]pyrazin-1-yl)-N-(2,2,2-trifluoroethyl)pyrrolidine-1-sulfonamide (prepared using ZZ from 2,2,2-trifluoroethanamine and TEA, AAA with Example #36, Step F, and D with NaOH). [Table 2, Method 66, $R_t$ = 15.8 min, or = positive] | 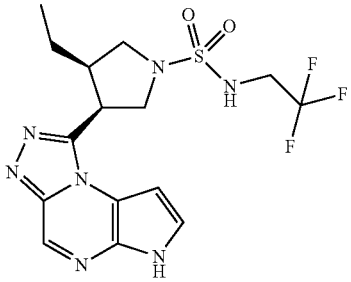 | AA.1.158 | 1.85 (a) | 418 |
| (cis)-3-ethyl-4-(3H-imidazo[1,2-a]pyrrolo[2,3-e]pyrazin-8-yl)-N-(2,2,2-trifluoroethyl)pyrrolidine-1-carboxamide (prepared using J.1 with Preparation #F.1.1 and 2,2,2-trifluoroethanamine, and D with NaOH). [Table 2, Method 69, $R_t$ = 11.2 min, or = positive] | 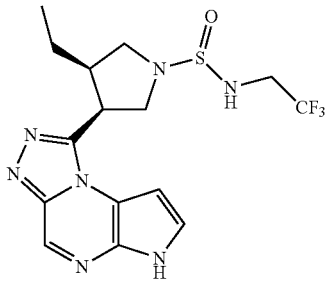 | AA.1.159 | 1.52 (a) | 381 |
| (cis)-3-ethyl-4-(3H-imidazo[1,2-a]pyrrolo[2,3-e]pyrazin-8-yl)-N-(2,2,2-trifluoroethyl)pyrrolidine-1-carboxamide (prepared using J.1 with Preparation #F.1.1 and 2,2,2-trifluoroethanamine, and D with NaOH). [Table 2, Method 69, $R_t$ = 15.5 min, or = negative] | 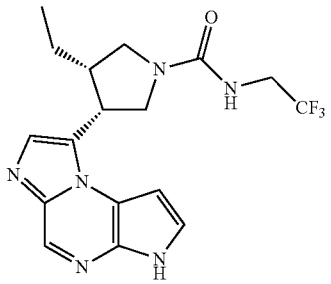 | AA.1.160 | 1.52 (a) | 381 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| 1-((1,2,4)-4-(4,4-difluorocyclohexyloxy)-2-ethylcyclopentyl)-6H-pyrrolo[2,3-e][1,2,4]triazolo[4,3-a]pyrazine (prepared using II from Example #22 Step C with 4-nitrobenzoic acid, SS with NaOH, VV, FFF with 4,4-difluorocyclohexanone [Small Molecule], Z with NaOH, A with Example #1 Step D, HATU and TEA, B with DIEA, D with NaOH) [Table 2, Method 28, $R_t$ = 10.1 min, or = negative] | 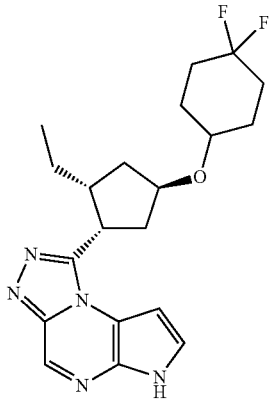 | AA.1.161 | 2.07 (b) | 390 |
| 1-((1,2,4)-4-(4,4-difluorocyclohexyloxy)-2-ethylcyclopentyl)-6H-pyrrolo[2,3-e][1,2,4]triazolo[4,3-a]pyrazine (prepared using II from Example #22 Step C with 4-nitrobenzoic acid, SS with NaOH, VV, FFF with 4,4-difluorocyclohexanone [Small Molecule], Z with NaOH, A with Example #1 Step D, HATU and TEA, B with DIEA, D with NaOH) [Table 2, Method 28, $R_t$ = 15.1 min, or = negative] | 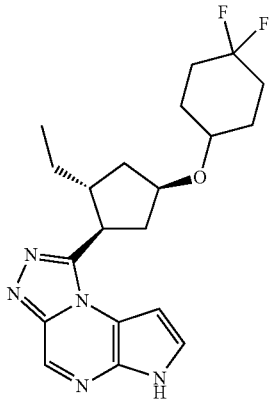 | AA.1.162 | 2.05 (b) | 390 |
| 1((1,2,4)-2-ethyl-4-((1,4)-4-(trifluoromethyl)cyclohexyloxy)cyclopentyl)-6H-pyrrolo[2,3-e][1,2,4]triazolo[4,3-a]pyrazine (prepared using II from Example #22 Step C with 4-nitrobenzoic acid, SS with NaOH, VV, FFF with 4-trifluoromethylcyclohexanone [Matrix], Z with NaOH, A with Example #1 Step D, HATU and TEA, B with DIEA, D with NaOH) [Table 2, Method 58, $R_t$ = 7.8 min, or = negative] | 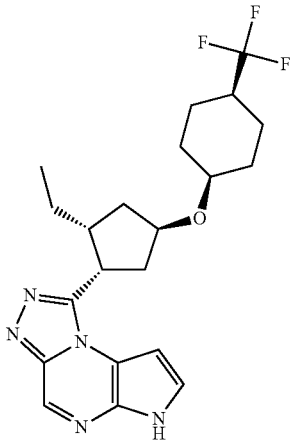 | AA..1.163 | 2.34 (b) | 422 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| 1((1,2,4)-2-ethyl-4-((1,4)-4-(trifluoromethyl)cyclohexyloxy)cyclopentyl)-6H-pyrrolo[2,3-e][1,2,4]triazolo[4,3-a]pyrazine (prepared using II from Example #22 Step C with 4-nitrobenzoic acid, SS with NaOH, VV, FFF with 4-trifluoromethylcyclohexanone [Matrix], Z with NaOH, A with Example #1 Step D, HATU and TEA, B with DIEA, D with NaOH) [Table 2, Method 51, $R_t$ = 14.6 min, or = negative] | 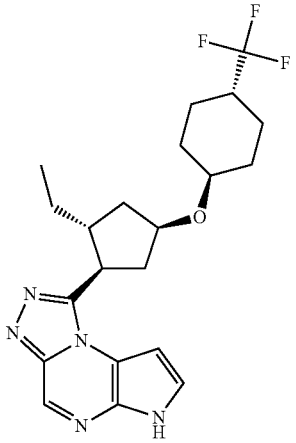 | AA.1.164 | 2.22 (b) | 422 |
| 1((1,2,4)-2-ethyl-4-((1,4)-4-(trifluoromethyl)cyclohexyloxy)cyclopentyl)-6H-pyrrolo[2,3-e][1,2,4]triazolo[4,3-a]pyrazine (prepared using II from Example #22 Step C with 4-nitrobenzoic acid, SS with NaOH, VV, FFF with 4-trifluoromethylcyclohexanone [Matrix], Z with NaOH, A with Example #1 Step D, HATU and TEA, B with DIEA, D with NaOH) [Table 2, Method 58, $R_t$ = 14.6 min, or = negative] | 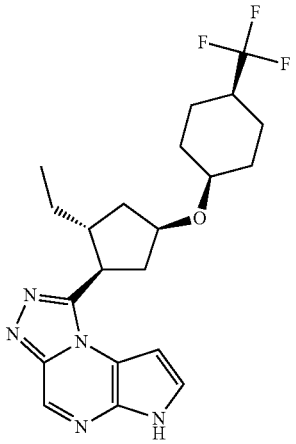 | AA.1.165 | 2.29 (b) | 422 |
| 1((1,2,4)-2-ethyl-4-((1,4)-4-(trifluoromethyl)cyclohexyloxy)cyclopentyl)-6H-pyrrolo[2,3-e][1,2,4]triazolo[4,3-a]pyrazine (prepared using II from Example #22 Step C with 4-nitrobenzoic acid, SS with NaOH, VV, FFF with 4-trifluoromethylcyclohexanone [Matrix], Z with NaOH, A with Example #1 Step D, HATU and TEA, B with DIEA, D with NaOH) [Table 2, Method 51, $R_t$ = 15.8 min, or = negative] | 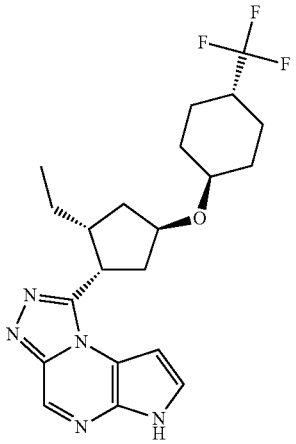 | AA.1.166 | 2.22 (b) | 422 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| (1,4)-4-((1,3,4)-3-ethyl-4-(6H-pyrrolo[2,3-e][1,2,4]triazolo[4,3-a]pyrazin-1-yl)cyclopentyloxy)cyclohexane-carbonitrile (prepared using II from Example #22 Step C with 4-nitrobenzoic acid, SS with NaOH, VV, FFF with 4-oxocyclohexanecarbonitrile [Beta Pharma], Z with NaOH, A with Example #1 Step D, HATU and TEA, B with DIEA, D with NaOH) [Table 2, Method 57, $R_t$ = 14.3 min, or = negative] | 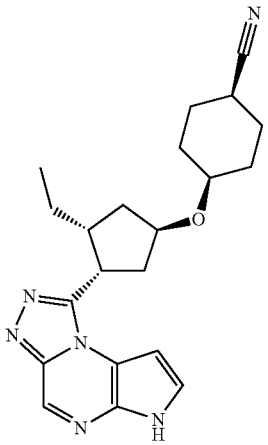 | AA.1.167 | 1.80 (b) | 379 |
| (1,4)-4-((1,3,4)-3-ethyl-4-(6H-pyrrolo[2,3-e][1,2,4]triazolo[4,3-a]pyrazin-1-yl)cyclopentyloxy)cyclohexane-carbonitrile (prepared using II from Example #22 Step C with 4-nitrobenzoic acid, SS with NaOH, VV, FFF with 4-oxocyclohexanecarbonitrile [Beta Pharma], Z with NaOH, A with Example #1 Step D, HATU and TEA, B with DIEA, D with NaOH) [Table 2, Method 57, $R_t$ = 19.5 min, or = negative] | 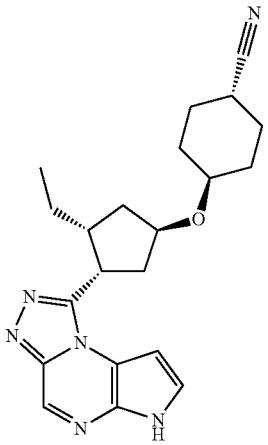 | AA.1.168 | 1.80 (b) | 379 |
| (cis-3-(3H-imidazo[1,2-a]pyrrolo[2,3-e]pyrazin-8-yl)cyclobutyl)methanamine (prepared from Preparation #36 using N, R with trimethylsilyl diazomethane, S with Example #3 Step E, E with TFA, KKKK with 2,2,3,3,3-pentafluoropropanoic anhydride, D with NaOH, F.1 with HBr in AcOH) [Table 2, Method 71, $R_t$ = 29.8 min] | 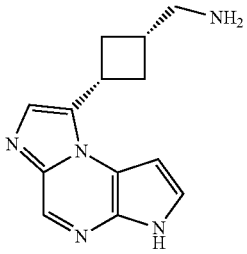 | AA.1.169 | 2.10 (r) | 242 |
| (trans-3-(3H-imidazo[1,2-a]pyrrolo[2,3-e]pyrazin-8-yl)cyclobutyl)methanamine (prepared from Preparation #36 using N, R with trimethylsilyl diazomethane, S with Example #3 Step E, E with TFA, KKKK with 2,2,3,3,3-pentafluoropropanoic anhydride, D with NaOH, F.1 with HBr in AcOH) [Table 2, Method 71, $R_t$ = 27.9 min] | 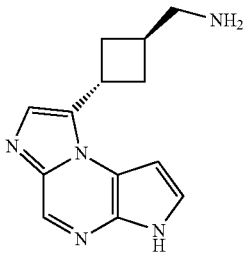 | AA.1.170 | 2.10 (r) | 242 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| N-((5-(3H-imidazo[1,2-a]pyrrolo[2,3-e]pyrazin-8-yl)-4-methyltetrahydrofuran-2-yl)methyl)-3,3,3-trifluoropropane-1-sulfonamide (prepared using E with HCl from Preparation #43, K with 3,3,3-trifluoropropane-1-sulfonyl chloride (Matrix), Z with NaOH, H with N,O-dimethylhydroxylamine, hydrochloric acid, MMMM with methylmagnesium bromide, M.1, LLLL, S from Example #3 Step E, E with TFA, KKKK with TFA & TFAA, D with $Na_2CO_3$) [Table 2, Method 51, $R_t$ = 46.2 min, or = positive] | 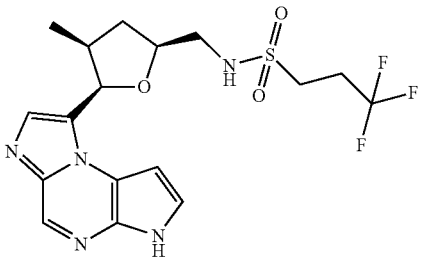 | AA.171 | 1.72 (a) | 432 |
| N-((5-(3H-imidazo[1,2-a]pyrrolo[2,3-e]pyrazin-8-yl)-4-methyltetrahydrofuran-2-yl)methyl)-3,3,3-trifluoropropane-1-sulfonamide (prepared using E with HCl from Preparation #43, K with 3,3,3-trifluoropropane-1-sulfonyl chloride (Matrix), Z with NaOH, H with N,O-dimethylhydroxylamine, Hydrochloric Acid, MMMM with methylmagnesium bromide, M.1, LLLL, S from Example #3 Step E, E with TFA, KKKK with TFA & TFAA, D with $Na_2CO_3$) [Table 2, Method 51, $R_t$ = 41.2 min, or = negative] | 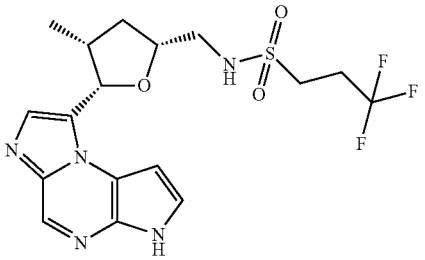 | AA.172 | 1.72 (a) | 432 |
| 3-ethyl-1-(morpholinosulfonylmethyl)-4-(6H-pyrrolo[2,3-e][1,2,4]triazolo[4,3-a]pyrazin-1-yl)cyclopentanol (prepared using NNNN with Preparation #41 and Example 35 Step G, LL) [Table 2, Method 52, $R_t$ = 12 min, or = negative] | 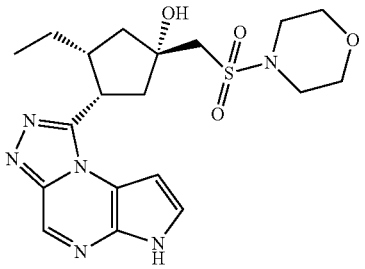 | AA.173 | 1.63 (a) | 435 |
| 3-ethyl-1-(morpholinosulfonylmethyl)-4-(6H-pyrrolo[2,3-e][1,2,4]triazolo[4,3-a]pyrazin-1-yl)cyclopentanol (prepared using NNNN with Preparation #41 and Example 35 Step G, LL) [Table 2, Method 52, $R_t$ = 8.9 min, or = negative] | 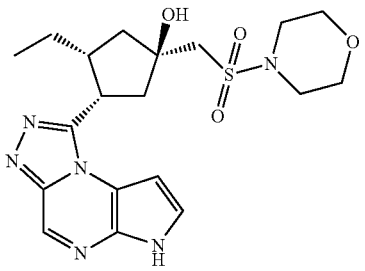 | AA.174 | 1.60 (a) | 435 |

TABLE AA.1-continued

| Examples prepared using General Procedure AA | | | | |
|---|---|---|---|---|
| Stereoisomers [Chiral Separation Method] | Structure | Ex. # | $R_t$ min (method) | m/z ESI+ $(M + H)^+$ |
| 3-ethyl-1-(morpholinosulfonylmethyl)-4-(6H-pyrrolo[2,3-e][1,2,4]triazolo[4,3-a]pyrazin-1-yl)cyclopentanol (prepared using NNNN with Preparation #41 and Example 35 Step G, LL) [Table 2, Method 53, $R_t$ = 18.7 min, or = negative] | 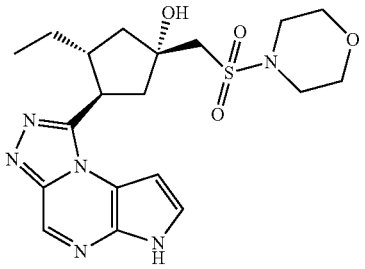 | AA.175 | 1.56 (a) | 435 |
| 8-(2-methyl-4-(tetrahydro-2H-pyran-4-yloxy)cyclopentyl)-3H-imidazo[1,2-a]pyrrolo[2,3-e]pyrazine (prepared using P from Example #24 Step H, VV, FFF with dihydro-2H-pyran-4(3H)-one, Z with NaOH, R, S from Example #3 Step E, E with TFA, KKKK with PFPAA, D with NaOH) [Table 2, Method 21, $R_t$ = 17.6 min, or = negative] | 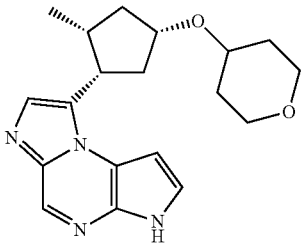 | AA.176 | 1. 60 (a) | 341 |
| 8-(2-methyl-4-(tetrahydro-2H-pyran-4-yloxy)cyclopentyl)-3H-imidazo[1,2-a]pyrrolo[2,3-e]pyrazine (prepared using P from Example #24 Step H, VV, FFF with dihydro-2H-pyran-4(3H)-one, Z with NaOH, R, S from Example #3 Step E, E with TFA, KKKK with PFPAA, D with NaOH) [Table 2, Method 21, $R_t$ = 5.1 min, or = negative] | 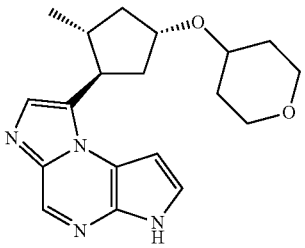 | AA.177 | 1.65 (a) | 341 |
| 8-(2-methyl-4-(tetrahydro-2H-pyran-4-yloxy)cyclopentyl)-3H-imidazo[1,2-a]pyrrolo[2,3-e]pyrazine (prepared using P from Example #24 Step H, II with 4-nitrobenzoic acid, SS, VV, FFF with dihydro-2H-pyran-4(3H)-one, Z with NaOH, R, S from Example #3 Step E, E with TFA, KKKK with PFPAA, D with NaOH) [Table 2, Method 28, $R_t$ = 18.6 min, or = negative] | 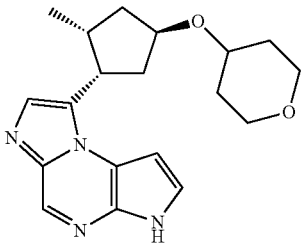 | AA.178 | 1.85 (a) | 341 |
| N-(3-methyl-4-(7-methyl-3H-imidazo[1,2-a]pyrrolo[2,3-e]pyrazin-8-yl)cyclopentyl)cyclopropane-sulfonamide (prepared using LLLL from Preparation #M.1.1, S from Example #3 Step E, E with TFA, T with Lawesson's Reagent, D with NaOH) [Table 2, Method 6, $R_t$ = 14.2 min, or = negative] | 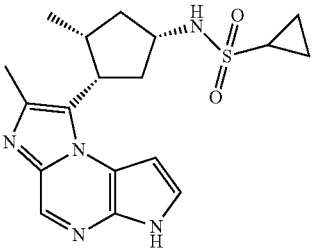 | AA.179 | 1.66 (a) | 374 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| N-(3-methyl-4-(7-methyl-3H-imidazo[1,2-a]pyrrolo[2,3-e]pyrazin-8-yl)cyclopentyl)cyclopropane-sulfonamide (prepared using LLLL from Preparation #M.1.1, S from Example #3 Step E, E with TFA, T with Lawesson's Reagent, D with NaOH) [Table 2, Method 6, $R_t$ = 9.3 min, or = positive | 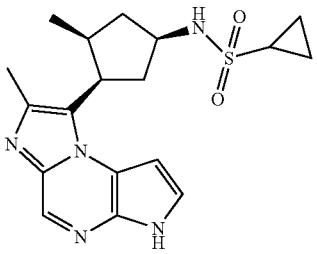 | AA.180 | 1.66 (a) | 374 |
| N,N-dibenzyl-3-(3H-imidazo[1,2-a]pyrrolo[2,3-e]pyrazin-8-yl)cyclopentanamine (prepared using X from 3-oxocyclopentanecarboxylic acid and dibenzylamine, FFFFF, GGGGG with Preparation #E.1.1, KKKK with PFPAA, D with NaOH, Y with $Pd(OH)_2$) [Table 2, Method 59, $R_t$ = 10.5 min, or = ND] | 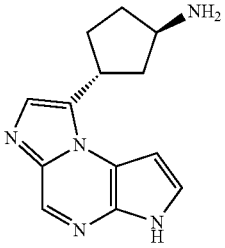 | AA.1.181 | 1.18 (b) | 242 |
| N,N-dibenzyl-3-(3H-imidazo[1,2-a]pyrrolo[2,3-e]pyrazin-8-yl)cyclopentanamine (prepared using X from 3-oxocyclopentanecarboxylic acid and dibenzylamine, FFFFF, GGGGG with Preparation #E.1.1, KKKK with PFPAA, D with NaOH, Y with $Pd(OH)_2$) [Table 2, Method 59, $R_t$ = 12.0 min, or = ND] | 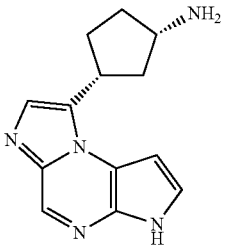 | AA.1.182 | 1.17 (b) | 242 |
| N,N-dibenzyl-3-(3H-imidazo[1,2-a]pyrrolo[2,3-e]pyrazin-8-yl)cyclopentanamine (prepared using X from 3-oxocyclopentanecarboxylic acid and dibenzylamine, FFFFF, GGGGG with Preparation #E.1.1, KKKK with PFPAA, D with NaOH, Y with $Pd(OH)_2$) [Table 2, Method 59, $R_t$ = 13.5 min, or = ND] | 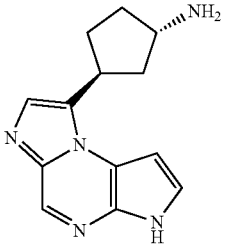 | AA.1.183 | 1.11 (b) | 242 |

TABLE AA.1-continued

Examples prepared using General Procedure AA

| Stereoisomers [Chiral Separation Method] | Structure | Ex. # | $R_t$ min (method) | m/z ESI+ $(M + H)^+$ |
|---|---|---|---|---|
| N,N-dibenzyl-3-(3H-imidazo[1,2-a]pyrrolo[2,3-e]pyrazin-8-yl)cyclopentanamine (prepared using X from 3-oxocyclopentanecarboxylic acid and dibenzylamine, FFFFF, GGGGG with Preparation #E.1.1, KKKK with PFPAA, D with NaOH, Y with $Pd(OH)_2$) [Table 2, Method 59, $R_t$ = 17.1 min, or = ND] | 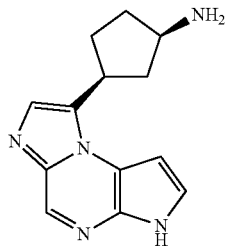 | AA.1.184 | 1.17 (b) | 242 |
| N-(2-cyclopropylethyl)-N-((1S,3R,4S)-3-ethyl-4-(6H-pyrrolo[2,3-e][1,2,4]triazolo[4,3-a]pyrazin-1-yl)cyclopentyl)oxetan-3-amine (prepared using X from Preparation #25 and oxetan-3-amine [Synthonix], X using 2-cyclopropylacetaldehyde [Anichem], and D with NaOH [Table 2, Method 55, $R_t$ = 22.7 min, or = negative] | 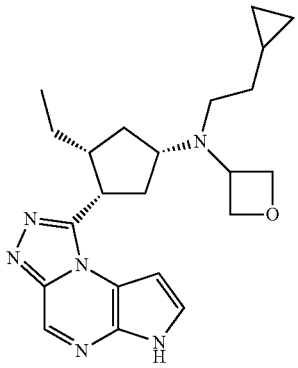 | AA.1.185* | 1.38 (a) | 395 |
| N-(2-cyclopropylethyl)-N-((1S,3R,4S)-3-ethyl-4-(6H-pyrrolo[2,3-e][1,2,4]triazolo[4,3-a]pyrazin-1-yl)cyclopentyl)oxetan-3-amine (prepared using X from Preparation #25 and oxetan-3-amine [Synthonix], X using cyclopropanecarbaldehyde, and D with NaOH [Table 2, Method 55, $R_t$ = 15.9 min, or = negative] | 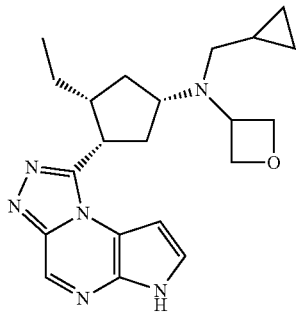 | AA.1.186* | 1.21 (a) | 381 |

General Procedure BB: Acidic Hydrolysis of an Acetyl Protected Amine

To a solution of an N-acetamide (preferably 1 equiv) in an organic solvent (such as 1,4-dioxane) is added an acid, such as 6 N aqueous HCl (3-100 equiv, preferably 30-40 equiv). The reaction mixture is heated at about 60-100° C. (preferably about 90-100° C.) for about 1-24 h (preferably about 16 h). The reaction mixture is allowed to cool to ambient temperature before it is partitioned between an organic solvent (such as EtOAc or DCM) and aqueous base (such as $NaHCO_3$, $Na_2CO_3$ or NaOH, preferably $NaHCO_3$) and the aqueous layer is optionally extracted with additional organic solvent (such as EtOAc or DCM). The organic layer is dried over anhydrous $MgSO_4$ or $Na_2SO_4$, filtered, and concd under reduced pressure.

Illustration of General Procedure BB

Preparation #BB.1*: (1S,3R,4S)-3-ethyl-4-(6-tosyl-6H-pyrrolo[2,3-e][1,2,4]triazolo[4,3-a]pyrazin-1-yl) cyclopentanamine

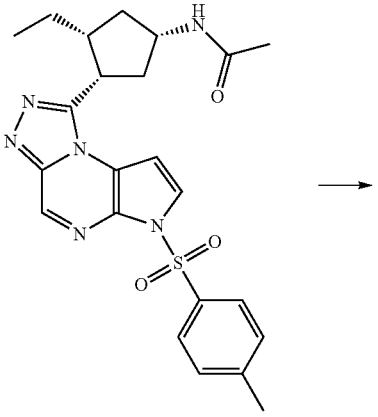

-continued

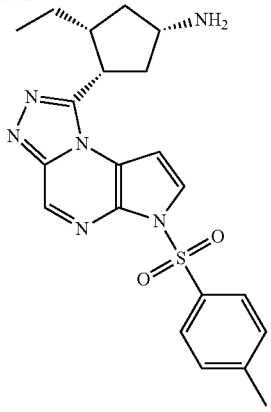

To a solution of N-((1S,3R,4S)-3-ethyl-4-(6-tosyl-6H-pyrrolo[2,3-e][1,2,4]triazolo[4,3-a]pyrazin-1-yl)cyclopentyl)acetamide (6.0 g, 12.86 mmol, Example #8, Step L) in 1,4-dioxane (78 mL) was added aqueous HCl (6 N, 75 mL, 450 mmol). The reaction mixture was heated at about 95° C. for about 16 h. The reaction was cooled to ambient temperature and the solvent was removed under reduced pressure. The residue was diluted with DCM (50 mL) and washed with saturated aqueous $NaHCO_3$ (100 mL). The aqueous portion was extracted with additional DCM (3×50 mL) and the combined organic layers were dried over anhydrous $MgSO_4$, filtered, and concd under reduced pressure. The crude material was purified by silica gel chromatography eluting with a gradient of 0-100% DCM/MeOH/$NH_4OH$ (950:45:5) in DCM to give (1S,3R,4S)-3-ethyl-4-(6-tosyl-6H-pyrrolo[2,3-e][1,2,4]triazolo[4,3-a]pyrazin-1-yl)cyclopentanamine (3.05 g, 56%) as a tan solid: LC/MS (Table 1, Method a) $R_t$=1.85 min; MS m/z: 425 $(M+H)^+$.

General Procedure CC: Formation of a Sulfamoyl Chloride

A round bottom flask is charged with an amine or amine salt (preferably 1 equiv) in an organic solvent (for example, DCM or toluene or toluene/DCM). If an amine salt is used, a base such as TEA or DIEA, preferably DIEA (1-10 equiv, preferably 2.5 equiv) is added and the reaction is stirred for about 1-20 min, (preferably about 5 min). The reaction mixture is then cooled to about −50-20° C., (preferably about −30° C.) for about 1-10 min (preferably about 5 min). Sulfuryl chloride or a solution of sulfuryl chloride (such as 1 M in DCM), preferably sulfuryl chloride (1-10 equiv, preferably 3.5 equiv) is added dropwise to the reaction mixture. The reaction mixture is stirred at about −50-0° C. (preferably about −30° C.) for about 0.5-4 h (preferably about 1 h) then is allowed to warm to ambient temperature and is stirred for about 1-24 h (preferably about 5 h). The reaction is then diluted with an organic solvent (such as DCM, EtOAc or toluene), and is washed with an aqueous solution of HCl (such as 0.1-6 M, preferably 1 M). Optionally, the reaction is poured over crushed ice and the layers are separated. The organic extracts are optionally washed with water and/or brine, dried over anhydrous $Na_2SO_4$ or $MgSO_4$, filtered or decanted, and concd under reduced pressure.

Illustration of General Procedure CC

Preparation #CC.1: azetidine-1-sulfonyl chloride

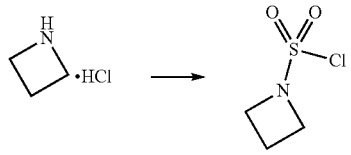

An oven dried flask is charged with azetidine hydrochloride (2.00 g, 21.38 mmol), DIEA (5.60 mL, 32.10 mmol), and DCM (50 mL). The reaction mixture was stirred for about 5 min at ambient temperature and then cooled to about −30° C. in a dry ice/MeCN bath for about 5 min. Sulfuryl chloride (4.30 mL, 53.60 mmol, Acros) was added dropwise over about 5 min. The reaction mixture was stirred at about −30° C. for about 1 h, then at ambient temperature for about 5 h. The reaction mixture was diluted with aqueous HCl (1 N, 15 mL). The layers were separated and the aqueous layer was extracted with DCM (10 mL). The combined organic layers were washed with aqueous HCl (1 N, 10 mL) and brine (20 mL). The organic layers were dried over anhydrous $MgSO_4$, filtered, and the solvent was removed under reduced pressure to give azetidine-1-sulfonyl chloride (1.86 g, 56%): $^1H$ NMR ($CDCl_3$) δ 4.25-4.01 (m, 4H), 2.51-2.29 (m, 2H).

General Procedure DD: Formation of a Sulfonylurea

To a solution of an amine (preferably 1 equiv) and a base such as TEA, DIEA, $Na_2CO_3$, or $K_2CO_3$ (1-20 equiv, preferably 2.5 equiv of TEA) in an organic solvent (such as DMF, DMA, DCM, THF, or 1,4-dioxane, preferably DMF) at about −10° C. to ambient temperature (preferably about 0° C.) is added a sulfamoyl chloride (1-5 equiv, preferably 2.2 equiv). The reaction mixture is stirred for about 1-48 h (preferably about 2-4 h) at ambient temperature. In cases where the reaction does not proceed to completion as monitored by TLC, LC/MS, or HPLC, additional sulfamoyl chloride is added portionwise (1-20 equiv in total, preferably 3 equiv per addition) to the reaction mixture about every 12-72 h (preferably about every 24 h) and the reaction mixture is stirred at ambient temperature until progress of the reaction has halted as monitored by TLC, LC/MS, or HPLC. The reaction mixture is concd to dryness under reduced pressure and/or diluted with an organic solvent (such as EtOAc or DCM) and water. The combined organic extracts are optionally washed with water and/or brine, dried over anhydrous $Na_2SO_4$ or $MgSO_4$, filtered, or decanted, and concd under reduced pressure. Optionally, the reaction is diluted with water and the solid is collected by vacuum filtration, washed with additional water, and dried under vacuum.

Illustration of General Procedure DD

Preparation #DD.1* : N-((1S,3R,4S)-3-ethyl-4-(6-tosyl-6H-pyrrolo[2,3-e][1,2,4]triazolo[4,3-a]pyrazin-1-yl)cyclopentyl)azetidine-1-sulfonamide

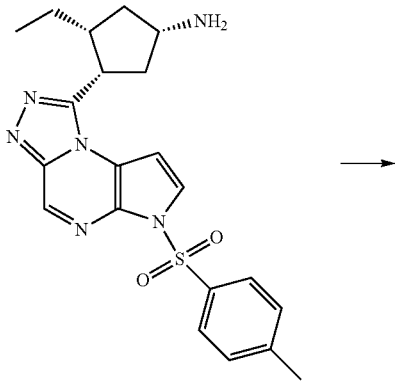

-continued

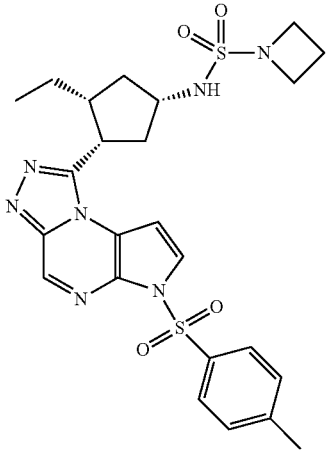

A flask was charged with (1S,3R,4S)-3-ethyl-4-(6-tosyl-6H-pyrrolo[2,3-e][1,2,4]triazolo[4,3-a]pyrazin-1-yl)cyclopentanamine (0.200 g, 0.471 mmol, Example #8, Step M) and DMF (4 mL). The solution was cooled to about 0° C. followed by the addition of TEA (0.16 mL, 1.2 mmol) and azetidine-1-sulfonyl chloride (0.165 g, 1.06 mmol, Preparation #CC.1). The reaction mixture was warmed to ambient temperature and was stirred for about 2 h. The solvent was removed under reduced pressure and DCM (10 mL) was added to the resulting residue. The organic solution was washed with water and brine (5 mL each). The combined organics were dried over anhydrous $MgSO_4$, filtered, and concd under reduced pressure to give a brown oil. The crude material was purified by silica gel chromatography eluting with a gradient of 0-70% EtOAc in DCM to afford N-((1S,3R,4S)-3-ethyl-4-(6-tosyl-6H-pyrrolo[2,3-e][1,2,4]triazolo[4,3-a]pyrazin-1-yl)-cyclopentyl)azetidine-1-sulfonamide (0.20 g, 77%) as a white solid: LC/MS (Table 1, Method a) $R_t$=2.39 min; MS m/z: 544 $(M+H)^+$.

TABLE DD.1

Example prepared from 1-((3R,4R)-4-methylpiperidin-3-yl)-6H-imidazo[1,5-a]pyrrolo[2,3-e]pyrazine hydrochloride (Example #5, Step J) using General Procedure DD

| Sulfonyl chloride | Product | Example # | $R_t$ min (Table 1, Method) | m/z ESI+ $(M + H)^+$ |
|---|---|---|---|---|
| pyrrolidine-1-sulfonyl chloride [ChemBridge-BB] | 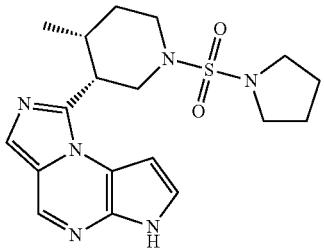 | DD.1.1* | 1.79 (b) | 389 |

TABLE DD.2

| Example prepared from (R)-1-(piperidin-3-yl)-6H-imidazo[1,5-a]pyrrolo[2,3-e]pyrazine hydrochloride (Example #6, Step H) using General Procedure DD | | | | |
|---|---|---|---|---|
| Sulfonyl chloride | Product | Example # | $R_t$ min (Table 1, Method) | m/z ESI+ $(M + H)^+$ |
| pyrrolidine-1-sulfonyl chloride [ChemBridge-BB] | 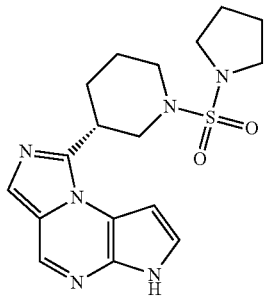 | DD.2.1* | 1.67 (b) | 375 |

General Procedure EE: Ether Formation from a Trichloroacetimidate Derivative

To an alcohol (preferably 1 equiv) in a mixture of organic solvents such as DCM and cyclohexane (1:1 to 1:5, preferably 1:2) at about −10-5° C. (preferably about 0° C.) is added a 2,2,2-trichloroacetimidate derivative (1-3 equiv, preferably 1.6 equiv) followed by a slow addition of an acid such as p-toluenesulfonic acid or trifluoromethanesulfonic acid (0.05-1 equiv, preferably 0.08-0.1 equiv). The reaction mixture is stirred at about −10-5° C. (preferably about 0° C.) for about 5-60 min (preferably about 30 min). The ice bath is removed and the reaction mixture is stirred at ambient temperature for about 2-24 h (preferably about 16 h). The suspension is poured into ice water and stirred for about 5-60 min (preferably about 30 min). The suspension is either filtered while washing with an organic solvent such as DCM or diluted with an organic solvent such as DCM. The layers are separated and the aqueous layer is extracted with an organic solvent such as DCM. The combined organic layers are washed with water, dried over anhydrous $Na_2SO_4$ or $MgSO_4$, filtered and concd under reduced pressure.

Illustration of General Procedure EE

Preparation #EE.1: Ethyl 2-ethyl-4-(4-methoxybenzyloxy)cyclopentanecarboxylate

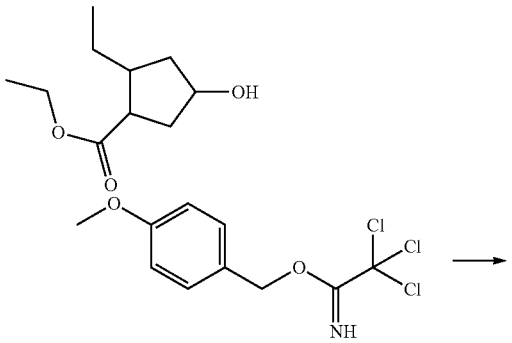

-continued

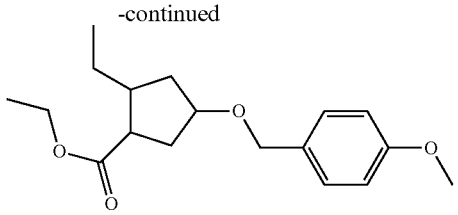

To a mixture of ethyl 2-ethyl-4-hydroxycyclopentanecarboxylate (37.78 g, 203 mmol, Preparation #P.1) in DCM (100 mL) and cyclohexane (200 mL) at about 0° C. was added 4-methoxybenzyl 2,2,2-trichloroacetimidate (93.58 g, 331 mmol) followed by dropwise addition of trifluoromethanesulfonic acid (1.6 mL, 18.0 mmol) over about 35 min. The reaction mixture was stirred at about 0° C. for about 30 min. The ice bath was removed and the reaction mixture was stirred at ambient temperature for about 16 h. The suspension was poured into ice-water (500 mL) and stirred for about 30 min. The solid was removed by filtration while washing with DCM (100 mL). The layers in the filtrate were separated and the aqueous layer was extracted with DCM (3×200 mL). The combined organic layers were washed with water (200 mL), dried over anhydrous $MgSO_4$, filtered, and concd under reduced pressure. The crude material was purified using silica gel chromatography eluting with a gradient of 0-100% DCM:EtOAc (95:5) in DCM to give ethyl 2-ethyl-4-(4-methoxybenzyloxy)cyclopentanecarboxylate (39.80 g, 64%): LC/MS (Table 1, Method b) $R_t$=2.90 min; MS m/z: 307 $(M+H)^+$.

General Procedure FF: Deprotection of a PMB Protected Alcohol

To a PMB protected alcohol (preferably 1 equiv) in an mixture of solvents such as DCM and water (1:1 to 7:1, preferably 5:1) is added 2,3-dichloro-5,6-dicyano-p-benzoquinone (1-2 equiv, preferably 1.2 equiv). The reaction mixture is stirred at ambient temperature for about 8-24 h (preferably about 16 h). The solid is removed by filtration while washing with an organic solvent such as DCM. The layers in the filtrate are separated and the organic layer is washed with saturated aqueous $NaHCO_3$ and brine, dried over anhydrous $Na_2SO_4$ or $MgSO_4$, filtered, and concd under reduced pressure.

Illustration of General Procedure FF

Preparation #FF.1: 3-ethyl-4-(6-tosyl-6H-pyrrolo[2,3-e][1,2,4]triazolo[4,3-a]pyrazin-1-yl)cyclopentanol

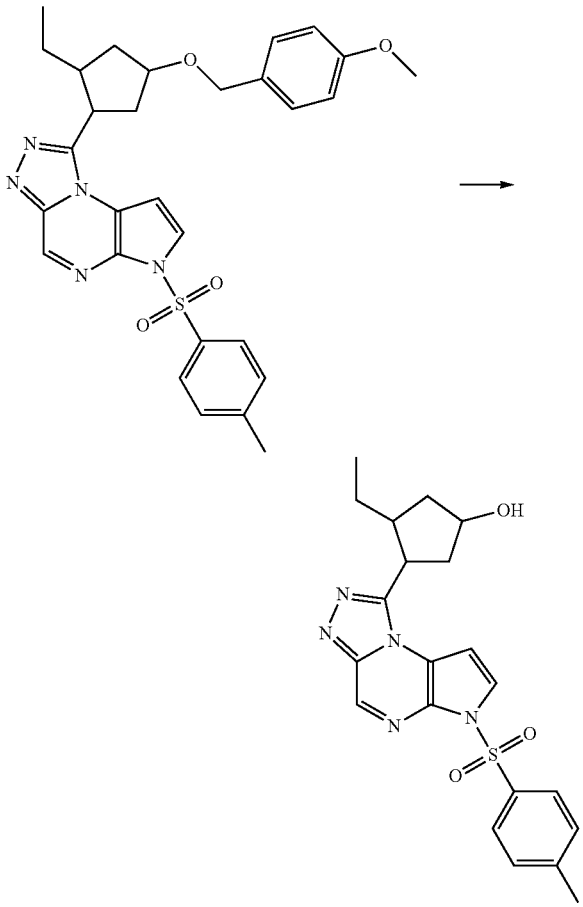

To 2-ethyl-4-(4-methoxybenzyloxy)cyclopentyl)-6-tosyl-6H-pyrrolo[2,3-e][1,2,4]triazolo[4,3-a]pyrazine (1.153 g, 2.11 mmol, prepared using Z from Preparation #EE.1, A from Example #1, Step D, HATU, and TEA, B with DIEA) in DCM (18 mL) and water (3.5 mL) was added 2,3-dichloro-5,6-dicyano-p-benzoquinone (0.576 g, 2.54 mmol). The reaction mixture was stirred at ambient temperature for about 16 h. The solid was removed by filtration while washing with DCM (150 mL). The organic layer was separated and washed with saturated aqueous $NaHCO_3$ (2×40 mL) and brine (40 mL), dried over anhydrous $MgSO_4$, filtered, and concd under reduced pressure. The residue was purified using silica gel chromatography (40 g) eluting with a gradient of 30-100% EtOAc in DCM to give 3-ethyl-4-(6-tosyl-6H-pyrrolo[2,3-e][1,2,4]triazolo[4,3-a]pyrazin-1-yl)cyclopentanol (0.672 g, 75%): LC/MS (Table 1, Method b) $R_t$=2.09 min; MS m/z: 426 $(M+H)^+$.

General Procedure GG: Formation of a Lactone

To a γ-alcohol carboxylic acid (preferably 1 equiv) in an organic solvent such as DCM is added a base (such as TEA, 3-5 equiv, preferably 3 equiv) and BOP-Cl (1-2 equiv, preferably 1.2 equiv). The reaction mixture is stirred at ambient temperature for about 1-5 h (preferably about 2 h). The reaction mixture is poured into an organic solvent (preferably $Et_2O$). The solid is removed by filtration while washing with an organic solvent such as $Et_2O$. The filtrate is concd under reduced pressure. Alternatively, the filtrate is washed with saturated aqueous $NaHCO_3$, 1 N aqueous citric acid, and brine, dried over anhydrous $Na_2SO_4$ or $MgSO_4$, filtered, and concd under reduced pressure.

Illustration of General Procedure GG

Preparation #GG.1*: (1S,4S,5R)-5-ethyl-2-oxabicyclo[2.2.1]heptan-3-one

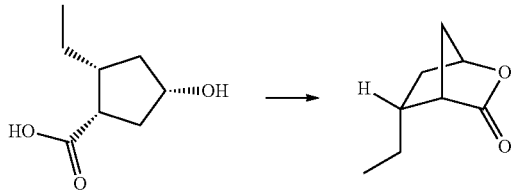

To (1S,2R,4S)-2-ethyl-4-hydroxycyclopentanecarboxylic acid (0.943 g, 5.96 mmol, Example #4, Step H) in DCM (60 mL) was added TEA (2.5 mL, 18 mmol) and BOP-Cl (1.82 g, 7.15 mmol). The reaction mixture was stirred at ambient temperature for about 2 h then poured into $Et_2O$ (350 mL). The solid was removed by filtration while washing with $Et_2O$ (50 mL). The filtrate was concd under reduced pressure to give a yellow oil which was dissolved in DCM (5 mL) and $Et_2O$ was added to give a solid. The supernatant was decanted and the solid was washed with additional $Et_2O$. The combined organic extracts were concd under reduced pressure to give (1S,4S,5R)-5-ethyl-2-oxabicyclo[2.2.1]heptan-3-one containing about 15 mol % TEA (0.912 g, 99% crude): $^1H$ NMR ($CDCl_3$) δ 4.85 (s, 1H), 2.88 (s, 1H), 2.19 (m, 2H), 2.08 (m, 1H), 1.69 (m, 1H), 1.41 (m, 3H), 0.97 (t, J=5.4, 3H).

General Procedure HH: Opening of a Lactone with an Amine or Hydrazine

To a lactone (preferably 1 equiv) in an organic solvent such as 1,4-dioxane or DCM (preferably 1,4-dioxane) is added a hydrazine (1-1.5 equiv, preferably 1 equiv). Alternatively, a lactone (preferably 1 equiv) is added to a solution of an HCl salt of an amine and DIEA (1-1.5 equiv, preferably 1 equiv) in an organic solvent or mixture of solvents (such as 1,4-dioxane, DCM, or DCM/DMF, preferably DCM). The reaction mixture is stirred at ambient temperature or heated at about 40-100° C. (preferably about 80° C. when 1,4-dioxane is used, reflux when DCM is used) for about 1-24 h (preferably about 16 h). If heating, the reaction mixture is cooled to ambient temperature. In cases where the reaction does not proceed to completion as monitored by TLC, LC/MS or HPLC, trimethylaluminum (1-8 equiv, preferably 3 equiv) is added dropwise neat or in solution (such as 2 M in chlorobenzene, 2 M in heptane, or 2 M in toluene, preferably 2M in toluene) after the optional addition of an organic solvent (such as 1,4-dioxane, DCM, or DMF, preferably 1,4-dioxane) and the reaction mixture is stirred at ambient temperature for about 0.25-16 h (preferably about 0.5 h). Optionally, trimethylaluminum neat or in solution as described above may be added from the onset of the reaction. Aqueous HCl (1 N, 3-10 equiv, preferably 8 equiv) is added dropwise and the reaction mixture is stirred for about 10-60 min (preferably about 30 min). The layers are separated and the aqueous layer is extracted with an organic solvent such as EtOAc or DCM (preferably EtOAc). The combined organic portions are washed with water, saturated aqueous $NaHCO_3$, brine and dried over anhydrous $Na_2SO_4$ or $MgSO_4$, filtered, and concd under reduced pressure.

Illustration of General Procedure HH

Preparation #HH.1*: (1S,2R,4S)-2-ethyl-4-hydroxy-N'-(5-tosyl-5H-pyrrolo[2,3-b]pyrazin-2-yl)cyclopentanecarbohydrazide

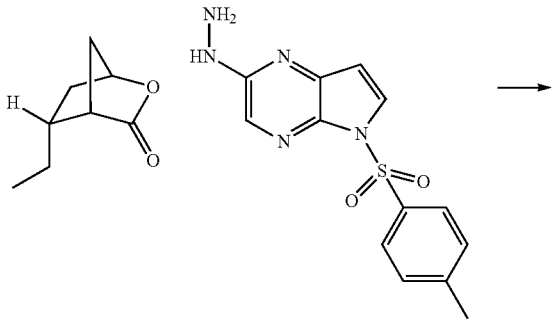

-continued

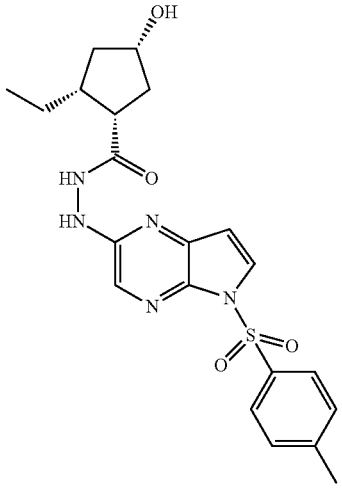

To (1S,4S,5R)-5-ethyl-2-oxabicyclo[2.2.1]heptan-3-one (0.835 g, 5.96 mmol, Preparation #GG.1) in 1,4-dioxane (12 mL) was added 2-hydrazinyl-5-tosyl-5H-pyrrolo[2,3-b]pyrazine (Example #1, Step D, 1.81 g, 5.96 mmol). The reaction mixture was heated at about 80° C. for about 16 h then cooled to ambient temperature. 1,4-Dioxane (25 mL) and trimethylaluminum (2 N in toluene, 9 mL, 18 mmol) were added sequentially. The reaction mixture was stirred at ambient temperature for about 30 min. Aqueous HCl (1 N, 50 mL) was added dropwise and the reaction mixture was stirred for about 30 min. The layers were separated. The aqueous portion was extracted with EtOAc (2×100 mL). The combined organic extracts were washed with water (10 mL), saturated aqueous $NaHCO_3$ (15 mL), brine (15 mL) and dried over anhydrous $MgSO_4$, filtered, and concd under reduced pressure. The residue was purified using silica gel chromatography (40 g) eluting with 100% EtOAc to give (1S,2R,4S)-2-ethyl-4-hydroxy-N'-(5-tosyl-5H-pyrrolo[2,3-b]pyrazin-2-yl)cyclopentanecarbohydrazide (1.887 g, 53%): LC/MS (Table 1, Method b) $R_t$=2.05 min; MS m/z: 444 $(M+H)^+$.

TABLE HH.1

Examples prepared from 1-((3R,4R)-4-methylpiperidin-3-yl)-6H-imidazo[1,5-a]pyrrolo[2,3-e]pyrazine hydrochloride (Example #5, Step J) using General Procedure HH with DIEA

| Lactone | Product | Example # | $R_t$ min (Table 1, Method) | m/z ESI+ $(M + H)^+$ |
|---|---|---|---|---|
| β-propiolactone | 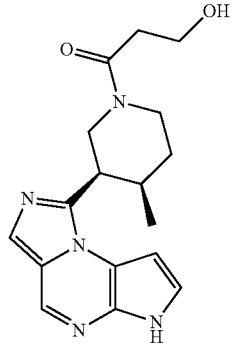 | HH.1.1* | 1.02 (b) | 328 |

General Procedure II: Mitsunobu Reaction of an Alcohol

To an alcohol (preferably 1 equiv) in an organic solvent such as THF, benzene, toluene, or 1,4-dioxane (preferably THF) is added a suitably acidic reactant (such as a carboxylic acid, a phenol or a heteroaryl alcohol, 1-3 equiv, preferably 1.5 equiv), followed by tri-n-butylphosphine, triphenylphosphine or polymer bound triphenylphosphine (preferably polymer bound triphenylphosphine, 1-3 equiv, preferably 1.5 equiv), and TEA (1-6 equiv, preferably 4.5 equiv). TMAD, 1,1'-(azodicarbonyl)dipiperidine, DIAD or DEAD (preferably DEAD, 1-3 equiv, preferably 1.5 equiv) is added dropwise. The reaction mixture is stirred at ambient temperature for about 5-48 h (preferably about 16 h). Alternatively, after about 0.1-24 h (preferably about 1 h), additional phosphine reagent (0.2-2 equiv, preferably 0.75 equiv) and TMAD, 1,1'-(azodicarbonyl)dipiperidine, DIAD or DEAD (0.2-1 equiv, preferably 0.75 equiv) are added to drive the reaction to completion. When polymer bound reagent is used, the reaction mixture is filtered and washed with a mixture of solvents such as DCM, EtOAc and MeOH (preferably DCM then MeOH). The filtrate is concd under reduced pressure. When no polymer bound reagent is used, the reaction mixture is diluted with an organic solvent such as DCM or EtOAc and then washed with water, saturated aqueous $NaHCO_3$, brine and dried over anhydrous $Na_2SO_4$ or $MgSO_4$, filtered, and concd under reduced pressure.

Illustration of General Procedure II

Preparation #II.1*: (1S,2R,4R)-4-(4-cyanophenoxy)-2-ethyl-N'-(5-tosyl-5H-pyrrolo[2,3-b]pyrazin-2-yl)cyclopentanecarbohydrazide

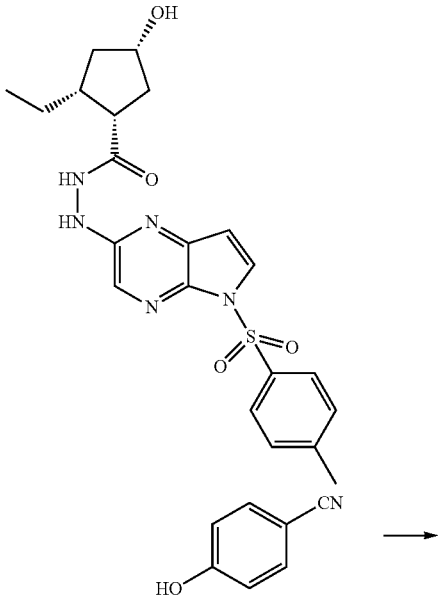

-continued

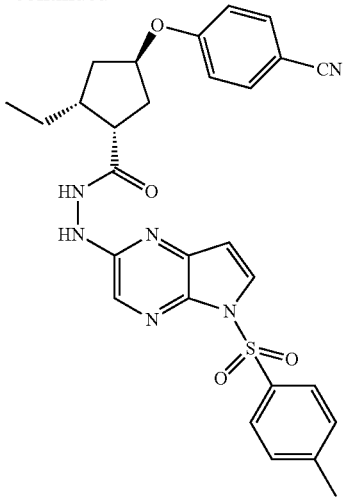

To (1S,2R,4S)-2-ethyl-4-hydroxy-N-(5-tosyl-5H-pyrrolo[2,3-1)]pyrazin-2-yl)cyclopentane-carbo-hydrazide (0.885 g, 1.99 mmol, Example #4, Step J) in THF (15 mL) was added 4-hydroxybenzonitrile (0.357 g, 2.99 mmol), triphenylphosphine (0.998 g, 2.99 mmol, polymer bound, 3 mmol/g), and TEA (1.3 mL, 9 mmol). DEAD (0.47 mL, 2.99 mmol) was added dropwise. The reaction mixture was stirred for about 1 h then additional triphenylphosphine (0.50 g, 1.50 mmol, polymer bound, 3 mmol/g) and DEAD (0.2 mL, 1.3 mmol) were added and the reaction mixture was stirred at ambient temperature for about 16 h. The solid was removed by filtration while washing with DCM (5×5 mL) then MeOH (4×5 mL). The filtrate was concd under reduced pressure and the residue was purified using silica gel chromatography (40 g) eluting with a gradient of 0-40% EtOAc in DCM to give (1S,2R,4R)-4-(4-cyanophenoxy)-2-ethyl-N'-(5-tosyl-5H-pyrrolo[2,3-b]pyrazin-2-yl)cyclopentanecarbohydrazide (0.958 g, 88%) as a yellow foam: LC/MS (Table 1, Method b) $R_t$=2.56 min; MS m/z: 545 $(M+H)^+$.

General Procedure JJ: Displacement of a Halide with an Alcohol

To an alcohol (preferably 1 equiv) in an organic solvent such as DMF, THF or 1,4-dioxane (preferably DMF) at about 0-25° C. (preferably ambient temperature) is added NaH (60% dispersion in mineral oil, 1-4 equiv, preferably 1.2 equiv) in portions. After about 2-60 min (preferably about 5 min), a halide (1-30 equiv, preferably 1.1 equiv) is added. The reaction mixture is heated at about 60-80° C. (preferably about 70° C.) for about 1-16 h (preferably about 2 h). After cooling to ambient temperature, ice-water is added to the reaction mixture or the reaction mixture is poured into ice water and then extracted with an organic solvent such as DCM or EtOAc (preferably DCM). The combined organic portions are concd under reduced pressure. Alternatively, the combined organic portions are washed with water, saturated aqueous $NaHCO_3$, brine and dried over anhydrous $Na_2SO_4$ or $MgSO_4$, filtered, and concd under reduced pressure.

Illustration of General Procedure JJ

Preparation #JJ.1: 5-(3-ethyl-4-(6-((2-(trimethylsilyl)ethoxy)methyl)-6H-pyrrolo[2,3-e][1,2,4]triazolo[4,3-a]pyrazin-1-yl)cyclopentyloxy)pyrazine-2-carbonitrile

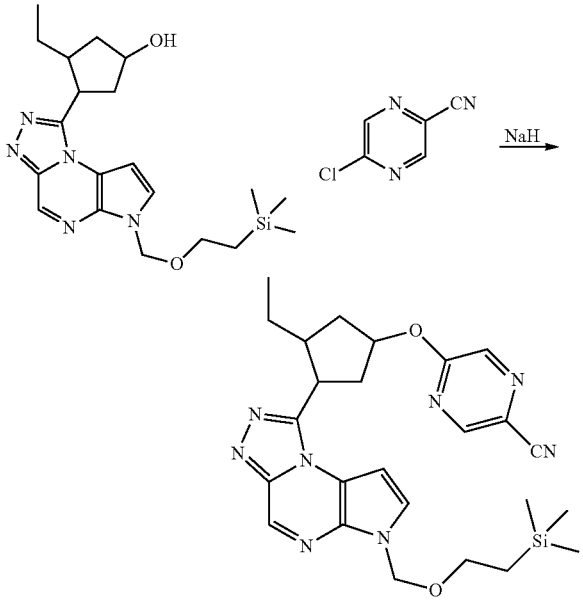

To 3-ethyl-4-(6-((2-(trimethylsilyl)ethoxy)methyl)-6H-pyrrolo[2,3-e][1,2,4]triazolo[4,3-a]pyrazin-1-yl)cyclopentanol (0.098 g, 0.24 mmol, prepared using FF from Preparation #KK.1) in DMF (1 mL) was added NaH (0.012 g, 0.29 mmol, 60% dispersion in mineral oil) portionwise. After about 5 min, 2-chloro-5-cyanopyrazine (0.039 g, 0.28 mmol, ArkPharm) was added. The reaction mixture was heated at about 70° C. for about 2 h. After cooling to ambient temperature, ice water (2 mL) was added and the mixture was extracted with DCM (3×5 mL). The organic layers were combined and the solvents were removed under reduced pressure. The residue was purified using silica gel chromatography (12 g) eluting with a gradient of 20-80% EtOAc in DCM to give 5-(3-ethyl-4-(6-((2-(trimethylsilyl)ethoxy)methyl)-6H-pyrrolo[2,3-e][1,2,4]triazolo[4,3-a]pyrazin-1-yl)cyclopentyloxy)pyrazine-2-carbonitrile (0.085 g, 69%): LC/MS (Table 1, Method b) $R_t$=2.84 min; MS m/z: 505 $(M+H)^+$.

General Procedure KK: SEM-Protection

To a pyrrole derivative (preferably 1 equiv) in an organic solvent (such as THF, 1,4-dioxane, or DMF, preferably 1,4-dioxane) at about 0-40° C. (preferably ambient temperature) is added NaH (60% dispersion in mineral oil) (1-3equiv, preferably 1.05 equiv) in portions. The reaction mixture is stirred for about 1-60 min (preferably about 30 min) SEM-Cl (1-3 equiv, preferably 1.5 equiv) is then added. After about 15 min-24 h (preferably about 30 min), the solvent is removed and the residue is partitioned between an organic solvent such as EtOAc and water. The layers are separated and the organic solvent is removed under reduced pressure to give the target compound. Alternatively, the reaction mixture is poured slowly into ice water with stirring to provide a suspension. Solids may be collected by filtration and dried to provide the target compound. Also, the filtrate may be partitioned between an organic solvent (such as EtOAc or DCM) and an aqueous base (such as saturated aqueous $NaHCO_3$ or saturated aqueous $Na_2SO_4$, preferably saturated aqueous $NaHCO_3$). The organic portion is separated and concd under reduced pressure to provide the target compound.

Illustration of General Procedure KK

Preparation #KK.1: 1-(2-ethyl-4-(4-methoxybenzyloxy)cyclopentyl)-6-((2-(trimethylsilyl)ethoxy)methyl)-6H-pyrrolo[2,3-e][1,2,4]triazolo[4,3-a]pyrazine

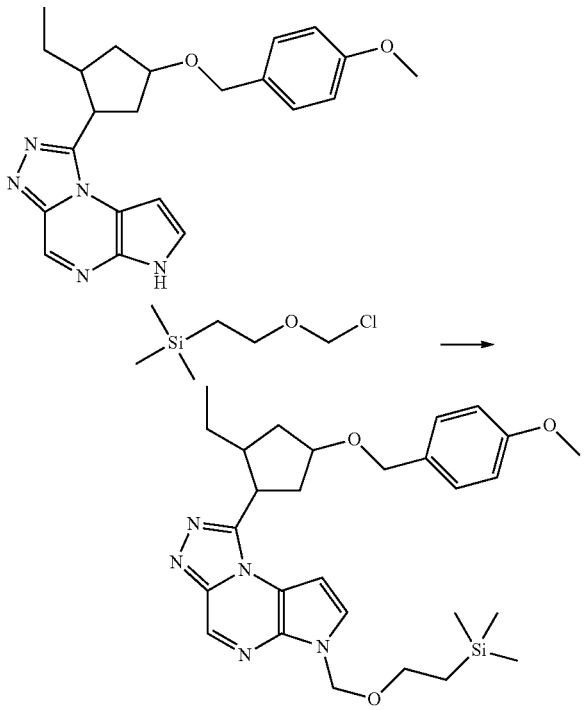

To a suspension of 1-(2-ethyl-4-(4-methoxybenzyloxy)cyclopentyl)-6H-pyrrolo[2,3-e][1,2,4]-triazolo[4,3-a]pyrazine (0.323 g, 0.825 mmol, prepared using Z from Preparation #EE.1, A from Example #1, Step D, HATU, and TEA, B with DIEA, D with NaOH) in 1,4-dioxane (2.5 mL) was added NaH (0.035 g, 0.866 mmol, 60% dispersion in mineral oil) in portions. The reaction mixture was stirred at ambient temperature for about 30 min. SEM-Cl (0.15 mL, 0.83 mmol) was added. After about 30 min, the solvent was removed and the residue was partitioned between EtOAc (12 mL) and water (2 mL). The organic layer was separated and concd under reduced pressure. The residue was purified using silica gel chromatography (40 g) eluting with a gradient of 0-60% EtOAc in DCM to give 1-(2-ethyl-4-(4-methoxybenzyloxy)cyclopentyl)-6-((2-(trimethylsilyl)ethoxy)methyl)-6H-pyrrolo[2,3-e][1,2,4]triazolo[4,3-a]pyrazine (0.372 g, 86%): LC/MS (Table 1, Method b) $R_t$=2.96 min; MS m/z: 522 $(M+H)^+$.

General Procedure LL: SEM-Deprotection

To a solution of a N-SEM-protected compound (preferably 1 equiv) in an organic solvent (such as DMF, 1,4-dioxane, or DCM, preferably DCM) is added TFA (5-70 equiv, preferably 50 equiv) and the reaction mixture is stirred at about 0-40° C. (preferably ambient temperature) for about 1-20 h (preferably about 1-4 h). Additional TFA (5-20 equiv, preferably 10 equiv) may be added. The resulting mixture is concd under reduced pressure and the residue is dissolved in an organic solvent such as 1,4-dioxane, MeOH or EtOH (preferably 1,4-dioxane). An aqueous base (such as NaOH or $NH_4OH$, preferably $NH_4OH$, 30-200 equiv, preferably 120 equiv) is added and the reaction mixture is heated at about 30-100° C. (preferably about 60° C.) for about 30 min-10 h (preferably about 30 min). The reaction mixture is cooled to ambient temperature, water is added and the product is isolated by filtration. Alternatively the mixture may be partitioned between an organic solvent (such as EtOAc or DCM) and an aqueous base (such as saturated aqueous $NaHCO_3$ or saturated aqueous $Na_2SO_4$, preferably saturated aqueous $NaHCO_3$). The organic portion is separated and concd under reduced pressure to provide the target compound. In some cases an intermediate hydroxymethylsulfonamide may be isolated.

Illustration of General Procedure LL

Preparation #LL.1: 5-(-3-ethyl-4-(6H-pyrrolo[2,3-e][1,2,4]triazolo[4,3-a]pyrazin-1-yl)cyclopentyloxy)pyrazine-2-carbonitrile

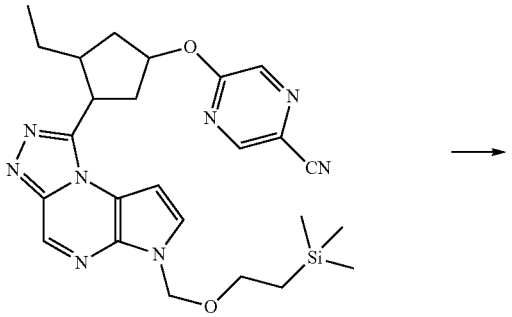

-continued

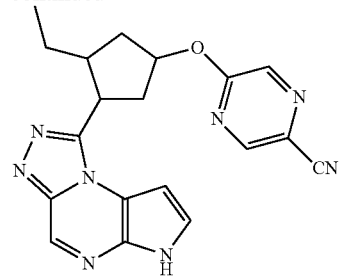

To 5-(3-ethyl-4-(6-((2-(trimethylsilyl)ethoxy)methyl)-6H-pyrrolo[2,3-e][1,2,4]triazolo[4,3-a]pyrazin-1-yl)cyclopentyloxy)pyrazine-2-carbonitrile (0.097 g, 0.19 mmol, Preparation #11.1) in DCM (2.5 mL) was added TFA (0.7 mL, 10 mmol). The reaction mixture was stirred at ambient temperature for about 1.5 h. The solvents were removed under reduced pressure and the residue was dissolved in 1,4-dioxane (1.3 mL). Ammonium hydroxide (28-30% aqueous ammonia, 2.5 mL, 24 mmol) was added and the reaction mixture was heated at about 60° C. for about 30 min then cooled to ambient temperature. Water (4 mL) was added and the precipitate was collected by filtration to give 5-(-3-ethyl-4-(6H-pyrrolo[2,3-e][1,2,4]triazolo[4,3-a]pyrazin-1-yl)cyclopentyloxy)pyrazine-2-carbonitrile (0.0628 g, 87%): LC/MS (Table 1, Method b) $R_t$=1.99 min; MS m/z: 375 $(M+H)^+$.

TABLE LL.1

Examples prepared using General Procedure LL

| Silyl protected pyrrole | Product | Ex # | $R_t$ min (Table 1, Method) | m/z ESI+ $(M + H)^+$ |
|---|---|---|---|---|
| N-((1S,3R,4S)-3-ethyl-4-(8-methyl-6-((2-(trimethylsilyl)ethoxy)methyl)-6H-pyrrolo[2,3-e][1,2,4]triazolo[4,3-a]pyrazin-1-yl)cyclopentyl)-N-((2-(trimethylsilyl)ethoxy)methyl)cyclopropanesulfonamide (Preparation #23) | 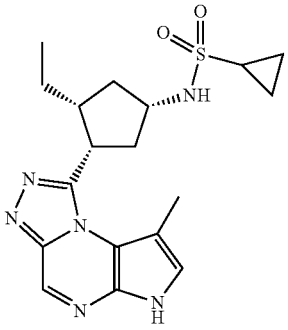 | LL.1.1* | 1.71 (a) | 389 |
| N-((1S,3R,4S)-3-ethyl-4-(8-methyl-6-((2-(trimethylsilyl)ethoxy)methyl)-6H-pyrrolo[2,3-e][1,2,4]triazolo[4,3-a]pyrazin-1-yl)cyclopentyl)-N-((2-(trimethylsilyl)ethoxy)methyl)cyclopropanesulfonamide (Preparation #23) | 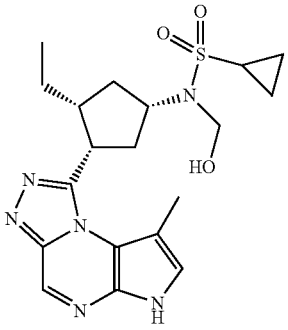 | LL.1.2* | 1.96 (a) | 419 |

TABLE LL.1-continued

| Examples prepared using General Procedure LL | | | | |
|---|---|---|---|---|
| Silyl protected pyrrole | Product | Ex # | $R_t$ min (Table 1, Method) | m/z ESI+ $(M + H)^+$ |
| N-((1S,3S,4R)-3-(8-cyano-6-((2-(trimethylsilyl)ethoxy)methyl)-6H-pyrrolo[2,3-e][1,2,4]triazolo[4,3-a]pyrazin-1-yl)-4-ethylcyclopentyl)cyclopropanesulfonamide (Preparation #HHH.1) | 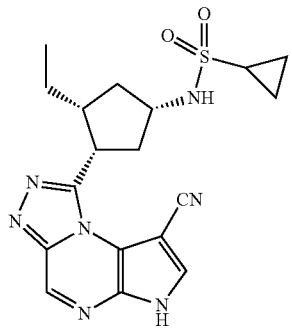 | LL.1.3* | 1.64 (b) | 400 |
| 1-((1S,2R,4R)-2-ethyl-4-(2,2,2-trifluoroethylsulfonyl)cyclopentyl)-6-((2-(trimethylsilyl)ethoxy)methyl)-6H-pyrrolo[2,3-e][1,2,4]triazolo[4,3-a]pyrazine (Preparation #LLL.1) | 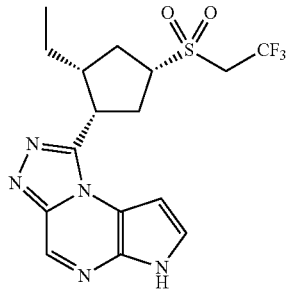 | LL.1.4 | 1.81 (a) | 402 |
| 3-fluoro-N-((1S,3R,4S)-3-methyl-4-(3-((2-(trimethylsilyl)ethoxy)methyl)-3H-imidazo[1,2-a]pyrrolo[2,3-e]pyrazin-8-yl)cyclopentyl)propane-1-sulfonamide (prepared using FFFFF from Preparation #33, GGGGG with Preparation #E.1.1, KKKK with PFPAA, D with NaOH, KK, Y; K with 3-fluoropropane-1-sulfonyl chloride [Hande]) | 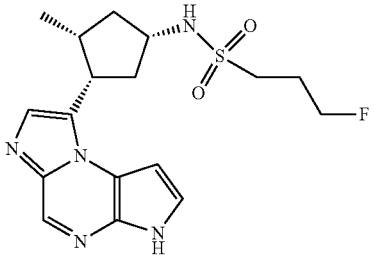 | LL.1.5* | 1.53 (b) | 380 |
| 3,3-difluoro-N-((1S,3R,4S)-3-methyl-4-(3-((2-(trimethylsilyl)ethoxy)methyl)-3H-imidazo[1,2-a]pyrrolo[2,3-e]pyrazin-8-yl)cyclopentyl)cyclobutane-1-sulfonamide (prepared using FFFFF with Preparation #33, GGGGG with Preparation #E.1.1, KKKK with PFPAA, D with NaOH, KK, Y, K with Preparation #34 and DIEA) | 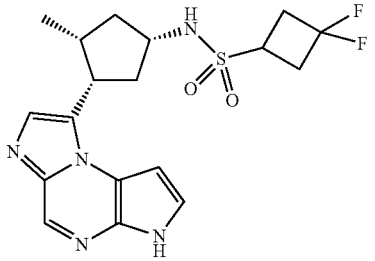 | LL.1.6* | 1.84 (a) | 410 |
| 3,3,3-trifluoro-N-methyl-N-((1S,3R,4S)-3-methyl-4-(3-((2-(trimethylsilyl)ethoxy)methyl)-3H-imidazo[1,2-a]pyrrolo[2,3-e]pyrazin-8-yl)cyclopentyl)propane-1-sulfonamide (prepared using FFFFF with Preparation #33, GGGGG with Preparation #E.1.1, KKKK with PFPAA, D with NaOH, KK, Y, K with 3,3,3-trifluoropropane-1-sulfonyl chloride (Matrix), S with iodomethane ) | 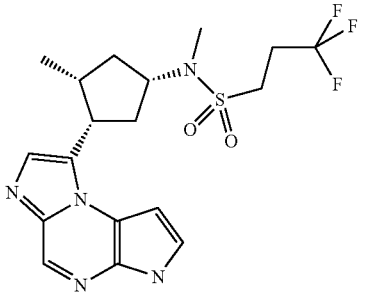 | LL.1.7* | 2.04 | 429 |

TABLE LL.1-continued

Examples prepared using General Procedure LL

| Silyl protected pyrrole | Product | Ex # | $R_t$ min (Table 1, Method) | m/z ESI+ $(M + H)^+$ |
|---|---|---|---|---|
| N-((1S,3R,4S)-3-methyl-4-(3-((2-(trimethylsilyl)ethoxy)methyl)-3H-imidazo[1,2-a]pyrrolo[2,3-e]pyrazin-8-yl)cyclopentyl)azetidine-1-sulfonamide (prepared using FFFFF with Preparation #33, GGGGG with Preparation #E.1.1, KKKK with PFPAA, D with NaOH, KK, Y, ZZ, AAA with azetidine) | 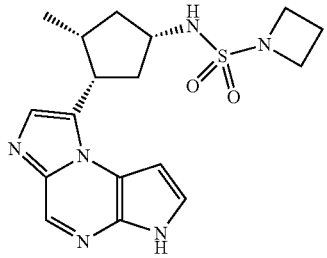 | LL.1.8* | 1.53 | 375 |
| 3-fluoro-N-((1S,3R,4S)-3-methyl-4-(3-((2-(trimethylsilyl)ethoxy)methyl)-3H-imidazo[1,2-a]pyrrolo[2,3-e]pyrazin-8-yl)cyclopentyl)azetidine-1-sulfonamide (prepared using FFFFF with Preparation #33, GGGGG with Preparation #E.1.1, KKKK with PFPAA, D with NaOH, KK, Y, ZZ, AAA with 3-fluoroazetidine hydrochloride [Parkway]) | 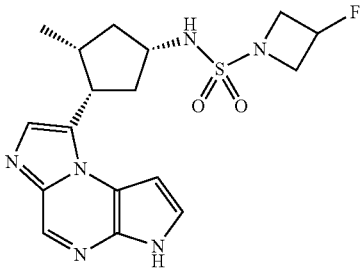 | LL.1.9* | 1.73 | 393 |
| 2-cyano-N-((1S,3R,4S)-3-methyl-4-(3-((2-(trimethylsilyl)ethoxy)methyl)-3H-imidazo[1,2-a]pyrrolo[2,3-e]pyrazin-8-yl)cyclopentyl)acetamide (prepared using FFFFF with Preparation #33, GGGGG with Preparation #E.1.1, KKKK with PFPAA, D with NaOH, KK, Y, H with cyanoacetic acid ) | 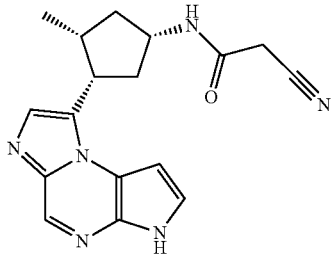 | LL.1.10* | 1.61 | 323 |
| 1-((1S,2R,4R)-4-(1H-pyrazol-1-yloxy)-2-ethylcyclopentyl)-6-((2-(trimethylsilyl)ethoxy)methyl)-6H-pyrrolo[2,3-e][1,2,4]triazolo[4,3-a]pyrazine (prepared from Example #35, Step H, using IIII and JJJJ with N-hydroxypyrazole (prepared according to *Journal of the Chemical Society, Perkin Transactions 1: Organic and Bio-Organic Chemistry* (1995), (3), 243-7). | 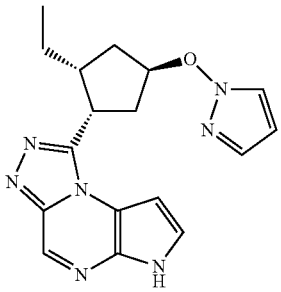 | LL.1.11 | 1.87 | 338 |
| (1R,3R,4S)-3-ethyl-4-(6-((2-(trimethylsilyl)ethoxy)methyl)-6H-pyrrolo[2,3-e][1,2,4]triazolo[4,3-a]pyrazin-1-yl)cyclopentanecarbonitrile (prepared from Example #35, step H, using IIII and JJJJ with sodium cyanide) | 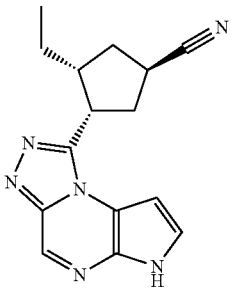 | LL.1.12 | 1.75 | 281 |

TABLE LL.1-continued

| Examples prepared using General Procedure LL | | | | |
|---|---|---|---|---|
| Silyl protected pyrrole | Product | Ex # | $R_t$ min (Table 1, Method) | m/z ESI+ $(M + H)^+$ |
| 1-((1S,2R,4S)-4-(3-cyclopropyl-1H-pyrazol-1-yl)-2-ethylcyclopentyl)-6-((2-(trimethylsilyl)ethoxy)methyl)-6H-pyrrolo[2,3-e][1,2,4]triazolo[4,3-a]pyrazine (prepared using JJJJ from Example #35 step I, with sodium hydride and 5-cyclopropyl-1H-pyrazole (ChemBridge)) | 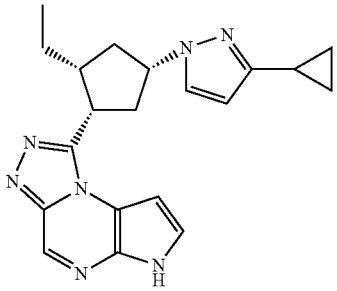 | LL.1.13 | 1.98 | 362 |
| 1-((1S,2R,4S)-4-(3-cyclopropyl-1H-pyrazol-1-yl)-2-ethylcyclopentyl)-6-((2-(trimethylsilyl)ethoxy)methyl)-6H-pyrrolo[2,3-e][1,2,4]triazolo[4,3-a]pyrazine (prepared from Example #35 step I, using JJJJ with sodium hydride and 5-cyclopropyl-1H-pyrazole (ChemBridge)) | 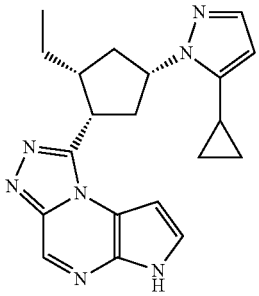 | LL.1.14 | 2.02 | 362 |
| 3-(-3-ethyl-4-(6-((2-(trimethylsilyl)ethoxy)methyl)-6H-pyrrolo[2,3-e][1,2,4]triazolo[4,3-a]pyrazin-1-yl)cyclopentyloxy)methyl)-5-methylisoxazole (Preparation #HHHH.1) | 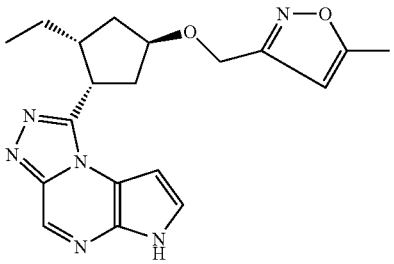 | LL.1.15 | 1.71 (b) | 367 |
| 4-(2-(3-ethyl-4-(6-((2-(trimethylsilyl)ethoxy)methyl)-6H-pyrrolo[2,3-e][1,2,4]triazolo[4,3-a]pyrazin-1-yl)cyclopentyloxy)ethyl)morpholine (prepared using HHHH from Example #35, step H and 4-(2-chloroethyl)morpholine [Beta Pharma] with KOH) | 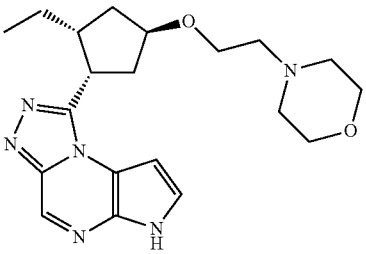 | LL.1.16 | 1.16 (b) | 385 |
| 1-(4-(2,2-difluoroethoxy)-2-ethylcyclopentyl)-6-((2-(trimethylsilyl)ethoxy)methyl)-6H-pyrrolo[2,3-e][1,2,4]triazolo[4,3-a]pyrazine (prepared using HHHH from Example #35 step H and 2-bromo-1,1-difluoroethane [Lancaster] with KOH) | 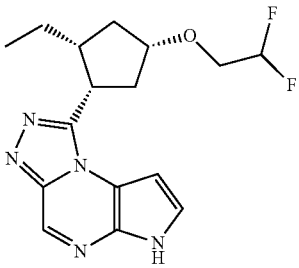 | LL.1.17 | 1.78 (b) | 336 |

TABLE LL.1-continued

| Examples prepared using General Procedure LL | | | | |
|---|---|---|---|---|
| Silyl protected pyrrole | Product | Ex # | $R_t$ min (Table 1, Method) | m/z ESI+ $(M + H)^+$ |
| 1-(4-(2,2-difluoroethoxy)-2-ethylcyclopentyl)-6-((2-(trimethylsilyl)ethoxy)methyl)-6H-pyrrolo[2,3-e][1,2,4]triazolo[4,3-a]pyrazine (prepared using HHHH from Example #35, step H and 2-bromo-1,1-difluoroethane [Lancaster] with KOH) | 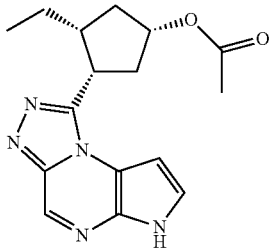 | LL.1.18 | 1.62 (b) | 314 |
| 1-(3-ethyl-4-(6-((2-(trimethylsilyl)ethoxy)methyl)-6H-pyrrolo[2,3-e][1,2,4]triazolo[4,3-a]pyrazin-1-yl)cyclopentyloxy)-2-methylpropan-2-ol (prepared using HHHH from Example #35, step H and 1-chloro-2-methyl-2-propanol with KOH) | 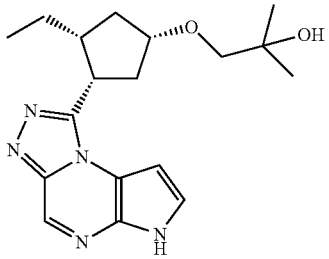 | LL.1.19 | 1.61 (b) | 344 |
| 4-(3-((2-(trimethylsilyl)ethoxy)methyl)-3H-imidazo[1,2-a]pyrrolo[2,3-e]pyrazin-8-yl)piperidine-1-carboximidamide (prepared using R from 1-(benzyloxycarbonyl)piperidine-4-carboxylic acid (Matrix), S with Example #3 Step E, E with TFA, KKKK with PFPAA, D with NaOH, KK, DDDDD, EEEEE) | 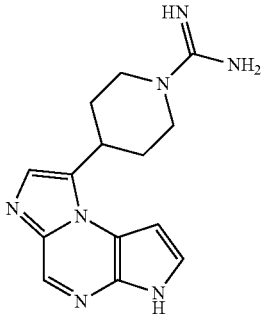 | LL.1.20 | 2.04 (r) | 284 |
| 8-cyclohexyl-1-methyl-3-((2-(trimethylsilyl)ethoxy)methyl)-3H-imidazo[1,2-a]pyrrolo[2,3-e]pyrazine (prepared using GGG with 8-cyclohexyl-3H-imidazo[1,2-a]pyrrolo[2,3-e]pyrazine (W02009152133A1), KK, VVV with 2,4,6-trimethyl-1,3,5,2,4,6-trioxatriborinane) | 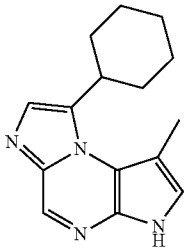 | LL.1.21 | 2.21 (a) | 255 |
| t-butyl 2-oxo-2-(4-(3-((2-(trimethylsilyl)ethoxy)methyl)-3H-imidazo[1,2-a]pyrrolo[2,3-e]pyrazin-8-yl)piperidin-1-yl)ethylcarbamate (prepared using R from 1-(benzyloxycarbonyl)piperidine-4-carboxylic acid (Matrix), S from Example #3 Step E, E with TFA, KKKK with PFPAA, D with NaOH, KK, DDDDD, H from 2-(t-butoxycarbonylamino)acetic acid) | 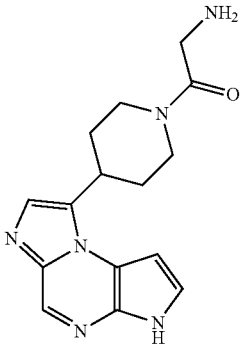 | LL.1.22 | 2.84 (r) | 299 |

TABLE LL.1-continued

Examples prepared using General Procedure LL

| Silyl protected pyrrole | Product | Ex # | $R_t$ min (Table 1, Method) | m/z ESI+ $(M + H)^+$ |
|---|---|---|---|---|
| (1S,3R,4S)-3-methyl-4-(3-((2-(trimethylsilyl)ethoxy)methyl)-3H-imidazo[1,2-a]pyrrolo[2,3-e]pyrazin-8-yl)cyclopentanamine (prepared using X from Example #24 Step H and dibenzyl amine, FFFFF, GGGGG from Preparation #E.1.1, KKKK with PFPAA, D with NaOH, KK, Y) | 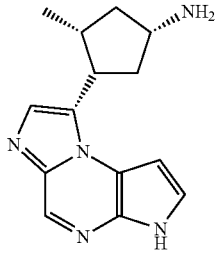 | LL.1.23 | 1.39 (a) | 256 |
| 2-(3-((1S,3R,4S)-3-methyl-4-(3-((2-(trimethylsilyl)ethoxy)methyl)-3H-imidazo[1,2-a]pyrrolo[2,3-e]pyrazin-8-yl)cyclopentylamino)oxetan-3-yl)acetonitrile (Preparation YYY.1) | 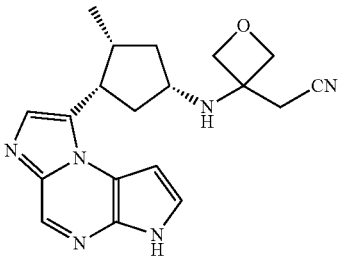 | LL.1.24 | 1.49 (a) | 351 |
| N-(2-cyclopropylethyl)-N-((1S,3R,4S)-3-methyl-4-(3-((2-(trimethylsilyl)ethoxy)methyl)-3H-imidazo[1,2-a]pyrrolo[2,3-e]pyrazin-8-yl)cyclopentyl)oxetan-3-amine (prepared using using X from Example #24 Step H and dibenzyl amine, FFFFF, GGGGG from Preparation #E.1.1), KKKK with PFPAA, D with NaOH, KK, Y, X with oxetan-3-one [PharmaBlock], X with 2-cyclopropylacetaldehyde [Anichem]) | 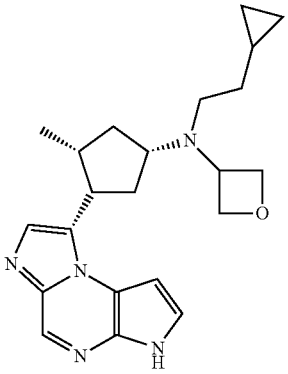 | LL.1.25 | 1.55 (a) | 380 |
| N-(cyclopropylmethyl)-N-((1S,3R,4S)-3-methyl-4-(3-((2-(trimethylsilyl)ethoxy)methyl)-3H-imidazo[1,2-a]pyrrolo[2,3-e]pyrazin-8-yl)cyclopentyl)oxetan-3-amine (prepared using using X from Example #24 Step H and dibenzyl amine, FFFFF, GGGGG from Preparation #E.1.1), KKKK with PFPAA, D with NaOH, KK, Y, X with oxetan-3-one [PharmaBlock], X with cyclopropanecarbaldehyde) | 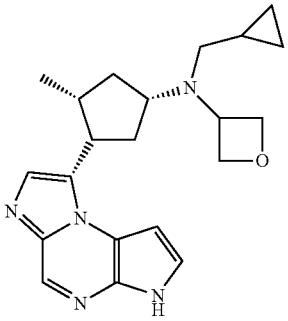 | LL.1.26 | 1.40 (a) | 366 |

General Procedure LL.1: SEM-Deprotection

A N-SEM-protected compound is dissolved or suspended in an organic solvent (such as DMF, 1,4-dioxane, THF, MeOH, or DCM, preferably DCM). TFA, camphorsulfonic acid, or HCl, preferably TFA (5-70 equiv, preferably 50 equiv) may be added and the reaction mixture is stirred at about 0-40° C. (preferably ambient temperature) for about 1-20 h (preferably about 1-4 h). Optionally, additional TFA (5-20 equiv, preferably 10 equiv) may be added. The resulting mixture is concentrated under reduced pressure. Alternatively, the solution or suspension of SEM-protected material may be treated with a fluoride source such as TBAF or $LiBF_4$, preferably TBAF (1-20 equiv, preferably 6 equiv). Optionally, a base such as aqueous NaOH, ethylenediamine, or aqueous $NH_4OH$ (1-200 equiv, preferably ethylenediamine, 2 equiv) may be added. The reaction mixture is heated at about 30-100° C. (preferably about 60° C.) for about 30 min-72 h (preferably about 24 h). The reaction mixture is cooled to ambient temperature. Optionally the volatiles are removed under reduced pressure. The reaction mixture is worked up using one of the following methods.

Method 1: The residue is dissolved in an organic solvent such as 1,4-dioxane, MeOH or EtOH (preferably 1,4-dioxane). A base such as aqueous NaOH, ethylenediamine, or aqueous $NH_4OH$ (preferably aqueous $NH_4OH$, 1-200 equiv, preferably 120 equiv) is added and the reaction mixture is heated at about 30-100° C. (preferably about 60° C.) for about 5 min-10 h (preferably about 30 min). The reaction mixture is cooled to ambient temperature, water is added and the product is isolated by filtration. Method 2: The mixture is partitioned between an organic solvent (such as EtOAc or DCM) and an aqueous base (such as saturated aqueous $NaHCO_3$ or saturated aqueous $Na_2SO_4$, preferably saturated aqueous $NaHCO_3$). The organic portion is separated and concentrated under reduced pressure to provide the target compound. Method 3: Optionally, water, aqueous $NaHCO_3$, or aqueous $NH_4Cl$ (preferably water) is added. The product may be isolated by filtration or the mixture may be extracted with an organic solvent (such as EtOAc or DCM). The organics are dried over $Na_2SO_4$ or $MgSO_4$, filtered, and concentrated under reduced pressure to provide the target compound. In some cases an intermediate hydroxymethylsulfonamide may be isolated.

Illustration of General Procedure LL.1

Preparation #LL.1.1: tert-butyl(trans-4-(6H-pyrrolo[2,3-e][1,2,4]triazolo[4,3-a]pyrazine-8-carboxamido)cyclohexyl)methylcarbamate

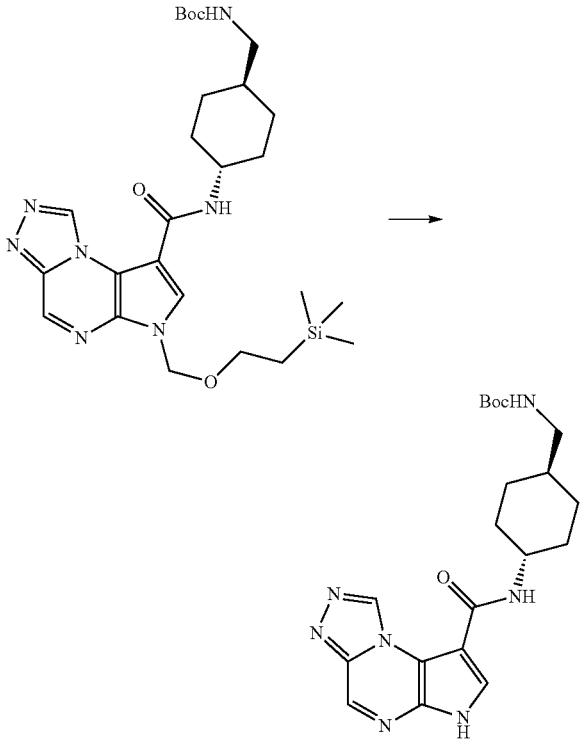

Ethylenediamine (0.011 mL, 0.16 mmol) was added to a solution of tert-butyl(trans-4-(6-((2-(trimethylsilyl)ethoxy)methyl)-6H-pyrrolo[2,3-e][1,2,4]triazolo[4,3-a]pyrazine-8-carboxamido)cyclohexyl)methylcarbamate (0.043 g, 0.079 mmol, prepared using Z from Preparation #AAAAA.1 and KOH, H with tert-butyl trans-4-aminocyclohexylmethylcarbamate [AMRI], HATU, and TEA) in THF (1 mL). TBAF (1.0 M solution in THF, 0.470 mL, 0.470 mmol) was added in one portion. The mixture was heated at about 60° C. After about 24 h, the solution was allowed to cool to ambient temperature and stirred for about 40 h. The volatiles were removed under reduced pressure. The residue was slurried in water (10 mL) and extracted with EtOAc (4×20 mL). The combined organic portions were washed with brine (10 mL), dried over $Na_2SO_4$, filtered, and concentrated under reduced pressure. The residue was purified by silica gel chromatography eluting with a gradient of 2-10% MeOH/DCM to give tert-butyl(trans-4-(6H-pyrrolo[2,3-e][1,2,4]triazolo[4,3-a]pyrazine-8-carboxamido)cyclohexyl)methylcarbamate (0.0094 g, 29%): LC/MS (Table 1, Method n) $R_t$=0.55 min; MS m/z: 414 $(M+H)^+$.

General Procedure MM: Halogenation of an Imidazole

To a solution of an imidazole (preferably 1 equiv) in an organic solvent (such as DCM, MeOH or THF, preferably THF) is added a halogenating reagent (such as bromine, pyridinium hydrobromide perbromide, NCS, NBS, or NIS) (0.9-1.1 equiv, preferably 1 equiv). The reaction is stirred at about −20-150° C. (preferably about 0-60° C.) for about 10 min-48 h (preferably about 30 min). The reaction mixture is then partitioned between an organic solvent (such as EtOAc, DCM or 1,4-dioxane, preferably EtOAc) and an aqueous base (such as saturated aqueous $NaHCO_3$ or saturated aqueous $Na_2CO_3$, preferably saturated aqueous $NaHCO_3$). The aqueous layer is optionally extracted with additional organic solvent (such as EtOAc or DCM). The combined organic layers may optionally be washed with brine and concd in vacuo or dried over anhydrous $Na_2SO_4$ or $MgSO_4$ and then decanted or filtered prior to concentrating under reduced pressure to give the tareagent, and mercury(II) acetate) in THF (10 mL) at about 0° C. was added a solution of NBS (0.12 g, 0.672 mmol) in THF (2 mL). After about 30 min, the reaction mixture was diluted with EtOAc (20 mL) and saturated aqueous $NaHCO_3$ (20 mL). The organic layer was separated, concd in vacuo, and purified by chromatography on silica gel (40 g) eluting with EtOAc:DCM:heptane (1:1:2) to provide 3-bromo-1-cyclohexyl-6-tosyl-6H-imidazo[1,5-a]pyrrolo[2,3-e]pyrazine (0.27 g 83%) as a tan solid: LC/MS (Table 1, Method a) $R_t$=3.12 min; MS m/z 473, 475 (1:1) $(M+H)^+$.

Preparation #MM.1: 3-bromo-1-cyclohexyl-6-tosyl-6H-imidazo[1,5-a]pyrrolo[2,3-e]pyrazine

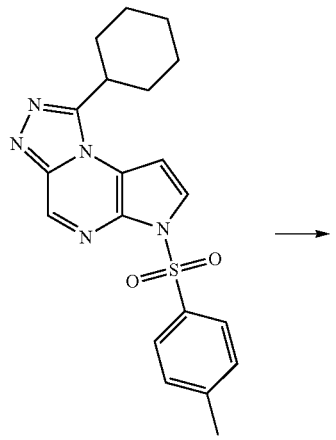

-continued

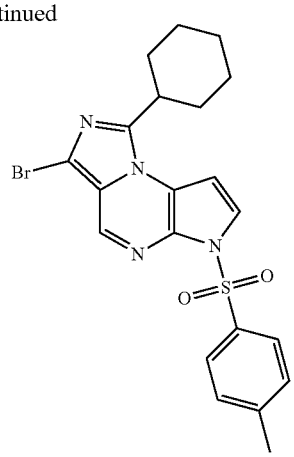

To a solution of 1-cyclohexyl-6-tosyl-6H-imidazo[1,5-a]pyrrolo[2,3-e]pyrazine (0.27 g, 0.67 mmol, prepared using Q from Preparation #13, Lawesson's reagent, and mercury (II) acetate) in THF (10 mL) at about 0° C. was added a solution of NBS (0.12 g, 0.672 mmol) in THF (2 mL). After about 30 min, the reaction mixture was diluted with EtOAc (20 mL) and saturated aqueous $NaHCO_3$ (20 mL). The organic layer was separated, concd in vacuo, and purified by chromatography on silica gel (40 g) eluting with EtOAc:DCM:heptane (1:1:2) to provide 3-bromo-1-cyclohexyl-6-tosyl-6H-imidazo[1,5-a]pyrrolo[2,3-e]pyrazine (0.27 g 83%) as a tan solid: LC/MS (Table 1, Method a) $R_t$=3.12 min; MS m/z 473, 475 (1:1) $(M+H)^+$.

General Procedure NN: Formation of an Amide from a Carboxylic Acid and an Amine with Loss of a Sulfonamide Protecting Group To mixture of a 1-substituted 6-tosyl-6H-pyrrolo[2,3-e][1,2,4]triazolo[4,3-a]pyrazine with a pendant amino group (preferably 1 equiv) and a carboxylic acid (1-2 equiv, preferably 1.5 equiv) in a solvent (such as DMF or THF, preferably DMF) is added a coupling agent such as EDC•HCl or HATU (1.0-2.0 equiv, preferably 1.2 equiv) with an organic base (such as TEA or DIEA, 1-5 equiv, preferably 2 equiv). If EDC•HCl is used as the coupling reagent, HOBT (1-3 equiv, preferably 1.2 equiv) is added. After about 1-72 h (preferably about 18 h) at about 20-60° C. (preferably ambient temperature), water is added and the aqueous layer is extracted with an organic solvent such as EtOAc or DCM. The combined organic layers are dried over anhydrous $Na_2SO_4$ or $MgSO_4$, filtered or decanted, and concd under reduced pressure. Intermediates and final compounds prepared via this General Procedure can be optionally purified using one or more of the Purification Methods described above.

Illustration of General Procedure NN

Example #NN.1.1

N-((1-((6H-pyrrolo[2,3-e][1,2,4]triazolo[4,3-a]pyrazin-1-yl)methyl)cyclobutyl)methyl)-2-cyanoacetamide

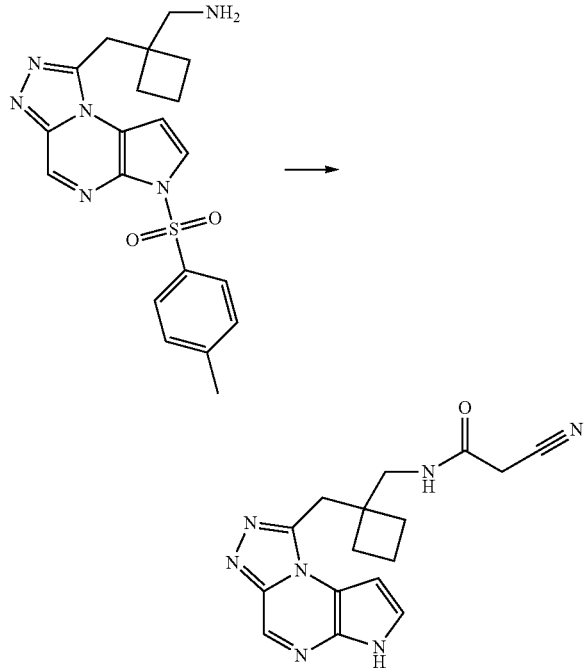

To a solution of (1-((6-tosyl-6H-pyrrolo[2,3-e][1,2,4]triazolo[4,3-a]pyrazin-1-yl)methyl)-cyclobutyl)methanamine (0.225 g, 0.548 mmol) (prepared using A from Example #1, Step D, 2-(1-(tert-butoxycarbonylamino)cyclobutyl)acetic acid [prepared as described WO9921824A1], EDC•HCl, B with TEA, E with 4.0 M HCl in 1,4-dioxane) in DMF (10 mL) was added cyanoacetic acid (0.070 g, 0.822 mmol), HOBt (0.101 g, 0.658 mmol), EDC•HCl (0.126 g, 0.658 mmol) and DIEA (0.190 mL, 1.096 mmol) to give a brown solution. The mixture was stirred at ambient temperature for about 18 h. Water (20 mL) was added and the mixture was extracted with EtOAc (3×25 mL). The combined organic layers were dried over anhydrous $MgSO_4$, filtered, and concd in vacuo. The crude material was purified by flash chromatography on silica gel eluting with a gradient of 0-10% MeOH in DCM to give N-((1-((6H-pyrrolo[2,3-e][1,2,4]triazolo[4,3-a]pyrazin-1-yl)methyl)cyclobutyl)methyl)-2-cyanoacetamide as an off-white solid (0.030 g, 17%): LC/MS (Table 1, Method a) $R_t$=1.48 min; MS m/z: 324 $(M+H)^+$.

TABLE NN.1

Examples prepared using General Procedure NN with cyanoacetic acid

| Amine | Product | Ex. # | $R_t$ min (Table 1, Method) | m/z ESI+ $(M + H)^+$ |
|---|---|---|---|---|
| 1-((6-tosyl-6H-pyrrolo[2,3-e][1,2,4]triazolo[4,3-a]pyrazin-1-yl)methyl)cyclobutanamine (prepared using A from Example #1, Step D and 2-(1-(tert-butoxycarbonylamino)cyclo-butyl) acetic acid [prepared as described in *Eur. J. Med. Chem,* 1999, 34, 363]EDC•HCl, B with TEA, E with HCl) | 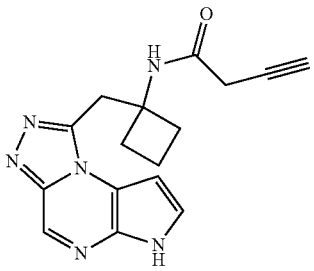 | NN.1.2 | 1.40 (a) | 310 |

General Procedure OO: Cyclization with $POCl_3$

To a solution of a urea, an amide, or a hydrazide (1-3 equiv, preferably 2 equiv) neat or in an organic solvent (for example, 1,4-dioxane) is added $POCl_3$ (10-200 equiv, preferably 100 equiv). The mixture is heated at about 25-100° C. (preferably about 60° C.) for about 1-16 h (preferably about 1-3h). The reaction mixture is cooled to ambient temperature and ice is added. Following dissolution, the pH of the mixture is adjusted to about 7 with a base such as aqueous NaOH. If the product precipitates from the reaction mixture it can be collected by filtration. Alternatively the product can be extracted into an organic solvent (such as EtOAc or DCM) and the organic layers may be optionally washed with aqueous base (such as saturated aqueous $NaHCO_3$) and/or brine, dried over anhydrous $Na_2SO_4$ or $MgSO_4$, then decanted or filtered prior to concentrating under reduced pressure.

Preparation #OO.1: N-((3S,5R)-5-methyl-1-(6-tosyl-6H-imidazo[1,5-a]pyrrolo[2,3-e]pyrazin-1-yl)pyrrolidin-3-yl)cyclopropanesulfonamide

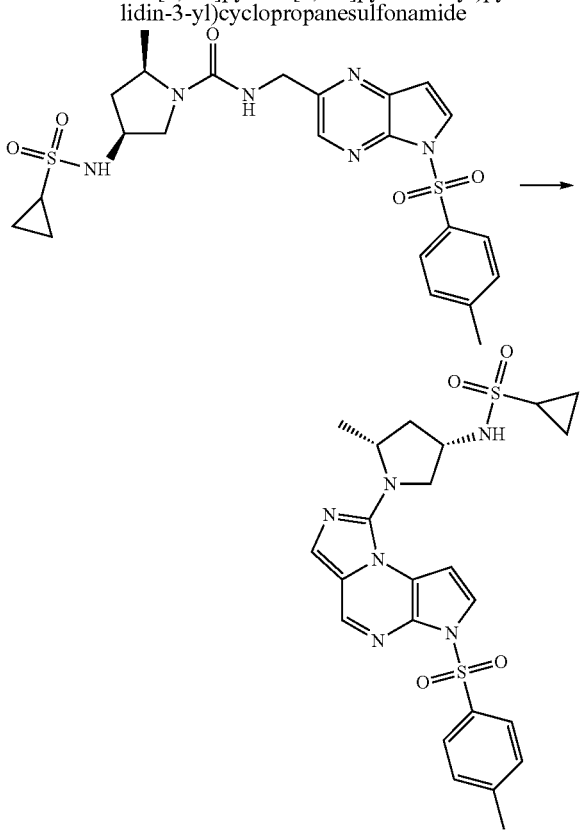

A flask was charged with (2R,4S)-4-(cyclopropanesulfonamido)-2-methyl-N-((5-tosyl-5H-pyrrolo[2,3-b]pyrazin-2-yl)methyl)pyrrolidine-1-carboxamide (0.11 g, 0.207 mmol, prepared using E from Preparation #14 and J from Example #5 Step C and CDI) and $POCl_3$ (1.9 mL, 21 mmol). The reaction mixture was heated to about 60° C. resulting in a homogeneous mixture. After about 2 h, the reaction mixture was cooled to ambient temperature and crushed ice was added. After the ice had melted, 2 N aqueous NaOH was added until a pH of about 7 was obtained. The resulting precipitate was collected by filtration and dried in vacuo to provide N-((3S,5R)-5-methyl-1-(6-tosyl-6H-imidazo[1,5-a]pyrrolo[2,3-e]pyrazin-1-yl)pyrrolidin-3-yl)cyclopropanesulfonamide (0.10 g, 94%) as a tan solid: LC/MS (Table 1, Method a) $R_t$=2.14 min; MS m/z: 515 $(M+H)^+$.

General Procedure OO.1: Cyclization with $POCl_3$

To a urea, an amide, or a hydrazide, neat or in an organic solvent (such as 1,4-dioxane, DCE, or toluene), is added $POCl_3$ (3-200 equiv, preferably 100 equiv). The mixture is heated at about 25-110° C. (preferably about 100° C.) for about 1-16 h (preferably about 1-3 h). The reaction mixture is allowed to cool to ambient temperature. The reaction mixture may be added to ice or ice may be added. Alternatively, the volatiles may be removed under reduced pressure. Optionally, DCM is added followed by slow addition of MeOH and then the mixture is concentrated under reduced pressure. An aqueous layer such as water or aqueous HCl is added and an organic solvent such as 1,4-dioxane may be added and the solution may be warmed to about 30-110° C. (preferably about 100° C.) for about 0.5-6 h (preferably about 3h). Following concentration under reduced pressure, the pH of the mixture may be adjusted with a base such as aqueous NaOH or $NaHCO_3$ (preferably to about pH 7) and an organic solvent such as EtOAc or DCM is added. The product may be collected by filtration or extracted into an organic solvent (such as EtOAc or DCM). The organic layers may be optionally washed with aqueous base (such as saturated aqueous $NaHCO_3$) and/or brine, dried over anhydrous $Na_2SO_4$ or $MgSO_4$, and then decanted or filtered prior to concentrating under reduced pressure.

Preparation #OO.1.1: 3-tosyl-3H-imidazo[1,2-a]pyrrolo[2,3-e]pyrazin-8-amine

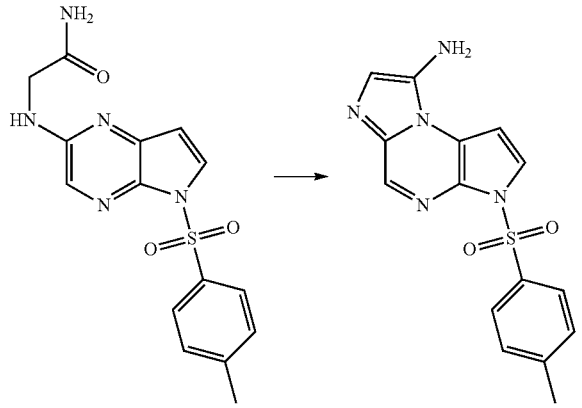

To 2-(5-tosyl-5H-pyrrolo[3,2-b]pyrazin-2-ylamino)acetamide (0.845 g, 2.45 mmol, prepared using E from Preparation #S.1.1 and HCl) under nitrogen was added $POCl_3$ (5.0 mL, 54 mmol). After about 15 min, a reflux condenser was attached and the mixture was warmed to about 100° C. After about 2 h, the solution was allowed to cool to ambient temperature. The mixture was concd under reduced pressure. The residue was slurried in DCM (10 mL) and slowly treated with MeOH (10 mL). The reaction mixture was stirred for about 5 min then concd under reduced pressure. The residue was dissolved in MeOH (20 mL) and then concentrated under reduced pressure. The residue was dissolved in 1,4-dioxane (5 mL) and 2N aqueous HCl (5 mL). The solution was warmed to about 100° C. for about 3 h. The solution was allowed to cool to ambient temperature and the volatiles were removed under reduced pressure. The aqueous mixture was slurried in saturated aqueous $NaHCO_3$/water (1:1, 100 mL) and DCM (50 mL). The solid was collected by filtration, rinsed with water and DCM, and dried to afford 3-tosyl-3H-imidazo[1,2-a]pyrrolo[2,3-e]pyrazin-8-amine (0.343 g, 43%): LC/MS (Table 1, Method n) $R_t$=0.56 min; MS m/z: 328 $(M+H)^+$.

General Procedure PP: Reaction of an Amine with an Aryl Boronic Acid

To a solution of a boronic acid (preferably 1-3 equiv) in an organic solvent (such as DCM or MeCN) is added an organic base, such as DIEA (1-5 equiv, preferably 1 equiv), an inorganic catalyst (such as copper (II) acetate monohydrate (0.1 to 0.5 equiv, preferably 0.25 equiv), an amine (preferably 1 equiv) and a drying reagent (such as 4 Å molecular sieves). The reaction mixture is purged with oxygen (1-5 times, preferably 3 times) and heated at about 20-60° C. (preferably about 40-50° C.) for about 1-24 h (preferably about 18 h) under an atmosphere of oxygen. If the reaction does not reach completion, additional inorganic catalyst (such as copper (II) acetate monohydrate (0.1 to 0.5 equiv, preferably 0.25 equiv) may be added. The reaction mixture is allowed to cool to ambient temperature before it is concd under reduced pressure Illustration of General Procedure PP Preparation #PP.1*: 3-((1S,3R,4S)-3-methyl-4-(6-tosyl-6H-pyrrolo[2,3-e][1,2,4]triazolo[4,3-a]pyrazin-1-yl)cyclopentylamino)benzonitrile

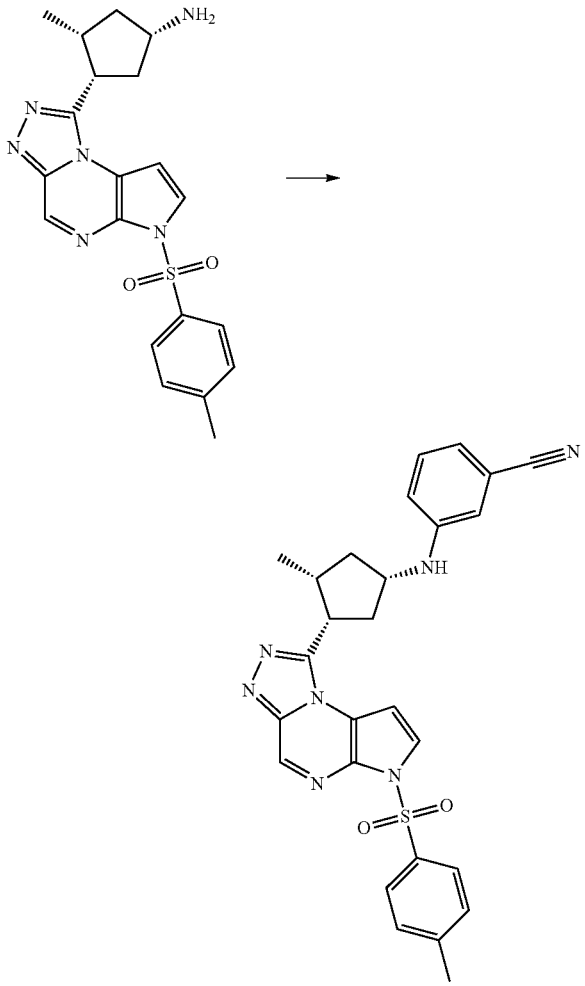

To a solution of 3-cyanophenylboronic acid (0.143 g, 0.974 mmol) in DCM (4 mL) was added copper (II) acetate monohydrate (0.013 g, 0.122 mmol) and 4 Å molecular sieves. The reaction mixture was purged 3 times with oxygen. A solution of (1S,3R,4S)-3-methyl-4-(6-tosyl-6H-pyrrolo[2,3-e][1,2,4]-triazolo[4,3-a]pyrazin-1-yl)cyclopentanamine (0.20 g, 0.48 mmol, Preparation #19.2) and DIEA (0.085 mL, 0.487 mmol) in MeCN (1 mL) was added and the reaction mixture was heated at about 45° C. for about 18 h. Additional copper (II) acetate monohydrate (0.013 g, 0.122 mmol) was added and the reaction mixture was stirred for about 4 h. The reaction mixture was filtered through a pad of Celite® and concd under reduced pressure. The crude material was purified by silica gel chromatography eluting with a gradient of 0-60% EtOAc in DCM to give 3-((1S,3R,4S)-3-methyl-4-(6-tosyl-6H-pyrrolo[2,3-e][1,2,4]triazolo[4,3-a]pyrazin-1-yl)cyclopentylamino)benzonitrile (0.16 g, 48%) as a dark brown solid: LC/MS (Table 1, Method c) $R_t$=1.54 min; MS m/z: 512 $(M+H)^+$.

General Procedure QQ: Formation of a Urea from an Amine and an Isocyanate

To a flask containing an amine or an amine salt (1 equiv) in an organic solvent (such as THF, DCM, or MeCN, preferably DCM) is optionally added a base (such as DIEA or TEA, preferably DIEA, 1-3 equiv, preferably 1 equiv) and the reaction mixture is stirred at ambient temperature for about 0-30 min (preferably about 5 min) An isocyanate (1-5 equiv, preferably 1 equiv) is added and the mixture is stirred at about 10-60° C. (preferably ambient temperature) for about 1-24 h (preferably about 18 h). The organic solvent is optionally removed under reduced pressure unless MeCN is used in which case the solvent is preferably removed under reduced pressure. The crude material can be partitioned between an organic solvent (such as EtOAc or DCM) and water, an aqueous base (such as saturated aqueous $NaHCO_3$) or brine. The layers are separated and the aqueous layer is optionally washed with an organic solvent (such as EtOAc or DCM). The combined organic extracts are dried over anhydrous $Na_2SO_4$ or $MgSO_4$, filtered, and concd under reduced pressure to give the target compound.

Illustration of General Procedure QQ

Example #QQ.1.1*

(3R,4R)-N-(2,4-difluorophenyl)-3-(6H -imidazo[1,5-a]pyrrolo[2,3-e]pyrazin-1-yl)-4-methylpiperidine-1-carboxamide

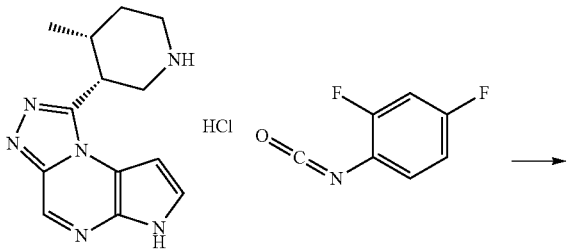

-continued

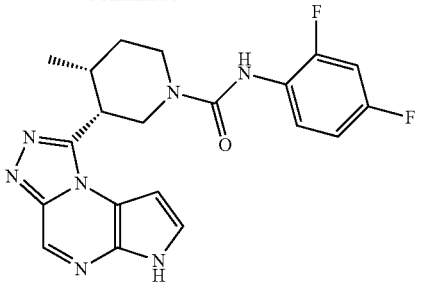

A round bottom flask was charged with 1-((3R,4R)-4-methylpiperidin-3-yl)-6H-imidazo[1,5-a]pyrrolo[2,3-e]pyrazine hydrochloride (0.05 g, 0.17 mmol, Example #5 Step J) and DIEA (0.03 mL, 0.17 mmol) in DCM (1.6 mL). The reaction mixture was stirred for about 5 min at ambient temperature then 2,4-difluoro-1-isocyanatobenzene (0.02 mL, 0.17 mmol) was added and the reaction mixture was stirred at ambient temperature for about 18 h. The reaction mixture was diluted with DCM (5 mL) and washed with water (2 mL). The aqueous layer was back extracted with DCM (2 mL). The combined organic layers were dried over anhydrous $MgSO_4$, filtered, and concd under reduced pressure. The material was purified by RP-HPLC (Table 1, Method e) to afford (3R,4R)-N-(2,4-difluorophenyl)-3-(6H-imidazo[1,5-a]pyrrolo[2,3-e]pyrazin-1-yl)-4-methylpiperidine-1-carboxamide (0.014 g, 20%): LC/MS (Table 1, Method j) $R_t$=1.77 min; MS m/z 411 $(M+H)^+$.

TABLE QQ.1

Examples prepared from 1-((3R,4R)-4-methylpiperidin-3-yl)-6H-imidazo[1,5-a]pyrrolo[2,3-e]pyrazine hydrochloride (Example #5 Step J) using General Procedure QQ

| Isocyanate | Product | Example # | $R_t$ min (Table 1, Method) | m/z ESI+ $(M+H)^+$ |
|---|---|---|---|---|
| 2-(4-isocyanatophenyl)-acetonitrile | 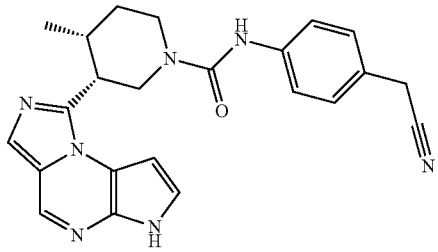 | QQ.1.2* | 1.69 (b) | 414 |
| 3-isocyanatobenzonitrile | 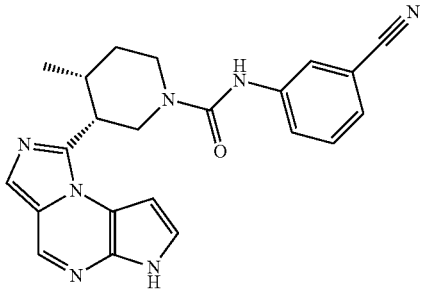 | QQ.1.3* | 1.76 (b) | 400 |

TABLE QQ.1-continued

Examples prepared from 1-((3R,4R)-4-methylpiperidin-3-yl)-6H-imidazo[1,5-a]pyrrolo[2,3-e]pyrazine hydrochloride (Example #5 Step J) using General Procedure QQ

| Isocyanate | Product | Example # | $R_t$ min (Table 1, Method) | m/z ESI+ $(M+H)^+$ |
|---|---|---|---|---|
| 4-isocyanatobenzonitrile | 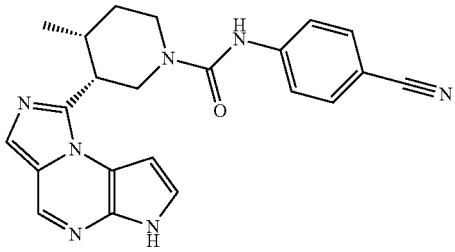 | QQ.1.4* | 1.74 (b) | 400 |

General Procedure RR: Formation of a Urea from an Amine, a Heteroaryl Amine and Phenyl Chloroformate To a flask containing a heteroaryl amine (1-6 equiv, preferably 2.1 equiv) in an organic solvent or mixture of solvents (such as THF/MeCN, THF, DCM, or MeCN, preferably MeCN), a base such as pyridine, DIEA or TEA, preferably TEA (1-6 equiv, preferably 2 equiv) and DMAP (0.1-0.6 equiv, preferably 0.2 equiv) is added phenyl chloroformate (1-6 equiv, preferably 2.0 equiv) at about −5-25° C. (preferably about 0° C.). The reaction mixture is warmed to ambient temperature and stirred for about 1-4 h (preferably about 3 h). The organic solvent is optionally removed under reduced pressure. The crude material can be partitioned between an organic solvent such as EtOAc, DCM or $Et_2O$ (preferably $Et_2O$) and water or brine. The layers are separated and the organic layer is optionally washed with water or brine, dried over anhydrous $Na_2SO_4$ or $MgSO_4$, filtered, and concd under reduced pressure to give the crude carbamate. The crude carbamate is dissolved in an organic solvent such as MeCN, THF or DMF (preferably MeCN) and added to a solution of amine or amine salt (1-2 equiv, preferably 1 equiv), and a base such as pyridine, TEA or DIEA (preferably DIEA, 1-2 equiv, preferably 1 equiv) in an organic solvent such as MeCN, THF or DMF (preferably MeCN) and stirred at about 25-80° C. (preferably about 70° C.) for about 0.5-48 h (preferably about 2-18 h). The solvent is optionally removed under reduced pressure. The crude material can be partitioned between an organic solvent (such as EtOAc or DCM) and water, an aqueous base (such as aqueous $NaHCO_3$) or brine. The layers are separated and the organic layer is optionally washed with water, an aqueous base (such as saturated aqueous $NaHCO_3$) and/or brine, dried over anhydrous $Na_2SO_4$ or $MgSO_4$, filtered, and concd under reduced pressure to give the target compound.

Illustration of General Procedure RR

Example #RR.1.1*

(3R,4R)-3-(6H-imidazo[1,5-a]pyrrolo[2,3-e]pyrazin-1-yl)-4-methyl-N-(pyrimidin-4-yl)piperidine-1-carboxamide

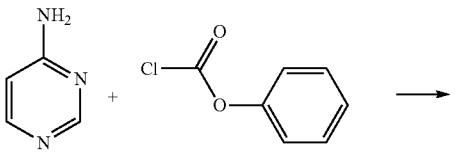

-continued

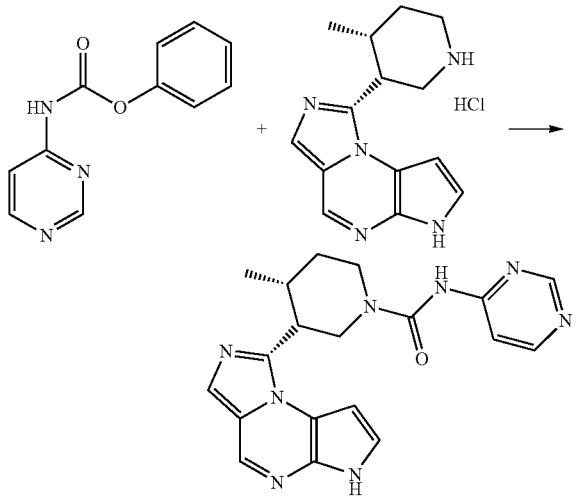

To solution of 4-aminopyrimidine (0.04 g, 0.43 mmol), TEA (0.07 mL, 0.47 mmol) and DMAP (0.006 g, 0.05 mmol), in MeCN (1 mL) at about 0° C. was added phenyl chloroformate (0.05 mL, 0.41 mmol). The reaction mixture was warmed to ambient temperature and stirred for about 3 h. To the reaction mixture was added water (2 mL) and $Et_2O$ (5 mL). The organic layer was separated, washed with water (2 mL), dried over anhydrous $MgSO_4$, filtered, and concd under reduced pressure to provide the crude carbamate. The carbamate was dissolved in MeCN (1 mL) and to it was added a solution of 1-((3R,4R)-4-methylpiperidin-3-yl)-6H-imidazo[1,5-a]pyrrolo[2,3-e]pyrazine hydrochloride (0.06 g, 0.21 mmol, Example #5 Step J) and DIEA (0.04 mL, 0.21 mmol) in MeCN (1 mL). The reaction mixture was heated to about 70° C. for about 2 h. The solvent was removed under reduced pressure. The crude residue was dissolved in DCM (5 mL) and washed with water (2 mL), brine (3 mL), dried over anhydrous $MgSO_4$, filtered, and concd under reduced pressure. The crude material was purified by RP-HPLC (Table 1, Method e) to give (3R,4R)-3-(6H-imidazo[1,5-a]pyrrolo[2,3-e]pyrazin-1-yl)-4-methyl-N-(pyrimidin-4-yl)piperidine-1-carboxamide (0.007 g, 9%): LC/MS (Table 1, Method b) $R_t$=1.40 min; MS m/z 377 $(M+H)^+$.

TABLE RR.1

Examples prepared from 1-((3R,4R)-4-methylpiperidin-3-yl)-6H-imidazo[1,5-a]pyrrolo[2,3-e]pyrazinehydrochloride (Example #5 Step J) using General Procedure RR

| Heteroaryl amine | Product | Example # | $R_t$ min (Table 1, Method) | m/z ESI+ $(M + H)^+$ |
|---|---|---|---|---|
| pyrimidin-2-amine | 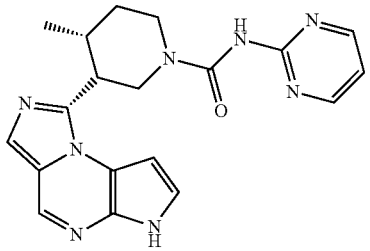 | RR.1.2* | 1.29 (b) | 377 |
| pyridin-2-amine | 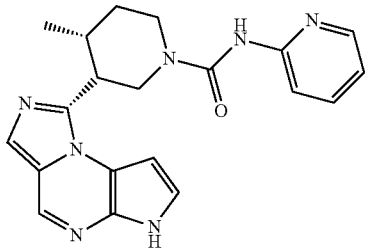 | RR.1.3* | 1.95 (b) | 376 |
| pyrazin-2-amine | 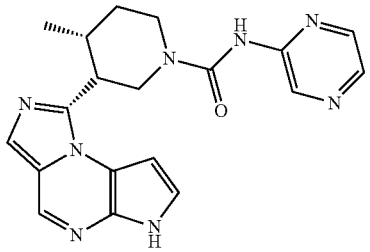 | RR.1.4* | 1.41 (b) | 377 |

General Procedure SS: Hydrolysis of an Ester to an Alcohol

A solution of an ester (preferably 1 equiv) in an organic solvent such as THF, MeOH, or EtOH (preferably MeOH) is added to a base in an organic solvent (such as NaOH in MeOH) or aqueous base (such as $Na_2CO_3$ or NaOH) (1-20 equiv, preferably 2-10 equiv). The reaction mixture is stirred at ambient temperature for about 1-16 h (preferably about 3 h). The mixture is partitioned between an organic solvent (such as EtOAc or DCM) and an aqueous base (such as saturated aqueous $NaHCO_3$ or saturated aqueous $Na_2CO_3$, preferably saturated aqueous $NaHCO_3$). The organic layer is separated, dried over anhydrous $Na_2SO_4$ or $MgSO_4$, filtered, and concd under reduced pressure to provide the target compound.

Illustration of General Procedure SS

Preparation #SS.1: 3-ethyl-4-(6-((2-(trimethylsilyl)ethoxy)methyl)-6H-pyrrolo[2,3-e][1,2,4]triazolo[4,3-a]pyrazin-1-yl)cyclopentanol

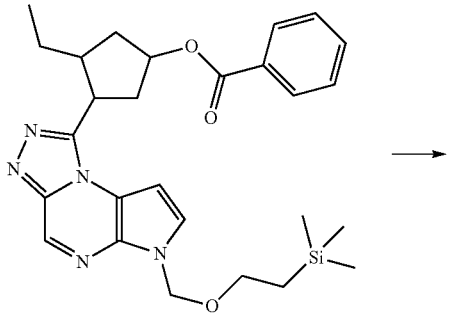

-continued

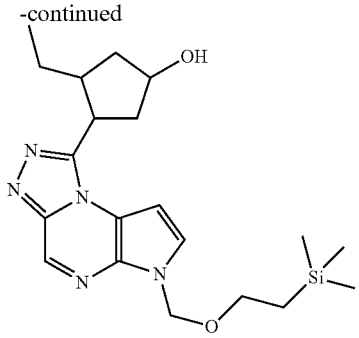

To a solution of NaOH (0.088 g, 2.20 mmol) in MeOH (8 mL) was added a solution of 3-ethyl-4-(6-((2-(trimethylsilyl)ethoxy)methyl)-6H-pyrrolo[2,3-e][1,2,4]triazolo[4,3-a]pyrazin-1-yl)cyclopentyl benzoate (0.158 g, 0.312 mmol, prepared using KK from Preparation #20.2) in MeOH (2 mL). The reaction mixture was stirred at ambient temperature for about 3 h. The solvent was removed under reduced pressure and DCM (150 mL) was added. The organic layer was washed with water (5 mL), saturated aqueous $NaHCO_3$ (15 mL), brine (15 mL), and dried over anhydrous $MgSO_4$, filtered, and concd under reduced pressure to give 3-ethyl-4-(6-((2-(trimethylsilyl)ethoxy)methyl)-6H-pyrrolo[2,3-e][1,2,4]triazolo[4,3-a]pyrazin-1-yl)cyclopentanol (0.123 g, 98%) as clear oil: LC/MS (Table 1, Method b) $R_t$=2.34 min; MS m/z: 402 $(M+H)^+$.

General Procedure TT: Acid-Mediated Conversion of an Ester to a Carboxylic Acid

To a solution of an ester (preferably 1 equiv) in an organic solvent such as 1,4-dioxane or THF (preferably 1,4-dioxane) is added HCl (0.5-12 N, preferably 1-6 N aqueous; 5-100 equiv, preferably 10-20 equiv). The reaction is heated at about 30-120° C. (preferably about 60° C.) for about 12-120 h (preferably about 36-72 h). In any case where an additional acid labile group is present (for example, a Boc group) this group may also be cleaved during the reaction. The reaction mixture is concd under reduced pressure and the pH is adjusted to about 8 with an aqueous inorganic base such as $NaHCO_3$ or $Na_2CO_3$ (preferably saturated aqueous $NaHCO_3$) and the aqueous phase is extracted with an organic solvent such as DCM or EtOAc (preferably EtOAc). The organic extract is optionally washed with brine, dried over a drying agent such as anhydrous $MgSO_4$ or $Na_2SO_4$ (preferably anhydrous $MgSO_4$) and concd under reduced pressure to yield the target compound.

Illustration of General Procedure TT

Preparation #TT.1: 4-(dibenzylamino)-2-methylcyclopentanecarboxylic acid

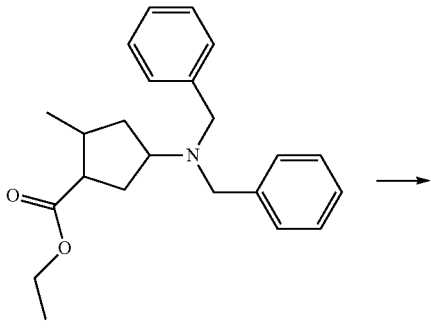

-continued

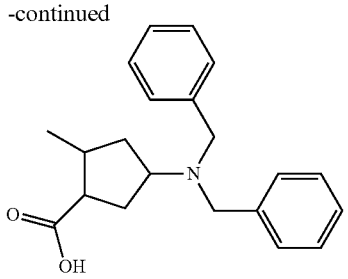

Ethyl 4-(dibenzylamino)-2-methylcyclopentanecarboxylate (3.65 g, 10.38 mmol) was dissolved in a mixture of HC; (6 N aqueous, 20 mL) and 1,4-dioxane (50 mL) and the resulting mixture was heated at about 60° C. for about 72 h. The organic solvent was removed under reduced pressure. The aqueous phase was neutralized by the addition of saturated aqueous $NaHCO_3$ (40 mL) and extracted with EtOAc (50 mL). The organic phase was washed with brine (40 mL), dried over anhydrous $MgSO_4$ and coned under reduced pressure to yield 4-(dibenzylamino)-2-methylcyclopentanecarboxylic acid (3.3 g, 98%) as a white amorphous solid: LC/MS (Table 1, Method a) $R_t$=1.66 min.; MS m/z 324 $(M+H)^+$. The procedure in Step A, Preparation #33 was utilized to provide (1S,2R,4S)-4-(dibenzylamino)-2-methylcyclopentanecarboxylic acid.

General Procedure UU: Formation of 2,2,2-trichloroacetimidate

To a mixture of an alcohol (preferably 1 equiv) in an organic solvent (such as $Et_2O$, heptane or DCM, preferably DCM) at about −20° C. to 30° C. (preferably about 0° C.) is added an aqueous base (such as aqueous sodium hydroxide or potassium hydroxide, preferably aqueous potassium hydroxide, 1-20 equiv, preferably 10 equiv). A catalytic amount of phase transfer reagent (preferably tetrabutylammonium hydrogen sulfate, 0.01-0.5 equiv, preferably 0.1 equiv) is added followed by 2,2,2-trichloroacetonitrile (1-10 equiv, preferably 5 equiv). The reaction mixture is allowed to warm to ambient temperature and stirred at about 15-60° C. (preferably ambient temperature) for about 5-48 h (preferably about 14 h). The layers are separated and the aqueous layer is extracted with an organic solvent (such as $Et_2O$, EtOAc or DCM, preferably DCM). The combined organic layers are washed with water, an aqueous base (such as saturated aqueous $Na_2CO_3$ or $NaHCO_3$) or brine, dried over anhydrous $Na_2SO_4$ or $MgSO_4$, filtered, and concd under reduced pressure. Alternatively, an organic base (such as DBU) may be used as the base for this reaction. In this case, to a mixture of an alcohol (preferably 1 equiv) in an organic solvent (such as $Et_2O$, heptane or DCM, preferably DCM) at about −20° C. to 30° C. (preferably about 0° C.) is added 2,2,2-trichloroacetonitrile (1-10 equiv, preferably 5 equiv), followed by an organic base preferably DBU (0.2-1 equiv, preferably about 0.4 equiv). The reaction mixture is stirred at about −20-30° C. (preferably about 0° C.) for about 0.5-10 h (preferably about 1 h) then concd.

Illustration of General Procedure UU

Preparation #UU.1: ethyl 2-ethyl-4-(2,2,2-trichloro-1-iminoethoxy)cyclopentanecarboxylate

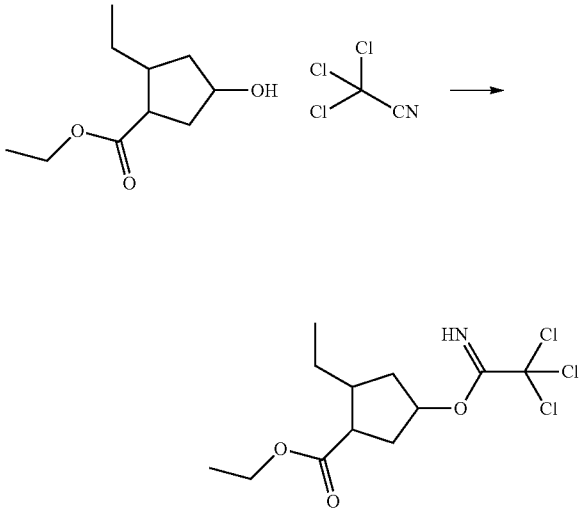

To ethyl 2-ethyl-4-hydroxycyclopentanecarboxylate (3.52 g, 18.9 mmol, Preparation #P.1) in DCM (21 mL) at about 0° C. was added aqueous potassium hydroxide (50%, 21 mL, 189 mmol), tetrabutylammonium hydrogen sulfate (0.64 g, 1.891 mmol) and 2,2,2-trichloroacetonitrile (9.5 mL, 95 mmol). The reaction mixture was allowed to warm to ambient temperature and stirred at ambient temperature for about 14 h. The layers were separated and the aqueous layer was extracted with DCM (4×60 mL). The combined organic layers were washed with water (2×50 mL), brine (60 mL), dried over anhydrous $MgSO_4$, filtered and concd under reduced pressure. The material was purified by silica gel chromatography eluting with a gradient of 15-50% EtOAc in heptane to afford ethyl 2-ethyl-4-(2,2,2-trichloro-1-iminoethoxy)cyclopentanecarboxylate (2.80 g, 45%) as a colorless oil: LC/MS (Table 1, Method b) $R_t$=2.91 min; MS m/z: 330 $(M+H)^+$.

General Procedure VV: TBDMS-Protection of an Alcohol

To a mixture of an alcohol (preferably 1 equiv) in an organic solvent (preferably DMF) is added TBDMS-Cl (1-5 equiv, preferably 1.2 equiv) and imidazole (1-10 equiv, preferably 2.5 equiv). The reaction mixture is stirred at about 10-60° C. (preferably ambient temperature) for about 1-24 h (preferably about 3h). An organic solvent is added (such as heptane, hexane or pentane, preferably heptane). The layers are separated and the bottom layer (DMF layer) is extracted with an organic solvent (such as pentane, hexane or heptane, preferably heptane). The combined extracts are washed with water, an aqueous base (such as saturated aqueous $NaHCO_3$) or brine, dried over anhydrous $Na_2SO_4$ or $MgSO_4$, filtered, and concd under reduced pressure.

Illustration of General Procedure VV

Preparation #VV.1: Ethyl 4-(tert-butyldimethylsilyloxy)-2-ethylcyclopentanecarboxylate

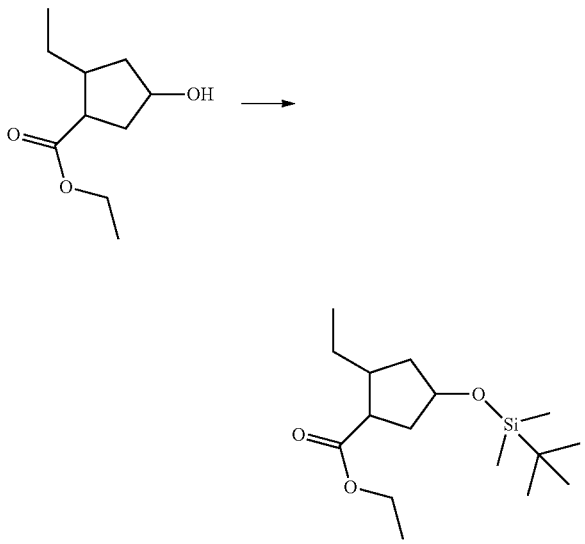

To a solution of ethyl 2-ethyl-4-hydroxycyclopentanecarboxylate (4.97 g, 26.7 mmol, prepared using II from Preparation #P.1, SS with NaOH)) in DMF (9 mL) was added TBDMS-Cl (4.83 g, 32.1 mmol) and imidazole (4.55 g, 66.8 mmol). The reaction mixture was stirred at ambient temperature for about 3 h. Heptane (30 mL) was added. The layers were separated and the bottom layer (DMF layer) was extracted with heptane (3×30 mL). The combined organic extracts were washed with water (2×30 mL), brine (30 mL), dried over anhydrous $MgSO_4$, filtered and concd under reduced pressure. The material was purified by silica gel chromatography eluting with a gradient of 0-15% EtOAc in heptane to afford ethyl 4-(tert-butyldimethylsilyloxy)-2-ethylcyclopentanecarboxylate (5.16 g, 64%) as a colorless oil: $^1H$ NMR (400 MHz, $CDCl_3$) δ 4.45 (m, 1H), 4.11 (m, 2H), 3.08 (m, 1H), 2.34 (m, 1H), 2.18 (m, 1H), 1.75 (m, 2H), 1.57 (m, 1H), 1.41 (m, 1H), 1.25 (m, 3H), 1.10 (m, 1H), 0.90 (m, 3H), 0.87 (s, 9H), 0.03 (s, 6H).

General Procedure WW: Formation of a Ketal

To a solution of a ketone (preferably 1 equiv), an organic solvent (such as DCM, DCE, or toluene, preferably DCM), a diol such as ethylene glycol (1-3 equiv, preferably 2 equiv), and an acid such as p-toluenesulfonic acid monohydrate (0.1-0.5 equiv, preferably 0.2 equiv) is optionally added a dehydrating agent such as triethylorthoformate or trimethylorthoformate (preferably triethylorthoformate, 1-4 equiv, preferably 1.5 equiv) The reaction mixture is stirred at rt to about 110° C. (preferably rt in the presence of a dehydrating agent such as triethylorthoformate or preferably about 110° C. in the absence of a dehydrating agent) for about 16-96 h (preferably about 24 h). If heated, the reaction mixture is cooled to rt. The reaction mixture is worked up using one of the following methods. Method 1: Water is added to the reaction mixture, the layers are separated, and the organic solution is optionally washed with brine, dried over anhydrous $Na_2SO_4$ or $MgSO_4$, then decanted or filtered prior to concentrating under reduced pressure. Method 2: The reaction mixture is concd under reduced pressure and purified directly.

Illustration of General Procedure WW

Preparation #WW.1: ethyl 2-ethyl-4-oxocyclopentanecarboxylate

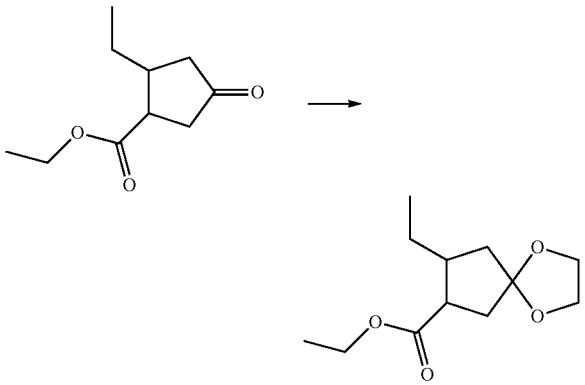

A round bottom flask was charged with ethyl 2-ethyl-4-oxocyclopentanecarboxylate (1.5 g, 8.1 mmol, Example #22, Step B) in DCM (22 mL). To the flask were added ethylene glycol (0.91 mL, 16 mmol), triethylorthoformate (2.0 mL, 12 mmol), and p-toluenesulfonic acid monohydrate (0.31 g, 1.6 mmol). The reaction mixture was stirred at rt for about 24 h. The solution was concd under reduced pressure to give a brown oil that was dissolved in minimal EtOAc and purified by silica gel chromatography (Silicycle 25 g column) eluting with a gradient of 0-50% EtOAc in heptane to give ethyl 2-ethyl-4-oxocyclopentanecarboxylate (1.6 g, 83%) as a light yellow oil: LC/MS (Table 1, Method c) MS m/z 229 (M+H); $^1$H NMR ($CDCl_3$) δ 4.14 (q, 2H), 3.90 (m, 4H), 2.99 (q, 1H), 2.32-2.27 (m, 1H), 2.26-2.11 (m, 1H), 2.05-1.99 (m, 1H), 1.96-1.91 (m, 1H), 1.83-1.78 (m, 1H), 1.46-1.39 (m, 1H), 1.31-1.24 (m, 1H), 1.26 (t, 3H), 0.90 (t, 3H).

General Procedure XX: Palladium Catalyzed Coupling of a Hydrazone

To a mixture of a substituted 5-chloro-4-(hydrazonomethyl)-1H-pyrrolo[2,3-b]pyridine (1 equiv) in an organic solvent (preferably NMP) is added a base (such as $K_2CO_3$ or sodium tert-butoxide, preferably sodium tert-butoxide [1-4 equiv, preferably 2.5 equiv]) a palladium catalyst (preferably palladium acetate [0.01-0.2 equiv, preferably 0.1 equiv]) and a ligand (preferably (R)-1-[(S)-2-(dicyclohexylphosphino) ferrocenyl]ethyl-di-tert-butylphosphine [0.01-0.2 equiv, preferably 0.1 equiv]). The reaction mixture is heated thermally or in a microwave (preferably in a microwave) at about 100-165° C. (preferably 150° C. for about 10 min-6 h (preferably about 2 h)). The reaction mixture is filtered through a pad of Celite® washing with an organic solvent (such as EtOAc or DCM, preferably EtOAc) and concd under reduced pressure to remove wash solvent. The crude material is optionally resubmitted to the reaction conditions. Then the crude material is partitioned between an organic solvent (such as EtOAc or DCM, preferably EtOAc) and water and the aqueous phase is extracted with an organic solvent (such as EtOAc or DCM, preferably EtOAc), washed with water and/or brine, dried over anhydrous $MgSO_4$, filtered and concd under reduced pressure.

Illustration of General Procedure XX

Preparation #XX.1: tert-butyl benzyl(4-(3,6-dihydro-pyrazolo[4,3-d]pyrrolo[2,3-b]pyridine-1-yl) bicyclo[2.2.2]octan-1-yl)carbamate

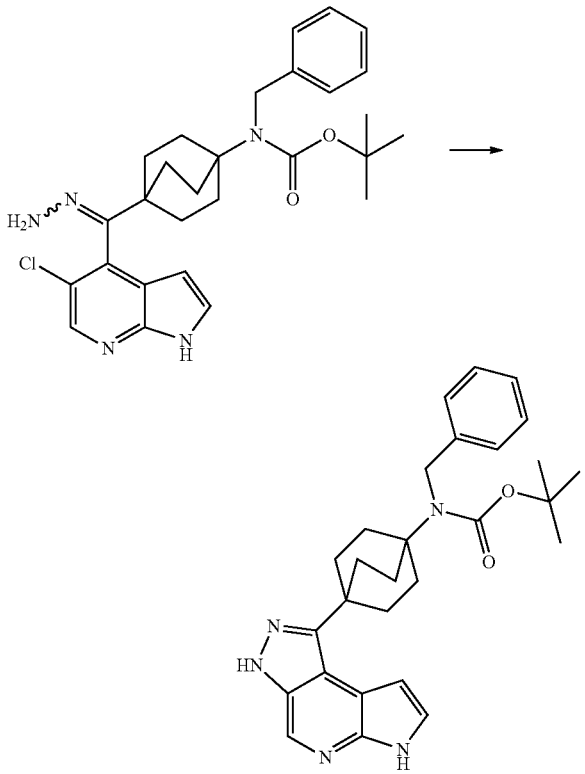

A microwave reaction vial was charged with tert-butyl benzyl(4-((5-chloro-1H-pyrrolo[2,3-b]pyridin-4-)(hydrazono)methyl)bicyclo[2.2.2]octan-1-yl)carbamate (0.700 g, 1.38 mmol, Example #29 Step G) and NMP (11 mL). Sodium tert-butoxide (0.331 g, 3.44 mmol), palladium acetate (0.031 g, 0.138 mmol) and (R)-1-[(S)-2-(dicyclohexylphosphino)ferrocenyl]ethyl-di-tert-butylphosphine (0.076 g, 0.138 mmol) were each added sequentially. The reaction mixture was heated in a Biotage microwave at about 150° C. for about 2 h (250 psi maximum pressure, 1 min ramp, 150 max watts). The reaction mixture was filtered through a pad of Celite® washing with EtOAc (about 15 mL), and the EtOAc was removed under reduced pressure. The remaining material was transferred to a microwave vial and sodium tert-butoxide (0.331 g, 3.44 mmol), palladium acetate (0.031 g, 0.138 mmol) and (R)-1-[(S)-2-(dicyclohexylphosphino)ferrocenyl]-ethyl-di-tert-butylphosphine (0.076 g, 0.138 mmol) were added. The reaction mixture was heated in a Biotage microwave at about 160° C. for about 2 h (250 psi maximum pressure, 1 min ramp, 150 max watts). The reaction mixture was through a pad of Celite® washing with EtOAc (about 20 mL). Water (15 mL) was added and the layers were separated. The aqueous layer was extracted with EtOAc (2×10 mL) and the combined organics were washed with water (3×10 mL) and brine (5×15 mL), dried over anhydrous $MgSO_4$, filtered and concd under reduced pressure. The remaining dark residue was purified by silica gel chromatography eluting with a gradient of 10-100% EtOAc in heptane to give tert-butyl benzyl(4-(3,6-dihydropyrazolo[4,3-d]pyrrolo[2,3-b]pyridine-1-yl)bicyclo[2.2.2]octan-1-yl)carbamate with 0.5 eq EtOAc as an excipient (0.281 g, 39.5%) as a light brown solid: LC/MS (Table 1, Method b) $R_t$=2.57 min; MS m/z: 472 $(M+H)^+$.

General Procedure YY: Michael Addition of an Amine, Amine Salt or Heterocycle to an α,β-Unsaturated Sulfonamide To a mixture of an α,β-unsaturated sulfonamide (1-3 equiv, preferably 1.0 equiv) and an amine, amine salt or heterocycle (1-10 equiv, preferably 4 equiv) in an organic solvent or mixture of solvents (such as THF, n-PrOH, water, EtOH, THF/PrOH, THF/EtOH, preferably n-PrOH) is optionally added a base (such as DIEA or TEA 0-25 equiv, preferably DIEA 10-20 equiv). The mixture is stirred at about 25-100° C. (preferably about 60-80° C.) for about 2-72 h (preferably about 18-20 h). In cases where the reaction does not proceed to completion as monitored by LC/MS, HPLC, and/or TLC; additional amine, amine salt or heterocycle (1-10 equiv, preferably 2 equiv) and/or a cosolvent (such as EtOH) may be added. The reaction is continued at about 25-100° C. (preferably about 80° C.) for about 1-24 h (preferably about 1-2 h). In cases where there is a base-labile protecting group present (for example, a tosyl), the compound may be deprotected. The reaction mixture is allowed to reach ambient temperature and the organic solvent is optionally removed under reduced pressure. The crude material can be partitioned between an organic solvent (such as EtOAc or DCM) and water, an aqueous base (such as saturated aqueous $NaHCO_3$) or brine. The layers are separated and the organic layer is optionally washed with water, an aqueous base (such as saturated aqueous $NaHCO_3$) or brine, dried over anhydrous $Na_2SO_4$ or $MgSO_4$, filtered, and concd under reduced pressure to give the target compound.

Illustration of General Procedure YY

Example #YY.1.1*

2-(4-cyano-1H-pyrazol-1-yl)-N-((1S,3R,4S)-3-ethyl-4-(6H-pyrrolo[2,3-e][1,2,4]triazolo[4,3-a]pyrazin-1-yl)cyclopentyl)ethanesulfonamide

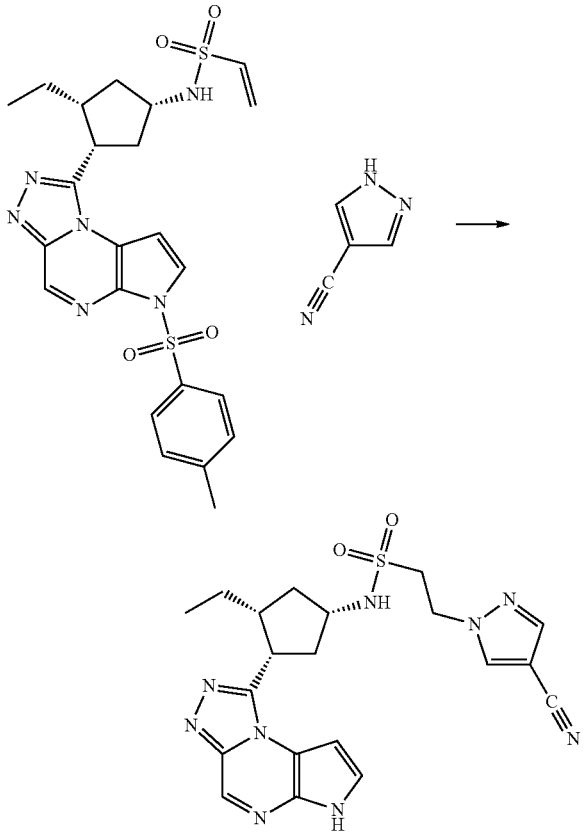

A mixture of N-((1S,3R,4S)-3-ethyl-4-(6-tosyl-6H-pyrrolo[2,3-e][1,2,4]triazolo[4,3-a]pyrazin-1-yl)cyclopentyl)ethenesulfonamide (0.065 g, 0.13 mmol, prepared using K.1 from Example #8 Step M and 2-chloroethanesulfonyl chloride with TEA), DIEA (0.30 mL, 1.7 mmol) and 1H-pyrazole-4-carbonitrile (0.047 g, 0.51 mmol, American Custom Chemicals Corp) in n-PrOH (2.0 mL) was stirred for about 2 h at about 60° C. then at about 80° C. for about 18 h. The reaction mixture was cooled to ambient temperature and concd under reduced pressure. The crude residue was dissolved in DCM (10 mL), washed with saturated $NaHCO_3$ (5 mL), dried over anhydrous $MgSO_4$, filtered, and concd under reduced pressure. The crude material was purified by silica gel chromatography eluting with a gradient of 0-5% MeOH in DCM to give 2-(4-cyano-1H-pyrazol-1-yl)-N-((1S,3R,4S)-3-ethyl-4-(6H-pyrrolo[2,3-e][1,2,4]triazolo[4,3-a]pyrazin-1-yl)cyclopentyl)ethanesulfonamide (0.024 g, 42%): LC/MS (Table 1, Method b) $R_t$=1.63 min; MS m/z: 454 $(M+H)^+$.

TABLE YY.1

Examples prepared from N-((1S,3R,4S)-3-ethyl-4-(6H-pyrrolo[2,3-e][1,2,4]triazolo[4,3-a]pyrazin-1-yl)cyclopenty1)-2-(1H-1,2,4-triazol-1-yl)ethanesulfonamide (prepared using K.1 from Example #8 Step M and 2-chloroethanesulfonyl chloride with TEA) using General Procedure YY

| Amine | Structure | Ex. # | (Table 1, Method) $R_t$ min (method) | m/z ESI+ $(M + H)^+$ |
|---|---|---|---|---|
| 1H-1,2,4-triazole | 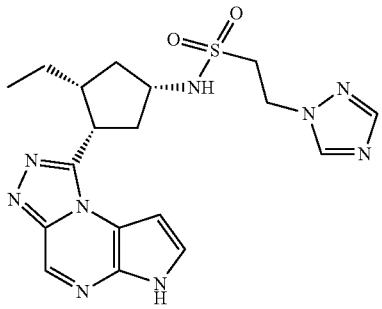 | YY.1.2* | 1.41 (b) | 430 |

General Procedure ZZ: Formation of an Oxazolidinone Sulfonourea

To a mixture of an amine or an amine salt (1 equiv) and 2-chloroethyl chlorosulfonylcarbamate (prepared as detailed in Bioorg. Med. Chem. Lett., 2006 16, 3367-3370) (1-3 equiv, preferably 1 equiv) in an organic solvent (preferably DCM) is added a base (such as DIEA or TEA, preferably TEA [2-5 equiv, preferably 3 equiv]) and optionally DMAP (1-3 equiv, preferably 1 equiv) and stirred at ambient temperature for about 10 min-6 h (preferably about 1 h). The solvent is removed under reduced pressure. In cases where DMAP is used, the crude material can be partitioned between an organic solvent (such as EtOAc or DCM) and water or brine, dried over anhydrous $MgSO_4$, filtered and concd under reduced pressure.

Illustration of General Procedure ZZ

Preparation #ZZ.1*: N-((1S,3R,4S)-3-ethyl-4-(6-tosyl-6H-pyrrolo[2,3-e][1,2,4]triazolo[4,3-a]pyrazin-1-yl)cyclopentyl)-2-oxooxazolidine-3-sulfonamide

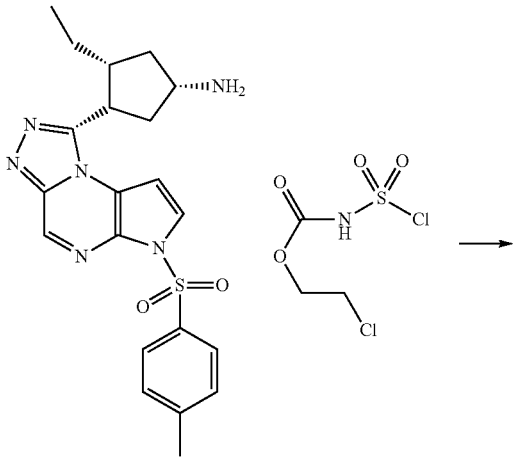

-continued

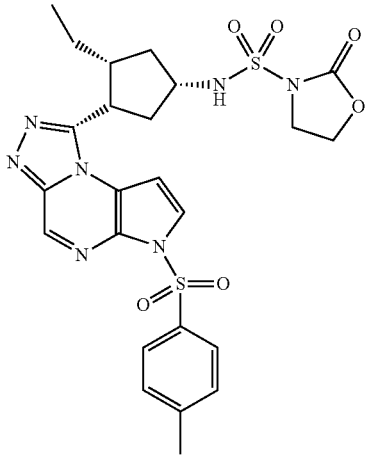

To a mixture of 2-chloroethyl chlorosulfonylcarbamate (prepared as detailed in Bioorg. Med. Chem. Lett., 2006 16, 3367-3370; 0.052 g, 0.236 mmol) and (1S,3R,4S)-3-ethyl-4-(6-tosyl-6H-pyrrolo[2,3-e][1,2,4]triazolo[4,3-a]pyrazin-1-yl)cyclopentanamine (0.100 g, 0.236 mmol, Example #8 Step M) in DCM (2.4 mL) was added TEA (0.098 mL, 0.71 mmol) and the reaction mixture was stirred at ambient temperature for about 1 h. The reaction mixture was concd under reduced pressure to give N-((1S,3R,4S)-3-ethyl-4-(6-tosyl-6H-pyrrolo[2,3-e][1,2,4]triazolo[4,3-a]pyrazin-1-yl)cyclopentyl)-2-oxooxazolidine-3-sulfonamide (0.098 g, 65%) as a light brown solid: LC/MS (Table 1, Method a) $R_t$=2.18 min; MS m/z 574 $(M+H)^+$.

General Procedure AAA: Formation of a Sulfonylurea from an Oxazolidinone Sulfonourea To a solution of an oxazolidinone (preferably 1 equiv) in an organic solvent (preferably MeCN) is added an amine or a hydrochloride salt of an amine (1-2 equiv, preferably 1.5 equiv) and an organic base, such as TEA or DIEA (1-4 equiv, preferably 2 equiv). The reaction is irradiated in the microwave at about 100-150° C. (preferably 120° C.) for about 0.5-1 h (preferably 0.5 h). The reaction mixture is cooled to ambient temperature and is optionally concd under reduced pressure to give a residue. The reaction mixture or residue is optionally partitioned between an organic solvent (such as DCM or EtOAc, preferably EtOAc), water, an aqueous solution (such as saturated aqueous $NaHCO_3$ or saturated aqueous ammonium chloride (preferably saturated aqueous ammonium chloride) or brine. The layers are separated and the organic layer is dried over anhydrous $Na_2SO_4$ or MgSO4, filtered, and concd under reduced pressure to give a sulfonylurea.

Illustration of General Procedure AAA

Preparation #AAA.1*: (R)-N-((1S,3R,4S)-3-methyl-4-(6-tosyl-6H-imidazo[1,5-a]pyrrolo[2,3-e]pyrazin-1-yl)cyclopentyl)-2-(trifluoromethyl)pyrrolidine-1-sulfonamide

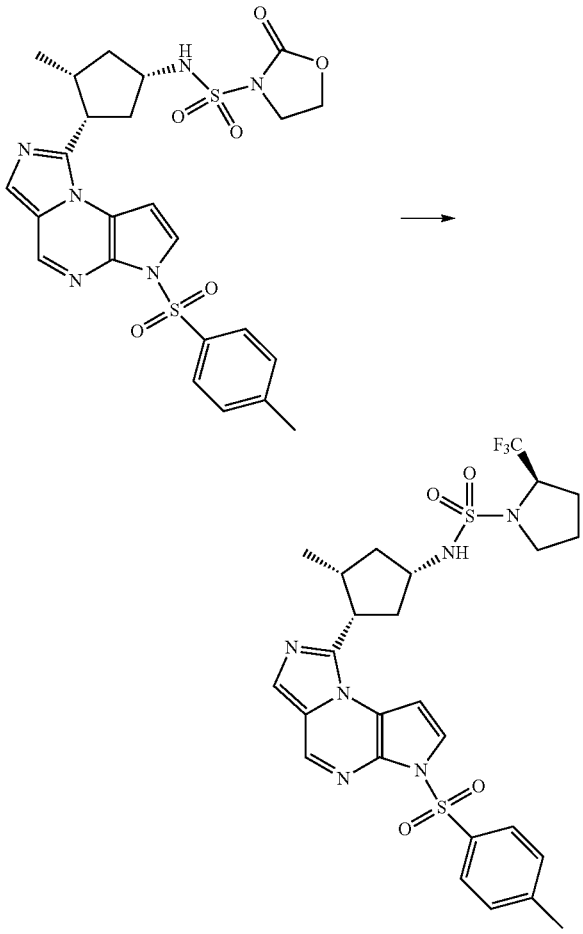

To a solution of N-((1S,3R,4S)-3-methyl-4-(6-tosyl-6H-imidazo[1,5-a]pyrrolo[2,3-e]pyrazin-1-yl)cyclopentyl)-2-oxooxazolidine-3-sulfonamide (0.200 g, 0.261 mmol, prepared from 5-tosyl-5H-pyrrolo[2,3-b]pyrazin-2-yl) methanamine hydrochloride (WO2009152133) and (1S,2R, 4S)-4-acetamido-2-methylcyclopentanecarboxylic acid [prepared from ethyl 4-amino-2-methyl-cyclopentanecarboxylate (WO2009152133) using G, AA, and Z] using H, OO, BB, and ZZ) and (R)-2-trifluoromethylpyrrolidine (0.055 g, 0.392 mmol) in MeCN (1.4 mL) was added TEA (0.073 mL, 0.523 mmol). The reaction was irradiated in a CEM microwave at about 120° C. for about 0.5 h. The reaction mixture was cooled to ambient temperature and concd under reduced pressure to afford a residue. The crude material was purified by silica gel chromatography eluting with a gradient of 0-70% EtOAc in DCM to afford (R)-N-((1S,3R,4S)-3-methyl-4-(6-tosyl-6H-imidazo[1,5-a]pyrrolo[2,3-e]pyrazin-1-yl)cyclopentyl)-2-(trifluoromethyl)pyrrolidine-1-sulfonamide (0.12 g, 75%, 72% purity) as an off-white solid: LC/MS (Table 1, Method a) $R_t$=2.79 min; MS m/z: 611 $(M+H)^+$.

General Procedure BBB: Reduction of a Nitro Group

To a solution of a nitro-containing compound (preferably 1 equiv) in an organic solvent (preferably EtOH) is added tin (II) chloride dihydrate (1-3 equiv, preferably 1 equiv) and the reaction is stirred at about 25-80° C. (preferably at about 75° C.) for about 0.5-24 h (preferably about 1-2 h). Optionally, additional portions of tin (II) chloride dihydrate (1-5 equiv, preferably 2 equiv) can be added to the reaction mixture and heating can be continued for about 0.5-24 h (preferably about 5-14 h). The reaction mixture is concd under reduced pressure. The crude mixture may be diluted with an organic solvent (for example, EtOAc or DCM) and aqueous base (such as 1 N NaOH or saturated aqueous $NaHCO_3$). The layers are separated and the aqueous layer is extracted with an organic solvent (such as EtOAc and/or DCM). The combined organic layers are optionally washed with brine, dried over anhydrous $MgSO_4$, filtered and concd under reduced pressure.

Illustration of General Procedure BBB

Preparation #BBB.1: N-4-cyclohexyl-1-tosyl-1H-pyrrolo[2,3-b]pyridine-4,5-diamine

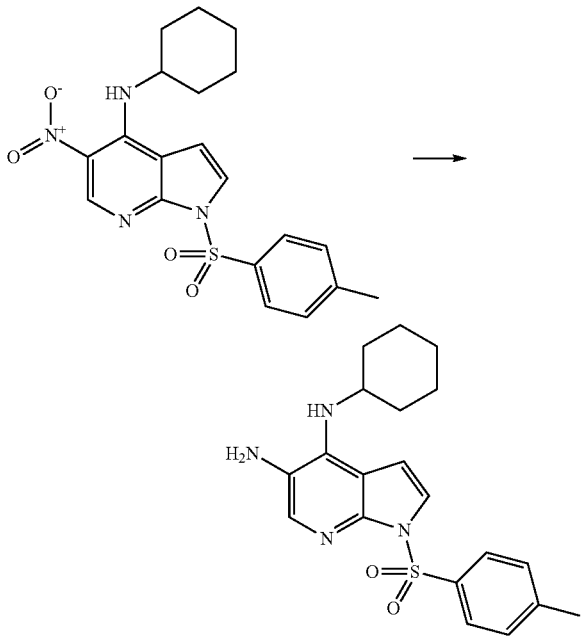

To a mixture of N-cyclohexyl-5-nitro-1-tosyl-1H-pyrrolo[2,3-b]pyridin-4-amine (0.111 g, 0.268 mmol, prepared using K.1 from Example #21 Step D with 4-methylbenzene-1-sulfonyl chloride, L with cyclohexylamine) in EtOH (2.5 mL) was added tin (II) chloride dihydrate (0.060 g, 0.268 mmol). The reaction mixture was heated at about 75° C. for about 75 min. Tin (II) chloride dihydrate (0.030 g, 0.134 mmol) was added and the reaction mixture was heated at about 75° C. for about 5 h. Additional tin (II) chloride dihydrate (0.060 g, 0.268 mmol) was added and the reaction mixture was heated at about 75° C. for about 14 h. The solvent was removed under reduced pressure. The residue was diluted with EtOAc (25 mL) and washed with saturated aqueous $NaHCO_3$ (25 mL) and brine (25 mL). The organic portion was separated. The aqueous portion was extracted with EtOAc (3×25 mL). The organic extracts were combined, dried over $MgSO_4$, filtered, and concd under reduced pressure to give N-4-cyclohexyl-1-tosyl-1H-pyrrolo[2,3-b]pyridine-4,5-diamine (0.081 g, 79%) as a brown oil: LC/MS (Table 1, Method n) $R_t$=0.82 min; MS m/z 385 $(M+H)^+$.

General Procedure CCC: Formation of an Amide

To a mixture of an amine or amine salt (1 equiv) in an organic solvent (for example, DCM or THF, preferably DCM) at about 0-25° C. (preferably 0° C.) is added and organic base (TEA or DIEPA, preferably TEA) (neat or as a solution in an organic solvent (preferably DCM)), 1-3 equiv (preferably 1 equiv) and an acylating agent (for example, an anhydride or an acid chloride) (preferably an anhydride) (neat or as a solution in an organic solvent (preferably DCM)), 1-3 equiv (preferably 1 equiv). The reaction mixture is stirred at ambient temperature for about 5 min-6 h (preferably about 10 min). The reaction mixture is optionally washed with saturated aqueous $NaHCO_3$, water, or brine, dried over $MgSO_4$, filtered, and concd under reduced pressure.

Illustration of General Procedure CCC

Preparation #CCC.1: N-(4-(cyclohexylamino)-1-tosyl-1H-pyrrolo[2,3-b]pyridin-5-yl)-2,2,2-trifluoroacetamide

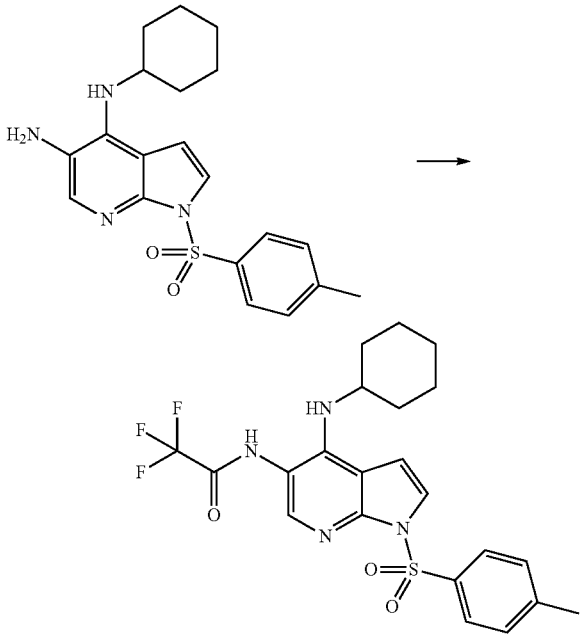

To a 0° C. solution of N-4-cyclohexyl-1-tosyl-1H-pyrrolo[2,3-b]pyridine-4,5-diamine (Preparation #BBB.1, 0.080 g, 0.208 mmol) in DCM (2.0 mL) was added TEA (2 M in DCM, 0.104 mL, 0.208 mmol) and TFAA (2 M in DCM, 0.104 mL, 0.208 mmol). The reaction mixture was stirred for about 10 min. The reaction mixture was washed with saturated aqueous $NaHCO_3$ (2 mL) and water (2 mL), dried over anhydrous $MgSO_4$, filtered and concd under reduced pressure to give N-(4-(cyclohexylamino)-1-tosyl-1H-pyrrolo[2,3-b]pyridin-5-yl)-2,2,2-trifluoroacetamide with 40 mol % dichloromethane as an excipient (0.089 g, 83%, 90% purity) as a brown solid: LC/MS (Table 1, Method n) $R_t$=0.88 min; MS m/z 481 $(M+H)^+$.

General Procedure DDD: Cyclization to Form a Fused Imidazole

To a solution of a diamine (preferably 1 equiv) in an organic solvent such as DMF, DCM, 1,4-dioxane, or MeOH (preferably MeOH) is added the corresponding cyclization reagent such as TMOF (1-10 equiv, preferably 1-2 equiv.). (A catalytic amount of acid, such as TsOH (0.005-0.5 equiv, preferably 0.01 equiv) is optionally added to the reaction mixture when TMOF is used). Alternatively, a solution of an ortho-substituted amidoaminoaryl or heteroaryl compound (preferably 1 equiv) is cyclized in an organic solvent such as DMF or THF using a dehydrating agent such as TPP, $POCl_3$ or HCl (5-100 equiv, preferably 10 equiv of TPP). The reaction mixture is heated at about 25-120° C. (preferably about 65° C.) for about 1-24 h (preferably about 12-16 h), cooled to ambient temperature and optionally concd under reduced pressure to give a residue. The residue is partitioned between an organic solvent (such as DCM or EtOAc, preferably EtOAc), water, an aqueous base (such as saturated aqueous $NaHCO_3$) and/or brine. The layers are separated and the organic layer is optionally washed with water, an aqueous base (such as saturated aqueous $NaHCO_3$) and/or brine, dried over anhydrous $Na_2SO_4$ or $MgSO_4$, filtered, and concd under reduced pressure.

Illustration of General Procedure DDD

Preparation #DDD.1: N-(3-ethyl-4-(6-tosylimidazo[4,5-d]pyrrolo[2,3-b]pyridin-1(6H)-yl)cyclopentyl) cyclopropanesulfonamide

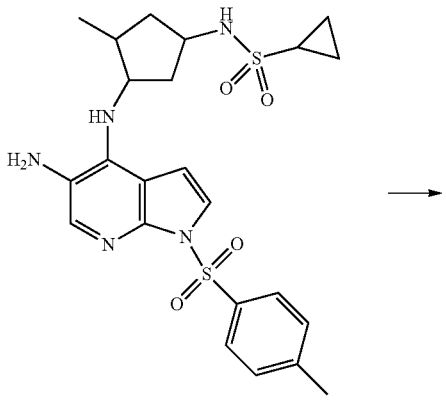

-continued

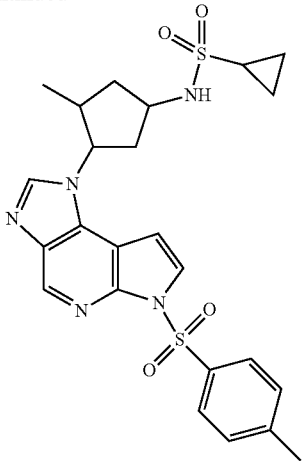

To a solution of N-(3-(5-amino-1-tosyl-1H-pyrrolo[2,3-b]pyridin-4-ylamino)-4-ethylcyclopentyl)cyclopropanesulfonamide (0.095 g, 75% purity, 0.142 mmol, prepared using L from Preparation #27 and Preparation #000.1 with DIEA, K.1 with TsCl and NaH, and BBB) and TMOF (0.016 mL, 0.147 mmol) in MeOH (3.09 mL) was added toluene-4-sulfonic acid hydrate (0.0003 g, 0.0015 mmol). The reaction was heated at about 65° C. for about 14 h. The reaction was cooled to ambient temperature and concd under reduced pressure to give a crude solid. The solid was dissolved in EtOAc (10 mL) and was washed with saturated aqueous $NaHCO_3$ (5 mL), water (5 mL), and brine (5 mL). The organic portion was separated and dried over anhydrous $MgSO_4$, filtered, and concd under reduced pressure to afford N-(3-ethyl-4-(6-tosylimidazo[4,5-d]pyrrolo[2,3-b]pyridin-1(6H)-yl)cyclopentyl)cyclopropanesulfonamide (0.075 g, 99%) as a yellow solid: LC/MS (Table 1, Method a) $R_t$=2.15 min; MS m/z: 514 $(M+H)^+$.

General Procedure EEE: Formation of a Sulfonyl Chloride

To a solution of a sulfonic acid or the potassium salt of a sulfonate (preferably 1 equiv) in thionyl chloride (2-30 equiv, preferably 20-25 equiv) is added DMF (0.01-0.10 equiv, preferably 0.09 equiv). The reaction is heated at about 50-100° C. (preferably about 80° C.) for about 8-24 h (preferably about 12-16 h). The reaction mixture is cooled to 0-25° C. (preferably about 0° C.) and is diluted with water. The reaction mixture is partitioned between an organic solvent (such as DCM or EtOAc) and water or brine. The layers are separated and the organic layer is optionally washed with water and/or brine, dried over anhydrous $Na_2SO_4$ or $MgSO_4$, filtered, and concd under reduced.

Illustration of General Procedure EEE

Preparation #EEE.1: 1-ethylcyclopropane-1-sulfonyl chloride

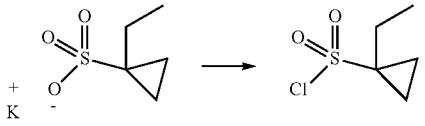

To a mixture of potassium 1-ethylcyclopropane-1-sulfonate (0.420 g, 2.23 mmol, Preparation #JJJ.1) in thionyl chloride (3.58 mL, 49.1 mmol) was added DMF (0.016 mL, 0.20 mmol). The reaction was heated at about 80° C. for about 16 h. The reaction was cooled to 0° C. before the slow addition of water (10 mL). The reaction mixture was diluted with DCM (20 mL). The layers were separated and the aqueous portion was extracted with DCM (3×10 mL). The combined organic layers were separated, dried over anhydrous $MgSO_4$, filtered, and concd under reduced pressure to afford crude 1-ethylcyclopropane-1-sulfonyl chloride (0.52 g, 83% yield, 60% purity) as an orange oil: $^1$H NMR (400 MHz, DMSO) d 2.09 (q, J=7.4, 2H), 1.62-1.60 (m, 2H), 1.45-1.39 (m, 2H), 0.91 (t, J=7.5, 3H).

General Procedure FFF: Generation of an Ether Under Reductive Conditions

To a solution of a TBDMS ether (1.0 equiv) in MeCN at ambient temperature is added triethyl silane (1-2 equiv preferably 1.5 equiv), and bismuth (III) bromide (0.05-0.2 equiv, preferably 0.06 equiv). The reaction is stirred at about 25-60° C. (preferably about 25° C.) for about 0.5-5 min (preferably 1-3 min). To the reaction mixture is added an aldehyde or ketone (1-6 equiv, preferably 1.5 equiv) that can be optionally dried over anhydrous $Na_2SO_4$ or $MgSO_4$. In cases where the reaction does not proceed to completion as monitored by TLC, additional triethyl silane (1-2 equiv preferably 1.5 equiv) and/or bismuth (III) bromide (0.05-0.2 equiv, preferably 0.06 equiv) and/or aldehyde or ketone (1-6 equiv, preferably 1.5 equiv) can be added. The reaction is continued at about 25-60° C. (preferably about 25° C.) for about 15 min-24 h (preferably about 1 h). The reaction is worked up using one of the following methods. Method 1: The reaction mixture is filtered through a pad of Celite®. The pad of Celite® can be rinsed with additional organic solvent (preferably heptane or MeCN) and the filtrate is concd under reduced pressure. Method 2: The reaction mixture is filtered through an Acrodisc® and the filtrate is concd under reduced pressure.

Illustration of General Procedure FFF

Preparation #FFF.1: ethyl 2-ethyl-4-(tetrahydro-2H-pyran-4-yloxy)cyclopentanecarboxylate

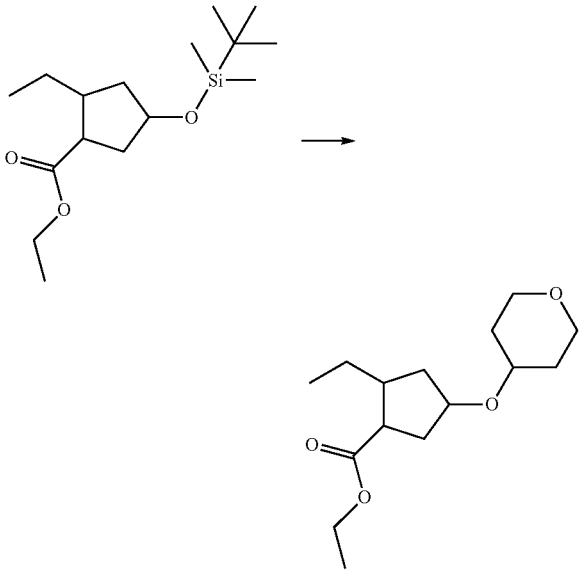

To a solution of ethyl 4-(tert-butyldimethylsilyloxy)-2-ethylcyclopentanecarboxylate (0.200 g, 0.666 mmol, Example #22 Step D) in MeCN (4.5 mL) was added triethylsilane (0.160 mL, 1.00 mmol) and bismuth(III) bromide (0.020 g, 0.045 mmol). The reaction mixture was stirred at ambient temperature for about 1 min followed by dropwise addition of dihydro-2H-pyran-4(3H)-one (0.100 g, 0.998 mmol). The reaction mixture was stirred at ambient temperature for about 15 min. The reaction was filtered through an Acrodisc® and the solvent was removed under reduced pressure. The crude material was purified by silica gel chromatography using a gradient of 10-100% EtOAc in heptane to give ethyl 2-ethyl-4-(tetrahydro-2H-pyran-4-yloxy)cyclopentanecarboxylate (0.253 g, 94%) as a colorless oil; $^1$H NMR (400 MHz, $CDCl_3$) δ 4.13 (q, J=7.1, 2H), 4.05-3.98 (m, 1H), 3.98-3.88 (m, 2H), 3.58-3.47 (m, 1H), 3.46-3.36 (m, 2H), 2.80 (q, J=8.5, 1H), 2.16 (dt, J=13.3, 7.7, 1H), 2.09-1.93 (m, 3H), 1.90-1.81 (m, 2H), 1.62-1.49 (m, 3H), 1.43 (ddd, J=11.1, 7.4, 5.2, 1H), 1.33-1.22 (m, 4H), 0.92-0.83 (m, 3H).

General Procedure GGG: Iodination of a Pyrrole Based Heterocycle

To a pyrrole based heterocycle (preferably 1 equiv) in an organic solvent such as DMF is added a base such as KOH (1-10 equiv, preferably 3equiv) at about 0° C. to 40° C. (preferably at ambient temperature) and the mixture is stirred for about 2-45 min (preferably about 5 min). Iodine (0.95-1.2 equiv, preferably 1.0 equiv) is added in small portions and the mixture is stirred for 10-100 min. (preferably about 30 min). The mixture is added drop-wise into saturated aqueous ammonium chloride (10 mL for every 1 mL of DMF used) and the target compound is collected by filtration, washed with additional water and dried.

Illustration of General Procedure GGG

Preparation #GGG.1: N-((1S,3R,4S)-3-ethyl-4-(8-iodo-6H-pyrrolo[2,3-e][1,2,4]triazolo[4,3-a]pyrazin-1-yl)cyclopentyl)cyclopropanesulfonamide

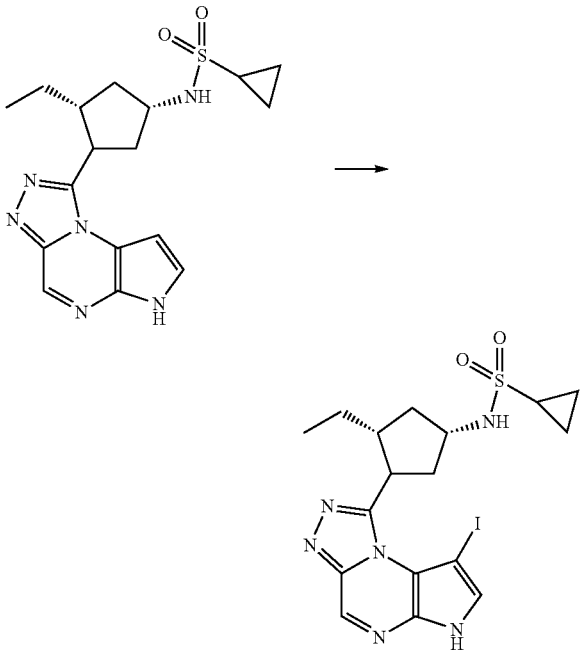

To a solution of N-((1S,3R,4S)-3-ethyl-4-(6H-pyrrolo[2,3-e][1,2,4]triazolo[4,3-a]pyrazin-1-yl)cyclopentyl)cyclopropanesulfonamide (0.396 g, 1.06 mmol, prepared as detailed in WO2009152133) in DMF (20 mL) was added KOH (0.190 g, 3.38 mmol). The mixture was stirred at rt for 5 min. Iodine (0.268 g, 1.058 mmol) was added in small portions and the reaction mixture was stirred at rt for 30 min. The mixture was added dropwise into a saturated aqueous ammonium chloride (200 mL). The precipitate was collected by filtration, washed with water, and dried to give N-((1S,3R,4S)-3-ethyl-4-(8-iodo-6H-pyrrolo[2,3-e][1,2,4]triazolo[4,3-a]pyrazin-1-yl)cyclopentyl)cyclopropanesulfonamide (0.494 g, 93%) as an off-white solid: LC/MS (Table 1, Method a) $R_t$=1.83 min; MS m/z 501 $(M+H)^+$.

General Procedure GGG.1: Iodination, Chlorination or Bromination of a Pyrrole Based Heterocycle To a pyrrole based heterocycle (preferably 1 equiv) in an organic solvent such as DMF, THF, MeCN, MeOH, AcOH, $CHCl_3$, or DCM (preferably DMF) is optionally added a base such as TEA, NaOAc, $K_2CO_3$, or KOH (1-10 equiv) at about 0-40° C. (preferably at 0° C.) and the mixture is stirred for about 2-45 min (preferably about 5 min). A halogen source such as $I_2$, $Br_2$, NBS, pyridinium tribromide, NCS, or NIS (0.95-1.2 equiv, preferably 1.0 equiv) is added portion-wise, dropwise neat, or as a solution in a solvent such as DMF. If cooling the ice bath is removed and the mixture is stirred for about 0.1-2 h (preferably about 40 min) at rt. Optionally, a reagent such as sodium thiosulfate or sodium bisulfite as a solution in water may be added or the reaction mixture is added to the solution and the reaction mixture stirred for about 5-60 min (preferably about 30 min). The mixture may be diluted with or added into water or saturated aqueous $NH_4Cl$ (preferably using 10 mL of water per 1 mL of DMF). The target compound may be collected by filtration or extracted using an organic solvent such as EtOAc or DCM, dried over $Na_2SO_4$ or $MgSO_4$, filtered, and concentrated under reduced pressure.

Illustration of General Procedure GGG.1

Preparation #GGG.1.1: 8-iodo-6H-pyrrolo[2,3-e][1,2,4]triazolo[4,3-a]pyrazine

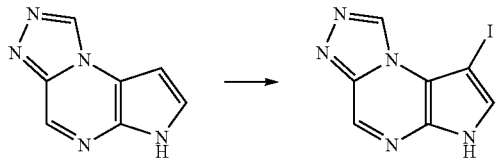

A solution of 6H-pyrrolo[2,3-e][1,2,4]triazolo[4,3-a]pyrazine (0.500 g, 3.14 mmol, prepared using D from Preparation #BBBBB.1 and NaOH) and DMF (16 mL) under nitrogen was cooled to about 0° C. The mixture was stirred for about 5 min. N-Iodosuccinimide (0.707 g, 3.14 mmol) was added. After about 40 min, 5% aq. sodium thiosulfate (10 mL) was added. The cold bath was removed. After stirring for about 30 min, water (15 mL) was added. The solid was collected by filtration. The filter cake was washed with water (2×5 mL). The aqueous layer was extracted with EtOAc (4×50 mL). The combined organics were dried over $Na_2SO_4$, filtered, and concentrated under reduced pressure. The residue was slurried in water (10 mL)

and then filtered, rinsing with water (2×1 mL). The solid was dried in vacuo to afford a brown solid (0.689 g) containing an approximate 4:1 ratio of mono- to di-iodinated material. 8-iodo-6H-pyrrolo[2,3-e][1,2,4]triazolo[4,3-a]pyrazine (0.506 g, 57%): LC/MS (Table 1, Method n) $R_t$=0.39 min; MS m/z 286 $(M+H)^+$.

General Procedure HHH: Cyanation of a Heterocycle

To a solution of a heteroaryl halide (preferably 1 equiv) in an organic solvent (such as 1,4-dioxane, NMP or DMF, preferably DMF) is added potassium cyanide (1-4 equiv, preferably 2.5 equiv), copper(I) iodide (1-4 equiv, preferably 2.5 equiv), tetrakis(triphenylphosphine)palladium(0) (0.01-0.05 equiv, preferably 0.01 equiv) and 18-crown-6 (0.01-1.0 equiv, preferably 0.06-0.07 equiv). The reaction is heated at about 25-120° C. (preferably about 110° C.) for about 0.5-10 h (preferably about 4 h). The reaction is cooled to rt and the organic solvent is optionally removed under reduced pressure. The crude material can be partitioned between an organic solvent (such as EtOAc or DCM) and water, an aqueous base (such as saturated aqueous $NaHCO_3$) or brine. The layers are separated and the aqueous layer is optionally washed with an organic solvent (such as EtOAc or DCM). The combined organic extracts are dried over anhydrous $Na_2SO_4$ or $MgSO_4$, filtered, and concd under reduced pressure.

Illustration of General Procedure HHH

Preparation #HHH.1*: N-((1S,3S,4R)-3-(8-cyano-6-((2-(trimethylsilyl)ethoxy) methyl)-6H-pyrrolo[2,3-e][1,2,4]triazolo[4,3-a]pyrazin-1-yl)-4-ethylcyclopentyl)cyclopropanesulfonamide

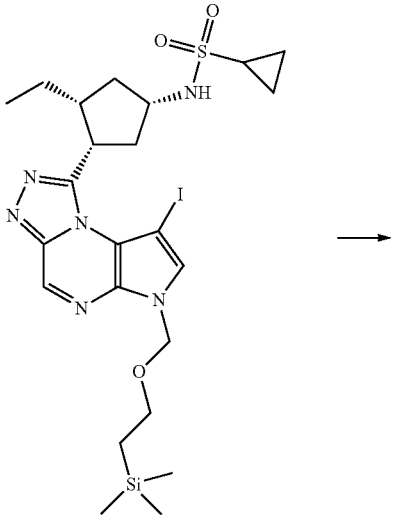

-continued

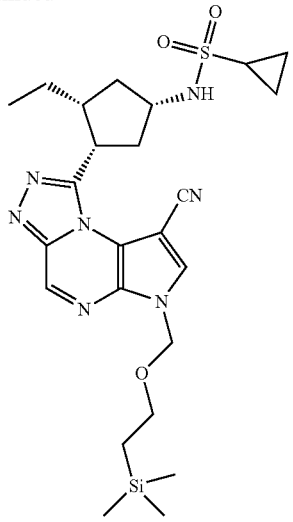

To a solution of N-((1S,3R,4S)-3-ethyl-4-(8-iodo-6-((2-(trimethylsilyl)ethoxy)methyl)-6H-pyrrolo[2,3-e][1,2,4]triazolo[4,3-a]pyrazin-1-yl)cyclopentyl)cyclopropanesulfonamide (0.1 g, 0.16 mmol, prepared using KK from Preparation #GGG.1) in DMF (1.2 mL) was added potassium cyanide (0.03 g, 0.40 mmol), copper(I) iodide (0.076 g, 0.40 mmol), tetrakis(triphenyl-phosphine)palladium(0) (0.002 g, 0.002 mmol) and 18-crown-6 (0.003 g, 0.01 mmol). The reaction mixture was stirred at about 110° C. for about 4 h and cooled to ambient temperature. The solvent was removed under reduced pressure. The residue was partitioned between EtOAc (15 mL) and water (8 mL). The aqueous layer was further extracted with EtOAc (15 mL). The combined organic layers were dried with $MgSO_4$, filtered, and concd under reduced pressure to give N-((1S,3S,4R)-3-(8-cyano-6-((2-(trimethylsilyl)ethoxy)methyl)-6H-pyrrolo[2,3-e][1,2,4]triazolo[4,3-a]pyrazin-1-yl)-4-ethylcyclopentyl)cyclopropanesulfonamide (0.069 g, 82%): LC/MS (Table 1, Method b) $R_t$=2.50 min; MS m/z: 530 $(M+H)^+$.

General Procedure III: Horner-Wadsworth-Emmons Reaction of a Ketone

To a flask charged with a base (preferably NaH) (1-5 equiv, preferably 1.2 equiv) in an organic solvent (preferably THF) at about 0-50° C. (preferably rt) is added a beta-ketophosphonate (1-5 equiv, preferably 1.25 equiv). After the evolution of hydrogen gas has ceased a solution of a ketone (preferably 1 equiv) in an organic solvent (preferably THF) is added. After about 1-20 h (preferably about 4 h) the reaction mixture is partitioned between an organic solvent (such as DCM or EtOAc, preferably EtOAc) and an aqueous phase such as saturated aqueous $NaHCO_3$. The organic layer is separated and optionally washed with brine, dried over anhydrous $Na_2SO_4$ or $MgSO_4$, filtered, and concd under reduced pressure.

Illustration of General Procedure III

Preparation #III.1: (E)-ethyl 2-((3R,4S)-3-ethyl-4-(6-tosyl-6H-pyrrolo[2,3-e][1,2,4]triazolo[4,3-a]pyrazin-1-yl)cyclopentylidene)acetate

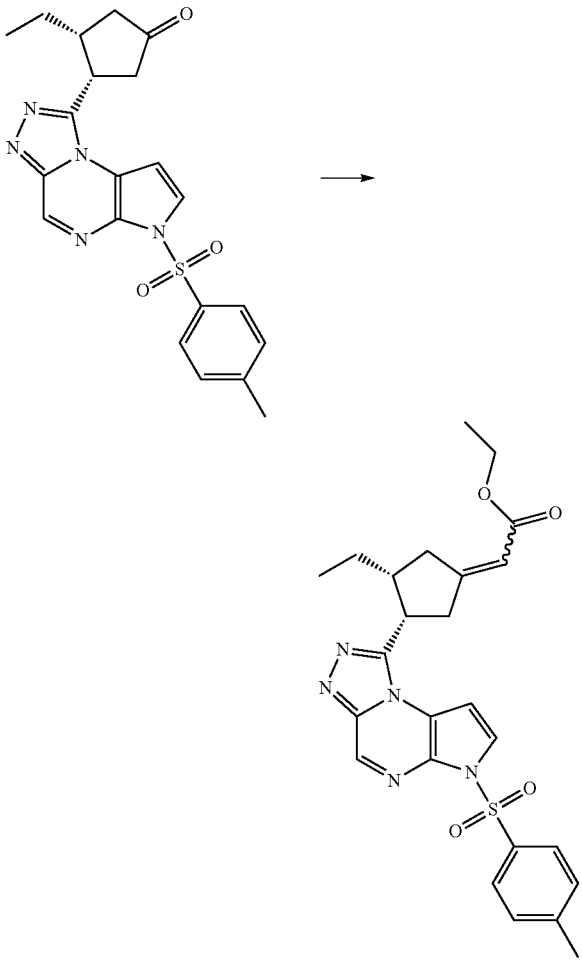

To a slurry of NaH (0.034 g, 0.85 mmol) in THF (5 mL) was added ethyl 2-(diethoxyphosphoryl)acetate (0.177 mL, 0.886 mmol) at rt. After about 30 min, a solution of (3R,4S)-3-ethyl-4-(6-tosyl-6H-pyrrolo[2,3-e][1,2,4]triazolo[4,3-a]pyrazin-1-yl)cyclopentanone (0.300 g, 0.708 mmol, Preparation #25) in THF (1 mL) was added. After about 4 h, EtOAc (20 mL) and saturated aqueous $NaHCO_3$ (20 mL) were added. The organic layer was separated, concd in vacuo, and purified by chromatography on silica gel (40 g) eluting with EtOAc/heptane/DCM (2:1:1) to provide (E)-ethyl 2-((3R,4S)-3-ethyl-4-(6-tosyl-6H-pyrrolo[2,3-e][1,2,4]triazolo[4,3-a]pyrazin-1-yl)cyclopentylidene)acetate (0.260 g, 74%). LC/MS (Table 1, Method a) $R_t$=2.54 min; MS m/z: 494 $(M+H)^+$.

General Procedure JJJ: Formation of a Potassium Sulfonate

To a solution of a sulfonate (preferably 1 equiv) in an organic solvent (preferably 1,4-dioxane) and water is added potassium thiocyanate (1-3 equiv, preferably 1 equiv). The reaction is heated at about 80-100° C. (preferably about 100° C.) for about 5-24 h (preferably about 16 h). The reaction mixture is cooled to ambient temperature and is concd under reduced pressure.

Illustration of General Procedure JJJ

Preparation #JJJ.1: potassium 1-ethylcyclopropane-1-sulfonate

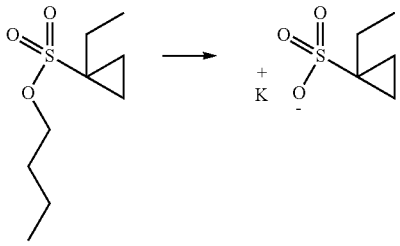

To a solution of butyl 1-ethylcyclopropane-1-sulfonate (0.46 g, 2.23 mmol prepared from Preparation #6 Step A and ethyl iodide using KKK) in 1,4-dioxane (2.79 mL) and water (2.79 mL) was added potassium thiocyanate (0.12 mL, 2.23 mmol). The reaction is heated to about 100° C. for about 16 h. The reaction mixture was cooled to ambient temperature and was concd under reduced pressure to afford potassium 1-ethylcyclopropane-1-sulfonate (0.42 g, 100%) as a white crystalline solid: $^1H$ NMR (400 MHz, DMSO) d 1.70-1.58 (m, 2H), 0.89 (t, J=7.5, 3H), 0.80 (q, J=3.8, 2H), 0.32 (q, J=3.8, 2H).

General Procedure KKK: Alkylation of a Sulfonate

To a solution of a sulfonate (preferably 1 equiv) in an organic solvent (preferably THF), cooled to about −78-0° C. (preferably −78° C.) is added an organic base such as n-BuLi, KHMDS, or LDA (preferably n-BuLi) (1-3 equiv, preferably 1 equiv) and an alkylating reagent such as iodomethane, iodoethane, or trifluoroethyl iodide (1-5 equiv, preferably 1.2 equiv). The reaction is stirred at about −78-25° C. (preferably −78° C.) for about 1-24 h (preferably 2 h). Optionally, the reaction is warmed to ambient temperature and stirred for about 1-24 h (preferably 2 h). The reaction mixture is quenched by the addition of saturated aqueous ammonium chloride. The reaction mixture is partitioned between an organic solvent (such as DCM or EtOAc) and water or brine. The layers are separated and the organic layer is optionally washed with water and/or brine, dried over anhydrous $Na_2SO_4$ or $MgSO_4$, filtered, and concd under reduced pressure.

Illustration of General Procedure KKK

Preparation #KKK.1: butyl 1-methylcyclopropane-1-sulfonate

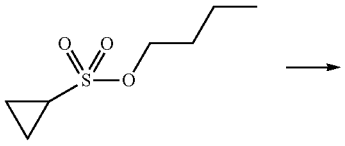

-continued

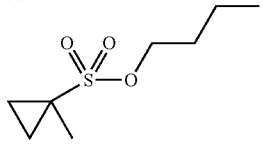

To a solution of butyl cyclopropanesulfonate (1.5 g, 8.4 mmol, Preparation #6 Step A) in THF (8 mL) at about −78° C. was added n-BuLi (1.6 M in hexanes, 5.26 mL, 8.42 mmol) and iodomethane (0.684 mL, 10.9 mmol) simultaneously. The resulting mixture was stirred at about −78° C. for about 2 h and then at ambient temperature for about 2 h. The reaction was quenched by the addition of saturated aqueous $NH_4Cl$ (7 mL) and the layers were separated. The aqueous layer was extracted with EtOAc (15 mL) and the combined organic extracts were dried over anhydrous $MgSO_4$, filtered, and concd under reduced pressure. The residue was purified by silica gel column chromatography eluting with 5 to 25% EtOAc in heptanes to yield butyl 1-methylcyclopropane-1-sulfonate (0.8 g, 49%) as a colorless oil. $^1$H NMR (DMSO-$d_6$) δ 4.17 (t, 2H), 1.62 (m, 2H), 1.43 (s, 3H), 1.35 (m, 2H), 1.22 (m, 2H), 0.94 (m, 2H), 0.88 (t, 3H).

General Procedure LLL: Oxidation of a Thioether to a Sulfone

To a solution of a thioether (preferably 1 equiv) in an organic solvent (preferably DCM) is added an oxidant (such as m-CPBA, oxone, preferably m-CPBA) (1-4 equiv, preferably 2 equiv). The reaction is stirred at ambient temperature for about 0.25-24 h (preferably about 0.5 h). The reaction mixture is optionally filtered, washed with additional DCM, and the filtrate is concd under reduced pressure. The reaction mixture is optionally quenched with the addition of an aqueous base (such as saturated aqueous $NaHCO_3$) and partitioned between an organic solvent (such as DCM or EtOAc, preferably DCM). The layers are separated and optionally washed with water and/or brine, dried over anhydrous $Na_2SO_4$ or $MgSO_4$, filtered, and concd under reduced pressure to give a sulfone.

Illustration of General Procedure LLL

Preparation #LLL.1: 1-(2-ethyl-4-(2,2,2-trifluoroethylsulfonyl)cyclopentyl)-6-((2-(trimethylsilyl)ethoxy)methyl)-6H-pyrrolo[2,3-e][1,2,4]triazolo[4,3-a]pyrazine

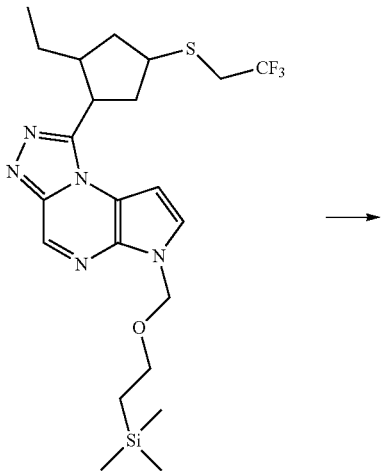

-continued

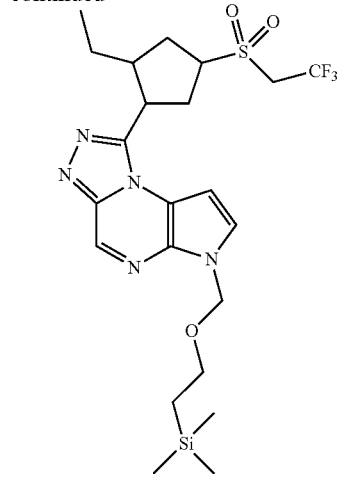

To a mixture of 1-(2-ethyl-4-(2,2,2-trifluoroethylthio)cyclopentyl)-6-((2-(trimethylsilyl)ethoxy)methyl)-6H-pyrrolo[2,3-e][1,2,4]triazolo[4,3-a]pyrazine (0.100 g, 0.200 mmol, Preparation #MMM.1) in DCM (0.667 mL) was added m-CPBA (0.090 g, 0.400 mmol). The reaction stirred at ambient temperature for about 0.5 h. The reaction mixture was quenched by the addition of saturated aqueous $NaHCO_3$ (5 mL). The aqueous portion was extracted with DCM (2×10 mL). The combined organic layers were separated, dried over anhydrous $MgSO_4$, filtered, and concd under reduced pressure. The crude material was purified by silica gel chromatography eluting with a gradient of 0-60% EtOAc in DCM to afford 1-2-ethyl-4-(2,2,2-trifluoroethylsulfonyl)cyclopentyl)-6-((2-(trimethylsilyl)ethoxy)methyl)-6H-pyrrolo[2,3-e][1,2,4]triazolo[4,3-a]pyrazine (0.095 g, 89%, 93% purity) as a clear oil: LC/MS (Table 1, Method a) $R_t$=2.63 min; MS m/z: 532 $(M+H)^+$.

General Procedure MMM: Mitsunobu Reaction Using a Thiol

To a solution of an azodicarboxylate such as DIAD, DEAD, or TMAD (preferably DIAD) (1-2 equiv, preferably 1.2 equiv) in an organic solvent (preferably THF) is added a phosphine reagent such as $PPh_3$ or $P(n\text{-}Bu)_3$ (preferably $P(n\text{-}Bu)_3$) (1-2 equiv, preferably 1.2 equiv), an alcohol (preferably 1 equiv), TEA (1-2 equiv, preferably 1.2 equiv) and a thiol (1-1.5 equiv, preferably 1.2 equiv). The reaction is stirred at ambient temperature for about 1-24 h (preferably 16 h). The reaction mixture is optionally concd under reduced pressure to give a residue. The reaction mixture or residue is partitioned between an organic solvent (such as DCM or EtOAc, preferably EtOAc) and water, an aqueous base (such as saturated aqueous $NaHCO_3$) or brine. The layers are separated and the organic layer is optionally washed with water, an aqueous base (such as saturated aqueous $NaHCO_3$) and/or brine, dried over anhydrous $Na_2SO_4$ or $MgSO_4$, filtered, and concd under reduced pressure to give a thioether.

Illustration of General Procedure MMM

Preparation #MMM.1: 1-(2-ethyl-4-(2,2,2-trifluoroethylthio)cyclopentyl)-6-((2-(trimethylsilyl)ethoxy)methyl)-6H-pyrrolo[2,3-e][1,2,4]triazolo[4,3-a]pyrazine

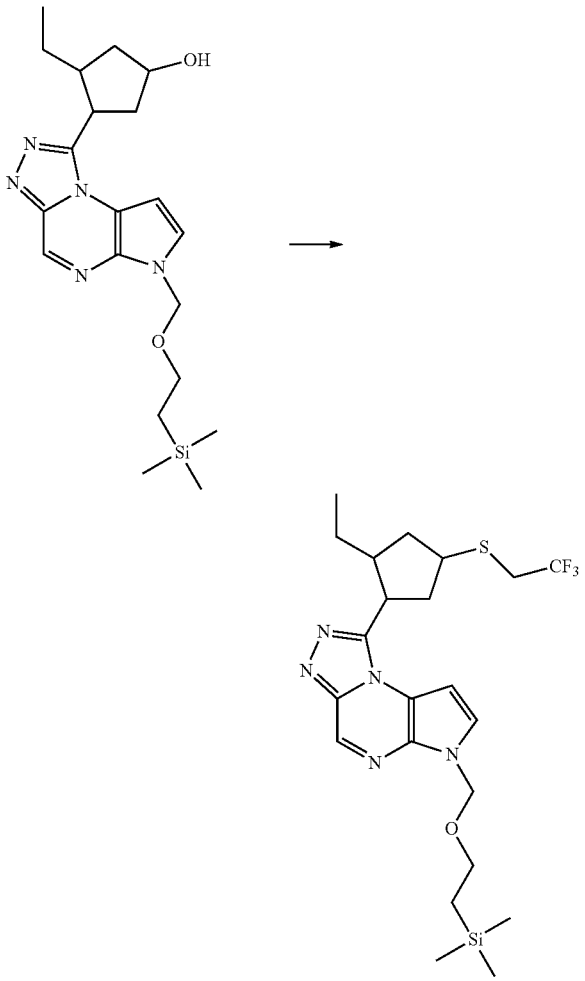

An oven-dried flask was charged with DIAD (0.177 mL, 0.896 mmol) and THF (3.74 mL). The reaction flask was cooled to 0° C. before the addition of $P(n\text{-}Bu)_3$ (0.221 mL, 0.896 mmol), 3-ethyl-4-(6-((2-(trimethylsilyl)ethoxy)methyl)-6H-pyrrolo[2,3-e][1,2,4]triazolo[4,3-a]pyrazin-1-yl)cyclopentanol (0.300 g, 0.747 mmol, prepared from Preparation #20 using KK and SS), TEA (0.125 mL, 0.896 mmol) and 2,2,2-trifluoroethanthiol (0.080 mL, 0.896 mmol). The reaction was stirred at ambient temperature for about 16 h. The reaction mixture was partitioned between water (10 mL) and EtOAc (10 mL). The aqueous layer was extracted with EtOAc (3×10 mL). The combined organic layers were dried over anhydrous $MgSO_4$, filtered, and concd under reduced pressure to afford a crude oil. The crude material was purified by silica gel chromatography eluting with a gradient of 0-60% EtOAc in DCM to afford 1-(2-ethyl-4-(2,2,2-trifluoroethylthio)cyclopentyl)-6-((2-(trimethylsilyl)ethoxy)methyl)-6H-pyrrolo[2,3-e][1,2,4]triazolo[4,3-a]pyrazine (0.165 g, 44%) as an orange solid: LC/MS (Table 1, Method a) $R_t$=3.02 min; MS m/z: 500 $(M+H)^+$.

General Procedure NNN: Curtius Rearrangement to Form an Isocyanate

To a solution of a carboxylic acid (preferably 1 equiv) in an organic solvent such as t-BuOH or toluene (preferably t-BuOH) is added DPPA (1-3equiv, preferably 1-1.1 equiv) and an organic base such as TEA (2-4 equiv, 2.2 equiv). The reaction is stirred at about 25-110° C. (preferably about 70° C. for t-BuOH and 110° C. for toluene) for about 0.5-16 h (preferably about 2 h). The reaction mixture is cooled to ambient temperature and is optionally concd under reduced pressure to give a residue. The reaction mixture or residue is optionally partitioned between an organic solvent (such as DCM or EtOAc) and water, an aqueous base (such as saturated aqueous $NaHCO_3$) or brine. The layers are separated and the organic layer is dried over anhydrous $Na_2SO_4$ or $MgSO_4$, filtered, and concd under reduced pressure.

Illustration of General Procedure NNN

Preparation #NNN.1: N-(3-isocyanato-4-methylcyclopentyl)cyclopropanesulfonamide

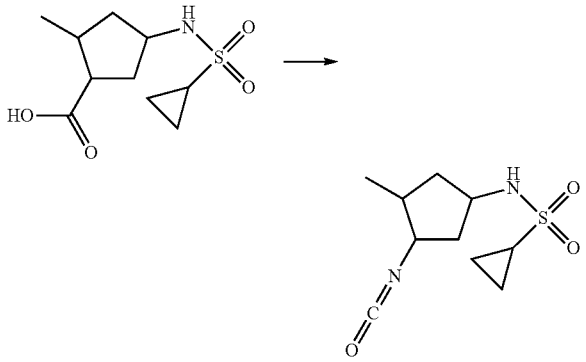

To a solution of 4-(cyclopropanesulfonamido)-2-methylcyclopentanecarboxylic acid (4.10 g, 16.58 mmol, prepared from Example #24 Step I using Y, K, and Z) and DPPA (3.58 mL, 16.58 mmol) in t-BuOH (55 mL) was added TEA (5.0 mL, 36.5 mmol). The reaction was heated to about 70° C. for about 2 h then cooled to ambient temperature and concd under reduced pressure to afford a crude residue. The crude material was purified by silica gel chromatography eluting with a gradient of 0-10% MeOH in DCM to afford N-(3-isocyanato-4-methylcyclopentyl)cyclopropanesulfonamide (3.25 g, 80%) as a white solid: LC/MS (Table 1, Method n) $R_t$=0.49 min; MS m/z: 245 $(M+H)^+$.

General Procedure OOO: Hydrolysis of an Isocyanate

To a mixture of an isocyanate (preferably 1 equiv) in an organic solvent (preferably THF) is added an aqueous base or acid (such as aqueous NaOH, LiOH, or HCl) (10-50 equiv, preferably 20 equiv). The reaction is heated at about 30-100° C. for about 5-36 h (preferably about 50° C. for about 16 h). The reaction is cooled to ambient temperature and the reaction mixture is partitioned between an organic solvent (such as DCM or EtOAc) and water, an aqueous base (such as saturated aqueous $NaHCO_3$) or brine. The layers are separated and the organic layer is optionally washed with water and or brine, dried over anhydrous $Na_2SO_4$ or $MgSO_4$, filtered, and concd under reduced pressure.

Illustration of General Procedure OOO

Preparation #OOO.1: N-(3-amino-4-methylcyclopentyl)cyclopropanesulfonamide

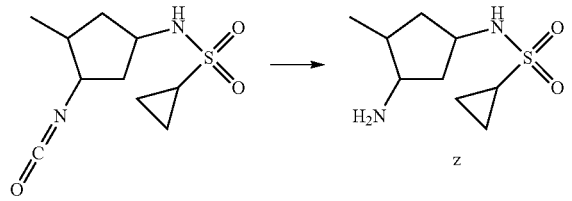

To a mixture of N-(3-isocyanato-4-methylcyclopentyl) cyclopropanesulfonamide (1.00 g, 4.09 mmol, Preparation #NNN.1) in THF (2.0 mL) was added aqueous LiOH (4 N, 20.5 mL, 82 mmol). The reaction was heated to about 50° C. for about 16 h, cooled to ambient temperature and partitioned between water (5 mL) and EtOAc (10 mL). The organic portion was separated and the aqueous portion was extracted with DCM (3×20 mL). The combined organic extracts were dried over anhydrous $MgSO_4$, filtered, and concd under reduced pressure to give crude N-(3-amino-4-methylcyclopentyl)cyclopropanesulfonamide (0.66 g, 74%) as a white solid: LC/MS (Table 1, Method n) $R_t$=0.020 min; MS m/z: 219 $(M+H)^+$.

General Procedure PPP: Formation of an Oxime Ether from a Ketone

To a solution of a ketone (preferably 1 equiv) in an organic solvent (preferably EtOH) is added an O-alkyl hydroxylamine (1-10 equiv, preferably about 1 equiv). If the O-alkyl hydroxylamine is a hydrochloride salt, an organic base is added such as TEA or DIEA (preferably TEA, 1-5 equiv, preferably about 1.5 equiv). The reaction mixture is stirred at ambient temperature for about 12-24 h (preferably about 18 h). In cases where the reaction does not proceed to completion as monitored by TLC, LC/MS, or HPLC, additional O-alkyl hydroxylamine may be added (1-10 equiv, preferably about 1 equiv). The reaction is stirred at ambient temperature for about 1-24 h (preferably about 5 h). The solvent is removed under reduced pressure.

Illustration of General Procedure PPP

Example #PPP.1.1

(3R,4S)-3-ethyl-4-(6H-pyrrolo[2,3-e][1,2,4]triazolo[4,3-a]pyrazin-1-yl)cyclopentanone O-cyclopropylmethyl oxime

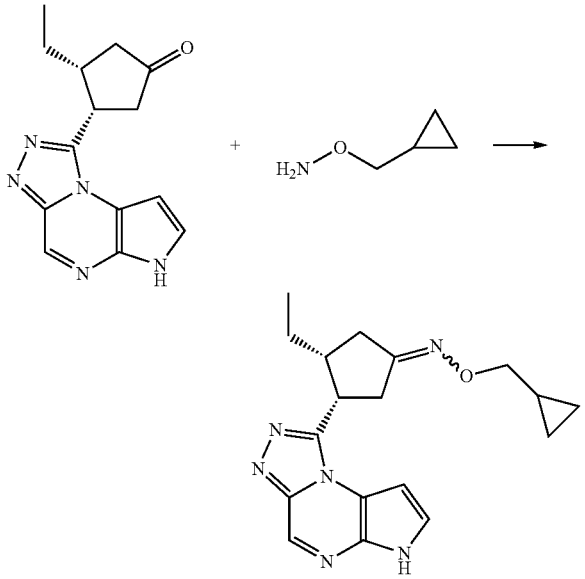

To a solution of (3R,4S)-3-ethyl-4-(6H-pyrrolo[2,3-e][1,2,4]triazolo[4,3-a]pyrazin-1-yl)cyclopentanone (0.05 g, 0.19 mmol, Example #AA.1.59) in EtOH (1 mL) was added TEA (0.04 mL, 0.28 mmol) and O-(cyclopropylmethyl) hydroxylamine hydrochloride (0.02 g, 0.19 mmol, Huhu Technologies). The reaction mixture was stirred for about 18 h at ambient temperature. Additional O-(cyclopropylmethyl) hydroxylamine hydrochloride (0.02 g, 0.19 mmol, Huhu Technologies) was added. The reaction was stirred at ambient temperature for about 5 h. The solvent was removed under reduced pressure. The crude material was purified by silica gel chromatography eluting with a gradient of 1-10% MeOH in DCM to afford (3R,4S)-3-ethyl-4-(6H-pyrrolo[2,3-e][1,2,4]triazolo[4,3-a]pyrazin-1-yl)cyclopentanone O-cyclopropylmethyl oxime (0.051 g, 80%): LC/MS (Table 1, Method a) $R_t$=1.94 min; MS m/z: 339 $(M+H)^+$.

TABLE PPP.1

Examples prepared using PPP and (3R,4S)-3-ethyl-4-(6H-pyrrolo[2,3-e][1,2,4]triazolo[4,3-a]pyrazin-1-yl)cyclopentanone (Example #AA.1.59)

| Hydroxylamine | Structure | Ex. # | $R_t$ min (Table 1 method) | m/z ESI+ $(M + H)^+$ |
|---|---|---|---|---|
| O-(2-(methylsulfonyl)ethyl) hydroxylamine (Huhu Technologies) | 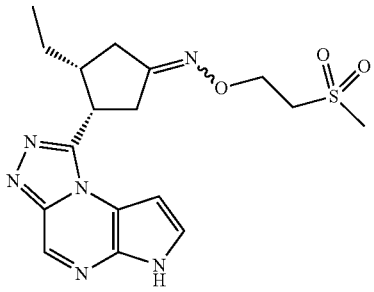 | PPP.1.2 | 1.63 (a) | 391 |

TABLE PPP.1-continued

Examples prepared using PPP and (3R,4S)-3-ethyl-4-(6H-pyrrolo[2,3-e][1,2,4]triazolo[4,3-a]pyrazin-1-yl)cyclopentanone (Example #AA.1.59)

| Hydroxylamine | Structure | Ex. # | $R_t$ min (Table 1 method) | m/z ESI+ $(M + H)^+$ |
|---|---|---|---|---|
| O-(cyclobutylmethyl)hydroxylamine (Huhu Technologies) | 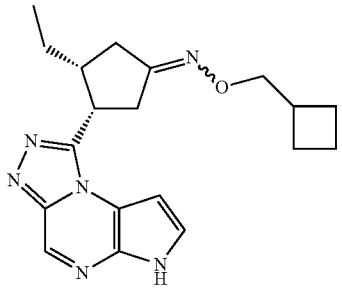 | PPP.1.3 | 2.15-2 .12 (a) | 353 |
| O-(tetrahydro-2H-pyran-4-yl)hydroxylamine (Huhu Technologies) | 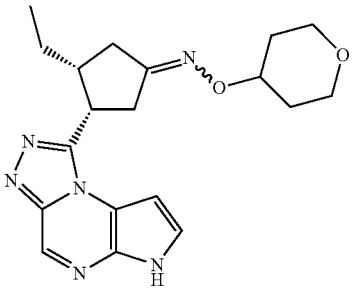 | PPP.1.4 | 1.72 (a) | 369 |

General Procedure QQQ: Acid-Mediated Conversion of a T-Butyl Ester to a Carboxylic Acid with TFA To a t-butyl ester (preferably 1 equiv) is added TFA (10-400 equiv, preferably 200-250 equiv). The reaction is maintained at about −20-60° C. (preferably about 25° C.) for about 0.5-16 h (preferably about 1 h). In any case where an additional acid labile group is present (for example, a Boc group) this group may also be cleaved during the reaction. The reaction mixture is concd under reduced pressure. The resulting residue can be used without further purification or dissolved in an organic solvent such as DCM or EtOAc (preferably DCM) and is washed with an aqueous inorganic base such as $NaHCO_3$ or $Na_2CO_3$ (preferably saturated aqueous $NaHCO_3$). The organic layer is optionally washed with brine, dried over anhydrous $MgSO_4$ or $Na_2SO_4$, and concd under reduced pressure to yield the target compound.

Illustration of General Procedure QQQ

Preparation #QQQ.1: 4-(cyclopropanesulfonamidomethyl)-2-ethylcyclopentanecarboxylic acid

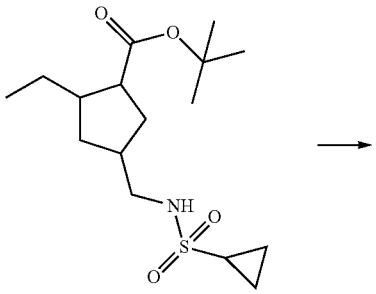

-continued

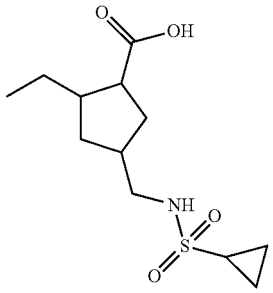

tert-Butyl 4-(cyclopropanesulfonamidomethyl)-2-ethylcyclopentanecarboxylate (0.080 g, 0.241 mmol, prepared using K from Preparation #21 and cyclopropylsulfonyl chloride) in TFA (4 mL, 51.9 mmol) was stirred at about 25° C. for about 1 h. The organic solvent was removed under reduced pressure to yield crude 4-(cyclopropanesulfonamidomethyl)-2-ethylcyclopentanecarboxylic acid (0.066 g, 100%): LC/MS (Table 1, Method b) $R_t$=1.81 min; MS m/z: 276 $(M+H)^+$.

General Procedure RRR: Reduction of an Alkyne to an Alkene

To a flask charged with a hydrogenation catalyst (preferably Lindlar catalyst) (0.001 to 1 equiv, preferably 0.01 equiv) is added a solvent (preferably THF) and an additive to prevent over-reduction (such as pyridine or quinoline, preferably pyridine) in a ratio of 5:1 to 20:1 (preferably 10:1) followed by an alkyne (1 equiv). The reaction mixture is sparged with hydrogen for about 5-30 min (preferably about 10 min) and an atmosphere of hydrogen is maintained via balloon. After about 1-40 h (preferably about 15 h) the reaction mixture is filtered, diluted with an organic solvent (preferably $Et_2O$) and washed with saturated aqueous $CuSO_4$, followed by water. The organic layer is separated, dried over anhydrous $Na_2SO_4$ or $MgSO_4$, filtered, and concd under reduced pressure.

Illustration of General Procedure RRR

Preparation #RRR.1: (Z)-ethyl pent-2-enoate

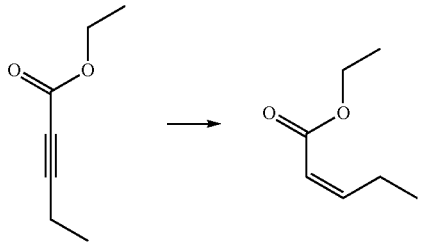

To a slurry of Lindlar catalyst (0.844 g, 0.396 mmol) in THF (100 mL) and pyridine (10.00 mL) was added ethyl pent-2-ynoate (5.22 mL, 39.6 mmol). The reaction mixture was sparged with hydrogen for about 10 min and an atmosphere of hydrogen was maintained via balloon. After about 15 h the reaction mixture was filtered through a pad of Celite®, diluted with $Et_2O$ (30 mL) and washed with saturated aqueous $CuSO_4$ (40 mL), followed by water (40 mL). The organic layer was separated, dried over anhydrous $MgSO_4$, filtered, and concd in vacuo to provide crude (Z)-ethyl pent-2-enoate (5 g, 98%). $^1H$ NMR (DMSO-$d_6$) δ 1.05 (t, 3H), 1.28 (t, 3H), 2.65 (m, 2H), 4.18 (q, 2H), 5.72 (m, 1H), 6.21 (m, 1H).

General Procedure SSS: 1,3-Dipolar Cycloaddition to Form a Pyrrolidine

To a solution of a 1,3-dipole precursor (0.5-3equiv, preferably 1 equiv) and a dipolarophile (0.5-3equiv, preferably 1 equiv) in an organic solvent (preferably DCM) at about 0-45° C. (preferably rt) is added an acid (preferably TFA) (0.001-1 equiv, preferably 0.01 equiv). After about 1-60 h (preferably about 48 h) the mixture is concd in vacuo to provide the crude cyclo-adduct.

Illustration of General Procedure SSS

Preparation #SSS.1: cis-ethyl 1-benzyl-4-ethylpyrrolidine-3-carboxylate

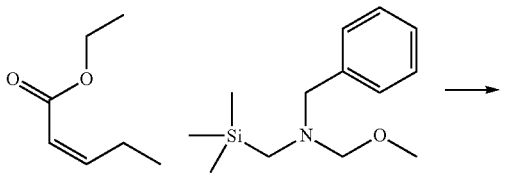

-continued

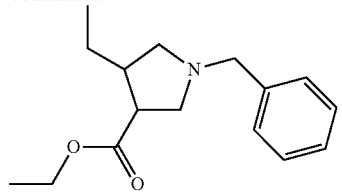

To a solution of N-benzyl-1-methoxy-N-((trimethylsilyl) methyl)methanamine (9.98 mL, 39.0 mmol), and (Z)-ethyl pent-2-enoate (5 g, 39.0 mmol, Preparation #RRR.1) in DCM (50 mL) was added TFA (0.030 mL, 0.390 mmol) at rt. After about 2 d, the reaction mixture was concd in vacuo to provide crude cis-ethyl 1-benzyl-4-ethylpyrrolidine-3-carboxylate (9.8 g, 96%) as an oil. LC/MS (Table 1, Method a) $R_t$=0.51 min; MS m/z: 262 $(M+H)^+$.

General Procedure TTT: Hydrogenation of an Azide to an Amine

To an azide (preferably 1 equiv) in EtOH, MeOH, EtOAc or THF (preferably EtOH), a catalyst such as 20 wt % palladium hydroxide on carbon or 10% wt palladium on carbon (preferably palladium hydroxide on carbon, 0.05-0.5 eq., preferably 0.15 equiv) is added and the mixture is stirred at ambient temperature under atmospheric pressure of hydrogen for 1-24 h, preferably about 2 h. The catalyst is removed by filtration through a pad of Celite® and the filtrate is concd under reduced pressure to yield the desired product.

Illustration of General Procedure TTT

Preparation #TTT.1: (3S,5R)-5-ethyl-1-(3H-imidazo[1,2-a]pyrrolo[2,3-e]pyrazin-8-yl)pyrrolidin-3-amine

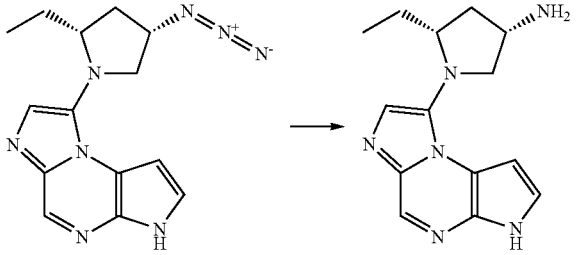

To the solution of 8-((2R,4S)-4-azido-2-ethylpyrrolidin-1-yl)-3H-imidazo[1,2-a]pyrrolo[2,3-e]pyrazine (0.136 g, 0.459 mmol, prepared using S from Example #3 Step E and tert-butyl bromoacetate, E with HCl, H with (2R,4S)-4-azido-2-methylpyrrolidine (prepared from (2R,4S)-tert-butyl 4-azido-2-methylpyrrolidine-1-carboxylate as detailed in Rosen, T.; Chu, D. T. W.; Lico, I. M.; Fernandes, P. B.; Marsh, K.; Shen, L.; Cepa, V. G.; Pernet, A. G. J. Med. Chem. 1988, 31, 1598-1611, then E with HCl), OO, D with NaOH) in EtOH (15 mL), 20% palladium hydroxide on carbon (0.05 g, 0.071 mmol) was added and the reaction mixture was stirred under atmospheric pressure of hydrogen for 2 h. The catalyst was removed by filtration through a pad of Celite® and the solvent was removed under reduced pressure to yield (3S,5R)-5-ethyl-1-(3H-imidazo[1,2-a]pyrrolo[2,3-e]pyrazin-8-yl)pyrrolidin-3-amine (0.11 g, 89%) as an off-white amorphous solid. LC/MS (Table 1, Method a) $R_t$=1.00 min; MS m/z 271 $(M+H)^+$.

General Procedure UUU: Reaction of an Aryl or Heteroaryl Halide with a Boronic Acid or Boronate Ester Followed by Tosyl Deprotection To a mixture of an aryl halide (preferably 1 equiv), a boronic acid or boronate ester (1-1.75 equiv, preferably 1.1 equiv), and an inorganic base (for example, potassium fluoride, sodium carbonate or cesium carbonate, preferably cesium carbonate (2-16 equiv, preferably 2.5 equiv) in a solvent (for example THF, DME, DMF, 1,4-dioxane, DME/water, 1,4-dioxane/water, toluene/EtOH/water, 1,4-dioxane/EtOH/water, water; preferably 1,4-dioxane/EtOH/water) is added a palladium catalyst (for example tris(benzylideneacetone)dipalladium(0), tetrakis(triphenylphosphine)palladium(0), bis(acetato)triphenylphosphinepalladium(II), polymer-bound FibreCat™ 1032, (1,1'-bis(diphenylphosphino) ferrocene)dichloropalladium(II) complex with DCM, or dichlorobis(triphenylphosphine)palladium(II); preferably dichlorobis(triphenylphosphine)palladium(II) (0.01-0.20 equiv, preferably 0.1 equiv)). The reaction mixture is heated at about 40-120° C. (preferably about 60° C.) for about 1-24 h (preferably about 6 h) thermally, or at about 100-200° C. (preferably about 120° C. for about 5-60 min (preferably about 20 min) in a microwave (preferably 5 min ramp time, 300 Watts max power, 250 psi max pressure). The reaction mixture is allowed to cool to ambient temperature and is worked up using one of the following methods. Method 1. For reactions containing water, the reaction mixture may be diluted with an organic solvent (such as DCM or EtOAc). The layers are separated, the organic solution is optionally washed with water and/or brine, dried over anhydrous $MgSO_4$ or $Na_2SO_4$, filtered, and the solvent is removed under reduced pressure to give the intermediate. Method 2. The reaction mixture is concd under reduced pressure and optionally purified using one or more of the Purification Methods described above to give the intermediate. To the intermediate are added an organic solvent (such as 1,4-dioxane, MeOH, or THF/MeOH, preferably 1,4-dioxane) and an aqueous base (such as aqueous $Na_2CO_3$ or aqueous NaOH, 1-30 equiv, preferably 2-3 equiv for aqueous NaOH, preferably 15-20 equiv for aqueous $Na_2CO_3$). The mixture is stirred at about 25-100° C. (preferably about 60° C.) for about 1-72 h (preferably about 1-16 h) thermally or at about 80-200° C. (preferably about 100° C.) for about 10-60 min (preferably about 15 min) in a microwave (preferably 5 min ramp time, 300 Watts max power, 250 psi max pressure). In cases where the reaction does not proceed to completion as monitored by TLC, LC/MS, or HPLC, additional aqueous base (such as aqueous $Na_2CO_3$, 10-20 equiv, preferably 10 equiv or aqueous NaOH, 1-5 equiv, preferably 1-2 equiv) and/or a cosolvent (such as EtOH) are added. The reaction is continued at about 25-100° C. (preferably about 60° C.) for about 0.25-3 h (preferably about 1-2 h) thermally or at about 80-100° C. (preferably about 100° C.) for about 10-60 min (preferably about 15 min) in a microwave. In any case where an additional base labile group is present (for example, an ester or a cyano group), this group may also be hydrolyzed. The reaction is worked up using one of the following methods. Method 1. The organic solvent is optionally removed under reduced pressure and the aqueous solution is neutralized with the addition of a suitable aqueous acid (such as aqueous HCl). A suitable organic solvent (such as EtOAc or DCM) and water are added, the layers are separated, and the organic solution is dried over anhydrous $Na_2SO_4$ or $MgSO_4$, filtered, and concd to dryness under reduced pressure to give the target compound. Method 2. The organic solvent is optionally removed under reduced pressure, a suitable organic solvent (such as EtOAc or DCM) and water are added, the layers are separated, and the organic solution is dried over anhydrous $Na_2SO_4$ or $MgSO_4$, filtered, and concd to dryness under reduced pressure to give the target compound. Method 3. The reaction mixture is concd under reduced pressure and directly purified by one of the subsequent methods to give the target compound.

Illustration of General Procedure UUU

Example #UUU.1

1-cyclohexyl-3-(4-(methylsulfonyl)phenyl)-6H-imidazo[1,5-a]pyrrolo[2,3-e]pyrazine

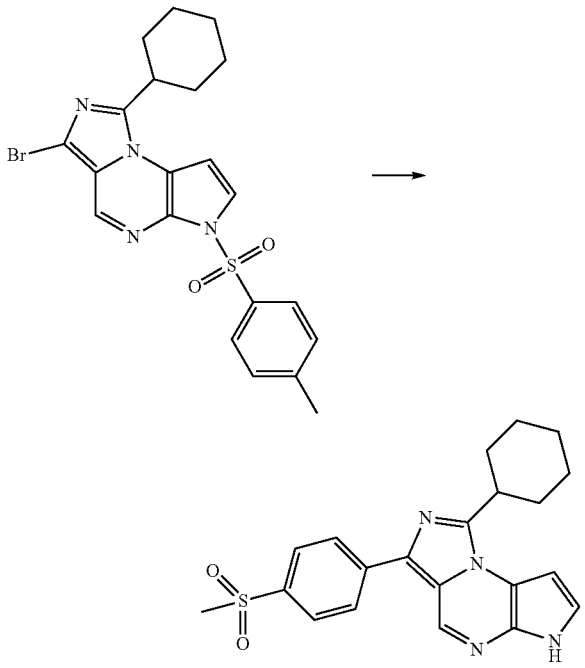

A microwave vial was charged with 3-bromo-1-cyclohexyl-6-tosyl-6H-imidazo[1,5-a]pyrrolo[2,3-e]pyrazine (0.050 g, 0.11 mmol, Preparation #MM.1), 4-(methylsulfonyl)phenylboronic acid (0.023 g, 0.12 mmol, Acros), cesium carbonate (0.086 g, 0.26 mmol), dichlorobis(triphenylphosphine)palladium(II) (0.0066 g, 0.0000094 mmol), and 1,4-dioxane (0.42 mL), EtOH (0.42 mL), and water (0.21 mL). The vial was capped and the mixture was heated to about 120° C. for about 20 min (5 min ramp time, 300 Watts max power, 250 psi max pressure) in a microwave. The reaction mixture was concd under reduced pressure to give a solid that was dissolved in 1,4-dioxane (1.0 mL) and transferred to a microwave vial. Aqueous 2 N NaOH (0.11 mL, 0.21 mmol) was added and the vial was capped. The solution was heated to about 100° C. for about 15 min in a microwave (300 W max power, 250 psi max pressure, 5 min ramp time). DCM (10 mL) and saturated aqueous $NH_4Cl$ (5 mL) were added to the reaction solution. The layers were separated and the aqueous solution was extracted with additional DCM (5 mL). The combined extracts were dried over anhydrous $MgSO_4$, filtered, and concentrated to dryness under reduced pressure to give a light brown solid. Upon addition of DCM (1 mL), a yellow precipitate formed that was collected by vacuum filtration and dried overnight on a Buchner funnel to give 1-cyclohexyl-3-(4-(methylsulfonyl)phenyl)-6H-imidazo[1,5-a]pyrrolo[2,3-e]pyrazine (0.017 g, 41%): LC/MS (Table 1, Method a) $R_t$=2.39 min; MS m/z: 395 $(M+H)^+$.

TABLE UUU.1

Examples prepared from 3-bromo-1-cyclohexy1-6-tosyl-6H-imidazo[1,5-a]pyrrolo[2,3-e]pyrazine (Preparation #MM.1) using General Procedure UUU

| Boronic acid or boronate ester | Product | Example # | $R_t$ min (Table 1, Method) | m/z ESI+ $(M + H)^+$ |
|---|---|---|---|---|
| N-(4-(4,4,5,5-tetramethyl-1,3,2-dioxaborolan-2-yl)phenyl)methanesulfonamide | 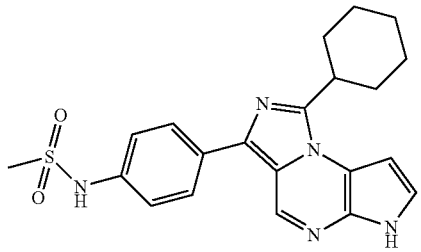 | UUU.1.1 | 2.25 (a) | 410 |

General Procedure VVV: Reaction of an Aryl or Heteroaryl Halide with a Boronic Acid or Boronate Ester To a mixture of an aryl halide (preferably 1 equiv), a boronic acid or boronate ester (1-1.75 equiv, preferably 1.1 equiv), and an inorganic base (for example, potassium fluoride, sodium carbonate or cesium carbonate, preferably cesium carbonate) (1.1-16 equiv, preferably 2 equiv) in a solvent (for example THF, DME, DMF, 1,4-dioxane, DME/water, 1,4-dioxane/water, toluene/EtOH/water, 1,4-dioxane/EtOH/water or water; preferably 1,4-dioxane) is added a palladium catalyst (for example tris(benzylideneacetone) dipalladium(0), tetrakis(triphenylphosphine)palladium(0), bis(acetato)triphenylphosphinepalladium(II), polymer-bound FibreCat™ 1032, (1,1'-bis(diphenylphosphino)ferrocene)dichloropalladium(II) complex with DCM, or dichlorobis(triphenylphosphine)palladium(II); preferably tris (benzylideneacetone)dipalladium(0), 0.01-0.20 equiv, preferably 0.1 equiv) and a ligand (for example tricyclohexylphosphine, tri-t-butyl-phosphane; preferably tricyclohexylphosphine (0.01-1.0 equiv, preferably 0.16 equiv)) is added optionally. The reaction mixture is heated at about 40-120° C. (preferably about 85° C.) for about 1-24 h (preferably about 2 h) thermally, or at about 100-200° C. (preferably about 120° C.) for about 5-60 min (preferably about 20 min) in a microwave (preferably 5 min ramp time, 300 Watts max power, 250 psi max pressure). The reaction mixture is allowed to cool to ambient temperature and is worked up using one of the following methods. Method 1. For reactions containing water, the reaction mixture may be diluted with an organic solvent (such as DCM or EtOAc). The layers are separated, the organic solution is optionally washed with water and/or brine, dried over anhydrous $MgSO_4$ or $Na_2SO_4$, filtered, and the solvent is removed under reduced pressure to give the desired compound. Method 2. The reaction mixture is concd under reduced pressure and optionally purified using one or more of the Purification Methods described above to give the desired compound. Method 3. The catalyst is removed by filtration and the filtrate is concentrated under reduced pressure.

Illustration of General Procedure VVV

Preparation #VVV.1: 8-cyclohexyl-1-methyl-3-((2-(trimethylsilyl)ethoxy)methyl)-3H-imidazo[1,2-a] pyrrolo[2,3-e]pyrazine

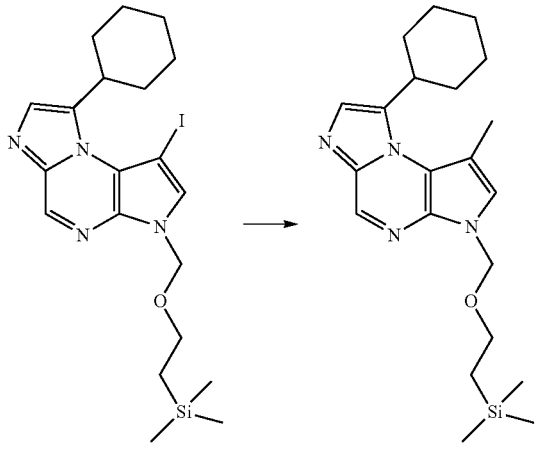

To the solution of 8-cyclohexyl-1-iodo-3-((2-(trimethylsilyl)ethoxy)methyl)-3H-imidazo[1,2-a]pyrrolo[2,3-e]pyrazine (0.100 g, 0.201 mmol, prepared using GGG with 8-cyclohexyl-3H-imidazo[1,2-a]pyrrolo[2,3-e]pyrazine [WO2009152133A1], KK) in 1,4-dioxane (1 mL) was added cesium carbonate (0.131 g, 0.403 mmol), tricyclohexylphosphine (20 wt % solution in toluene, 0.045 g, 0.032 mmol), $Pd_2(dba)_3$ (0.018 g, 0.020 mmol) and trimethylborate (0.033 g, 0.262 mmol). The mixture was degassed and heated at about 85° C. for about 2 h. The catalyst was filtered off. The filtrate was concentrated and purified by RP-HPLC (Table 1, Method s) to give 8-cyclohexyl-1-methyl-3-((2-(trimethylsilyl)ethoxy)methyl)-3H-imidazo[1,2-a]pyrrolo[2,3-e]pyrazine (0.032 g, 41%) as a clear oil: LC/MS (Table 1, Method b) $R_t$=3.41 min; MS m/z: 385 $(M+H)^+$.

General Procedure WWW: Formation of a Carbamate

To an amine (2-10 equiv, preferably 5 equiv) and DMAP (0-5 equiv, preferably 2 equiv) in an organic solvent (such as THF or 1,4-dioxane, preferably 1,4-dioxane) at about −20° C. to 80° C. (preferably about 40° C.) is added a carbonate or a solution of a carbonate (preferably 1 equiv) in an organic solvent (such as THF or 1,4 dioxane, preferably 1,4-dioxane). After about 1-16 h (preferably about 2 h), the reaction mixture is either concd under reduced pressure or optionally diluted with an organic solvent (such as $Et_2O$, EtOAc or DCM, preferably EtOAc), washed with water and an aqueous base (such as saturated aqueous $Na_2CO_3$ or $NaHCO_3$ and brine, dried over anhydrous $Na_2SO_4$ or $MgSO_4$, filtered, and concd under reduced pressure.

Illustration of General Procedure WWW

Preparation #WWW.1: (1S,3R,4S)-3-ethyl-4-(6-tosyl-6H-pyrrolo[2,3-e][1,2,4]triazolo[4,3-a]pyrazin-1-yl)cyclopentyl phenylcarbamate

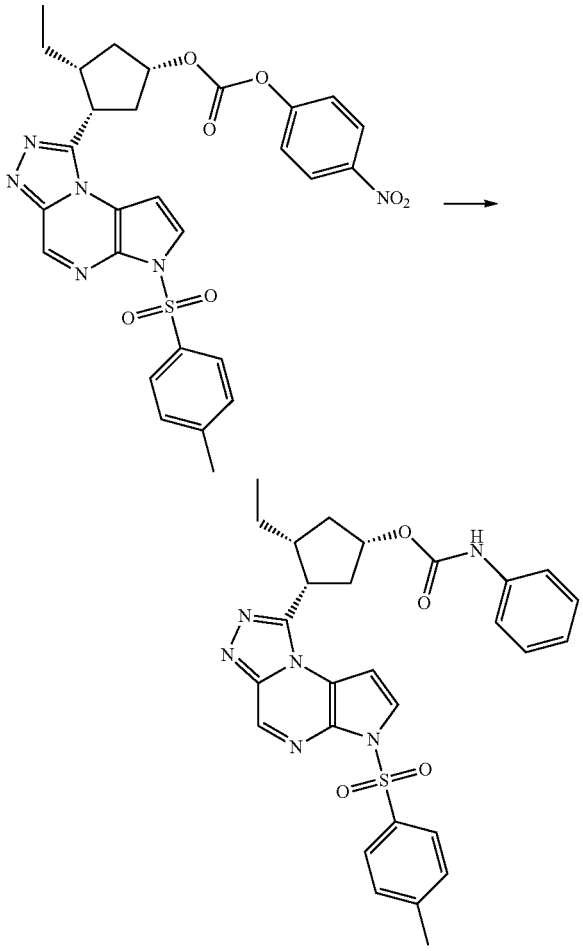

To aniline (0.063 g, 0.677 mmol) and DMAP (0.033 g, 0.271 mmol) in 1,4-dioxane (1 mL) at about 40° C. was added a solution of (1S,3R,4S)-3-ethyl-4-(6-tosyl-6H-pyrrolo[2,3-e][1,2,4]triazolo[4,3-a]pyrazin-1-yl)cyclopentyl 4-nitrophenyl carbonate (0.080 g, 0.135 mmol, prepared from Example #42 Step N) in 1,4-dioxane (1 mL). After about 2 h, the solvent was removed and the residue was purified by silica gel chromatography (12 g) eluting with 0-40% EtOAc in DCM to give (1S,3R,4S)-3-ethyl-4-(6-tosyl-6H-pyrrolo[2,3-e][1,2,4]triazolo[4,3-a]pyrazin-1-yl) cyclopentyl phenylcarbamate (0.0468 g, 63%): LC/MS (Table 1, Method b) $R_t$=2.58 min; MS m/z: 545 $(M+H)^+$.

General Procedure XXX: Urea Formation with Loss of Protecting Group

To a solution or slurry of an amine or amine salt (1-3 equiv, preferably 1-2 equiv) in an organic solvent such as DCM, THF, or DMF (preferably THF) at about 20-80° C. (preferably about 20° C.) is optionally added an organic base, such as TEA, DIEA, pyridine (preferably DIEA) (1-10 equiv, preferably 1-5 equiv) followed by CDI (1-5 equiv, preferably 1 equiv). After about 0.5-24 h (preferably about 1-3 h), a second amine or amine salt (1-10 equiv, preferably 1-3 equiv) is added neat or as a solution or slurry in an organic solvent such as DCM, THF, or DMF (preferably THF). The reaction is held at about 20-80° C. for about 2-24 h (preferably about 16 h). If the reaction is not complete, the reaction may be heated at about 40-80° C. (preferably 55° C.). In addition, additional amine or amine salt (1-50 equiv, preferably 20 equiv), and/or DMAP (1-10 equiv, preferably 1 equiv) may be added. The reaction is held at about 20-80° C. for about 24-96 h (preferably 72 h). This may be repeated if the reaction is not complete by TLC, LC/MS, or HPLC. The reaction mixture is cooled to ambient temperature. The reaction mixture is optionally partitioned between an organic solvent (such as EtOAc or DCM) and an aqueous base (such as saturated aqueous $NaHCO_3$ or saturated aqueous $Na_2CO_3$, preferably saturated aqueous $NaHCO_3$). Alternatively, the reaction mixture is concd under reduced pressure and the residue is partitioned as above. In either case, the aqueous layer is then optionally extracted with additional organic solvent such as EtOAc or DCM. The combined organic layers may optionally be washed with brine and concd in vacuo or dried over anhydrous $Na_2SO_4$ or $MgSO_4$ and then decanted or filtered prior to concentrating under reduced pressure. Optionally, the reaction mixture is concd under reduced pressure and the residue is directly purified.

Illustration of General Procedure XXX Preparation #XXX.1: (cis)-3-ethyl-4-(6H-pyrrolo[2,3-e][1,2,4] triazolo[4,3-a]pyrazin-1-yl)-N-((tetrahydro-2H-pyran-4-yl)methyl)pyrrolidine-1-carboxamide

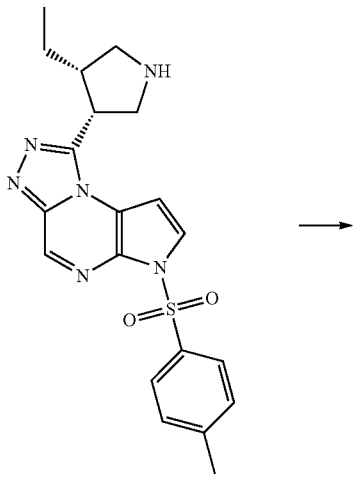

-continued

CIS

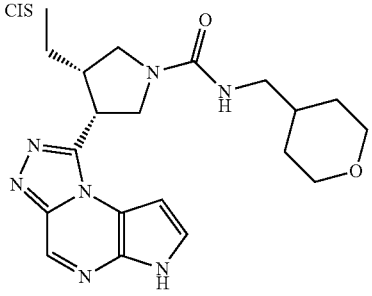

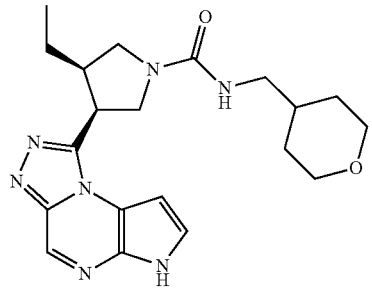

To a solution of 1-((cis)-4-ethylpyrrolidin-3-yl)-6-tosyl-6H-pyrrolo[2,3-e][1,2,4]triazolo[4,3-a] pyrazine•hydrochloride (0.075 g, 0.168 mmol, Example #36, step F) in THF (1.00 mL) was added DIEA (0.150 mL, 0.861 mmol) and CDI (0.027 g, 0.168 mmol). After about 1 h, 4-aminomethyltetrahydropyran (0.020 g, 0.17 mmol, Acros) was added and the reaction mixture was stirred at ambient temperature for about 16 h. The reaction mixture was heated at about 55° C. for about 24 h. DMAP (0.021 g, 0.168 mmol) was added and continued stirring at about 55° C. for about 48 h. 4-aminomethyltetrahydropyran (0.400 g, 3.47 mmol, Acros) was added and continued stirring at about 55° C. for about 24 h. The solvent was removed under reduced pressure. The crude material was purified by RP-HPLC (Table 1, Method m) to afford (cis)-3-ethyl-4-(6H-pyrrolo[2,3-e][1,2,4]triazolo[4,3-a]pyrazin-1-yl)-N-((tetrahydro-2H-pyran-4-yl)methyl)pyrrolidine-1-carboxamide (0.007 g, 10%) as product: LC/MS (Table 1, Method a) $R_t$=1.32 min; MS m/z: 398 $(M+H)^+$.

TABLE XXX.1

Urea formation with loss of protecting group (prepared from Example #36, step F) using General Procedure XXX

| Starting material amine | Product | Ex # | $R_t$ min (Table 1, Method) | m/z ESI+ $(M + H)^+$ |
|---|---|---|---|---|
| cyclopropylmethanamine | 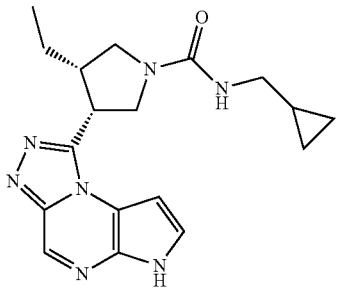 | XXX.1 | 1.62 (a) | 354 |
| | 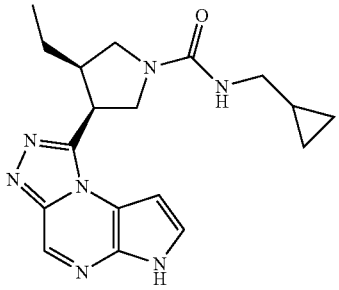 | | | |

General Procedure YYY: Michael addition

To a mixture of a nucleophile (such as an amine or an alcohol, preferably 1 equiv) and a Michael acceptor (0.5-30 equiv, preferably 2-5 equiv) optionally in an organic solvent (such as DMF, EtOH or MeCN, preferably DMF) is optionally added an organic base (such as TEA, DIEA, or DBU, preferably DBU, 1-5 equiv, preferably 1-2 equiv). The reaction mixture is heated at about 20-120° C. (preferably about 80° C.) for about 2-60 h (preferably about 12-16 h). Optionally additional Michael acceptor (0.5-30 equiv, preferably 2-5 equiv) is added followed by optional addition of an organic base (such as TEA, DIEA, or DBU, preferably DBU, 1-5 equiv, preferably 1-2 equiv) and the reaction mixture is heated at about 20-120° C. (preferably about 80° C.) for about 2-60 h (preferably about 2-5 h). In cases where the reaction does not proceed to completion as monitored by TLC, LC/MS, or HPLC, the reaction mixture is resubjected to the previously described conditions. The reaction mixture is then cooled to ambient temperature. Optionally, DCM is added and the suspension is filtered. The reaction mixture or the optional filtrate is concentrated under reduced pressure.

Illustration of General Procedure YYY

Preparation #YYY.1: 2-(3-((1S,3S,4R)-3-(3H-imidazo[1,2-a]pyrrolo[2,3-e]pyrazin-8-yl)-4-methylcyclopentylamino)oxetan-3-yl)acetonitrile

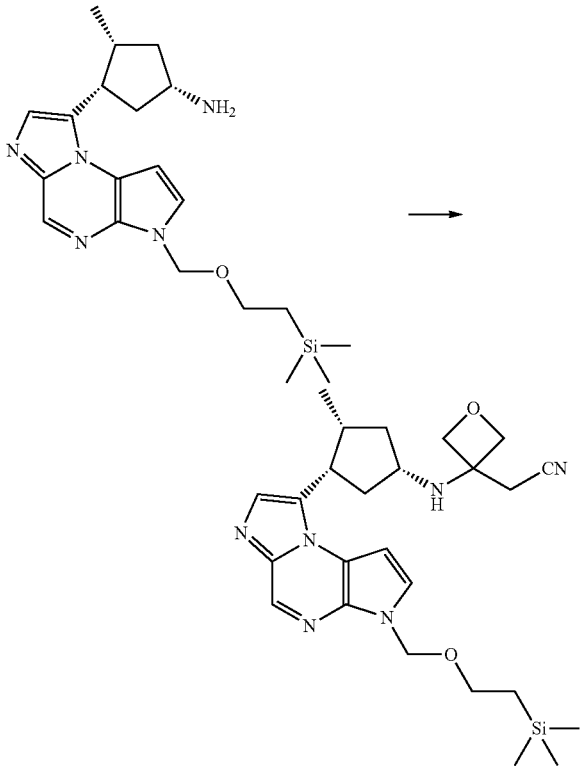

To a solution of (1S,3R,4S)-3-methyl-4-(3-((2-(trimethylsilyl)ethoxy)methyl)-3H-imidazo[1,2-a]pyrrolo[2,3-e]pyrazin-8-yl)cyclopentanamine (0.605 g, 1.569 mmol, prepared using FFFFF from Preparation #33, GGGGG with Preparation #E.1.1, KKKK with PFPAA, D with NaOH, KK, Y) in DMF (6 mL) was added 2-(oxetan-3-ylidene)acetonitrile (0.298 g, 3.14 mmol, J. Med. Chem. 2010, 53(8), 3227) and the reaction mixture was heated at about 80° C. for about 15 h. 2-(Oxetan-3-ylidene)acetonitrile (0.149 g, 1.569 mmol) was added and the reaction mixture was heated at about 80° C. for about 3.5 h. The reaction mixture was cooled to ambient temperature, concentrated in vacuo and the residue was purified by silica gel chromatography eluting with 0% to 10% MeOH in DCM. A second purification by silica gel chromatography eluting with 50% to 100% EtOAc in heptane followed by 10% MeOH in DCM yielded 2-(3-((1S,3S,4R)-3-(3H-imidazo[1,2-a]pyrrolo[2,3-e]pyrazin-8-yl)-4-methylcyclopentylamino)oxetan-3-yl)acetonitrile (0.262 g, 33%) as a sticky brown solid: LC/MS (Table 1, Method n) $R_t$=0.75 min; MS m/z 481 $(M+H)^+$.

General Procedure ZZZ: Grignard or Alkyl Lithium Addition to a Carbonyl-Containing Compound A solution of a carbonyl-containing compound (preferably 1 equiv) in an organic solvent (such as THF, 1,4-dioxane, $Et_2O$, preferably THF) was cooled to about −78° C.-50° C. (preferably about 0° C.) followed by the optional addition of an additive such as lithium chloride (1-10 equiv, preferably 4 equiv) in an organic solvent (such as THF or $Et_2O$, preferably THF). To the reaction solution is added a solution of a Grignard reagent or alkyl lithium in an organic solvent (such as THF or $Et_2O$, preferably $Et_2O$) and the resulting mixture is stirred at about −78° C.-50° C. for about 15 min-2 h (preferably about 0° C. for about 20 min) and then is optionally warmed to ambient temperature and stirred for about 2-16 h (preferably about 4 h). In cases where the reaction did not proceed to completion, an additional portion or portions of a solution of a Grignard reagent or alkyl lithium in an organic solvent (such as THF or $Et_2O$, preferably $Et_2O$) was added to drive the reaction to completion. The reaction mixture is then optionally cooled to about −78° C.-0° C. (preferably about −78° C.) and is quenched with the addition of a saturated aqueous solution of $NH_4Cl$. The mixture is optionally stirred for about 5-30 min (preferably about 5 min) followed by the addition of an organic solvent (such as EtOAc or DCM). The layers are separated and the organic solution is dried over anhydrous $MgSO_4$, filtered, and concentrated under reduced pressure.

Illustration of General Procedure ZZZ

Example #ZZZ.1

1-((1R,3R,4S)-3-ethyl-4-(6H-pyrrolo[2,3-e][1,2,4]triazolo[4,3-a]pyrazin-1-yl)cyclopentyl)-2-methylpropan-2-ol

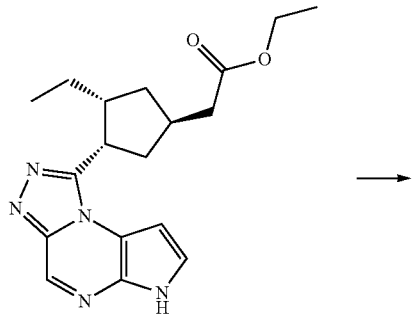

-continued

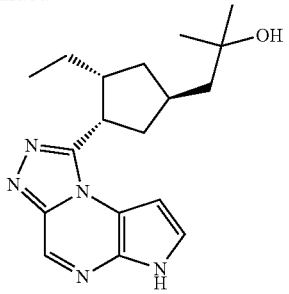

To a solution of ethyl 2-((1R,3R,4S)-3-ethyl-4-(6H-pyrrolo[2,3-e][1,2,4]triazolo[4,3-a]pyrazin-1-yl)cyclopentyl) acetate (0.166 g, 0.486 mmol, Example #38, Step H) in THF (4 mL) at about 0° C. was added lithium chloride in THF (0.5 M, 3.9 mL) followed by methylmagnesium bromide in $Et_2O$ (3.0 M, 0.65 mL). After about 20 min the reaction mixture was allowed to warm to rt. After about 4 h the reaction mixture was cooled to about −78° C. and saturated aqueous $NH_4Cl$ (about 5 mL) was added. After about 5 min the reaction mixture was allowed to warm to rt and EtOAc (about 10 mL) was added. The layers were separated and the organic solution was dried over anhydrous $MgSO_4$, filtered, and concentrated under reduced pressure. The crude material was purified by silica gel chromatography eluting with EtOAc/MeOH to provide 1-((1R,3R,4S)-3-ethyl-4-(6H-pyrrolo[2,3-e][1,2,4]triazolo[4,3-a]pyrazin-1-yl)cyclopentyl)-2-methylpropan-2-ol (0.118 g, 74%) as a foam: LC/MS (Table 1, Method a) $R_t$=1.64 min; MS m/z 328 $(M+H)^+$.

General Procedure AAAA: Deprotection of a Sulfonamide with DBU

To a flask containing a sulfonamide, for example, a sulfonyl-protected pyrrole, (preferably 1 equiv) in an organic solvent (such as 1,4-dioxane, MeOH, or THF/MeOH, MeCN, preferably MeCN) is added DBU (1-30 equiv, preferably 5-6 equiv). The mixture is stirred at about 20-100° C. (preferably about rt) for about 1-72 h (preferably about 24 h). In cases where the reaction does not proceed to completion as monitored by TLC, LC/MS, or HPLC the reaction is heated at about 30-100° C. (preferably about 45° C.) for about 1-48 h (preferably about 12-24 h). In cases where the reaction does not proceed to completion as monitored by TLC, LC/MS, or HPLC, additional DBU (1-20 equiv, preferably 1 equiv) is added. This may be repeated if the reaction is not complete by TLC, LC/MS, or HPLC. The reaction is cooled to rt and worked up using one of the following methods. Method 1. The organic solvent is optionally removed under reduced pressure, a suitable organic solvent (such as EtOAc or DCM) and water or brine are added, the layers are separated, and the organic solution is dried over anhydrous $Na_2SO_4$ or $MgSO_4$, filtered, and concd to dryness under reduced pressure to give the target compound. Method 2. The reaction mixture is concd under reduced pressure and directly purified by one of the subsequent methods.

TABLE ZZZ.1

Examples prepared using General Procedure ZZZ with methylmagnesium bromide

| Ester | Product | Ex # | $R_t$ min (Table 1, Method) | m/z ESI+ $(M + H)^+$ |
|---|---|---|---|---|
| ethyl 2-((1S,3R,4R)-3-ethyl-4-(6H-pyrrolo[2,3-e][1,2,4]triazolo[4,3-a]pyrazin-1-yl)cyclopentyl)acetate (prepared from Preparation #BBBB.1*, using W.1, from Preparation #BBBB.1, AA, Table 2, method 3) | 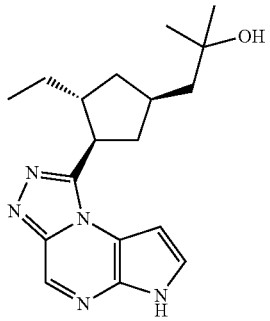 | ZZZ.1.1* | 1.63 (a) | 328 |
| ethyl 2-((lR,3R,4S)-3-ethy1-4-(3-(trifluoromethyl)-6H-imidazo[1,5-a]pyrrolo[2,3-e]pyrazin-1-yl)cyclopentyl)acetate (Example #BBBB.1.1*) | 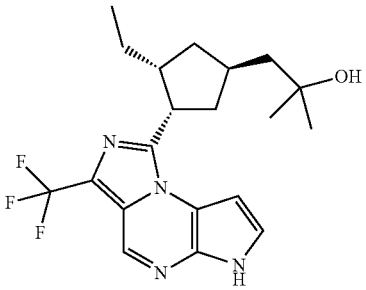 | ZZZ.1.2* | 2.33 (a) | 395 |

Illustration of General Procedure AAAA

Preparation #AAAA.1: (E/Z)-ethyl 2-((3R,4S)-3-ethyl-4-(6H-pyrrolo[2,3-e][1,2,4]triazolo[4,3-a]pyrazin-1-yl)cyclopentylidene)acetate

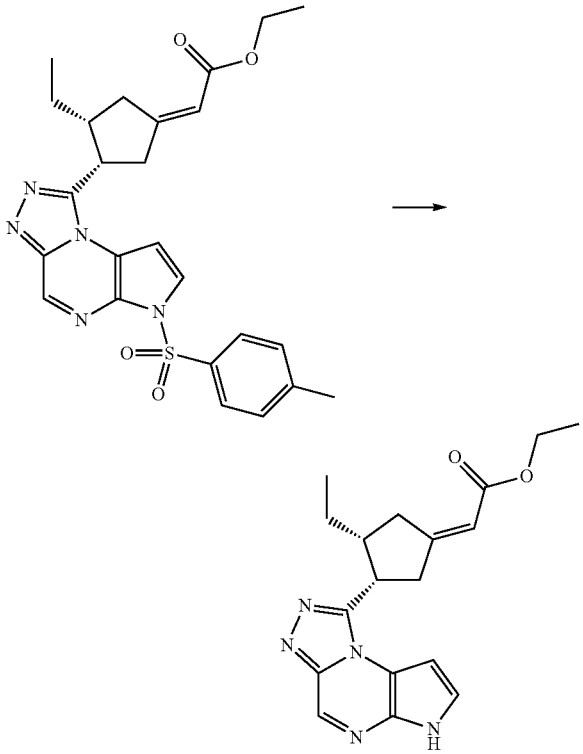

To a solution of (E/Z)-ethyl 2-((3R,4S)-3-ethyl-4-(6-tosyl-6H-pyrrolo[2,3-e][1,2,4]triazolo[4,3-a]pyrazin-1-yl)cyclopentylidene)acetate (2.00 g, 4.05 mmol, Preparation #III.1) in MeCN (20 mL) was added DBU (3.70 mL, 24.51 mmol). The reaction mixture was stirred at rt for about 16 h. The reaction mixture was heated at about 45° C. for about 24 h. DBU (1.00 mL, 6.63 mmol) was added and continued heating at about 45° C. for about 24 h. Additional DBU (1.00 mL, 6.63 mmol) was added and continued heating at about 45° C. for about 24 h. The reaction mixture was cooled to rt and the solvent was removed under reduced pressure. The crude material was purified via flash chromatography on silica gel eluting with a gradient of 0-10% MeOH in DCM to afford (E/Z)-ethyl 2-((3R,4S)-3-ethyl-4-(6H-pyrrolo[2,3-e][1,2,4]triazolo[4,3-a]pyrazin-1-yl)cyclopentylidene)acetate (0.70 g, 51%) as a brown foam: LC/MS (Table 1, Method b) $R_t$=1.90-1.95 min; MS m/z: 340 $(M+H)^+$.

General Procedure BBBB: Deprotection of a Sulfonamide with TBAF

To a solution of a sulfonamide (preferably 1 equiv) in an organic solvent (preferably THF) at about −30 to 65° C. (preferably 0° C.) is added TBAF (1-10 equiv, preferably 3 equiv). Additional TBAF (1-10 equiv, preferably 3 equiv) can be added to drive the reaction to completion. Once the reaction has preceded to an acceptable level the reaction mixture is partitioned between an organic solvent (such as DCM or EtOAc, preferably EtOAc) and an aqueous phase (such as water or brine). The organic layer is separated and optionally washed with brine, dried over anhydrous $Na_2SO_4$ or $MgSO_4$, and/or filtered prior to concentrating under reduced pressure.

Illustration of General Procedure BBBB

Preparation #BBBB.1*: Ethyl 2-03R,4S)-3-ethyl-4-(6H-pyrrolo[2,3-e][1,2,4]triazolo[4,3-a]pyrazin-1-yl)cyclopentylidene)acetate

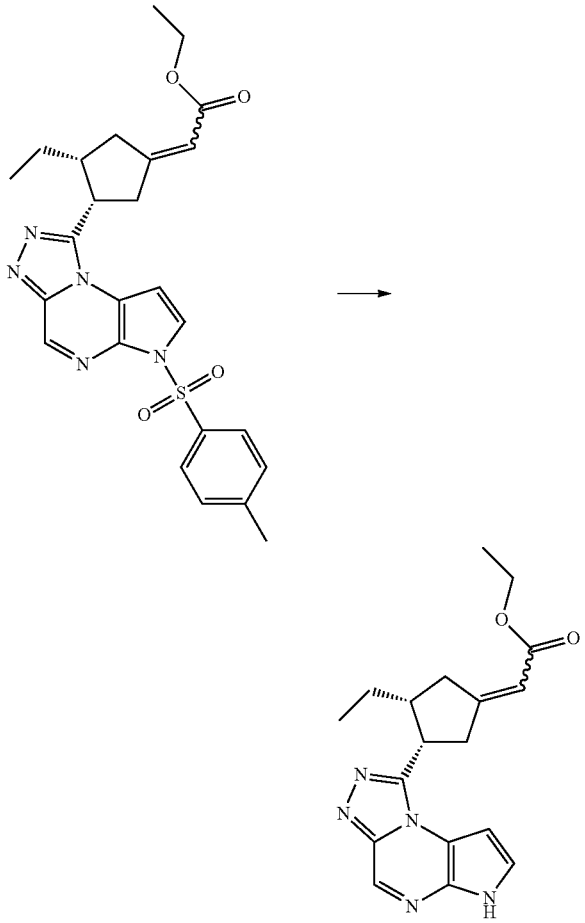

To a solution of ethyl 2-((3R,4S)-3-ethyl-4-(6-tosyl-6H-pyrrolo[2,3-e][1,2,4]triazolo [4,3-a]pyrazin-1-yl)cyclopentylidene)acetate (1.9 g, 3.85 mmol, Preparation #III.1) in THF (30 mL) at about 0° C. was added a solution of TBAF (11.55 mL, 11.55 mmol, 1M in THF). After about 30 min additional TBAF (7.70 mL, 7.70 mmol, 1M in THF) was added. After about 1 h EtOAc and brine were added to the reaction mixture. The organic layer was separated, concd in vacuo and purified by chromatography on silica gel eluting with EtOAc to provide ethyl 2-((3R,4S)-3-ethyl-4-(6H-pyrrolo[2,3-e][1,2,4]triazolo[4,3-a]pyrazin-1-yl)cyclopentylidene)acetate (1.3 g, 100%) as a mixture of stereoisomers. LC/MS (Table 1, Method a) $R_t$=1.86 and 1.90 min.; MS m/z: 340 $(M+H)^+$.

TABLE BBBB.1

Examples prepared using General Procedure BBBB

| Sulfonamide | Product | Example # | R, min (Table 1, Method) | m/z ESI+ $(M + H)^+$ |
|---|---|---|---|---|
| ethyl 2-((1R,3R,4S)-3-ethyl-4-(6-tosyl-3-(trifluoromethyl)-6H-imidazo[1,5-a]pyrrolo[2,3-e]pyrazin-1-yl)cyclopentyl)acetate (prepared using H with Preparation #32 Preparation #31 HATU, and DIEA, and OO) | 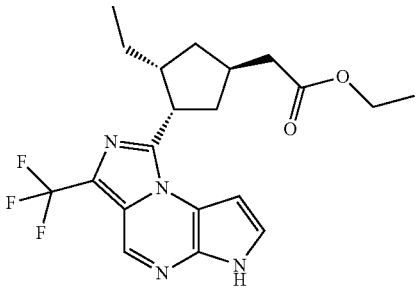 | BBBB.1.1 | 2.62 (a) | 409 |
| N-((1S,3R,4S)-3-ethyl-4-(6-tosyl-3-(2,2,2-trifluoroethyl)-6H-imidazo[1,5-a]pyrrolo[2,3-e]pyrazin-1-yl)cyclopentyl)cyclopropanesulfonamide (prepared using H with Preparation #30 and Preparation #Z.1, and OO) | 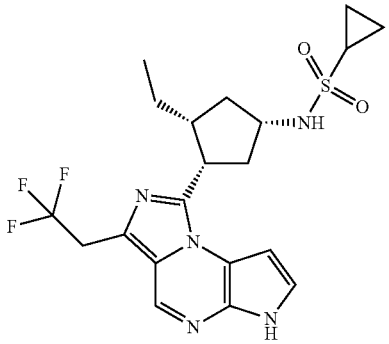 | BBBB.1.X | 2.04 (a) | 456 |

General Procedure CCCC: Deprotection of a Sulfonamide with KCN

To a flask containing a sulfonamide, for example, a sulfonyl-protected pyrrole, (preferably 1 equiv) in an organic solvent (such as 1,4-dioxane, MeOH, or THF, preferably MeOH) is added KCN (1-3equiv, preferably 2.2 equiv) as a solution in an organic solvent (such as 1,4-dioxane, MeOH, or THF, preferably MeOH) or as a solid. The mixture is stirred at ambient temperature for about 1-18 h (preferably about 16 h). The organic solvent is optionally removed under reduced pressure and a suitable organic solvent (such as EtOAc or DCM) and water are added. The layers are separated and the organic solution is dried over anhydrous $Na_2SO_4$ or $MgSO_4$, filtered or decanted, and concd to dryness under reduced pressure and directly purified by one of the subsequent methods.

Illustration of General Procedure CCCC

Preparation #CCCC.1: 3-ethyl-4-(6H-pyrrolo[2,3-e][1,2,4]triazolo[4,3-a]pyrazin-1-yl)cyclopentyl benzoate

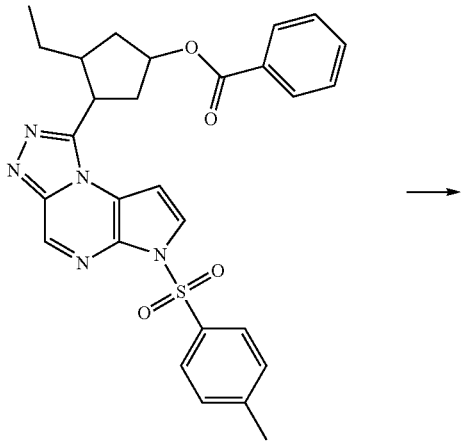

-continued

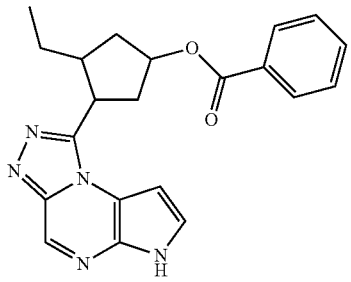

To a mixture of 3-ethyl-4-(6-tosyl-6H-pyrrolo[2,3-e][1,2,4]triazolo[4,3-a]pyrazin-1-yl)cyclopentyl benzoate (5.00 g, 7.84 mmol, prepared using II from Example #4 Step J with benzoic acid and B) in MeOH (16 mL) was added a solution of potassium cyanide (0.74 mL, 17 mmol) in MeOH (16 mL). The reaction was stirred at ambient temperature for about 16 h. The reaction mixture was concd under reduced pressure to afford a residue. The residue was partitioned between water (20 mL) and DCM (20 mL). The layers were separated and the aqueous layer was extracted with DCM (3×10 mL). The extract was then washed with saturated aqueous $NaHCO_3$, dried over anhydrous $MgSO_4$, filtered, and concd under reduced pressure to afford a crude oil. The crude material was purified by silica gel chromatography eluting with a gradient of 0-10% MeOH in DCM to 3-ethyl-4-(6H-pyrrolo[2,3-e][1,2,4]triazolo[4,3-a]pyrazin-1-yl)cyclopentyl benzoate (2.30 g, 78%) as a solid. LC/MS (Table 1, Method a) $R_t$=2.08 min; MS m/z: 376 $(M+H)^+$.

General Procedure DDDD: Formation of an Oxadiazole

To a solution of a carboxylic ester (preferably 1 equiv) in an organic solvent (such as DMF, NMP, THF, MeOH/toluene, p-Dioxane, or MeOH, preferably MeOH/toluene) is added a base (such as $K_2CO_3$ or $Cs_2CO_3$, 2-10 equiv, preferably 2-4 equiv) and an acetimidamide (1-20 equiv, preferably 4-10 equiv). The reaction mixture is heated at about 100-160° C. (preferably about 130° C.) for about 15 min to 2 h (preferably about 45 min) under microwave irradiation. In cases where the reaction does not proceed to completion as monitored by TLC, LC/MS, or HPLC, additional acetimidamide (1-20 equiv, preferably 3-10 equiv) and/or base (such as $K_2CO_3$ or $Cs_2CO_3$, 2-10 equiv, preferably 2-4 equiv) may be added. The reaction mixture is heated at about 100-160° C. (preferably about 130-140° C.) for about 15 min to 2 h (preferably about 45 min) under microwave irradiation. The additional heating with or without addition of acetimidamide and/or base is optionally repeated. Alternatively, a solution of an acetimidamide (1-20 equiv, preferably 4-10 equiv) in an organic solvent (such as THF or p-dioxane, preferably THF) is added a base (such as NaH, 1-5 equiv, preferably 3 equiv). After about 0.5-2 h (preferably about 0.5 h), a carboxylic ester (preferably 1 equiv) is added. After about 0.25-3 h (preferably about 0.25 h), the reaction mixture is heated at about 40-120° C. (preferably about 70° C.) for about 1-48 h (preferably about 4 h). If the reaction is heated the reaction mixture is cooled to ambient temperature. The reaction is worked up using one of the following methods. Method 1. The organic solvent is optionally removed under reduced pressure, a suitable organic solvent (such as EtOAc or DCM) and water, brine or saturated $NH_4Cl$ are added, the layers are separated. The organic solution is washed with water, brine or saturated $NH_4Cl$ and the organic solution is dried over anhydrous $Na_2SO_4$ or $MgSO_4$, filtered, and concd to dryness under reduced pressure to give the target compound. Method 2. The reaction mixture is concd under reduced pressure and directly purified.

TABLE CCCC.1

Examples prepared using General Procedure D with KCN

| Sulfonamide | Product | Ex # | $R_t$ min (Table 1, Method) | m/z ESI+ $(M + H)^+$ |
|---|---|---|---|---|
| N-((1S,3R,4S)-3-ethyl-4-(6-tosyl-6H-pyrrolo[2,3-e][1,2,4]triazolo[4,3-a]pyrazin-1-yl)cyclopentyl)-N-((5-methylisoxazol-3-yl)methyl)oxetan-3-amine (prepared using X from Example #8 Step M with oxetan-3-one [PharmaBlock], and X with 5-methylisoxazole-3-carbaldehyde) | 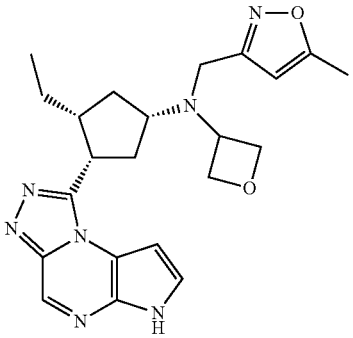 | CCCC.1.1* | 1.57 (a) | 422 |

Illustration of General Procedure DDDD

Preparation #DDDD.1: (5-(((1S,3R,4S)-3-ethyl-4-(6H-pyrrolo[2,3-e][1,2,4]triazolo[4,3-a]pyrazin-1-yl)cyclopentyl)methyl)-1,2,4-oxadiazol-3-yl)methanol

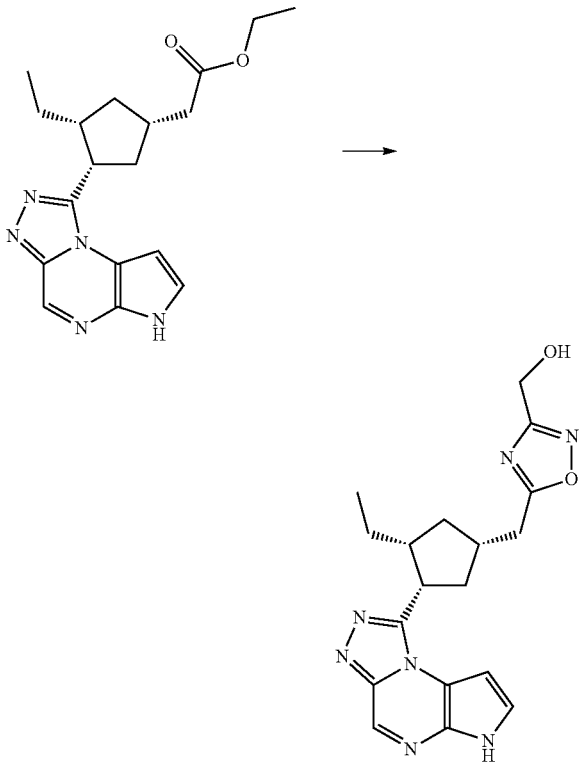

To a solution of ethyl 2-((1S,3R,4S)-3-ethyl-4-(6H-pyrrolo[2,3-e][1,2,4]triazolo[4,3-a]pyrazin-1-yl)cyclopentyl) acetate (0.195 g, 0.571 mmol, Example #38, Step H) in toluene (1.00 mL) and MeOH (1.000 mL) were added (Z)-N',2-dihydroxyacetimidamide (0.515 g, 5.71 mmol, Tyger) and $K_2CO_3$ (0.195 g, 1.41 mmol). The reaction was heated in a CEM microwave at about 130° C. twice at about 45 min each (250 psi maximum pressure, 1 min ramp, 300 max watts). (Z)-N',2-dihydroxy acetimidamide (0.200 g, 2.22 mmol, Tyger) was added and the reaction mixture was heated in a CEM microwave at about 140° C. for about 45 min (250 psi maximum pressure, 1 min ramp, 300 max watts). (Z)-N',2-dihydroxyacetimidamide (0.200 g, 2.22 mmol, Tyger) and $K_2CO_3$ (0.100 g, 0.725 mmol) were added, and the reaction mixture was heated in a CEM microwave at about 140° C. for about 45 min (250 psi maximum pressure, 1 min ramp, 300 max watts). The solvent was removed under reduced pressure. The residue was dissolved with water (20 mL) and EtOAc (50 mL). The aqueous layer was extracted with EtOAc (5×50 mL). The combined organic layers were dried over anhydrous $MgSO_4$, filtered, and concd to give a yellow residue. The crude material was purified via flash chromatography on silica gel eluting with a gradient of 0-10% MeOH in EtOAc to afford (5-(((1S,3R,4S)-3-ethyl-4-(6H-pyrrolo[2,3-e][1,2,4]triazolo[4,3-a]pyrazin-1-yl)cyclopentyl)methyl)-1,2,4-oxadiazol-3-yl)methanol (0.042 g, 20%) as a yellow solid: LC/MS (Table 1, Method a) $R_t$=1.67 min; MS m/z: 368 $(M+H)^+$.

TABLE DDDD.1

Examples prepared using General Procedure DDDD with (Z)-N'-hydroxy-methoxyacetimidamide

| Ester | Product | Ex # | $R_t$ min (Table 1, Method) | m/z ESI+ $(M + H)^+$ |
|---|---|---|---|---|
| ethyl 2-((1R,3R,4S)-3-ethyl-4-(6-tosyl-3-(trifluoromethyl)-6H-imidazo[1,5-a]pyrrolo[2,3-e]pyrazin-1-yl)cyclopentyl)acetate (Example #BBBB.1.1*) | 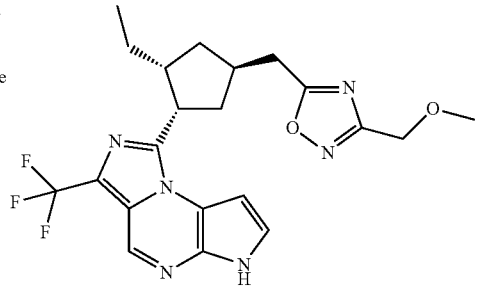 | DDDD.1.1* | 2.41 (a) | 449 |

General Procedure EEEE: Formation of a Urea Using Phosgene

To a solution of phosgene (1-1.5 equiv, preferably 1.2 equiv, 20% solution in toluene) in an organic solution (such as DCM), under an inert atmosphere at about 0° C. is added solution or slurry of an amine or amine salt (preferably 1 equiv) in an organic solvent (such as DCM, THF, or 1,4-dioxane, preferably DCM) and an organic base (such as TEA, DIEA, pyridine, 1-10 equiv, preferably 5 equiv, preferably TEA). After about 0.5-24 h (preferably about 40 min) at about 0° C., a second amine or amine salt (1-10 equiv, preferably 1-3 equiv) is added neat or as a solution or slurry in an organic solvent (such as DCM, THF, or DMF, preferably DCM) and an organic base (such as TEA, DIEA, pyridine, 1-10 equiv, preferably 5 equiv, preferably TEA). The reaction mixture is stirred at about 0° C. for 0.5-24 h (preferably 45 min). An aqueous base (such as aqueous $NH_4OH$ or saturated aqueous $Na_2CO_3$) is added with the optional addition of an organic solvent such as EtOAc or DCM. The aqueous layer is then optionally extracted with additional organic solvent (such as EtOAc or DCM). The combined organic layers may optionally be washed with water or brine and concd in vacuo or dried over anhydrous $Na_2SO_4$ or $MgSO_4$ and then decanted or filtered prior to concentrating under reduced pressure to give the target compound.

Illustration of General Procedure EEEE

Preparation #EEEE.1: (3,3-difluoroazetidin-1-yl)((cis)-3-ethyl-4-(6-tosyl-6H-pyrrolo[2,3-e][1,2,4]triazolo[4,3-a]pyrazin-1-yl)pyrrolidin-1-yl)methanone

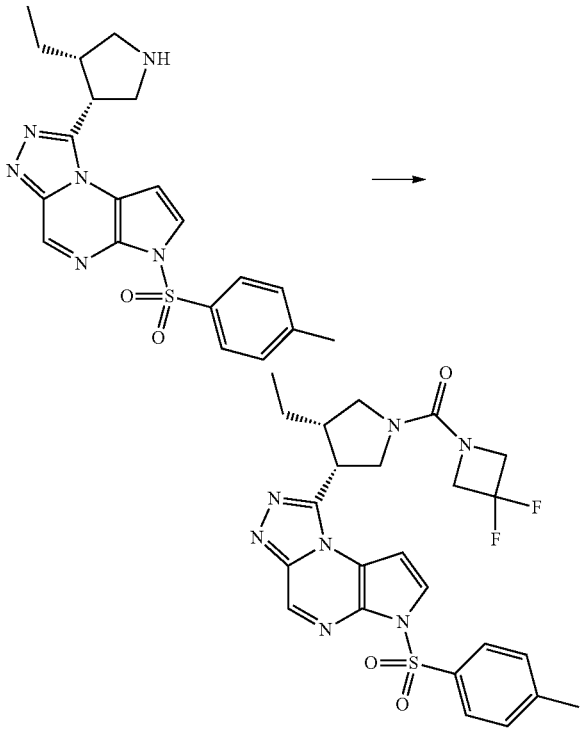

To a solution of phosgene (0.400 mL, 0.761 mmol, 20% in toluene) in DCM (1.5 mL) under a balloon of $N_2$ at about 0° C. were added a solution of 1-((cis)-4-ethylpyrrolidin-3-yl)-6-tosyl-6H-pyrrolo[2,3-e][1,2,4]triazolo[4,3-a]pyrazine (0.250 g, 0.609 mmol, Example #36, step F) in DCM (5.0 mL) and TEA (0.430 mL, 3.08 mmol). After about 40 min, at about 0° C., a solution of 3,3-difluoroazetidine•hydrochloride (0.095 g, 0.731 mmol, Matrix) and TEA (0.430 mL, 3.08 mmol) in DCM (5.0 mL) were added dropwise and stirred at about 0° C. for about 45 min. Saturated aqueous sodium bicarbonate (2 mL) was added and the layers were separated. The aqueous layer was extracted with DCM (2×30 mL). The combined organic layers were washed with water (25 mL), dried over anhydrous $MgSO_4$, filtered, and concd to give a brown residue. The crude material was purified via flash chromatography on silica gel eluting with a gradient of 0-10% MeOH in DCM to afford (3,3-difluoroazetidin-1-yl)((cis)-3-ethyl-4-(6-tosyl-6H-pyrrolo[2,3-e][1,2,4]triazolo[4,3-a]pyrazin-1-yl)pyrrolidin-1-yl)methanone (0.208 g, 65%) as a brown residue: LC/MS (Table 1, Method a) $R_t$=2.17 min; MS m/z: 530 $(M+H)^+$.

General Procedure FFFF: Formation of an Amide from an Ester

To a pressure reactor charged with an ester (preferably 1 equiv) is added a solution of ammonia in a protic solvent (such as ethanol, methanol or water, preferably methanol). The reactor is sealed and the temperature is maintained at about ambient temperature to about 200° C. (preferably about 85° C.). After about 1 to 10 days (preferably about 2 days) the reaction mixture is cooled to rt and the reaction mixture is concd in vacuo to provide the crude amide.

Illustration of General Procedure FFFF

Example #FFFF.1

4-(3-ethyl-4-(6H-pyrrolo[2,3-e][1,2,4]triazolo[4,3-a]pyrazin-1-yl)cyclopentyl)butanamide

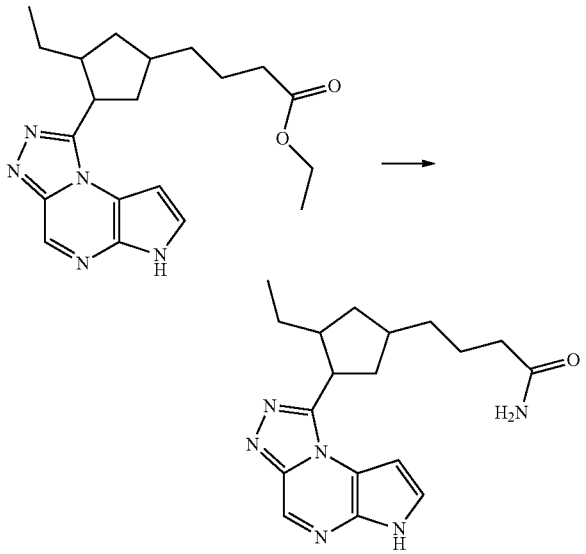

Ethyl 4-(3-ethyl-4-(6H-pyrrolo[2,3-e][1,2,4]triazolo[4,3-a]pyrazin-1-yl)cyclopentyl)butanoate (0.080 g, 0.217 mmol, prepared using III from Preparation #25 and (E)-ethyl 4-(diethoxyphosphoryl)but-2-enoate, W) and ammonia (7 N in MeOH, 6.2 mL, 43.3 mmol). The reaction vessel was sealed and heated to about 85° C. After about 2 days the tube was cooled to rt and the reaction mixture was concd in vacuo to provide 4-((3R,4S)-3-ethyl-4-(6H-pyrrolo[2,3-e][1,2,4]triazolo[4,3-a]pyrazin-1-yl)cyclopentyl)butanamide (0.074 g, 100%) as a solid which was used without further purification: LC/MS (Table 1, Method c) $R_t$=0.50 min.; MS m/z: 341 $(M+H)^+$.

General Procedure GGGG: Formation of a Nitrile from a Primary Amide

To solution of a primary amide (preferably 1 equiv) in an organic solvent (such as DCM, THF, DCE, preferably DCM) is added a dehydrating reagent (such as TFAA or $SOCl_2$, preferably TFAA) (1-20 equiv, preferably 10 equiv). After about 1-20 h (preferably about 4 h) at 10 to 60° C. (preferably ambient temperature) the reaction mixture is concd in vacuo.

Illustration of General Procedure GGGG

Example #GGGG.1

4-((1S,3R,4S)-3-ethyl-4-(6H-pyrrolo[2,3-e][1,2,4]triazolo[4,3-a]pyrazin-1-yl)cyclopentyl)butanenitrile and 4-((1R,3R,4S)-3-ethyl-4-(6H-pyrrolo[2,3-e][1,2,4]triazolo[4,3-a]pyrazin-1-yl)cyclopentyl)butanenitrile

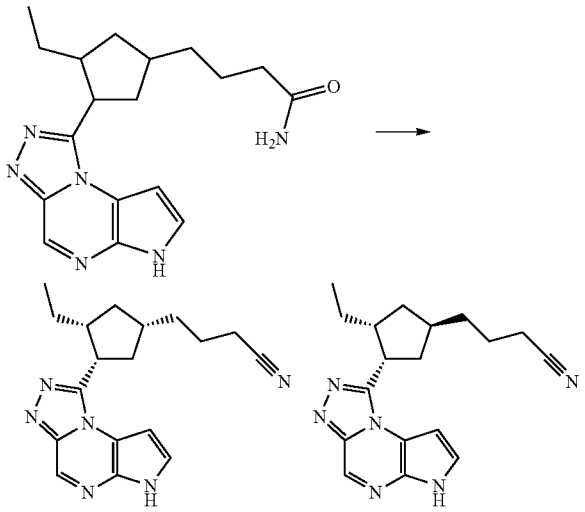

To a solution of 4-(3-ethyl-4-(6H-pyrrolo[2,3-e][1,2,4]triazolo[4,3-a]pyrazin-1-yl)cyclopentyl)butanamide (0.090 g, 0.264 mmol, Example #FFFF.1) in DCM (3 mL) was added TFAA (0.373 mL, 2.64 mmol). After about 4 h at ambient temperature the reaction mixture was concd in vacuo and purified by chiral preparative HPLC (Table 2, Method 33) to provide 4-((1S,3R,4S)-3-ethyl-4-(6H-pyrrolo[2,3-e][1,2,4]triazolo[4,3-a]pyrazin-1-yl)cyclopentyl)butanenitrile (0.013 g, 15%) (rt=16.1 min, or =neg) LC/MS (Table 1, Method a) $R_t$=1.79 min; MS m/z: 323 $(M+H)^+$ and 4-((1R,3R,4S)-3-ethyl-4-(6H-pyrrolo[2,3-e][1,2,4]triazolo[4,3-a]pyrazin-1-yl)cyclopentyl)butanenitrile (0.010 g, 12%) (rt=13.7 min, or =neg) LC/MS (Table 1, Method a) $R_t$=1.79 min; MS m/z: 323 $(M+H)^+$ as solids.

General Procedure HHHH: O-Alkylation with KOH or NaOH and TBAB

To an alcohol (preferably 1 equiv) is added an aqueous base (such as 50% w/v KOH or 50% w/v NaOH, 1-60 equiv, preferably 11-24 equiv) and a solvent (such as 1,4-dioxane or THF, preferably 1,4-dioxane) and the reaction mixture is heated to about 45-100° C. (preferably about 70° C.). To the reaction mixture is added an alkyl halide or mesylate (1-30 equiv, preferably 8-16 equiv), and TBAB (0.05-2 equiv, preferably 0.08-1.6 equiv) and stirred for about 8-48 h (preferably about 24 h). Alternatively, the order of addition may be reversed. In cases where the reaction does not proceed to completion as monitored by TLC, LC/MS, or HPLC, the reaction may be re-subjected to heating at about 25-100° C. (preferably about 70° C.) for about 2-48 h (preferably about 8-24 h) with the optional addition of more base (such as 50% w/w aqueous KOH or 50% w/w aqueous NaOH, 1-60 equiv, preferably 11-24 equiv), solvent (such as 1,4-dioxane or THF preferably 1,4-dioxane), alkyl halide or mesylate (1-30 equiv, preferably 8-16 equiv), and/or TBAB (0.05-2 equiv, preferably 0.08-1.5 equiv). This process is repeated until the reaction proceeds no further. After cooling to ambient temperature, the reaction is worked up using one of the following methods. Method 1: An organic solvent such as EtOAc or DCM is added with the optional addition of water or brine and the layers are separated. The aqueous layer is then optionally extracted with additional organic solvent such as EtOAc or DCM. The combined organic layers are optionally washed with brine or water, dried over anhydrous $MgSO_4$ or $Na_2SO_4$, filtered or decanted, and concd under reduced pressure. Method 2: A reaction mixture containing a precipitate may be filtered. To the filtrate is added an organic solvent such as EtOAc or DCM with the optional addition of water or brine and the layers are separated. The aqueous layer is then optionally extracted with additional organic solvent such as EtOAc or DCM. The combined organic layers are optionally washed with brine or water, dried over anhydrous $MgSO_4$ or $Na_2SO_4$, filtered or decanted, and concd under reduced pressure.

Illustration of General Procedure HHHH

Preparation #HHHH.1: 3-(((1R,3R,4S)-3-ethyl-4-(6-((2-(trimethylsilyl)ethoxy)methyl)-6H-pyrrolo[2,3-e][1,2,4]triazolo[4,3-a]pyrazin-1-yl)cyclopentyloxy)methyl)-5-methylisoxazole

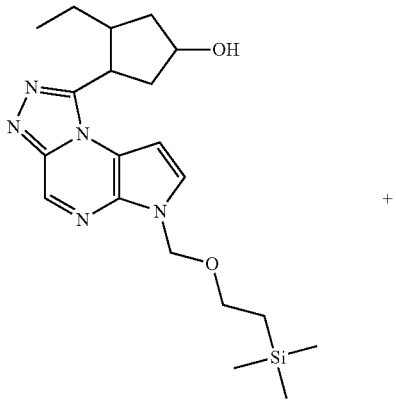

-continued

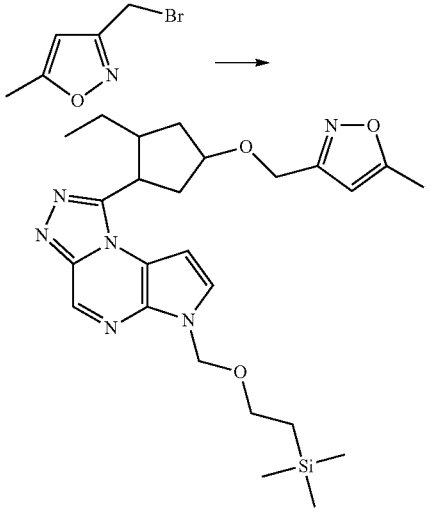

A mixture of 3-ethyl-4-(6-((2-(trimethylsilyl)ethoxy)methyl)-6H-pyrrolo[2,3-e][1,2,4]triazolo[4,3-a]pyrazin-1-yl)cyclopentanol (0.072 g, 0.179 mmol, Example #35, Step H), KOH aqueous (50% w/v 0.118 g, 2.10 mmol) and 1,4-dioxane (0.1 mL) was heated to about 70° C. To the reaction mixture was added 3-(bromomethyl)-5-methylisoxazole (0.063 g, 0.359 mmol, Maybridge) and TBAB (0.004 g, 0.01 mmol) and the reaction mixture was stirred for about 24 h. To the reaction mixture was added 3-(bromomethyl)-5-methylisoxazole (0.063 g, 0.36 mmol, Maybridge) and aqueous KOH (50% w/v 0.118 g, 2.10 mmol) and stirring was continued for about 24 h. The reaction was cooled to ambient temperature and EtOAc (10 mL) and water (5 mL) were added. The layers were separated and the aqueous layer was extracted with EtOAc (10 mL). The combined organic layers were dried over anhydrous $MgSO_4$, filtered, and concd under reduced pressure. The crude material was purified by silica gel chromatography eluting with a gradient of 0-5% MeOH in DCM to give 3-(((1R,3R,4S)-3-ethyl-4-(6-((2-(trimethylsilyl)ethoxy)methyl)-6H-pyrrolo[2,3-e][1,2,4]triazolo[4,3-a]pyrazin-1-yl)cyclopentyloxy)methyl)-5-methylisoxazole (0.064 g, 72%): LC/MS (Table 1, Method b) $R_t$=2.58 min; MS m/z: 497 $(M+H)^+$.

General Procedure IIII: Formation of a Mesylate

To a solution of an alcohol (preferably 1 equiv) in an organic solvent such as DCM an organic base such as TEA or Hunig's base (1-4 equiv, preferably 2 equiv) is added at about 0-40° C. (preferably room temperature) followed by a dropwise addition at this temperature of mesyl chloride (1-2 equiv preferably 1.1 equiv). In cases where the reaction mixture is cooled to below rt, it is stirred at this temperature for about 1-3 h (preferably about 2 h) and then optionally warmed up to ambient temperature while stirring overnight. The product could be worked up by one of the following methods. 1) The reaction mixture is concentrated. 2) The reaction mixture is washed with saturated aqueous $NaHCO_3$ and brine, dried over anhydrous $MgSO_4$, filtered, and concentrated.

Illustration of General Procedure IIII

Preparation #IIII.1: 3-ethyl-4-(6-((2-(trimethylsilyl)ethoxy)methyl)-6H-pyrrolo[2,3-e][1,2,4]triazolo[4,3-a]pyrazin-1-yl)cyclopentyl methanesulfonate

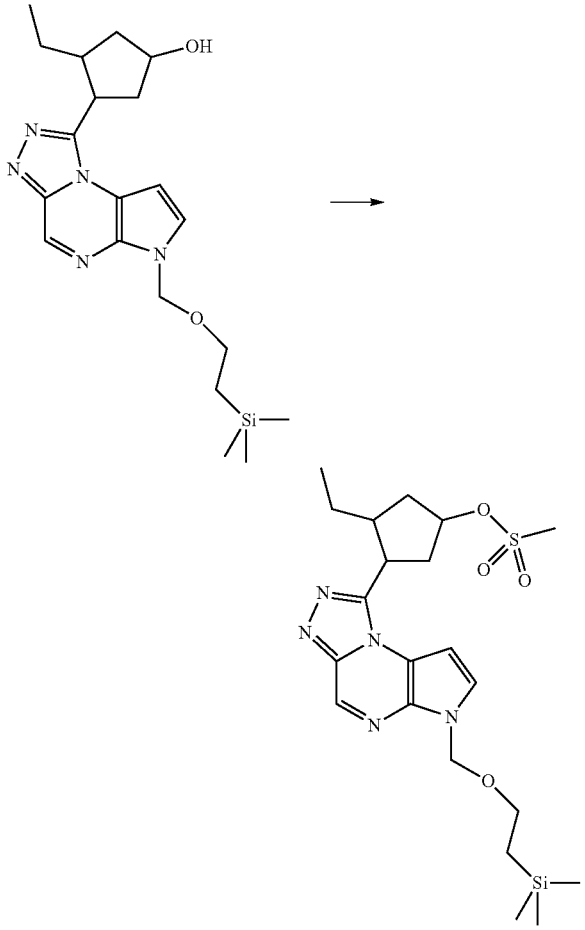

Mesyl chloride (0.067 mL, 0.866 mmol) was added dropwise to a solution of 3-ethyl-4-(6-((2-(trimethylsilyl)ethoxy)methyl)-6H-pyrrolo[2,3-e][1,2,4]triazolo[4,3-a]pyrazin-1-yl)cyclopentanone (0.316 g, 0.787 mmol, Example #35 Step H) and TEA (0.219 mL, 1.57 mmol) in DCM (8 mL), and the reaction mixture was stirred at rt overnight. The solvent was removed under reduced pressure and the residue purified by silica gel column chromatography (0 to 60% EtOAc in DCM) to yield 3-ethyl-4-(6-((2-(trimethylsilyl)ethoxy)methyl)-6H-pyrrolo[2,3-e][1,2,4]triazolo[4,3-a]pyrazin-1-yl)cyclopentyl methanesulfonate (0.29 g, 77%) as a white amorphous solid: LC/MS (Table 1, Method a) $R_t$=2.53 min; MS m/z 480 $(M+H)^+$.

General Procedure JJJJ: Displacement of an Alkyl Mesylate, Tosylate, or Halide with a Nucleophile A round bottom flask is charged with an alkyl mesylate, tosylate, or halide (preferably 1 equiv) and an organic solvent such as DMF, DMA, NMP or DMSO (preferably DMF). To the reaction flask is added the sodium or potassium salt (preferably the sodium salt) of the nucleophile such as, but not limited to, an azide, cyanide, thioacetate, pyrazole and triazole (1-10 equiv, preferably 5.0 equiv) in portions. When the nucleophile is not already the sodium or potassium salt, a base such as 60% NaH in mineral oil (1-10 equiv, preferably an equimolar amount to the nucleophile used) is added. The mixture is stirred at about 10-100° C.

(preferably ambient temperature) for about 1-24 h (preferably about 20 h). If the reaction does not go to completion as monitored by HPLC, LC/MS, or TLC, additional nucleophile and/or base is used (5-300% of the original amount used, preferably 10%) may be added and the reaction is continued for about 0.5-24 h (preferably about 2 h). The reaction is partitioned between an organic solvent such as EtOAc or DCM (preferably EtOAc) and water. The layers are separated and the organic solution is dried over anhydrous $MgSO_4$ or $Na_2SO_4$, filtered, and concentrated under reduced pressure to provide the target compound.

Illustration of General Procedure JJJJ

Preparation #JJJJ.1: 1-((1S,2R,4R)-4-azido -2-ethylcyclopentyl)-6-((2-(trimethylsilyl)ethoxy)methyl)-6H-pyrrolo[2,3-e][1,2,4]triazolo[4,3-a]pyrazine

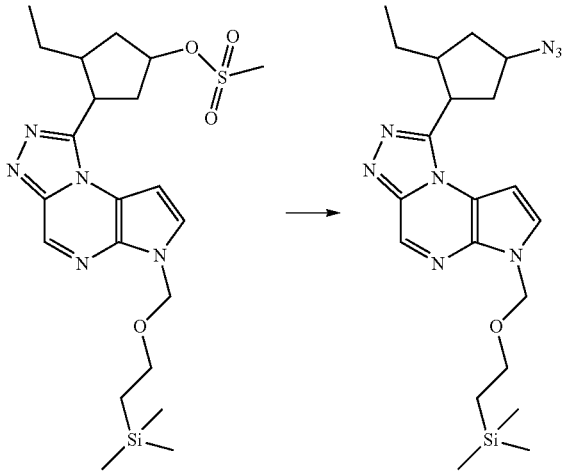

A round bottom flask was charged with 3-ethyl-4-(6-((2-(trimethylsilyl)ethoxy)methyl)-6H-pyrrolo[2,3-e][1,2,4]triazolo[4,3-a]pyrazin-1-yl)cyclopentyl methanesulfonate (0.83 g, 1.7 mmol, Preparation #IIII.1) and DMF (7.0 mL). To the reaction flask was added sodium azide (0.56 g, 8.6 mmol). The mixture was stirred at ambient temperature for about 20 h. Another portion of sodium azide (0.056 g, 0.86 mmol) was added and the reaction was stirred for about 2 h. The reaction was partitioned between EtOAc (20 mL) and water (20 mL). The layers were separated and the organic solution was dried over anhydrous MgSO4, filtered, and concentrated under reduced pressure to give 1-(-4-azido-2-ethylcyclopentyl)-6-((2-(trimethylsilyl)ethoxy)methyl)-6H-pyrrolo[2,3-e][1,2,4]triazolo[4,3-a]pyrazine (0.65 g, 88%) as a brown oil: LC/MS (Table 1, Method b) $R_t$=2.85 min; MS m/z: 427 $(M+H)^+$.

General Procedure KKKK: Cyclization of a Ketone Using TFAA or PFPAA

To a ketone (preferably 1 equiv) optionally dissolved in an organic solvent such as acetonitrile or DCM (preferably acetonitrile) is added TFA/TFAA (2-100 equiv/10-60 equiv, preferably 2 equiv/10 equiv) or PFPAA (2-30 equiv, preferably 10 equiv) or 2,2,3,3,3-pentafluoropropanoic acid/PFPAA (1-10 equiv/5-50 equiv, preferably 2 equiv/10 equiv) at about 0° C. to 50° C. (preferably ambient temperature). The reaction is warmed and stirred at about 0° C. to about 80° C. (preferably about 60° C.) for about 0.5-48 h (preferably about 2-4 h). Additional TFAA or PFPAA (2-10 equiv) can be added to complete the reaction. MeOH is optionally added to quench the reaction. The reaction mixture is concentrated under reduced pressure. Alternatively, the crude mixture may be optionally concentrated before partitioning between an aqueous solution of an inorganic base (for example aqueous $NaHCO_3$ or $K_2CO_3$) and an organic solvent (for example EtOAc or DCM). The layers are separated and the aqueous layer is extracted further with organic solvent (such as EtOAc and/or DCM). The combined organic layers are optionally washed with brine, dried over anhydrous $MgSO_4$ or $Na_2SO_4$, filtered, and concentrated to dryness under reduced pressure.

Illustration of General Procedure KKKK

Preparation #KKKK.1: 3-Tosyl-8-(2-tosyl-2-azaspiro[3.3]heptan-6-yl)-3H-imidazo[1,2-a]pyrrolo[2,3-e]pyrazine

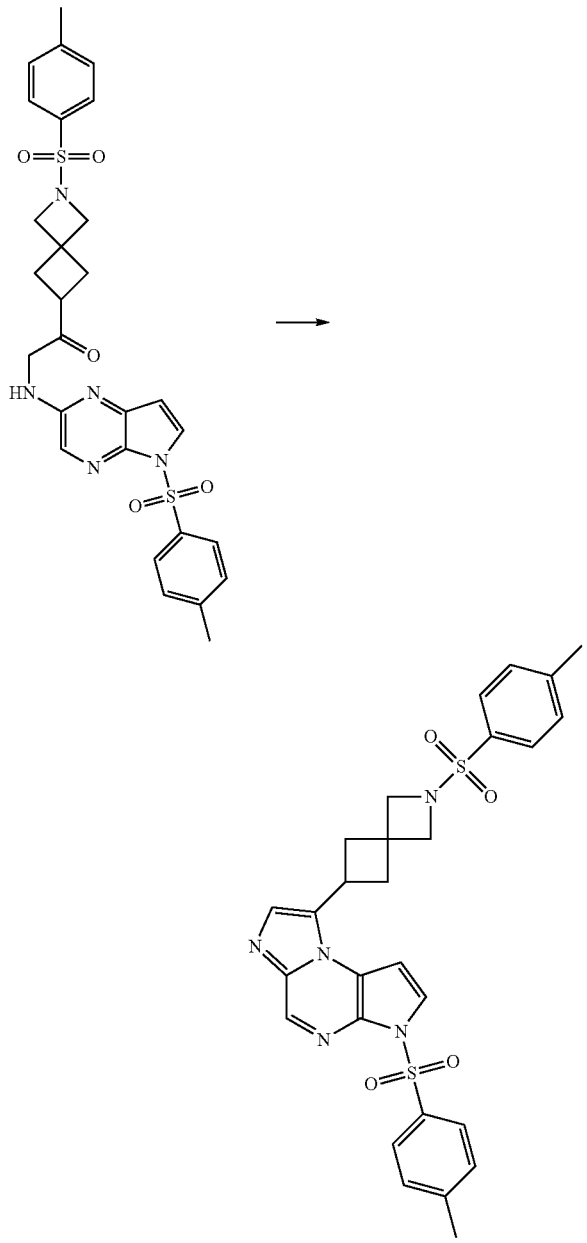

To a solution of 2-(5-tosyl-5H-pyrrolo[2,3-b]pyrazin-2-ylamino)-1-(2-tosyl-2-azaspiro[3.3]heptan-6-yl)ethanone (0.631 g, 1.089 mmol, prepared using R with 2-tosyl-2-azaspiro[3.3]heptane-6-carboxylic acid [prepared as described in J. Org. Chem, 2010, 75, 5941] and trimethylsilyl diazomethane, S with Example #3 Step E, E with TFA) in MeCN (5 mL) was added PFPAA (2.15 mL, 10.9 mmol). The mixture was heated at about 60° C. for about 2 h. The reaction mixture was partitioned between DCM (30 mL) and saturated aqueous $NaHCO_3$ (50 mL). The layers were separated and the aqueous layer was extracted further with DCM (2×30 mL). The combined organic layers were dried over anhydrous $MgSO_4$, filtered, and concentrated to dryness under reduced pressure. The crude material was purified using silica gel flash chromatography eluting with a gradient of 50-100% EtOAc in heptane to give 3-tosyl-8-(2-tosyl-2-azaspiro[3.3]heptan-6-yl)-3H-imidazo[1,2-a]pyrrolo[2,3-e]pyrazine (0.467 g, 76%) as a white solid: LC/MS (Table 1, Method b) $R_t$=2.53 min; MS m/z 562 $(M+H)^+$.

General Procedure LLLL: Formation of a Bromoketone from a Ketone or an Aldehyde

To a ketone or an aldehyde (preferably 1 equiv) in an organic solvent (DCM or DCE, preferably DCM) at about −20 to 20° C. (preferably about 0° C.), an organic base such as TEA or DIEA (preferably DIEA, 1-20 equiv, preferably 5-10 equiv) is added, followed by addition of trimethylsilyl trifluoromethanesulfonate (1-8 equiv, preferably 4.5 equiv). The reaction is stirred at the same temperature for about 0.5 to 6 h (preferably about 1 h). A suitable organic solvent (such as EtOAc or DCM) is optionally added. An aqueous solution (such as saturated aqueous $NaHCO_3$ or water) is added. The layers are separated, the aqueous layer is optionally extracted with additional organic solvent (such as EtOAc or DCM) and the organic layer or combined organic layers are dried over anhydrous $Na_2SO_4$ or $MgSO_4$, filtered, and concd under reduced pressure to give a TMS-protected enol intermediate. The intermediate is dissolved in an organic solvent (DCM or DCE, preferably DCM) at about −20 to 60° C. (preferably rt) and an inorganic base such as $NaHCO_3$ or $Na_2CO_3$ (preferably $NaHCO_3$, 1-20 equiv, preferably 4 equiv) and NBS (1-3 equiv, preferably 1 equiv) are added. The reaction is stirred at the same temperature for about 1-48 h (preferably about 18 h). A suitable organic solvent (such as EtOAc or DCM) and an aqueous solution (such as saturated aqueous $NaHCO_3$ or water) are added, the layers are separated, and the organic solution is dried over anhydrous $Na_2SO_4$ or $MgSO_4$, filtered, and concd under reduced pressure.

Illustration of General Procedure LLLL

Preparation #LLLL.1: t-butyl-(cis-5-(2-bromoacetyl)-4-methyltetrahydrofuran-2-yl)methyl(3,3,3-trifluoropropylsulfonyl)carbamate

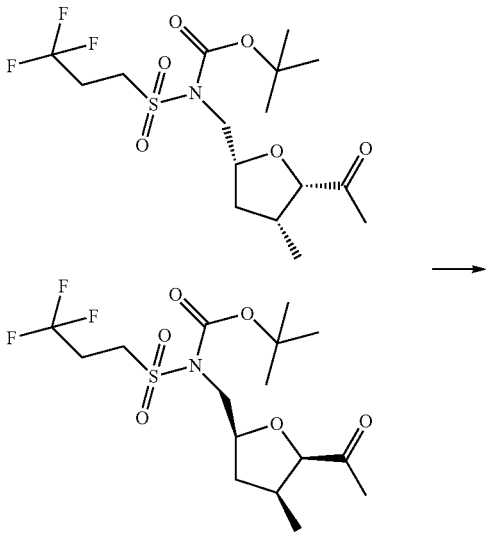

-continued

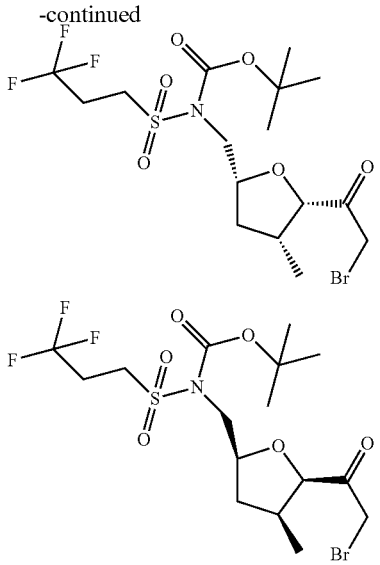

To a solution of t-butyl(cis-5-acetyl-4-methyltetrahydrofuran-2-yl)methyl(3,3,3-trifluoropropylsulfonyl)carbamate (0.54 g, 1.3 mmol, prepared using M.1 from Preparation #MMMM.1) in DCM (5 mL) at about 0° C. was added DIEA (2.03 mL, 11.6 mmol) and trimethylsilyl trifluoromethanesulfonate (1.06 mL, 5.82 mmol). The reaction was stirred at about 0° C. for about 1 h. Saturated aqueous $NaHCO_3$ (10 mL) was added and the layers were separated. The aqueous layer was extracted with DCM (2×10 mL). The combined organic extracts were dried over anhydrous $MgSO_4$, filtered, and concd under reduced pressure. The residue was dissolved in DCM (5 mL) and $NaHCO_3$ (0.435 g, 5.17 mmol) and NBS (0.230 g, 1.294 mmol) were added. The reaction was stirred at ambient temperature for about 18 h. The reaction mixture was partitioned between water (30 mL) and DCM (30 mL). The aqueous layer was extracted with DCM (2×30 mL). The combined organic extracts were dried over anhydrous $MgSO_4$, filtered, and concd under reduced pressure. The product was purified by silica gel chromatography eluting with a gradient of 0-30% EtOAc in heptane to give t-butyl-(cis-5-(2-bromoacetyl)-4-methyltetrahydrofuran-2-yl)methyl(3,3,3-trifluoropropylsulfonyl)carbamate (0.472 g, 73%) as a yellow solid: LC/MS (Table 1, Method b) $R_t$=2.76 min; MS m/z: 494, 496 $(M-H)^-$.

General Procedure MMMM: Formation of a Ketone from a Weinreb Amide

To a Weinreb amide (preferably 1 equiv) in an organic solvent (for example DCM, MeCN, 1,4-dioxane or THF, preferably THF) is added a Grignard or an alkyl lithium reagent (1-10.0 equiv, preferably 6 equiv) at about −30 to 40° C. (preferably about −10° C.). The reaction mixture is stirred at about −30 to 40° C. (preferably about −10° C.) for about 1-24 h (preferably about 5 h). The reaction mixture is quenched with an aqueous acid (such as aqueous HCl) and then water, partitioned between an organic solvent (such as $Et_2O$, EtOAc or DCM) and water. The layers are separated and the aqueous layer is extracted with additional organic solvent and the combined organic layers may be optionally washed with brine. The organic layer is optionally dried over anhydrous $Na_2SO_4$ or $MgSO_4$, and then decanted or filtered prior to concentrating under reduced pressure.

Illustration of General Procedure MMMM

Preparation #MMMM.1: N-((cis-5-acetyl-4-methyltetrahydrofuran-2-yl)methyl)-3,3,3-trifluoropropane-1-sulfonamide

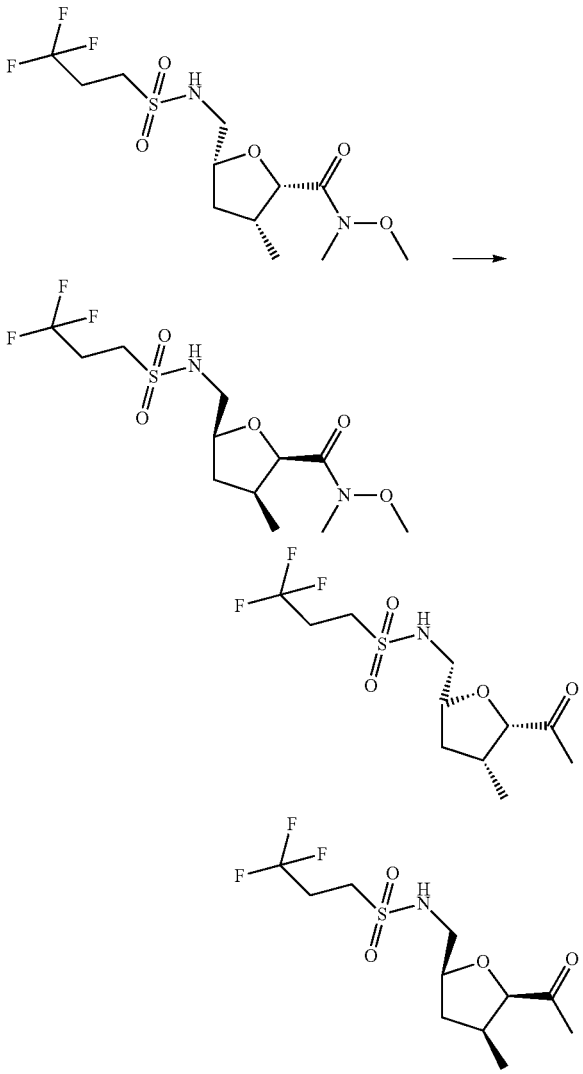

To a solution of cis-N-methoxy-N,3-dimethyl-5-((3,3,3-trifluoropropylsulfonamido)methyl)tetrahydrofuran-2-carboxamide (0.70 g, 1.9 mmol, prepared using E from Preparation #43 with HCl, K with 3,3,3-trifluoropropane-1-sulfonyl chloride (Matrix), Z with NaOH, H with N,O-dimethylhydroxylamine hydrochloric acid) in THF (5 mL) was added methylmagnesium bromide (3 N in $Et_2O$, 3.86 mL, 11.6 mmol) dropwise at about −10° C. The reaction mixture was stirred at about −10° C. for about 5 h. Aqueous HCl (1 N, 9.66 mL, 9.66 mmol) was added to quench the reaction. The reaction mixture was partitioned between water (10 mL) and DCM (20 mL). The layers were separated and the aqueous layer was extracted with DCM (2×20 mL). The combined organic extracts were concd under reduced pressure. The product was purified by silica gel chromatography eluting with a gradient of 0-100% EtOAc in heptane to give N-((cis-5-acetyl-4-methyltetrahydrofuran-2-yl)methyl)-3,3,3-trifluoropropane-1-sulfonamide (0.57 g, 93%) as a clear oil: LC/MS (Table 1, Method b) $R_t$=2.02 min; MS m/z: 318 $(M+H)^+$.

General Procedure NNNN: Formation of β-Hydroxysulfonamide from a Ketone

To an optionally substituted methyl sulfonamide (1-8 equiv, preferably 1.5 equiv) in an organic solvent (DCM or THF, preferably THF) at about −20 to 20° C. (preferably about 0° C.), an alkyl lithium reagent (for example n-BuLi, t-BuLi or LDA (preferably n-BuLi, 1-20 equiv, preferably 1-2 equiv) is added. The reaction is stirred at about −20 to 20° C. (preferably about 0° C.) for about 0.5-72 h (preferably about 1 h). The resulting solution is added dropwise to a solution of ketone (preferably 1.0 equiv) in an organic solvent (DCM or THF, preferably THF) at about −20 to 20° C. (preferably about 0-5° C.). The reaction is stirred at about −20 to 20° C. (preferably about 0-5° C.) for about 1-72 h (preferably about 48 h). A suitable organic solvent (such as EtOAc or DCM) and an aqueous solution (such as saturated aqueous $NaHCO_3$ or water) are added, the layers are separated, and the organic solution is dried over anhydrous $Na_2SO_4$ or $MgSO_4$, filtered, and concd under reduced pressure.

Illustration of General Procedure NNNN

Preparation #NNNN.1: 3-Ethyl-1-(morpholinosulfonylmethyl)-4-(6-((2-(trimethylsilyl)ethoxy)methyl)-6H-pyrrolo[2,3-e][1,2,4]triazolo[4,3-a]pyrazin-1-yl)cyclopentanol

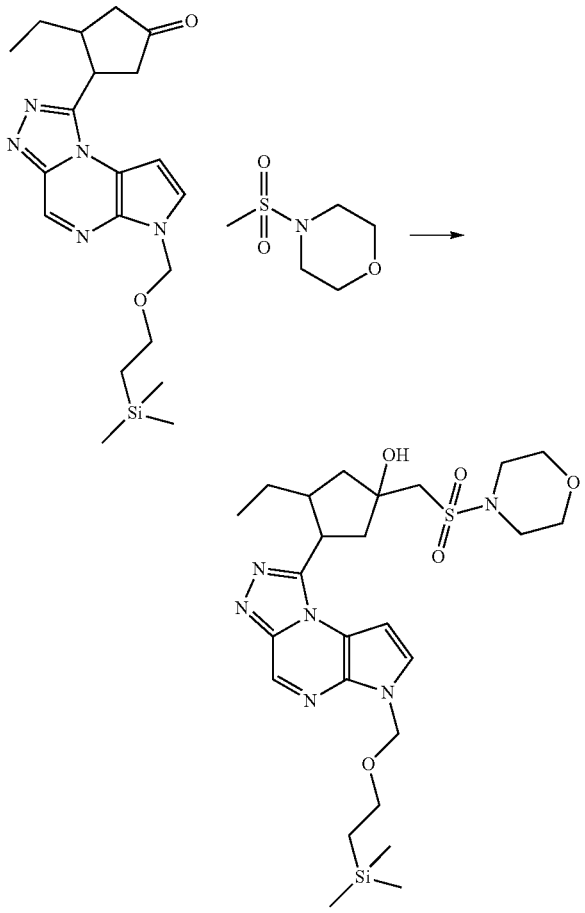

To a solution of 4-(methylsulfonyl)morpholine (0.217 g, 1.314 mmol, Preparation #41) in THF (4 mL) at about 0° C. was added n-BuLi (2.5 M in hexanes, 0.53 mL, 1.3 mmol). The reaction mixture was stirred at about 0° C. for about 1 h. The resulting solution was added dropwise to a solution of 3-ethyl-4-(6-((2-(trimethylsilyl)ethoxy)methyl)-6H-pyrrolo[2,3-e][1,2,4]triazolo[4,3-a]pyrazin-1-yl)cyclopentanone (0.350 g, 0.876 mmol, Example #35 Step G) in THF (4 mL) at about 0° C. The reaction mixture was maintained at about 4° C. in a refrigerator for about 48 h. The reaction mixture was partitioned between water (5 mL) and DCM (5 mL) The layers were separated and the aqueous solution was extracted with DCM (2×5 mL). The combined organic extracts were concd under reduced pressure. The product was purified by silica gel chromatography eluting with a gradient of 0-2% MeOH/DCM, then by RP-HPLC (Table 1, Method 1) to give 3-ethyl-1-(morpholinosulfonylmethyl)-4-(6-((2-(trimethylsilyl)ethoxy)methyl)-6H-pyrrolo[2,3-e][1,2,4]triazolo[4,3-a]pyrazin-1-yl)cyclopentanol (0.17 g, 34%) as a yellow oil: LC/MS (Table 1, Method b) $R_t$=2.32 & 2.42 min; MS m/z: 565 $(M+H)^+$.

General Procedure OOOO: Formation of a Carbonate

To an alcohol (preferably 1 equiv) in an organic solvent (preferably pyridine) at about −20° C. to 80° C. (preferably ambient temperature) is added DMAP (0.1-5 equiv, preferably 0.3 equiv) and a chloroformate (1-10 equiv, preferably 2 equiv). The reaction mixture is stirred at about −20° C. to 80° C. (preferably ambient temperature) for about 1-16 h (preferably about 1 h). The reaction mixture is either concd under reduced pressure or optionally filtered, diluted with an organic solvent (preferably EtOAc), washed with water and an aqueous base (such as saturated aqueous $Na_2CO_3$ or $NaHCO_3$) or saturated brine, dried over anhydrous $Na_2SO_4$ or $MgSO_4$, filtered, and concd under reduced pressure.

Illustration of General Procedure OOOO

Preparation #OOOO.1: (1R,3R,4S)-3-ethyl-4-(6-tosyl-6H-pyrrolo[2,3-e][1,2,4]triazolo[4,3-a]pyrazin-1-yl)cyclopentyl-4-nitrophenyl carbonate

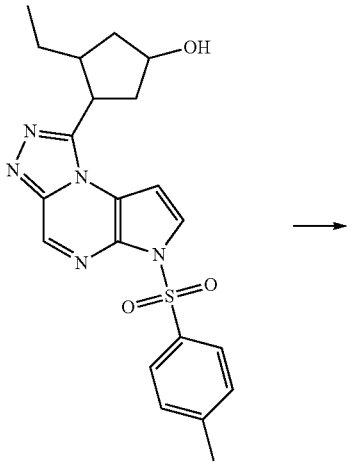

-continued

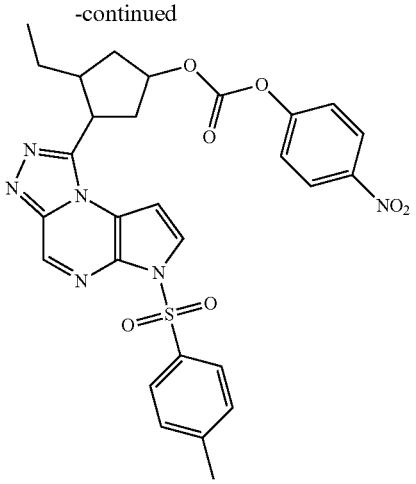

To a scalemic mixture enriched in (1R,3R,4S)-3-ethyl-4-(6-tosyl-6H-pyrrolo[2,3-e][1,2,4]triazolo[4,3-a]pyrazin-1-yl)cyclopentanol (1.20 g, 2.82 mmol, Example #41, Step N) in pyridine (10 mL) was added DMAP (0.103 g, 0.846 mmol) and 4-nitrophenyl chloroformate (0.853 g, 4.23 mmol). The resulting mixture was stirred at ambient temperature for about 1 h. The reaction mixture was concentrated and purified using silica gel chromatography eluting with 0-30% EtOAc in DCM to give a scalemic mixture enriched in (1R,3R,4S)-3-ethyl-4-(6-tosyl-6H-pyrrolo[2,3-e][1,2,4]triazolo[4,3-a]pyrazin-1-yl)cyclopentyl 4-nitrophenyl carbonate (0.72 g. 43%): LC/MS (Table 1, Method b) $R_t$=2.64 min; MS m/z: 591 $(M+H)^+$.

General Procedure PPPP: Formation of a Carbamate Followed by Sulfonamide Hydrolysis To a carbonate (preferably 1 equiv) in an organic solvent (preferably 1,4-dioxane) at about −20 to 60° C. (preferably at ambient temperature) is added an amine (2-10 equiv, preferably 5 equiv) and optionally DMAP (0-5 equiv, preferably 0 equiv). After about 1-16 h (preferably about 1 h), aqueous sodium hydroxide (1-2 N, preferably 1 N; 1-10 eq, preferably 4 equiv) is added. The reaction mixture is stirred at about 25-100° C. (preferably about 60° C.) for about 10 min-5 h (preferably about 30 min) and, if the reaction was heated, cooled to ambient temperature. The reaction mixture is either concd under reduced pressure or the layers are separated and the aqueous layer is extracted with an organic solvent (preferably DCM). The combined organic extracts are washed with water, an aqueous base (such as saturated aqueous $Na_2CO_3$ or $NaHCO_3$), or saturated brine, dried over anhydrous $Na_2SO_4$ or $MgSO_4$, filtered, and then concd under reduced pressure.

Preparation #PPPP.1: (1R,3R,4S)-3-ethyl-4-(6H-pyrrolo[2,3-e][1,2,4]triazolo[4,3-a]pyrazin-1-yl)cyclopentyl cyclopropylcarbamate

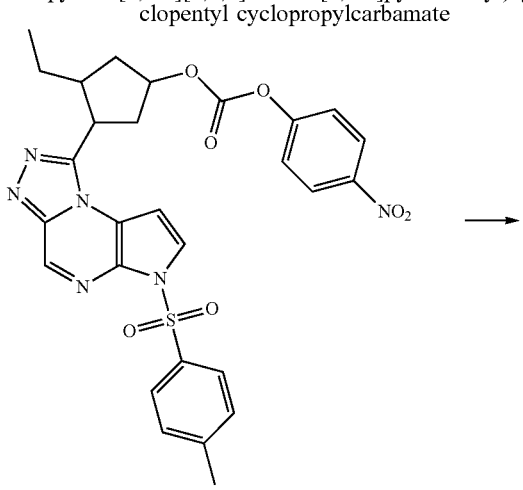

-continued

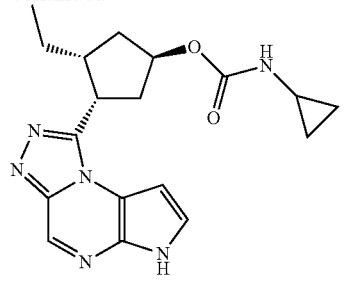

To a scalemic mixture enriched in (1R,3R,4S)-3-ethyl-4-(6-tosyl-6H-pyrrolo[2,3-e][1,2,4]triazolo[4,3-a]pyrazin-1-yl)cyclopentyl 4-nitrophenyl carbonate (Example #41 Step O, 0.211 g, 0.357 mmol) in 1,4-dioxane (1.5 mL) was added cyclopropylamine (0.102 g, 1.79 mmol). After about 1 h, 1N aqueous sodium hydroxide (1.5 mL, 1.5 mmol) was added and the reaction mixture was heated at about 60° C. for about 30 min then cooled to ambient temperature. The layers were separated and the aqueous layer was extracted with DCM (3×5 mL). The combined organic layers were concd under reduced pressure. The residue was purified by silica gel chromatography eluting with 0-10% MeOH in EtOAc to give (1R,3R,4S)-3-ethyl-4-(6H-pyrrolo[2,3-e][1,2,4]triazolo[4,3-a]pyrazin-1-yl)cyclopentyl cyclopropylcarbamate (0.085 g, 67%): LC/MS (Table 1, Method b) $R_t$=1.73 min; MS m/z: 355 $(M+H)^+$.

TABLE PPPP.1

Examples prepared from a scalemic mixture enriched in (1R,3R,4S)-3-ethyl-4-(6-tosyl-6H-pyrrolo[2,3-e][1,2,4]triazolo[4,3-a]pyrazin-1-yl)cyclopentyl 4-nitrophenyl carbonate (Example #41 Step O)

| Amine | Product | Example # | $R_t$ min (Table 2, Method) | m/z ESI+ $(M + H)^+$ |
|---|---|---|---|---|
| 3,3-difluoroazetidine hydrochloride [Matrix] | 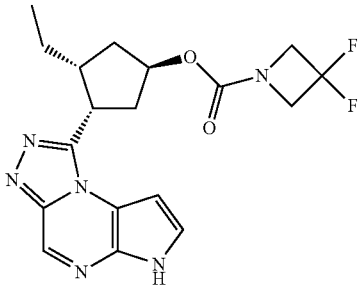 | PPPP.1.1 | 1.94 (b) | 391 |
| 2-aminoacetonitrile | 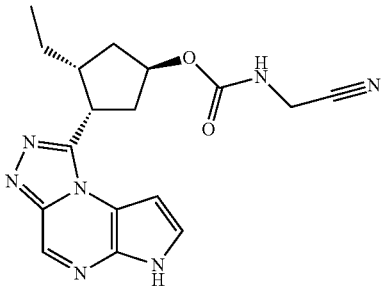 | PPPP.1.2 | 1.64 (b) | 354 |
| dimethylamine | 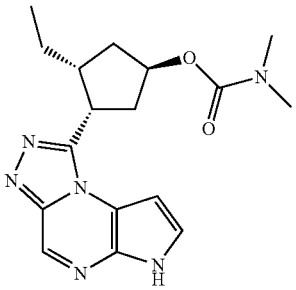 | PPPP.1.3 | 1.75 (b) | 343 |

TABLE PPPP.1-continued
Examples prepared from a scalemic mixture enriched in (1R,3R,4S)-3-ethyl-4-(6-tosyl-6H-pyrrolo[2,3-e][1,2,4]triazolo[4,3-a]pyrazin-1-yl)cyclopentyl 4-nitrophenyl carbonate (Example #41 Step O)
| Amine | Product | Example # | $R_t$ min (Table 2, Method) | m/z ESI+ $(M + H)^+$ |
|---|---|---|---|---|
| oxetan-3-amine | 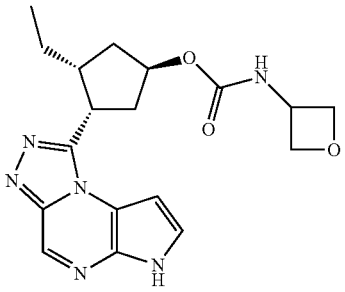 | PPPP.1.4 | 1.54 (b) | 371 |
| cyclobutanamine | 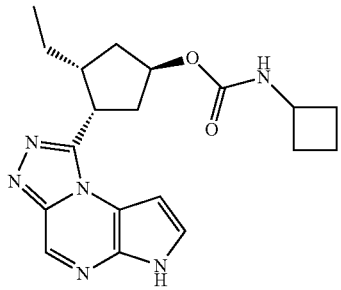 | PPPP.1.5 | 1.89 (b) | 369 |
| 2-aminoacetonitrile | 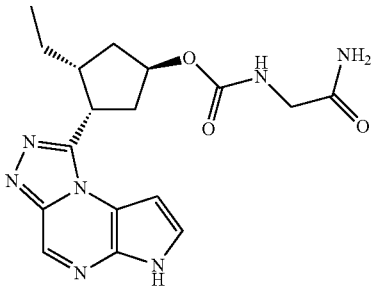 | PPPP.1.6 | 1.42 (b) | 372 |
| piperidin-4-ol | 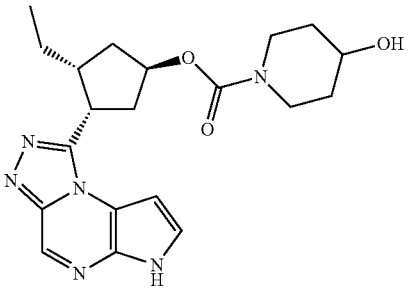 | PPPP.1.7 | 1.39 (b) | 399 |
| 2,2,2-trifluoroethanamine | 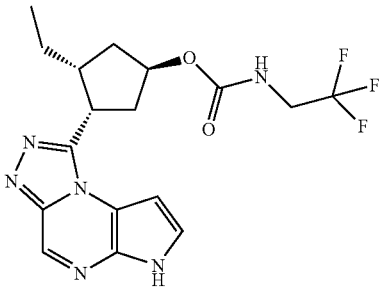 | PPPP.1.8 | 1.80 (b) | 397 |

TABLE PPPP.2
Examples prepared from a scalemic mixture enriched in (1S,3R,4S)-3-ethyl-4-(6H-pyrrolo[2,3-e][1,2,4]triazolo[4,3-a]pyrazin-1-yl)cyclopentyl cyclobutylcarbamate (Example #42 Step N)
| Amines | Product | Example # | $R_t$ min (Table 2, Method) | m/z ESI+ $(M + H)^+$ |
|---|---|---|---|---|
| dimethylamine | 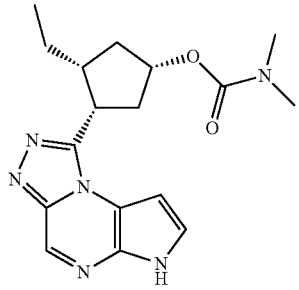 | PPPP.2.1 | 1.66 (b) | 343 |
| cyclobutanamine | 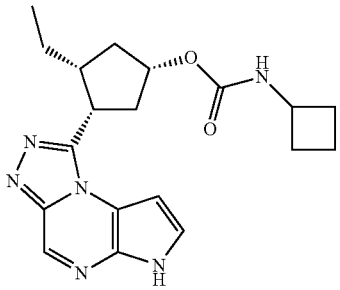 | PPPP.2.2 | 1.17 (c) | 369 |
| piperidin-4-ol | 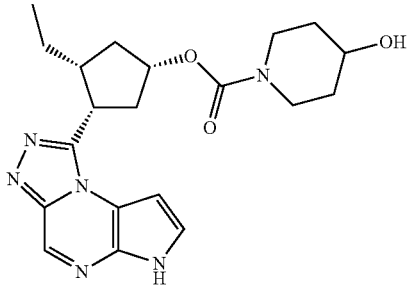 | PPPP.2.3 | 1.63 (b) | 399 |
| 2-aminoacetonitrile | 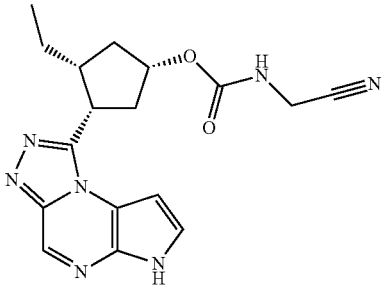 | PPPP.2.4 | 1.67 (b) | 354 |
| cyclopropanamine | 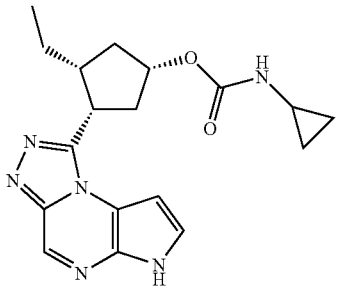 | PPPP.2.5 | 1.75 (b) | 355 |

TABLE PPPP.2-continued

Examples prepared from a scalemic mixture enriched in (1S,3R,4S)-3-ethyl-4-(6H-pyrrolo[2,3-e][1,2,4]triazolo[4,3-a]pyrazin-1-yl)cyclopentyl cyclobutylcarbamate (Example #42 Step N)

| Amines | Product | Example # | $R_t$ min (Table 2, Method) | m/z ESI+ $(M + H)^+$ |
|---|---|---|---|---|
| 2,2,2-trifluoroethanamine | 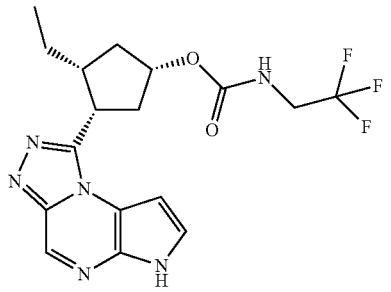 | PPPP.2.6 | 1.90 (b) | 397 |
| 3,3-difluoroazetidine hydrochloride [Matrix] | 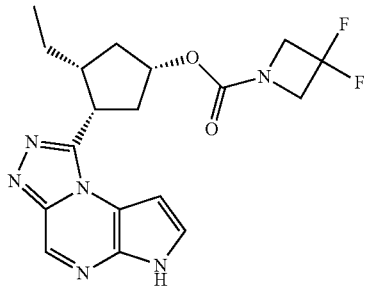 | PPPP.2.7 | 1.91 (b) | 391 |
| piperidine-4-carbonitrile | 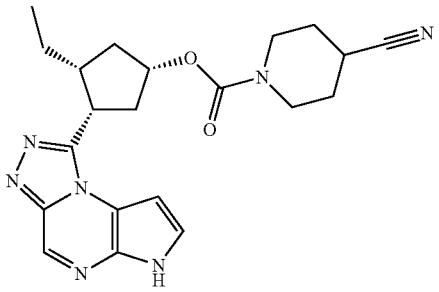 | PPPP.2.8 | 1.81(b) | 408 |
| azetidine-3-carbonitrile hydrochloride [Astatech] | 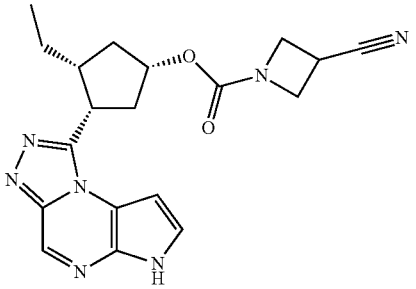 | PPPP.2.9 | 1.76 (b) | 380 |
| phenylmethanamine | 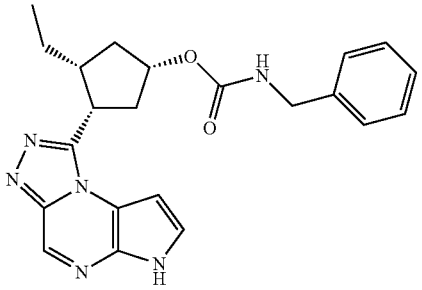 | PPPP.2.10 | 2.01 (b) | 405 |

TABLE PPPP.2-continued

Examples prepared from a scalemic mixture enriched in (1S,3R,4S)-3-ethyl-4-(6H-pyrrolo[2,3-e][1,2,4]triazolo[4,3-a]pyrazin-1-yl)cyclopentyl cyclobutylcarbamate (Example #42 Step N)

| Amines | Product | Example # | $R_t$ min (Table 2, Method) | m/z ESI+ $(M + H)^+$ |
|---|---|---|---|---|
| oxetan-3-amine | 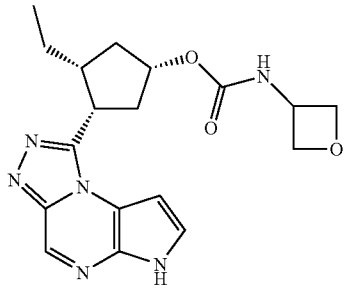 | PPPP.2.11 | 1.62 (b) | 371 |
| 1-aminocyclo-propanecarbonitrile hydrochloride [Astatech] | 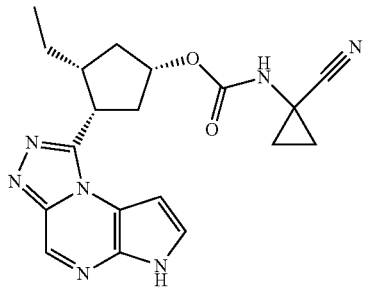 | PPPP.2.12 | 1.77 (b) | 380 |
| 3-methyloxetan-3-amine [Synthorax] | 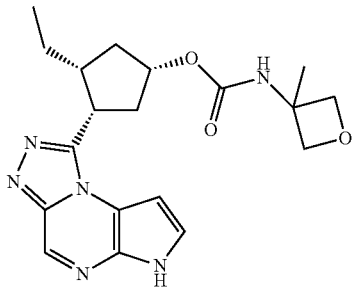 | PPPP.2.13 | 1.69 (b) | 385 |
| (R)-pyrrolidin-3-ol | 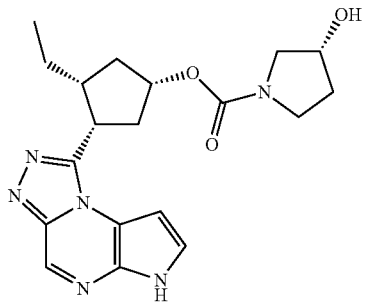 | PPPP.2.14 | 1.62 (b) | 385 |

TABLE PPPP.2-continued

Examples prepared from a scalemic mixture enriched in (1S,3R,4S)-3-ethyl-4-(6H-pyrrolo[2,3-e][1,2,4]triazolo[4,3-a]pyrazin-1-yl)cyclopentyl cyclobutylcarbamate (Example #42 Step N)

| Amines | Product | Example # | $R_t$ min (Table 2, Method) | m/z ESI+ $(M + H)^+$ |
|---|---|---|---|---|
| (S)-pyrrolidin-3-ol | 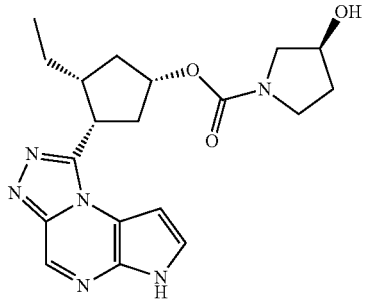 | PPPP.2.15 | 1.61 (b) | 385 |
| 4-fluoropiperidine hydrochloride | 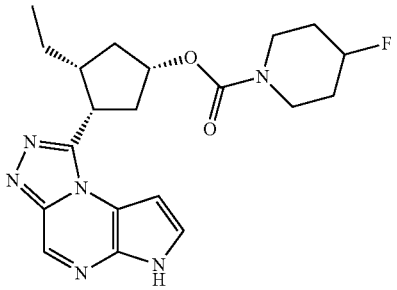 | PPPP.2.16 | 1.92 (b) | 401 |
| 2,2-difluoroethanamine [Matrix] | 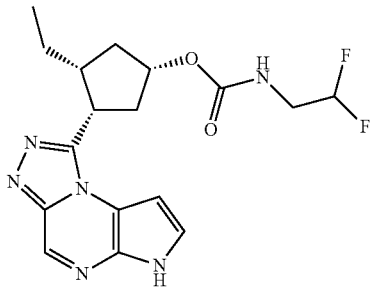 | PPPP.2.17 | 1.82 (b) | 379 |
| piperidine | 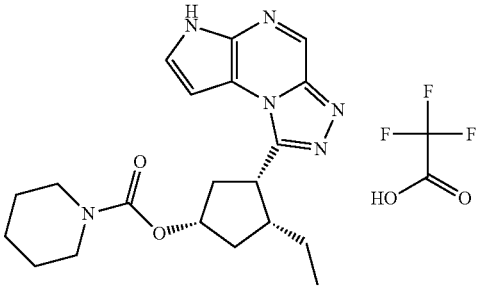 | PPPP.2.18 | 1.41 (v) | 383 |
| 3 -fluoroazetidine hydrochloride [Acesys] | 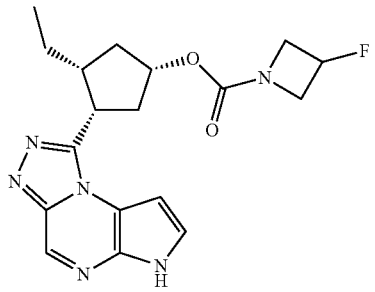 | PPPP.2.19 | 1.81 (b) | 373 |

TABLE PPPP.2-continued

Examples prepared from a scalemic mixture enriched in (1S,3R,4S)-3-ethyl-4-(6H-pyrrolo[2,3-e][1,2,4]triazolo[4,3-a]pyrazin-1-yl)cyclopentyl cyclobutylcarbamate (Example #42 Step N)

| Amines | Product | Example # | $R_t$ min (Table 2, Method) | m/z ESI+ $(M + H)^+$ |
|---|---|---|---|---|
| 1-methylcyclobutanamine [Matrix] | 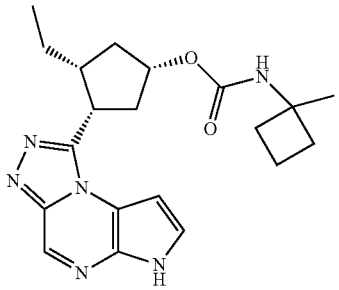 | PPPP.2.20 | 1.98 (b) | 383 |
| 1-(aminomethyl)cyclo-propanol [ChemPacific] | 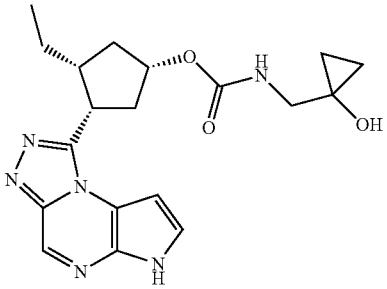 | PPPP.2.21 | 1.72 (b) | 385 |
| N-methyloxetan-3-amine [Synthonix] | 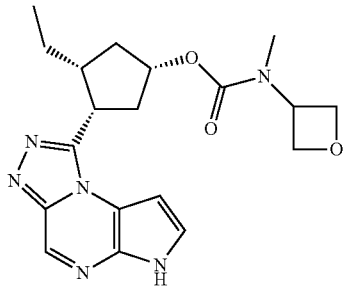 | PPPP.2.22 | 1.68 (b) | 385 |
| (3-methyloxetan-3-yl)methanamine [Synthonix] | 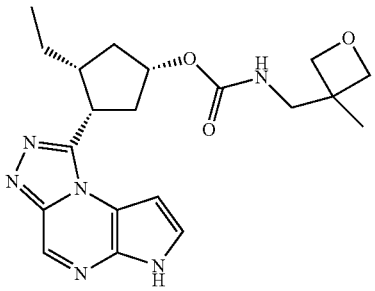 | PPPP.2.23 | 1.68 (b) | 399 |
| 2-methylpropan-2-amine | 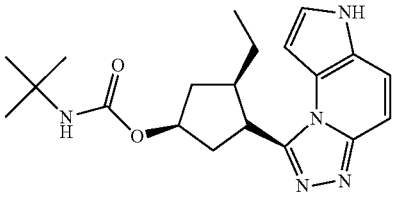 | PPPP.2.24 | 0.81 (u) | 371 |

TABLE PPPP.2-continued

Examples prepared from a scalemic mixture enriched in (1S,3R,4S)-3-ethyl-4-(6H-pyrrolo[2,3-e][1,2,4]triazolo[4,3-a]pyrazin-1-yl)cyclopentyl cyclobutylcarbamate (Example #42 Step N)

| Amines | Product | Example # | $R_t$ min (Table 2, Method) | m/z ESI+ $(M + H)^+$ |
|---|---|---|---|---|
| 2,2-dimethylpropan-1-amine | 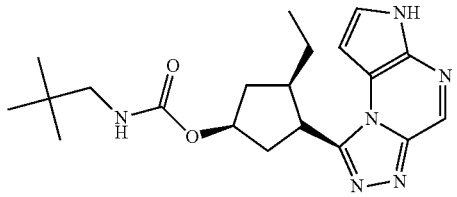 | PPPP.2.25 | 0.84 (u) | 385 |
| 2-methoxyethanamine | 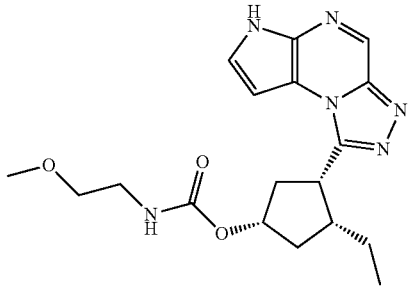 | PPPP.2.26 | 0.66 (u) | 373 |
| (3,5-bis(trifluoromethyl)phenyl) methanamine | 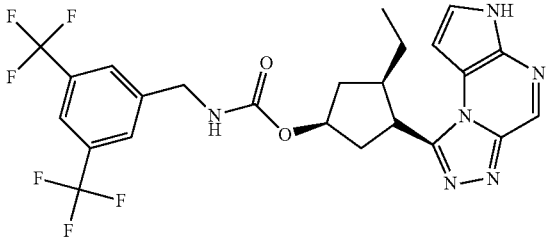 | PPPP.2.27 | 0.96 (u) | 541 |
| N1,N1,N2-trimethylethane-1,2-diamine | 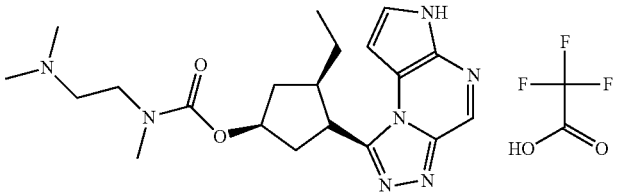 | PPPP.2.28 | 0.56 (u) | 400 |
| N1,N1,N3-trimethylpropane-1,3-diamine | 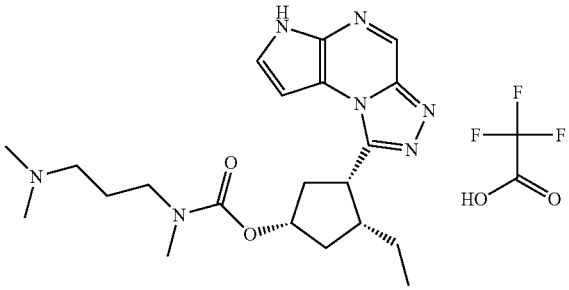 | PPPP.2.29 | 0.59 (u) | 414 |
| N-benzylpropan-2-amine | 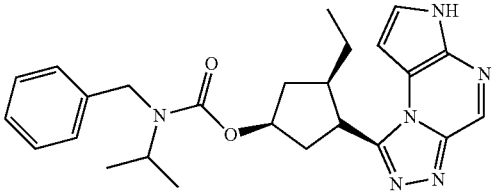 | PPPP.2.30 | 0.92 (u) | 447 |

TABLE PPPP.2-continued

Examples prepared from a scalemic mixture enriched in (1S,3R,4S)-3-ethyl-4-(6H-pyrrolo[2,3-e][1,2,4]triazolo[4,3-a]pyrazin-1-yl)cyclopentyl cyclobutylcarbamate (Example #42 Step N)

| Amines | Product | Example # | $R_t$ min (Table 2, Method) | m/z ESI+ $(M + H)^+$ |
|---|---|---|---|---|
| (R)-piperidin-3-ol | 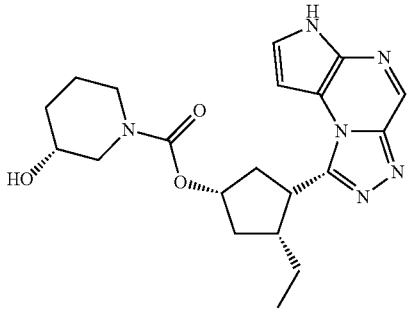 | PPPP.2.31 | 0.70 (u) | 399 |
| 1-methylpiperazine | 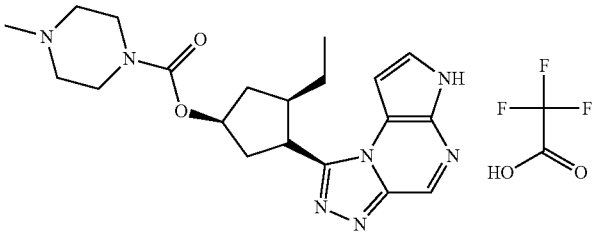 | PPP.2.32 | 0.53 (u) | 398 |
| 1-(piperazin-1-yl)ethanone | 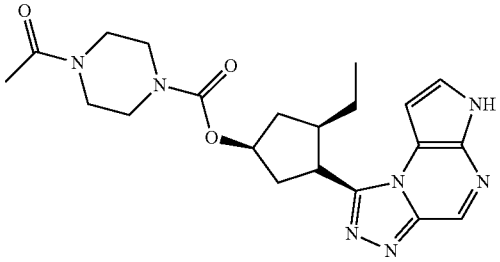 | PPPP.2.33 | 0.66 (u) | 426 |
| 1-(2-fluorophenyl)piperazine | 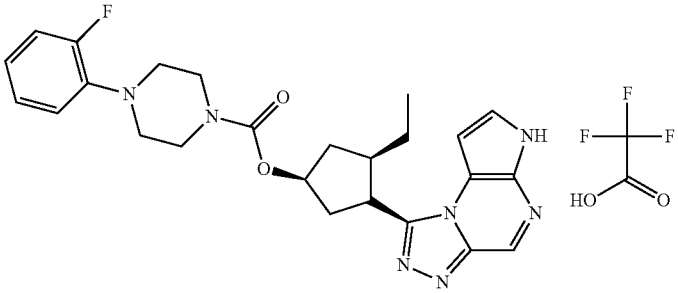 | PPPP.2.34 | 0.89 (u) | 478 |
| pyridin-2-ylmethanamine | 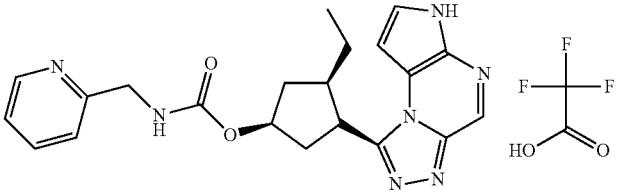 | PPPP.2.35 | 0.54 (u) | 406 |

TABLE PPPP.2-continued

Examples prepared from a scalemic mixture enriched in (1S,3R,4S)-3-ethyl-4-(6H-pyrrolo[2,3-e][1,2,4]triazolo[4,3-a]pyrazin-1-yl)cyclopentyl cyclobutylcarbamate (Example #42 Step N)

| Amines | Product | Example # | $R_t$ min (Table 2, Method) | m/z ESI+ $(M + H)^+$ |
|---|---|---|---|---|
| pyridin-3-ylmethanamine | 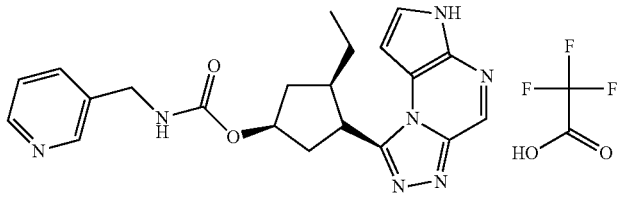 | PPPP.2.36 | 0.54 (u) | 406 |
| pyridin-4-ylmethanamine | 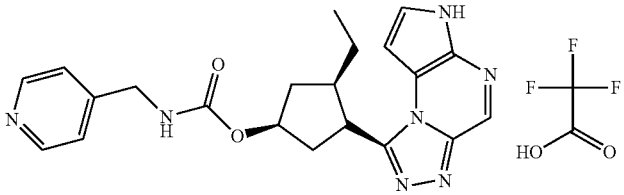 | PPPP.2.37 | 0.54 (u) | 406 |
| 2-methylpropan-1-amine | 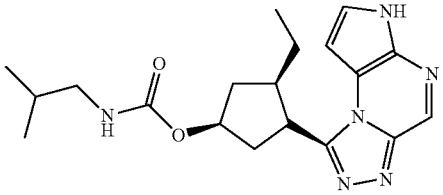 | PPPP.2.38 | 0.80 (u) | 371 |
| (S)-(tetrahydrofuran-2-yl)methanamine | 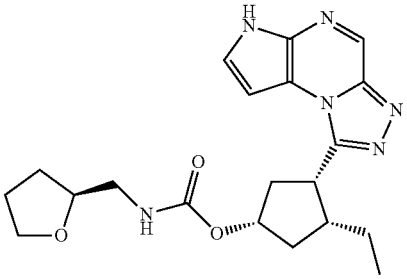 | PPPP.2.39 | 0.71 (u) | 399 |
| (R)-(tetrahydrofuran-2-yl)methanamine | 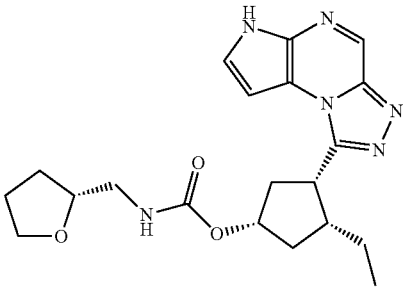 | PPPP.2.40 | 0.71 (u) | 399 |

TABLE PPPP.2-continued

Examples prepared from a scalemic mixture enriched in (1S,3R,4S)-3-ethyl-4-(6H-pyrrolo[2,3-e][1,2,4]triazolo[4,3-a]pyrazin-1-yl)cyclopentyl cyclobutylcarbamate (Example #42 Step N)

| Amines | Product | Example # | $R_t$ min (Table 2, Method) | m/z ESI+ $(M + H)^+$ |
|---|---|---|---|---|
| 3-(cyclopropylamino) propanenitrile | 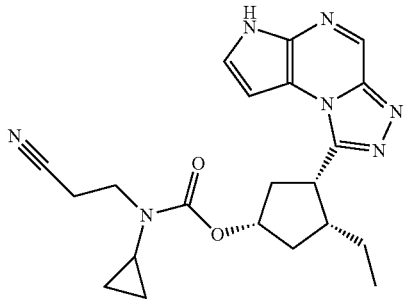 | PPPP.2.41 | 0.72 (u) | 408 |
| diisobutylamine | 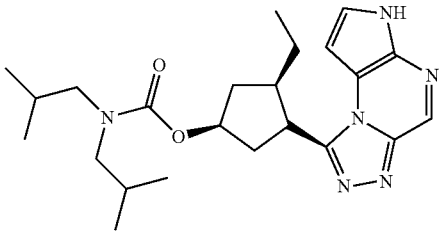 | PPPP.2.42 | 0.97 (u) | 427 |
| azetidine | 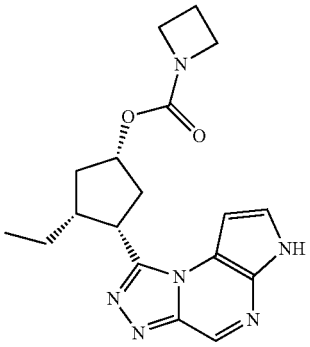 | PPPP.2.43 | 0.72 (u) | 355 |
| 2-methoxy-N-methylethanamine | 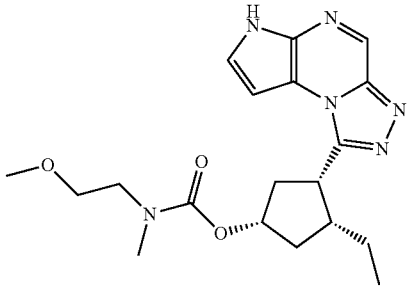 | PPPP.2.44 | 0.72 (u) | 387 |
| morpholine | 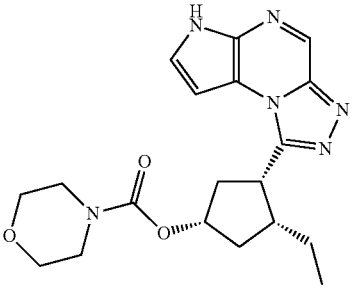 | PPPP.2.45 | 0.70 (u) | 385 |

TABLE PPPP.2-continued

Examples prepared from a scalemic mixture enriched in (1S,3R,4S)-3-ethyl-4-(6H-pyrrolo[2,3-e][1,2,4]triazolo[4,3-a]pyrazin-1-yl)cyclopentyl cyclobutylcarbamate (Example #42 Step N)

| Amines | Product | Example # | $R_t$ min (Table 2, Method) | m/z ESI+ $(M + H)^+$ |
|---|---|---|---|---|
| thiomorpholine | 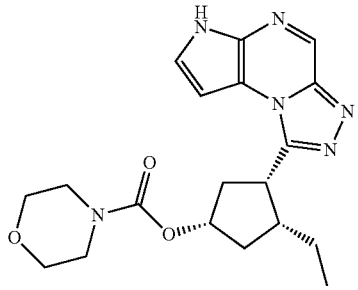 | PPPP.2.46 | 0.78 (u) | 401 |
| N1,N1-dimethylethane-1,2-diamine | 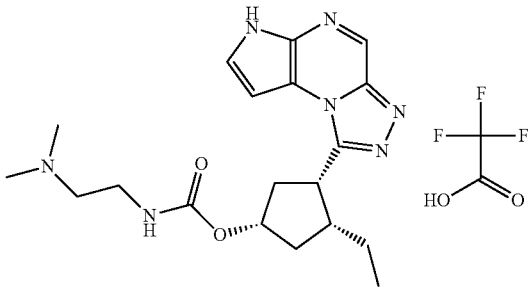 | PPPP.2.47 | 0.53 (u) | 386 |
| N1,N1-dimethylpropane-1,3-diamine | 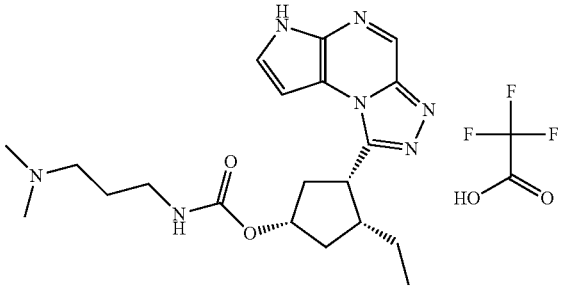 | PPPP.2.48 | 0.54 (u) | 400 |
| 2-(pyrrolidin-1-yl)ethanamine | 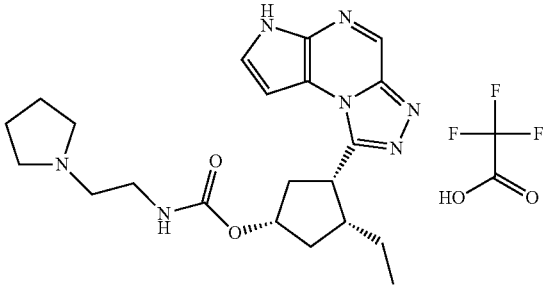 | PPPP.2.49 | 0.55 (u) | 412 |
| 3-(pyrrolidin-1-yl)propan-1-amine | 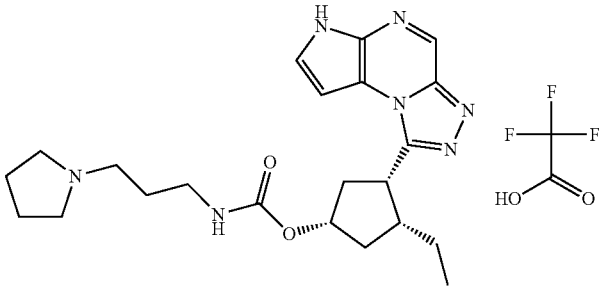 | PPPP.2.50 | 0.56 (u) | 426 |

TABLE PPPP.2-continued

Examples prepared from a scalemic mixture enriched in (1S,3R,4S)-3-ethyl-4-(6H-pyrrolo[2,3-e][1,2,4]triazolo[4,3-a]pyrazin-1-yl)cyclopentyl cyclobutylcarbamate (Example #42 Step N)

| Amines | Product | Example # | $R_t$ min (Table 2, Method) | m/z ESI+ $(M + H)^+$ |
|---|---|---|---|---|
| 2-(piperidin-1-yl)ethanamine | 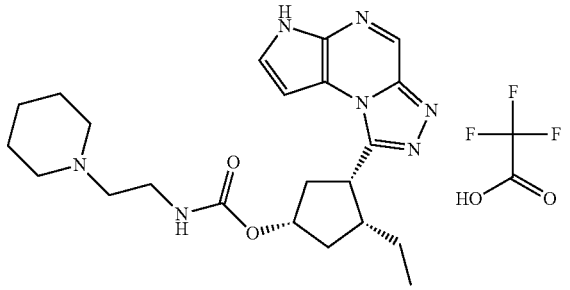 | PPPP.2.51 | 0.57 (u) | 426 |
| 3-(piperidin-1-yl)propan-1-amine | 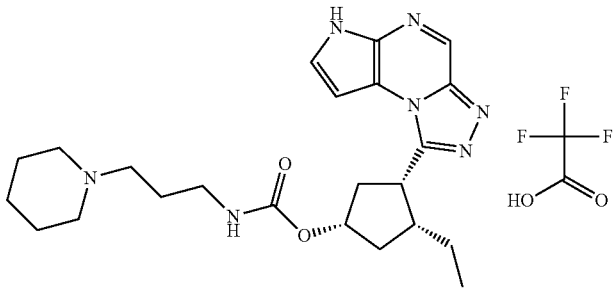 | PPPP.2.52 | 0.58 (u) | 440 |
| 2-morpholinoethanamine | 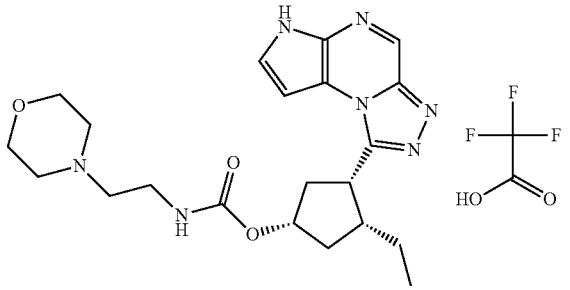 | PPPP.2.53 | 0.54 (u) | 428 |
| 3 -morpholinopropan-1-amine | 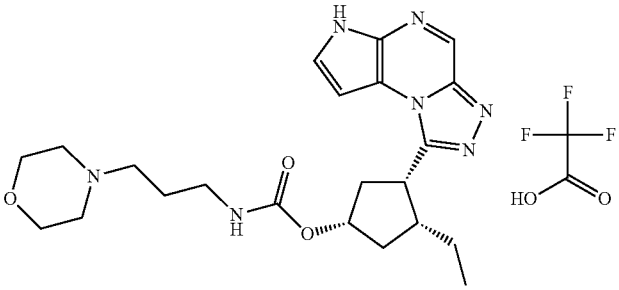 | PPPP.2.54 | 0.55 (u) | 442 |

General Procedure QQQQ: Oxidation of an Alkyl Thioacetate to an Alkyl Sulfonic Acid To a mixture of the alkyl thioacetate (preferably 1 equiv) and formic acid (30-100 equiv, preferably 36 equiv) and aqueous $H_2O_2$ (~30%, 3-10 equiv, preferably 5 equiv) are added dropwise. The reaction is stirred at ambient temperature for about 1-8 h (preferably about 2 h). The reaction is quenched with saturated aqueous $Na_2S_2O_3$ and is extracted with an organic solvent such as DCM. The organic extract is concd under reduced pressure. The resulting residue is optionally partitioned between an organic solvent such as EtOAc and brine. The aqueous extract is concd under reduced pressure and the resulting residue is optionally triturated in an organic solvent or mixture of organic solvents such as MeOH, DCM or MeOH/DCM (preferably MeOH/DCM) and filtered. The filtrate is concd under reduced pressure and optionally purified.

Illustration of General Procedure QQQQ

Preparation #QQQQ.1: (1S,3R,4S)-3-ethyl-4-(6-tosyl-6H-pyrrolo[2,3-e][1,2,4]triazolo[4,3-a]pyrazin-1-yl)cyclopentane-1-sulfonic acid

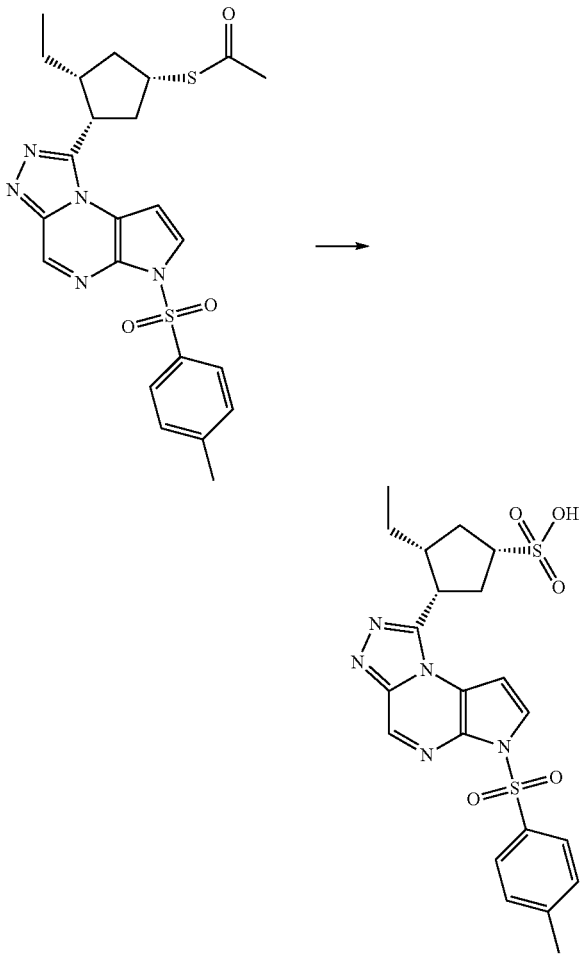

To a mixture of S-(1S,3R,4S)-3-ethyl-4-(6-tosyl-6H-pyrrolo[2,3-e][1,2,4]triazolo[4,3-a]pyrazin-1-yl)cyclopentyl ethanethioate (0.28 g, 0.58 mmol, prepared using P from Preparation #25, Step E and DIBAL-H; IIII, and JJJJ with potassium thioacetate) and formic acid (0.80 mL, 20.8 mmol) was added aqueous $H_2O_2$ (~30%, 0.30 mL, 2.9 mmol) dropwise. The reaction was stirred at ambient temperature for about 2 h. The reaction was quenched with saturated aqueous $Na_2S_2O_3$ (25 mL) and extracted with DCM (2×25 mL). The combined extracts were concd under reduced pressure. The resulting residue was partitioned between EtOAc and brine (25 mL each). The aqueous extract was concd under reduced pressure. The resulting residue was partially dissolved in MeOH/DCM (1:1, 50 mL), filtered and concd under reduced pressure. The resulting residue was purified by RP-HPLC (Table 1, Method y) to give (1S,3R,4S)-3-ethyl-4-(6-tosyl-6H-pyrrolo[2,3-e][1,2,4]triazolo[4,3-a]pyrazin-1-yl)cyclopentane-1-sulfonic acid (0.058 g, 20%) as an off-white solid: LC/MS (Table 1, Method b) $R_t$=1.60 min; MS m/z: 490 $(M+H)^+$.

General Procedure RRRR: Cyclization of a Diamine with Cyanogen Bromide

To a mixture of a substituted diamine (1 equiv) in an organic solvent (for example, MeOH or EtOH, preferably MeOH) is added cyanogen bromide or cyanogen bromide in MeCN (1-10 equiv, preferably 8.0 equiv). The mixture is stirred at ambient temperature for about 1-24 h (preferably about 16 h) and the solvent is removed under reduced pressure.

Illustration of General Procedure RRRR

Preparation #RRRR.1*: N-((1S,3S,4R)-3-(2-amino-6-tosylimidazo[4,5-d]pyrrolo[2,3-b]pyridin-1(6H)-yl)-4-ethylcyclopentyl)cyclopropanesulfonamide

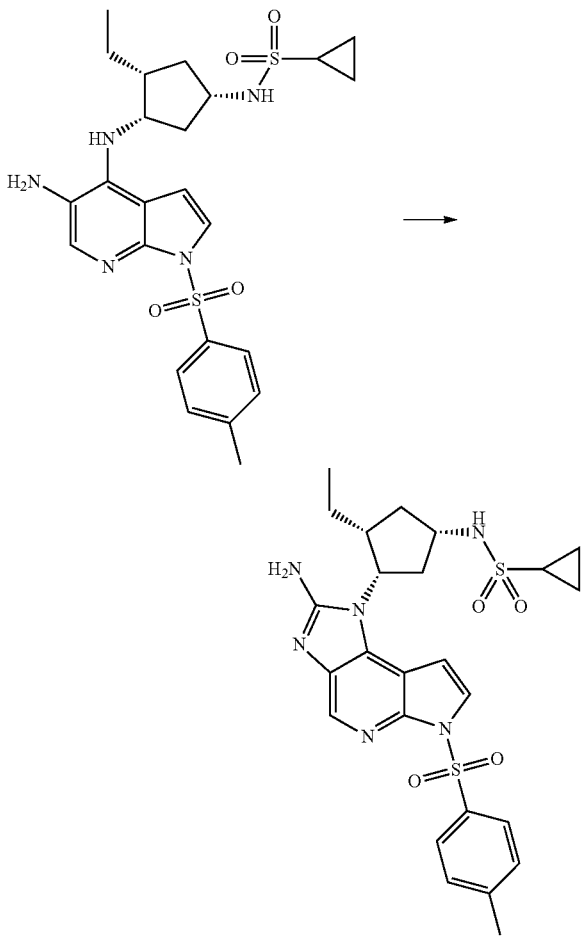

To a solution of N-((1S,3S,4R)-3-(5-amino-1-tosyl-1H-pyrrolo[2,3-b]pyridin-4-ylamino)-4-ethylcyclopentyl)cyclopropanesulfonamide (0.200 g, 0.301 mmol, Example #23 Step I) in MeOH (3.0 mL) was added cyanogen bromide (5 M in MeCN, 0.482 mL, 2.41 mmol) dropwise. The reaction was stirred at ambient temperature for about 16 h. The solvent was removed under reduced pressure and the residue was purified by silica gel chromatography eluting with a gradient of 0-10% MeOH in DCM to give N-((1S,3S,4R)-3-(2-amino-6-tosylimidazo[4,5-d]pyrrolo[2,3-b]pyridin-1(6H)-yl)-4-ethylcyclopentyl)cyclopropane-sulfonamide (0.11 g, 67%) as a brown solid: LC/MS (Table 1, Method a) $R_t$=2.00 min; MS m/z: 543 $(M+H)^+$.

General Procedure SSSS: Cyclization of a Diamine with $NaNO_2$

A mixture of a diamine (preferably 1 equiv) and an acidic aqueous solution (such as 6 M HCl in water) is cooled to about 0° C. Then an aqueous solution of $NaNO_2$ (1-5 equiv, preferably 1-2 equiv) is added and the reaction is maintained at about 0° C. for about 1-6 h (preferably about 2-3 h) and then warmed slowly to rt or is allowed to warm slowly to rt immediately following the addition. After about 1-18 h (preferably about 12-16 h), the reaction is filtered, while washing with water, to collect the solid.

Illustration of General Procedure SSSS

Preparation #SSSS.1*: N-((1S,3R,4S)-3-ethyl-4-(6-tosylpyrrolo[2,3-b][1,2,3]triazolo[4,5-d]pyridin-1(6H)-yl)cyclopentyl)cyclopropanesulfonamide

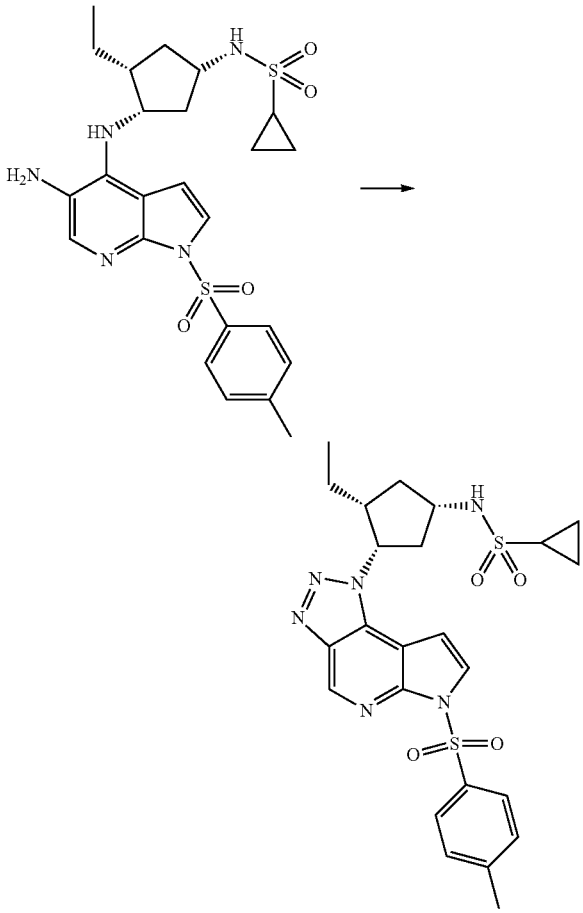

A mixture of N-((1S,3S,4R)-3-(5-amino-1-tosyl-1H-pyrrolo[2,3-b]pyridin-4-ylamino)-4-ethylcyclopentyl)cyclopropanesulfonamide (0.15 g, 0.23 mmol, Example #23 Step I) and aqueous HCl (6 N, 1.0 mL, 6.00 mmol) was cooled to about 0° C. A solution of $NaNO_2$ (0.022 g, 0.32 mmol) in water (0.2 mL) was added and the reaction was stirred at about 0° C. After about 3 h, the reaction was warmed to rt. After about 15.5 h, the reaction was filtered to collect the yellow solid by vacuum filtration, while washing with water (10 mL). The crude solid was purified by silica gel chromatograpy eluting with 0-20% EtOAc in DCM to give N-((1S,3R,4S)-3-ethyl-4-(6-tosylpyrrolo[2,3-b][1,2,3]triazolo[4,5-d]pyridin-1(6H)-yl)cyclopentyl)cyclopropanesulfonamide (0.088 g, 74%): LC/MS (Table 1, Method a) $R_t$=2.44 min; MS m/z: 529 $(M+H)^+$.

General Procedure TTTT: Formation of a Squaramide

A mixture of a 3-amino-4-methoxycyclobut-3-ene-1,2-dione (preferably 1 equiv), an amine (1-5 equiv, preferably 2 equiv), an organic base such as DIEA or TEA (1-10 equiv, preferably 5-6 equiv of DIEA), and a suitable organic solvent such as MeOH or DCE (preferably MeOH) was heated at about 40 to 65° C. (preferably about 50° C.). After about 1-24 h (preferably about 12-18 h), the reaction is filtered, while washing with water, to collect the solid.

Illustration of General Procedure TTTT

Preparation #TTTT.1*: 3-((1S,3R,4S)-3-ethyl-4-(6-tosyl-6H-pyrrolo[2,3-e][1,2,4]triazolo[4,3-a]pyrazin-1-yl)cyclopentylamino)-4-(3,3,3-trifluoropropylamino)cyclobut-3-ene-1,2-dione

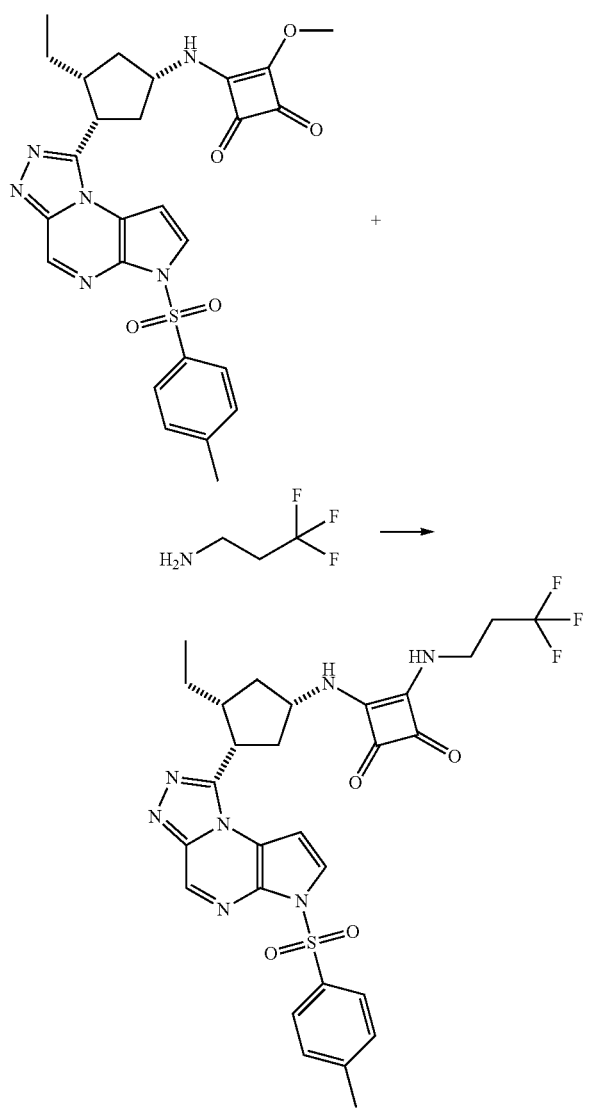

A mixture of 3-((1S,3R,4S)-3-ethyl-4-(6-tosyl-6H-pyrrolo[2,3-e][1,2,4]triazolo[4,3-a]pyrazin-1-yl)cyclopentylamino)-4-methoxycyclobut-3-ene-1,2-dione (0.090 g, 0.17 mmol, Preparation #29), 3,3,3-trifluoropropan-1-amine hydrochloride (0.050 g, 0.337 mmol, Fluorochem Limited), DIEA (0.18 mL, 1.0 mmol) and MeOH (1.2 mL) was heated at about 50° C. After about 18 h, the reaction was cooled to rt. The solid was collected via vacuum filtration, while washing with MeOH (about 3-5 mL), and then dried in a vacuum oven at about 60° C. to give 3-((1S,3R,4S)-3-ethyl-4-(6-tosyl-6H-pyrrolo[2,3-e][1,2,4]triazolo[4,3-a]pyrazin-1-yl)cyclopentylamino)-4-(3,3,3-trifluoropropylamino)cyclobut-3-ene-1,2-dione (0.083 g, 79%) as an off-white solid: LC/MS (Table 1, Method a) $R_t$=2.27 min; MS m/z: 616 $(M+H)^+$.

General Procedure UUUU: Reduction of an Azide to an Amine

To a solution of an azide (preferably 1 equiv) in a suitable organic solvent (such as THF or 1,4-dioxane, preferably THF) and water is added triphenylphosphine (1-2 equiv, preferably 1.2 equiv). The reaction mixture is stirred at about room temperature −80° C. (preferably about 45° C.) for about 1-24 h (preferably about 7 h). If heated, the reaction mixture is cooled to room temperature. The reaction mixture is worked up using one of the following methods. Method 1. The reaction mixture is diluted in an organic solvent (such as DCM or EtOAc) and water is added. The layers are separated and the organic solution is optionally washed with water and/or brine, dried over anhydrous $MgSO_4$ or $Na_2SO_4$, filtered, and the solvent is removed under reduced pressure. Method 2. The reaction mixture is concentrated under reduced pressure.

Illustration of General Procedure UUUU

Preparation #UUUU.1: 3-ethyl-4-(6-((2-(trimethylsilyl)ethoxy)methyl)-6H-pyrrolo[2,3-e][1,2,4]triazolo[4,3-a]pyrazin-1-yl)cyclopentanamine

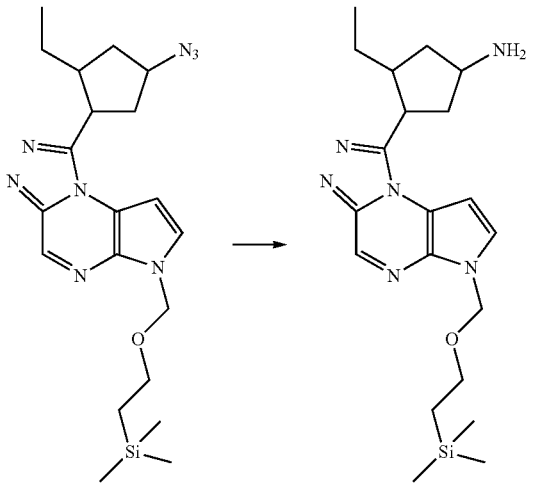

A round bottom flask was charged with 1-(-4-azido-2-ethylcyclopentyl)-6-((2-(trimethylsilyl)ethoxy)methyl)-6H-pyrrolo[2,3-e][1,2,4]triazolo[4,3-a]pyrazine (0.650 g, 1.52 mmol, prepared using D from Preparation #25 with NaOH, KK, P with $NaBH_4$, IIII, JJJJ with $NaN_3$), THF (8.0 mL), and water (1.6 mL). To the flask was added triphenylphosphine (0.480 g, 1.83 mmol). The reaction mixture was heated to about 45° C. for about 7 h. The reaction mixture was cooled to room temperature and EtOAc (20 mL) and water (15 mL) were added. The layers were separated and the organic solution was dried over anhydrous $MgSO_4$, filtered, and concentrated under reduced pressure to give an oil that solidified upon standing. The crude material was purified via flash silica gel chromatography eluting with a gradient of 1-10% DCM/MeOH/DEA (900:90:10) in DCM. The product containing fractions were combined and concentrated under reduced pressure to give an oil that was then dried on a vacuum pump overnight to give 3-ethyl-4-(6((2-(trimethylsilyl)ethoxy)methyl)-6H-pyrrolo[2,3-e][1,2,4]triazolo[4,3-a]pyrazin-1-yl)cyclopentanamine as a tacky oil (0.49 g, 80%): LC/MS (Table 1, Method b) $R_t$=1.85 min; MS m/z 401 $(M+H)^+$.

General Procedure VVVV: Formation of a Ketone from a Heteroaryl Halide

To a solution of a heteroaryl halide (preferably 1 equiv) in an organic solvent (for example THF) at about −100° C. to 0° C. (preferably about −78° C.) is added an alkyl lithium base (1-2 equiv) (preferably sec-butyllithium, 1.3 equiv) dropwise. The reaction mixture is stirred at about −100° C. to 0° C. (preferably about −78° C.) for about 15 min to 5 h (preferably about 1 h). A solution of an acylating agent (such as an acid chloride, Weinreb amide or acylimidazole for example, preferably an acid chloride, 1-3 equiv, preferably 1.5 equiv). The reaction mixture is allowed to reach ambient temperature and water is added. The layers are separated and the aqueous layer is then extracted with an organic solvent such as DCM or EtOAc. The combined organic layers are then washed with water and/or brine, dried over anhydrous $MgSO_4$ or $NaSO_4$, filtered and concentrated under reduced pressure.

Illustration of General Procedure VVVV

Preparation #VVVV.1: tert-butyl 4-(2-(5-chloro-1-(triisopropylsilyl)-1H-pyrrolo[2,3-b]pyridin-4-yl)-2-oxoethyl)piperidine-1-carboxylate

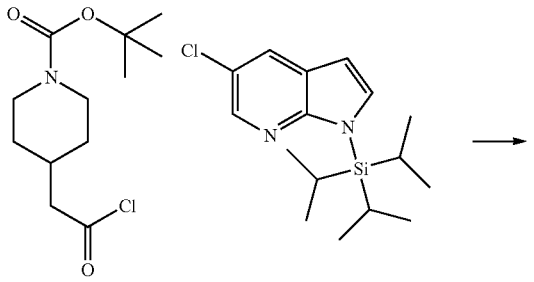

-continued

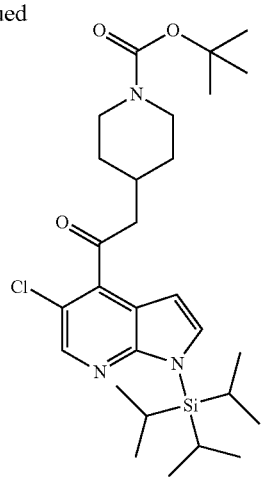

To a solution of 5-chloro-1-(triisopropylsilyl)-1H-pyrrolo[2,3-b]pyridine (0.338 g, 1.09 mmol, Adesis) in THF (5.5 mL) at about −78° C. was added sec-butyllithium (1.015 mL, 1.421 mmol) drop-wise. The reaction mixture was stirred at about −78° C. for about 1 h then a suspension of tert-butyl 4-(2-chloro-2-oxoethyl)piperidine-1-carboxylate (0.429 g, 1.64 mmol, Preparation #WWWW.1) in THF (2 mL) was added. The reaction mixture was stirred at about −78° C. for about 1 h then allowed to reach ambient temperature. Water (5 mL) was added and the product was extracted into DCM (3×10 mL). The combined organic extracts were washed with brine and dried over anhydrous $MgSO_4$, filtered, and concentrated under reduced pressure. The crude material was purified by silica gel chromatography eluting with 0-30% EtOAc in heptane to afford tert-butyl 4-(2-(5-chloro-1-(triisopropylsilyl)-1H-pyrrolo[2,3-b]pyridin-4-yl)-2-oxoethyl)piperidine-1-carboxylate (0.147 g, 25%) as a colorless oil: LC/MS (Table 1, Method r) $R_t$=3.97 min; MS m/z: 534/536 $(M+H)^+$ General Procedure WWWW: Formation of an Acid Chloride To a solution of a carboxylic acid (preferably 1 equiv) in an organic solvent (for example DCM or DCE, preferably DCM) is added oxalyl chloride (1-5 equiv, preferably 1-2 equiv) and N,N-dimethylformamide (0.05-0.5 equiv, preferably 0.1 equiv). The reaction mixture is stirred at about 0 to 50° C. (preferably ambient temperature) for about 30 min to 15 h (preferably 3 h). The solvent is removed under reduced pressure and the residue is in the next step without further purification.

Illustration of General Procedure WWWW

Preparation #WWWW.1: tert-butyl 4-(2-chloro-2-oxoethyl)piperidine-1-carboxylate

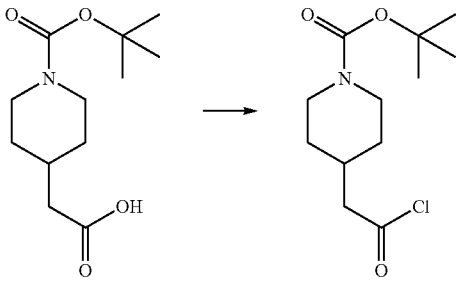

To a solution of 2-(1-(tert-butoxycarbonyl)piperidin-4-yl) acetic acid (3.84 g, 15.78 mmol) (prepared using M from ethyl 2-(piperidin-4-yl)acetate (Oakwood), Z) in DCM (79 mL) at ambient temperature were added oxalyl chloride (1.658 mL, 18.94 mmol) and DMF (0.115 g, 1.58 mmol). The reaction mixture was stirred at ambient temperature for about 3 h. The solvent was removed under reduced pressure to afford tert-butyl 4-(2-chloro-2-oxoethyl)piperidine-1-carboxylate (4.13 g, 100%) as a light yellow solid. The product was used in the next step without further purification.

General Procedure XXXX: Formation of a hydrazone

To a mixture of a ketone (preferably 1 equiv) in an organic solvent (preferably EtOH) are added a hydrazine (5-100 equiv, preferably 45-55 equiv) and acetic acid (1-10 equiv, preferably 4-6 equiv). The reaction mixture is stirred at ambient temperature to reflux (preferably at reflux) for about 1-24 h (preferably about 16 h). The solvent is removed under reduced pressure and the crude material is taken up in an organic solvent (such as DCM) and dried over anhydrous $MgSO_4$ or $NaSO_4$. The solvent is removed under reduced pressure.

Illustration of General Procedure XXXX

Preparation #XXXX.1: tert-butyl 4-(2-(5-chloro-1H-pyrrolo[2,3-b]pyridin-4-yl)-2-hydrazonoethyl) piperidine-1-carboxylate

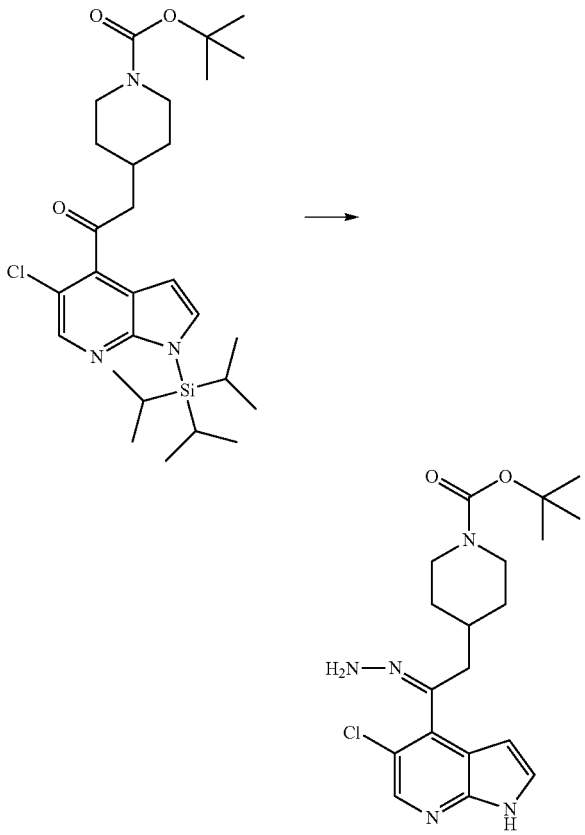

To a suspension of tert-butyl 4-(2-(5-chloro-1-(triisopropylsilyl)-1H-pyrrolo[2,3-b]pyridin-4-yl)-2-oxoethyl)piperidine-1-carboxylate (1.00 g, 1.87 mmol) in EtOH (6.4 mL) were added anhydrous hydrazine (2.94 mL, 94.0 mmol) and AcOH (0.536 mL, 9.36 mmol). The reaction mixture was stirred at reflux for about 16 h. The solvent was removed under reduced pressure and the crude material was taken up in DCM and dried over anhydrous $MgSO_4$. The solvent was removed and DCM (3 mL) was added. The solid was removed by filtration and the filtrate was purified by silica gel chromatography eluting with 0-10% MeOH in DCM to afford tert-butyl 4-(2-(5-chloro-1H-pyrrolo[2,3-b]pyridin-4-yl)-2-hydrazonoethyl)piperidine-1-carboxylate (0.324 g, 44%) as a white solid consisting of a 1/1 mixture of E/Z isomers: LC/MS (Table 1, Method r) $R_t$=1.46 and 1.53 min; MS m/z: 392/394 and 392/394 $(M+H)^+$.

General Procedure YYYY: Cyclization with an α-haloaldehyde

To an α-haloaldehyde (1-20 equiv, preferably 1.5 equiv) and a protected 2-amino-5H-pyrrolo[2,3-b]pyrazine (preferably 1 equiv) is optionally added an organic solvent such a DCE, DMF, 1,4-dioxane, EtOH, n-butanol, or toluene (preferably n-butanol or 1,4-dioxane) with or without an acid catalyst such as TsOH or sulfuric acid (0.05-0.2 equiv). The reaction mixture is stirred at about room temperature −150° C. (preferably about 90° C.) for about 30 min-72 h (preferably about 48 h). Optionally the reaction mixture can be subjected to microwave heating at about 100-150° C. (preferably about 130° C.) for about 30 min-15 h (preferably about 9 h). In cases where the reaction does not proceed to completion as monitored by TLC, LC/MS, or HPLC, the reaction may be re-subjected to heating at about 25-100° C. (preferably about 70° C.) for about 2-48 h (preferably about 8-24 h) with the optional addition of. In cases where the reaction does not proceed to completion as monitored by TLC, LC/MS, or HPLC, an additional portion or portions of an α-haloaldehyde (1-20 equiv, preferably 2.5 equiv) in an organic solvent such as 1,4-dioxane can be added and the reaction continued at about rt −150° C. (preferably about 125° C.). The volatiles are removed under reduced pressure. Optionally the crude mixture is diluted with water, aqueous $NH_4Cl$, or aqueous $NaHCO_3$. The product may be isolated by filtration or an organic solvent (for example, EtOAc or DCM) may be added. The layers are separated and the aqueous layer may be extracted further with an organic solvent (such as EtOAc and/or DCM). The combined organic layers are optionally washed with additional aqueous solutions such as aqueous $NH_4Cl$, aqueous $NaHCO_3$, water, and/or brine, dried over anhydrous $Na_2SO_4$ or $MgSO_4$, filtered, and concentrated to dryness under reduced pressure.

Illustration of General Procedure YYYY

Preparation #YYYY.1: ethyl 3-tosyl-3H-imidazo[1,2-a]pyrrolo[2,3-e]pyrazine-8-carboxylate

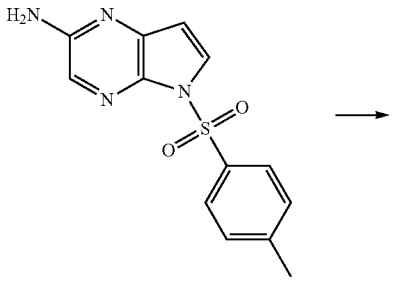

-continued

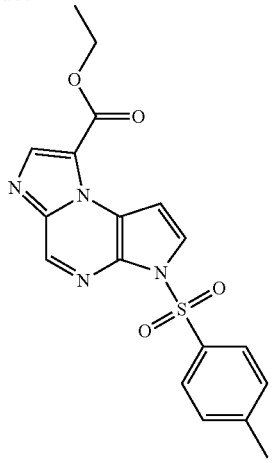

A solution of ethyl 2-chloro-3-oxopropanoate (1.60 g, 7.65 mmol, prepared as described in US2009005359A1) and 1,4-dioxane (10.0 mL) was added to 5-tosyl-5H-pyrrolo[3,2-b]pyrazin-2-amine (1.45 g, 5.03 mmol, Preparation #E.1.1) under nitrogen. Anhydrous butan-1-ol (30.0 mL) was added, a reflux condenser was attached, and the system was sealed. After about 30 min, the mixture was warmed to about 80° C. The solution was allowed to cool to ambient temperature. A solution of ethyl 2-chloro-3-oxopropanoate (2.78 g, 13.3 mmol) and 1,4-dioxane (5 mL) was added. After about 30 min, the reaction mixture was warmed to about 80° C. After about 30 min, the mixture was warmed to about 125° C. After about 48 h, the brown solution was allowed to cool to ambient temperature. The volatiles were removed under reduced pressure. The residue was purified by silica gel chromatography eluting with a gradient of 5-50% EtOAc in heptane to give ethyl 3-tosyl-3H-imidazo[1,2-a]pyrrolo[2,3-e]pyrazine-8-carboxylate (1.16 g, 60%): LC/MS (Table 1, Method b) $R_t$=2.52 min; MS m/z 385 $(M+H)^+$.

General Procedure ZZZZ: Cyclization with $SOCl_2$

To the amide, urea, hydrazide, or ketone (preferably 1 equiv), neat or as a solution in an organic solvent such as 1,4-dioxane, DCE, or toluene (preferably 1,4-dioxane), optionally with a buffering co-solvent such as pyridine or TEA (preferably TEA) is added dropwise $SOCl_2$ (1.3-200 equiv, preferably 3 equiv) either neat or as a solution in an organic solvent such as 1,4-dioxane, DCE, or toluene. Optionally, the reaction vessel is cooled to about −10 to 25° C. (preferably about 0° C.) during the addition. Alternatively, the order of addition may be reversed. The reaction mixture is warmed to about 30 to 100° C. (preferably about 80° C.) for about 0.5 to 24 h (preferably about 2 h). The reaction mixture is allowed to cool to ambient temperature. The volatiles are optionally removed under reduced pressure and an organic solvent such as DCM, 1,4-dioxane, or EtOAc (preferably EtOAc) is added. The organic layer is washed with an aqueous solution such as aqueous HCl, aqueous NaOH, aqueous $NaHCO_3$, aqueous $NH_4Cl$, aqueous $Na_2CO_3$, or water (preferably aqueous $Na_2CO_3$), with optional cooling, and the product is isolated using one or more of the Purification Methods described above. Optionally, subsequent removal of protecting groups can be performed using General Procedures listed above.

Preparation #ZZZZ.1: tert-butyl(trans-4-((6H-pyrrolo[2,3-e][1,2,4]triazolo[4,3-a]pyrazin-1-yl)methyl) cyclohexyl)methylcarbamate

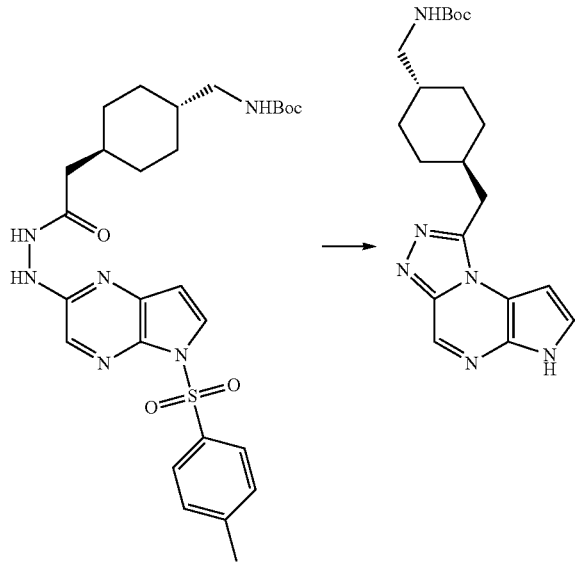

Thionyl chloride (0.030 mL, 0.41 mmol) was added dropwise to a solution of tert-butyl(trans-4-(2-oxo-2-(2-(5-tosyl-5H-pyrrolo[2,3-b]pyrazin-2-yl)hydrazinyl)ethyl)cyclohexyl)methyl-carbamate (0.127 g, 0.228 mmol, prepared using M from trans-(4-aminomethylcyclohexyl)acetic acid hydrochloride [AstaTech], H from Example #1, Step D, HATU, TEA), TEA (0.160 mL, 1.15 mmol), and 1,4-dioxane (2.3 mL) under nitrogen. A reflux condenser was attached and the reaction mixture was warmed to about 80° C. After about 2 h, the solution was cooled to ambient temperature and aqueous $Na_2CO_3$ (2 M, 3.4 mL, 6.8 mmol) was added and the biphasic mixture was warmed to about 80° C. After about 2 h, aqueous NaOH (2 M, 0.570 mL, 1.14 mmol) was added due to slow rate of deprotection. After about 17 h, the mixture was allowed to cool to ambient temperature. The reaction solution was diluted with water (5 mL) and then extracted with EtOAc (2×10 mL). The combined organics were dried over anhydrous $Na_2SO_4$, filtered, and concentrated under reduced pressure. The residue was purified by silica gel chromatography eluting with a gradient of 2-8% MeOH in DCM to give tert-butyl(trans-4-((6H-pyrrolo[2,3-e][1,2,4]triazolo[4,3-a]pyrazin-1-yl)methyl)cyclohexyl) methylcarbamate (0.0565 g, 63%): LC/MS (Table 1, Method a) $R_t$=1.85 min; MS m/z: 385 $(M+H)^+$.

General Procedure AAAAA: Formation of a Carboxylic Acid or Ester from an Aryl Halide An aryl or heteroaryl halide (preferably 1 equiv) is dissolved or suspended in an organic solvent such as DMF, 1,4-dioxane, THF, $Et_2O$, or toluene (preferably DMF or THF). The halide may be transmetallated using a base such a n-, t-, or sec-butyllithium (1-3 equiv) or a Grignard reagent such as isopropyl magnesium bromide (1-3 equiv) and then trapped with $CO_2$ to afford the carboxylic acid following an acidic workup. Alternatively, the solution of the aryl or heteroaryl halide may be treated with a base such as $Cs_2CO_3$, $K_2CO_3$, or TEA (1-10 equiv, preferably TEA, 2 equiv). Optionally, MeOH, (1-200 equiv, preferably 50 equiv) is added. A palladium source such a [1,1'-bis(diphenylphosphino)ferrocene]-dichloropalladium(II)-$CH_2Cl_2$ adduct, [1,1'-bis(diphenylphosphino)ferrocene]-dichloropalladium (II), bis(triphenylphosphine)dichloropalladium, or tetrakis(triphenylphosphinepalladium(0) (0.02-1 equiv, preferably [1,1'-bis(diphenylphosphino)ferrocene]-dichloropalladium(II)-$CH_2Cl_2$ adduct, 0.1 equiv) is added. The mixture is placed under a CO atmosphere and then warmed to about 40-120° C. (preferably about 100° C.) for about 0.5-24 h (preferably about 4.5 h). The reaction is optionally quenched using sodium methoxide or aqueous NaOH (1-100 equiv) and an organic solvent (for example, EtOAc or DCM) is added. The layers are separated and the aqueous layer may be extracted further with an organic solvent (such as EtOAc and/or DCM). The combined organic layers are optionally washed with additional aqueous solutions such as brine, dried over anhydrous $Na_2SO_4$ or $MgSO_4$, filtered, and concentrated to dryness under reduced pressure.

Illustration of General Procedure AAAAA

Preparation #AAAAA.1: methyl 6-((2-(trimethylsilyl)ethoxy) methyl)-6H-pyrrolo[2,3-e][1,2,4]triazolo [4,3-a]pyrazine-8-carboxylate

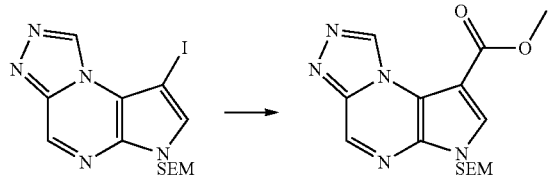

To a solution of 8-iodo-6-((2-(trimethylsilyl)ethoxy) methyl)-6H-pyrrolo[2,3-e][1,2,4]triazolo[4,3-a]pyrazine (0.050 g, 0.12 mmol, prepared using KK from Preparation #GGG.1.1 and NaH), TEA (0.034 mL, 0.24 mmol), MeOH (0.25 mL, 6.2 mmol), and DMF (0.6 mL) purged with nitrogen was added [1,1'-bis(diphenylphosphino)ferrocene] dichloropalladium(II) (0.0098 g, 0.012 mmol). The mixture was purged with CO and a balloon of CO was attached to the reaction vessel. The mixture was warmed to about 100° C. After about 4.5 h, the solution was allowed to cool to ambient temperature. Water (5 mL) was added and the mixture was extracted with EtOAc (2×10 mL). The combined organics were dried over anhydrous $Na_2SO_4$, filtered, and concentrated under reduced pressure. The crude material was purified by silica gel chromatography eluting with a gradient of 25-75% EtOAc/heptane over 30 min to afford methyl 6-((2-(trimethylsilyl)ethoxy)methyl)-6H-pyrrolo[2,3-e][1,2,4]triazolo[4,3-a]pyrazine-8-carboxylate (0.0311 g, 74%): LC/MS (Table 1, Method n) $R_t$=0.74 min; MS m/z: 348 $(M+H)^+$.

General Procedure BBBBB: Cyclization with an Orthoester

To an orthoester (1-20 equiv, preferably 10 equiv) and a protected 2-hydrazinyl-5H-pyrrolo[2,3-b]pyrazine (preferably 1 equiv) is optionally added an organic solvent such a DCE, DMF, 1,4-dioxane, or toluene (preferably DMF) with or without an acid catalyst such as TsOH or TFA (0.05-0.2 equiv). The mixture may be left at ambient temperature or warmed at about 30-100° C. (preferably about 100° C.) for about 0.5-24 h (preferably about 17 h). The volatiles may be removed under reduced pressure. Optionally, the crude mixture may be diluted with water, aqueous $NH_4Cl$, or aqueous $NaHCO_3$. The product may be isolated by filtration and an organic solvent (for example, EtOAc or DCM) may be added. Alternatively, an organic solvent may be added directly to the aqueous mixture. The layers are separated and the aqueous layer may be extracted further with an organic solvent (such as EtOAc and/or DCM). The combined organic layers are optionally washed with additional aqueous solutions such as aqueous $NH_4Cl$, aqueous $NaHCO_3$, water, and/or brine, dried over anhydrous $Na_2SO_4$ or $MgSO_4$, filtered, and concentrated to dryness under reduced pressure.

Illustration of General Procedure BBBBB

Preparation #BBBBB.1: 6-tosyl-6H-pyrrolo[2,3-e][1,2,4]triazolo[4,3-a]pyrazine

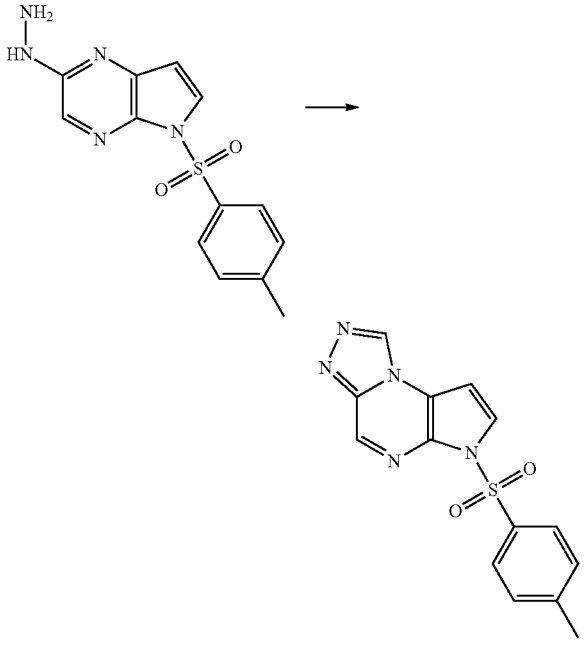

Triethyl orthoformate (76.0 mL, 456 mmol) was added to a mixture of 2-hydrazinyl-5-tosyl-5H-pyrrolo[2,3-b]pyrazine (13.8 g, 45.4 mmol, Example #1, Step D) and DMF (45 mL) under nitrogen. A reflux condenser was attached and the mixture was warmed to about 100° C. After about 17 h, the solution was allowed to cool to ambient temperature. The volatiles were removed under reduced pressure. The residue was slurried in water (100 mL) and then filtered, rinsing with water. The aqueous phase was extracted with EtOAc (200 mL). The organics were dried over anhydrous $Na_2SO_4$, filtered, and concentrated. The material was combined with the precipitate and then purified by silica gel chromatography eluting with a gradient of 0-5% MeOH in DCM to give 6-tosyl-6H-pyrrolo[2,3-e][1,2,4]triazolo[4,3-a]pyrazine (10.4 g, 73%): LC/MS (Table 1, Method n) $R_t$=0.59 min; MS m/z 314 $(M+H)^+$.

General Procedure CCCCC: Stille Coupling of an Aryl or Heteroaryl Halide

To a degassed solution of a aryl, heteroaryl, or vinyl stannane (preferably 1.3 equiv) and an aryl, heteroaryl or alkeneyl halide (preferably 1 equiv) in an organic solvent such as DMF, 1,4-dioxane, or toluene (preferably DMF) may be added a base such as $Cs_2CO_3$, $K_2CO_3$, or TEA (1-10 equiv). Optionally, additives such as LiCl (1-10 equiv, preferably 3 equiv), CsF (1-10 equiv, preferably 1.5 equiv), and/or CuI (0.05-0.5 equiv, preferably 0.2 equiv) may be added. A palladium(0) source such a tetrakis(triphenylphosphine)palladium(0), bis(dibenzylideneacetone)palladium or a palladium(II) source such as bis(triphenylphosphine)palladium(II) chloride or palladium acetate is added (0.01-0.2 equiv, preferably tetrakis (triphenylphosphine)palladium(0), preferably 0.1 equiv). The mixture is warmed at about 40 to 150° C. (preferably about 80° C.) either thermally or using a microwave for about 0.5 to 72 h (preferably about 4 h). The solution is cooled to rt and volatiles may be removed under reduced pressure and the crude mixture diluted with water, aqueous $NH_4Cl$, aqueous $NaHCO_3$ and an organic solvent such as EtOAc or DCM. If a solid was present, the resulting reaction mixture was filtered to remove it. The resulting layers of the filtrate are separated and the aqueous layer may be extracted with additional organic solvent. The combined organic layers are optionally washed with additional aqueous solutions such as brine, then dried over anhydrous $Na_2SO_4$ or $MgSO_4$, filtered, and concentrated to dryness under reduced pressure.

Illustration of General Procedure CCCCC

Preparation #CCCCC.1: 8-(2-(4-methylpiperazin-1-yl)pyrimidin-4-yl)-6-tosyl-6H-pyrrolo[2,3-e][1,2,4]triazolo[4,3-a]pyrazine

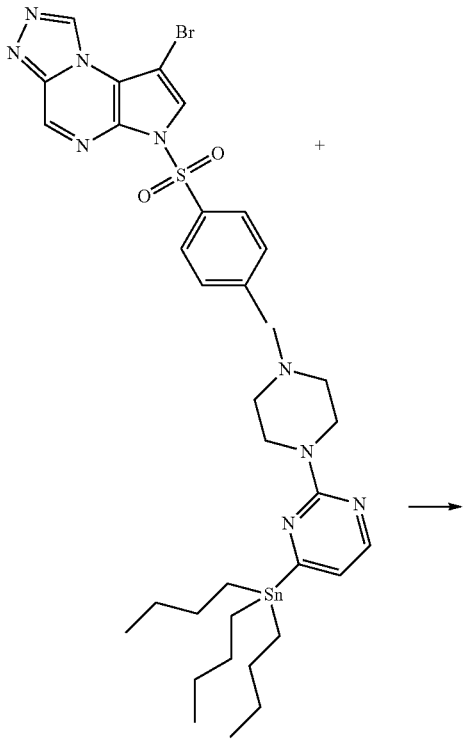

-continued

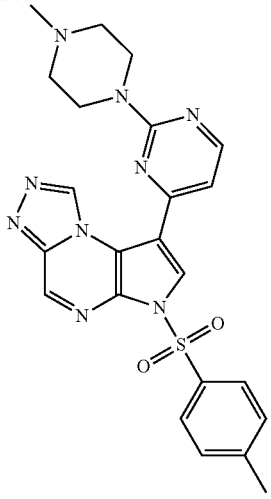

A vial containing 8-bromo-6-tosyl-6H-pyrrolo[2,3-e][1,2,4]triazolo[4,3-a]pyrazine (0.030 g, 0.076 mmol, prepared using D from Preparation #BBBBB.1 and NaOH, GGG.1 with NBS, K.1 with TsCl and NaH), 2-(4-methylpiperazin-1-yl)-4-(tributylstannyl)pyrimidine (0.054 g, 0.12 mmol, Preparation #39), LiCl (0.010 g, 0.24 mmol), CuI (0.003 g, 0.02 mmol), CsF (0.017 g, 0.12 mmol), and tetrakis(triphenylphosphine)palladium(0) (0.009 g, 0.008 mmol) under nitrogen was evacuated and then back-filled with nitrogen. 1,4-Dioxane (0.5 mL) was added and nitrogen was bubbled through the mixture for about 30 min. The reaction vessel was sealed and the mixture was warmed to about 80° C. After about 4 h, the mixture was allowed to cool to ambient temperature. The mixture was diluted with water (5 mL) and EtOAc (5 mL) and then filtered through a syringe filter. The layers were separated and the aqueous phase was extracted with EtOAc (5 mL). The combined organics were concentrated under reduced pressure. The residue was purified by silica gel chromatography eluting with a gradient of 0-10% MeOH in DCM over 40 min to afford 8-(2-(4-methylpiperazin-1-yl)pyrimidin-4-yl)-6-tosyl-6H-pyrrolo[2,3-e][1,2,4]triazolo[4,3-a]pyrazine (0.026 g, 69%): LC/MS (Table 1, Method n) $R_t$=0.56 min; MS m/z 490 $(M+H)^+$.

General Procedure DDDDD: Deprotection of a Cbz-Protected Amine Using a Silane

A solution of Cbz-protected amine (preferably 1 equiv) and a silane (for example triethylsilane, t-$BuMe_2SiH$ (preferably triethylsilane, 10-500 equiv, preferably 100 equiv)) is added an organic base such as TEA or DIEA (preferably TEA, 0.1-10 equiv, preferably 0.2 equiv), and a palladium catalyst (for example palladium (II) chloride, palladium (II) acetate, tris(benzylideneacetone)dipalladium(0), bis(acetato)triphenylphosphinepalladium(II), or dichlorobis(triphenylphosphine)palladium(II); preferably palladium (II) chloride, 0.01-0.20 equiv, preferably 0.1 equiv). The reaction is heated at about 40 to 180° C. (preferably about 120° C.) for about 1 to 48 h (preferably about 8 h). The catalyst is removed by filtration and the filtrate is concentrated under reduced pressure. The reaction mixture is optionally worked up by adding a suitable organic solvent (such as EtOAc or DCM) and water. The layers are separated, and the organic solution is dried over anhydrous $Na_2SO_4$ or $MgSO_4$, filtered, and concd under reduced pressure to give the target compound.

Illustration of General Procedure DDDDD

Preparation #DDDDD.1: 8-(piperidin-4-yl)-3-((2-(trimethylsilyl)ethoxy)methyl)-3H-imidazo[1,2-a]pyrrolo[2,3-e]pyrazine

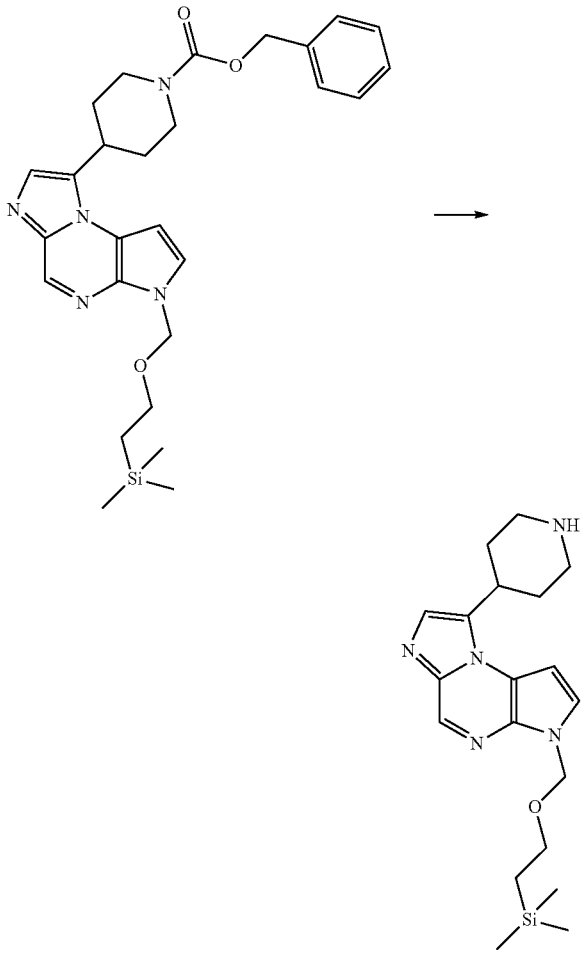

A solution of benzyl 4-(3-((2-(trimethylsilyl)ethoxy)methyl)-3H-imidazo[1,2-a]pyrrolo[2,3-e]pyrazin-8-yl)piperidine-1-carboxylate (0.580 g, 1.15 mmol, prepared using R from 1-(benzyloxycarbonyl)piperidine-4-carboxylic acid (Matrix), S from Example #3 Step E, E with TFA, KKKK with PFPAA, D with NaOH, KK), TEA (0.03 mL, 0.229 mmol), palladium (II) chloride (0.020 g, 0.115 mmol) in triethylsilane (18.3 mL, 115 mmol) was heated at about 120° C. for about 8 h. The catalyst was removed by filtration and the filtrate was concentrated under reduced pressure. The product was purified by silica gel chromatography eluting with a gradient of 0-10% (90:9:1) (MeOH/DCM/DEA) in DCM to give 8-(piperidin-4-yl)-3-((2-(trimethylsilyl)ethoxy)methyl)-3H-imidazo[1,2-a]pyrrolo[2,3-e]pyrazine (0.234 g, 55%) as a brown oil: LC/MS (Table 1, Method b) $R_t$=1.93 min; MS m/z: 372 $(M+H)^+$.

General Procedure EEEEE: Formation of a Guanidine

To an amine (preferably 1 equiv) in an organic solvent (for example DMF, MeCN, 1,4-dioxane or THF, preferably DMF) is added an aqueous base (for example aqueous $Na_2CO_3$, NaOH, $K_2CO_3$ or $NaHCO_3$; (preferably $Na_2CO_3$, 2-20 equiv, preferably 2-10 equiv)) or an organic base such as TEA or DIEA (preferably DIEA, 1-5 equiv, preferably 4 equiv) and addition of 1H-pyrazole-1-carboximidamide hydrochloride (1-10.0 equiv, preferably 3equiv). The reaction is stirred at about 10-40° C. (preferably rt) for about 2-90 h (preferably about 72 h) and worked up using one of the following methods. Method 1: An organic solvent (such as $Et_2O$, EtOAc or DCM) and water are added and the layers are separated. The aqueous layer is extracted with additional organic solvent and the combined organic layers may be optionally washed with brine, dried over anhydrous $Na_2SO_4$ or $MgSO_4$, and then decanted or filtered prior to concentrating under reduced pressure. Method 2: The reaction mixture is directly purified.

Illustration of General Procedure EEEEE

Preparation #EEEEE.1: 4-(3-((2-(trimethylsilyl) ethoxy)methyl)-3H-imidazo[1,2-a]pyrrolo[2,3-e] pyrazin-8-yl)piperidine-1-carboximidamide

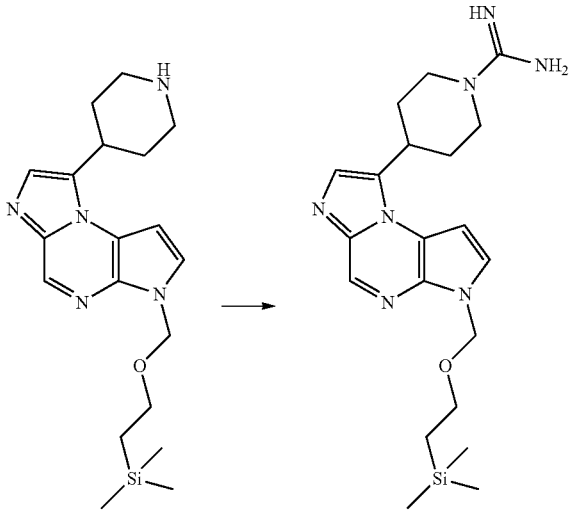

A solution of 8-(piperidin-4-yl)-3-((2-(trimethylsilyl) ethoxy)methyl)-3H-imidazo[1,2-a]pyrrolo[2,3-e]pyrazine (0.100 g, 0.269 mmol, Preparation #DDDDD.1), 1H-pyrazole-1-carboximidamid, hydrochloride (0.118 g, 0.807 mmol) and DIEA (0.188 mL, 1.08 mmol) in DMF (2 mL) was stirred at rt for about 72 h. The reaction mixture was purified by RP-HPLC (Table 1, Method 1) to give 4-(3-((2-(trimethylsilyl)ethoxy)methyl)-3H-imidazo[1,2-a]pyrrolo [2,3-e]pyrazin-8-yl)piperidine-1-carboximidamide (0.037 g, 33%) as a brown oil: LC/MS (Table 1, Method b) $R_t$=1.82 min; MS m/z: 414 $(M+H)^+$.

General Procedure FFFFF: Formation of a Sulfoxonium Ylide

To a suspension of a carboxylic acid (preferably 1 equiv) in an organic solvent (such as THF, 2-methyl tetrahydrofuran, or MTBE, preferably THF) is added an organic base such as Hunig's base or TEA (preferably TEA) (1.2-3.5 equiv, preferably 3.5 equiv) and activating agent such as DCC or HATU (preferably HATU) (1-1.5 equiv, preferably 1.01 equiv). The reaction is stirred at 10 to 40° C. preferably ambient temperature for about 1-20 h (preferably about 1-2 h). In a separate flask, trimethylsulfoxonium chloride (1.25-5 equiv, preferably 3 equiv) is added to a suspension of a base such as sodium tert-butoxide or potassium tert-butoxide (3-5 equiv, preferably 3.15 equiv) in an organic solvent (such as THF, 2-methyl tetrahydrofuran, or MTBE, preferably THF). The reaction is stirred at about 60 to 70° C. (preferably 65° C.) for about 2-4 h (preferably about 3 h). The suspension is cooled to about −5 to 5° C. and the above activated ester solution is added dropwise over about 20-60 min. The reaction mixture is stirred at about −5 to 5° C. for about 1-20 h (preferably about 1-2 h). The reaction mixture is quenched with water dropwise at about 0 to 40° C. (preferably ambient temperature) over about 2-50 min and stirred for about 0.2-20 h (preferably about 18 h at ambient temperature. The reaction may be concentrated under reduced pressure to remove volatiles and then partitioned between an organic solvent (such as EtOAc) and water. The aqueous layer can be optionally extracted with additional organic solvent such as EtOAc. The combined organic layer is washed with water, dried over anhydrous $Na_2SO_4$ or $MgSO_4$, filtered, concentrated under reduced pressure to give the target compound.

Illustration of General Procedure FFFFF

Preparation #FFFFF.1: 2-(4-(Dibenzylamino)cyclohexyl)-dimethylsulfoxonium-2-oxo-ethylide

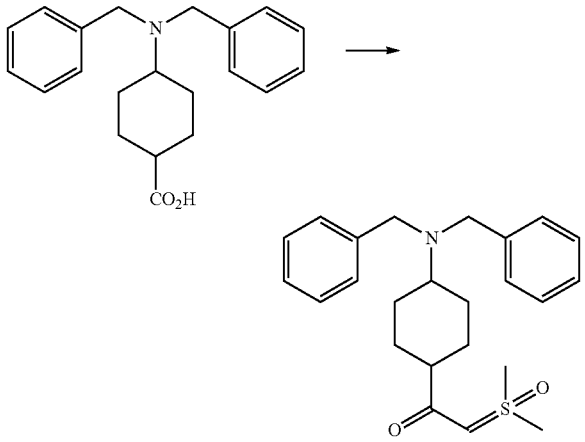

To a 250 mL flask, 4-(dibenzylamino)cyclohexanecarboxylic acid (5.6 g, 17.3 mmol), HATU (6.75 g, 17.4 mmol) and TEA (8.45 mL, 60.6 mmol) in THF (60 mL) were added to give a white suspension. The reaction mixture was stirred at ambient temperature for about 1 h. To a 500 mL flask, trimethylsulfoxonium chloride (6.82 g, 51.9 mmol) and potassium tert-butoxide (6.44 g, 54.5 mmol) in THF (60 mL) were added to give another white suspension. The reaction mixture was stirred at about 65° C. for about 3 h. The reaction mixture was cooled to about 5° C. The above activated ester solution was added dropwise over about 50 min. The reaction mixture was stirred at about 0-5° C. for about 90 min. The reaction mixture was quenched by the addition of water (120 mL) dropwise at about 0-5° C. over about 25 min. The reaction mixture was stirred at about 0-5°

C. for about 30 min, then at ambient temperature for about 18 h. The mixture was concd under reduced pressure to give a white suspension. The suspension was partitioned between EtOAc (300 mL) and water (200 mL). The aqueous layer was extracted with EtOAc (2×100 mL). The combined organic layer was washed with water (50 mL) and brine (3×40 mL). The organic layer was dried over anhydrous $Na_2SO_4$ and concd under reduced pressure. The residue was dissolved in hot MeOH (100 mL) and concd under reduced pressure. The oil was dissolved in hot MeOH (60 mL) and concd to give a white solid. The solid was dissolved in MeOH (36 mL) and water (12 mL) at about 55° C. The solution was cooled to ambient temperature, then to about 5° C. Additional 3:1 MeOH/water (40 mL) was added to the suspension. The suspension was filtered, washed with 1:1 MeOH/water (20 mL) then with heptane (20 mL). The collected wet cake was dried in a heated vacuum oven at about 60° C. for about 72 h to 2-(4-(dibenzylamino)cyclohexyl)dimethylsulfoxonium-2-oxo-ethylide (5.44 g, 79%) as white solid: LC/MS (Table 1, Method a) $R_t$=1.42, 1.45 min; MS m/z 398 $(M+H)^+$.

General Procedure GGGGG: Reaction of a Sulfoxonium Ylide with an Amine

To a mixture of sulfoxonium ylide (preferably 1 equiv) and an amine (0.7-2 equiv, preferably 1.2 equiv) is added a catalyst (such as $[Ir(COD)Cl]_2$, $[(COD)Ir(OMe)]_2$, (COD)Ir (a-cac), $Ir(COD)_2BF_4$, $Ir(COD)_2BArF$, $Rh_2(OAc)_2$, $Rh_2(TFA)_4$, $[Ru(cym)Cl_2]_2$, $RuCl_2(PPh_3)_3$, $RuCl_2(DMSO)_4$, preferably $[Ir(COD)Cl]_2$ (0.01-0.1 equiv, preferably 0.04 equiv)). A degassed organic solvent (such as DCM, DCE, MeCN, THF, 2-methyl tetrahydrofuran, $CHCl_3$, toluene, or DMF, preferably DCE) is added. The reaction is purged with $N_2$ for about 10-20 min and stirred at about 20-90° C. (preferably about 70° C.) for about 1-96 h (preferably about 3-6 h). Optionally, additional catalyst (preferably $[Ir(COD)Cl]_2$ equiv) may be added to the reaction mixture in cases where the reaction does not proceed to completion as monitored by TLC, LC/MS, or HPLC. Once the reaction has proceeded to an acceptable level, the reaction mixture can be concd in vacuo to provide the product.

Illustration of General Procedure GGGGG

Preparation #GGGGG.1: 1-(4-(dibenzylamino)cyclohexyl)-2-(5-tosyl-5H-pyrrolo[2,3-b]pyrazin-2-ylamino)ethanone

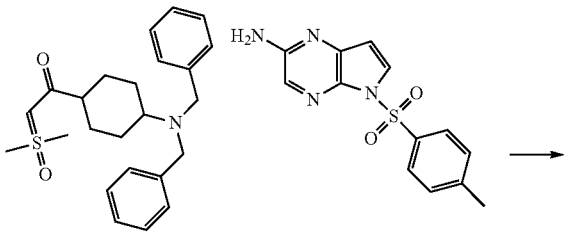

-continued

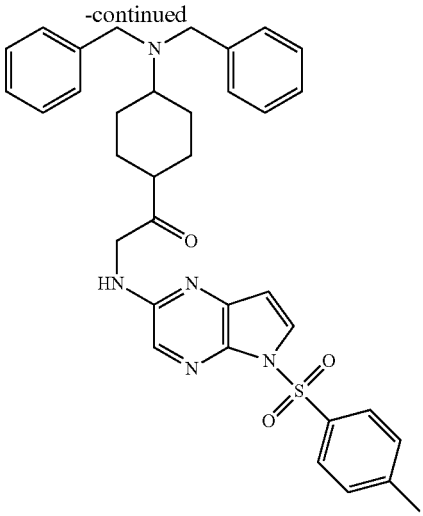

To a 100 mL 2-neck round-bottomed flask, 2-(4-(dibenzylamino)cyclohexyl)-dimethylsulfoxonium-2-oxo-ethylide (5.4 g, 13.6 mmol, Preparation #FFFFF.1), 5-tosyl-5H-pyrrolo[2,3-b]pyrazin-2-amine (4.7 g, 16.3 mmol, Preparation #E.1.1), and $[Ir(COD)Cl]_2$ (0.365 g, 0.543 mmol, Alfa Aesar) were added. The reaction vessel was purged with $N_2$ for about 10 min. To the reaction vessel, degassed DCE (25 mL) was added via syringe. The reaction mixture was purged with $N_2$ for about 10 min and stirred under an atmosphere of $N_2$ at about 70° C. for about 3 h. The reaction mixture was allowed to cool to ambient temperature. The solvent was removed under reduced pressure. The residue was purified by silica gel flash chromatography eluting with a gradient of 5-70% EtOAc in heptane to yield 1-(4-(dibenzylamino)cyclohexyl)-2-(5-tosyl-5H-pyrrolo[2,3-b]pyrazin-2-ylamino)ethanone (5.8 g, 65%) as glassy solid: LC/MS (Table 1, Method a) $R_t$=3.24 and 3.26 min; MS m/z 608 $(M+H)^+$.

Example #1

Example #1.1: N,N-diethyl-1-((1S,3R,4R)-3-ethyl-4-(6H-pyrrolo[2,3-e][1,2,4]triazolo[4,3-a]pyrazin-1-yl)cyclopentyl)methanesulfonamide, Example #1.2: N,N-diethyl-1-((1R,3S,4S)-3-ethyl-4-(6H-pyrrolo[2,3-e][1,2,4]triazolo[4,3-a]pyrazin-1-yl)cyclopentyl)methanesulfonamide, Example #1.3: N,N-diethyl-1-((1S,3S,4S)-3-ethyl-4-(6H-pyrrolo[2,3-e][1,2,4]triazolo[4,3-a]pyrazin-1-yl)cyclopentyl)methanesulfonamide, Example #1.4: N,N-diethyl-1-((1R,3R,4R)-3-ethyl-4-(6H-pyrrolo[2,3-e][1,2,4]triazolo[4,3-a]pyrazin-1-yl)cyclopentyl)methanesulfonamide, Example #1.5: N,N-diethyl-1-((1S,3S,4R)-3-ethyl-4-(6H-pyrrolo[2,3-e][1,2,4]triazolo[4,3-a]pyrazin-1-yl)cyclopentyl)methanesulfonamide, and Example #1.6: N,N-diethyl-1-((1R,3S,4R)-3-ethyl-4-(6H-pyrrolo[2,3-e][1,2,4]triazolo[4,3-a]pyrazin-1-yl)cyclopentyl)methanesulfonamide

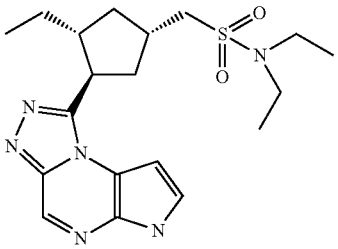

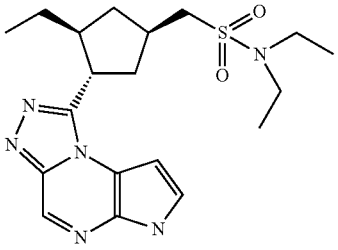

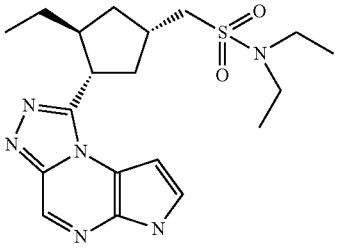

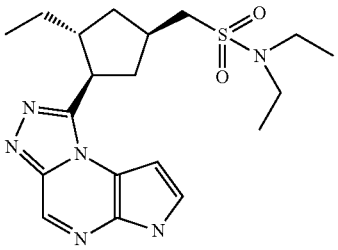

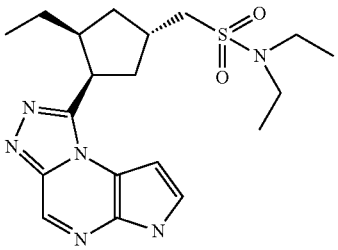

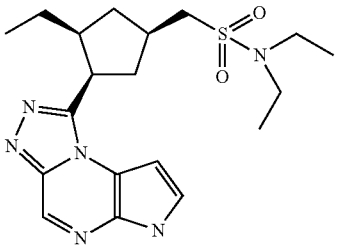

Step A: 5-bromo-3-((trimethylsilyl)ethynyl)pyrazin-2-amine

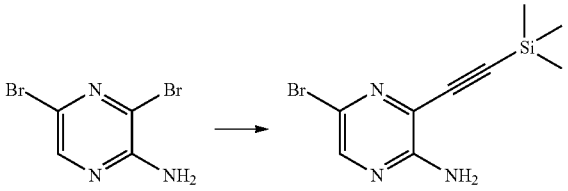

To a solution of 3,5-dibromopyrazin-2-amine (125 g, 494 mmol), TEA (207.0 mL, 1483 mmol), and copper (I) iodide (0.941 g, 4.94 mmol) in THF (1255 mL) was added $PdCl_2(PPh_3)_2$ (3.47 g, 4.94 mmol). The reaction mixture was cooled at about −5-0° C. and a solution of (trimethylsilyl) acetylene (65.0 mL, 470 mmol) in THF (157 mL) was added dropwise over about 15 min. The reaction mixture was stirred at about −5-0° C. for about 1.5 h and then allowed to warm to rt overnight. The reaction mixture was then filtered through a Celite® pad and washed with THF until no further product eluted. The filtrate was concd under reduced pressure to give a brown-orange solid. The solid was triturated and sonicated with warm petroleum ether (b.p. 30-60° C., 400 mL), cooled to rt, collected, washed with petroleum ether (b.p. 30-60° C.; 2×60 mL), and dried to give 5-bromo-3-((trimethylsilyl)ethynyl)pyrazin-2-amine (124 g, 93%, 93% purity) as a brown solid: LC/MS (Table 1, Method b) $R_t$=2.51 min; MS m/z: 270, 272 $(M+H)^+$.

Step B: 2-bromo-5-tosyl-5H-pyrrolo[2,3-b]pyrazine

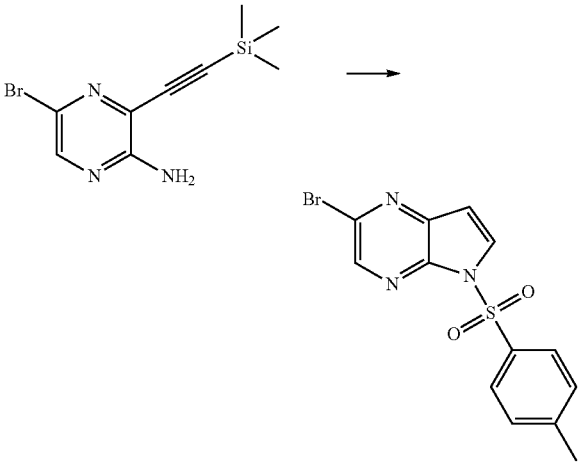

To a solution of 5-bromo-3-((trimethylsilyl)ethynyl) pyrazin-2-amine (3.00 g, 11.1 mmol) in DMF (60 mL) at about 0° C. was added NaH (60% dispersion in mineral oil, 0.577 g, 14.4 mmol) in three portions. After about 15 min, p-toluenesulfonyl chloride (2.75 g, 14.4 mmol) was added and the reaction was allowed to warm slowly to ambient temperature. After about 16 h, the reaction mixture was poured onto ice-cold water (120 mL) and the precipitate was collected by vacuum filtration. The crude solid was dissolved in DCM (15 mL) and purified by silica gel chromatography eluting with DCM to give 2-bromo-5-tosyl-5H-pyrrolo[2,3-b]pyrazine (2.16 g, 52%): LC/MS (Table 1, Method c) $R_t$=1.58 min; MS m/z: 352, 354 $(M+H)^+$.

Step C: tert-butyl 2-(5-tosyl-5H-pyrrolo[2,3-b]pyrazin-2-yl)hydrazinecarboxylate and tert-butyl 1-(5-tosyl-5H-pyrrolo[2,3-b]pyrazin-2-yl)hydrazinecarboxylate

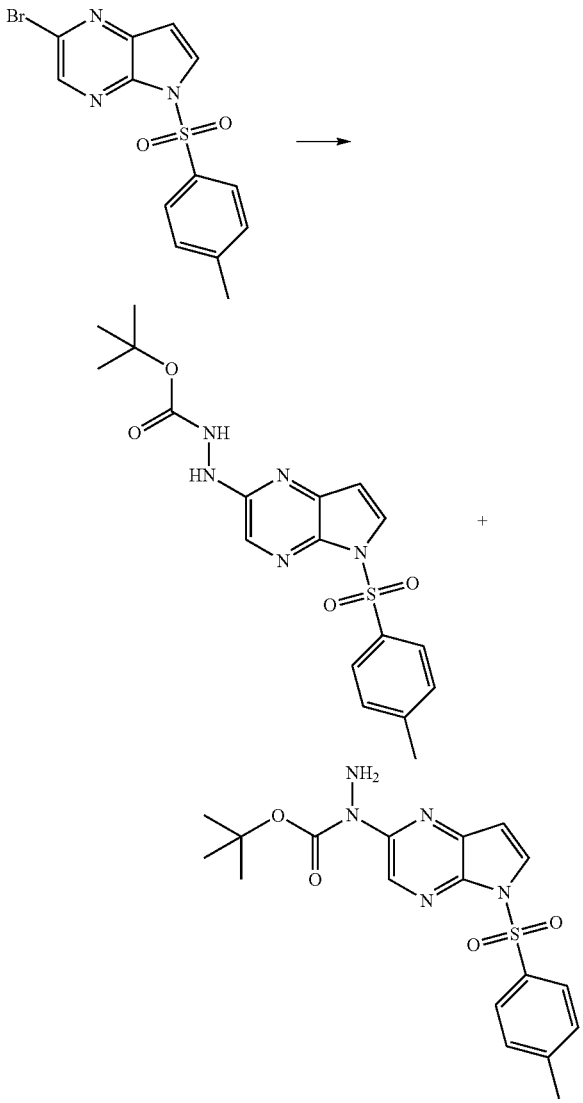

To a flask was added $Pd_2(dba)_3$ (3.90 g, 4.26 mmol), di-tert-butyl-(2',4',6'-triisopropylbiphenyl-2-yl)phosphane (3.62 g, 8.52 mmol), and 1,4-dioxane (453 mL). The catalyst-ligand mixture was degassed via vacuum/nitrogen purge (3 times) and heated at about 80° C. for about 10 min and cooled to ambient temperature. Then 2-bromo-5-tosyl-5H-pyrrolo[2,3-b]pyrazine (30.0 g, 85 mmol), tert-butyl hydrazinecarboxylate (16.9 g, 128 mmol), and NaOt-Bu (12.28 g, 128 mmol) were added. After an additional vacuum/nitrogen purge, the reaction was heated at about 80° C. After about 50 min, the reaction mixture was cooled to ambient temperature and filtered through a pad of silica gel (6 cm in height×6 cm in diameter), topped with Celite® (1 cm in height×6 cm in diameter), while washing with EtOAc (3×150 mL). Water (300 mL) was added to the filtrate and the organic layer was separated. The aqueous layer was extracted with additional EtOAc (3×200 mL). The combined organic extracts were washed with saturated aqueous $NH_4Cl$, saturated aqueous $NaHCO_3$, and brine (400 mL each), dried over anhydrous $MgSO_4$, filtered, and concd under reduced pressure to give a dark brown oil (45 g). The brown oil was dissolved in DCM (250 mL), silica gel (200 g) was added, and the mixture was concd under reduced pressure. The resulting silica mixture was purified using silica gel chromatography eluting with a gradient of 25-65% EtOAc in heptane to give a mixture of tert-butyl 2-(5-tosyl-5H-pyrrolo[2,3-b]pyrazin-2-yl)hydrazinecarboxylate [major regioisomer] and tert-butyl 1-(5-tosyl-5H-pyrrolo[2,3-b]pyrazin-2-yl)hydrazinecarboxylate [minor regioisomer] (18.8 g, 50%): LC/MS (Table 1, Method c) $R_t$=1.47 min; MS m/z: 404 $(M+H)^+$.

Step D: 2-hydrazinyl-5-tosyl-5H-pyrrolo[2,3-b]pyrazine

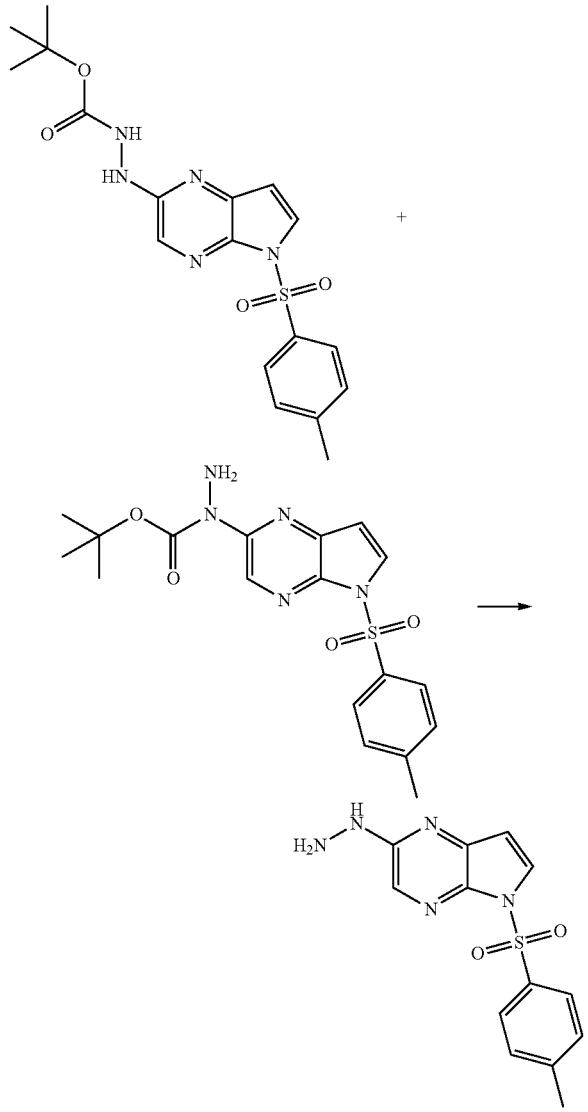

To a mixture of tert-butyl 2-(5-tosyl-5H-pyrrolo[2,3-b]pyrazin-2-yl)hydrazinecarboxylate and tert-butyl 1-(5-tosyl- 5H-pyrrolo[2,3-b]pyrazin-2-yl)hydrazinecarboxylate (49.2 g, 122 mmol) in 1,4-dioxane (290 mL) was added HCl (4 M in 1,4-dioxane, 226 mL, 902 mmol). The reaction was heated at about 60° C. for about 2.5 h and then cooled to about 15-20° C. The solid was collected by vacuum filtration, washed with EtOAc (3×50 mL), and then triturated with $Et_2O$ (60 mL), collected by vacuum filtration and dried to a constant weight under vacuum to yield 35.6 g of solid. The solid was stirred with a mixture of saturated aqueous $NaHCO_3$ and EtOAc (1:1, 400 mL). After about 1 h, the solid was collected by vacuum filtration, washed with ice cold water (3×30 mL) and EtOAc (3×30 mL), and dried in a vacuum oven to a constant weight to afford 2-hydrazinyl-5-tosyl-5H-pyrrolo[2,3-b]pyrazine as a tan solid (21.2 g, 57%): LC/MS (Table 1, Method a) $R_t$=1.88 min; MS m/z: 304 $(M+H)^+$.

Step E: sodium 4-(ethoxycarbonyl)-3-ethyl-2-(methoxycarbonyl)cyclopenta-1,3-dienolate

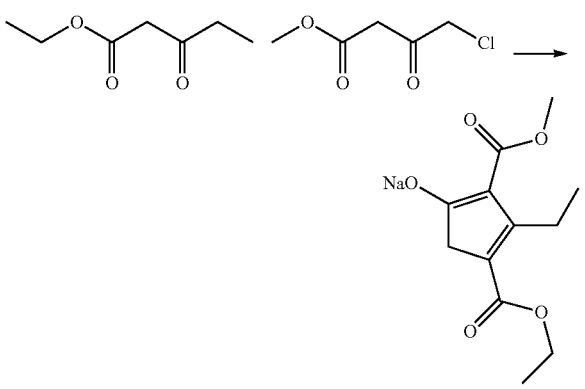

A round bottom flask was charged with THF (1.5 L) followed by the portionwise addition of NaH (60% dispersion in mineral oil, 70.0 g, 1.75 mol). Additional THF (500 mL) was added and the resulting mixture was cooled to about −10° C. and ethyl propionylacetate (250 mL, 1.80 mol) was added dropwise over about 1 h in order to keep internal temperature below about 10° C. The resulting mixture was stirred at ambient temperature for about 0.5 h to give a clear yellow solution, and methyl 4-chloroacetoacetate (100 mL, 0.88 mol) was added dropwise over about 5 min. The resulting mixture was heated at about 50° C. for about 19 h to give a reddish orange suspension. The reaction mixture was cooled to ambient temperature, concd under reduced pressure and the resulting liquid was transferred to a beaker and diluted with water (350 mL). The mixture was stirred in an ice bath for about 2 h. The solid was collected by vacuum filtration and the filter cake was rinsed with water (150 mL) and dried under vacuum for about 1 h. The solid was suspended in $Et_2O$ (1.5 L), filtered, washed with $Et_2O$ (1.5 L), and dried under vacuum. The resulting solid was azeotroped with toluene (1 L) to give a solid that was re-suspended in $Et_2O$ (1 L) and collected by vacuum filtration. The filter cake was washed with $Et_2O$ (500 mL) and dried under vacuum to give sodium 4-(ethoxycarbonyl)-3-ethyl-2-(methoxycarbonyl)cyclopenta-1,3-dienolate (204.2 g, 89%) as beige solid: $^1H$ NMR (DMSO-$d_6$) δ 3.94 (q, J=7.1 Hz, 2H), 3.46 (s, 3H), 3.04 (q, J=7.2 Hz, 2H), 2.66 (s, 2H), 1.13 (t, J=7.1 Hz, 3H), 0.99 (t, J=7.3Hz, 3H).

Step F: ethyl 2-ethyl-4-oxocyclopent-2-enecarboxylate

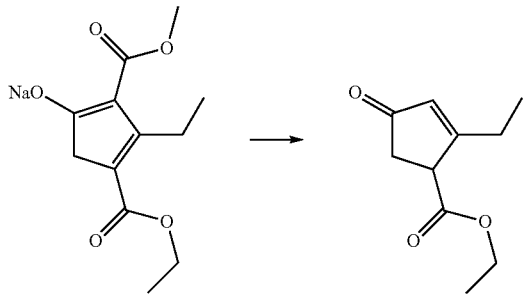

A 5 liter round bottom flask was charged with sodium 4-(ethoxycarbonyl)-3-ethyl-2-(methoxycarbonyl)cyclopenta-1,3-dienolate (316 g, 1205 mmol), KCl (126 g, 1687 mmol, JT-Baker), AcOH (241 mL, 4218 mmol, JT-Baker), toluene (1850 mL) and water (130 mL). The reaction was heated at reflux for about 6 h then cooled to ambient temperature and added dropwise to $NaHCO_3$ (8% aqueous, 3.5 L). The resulting biphasic mixture was extracted with MTBE (2×1.5 L). The combined organic layers were washed with brine (1 L), dried over anhydrous $MgSO_4$ and concd under reduced pressure to give 191 g of crude material that was purified by vacuum distillation (97-99° C., 0.600 mm Hg) to give ethyl 2-ethyl-4-oxocyclopent-2-enecarboxylate (160 g, 69%): $^1H$ NMR ($CDCl_3$) δ 6.04 (m, 1H), 4.26-4.15 (m, 2H), 3.76-3.69 (m, 1H), 2.75-2.57 (m, 2H), 2.56-2.44 (m, 2H), 1.32-1.26 (m, 3H), 1.23-1.18 (m, 3H).

Step G: ethyl 2-ethyl-4-oxocyclopentanecarboxylate

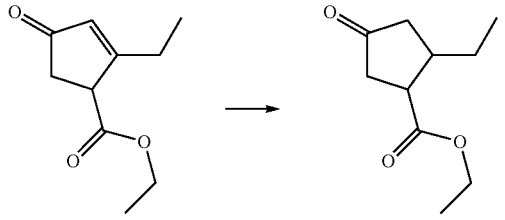

A round bottom flask was charged with 10 wt % Pd/C (10 g, 9.4 mmol). The flask was cooled to about 0° C. and EtOAc (400 mL) was added under a nitrogen atmosphere. The cooling bath was removed and ethyl 2-ethyl-4-oxocyclopent-2-enecarboxylate (47.8 g, 263 mmol) was added. Hydrogen gas was bubbled through the mixture for about 5 min and the mixture was then stirred under a hydrogen atmosphere for about 48 h. The hydrogen source was removed and the mixture was bubbled with nitrogen for about 5 min and was filtered through a pad of Celite®. The filter cake was rinsed with EtOAc (400 mL). The filtrate was concd under reduced pressure to give ethyl 2-ethyl-4-oxocyclopentanecarboxylate (about 9:1 mixture cis: trans) (48.0 g, 99%) as a yellow liquid: $^1H$ NMR ($CDCl_3$) δ 4.23-4.10 (m, 2H), 3.22 (m, 1H), 2.59-2.50 (m, 1H), 2.44-2.28 (m, 3H), 2.26-2.16 (m, 1H), 1.58-1.46 (m, 1H), 1.41-1.30 (m, 1H), 1.30-1.23 (m, 3H), 1.02-0.91 (m, 3H).

Step H: ethyl 2-ethyl-4-methylenecyclopentanecarboxylate

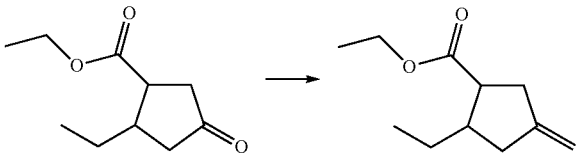

A solution of KOt-Bu (3.65 g, 32.6 mmol) and methyltriphenylphosphonium bromide (11.6 g, 32.6 mmol) in THF (69.5 mL) was cooled to about −10° C. A solution of ethyl 2-ethyl-4-oxocyclopentanecarboxylate (4.00 g, 21.7 mmol) in THF (17.4 mL) was added dropwise while the temperature was kept at about 0° C. The reaction mixture was allowed to warm to ambient temperature and stirred for about 16 h. The insoluble material was removed by filtration. The filtrate was concd under reduced pressure. The resulting material was purified by silica gel (120 g) chromatography eluting with a gradient of 0-20% EtOAc in heptane to provide ethyl 2-ethyl-4-methylenecyclopentanecarboxylate (2.55 g, 64%) as a colorless liquid: $^1$H NMR (d-DMSO) δ 4.88-4.78 (m, 2H), 4.16-3.96 (m, 2H), 2.66-2.31 (m, 4H), 2.24-1.82 (m, 2H), 1.50 (m, 1H), 1.35-1.22 (m, 1H), 1.18 (t, 3H), 0.85 (m, 3H).

Step I: ethyl 2-ethyl-4-(mercaptomethyl)cyclopentanecarboxylate

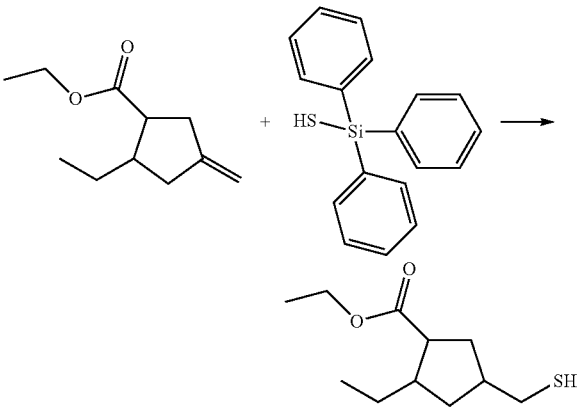

Ethyl 2-ethyl-4-methylenecyclopentanecarboxylate (0.720 g, 3.95 mmol), triphenylsilanethiol (1.329 g, 4.54 mmol) and 2,2'-azobis(2-methylpropionitrile) (0.195 g, 1.185 mmol) in toluene (3.95 mL) was heated at reflux for about 6 h. The reaction mixture was cooled to ambient temperature and then concd under reduced pressure. The material was purified by silica gel (40 g) chromatography eluting with a gradient of 0-10% EtOAc in heptane to give a colorless oil. The resulting oil was dissolved in DCM (4 mL) and TFA (1.52 mL, 19.7 mmol) was added. After stirring at ambient temperature for about 1 h, the solvent was removed under reduced pressure. The material was purified by silica gel (40 g) chromatography eluting with a gradient of 0-15% EtOAc in heptane to provide ethyl 2-ethyl-4-(mercaptomethyl)cyclopentanecarboxylate (0.620 g, 72%) as a colorless oil: $^1$H NMR (DMSO-$d_6$) δ 4.13-4.01 (m, 2H), 2.50-2.30 (m, 3H), 2.24 (m, 1H), 2.15-1.87 (m, 3H), 1.66-1.54 (m, 1H), 1.50-1.37 (m, 2H), 1.31-1.23 (m, 2H), 1.17 (t, 3H), 0.83 (m, 3H).

Step J: (3-(ethoxycarbonyl)-4-ethylcyclopentyl) methanesulfonic acid

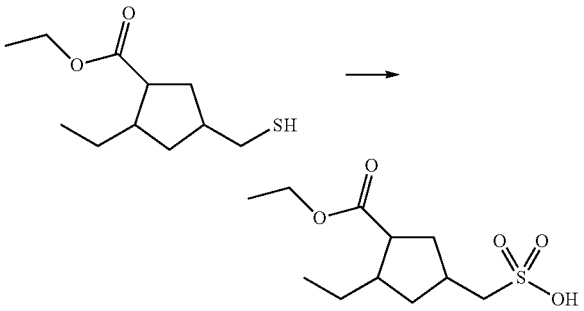

To a stirred solution of ethyl 2-ethyl-4-(mercaptomethyl) cyclopentanecarboxylate (2.50 g, 11.6 mmol) in DCM (50.7 mL) was added dropwise ethaneperoxoic acid (7.29 mL, 34.7 mmol) at about 0° C. The reaction mixture was warmed to ambient temperature and stirred for about 16 h. The solution was concd under reduced pressure to yield crude (3-(ethoxycarbonyl)-4-ethylcyclopentyl)methanesulfonic acid (3.18 g, 104%) as a dark brown oil: LC/MS (Table 1, Method b) $R_t$=1.39 min; MS m/z: 265 $(M+H)^+$.

Step K: ethyl 4-((N,N-diethylsulfamoyl)methyl)-2-ethylcyclopentanecarboxylate

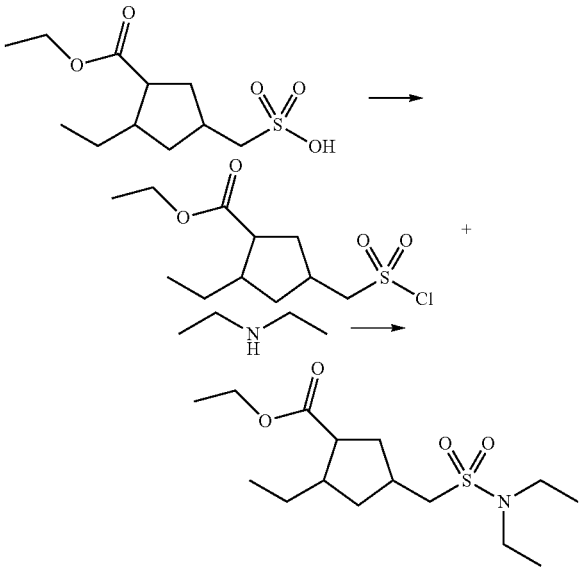

A solution of (3-(ethoxycarbonyl)-4-ethylcyclopentyl) methanesulfonic acid (3.18 g, 12.03 mmol) in DCM (10 mL) and DMF (10 mL) was cooled to about 0° C. Oxalyl chloride (24.1 mL, 48.1 mmol) was added dropwise while the temperature was kept at about 0° C. After the addition was complete, the reaction mixture was warmed to ambient temperature and stirred for about 1 h. The solvent was removed under reduced pressure. The residue was dissolved in DMF (10 mL) and then added dropwise to a solution of TEA (2.51 mL, 18.03 mmol) and diethylamine (0.937 mL, 9.02 mmol) in DMF (10 mL) at about 0° C. The reaction mixture was stirred at ambient temperature for about 16 h. The solvent was removed under reduced pressure. The material was purified by silica gel (120 g) chromatography eluting with a gradient of 10-60% EtOAc in heptane to provide ethyl 4-((N,N-diethylsulfamoyl)methyl)-2-ethylcyclopentanecarboxylate (0.570 g, 30%) as a yellow oil: LC/MS (Table 1, Method b) $R_t$=2.60 min; MS m/z: 320 $(M+H)^+$.

Step L: 4-((N,N-diethylsulfamoyl)methyl)-2-ethylcyclopentanecarboxylic acid

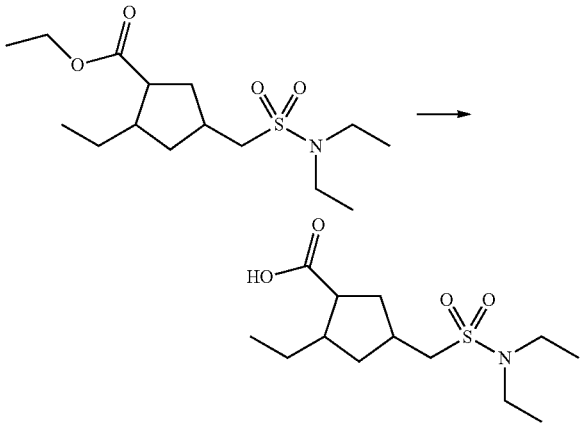

A mixture of ethyl 4-((N,N-diethylsulfamoyl)methyl)-2-ethylcyclopentanecarboxylate (0.570 g, 1.784 mmol) in NaOH (1 N aqueous, 10 mL, 10 mmol) was stirred at ambient temperature for about 72 h. The mixture was partitioned with DCM (10 mL). The aqueous phase was acidified to about pH=4 by addition of 6 N aqueous HCl. The solution was partitioned with DCM (10 mL). The aqueous phase was washed with DCM (2×10 mL). The organic layers were combined, dried over anhydrous $MgSO_4$, and concd under reduced pressure to give 4-((N,N-diethylsulfamoyl)methyl)-2-ethylcyclopentanecarboxylic acid (0.375 g, 72%) as yellow oil: LC/MS (Table 1, Method b) $R_t$=1.95 min; MS m/z: 292 $(M+H)^+$.

Step M: N,N-diethyl-1-(3-ethyl-4-(2-(5-tosyl-5H-pyrrolo[2,3-b]pyrazin-2-yl)hydrazinecarbonyl)cyclopentyl)methanesulfonamide

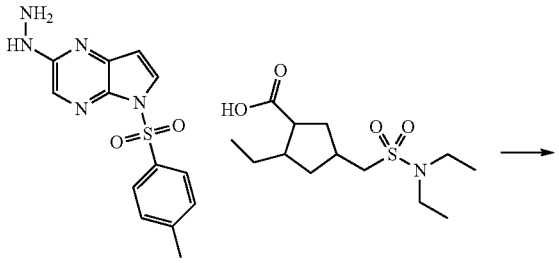

-continued

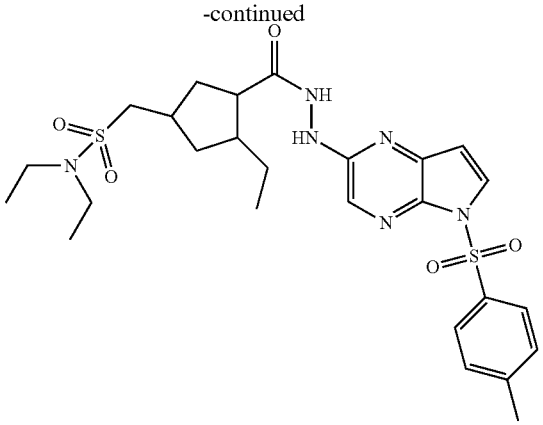

To a suspension of 2-hydrazinyl-5-tosyl-5H-pyrrolo[2,3-b]pyrazine (0.390 g, 1.287 mmol, Example #1 Step D), 4-((N,N-diethylsulfamoyl)methyl)-2-ethylcyclopentanecarboxylic acid (0.375 g, 1.287 mmol), and HATU (0.538 g, 1.416 mmol) in DCM (6.4 mL) was added TEA (0.538 mL, 3.86 mmol). The reaction mixture was stirred at ambient temperature for about 1 h. The reaction mixture was partitioned between water (50 mL) and DCM (50 mL). The aqueous layer was extracted with DCM (2×50 mL). The organic layers were combined and concd under reduced pressure. The material was purified by silica gel (120 g) chromatography eluting with a gradient of 20-100% EtOAc in DCM to provide N,N-diethyl-1-(3-ethyl-4-(2-(5-tosyl-5H-pyrrolo[2,3-b]pyrazin-2-yl)hydrazinecarbonyl)cyclopentyl)methanesulfonamide (0.730 g, 98%) as a brown solid: LC/MS (Table 1, Method b) $R_t$=2.39 min; MS m/z: 577 $(M+H)^+$.

Step N: N,N-diethyl-1-(3-ethyl-4-(6H-pyrrolo[2,3-e][1,2,4]triazolo[4,3-a]pyrazin-1-yl)cyclopentyl)methanesulfonamide

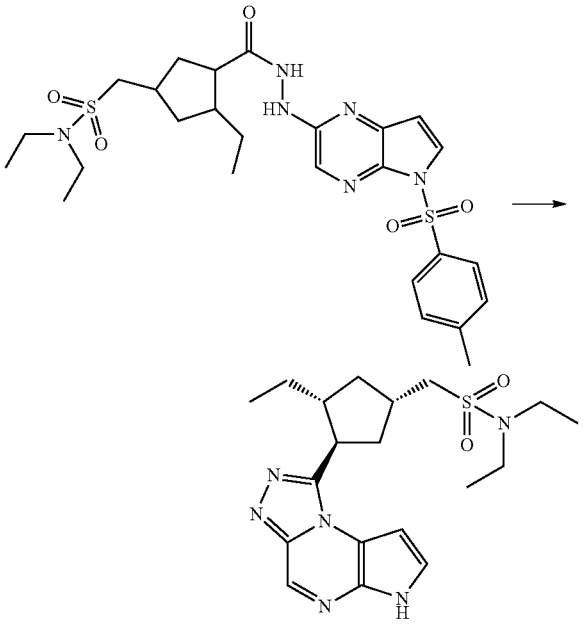

-continued

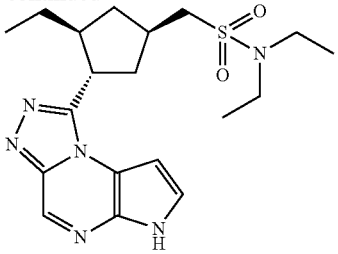

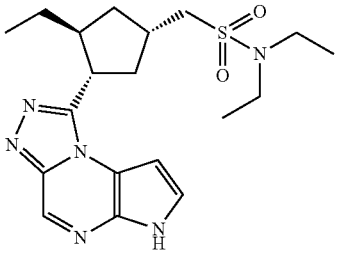

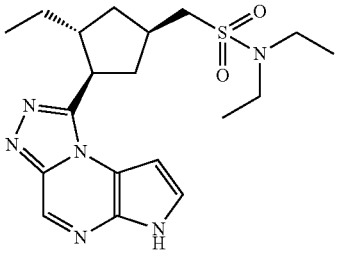

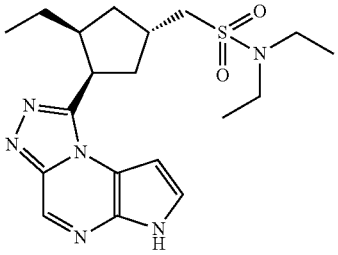

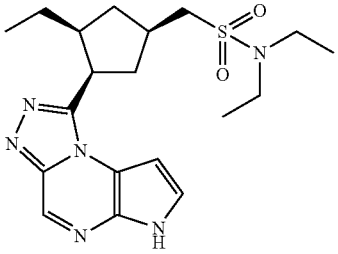

To a mixture of N,N-diethyl-1-(3-ethyl-4-(2-(5-tosyl-5H-pyrrolo[2,3-b]pyrazin-2-yl)hydrazinecarbonyl)cyclopentyl) methanesulfonamide (0.730 g, 1.27 mmol) and TEA (0.529 mL, 3.80 mmol) in 1,4-dioxane (12.7 mL) was added $SOCl_2$ (0.185 mL, 2.53 mmol). The reaction mixture was heated at about 80° C. for about 2 h. The reaction mixture was cooled to ambient temperature and partitioned between saturated aqueous $NaHCO_3$ (30 mL) and DCM (30 mL). The aqueous layer was washed with DCM (2×30 mL). The organic layers were combined, concd under reduced pressure, and purified by silica gel (80 g) chromatography eluting with a gradient of 0-60% MeOH in DCM to give a brown solid. The resulting solid was suspended in $Na_2CO_3$ (2 M aqueous, 2 mL), EtOH (2 mL) and 1,4-dioxane (2 mL). The reaction mixture was heated at about 60° C. for about 16 h. The reaction mixture was cooled to ambient temperature and purified by RP-HPLC (Table 1, Method d) to afford N,N-diethyl-1-(3-ethyl-4-(6H-pyrrolo[2,3-e][1,2,4]triazolo[4,3-a]pyrazin-1-yl)cyclopentyl)methanesulfonamide (0.300 g, 58%) as a tan solid: LC/MS (Table 1, Method b) $R_t$=1.89 min; MS m/z: 405 $(M+H)^+$. The solid was further purified by using General Procedure AA to give N,N-diethyl-1-((1S,3R,4R)-3-ethyl-4-(6H-pyrrolo[2,3-e][1,2,4]triazolo[4,3-a]pyrazin-1-yl)cyclopentyl)methanesulfonamide (Table 2, Method 27, $R_t$=11.8 min, or =negative) (0.021 g, 7%) [Example #1.1]; N,N-diethyl-1-((1R,3S,4S)-3-ethyl-4-(6H-pyrrolo[2,3-e][1,2,4]triazolo[4,3-a]pyrazin-1-yl)cyclopentyl)methane-sulfonamide (Table 2, Method 27, $R_t$=11.1 min, or =positive) (0.018 g, 6%) [Example #1.2]; N,N-diethyl-1-((1S,3S,4S)-3-ethyl-4-(6H-pyrrolo[2,3-e][1,2,4]triazolo[4,3-a]pyrazin-1-yl)cyclo-pentyl)methanesulfonamide (Table 2, Method 27, $R_t$=10.7 min, or =positive) (0.018 g, 6%) [Example #1.3]; N,N-diethyl-1-((1R,3R,4R)-3-ethyl-4-(6H-pyrrolo[2,3-e][1,2,4]triazolo[4,3-a]pyrazin-1-yl)cyclopentyl)methanesulfonamide (Table 2, Method 28, $R_t$=20.1 min, or =negative) (0.031 g, 11%) [Example #1.4]; N,N-diethyl-1-((1S,3S,4R)-3-ethyl-4-(6H-pyrrolo[2,3-e][1,2,4]triazolo[4,3-a]pyrazin-1-yl)cyclopentyl)methanesulfonamide (Table 2, Method 27, $R_t$=12.8 min, or =positive) (0.002 g, 1%) [Example #1.5]; and N,N-diethyl-1-((1R,3S,4R)-3-ethyl-4-(6H-pyrrolo[2,3-e][1,2,4]triazolo[4,3-a]pyrazin-1-yl)cyclopentyl)methanesulfonamide (Table 2, Method 27, $R_t$=12.8 min, or =positive) (0.001 g, 1%) [Example #1.6].

Example #2*

N-((1R,3R)-3-(6H-pyrrolo[2,3-e][1,2,4]triazolo[4,3-a]pyrazin-1-yl)cyclopentyl)aniline

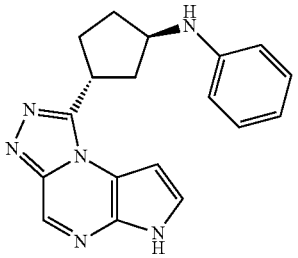

Step A: 5-bromo-3-((trimethylsilyl)ethynyl)pyrazin-2-amine

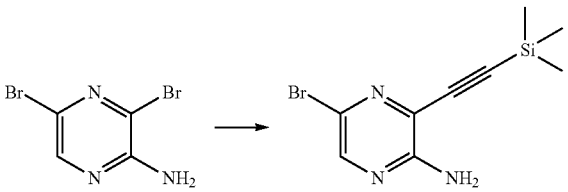

To a solution of 3,5-dibromopyrazin-2-amine (125 g, 494 mmol), TEA (207.0 mL, 1483 mmol), and copper (I) iodide (0.941 g, 4.94 mmol) in THF (1255 mL) was added $PdCl_2(PPh_3)_2$ (3.47 g, 4.94 mmol). The reaction mixture was cooled at about −5-0° C. and a solution of (trimethylsilyl) acetylene (65.0 mL, 470 mmol) in THF (157 mL) was added dropwise over about 15 min. The reaction mixture was stirred at about −5-0° C. for about 1.5 h and then allowed to warm to rt overnight. The reaction mixture was then filtered through a Celite® pad and washed with THF until no further product eluted. The filtrate was concd under reduced pressure to give a brown-orange solid. The solid was triturated and sonicated with warm petroleum ether (b.p. 30-60° C., 400 mL), cooled to rt, collected, washed with petroleum ether (b.p. 30-60° C.; 2×60 mL), and dried to give 5-bromo-3-((trimethylsilyl)ethynyl)pyrazin-2-amine (124 g, 93%, 93% purity) as a brown solid: LC/MS (Table 1, Method b) $R_t$=2.51 min; MS m/z: 270, 272 $(M+H)^+$.

Step B: 2-bromo-5-tosyl-5H-pyrrolo[2,3-b]pyrazine

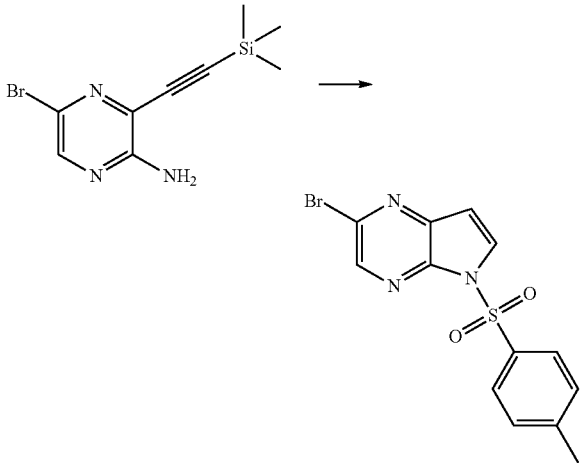

To a solution of 5-bromo-3-((trimethylsilyl)ethynyl) pyrazin-2-amine (3.00 g, 11.1 mmol) in DMF (60 mL) at about 0° C. was added NaH (60% dispersion in mineral oil, 0.577 g, 14.4 mmol) in three portions. After about 15 min, p-toluenesulfonyl chloride (2.75 g, 14.4 mmol) was added and the reaction was allowed to warm slowly to ambient temperature. After about 16 h, the reaction mixture was poured onto ice-cold water (120 mL) and the precipitate was collected by vacuum filtration. The crude solid was dissolved in DCM (15 mL) and purified by silica gel chromatography eluting with DCM to give 2-bromo-5-tosyl-5H-pyrrolo[2,3-b]pyrazine (2.16 g, 52%): LC/MS (Table 1, Method c) $R_t$=1.58 min; MS m/z: 352, 354 $(M+H)^+$.

Step C: tert-butyl 2-(5-tosyl-5H-pyrrolo[2,3-b] pyrazin-2-yl)hydrazinecarboxylate and tert-butyl 1-(5-tosyl-5H-pyrrolo[2,3-b]pyrazin-2-yl)hydrazinecarboxylate

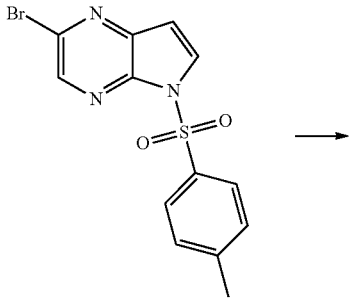

-continued

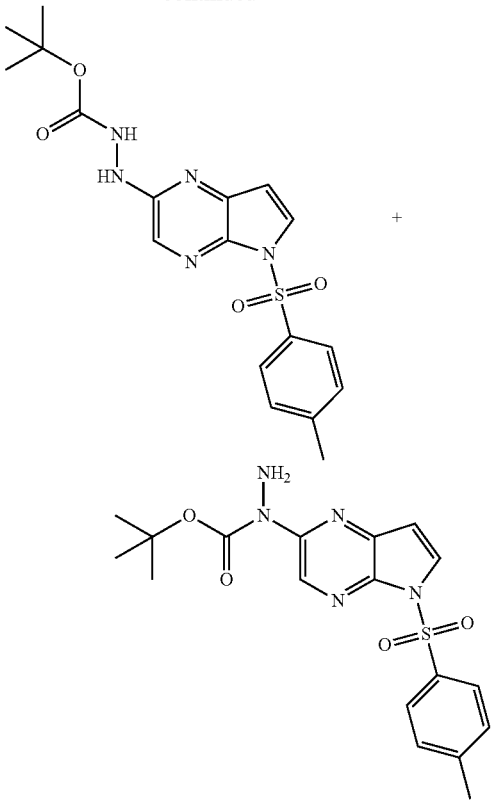

To a flask was added $Pd_2(dba)_3$ (3.90 g, 4.26 mmol), di-tert-butyl-(2',4',6'-triisopropylbiphenyl-2-yl)phosphane (3.62 g, 8.52 mmol), and 1,4-dioxane (453 mL). The catalyst-ligand mixture was degassed via vacuum/nitrogen purge (3 times) and heated at about 80° C. for about 10 min. Then 2-bromo-5-tosyl-5H-pyrrolo[2,3-b]pyrazine (30.0 g, 85 mmol), tert-butyl hydrazinecarboxylate (16.9 g, 128 mmol), and NaOt-Bu (12.28 g, 128 mmol) were added. After an additional vacuum/nitrogen purge, the reaction was heated at about 80° C. After about 50 min, the reaction mixture was cooled to ambient temperature and filtered through a pad of silica gel (6 cm in height×6 cm in diameter), topped with Celite® (1 cm in height×6 cm in diameter), while washing with EtOAc (3×150 mL). Water (300 mL) was added to the filtrate and the organic layer was separated. The aqueous layer was extracted with additional EtOAc (3×200 mL). The combined organic extracts were washed with saturated aqueous $NH_4Cl$, saturated aqueous $NaHCO_3$, and brine (400 mL each), dried over anhydrous $MgSO_4$, filtered, and concd under reduced pressure to give a dark brown oil (45 g). The brown oil was dissolved in DCM (250 mL), silica gel (200 g) was added, and the mixture was concd under reduced pressure. The resulting silica mixture was purified using silica gel chromatography eluting with a gradient of 25-65% EtOAc in heptane to give a mixture of tert-butyl 2-(5-tosyl-5H-pyrrolo[2,3-b]pyrazin-2-yl)hydrazinecarboxylate [major regioisomer] and tert-butyl 1-(5-tosyl-5H-pyrrolo[2,3-b]pyrazin-2-yl)hydrazinecarboxylate [minor regioisomer] (18.8 g, 50%): LC/MS (Table 1, Method c) $R_t$=1.47 min; MS m/z: 404 $(M+H)^+$.

Step D: 2-hydrazinyl-5-tosyl-5H-pyrrolo[2,3-b] pyrazine

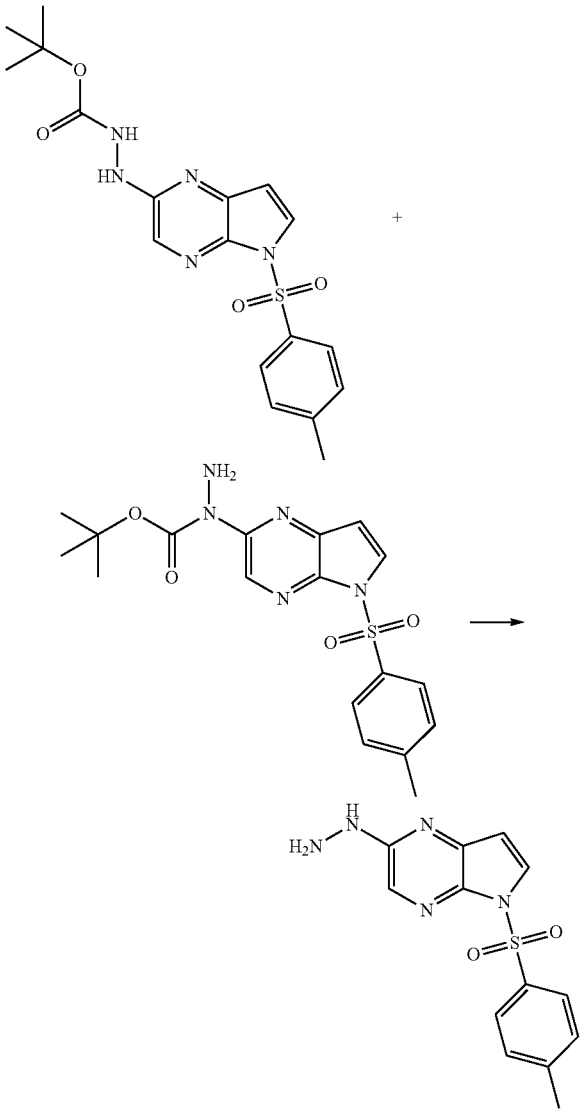

To a mixture of tert-butyl 2-(5-tosyl-5H-pyrrolo[2,3-b] pyrazin-2-yl)hydrazinecarboxylate and tert-butyl 1-(5-tosyl-5H-pyrrolo[2,3-b]pyrazin-2-yl)hydrazinecarboxylate (49.2 g, 122 mmol) in 1,4-dioxane (290 mL) was added HCl (4 M in 1,4-dioxane, 226 mL, 902 mmol). The reaction was heated at about 60° C. for about 2.5 h and then cooled to about 15-20° C. The solid was collected by vacuum filtration, washed with EtOAc (3×50 mL), and then triturated with $Et_2O$ (60 mL), collected by vacuum filtration and dried to a constant weight under vacuum to yield 35.6 g of solid. The solid was stirred with a mixture of saturated aqueous $NaHCO_3$ and EtOAc (1:1, 400 mL). After about 1 h, the solid was collected by vacuum filtration, washed with ice cold water (3×30 mL) and EtOAc (3×30 mL), and dried in a vacuum oven to a constant weight to afford 2-hydrazinyl-5-tosyl-5H-pyrrolo[2,3-b]pyrazine as a tan solid (21.2 g, 57%): LC/MS (Table 1, Method a) $R_t$=1.88 min; MS m/z: 304 $(M+H)^+$.

Step E: tert-butyl (1R,3R)-3-(2-(5-tosyl-5H-pyrrolo [2,3-b]pyrazin-2-yl)hydrazinecarbonyl)cyclopentyl-carbamate

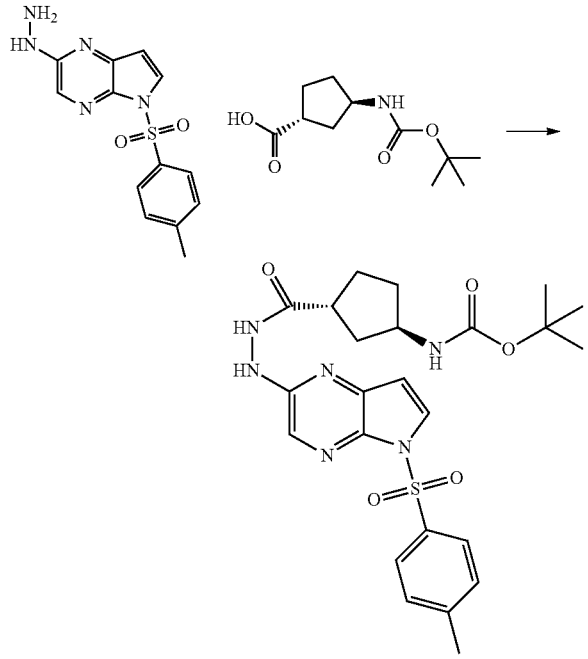

To (1R,3R)-3-(tert-butoxycarbonylamino)cyclopentanecarboxylic acid (2.25 g, 9.81 mmol, Acros) in DCM (98 mL) was added 2-hydrazinyl-5-tosyl-5H-pyrrolo[2,3-b] pyrazine (2.98 g, 9.81 mmol), HATU (3.73 g, 9.81 mmol) and TEA (5.5 mL, 39 mmol). The reaction mixture was stirred at ambient temperature for about 4 h then diluted with DCM (300 mL). The reaction mixture was washed with water (2×80 mL), saturated aqueous $NaHCO_3$ (80 mL), dried over anhydrous $MgSO_4$, filtered, and concd under reduced pressure. The residue was purified using silica gel chromatography (220 g) eluting with a gradient of 50-100% EtOAc in DCM give tert-butyl (1R,3R)-3-(2-(5-tosyl-5H-pyrrolo[2,3-b]pyrazin-2-yl)hydrazinecarbonyl)cyclopentyl-carbamate (5.03 g, 100%) as a brown solid: LC/MS (Table 1, Method b) $R_t$=2.18 min; MS m/z: 513 $(M-H)^-$ Step F: (1R,3R)-3-(6-tosyl-6H-pyrrolo[2,3-e][1,2,4] triazolo[4,3-a]pyrazin-1-yl)cyclopentanamine

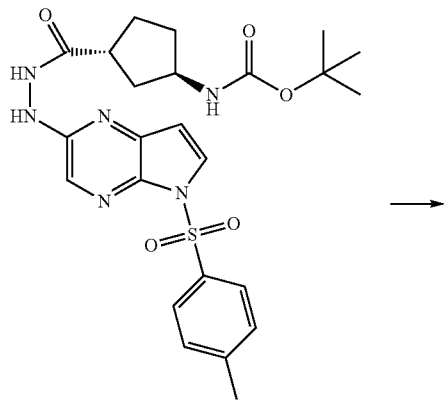

-continued

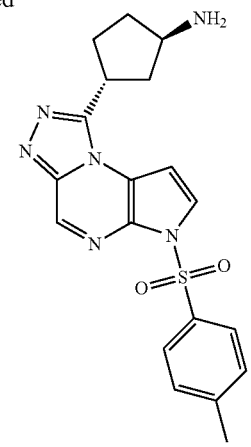

To tert-butyl (1R,3R)-3-(2-(5-tosyl-5H-pyrrolo[2,3-b]pyrazin-2-yl)hydrazinecarbonyl)cyclo-pentylcarbamate (5.03 g, 9.78 mmol) in 1,4-dioxane (103 mL) was added DIEA (7.2 mL, 41 mmol) and $SOCl_2$ (2.3 mL, 31 mmol). The reaction mixture was heated at about 80° C. for about 1 h. The solvent was removed under reduced pressure and the residue was purified using silica gel chromatography (330 g) eluting with a gradient of 0-20% MeOH in DCM to give (1R,3R)-3-(6-tosyl-6H-pyrrolo[2,3-e][1,2,4]triazolo[4,3-a]pyrazin-1-yl)cyclopentanamine (2.65 g, 68%): LC/MS (Table 1, Method b) $R_t$=1.55 min; MS m/z: 397 $(M+H)^+$.

Step G: N-((1R,3R)-3-(6-tosyl-6H-pyrrolo[2,3-e][1,2,4]triazolo[4,3-a]pyrazin-1-yl)cyclopentyl)aniline

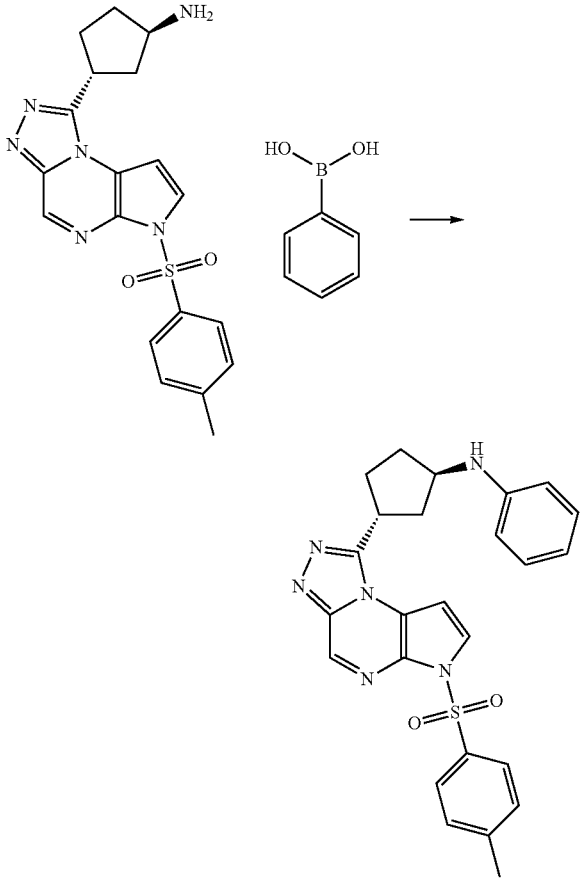

A 100 mL round bottom flask was sequentially charged with phenylboronic acid (0.123 g, 1.01 mmol), diacetoxycopper monohydrate (0.010 g, 0.05 mmol), powdered 4 Å molecular sieves (0.375 g) and DCM (4 mL). The reaction mixture was stirred for about 10 min then a suspension of (1R,3R)-3-(6-tosyl-6H-pyrrolo[2,3-e][1,2,4]triazolo[4,3-a]pyrazin-1-yl)cyclopentanamine (0.20 g, 0.50 mmol) in DCM (2 mL) and MeCN (2 mL) was added. The flask was fitted with an oxygen balloon. The flask was purged with oxygen and then heated at about 40° C. for about 18 h. Additional diacetoxycopper monohydrate (0.010 g, 0.05 mmol) was added and the reaction mixture was heated at about 45° C. under an atomosphere of oxygen for about 3 days. DCM (50 mL) was added and the reaction mixture was filtered through a pad of Celite® while washing with DCM (20 mL). The filtrate was concd under reduced pressure and the residue was purified using silica gel chromatography (20 g) eluting with a gradient of 30-80% EtOAc in DCM to give N-((1R,3R)-3-(6-tosyl-6H-pyrrolo[2,3-e][1,2,4]triazolo[4,3-a]pyrazin-1-yl)cyclopentyl)aniline (0.106 g, 45%): LC/MS (Table 1, Method b) $R_t$=2.39 min; MS m/z: 473 $(M+H)^+$.

Step H: N-((1R,3R)-3-(6H-pyrrolo[2,3-e][1,2,4]triazolo[4,3-a]pyrazin-1-yl)cyclopentyl)aniline

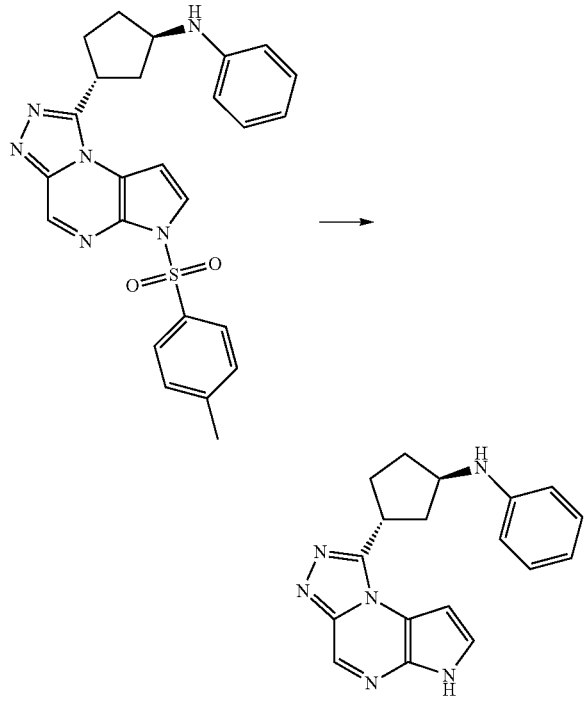

To N-((1R,3R)-3-(6-tosyl-6H-pyrrolo[2,3-e][1,2,4]triazolo[4,3-a]pyrazin-1-yl)cyclopentyl)aniline (0.106 g, 0.224 mmol) in 1,4-dioxane (1 mL) was added NaOH (1 N aqueous, 1.12 mL, 1.12 mmol). The reaction mixture was heated at about 60° C. for about 1 h. AcOH (0.5 mL) was added and the crude reaction mixture was purified by RP-HPLC (Table 1, Method j) to give N-((1R,3R)-3-(6H-pyrrolo[2,3-e][1,2,4]triazolo[4,3-a]pyrazin-1-yl)cyclopentyl)aniline (0.053 g, 74%) as a light yellow solid: LC/MS (Table 1, Method b) $R_t$=1.84 min; MS m/z: 319 $(M+H)^+$.

Example #3*

(R)-(3-(3H-imidazo[1,2-a]pyrrolo[2,3-e]pyrazin-8-yl)piperidin-1-yl)(3,3-difluorocyclobutyl)methanone

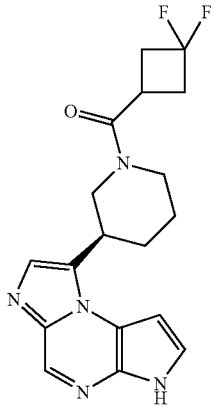

Step A: 5-bromo-3-((trimethylsilyl)ethynyl)pyrazin-2-amine

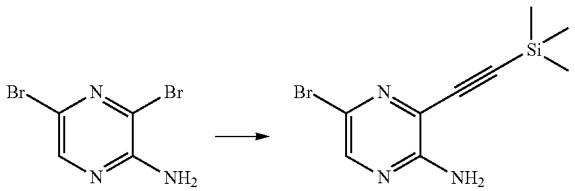

To a solution of 3,5-dibromopyrazin-2-amine (125 g, 494 mmol), TEA (207.0 mL, 1483 mmol), and copper (I) iodide (0.941 g, 4.94 mmol) in THF (1255 mL) was added $PdCl_2(PPh_3)_2$ (3.47 g, 4.94 mmol). The reaction mixture was cooled at about −5-0° C. and a solution of (trimethylsilyl) acetylene (65.0 mL, 470 mmol) in THF (157 mL) was added dropwise over about 15 min. The reaction mixture was stirred at about −5-0° C. for about 1.5 h and then allowed to warm to rt overnight. The reaction mixture was then filtered through a Celite® pad and washed with THF until no further product eluted. The filtrate was concd under reduced pressure to give a brown-orange solid. The solid was triturated and sonicated with warm petroleum ether (b.p. 30-60° C., 400 mL), cooled to rt, collected, washed with petroleum ether (b.p. 30-60° C.; 2×60 mL), and dried to give 5-bromo-3-((trimethylsilyl)ethynyl)pyrazin-2-amine (124 g, 93%, 93% purity) as a brown solid: LC/MS (Table 1, Method b) $R_t$=2.51 min; MS m/z: 270, 272 $(M+H)^+$.

Step B: 2-bromo-5-tosyl-5H-pyrrolo[2,3-b]pyrazine

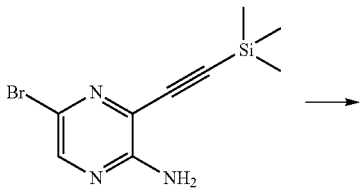

-continued

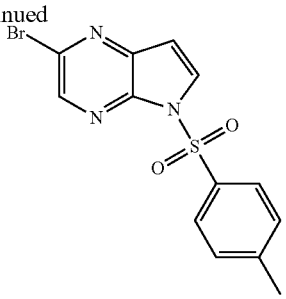

To a solution of 5-bromo-3-((trimethylsilyl)ethynyl) pyrazin-2-amine (3.00 g, 11.1 mmol) in DMF (60 mL) at about 0° C. was added NaH (60% dispersion in mineral oil, 0.577 g, 14.4 mmol) in three portions. After about 15 min, p-toluenesulfonyl chloride (2.75 g, 14.4 mmol) was added and the reaction was allowed to warm slowly to ambient temperature. After about 16 h, the reaction mixture was poured onto ice-cold water (120 mL) and the precipitate was collected by vacuum filtration. The crude solid was dissolved in DCM (15 mL) and purified by silica gel chromatography eluting with DCM to give 2-bromo-5-tosyl-5H-pyrrolo[2,3-b]pyrazine (2.16 g, 52%): LC/MS (Table 1, Method c) $R_t$=1.58 min; MS m/z: 352, 354 $(M+H)^+$.

Step C: methyl 5-tosyl-5H-pyrrolo[2,3-b]pyrazine-2-carboxylate

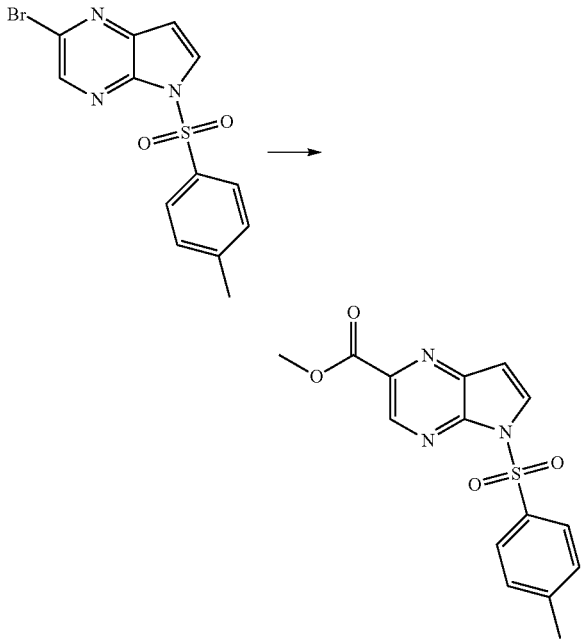

CO was bubbled into an orange solution of 2-bromo-5-tosyl-5H-pyrrolo[2,3-b]pyrazine (50.0 g, 142 mmol) in DMF (2.50 L) within a 5 L round bottom flask for about 2 min. Bis(triphenylphosphine)-palladium(II) dichloride (9.96 g, 14.2 mmol), TEA (59 mL, 423 mmol) and MeOH (173.0 mL, 4259 mmol) were added and the flask was fitted with a balloon of CO. The mixture was heated at about 95° C. under an atmosphere of CO (1 atmosphere). After stirring overnight, the reaction mixture was cooled to ambient temperature overnight and poured into ice water (3.2 L). The mixture was stirred for about 10 min and the precipitate was collected by filtration, while washing with water, and dried for 1 h. The crude material was dissolved in DCM, separated from residual water, dried over anhydrous $MgSO_4$, filtered, added silica gel, and concd under reduced pressure to prepare for chromatography. The crude material was purified by silica gel column chromatography eluting with 0-5% MeOH in DCM to yield methyl 5-tosyl-5H-pyrrolo[2,3-b]pyrazine-2-carboxylate with 5 mol % DCM as an excipient (40.7 g, 86%, 93% purity): LC/MS (Table 1, Method a) $R_t$=2.35 min; MS m/z 332 $(M+H)^+$.

Step D: 5-tosyl-5H-pyrrolo[2,3-b]pyrazine-2-carboxylic acid

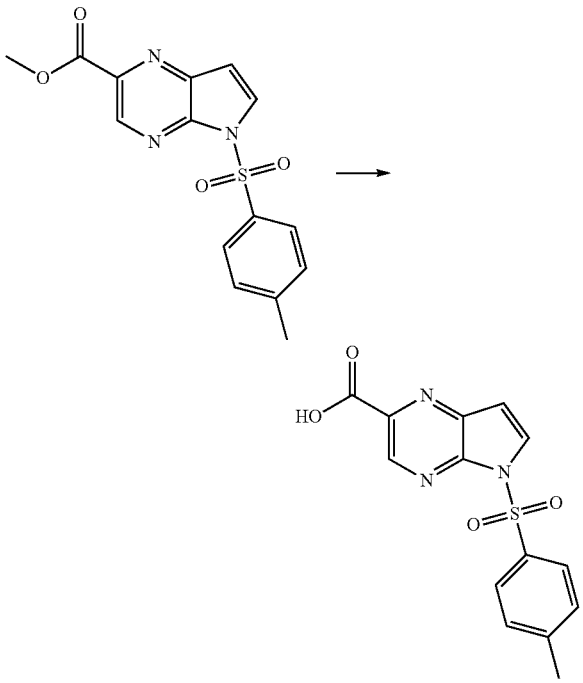

HCl (6 N aqueous, 714 mL) was added to a yellow solution of methyl 5-tosyl-5H-pyrrolo[2,3-b]pyrazine-2-carboxylate (17.8 g, 53.6 mmol) in 1,4-dioxane (715 mL) within a 2 L round bottom flask, and the mixture was heated at about 60° C. for about 16 h. The reaction mixture was cooled to ambient temperature. The organic solvent was removed under reduced pressure and the precipitate was collected, washed with water, and dried to yield 5-tosyl-5H-pyrrolo[2,3-b]pyrazine-2-carboxylic acid (14.4 g, 85%) as a yellow solid: LC/MS (Table 1, Method a) $R_t$=1.63 min; MS m/z 316 $(M-H)^-$.

Step E: tert-butyl 5-tosyl-5H-pyrrolo[2,3-b]pyrazin-2-ylcarbamate

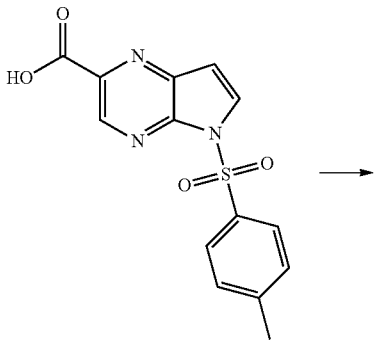

-continued

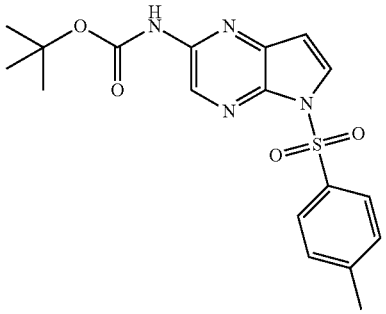

In a 500 mL round bottom flask, 5-tosyl-5H-pyrrolo[2,3-b]pyrazine-2-carboxylic acid (14.4 g, 45.3 mmol), diphenylphosphoryl azide (9.78 mL, 45.3 mmol) and TEA (13.9 mL, 100 mmol) in t-BuOH (200 mL) were added to give an orange suspension. The mixture was heated at about 70° C. for about 16 h, cooled to ambient temperature and the insoluble material was removed by filtration. The solvent was removed under reduced pressure and the crude material was purified by silica gel column chromatography eluting with 25-60% EtOAc in heptane to yield tert-butyl 5-tosyl-5H-pyrrolo[2,3-b]pyrazin-2-ylcarbamate (9.75 g, 54%) as an off-white solid: LC/MS (Table 1, Method a) $R_t$=2.79 min; MS m/z 389 $(M+H)^+$.

Step F: (R)-1-(benzyloxycarbonyl)piperidine-3-carboxylic acid

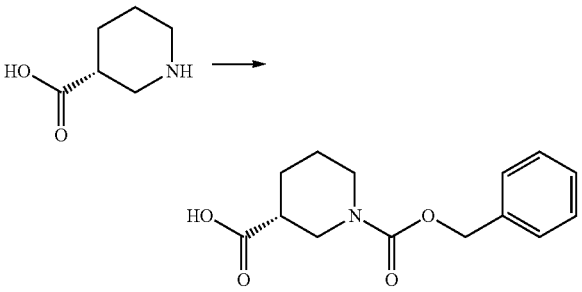

A mixture of (R)-piperidine-3-carboxylic acid (3.0 g, 23 mmol), benzyl 2,5-dioxopyrrolidin-1-yl carbonate (5.79 g, 23.2 mmol) and $Na_2CO_3$ (6.15 g, 58.1 mmol) was stirred in water and 1,4-dioxane (1:1, 200 mL) at ambient temperature for about 96 h. The organic solvent was removed under reduced pressure. The aqueous layer was acidified with 1 N aqueous HCl and extracted with EtOAc (2×100 mL). The organic phase was washed with brine (150 mL), dried over anhydrous $MgSO_4$ and concd under reduced pressure to yield crude (R)-1-(benzyloxycarbonyl)-piperidine-3-carboxylic acid (11.6 g, 191%) as a white solid: LC/MS (Table 1, Method a) $R_t$=1.80 min; MS m/z 264 $(M+H)^+$.

Step G: (R)-8-(piperidin-3-yl)-3H-imidazo[1,2-a]pyrrolo[2,3-e]pyrazine hydrobromide and (S)-8-(piperidin-3-yl)-3H-imidazo[1,2-a]pyrrolo[2,3-e]pyrazine hydrobromide

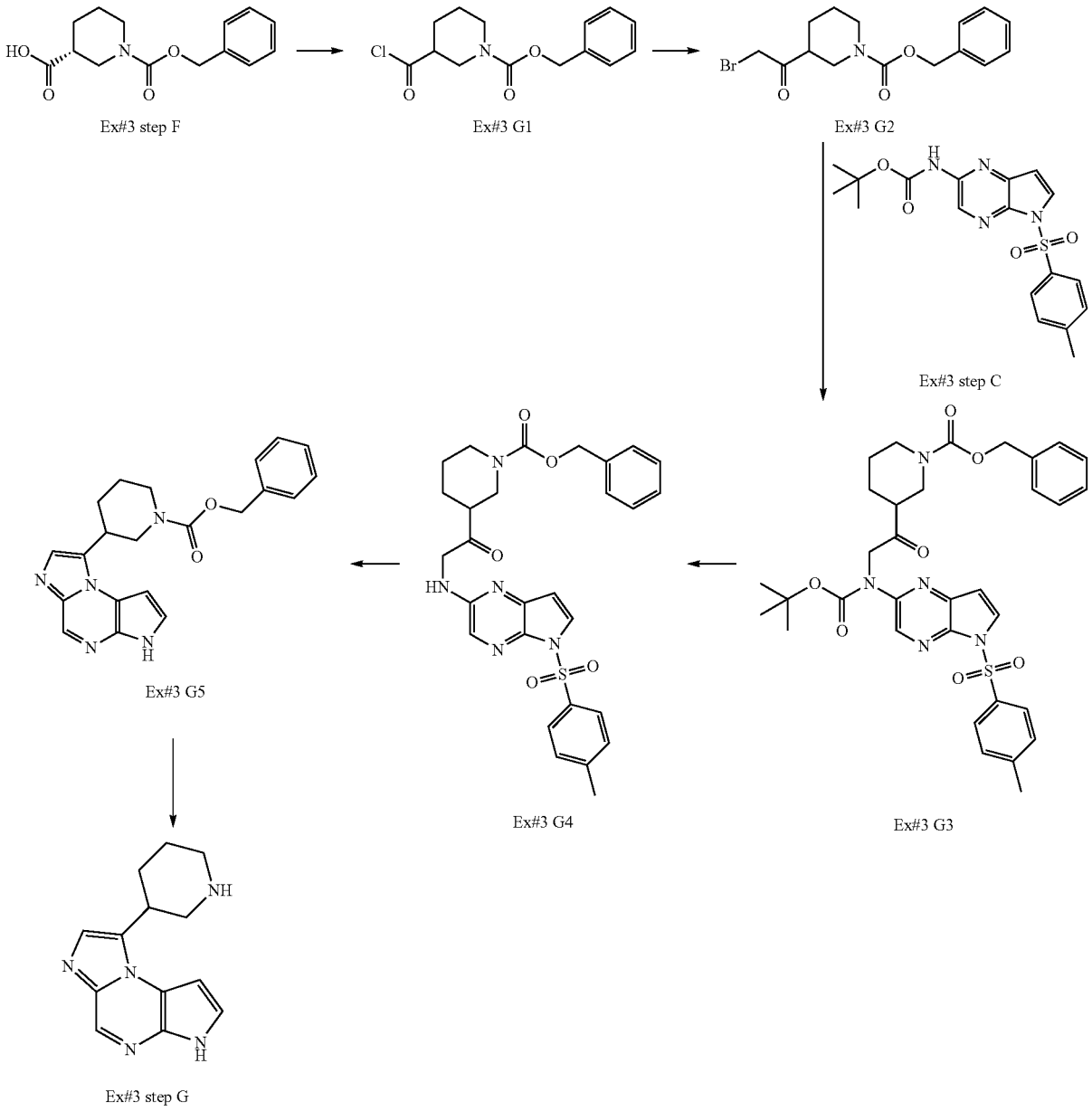

Oxalyl chloride (8.41 mL, 96 mmol) was added to a solution of (R)-1-(benzyloxycarbonyl)piperidine-3-carboxylic acid (11.5 g, 43.7 mmol, Ex#3, step F) in DCM (120 mL) followed by a dropwise addition of DMF (0.5 mL, 6.55 mmol). The resulting mixture was stirred at ambient temperature for about 14 h. The solvent was removed under reduced pressure to yield a crude acid chloride (Ex#3 G1) as a yellow semi-solid, which was dissolved in THF and MeCN (1:1, 160 mL) and added to trimethylsilyldiazomethane (2 M in $Et_2O$, 78 mL, 155 mmol) in THF and MeCN (1:1, 160 mL) at about 0° C. The reaction mixture was stirred at about 0° C. for about 2 h after the completion of the addition. The reaction mixture was then quenched by a dropwise addition of HBr (48% aqueous, 40 mL, 354 mmol). The organic solvents were removed under reduced pressure and the residue dissolved in EtOAc (100 mL). The organic phase was washed with saturated aqueous $NaHCO_3$ (100 mL), and brine (25 mL), dried over anhydrous $MgSO_4$, filtered, and concd under reduced pressure. The residue was purified by silica gel chromatography eluting with 5 to 45% EtOAc in heptane to yield the crude benzyl 3-(2-bromoacetyl)piperidine-1-carboxylate (Ex#3 G2) as a colorless oil. To a mixture of NaH (60% dispersion in mineral oil, 0.55 g, 14 mmol) in DMF (20 mL) was added dropwise a solution of tert-butyl 5-tosyl-5H-pyrrolo[2,3-b]pyrazin-2-ylcarbamate (Ex#3 step F) (5.00 g, 12.9 mmol) in DMF (20 mL) at about 0° C. The reaction mixture was stirred at this temperature for about 30 min and was then added dropwise to a solution of crude benzyl 3-(2-bromoacetyl)piperidine-1-carboxylate (Ex#3 G2) (5.26 g, 15.5 mmol) in DMF (40 mL) at about 0° C. The mixture was stirred for about 3 h while warming to ambient temperature. The solvent was removed under reduced pressure and the residue partitioned between saturated aqueous $NH_4Cl$ and EtOAc (70 mL each). The organic phase was further washed with brine (60 mL), dried over anhydrous $MgSO_4$, filtered, and concd under reduced pressure to yield crude Boc-protected aminomethylketone (Ex#3 G3) as a yellow oil that was used in the next step without further purification. The oil was dissolved in HCl (4 N in 1,4-dioxane, 40 mL) and the solution was stirred at ambient temperature for about 2 h. The solvent was removed under reduced pressure and the residue partitioned between saturated aqueous $NaHCO_3$ and DCM (200 mL each). The organic phase was washed with brine (150 mL), dried over anhydrous $MgSO_4$, filtered, and concd under reduced pressure to yield crude aminomethylketone (Ex#3 G4) as a brown amorphous solid. It was dissolved in 1,4-dioxane (100 mL) and Lawesson's reagent (1.94 g, 4.80 mmol) was added. The reaction mixture was heated at about 60° C. for about 2 h. NaOH (2 N aqueous, 3 mL) was added and heating was continued at about 90° C. for about 4 h. The organic solvent was removed under reduced pressure and saturated aqueous $NH_4Cl$ (120 mL) was added. The aqueous phase was extracted with DCM (2×100 mL) and the combined organic extracts were dried over anhydrous $MgSO_4$, filtered, and concd under reduced pressure. The crude material was purified by silica gel column chromatography eluting with 0-10% MeOH in DCM to yield crude imidazo[1,2-a]pyrrolo[2,3-e]pyrazine (Ex#3 G5) as a yellow amorphous solid. It was suspended in HBr (33% in AcOH, 10 mL). The resulting mixture was stirred for about 10 min and then was diluted with EtOAc (80 mL). The precipitate was collected by filtration and exhaustively washed with EtOAc to yield (R)-8-(piperidin-3-yl)-3H-imidazo[1,2-a]pyrrolo[2,3-e]pyrazine hydrobromide and (S)-8-(piperidin-3-yl)-3H-imidazo[1,2-a]pyrrolo[2,3-e]pyrazine hydrobromide [er=80:20](2.61 g, 62.9% overall) as a yellow solid: LC/MS (Table 1, Method a) $R_t$=0.63 min; MS m/z 242 $(M+H)^+$; chiral analytical LC (Table 1, Method 29) $R_t$=17.75 min, or =negative and $R_t$=20.33 min, or =positive.

Step H: (R)-(3-(3H-imidazo[1,2-a]pyrrolo[2,3-e]pyrazin-8-yl)piperidin-1-yl)(3,3-difluorocyclobutyl)methanone

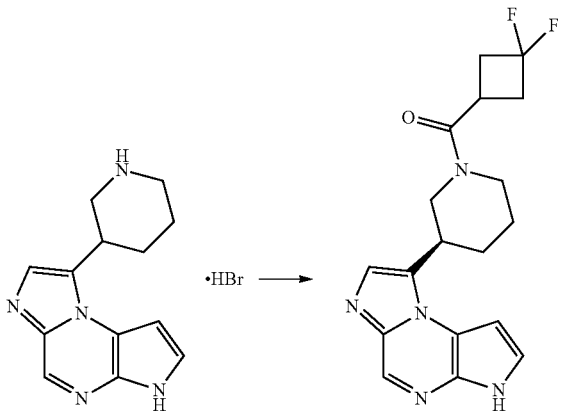

To a solution of (R)-8-(piperidin-3-yl)-3H-imidazo[1,2-a]pyrrolo[2,3-e]pyrazine hydrobromide and (S)-8-(piperidin-3-yl)-3H-imidazo[1,2-a]pyrrolo[2,3-e]pyrazine hydrobromide [er=80:20](0.30 g, 0.93 mmol), DIEA (0.52 mL, 3.0 mmol) and 3,3-difluorocyclobutanecarboxylic acid (0.35 g, 3.1 mmol, Waterstone) in DMF (4 mL) was added EDC•HCl (0.21 g, 1.1 mmol). The reaction was stirred at about 25° C. for about 4 h. The reaction was partitioned with aqueous $Na_2CO_3$ (2 M, 25 mL) and DCM (25 mL). The organic layer was separated, dried over anhydrous $Na_2SO_4$, filtered, and concd in vacuo. The resulting residue was purified on silica gel (12 g) using 0-5% MeOH in DCM followed by purification using General Procedure AA (Table 2, Method 23, $R_t$=16.4 min, or =positive) to give (R)-(3-(3H-imidazo[1,2-a]pyrrolo[2,3-e]pyrazin-8-yl)piperidin-1-yl)(3,3-difluorocyclobutyl)-methanone (0.10 g, 30%): LC/MS (Table 1, Method b) $R_t$=1.85 min; MS m/z: 360 $(M+H)^+$.

Example #4*

4-((1R,3R,4S)-3-ethyl-4-(6H-pyrrolo[2,3-e][1,2,4]triazolo[4,3-a]pyrazin-1-yl)cyclopentyloxy)benzonitrile

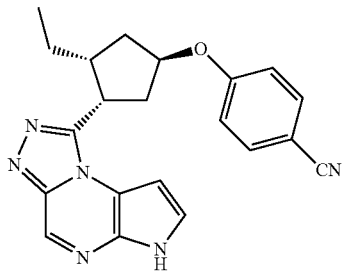

Step A: 5-bromo-3-((trimethylsilyl)ethynyl)pyrazin-2-amine

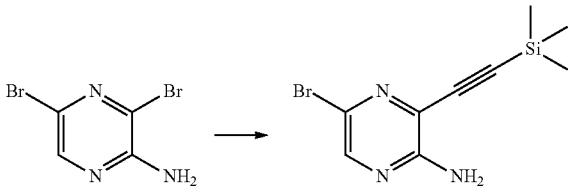

To a solution of 3,5-dibromopyrazin-2-amine (125 g, 494 mmol), TEA (207.0 mL, 1483 mmol), and copper (I) iodide (0.941 g, 4.94 mmol) in THF (1255 mL) was added $PdCl_2(PPh_3)_2$ (3.47 g, 4.94 mmol). The reaction mixture was cooled at about −5-0° C. and a solution of (trimethylsilyl) acetylene (65.0 mL, 470 mmol) in THF (157 mL) was added dropwise over about 15 min. The reaction mixture was stirred at about −5-0° C. for about 1.5 h and then allowed to warm to rt overnight. The reaction mixture was then filtered through a Celite® pad and washed with THF until no further product eluted. The filtrate was concd under reduced pressure to give a brown-orange solid. The solid was triturated and sonicated with warm petroleum ether (b.p. 30-60° C., 400 mL), cooled to rt, collected, washed with petroleum ether (b.p. 30-60° C.; 2×60 mL), and dried to give 5-bromo-3-((trimethylsilyl)ethynyl)pyrazin-2-amine (124 g, 93%, 93% purity) as a brown solid: LC/MS (Table 1, Method b) $R_t$=2.51 min; MS m/z: 270, 272 $(M+H)^+$.

Step B: 2-bromo-5-tosyl-5H-pyrrolo[2,3-b]pyrazine

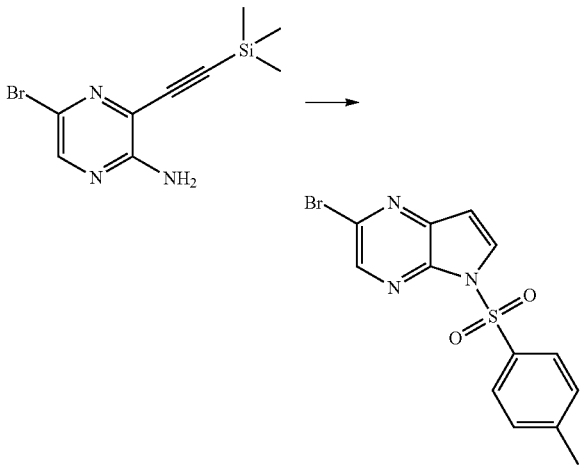

To a solution of 5-bromo-3-((trimethylsilyl)ethynyl) pyrazin-2-amine (3.00 g, 11.1 mmol) in DMF (60 mL) at about 0° C. was added NaH (60% dispersion in mineral oil, 0.577 g, 14.4 mmol) in three portions. After about 15 min, p-toluenesulfonyl chloride (2.75 g, 14.4 mmol) was added and the reaction was allowed to warm slowly to ambient temperature. After about 16 h, the reaction mixture was poured onto ice-cold water (120 mL) and the precipitate was collected by vacuum filtration. The crude solid was dissolved in DCM (15 mL) and purified by silica gel chromatography eluting with DCM to give 2-bromo-5-tosyl-5H-pyrrolo[2,3-b]pyrazine (2.16 g, 52%): LC/MS (Table 1, Method c) $R_t$=1.58 min; MS m/z: 352, 354 $(M+H)^+$.

Step C: tert-butyl 2-(5-tosyl-5H-pyrrolo[2,3-b] pyrazin-2-yl)hydrazinecarboxylate and tert-butyl 1-(5-tosyl-5H-pyrrolo[2,3-b]pyrazin-2-yl)hydrazinecarboxylate

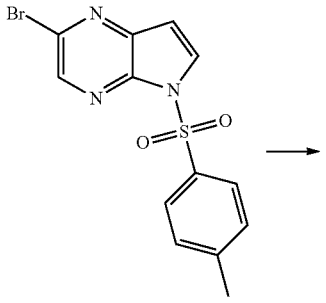

-continued

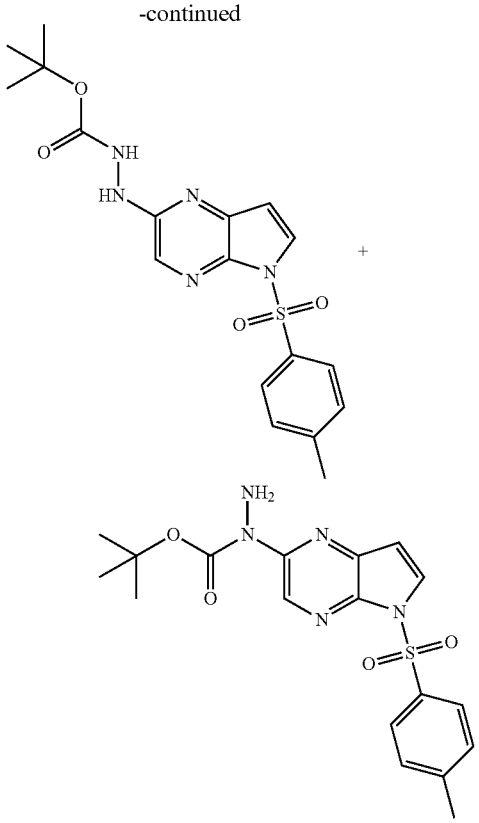

To a flask was added $Pd_2(dba)_3$ (3.90 g, 4.26 mmol), di-tert-butyl-(2',4',6'-triisopropylbiphenyl-2-yl)phosphane (3.62 g, 8.52 mmol), and 1,4-dioxane (453 mL). The catalyst-ligand mixture was degassed via vacuum/nitrogen purge (3 times) and heated at about 80° C. for about 10 min. Then 2-bromo-5-tosyl-5H-pyrrolo[2,3-b]pyrazine (30.0 g, 85 mmol), tert-butyl hydrazinecarboxylate (16.9 g, 128 mmol), and NaOt-Bu (12.28 g, 128 mmol) were added. After an additional vacuum/nitrogen purge, the reaction was heated at about 80° C. After about 50 min, the reaction mixture was cooled to ambient temperature and filtered through a pad of silica gel (6 cm in height×6 cm in diameter), topped with Celite® (1 cm in height×6 cm in diameter), while washing with EtOAc (3×150 mL). Water (300 mL) was added to the filtrate and the organic layer was separated. The aqueous layer was extracted with additional EtOAc (3×200 mL). The combined organic extracts were washed with saturated aqueous $NH_4Cl$, saturated aqueous $NaHCO_3$, and brine (400 mL each), dried over anhydrous $MgSO_4$, filtered, and concd under reduced pressure to give a dark brown oil (45 g). The brown oil was dissolved in DCM (250 mL), silica gel (200 g) was added, and the mixture was concd under reduced pressure. The resulting silica mixture was purified using silica gel chromatography eluting with a gradient of 25-65% EtOAc in heptane to give a mixture of tert-butyl 2-(5-tosyl-5H-pyrrolo[2,3-b]pyrazin-2-yl)hydrazinecarboxylate [major regioisomer] and tert-butyl 1-(5-tosyl-5H-pyrrolo[2,3-b]pyrazin-2-yl)hydrazinecarboxylate [minor regioisomer] (18.8 g, 50%): LC/MS (Table 1, Method c) $R_t$=1.47 min; MS m/z: 404 $(M+H)^+$.

Step D: 2-hydrazinyl-5-tosyl-5H-pyrrolo[2,3-b] pyrazine

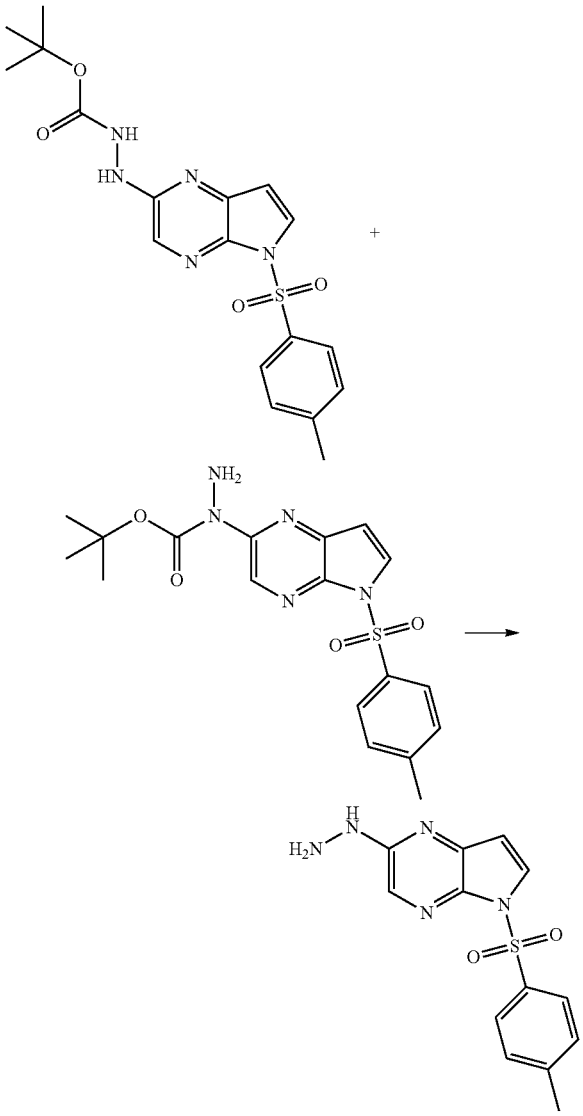

To a mixture of tert-butyl 2-(5-tosyl-5H-pyrrolo[2,3-b] pyrazin-2-yl)hydrazinecarboxylate and tert-butyl 1-(5-tosyl-5H-pyrrolo[2,3-b]pyrazin-2-yl)hydrazinecarboxylate (49.2 g, 122 mmol) in 1,4-dioxane (290 mL) was added HCl (4 M in 1,4-dioxane, 226 mL, 902 mmol). The reaction was heated at about 60° C. for about 2.5 h and then cooled to about 15-20° C. The solid was collected by vacuum filtration, washed with EtOAc (3×50 mL), and then triturated with $Et_2O$ (60 mL), collected by vacuum filtration and dried to a constant weight under vacuum to yield 35.6 g of solid. The solid was stirred with a mixture of saturated aqueous $NaHCO_3$ and EtOAc (1:1, 400 mL). After about 1 h, the solid was collected by vacuum filtration, washed with ice cold water (3×30 mL) and EtOAc (3×30 mL), and dried in a vacuum oven to a constant weight to afford 2-hydrazinyl-5-tosyl-5H-pyrrolo[2,3-b]pyrazine as a tan solid (21.2 g, 57%): LC/MS (Table 1, Method a) $R_t$=1.88 min; MS m/z: 304 $(M+H)^+$.

Step E: sodium 4-(ethoxycarbonyl)-3-ethyl-2-(methoxycarbonyl)cyclopenta-1,3-dienolate

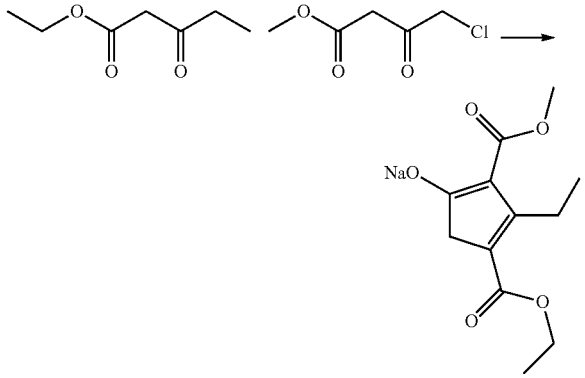

A round bottom flask was charged with THF (1.5 L) followed by the portionwise addition of NaH (60% dispersion in mineral oil, 70.0 g, 1.75 mol). Additional THF (500 mL) was added and the resulting mixture was cooled to about −10° C. and ethyl propionylacetate (250 mL, 1.80 mol) was added dropwise over about 1 h in order to keep the internal temperature below about 10° C. The resulting mixture was stirred at ambient temperature for about 0.5 h to give a clear yellow solution, and methyl 4-chloroacetoacetate (100 mL, 0.88 mol) was added dropwise over about 5 min. The resulting mixture was heated at about 50° C. for about 19 h to give a reddish orange suspension. The reaction mixture was cooled to ambient temperature, concd under reduced pressure and the resulting liquid was transferred to a beaker and diluted with water (350 mL). The mixture was stirred in an ice bath for about 2 h. The solid was collected by vacuum filtration and the filter cake was rinsed with water (150 mL) and dried under vacuum for about 1 h. The solid was suspended in $Et_2O$ (1.5 L), filtered, washed with $Et_2O$ (1.5 L), and dried under vacuum. The resulting solid was azeotroped with toluene (1 L) to give a solid that was re-suspended in $Et_2O$ (1 L) and collected by vacuum filtration. The filter cake was washed with $Et_2O$ (500 mL) and dried under vacuum to give sodium 4-(ethoxycarbonyl)-3-ethyl-2-(methoxycarbonyl)cyclopenta-1,3-dienolate (204.2 g, 89%) as beige solid: $^1H$ NMR (DMSO-$d_6$) δ 3.94 (q, J=7.1 Hz, 2H), 3.46 (s, 3H), 3.04 (q, J=7.2 Hz, 2H), 2.66 (s, 2H), 1.13 (t, J=7.1 Hz, 3H), 0.99 (t, J=7.3 Hz, 3H).

Step F: ethyl 2-ethyl-4-oxocyclopent-2-enecarboxylate

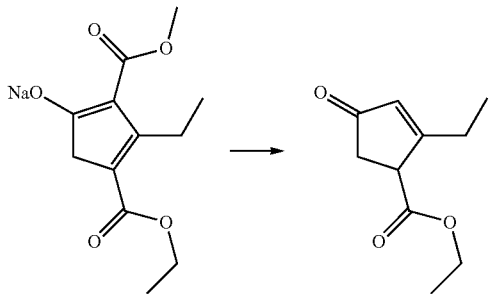

A 5 L round bottom flask was charged with sodium 4-(ethoxycarbonyl)-3-ethyl-2-(methoxycarbonyl)cyclopenta-1,3-dienolate (316 g, 1205 mmol), KCl (126 g, 1687 mmol, JT-Baker), AcOH (241 mL, 4218 mmol, JT-Baker), toluene (1850 mL) and water (130 mL). The reaction was heated at reflux for about 6 h then cooled to ambient temperature and added dropwise to $NaHCO_3$ (8% aqueous, 3.5 L). The resulting biphasic mixture was extracted with MTBE (2×1.5 L). The combined organic layers were washed with brine (1 L), dried over anhydrous $MgSO_4$ and concd under reduced pressure to give 191 g of crude material that was purified by vacuum distillation (97-99° C., 0.600 mm Hg) to give ethyl 2-ethyl-4-oxocyclopent-2-enecarboxylate (160 g, 69%): $^1$H NMR ($CDCl_3$) δ 6.04 (m, 1H), 4.26-4.15 (m, 2H), 3.76-3.69 (m, 1H), 2.75-2.57 (m, 2H), 2.56-2.44 (m, 2H), 1.32-1.26 (m, 3H), 1.23-1.18 (m, 3H).

Step G: (1S,2R,4S)-ethyl 2-ethyl-4-hydroxycyclopentanecarboxylate

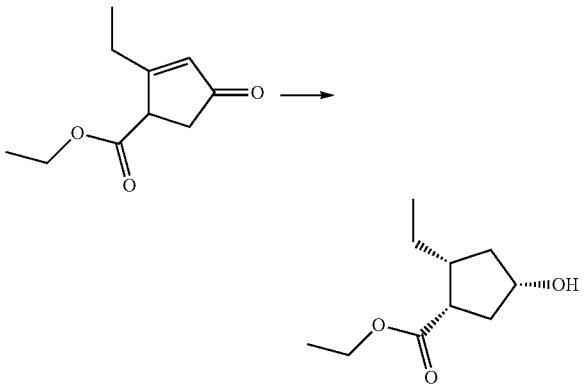

A mixture of copper (I) chloride (0.136 g, 1.37 mmol), (S)-(−)-2,2'-bis(diphenylphosphino)-1,1'-binaphthyl (0.854 g, 1.37 mmol), and NaOt-Bu (0.132 g, 1.37 mmol) in toluene (50 mL) was stirred at ambient temperature for about 15 min then cooled to about 5° C. and polymethylhydrosiloxane (12 mL, 55 mmol) was added. The reaction mixture was stirred for about 40 min at about 5° C. then cooled to about −12° C. A solution of ethyl 2-ethyl-4-oxocyclopent-2-enecarboxylate (5.00 g, 27.4 mmol) and t-BuOH (14 mL, 148 mmol) in toluene (50 mL) was added in one portion and the reaction mixture was stirred for about 16 h at about −12° C. The reaction mixture was quenched by the addition of MeOH (50 mL). The solvents were removed under reduced pressure. The residue was dissolved in MeOH (35 mL) and filtered through a pad of Celite®. The filtrate was concd under reduced pressure and the residue was triturated with EtOAc (100 mL) and filtered. The filtrate was concd under reduced pressure and the residue was purified using silica gel chromatography (280 g) eluting with a gradient of 0-10% EtOAc in heptane to give (1S,2R,4S)-ethyl 2-ethyl-4-hydroxycyclopentanecarboxylate (1.11 g, 22%): $^1$H NMR ($CDCl_3$) δ 4.30 (m, 1H), 4.24-4.08 (m, 2H), 2.88 (td, J=2.1, 7.1 Hz, 1H), 2.40 (dt, J=7.8, 14.0 Hz, 1H), 2.08-1.91 (m, 3H), 1.52-1.31 (m, 3H), 1.29 (t, J=7.1 Hz, 3H), 0.94 (t, J=7.4 Hz, 3H).

Step H: (1S,2R,4S)-2-ethyl-4-hydroxycyclopentanecarboxylic acid

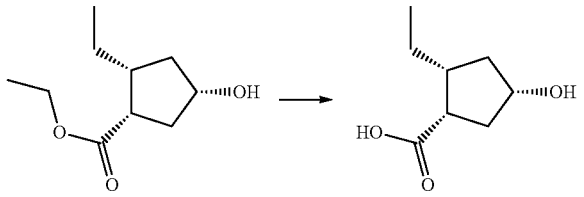

NaOH (1 N aqueous, 12 mL, 12 mmol) was added to (1S,2R,4S)-ethyl 2-ethyl-4-hydroxycyclopentanecarboxylate (1.11 g, 5.96 mmol). The reaction mixture was stirred at ambient temperature for about 3 days and then extracted with $Et_2O$ (3×25 mL). The $Et_2O$ extracts were discarded and the aqueous portion was cooled to about 0° C. HCl (5 N aqueous) was slowly added to bring the pH to about 2. The resulting aqueous suspension was extracted with EtOAc (3×40 mL). The combined organic layers were washed with brine (2×80 mL), dried over anhydrous $MgSO_4$, filtered, and concd under reduced pressure to give (1S,2R,4S)-2-ethyl-4-hydroxycyclopentanecarboxylic acid (0.943 g, 100%) as clear oil: $^1$H NMR ($CDCl_3$) δ 4.36 (tdd, J=2.6, 4.9, 7.4, 1H), 2.95 (td, J=2.4, 7.3, 1H), 2.41 (dt, J=7.7, 14.1, 1H), 2.16-1.94 (m, 3H), 1.65-1.49 (m, 1H), 1.49-1.32 (m, 2H), 0.96 (q, J=7.4, 3H).

Step I: (1S,4S,5R)-5-ethyl-2-oxabicyclo[2.2.1]heptan-3-one

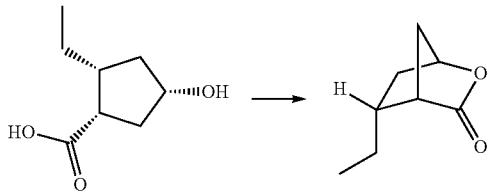

To (1S,2R,4S)-2-ethyl-4-hydroxycyclopentanecarboxylic acid (0.943 g, 5.96 mmol) in DCM (60 mL) was added TEA (2.5 mL, 18 mmol) and BOP-Cl (1.821 g, 7.15 mmol). The reaction mixture was stirred at ambient temperature for about 2 h then poured into $Et_2O$ (350 mL). The solid was removed by filtration while washing with $Et_2O$ (50 mL). The filtrate was coned under reduced pressure to give a yellow oil which was dissolved in DCM (5 mL) and $Et_2O$ was added to give a solid. The supernatant was decanted and the solid was washed with additional $Et_2O$. The combined organic extracts were coned under reduced pressure to give crude (1S,4S,5R)-5-ethyl-2-oxabicyclo[2.2.1]heptan-3-one containing about 15 mol % TEA (0.912 g, 99%): $^1$H NMR ($CDCl_3$) δ 4.85 (s, 1H), 2.88 (s, 1H), 2.19 (m, 2H), 2.08 (m, 1H), 1.69 (m, 1H), 1.41 (m, 3H), 0.97 (t, J=5.4, 3H).

Step J: (1S,2R,4S)-2-ethyl-4-hydroxy-N'-(5-tosyl-5H-pyrrolo[2,3-b]pyrazin-2-yl)cyclopentanecarbohydrazide

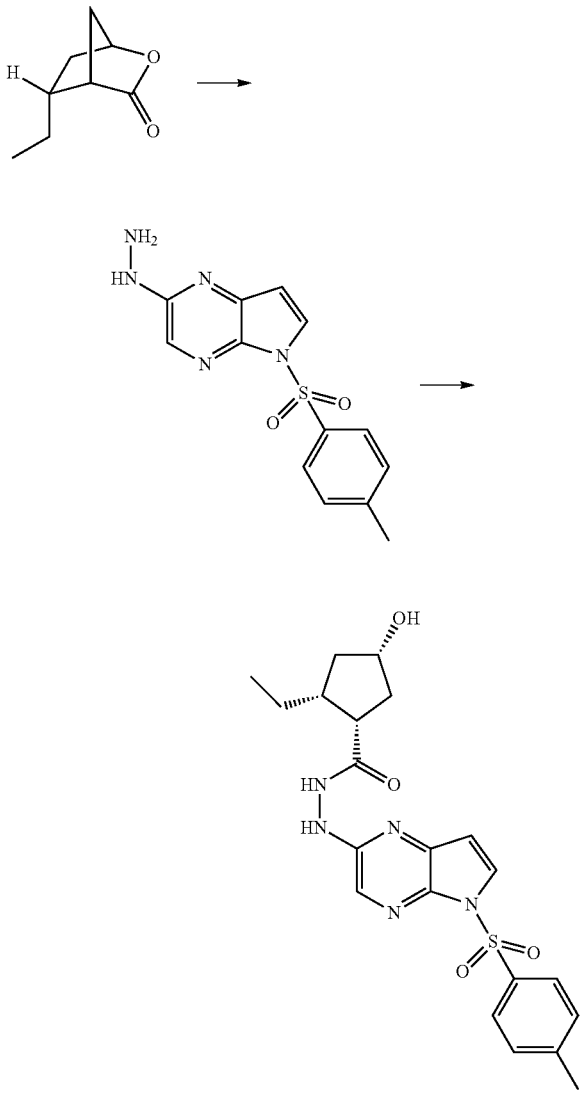

To (1S,4S,5R)-5-ethyl-2-oxabicyclo[2.2.1]heptan-3-one (0.835 g, 5.96 mmol) in 1,4-dioxane (12 mL) was added 2-hydrazinyl-5-tosyl-5H-pyrrolo[2,3-b]pyrazine (step D, 1.810 g, 5.96 mmol). The reaction mixture was heated at about 80° C. for about 16 h then cooled to ambient temperature. 1,4-Dioxane (25 mL) and trimethylaluminum (2 N in toluene, 9 mL, 18 mmol) were added sequentially. The reaction mixture was stirred at ambient temperature for about 30 min then HCl (1 N aqueous, 50 mL) was added dropwise and the reaction mixture was stirred for about 30 min. The layers were separated and the aqueous portion was extracted with EtOAc (2×100 mL). The combined organic extracts were washed with water (10 mL), saturated aqueous $NaHCO_3$ (15 mL), brine (15 mL) and dried over anhydrous $MgSO_4$, filtered, and coned under reduced pressure. The residue was purified using silica gel chromatography (40 g) eluting with 100% EtOAc to give (1S,2R,4S)-2-ethyl-4-hydroxy-N'-(5-tosyl-5H-pyrrolo[2,3-b]pyrazin-2-yl)cyclopentanecarbohydrazide (1.887 g, 71%): LC/MS (Table 1, Method b) $R_t$=2.05 min; MS m/z: 444 $(M+H)^+$.

Step K: (1S,2R,4R)-4-(4-cyanophenoxy)-2-ethyl-N'-(5-tosyl-5H-pyrrolo[2,3-b]pyrazin-2-yl)cyclopentanecarbohydrazide

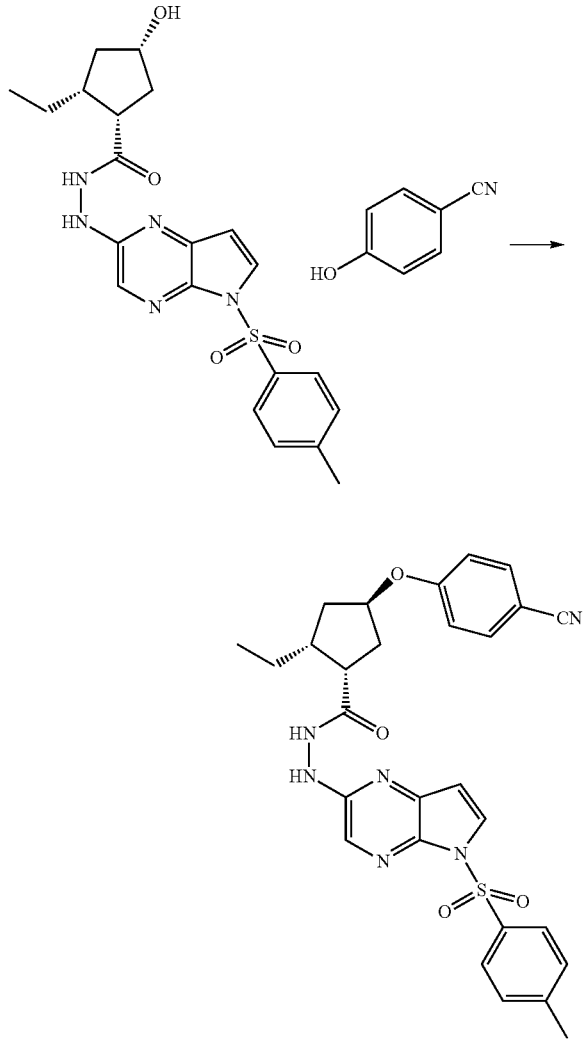

To (1S,2R,4S)-2-ethyl-4-hydroxy-N-(5-tosyl-5H-pyrrolo[2,3-b]pyrazin-2-yl)cyclopentanecarbohydrazide (0.885 g, 1.99 mmol) in THF (15 mL) was added 4-hydroxybenzonitrile (0.357 g, 2.99 mmol), triphenylphosphine (0.998 g, 2.99 mmol, polymer bound, 3 mmol/g), and TEA (1.3 mL, 9 mmol). DEAD (0.47 mL, 2.99 mmol) was added dropwise. The reaction mixture was stirred for about 1 h then additional triphenylphosphine (0.50 g, 1.5 mmol, polymer bound, 3mmol/g) and DEAD (0.2 mL, 1.3 mmol) were added and the reaction mixture was stirred at ambient temperature for about 16 h. The solid was removed by filtration while washing with DCM (5×5 mL) then MeOH (4×5 mL). The filtrate was concd under reduced pressure and the residue was purified using silica gel chromatography (40 g) eluting with a gradient of 0-40% EtOAc in DCM to give (1S,2R,4R)-4-(4-cyanophenoxy)-2-ethyl-N'-(5-tosyl-5H-pyrrolo[2,3-b]pyrazin-2-yl)cyclopentanecarbohydrazide (0.958 g, 88%) as a yellow foam: LC/MS (Table 1, Method b) $R_t$=2.56 min; MS m/z: 545 $(M+H)^+$.

Step L: 4-01R,3R,4S)-3-ethyl-4-(6-tosyl-6H-pyrrolo[2,3-e][1,2,4]triazolo[4,3-a]pyrazin-1-yl)cyclopentyloxy)benzonitrite

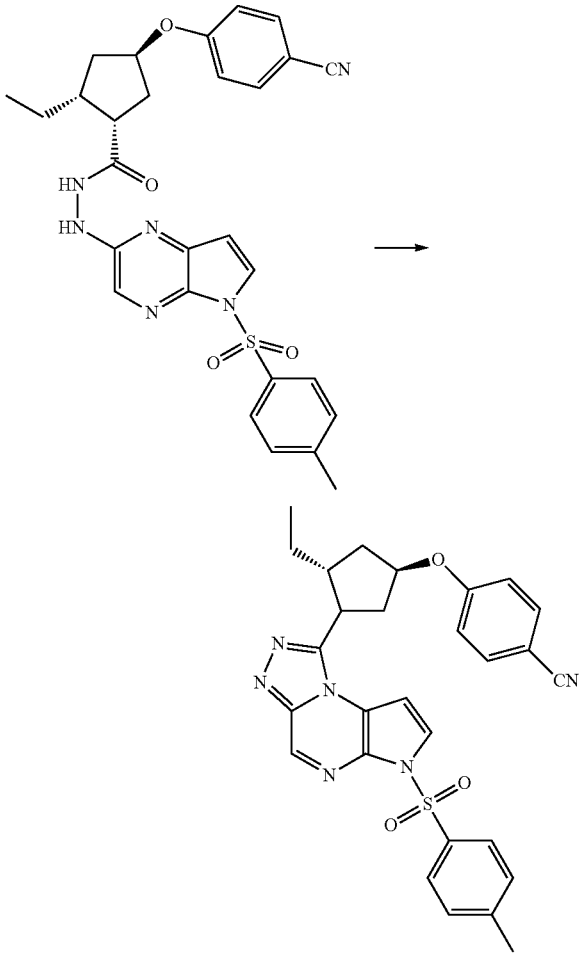

To (1S,2R,4R)-4-(4-cyanophenoxy)-2-ethyl-N-(5-tosyl-5H-pyrrolo[2,3-b]pyrazin-2-yl)cyclopentanecarbohydrazide (0.958 g, 1.76 mmol) in 1,4-dioxane (18 mL) was added DIEA (1.2 mL, 7.0 mmol) and thionyl chloride (0.4 mL, 5.3 mmol). The reaction mixture was heated at about 80° C. for about 2 h. The solvent was removed under reduced pressure and the residue was purified using silica gel chromatography (80 g) eluting with a gradient of 20-80% EtOAc in DCM to give 4-((1R,3R,4S)-3-ethyl-4-(6-tosyl-6H-pyrrolo[2,3-e][1,2,4]triazolo[4,3-a]pyrazin-1-yl)cyclopentyloxy)benzonitrile (0.620 g, 67%): LC/MS (Table 1, Method b) $R_t$=2.65 min; MS m/z: 527 $(M+H)^+$.

Step M: 4-((1R,3R,4S)-3-ethyl-4-(6H-pyrrolo[2,3-e][1,2,4]triazolo[4,3-a]pyrazin-1-yl)cyclopentyloxy)benzonitrile

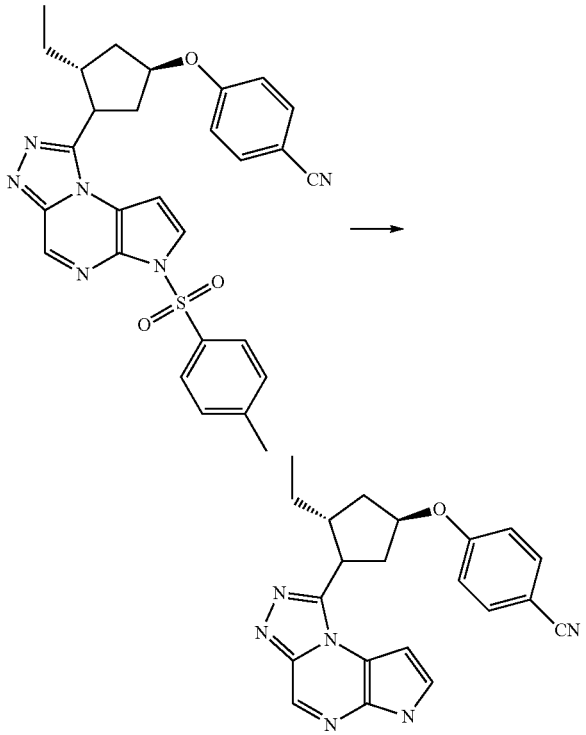

To 4-((1R,3R,4S)-3-ethyl-4-(6-tosyl-6H-pyrrolo[2,3-e][1,2,4]triazolo[4,3-a]pyrazin-1-yl)cyclo-pentyloxy)benzonitrile (0.826 g, 1.57 mmol) in 1,4-dioxane (16 mL) was added $Na_2CO_3$ (2 N aqueous solution, 16 mL, 31 mmol). The reaction mixture was heated at about 80° C. for about 16 h. The layers were separated and the aqueous portion was extracted with EtOAc (3×40 mL). The combined organic layers were washed with saturated aqueous $NaHCO_3$ (2×30 mL), brine (30 mL), dried over anhydrous $MgSO_4$, filtered, and concd under reduced pressure. The residue was purified by using General Procedure AA (Table 2, Method 17, $R_t$=19.2 min, or =negative) to give 4-((1R,3R,4S)-3-ethyl-4-(6H-pyrrolo[2,3-e][1,2,4]triazolo[4,3-a]pyrazin-1-yl)cyclopentyloxy)benzonitrile (0.298 g, 51%): LC/MS (Table 1, Method b) $R_t$=2.07 min; MS m/z: 373 $(M+H)^+$.

Example #5*

N-(43R,4R)-3-(6H-imidazo[1,5-a]pyrrolo[2,3-e]pyrazin-1-yl)-4-methylpiperidin-1-yl)(pyrrolidin-1-yl)methylene)cyanamide

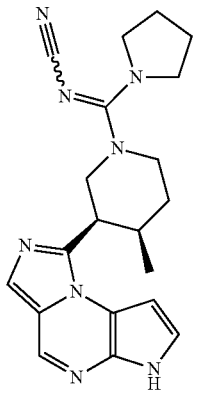

Step A: 5-bromo-3-((trimethylsilyl)ethynyl)pyrazin-2-amine

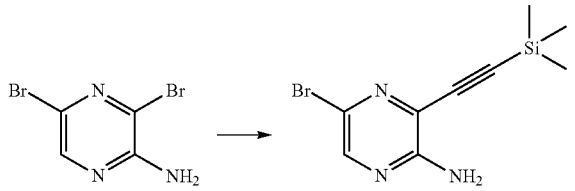

To a solution of 3,5-dibromopyrazin-2-amine (125 g, 494 mmol), TEA (207.0 mL, 1483 mmol), and copper (I) iodide (0.941 g, 4.94 mmol) in THF (1255 mL) was added $PdCl_2(PPh_3)_2$ (3.47 g, 4.94 mmol). The reaction mixture was cooled at about −5-0° C. and a solution of (trimethylsilyl) acetylene (65.0 mL, 470 mmol) in THF (157 mL) was added dropwise over about 15 min. The reaction mixture was stirred at about −5-0° C. for about 1.5 h and then allowed to warm to rt overnight. The reaction mixture was then filtered through a Celite® pad and washed with THF until no further product eluted. The filtrate was concd under reduced pressure to give a brown-orange solid. The solid was triturated and sonicated with warm petroleum ether (b.p. 30-60° C., 400 mL), cooled to rt, collected, washed with petroleum ether (b.p. 30-60° C.; 2×60 mL), and dried to give 5-bromo-3-((trimethylsilyl)ethynyl)pyrazin-2-amine (124 g, 93%, 93% purity) as a brown solid: LC/MS (Table 1, Method b) $R_t$=2.51 min; MS m/z: 270, 272 $(M+H)^+$.

Step B: 2-bromo-5-tosyl-5H-pyrrolo[2,3-b]pyrazine

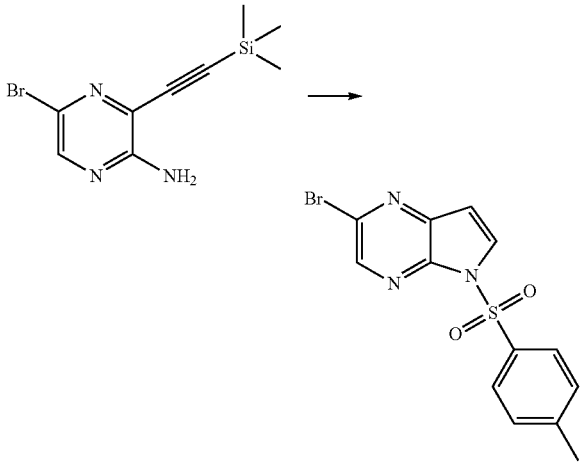

To a solution of 5-bromo-3-((trimethylsilyl)ethynyl) pyrazin-2-amine (3.00 g, 11.1 mmol) in DMF (60 mL) at about 0° C. was added NaH (60% dispersion in mineral oil, 0.577 g, 14.4 mmol) in three portions. After about 15 min, p-toluenesulfonyl chloride (2.75 g, 14.4 mmol) was added and the reaction was allowed to warm slowly to ambient temperature. After about 16 h, the reaction mixture was poured onto ice-cold water (120 mL) and the precipitate was collected by vacuum filtration. The crude solid was dissolved in DCM (15 mL) and purified by silica gel chromatography eluting with DCM to give 2-bromo-5-tosyl-5H-pyrrolo[2,3-b]pyrazine (2.16 g, 52%): LC/MS (Table 1, Method c) $R_t$=1.58 min; MS m/z: 352, 354 $(M+H)^+$.

Step C: (5-tosyl-5H-pyrrolo[2,3-b]pyrazin-2-yl) methanamine hydrochloride

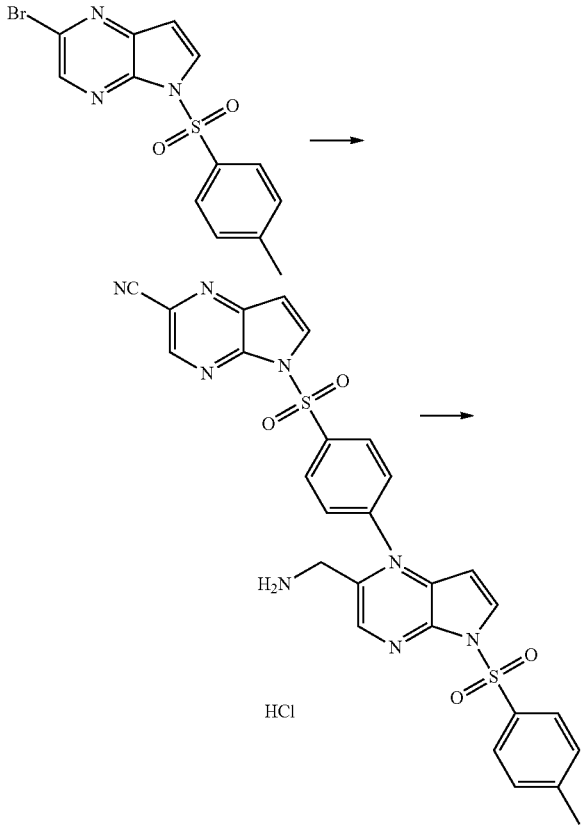

A 5 L reactor was charged with 2-bromo-5-tosyl-5H-pyrrolo[2,3-b]pyrazine (98.8 g, 281 mmol), zinc dust (3.50 g, 53.3 mmol), palladium(II) trifluoroacetate (4.0 g, 12 mmol), and racemic-2-(di-t-butylphosphino)-1,1'-binapthyl (9.8 g, 24.7 mmol). The flask was equipped with a powder addition device into which zinc cyanide (10.0 g, 157 mmol) was placed to be added at a later step. The vessel was purged with argon for no longer than about 30 min and then argon sparged DMA (2 L) was added to the reactor. The mixture was stirred and heated to about 50° C. while maintaining an argon atmosphere. The resulting dark brown solution was further heated to about 95° C. while adding the zinc cyanide, from the powder addition device, portionwise over about 15 min. Upon reaching about 95° C., the brown mixture was stirred for about an additional 16 h. The reaction mixture was cooled to ambient temperature, resulting in the precipitation of salts. The mixture was filtered through a Buchner funnel containing filter-aid and the filter cake was washed with DMA (20 mL). A solution of the crude product in DMA was added to cold (<10° C.) water (16 L) and stirred for about 30 min. The resulting suspension was filtered and the filter cake was rinsed again with water (1 L). The resulting wet cake was dried in a vacuum oven at about 50° C. The crude solid was dissolved in DCM (1.5 L) and further dried over anhydrous $MgSO_4$. After filtration, the solution was passed through a pad of silica (140 g), using DCM as the eluent until only predominantly impurities were detected eluting off the pad. The solvent was removed under reduced pressure and the crude solid was triturated with MeOH/DCM (4:1, 10 volumes of solvent per gram of crude solid) at ambient temperature for about 5 h. The solid was filtered and washed with MeOH (300 mL). The product was dried in a vacuum oven to provide 5-tosyl-5H-pyrrolo[2,3-b]pyrazine-2-carbonitrile (58.8 g, 70%) as a white solid: $^1$H NMR ($CDCl_3$) δ 8.67 (s, 1H), 8.21 (d, J=4.2 Hz, 1H), 8.07 (d, J=8.4 Hz, 2H), 7.34 (d, J=8.1 Hz, 2H), 6.89 (d, J=4.2 Hz, 1H), 2.42 (s, 3H). A 2-L 316-stainless steel pressure reactor was charged with 5 wt % Pd/C (15.4 g of 63.6 wt % water wet material, 5.6 g dry basis, 2.6 mmol Johnson Matthey A503032-5), 5-tosyl-5H-pyrrolo[2,3-b]pyrazine-2-carbonitrile (55 g, 184 mmol), THF (1.1 L), deionized water (165 mL), HCl (37 wt % aqueous, 30 mL, 369 mmol) and quinoline (1.1 mL, 9.0 mmol). The vessel was purged, pressurized, and maintained at 40 psi with hydrogen supplied from a high pressure reservoir. The mixture was vigorously agitated at about 25° C. After about 5 h the reactor was vented and purged with nitrogen to remove most of the dissolved hydrogen, and the reaction mixture was filtered to remove the catalyst. The reactor and catalyst cake were rinsed with THF:water (1:1, 2×40 mL). The combined filtrate and rinses were concd and EtOH (500 mL) was added then removed under reduced pressure. After two further azeotropes using EtOH (2×500 mL), the crude residue was concd under reduced pressure to give a residue (76 g) that was suspended in EtOH (550 mL) and stirred at ambient temperature for about 4 h. The solid was collected by filtration and washed with cold EtOH (50 mL). The wet cake was dried in a vacuum oven to provide (5-tosyl-5H-pyrrolo[2,3-b]pyrazin-2-yl)methanamine hydrochloride (51.2 g, 82%) as a white solid: LC/MS (Table 1, Method a) $R_t$=1.44 min; MS m/z: 303 $(M+H)^+$.

Step D: 4-methylpiperidine-3-carboxylic acid hydrochloride

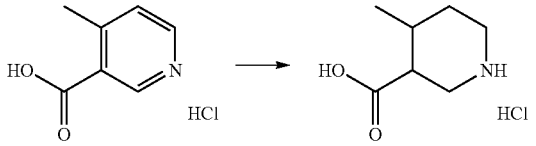

AcOH (380 mL) was added to 4-methylnicotinic acid hydrochloride (50.5 g, 291 mmol, Maybridge) and $PtO_2$ (5.05 g, 22.2 mmol, Johnson Matthey) in a 600 mL stainless steel reactor. The mixture was stirred under 220 psi of hydrogen at ambient temperature for about 14 hr. The supernatant solution was filtered through a nylon membrane and rinsed with enough AcOH until only the catalyst remained. The filtrate was concd under reduced pressure to give a clear oil that solidified upon cooling to ambient temperature to give crude 4-methylpiperidine-3-carboxylic acid with AcOH as an excipient (88.94 g, 170% crude): LC/MS (Table 1, Method b) Rt=0.44 min; MS m/z: 144 $(M+H)^+$.

Step E: (3R,4R)-ethyl 4-methylpiperidine-3-carboxylate (2S,3S)-2,3-dihydroxysuccinate

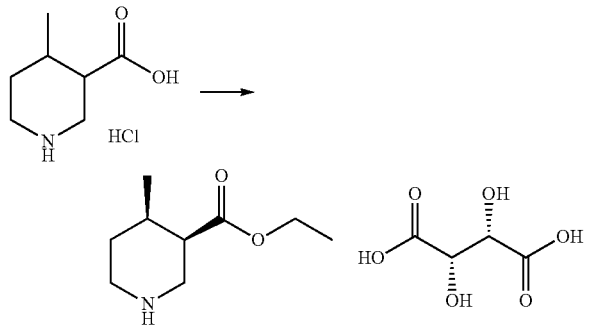

Crude racemic 4-methylpiperidine-3-carboxylic acid hydrochloride (~70% chemical purity, approximately 15:1 cis:trans) in AcOH (2:1, 300 g) was dissolved in EtOH (1500 mL) and sparged with HCl (gas) for about 15 min. The reaction mixture was fitted with a balloon to allow for expansion then heated to about 85° C. After about 48 h, the reaction mixture was cooled to ambient temperature and concd in vacuo to provide a thick syrup containing racemic ethyl 4-methylpiperidine-3-carboxylic acid hydrochloride (260 g). To this ester was added $CHCl_3$ (1000 mL) followed by saturated aqueous $NaHCO_3$ (500 mL) and $NH_4OH$ (15% aqueous, 500 mL). The organic layer was separated and the aqueous layer was further extracted with $CHCl_3$ (1000 mL). The combined organic layers were dried over anhydrous $Na_2SO_4$, filtered, and then concd in vacuo to provide crude ethyl 4-methylpiperidine-3-carboxylate (200 g) as an oil. To a slurry of (2S,3S)-2,3-dihydroxysuccinic acid (150 g, 1001 mmol) in MeOH (200 mL) was added a solution of crude ethyl 4-methylpiperidine-3-carboxylate (200 g, 1168 mmol) in EtOAc (3000 mL). The mixture was stirred rapidly for about 3 h and the resulting solids were collected by filtration to provide the (2S,3S)-2,3-dihydroxysuccinate salt as a white solid (245 g) (approximately 15:1 cis:trans, er=48:52 for cis stereoisomers). The solids were dissolved in MeOH (1000 mL) and EtOAc (3000 mL) was slowly added until solids began to form. After about 30 min, the solids were collected by filtration and partially dried in vacuo to provide a stereo-enriched mixture containing (3R,4R)-ethyl 4-methylpiperidine-3-carboxylate (2S,3S)-2,3-dihydroxysuccinate as a white solid (145 g) (approximately 15:1 cis:trans, er=60:40 for (3R,4R):(3S,4S) enantiomers). The above solids were dissolved in MeOH (1000 mL) and divided into four lots. Each lot (250 mL) was diluted with MeOH (500 mL) and EtOAc (3000 mL) was slowly added to the solution until solids formed. After about 4-15 h, the solids were collected by filtration and dried in vacuo to provide multiple lots of partially resolved (3R,4R)-ethyl 4-methylpiperidine-3-carboxylate (2S,3S)-2,3-dihydroxysuccinate, these were combined and dissolved in MeOH (1000 mL) and EtOAc (4000 mL) was slowly added. After stirring for about 1 h the solids were collected by filtration to provide (3R,4R)-ethyl 4-methylpiperidine-3-carboxylate (2S,3S)-2,3-dihydroxysuccinate (4.5 g) (approximately 15:1 cis:trans, er=98:2 for (3R,4R):(3S,4S) enantiomers), chiral analytical LC (Table 2, Method 30) minor isomer $R_t$=12.2 min; MS m/z: 343

(M+(2S,3S)-2,3-dihydroxysuccinate+Na)$^+$; major isomer $R_t$=10.6 min; MS m/z: 343 (M+(2S,3S)-2,3-dihydroxysuccinate+Na)$^+$ Step F: (3R,4R)-1-(tert-butoxycarbonyl)-4-methylpiperidine-3-carboxylic acid

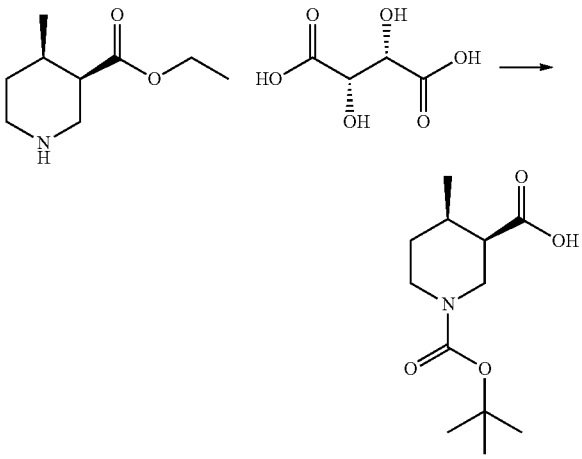

To a flask charged with (3R,4R)-ethyl 4-methylpiperidine-3-carboxylate (2S,3S)-2,3-dihydroxysuccinate (36.9 g, 115 mmol) was added a solution of HCl (6 N aqueous, 191 mL). The reaction mixture was heated to about 60° C. After about 2 h, the reaction mixture was heated to about 90° C. After about 4 h the reaction mixture was cooled to ambient temperature and concd in vacuo. To the residue was added $NaHCO_3$ (122 g, 1148 mmol) and di-tert-butyl dicarbonate (37.6 g, 172 mmol) followed by a mixture of 1,4-dioxane (500 mL) and water (500 mL). After about 2 h, $Et_2O$ (500 mL) and water (500 mL) were added to the reaction mixture. The pH was adjusted to about 4 with 1 N aqueous HCl. The organic layer was separated, dried over anhydrous $Na_2SO_4$, filtered, and concd in vacuo to provide a white solid. The solid was slurried in heptane and filtered to provide (3R,4R)-1-(tert-butoxycarbonyl)-4-methylpiperidine-3-carboxylic acid (25 g, 89%) as a white solid: LC/MS (Table 1, Method b) $R_t$=1.90 min; MS m/z: 244 (M+H)$^+$.

Step G: (3R,4R)-tert-butyl 4-methyl-3-((5-tosyl-5H-pyrrolo[2,3-b]pyrazin-2-yl)methylcarbamoyl)piperidine-1-carboxylate

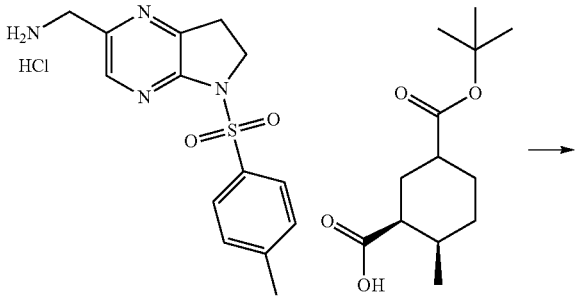

-continued

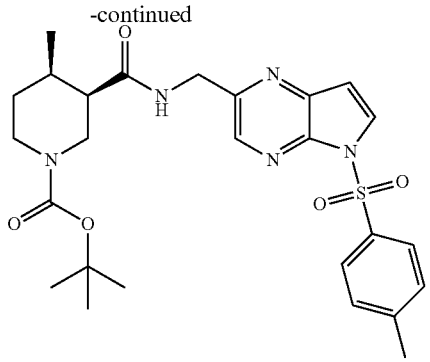

To a slurry of (5-tosyl-5H-pyrrolo[2,3-b]pyrazin-2-yl) methanamine hydrochloride (34.0 g, 100 mmol, Example #5, Step C), (3R,4R)-1-(tert-butoxycarbonyl)-4-methylpiperidine-3-carboxylic acid (24.43 g, 100 mmol) and HATU (38.2 g, 100 mmol) in DCM (700 mL) was added DIEA (52.6 mL, 301 mmol). The reaction was stirred at ambient temperature for about 45 min. The reaction was washed with saturated aqueous $NaHCO_3$ (300 mL). The organic layer was separated, dried over anhydrous $Na_2SO_4$, filtered then concd in vacuo. The resulting residue was purified by chromatography on silica gel (330 g) using 33-100% EtOAc in heptane to give (3R,4R)-tert-butyl-4-methyl-3-((5-tosyl-5H-pyrrolo[2,3-b]pyrazin-2-yl)methylcarbamoyl)piperidine-1-carboxylate (53 g, 100%) as a pale-yellow foam: LC/MS (Table 1, Method b) $R_t$=2.40 min; MS m/z: 528 (M+H)$^+$.

Step H: (3R,4R)-tert-butyl 4-methyl-3-(6-tosyl-6H-imidazo[1,5-a]pyrrolo[2,3-e]pyrazin-1-yl)piperidine-1-carboxylate

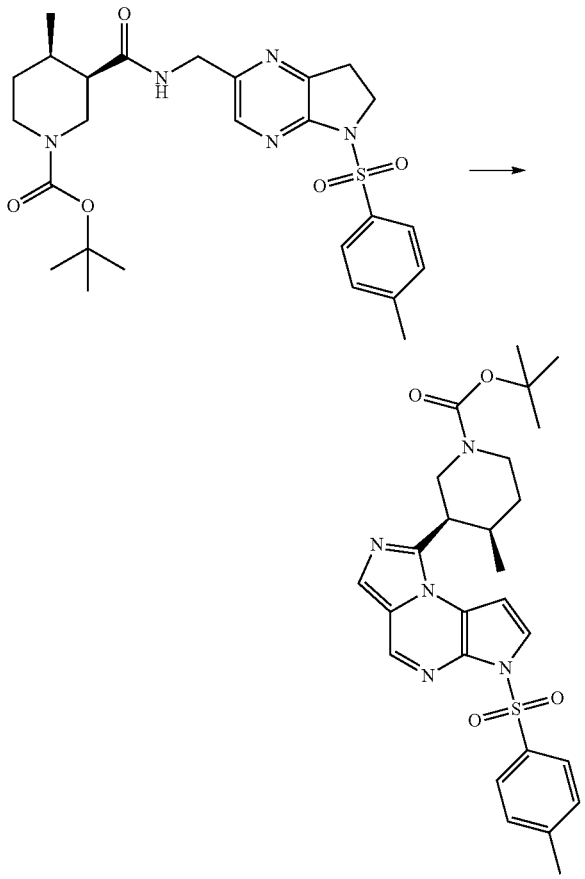

A mixture of (3R,4R)-tert-butyl-4-methyl-3-((5-tosyl-5H-pyrrolo[2,3-b]pyrazin-2-yl)methyl-carbamoyl)-piperidine-1-carboxylate (53 g, 100 mmol) and Lawesson's reagent (22.4 g, 55.2 mmol) in 1,4-dioxane (500 mL) was heated at about 80° C. for about 1 h. The reaction was allowed to cool to ambient temperature and then was partitioned between EtOAc (1000 mL) and saturated aqueous $NaHCO_3$ (700 mL). The organic layer was washed with additional saturated aqueous $NaHCO_3$ (700 mL), dried over anhydrous $Na_2SO_4$, filtered then concd in vacuo. The resulting residue was dissolved in 1,4-dioxane (500 mL) then mercury (II) trifluoroacetate (54.0 g, 127 mmol) was added. The reaction was stirred at about 25° C. for about 1 h. The reaction was partitioned with saturated aqueous $Na_2S_2O_3$ (500 mL)/water (500 mL) with DCM (1000 mL). The layers were filtered through Celite® and the Celite® pad was washed with DCM (500 mL). The combined layers were separated then the organic layer was washed with saturated aqueous $NaHCO_3$ (800 mL). The organic layer was separated, dried over anhydrous $Na_2SO_4$, filtered, and then coned in vacuo. The resulting residue was purified on silica gel (330 g) using 0-40% EtOAc in DCM to give (3R,4R)-tert-butyl 4-methyl-3-(6-tosyl-6H-imidazo[1,5-a]pyrrolo[2,3-e]pyrazin-1-yl)piperidine-1-carboxylate (40.5 g, 79%) as a yellow foam: LC/MS (Table 1, Method b) $R_t$=2.62 min; MS m/z: 510 $(M+H)^+$.

Step I: (3R,4R)-tert-butyl-3-(6H-imidazo[1,5-a]pyrrolo[2,3-e]pyrazin-1-yl)-4-methylpiperidine-1-carboxylate

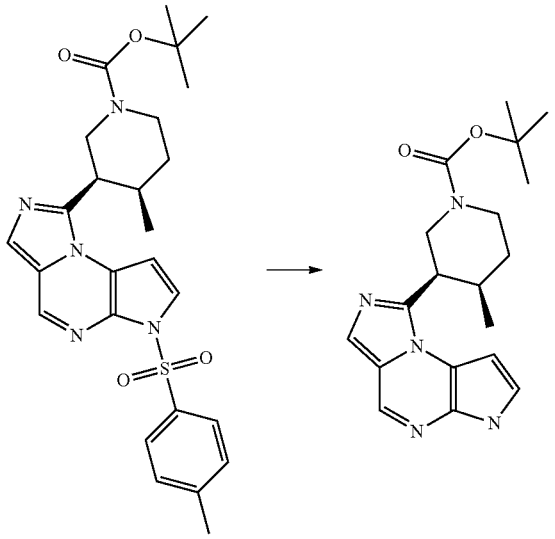

To a solution of (3R,4R)-tert-butyl 4-methyl-3-(6-tosyl-6H-imidazo[1,5-a]pyrrolo[2,3-e]pyrazin-1-yl)piperidine-1-carboxylate (40 g, 78 mmol) in 1,4-dioxane (160 mL) was added NaOH (1 N aqueous, 157 mL). The mixture was heated at about 60° C. for about 1 h. The mixture was allowed to cool to ambient temperature. The mixture was partitioned with HCl (4 N aqueous, 50 mL) and extracted with DCM (2×300 mL). The combined organic extracts were washed with brine (400 mL), dried over anhydrous $Na_2SO_4$, filtered then coned in vacuo. The product was purified on silica gel (330 g) using 1-5% MeOH in DCM to give (3R,4R)-tert-butyl 3-(6H-imidazo[1,5-a]pyrrolo[2,3-e]pyrazin-1-yl)-4-methylpiperidine-1-carboxylate (30 g, 99%): LC/MS (Table 1, Method b) $R_t$=2.00 min; MS m/z: 356 $(M+H)^+$.

Step J: 1-((3R,4R)-4-methylpiperidin-3-yl)-6H-imidazo[1,5-a]pyrrolo[2,3-e]pyrazine hydrochloride

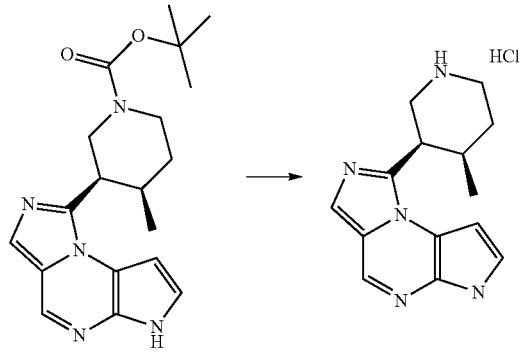

To a solution of (3R,4R)-tert-butyl 3-(6H-imidazo[1,5-a]pyrrolo[2,3-e]pyrazin-1-yl)-4-methyl-piperidine-1-carboxylate (27.9 g, 78 mmol) in 1,4-dioxane (400 mL) was added HCl (4 N in 1,4-dioxane, 58.9 mL, 235 mmol). The resulting suspension was heated at about 60° C. for about 1 h. The reaction was allowed to cool to ambient temperature and then was filtered, washed with 1,4-dioxane (100 mL) followed by $Et_2O$ (100 mL), to give 1-((3R,4R)-4-methylpiperidin-3-yl)-6H-imidazo[1,5-a]pyrrolo[2,3-e]pyrazine hydrochloride (20.6 g, 89%) as a tan solid: LC/MS (Table 1, Method b) $R_t$=1.27 min; MS m/z: 256 $(M+H)^+$.

Step K: N-(((3R,4R)-3-(6H-imidazo[1,5-a]pyrrolo[2,3-e]pyrazin-1-yl)-4-methylpiperidin-1-yl)(pyrrolidin-1-yl)methylene)cyanamide

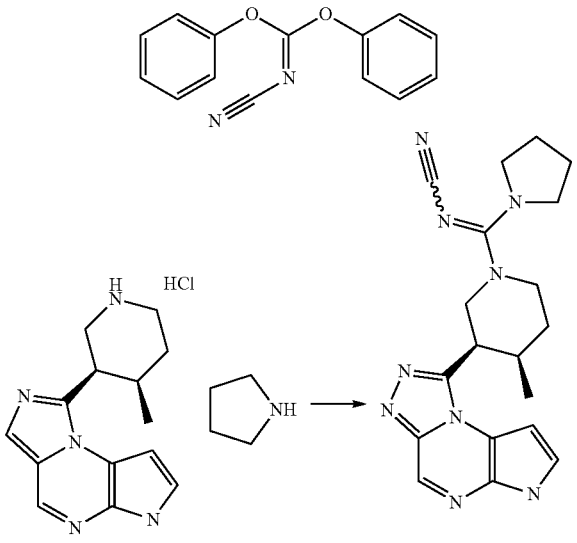

To a solution of diphenyl cyanocarbonimidate (0.163 g, 0.685 mmol) and DIEA (0.239 mL, 1.371 mmol) in MeCN (5 mL) was added 1-((3R,4R)-4-methylpiperidin-3-yl)-6H-imidazo[1,5-a]pyrrolo[2,3-e]pyrazine hydrochloride (0.20 g, 0.68 mmol). The reaction was heated at about 80° C. for about 2 h. The reaction mixture was concd in vacuo. The residue was dissolved in pyrrolidine (1.0 mL, 12 mmol) and transferred to a sealed microwave vessel. The reaction was heated at about 120° C. for about 30 min in a CEM microwave. The reaction mixture was concd in vacuo and purified by RP-HPLC (Table 1, Method i) to give N-(((3R, 4R)-3-(6H-imidazo[1,5-a]pyrrolo[2,3-e]pyrazin-1-yl)-4-methylpiperidin-1-yl)(pyrrolidin-1-yl)-methylene)cyanamide (0.030 g, 11%): LC/MS (Table 1, Method b) $R_t$=1.62 min; m/z: 377 $(M+H)^+$ Example #6*

(R)-(3-(6H-imidazo[1,5-a]pyrrolo[2,3-e]pyrazin-1-yl)piperidin-1-yl)(4,4-difluoropiperidin-1-yl)methanone

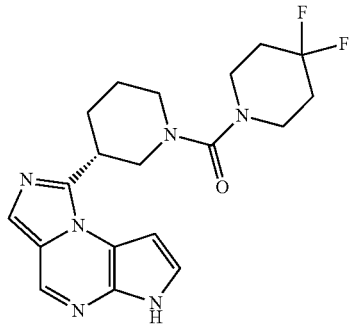

Step A: 5-bromo-3-((trimethylsilyl)ethynyl)pyrazin-2-amine

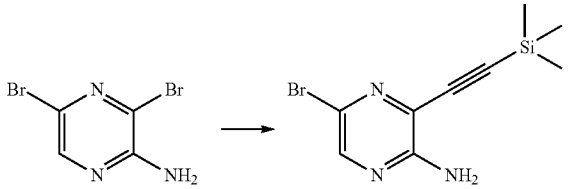

To a solution of 3,5-dibromopyrazin-2-amine (125 g, 494 mmol), TEA (207.0 mL, 1483 mmol), and copper (I) iodide (0.941 g, 4.94 mmol) in THF (1255 mL) was added $PdCl_2(PPh_3)_2$ (3.47 g, 4.94 mmol). The reaction mixture was cooled at about −5-0° C. and a solution of (trimethylsilyl) acetylene (65.0 mL, 470 mmol) in THF (157 mL) was added dropwise over about 15 min. The reaction mixture was stirred at about −5-0° C. for about 1.5 h and then allowed to warm to rt overnight. The reaction mixture was then filtered through a Celite® pad and washed with THF until no further product eluted. The filtrate was concd under reduced pressure to give a brown-orange solid. The solid was triturated and sonicated with warm petroleum ether (b.p. 30-60° C., 400 mL), cooled to rt, collected, washed with petroleum ether (b.p. 30-60° C.; 2×60 mL), and dried to give 5-bromo-3-((trimethylsilyl)ethynyl)pyrazin-2-amine (124 g, 93%, 93% purity) as a brown solid: LC/MS (Table 1, Method b) $R_t$=2.51 min; MS m/z: 270, 272 $(M+H)^+$.

Step B: 2-bromo-5-tosyl-5H-pyrrolo[2,3-b]pyrazine

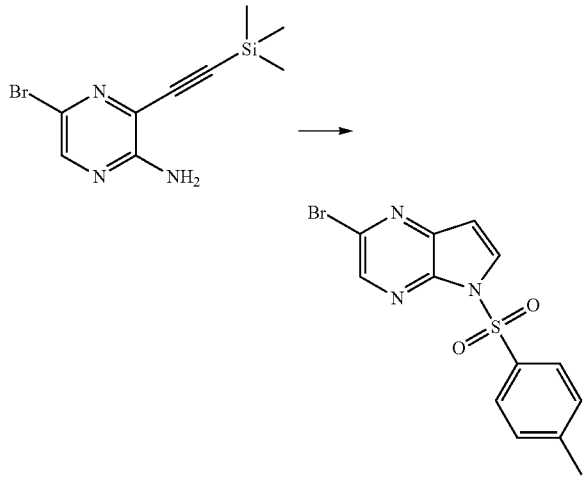

To a solution of 5-bromo-3-((trimethylsilyl)ethynyl) pyrazin-2-amine (3.00 g, 11.1 mmol) in DMF (60 mL) at about 0° C. was added NaH (60% dispersion in mineral oil, 0.577 g, 14.4 mmol) in three portions. After about 15 min, p-toluenesulfonyl chloride (2.75 g, 14.4 mmol) was added and the reaction was allowed to warm slowly to ambient temperature. After about 16 h, the reaction mixture was poured onto ice-cold water (120 mL) and the precipitate was collected by vacuum filtration. The crude solid was dissolved in DCM (15 mL) and purified by silica gel chromatography eluting with DCM to give 2-bromo-5-tosyl-5H-pyrrolo[2,3-b]pyrazine (2.16 g, 52%): LC/MS (Table 1, Method c) $R_t$=1.58 min; MS m/z: 352, 354 $(M+H)^+$.

Step C: (5-tosyl-5H-pyrrolo[2,3-b]pyrazin-2-yl) methanamine hydrochloride

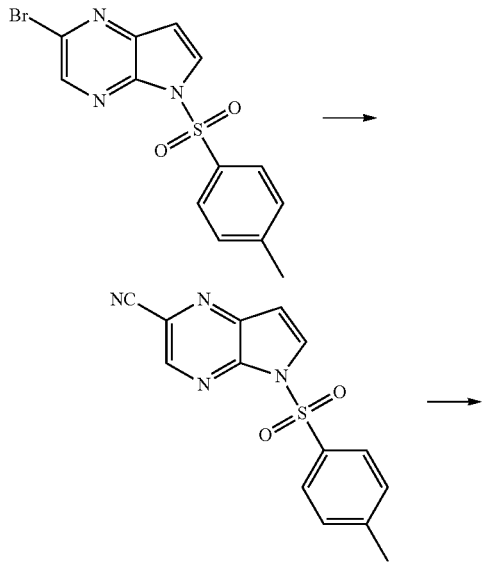

-continued

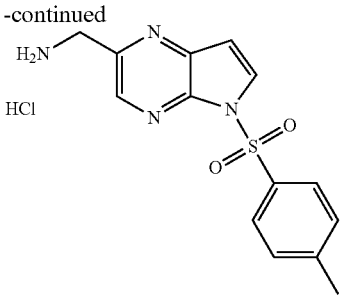

A 5 L reactor was charged with 2-bromo-5-tosyl-5H-pyrrolo[2,3-b]pyrazine (98.8 g, 281 mmol), zinc dust (3.50 g, 53.3 mmol), palladium(II) trifluoroacetate (4.0 g, 12 mmol), and racemic-2-(di-t-butylphosphino)-1,1'-binapthyl (9.8 g, 24.7 mmol). The flask was equipped with a powder addition device into which zinc cyanide (10.0 g, 157 mmol) was placed to be added later. The vessel was purged with argon for no longer than about 30 min and then argon sparged DMA (2 L) was added to the reactor. The mixture was stirred and heated to about 50° C. while maintaining an argon atmosphere. The resulting dark brown solution was further heated to about 95° C. while adding the zinc cyanide, from the powder addition device, portionwise over about 15 min. Upon reaching about 95° C., the brown mixture was stirred for about an additional 16 h. The reaction mixture was cooled to ambient temperature, resulting in the precipitation of salts. The mixture was filtered through a Buchner funnel containing filter-aid and the filter cake was washed with DMA (20 mL). A solution of the crude product in DMA was added to cold (<10° C.) water (16 L) and stirred for about 30 min. The resulting suspension was filtered and the filter cake was rinsed again with water (1 L). The resulting wet cake was dried in a vacuum oven at about 50° C. The crude solid was dissolved in DCM (1.5 L) and further dried over anhydrous $MgSO_4$. After filtration, the solution was passed through a pad of silica (140 g), washing with additional solvent until only predominantly impurities were detected eluting off the pad. The solvent was removed under reduced pressure and the crude solid was triturated with MeOH/DCM (4:1, 10 volumes of solvent per gram of crude solid) at ambient temperature for about 5 h. The solid was filtered and washed with MeOH (300 mL). The product was dried in a vacuum oven to provide 5-tosyl-5H-pyrrolo[2,3-b]pyrazine-2-carbonitrile (58.8 g, 70%) as a white solid: $^1$H NMR ($CDCl_3$) δ 8.67 (s, 1H), 8.21 (d, J=4.2 Hz, 1H), 8.07 (d, J=8.4 Hz, 2H), 7.34 (d, J=8.1 Hz, 2H), 6.89 (d, J=4.2 Hz, 1H), 2.42 (s, 3H). A 2-L 316-stainless steel pressure reactor was charged with 5 wt % Pd/C (15.4 g of 63.6 wt % water wet material, 5.6 g dry basis, 2.6 mmol, Johnson Matthey A503032-5), 5-tosyl-5H-pyrrolo[2,3-b]pyrazine-2-carbonitrile (55 g, 184 mmol), THF (1.1 L), deionized water (165 mL), HCl (37 wt % aqueous, 30 mL, 369 mmol) and quinoline (1.1 mL, 9.0 mmol). The vessel was purged, pressurized, and maintained at 40 psi with hydrogen supplied from a high pressure reservoir. The mixture was vigorously agitated at about 25° C. After about 5 h the reactor was vented and purged with nitrogen to remove most of the dissolved hydrogen, and the reaction mixture was filtered to remove the catalyst. The reactor and catalyst cake were rinsed with THF:water (1:1, 2×40 mL). The combined filtrate and rinses were concd and EtOH (500 mL) was added. After two additional solvent switches with EtOH (2×500 mL), the crude residue was concd under reduced pressure to give a residue (76 g) that was suspended in EtOH (550 mL) and stirred at ambient temperature for about 4 h. The solid was collected by filtration and washed with cold EtOH (50 mL). The wet cake was dried in a vacuum oven to provide (5-tosyl-5H-pyrrolo[2,3-b]pyrazin-2-yl)methanamine hydrochloride (51.2 g, 82%) as a white solid: LC/MS (Table 1, Method a) $R_t$=1.44 min; MS m/z: 303 $(M+H)^+$.

Step D: (R)-tert-butyl 3-((5-tosyl-5H-pyrrolo[2,3-b]pyrazin-2-yl)methylcarbamoyl)-piperidine-1-carboxylate

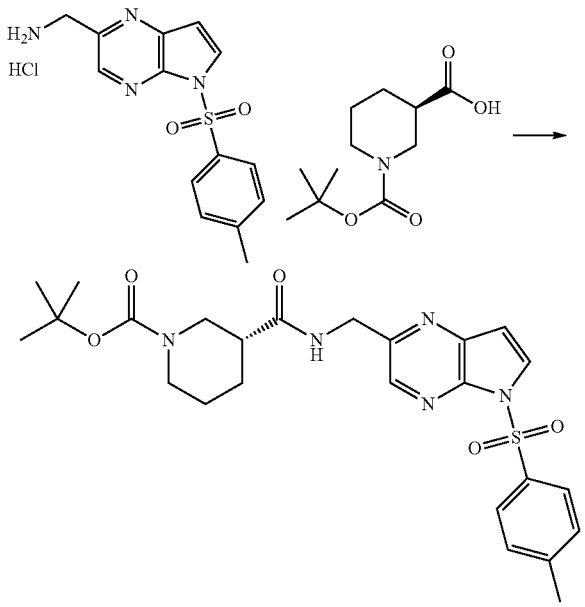

To a solution of (5-tosyl-5H-pyrrolo[2,3-b]pyrazin-2-yl)methanamine hydrochloride (5 g, 14.7 mmol) in DCM (78 mL) was added DIEA (7.7 mL, 44.3 mmol) and stirred at ambient temperature for about 10 min followed by the addition of (R)-N-Boc-piperidine-3-carboxylic acid (3.38 g, 14.7 mmol, CNH-Technologies) and HATU (5.61 g, 14.7 mmol). The mixture was stirred for about 1 h at ambient temperature and to it was added water (30 mL) and the layers were separated. The organic layer was washed with saturated aqueous $NaHCO_3$ (30 mL) and brine (30 mL), dried over anhydrous $MgSO_4$, filtered, and concd under reduced pressure. The crude material was purified by silica gel chromatography eluting with a gradient of 0-5% MeOH in DCM to afford crude (R)-tert-butyl 3-((5-tosyl-5H-pyrrolo[2,3-b]pyrazin-2-yl)methylcarbamoyl)piperidine-1-carboxylate (7.58 g, 94%): LC/MS (Table 1, Method b) $R_t$=2.30 min; MS m/z: 514 $(M+H)^+$.

Step E: (R)-tert-butyl 3-((5-tosyl-5H-pyrrolo[2,3-b]pyrazin-2-yl)methylcarbamothioyl)-piperidine-1-carboxylate

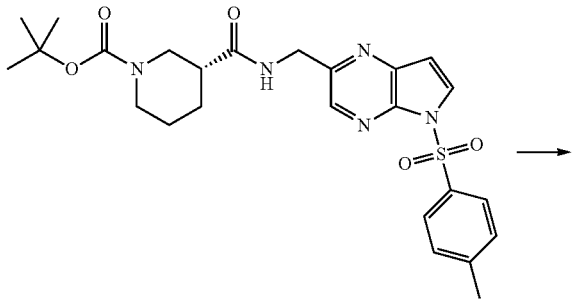

-continued

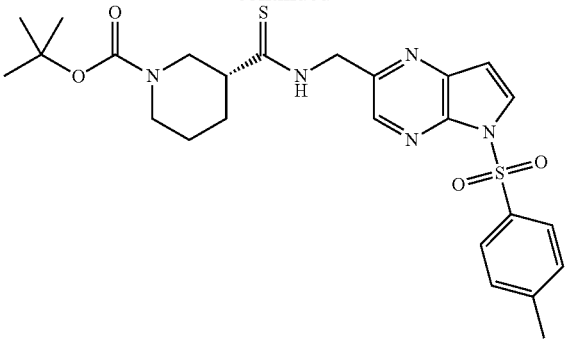

To a solution of (R)-tert-butyl 3-((5-tosyl-5H-pyrrolo[2,3-b]pyrazin-2-yl)methylcarbamoyl)-piperidine-1-carboxylate (7.58 g, 13.8 mmol) in 1,4-dioxane (130 mL) was added Lawesson's reagent (3.37 g, 8.32 mmol) and the reaction mixture was heated to about 60° C. for about 2 h then cooled to ambient temperature and concd under reduced pressure. The crude residue was dissolved with EtOAc (40 mL) and washed with saturated aqueous $NaHCO_3$, (3×40 mL), brine (30 mL), dried over anhydrous $MgSO_4$, filtered, and concd under reduced pressure. The crude material was purified by silica gel chromatography eluting with a gradient of 0-5% MeOH in DCM to afford (R)-tert-butyl 3-((5-tosyl-5H-pyrrolo[2,3-b]pyrazin-2-yl)methylcarbamothioyl)piperidine-1-carboxylate (5.6 g, 74%, UV purity 97%): LC/MS (Table 1, Method b) $R_t$=2.60 min; MS m/z: 530 $(M+H)^+$.

Step F: (R)-tert-butyl 3-(6-tosyl-6H-imidazo[1,5-a]pyrrolo[2,3-e]pyrazin-1-yl)piperidine-1-carboxylate

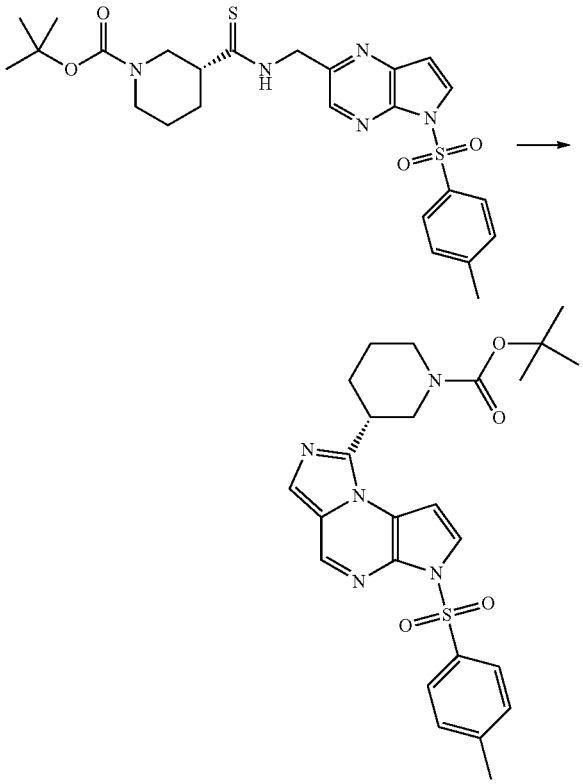

To a solution of (R)-tert-butyl 3-((5-tosyl-5H-pyrrolo[2,3-b]pyrazin-2-yl)methylcarbamothioyl)-piperidine-1-carboxylate (5.61 g, 10.3 mmol) in 1,4-dioxane (96 mL) was added mercury (II) trifluoroacetate (4.38 g, 10.3 mmol) and the reaction mixture was stirred at ambient temperature for about 2 h then filtered through a pad of Celite®. The Celite® pad was rinsed with EtOAc (50 mL) and the filtrate was concd under reduced pressure. The crude residue was dissolved in EtOAc (40 mL) and the organic phase was washed with saturated aqueous $NaHCO_3$ (2×40 mL), brine (30 mL), dried over anhydrous $MgSO_4$, filtered, and concd under reduced pressure. The crude material was purified by silica gel chromatography eluting with a gradient of 0-5% MeOH in DCM to afford (R)-tert-butyl 3-(6-tosyl-6H-imidazo[1,5-a]pyrrolo[2,3-e]pyrazin-1-yl)piperidine-1-carboxylate (4.4 g, 87%): LC/MS (Table 1, Method b) $R_t$=2.49 min; MS m/z: 496 $(M+H)^+$.

Step G: (R)-tert-butyl 3-(6H-imidazo[1,5-a]pyrrolo[2,3-e]pyrazin-1-yl)piperidine-1-carboxylate

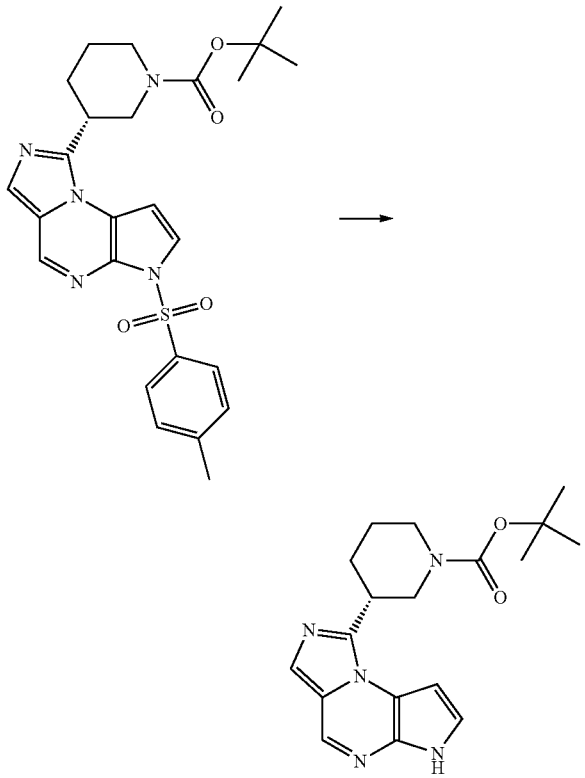

To a solution of (R)-tert-butyl 3-(6-tosyl-6H-imidazo[1,5-a]pyrrolo[2,3-e]pyrazin-1-yl)piperidine-1-carboxylate (4.44 g, 8.96 mmol) in 1,4-dioxane (54 mL) was added NaOH (2 N aqueous, 8.9 mL, 18 mmol), and the resulting mixture was heated at about 60° C. for about 3 h. The reaction was cooled to ambient temperature and EtOAc (30 mL) and saturated aqueous $NH_4Cl$ (20 mL) were added. The organic layer was separated and the aqueous layer was further extracted with EtOAc (40 mL). The combined organic layers were washed with brine (40 mL), dried over anhydrous $MgSO_4$, filtered, and concd under reduced pressure. The material was purified by silica gel chromatography eluting with a gradient of 0-10% MeOH in DCM to afford (R)-tert-butyl 3-(6H-imidazo[1,5-a]pyrrolo[2,3-e]pyrazin-1-yl)piperidine-1-carboxylate (2.80 g, 92%): LC/MS (Table 1, Method b) $R_t$=1.85 min; MS m/z: 342 $(M+H)^+$.

Step H: (R)-1-(piperidin-3-yl)-6H-imidazo[1,5-a]pyrrolo[2,3-e]pyrazine hydrochloride

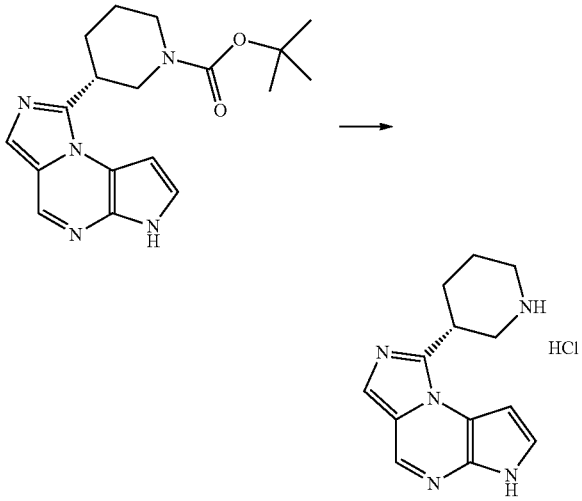

A round bottom flask was charged with (R)-tert-butyl 3-(6H-imidazo[1,5-a]pyrrolo[2,3-e]pyrazin-1-yl)piperidine-1-carboxylate (2.8 g, 8.20 mmol), 1,4-dioxane (24 mL) and HCl (4 N in 1,4-dioxane, 6.2 mL, 24.6 mmol). The reaction mixture was heated at about 60° C. for about 18 h. The reaction mixture was cooled to ambient temperature, $Et_2O$ (40 mL) was added and the mixture was stirred for about 15 min. The solid was collected by vacuum filtration and washed with $Et_2O$ (50 mL) then dried in a vacuum oven at about 60° C. to afford (R)-1-(piperidin-3-yl)-6H-imidazo[1,5-a]pyrrolo[2,3-e]pyrazine hydrochloride as an off-white solid (2.4 g, 94%): LC/MS (Table 1, Method b) $R_t$=0.81 min; MS m/z 242 $(M+H)^+$.

Step I: (R)-(3-(6H-imidazo[1,5-a]pyrrolo[2,3-e]pyrazin-1-yl)piperidin-1-yl)(4,4-difluoropiperidin-1-yl)methanone

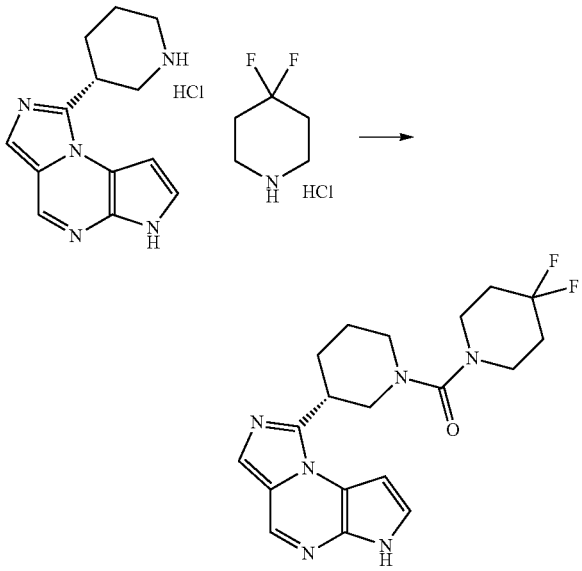

To a solution of (R)-1-(piperidin-3-yl)-6H-imidazo[1,5-a]pyrrolo[2,3-e]pyrazine hydrochloride (0.24 g, 0.76 mmol) in pyridine (7.2 mL) was added CDI (0.14 g, 0.87 mmol) and the reaction mixture was stirred at about 50° C. for about 2 h. Additional CDI (0.02 g, 0.14 mmol) was added and the reaction mixture was stirred for about 1 h. To the reaction mixture was added 4,4-difluoropiperidine hydrochloride (0.12 g, 0.76 mmol). The reaction mixture was heated to about 55° C. for about 1 h, cooled to ambient temperature, and stirred for about 2 d. The solvent was removed under reduced pressure and the crude residue dissolved with DCM (5 mL) and washed with water (2 mL). The aqueous layer was back extracted with DCM (2 mL). The combined organic extracts were washed with brine (3 mL), dried over anhydrous $MgSO_4$, filtered, and concd under reduced pressure. The crude material was purified by silica gel chromatography eluting with a gradient of 0-5% MeOH in DCM to afford (R)-(3-(6H-imidazo[1,5-a]pyrrolo[2,3-e]pyrazin-1-yl)piperidin-1-yl)(4,4-difluoropiperidin-1-yl)methanone (0.146 g, 49%) as an off white solid: LC/MS (Table 1, Method b) $R_t$=1.70 min; MS m/z: 389 $(M+H)^+$.

Example #7

N-((1S,3S,4R)-3-(3H-imidazo[1,2-a]pyrrolo[2,3-e]pyrazin-8-yl)-4-methylcyclopentyl)-3,3,3-trifluoropropane-1-sulfonamide

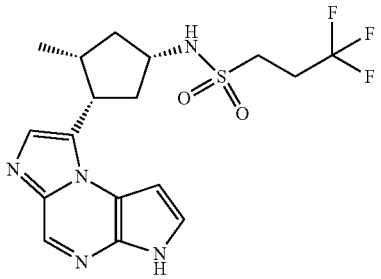

Step A: 5-Bromo-3-((trimethylsilyl)ethynyl)pyrazin-2-amine

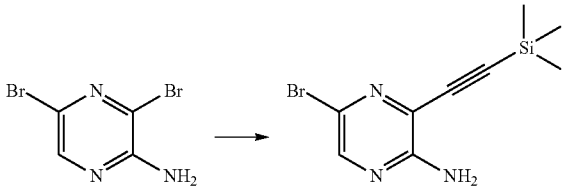

To a solution of 3,5-dibromopyrazin-2-amine (125 g, 494 mmol), TEA (207.0 mL, 1483 mmol), and copper (I) iodide (0.941 g, 4.94 mmol) in THF (1255 mL) was added $PdCl_2(PPh_3)_2$ (3.47 g, 4.94 mmol). The reaction mixture was cooled at about −5-0° C. and a solution of (trimethylsilyl) acetylene (65.0 mL, 470 mmol) in THF (157 mL) was added dropwise over about 15 min. The reaction mixture was stirred at about −5-0° C. for about 1.5 h and then allowed to warm to rt overnight. The reaction mixture was then filtered through a Celite® pad and washed with THF until no further product eluted. The filtrate was concd under reduced pressure to give a brown-orange solid. The solid was triturated and sonicated with warm petroleum ether (b.p. 30-60° C., 400 mL), cooled to rt, collected, washed with petroleum ether (b.p. 30-60° C.; 2×60 mL), and dried to give 5-bromo-3-((trimethylsilyl)ethynyl)pyrazin-2-amine (124 g, 93%, 93% purity) as a brown solid: LC/MS (Table 1, Method b) $R_t$=2.51 min; MS m/z: 270, 272 $(M+H)^+$.

Step B: 2-Bromo-5-tosyl-5H-pyrrolo[2,3-b]pyrazine

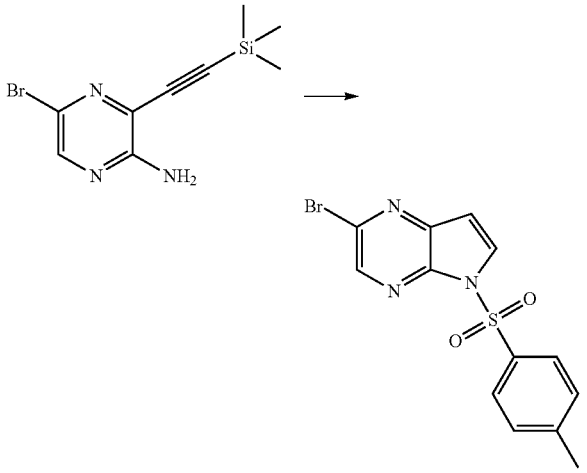

To a solution of 5-bromo-3-((trimethylsilyl)ethynyl) pyrazin-2-amine (3.00 g, 11.1 mmol) in DMF (60 mL) at about 0° C. was added NaH (60% dispersion in mineral oil, 0.577 g, 14.4 mmol) in three portions. After about 15 min, p-toluenesulfonyl chloride (2.75 g, 14.4 mmol) was added and the reaction was allowed to warm slowly to ambient temperature. After about 16 h, the reaction mixture was poured onto ice-cold water (120 mL) and the precipitate was collected by vacuum filtration. The crude solid was dissolved in DCM (15 mL) and purified by silica gel chromatography eluting with DCM to give 2-bromo-5-tosyl-5H-pyrrolo[2,3-b]pyrazine (2.16 g, 52%): LC/MS (Table 1, Method c) $R_t$=1.58 min; MS m/z: 352, 354 $(M+H)^+$.

Step C: tert-Butyl 5-tosyl-5H-pyrrolo[2,3-b]pyrazin-2-ylcarbamate

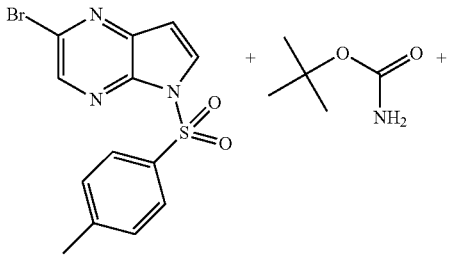

-continued

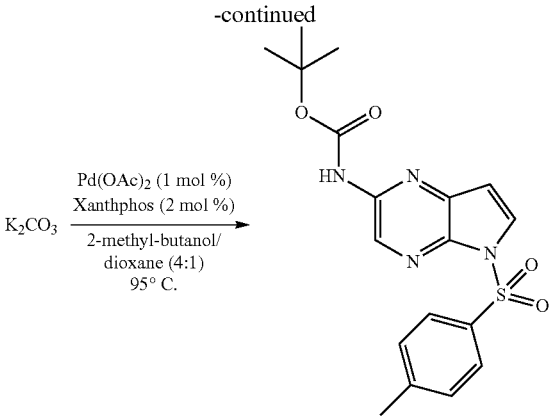

2-Bromo-5-tosyl-5H-pyrrolo[2,3-b]pyrazine (30.0 g, 85 mmol), tert-butyl carbamate (14.9 g, 128 mmol), 325 mesh potassium carbonate (35.3 g, 256 mmol), palladium acetate (0.19 g, 0.85 mmol) and 9,9-dimethyl-4,5-bis(diphenylphosphino)xanthene (Xantphos) (0.99 g, 1.70 mmol) were charged to a three-neck, 1 L cylindrical reactor equipped with an over head stirrer, thermocouple and a reflux condenser. The solids were purged with argon for not less than 120 min. 2-methyl-butanol (240 mL) and 1,4-dioxane (60 mL) were charged to a separate 500 mL round bottom flask and purged with argon for not less than 60 min. The solvent mixture was transferred to the 1 L flask using a cannula under a positive pressure of argon, the temperature was raised to about 95° C. and the reaction mixture was stirred for about 3 h under a positive pressure of argon. The reaction mixture was cooled to about 40° C., THF (100 mL) was added and filtered through a 2 inch pad of celite. The reaction mixture was split into 2 equal batches (about 200 mL) and each of the batches were purified separately. Each batch was diluted with THF (250 mL) and was transferred to a 1 L cylindrical flask equipped with a magnetic stir bar. A solution of L-cysteine (0.76 g), potassium bicarbonate (1.52 g) and sodium chloride (0.76 g) in water (250 mL) was added to the above flask and was allowed to stir for about 2-4 h. The aqueous layer was separated. Formation of a rag layer was observed that was kept with the organic layer. The organic layer was washed with saturated sodium chloride solution (100 mL) and the aqueous layer was separated. Charcoal (0.76 g) was added to the flask, stirred for about 2-4 h, filtered through a 2 inch pad of celite, rinsed with THF (30 mL) and concentrated in vacuo at about 60° C. to obtain an oil/solid slurry. A mixture of isopropanol (50 mL) and heptanes (15 mL) were added to the oil/solid slurry and concentrated in vacuo to obtain light yellow colored solid. Isopropanol (90 mL) was added to the solid, heated to about 60° C. and mixed for about 1 h. The mixture was allowed to cool to room temperature with stirring, solids were filtered off, rinsed with heptane (40 mL) and dried overnight in a vacuum oven at about 50° C. The 2 batches were combined to obtain tert-butyl 5-tosyl-5H-pyrrolo[2,3-b]pyrazin-2-ylcarbamate (12.87 g), as a light yellow colored solid. $^1H$ NMR (400 MHz, DMSO) δ 10.11 (s, 1H), 8.77 (s, 1H), 8.16 (d, J=4.1 Hz, 1H), 7.99-7.92 (m, 2H), 7.40 (d, J=8.4 Hz, 2H), 6.83 (d, J=4.1 Hz, 1H), 2.32 (s, 3H), 1.46 (s, 9H).

Step D: 5-Tosyl-5H-pyrrolo[2,3-b]pyrazin-2-amine

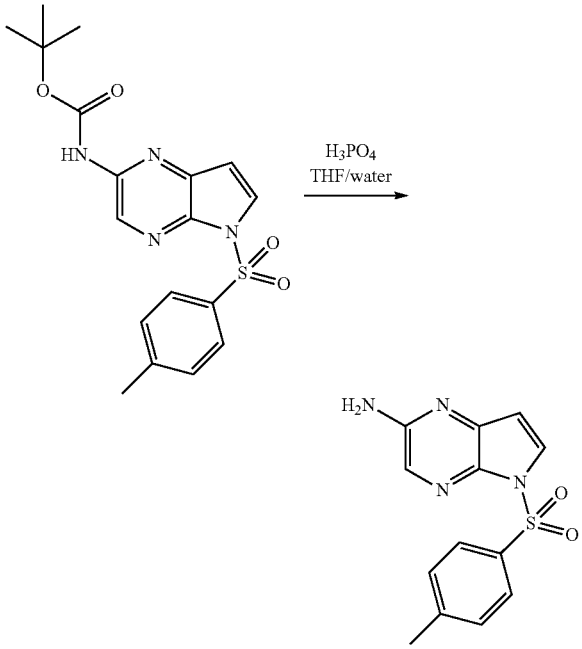

tert-Butyl 5-tosyl-5H-pyrrolo[2,3-b]pyrazin-2-ylcarbamate (14.0 g, 36.0 mmol) and tetrahydrofuran (28 mL) were charged to a 500 mL round bottom flask containing a magnetic stir bar. Phosphoric acid (10 equiv, 85%, 20.8 ml, 360 mmol) was added over about 5 minutes via needle and syringe. Upon addition, effervescing occurred and solids formed. The resultant slurry was heated to about 65° C. (bath temperature); upon reaching temperature all solids dissolved. After about 1 hr, there was no starting material present. The hot reaction mixture was diluted with tetrahydrofuran (115 mL); then the solution was allowed to cool to room temperature. A solution of potassium phosphate tribasic (35.3 g, 360 mmol) in water (145 mL) was prepared and added to the mixture over about 20 minutes with vigorous stirring. The biphasic mixture was transferred to a separatory funnel using THF and water. The layers were separated and the organic layer was transferred to a 500 mL round bottom flask. Water (100 mL) was added to the flask and the organics are removed under reduced pressure. This resulted in a suspension of solids in water, which was allowed to slurry for about 30 minutes. The solids were isolated by vacuum filtration and placed in a vacuum oven to dry (oven temperature about 50° C.) for about 16 hours. 5-Tosyl-5H-pyrrolo[2,3-b]pyrazin-2-amine was isolated as an off white solid (10.1 g, 97%). $^1$H NMR (400 MHz, $d_6$-DMSO) δ 7.88-7.84 (m, 3H), 7.64 (s, 1H), 7.39 (d, J=8.4, 2H), 6.55 (d, J=4.0, 1H), 6.31 (s, 2H), 2.33 (s, 3H)

Step E: Sodium 4-(ethoxycarbonyl)-2-(methoxycarbonyl)-3-methylcyclopenta-1,3-dienolate

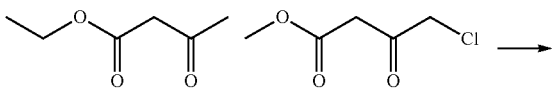

-continued

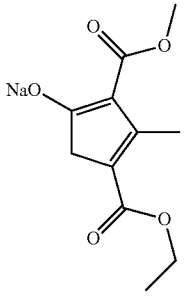

In a 12 L round bottom flask, NaH (60% dispersion in mineral oil, 159 g, 3985 mmol) was added in portions to stirred anhydrous THF (4004 mL) to give a gray suspension. The mixture was cooled to about 5° C. in an ice/salt bath before ethyl acetoacetate (506 mL, 3985 mmol, Alfa Aesar) in anhydrous THF (200 mL) was added dropwise via an addition funnel over about 1 h during which time the temperature gradually increased to about 18° C. After the addition was complete, the reaction was stirred at ambient temperature for about 1 h and then a solution of methyl 4-chloroacetoacetate (230 mL, 1993 mmol, Oakwood) in anhydrous THF (200 mL) was added dropwise via an addition funnel over about 1 h. The resulting mixture was stirred at ambient temperature for about 2 h and then heated at about 50° C. for about 16 h. The reaction mixture was concd in vacuo. The orange solid was cooled to about 5° C. and an ice/water mixture (2 L) was added. The suspension was mixed by rotating on the rotovap without vacuum for about 30 min. The solid was collected by filtration and washed with ice-cold water (750 mL). Once most of the solvent (about 90%) had been removed, the wet solid was triturated with MeCN (750 mL), stirred for about 30 min and then the solid was collected by filtration while washing with $Et_2O$ (2×500 mL). The solid was dried in air for about 16 h and then in vacuo at about 55° C. to give sodium 4-(ethoxycarbonyl)-2-(methoxycarbonyl)-3-methylcyclopenta-1,3-dienolate (485 g, 98%): $^1$H NMR (DMSO-$d_6$) δ 3.95 (q, J=7.1 Hz, 2H), 3.48 (s, 3H), 2.69 (q, J=2.0 Hz, 2H), 2.47 (t, J=2.1 Hz, 3H), 1.15 (t, J=7.1 Hz, 3H).

Step F: Ethyl 2-methyl-4-oxocyclopent-2-enecarboxylate

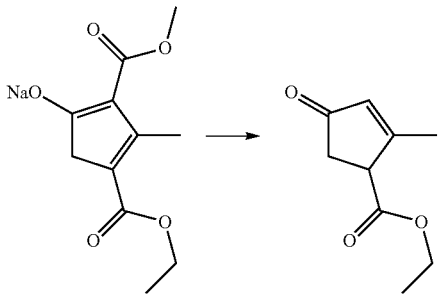

In a 5 L round bottom flask, sodium 4-(ethoxycarbonyl)-2-(methoxycarbonyl)-3-methylcyclo-penta-1,3-dienolate (485 g, 1954 mmol), KCl (204 g, 2736 mmol, JT Baker), and AcOH (392 mL, 6839 mmol, JT Baker) in toluene (1200 mL) and water (1200 mL) were heated at reflux for about 6 h. The reaction mixture was allowed to cool to ambient temperature for about 16 h. The reaction mixture was then poured into a 12 L flask and diluted with water (3 L). Solid $NaHCO_3$ (450 g, 5.3 mol) was added cautiously portionwise with stirring over about 1 h. After an additional about 30 min of stirring, the basic aqueous phase was separated and further extracted with $Et_2O$ (4×400 mL). The combined organic layers were washed with water (4×500 mL) and saturated brine (500 mL), dried over anhydrous $MgSO_4$, filtered, and concd under reduced pressure to yield a yellow oil that was purified by vacuum distillation (about 92-94° C. at about 0.4 mmHg) to give ethyl 2-methyl-4-oxocyclopent-2-enecarboxylate (229 g, 69%) as a yellow oil: $^1$H NMR ($CDCl_3$) δ 6.04-6.01 (m, 1H), 4.26-4.17 (m, 2H), 3.67 (m, 1H), 2.72 (m, 1H), 2.62 (m, 1H), 2.16 (s, 3H), 1.32-1.27 (t, J=7.1 Hz, 3H).

Step G: Ethyl 2-methyl-4-oxocyclopentanecarboxylate

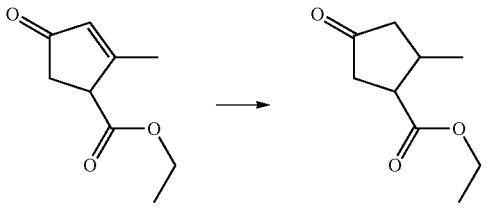

EtOAc (580 mL) was added to a round bottom flask charged with 10 wt % Pd/C (7.6 g, 7.1 mmol) at about 0° C., under a nitrogen atmosphere. The cooling bath was removed and ethyl 2-methyl-4-oxocyclopent-2-enecarboxylate (60.0 g, 357 mmol) was added. Hydrogen gas was bubbled through the mixture for about 5 min and the mixture was then stirred under a hydrogen atmosphere (1 atmosphere) for about 48 h. The hydrogen source was removed and the mixture was bubbled with nitrogen for about 5 min and was filtered through a pad of Celite®. The filter cake was rinsed with EtOAc (500 mL). The filtrate was concd under reduced pressure to give ethyl 2-methyl-4-oxocyclopentanecarboxylate (59.9 g, 99%) as a yellow liquid: $^1$H NMR ($CDCl_3$) δ 4.23-4.14 (m, 2H), 3.18 (ddd, J=5.6, 6.8, 8.1 Hz, 1H), 2.73-2.65 (m, 1H), 2.60 (ddd, J=1.7, 5.5, 18.7 Hz, 1H), 2.42-2.29 (m, 2H), 2.15 (ddd, J=1.7, 7.9, 18.3 Hz, 1H), 1.29 (t, J=7.1 Hz, 3H), 1.07 (d, J=7.0 Hz, 3H).

Step H: Ethyl 4-(dibenzylamino)-2-methylcyclopentanecarboxylate

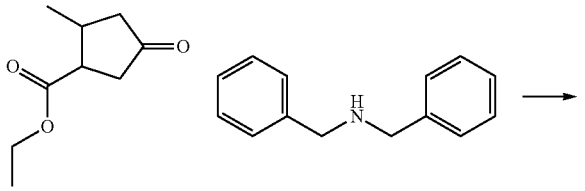

-continued

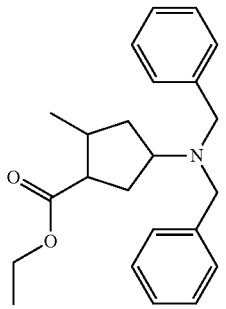

A round bottom flask was charged with ethyl 2-methyl-4-oxocyclopentanecarboxylate (10.0 g, 58.8 mmol) and DCE (180 mL). The solution was cooled to about 0° C. and AcOH (5.7 mL, 100 mmol) and dibenzylamine (11.3 mL, 58.8 mmol) were added dropwise, resulting in formation of a thick suspension. The reaction mixture was warmed to about 10° C. and sodium triacetoxyborohydride (21.2 g, 100 mmol) was added portionwise and the reaction mixture was stirred at ambient temperature for about 20 h. The reaction mixture was slowly poured into stirred saturated aqueous $NaHCO_3$ (300 mL) and was stirred for about 20 min. The layers were separated and the aqueous phase was extracted with DCM (3×100 mL). The combined organic extracts were washed with brine (2×100 mL), dried over anhydrous $Na_2SO_4$, and concd under reduced pressure. The crude yellow oil was purified via flash column chromatography eluting with a gradient of 0-30% EtOAc in heptane to give ethyl 4-(dibenzylamino)-2-methylcyclopentanecarboxylate (15.5 g, 75%) as a colorless oil: $^1$H NMR (pyridine-$d_5$) δ 7.53 (dd, J=0.9, 7.9 Hz, 4H), 7.43-7.35 (m, 4H), 7.33-7.25 (m, 2H), 4.22-4.06 (m, 2H), 3.79 (d, J=14.2 Hz, 2H), 3.70 (d, J=14.2 Hz, 2H), 3.34-3.22 (m, 1H), 2.76 (dd, J=7.9, 16.6 Hz, 1H), 2.25-2.13 (m, 1H), 2.09-1.94 (m, 2H), 1.88-1.79 (m, 1H), 1.52 (dd, J=10.5, 22.5 Hz, 1H), 1.16 (t, J=7.1 Hz, 3H), 0.98 (d, J=7.0 Hz, 3H).

Step I: 4-(Dibenzylamino)-2-methylcyclopentanecarboxylic acid

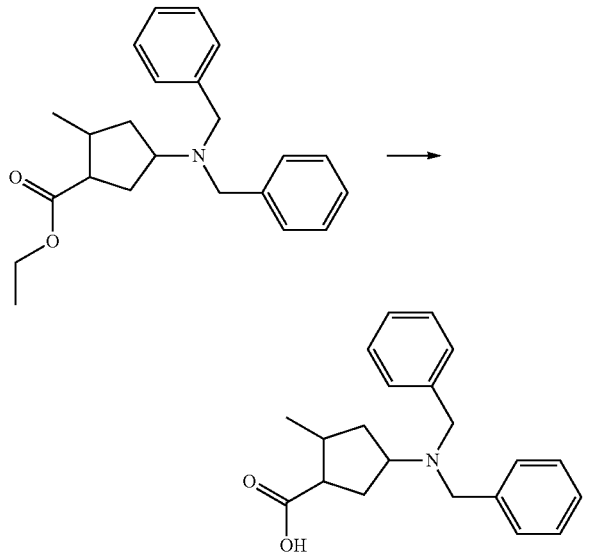

Ethyl 4-(dibenzylamino)-2-methylcyclopentanecarboxylate (3.65 g, 10.38 mmol) was dissolved in a mixture of HCl (6 N aqueous, 20 mL) and 1,4-dioxane (50 mL) and the resulting mixture was heated at about 60° C. for about 72 h. The organic solvent was removed under reduced pressure. The aqueous phase was neutralized by the addition of saturated aqueous $NaHCO_3$ (40 mL) and extracted with EtOAc (50 mL). The organic phase was washed with brine (40 mL), dried over anhydrous $MgSO_4$ and concd under reduced pressure to yield 4-(dibenzylamino)-2-methylcyclopentanecarboxylic acid (3.3 g, 98%) as a white amorphous solid: LC/MS (Table 1, Method a) $R_t$=1.66 min; MS m/z 324 $(M+H)^+$.

Step J: 2-(2-Methyl-4-(dibenzylamino)cyclopentyl) dimethylsulfoxonium-2-oxo-ethylide

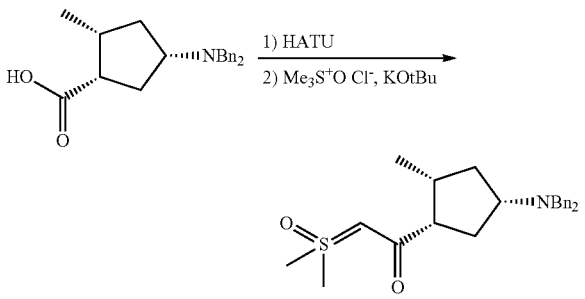

Trimethylsulfoxonium chloride (26.1 g, 198 mmol), THF (202 ml), and potassium tert-butoxide (23.35 g, 202 mmol) were added to a 500 mL jacketed flask under a nitrogen blanket. The suspension was stirred for about 2 hours at about 65° C. before being cooled to about 0° C. In a separate flask, (1S,2R,4S)-4-(dibenzylamino)-2-methylcyclopentanecarboxylic acid (21.4 g, 66.2 mmol) was dissolved in THF (134 ml). HATU (31.4 g, 83 mmol) and triethylamine (11.53 ml, 83 mmol) were added and the solution and mixed for about 4 h. With the sulfur ylide suspension maintained between about 0 and −5° C., the activated ester solution was filtered and then added dropwise over about 3 h to the ylide suspension. The resultant bright yellow suspension was stirred for about 8 h at about 5° C. Water (340 mL) and THF (30 mL) were added, and the mixture stirred for about 30 min at about 25° C. Aqueous sodium chloride (15% w/v, 60 mL) was added to the solution and the layers separated. The aqueous layer was extracted with EtOAc (60 mL). The combined organic layers were washed with aqueous NaCl (15% w/v, 3×100 mL). The solution was concentrated and the crude oil was dissolved in methanol (150 mL) and water (150 mL) was added to the slurry which is stirred for about 1 h at ambient temperature before being cooled to about 10° C. and stirred overnight. The white solid was filtered and washed with chilled 1:1 MeOH/H2O (20 mL) and water (60 mL). The solid was dried in the vacuum oven to afford 2-(2-methyl-4-(dibenzylamino)cyclopentyl)-dimethylsulfoxonium-2-oxo-ethylide (23.8 g, 90% yield). $^1$H NMR (400 MHz, DMSO) δ 7.30 (ddd, J=15.0, 10.7, 4.6 Hz, 8H), 7.21-7.14 (m, 2H), 4.67 (s, 1H), 3.71-3.52 (m, 4H), 3.39 (d, J=3.9 Hz, 6H), 3.13-2.99 (m, 1H), 2.48-2.39 (m, 1H), 2.05-1.84 (m, 2H), 1.82-1.66 (m, 2H), 1.43-1.30 (m, 1H), 0.90 (d, J=6.9 Hz, 3H).

Step K: 1-((1S,2R,4S)-4-(dibenzylamino)-2-methylcyclopentyl)-2-(5-tosyl-5H-pyrrolo[2,3-b]pyrazin-2-ylamino)ethanone

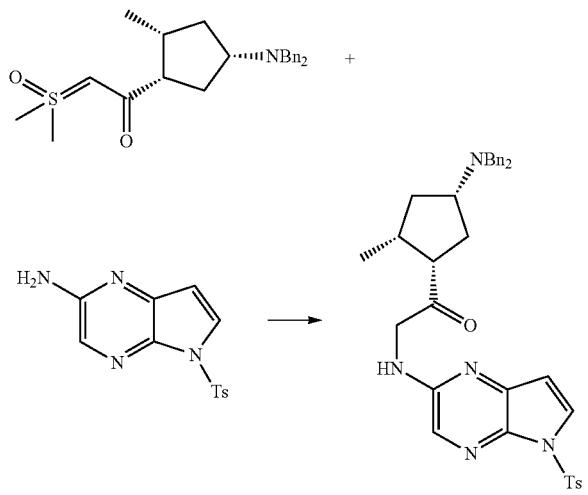

To a 40 mL vial, 2-(2-methyl-4-(dibenzylamino)cyclopentyl)-dimethylsulfoxonium-2-oxo-ethylide (4.02 g, 10.1 mmol), 5-tosyl-5H-pyrrolo[2,3-b]pyrazin-2-amine (2.92 g, 10.1 mmol), and chloro (1,5-cyclooctadiene) iridium(I) dimer (0.17 g, 0.3 mmol, Alfa Aesar) was added. The reaction vessel was purged with $N_2$ for about 10 min. To the reaction vessel, degassed $CH_3Cl$ (13 mL) was added via syringe. The reaction mixture was purged with $N_2$ for about 10 min and stirred under an atmosphere of $N_2$ at about 70° C. for about 68 h. The reaction mixture was allowed to cool to ambient temperature. The reaction mixture was purified by silica gel flash chromatography eluting with a gradient of 0-25% EtOAc in heptane to yield 1-((1S,2R,4S)-4-(dibenzylamino)-2-methylcyclopentyl)-2-(5-tosyl-5H-pyrrolo[2,3-b]pyrazin-2-ylamino)ethanone (8.61 g, 56%) as tan foam. $^1$H NMR (400 MHz, DMSO) δ 7.91-7.80 (m, 4H), 7.42-7.34 (m, 2H), 7.33-7.23 (m, 9H), 7.21-7.13 (m, 2H), 6.52 (d, J=3.5 Hz, 1H), 4.23-4.04 (m, 2H), 3.63-3.48 (m, 4H), 3.19-3.09 (m, 1H), 3.08-2.99 (m, 1H), 2.32 (s, 3H), 2.29-2.18 (m, 1H), 1.94-1.71 (m, 3H), 1.37-1.23 (m, 1H), 0.86 (d, J=7.8 Hz, 3H).

Step L: (1S,3S,4R)-N,N-dibenzyl-3-(3H-imidazo[1,2-a]pyrrolo[2,3-e]pyrazin-8-yl)-4-methylcyclopentanamine

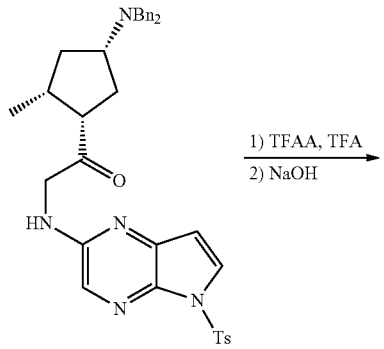

-continued

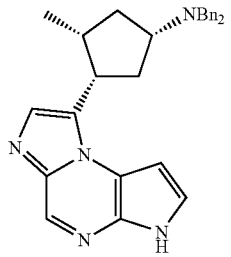

To a 250 mL round-bottomed flask 1-((1S,2R,4S)-4-(dibenzylamino)-2-methylcyclopentyl)-2-(5-tosyl-5H-pyrrolo[2,3-b]pyrazin-2-ylamino)ethanone (11.2 g, 17.51 mmol) in acetonitrile (60 ml) was added. The mixture was cooled with an ice bath and TFA (2.70 ml, 35.0 mmol) and TFAA (24.46 ml, 175 mmol) was added. The resulting mixture was warmed and stirred at about 40° C. for about 42 h. The reaction was then cooled in an ice bath and quenched with methanol (7 mL). After warming to ambient temperature and stirring for about 1 h, it was poured into ethyl acetate (100 mL) and aqueous sodium carbonate (10% w/v, 200 mL). The layers were separated and the organic layer concentrated. The residue was dissolved in THF (120 ml) and 2N sodium hydroxide (35.0 ml, 70.0 mmol) was added. The reaction mixture was warmed to about 60° C. and stirred for about 16 h. After cooling to ambient temperature, 2-methyl-tetrahydrofuran (100 mL) and brine (100 mL) were added and the layers separated. The aqueous layer was extracted with 2-methyl-tetrahydrofuran (50 mL) and the combined organic layers washed with brine (50 mL). The organic layer was concentrated, dissolved in EtOH (100 mL) and treated with charcoal (500 mg) for about 1 h. The charcoal was filtered off and the ethanol removed under reduced pressure. The residue was taken up in $CHCl_3$ (50 mL) warmed to about 50° C. and heptane (50 mL) was added. After cooling to ambient temperature, the product was collected, washed with 1:2 $CHCl_3$:heptane (30 mL) and dried in a vacuum oven to afford (1S,3S,4R)-N,N-dibenzyl-3-(3H-imidazo[1,2-a]pyrrolo[2,3-e]pyrazin-8-yl)-4-methylcyclopentanamine as a tan solid (5.1 g, 67%) $^1$H NMR (400 MHz, DMSO) δ 12.18 (s, 1H), 8.52 (s, 1H), 7.60 (s, 1H), 7.44-7.29 (m, 8H), 7.22 (t, J=7.2 Hz, 2H), 6.84 (d, J=3.4 Hz, 1H), 3.86 (dd, J=17.6, 8.8 Hz, 1H), 3.77-3.59 (m, 4H), 3.41-3.17 (m, 2H), 2.64-2.53 (m, 1H), 2.32-2.06 (m, 3H), 1.49-1.30 (m, 1H), 0.40 (d, J=7.0 Hz, 3H).

Step M: (1S,3S,4R)-3-(3H-imidazo[1,2-a]pyrrolo[2,3-e]pyrazin-8-yl)-4-methylcyclopentanamine hydrochloride

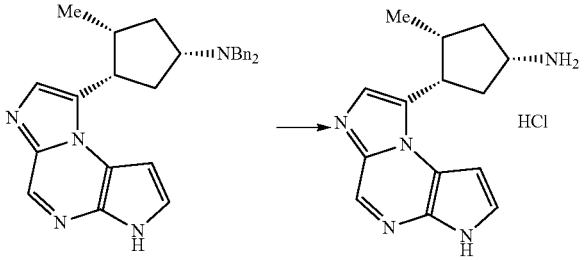

To a 1.8 L stainless steel pressure bottle (1S,3S,4R)-N,N-dibenzyl-3-(3H-imidazo[1,2-a]pyrrolo[2,3-e]pyrazin-8-yl)-4-methylcyclopentanamine (49 g, 112 mmol), 10% $Pd(OH)_2/C$ (20 g, Johnson Mathey) and ethanol (750 ml) was added under nitrogen. The reactor was purged with nitrogen then hydrogen. The vessel was pressurized with hydrogen to about 30 psig. The mixture was agitated for about 22 hrs at about 50° C. After cooling to ambient temperature, the reaction was filtered through a buchner funnel containing a glass fiber filter to remove the catalyst. Conc. HCl (12 M, 16.7 mL) was added and concentrated under reduced pressure. The residue was suspended in ethanol (100 mL) and EtOAc (100 mL), the solids collected by filtration, washed with 1:1 EtOAc:EtOH (30 mL) and dried in a vacuum oven to afford (1S,3S,4R)-3-(3H-imidazo[1,2-a]pyrrolo[2,3-e]pyrazin-8-yl)-4-methylcyclopentanamine hydrochloride as an off-white solid (33.3 g, 86%). $^1$H NMR (400 MHz, DMSO) δ 13.11 (s, 1H), 8.90 (s, 1H), 8.65-8.42 (m, 4H), 7.88 (t, J=3.1 Hz, 1H), 7.21 (s, 1H), 4.20 (dd, J=17.3, 8.6 Hz, 1H), 3.75-3.52 (m, 1H), 2.77-2.63 (m, 1H), 2.61-2.52 (m, 1H), 2.33 (ddd, J=31.4, 17.8, 8.8 Hz, 2H), 1.54 (dt, J=12.7, 6.4 Hz, 1H), 0.50 (d, J=7.0 Hz, 3H).

Step N: N-((1S,3S,4R)-3-(3H-imidazo[1,2-a]pyrrolo[2,3-e]pyrazin-8-yl)-4-methylcyclopentyl)-3,3,3-trifluoropropane-1-sulfonamide

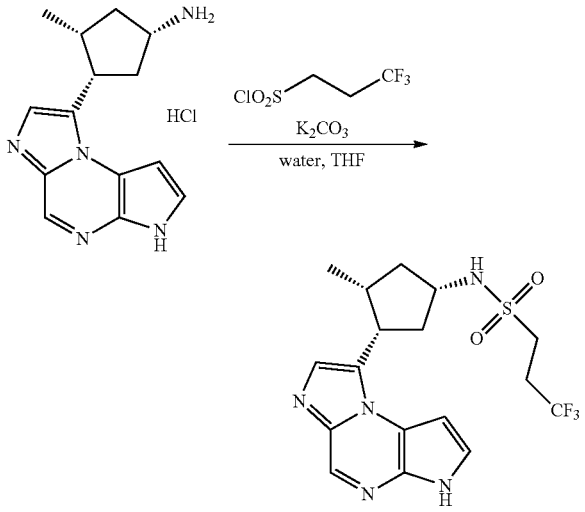

To a 2 L flask (1S,3S,4R)-3-(3H-imidazo[1,2-a]pyrrolo[2,3-e]pyrazin-8-yl)-4-methylcyclopentanamine hydrochloride (248.0 g, 733 mmol), water (1240 ml), THF (124 ml) and activated carbon (24.12 g) was added and stirred for about 10 min. The resulting mixture was filtered through celite rinsing with a mixture of water (100 mL) and THF (24 mL). Potassium carbonate (668 g, 4836 mmol) and THF (1736 ml) were added and a solution of 3,3,3-trifluoropropane-1-sulfonyl chloride (315 g, 1524 mmol, Matrix) in THF (620 ml) was added over about 1 hr. After cooling to ambient temperature the layers were separated and the aqueous layer extracted with THF (500 mL). The combined organic layers were washed with aqueous ammonium chloride (3×100 mL) and concentrated to approximately 1 L. Water (1770 mL) was added slowly at about 50° C. and the slurry cooled to about 23° C. The solids were collected by filtration, washed with 35% THF in water (750 mL) and dried in a vacuum oven. The crude material was dissolved in MeOH (4.5 L) and treated with activated carbon (28.3 g).

After filtering through celite and rinsing with MeOH (500 mL), the solution was concentrated under reduced pressure to approximately 1 L and water (800 mL) was added slowly at about 50° C. then cooled to 35° C. when additional water (360 mL) was added. The product was collected by filtration, washed with 1:1 MeOH:water (2×350 mL) and dried in a vacuum oven to afford N-((1S,3S,4R)-3-(3H-imidazo[1,2-a]pyrrolo[2,3-e]pyrazin-8-yl)-4-methylcyclopentyl)-3,3,3-trifluoropropane-1-sulfonamide (215.3 g, 71%) as a white crystalline solid (m.p. 225° C.). $^1$H NMR (400 MHz, DMSO) δ 11.99 (bs, 1H), 8.30 (s, 1H), 7.40 (bs, 1H), 7.38 (s, 1H), 7.27-7.07 (m, 1H), 6.62 (d, J=3.4 Hz, 1H), 3.75 (dt, J=10.1, 7.8 Hz, 1H), 3.70-3.55 (m, 1H), 3.15-3.02 (m, 2H), 2.61-2.40 (m, 2H), 2.40-2.29 (m, 1H), 2.23 (dd, J=13.3, 6.9 Hz, 1H), 2.16-2.03 (m, 1H), 1.94-1.77 (m, 1H), 1.20-0.99 (m, 1H), 0.17 (d, J=7.0 Hz, 3H).

Example #8*

2-((1S,3R,4S)-3-ethyl-4-(6H-pyrrolo[2,3-e][1,2,4]triazolo[4,3-a]pyrazin-1-yl)cyclopentylamino)thiazole-5-carbonitrile

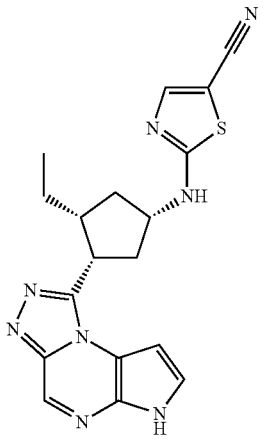

Step A: 5-bromo-3-((trimethylsilyl)ethynyl)pyrazin-2-amine

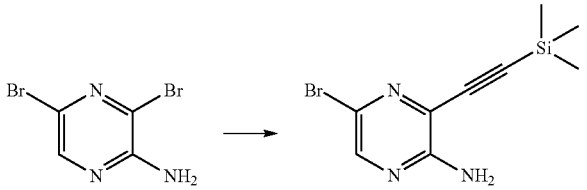

To a solution of 3,5-dibromopyrazin-2-amine (125 g, 494 mmol), TEA (207.0 mL, 1483 mmol), and copper (I) iodide (0.941 g, 4.94 mmol) in THF (1255 mL) was added $PdCl_2(PPh_3)_2$ (3.47 g, 4.94 mmol). The reaction mixture was cooled at about −5-0° C. and a solution of (trimethylsilyl) acetylene (65.0 mL, 470 mmol) in THF (157 mL) was added dropwise over about 15 min. The reaction mixture was stirred at about −5-0° C. for about 1.5 h and then allowed to warm to rt overnight. The reaction mixture was then filtered through a Celite® pad and washed with THF until no further product eluted. The filtrate was concd under reduced pressure to give a brown-orange solid. The solid was triturated and sonicated with warm petroleum ether (b.p. 30-60° C., 400 mL), cooled to rt, collected, washed with petroleum ether (b.p. 30-60° C.; 2×60 mL), and dried to give 5-bromo-3-((trimethylsilyl)ethynyl)pyrazin-2-amine (124 g, 93%, 93% purity) as a brown solid: LC/MS (Table 1, Method b) $R_t$=2.51 min; MS m/z: 270, 272 $(M+H)^+$.

Step B: 2-bromo-5-tosyl-5H-pyrrolo[2,3-b]pyrazine

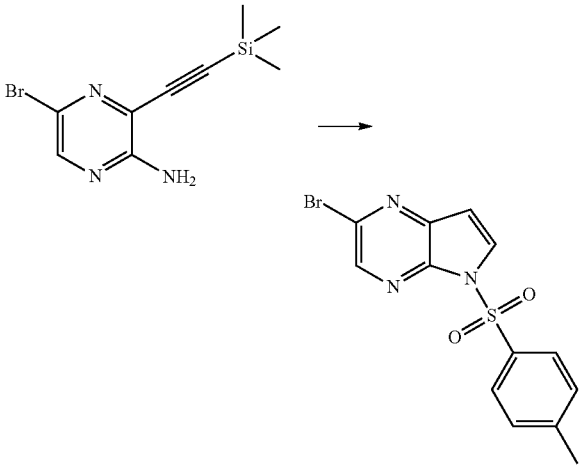

To a solution of 5-bromo-3-((trimethylsilyl)ethynyl) pyrazin-2-amine (3.00 g, 11.1 mmol) in DMF (60 mL) at about 0° C. was added NaH (60% dispersion in mineral oil, 0.577 g, 14.4 mmol) in three portions. After about 15 min, p-toluenesulfonyl chloride (2.75 g, 14.4 mmol) was added and the reaction was allowed to warm slowly to ambient temperature. After about 16 h, the reaction mixture was poured onto ice-cold water (120 mL) and the precipitate was collected by vacuum filtration. The crude solid was dissolved in DCM (15 mL) and purified by silica gel chromatography eluting with DCM to give 2-bromo-5-tosyl-5H-pyrrolo[2,3-b]pyrazine (2.16 g, 52%): LC/MS (Table 1, Method c) $R_t$=1.58 min; MS m/z: 352, 354 $(M+H)^+$.

Step C: tert-butyl 2-(5-tosyl-5H-pyrrolo[2,3-b]pyrazin-2-yl)hydrazinecarboxylate and tert-butyl 1-(5-tosyl-5H-pyrrolo[2,3-b]pyrazin-2-yl)hydrazinecarboxylate

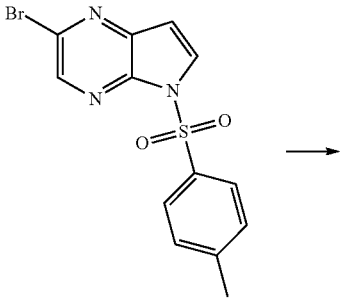

-continued

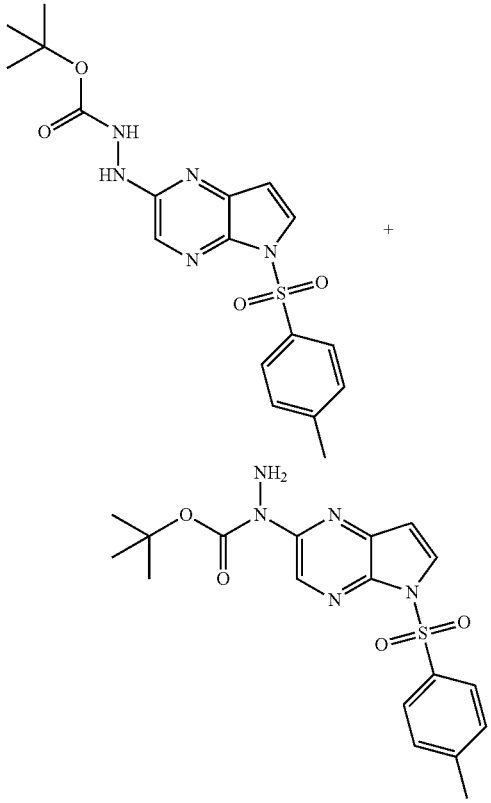

To a flask was added $Pd_2(dba)_3$ (3.90 g, 4.26 mmol), di-tert-butyl-(2',4',6'-triisopropylbiphenyl-2-yl)phosphane (3.62 g, 8.52 mmol), and 1,4-dioxane (453 mL). The catalyst-ligand mixture was degassed via vacuum/nitrogen purge (3 times) and heated at about 80° C. for about 10 min. Then 2-bromo-5-tosyl-5H-pyrrolo[2,3-b]pyrazine (30.0 g, 85 mmol), tert-butyl hydrazinecarboxylate (16.9 g, 128 mmol), and NaOt-Bu (12.28 g, 128 mmol) were added. After an additional vacuum/nitrogen purge, the reaction was heated at about 80° C. After about 50 min, the reaction mixture was cooled to ambient temperature and filtered through a pad of silica gel (6 cm in height×6 cm in diameter), topped with Celite® (1 cm in height×6 cm in diameter), while washing with EtOAc (3×150 mL). Water (300 mL) was added to the filtrate and the organic layer was separated. The aqueous layer was extracted with additional EtOAc (3×200 mL). The combined organic extracts were washed with saturated aqueous $NH_4Cl$, saturated aqueous $NaHCO_3$, and brine (400 mL each), dried over anhydrous $MgSO_4$, filtered, and concd under reduced pressure to give a dark brown oil (45 g). The brown oil was dissolved in DCM (250 mL), silica gel (200 g) was added, and the mixture was concd under reduced pressure. The resulting silica mixture was purified using silica gel chromatography eluting with a gradient of 25-65% EtOAc in heptane to give a mixture of tert-butyl 2-(5-tosyl-5H-pyrrolo[2,3-b]pyrazin-2-yl)hydrazinecarboxylate [major regioisomer] and tert-butyl 1-(5-tosyl-5H-pyrrolo[2,3-b]pyrazin-2-yl)hydrazinecarboxylate [minor regioisomer] (18.8 g, 50%): LC/MS (Table 1, Method c) $R_t$=1.47 min; MS m/z: 404 $(M+H)^+$.

Step D: 2-hydrazinyl-5-tosyl-5H-pyrrolo[2,3-b]pyrazine

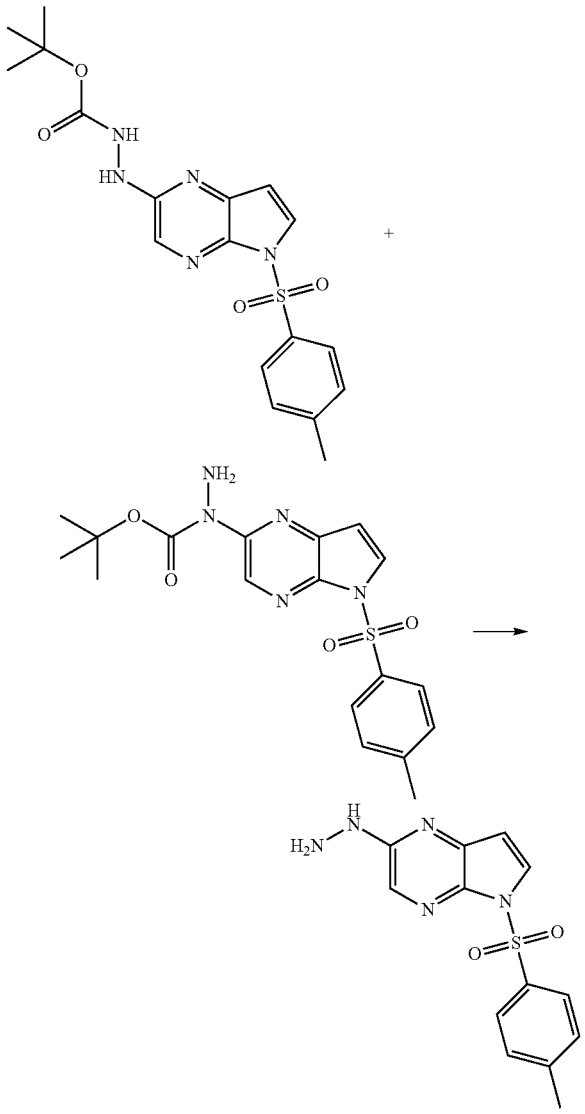

To a mixture of tert-butyl 2-(5-tosyl-5H-pyrrolo[2,3-b]pyrazin-2-yl)hydrazinecarboxylate and tert-butyl 1-(5-tosyl-5H-pyrrolo[2,3-b]pyrazin-2-yl)hydrazinecarboxylate (49.2 g, 122 mmol) in 1,4-dioxane (290 mL) was added HCl (4 M in 1,4-dioxane, 226 mL, 902 mmol). The reaction was heated at about 60° C. for about 2.5 h and then cooled to about 15-20° C. The solid was collected by vacuum filtration, washed with EtOAc (3×50 mL), and then triturated with $Et_2O$ (60 mL), collected by vacuum filtration and dried to a constant weight under vacuum to yield 35.6 g of solid. The solid was stirred with a mixture of saturated aqueous $NaHCO_3$ and EtOAc (1:1, 400 mL). After about 1 h, the solid was collected by vacuum filtration, washed with ice cold water (3×30 mL) and EtOAc (3×30 mL), and dried in a vacuum oven to a constant weight to afford 2-hydrazinyl-5-tosyl-5H-pyrrolo[2,3-b]pyrazine as a tan solid (21.2 g, 57%): LC/MS (Table 1, Method a) $R_t$=1.88 min; MS m/z: 304 $(M+H)^+$.

Step E: sodium 4-(ethoxycarbonyl)-3-ethyl-2-(methoxycarbonyl)cyclopenta-1,3-dienolate

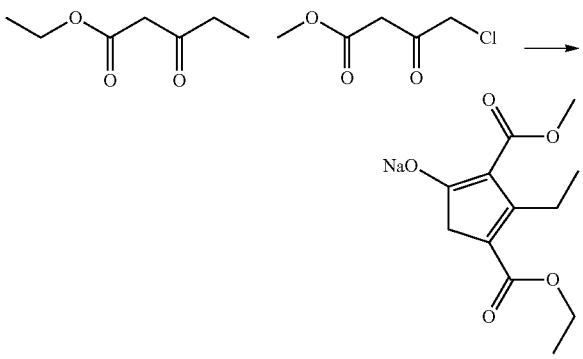

A round bottom flask was charged with THF (1.5 L) followed by the portionwise addition of NaH (60% dispersion in mineral oil, 70.0 g, 1.75 mol). Additional THF (500 mL) was added and the resulting mixture was cooled to about −10° C. and ethyl propionylacetate (250 mL, 1.80 mol) was added dropwise over about 1 h in order to keep internal temperature below about 10° C. The resulting mixture was stirred at ambient temperature for about 0.5 h to give a clear yellow solution, and methyl 4-chloroacetoacetate (100 mL, 0.88 mol) was added dropwise over about 5 min. The resulting mixture was heated at about 50° C. for about 19 h to give a reddish orange suspension. The reaction mixture was cooled to ambient temperature, concd under reduced pressure and the resulting liquid was transferred to a beaker and diluted with water (350 mL). The mixture was stirred in an ice bath for about 2 h. The solid was collected by vacuum filtration and the filter cake was rinsed with water (150 mL) and dried under vacuum for about 1 h. The solid was suspended in $Et_2O$ (1.5 L), filtered, washed with $Et_2O$ (1.5 L), and dried under vacuum. The resulting solid was azeotroped with toluene (1 L) to give a solid that was re-suspended in $Et_2O$ (1 L) and collected by vacuum filtration. The filter cake was washed with $Et_2O$ (500 mL) and dried under vacuum to give sodium 4-(ethoxycarbonyl)-3-ethyl-2-(methoxycarbonyl)cyclopenta-1,3-dienolate (204.2 g, 89%) as a beige solid: $^1$H NMR (DMSO-$d_6$) δ 3.94 (q, J=7.1 Hz, 2H), 3.46 (s, 3H), 3.04 (q, J=7.2 Hz, 2H), 2.66 (s, 2H), 1.13 (t, J=7.1 Hz, 3H), 0.99 (t, J=7.3 Hz, 3H).

Step F: ethyl 2-ethyl-4-oxocyclopent-2-enecarboxylate

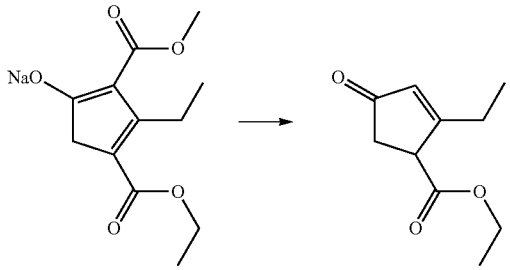

A 5 L round bottom flask was charged with sodium 4-(ethoxycarbonyl)-3-ethyl-2-(methoxycarbonyl)cyclopenta-1,3-dienolate (316 g, 1205 mmol), KCl (126 g, 1687 mmol, JT-Baker), AcOH (241 mL, 4218 mmol, JT-Baker), toluene (1850 mL) and water (130 mL). The reaction was heated at reflux for about 6 h then cooled to ambient temperature and added dropwise to $NaHCO_3$ (8% w/v aqueous, 3.5 L). The resulting biphasic mixture was extracted with MTBE (2×1.5 L). The combined organic layers were washed with brine (1 L), dried over anhydrous $MgSO_4$ and concd under reduced pressure to give 191 g of crude material that was purified by vacuum distillation (97-99° C., 0.600 mm Hg) to give ethyl 2-ethyl-4-oxocyclopent-2-enecarboxylate (160 g, 69%): $^1$H NMR ($CDCl_3$) δ 6.04 (m, 1H), 4.26-4.15 (m, 2H), 3.76-3.69 (m, 1H), 2.75-2.57 (m, 2H), 2.56-2.44 (m, 2H), 1.32-1.26 (m, 3H), 1.23-1.18 (m, 3H).

Step G: ethyl 2-ethyl-4-oxocyclopentanecarboxylate

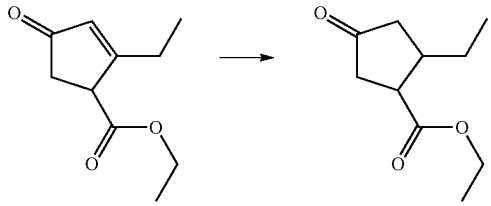

A round bottom flask was charged with 10 wt % Pd/C (10 g, 9.4 mmol). The flask was cooled to about 0° C. and EtOAc (400 mL) was added under a nitrogen atmosphere. The cooling bath was removed and ethyl 2-ethyl-4-oxocyclopent-2-enecarboxylate (47.8 g, 263 mmol) was added. Hydrogen gas was bubbled through the mixture for about 5 min and the mixture was then stirred under a hydrogen atmosphere for about 48 h. The hydrogen source was removed and the mixture was bubbled with nitrogen for about 5 min and was filtered through a pad of Celite®. The filter cake was rinsed with EtOAc (400 mL). The filtrate was coned under reduced pressure to give ethyl 2-ethyl-4-oxocyclopentanecarboxylate (about 9:1 mixture cis:trans) (48.0 g, 99%) as a yellow liquid: $^1$H NMR ($CDCl_3$) δ 4.23-4.10 (m, 2H), 3.22 (m, 1H), 2.59-2.50 (m, 1H), 2.44-2.28 (m, 3H), 2.26-2.16 (m, 1H), 1.58-1.46 (m, 1H), 1.41-1.30 (m, 1H), 1.30-1.23 (m, 3H), 1.02-0.91 (m, 3H).

Step H: ethyl 4-(dibenzylamino)-2-ethylcyclopentanecarboxylate

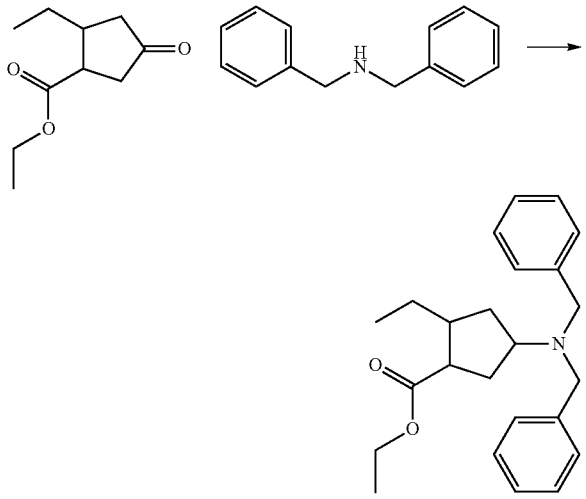

A round bottom flask was charged with ethyl 2-ethyl-4-oxocyclopentanecarboxylate (95.9 g, 521 mmol) and DCE (1.8 L). The solution was cooled to about 0° C. and AcOH (45 mL, 780 mmol) and dibenzylamine (120 mL, 625 mmol) were added dropwise, resulting in the formation of a thick suspension. The reaction mixture was warmed to about 10° C. and additional DCE (500 mL) was added. Sodium triacetoxyborohydride (166 g, 781 mmol) was added portionwise and the reaction mixture was stirred at ambient temperature for about 20 h. The reaction mixture was slowly poured into stirred saturated aqueous $NaHCO_3$ (1.5 L), followed by the portionwise addition of solid $NaHCO_3$ (175 g). The mixture was stirred for about 2 h and the organic layer was separated, dried over anhydrous $Na_2SO_4$, and coned under reduced pressure. The crude yellow oil was purified by silica gel chromatography eluting with 0-20% EtOAc in heptane to yield ethyl 4-(dibenzylamino)-2-ethylcyclopentanecarboxylate (136.6 g, 72%) as a white solid: LC/MS (Table 1, Method a) $R_t$=3.26 min; MS m/z: 366 $(M+H)^+$ Step I: ethyl 4-amino-2-ethylcyclopentanecarboxylate

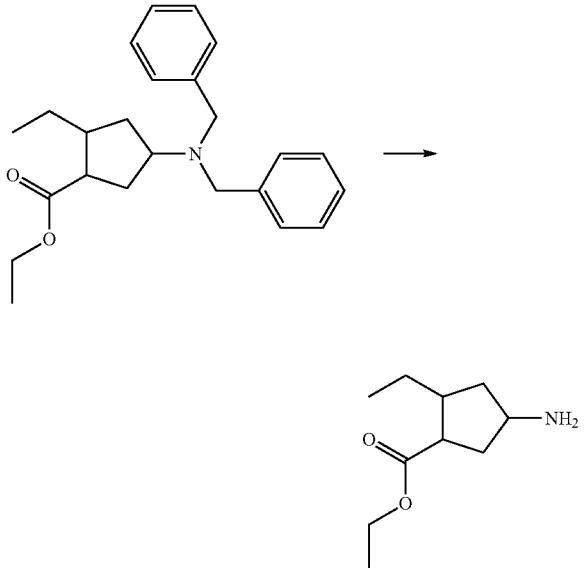

To a vessel containing a slurry of 20 wt % $Pd(OH)_2$ on C (12.9 g, 18.4 mmol) in EtOH (1.0 L) was added ethyl 4-(dibenzylamino)-2-ethylcyclopentanecarboxylate (129 g, 352 mmol). The reaction was shaken for about 90 min at about 50° C. under about 30 psi of hydrogen. After removal of the hydrogen source, a nitrogen atmosphere was introduced and the resulting mixture was filtered through a pad of Celite® and the filtrate was coned under reduced pressure to give ethyl 4-amino-2-ethylcyclopentanecarboxylate (64.5 g, 99%) as a yellow syrup: $^1H$ NMR ($CDCl_3$) δ 4.03-3.88 (m, 2H), 3.17 (m, 1H), 2.68 (m, 1H), 2.09-2.02 (m, 2H), 2.02-1.94 (m, 2H), 1.84 (m, 1H), 1.58-1.48 (m, 1H), 1.32-1.18 (m, 1H), 1.09 (m, 3H), 1.03 (m, 2H), 0.78-0.69 (m, 3H).

Step J: (1S,2R,4S)-ethyl 4-acetamido-2-ethylcyclopentanecarboxylate

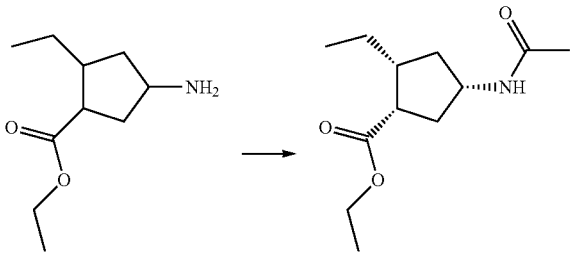

A solution of ethyl 4-amino-2-ethylcyclopentanecarboxylate (49.0 g, 264 mmol) in pyridine (214 mL, 2645 mmol) was cooled to about 0° C. Acetic anhydride (125 mL, 1322 mmol) was added and stirring was continued at about 0° C. for about 15 min. The resulting solution was warmed to ambient temperature and stirred for about 12 h. The reaction was concd under reduced pressure and EtOAc (500 mL) and HCl (1 N aqueous, 200 mL) were added. The layers were separated and the organic layer was washed with HCl (1 N aqueous, 200 mL), saturated aqueous $NaHCO_3$ (2×200 mL) and brine (150 mL), dried over anhydrous $MgSO_4$, filtered through a pad of Florisil® while washing with EtOAc (600 mL), and concd under reduced pressure to give an off-white solid (52 g) that was purified by using General Procedure AA (Table 2, Method 24, $R_t$=8.2 min, or =positive) to give (1S,2R,4S)-ethyl 4-acetamido-2-ethylcyclopentanecarboxylate (20.3 g, 34%): LC/MS (Table 1, Method a) $R_t$=1.82 min; MS m/z: 228 $(M+H)^+$.

Step K: (1S,2R,4S)-4-acetamido-2-ethylcyclopentanecarboxylic acid

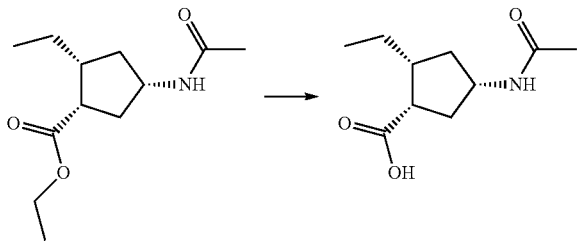

To a flask containing (1S,2R,4S)-ethyl 4-acetamido-2-ethylcyclopentanecarboxylate (9.44 g, 41.5 mmol) was added NaOH (2 N aqueous, 141 mL, 282 mmol). After stirring at ambient temperature for about 12 h, the reaction was acidified to about pH 1 by the addition of 6 N aqueous HCl (50 mL) and extracted with EtOAc (3×500 mL). The combined organic layers were washed with brine (100 mL), dried over anhydrous $MgSO_4$, filtered, and concd under reduced pressure to give crude (1S,2R,4S)-4-acetamido-2-ethylcyclopentanecarboxylic acid (7.25 g, 88%): LC/MS (Table 1, Method a) $R_t$=1.51 min; MS m/z: 200 $(M-H)^+$.

Step L: N-((1S,3R,4S)-3-ethyl-4-(6-tosyl-6H-pyrrolo[2,3-e][1,2,4]triazolo[4,3-a]pyrazin-1-yl)cyclopentyl)acetamide

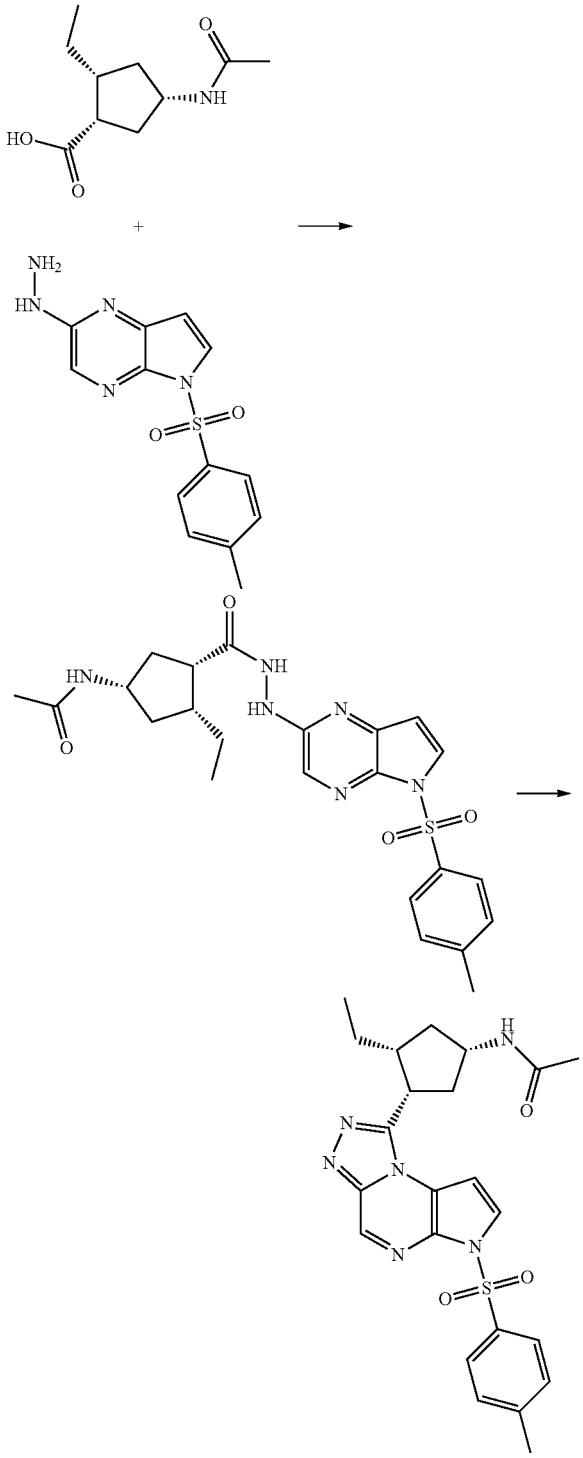

To a mixture of (1S,2R,4S)-4-acetamido-2-ethylcyclopentanecarboxylic acid (3.03 g, 15.2 mmol) in DCM (90 mL) was added 2-hydrazinyl-5-tosyl-5H-pyrrolo[2,3-b]pyrazine (4.20 g, 13.8 mmol, Example #4, Step D), HATU (5.53 g, 14.5 mmol) and TEA (7.72 mL, 55.4 mmol). After stirring at ambient temperature for about 2 h, the reaction was diluted with water (60 mL). The layers were separated and the aqueous layer was extracted with DCM (3×50 mL). The combined organic layers were washed with brine (50 mL), dried over anhydrous $MgSO_4$, filtered, and concd under reduced pressure. The crude material was purified by silica gel chromatography eluting with a gradient of 0-5% MeOH in DCM to give N-((1S,3R,4S)-3-ethyl-4-(2-(5-tosyl-5H-pyrrolo[2,3-b]pyrazin-2-yl)hydrazinecarbonyl)cyclopentyl)acetamide (7.0 g, 90%, 87% purity) as a tan foam: LC/MS (Table 1, Method a) $R_t$=1.96 min; MS m/z: 485 $(M+H)^+$. To a solution of impure N-((1S,3R,4S)-3-ethyl-4-(2-(5-tosyl-5H-pyrrolo[2,3-b]pyrazin-2-yl)hydrazinecarbonyl)-cyclo-pentyl)acetamide (9.40 g, 19.4 mmol) in 1,4-dioxane (100 mL) was added TEA (8 mL, 58 mmol) and thionyl chloride (1.9 mL, 27.1 mmol). The reaction mixture was heated at about 80° C. for about 2 h, and then cooled to about 0° C. and saturated aqueous $NaHCO_3$ and EtOAc (100 mL each) were added. The layers were separated and the aqueous layer was extracted with additional EtOAc (2×100 mL). The combined organic layers were washed with brine (100 mL), dried over anhydrous $MgSO_4$, filtered, and concd under reduced pressure. The crude material was purified by silica gel chromatography eluting with a gradient of 50-100% EtOAc/MeOH/$Et_2NH$ (90:9:1) in EtOAc to give N-((1S,3R,4S)-3-ethyl-4-(6-tosyl-6H-pyrrolo[2,3-e][1,2,4]triazolo[4,3-a]pyrazin-1-yl)cyclopentyl)acetamide (6.00 g, 66%): LC/MS (Table 1, Method a) $R_t$=2.03 min; MS m/z: 467 $(M+H)^+$.

Step M: (1S,3R,4S)-3-ethyl-4-(6-tosyl-6H-pyrrolo[2,3-e][1,2,4]triazolo[4,3-a]pyrazin-1-yl)cyclopentanamine

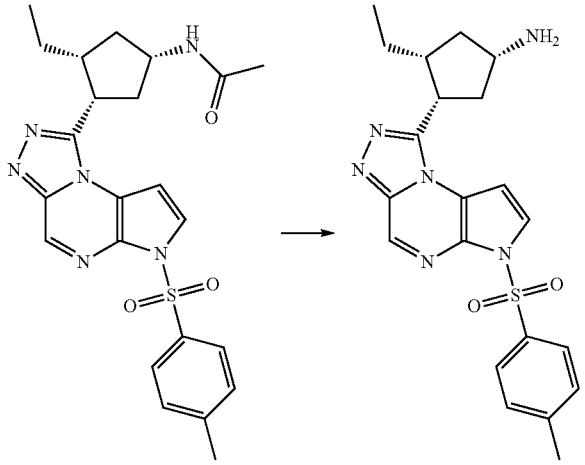

To a solution of N-((1S,3R,4S)-3-ethyl-4-(6-tosyl-6H-pyrrolo[2,3-e][1,2,4]triazolo[4,3-a]pyrazin-1-yl)cyclopentyl)acetamide (6.0 g, 12.86 mmol, Example #8 Step L) in 1,4-dioxane (78 mL) was added HCl (6 N aqueous, 75 mL, 450 mmol). The reaction mixture was heated at about 95° C. for about 16 h. The reaction was cooled to ambient temperature and the solvent was removed under reduced pressure. The residue was diluted with DCM (50 mL) and washed with saturated aqueous $NaHCO_3$ (100 mL). The aqueous portion was extracted with additional DCM (3×50 mL) and the combined organic layers were dried over anhydrous $MgSO_4$, filtered, and concd under reduced pressure. The crude material was purified by silica gel chromatography eluting with a gradient of 0-100% DCM/MeOH/$NH_4OH$ (950:45:5) in DCM to give (1S,3R,4S)-3-ethyl-4-(6-tosyl-6H-pyrrolo[2,3-e][1,2,4]triazolo[4,3-a]pyrazin-1-yl)cyclopentanamine (3.05 g, 56%) as a tan solid: LC/MS (Table 1, Method a) $R_t$=1.85 min; MS m/z: 425 $(M+H)^+$.

Step N: 2-((1S,3R,4S)-3-ethyl-4-(6-tosyl-6H-pyrrolo[2,3-e][1,2,4]triazolo[4,3-a]pyrazin-1-yl)cyclopentylamino)thiazole-5-carbonitrile

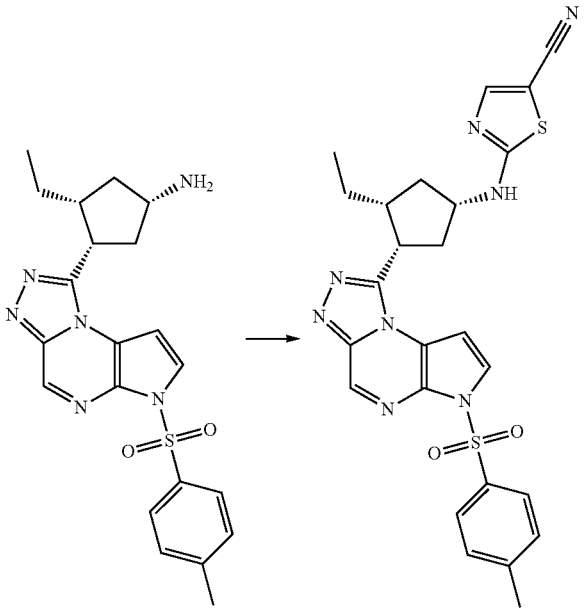

A mixture of (1S,3R,4S)-3-ethyl-4-(6-tosyl-6H-pyrrolo[2,3-e][1,2,4]triazolo[4,3-a]pyrazin-1-yl)cyclopentanamine (0.20 g, 0.47 mmol), EtOH (1.3 mL), DIEA (0.33 mL, 1.88 mmol), and 2-chlorothiazole-5-carbonitrile (0.082 g, 0.56 mmol, Ark Pharm) was heated in a CEM microwave at about 150° C. for about 30 min (250 psi maximum pressure, 5 min maximum ramp, 300 maximum watts). The reaction mixture was cooled to ambient temperature and concd under reduced pressure. The crude oil was dissolved in DCM (10 mL) and washed with water (2×10 mL). The organic layer was dried over anhydrous $MgSO_4$, filtered, and concd under reduced pressure. The crude mixture was purified by silica gel chromatography eluting with a gradient of 0-70% EtOAc in DCM to give 2-((1S,3R,4S)-3-ethyl-4-(6-tosyl-6H-pyrrolo[2,3-e][1,2,4]triazolo[4,3-a]pyrazin-1-yl)cyclopentylamino)thiazole-5-carbonitrile (0.21 g, 84%): LC/MS (Table 1, Method c) $R_t$=1.53 min; MS m/z: 533 $(M+H)^+$.

Step O: 2-((1S,3R,4S)-3-ethyl-4-(6H-pyrrolo[2,3-e][1,2,4]triazolo[4,3-a]pyrazin-1-yl)cyclopentylamino)thiazole-5-carbonitrile

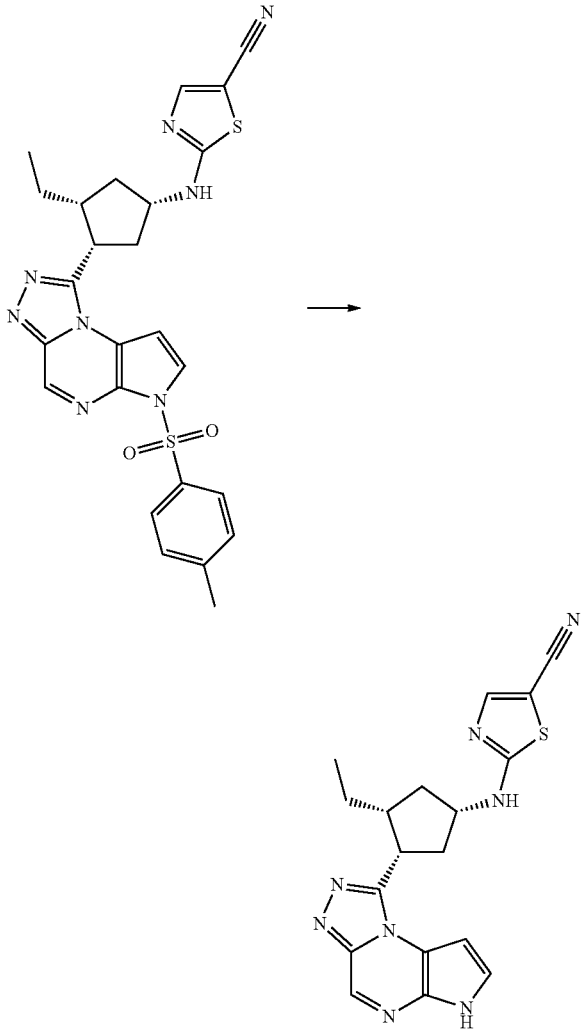

A mixture of 2-((1S,3R,4S)-3-ethyl-4-(6-tosyl-6H-pyrrolo[2,3-e][1,2,4]triazolo[4,3-a]pyrazin-1-yl)cyclopentylamino)thiazole-5-carbonitrile (0.21 g, 0.39 mmol), 1,4-dioxane (4.5 mL), EtOH (3.5 mL) and $Na_2CO_3$ (2 N aqueous, 5.8 mL, 15.7 mmol) was heated at about 50° C. for about 12 h. The reaction mixture was neutralized to pH 7 by the addition of AcOH (0.3 mL), washed with water (2×5 mL) and extracted with DCM (3×5 mL). The organic layer was dried over anhydrous $MgSO_4$, filtered, and concd under reduced pressure. The crude material was purified by silica gel chromatography eluting with a gradient of 0-5% MeOH in DCM to give 2-((1S,3R,4S)-3-ethyl-4-(6H-pyrrolo[2,3-e][1,2,4]triazolo [4,3-a]pyrazin-1-yl)cyclopentylamino)-thiazole-5-carbonitrile (0.09 g, 60%): LC/MS (Table 1, Method c) $R_t$=1.95 min; MS m/z: 379 $(M+H)^+$.

Example #9

N-(4-(6H-pyrrolo[2,3-e][1,2,4]triazolo[4,3-a]pyrazin-1-yl)bicyclo[2.2.2]octan-1-yl)pyrrolidine-1-sulfonamide

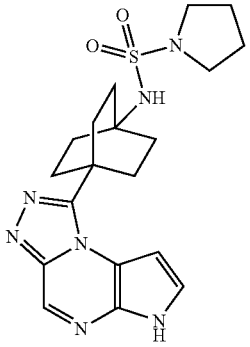

Step A: 5-bromo-3-((trimethylsilyl)ethynyl)pyrazin-2-amine

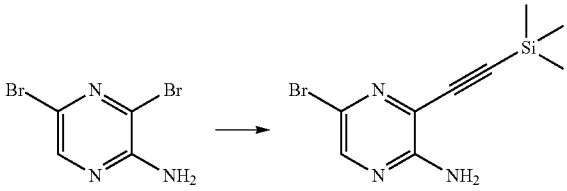

To a solution of 3,5-dibromopyrazin-2-amine (125 g, 494 mmol), TEA (207.0 mL, 1483 mmol), and copper (I) iodide (0.941 g, 4.94 mmol) in THF (1255 mL) was added $PdCl_2(PPh_3)_2$ (3.47 g, 4.94 mmol). The reaction mixture was cooled at about −5-0° C. and a solution of (trimethylsilyl) acetylene (65.0 mL, 470 mmol) in THF (157 mL) was added dropwise over about 15 min. The reaction mixture was stirred at about −5-0° C. for about 1.5 h and then allowed to warm to rt overnight. The reaction mixture was then filtered through a Celite® pad and washed with THF until no further product eluted. The filtrate was concd under reduced pressure to give a brown-orange solid. The solid was triturated and sonicated with warm petroleum ether (b.p. 30-60° C., 400 mL), cooled to rt, collected, washed with petroleum ether (b.p. 30-60° C.; 2×60 mL), and dried to give 5-bromo-3-((trimethylsilyl)ethynyl)pyrazin-2-amine (124 g, 93%, 93% purity) as a brown solid: LC/MS (Table 1, Method b) $R_t$=2.51 min; MS m/z: 270, 272 $(M+H)^+$.

Step B: 2-bromo-5-tosyl-5H-pyrrolo[2,3-b]pyrazine

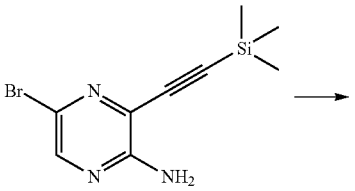

-continued

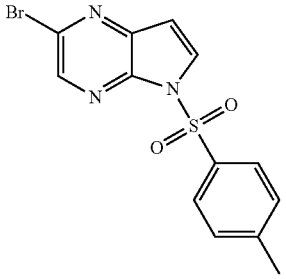

To a solution of 5-bromo-3-((trimethylsilyl)ethynyl) pyrazin-2-amine (3.00 g, 11.1 mmol) in DMF (60 mL) at about 0° C. was added NaH (60% dispersion in mineral oil, 0.577 g, 14.4 mmol) in three portions. After about 15 min, p-toluenesulfonyl chloride (2.75 g, 14.4 mmol) was added and the reaction was allowed to warm slowly to ambient temperature. After about 16 h, the reaction mixture was poured onto ice-cold water (120 mL) and the precipitate was collected by vacuum filtration. The crude solid was dissolved in DCM (15 mL) and purified by silica gel chromatography eluting with DCM to give 2-bromo-5-tosyl-5H-pyrrolo[2,3-b]pyrazine (2.16 g, 52%): LC/MS (Table 1, Method c) $R_t$=1.58 min; MS m/z: 352, 354 $(M+H)^+$.

Step C: tert-butyl 2-(5-tosyl-5H-pyrrolo[2,3-b]pyrazin-2-yl)hydrazinecarboxylate and tert-butyl 1-(5-tosyl-5H-pyrrolo[2,3-b]pyrazin-2-yl)hydrazinecarboxylate

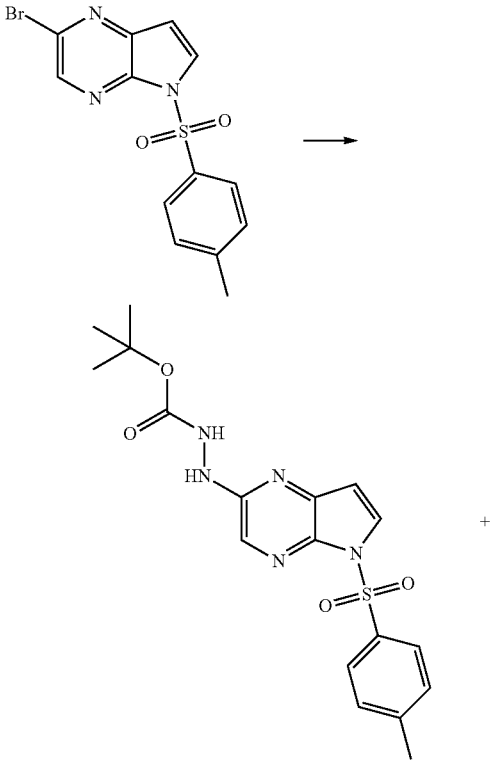

-continued

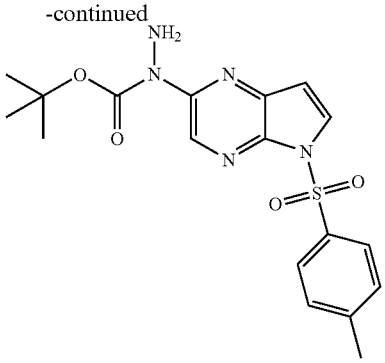

To a flask was added $Pd_2(dba)_3$ (3.90 g, 4.26 mmol), di-tert-butyl-(2',4',6'-triisopropylbiphenyl-2-yl)phosphane (3.62 g, 8.52 mmol), and 1,4-dioxane (453 mL). The catalyst-ligand mixture was degassed via vacuum/nitrogen purge (3 times) and heated at about 80° C. for about 10 min. Then 2-bromo-5-tosyl-5H-pyrrolo[2,3-b]pyrazine (30.0 g, 85 mmol), tert-butyl hydrazinecarboxylate (16.9 g, 128 mmol), and NaOt-Bu (12.28 g, 128 mmol) were added. After an additional vacuum/nitrogen purge, the reaction was heated at about 80° C. After about 50 min, the reaction mixture was cooled to ambient temperature and filtered through a pad of silica gel (6 cm in height×6 cm in diameter), topped with Celite® (1 cm in height×6 cm in diameter), while washing with EtOAc (3×150 mL). Water (300 mL) was added to the filtrate and the organic layer was separated. The aqueous layer was extracted with additional EtOAc (3×200 mL). The combined organic extracts were washed with saturated aqueous $NH_4Cl$, saturated aqueous $NaHCO_3$, and brine (400 mL each), dried over anhydrous $MgSO_4$, filtered, and concd under reduced pressure to give a dark brown oil (45 g). The brown oil was dissolved in DCM (250 mL), silica gel (200 g) was added, and the mixture was concd under reduced pressure. The resulting silica mixture was purified using silica gel chromatography eluting with a gradient of 25-65% EtOAc in heptane to give a mixture of tert-butyl 2-(5-tosyl-5H-pyrrolo[2,3-b]pyrazin-2-yl)hydrazinecarboxylate [major regioisomer] and tert-butyl 1-(5-tosyl-5H-pyrrolo[2,3-b]pyrazin-2-yl)hydrazinecarboxylate [minor regioisomer] (18.8 g, 50%): LC/MS (Table 1, Method c) $R_t$=1.47 min; MS m/z: 404 $(M+H)^+$.

Step D: 2-hydrazinyl-5-tosyl-5H-pyrrolo[2,3-b] pyrazine

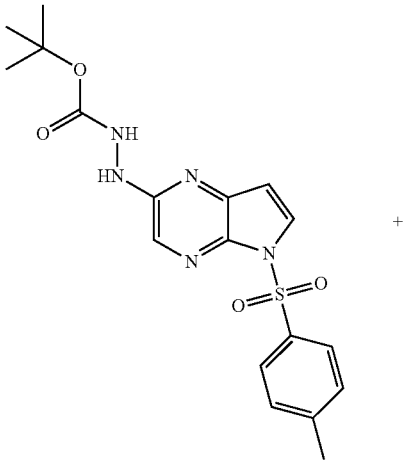

-continued

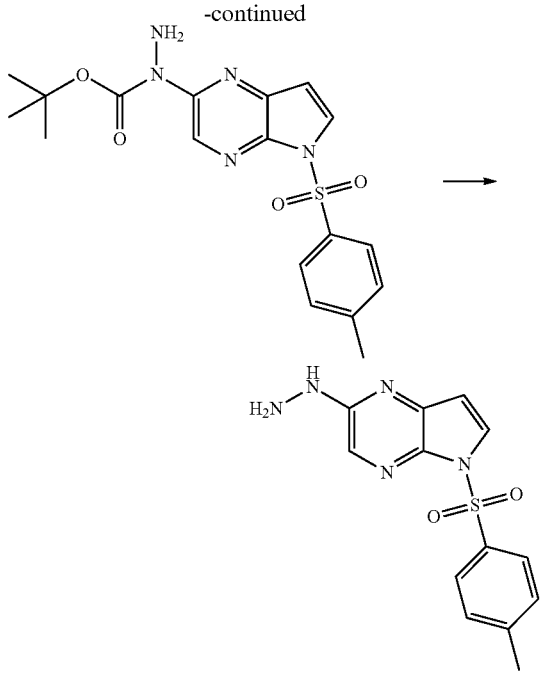

HCl (4 M in 1,4-dioxane, 226 mL, 902 mmol) was added to a mixture of tert-butyl 2-(5-tosyl-5H-pyrrolo[2,3-b] pyrazin-2-yl)hydrazinecarboxylate and tert-butyl 1-(5-tosyl-5H-pyrrolo[2,3-b]pyrazin-2-yl)hydrazinecarboxylate (49.2 g, 122 mmol) in 1,4-dioxane (290 mL). The reaction was heated at about 60° C. for about 2.5 h and then cooled to about 15-20° C. The solid was collected by vacuum filtration, washed with EtOAc (3×50 mL), and then triturated with $Et_2O$ (60 mL), collected by vacuum filtration and dried to a constant weight under vacuum to yield 35.6 g of crude solid. The solid was stirred with a mixture of saturated aqueous $NaHCO_3$ and EtOAc (1:1, 400 mL). After about 1 h, the solid was collected by vacuum filtration, washed with ice cold water (3×30 mL) and EtOAc (3×30 mL), and dried in a vacuum oven to a constant weight to afford 2-hydrazinyl-5-tosyl-5H-pyrrolo[2,3-b]pyrazine as a tan solid (21.2 g, 57%): LC/MS (Table 1, Method a) $R_t$=1.88 min; MS m/z: 304 $(M+H)^+$.

Step E: tert-butyl 4-(2-(5-tosyl-5H-pyrrolo[2,3-b] pyrazin-2-yl)hydrazinecarbonyl)bicyclo[2.2.2]octan-1-ylcarbamate

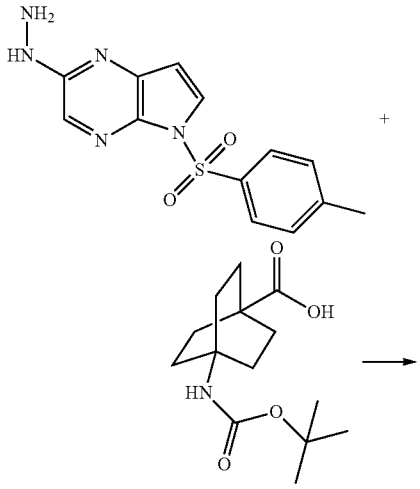

-continued

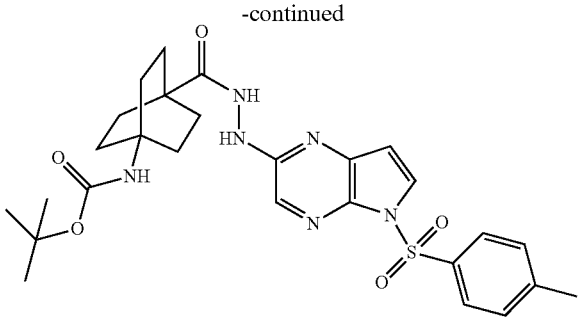

A round bottom flask was charged with 2-hydrazinyl-5-tosyl-5H-pyrrolo[2,3-b]pyrazine (3.75 g, 11.1 mmol), 4-(tert-butoxycarbonylamino)bicyclo[2.2.2]octane-1-carboxylic acid (3.0 g, 11 mmol, Prime Organics), HATU (4.23 g, 11.1 mmol), TEA (6.2 mL, 44 mmol), and DCM (65 mL). The reaction mixture was stirred at ambient temperature for about 16 h. The reaction mixture was diluted with water (30 mL) and the initial layers that formed were separated. The remaining aqueous emulsion was filtered through Celite®. The filtrate layers were separated and the aqueous layer was extracted with additional DCM (60 mL). The organic layer was washed with water (3×50 mL), dried over anhydrous $MgSO_4$, filtered, and concd under reduced pressure. The crude material was purified by silica gel chromatography eluting with a gradient of 0-100% EtOAc in DCM to afford tert-butyl 4-(2-(5-tosyl-5H-pyrrolo[2,3-b]pyrazin-2-yl)hydrazinecarbonyl)bicyclo[2.2.2]octan-1-ylcarbamate as a brown amorphous solid (5.38 g, 87%): LC/MS (Table 1, Method a) $R_t$=2.40 min; MS m/z 555 $(M+H)^+$.

Step F: 4-((6-tosyl-6H-pyrrolo[2,3-e][1,2,4]triazolo[4,3-a]pyrazin-1-yl)bicyclo[2.2.2]octan-1-amine

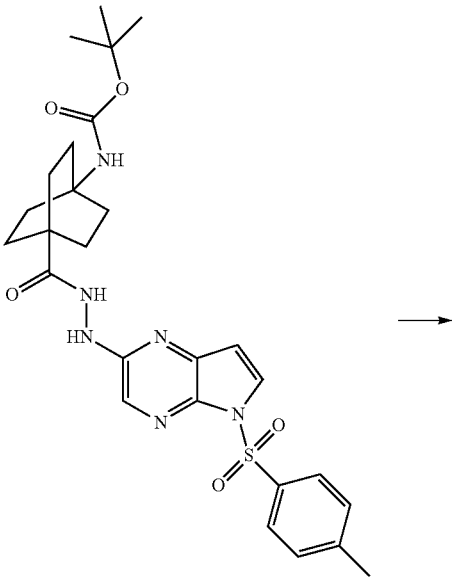

-continued

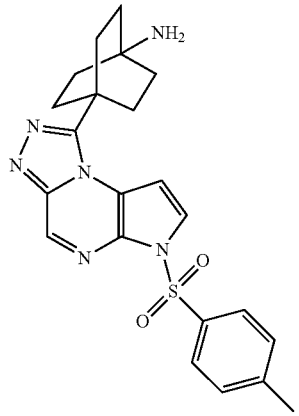

To a solution of tert-butyl 4-(2-(5-tosyl-5H-pyrrolo[2,3-b]pyrazin-2-yl)hydrazinecarbonyl)-bicyclo[2.2.2]octan-1-yl-carbamate (6.1 g, 11.0 mmol), TEA (6.1 mL, 44.0 mmol) in 1,4-dioxane (110 mL) was added $SOCl_2$ (2.0 mL, 27.5 mmol). The reaction mixture was heated at about 80° C. for about 2 h then cooled to ambient temperature. The reaction mixture was washed with saturated aqueous $NaHCO_3$ (3×50 mL). The aqueous portion was filtered to give 4-(6-tosyl-6H-pyrrolo[2,3-e][1,2,4]triazolo[4,3-a]pyrazin-1-yl)bicyclo[2.2.2]-octan-1-amine as a brown solid (1.17 g, 24%): LC/MS (Table 1, Method a) $R_t$=1.28 min; MS m/z: 437 $(M+H)^+$. The remaining filtrate was extracted with EtOAc (10 mL). The organic layer was dried over anhydrous $MgSO_4$, filtered, and concd under reduced pressure to afford crude tert-butyl 4-(6-tosyl-6H-pyrrolo[2,3-e][1,2,4]triazolo[4,3-a]pyrazin-1-yl)bicyclo[2.2.2]octan-1-ylcarbamate (3.5 g). The crude Boc-protected material was dissolved in 1,4-dioxane (38 mL) and HCl (4 N in 1,4-dioxane, 8 mL) was added. The reaction mixture was heated at about 50° C. for about 3 h. The precipitate formed was filtered, dissolved in DCM (50 mL), and washed with saturated aqueous $NaHCO_3$ (3×20 mL). The layers were separated and the organic portion was dried over anhydrous $MgSO_4$, filtered, and concd under reduced pressure to give additional 4-(6-tosyl-6H-pyrrolo[2,3-e][1,2,4]triazolo[4,3-a]pyrazin-1-yl)bicyclo[2.2.2]octan-1-amine as a brown solid (2.3 g, 50% over 2 steps): LC/MS (Table 1, Method a) $R_t$=1.28 min; MS m/z: 437 $(M+H)^+$.

Step G: N-(4-(6H-pyrrolo[2,3-e][1,2,4]triazolo[4,3-a]pyrazin-1-yl)bicyclo[2.2.2]octan-1-yl)pyrrolidine-1-sulfonamide

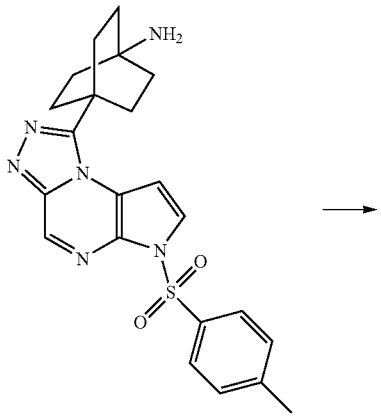

-continued

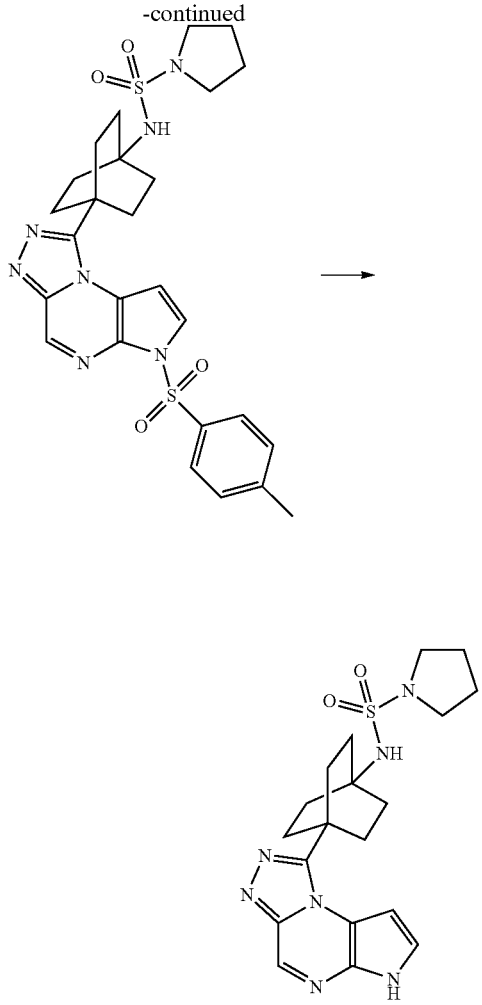

A round bottom flask was charged with 4-(6-tosyl-6H-pyrrolo[2,3-e][1,2,4]triazolo[4,3-a]pyrazin-1-yl)bicyclo[2.2.2]octan-1-amine (0.12 g, 0.28 mmol), DIEA (0.48 mL, 2.8 mmol) in DMA (2.75 mL). Pyrrolidine-1-sulfonyl chloride (0.07 g, 0.41 mmol, Matrix) was added dropwise and reaction mixture was stirred at ambient temperature for about 1 h. $K_2CO_3$ (0.190 g, 1.37 mmol) was added and the reaction mixture was stirred at ambient temperature for about 16 h. The solvent was removed under reduced pressure. The crude material was purified by flash chromatography on silica gel eluting with a gradient of 0-10% MeOH in DCM to give N-(4-(6-tosyl-6H-pyrrolo[2,3-e][1,2,4]triazolo[4,3-a]pyrazin-1-yl)bicyclo[2.2.2]octan-1-yl)pyrrolidine-1-sulfonamide, which was dissolved in NaOH (1 N aqueous, 1.10 mL, 1.10 mmol) and 1,4-dioxane (1 mL) and heated at about 50° C. for about 1 h. The crude material was purified by preparative reverse phase HPLC (Table 2, Method 1) to give N-(4-(6H-pyrrolo[2,3-e][1,2,4]triazolo[4,3-a]pyrazin-1-yl)bicyclo[2.2.2]octan-1-yl)pyrrolidine-1-sulfonamide (0.042 g, 37%) as a white solid: LC/MS (Table 1, Method a) $R_t$=1.81 min; MS m/z 416 $(M+H)^+$.

Example #10*

(3R,4R)-phenyl 3-(6H-imidazo[1,5-a]pyrrolo[2,3-e]pyrazin-1-yl)-4-methylpiperidine-1-carboxylate

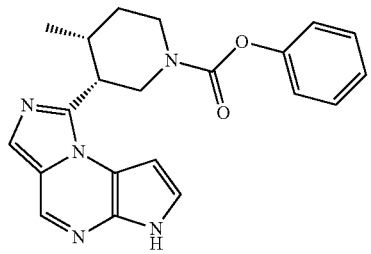

Step A: 5-bromo-3-((trimethylsilyl)ethynyl)pyrazin-2-amine

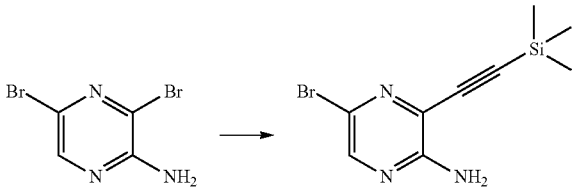

To a solution of 3,5-dibromopyrazin-2-amine (125 g, 494 mmol), TEA (207.0 mL, 1483 mmol), and copper (I) iodide (0.941 g, 4.94 mmol) in THF (1255 mL) was added $PdCl_2(PPh_3)_2$ (3.47 g, 4.94 mmol). The reaction mixture was cooled at about −5-0° C. and a solution of (trimethylsilyl) acetylene (65.0 mL, 470 mmol) in THF (157 mL) was added dropwise over about 15 min. The reaction mixture was stirred at about −5-0° C. for about 1.5 h and then allowed to warm to rt overnight. The reaction mixture was then filtered through a Celite® pad and washed with THF until no further product eluted. The filtrate was concd under reduced pressure to give a brown-orange solid. The solid was triturated and sonicated with warm petroleum ether (b.p. 30-60° C., 400 mL), cooled to rt, collected, washed with petroleum ether (b.p. 30-60° C.; 2×60 mL), and dried to give 5-bromo-3-((trimethylsilyl)ethynyl)pyrazin-2-amine (124 g, 93%, 93% purity) as a brown solid: LC/MS (Table 1, Method b) $R_t$=2.51 min; MS m/z: 270, 272 $(M+H)^+$.

Step B: 2-bromo-5-tosyl-5H-pyrrolo[2,3-b]pyrazine

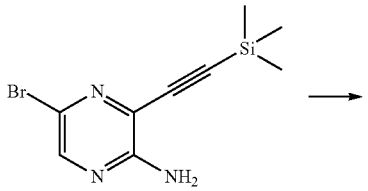

-continued

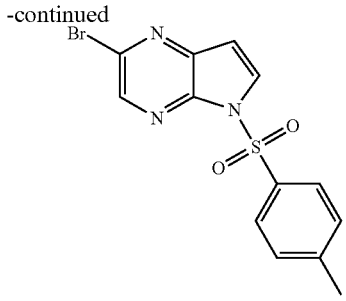

To a solution of 5-bromo-3-((trimethylsilyl)ethynyl) pyrazin-2-amine (3.00 g, 11.1 mmol) in DMF (60 mL) at about 0° C. was added NaH (60% dispersion in mineral oil, 0.577 g, 14.4 mmol) in three portions. After about 15 min, p-toluenesulfonyl chloride (2.75 g, 14.4 mmol) was added and the reaction was allowed to warm slowly to ambient temperature. After about 16 h, the reaction mixture was poured onto ice-cold water (120 mL) and the precipitate was collected by vacuum filtration. The crude solid was dissolved in DCM (15 mL) and purified by silica gel chromatography eluting with DCM to give 2-bromo-5-tosyl-5H-pyrrolo[2,3-b]pyrazine (2.16 g, 52%): LC/MS (Table 1, Method c) $R_t$=1.58 min; MS m/z: 352, 354 $(M+H)^+$.

Step C: (5-tosyl-5H-pyrrolo[2,3-b]pyrazin-2-yl) methanamine hydrochloride

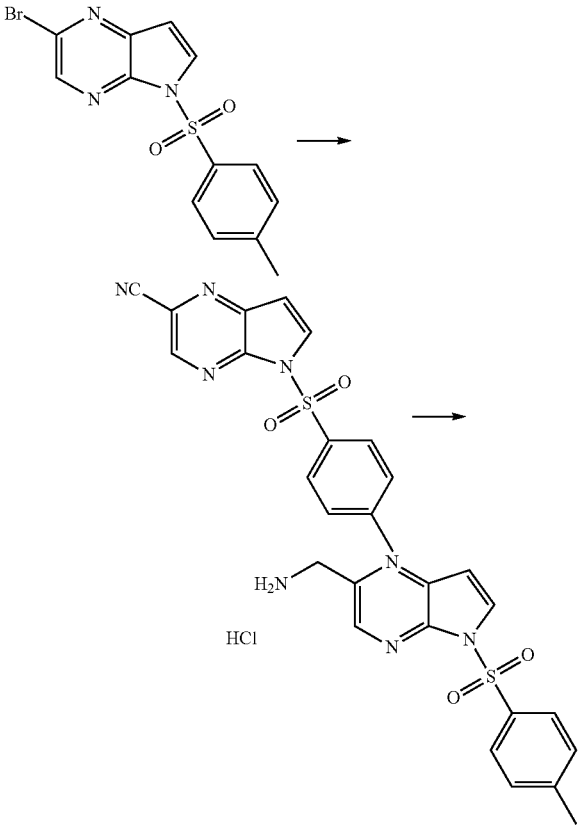

A 5 L reactor was charged with 2-bromo-5-tosyl-5H-pyrrolo[2,3-b]pyrazine (98.8 g, 281 mmol), zinc dust (3.50 g, 53.3 mmol), palladium(II) trifluoroacetate (4.0 g, 12 mmol), and racemic-2-(di-t-butylphosphino)-1,1'-binapthyl (9.8 g, 24.7 mmol). The flask was equipped with a powder addition device into which zinc cyanide (10.0 g, 157 mmol) was placed to be added at a later step. The vessel was purged with argon for no longer than about 30 min and then argon sparged DMA (2 L) was added to the reactor. The mixture was stirred and heated to about 50° C. while maintaining an argon atmosphere. The resulting dark brown solution was further heated to about 95° C. while adding the zinc cyanide, from the powder addition device, portionwise over about 15 min. Upon reaching about 95° C., the brown mixture was stirred for about an additional 16 h. The reaction mixture was cooled to ambient temperature, resulting in the precipitation of salts. The mixture was filtered through a Buchner funnel containing filter-aid and the filter cake was washed with DMA (20 mL). A solution of the crude product in DMA was added to cold (<10° C.) water (16 L) and stirred for about 30 min. The resulting suspension was filtered and the filter cake was rinsed again with water (1 L). The resulting wet cake was dried in a vacuum oven at about 50° C. The crude solid was dissolved in DCM (1.5 L) and further dried over anhydrous $MgSO_4$. After filtration, the solution was passed through a pad of silica (140 g), using DCM as the eluent until only predominantly impurities were detected eluting off the pad. The solvent was removed under reduced pressure and the crude solid was triturated with MeOH/DCM (4:1, 10 volumes of solvent per gram of crude solid) at ambient temperature for about 5 h. The solid was filtered and washed with MeOH (300 mL). The product was dried in a vacuum oven to provide 5-tosyl-5H-pyrrolo[2,3-b]pyrazine-2-carbonitrile (58.8 g, 70%) as a white solid: $^1$H NMR ($CDCl_3$) δ 8.67 (s, 1H), 8.21 (d, J=4.2 Hz, 1H), 8.07 (d, J=8.4 Hz, 2H), 7.34 (d, J=8.1 Hz, 2H), 6.89 (d, J=4.2 Hz, 1H), 2.42 (s, 3H). A 2-L 316-stainless steel pressure reactor was charged with 5 wt % Pd/C (15.4 g of 63.6 wt % water wet material, 5.6 g dry basis, 2.6 mmol Johnson Matthey A503032-5), 5-tosyl-5H-pyrrolo[2,3-b]pyrazine-2-carbonitrile (55 g, 184 mmol), THF (1.1 L), deionized water (165 mL), HCl (37 wt % aqueous, 30 mL, 369 mmol) and quinoline (1.1 mL, 9.0 mmol). The vessel was purged, pressurized, and maintained at 40 psi with hydrogen supplied from a high pressure reservoir. The mixture was vigorously agitated at about 25° C. After about 5 h the reactor was vented and purged with nitrogen to remove most of the dissolved hydrogen, and the reaction mixture was filtered to remove the catalyst. The reactor and catalyst cake were rinsed with THF:water (1:1, 2×40 mL). The combined filtrate and rinses were concd and EtOH (500 mL) was added then removed under reduced pressure. After two further azeotropes using EtOH (2×500 mL), the crude residue was concd under reduced pressure to give a residue (76 g) that was suspended in EtOH (550 mL) and stirred at ambient temperature for about 4 h. The solid was collected by filtration and washed with cold EtOH (50 mL). The wet cake was dried in a vacuum oven to provide (5-tosyl-5H-pyrrolo[2,3-b]pyrazin-2-yl)methanamine hydrochloride (51.2 g, 82%) as a white solid: LC/MS (Table 1, Method a) $R_t$=1.44 min; MS m/z: 303 $(M+H)^+$.

Step D: 4-methylpiperidine-3-carboxylic acid hydrochloride

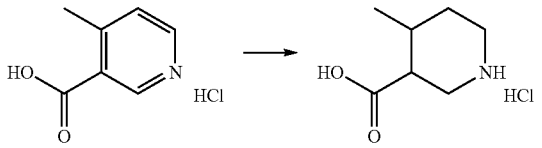

AcOH (380 mL) was added to 4-methylnicotinic acid hydrochloride (50.5 g, 291 mmol, Maybridge) and $PtO_2$ (5.05 g, 22.2 mmol, Johnson Matthey) in a 600 mL stainless steel reactor. The mixture was stirred under 220 psi of hydrogen at ambient temperature for about 14 hr. The supernatant solution was filtered through a nylon membrane and rinsed with enough AcOH until only the catalyst remained. The filtrate was concd under reduced pressure to give a clear oil that solidified upon cooling to ambient temperature to give crude 4-methylpiperidine-3-carboxylic acid with AcOH as an excipient (88.94 g, 170%): LC/MS (Table 1, Method b) Rt=0.44 min; MS m/z: 144 $(M+H)^+$.

Step E: (3R,4R)-ethyl 4-methylpiperidine-3-carboxylate(2S,3S)-2,3-dihydroxysuccinate

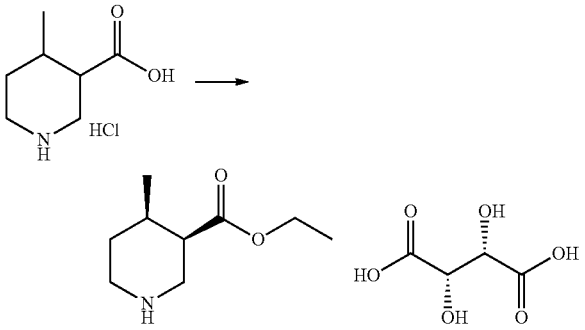

Crude racemic 4-methylpiperidine-3-carboxylic acid hydrochloride (~70% chemical purity, approximately 15:1 cis:trans) in AcOH (2:1, 300 g) was dissolved in EtOH (1500 mL) and sparged with HCl (gas) for about 15 min. The reaction mixture was fitted with a balloon to allow for expansion then heated to about 85° C. After about 48 h, the reaction mixture was cooled to ambient temperature and concd in vacuo to provide a thick syrup containing racemic ethyl 4-methylpiperidine-3-carboxylic acid hydrochloride (260 g). To this ester was added $CHCl_3$ (1000 mL) followed by saturated aqueous $NaHCO_3$ (500 mL) and $NH_4OH$ (15% aqueous, 500 mL). The organic layer was separated and the aqueous layer was further extracted with $CHCl_3$ (1000 mL). The combined organic layers were dried over anhydrous $Na_2SO_4$, filtered, and then concd in vacuo to provide crude ethyl 4-methylpiperidine-3-carboxylate (200 g) as an oil. To a slurry of (2S,3S)-2,3-dihydroxysuccinic acid (150 g, 1001 mmol) in MeOH (200 mL) was added a solution of crude ethyl 4-methylpiperidine-3-carboxylate (200 g, 1168 mmol) in EtOAc (3000 mL). The mixture was stirred rapidly for about 3 h and the resulting solids were collected by filtration to provide the (2S,3S)-2,3-dihydroxysuccinate salt as a white solid (245 g) (approximately 15:1 cis:trans, er=48:52 for cis stereoisomers). The solids were dissolved in MeOH (1000 mL) and EtOAc (3000 mL) was slowly added until solids began to form. After about 30 min, the solids were collected by filtration and partially dried in vacuo to provide a stereo-enriched mixture containing (3R,4R)-ethyl 4-methylpiperidine-3-carboxylate (2S,3S)-2,3-dihydroxysuccinate as a white solid (145 g) (approximately 15:1 cis:trans, er=60:40 for (3R,4R):(3S,4S) enantiomers). The above solids were dissolved in MeOH (1000 mL) and divided into four lots. Each lot (250 mL) was diluted with MeOH (500 mL) and EtOAc (3000 mL) was slowly added to the solution until solids formed. After about 4-15 h, the solids were collected by filtration and dried in vacuo to provide multiple lots of partially resolved (3R,4R)-ethyl 4-methylpiperidine-3-carboxylate (2S,3S)-2,3-dihydroxysuccinate, these were combined and dissolved in MeOH (1000 mL) and EtOAc (4000 mL) was slowly added. After stirring for about 1 h the solids were collected by filtration to provide (3R,4R)-ethyl 4-methylpiperidine-3-carboxylate (2S,3S)-2,3-dihydroxysuccinate (4.5 g) (approximately 15:1 cis:trans, er=98:2 for (3R,4R):(3S,4S) enantiomers), chiral analytical LC (Table 2, Method 30) minor isomer $R_t$=12.2 min; MS m/z: 343 $(M+(2S,3S)\text{-}2,3\text{-dihydroxysuccinate}+Na)^+$; major isomer $R_t$=10.6 min; MS m/z: 343 $(M+(2S,3S)\text{-}2,3\text{-dihydroxysuccinate}+Na)^+$ Step F: (3R,4R)-1-(tert-butoxycarbonyl)-4-methylpiperidine-3-carboxylic acid

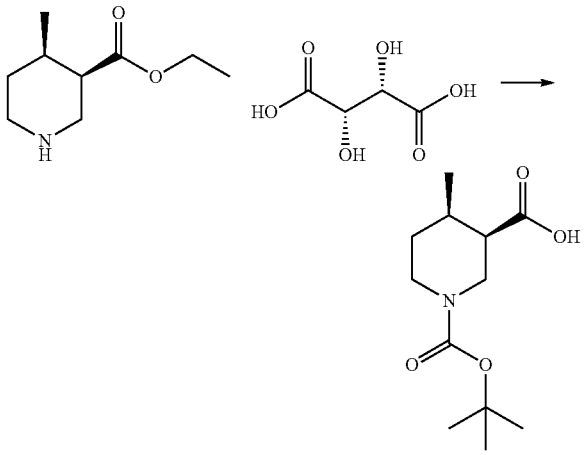

To a flask charged with (3R,4R)-ethyl 4-methylpiperidine-3-carboxylate (2S,3S)-2,3-dihydroxysuccinate (36.9 g, 115 mmol) was added a solution of HCl (6 N aqueous, 191 mL). The reaction mixture was heated to about 60° C. After about 2 h, the reaction mixture was heated to about 90° C. After about 4 h the reaction mixture was cooled to ambient temperature and concd in vacuo. To the residue was added $NaHCO_3$ (122 g, 1148 mmol) and di-tert-butyl dicarbonate (37.6 g, 172 mmol) followed by a mixture of 1,4-dioxane (500 mL) and water (500 mL). After about 2 h, $Et_2O$ (500 mL) and water (500 mL) were added to the reaction mixture. The pH was adjusted to about 4 with 1 N aqueous HCl. The organic layer was separated, dried over anhydrous $Na_2SO_4$, filtered, and concd in vacuo to provide a white solid. The solid was slurried in heptane and filtered to provide (3R,4R)-1-(tert-butoxycarbonyl)-4-methylpiperidine-3-carboxylic acid (25 g, 89%) as a white solid: LC/MS (Table 1, Method b) $R_t$=1.90 min; MS m/z: 244 $(M+H)^+$.

Step G: (3R,4R)-tert-butyl 4-methyl-3-((5-tosyl-5H-pyrrolo[2,3-b]pyrazin-2-yl)methylcarbamoyl)piperidine-1-carboxylate

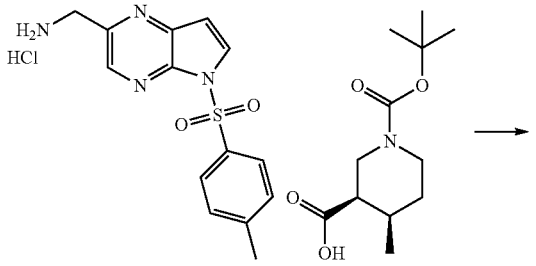

-continued

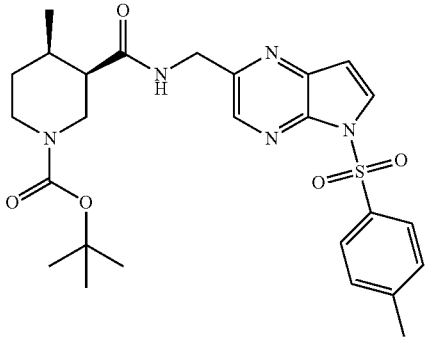

To a slurry of (5-tosyl-5H-pyrrolo[2,3-b]pyrazin-2-yl) methanamine hydrochloride (34.0 g, 100 mmol, Example #5, Step C), (3R,4R)-1-(tert-butoxycarbonyl)-4-methylpiperidine-3-carboxylic acid (24.43 g, 100 mmol) and HATU (38.2 g, 100 mmol) in DCM (700 mL) was added DIEA (52.6 mL, 301 mmol). The reaction was stirred at ambient temperature for about 45 min. The reaction was washed with saturated aqueous $NaHCO_3$ (300 mL). The organic layer was separated, dried over anhydrous $Na_2SO_4$, filtered then concd in vacuo. The resulting residue was purified by chromatography on silica gel (330 g) using 33-100% EtOAc in heptane to give (3R,4R)-tert-butyl-4-methyl-3-((5-tosyl-5H-pyrrolo[2,3-b]pyrazin-2-yl)methylcarbamoyl)piperidine-1-carboxylate (53 g, 96%) as a pale-yellow foam: LC/MS (Table 1, Method b) $R_t$=2.40 min; MS m/z: 528 $(M+H)^+$.

Step H: (3R,4R)-tert-butyl 4-methyl-3-(6-tosyl-6H-imidazo[1,5-a]pyrrolo[2,3-e]pyrazin-1-yl)piperidine-1-carboxylate

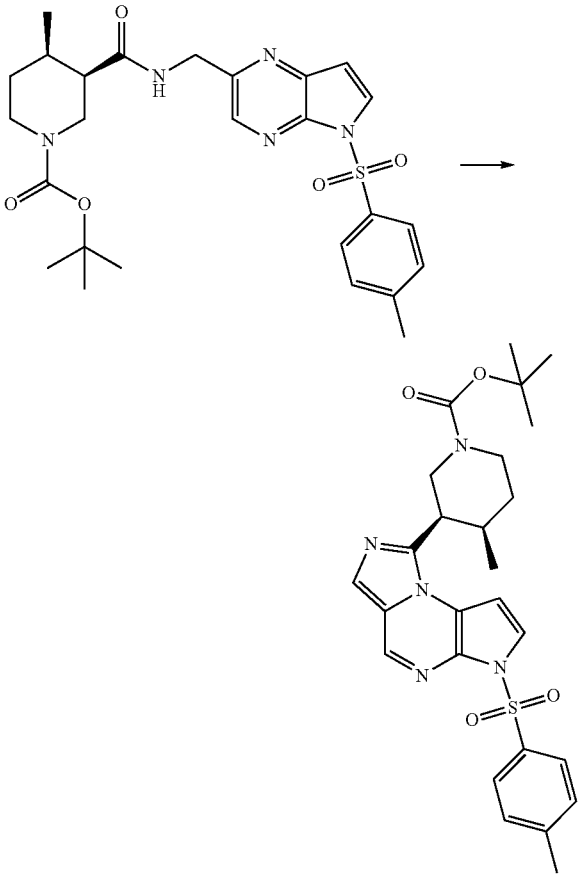

A mixture of (3R,4R)-tert-butyl-4-methyl-3-((5-tosyl-5H-pyrrolo[2,3-b]pyrazin-2-yl)methyl-carbamoyl)-piperidine-1-carboxylate (53 g, 100 mmol) and Lawesson's reagent (22.4 g, 55.2 mmol) in 1,4-dioxane (500 mL) was heated at about 80° C. for about 1 h. The reaction was allowed to cool to ambient temperature and then was partitioned between EtOAc (1000 mL) and saturated aqueous $NaHCO_3$ (700 mL). The organic layer was washed with additional saturated aqueous $NaHCO_3$ (700 mL), dried over anhydrous $Na_2SO_4$, filtered then concd in vacuo. The resulting residue was dissolved in 1,4-dioxane (500 mL) then mercury (II) trifluoroacetate (54.0 g, 127 mmol) was added. The reaction was stirred at about 25° C. for about 1 h. The reaction was partitioned with saturated aqueous $Na_2S_2O_3$ (500 mL)/water (500 mL) with DCM (1000 mL). The layers were filtered through Celite® and the Celite® pad was washed with DCM (500 mL). The combined layers were separated then the organic layer was washed with saturated aqueous $NaHCO_3$ (800 mL). The organic layer was separated, dried over anhydrous $Na_2SO_4$, filtered, and then concd in vacuo. The resulting residue was purified on silica gel (330 g) using 0-40% EtOAc in DCM to give (3R,4R)-tert-butyl 4-methyl-3-(6-tosyl-6H-imidazo[1,5-a]pyrrolo[2,3-e]pyrazin-1-yl)piperidine-1-carboxylate (40.5 g, 79%) as a yellow foam: LC/MS (Table 1, Method b) $R_t$=2.62 min; MS m/z: 510 $(M+H)^+$.

Step I: (3R,4R)-tert-butyl-3-(6H-imidazo[1,5-a]pyrrolo[2,3-e]pyrazin-1-yl)-4-methylpiperidine-1-carboxylate

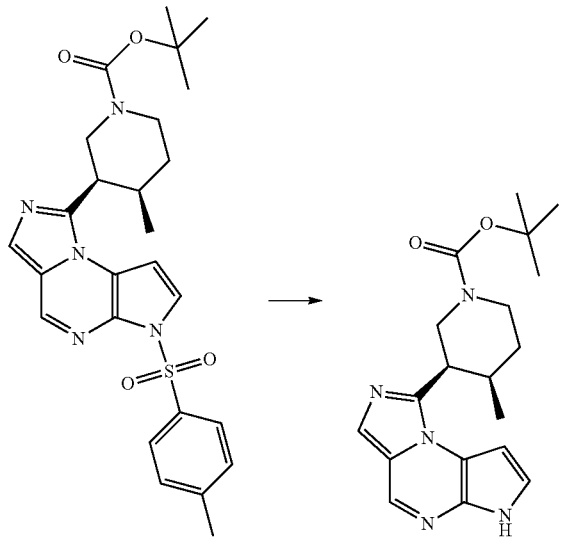

To a solution of (3R,4R)-tert-butyl 4-methyl-3-(6-tosyl-6H-imidazo[1,5-a]pyrrolo[2,3-e]pyrazin-1-yl)piperidine-1-carboxylate (40 g, 78 mmol) in 1,4-dioxane (160 mL) was added NaOH (1 N aqueous, 157 mL). The mixture was heated at about 60° C. for about 1 h. The mixture was allowed to cool to ambient temperature. The mixture was partitioned with HCl (4 N aqueous, 50 mL) and extracted with DCM (2×300 mL). The combined organic extracts were washed with brine (400 mL), dried over anhydrous $Na_2SO_4$, filtered then concd in vacuo. The product was purified on silica gel (330 g) using 1-5% MeOH in DCM to give (3R,4R)-tert-butyl 3-(6H-imidazo[1,5-a]pyrrolo[2,3-e]

pyrazin-1-yl)-4-methylpiperidine-1-carboxylate (30 g, 99%): LC/MS (Table 1, Method b) $R_t$=2.00 min; MS m/z: 356 $(M+H)^+$.

Step J: 1-((3R,4R)-4-methylpiperidin-3-yl)-6H-imidazo[1,5-a]pyrrolo[2,3-e]pyrazine hydrochloride

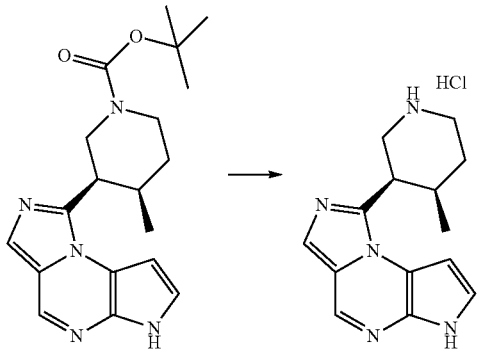

To a solution of (3R,4R)-tert-butyl 3-(6H-imidazo[1,5-a]pyrrolo[2,3-e]pyrazin-1-yl)-4-methyl-piperidine-1-carboxylate (27.9 g, 78 mmol) in 1,4-dioxane (400 mL) was added HCl (4 N in 1,4-dioxane, 58.9 mL, 235 mmol). The resulting suspension was heated at about 60° C. for about 1 h. The reaction was allowed to cool to ambient temperature and then was filtered, washed with 1,4-dioxane (100 mL) followed by $Et_2O$ (100 mL), to give 1-((3R,4R)-4-methylpiperidin-3-yl)-6H-imidazo[1,5-a]pyrrolo[2,3-e]pyrazine hydrochloride (20.6 g, 89%) as a tan solid: LC/MS (Table 1, Method b) $R_t$=1.27 min; MS m/z: 256 $(M+H)^+$.

Step K: (3R,4R)-phenyl 3-(6H-imidazo[1,5-a]pyrrolo[2,3-e]pyrazin-1-yl)-4-methylpiperidine-1-carboxylate

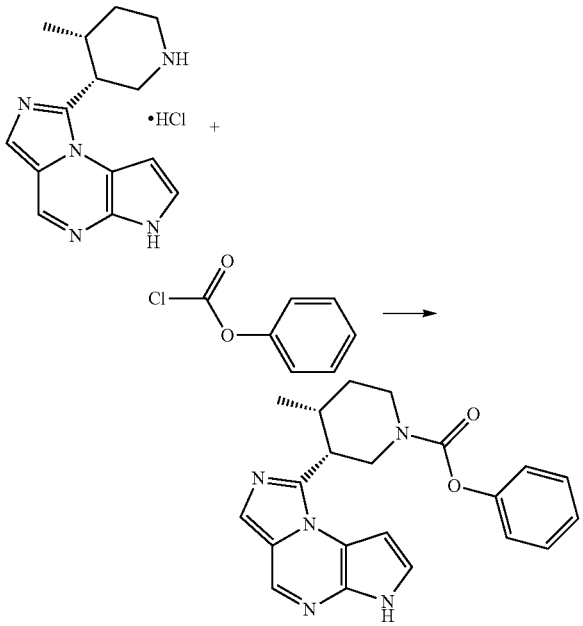

To a solution of 1-((3R,4R)-4-methylpiperidin-3-yl)-6H-imidazo[1,5-a]pyrrolo[2,3-e]pyrazine hydrochloride (0.06 g, 0.21 mmol) in MeCN (1 mL) at about 0° C. was added TEA (0.06 mL, 0.41 mmol), THF (0.6 mL) and DMAP (0.006 g, 0.050 mmol) then phenyl chloroformate (0.026 mL, 0.206 mmol) and stirred for about 1 h. The reaction mixture was warmed to ambient temperature and concd under reduced pressure. The crude residue was dissolved in DCM (3 mL) and washed with water (2 mL), dried over anhydrous $MgSO_4$, filtered, and concd under reduced pressure. The crude residue was dissolved in DCM (5 mL) and washed with water (2 mL) and brine (2 mL), dried over anhydrous $MgSO_4$, filtered, and concd under reduced pressure. The material was purified by RP-HPLC (Table 1, Method g) to give (3R,4R)-phenyl 3-(6H-imidazo[1,5-a]pyrrolo[2,3-e]pyrazin-1-yl)-4-methylpiperidine-1-carboxylate (0.010 g, 11%): LC/MS (Table 1, Method b) $R_t$=1.95 min; MS m/z 376 $(M+H)^+$.

Example #11*

(R)-cyclopentyl 3-(6H-imidazo[1,5-a]pyrrolo[2,3-e]pyrazin-1-yl)piperidine-1-carboxylate

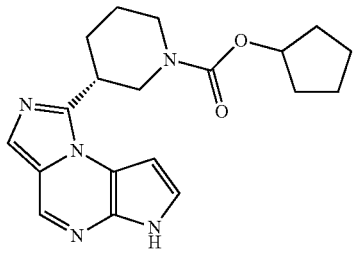

Step A: 5-bromo-3-((trimethylsilyl)ethynyl)pyrazin-2-amine

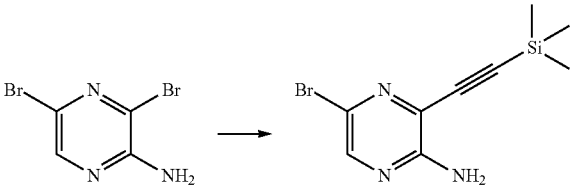

To a solution of 3,5-dibromopyrazin-2-amine (125 g, 494 mmol), TEA (207.0 mL, 1483 mmol), and copper (I) iodide (0.941 g, 4.94 mmol) in THF (1255 mL) was added $PdCl_2(PPh_3)_2$ (3.47 g, 4.94 mmol). The reaction mixture was cooled at about −5-0° C. and a solution of (trimethylsilyl) acetylene (65.0 mL, 470 mmol) in THF (157 mL) was added dropwise over about 15 min. The reaction mixture was stirred at about −5-0° C. for about 1.5 h and then allowed to warm to rt overnight. The reaction mixture was then filtered through a Celite® pad and washed with THF until no further product eluted. The filtrate was concd under reduced pressure to give a brown-orange solid. The solid was triturated and sonicated with warm petroleum ether (b.p. 30-60° C., 400 mL), cooled to rt, collected, washed with petroleum ether (b.p. 30-60° C.; 2×60 mL), and dried to give 5-bromo-3-((trimethylsilyl)ethynyl)pyrazin-2-amine (124 g, 93%, 93% purity) as a brown solid: LC/MS (Table 1, Method b) $R_t$=2.51 min; MS m/z: 270, 272 $(M+H)^+$.

Step B: 2-bromo-5-tosyl-5H-pyrrolo[2,3-b]pyrazine

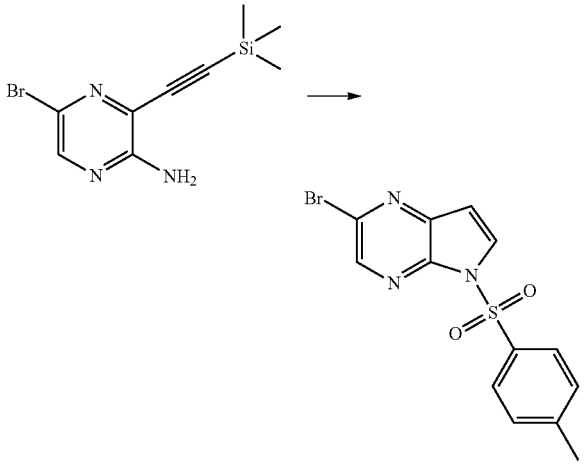

To a solution of 5-bromo-3-((trimethylsilyl)ethynyl) pyrazin-2-amine (3.00 g, 11.1 mmol) in DMF (60 mL) at about 0° C. was added NaH (60% dispersion in mineral oil, 0.577 g, 14.4 mmol) in three portions. After about 15 min, p-toluenesulfonyl chloride (2.75 g, 14.4 mmol) was added and the reaction was allowed to warm slowly to ambient temperature. After about 16 h, the reaction mixture was poured onto ice-cold water (120 mL) and the precipitate was collected by vacuum filtration. The crude solid was dissolved in DCM (15 mL) and purified by silica gel chromatography eluting with DCM to give 2-bromo-5-tosyl-5H-pyrrolo[2,3-b]pyrazine (2.16 g, 52%): LC/MS (Table 1, Method c) $R_t$=1.58 min; MS m/z: 352, 354 $(M+H)^+$.

Step C: (5-tosyl-5H-pyrrolo[2,3-b]pyrazin-2-yl) methanamine hydrochloride

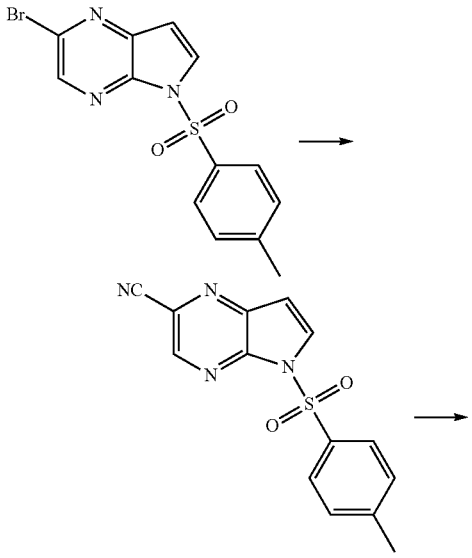

-continued

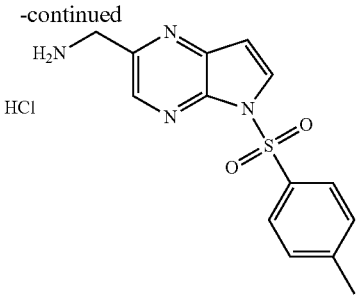

A 5 L reactor was charged with 2-bromo-5-tosyl-5H-pyrrolo[2,3-b]pyrazine (98.8 g, 281 mmol), zinc dust (3.50 g, 53.3 mmol), palladium(II) trifluoroacetate (4.0 g, 12 mmol), and racemic-2-(di-t-butylphosphino)-1,1'-binapthyl (9.8 g, 24.7 mmol). The flask was equipped with a powder addition device into which zinc cyanide (10.0 g, 157 mmol) was placed to be added at a later step. The vessel was purged with argon for no longer than about 30 min and then argon sparged DMA (2 L) was added to the reactor. The mixture was stirred and heated to about 50° C. while maintaining an argon atmosphere. The resulting dark brown solution was further heated to about 95° C. while adding the zinc cyanide, from the powder addition device, portionwise over about 15 min. Upon reaching about 95° C., the brown mixture was stirred for about an additional 16 h. The reaction mixture was cooled to ambient temperature, resulting in the precipitation of salts. The mixture was filtered through a Buchner funnel containing filter-aid and the filter cake was washed with DMA (20 mL). A solution of the crude product in DMA was added to cold (<10° C.) water (16 L) and stirred for about 30 min. The resulting suspension was filtered and the filter cake was rinsed again with water (1 L). The resulting wet cake was dried in a vacuum oven at about 50° C. The crude solid was dissolved in DCM (1.5 L) and further dried over anhydrous $MgSO_4$. After filtration, the solution was passed through a pad of silica (140 g), washed with additional solvent until only predominantly impurities were detected eluting off the pad. The solvent was removed and the crude solid was triturated with MeOH/DCM (4:1, 10 volumes of solvent per gram of crude solid) at ambient temperature for about 5 h. The solid was filtered and washed with MeOH (300 mL). The product was dried in a vacuum oven to provide 5-tosyl-5H-pyrrolo[2,3-b]pyrazine-2-carbonitrile (58.8 g, 70%) as a white solid: $^1H$ NMR ($CDCl_3$) δ 8.67 (s, 1H), 8.21 (d, J=4.2 Hz, 1H), 8.07 (d, J=8.4 Hz, 2H), 7.34 (d, J=8.1 Hz, 2H), 6.89 (d, J=4.2 Hz, 1H), 2.42 (s, 3H). A 2 L 316-stainless steel pressure reactor was charged with 5 wt % Pd/C (15.4 g of 63.6 wt % water wet material, 5.6 g dry basis, 2.6 mmol, Johnson Matthey A503032-5), 5-tosyl-5H-pyrrolo[2,3-b]pyrazine-2-carbonitrile (55 g, 184 mmol), THF (1.1 L), deionized water (165 mL), HCl (37 wt % aqueous, 30 mL, 369 mmol) and quinoline (1.1 mL, 9.0 mmol). The vessel was purged, pressurized, and maintained at 40 psi with hydrogen supplied from a high pressure reservoir. The mixture was vigorously agitated at about 25° C. After about 5 h the reactor was vented and purged with nitrogen to remove most of the dissolved hydrogen, and the reaction mixture was filtered to remove the catalyst. The reactor and catalyst cake were rinsed with THF:water (1:1, 2×40 mL). The combined filtrate and rinses were concd and EtOH (500 mL) was added. After two additional solvent switches with EtOH (2×500 mL), the crude residue was concd under reduced pressure to give a residue (76 g) that was suspended in EtOH (550 mL) and stirred at ambient temperature for about 4 h. The solid was collected by filtration and washed with cold EtOH (50 mL). The wet cake was dried in a vacuum oven to provide (5-tosyl-5H-pyrrolo

[2,3-b]pyrazin-2-yl)methanamine hydrochloride (51.2 g, 82%) as a white solid: LC/MS (Table 1, Method a) $R_t$=1.44 min; MS m/z: 303 $(M+H)^+$.

Step D: (R)-tert-butyl 3-((5-tosyl-5H-pyrrolo[2,3-b]pyrazin-2-yl)methylcarbamoyl)piperidine-1-carboxylate

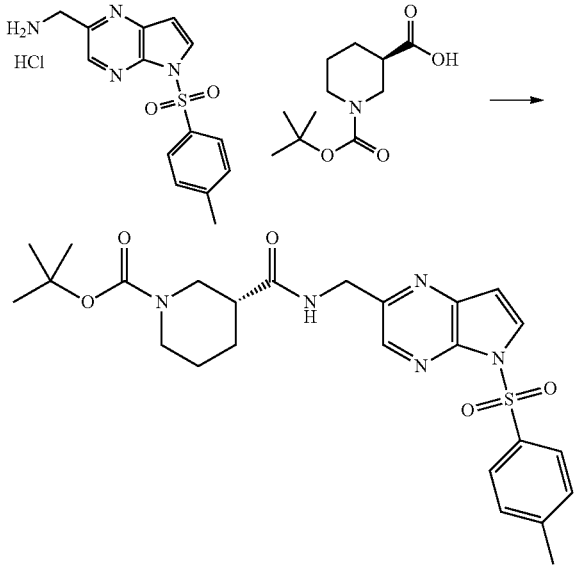

DIEA (7.7 mL, 44.3 mmol) was added to a solution of (5-tosyl-5H-pyrrolo[2,3-b]pyrazin-2-yl)methanamine hydrochloride (5 g, 14.7 mmol) in DCM (78 mL) and the reaction was stirred at ambient temperature for about 10 min followed by the addition of (R)-N-Boc-piperidine-3-carboxylic acid (3.38 g, 14.7 mmol, CNH-Technologies) and HATU (5.61 g, 14.7 mmol). The mixture was stirred for about 1 h, then water (30 mL) was added, and the layers were separated. The organic layer was washed with saturated aqueous $NaHCO_3$ (30 mL) and brine (30 mL), dried over anhydrous $MgSO_4$, filtered, and concd under reduced pressure. The crude material was purified by silica gel chromatography eluting with a gradient of 0-5% MeOH in DCM to afford crude (R)-tert-butyl 3-((5-tosyl-5H-pyrrolo[2,3-b]pyrazin-2-yl)methylcarbamoyl)piperidine-1-carboxylate (7.58 g, 94%): LC/MS (Table 1, Method b) $R_t$=2.30 min; MS m/z: 514 $(M+H)^+$.

Step E: (R)-tert-butyl 3-((5-tosyl-5H-pyrrolo[2,3-b]pyrazin-2-yl)methylcarbamothioyl)-piperidine-1-carboxylate

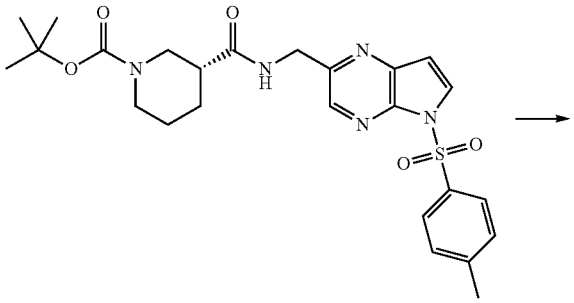

-continued

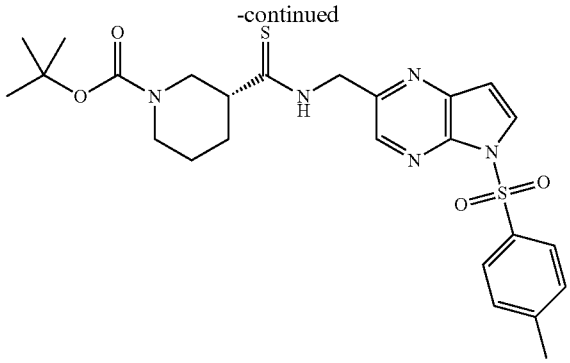

To a solution of (R)-tert-butyl 3-((5-tosyl-5H-pyrrolo[2,3-b]pyrazin-2-yl)methylcarbamoyl)-piperidine-1-carboxylate (7.58 g, 13.8 mmol) in 1,4-dioxane (130 mL) was added Lawesson's reagent (3.37 g, 8.32 mmol) and the reaction mixture was heated to about 60° C. for about 2 h then cooled to ambient temperature and concd under reduced pressure. The crude residue was dissolved in EtOAc (40 mL) and washed with saturated aqueous $NaHCO_3$, (3×40 mL), brine (30 mL), dried over anhydrous $MgSO_4$, filtered, and concd under reduced pressure. The crude material was purified by silica gel chromatography eluting with a gradient of 0-5% MeOH in DCM to afford (R)-tert-butyl 3-((5-tosyl-5H-pyrrolo[2,3-b]pyrazin-2-yl)methylcarbamothioyl)piperidine-1-carboxylate (5.6 g, 74%, UV purity 97%): LC/MS (Table 1, Method b) $R_t$=2.60 min; MS m/z: 530 $(M+H)^+$.

Step F: (R)-tert-butyl 3-(6-tosyl-6H-imidazo[1,5-a]pyrrolo[2,3-e]pyrazin-1-yl)piperidine-1-carboxylate

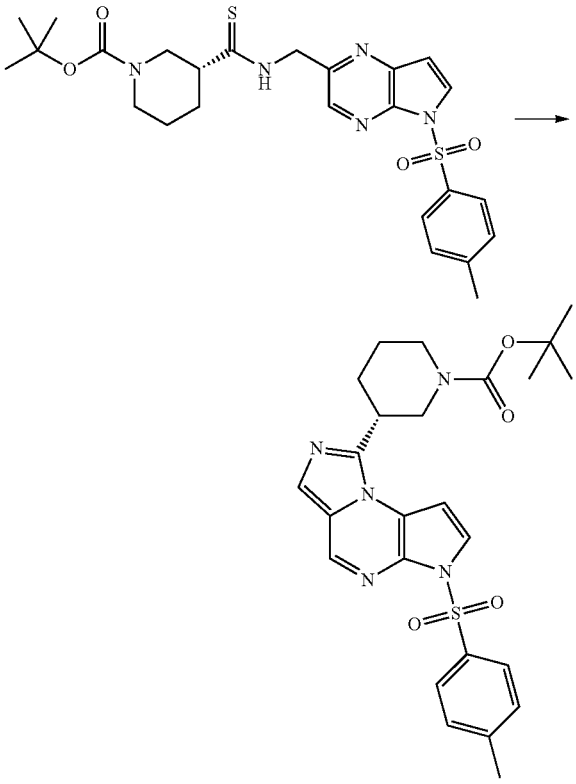

To a solution of (R)-tert-butyl 3-((5-tosyl-5H-pyrrolo[2,3-b]pyrazin-2-yl)methylcarbamothioyl)-piperidine-1-carboxylate (5.61 g, 10.3 mmol) in 1,4-dioxane (96 mL) was added mercury (II) trifluoroacetate (4.38 g, 10.3 mmol). The reaction mixture was stirred at ambient temperature for about 2 h then filtered through a pad of Celite®. The Celite® pad was rinsed with EtOAc (50 mL) and the filtrate was concd under reduced pressure. The crude residue was dissolved in EtOAc (40 mL) and the organic phase was washed with saturated aqueous $NaHCO_3$ (2×40 mL) and brine (30 mL), dried over anhydrous $MgSO_4$, filtered, and coned under reduced pressure. The crude material was purified by silica gel chromatography eluting with a gradient of 0-5% MeOH in DCM to afford (R)-tert-butyl 3-(6-tosyl-6H-imidazo[1,5-a]pyrrolo[2,3-e]pyrazin-1-yl)piperidine-1-carboxylate (4.4 g, 87%): LC/MS (Table 1, Method b) $R_t$=2.49 min; MS m/z: 496 $(M+H)^+$.

Step G: (R)-tert-butyl 3-(6H-imidazo[1,5-a]pyrrolo[2,3-e]pyrazin-1-yl)piperidine-1-carboxylate

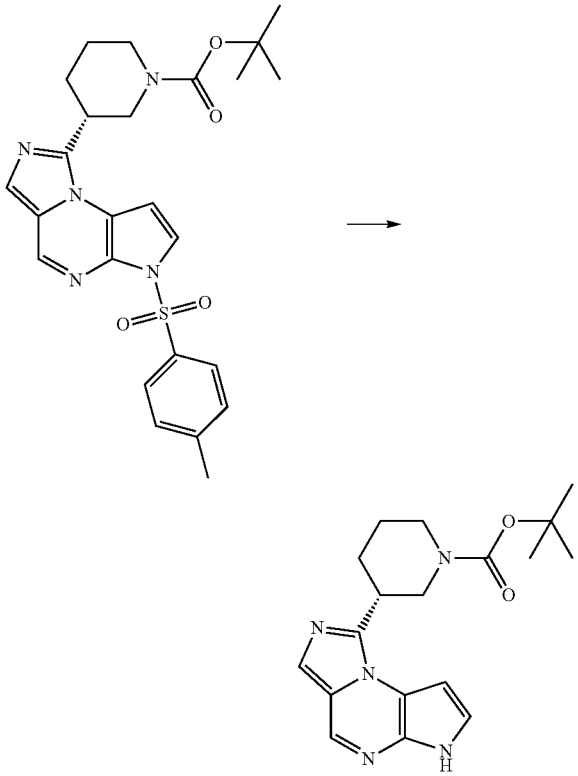

To a solution of (R)-tert-butyl 3-(6-tosyl-6H-imidazo[1,5-a]pyrrolo[2,3-e]pyrazin-1-yl)piperidine-1-carboxylate (4.44 g, 8.96 mmol) in 1,4-dioxane (54 mL) was added NaOH (2 N aqueous, 8.9 mL, 18 mmol), and the resulting mixture was heated at about 60° C. for about 3 h. The reaction was cooled to ambient temperature and EtOAc (30 mL) and saturated aqueous $NH_4Cl$ (20 mL) were added. The organic layer was separated and the aqueous layer was further extracted with EtOAc (40 mL). The combined organic layers were washed with brine (40 mL), dried over anhydrous $MgSO_4$, filtered, and coned under reduced pressure. The material was purified by silica gel chromatography eluting with a gradient of 0-10% MeOH in DCM to afford (R)-tert-butyl 3-(6H-imidazo[1,5-a]pyrrolo[2,3-e]pyrazin-1-yl)piperidine-1-carboxylate (2.80 g, 92%): LC/MS (Table 1, Method b) $R_t$=1.85 min; MS m/z: 342 $(M+H)^+$.

Step H: (R)-1-(piperidin-3-yl)-6H-imidazo[1,5-a]pyrrolo[2,3-e]pyrazine hydrochloride

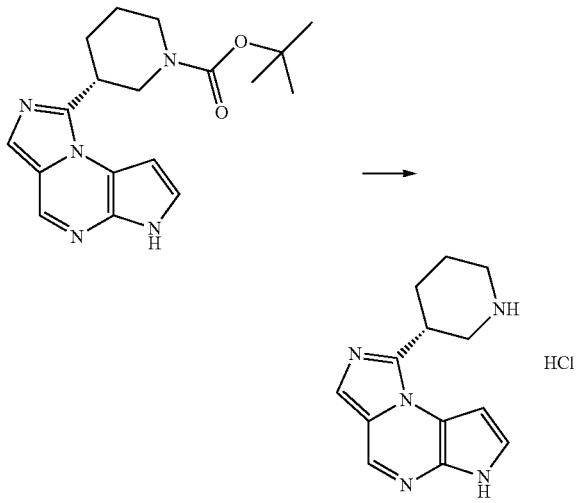

A round bottom flask was charged with (R)-tert-butyl 3-(6H-imidazo[1,5-a]pyrrolo[2,3-e]pyrazin-1-yl)piperidine-1-carboxylate (2.8 g, 8.20 mmol), 1,4-dioxane (24 mL) and HCl (4 N in 1,4-dioxane, 6.2 mL, 24.6 mmol). The reaction mixture was heated at about 60° C. for about 18 h. The reaction mixture was cooled to ambient temperature and $Et_2O$ (40 mL) was added and the mixture was stirred for about 15 min. The solid was collected by vacuum filtration, while washed with $Et_2O$ (50 mL), and then dried in a vacuum oven at about 60° C. to afford (R)-1-(piperidin-3-yl)-6H-imidazo[1,5-a]pyrrolo[2,3-e]pyrazine hydrochloride (2.4 g, 94%) as an off-white solid: LC/MS (Table 1, Method b) $R_t$=0.81 min; MS m/z 242 $(M+H)^+$.

Step I: (R)-cyclopentyl 3-(6H-imidazo[1,5-a]pyrrolo[2,3-e]pyrazin-1-yl)piperidine-1-carboxylate

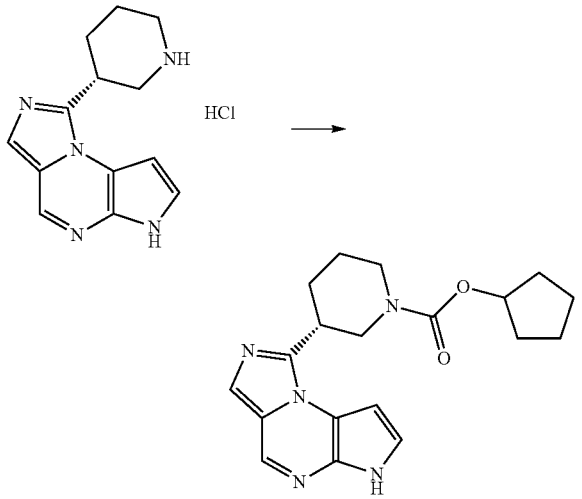

To a solution of (R)-1-(piperidin-3-yl)-6H-imidazo[1,5-a]pyrrolo[2,3-e]pyrazine hydrochloride (0.06 g, 0.19 mmol) in THF (1 mL) was added TEA (0.08 mL, 0.57 mmol) and the reaction was stirred at ambient temperature for about 10 min. To the reaction mixture was added cyclopentyl chloroformate (0.02 mL, 0.15 mmol, Waterstone) and the mixture was stirred at about 45° C. for about 18 h. The reaction mixture was cooled to ambient temperature and concd under reduced pressure. The crude material was dissolved in DCM (5 mL) and washed with water (5 mL). The organic layer was separated and the aqueous layer was back extracted with DCM (2 mL). The combined organic extracts were dried over anhydrous $MgSO_4$, filtered, and concd under reduced pressure. The material was purified by silica gel chromatography eluting with a gradient of 0-5% MeOH in DCM to afford (R)-cyclopentyl 3-(6H-imidazo[1,5-a]pyrrolo[2,3-e]pyrazin-1-yl)piperidine-1-carboxylate (0.015 g, 21%): LC/MS (Table 1, Method b) $R_t$=1.87 min; MS m/z: 354 $(M+H)^+$.

Example #12

(E)-3-(1-cyclohexyl-6H-imidazo[1,5-a]pyrrolo[2,3-e]pyrazin-3-yl)acrylic acid

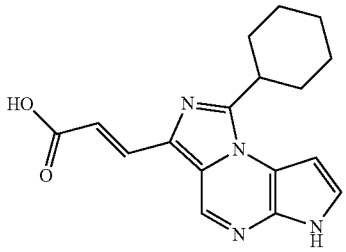

Step A: (E)-ethyl 3-(1-cyclohexyl-6-tosyl-6H-imidazo[1,5-a]pyrrolo[2,3-e]pyrazin-3-yl)acrylate

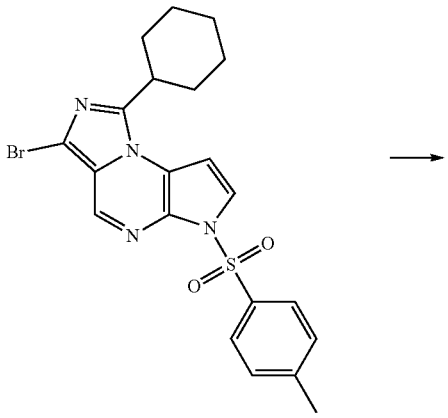

-continued

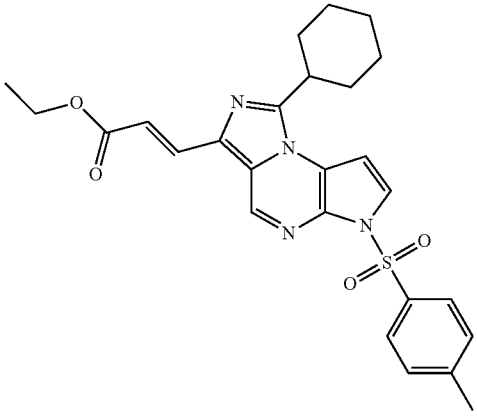

To a solution of 3-bromo-1-cyclohexyl-6-tosyl-6H-imidazo[1,5-a]pyrrolo[2,3-e]pyrazine (0.026 g, 0.056 mmol, Preparation #MM.1) and PdCl2(dppf)•DCM adduct (0.005 g, 0.006 mmol) in THF (1 mL) was added (E)-ethyl 3-(4,4,5,5-tetramethyl-1,3,2-dioxaborolan-2-yl)acrylate (0.052 g, 0.23 mmol) and $Na_2CO_3$ (0.021 g, 0.20 mmol) followed by water (0.25 mL). The reaction mixture was heated to about 65° C. After about 15 h, the reaction mixture was cooled to ambient temperature and directly purified by chromatography on silica gel (12 g) eluting with 20-80% EtOAc:DCM (1:1) in heptane to provide (E)-ethyl 3-(1-cyclohexyl-6-tosyl-6H-imidazo[1,5-a]pyrrolo[2,3-e]pyrazin-3-yl)acrylate (0.045 g, 70%) as a yellow solid: LC/MS (Table 1, Method a) $R_t$=3.15 min; MS m/z: 493 $(M+H)^+$.

Step B: (E)-3-(1-cyclohexyl-6H-imidazo[1,5-a]pyrrolo[2,3-e]pyrazin-3-yl)acrylic acid

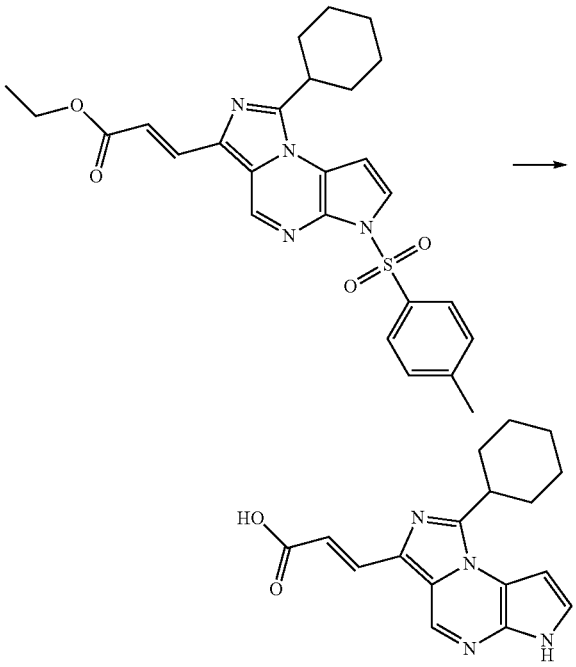

To a solution of (E)-ethyl 3-(1-cyclohexyl-6-tosyl-6H-imidazo[1,5-a]pyrrolo[2,3-e]pyrazin-3-yl)acrylate (0.064 g, 0.13 mmol) in 1,4-dioxane (5 mL) was added NaOH (2 N aqueous, 1.30 mL, 2.60 mmol). The reaction mixture was heated to about 65° C. After about 15 h, the reaction mixture was cooled to ambient temperature and the pH of the reaction mixture was adjusted to about pH 1 with concentrated HCl. The mixture was partially concd in vacuo to remove the 1,4-dioxane and the resulting yellow solid was collected by filtration and dried in vacuo to provide (E)-3-(1-cyclohexyl-6H-imidazo[1,5-a]pyrrolo[2,3-e]pyrazin-3-yl)acrylic acid (0.015 g, 37.2%): LC/MS (Table 1, Method a) $R_t$=1.85 min; MS m/z: 311 $(M+H)^+$.

Example #13

3-(1-cyclohexyl-6H-imidazo[1,5-a]pyrrolo[2,3-e]pyrazin-3-yl)propanoic acid

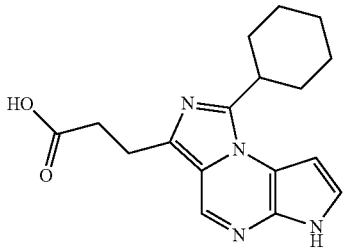

To solution of ethyl 3-(1-cyclohexyl-6-tosyl-6H-imidazo[1,5-a]pyrrolo[2,3-e]pyrazin-3-yl)propanoate (0.031 g, 0.063 mmol, prepared using W from Example #12 Step A) in 1,4-dioxane (3 mL) was added NaOH (2 N aqueous, 1.57 mL, 3.13 mmol). The reaction mixture was heated to about 65° C. After about 2 h, the reaction mixture was cooled to ambient temperature and the pH of the mixture was adjusted to about 1 with 1 N aqueous HCl. The reaction mixture was concd in vacuo and purified by chromatography on silica gel (12 g) eluting with 2-10% MeOH in DCM to provide 3-(1-cyclohexyl-6H-imidazo[1,5-a]pyrrolo[2,3-e]pyrazin-3-yl)propanoic acid (0.005 g, 26%) as a tan solid: LC/MS (Table 1, Method a) $R_t$=1.68 min; MS m/z: 313 $(M+H)^+$.

Example #14*

N-((1S,3R,4S)-3-ethyl-4-(3-(3-hydroxypropyl)-6H-imidazo[1,5-a]pyrrolo[2,3-e]pyrazin-1-yl)cyclopentyl)cyclopropanesulfonamide

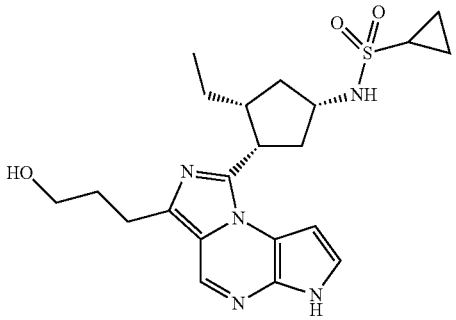

To a solution of N-((1S,3S,4R)-3-(3-allyl-6-tosyl-6H-imidazo[1,5-a]pyrrolo[2,3-e]pyrazin-1-yl)-4-ethylcyclopentyl)cyclopropanesulfonamide (0.090 g, 0.16 mmol, prepared using H with Preparation #12, Preparation #Z.1, HATU and DIEA, and Q with Lawesson's reagent and mercury (II) trifluoroacetate) in THF (3 mL) at about 0° C. was added $BH_3$•DMS (2 M in THF, 0.040 mL, 0.079 mmol). After about 2 h, additional $BH_3$•DMS (2 M in THF, 0.040 mL, 0.079 mmol) was added to the reaction mixture. After about 6 h total, a premixed solution of $H_2O_2$ (30% aqueous, 0.324 mL, 3.17 mmol) and NaOH (2 N aqueous, 0.793 mL, 1.58 mmol) was added to the reaction mixture. After stirring for about 15 h, EtOAc (20 mL) and water (20 mL) were added to the reaction mixture. The organic layer was separated, washed with brine (20 mL), and concd in vacuo. The crude residue was purified by chromatography on silica gel (12 g) eluting with EtOAc to provide N-((1S,3R,4S)-3-ethyl-4-(3-(3-hydroxypropyl)-6H-imidazo[1,5-a]pyrrolo[2,3-e]pyrazin-1-yl)cyclopentyl)cyclopropanesulfonamide (0.025 g, 37%) as a white solid: LC/MS (Table 1, Method a) $R_t$=1.70 min; MS m/z: 432 $(M+H)^+$.

Example #15

N-(1-(6H-imidazo[1,5-a]pyrrolo[2,3-e]pyrazin-1-yl)pyrrolidin-3-yl)cyclopropanesulfonamide

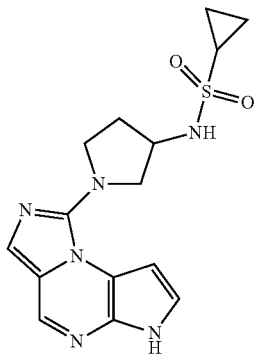

To a solution of tert-butyl 1-(6H-imidazo[1,5-a]pyrrolo[2,3-e]pyrazin-1-yl)pyrrolidin-3-ylcarbamate (0.175 g, 0.511 mmol, Example #D.1.42) in DCM (10 mL) was added HCl (4 N in 1,4-dioxane, 1.28 mL, 5.11 mmol). After about 4 h at ambient temperature, the reaction mixture was concd in vacuo. The residue was suspended in DCM (10 mL) and DIEA (0.446 mL, 2.56 mmol) was added to the reaction mixture resulting in a nearly homogeneous mixture. To the mixture was added cyclopropanesulfonyl chloride (0.079 g, 0.56 mmol). After about 2 h at ambient temperature, additional cyclopropane-sulfonyl chloride (0.079 g, 0.56 mmol) was added. After about 6 h at ambient temperature, saturated aqueous $NaHCO_3$ (10 mL) was added to the reaction mixture. The organic layer was separated and the aqueous layer was extracted with DCM (3×10 mL). The combined organic layers were concd in vacuo and purified by chromatography on silica gel (40 g) eluting with 50-90% MeCN in DCM to provide N-(1-(6H-imidazo[1,5-a]pyrrolo[2,3-e]pyrazin-1-yl)pyrrolidin-3-yl)cyclopropane-sulfonamide (0.125 g, 70%) as a tan solid: LC/MS (Table 1, Method a) $R_t$=1.42 min; MS m/z: 347 $(M+H)^+$.

Example #16

1-cyclohexyl-3-phenyl-6H-imidazo[1,5-a]pyrrolo[2,3-e]pyrazine

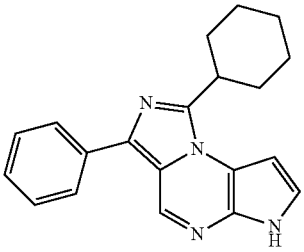

To a solution of 3-bromo-1-cyclohexyl-6-tosyl-6H-imidazo[1,5-a]pyrrolo[2,3-e]pyrazine (0.27 g, 0.056 mmol, Preparation #MM.1) and PdCl2(dppf)•DCM adduct (0.0046 g, 0.0056 mmol) in THF (1 mL) was added a solution of phenylboronic acid (0.12 g, 0.098 mmol) and $Na_2CO_3$ (0.009 g, 0.084 mmol) in water (0.25 mL). The reaction mixture was heated to about 60° C. After about 6 h, the reaction mixture was cooled to ambient temperature and was diluted with EtOAc (5 mL) and brine (5 mL). The organic layer was separated and concd in vacuo. The residue was dissolved in 1,4-dioxane (5 mL) and NaOH (2 N aqueous, 1 mL) was added. The reaction mixture was heated to about 65° C. After about 15 h, the reaction mixture was cooled to ambient temperature and HCl (1 N aqueous, 3 mL) and EtOAc (5 mL) were added. The organic layer was separated, concd in vacuo, and the residue was purified by chromatography on silica gel (12 g) eluting with 20-80% EtOAc in DCM to provide 1-cyclohexyl-3-phenyl-6H-imidazo[1,5-a]pyrrolo[2,3-e]pyrazine (0.005 g, 28%) as a solid: LC/MS (Table 1, Method a) $R_t$=2.75 min; MS m/z: 317 $(M+H)^+$.

Example #17*

N-((1S,3R,4S)-3-ethyl-4-(3-(hydroxymethyl)-6H-imidazo[1,5-a]pyrrolo[2,3-e]pyrazin-1-yl)cyclopentyl)cyclopropanesulfonamide

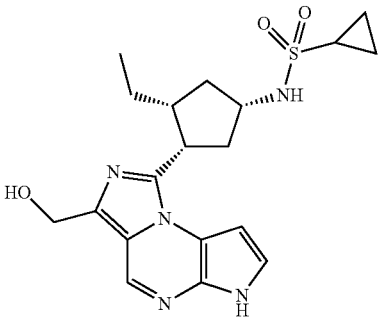

To a solution of N-((1S,3S,4R)-3-(3-allyl-6-tosyl-6H-imidazo[1,5-a]pyrrolo[2,3-e]pyrazin-1-yl)-4-ethylcyclopentyl) cyclopropanesulfonamide (0.17 g, 0.299 mmol, prepared using H with Preparation #12, Preparation #Z.1, HATU and DIEA, and Q with Lawesson's reagent and mercury (II) trifluoroacetate) in 1,4-dioxane (5 mL) and water (1.7 mL) was added sodium periodate (0.26 g, 1.2 mmol) followed by osmium tetroxide (4 wt % in water, 0.117 mL, 0.015 mmol). After about 48 h at ambient temperature, the reaction mixture was diluted with water (about 50 mL) and EtOAc (30 mL). The organic layer was separated, dried over anhydrous $Na_2SO_4$, filtered, and concd in vacuo. The crude aldehyde was dissolved in EtOH (10 mL) and $NaBH_4$ (0.023 g, 0.599 mmol) was added to the reaction mixture. After about 2 h at ambient temperature, HCl (1 N aqueous, about 3 mL) was added. After stirring for about 30 min, the reaction mixture was concd in vacuo. The residue was partitioned between EtOAc (30 mL) and saturated aqueous $NaHCO_3$ (30 mL). The organic layer was separated, dried over anhydrous $Na_2SO_4$, filtered, and concd in vacuo. The crude alcohol was dissolved in 1,4-dioxane (10 mL) and NaOH (2 N aqueous, 1.5 mL, 2.99 mmol) was added. The reaction mixture was heated to about 80° C. After about 4 h, the reaction mixture was cooled to ambient temperature and diluted with EtOAc (30 mL) and saturated aqueous $NH_4Cl$ (30 mL). The organic layer was separated, concd in vacuo, and purified by chromatography on silica gel eluting with 10-50% MeCN in DCM to provide N-((1S,3R,4S)-3-ethyl-4-(3-(hydroxymethyl)-6H-imidazo[1,5-a]pyrrolo[2,3-e]pyrazin-1-yl)cyclopentyl)cyclopropanesulfonamide (0.007 g, 6%) as a yellow solid: LC/MS (Table 1, Method a) $R_t$=1.59 min; MS m/z: 404 $(M+H)^+$.

Example #18*

N-((1S,3R,4S)-3-ethyl-4-(3-(2-hydroxyethyl)-6H-imidazo[1,5-a]pyrrolo[2,3-e]pyrazin-1-yl)cyclopentyl)cyclopropanesulfonamide

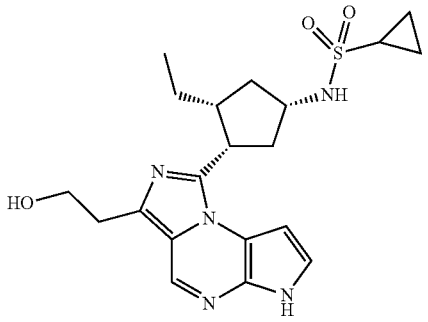

To a solution of N-((1S,3S,4R)-3-(3-allyl-6-tosyl-6H-imidazo[1,5-a]pyrrolo[2,3-e]pyrazin-1-yl)-4-ethylcyclopentyl) cyclopropanesulfonamide (0.170 g, 0.299 mmol, prepared using H with Preparation #12, Preparation #Z.1, HATU and DIEA, Q with Lawesson's reagent and mercury (II) trifluoroactate) in 1,4-dioxane (5 mL) and water (1.67 mL) was added sodium periodate (0.26 g, 1.198 mmol) followed by osmium tetroxide (4 wt % in water, 0.12 mL, 0.015 mmol). After about 4 h at ambient temperature, the reaction mixture was diluted with water (about 50 mL) and the resulting precipitate was collected by filtration. The crude aldehyde was dissolved in EtOH (10 mL) and $NaBH_4$ (0.023 g, 0.60 mmol) was added to the reaction mixture. After about 2 h at ambient temperature, HCl (1 N aqueous, about 3 mL) was added to the reaction mixture. After stirring for about 30 min, the reaction mixture was concd in vacuo. The residue was partitioned between EtOAc (20 mL) and saturated aqueous $NaHCO_3$ (20 mL). The organic layer was separated, dried over anhydrous $Na_2SO_4$, filtered, and concd in vacuo.

The crude alcohol was dissolved in 1,4-dioxane (10 mL) and NaOH (2 N aqueous, 1.50 mL, 2.99 mmol) was added. The reaction mixture was heated to about 80° C. After about 4 h, the reaction mixture was cooled to ambient temperature and diluted with EtOAc (30 mL) and saturated aqueous $NH_4Cl$ (30 mL). The organic layer was separated, concd in vacuo, and purified by chromatography on silica gel (40 g) eluting with 5% MeOH in DCM to provide N-((1S,3R,4S)-3-ethyl-4-(3-(2-hydroxyethyl)-6H-imidazo[1,5-a]pyrrolo[2,3-e]pyrazin-1-yl)cyclopentyl)cyclopropanesulfonamide (0.025 g, 20%) as a yellow solid: LC/MS (Table 1, Method a) $R_t$=1.67 min; MS m/z: 418 $(M+H)^+$.

Example #19*

N-((1S,3R,4S)-3-ethyl-4-(3-(2-(methylsulfonyl)ethyl)-6H-imidazo[1,5-a]pyrrolo[2,3-e]pyrazin-1-yl)cyclopentyl)cyclopropanesulfonamide

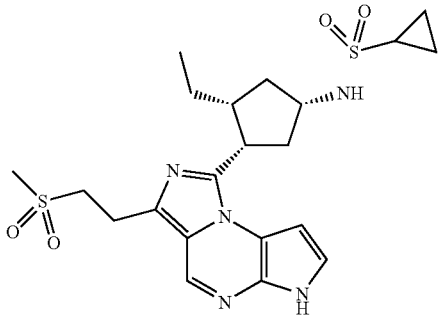

To a solution of N-((1S,3S,4R)-3-(3-allyl-6-tosyl-6H-imidazo[1,5-a]pyrrolo[2,3-e]pyrazin-1-yl)-4-ethylcyclopentyl)cyclopropanesulfonamide (0.28 g, 0.48 mmol, prepared using H with Preparation #12, Preparation #Z.1, HATU and DIEA, Q with Lawesson's reagent and mercury (II) trifluoroacetate) in 1,4-dioxane (5 mL) and water (1.5 mL) was added sodium periodate (0.21 g, 0.97 mmol) followed by osmium tetroxide (4 wt % in water, 0.19 mL, 0.024 mmol). After about 4 h, the reaction mixture was diluted with DCM (10 mL) and water (10 mL), the organic layer was separated and concd in vacuo. The crude aldehyde was dissolved in EtOH (5 mL) and $NaBH_4$ (0.18 g, 4.8 mmol) was added to the reaction mixture. After about 4 h, HCl (1 N aqueous, 10 mL) and DCM (20 mL) were added to the reaction mixture. The organic layer was separated and concd in vacuo. The residue was purified by silica gel chromatography eluting with EtOAc in DCM to give crude alcohol (0.061 g). To a solution of the crude alcohol in DCM (1 mL) was added DIEA (0.047 mL, 0.27 mmol) followed by methanesulfonyl chloride (0.0092 mL, 0.12 mmol). After about 2 h, the reaction mixture was diluted with DCM (10 mL) and saturated aqueous $NaHCO_3$ (10 mL). The organic layer was separated, concd in vacuo, and diluted with DMF (1.0 mL). Sodium methanethiolate (0.075 g, 1.1 mmol) was added to the reaction mixture. After stirring at ambient temperature for about 15 h, the reaction mixture was heated to about 50° C. After about 4 h, the reaction mixture was cooled to ambient temperature and diluted with DCM (10 mL) and saturated aqueous $NaHCO_3$ (10 mL). The organic layer was separated, concd in vacuo, and purified by chromatography on silica gel (40 g) eluting with 20-80% MeCN in DCM. The fractions containing the thioether were combined and concd in vacuo. The crude thioether was dissolved in DCM (1 mL) and treated with OXONE® tetrabutylammonium salt (0.114 g, 0.320 mmol). After about 4 h, the reaction mixture was diluted with DMSO (1 mL) and partially concd in vacuo to remove DCM. The crude mixture was purified by RP-HPLC (Table 1, Method k). The fractions containing the desired sulfone were combined and concd in vacuo. The residue was further purified by chromatography on silica gel (12 g) eluting with 5% MeOH in DCM to provide N-((1S,3R,4S)-3-ethyl-4-(3-(2-(methylsulfonyl)ethyl)-6H-imidazo[1,5-a]pyrrolo[2,3-e]pyrazin-1-yl)cyclopentyl)cyclopropanesulfonamide (0.002 g, 1.4%) as a solid: LC/MS (Table 1, Method a) $R_t$=1.82 min; MS m/z: 480 $(M+H)^+$.

Example #20

(cis-3-ethyl-4-(6H-pyrrolo[2,3-e][1,2,4]triazolo[4,3-a]pyrazin-1-yl)cyclopentyl)methanol

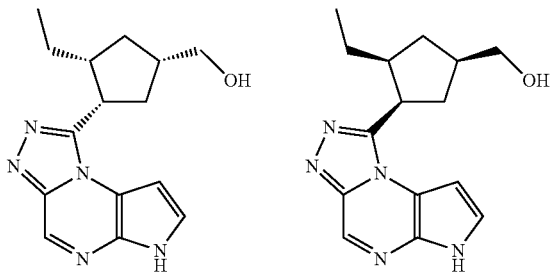

To a solution of 5-((cis-3-ethyl-4-(6-tosyl-6H-pyrrolo[2,3-e][1,2,4]triazolo[4,3-a]pyrazin-1-yl)cyclopentyl)methoxy)pyrazine-2-carbonitrile (0.145 g, 0.267 mmol, prepared using P from Preparation #11 with LAH, JJ with 5-chloropyrazine-2-carbonitrile [ArkPharm], TT with TFA, A from Example #1 Step D, HATU, and TEA, B with TEA) in 1,4-dioxane (2.7 mL) was added $Na_2CO_3$ (2 N aqueous, 2.7 mL). The reaction was heated at about 50° C. for about 16 h. EtOH (2 mL) was added to the reaction mixture. The reaction was kept at about 50° C. for about 16 h and then cooled to ambient temperature. The material was purified by RP-HPLC (Table 1, Method d) to give (cis-3-ethyl-4-(6H-pyrrolo[2,3-e][1,2,4]triazolo[4,3-a]pyrazin-1-yl)cyclopentyl)methanol (0.024 g, 31%) as the product: LC/MS (Table 1, Method b) $R_t$=1.63 min; MS m/z 286 $(M+H)^+$.

Example #21

1-cyclohexyl-1,6-dihydroimidazo[4,5-d]pyrrolo[2,3-b]pyridine

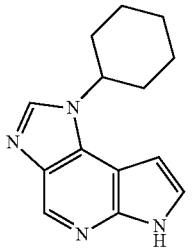

Step A: 4-chloro-3-iodo-5-nitropyridin-2-amine

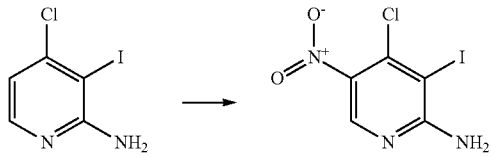

A solution of 4-chloro-3-iodopyridin-2-amine (4.00 g, 15.7 mmol, Adesis) in concd $H_2SO_4$ (45 mL) was cooled to about 0° C. in an ice bath. Potassium nitrate (3.50 g, 34.6 mmol) was added in four portions over about 10 min. The resulting solution was stirred at about 0° C. for about 1 h, then at ambient temperature for about 4 h. The reaction mixture was slowly poured over crushed ice (total volume 1 L) resulting in formation of a solid that was collected by vacuum filtration and dried under vacuum to give 4-chloro-3-iodo-5-nitropyridin-2-amine (2.2 g, 47%) as a yellow solid: LC/MS (Table 1, Method c) $R_t$=1.48 min; MS m/z 298 $(M-H)^-$.

Step B: 4-chloro-5-nitro-3-((trimethylsilyl)ethynyl) pyridin-2-amine

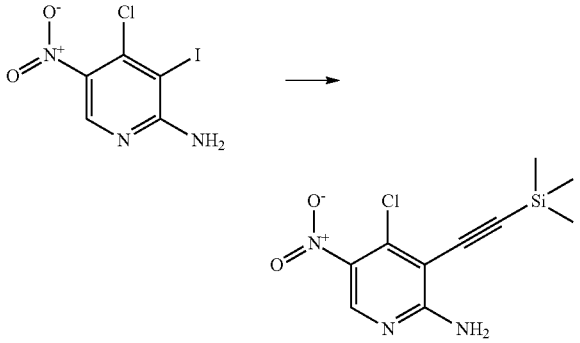

To a solution of 4-chloro-3-iodo-5-nitropyridin-2-amine (5.30 g, 17.7 mmol) in THF (90 mL) was added TEA (15.0 mL, 108 mmol). The reaction mixture was degassed and purged with nitrogen 3 times. Bis(triphenylphosphine)-palladium(II) dichloride (0.62 g, 0.88 mmol, Strem), copper(I) iodide (0.17 g, 0.89 mmol), and trimethylsilylacetylene (5.4 mL, 39 mmol) were added to the reaction mixture, degassed, and purged 3 times with nitrogen. The reaction was heated at about 60° C. for about 16 h. The reaction mixture was cooled to ambient temperature. The reaction mixture was filtered and washed with THF (200 mL). The filtrate was concd under reduced pressure. DCM (100 mL) was added to the residue and the precipitate that formed was filtered and collected to give 4-chloro-5-nitro-3-((trimethylsilyl)ethynyl)pyridin-2-amine (0.77 g). The remaining filtrate was concd under reduced pressure and the crude material was purified by flash chromatography on silica gel eluting with a gradient of 0-100% EtOAc in DCM. The purified material was combined with the 0.77 g of precipitate to afford 4-chloro-5-nitro-3-((trimethylsilyl)ethynyl)pyridin-2-amine (2.22 g, 47%) as a yellow solid: LC/MS (Table 1, Method c) $R_t$=1.62 min; MS m/z 268 $(M-H)^-$.

Step C: 4-chloro-3-ethynyl-5-nitropyridin-2-amine

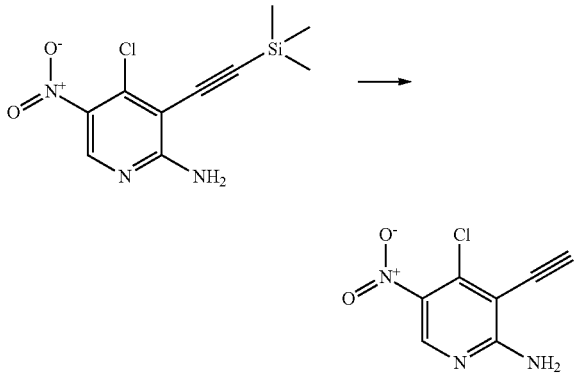

To a solution of 4-chloro-5-nitro-3-((trimethylsilyl)ethynyl)pyridin-2-amine (2.36 g, 8.76 mmol) in DMF (30 mL) was added potassium fluoride on alumina (40 wt %, 3.2 g, 22 mmol). The suspension was stirred at about ambient temperature for about 2 h. Activated charcoal (0.23 g) was added and the suspension was filtered though Celite®, washed with DMF (200 mL). The solvent was removed under reduced pressure and the residue was triturated with petroleum ether (50 mL, b.p. 30-60° C.). The solid was filtered, washed with petroleum ether (4×25 mL, b.p. 30-60° C.), and dried in vacuo to give 4-chloro-3-ethynyl-5-nitropyridin-2-amine (2.12 g, 89%) as a brown solid: LC/MS (Table 1, Method c) $R_t$=1.32 min; MS m/z 196 $(M-H)^-$.

Step D: 4-chloro-5-nitro-1H-pyrrolo[2,3-b]pyridine

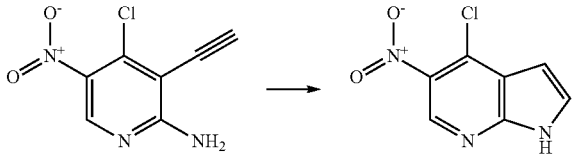

To a solution of 4-chloro-3-ethynyl-5-nitropyridin-2-amine (0.16 g, 0.81 mmol) in DMF (3 mL) was added chloro (1,5-cyclooctadiene)rhodium (I) dimer (0.02 g, 0.04 mmol) and tris(4-fluorophenyl)phosphine (0.128 g, 0.405 mmol). The reaction mixture was degassed by bubbling argon for 15 min. The reaction mixture was heated at about 80° C. for about 45 min. The solvent was removed under reduced pressure and the residue was suspended in ether (10 mL). The precipitate was collected by filtration and dried to give 4-chloro-5-nitro-1H-pyrrolo[2,3-b]pyridine (0.132 g, 83%, contains approximately 6% mol of DMF and approximately 3% mol of tris(4-fluorophenyl)phosphine) as a brown solid: LC/MS (Table 1, Method a) $R_t$=2.05 min; MS m/z 198 $(M+H)^+$.

Step E: N-cyclohexyl-5-nitro-1H-pyrrolo[2,3-b] pyridin-4-amine

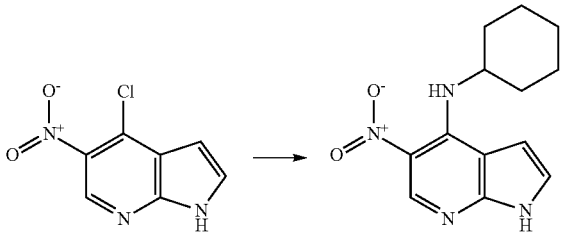

To a solution of 4-chloro-5-nitro-1H-pyrrolo[2,3-b]pyridine (0.182 g, 0.921 mmol) in DMF (5 mL) was added cyclohexylamine (0.55 g, 5.5 mmol). The reaction mixture was stirred at ambient temperature for about 2 h. The solvent was removed under reduced pressure and EtOAc (100 mL) and water (20 mL) were added. The layers were separated and the organic layer was washed with water (3×25 mL) and brine (20 mL), dried over anhydrous $MgSO_4$, filtered, and concd to give N-cyclohexyl-5-nitro-1H-pyrrolo[2,3-b]pyridin-4-amine (0.20, 57%) as a brown residue: LC/MS (Table 1, Method c) $R_t$=1.53 min; MS m/z 261 $(M+H)^+$.

Step F: N-cyclohexyl-1H-pyrrolo[2,3-b]pyridine-4, 5-diamine

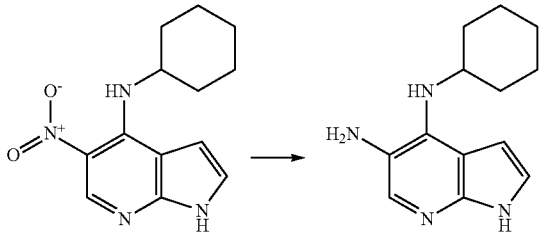

To a solution of N-cyclohexyl-5-nitro-1H-pyrrolo[2,3-b] pyridin-4-amine (0.15 g, 0.57 mmol) in EtOH (10 mL) was added tin (II) chloride dihydrate (0.65 g, 2.9 mmol). The reaction mixture was heated at about 55° C. for about 1 h. The solvent was removed under reduced pressure and EtOAc (75 mL) and saturated aqueous $NaHCO_3$ (25 mL) were added. The solid that formed was collected by vacuum filtration, washed with EtOAc (25 mL), and discarded. The filtrate was washed with saturated aqueous $NaHCO_3$ (3×20 mL), dried over anhydrous $MgSO_4$, filtered, and concd to give N-cyclohexyl-1H-pyrrolo[2,3-b]pyridine-4,5-diamine (0.107 g, 87%) as a brown residue: LC/MS (Table 1, Method c) $R_t$=1.21 min; MS m/z 231 $(M+H)^+$.

Step G: 1-cyclohexyl-1,6-dihydroimidazo[4,5-d] pyrrolo[2,3-b]pyridine

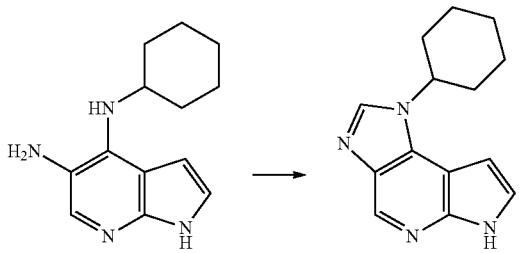

To a solution of N-cyclohexyl-1H-pyrrolo[2,3-b]pyridine-4,5-diamine (0.084 g, 0.36 mmol) in triethyl orthoformate (1 mL, 6 mmol) was added p-toluenesulfonic acid monohydrate (0.002 g, 0.011 mmol). The reaction mixture was heated at about 80° C. for about 1 h. p-Toluenesulfonic acid monohydrate (0.002 g, 0.011 mmol) was added and the reaction mixture was stirred at about 80° C. After about 1 h, p-toluenesulfonic acid monohydrate (0.002 g, 0.011 mmol) was added and the reaction mixture was stirred at about 80° C. for about 2 h. The reaction mixture was cooled to ambient temperature and concd under reduced pressure. The reaction was purified by RP-HPLC (Table 1, Method m) to give 1-cyclohexyl-1,6-dihydroimidazo[4,5-d]pyrrolo[2,3-b]pyridine (0.002 g, 2%) as a brown solid: LC/MS (Table 1, Method a) $R_t$=1.90 min; MS m/z 241 $(M+H)^+$.

Example #22

1-01S,2R,4S)-2-ethyl-4-(tetrahydro-2H-pyran-4-yloxy)cyclopentyl)-6H-pyrrolo[2,3-e][1,2,4]triazolo [4,3-a]pyrazine

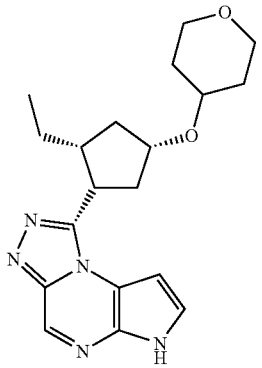

Step A: ethyl 2-ethyl-4-oxocyclopent-2-enecarboxylate

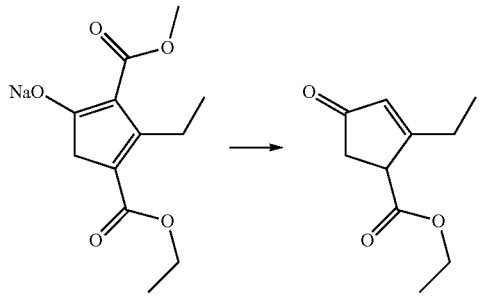

In a 5 L round bottom flask, sodium 4-(ethoxycarbonyl)-3-ethyl-2-(methoxycarbonyl)cyclopenta-1,3-dienolate (316 g, 1205 mmol, [Example #1, step E]), KCl (126 g, 1687 mmol), and AcOH (241 mL, 4218 mmol, JT Baker) in toluene (1850 mL) and water (130 mL) were heated at reflux for about 6 h. The reaction mixture was allowed to cool to ambient temperature for about 16 h. The reaction mixture was added dropwise to an aqueous solution of $NaHCO_3$ (3.5 L, 8%). The aqueous layer was extracted with MTBE (2×1.5 L). The combined organic layers were washed with brine (1 L), dried over anhydrous $MgSO_4$, filtered, and concd under reduced pressure. The crude material was purified by vacuum distillation (80-98° C., 0.6 mmHg) to give ethyl 2-ethyl-4-oxocyclopent-2-enecarboxylate (160.4 g, 69%): $^1$H NMR (400 MHz, $CDCl_3$) δ 6.05-6.02 (m, 1H), 4.28-4.14 (m, 2H), 3.75 (m, J=0.9, 1.8, 3.8, 6.7, 1H), 2.69 (dd, J=3.1, 18.4, 1H), 2.61 (dd, J=6.9, 18.4, 1H), 2.52 (dq, J=7.4, 24.2, 1H), 2.40 (dq, J=7.4, 16.1, 1H), 1.30 (t, J=7.2, 3H), 1.21 (t, J=7.4, 3H).

Step B: ethyl 2-ethyl-4-oxocyclopentanecarboxylate

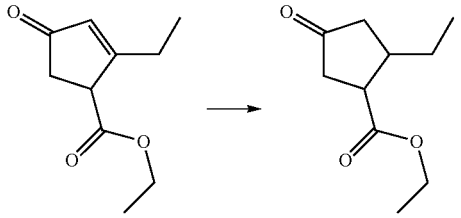

In a 1 L round-bottomed jacketed flask, copper(I) chloride (0.679 g, 6.86 mmol), (S)-(−)-2,2'-bis(diphenylphosphino)-1,1'-binaphthyl (4.27 g, 6.86 mmol), and sodium tert-butoxide (0.6.59 g, 6.86 mmol) in toluene (250 mL) were added to give a brown solution. The mixture was stirred at ambient temperature for 15 min after which the solution became brown. The solution was cooled to about 5° C. and polymethylhydrosiloxane (18.29 mL, 274 mmol) was added and the reaction mixture was stirred at about 5° C. for about 40 min. The solution was cooled to about −15° C. and a solution of ethyl 2-ethyl-4-oxocyclopent-2-enecarboxylate (25.00 g, 137 mmol) and tert-butyl alcohol (69.9 mL, 741 mmol) in toluene (250 mL) was added in one portion and the reaction stirred at about −15° C. for about 120 h. The reaction mixture was quenched by the addition of 1:1 ethanol/toluene (350 mL) and Celite® 545 (25 g). The mixture was stirred for about 3 h and allowed to warm to ambient temperature. The reaction mixture was concd in vacuo, chasing with heptane. Heptane (350 mL) was added to the residue and solids were removed by filtration. The filtrate was concd in vacuo and the crude product was purified by silica gel chromatography using a gradient of 10 to 50% EtOAc in heptane over 7 column volumes to give ethyl 2-ethyl-4-oxocyclopentanecarboxylate as a scalemic mixture of diastereomers, predominantly (1S,2R)-ethyl 2-ethyl-4-oxocyclopentanecarboxylate (13.68 g, 54%) as a colorless oil. $^1$H NMR (400 MHz, $CDCl_3$) δ 4.17 (qd, J=7.1, 1.5, 2H), 3.25-3.18 (m, 1H), 2.55 (m, J=4.7, 3.5, 1.7, 1H), 2.46-2.29 (m, 3H), 2.21 (m, J=11.6, 9.8, 1.3, 1H), 1.53 (m, J=14.8, 7.4, 6.1, 1H), 1.42-1.30 (m, 1H), 1.27 (t, J=7.1, 3H), 0.98 (t, J=7.4, 3H).

Step C: (ethyl 2-ethyl-4-hydroxycyclopentanecarboxylate

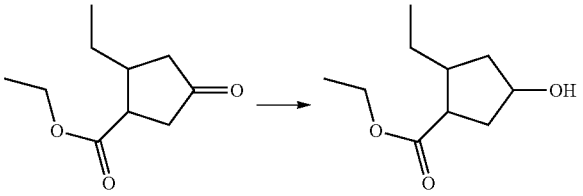

To a solution of ethyl 2-ethyl-4-oxocyclopentanecarboxylate (12.82 g, 69.6 mmol, 86% ee, predominantly 1S,2R) in MeOH (183 mL) was added sodium borohydride (3.29 g, 87 mmol) portion-wise. The suspension was stirred at ambient temperature for about 16 h. Saturated aqueous $NH_4Cl$ (200 mL) was added and the reaction was stirred for about 3 h. The white precipitate that formed was filtered and washed with $Et_2O$ (100 mL). The filtrate was poured into $Et_2O$ (300 mL). The solid was filtered and washed with $Et_2O$ (50 mL). The layers were separated and the aqueous layer was extracted with $Et_2O$ (2×150 mL). The combined organic layers were washed with brine (2×150 mL), dried over anhydrous $MgSO_4$, filtered and concd under reduce pressure (keeping bath temperature about 25° C. and vacuum >50 psi) to give a crude product as a thick light yellow oil. The oil was washed with pentane (5×80 mL). The combined pentane layers were dried over anhydrous $MgSO_4$, filtered and concd to give an oil which was purified by silica gel chromatography using 1:1 EtOAc:pentane to give ethyl 2-ethyl-4-hydroxycyclopentanecarboxylate as a scalemic mixture of diastereomers predominantly (1S,2R,4S)-ethyl 2-ethyl-4-hydroxycyclopentanecarboxylate (12.38 g, 96%) as a clear oil; $^1$H NMR (400 MHz, $CDCl_3$) δ 4.34-4.25 (m, 1H), 4.23-4.09 (m, 2H), 3.43-3.17 (m, 1H), 2.88 (td, J=7.1, 2.2, 1H), 2.40 (dt, J=14.0, 7.8, 1H), 2.09-1.91 (m, 3H), 1.33-1.24 (m, 4H), 0.95 (t, J=7.4, 3H).

Step D: (ethyl 4-(tert-butyldimethylsilyloxy)-2-ethylcyclopentanecarboxylate

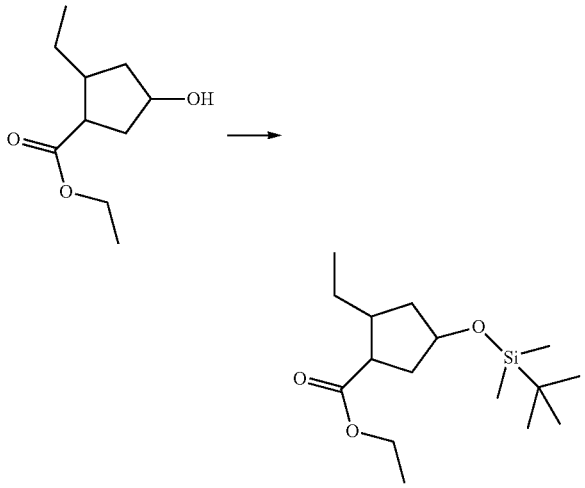

To a solution of ethyl 2-ethyl-4-hydroxycyclopentanecarboxylate (10.0 g, 53.7 mmol) in DMF (18 mL) was added TBDMS-Cl (9.72 g, 64.5 mmol) and imidazole (9.15 g, 134 mmol). The reaction mixture was stirred at ambient temperature for about 3 h. Heptane (50 mL) was added to the reaction and the layers were separated. The bottom layer was extracted with heptane (2×30 mL). The combined organic extracts were washed with water (2×30 mL), brine (30 mL), dried over anhydrous $MgSO_4$, filtered and concd to give ethyl 4-(tert-butyldimethylsilyloxy)-2-ethylcyclopentanecarboxylate (15.87 g, 52.8 mmol, 98%) as a colorless oil; $^1$H NMR (400 MHz, $CDCl_3$) δ 4.13 (m, 3H), 2.79 (m, 1H), 2.09 (m, 1H), 1.99 (m, 3H), 1.50-1.24 (m, 6H), 0.89 (m, 12H), 0.05 (s, 6H).

Step E: ethyl 2-ethyl-4-(tetrahydro-2H-pyran-4-yloxy)cyclopentanecarboxylate

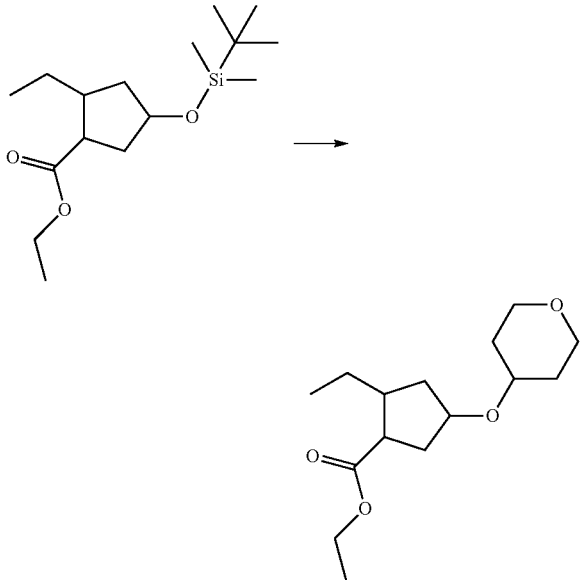

To a solution of ethyl 4-(tert-butyldimethylsilyloxy)-2-ethylcyclopentanecarboxylate (0.100 g, 0.333 mmol) in MeCN (2.2 mL) was added triethylsilane (0.080 mL, 0.499 mmol) and bismuth(III) bromide (0.010 g, 0.022 mmol). The reaction mixture was stirred at ambient temperature for about 1 min followed by dropwise addition of dihydro-2H-pyran-4(3H)-one (0.050 g, 0.499 mmol). The reaction mixture was stirred at ambient temperature for about 15 min. The reaction was filtered through an Acrodisc® and the solvent was removed under reduced pressure. To a solution of ethyl 4-(tert-butyldimethylsilyloxy)-2-ethylcyclopentanecarboxylate (0.200 g, 0.666 mmol) in MeCN (4.5 mL) was added triethylsilane (0.160 mL, 1.00 mmol) and bismuth(III) bromide (0.020 g, 0.045 mmol). The reaction mixture was stirred at ambient temperature for about 1 min followed by dropwise addition of dihydro-2H-pyran-4(3H)-one (0.100 g, 0.998 mmol). The reaction mixture was stirred at ambient temperature for about 15 min. The reaction was filtered through an Acrodisc® and the solvent was removed under reduced pressure. The residues were dissolved in DCM (2 mL) each, combined, and the crude material was purified by silica gel chromatography using a gradient of 10-100% EtOAc in heptane to give ethyl 2-ethyl-4-(tetrahydro-2H-pyran-4-yloxy)cyclopentanecarboxylate (0.253 g, 98%) as a colorless oil; $^1$H NMR (400 MHz, $CDCl_3$) δ 4.13 (q, J=7.1, 2H), 4.05-3.98 (m, 1H), 3.98-3.88 (m, 2H), 3.58-3.47 (m, 1H), 3.46-3.36 (m, 2H), 2.80 (q, J=8.5, 1H), 2.16 (dt, J=13.3, 7.7, 1H), 2.09-1.93 (m, 3H), 1.90-1.81 (m, 2H), 1.62-1.49 (m, 3H), 1.43 (ddd, J=11.1, 7.4, 5.2, 1H), 1.33-1.22 (m, 4H), 0.92-0.83 (m, 3H).

Step F: 2-ethyl-4-(tetrahydro-2H-pyran-4-yloxy) cyclopentanecarboxylic acid

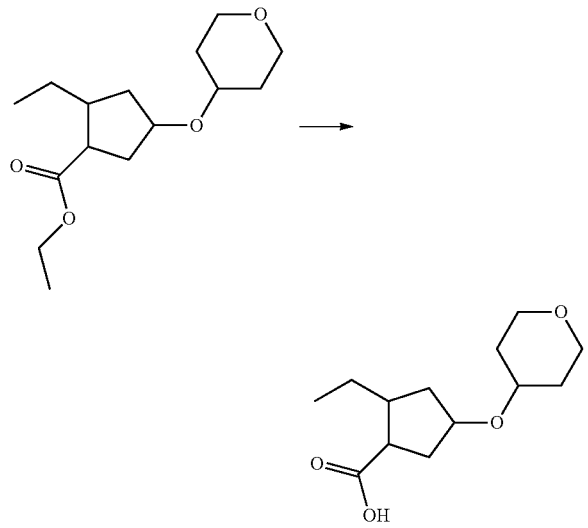

To a solution of ethyl 2-ethyl-4-(tetrahydro-2H-pyran-4-yloxy)cyclopentanecarboxylic acid (0.250 g, 0.925 mmol) in p-dioxane (15 mL) was added aqueous NaOH (1 M, 5.00 mL, 5.00 mmol) to give a colorless solution. The reaction was heated at about 70° C. for about 8 h. The reaction mixture was cooled to ambient temperature. The solvent was removed under reduced pressure. The solution was diluted with $Et_2O$ (30 mL). The layers were separated and the aqueous layer was extracted with $Et_2O$ (30 mL). The organic layer was set aside. The aqueous layer was acidified with 5 N HCl (2 mL) to about pH 2. The solution was diluted with $Et_2O$ (30 mL). The layers were separated and the aqueous layer was extracted with $Et_2O$ (3×30 mL). The combined organic extracts were dried over anhydrous $MgSO_4$, filtered and concd under reduced pressure to give 2-ethyl-4-(tetrahydro-2H-pyran-4-yloxy)cyclopentanecarboxylic acid containing 6 mol % of 1,4-dioxane as an excepient (0.194 g, 85%) as a colorless oil; LC/MS (Table 1, Method b) $R_t$=1.71 min; MS m/z: 243 $(M+H)^+$.

Step G: 2-ethyl-4-(tetrahydro-2H-pyran-4-yloxy)-N'-(5-tosyl-5H-pyrrolo[2,3-b]pyrazin-2-yl)cyclopentanecarbohydrazide

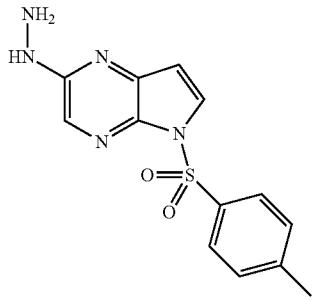

-continued

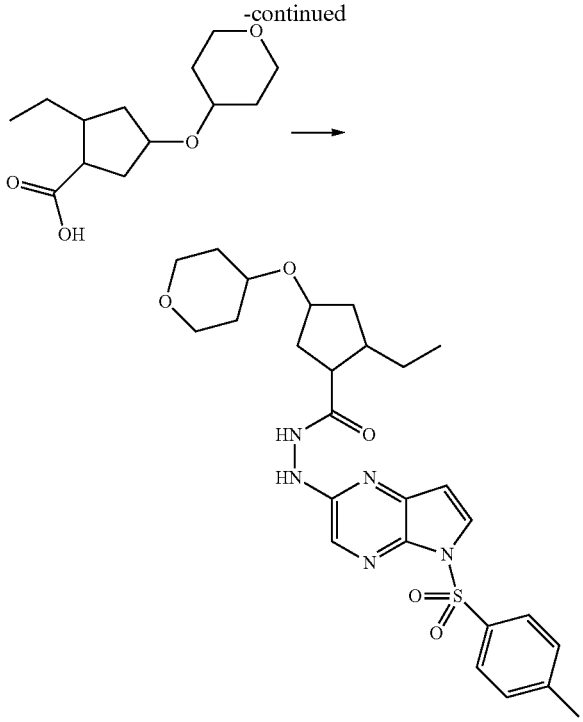

To a solution of 2-hydrazinyl-5-tosyl-5H-pyrrolo[2,3-b]pyrazine (0.233 g, 0.767 mmol, WO2009152133 Preparation #9) and 2-ethyl-4-(tetrahydro-2H-pyran-4-yloxy)cyclopentanecarboxylic acid (0.190 g, 0.767 mmol) in DCM (8.00 mL) was added HATU (0.350 g, 0.920 mmol, Novabiochem) and TEA (0.43 mL, 3.07 mmol). The resulting suspension was stirred at ambient temperature for about 4 h. The reaction was partitioned between DCM (50 mL) and water (25 mL) and the layers were separated. The organic layer was washed with water (2×25 mL) and brine (30 mL), dried over anhydrous $MgSO_4$, filtered, and concd to give a brown residue. The crude material was purified by silica gel chromatography using a gradient of 1-10% MeOH in DCM to give 2-ethyl-4-(tetrahydro-2H-pyran-4-yloxy)-N'-(5-tosyl-5H-pyrrolo[2,3-b]pyrazin-2-yl)cyclopentanecarbohydrazide (0.300 g, 74%); LC/MS (Table 1, Method b) $R_t$=2.20 min; MS m/z: 528 $(M+H)^+$.

Step H: 1-(2-ethyl-4-(tetrahydro-2H-pyran-4-yloxy)cyclopentyl)-6-tosyl-6H-pyrrolo[2,3-e][1,2,4]triazolo[4,3-a]pyrazine

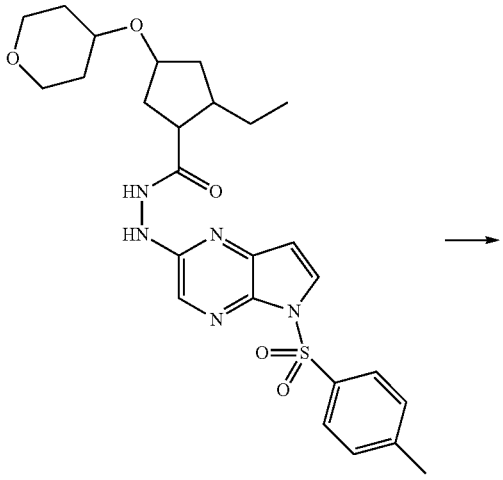

-continued

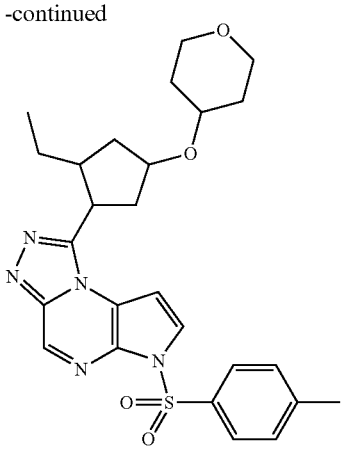

To a solution of 2-ethyl-4-(tetrahydro-2H-pyran-4-yloxy)-N-(5-tosyl-5H-pyrrolo[2,3-b]pyrazin-2-yl)cyclopentanecarbohydrazide (0.150 g, 0.284 mmol) in p-dioxane (5.00 mL) was added DIEA (0.200 mL, 1.146 mmol) and thionyl chloride (0.031 mL, 0.426 mmol). The reaction mixture was heated at about 80° C. for about 1 h, then cooled to ambient temperature. The reaction mixture was diluted with EtOAc (50 mL), washed with $H_2O$ (3×25 mL) and brine (2×25 mL). The aqueous layers were back extracted with EtOAc (2×30 mL). The combined organic layers were dried with anhydrous $MgSO_4$, filtered and concd to give 1-(2-ethyl-4-(tetrahydro-2H-pyran-4-yloxy)cyclopentyl)-6-tosyl-6H-pyrrolo[2,3-e][1,2,4]triazolo[4,3-a]pyrazine (0.145 g, 100%); LC/MS (Table 1, Method b) $R_t$=2.26 min; MS m/z: 510 $(M+H)^+$.

Step I: 1-((1S,2R,4S)-2-ethyl-4-(tetrahydro-2H-pyran-4-yloxy)cyclopentyl)-6H-pyrrolo[2,3-e][1,2,4]triazolo[4,3-a]pyrazine

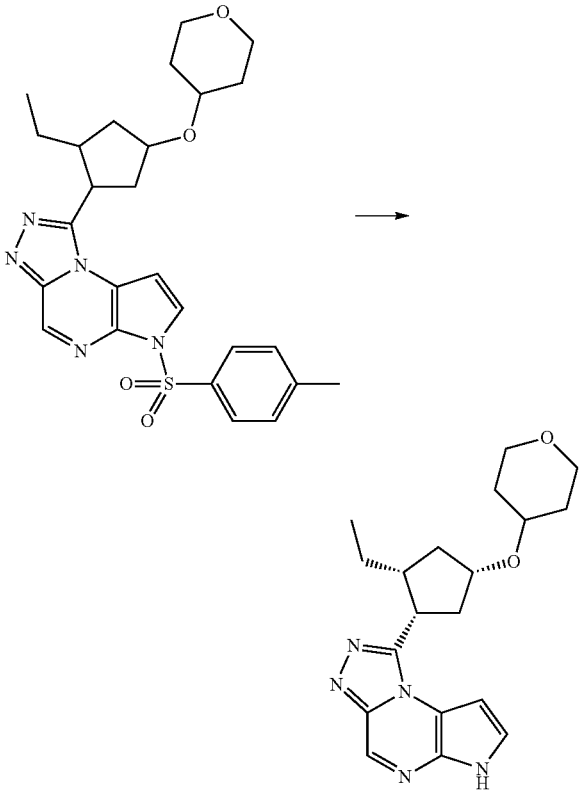

To a solution of 1-(2-ethyl-4-(tetrahydro-2H-pyran-4-yloxy)cyclopentyl)-6-tosyl-6H-pyrrolo[2,3-e][1,2,4]triazolo[4,3-a]pyrazine (0.145 g, 0.285 mmol) in p-dioxane (6.00 mL) was added an aqueous solution of NaOH (1 N, 1.50 mL, 1.50 mmol). The reaction mixture was stirred at about 55° C. for about 45 min, then cooled to ambient temperature. The reaction mixture was acidified to about pH 2 by the addition of aqueous HCl (1 N, 6 mL). The aqueous layer was extracted with DCM (3×20 mL). The combined organic layers were dried over anhydrous $MgSO_4$, filtered and concd to give a brown residue. The crude material was purified by silica gel chromatography using a gradient of 1-10% MeOH in DCM. The stereoisomers were separated using AA (Table 2, Method 32, $R_t$=15.5 min, or =negative) to give 1-((1S,2R,4S)-2-ethyl-4-(tetrahydro-2H-pyran-4-yloxy)cyclopentyl)-6H-pyrrolo[2,3-e][1,2,4]triazolo[4,3-a]pyrazine (0.048 g, 48%): LC/MS (Table 1, Method a) $R_t$=1.70 min; MS m/z: 356 $(M+H)^+$.

Example #23

N-((1S,3R,4S)-3-ethyl-4-(imidazo[4,5-d]pyrrolo[2,3-b]pyridin-1(6H)-yl)cyclopentyl)cyclopropanesulfonamide

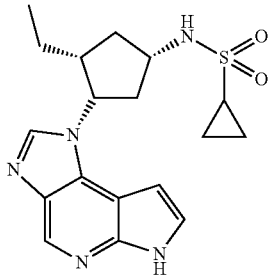

Step A: 4-chloro-3-iodo-5-nitropyridin-2-amine

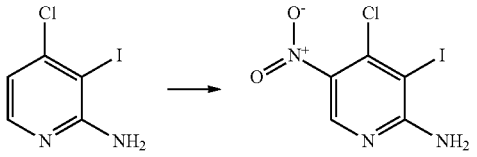

A solution of 4-chloro-3-iodopyridin-2-amine (0.25 g, 0.982 mmol, Boa Pharma) in concd $H_2SO_4$ (1.95 mL) was cooled to about 0° C. before the portion wise addition of potassium nitrate (0.21 g, 2.2 mmol) over 10 min. The reaction was stirred for about 4 h at about 0° C. The reaction mixture was slowly pipetted over a solution of ammonium hydroxide and crushed ice (10 mL) in an ice bath. The pH of the reaction was maintained above 9 by the incremental addition of ammonium hydroxide. The resulting precipitate is filtered and dried to afford 4-chloro-3-iodo-5-nitropyridin-2-amine (0.085 g, 29%) as a green-tinted solid LC/MS (Table 1, Method n) $R_t$=0.64 min; MS m/z: 298 $(M-H)^-$.

Step B: 4-chloro-5-nitro-3-((trimethylsilyl)ethynyl)pyridin-2-amine

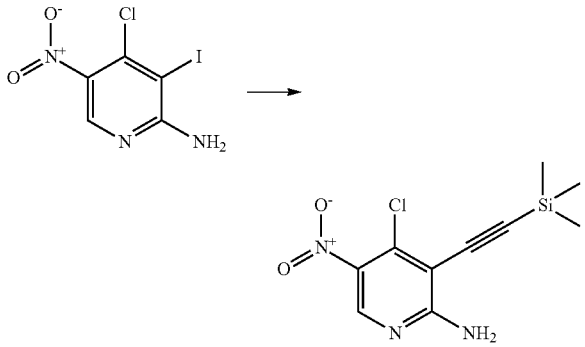

To a solution of 4-chloro-3-iodo-5-nitropyridin-2-amine (5.30 g, 17.7 mmol) in THF (90 mL) was added TEA (15.0 mL, 108 mmol). The reaction mixture was degassed and purged with nitrogen 3 times. Bis(triphenylphosphine)-palladium(II) dichloride (0.62 g, 0.88 mmol, Strem), copper(I) iodide (0.17 g, 0.89 mmol), and trimethylsilylacetylene (5.4 mL, 39 mmol) were added to the reaction mixture, degassed, and purged 3 times with nitrogen. The reaction was heated at about 60° C. for about 16 h. The reaction mixture was cooled to ambient temperature. The reaction mixture was filtered and washed with THF (200 mL). The filtrate was concd under reduced pressure. DCM (100 mL) was added to the residue and the precipitate that formed was filtered and collected to give 4-chloro-5-nitro-3-((trimethylsilyl)ethynyl)pyridin-2-amine (0.77 g). The remaining filtrate was concd under reduced pressure and the crude material was purified by flash chromatography on silica gel eluting with a gradient of 0-100% EtOAc in DCM. The purified material was combined with the 0.77 g of precipitate to afford 4-chloro-5-nitro-3-((trimethylsilyl)ethynyl)pyridin-2-amine (2.22 g, 47%) as a yellow solid: LC/MS (Table 1, Method c) $R_t$=1.62 min; MS m/z 268 $(M-H)^-$.

Step C: 4-chloro-3-ethynyl-5-nitropyridin-2-amine

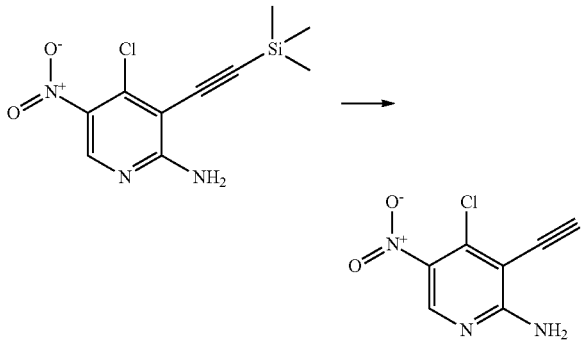

To a solution of 4-chloro-5-nitro-3-((trimethylsilyl)ethynyl)pyridin-2-amine (1.98 g, 7.34 mmol) in DMF (25 mL) was added potassium fluoride on alumina (40 wt %, 2.67 g, 18.35 mmol). The suspension was stirred at ambient temperature for about 1 h. Activated charcoal (0.3 g) was added and the suspension was filtered though Celite®, washing with DMF (150 mL). The solvent was removed under reduced pressure and the crude material was purified by silica gel chromatography eluting with a gradient of 0-10% MeOH in DCM to afford 4-chloro-3-ethynyl-5-nitropyridin-2-amine (1.03 g, 71%) as a yellow solid: LC/MS (Table 1, Method n) $R_t$=0.59 min; MS m/z: 196 $(M-H)^-$.

Step D: 4-chloro-5-nitro-1H-pyrrolo[2,3-b]pyridine

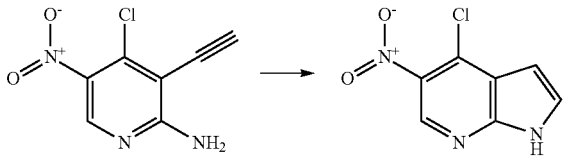

To a solution of 4-chloro-3-ethynyl-5-nitropyridin-2-amine (0.16 g, 0.81 mmol) in DMF (3 mL) was added chloro(1,5-cyclooctadiene)rhodium (I) dimer (0.02 g, 0.04 mmol) and tris(4-fluorophenyl)phosphine (0.128 g, 0.405 mmol). The reaction mixture was degassed by bubbling argon for 15 min. The reaction mixture was heated at about 80° C. for about 45 min. The solvent was removed under reduced pressure and the residue was suspended in ether (10 mL). The precipitate was collected by filtration and dried to give 4-chloro-5-nitro-1H-pyrrolo[2,3-b]pyridine (0.132 g, 83%, contains approximately 6% mol of DMF and approximately 3% mol of tris(4-fluorophenyl)phosphine) as a brown solid: LC/MS (Table 1, Method a) $R_t$=2.05 min; MS m/z 198 $(M+H)^+$.

Step E: N-((1S,3R,4S)-3-ethyl-4-isocyanatocyclopentyl)cyclopropanesulfonamide

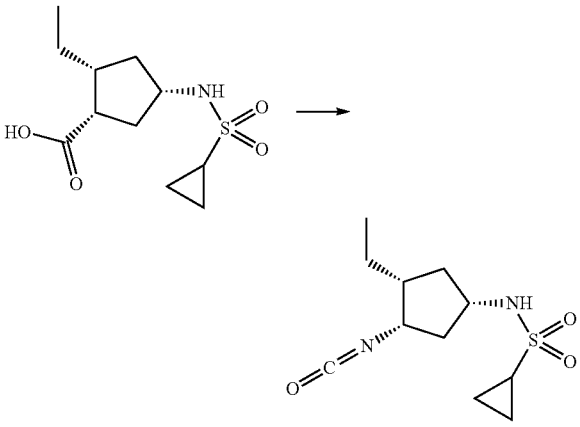

To a mixture of (1S,2R,4S)-4-(cyclopropanesulfonamido)-2-ethylcyclopentanecarboxylic acid (Preparation #Z.1, 1.00 g, 3.83 mmol) in t-BuOH (19.1 mL) was added DPPA (0.826 mL, 3.83 mmol) and TEA (1.17 mL, 8.42 mmol). The reaction mixture was heated at about 70° C. for about 45 min. The reaction mixture was cooled to ambient temperature and concd under reduced pressure. The crude material was purified by silica gel chromatography eluting with a gradient of 0-10% MeOH in DCM. The material was dried under reduced pressure to give N-((1S,3R,4S)-3-ethyl-4-isocyanatocyclopentyl)cyclopropanesulfonamide with 30 mol % of t-BuOH as an excipient (0.97 g, 98%) as a colorless oil: LC/MS (Table 1, Method n) $R_t$=0.56 min; MS m/z 259 $(M+H)^+$.

Step F: N-((1S,3S,4R)-3-amino-4-ethylcyclopentyl)cyclopropanesulfonamide hydrochloride

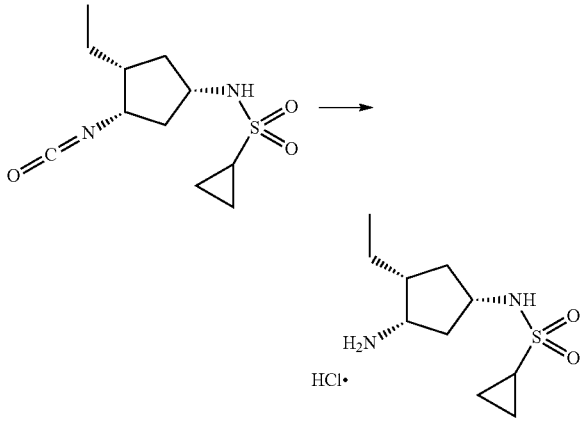

A mixture of N-((1S,3R,4S)-3-ethyl-4-isocyanatocyclopentyl)cyclopropanesulfonamide (0.972 g, 3.76 mmol) and aqueous HCl (6 N, 31.4 mL, 188 mmol) was heated at about 100° C. for about 60 h. Aqueous HCl (12 N, 5 mL) was added and the reaction mixture was heated at about 100° C. for about 18 h. The reaction mixture was cooled to ambient temperature and concd under reduced pressure. The residue was treated with $Et_2O$ (10 mL) and EtOAc (10 mL). The mixture was concd under reduced pressure. Water (5 mL) was added and the sample was lyophilized to give N-((1S,3S,4R)-3-amino-4-ethylcyclopentyl)cyclopropane-sulfonamide hydrochloride (0.859 g, 85%) as a white solid: LC/MS (Table 1, Method a) $R_t$=1.28 min; MS m/z 233 $(M+H)^+$.

Step G: N-((1S,3R,4S)-3-ethyl-4-(5-nitro-1H-pyrrolo[2,3-b]pyridin-4-ylamino)cyclopentyl)cyclopropanesulfonamide

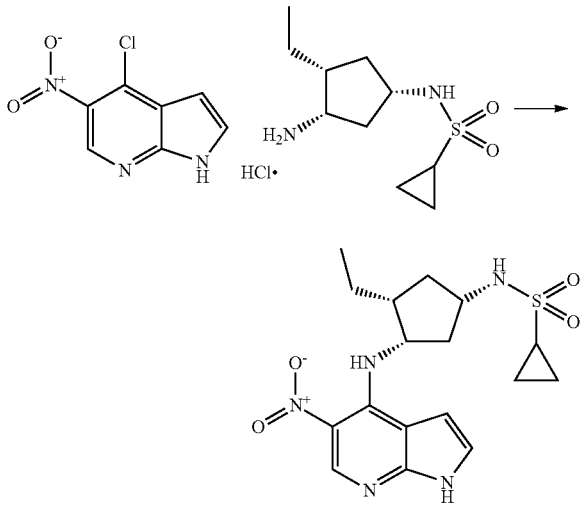

To a mixture of 4-chloro-5-nitro-1H-pyrrolo[2,3-b]pyridine (0.158 g, 0.800 mmol) in DMF (8.7 mL) was added DIEA (0.419 mL, 2.399 mmol) and N-((1S,3S,4R)-3-amino-4-ethylcyclopentyl) cyclopropanesulfonamide•hydrochloride (0.215 g, 0.800 mmol). The reaction mixture was heated at about 60° C. for about 60 h. The temperature was increased to about 70° C. for about 2 h then DIEA (0.279 mL, 1.599 mmol) and N-((1S,3S,4R)-3-amino-4-ethylcyclopentyl)cyclopropanesulfonamide hydrochloride (0.093 g, 0.346 mmol) were added. The reaction mixture was heated at about 70° C. for about 2 h. Additional N-((1S,3S,4R)-3-amino-4-ethylcyclopentyl)cyclopropanesulfonamide hydrochloride (0.060 g, 0.223 mmol) was added and the reaction mixture was heated at about 70° C. for about 30 min. Additional DIEA (0.279 mL, 1.599 mmol) was added and the reaction mixture was heated at about 70° C. for about 1 h. The reaction mixture was cooled to ambient temperature and concd in vacuo. The residue was dissolved in EtOAc (25 mL) and washed with water (20 mL). The organic layer was separated, dried over anhydrous $MgSO_4$, filtered, and concd under reduced pressure. The crude material was purified by silica gel chromatography eluting with a gradient of 0-5% MeOH in DCM to give N-((1S,3R,4S)-3-ethyl-4-(5-nitro-1H-pyrrolo[2,3-b]pyridin-4-ylamino)cyclopentyl)cyclopropanesulfonamide (0.134 g, 41%) as an orange solid: LC/MS (Table 1, Method n) $R_t$=0.66 min; MS m/z 394 $(M+H)^+$.

Step H: N-((1S,3R,4S)-3-ethyl-4-(5-nitro-1-tosyl-1H-pyrrolo[2,3-b]pyridin-4-ylamino)cyclopentyl) cyclopropanesulfonamide

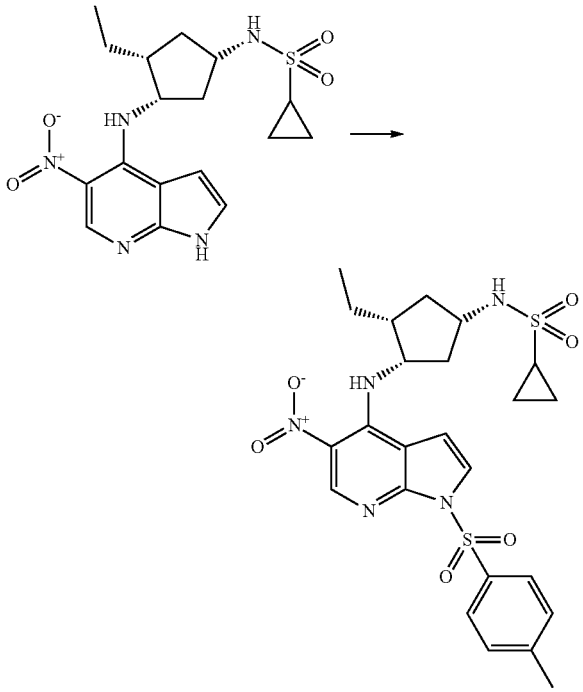

To a solution of N-((1S,3R,4S)-3-ethyl-4-(5-nitro-1H-pyrrolo[2,3-b]pyridin-4-ylamino)cyclopentyl)cyclopropanesulfonamide (0.123 g, 0.314 mmol) in DMF (3.0 mL) at about 0° C. was added NaH (60% in mineral oil, 0.015 g, 0.37 mmol). The reaction mixture was stirred for about 5 min. 4-Methylbenzene-1-sulfonyl chloride (0.060 g, 0.314 mmol) was added and the reaction mixture was stirred for about 30 min. Additional NaH (60% in mineral oil, 0.007 g, 0.18 mmol) was added and the reaction mixture was stirred for about 10 min. Additional NaH (60% in mineral oil, 0.005 g, 0.12 mmol) was added and the reaction mixture was stirred for about 15 min. Additional 4-methylbenzene-1-sulfonyl chloride (0.012 g, 0.063 mmol) was added and the reaction mixture was stirred for about 40 min. The reaction mixture was concd under reduced pressure. The residue was dissolved in EtOAc (25 mL) and washed with water (15 mL). The organic layer was separated, dried over anhydrous $MgSO_4$, filtered and concd under reduced pressure to give N-((1S,3R,4S)-3-ethyl-4-(5-nitro-1-tosyl-1H-pyrrolo[2,3-b]pyridin-4-ylamino)cyclopentyl)-cyclopropanesulfonamide (0.218 g) as a red-orange oil containing 40 mol % DMF and 1 equivalent EtOAc: LC/MS (Table 1, Method n) $R_t$=0.88 min; MS m/z 548 $(M+H)^+$.

Step I: N-((1S,3S,4R)-3-(5-amino-1-tosyl-1H-pyrrolo[2,3-b]pyridin-4-ylamino)-4-ethylcyclopentyl) cyclopropanesulfonamide

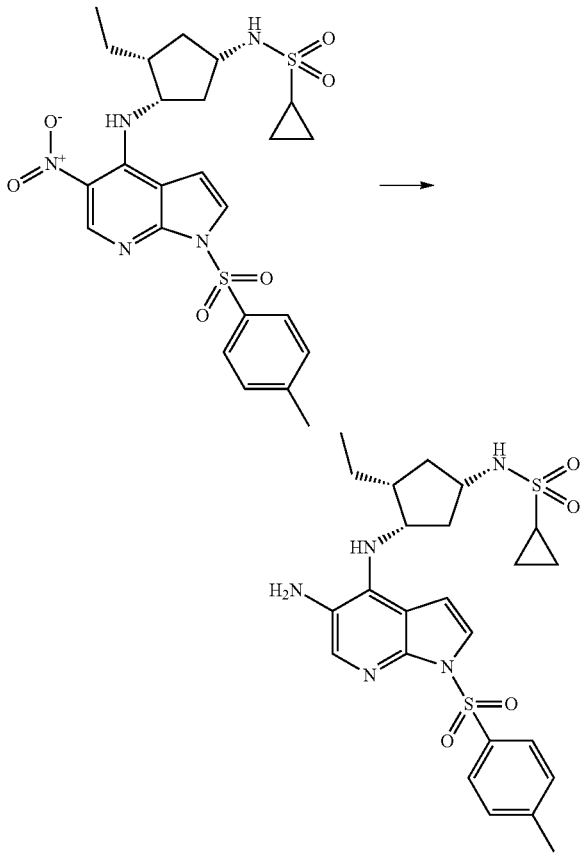

To a suspension of N-((1S,3R,4S)-3-ethyl-4-(5-nitro-1-tosyl-1H-pyrrolo[2,3-b]pyridin-4-ylamino)cyclopentyl)cyclopropanesulfonamide (0.172 g, 0.314 mmol) in EtOH (6 mL) was added tin (II) chloride dihydrate (0.142 g, 0.628 mmol). The reaction mixture was heated at about 75° C. for about 15 h. Tin (II) chloride dihydrate (0.128 g, 0.565 mmol) was added and the reaction mixture was heated at about 70° C. for about 40 min then heated at about 80° C. for about 3 h. The reaction was cooled to ambient temperature and the solvent was removed under reduced pressure. The reaction mixture was diluted with EtOAc (20 mL) and washed with 1N aqueous NaOH (10 mL), water (10 mL) and brine (10 mL). The organic layer was separated, dried over anhydrous $MgSO_4$, filtered and concd under reduced pressure. EtOH (10 mL) was added and the mixture was concd under reduced pressure to give N-((1S,3S,4R)-3-(5-amino-1-tosyl-1H-pyrrolo[2,3-b]pyridin-4-ylamino)-4-ethylcyclopentyl) cyclopropanesulfonamide (0.160 g, 98%) as a yellow oil: LC/MS (Table 1, Method n) $R_t$=0.75 min; MS m/z 518 $(M+H)^+$.

Step J: N-((1S,3R,4S)-3-ethyl-4-(6-tosylimidazo[4,5-d]pyrrolo[2,3-b]pyridin-1(6H)-yl)cyclopentyl) cyclopropanesulfonamide

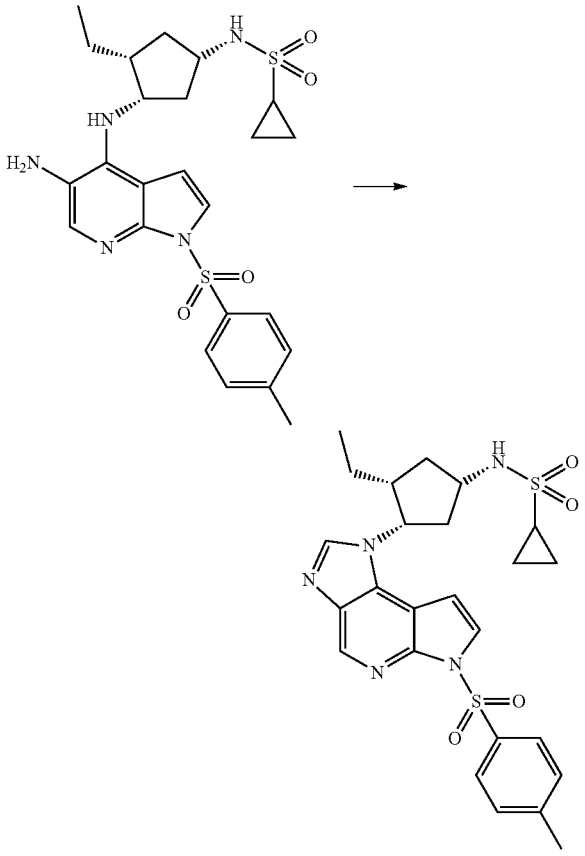

A mixture of N-((1S,3S,4R)-3-(5-amino-1-tosyl-1H-pyrrolo[2,3-b]pyridin-4-ylamino)-4-ethylcyclopentyl)cyclopropanesulfonamide (0.160 g, 0.309 mmol), trimethyl orthoformate (3.42 mL, 30.9 mmol) and toluene-4-sulfonic acid hydrate (0.006 g, 0.031 mmol) in MeOH (3.1 mL) was heated at about 65° C. for about 1 h then heated at about 60° C. for about 14 h. The reaction mixture was cooled to ambient temperature and concd under reduced pressure. The residue was dissolved in EtOAc (10 mL) and washed with saturated aqueous $NaHCO_3$ (5 mL), water (5 mL), and brine (5 mL). The organic layer was separated, dried over anhydrous $MgSO_4$, filtered and concd under reduced pressure to give N-((1S,3R,4S)-3-ethyl-4-(6-tosylimidazo[4,5-d]pyrrolo[2,3-b]pyridin-1(6H)-yl)cyclopentyl)cyclopropanesulfonamide as a yellow solid (0.130 g, 76%): LC/MS (Table 1, Method n) $R_t$=0.76 min; MS m/z 528 $(M+H)^+$.

Step K: N-((1S,3R,4S)-3-ethyl-4-(imidazo[4,5-d]pyrrolo[2,3-b]pyridin-1(6H)-yl)cyclopentyl)cyclopropanesulfonamide

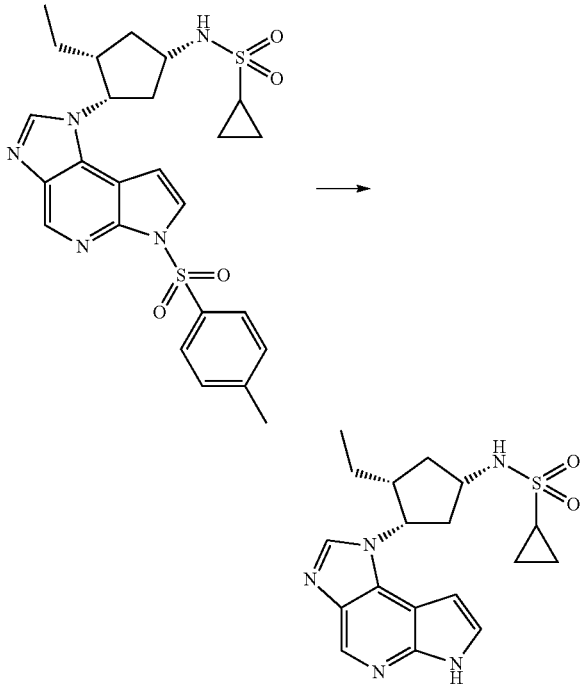

A mixture of N-((1S,3R,4S)-3-ethyl-4-(6-tosylimidazo[4,5-d]pyrrolo[2,3-b]pyridin-1(6H)-yl)cyclopentyl)cyclopropanesulfonamide (0.119 g, 0.214 mmol) and 1N aqueous NaOH (0.428 mL, 0.428 mmol) in 1,4-dioxane (2 mL) was heated at about 80° C. for about 40 min. Aqueous NaOH (1 N, 0.428 mL, 0.428 mmol) was added and the reaction mixture was heated at about 80° C. for about for 3.5 h. The reaction mixture was cooled to ambient temperature and concd under reduced pressure. The residue was dissolved in EtOAc (10 mL) and water (10 mL). The pH was adjusted to about 5 by the addition of 1 N aqueous HCl. The organic layer was separated, dried over anhydrous $MgSO_4$, filtered and concd under reduced pressure. The residue was triturated with $Et_2O$ (5 mL) and the solvent was removed by pippette. The residue was dried under reduced pressure to give a bright yellow solid that was purified by chiral chromatography [Table 2, Method 39, $R_t$=16.6 min, or =negative) to give N-((1S,3R,4S)-3-ethyl-4-(imidazo[4,5-d]pyrrolo[2,3-b]pyridin-1(6H)-yl)cyclopentyl)cyclopropanesulfonamide (0.036 g, 45%): LC/MS (Table 1, Method a) $R_t$=1.71 min; MS m/z 374 $(M+H)^+$.

Example #24

N-((1S,3S,4R)-3-(3H-imidazo[1,2-a]pyrrolo[2,3-e]pyrazin-8-yl)-4-methylcyclopentyl)cyclopropanesulfonamide

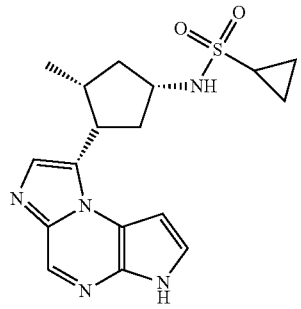

Step A: 5-bromo-3-((trimethylsilyl)ethynyl)pyrazin-2-amine

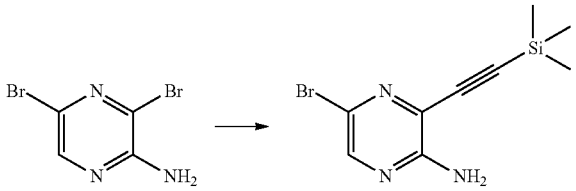

To a solution of 3,5-dibromopyrazin-2-amine (125 g, 494 mmol), TEA (207.0 mL, 1483 mmol), and copper (I) iodide (0.941 g, 4.94 mmol) in THF (1255 mL) was added $PdCl_2(PPh_3)_2$ (3.47 g, 4.94 mmol). The reaction mixture was cooled at about −5-0° C. and a solution of (trimethylsilyl) acetylene (65.0 mL, 470 mmol) in THF (157 mL) was added dropwise over about 15 min. The reaction mixture was stirred at about −5-0° C. for about 1.5 h and then allowed to warm to rt overnight. The reaction mixture was then filtered through a Celite® pad and washed with THF until no further product eluted. The filtrate was concd under reduced pressure to give a brown-orange solid. The solid was triturated and sonicated with warm petroleum ether (b.p. 30-60° C., 400 mL), cooled to rt, collected, washed with petroleum ether (b.p. 30-60° C.; 2×60 mL), and dried to give 5-bromo-3-((trimethylsilyl)ethynyl)pyrazin-2-amine (124 g, 93%, 93% purity) as a brown solid: LC/MS (Table 1, Method b) $R_t$=2.51 min; MS m/z: 270, 272 $(M+H)^+$.

Step B: 2-bromo-5-tosyl-5H-pyrrolo[2,3-b]pyrazine

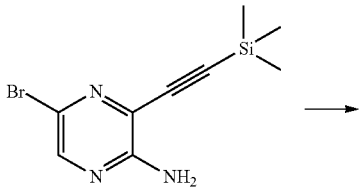

-continued

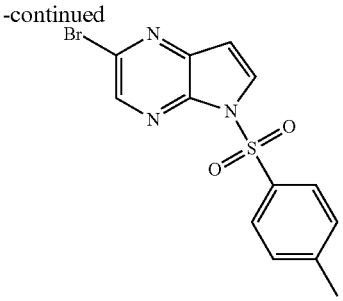

To a solution of 5-bromo-3-((trimethylsilyl)ethynyl) pyrazin-2-amine (3.00 g, 11.1 mmol) in DMF (60 mL) at about 0° C. was added NaH (60% dispersion in mineral oil, 0.577 g, 14.4 mmol) in three portions. After about 15 min, p-toluenesulfonyl chloride (2.75 g, 14.4 mmol) was added and the reaction was allowed to warm slowly to ambient temperature. After about 16 h, the reaction mixture was poured onto ice-cold water (120 mL) and the precipitate was collected by vacuum filtration. The crude solid was dissolved in DCM (15 mL) and purified by silica gel chromatography eluting with 100% DCM to give 2-bromo-5-tosyl-5H-pyrrolo[2,3-b]pyrazine (2.16 g, 52%): LC/MS (Table 1, Method c) $R_t$=1.58 min; MS m/z: 352, 354 $(M+H)^+$.

Step C: methyl 5-tosyl-5H-pyrrolo[2,3-b]pyrazine-2-carboxylate

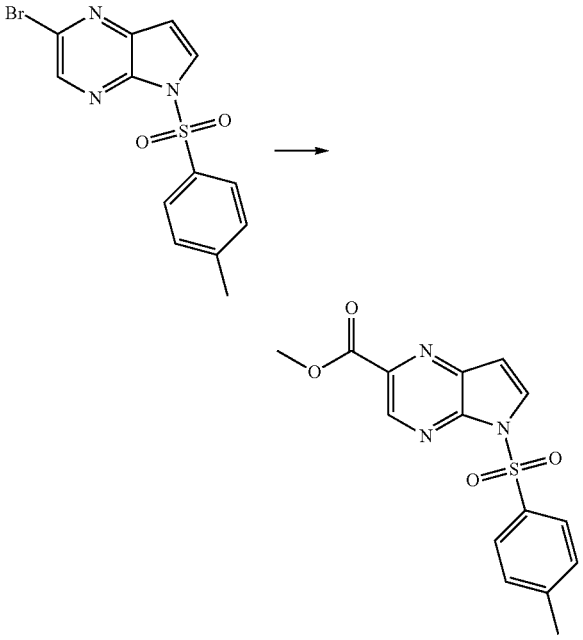

CO was bubbled into an orange solution of 2-bromo-5-tosyl-5H-pyrrolo[2,3-b]pyrazine (50.0 g, 142 mmol) in DMF (2.50 L) within a 5 L round bottom flask for about 2 min. Bis(triphenylphosphine)-palladium(II) dichloride (9.96 g, 14.2 mmol), TEA (59 mL, 423 mmol) and MeOH (173.0 mL, 4259 mmol) were added and the flask was fitted with a balloon of CO. The mixture was heated at about 95° C. under an atmosphere of CO (1 atmosphere). After stirring overnight, the reaction mixture was cooled to ambient temperature overnight and poured into ice water (3.2 L). The mixture was stirred for about 10 min and the precipitate was collected by filtration, while washing with water, and dried for 1 h. The crude material was dissolved in DCM, separated from residual water, dried over anhydrous $MgSO_4$, filtered, added silica gel, and concd under reduced pressure to prepare for chromatography. The crude material was purified by silica gel column chromatography eluting with 0-5% MeOH in DCM to yield methyl 5-tosyl-5H-pyrrolo[2,3-b]pyrazine-2-carboxylate with 5 mol % DCM as an excipient (40.7 g, 86%, 93% purity): LC/MS (Table 1, Method a) $R_t$=2.35 min; MS m/z 332 $(M+H)^+$.

Step D: 5-tosyl-5H-pyrrolo[2,3-b]pyrazine-2-carboxylic acid

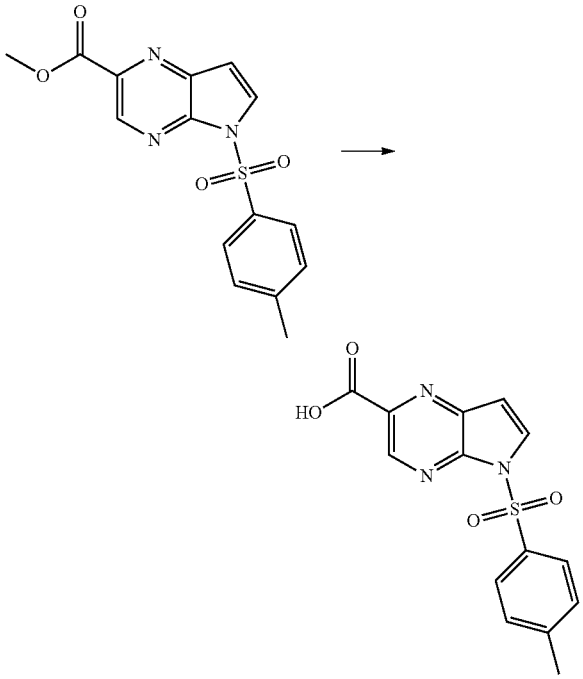

HCl (6 N aqueous, 714 mL) was added to a yellow solution of methyl 5-tosyl-5H-pyrrolo[2,3-b]pyrazine-2-carboxylate (17.8 g, 53.6 mmol) in 1,4-dioxane (715 mL) within a 2 L round bottom flask, and the mixture was heated at about 60° C. for about 16 h. The reaction mixture was cooled to ambient temperature. The organic solvent was removed under reduced pressure and the precipitate was collected, washed with water, and dried to yield 5-tosyl-5H-pyrrolo[2,3-b]pyrazine-2-carboxylic acid (14.4 g, 85%) as a yellow solid: LC/MS (Table 1, Method a) $R_t$=1.63 min; MS m/z 316 $(M-H)^-$.

Step E: tert-butyl 5-tosyl-5H-pyrrolo[2,3-b]pyrazin-2-ylcarbamate

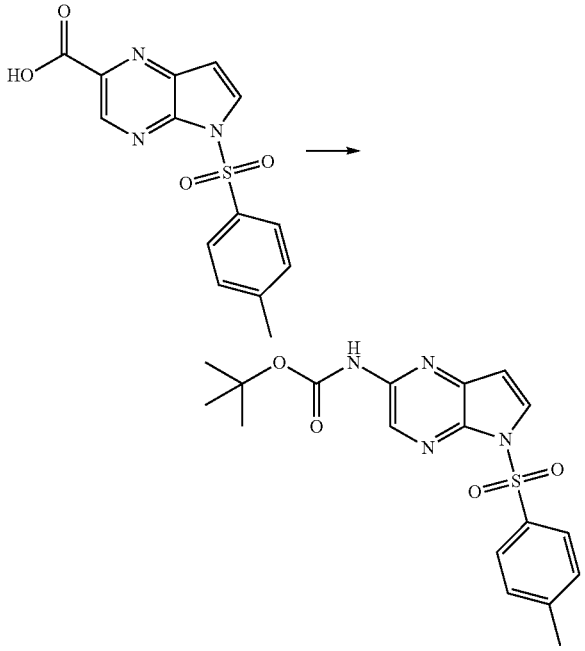

In a 500 mL round bottom flask, 5-tosyl-5H-pyrrolo[2,3-b]pyrazine-2-carboxylic acid (14.4 g, 45.3 mmol), DPPA (9.78 mL, 45.3 mmol) and TEA (13.9 mL, 100 mmol) in t-BuOH (200 mL) were added to give an orange suspension. The mixture was heated at about 70° C. for about 16 h, cooled to ambient temperature and the insoluble material was filtered. The solvent was removed under reduced pressure and the crude material was purified by silica gel column chromatography eluting with 25-60% EtOAc in heptane over 30 min to yield tert-butyl 5-tosyl-5H-pyrrolo[2,3-b]pyrazin-2-ylcarbamate (9.75 g, 54%) as an off-white solid: LC/MS (Table 1, Method a) $R_t$=2.79 min; MS m/z 389 $(M+H)^+$.

Step F: sodium 4-(ethoxycarbonyl)-2-(methoxycarbonyl)-3-methylcyclopenta-1,3-dienolate

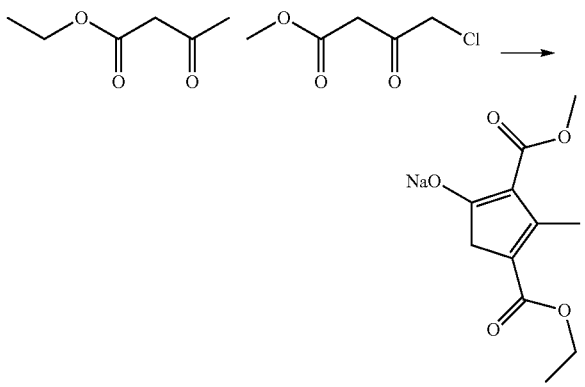

In a 12 L round bottom flask, NaH (60% dispersion in mineral oil, 159 g, 3985 mmol) was added in portions to stirred anhydrous THF (4004 mL) to give a gray suspension. The mixture was cooled to about 5° C. in an ice/salt bath before ethyl acetoacetate (506 mL, 3985 mmol, Alfa Aesar) in anhydrous THF (200 mL) was added dropwise via an addition funnel over about 1 h during which time the temperature gradually increased to about 18° C. After the addition was complete, the reaction was stirred at ambient temperature for about 1 h and then a solution of methyl 4-chloroacetoacetate (230 mL, 1993 mmol, Oakwood) in anhydrous THF (200 mL) was added dropwise via an addition funnel over about 1 h. The resulting mixture was stirred at ambient temperature for about 2 h and then heated at about 50° C. for about 16 h. The reaction mixture was concd in vacuo. The orange solid was cooled to about 5° C. and an ice/water mixture (2 L) was added. The suspension was mixed by rotating on the rotovap without vacuum for about 30 min. The solid was collected by filtration and washed with ice-cold water (750 mL). Once most of the solvent (about 90%) had been removed, the wet solid was triturated with MeCN (750 mL), stirred for about 30 min and then the solid was collected by filtration while washing with $Et_2O$ (2×500 mL). The solid was dried in air for about 16 h and then in vacuo at about 55° C. to give sodium 4-(ethoxycarbonyl)-2-(methoxycarbonyl)-3-methylcyclo-penta-1,3-dienolate (485 g, 98%): $^1$H NMR (DMSO-$d_6$) δ 3.95 (q, J=7.1 Hz, 2H), 3.48 (s, 3H), 2.69 (q, J=2.0 Hz, 2H), 2.47 (t, J=2.1 Hz, 3H), 1.15 (t, J=7.1 Hz, 3H).

Step G: ethyl
2-methyl-4-oxocyclopent-2-enecarboxylate

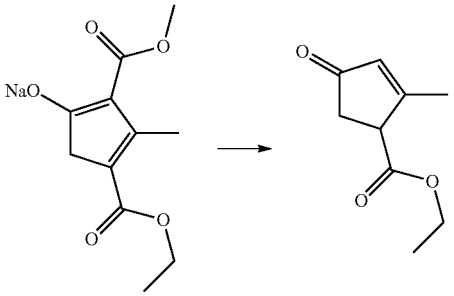

In a 5 L round bottom flask, sodium 4-(ethoxycarbonyl)-2-(methoxycarbonyl)-3-methylcyclo-penta-1,3-dienolate (485 g, 1954 mmol), KCl (204 g, 2736 mmol, JT Baker), and AcOH (392 mL, 6839 mmol, JT Baker) in toluene (1200 mL) and water (1200 mL) were heated at reflux for about 6 h. The reaction mixture was allowed to cool to ambient temperature for about 16 h. The reaction mixture was then poured into a 12 L flask and diluted with water (3 L). Solid $NaHCO_3$ (450 g, 5.3 mol) was added cautiously portionwise with stirring over about 1 h. After about an additional 30 min of stirring, the basic aqueous phase was separated and further extracted with $Et_2O$ (4×400 mL). The combined organic layers were washed with water (4×500 mL) and brine (500 mL), dried over anhydrous $MgSO_4$, filtered, and concd under reduced pressure to yield a yellow oil that was purified by vacuum distillation (92-94° C., 0.4 mmHg) to give ethyl 2-methyl-4-oxocyclopent-2-enecarboxylate (229 g, 69%) as a yellow oil: $^1$H NMR ($CDCl_3$) δ 6.04-6.01 (m, 1H), 4.26-4.17 (m, 2H), 3.67 (m, 1H), 2.72 (m, 1H), 2.62 (m, 1H), 2.16 (s, 3H), 1.32-1.27 (t, J=7.1 Hz, 3H).

Step H: ethyl
2-methyl-4-oxocyclopentanecarboxylate

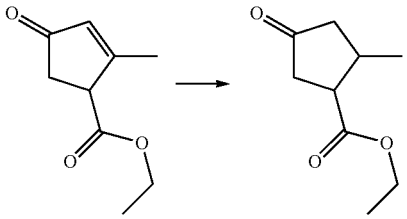

In a 1 L round bottom flask jacketed flask, copper(I) chloride (0.736 g, 7.43 mmol), (S)-(−)-2,2'-bis(diphenylphosphino)-1,1'-binaphthyl (4.63 g, 7.43 mmol), and sodium tert-butoxide (0.714 g, 7.43 mmol) in toluene (250 mL) were added to give a yellow solution. The mixture was stirred at ambient temperature for about 15 min. after which the solution became brown. The solution was cooled to about 5° C. and polymethylhydrosiloxane (14.86 mL, 223 mmol) was added and the solution was stirred at about 5° C. for about 40 min. The solution was cooled to about −15° C. and a solution of ethyl 2-methyl-4-oxocyclopent-2-enecarboxylate (25.00 g, 149 mmol) and tert-butyl alcohol (61.7 mL, 654 mmol) in toluene (250 mL) was added in one portion. The reaction was stirred at −15° C. for 144 h. The reaction mixture was quenched by the addition of 1:1 ethanol/toluene (350 mL) and Celite® 545 (25 g). The mixture was stirred and allowed to warm to ambient temperature. The reaction mixture was concd in vacuo, chasing with heptane. Heptane (350 mL) was added to the residue and solids were removed by filtration. The filtrate was concd in vacuo and the crude product was purified by silica gel chromatography using a gradient of 10 to 50% EtOAc in heptane over 7 column volumes to give ethyl 2-methyl-4-oxocyclopentanecarboxylate (scalemic mixture of diastereomers), predominantly (1S,2R)-ethyl 2-methyl-4-oxocyclopentanecarboxylate (11.2 g, 42% yield) as a color-less oil. $^1$H NMR (400 MHz, $CDCl_3$) δ 4.19 (qd, J=7.1, 0.6, 2H), 3.17 (ddd, J=8.1, 6.8, 5.6, 1H), 2.76-2.56 (m, 2H), 2.67-2.46 (m, 2H), 2.43-2.29 (m, 2H), 2.16 (ddd, J=18.3, 7.8, 1.7, 1H), 1.29 (t, J=7.2, 3H), 1.06 (d, J=7.0, 3H).

Step I: ethyl
4-(dibenzylamino)-2-methylcyclopentanecarboxylate

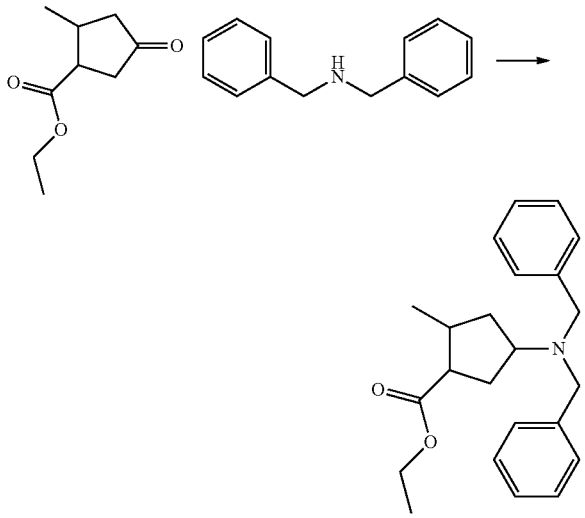

A round bottom flask was charged with ethyl 2-methyl-4-oxocyclopentanecarboxylate (10.0 g, 58.8 mmol) and DCE (180 mL). The solution was cooled to about 0° C. and AcOH (5.7 mL, 100 mmol) and dibenzylamine (11.3 mL, 58.8 mmol) were added dropwise, resulting in formation of a thick suspension. The reaction mixture was warmed to about 10° C. and sodium triacetoxyborohydride (21.2 g, 100 mmol) was added portionwise. The reaction mixture was stirred at ambient temperature for about 20 h then slowly poured into stirred saturated aqueous $NaHCO_3$ (300 mL) and stirred for about 20 min. The layers were separated and the aqueous phase was extracted with DCM (3×100 mL). The combined organic extracts were washed with brine (2×100 mL), dried over anhydrous $Na_2SO_4$, and concd under reduced pressure. The crude yellow oil was purified via silica gel chromatography eluting with a gradient of 0-30% EtOAc in heptane to give ethyl 4-(dibenzylamino)-2-methylcyclopentanecarboxylate (scalemic mixture of diastereomer), predominantly (1S,2R,4S)-ethyl 4-(dibenzylamino)-2-methylcyclopentanecarboxylate) (15.5 g, 75%) as a colorless oil: $^1$H NMR (pyridine-$d_5$) δ 7.53 (dd, J=0.9, 7.9 Hz, 4H), 7.43-7.35 (m, 4H), 7.33-7.25 (m, 2H), 4.22-4.06 (m, 2H), 3.79 (d, J=14.2 Hz, 2H), 3.70 (d, J=14.2 Hz, 2H), 3.34-3.22 (m, 1H), 2.76 (dd, J=7.9, 16.6 Hz, 1H), 2.25-2.13 (m, 1H), 2.09-1.94 (m, 2H), 1.88-1.79 (m, 1H), 1.52 (dd, J=10.5, 22.5 Hz, 1H), 1.16 (t, J=7.1 Hz, 3H), 0.98 (d, J=7.0 Hz, 3H).

Step J:
4-(dibenzylamino)-2-methylcyclopentanecarboxylic acid

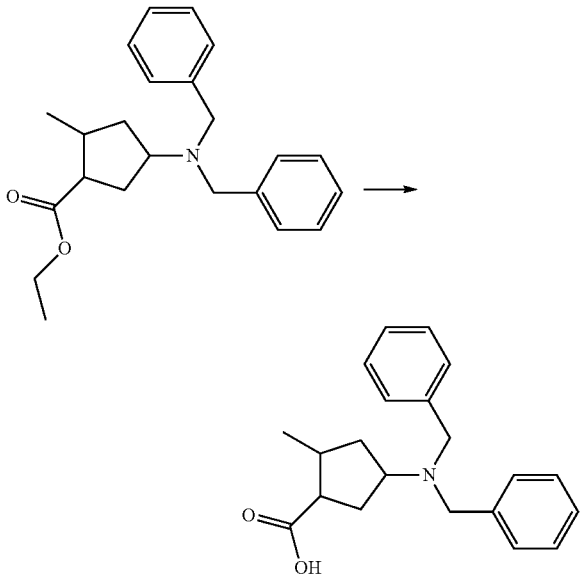

Ethyl 4-(dibenzylamino)-2-methylcyclopentanecarboxylate (3.65 g, 10.38 mmol) was dissolved in a mixture of HCl (6 N aqueous, 20 mL) and 1,4-dioxane (50 mL) and the resulting mixture was heated at about 60° C. for about 72 h. The organic solvent was removed under reduced pressure. The aqueous phase was neutralized by the addition of saturated aqueous $NaHCO_3$ (40 mL) and extracted with EtOAc (50 mL). The organic layer was washed with brine (40 mL), dried over anhydrous $MgSO_4$ and concd under reduced pressure to yield 4-(dibenzylamino)-2-methylcyclopentanecarboxylic acid (3.3 g, 98%) as a white amorphous solid: LC/MS (Table 1, Method a) $R_t$=1.66 min; MS m/z 324 $(M+H)^+$.

Step K: 2-bromo-1-(4-(dibenzylamino)-2-methylcyclopentyl)ethanone

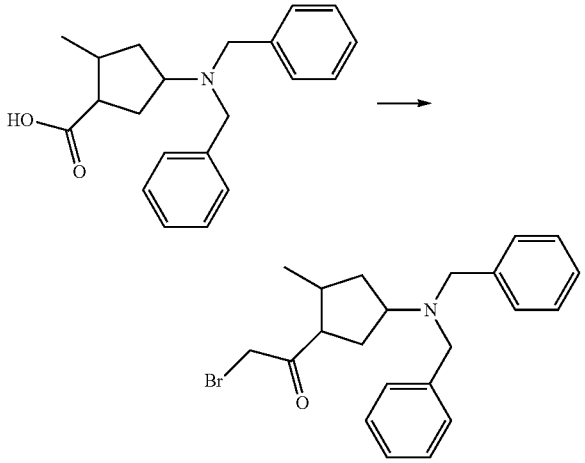

Oxalyl chloride (4.37 mL, 49.9 mmol) was slowly added to a solution of 4-(dibenzylamino)-2-methylcyclopentanecarboxylic acid (7.34 g, 22.7 mmol) in DCM (100 mL), (note: mild gas evolution) followed by a dropwise addition of DMF (0.26 mL, 3.41 mmol). The mixture was stirred at ambient temperature for about 14 h. The solvent was removed under reduced pressure to yield a beige amorphous solid, which was dissolved in THF and MeCN (1:1, 100 mL). The resulting solution was added to a solution of trimethylsilyldiazomethane (2 M in $Et_2O$, 39.7 mL, 79 mmol) in THF and MeCN (1:1, 100 mL) at about 0° C. The resulting mixture was stirred at about 0° C. for about 3 h and then was quenched by a dropwise addition of HBr (48% aqueous, 25 mL, 221 mmol). The resulting mixture was neutralized by a dropwise addition of saturated aqueous $NaHCO_3$ (300 mL) and the layers were separated. The organic layer was dried over anhydrous $MgSO_4$ and concd under reduced pressure. The residue was purified by silica gel chromatography eluting with 5% to 45% of EtOAc in heptane to yield 2-bromo-1-(4-(dibenzylamino)-2-methylcyclopentyl)ethanone (6.3 g, 69%) as a yellow oil: LC/MS (Table 1, Method a) $R_t$=2.90 min; MS m/z 400, 402 $(M+H)^+$.

Step L: tert-butyl 2-(4-(dibenzylamino)-2-methylcyclopentyl)-2-oxoethyl(5-tosyl-5H-pyrrolo[2,3-b]pyrazin-2-yl)carbamate

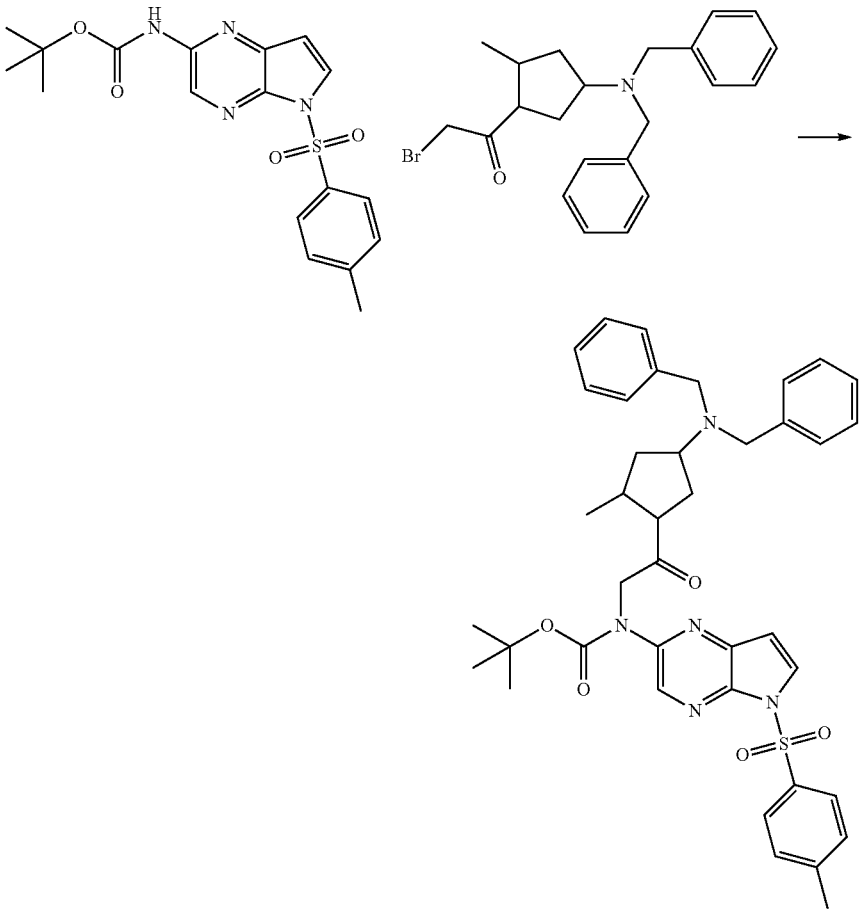

A solution of tert-butyl 5-tosyl-5H-pyrrolo[2,3-b]pyrazin-2-ylcarbamate (0.59 g, 1.519 mmol, Example #3 Step E) in DMF (5 mL) was added dropwise to a suspension of NaH (60% dispersion in mineral oil, 0.058 g, 1.45 mmol) in DMF (5 mL), at about 0° C. The resulting mixture was stirred at about 0° C. for about 30 min and then added dropwise to a solution of 2-bromo-1-(4-(dibenzylamino)-2-methylcyclopentyl)ethanone (0.73 g, 1.8 mmol) in DMF (10 mL) at about 0° C. The resulting mixture was stirred at about 0° C. for about 1 h and the solvent was removed under reduced pressure. The residue was partitioned between saturated aqueous $NaHCO_3$ and EtOAc (100 mL each). The organic phase was separated, dried over anhydrous $MgSO_4$ and concd under reduced pressure to yield tert-butyl 2-(4-(dibenzylamino)-2-methylcyclopentyl)-2-oxoethyl(5-tosyl-5H-pyrrolo[2,3-b]pyrazin-2-yl)carbamate (1.04 g, 97%) as a yellow amorphous solid: LC/MS (Table 1, Method a) $R_t$=3.30 min; MS m/z 708 $(M+H)^+$.

Step M: 1-(4-(dibenzylamino)-2-methylcyclopentyl)-2-(5-tosyl-5H-pyrrolo[2,3-b]pyrazin-2-ylamino)ethanone

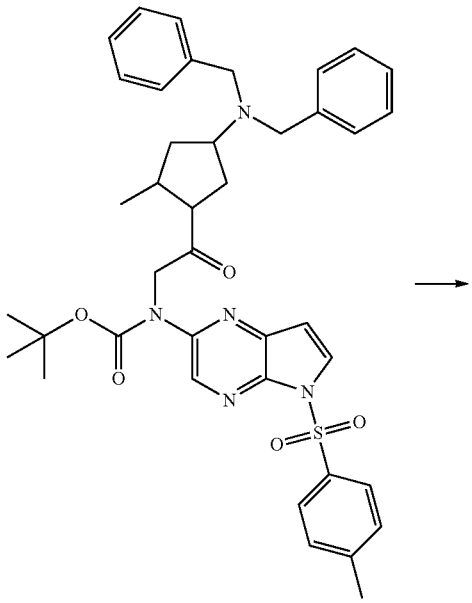

-continued

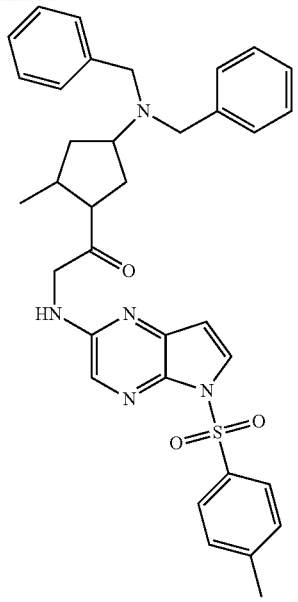

tert-Butyl 2-(4-(dibenzylamino)-2-methylcyclopentyl)-2-oxoethyl(5-tosyl-5H-pyrrolo[2,3-b]pyrazin-2-yl)carbamate (6.19 g, 8.75 mmol) was dissolved in HCl (4 N in 1,4-dioxane, 25 mL). The reaction mixture was stirred at ambient temperature for about 2 h. The solvent was removed under reduced pressure and the residue was partitioned between saturated aqueous $NaHCO_3$ and EtOAc (100 mL each). The organic phase was washed with brine (80 mL), dried over anhydrous $MgSO_4$ and concd under reduced pressure to yield 1-(4-(dibenzylamino)-2-methylcyclopentyl)-2-(5-tosyl-5H-pyrrolo[2,3-b]pyrazin-2-ylamino)ethanone (5.2 g, 98%) as a brown amorphous solid: LC/MS (Table 1, Method a) $R_t$=3.00 min; MS m/z 608 $(M+H)^+$.

Step N: N,N-dibenzyl-3-methyl-4-(3-tosyl-3H-imidazo[1,2-a]pyrrolo[2,3-e]pyrazin-8-yl)cyclopentanamine

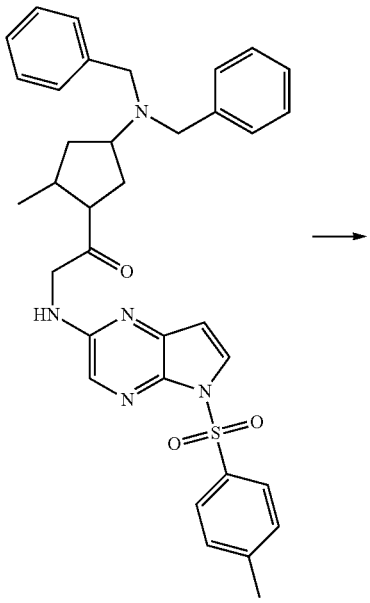

-continued

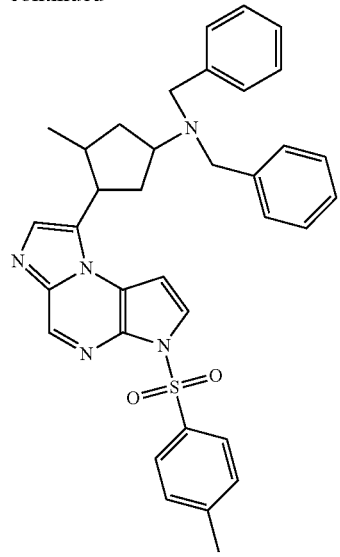

A mixture of 1-(4-(dibenzylamino)-2-methylcyclopentyl)-2-(5-tosyl-5H-pyrrolo[2,3-b]pyrazin-2-ylamino)ethanone (5.32 g, 8.75 mmol) and Lawesson's reagent (1.88 g, 4.64 mmol) was heated at about 60° C. for about 2 h. Lawesson's reagent (1.88 g, 4.64 mmol) was added. The reaction mixture was stirred at about 60° C. for about 1 h. The solvent was removed under reduced pressure and the residue was purified by silica gel chromatography eluting with a gradient of 0-8% MeOH in DCM to yield N,N-dibenzyl-3-methyl-4-(3-tosyl-3H-imidazo[1,2-a]pyrrolo[2,3-e]pyrazin-8-yl)cyclopentanamine (4.47 g, 87%) as a brown amorphous solid: LC/MS (Table 1, Method a) $R_t$=2.99 min; MS m/z 590 $(M+H)^+$.

Step O: N,N-dibenzyl-3-(3H-imidazo[1,2-a]pyrrolo[2,3-e]pyrazin-8-yl)-4-methylcyclopentanamine

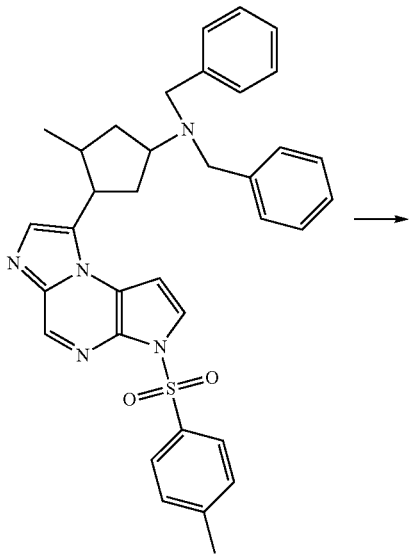

-continued

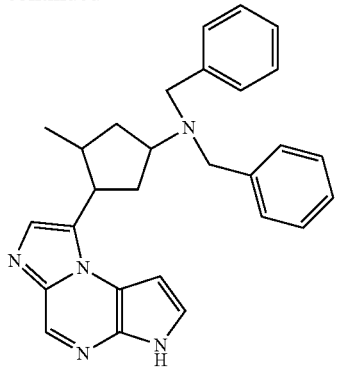

N,N-Dibenzyl-3-methyl-4-(3-tosyl-3H-imidazo[1,2-a]pyrrolo[2,3-e]pyrazin-8-yl)cyclopentan-amine (4.47 g, 7.58 mmol) was dissolved in 1,4-dioxane (40 mL). NaOH (2 N aqueous, 4 mL) was added and the reaction mixture was heated at about 90° C. for about 80 min. The organic solvent was removed under reduced pressure and the residue was treated with saturated aqueous $NH_4Cl$ (70 mL) and extracted with DCM (2×60 mL). The combined organic extracts were washed with brine (70 mL), dried over anhydrous $MgSO_4$ and concd under reduced pressure. The residue was purified by silica gel chromatography eluting with a gradient of 0-8% MeOH in DCM to yield N,N-dibenzyl-3-(3H-imidazo[1,2-a]pyrrolo[2,3-e]pyrazin-8-yl)-4-methylcyclopentan-amine (1.84 g, 56%) as a yellow oil: LC/MS (Table 1, Method a) $R_t$=2.31 min; MS m/z 436 $(M+H)^+$.

Step P: N,N-dibenzyl-3-methyl-4-(3-((2-(trimethylsilyl)ethoxy)methyl)-3H-imidazo[1,2-a]pyrrolo[2,3-e]pyrazin-8-yl)cyclopentanamine

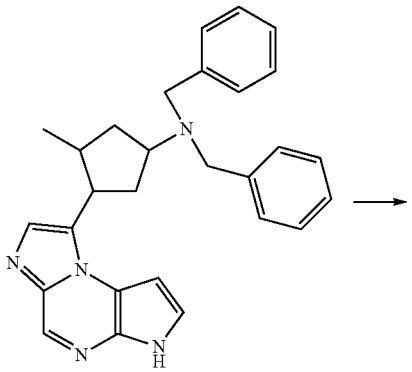

-continued

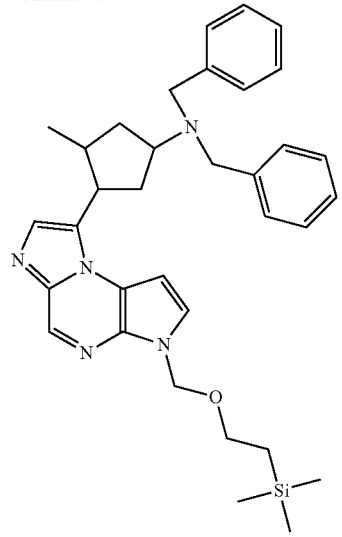

To the suspension of sodium hydride (60% dispersion in mineral oil, 0.382 g, 9.55 mmol) in DMF (50 mL) was added drop-wise a solution of N,N-dibenzyl-3-(3H-imidazo[1,2-a]pyrrolo[2,3-e]pyrazin-8-yl)-4-methylcyclopentanamine (3.96 g, 9.09 mmol) in DMF (50 mL) at 0° C. The resulting solution was stirred at ambient temperature for about 10 min. SEM chloride (1.774 mL, 10.0 mmol) was added drop-wise and the solution was stirred for about 1 h. The solvent was removed under reduced pressure and the residue was partitioned between water and EtOAc (200 mL each). The organic layer was washed with brine (100 mL), dried over anhydrous $MgSO_4$, filtered and concd. The residue was purified by silica gel chromatography eluting with 10-80% EtOAc in DCM to yield N,N-dibenzyl-3-methyl-4-(3-((2-(trimethylsilyl)ethoxy)methyl)-3H-imidazo[1,2-a]pyrrolo[2,3-e]pyrazin-8-yl)cyclopentanamine (3.1 g, 60% yield) as an off-white amorphous solid. LC/MS (Table 1, Method a) $R_t$=3.32 min; MS m/z 566 $(M+H)^+$.

Step Q: 3-Methyl-4-(3-((2-(trimethylsilyl)ethoxy)methyl)-3H-imidazo[1,2-a]pyrrolo[2,3-e]pyrazin-8-yl)cyclopentanamine

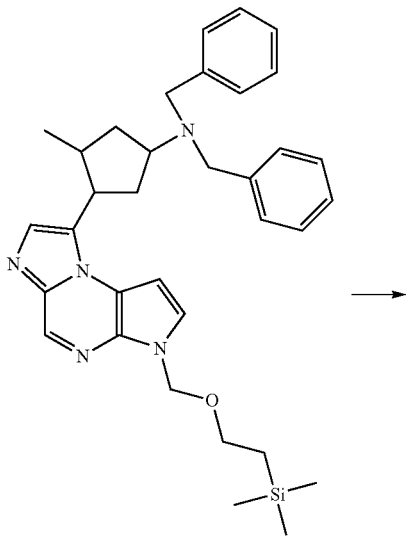

-continued

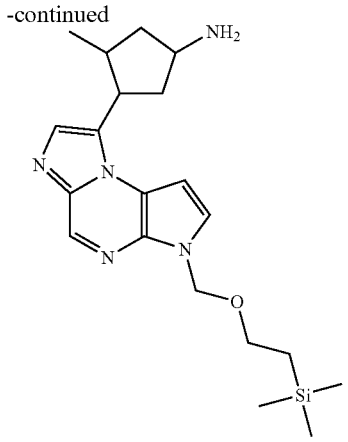

To a solution of N,N-dibenzyl-3-methyl-4-(3-((2-(trimethylsilyl)ethoxy)methyl)-3H-imidazo[1,2-a]pyrrolo[2,3-e]pyrazin-8-yl)cyclopentanamine (3.0 g, 5.30 mmol) in trifluoroethanol (200 mL) was added 20% wet palladium hydroxide on carbon (0.6 g, 4.27 mmol). The mixture was stirred under 40 psi of hydrogen at about 50° C. for about 90 min. The catalyst was removed by filtration through a pad of Celite® and the filtrate was concd under reduced pressure to yield 3-methyl-4-(3-((2-(trimethylsilyl)ethoxy)methyl)-3H-imidazo[1,2-a]pyrrolo[2,3-e]pyrazin-8-yl)cyclopentanamine (2.0 g, 98% yield) as a brown amorphous solid. LC/MS (Table 1, Method a) $R_t$=1.86 min; MS m/z 386 $(M+H)^+$.

Step R: N-(3-methyl-4-(3-((2-(trimethylsilyl)ethoxy)methyl)-3H-imidazo[1,2-a]pyrrolo[2,3-e]pyrazin-8-yl)cyclopentyl)cyclopropanesulfonamide

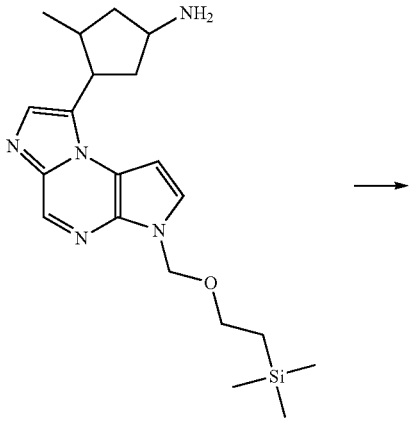

-continued

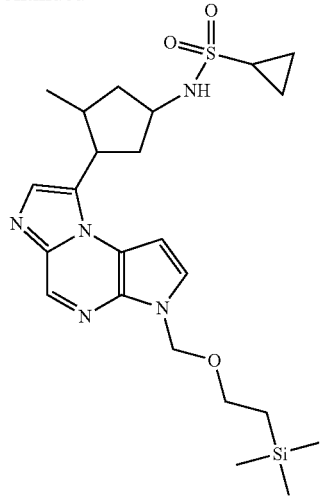

To a solution of 3-methyl-4-(3-((2-(trimethylsilyl)ethoxy)methyl)-3H-imidazo[1,2-a]pyrrolo[2,3-e]pyrazin-8-yl)cyclopentanamine (0.27 g, 0.7 mmol) and DIEA (0.18 mL, 1.05 mmol) in DCM (5 mL) was added cyclopropanesulfonyl chloride (0.098 g, 0.7 mmol) drop-wise. The resulting mixture was stirred at ambient temperature for about 1 h. Another 0.18 mL of DIEA and 0.098 g of cyclopropanesulfonyl chloride were added and the reaction was continued for about 3 h. The solvent was removed and the residue was partitioned between saturated aqueous ammonium chloride and EtOAc (20 mL each). The organic layer was washed with brine (10 mL), dried over anhydrous $MgSO_4$, filtered and concd. The residue was purified by silica gel chromatography (100% DCM for 5 min, then to 6% MeOH in DCM over next 30 min) to yield N-(3-methyl-4-(3-((2-(trimethylsilyl)ethoxy)methyl)-3H-imidazo[1,2-a]pyrrolo[2,3-e]pyrazin-8-yl)cyclopentyl)cyclopropanesulfonamide (0.18 g, 52% yield) as an off-white solid. LC/MS (Table 1, Method a) $R_t$=2.45 min; MS m/z 490 $(M+H)^+$.

Step S: N-((1S,3S,4R)-3-(3H-imidazo[1,2-a]pyrrolo[2,3-e]pyrazin-8-yl)-4-methylcyclopentyl)cyclopropanesulfonamide

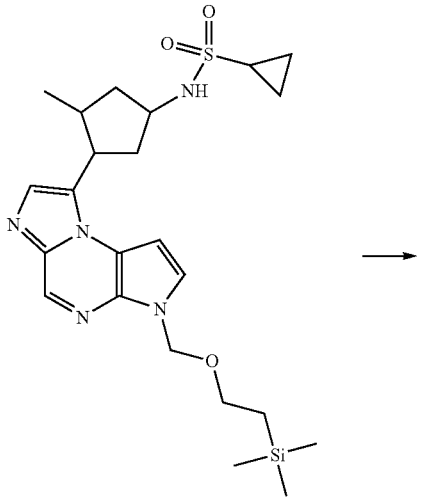

-continued

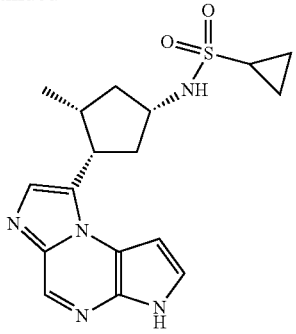

To the solution of 3-methyl-4-(3-((2-(trimethylsilyl) ethoxy)methyl)-3H-imidazo[1,2-a]pyrrolo[2,3-e]pyrazin-8-yl)cyclopentyl)cyclopropanesulfonamide (0.18 g, 0.368 mmol) in DCM (2.5 mL) was added TFA (0.9 mL). The resulting mixture was stirred at ambient temperature for about 2 h. The solvents were removed under reduced pressure and the residue dried under high vacuum. The residue was dissolved in 1,4-dioxane (3 mL) and 28% ammonium hydroxide solution in water (2.5 mL). The mixture was heated at about 60° C. for about 2 h. The solvents were removed under reduced pressure and the residue was purified by using general procedure AA (Table 2, Method 32, $R_t$=20.9 min, or =negative) to yield N-((1S,3S,4R)-3-(3H-imidazo[1,2-a]pyrrolo[2,3-e]pyrazin-8-yl)-4-methylcyclopentyl)cyclopropanesulfonamide (0.088 g, 66% yield) as a white solid. LC/MS (Table 1, Method a) $R_t$=1.52 min; MS m/z 360 $(M+H)^+$.

Example #25

N-((1S,3S,4R)-3-(3H-imidazo[1,2-a]pyrrolo[2,3-e] pyrazin-8-yl)-4-methylcyclopentyl)-3,3-difluoroazetidine-1-sulfonamide

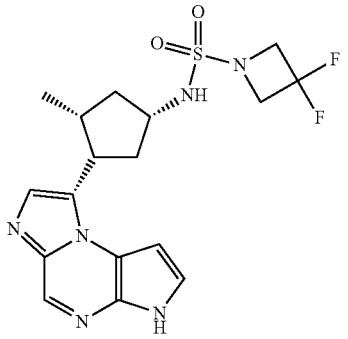

Step A: 5-bromo-3-((trimethylsilyl)ethynyl)pyrazin-2-amine

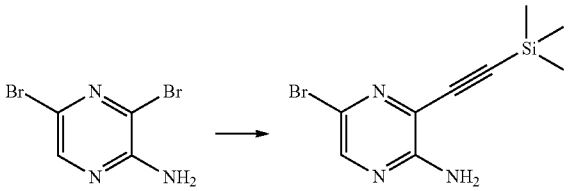

To a solution of 3,5-dibromopyrazin-2-amine (125 g, 494 mmol), TEA (207.0 mL, 1483 mmol), and copper (I) iodide (0.941 g, 4.94 mmol) in THF (1255 mL) was added $PdCl_2(PPh_3)_2$ (3.47 g, 4.94 mmol). The reaction mixture was cooled at about −5-0° C. and a solution of (trimethylsilyl) acetylene (65.0 mL, 470 mmol) in THF (157 mL) was added dropwise over about 15 min. The reaction mixture was stirred at about −5-0° C. for about 1.5 h and then allowed to warm to rt overnight. The reaction mixture was then filtered through a Celite® pad and washed with THF until no further product eluted. The filtrate was concd under reduced pressure to give a brown-orange solid. The solid was triturated and sonicated with warm petroleum ether (b.p. 30-60° C., 400 mL), cooled to rt, collected, washed with petroleum ether (b.p. 30-60° C.; 2×60 mL), and dried to give 5-bromo-3-((trimethylsilyl)ethynyl)pyrazin-2-amine (124 g, 93%, 93% purity) as a brown solid: LC/MS (Table 1, Method b) $R_t$=2.51 min; MS m/z: 270, 272 $(M+H)^+$.

Step B: 2-bromo-5-tosyl-5H-pyrrolo[2,3-b]pyrazine

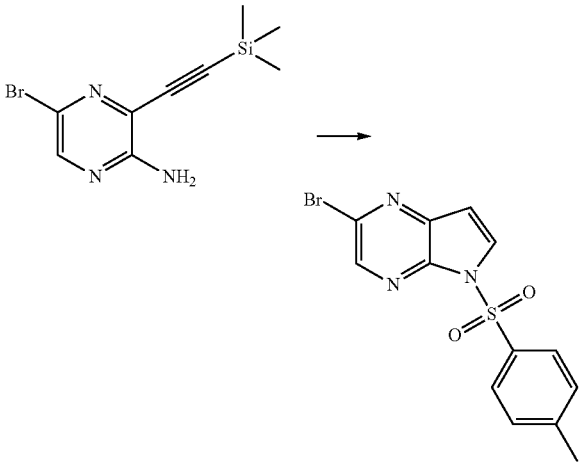

To a solution of 5-bromo-3-((trimethylsilyl)ethynyl) pyrazin-2-amine (3.00 g, 11.1 mmol) in DMF (60 mL) at about 0° C. was added NaH (60% dispersion in mineral oil, 0.577 g, 14.4 mmol) in three portions. After about 15 min, p-toluenesulfonyl chloride (2.75 g, 14.4 mmol) was added and the reaction was allowed to warm slowly to ambient temperature. After about 16 h, the reaction mixture was poured onto ice-cold water (120 mL) and the precipitate was collected by vacuum filtration. The crude solid was dissolved in DCM (15 mL) and purified by silica gel chromatography eluting with DCM to give 2-bromo-5-tosyl-5H-pyrrolo[2,3-b]pyrazine (2.16 g, 52%): LC/MS (Table 1, Method c) $R_t$=1.58 min; MS m/z: 352, 354 $(M+H)^+$.

Step C: methyl 5-tosyl-5H-pyrrolo[2,3-b]pyrazine-2-carboxylate

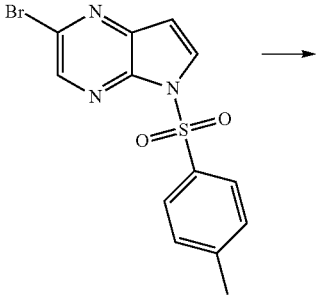

-continued

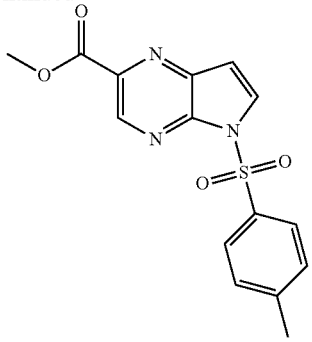

CO was bubbled into an orange solution of 2-bromo-5-tosyl-5H-pyrrolo[2,3-b]pyrazine (50.0 g, 142 mmol) in DMF (2.50 L) within a 5 L round bottom flask for about 2 min. Bis(triphenylphosphine)-palladium(II) dichloride (9.96 g, 14.2 mmol), TEA (59 mL, 423 mmol) and MeOH (173.0 mL, 4259 mmol) were added and the flask was fitted with a balloon of CO. The mixture was heated at about 95° C. under an atmosphere of CO (1 atmosphere). After stirring overnight, the reaction mixture was cooled to ambient temperature overnight and poured into ice water (3.2 L). The mixture was stirred for about 10 min and the precipitate was collected by filtration, while washing with water, and dried for 1 h. The crude material was dissolved in DCM, separated from residual water, dried over anhydrous $MgSO_4$, filtered, added silica gel, and concd under reduced pressure to prepare for chromatography. The crude material was purified by silica gel column chromatography eluting with 0-5% MeOH in DCM to yield methyl 5-tosyl-5H-pyrrolo[2,3-b]pyrazine-2-carboxylate with 5 mol % DCM as an excipient (40.7 g, 86%, 93% purity): LC/MS (Table 1, Method a) $R_t$=2.35 min; MS m/z 332 $(M+H)^+$.

Step D: 5-tosyl-5H-pyrrolo[2,3-b]pyrazine-2-carboxylic acid

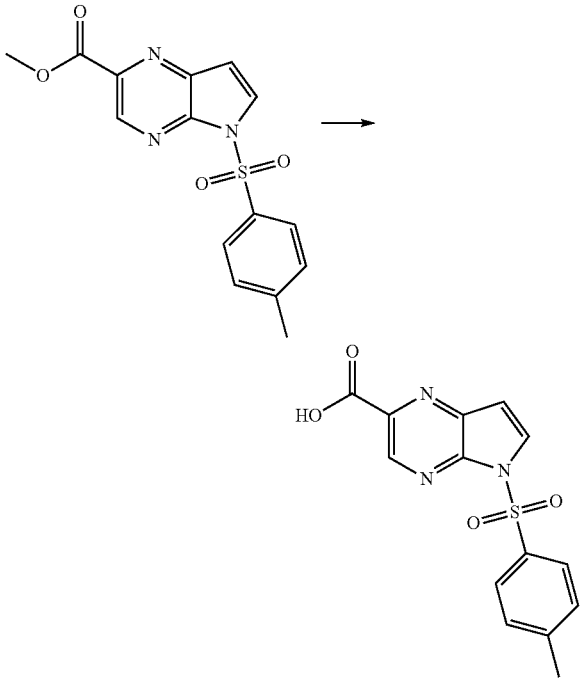

HCl (6 N aqueous, 714 mL) was added to a yellow solution of methyl 5-tosyl-5H-pyrrolo[2,3-b]pyrazine-2-carboxylate (17.8 g, 53.6 mmol) in 1,4-dioxane (715 mL) within a 2 L round bottom flask, and the mixture was heated at about 60° C. for about 16 h. The reaction mixture was cooled to ambient temperature. The organic solvent was removed under reduced pressure and the precipitate was collected, washed with water, and dried to yield 5-tosyl-5H-pyrrolo[2,3-b]pyrazine-2-carboxylic acid (14.4 g, 85%) as a yellow solid: LC/MS (Table 1, Method a) $R_t$=1.63 min; MS m/z 316 $(M-H)^-$.

Step E: tert-butyl 5-tosyl-5H-pyrrolo[2,3-b]pyrazin-2-ylcarbamate

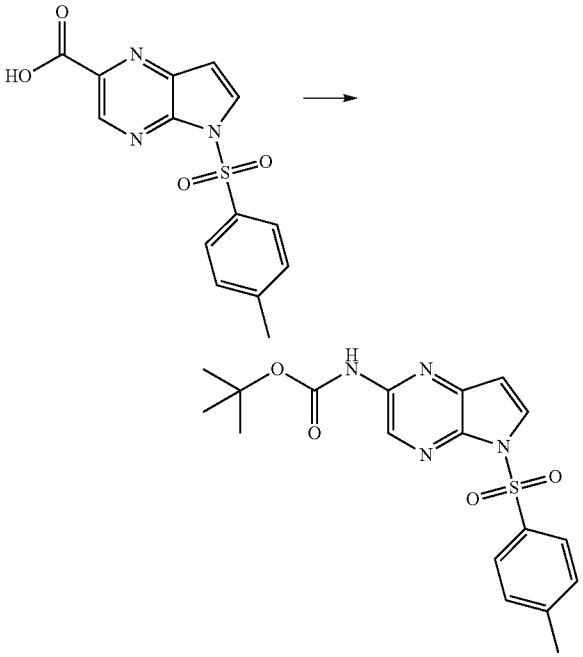

In a 500 mL round bottom flask, 5-tosyl-5H-pyrrolo[2,3-b]pyrazine-2-carboxylic acid (14.4 g, 45.3 mmol), DPPA (9.78 mL, 45.3 mmol) and TEA (13.9 mL, 100 mmol) in t-BuOH (200 mL) were added to give an orange suspension. The mixture was heated at about 70° C. for about 16 h, cooled to ambient temperature and the insoluble material was filtered. The solvent was removed under reduced pressure and the crude material was purified by silica gel column chromatography eluting with 25-60% EtOAc in heptane over 30 min to yield tert-butyl 5-tosyl-5H-pyrrolo[2,3-b]pyrazin-2-ylcarbamate (9.75 g, 54%) as an off-white solid: LC/MS (Table 1, Method a) $R_t$=2.79 min; MS m/z 389 $(M+H)^+$.

Step F: sodium 4-(ethoxycarbonyl)-2-(methoxycarbonyl)-3-methylcyclopenta-1,3-dienolate

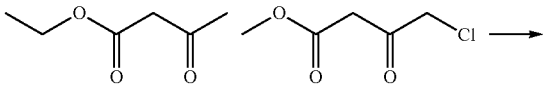

-continued

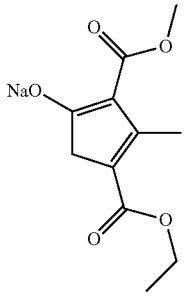

In a 12 L round bottom flask, NaH (60% dispersion in mineral oil, 159 g, 3985 mmol) was added in portions to stirred anhydrous THF (4004 mL) to give a gray suspension. The mixture was cooled to about 5° C. in an ice/salt bath before ethyl acetoacetate (506 mL, 3985 mmol, Alfa Aesar) in anhydrous THF (200 mL) was added dropwise via an addition funnel over about 1 h during which time the temperature gradually increased to about 18° C. After the addition was complete, the reaction was stirred at ambient temperature for about 1 h and then a solution of methyl 4-chloroacetoacetate (230 mL, 1993 mmol, Oakwood) in anhydrous THF (200 mL) was added dropwise via an addition funnel over about 1 h. The resulting mixture was stirred at ambient temperature for about 2 h and then heated at about 50° C. for about 16 h. The reaction mixture was concd in vacuo. The orange solid was cooled to about 5° C. and an ice/water mixture (2 L) was added. The suspension was mixed by rotating on the rotovap without vacuum for about 30 min. The solid was collected by filtration and washed with ice-cold water (750 mL). Once most of the solvent (about 90%) had been removed, the wet solid was triturated with MeCN (750 mL), stirred for about 30 min and then the solid was collected by filtration while washing with $Et_2O$ (2×500 mL). The solid was dried in air for about 16 h and then in vacuo at about 55° C. to give sodium 4-(ethoxycarbonyl)-2-(methoxycarbonyl)-3-methylcyclopenta-1,3-dienolate (485 g, 98%): $^1$H NMR (DMSO-$d_6$) δ 3.95 (q, J=7.1 Hz, 2H), 3.48 (s, 3H), 2.69 (q, J=2.0 Hz, 2H), 2.47 (t, J=2.1 Hz, 3H), 1.15 (t, J=7.1 Hz, 3H).

Step G: ethyl
2-methyl-4-oxocyclopent-2-enecarboxylate

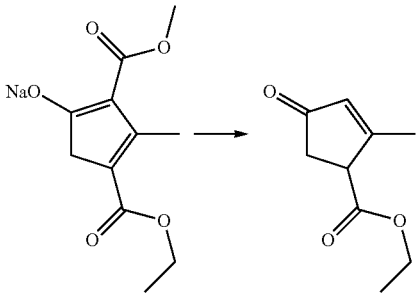

In a 5 L round bottom flask, sodium 4-(ethoxycarbonyl)-2-(methoxycarbonyl)-3-methylcyclo-penta-1,3-dienolate (485 g, 1954 mmol), KCl (204 g, 2736 mmol, JT Baker), and AcOH (392 mL, 6839 mmol, JT Baker) in toluene (1200 mL) and water (1200 mL) were heated at reflux for about 6 h. The reaction mixture was allowed to cool to ambient temperature for about 16 h. The reaction mixture was then poured into a 12 L flask and diluted with water (3 L). Solid $NaHCO_3$ (450 g, 5.3 mol) was added cautiously portionwise with stirring over about 1 h. After about an additional 30 min of stirring, the basic aqueous phase was separated and further extracted with $Et_2O$ (4×400 mL). The combined organic layers were washed with water (4×500 mL) and brine (500 mL), dried over anhydrous $MgSO_4$, filtered, and concd under reduced pressure to yield a yellow oil that was purified by vacuum distillation (92-94° C., 0.4 mmHg) to give ethyl 2-methyl-4-oxocyclopent-2-enecarboxylate (229 g, 69%) as a yellow oil: $^1$H NMR ($CDCl_3$) δ 6.04-6.01 (m, 1H), 4.26-4.17 (m, 2H), 3.67 (m, 1H), 2.72 (m, 1H), 2.62 (m, 1H), 2.16 (s, 3H), 1.32-1.27 (t, J=7.1 Hz, 3H).

Step H: ethyl
2-methyl-4-oxocyclopentanecarboxylate

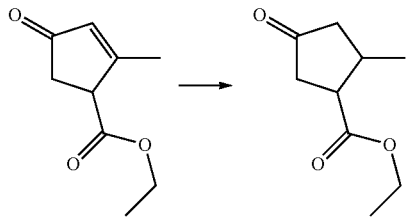

In a 1 L round-bottomed flask jacketed flask, copper(I) chloride (0.736 g, 7.43 mmol), (S)-(−)-2,2'-bis(diphenylphosphino)-1,1'-binaphthyl (4.63 g, 7.43 mmol), and sodium tert-butoxide (0.714 g, 7.43 mmol) in toluene (250 mL) were added to give a yellow solution. The mixture was stirred at ambient temperature for about 15 min. after which the solution became brown. The solution was cooled to about 5° C. and polymethylhydrosiloxane (14.86 mL, 223 mmol) was added and the solution was stirred at about 5° C. for about 40 min. The solution was cooled to about −15° C. and a solution of ethyl 2-methyl-4-oxocyclopent-2-enecarboxylate (25.00 g, 149 mmol) and tert-butyl alcohol (61.7 mL, 654 mmol) in toluene (250 mL) was added in one portion. The reaction stirred at −15° C. for 144 h. The reaction mixture was quenched by the addition of 1:1 ethanol/toluene (350 mL) and Celite® 545 (25 g). The mixture was stirred and allowed to warm to ambient temperature. The reaction mixture was concd in vacuo, chasing with heptane. Heptane (350 mL) was added to the residue and solids were removed by filtration. The filtrate was concd in vacuo and the crude product was purified by silica gel chromatography using a gradient of 10 to 50% EtOAc in heptane over 7 column volumes to give ethyl 2-methyl-4-oxocyclopentanecarboxylate (scalemic mixture of diastereomers), predominantly (1S,2R)-ethyl 2-methyl-4-oxocyclopentanecarboxylate (11.2 g, 42% yield) as a colorless oil. $^1$H NMR (400 MHz, $CDCl_3$) δ 4.19 (qd, J=7.1, 0.6, 2H), 3.17 (ddd, J=8.1, 6.8, 5.6, 1H), 2.76-2.56 (m, 2H), 2.67-2.46 (m, 2H), 2.43-2.29 (m, 2H), 2.16 (ddd, J=18.3, 7.8, 1.7, 1H), 1.29 (t, J=7.2, 3H), 1.06 (d, J=7.0, 3H).

Step I: ethyl 4-(dibenzylamino)-2-methylcyclopentanecarboxylate

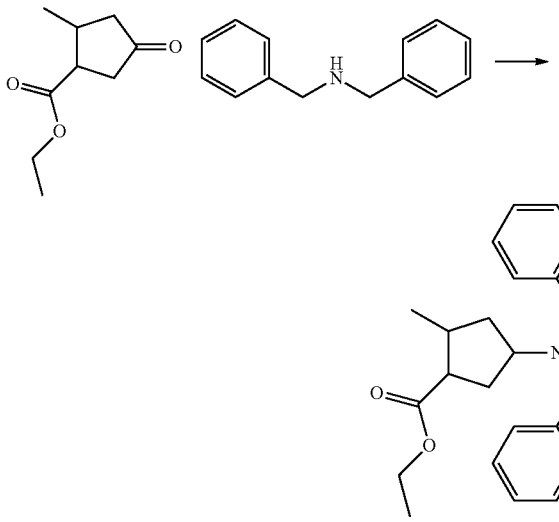

A round bottom flask was charged with ethyl 2-methyl-4-oxocyclopentanecarboxylate (10.0 g, 58.8 mmol) and DCE (180 mL). The solution was cooled to about 0° C. and AcOH (5.7 mL, 100 mmol) and dibenzylamine (11.3 mL, 58.8 mmol) were added dropwise, resulting in formation of a thick suspension. The reaction mixture was warmed to about 10° C. and sodium triacetoxyborohydride (21.2 g, 100 mmol) was added portionwise. The reaction mixture was stirred at ambient temperature for about 20 h then slowly poured into stirred saturated aqueous $NaHCO_3$ (300 mL) and stirred for about 20 min. The layers were separated and the aqueous phase was extracted with DCM (3×100 mL). The combined organic extracts were washed with brine (2×100 mL), dried over anhydrous $Na_2SO_4$, and concd under reduced pressure. The crude yellow oil was purified via silica gel chromatography eluting with a gradient of 0-30% EtOAc in heptane to give ethyl 4-(dibenzylamino)-2-methylcyclopentanecarboxylate (scalemic mixture of diastereomers), predominantly (1S,2R,4S) ethyl 4-(dibenzylamino)-2-methylcyclopentanecarboxylate (15.5 g, 75%) as a colorless oil: $^1$H NMR (pyridine-$d_5$) δ 7.53 (dd, J=0.9, 7.9 Hz, 4H), 7.43-7.35 (m, 4H), 7.33-7.25 (m, 2H), 4.22-4.06 (m, 2H), 3.79 (d, J=14.2 Hz, 2H), 3.70 (d, J=14.2 Hz, 2H), 3.34-3.22 (m, 1H), 2.76 (dd, J=7.9, 16.6 Hz, 1H), 2.25-2.13 (m, 1H), 2.09-1.94 (m, 2H), 1.88-1.79 (m, 1H), 1.52 (dd, J=10.5, 22.5 Hz, 1H), 1.16 (t, J=7.1 Hz, 3H), 0.98 (d, J=7.0 Hz, 3H).

Step J: 4-(dibenzylamino)-2-methylcyclopentanecarboxylic acid

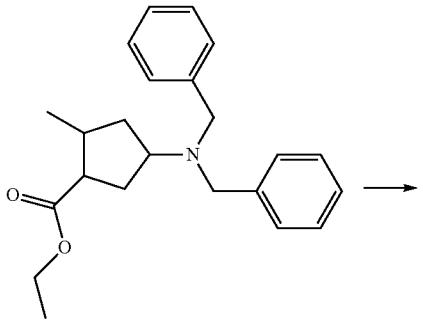

-continued

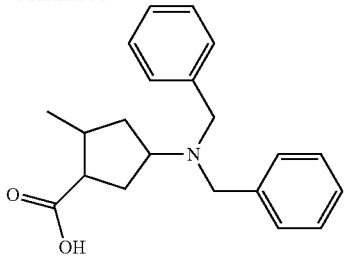

Ethyl 4-(dibenzylamino)-2-methylcyclopentanecarboxylate (3.65 g, 10.38 mmol) was dissolved in a mixture of HCl (6 N aqueous, 20 mL) and 1,4-dioxane (50 mL) and the resulting mixture was heated at about 60° C. for about 72 h. The organic solvent was removed under reduced pressure. The aqueous phase was neutralized by the addition of saturated aqueous $NaHCO_3$ (40 mL) and extracted with EtOAc (50 mL). The organic layer was washed with brine (40 mL), dried over anhydrous $MgSO_4$ and concd under reduced pressure to yield 4-(dibenzylamino)-2-methylcyclopentanecarboxylic acid (3.3 g, 98%) as a white amorphous solid: LC/MS (Table 1, Method a) $R_t$=1.66 min; MS m/z 324 $(M+H)^+$.

Step K: 2-bromo-1-(4-(dibenzylamino)-2-methylcyclopentyl)ethanone

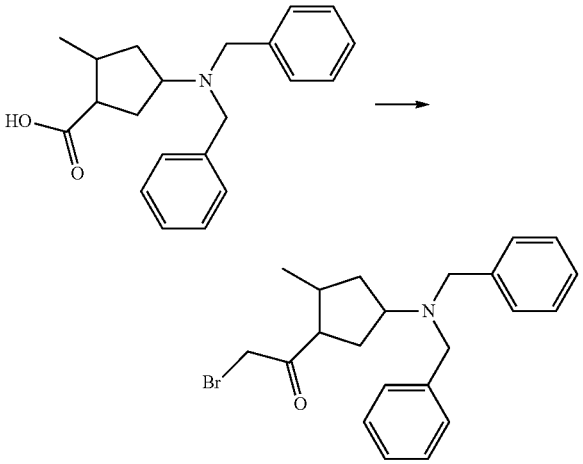

Oxalyl chloride (4.37 mL, 49.9 mmol) was slowly added to a solution of 4-(dibenzylamino)-2-methylcyclopentanecarboxylic acid (7.34 g, 22.7 mmol) in DCM (100 mL), (note: mild gas evolution) followed by a dropwise addition of DMF (0.26 mL, 3.41 mmol). The mixture was stirred at ambient temperature for about 14 h. The solvent was removed under reduced pressure to yield a beige amorphous solid, which was dissolved in THF and MeCN (1:1, 100 mL). The resulting solution was added to a solution of trimethylsilyldiazomethane (2 M in $Et_2O$, 39.7 mL, 79 mmol) in THF and MeCN (1:1, 100 mL) at about 0° C. The resulting mixture was stirred at about 0° C. for about 3 h and then was quenched by a dropwise addition of HBr (48% aqueous, 25 mL, 221 mmol). The resulting mixture was neutralized by a dropwise addition of saturated aqueous $NaHCO_3$ (300 mL) and the layers were separated. The organic layer was dried over anhydrous $MgSO_4$ and concd under reduced pressure. The residue was purified by silica gel chromatography eluting with 5% to 45% of EtOAc in heptane to yield 2-bromo-1-(4-(dibenzylamino)-2-methylcyclopentyl)ethanone (6.3 g, 69%) as a yellow oil: LC/MS (Table 1, Method a) $R_t$=2.90 min; MS m/z 400, 402 $(M+H)^+$.

Step L: tert-butyl 2-(4-(dibenzylamino)-2-methylcyclopentyl)-2-oxoethyl(5-tosyl-5H-pyrrolo[2,3-b]pyrazin-2-yl)carbamate

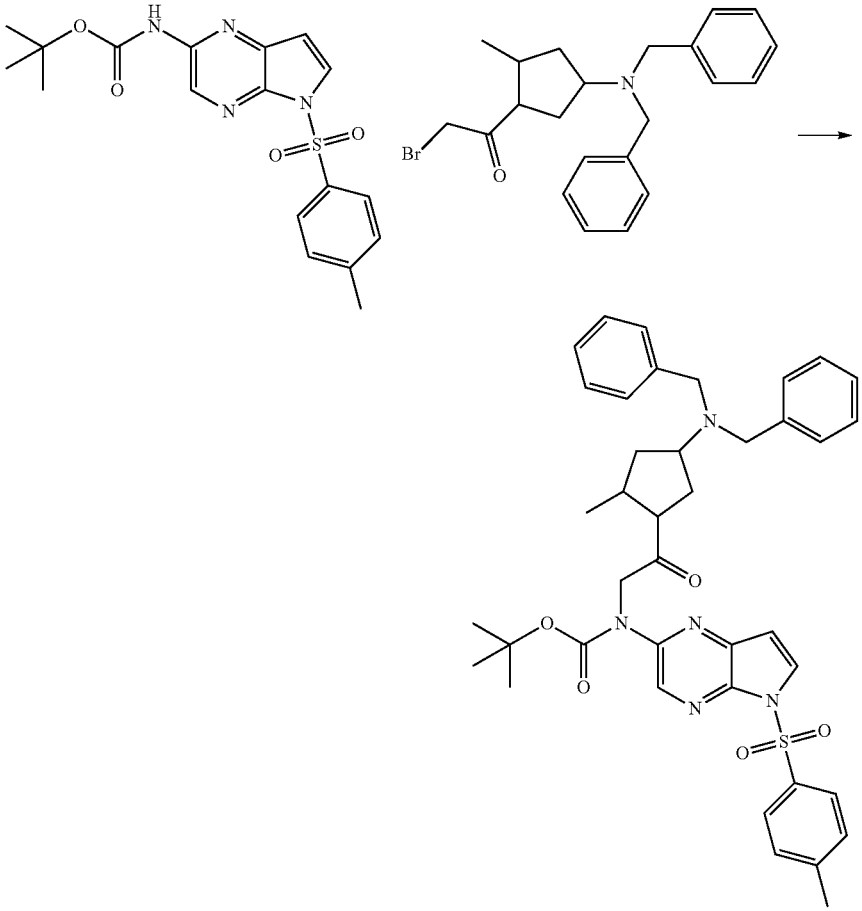

A solution of tert-butyl 5-tosyl-5H-pyrrolo[2,3-b]pyrazin-2-ylcarbamate (0.59 g, 1.519 mmol, Example #3 Step E) in DMF (5 mL) was added dropwise to a suspension of NaH (60% dispersion in mineral oil, 0.058 g, 1.45 mmol) in DMF (5 mL), at about 0° C. The resulting mixture was stirred at about 0° C. for about 30 min and then added dropwise to a solution of 2-bromo-1-(4-(dibenzylamino)-2-methylcyclopentyl)ethanone (0.73 g, 1.8 mmol) in DMF (10 mL) at about 0° C. The resulting mixture was stirred at about 0° C. for about 1 h and the solvent was removed under reduced pressure. The residue was partitioned between saturated aqueous $NaHCO_3$ and EtOAc (100 mL each). The organic phase was separated, dried over anhydrous $MgSO_4$ and concd under reduced pressure to yield tert-butyl 2-(4-(dibenzylamino)-2-methylcyclopentyl)-2-oxoethyl(5-tosyl-5H-pyrrolo[2,3-b]pyrazin-2-yl)carbamate (1.04 g, 97%) as a yellow amorphous solid: LC/MS (Table 1, Method a) $R_t$=3.30 min; MS m/z 708 $(M+H)^+$.

Step M: 1-(4-(dibenzylamino)-2-methylcyclopentyl)-2-(5-tosyl-5H-pyrrolo[2,3-b]pyrazin-2-ylamino)ethanone

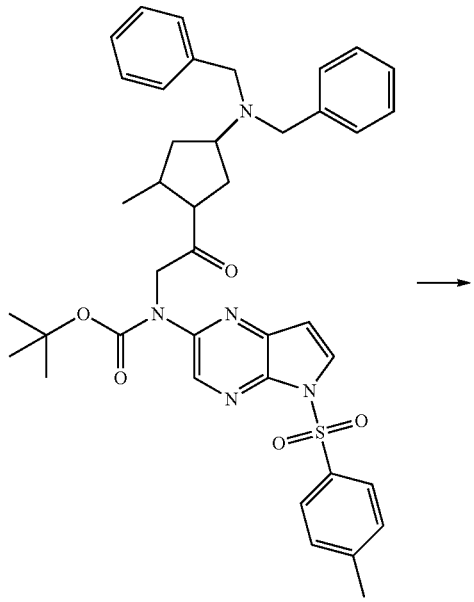

-continued

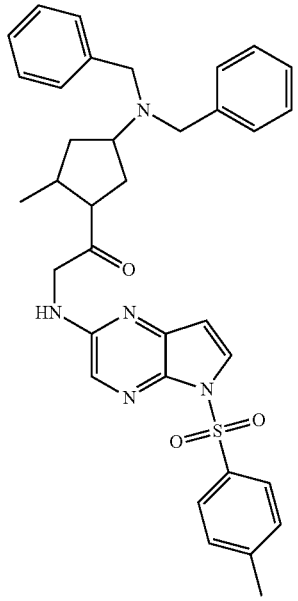

tert-Butyl 2-(4-(dibenzylamino)-2-methylcyclopentyl)-2-oxoethyl(5-tosyl-5H-pyrrolo[2,3-b]pyrazin-2-yl)carbamate (6.19 g, 8.75 mmol) was dissolved in HCl (4 N in 1,4-dioxane, 25 mL). The reaction mixture was stirred at ambient temperature for about 2 h. The solvent was removed under reduced pressure and the residue was partitioned between saturated aqueous $NaHCO_3$ and EtOAc (100 mL each). The organic phase was washed with brine (80 mL), dried over anhydrous $MgSO_4$ and concd under reduced pressure to yield 1-(4-(dibenzylamino)-2-methylcyclopentyl)-2-(5-tosyl-5H-pyrrolo[2,3-b]pyrazin-2-ylamino)ethanone (5.2 g, 98%) as a brown amorphous solid: LC/MS (Table 1, Method a) $R_t$=3.00 min; MS m/z 608 $(M+H)^+$.

Step N: N,N-dibenzyl-3-methyl-4-(3-tosyl-3H-imidazo[1,2-a]pyrrolo[2,3-e]pyrazin-8-yl)cyclopentanamine

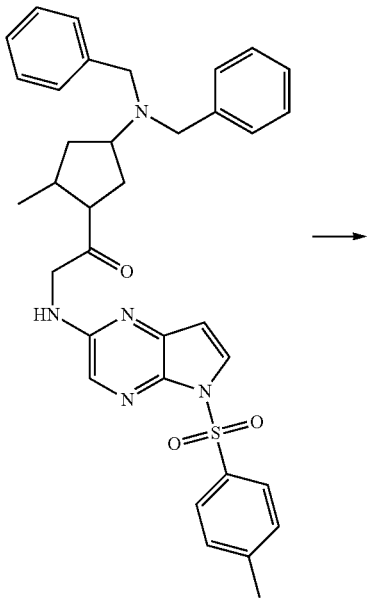

-continued

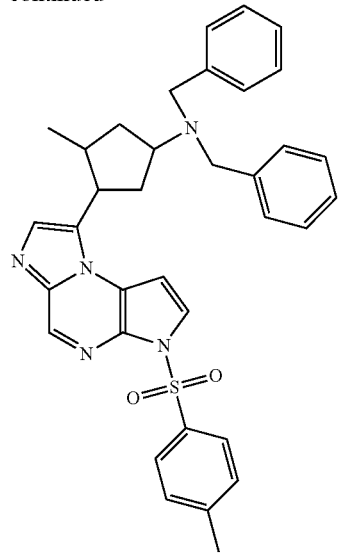

A mixture of 1-(4-(dibenzylamino)-2-methylcyclopentyl)-2-(5-tosyl-5H-pyrrolo[2,3-b]pyrazin-2-ylamino)ethanone (5.32 g, 8.75 mmol) and Lawesson's reagent (1.88 g, 4.64 mmol) was heated at about 60° C. for about 2 h. Additional Lawesson's reagent (1.88 g, 4.64 mmol) was added. The reaction mixture was stirred at about 60° C. for about 1 h. The solvent was removed under reduced pressure and the residue was purified by silica gel chromatography eluting with a gradient of 0-8% MeOH in DCM to yield N,N-dibenzyl-3-methyl-4-(3-tosyl-3H-imidazo[1,2-a]pyrrolo[2,3-e]pyrazin-8-yl)cyclopentanamine (4.47 g, 87%) as a brown amorphous solid: LC/MS (Table 1, Method a) $R_t$=2.99 min; MS m/z 590 $(M+H)^+$.

Step O: N,N-dibenzyl-3-(3H-imidazo[1,2-a]pyrrolo[2,3-e]pyrazin-8-yl)-4-methylcyclopentanamine

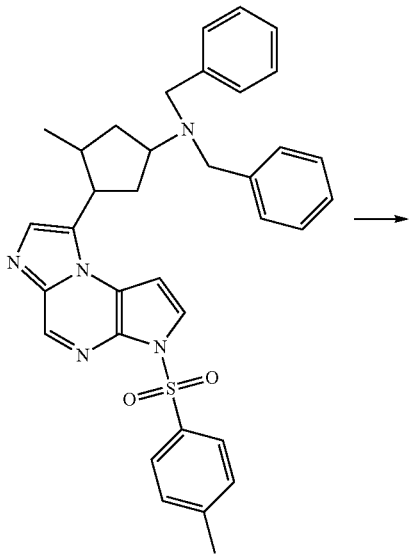

-continued

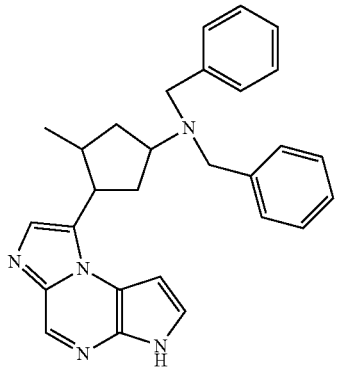

N,N-Dibenzyl-3-methyl-4-(3-tosyl-3H-imidazo[1,2-a]pyrrolo[2,3-e]pyrazin-8-yl)cyclopentan-amine (4.47 g, 7.58 mmol) was dissolved in 1,4-dioxane (40 mL). NaOH (2 N aqueous, 4 mL) was added and the reaction mixture was heated at about 90° C. for about 80 min. The organic solvent was removed under reduced pressure and the residue was treated with saturated aqueous $NH_4Cl$ (70 mL) and extracted with DCM (2×60 mL). The combined organic extracts were washed with brine (70 mL), dried over anhydrous $MgSO_4$ and concd under reduced pressure. The residue was purified by silica gel chromatography eluting with a gradient of 0-8% MeOH in DCM to yield N,N-dibenzyl-3-(3H-imidazo[1,2-a]pyrrolo[2,3-e]pyrazin-8-yl)-4-methylcyclopentan-amine (1.84 g, 56%) as a yellow oil: LC/MS (Table 1, Method a) $R_t$=2.31 min; MS m/z 436 $(M+H)^+$.

Step P: N,N-dibenzyl-3-methyl-4-(3-((2-(trimethylsilyl)ethoxy)methyl)-3H-imidazo[1,2-a]pyrrolo[2,3-e]pyrazin-8-yl)cyclopentanamine

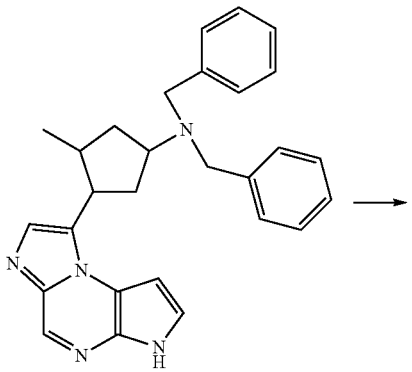

-continued

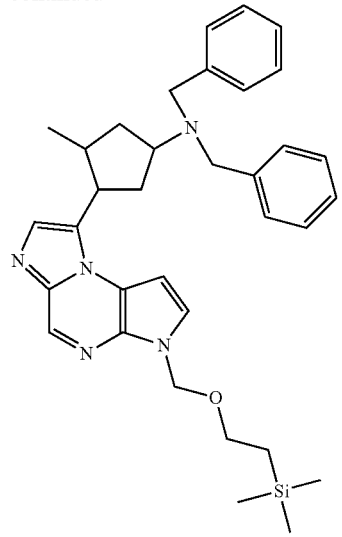

To the suspension of sodium hydride (60% dispersion in mineral oil, 0.382 g, 9.55 mmol) in DMF (50 mL) was added a solution of N,N-dibenzyl-3-(3H-imidazo[1,2-a]pyrrolo[2,3-e]pyrazin-8-yl)-4-methylcyclopentanamine (3.96 g, 9.09 mmol) in DMF (50 mL) drop-wise at about 0° C. The resulting solution was stirred at ambient temperature for about 10 min. SEM chloride (1.774 mL, 10.0 mmol) was added dropwise and the solution was stirred for about 1 h. The solvent was removed under reduced pressure and the residue was partitioned between water and EtOAc (200 mL each). The organic layer was washed with brine (100 mL), dried over anhydrous $MgSO_4$, filtered and concd. The residue was purified by silica gel column chromatography eluting with 10-80% EtOAc in DCM to yield N,N-dibenzyl-3-methyl-4-(3-((2-(trimethylsilyl)ethoxy)methyl)-3H-imidazo[1,2-a]pyrrolo[2,3-e]pyrazin-8-yl)cyclopentanamine (3.1 g, 60% yield) as an off-white amorphous solid. LC/MS (Table 1, Method a) $R_t$=3.32 min; MS m/z 566 $(M+H)^+$.

Step Q: 3-Methyl-4-(3-((2-(trimethylsilyl)ethoxy)methyl)-3H-imidazo[1,2-a]pyrrolo[2,3-e]pyrazin-8-yl)cyclopentanamine

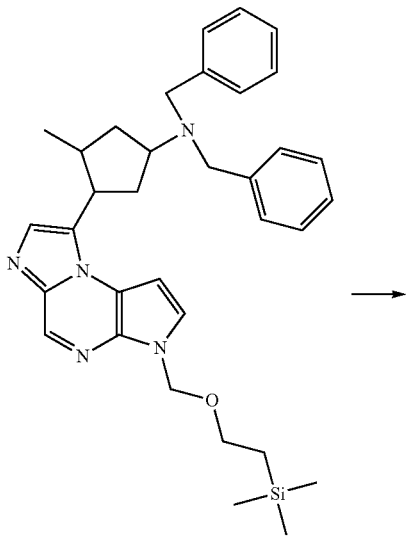

-continued

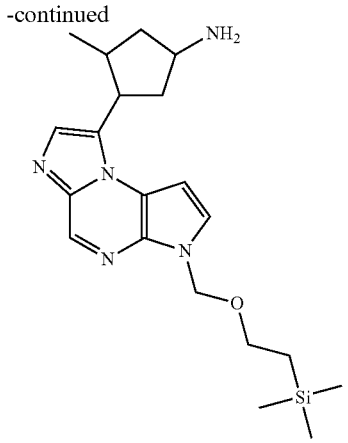

To a solution of N,N-dibenzyl-3-methyl-4-(3-((2-(trimethylsilyl)ethoxy)methyl)-3H-imidazo[1,2-a]pyrrolo[2,3-e]pyrazin-8-yl)cyclopentanamine (3.0 g, 5.30 mmol) in trifluoroethanol (200 mL) was added 20% wet palladium hydroxide on carbon (0.6 g, 4.27 mmol). The mixture was stirred under 40 psi of hydrogen at about 50° C. for about 90 min. The catalyst was removed by filtration through a pad of Celite® and the filtrate was concd under reduced pressure to yield 3-methyl-4-(3-((2-(trimethylsilyl)ethoxy)methyl)-3H-imidazo[1,2-a]pyrrolo[2,3-e]pyrazin-8-yl)cyclopentanamine (2.0 g, 98% yield) as a brown amorphous solid. LC/MS (Table 1, Method a) $R_t$=1.86 min; MS m/z 386 $(M+H)^+$.

Step R: N-3-methyl-4-(3-((2-(trimethylsilyl)ethoxy)methyl)-3H-imidazo[1,2-a]pyrrolo[2,3-e]pyrazin-8-yl)cyclopentyl)-2-oxooxazolidine-3-sulfonamide

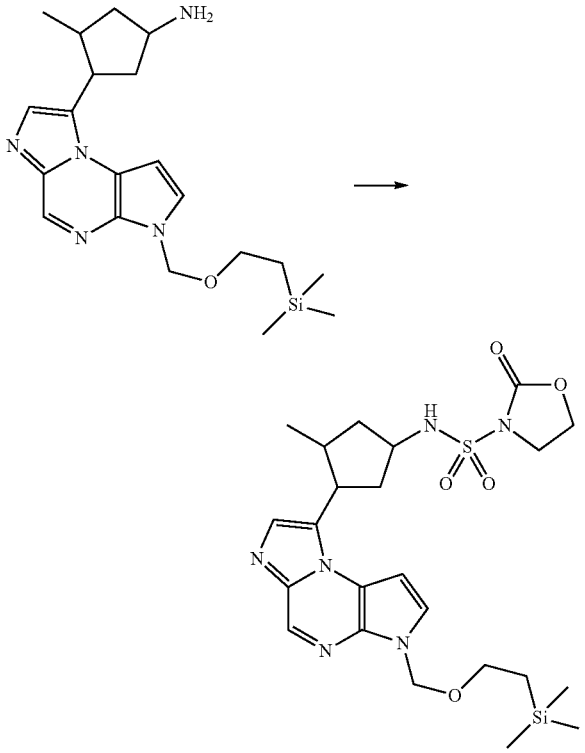

To a solution of 3-methyl-4-(3-((2-(trimethylsilyl)ethoxy)methyl)-3H-imidazo[1,2-a]pyrrolo[2,3-e]pyrazin-8-yl)cyclopentanamine (0.50 g, 1.3 mmol) and 2-chloroethyl chlorosulfonylcarbamate (0.288 g, 1.297 mmol, prepared as detailed in Biorg. Med. Chem. Lett, 2006 16, 3367-3370) in DCM (16 mL) was added TEA (0.542 mL, 3.89 mmol) dropwise. The mixture was stirred at ambient temperature for about 2 h. The solvent was removed under reduced pressure and the residue was partitioned between water and EtOAc (30 mL each). The organic layer was washed with brine (20 mL), dried over anhydrous $MgSO_4$, filtered and concd under reduced pressure. The residue was purified by silica gel chromatography (0% DCM for 5 min, then to 6% MeOH in DCM over the next 30 min.) to yield N-3-methyl-4-(3-((2-(trimethylsilyl)ethoxy)methyl)-3H-imidazo[1,2-a]pyrrolo[2,3-e]pyrazin-8-yl)cyclopentyl)-2-oxooxazolidine-3-sulfonamide (0.24 g, 35% yield) as an off-white solid. LC/MS (Table 1, Method a) $R_t$=2.42 min; MS m/z 535 $(M+H)^+$.

Step S: 3,3-difluoro-N-3-methyl-4-(3-((2-(trimethylsilyl)ethoxy)methyl)-3H-imidazo[1,2-a]pyrrolo[2,3-e]pyrazin-8-yl)cyclopentyl)azetidine-1-sulfonamide

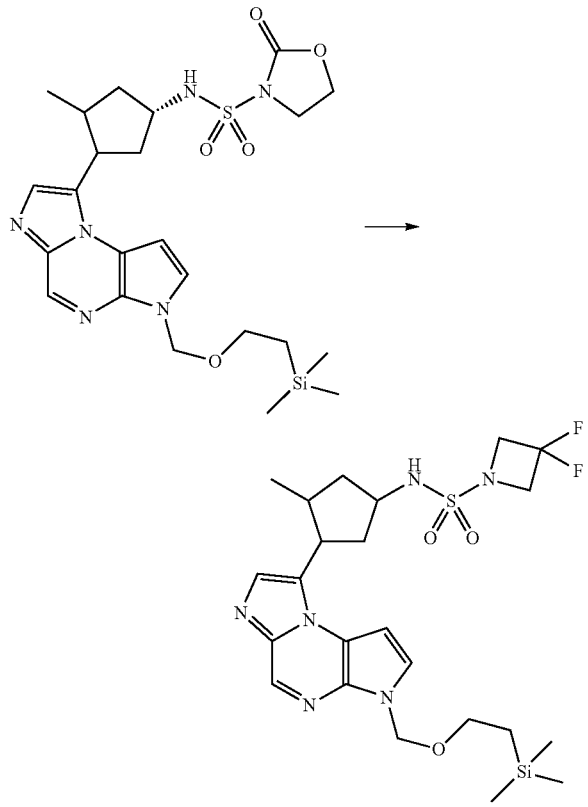

To a solution of 3-methyl-4-(3-((2-(trimethylsilyl)ethoxy)methyl)-3H-imidazo[1,2-a]pyrrolo[2,3-e]pyrazin-8-yl)cyclopentyl)-2-oxooxazolidine-3-sulfonamide (0.24 g, 0.449 mmol) in MeCN (1.5 mL) was added (3,3-difluoroazetidine hydrochloride (0.07 g, 0.539 mmol, Matirx Scientific) and DIEA (0.196 mL, 1.122 mmol). The mixture was heated in the microwave at about 120° C. for about 30 min. The solvent was removed under reduced pressure and the residue was partitioned between saturated solution of ammonium chloride in water and EtOAc (20 mL each). The organic layer was washed with brine (10 mL), dried over anhydrous $MgSO_4$, filtered and concd to yield 3,3-difluoro-N-3-methyl-4-(3-((2-(trimethylsilyl)ethoxy)methyl)-3H-imidazo[1,2-a]pyrrolo[2,3-e]pyrazin-8-yl)cyclopentyl)azetidine-1-sulfonamide (0.2 g, 82% yield) as an off-white amorphous solid. LC/MS (Table 1, Method a) $R_t$=2.61 min; MS m/z 541 $(M+H)^+$.

Step T: N-((1S,3S,4R)-3-(3H-imidazo[1,2-a]pyrrolo[2,3-e]pyrazin-8-yl)-4-methylcyclopentyl)-3,3-difluoroazetidine-1-sulfonamide

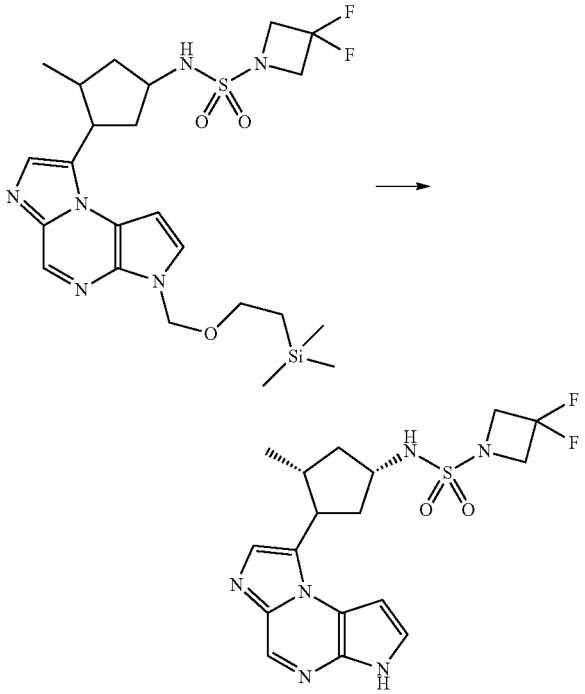

To a solution of 3,3-difluoro-N-3-methyl-4-(3-((2-trimethylsilyl)ethoxy)methyl-3H-imidazo[1,2-a]pyrrolo[2,3-e]pyrazin-8-yl)cyclopentyl)azetidine-1-sulfonamide (0.20 g, 0.370 mmol) in DCM (2.5 mL) was added TFA (0.9 mL) The resulting mixture was stirred at ambient temperature for about 2 h. The solvents were removed under reduced pressure and the residue was dried under high vacuum. The residue was dissolved in 1,4-dioxane (3 mL) and 28% ammonium hydroxide solution in water (2.5 mL) and the mixture was heated at about 60° C. for about 2 h. The solvents were removed under reduced pressure and the residue was purified by using general procedure AA (Table 2, Method 32, $R_t$=15.3 min, or =negative) to yield N-((1S,3S,4R)-3-(3H-imidazo[1,2-a]pyrrolo[2,3-e]pyrazin-8-yl)-4-methylcyclopentyl)-3,3-difluoroazetidine-1-sulfonamide (0.077 g, 51%) as a yellow solid. LC/MS (Table 1, Method a) $R_t$=1.75 min; MS m/z 411 $(M+H)^+$.

Example #26*

5-((3S,5R)-5-ethyl-1-(6H-imidazo[1,5-a]pyrrolo[2,3-e]pyrazin-1-yl)pyrrolidin-3-ylamino)pyrazine-2-carbonitrile oxalate

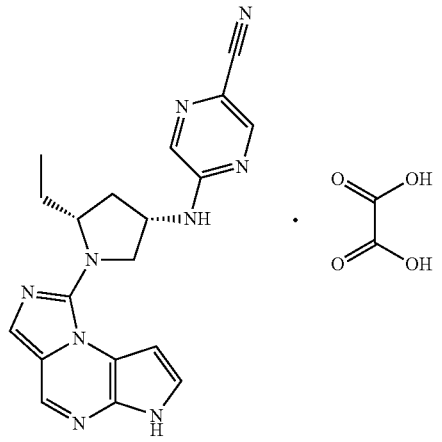

To slurry of palladium hydroxide on carbon (20 mol %, 0.082 g, 0.582 mmol) in EtOH (5 mL) was added a solution of 1-((2R,4S)-4-azido-2-ethylpyrrolidin-1-yl)-6H-imidazo[1,5-a]pyrrolo[2,3-e]pyrazine (0.115 g, 0.388 mmol, prepared using E from (2R,4S)-tert-butyl-4-azido-2-ethylpyrrolidine-1-carboxylate (synthesized as described in. J. Med. Chem. 1988, 31, 1598-1611) with HCl, J with Example #5, Step C, OO, D with NaOH) in EtOH (2 mL). The reaction mixture was sparged with hydrogen and an atmosphere of hydrogen was maintained via balloon. After about 2 h the reaction mixture was filtered and 5-chloropyrazine-2-carbonitrile (0.013 g, 0.019 mmol, ArkPharm) was added. The reaction mixture was heated at about 70° C. After about 7 h the reaction mixture was cooled to ambient temperature and diluted with water (5 mL). The resulting precipitate was collected by filtration to provide the product as the free base. The solid was dissolved in EtOAc (5 mL) and oxalic acid dihydrate (0.054 g, 0.43 mmol) was added. The solids were sonicated briefly with gentle heating. After cooling to ambient temperature, the solids were collected by filtration and dried in vacuo to provide 5-((3S,5R)-5-ethyl-1-(6H-imidazo[1,5-a]pyrrolo[2,3-e]pyrazin-1-yl)pyrrolidin-3-ylamino)pyrazine-2-carbonitrile oxylate, (0.100 g, 56%) as a tan solid: LC/MS (Table 1, Method a) $R_t$=1.80 min; MS m/z: 374 $(M+H)^+$.

Example #27*

N-((3S,5R)-5-ethyl-1-(6H-imidazo[1,5-a]pyrrolo[2,3-e]pyrazin-1-yl)pyrrolidin-3-yl)-3,3,3-trifluoropropane-1-sulfonamide

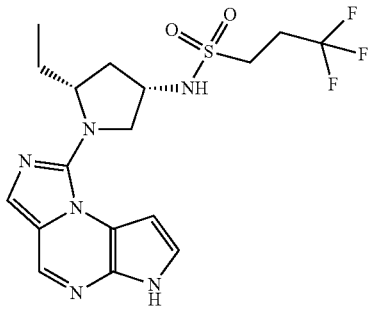

To slurry of palladium hydroxide on carbon (20 mol %, 0.013 g, 0.019 mmol) in EtOH (5 mL) was added a solution of 1-((2R,4S)-4-azido-2-ethylpyrrolidin-1-yl)-6H-imidazo[1,5-a]pyrrolo[2,3-e]pyrazine (0.110 g, 0.371 mmol, prepared using E from (2R,4S)-tert-butyl-4-azido-2-ethylpyrrolidine-1-carboxylate (synthesized as described in. J. Med. Chem. 1988, 31, 1598-1611) with HCl, J with Example #5, Step C, OO, D with NaOH) in EtOH (2 mL). The reaction mixture was sparged with hydrogen and an atmosphere of hydrogen was maintained via balloon. After about 2 h the reaction mixture was filtered and concd under reduced pressure The residue was dissolved in DCM (5 mL) and 3,3,3-trifluoropropane-1-sulfonyl chloride (0.080 g, 0.41 mmol, Matrix) was added. After about 15 h additional 3,3,3-trifluoropropane-1-sulfonyl chloride (80 mg, 0.408 mmol, Matrix) was added. After about 2 days the reaction mixture was partitioned between EtOAc (10 mL) and brine (10 mL). The organic layer was separated, dried over anhydrous $Na_2SO_4$, filtered, and concd under reduced pressure. The crude product was purified by chromatography on silica gel eluting with EtOAc to provide N-((3S,5R)-5-ethyl-1-(6H-imidazo[1,5-a]pyrrolo[2,3-e]pyrazin-1-yl)pyrrolidin-3-yl)-3,3,3-trifluoropropane-1-sulfonamide (0.025 g, 16%) as a brown solid: LC/MS (Table 1, Method a) $R_t$=1.81 min; MS m/z: 431 $(M+H)^+$.

Example #28

1-cyclohexyl-2,3,4,7-tetrahydro-1H-pyrrolo[2,3-h][1,6]naphthyridine

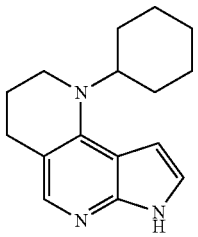

Step A: ethyl 4-chloro-1-(triisopropylsilyl)-1H-pyrrolo[2,3-b]pyridine-5-carboxylate

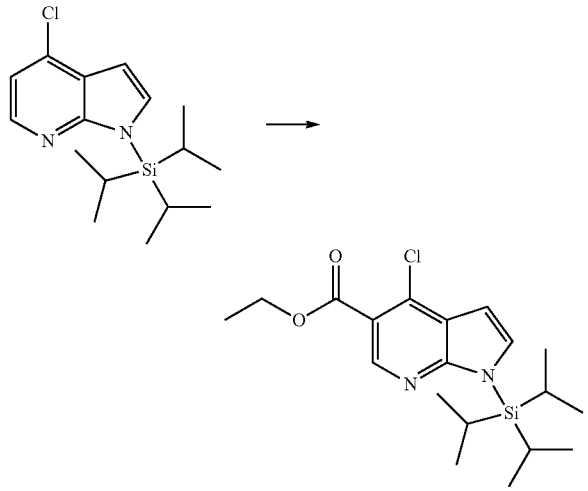

To a solution of 4-chloro-1-(triisopropylsilyl)-1H-pyrrolo[2,3-b]pyridine (3.03 g, 9.81 mmol, Adesis) in THF (49 mL) at about −78° C. was added sec-BuLi (1.4 M in cyclohexane, 15.4 mL, 21.6 mmol) dropwise. The reaction was stirred at about −78° C. for about 1 h before ethyl chloroformate (2.36 mL, 24.5 mmol) was added rapidly. The reaction mixture was allowed to warm to ambient temperature and was stirred for about 40 min. The reaction was quenched with saturated aqueous $NH_4Cl$ (25 mL). EtOAc (50 mL) and water (50 mL) were added and the layers were separated. The aqueous layer was extracted with EtOAc (2×20 mL) and the combined organic layers were washed with brine (2×20 mL). The organics were dried over anhydrous $Na_2SO_4$, filtered, and concd to dryness under reduced pressure to give a yellow oil. The oil was purified by silica gel chromatography eluting with a gradient of 0-10% EtOAc in heptane to give ethyl 4-chloro-1-(triisopropylsilyl)-1H-pyrrolo[2,3-b]pyridine-5-carboxylate (3.78 g, 98%) as a yellow oil: LC/MS (Table 1, Method b) $R_t$=3.98 min; MS m/z: 381 $(M+H)^+$.

Step B: ethyl 4-chloro-1H-pyrrolo[2,3-b]pyridine-5-carboxylate

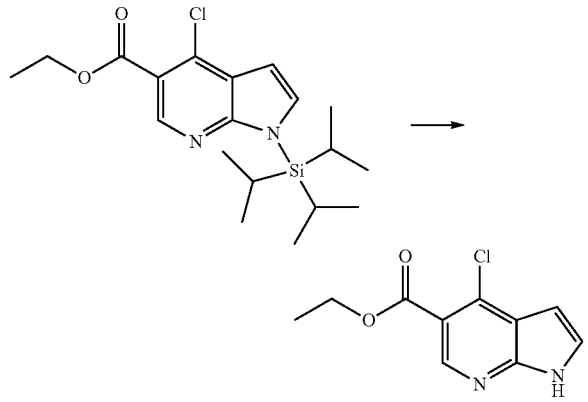

To a solution of ethyl 4-chloro-1-(triisopropylsilyl)-1H-pyrrolo[2,3-b]pyridine-5-carboxylate (4.30 g, 11.3 mmol) in THF (57 mL) at about 0° C. was added TBAF (1.0 M in THF, 12.6 mL, 12.6 mmol) dropwise and the reaction mixture was stirred at about 0° C. for about 1 h. The reaction was warmed to room temperature and stirred for about 30 min. The solvent was removed under reduced pressure and the resulting oil was partitioned between EtOAc and brine (100 mL each). The organic layer was dried over anhydrous $Na_2SO_4$, filtered and concd under reduced pressure. The residue was triturated with DCM and filtered to give ethyl 4-chloro-1H-pyrrolo[2,3-b]pyridine-5-carboxylate (1.32 g, 52%) as an off white solid: LC/MS (Table 1, Method b) $R_t$=2.07 min; MS m/z: 225 $(M+H)^+$.

Step C: ethyl 4-chloro-1-tosyl-1H-pyrrolo[2,3-b] pyridine-5-carboxylate

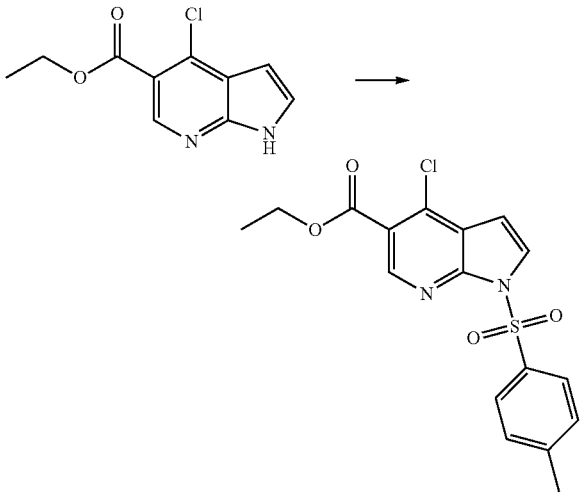

To a solution of ethyl 4-chloro-1H-pyrrolo[2,3-b]pyridine-5-carboxylate (1.32 g, 5.88 mmol) in DMF (39 mL) at about 0° C. was added sodium hydride (60% dispersion in mineral oil, 0.400 g, 10.00 mmol) and the reaction mixture was stirred at this temperature for about 15 min. A solution of 4-methyl-benzene-1-sulfonyl chloride (2.24 g, 11.8 mmol) in DMF (17 mL) was added dropwise and the reaction mixture was allowed to warm to ambient temperature for about 2 h. The reaction mixture was concd under reduced pressure and the residue was partitioned between EtOAc and water (25 mL each). The aqueous layer was extracted with EtOAc (2×25 mL) and the combined organic layers were washed with brine, dried over anhydrous $MgSO_4$, filtered, and concd under reduced pressure. The solid was triturated with heptane, and the precipitates were filtered to give ethyl 4-chloro-1-tosyl-1H-pyrrolo[2,3-b] pyridine-5-carboxylate (2.28 g, 102%, 90% purity) as a white solid: LCMS (Table 1, Method c) $R_t$=1.64 min; MS m/z: 379 $(M+H)^+$.

Step D: ethyl 4-(cyclohexylamino)-1-tosyl-1H-pyrrolo[2,3-b]pyridine-5-carboxylate

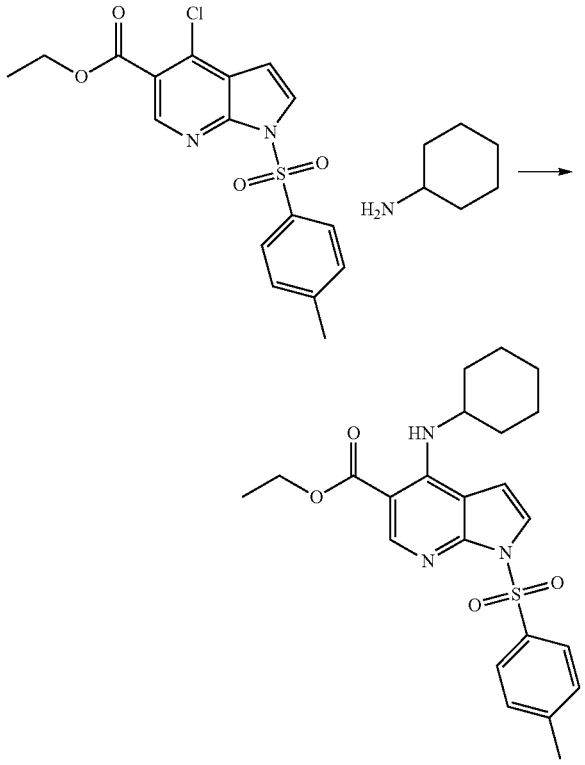

To a solution of ethyl 4-chloro-1-tosyl-1H-pyrrolo[2,3-b] pyridine-5-carboxylate (2.28 g, 5.42 mmol) in n-BuOH (21 mL) was added cyclohexanamine (1.24 mL, 10.8 mmol). The resulting solution was heated at about 110° C. for about 18 h. The reaction mixture was cooled to ambient temperature and diluted with water and DCM (50 mL each). The layers were separated and the organic layer was dried over anhydrous $Na_2SO_4$, filtered, and concd to dryness under reduced pressure. The residue was triturated with heptane and the precipitates were filtered to give ethyl 4-(cyclohexylamino)-1-tosyl-1H-pyrrolo[2,3-b]pyridine-5-carboxylate (1.74 g, 73%) as a light yellow solid: LC/MS (Table 1, Method b) $R_t$=3.18 min; MS m/z: 442 $(M+H)^+$.

Step E: (4-(cyclohexylamino)-1-tosyl-1H-pyrrolo[2,3-b]pyridin-5-yl)methanol

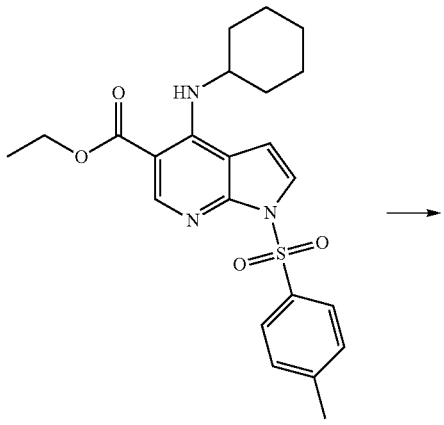

-continued

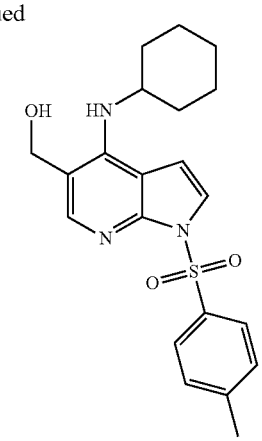

To a solution of ethyl 4-(cyclohexylamino)-1-tosyl-1H-pyrrolo[2,3-b]pyridine-5-carboxylate (1.71 g, 3.88 mmol) in toluene (43.1 mL) at about −78° C. was added DIBAL-H (1 M in hexanes, 6.60 mL, 6.60 mmol) dropwise. The reaction was stirred for about 1 h at about −78° C. and the reaction mixture was warmed to ambient temperature and stirred for about 1 h. The reaction was quenched with saturated aqueous potassium sodium tartrate (15 mL) and the mixture was stirred for about 1 h. EtOAc (25 mL) was added and the layers were separated. The organic layer was dried over anhydrous $Na_2SO_4$, filtered through a pad of silica gel while washing with EtOAc (20 mL), and the filtrate was concd under reduced pressure. The residue was purified by silica gel chromatography eluting with a gradient of 0-50% EtOAc in DCM to give (4-(cyclohexylamino)-1-tosyl-1H-pyrrolo[2,3-b]pyridin-5-yl)methanol (1.24 g, 80%) as an off white solid: LC/MS (Table 1, Method b) $R_t$=2.51 min; MS m/z: 400 $(M+H)^+$.

Step F: 4-(cyclohexylamino)-1-tosyl-1H-pyrrolo[2,3-b]pyridine-5-carbaldehyde

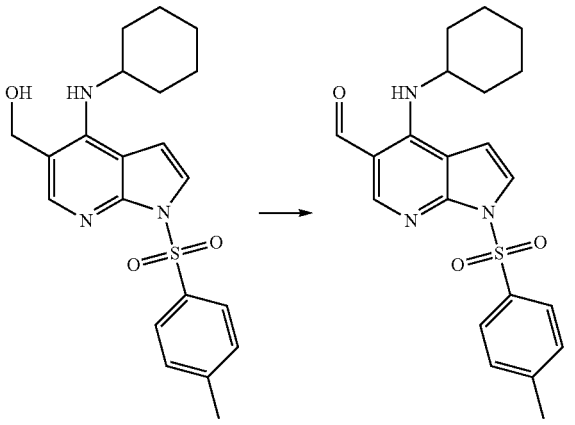

A mixture of (4-(cyclohexylamino)-1-tosyl-1H-pyrrolo[2,3-b]pyridin-5-yl)methanol (1.12 g, 2.80 mmol) and manganese dioxide (5.48 g, 63.1 mmol) in chloroform (70 mL) was stirred at ambient temperature for about 18 h. The reaction mixture was diluted with chloroform (100 mL) and the reaction mixture was filtered through a pad of Celite® while washing with chloroform (50 mL). The filtrate was concd under reduced pressure to give 4-(cyclohexylamino)-1-tosyl-1H-pyrrolo[2,3-b]pyridine-5-carbaldehyde (0.975 g, 87%) as an off white solid: LC/MS (Table 1, Method c) $R_t$=1.70 min; MS m/z: 398 $(M+H)^+$.

Step G: (E/Z)-5-(2-(1,3-dioxolan-2-yl)vinyl)-N-cyclohexyl-1-tosyl-1H-pyrrolo[2,3-b]pyridin-4-amine

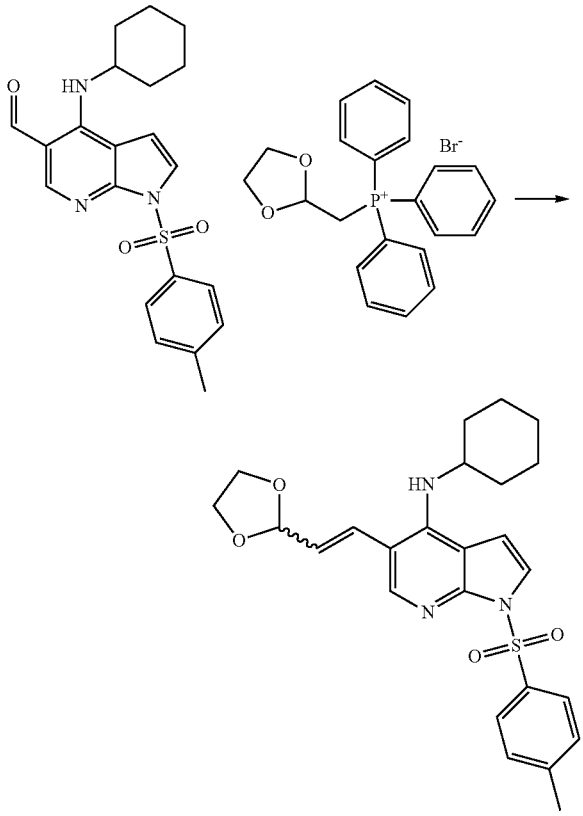

An oven dried flask under nitrogen was charged with ((1,3-dioxolan-2-yl)methyl)triphenylphosphonium bromide (2.23 g, 5.19 mmol) and THF (14 mL). The flask was cooled to about 0° C. in an ice bath and potassium tert-butoxide (0.591 g, 5.00 mmol) was added. The mixture was stirred for about 30 min at about 0° C. and a solution of 4-(cyclohexylamino)-1-tosyl-1H-pyrrolo[2,3-b]pyridine-5-carbaldehyde (0.750 g, 1.89 mmol) in THF (4 mL) was added dropwise over about 10 min. The reaction was allowed to warm to ambient temperature and stirred for about 16 h. Water (10 mL) was added and the reaction mixture was extracted with $Et_2O$ (3×10 mL). The combined organic extracts were dried over anhydrous $Na_2SO_4$, filtered, and concd under reduced pressure. The crude oil was purified by silica gel chromatography eluting 0-50% EtOAc in DCM to give 5-(2-(1,3-dioxolan-2-yl)vinyl)-N-cyclohexyl-1-tosyl-1H-pyrrolo[2,3-b]pyridin-4-amine (0.590 g, 67%) as a mixture of E and Z isomers: LC/MS (Table 1, Method c) $R_t$=1.69 min, 1.73 min; MS m/z: 468 $(M+H)^+$, 468 $(M+H)^+$.

Step H: 5-(2-(1,3-dioxolan-2-yl)ethyl)-N-cyclohexyl-1-tosyl-1H-pyrrolo[2,3-b]pyridin-4-amine

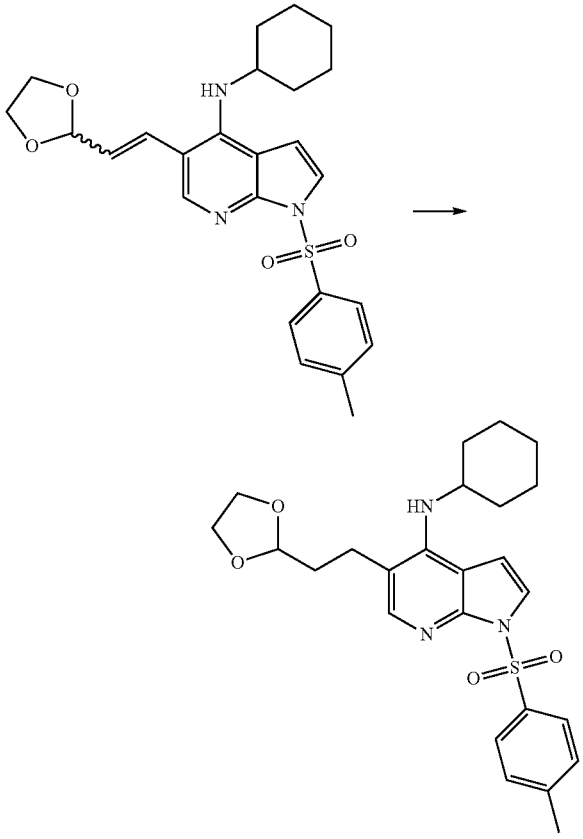

To a solution of (E/Z)-5-(2-(1,3-dioxolan-2-yl)vinyl)-N-cyclohexyl-1-tosyl-1H-pyrrolo[2,3-b]pyridin-4-amine (0.512 g, 1.10 mmol) in EtOAc (19 mL) was added palladium on carbon (10 mol %, 0.092 g, 0.086 mmol). The reaction mixture was purged with hydrogen and left under a hydrogen atmosphere using a balloon for about 1.5 h. The reaction mixture was filtered through a pad of Celite® while washing with EtOAc (10 mL) and the filtrate was concd under reduced pressure to give 5-(2-(1,3-dioxolan-2-yl)ethyl)-N-cyclohexyl-1-tosyl-1H-pyrrolo[2,3-b]pyridin-4-amine (0.499 g, 97%) as an off white foam: LC/MS (Table 1, Method b) $R_t$=2.84 min; MS m/z: 470 $(M+H)^+$.

Step I: 1-cyclohexyl-7-tosyl-2,3,4,7-tetrahydro-1H-pyrrolo[2,3-h]-[1,6]naphthyridine

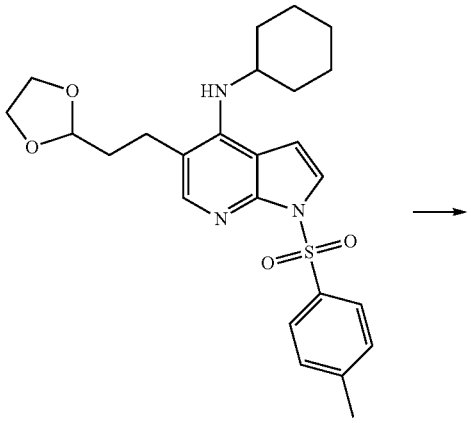

-continued

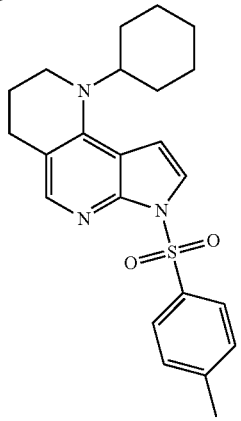

To a solution of 5-(2-(1,3-dioxolan-2-yl)ethyl)-N-cyclohexyl-1-tosyl-1H-pyrrolo[2,3-b]pyridin-4-amine (0.209 g, 0.445 mmol) in EtOH (2 mL) was added aqueous HCl (12 N, 0.186 mL, 2.23 mmol) dropwise. The mixture was heated at about 40° C. for about 2 h and then cooled to about 0° C. in an ice bath. Sodium borohydride (0.118 g, 3.12 mmol) was added portionwise and the mixture was warmed to ambient temperature. After about 2 h the solvent was removed under reduced pressure and the residue was partitioned between EtOAc and saturated aqueous $NaHCO_3$ (10 mL each). The aqueous phase was extracted with EtOAc (2×5 mL) and the combined organics were washed with water and brine (5 mL each), dried over anhydrous $Na_2SO_4$, filtered and concd under reduced pressure. The residue was purified by silica gel chromatography eluting with 0-50% EtOAc in heptane to give 1-cyclohexyl-7-tosyl-2,3,4,7-tetrahydro-1H-pyrrolo[2,3-h]-[1,6]naphthyridine (0.138 g, 75%) as a white solid: LC/MS (Table 1, Method b) $R_t$=3.01 min; MS m/z: 410 $(M+H)^+$.

Step J: 1-cyclohexyl-2,3,4,7-tetrahydro-1H-pyrrolo[2,3-h][1,6]naphthyridine

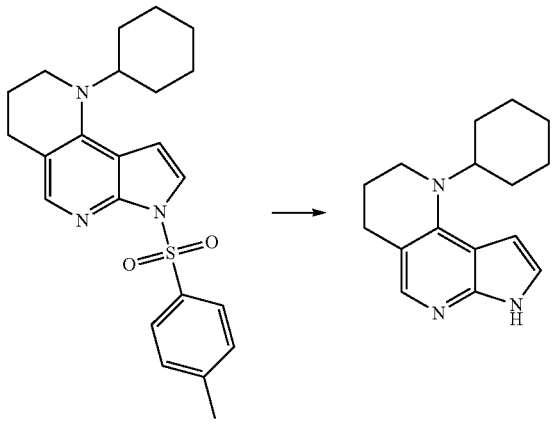

To a solution of 1-cyclohexyl-7-tosyl-2,3,4,7-tetrahydro-1H-pyrrolo[2,3-h][1,6]naphthyridine (0.132 g, 0.323 mmol) in 1,4-dioxane (2.2 mL) was added aqueous NaOH (2 N, 0.32 mL, 0.65 mmol). The reaction was heated at about 80° C. for about 96 h. Aqueous NaOH (5 N, 0.129 mL, 0.646 mmol) was added and the reaction was continued at about 80° C. for about 18 h. Aqueous NaOH (5 N, 0.065 mL, 0.323 mmol) was added and the reaction mixture was heated at about 100° C. for about 4 h. The reaction was cooled to ambient temperature, EtOAc and water were added (5 mL each) and the layers were separated. The aqueous layer was extracted with EtOAc (2×5 mL) and the combined organics were washed with water and brine (5 mL each), dried over anhydrous $Na_2SO_4$, filtered, and concd under reduced pressure. The residue was purified by silica gel chromatography eluting with a gradient of 0-100% (95/4.5/0.5) DCM/MeOH/DEA in DCM to give 1-cyclohexyl-2,3,4,7-tetrahydro-1H-pyrrolo[2,3-h][1,6]naphthyridine (0.052 g, 64%) as a tan solid: LC/MS (Table 1, Method b) $R_t$=1.88 min; MS m/z: 256 $(M+H)^+$.

Example #29

N-(4-(3,6-dihydropyrazolo[4,3-d]pyrrolo[2,3-b]pyridin-1-yl)bicyclo[2.2.2]octan-1-yl)cyclopropanesulfonamide

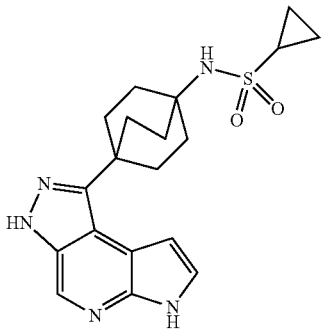

Step A: methyl 4-(tert-butoxycarbonylamino)bicyclo[2.2.2]octane-1-carboxylate

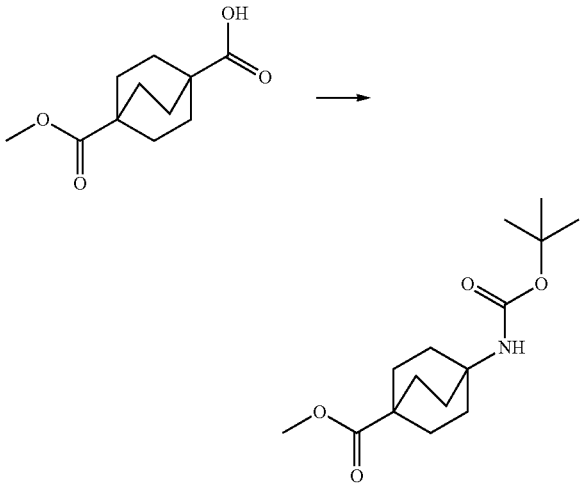

To a solution of 4-(methoxycarbonyl)bicyclo[2.2.2]octane-1-carboxylic acid (7.25 g, 34.2 mmol, Prime Organics) in toluene (150 mL) was added DPPA (7.37 mL, 34.2 mmol) and TEA (4.76 mL, 34.2 mmol) and the reaction mixture was stirred at ambient temperature for about 1 h. The reaction mixture was then heated at about 110° C. for about 1 h and tert-butanol (16.1 mL, 171 mmol) was added and the reaction was heated at about 110° C. for about 14 h. The reaction was cooled to ambient temperature and washed with saturated aqueous $NaHCO_3$ (2×50 mL) and brine (50 mL). The organics were dried over anhydrous $Na_2SO_4$, filtered and concd under reduced pressure. The crude material was purified by silica gel chromatography eluting with a gradient of 0-10% MeOH in DCM to give methyl 4-(tert-butoxycarbonylamino)bicyclo[2.2.2]octane-1-carboxylate (4.18 g, 43%) as a white solid: $^1$H NMR (400 MHz, $CDCl_3$) δ 4.32 (s, 1H), 3.63 (s, 3H), 1.95-1.76 (m, 12H), 1.42 (s, 9H).

Step B: methyl 4-(benzyl)tert-butoxycarbonyl)amino)bicyclo[2.2.2]octane-1-carboxylate

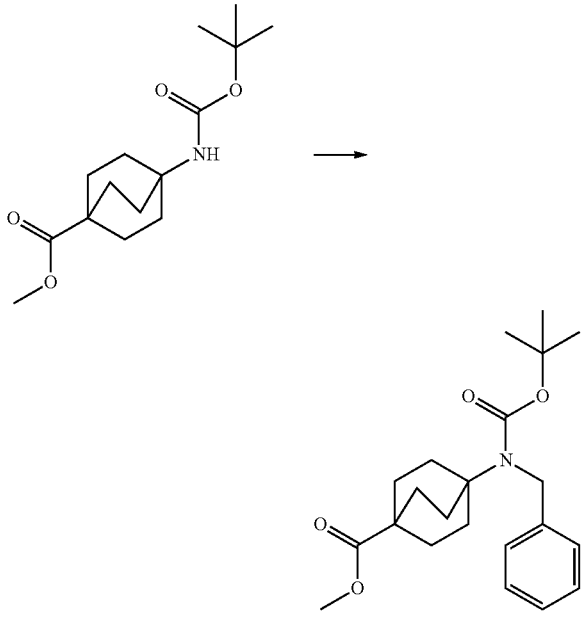

To a solution of methyl 4-(tert-butoxycarbonylamino)bicyclo[2.2.2]octane-1-carboxylate (2.50 g, 8.82 mmol) in DMF (42 mL) at about 0° C. was added sodium hydride (60% dispersion in mineral oil, 0.706 g, 17.6 mmol). The reaction mixture was stirred for about 30 min at about 0° C. and TBAI (0.652 g, 1.76 mmol) and benzyl bromide (2.10 mL, 17.7 mmol) were added. The reaction was warmed to ambient temperature and continued to stir for about 5 h. The solvent was removed under reduced pressure and the residue was taken up in DCM (50 mL) and water (30 mL). The layers were separated and the organic phase was washed with brine (30 mL), dried over anhydrous $MgSO_4$, filtered and concd under reduced pressure. The resulting oil was purified by silica gel chromatography eluting with a gradient of 0-30% EtOAc in heptane to give methyl 4-(benzyl(tert-butoxycarbonyl)amino)bicyclo[2.2.2]octane-1-carboxylate (2.71 g, 82%) as a clear colorless oil: LC/MS (Table 1, Method b) $R_t$=3.09 min; MS m/z: 374 $(M+H)^+$.

Step C: tert-butyl benzyl(4-(hydroxymethyl)bicyclo[2.2.2]octan-1-yl)carbamate

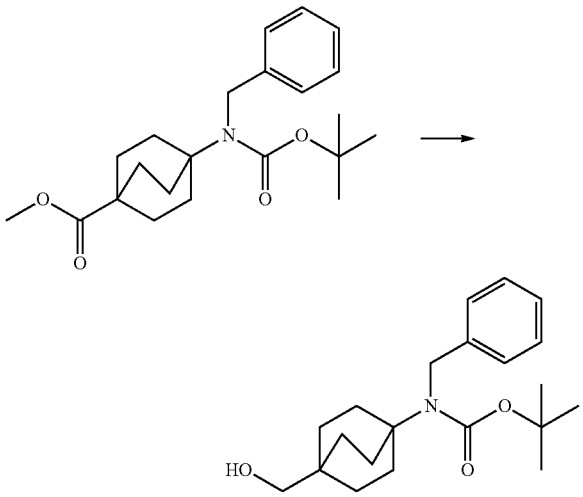

To a solution of methyl 4-(benzyl(tert-butoxycarbonyl)amino)bicyclo[2.2.2]octane-1-carboxylate (2.70 g, 7.23 mmol) in THF (24 mL) at about 0° C. was added lithium borohydride (0.350 g, 14.46 mmol). The reaction mixture was warmed to ambient temperature and stirred for about 16 h. The reaction was cooled to about 0° C. and water (15 mL) was carefully added. The reaction mixture was warmed to ambient temperature and was diluted with EtOAc (20 mL). The layers were separated and the organic layer was washed with brine (2×20 mL), dried over anhydrous $Na_2SO_4$, filtered and concd under reduced pressure to provide tert-butyl benzyl(4-(hydroxymethyl)bicyclo[2.2.2]octan-1-yl)carbamate (2.31 g, 92%) as an off white sticky foam: LC/MS (Table 1, Method b) $R_t$=2.67 min; MS m/z: 346 $(M+H)^+$.

Step D: tert-butyl benzyl(4-formylbicyclo[2.2.2]octan-1-yl)carbamate

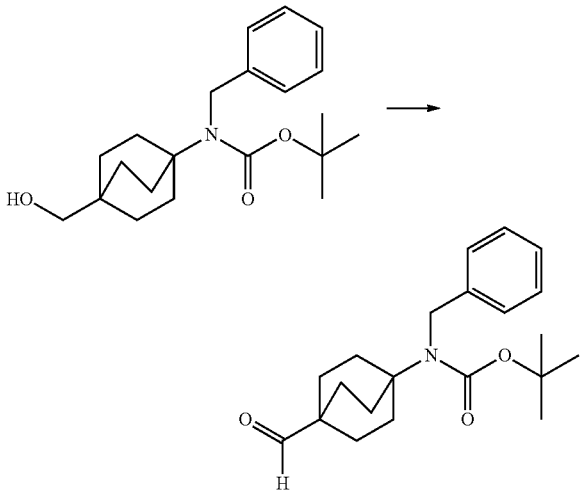

To a solution of tert-butyl benzyl(4-(hydroxymethyl)bicyclo[2.2.2]octan-1-yl) carbamate (2.30 g, 6.66 mmol) in DCM (17 mL) was added Dess-Martin periodinane (4.24 g, 9.99 mmol). After about 4 h, the reaction mixture was diluted with DCM (20 mL) and washed with saturated aqueous $NaHCO_3$ (2×30 mL), brine (30 mL), dried over anhydrous $MgSO_4$, filtered, and concd under reduced pressure. The resulting oil was purified by silica gel chromatography eluting with a gradient of 0-40% EtOAc in heptane to give tert-butyl benzyl (4-formylbicyclo[2.2.2]octan-1-yl) carbamate (1.10 g, 48%) as a clear colorless oil: LC/MS (Table 1, Method b) $R_t$=2.97 min; MS m/z: 344 $(M+H)^+$.

Step E: tert-butyl benzyl(4-((5-chloro-1-(triisopropylsilyl)-1H-pyrrolo[2,3-b]pyridin-4-yl)(hydroxy)methyl)bicyclo[2.2.2]octan-1-yl)carbamate

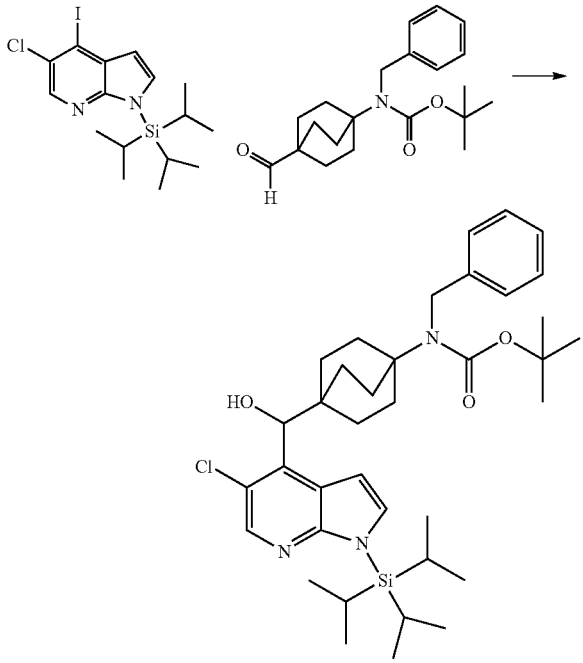

To a solution of 5-chloro-4-iodo-1-(triisopropylsilyl)-1H-pyrrolo[2,3-b]pyridine (1.33 g, 3.06 mmol, Adesis) in THF (25 mL) at about −78° C. was added n-BuLi (1.6 M solution in hexanes, 2.00 mL, 3.20 mmol) at such a rate that the internal temperature did not exceed about −70° C. The reaction mixture was stirred for about 45 min and a solution of tert-butyl benzyl(4-formylbicyclo[2.2.2]octan-1-yl)carbamate (1.05 g, 3.06 mmol) in THF (6 mL) was added dropwise. The reaction mixture was stirred at about −78° C. for about 1 h and was slowly warmed to ambient temperature and stirred for about 1 h. Saturated aqueous $NH_4Cl$ and EtOAc (10 mL each) were added and the layers were separated. The aqueous phase was extracted with EtOAc (2×10 mL) and the combined organics were washed with brine (10 mL), dried over anhydrous $MgSO_4$, filtered, and concd under reduced pressure. The remaining oil was purified by silica gel chromatography eluting with a gradient of 0-40% EtOAc in heptane to give tert-butyl benzyl(4-((5-chloro-1-(triisopropylsilyl)-1H-pyrrolo[2,3-b]pyridin-4-yl)(hydroxy)methyl)bicyclo[2.2.2]octan-1-yl)carbamate (1.27 g, 64%) as a clear colorless oil: LC/MS (Table 1, Method o) $R_t$=3.78 min; MS m/z: 652 $(M+H)^+$.

Step F: tert-butyl benzyl(4-(5-chloro-1-(triisopropylsilyl)-1H-pyrrolo[2,3-b]pyridine-4-carbonyl)bicyclo[2.2.2]octan-1-yl)carbamate

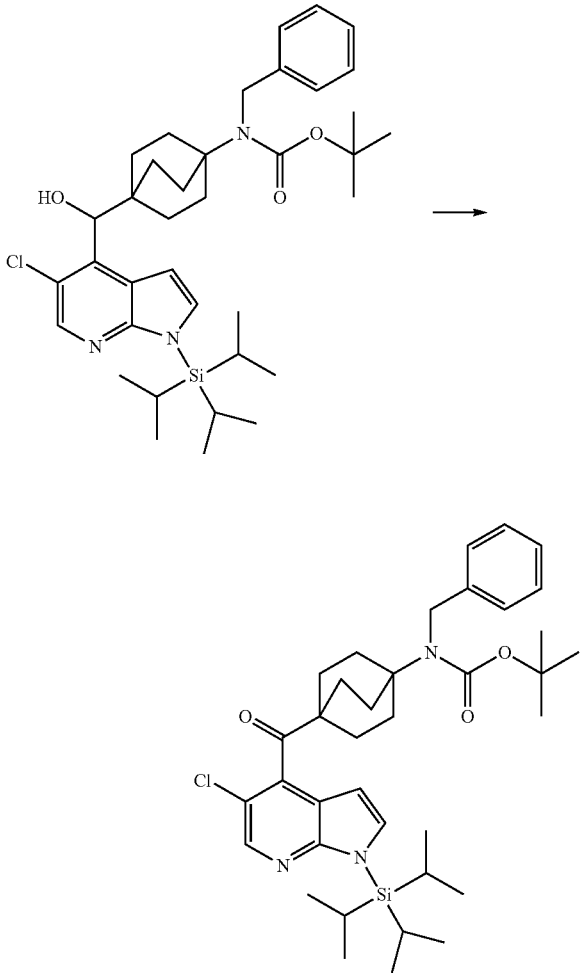

To a solution of tert-butyl benzyl(4-((5-chloro-1-(triisopropylsilyl)-1H-pyrrolo[2,3-b]pyridin-4-yl)(hydroxy)methyl)bicyclo[2.2.2]octan-1-yl)carbamate (1.26 g, 1.93 mmol) in DCM (10 mL) was added Dess-Martin periodinane (1.64 g, 3.86 mmol). The reaction was stirred at ambient temperature for about 3 h and was diluted with DCM (10 mL). The mixture was washed with saturated aqueous $NaHCO_3$ (2×15 mL), brine (15 mL), dried over anhydrous $MgSO_4$, filtered, and concd under reduced pressure. The resulting oil was purified by silica gel chromatography eluting with a gradient of 0-25% EtOAc in heptane to give tert-butyl benzyl(4-(5-chloro-1-(triisopropylsilyl)-1H-pyrrolo[2,3-b]pyridine-4-carbonyl)-bicyclo[2.2.2]octan-1-yl)carbamate (0.965 g, 77%) as a yellow oil: $^1$H NMR (400 MHz, $CDCl_3$) δ 8.15 (s, 1H), 7.32-7.24 (m, 3H), 7.23-7.08 (m, 3H), 6.23 (d, J=3.5, 1H), 4.53 (s, 2H), 2.13-2.03 (m, 6H), 1.95-1.83 (m, 6H), 1.81-1.74 (m, 3H), 1.41 (s, 9H), 1.12-1.06 (m, 18H).

Step G: tert-butyl benzyl(4-((5-chloro-1H-pyrrolo[2,3-b]pyridin-4-yl)-(hydrazono)-methyl)bicyclo[2.2.2]octan-1-yl)carbamate

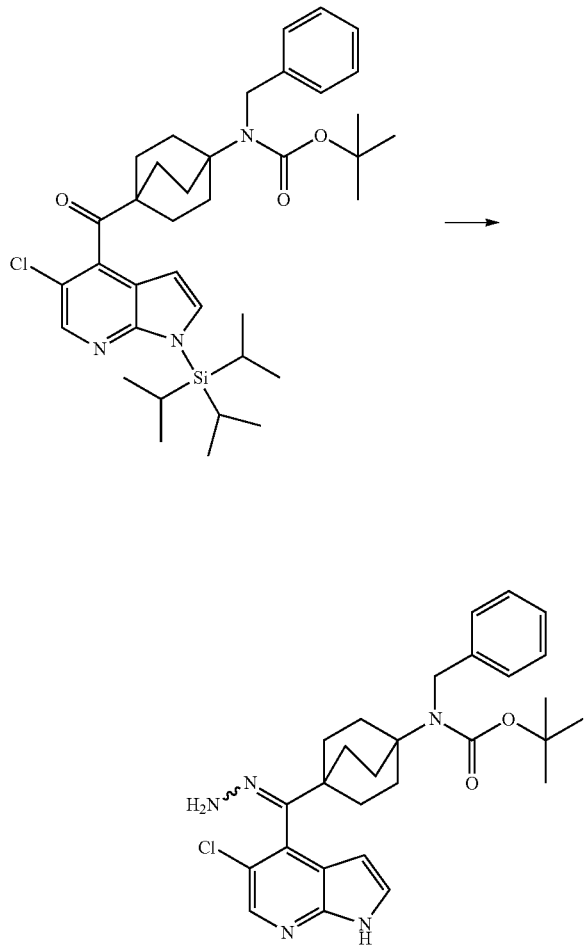

To a solution of tert-butyl benzyl(4-((5-chloro-1H-pyrrolo[2,3-b]pyridin-4-yl)(hydrazono)methyl)bicyclo[2.2.2]octan-1-yl)carbamate (0.765 g, 1.18 mmol) in EtOH (4 mL) were added hydrazine (1.85 mL, 58.8 mmol) and AcOH (0.337 mL, 5.88 mmol). The mixture was heated at about 80° C. for about 6 days. The reaction was cooled to ambient temperature and the solvent was removed under reduced pressure. EtOAc and water (5 mL each) were added and the layers were separated. The organic layer was washed with brine (5 mL), dried over anhydrous $MgSO_4$, filtered, and concd under reduced pressure. The oil was purified by silica gel chromatography eluting with a gradient of 0-10% MeOH in DCM to give tert-butyl benzyl(4-((5-chloro-1H-pyrrolo[2,3-b]pyridin-4-)(hydrazono)methyl)bicyclo[2.2.2]octan-1-yl)carbamate (0.631 g, 84%, 95% purity) as an off white solid: LC/MS (Table 1, Method b) $R_t$=2.72 min, MS m/z: 508 $(M+H)^+$.

Step H: tert-butyl benzyl(4-(3,6-dihydropyrazolo[4,3-d]pyrrolo[2,3-b]pyridine-1-yl)bicycle[2.2.2]octan-1-yl)carbamate

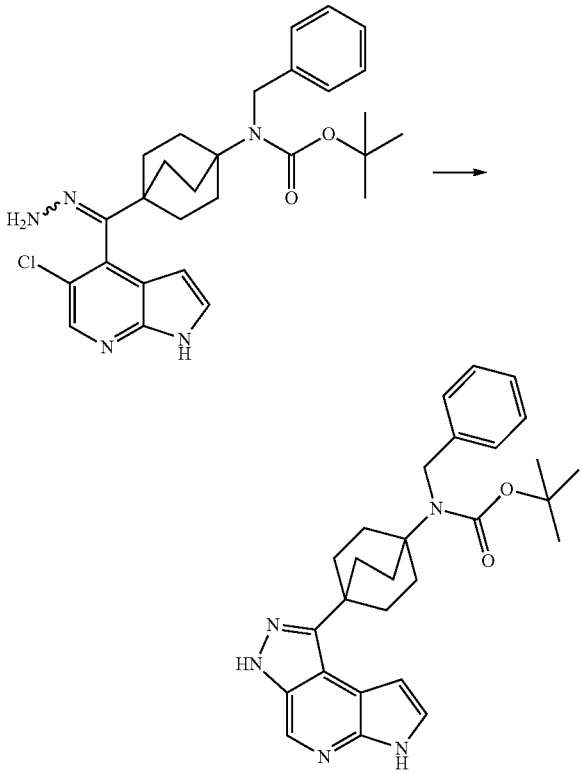

A microwave reaction vial was charged with tert-butyl benzyl(4-((5-chloro-1H-pyrrolo[2,3-b]pyridin-4-)(hydrazono)methyl)bicyclo[2.2.2]octan-1-yl)carbamate (0.700 g, 1.38 mmol) and NMP (11 mL). Sodium tert-butoxide (0.331 g, 3.44 mmol), palladium acetate (0.031 g, 0.14 mmol) and (R)-1-[(S)-2-(dicyclohexylphosphino)ferrocenyl]ethyl-di-tert-butylphosphine (0.076 g, 0.14 mmol) were each added sequentially in one portion to the solution. The reaction mixture was heated in a Biotage microwave at about 150° C. for about 2 h (250 psi maximum pressure, 1 min ramp, 150 max watts). The reaction mixture was filtered through a pad of Celite® while washing with EtOAc (15 mL), and the filtrate was concd under reduced pressure. The remaining material was transfered to a microwave vial and sodium tert-butoxide (0.331 g, 3.44 mmol), palladium acetate (0.031 g, 0.138 mmol) and (R)-1-[(S)-2-(dicyclohexylphosphino)ferrocenyl]-ethyl-di-tert-butylphosphine (0.076 g, 0.138 mmol) were added. The reaction mixture was heated in a Biotage microwave at about 160° C. for about 2 h (250 psi maximum pressure, 1 min ramp, 150 max watts). The reaction mixture was filtered through a pad of Celite® while washing with EtOAc (20 mL). Water (15 mL) was added and the layers were separated. The aqueous layer was extracted with EtOAc (2×10 mL) and the combined organic layers were washed with water (3×10 mL) and brine (5×15 mL), dried over anhydrous $MgSO_4$, filtered, and concd under reduced pressure. The dark residue was purified by silica gel chromatography eluting with a gradient of 10-100% EtOAc in heptane to give tert-butyl benzyl(4-(3,6-dihydropyrazolo[4,3-d]pyrrolo[2,3-b]pyridine-1-yl)bicycle[2.2.2]octan-1-yl)carbamate (0.281 g, 40%) as a light brown solid: LC/MS (Table 1, Method b) $R_t$=2.57 min; MS m/z: 472 $(M+H)^+$.

Step I: N-benzyl-4-(3,6-dihdropyrazolo[4,3-d]pyrrol[2,3-b]pyridine-1-yl)bicyclo[2.2.2]octan-1-amine hydrochloride

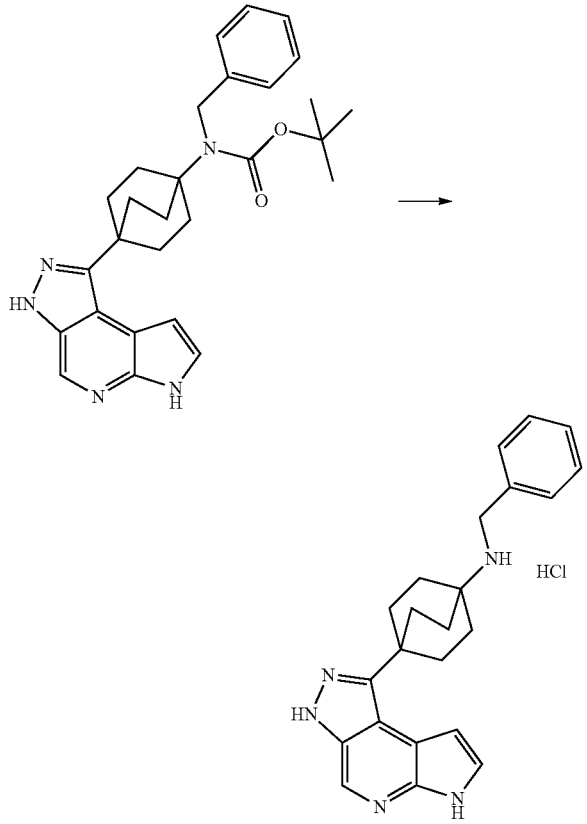

To a solution of tert-butyl benzyl(4-(3,6-dihydropyrazolo[4,3-a]pyrrolo[2,3-b]pyridin-1-yl)bicyclo[2.2.2]octan-1-yl)carbamate (0.280 g, 0.543 mmol) in 1,4-dioxane (4 mL) was added aqueous HCl (4 M in 1,4-dioxane, 0.58 mL, 2.3 mmol) and the reaction mixture was stirred at about 60° C. for about 2 h. The reaction was cooled to ambient temperature and the precipitates were filtered while washing with a minimal amount of $Et_2O$. The solid was dried under vacuum to give N-benzyl-4-(3,6-dihydropyrazolo[4,3-d]pyrrol[2,3-b]pyridine-1-yl)bicyclo[2.2.2]octan-1-amine hydrochloride (0.216 g, 98%) as a tan solid: LC/MS (Table 1, Method b) $R_t$=1.46 min; MS m/z: 372 $(M+H)^+$.

Step J: 4-(3,6-dihydropyrazolo[4,3-d]pyrrolo[2,3-b]pyridin-1-yl)bicyclo[2.2.2]octan-1-amine

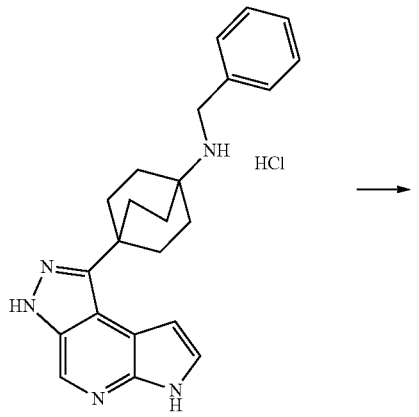

-continued

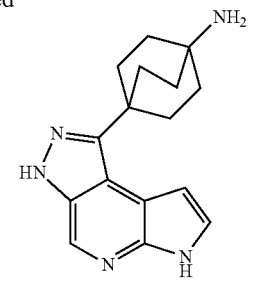

To a solution of N-benzyl-4-(3,6-dihydropyrazolo[4,3-d]pyrrolo[2,3-b]pyridin-1-yl)bicyclo[2.2.2]octan-1-amine hydrochloride (0.150 g, 0.368 mmol) in MeOH (6 mL) was added ammonium formate (0.116 g, 1.84 mmol) and 20% $PdOH_2$ on carbon (0.039 g, 0.055 mmol). The reaction mixture was heated at about 65° C. for about 2 h. The reaction mixture was filtered through a pad of Celite® while washing with EtOAc (about 10 mL) and the solvent was removed under reduced pressure. Water and EtOAc (10 mL each) were added and the layers were separated. The aqueous layer was extracted with EtOAc (5×5 mL) and the combined organics were dried over anhydrous $MgSO_4$, filtered, and concd under reduced pressure to give 4-(3,6-dihydropyrazolo[4,3-d]pyrrolo[2,3-b]pyridin-1-yl)bicyclo[2.2.2]octan-1-amine (0.073 g, 71%) as an off white foam: LC/MS (Table 1, Method b) $R_t$=1.08 min; MS m/z: 282 $(M+H)^+$.

Step K: N-(4-(3,6-dihydropyrazolo[4,3-d]pyrrolo[2,3-b]pyridin-1-yl)bicyclo[2.2.2]octan-1-yl)cyclopropanesulfonamide

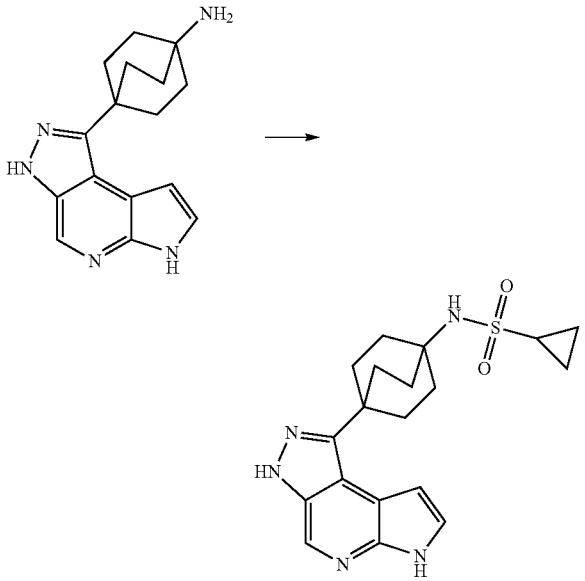

To a mixture of 4-(3,6-dihydropyrazolo[4,3-d]pyrrolo[2,3-b]pyridin-1-yl)bicyclo[2.2.2]octan-1-amine (0.075 g, 0.267 mmol) in DMF (2.5 mL) was added TEA (0.06 mL, 0.40 mmol) and cyclopropanesulfonyl chloride (0.027 mL, 0.27 mmol, Matrix). The reaction mixture was stirred at ambient temperature for about 16 h. Cyclopropanesulfonyl chloride (0.014 mL, 0.133 mmol, Matrix) was added to the reaction mixture and the reaction continued to stir at ambient temperature for about 4 h. The reaction mixture was diluted with water (10 mL) and extracted with DCM (3×10 mL). The combined organic layers were washed with brine (10 mL), dried over anhydrous $Na_2SO_4$, filtered, and concd under reduced pressure. The residue was purified by silica gel chromatography eluting with a gradient of 0-10% MeOH in DCM to give N-(4-(3,6-dihydropyrazolo[4,3-d]pyrrolo[2,3-b]pyridin-1-yl)bicyclo[2.2.2]octan-1-yl)cyclopropanesulfonamide (0.015 g, 15%) as a white solid: LC/MS (Table 1, Method b) $R_t$=1.72 min; MS m/z: 386 $(M+H)^+$.

Example #30 and 31

1-((1S,2S,4R)-2-ethyl-4-(4-methoxybenzyloxy)cyclopentyl)-3,6-dihydropyrazolo[4,3-d]pyrrolo[2,3-b]pyridine and 1-((1R,2R,4S)-2-ethyl-4-(4-methoxybenzyloxy)cyclopentyl)-3,6-dihydropyrazolo[4,3-d]pyrrolo[2,3-b]pyridine

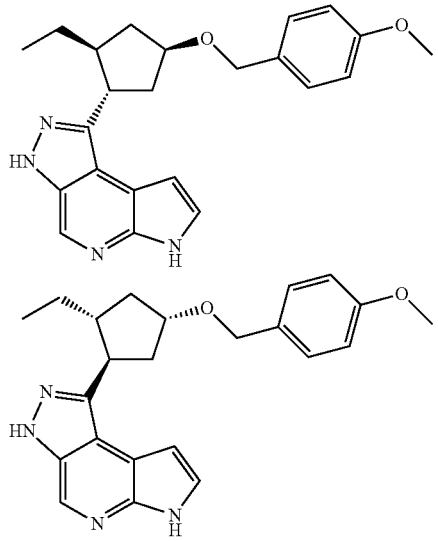

Step A: tert-butyl 2-ethyl-4-(4-methoxybenzyloxy)cyclopentanecarboxylate

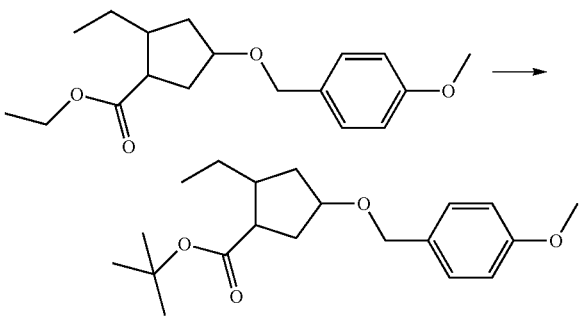

To a solution of ethyl 2-ethyl-4-(4-methoxybenzyloxy)cyclopentanecarboxylate (39.8 g, 130 mmol, Preparation #EE.1 predominantly 1S,2R,4S and 1R,2S,4R) in EtOH (286 mL) was added aqueous NaOH (2 N, 572 mL, 1140 mmol). The reaction mixture was stirred at about 50° C. for about 16 h. The reaction mixture was cooled to ambient temperature and the organic solvent was removed under reduced pressure. The aqueous layer was washed with $Et_2O$ (2×300 mL), cooled to about 0° C. in an ice bath and acidified to about pH 1 with aqueous HCl (5 N). The aqueous suspension was extracted with EtOAc (2×400 mL). The combined organics were washed with brine (200 mL), dried over anhydrous $MgSO_4$, filtered, and concd to give 34.5 g of crude solid. To a solution of the crude carboxylic acid (15.0 g, 53.9 mmol) in DMF (216 mL) was added iodomethane (6.71 mL, 108 mmol) and $K_2CO_3$ (14.9 g, 108 mmol). The reaction mixture was stirred at ambient temperature for about 48 h. Water and EtOAc (250 mL each) were added and the layers were separated. The aqueous layer was extracted with EtOAc (2×250 mL) and the combined organics were washed with water (250 mL), brine (3×250 mL), dried over anhydrous $MgSO_4$, filtered, and concd under reduced pressure. The oil was purified by silica gel chromatography eluting with a gradient of 0-50% EtOAc in heptane to give the methyl ester (14.1 g, 48.1 mmol) as a yellow oil. To a solution of methyl ester (14.1 g, 48.1 mmol) in THF (160 mL) was added potassium tert-butoxide (16.2 g, 144 mmol) and the reaction mixture was stirred at ambient temperature for about 18 h. Saturated aqueous $NH_4Cl$ (100 mL) was added and the reaction mixture was diluted with EtOAc (100 mL). The layers were separated and the organics were washed with brine (50 mL), dried over anhydrous $MgSO_4$, filtered and concd under reduced pressure. The remaining oil was purified by silica gel chromatography eluting with a gradient of 0-40% EtOAc in heptane to give tert-butyl 2-ethyl-4-(4-methoxybenzyloxy)cyclopentanecarboxylate (11.7 g, 73%, predominantly 1R,2R, 4S and 1S,2S, 4R) as a clear colorless oil: LC/MS (Table 1, Method c) $R_t$=1.95 min; MS m/z: 335 $(M+H)^+$.

Step B: 2-ethyl-4-(4-methoxybenzyloxy)cyclopentyl)methanol

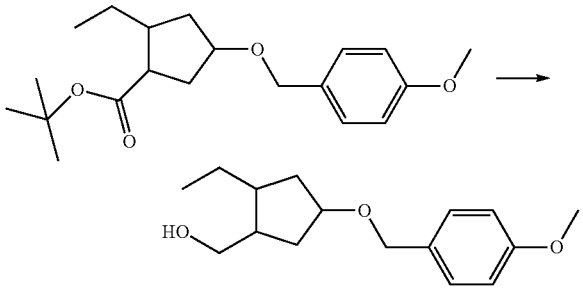

To a solution of tert-butyl 2-ethyl-4-(4-methoxybenzyloxy)cyclopentanecarboxylate (11.7 g, 35.0 mmol) in THF (175 mL) at to about 0° C. was added LAH (2 M in THF, 17.5 mL, 35.0 mmol) dropwise and the reaction mixture was slowly warmed to ambient temperature and stirred for about 1.5 h. The reaction was cooled to about 0° C. in an ice bath and quenched by a successive addition of water (150 mL dropwise), aqueous NaOH (1 N, 150 mL) and water (100 mL). The resulting mixture was warmed to ambient temperature and stirred for about 30 min. The mixture was filtered through a pad of Celite® while washing with $Et_2O$ (500 mL). The filtrate layers were separated. The organic layer was washed with brine (2×200 mL), dried over anhydrous $MgSO_4$, filtered, and concd under reduced pressure to give 2-ethyl-4-(4-methoxybenzyloxy)cyclopentyl)methanol (8.62 g, 93%) as a yellow oil: LC/MS (Table 1, Method b) $R_t$=2.29 min; MS m/z: 265 $(M+H)^+$.

Step C: 2-ethyl-4-(4-methoxybenzyloxy)cyclopentanecarbaldehyde

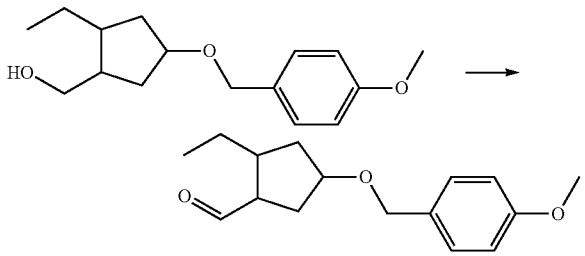

To a solution of 2-ethyl-4-(4-methoxybenzyloxy)cyclopentyl)methanol (8.60 g, 32.5 mmol) in DCM (163 mL) was added Dess-Martin periodinane (20.7 g, 48.8 mmol). The reaction mixture was stirred at ambient temperature for about 2.5 h. The reaction mixture was diluted with DCM (100 mL), washed with saturated aqueous $NaHCO_3$ (2×150 mL) and brine (150 mL), dried over anhydrous $MgSO_4$, filtered, and concd under reduced pressure. The resulting oil was purified by silica gel chromatography eluting with a gradient of 0-50% EtOAc in heptane to give 2-ethyl-4-(4-methoxybenzyloxy)cyclopentanecarbaldehyde (6.93 g, 81%) as a yellow oil: LC/MS (Table 1, Method b) $R_t$=2.59 min; MS m/z: 263 $(M+H)^+$.

Step D: (5-chloro-1-(triisopropylsilyl)-1H-pyrrolo[2,3-b]pyridin-4-yl)-2-ethyl-4-(4-methoxybenzyloxy)cyclopentyl)methanol

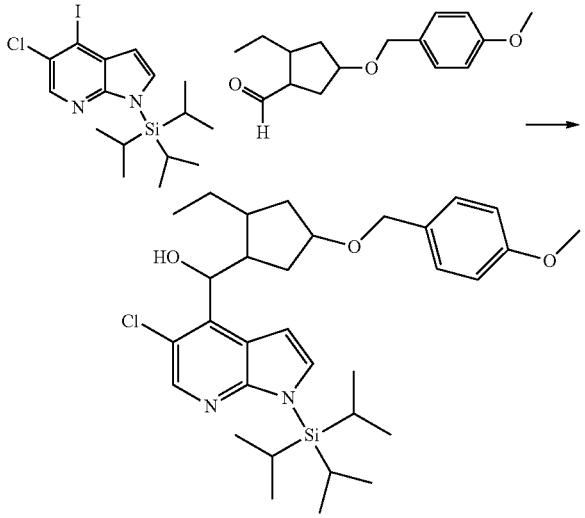

To a solution of 5-chloro-4-iodo-1-(triisopropylsilyl)-1H-pyrrolo[2,3-b]pyridine (4.99 g, 11.5 mmol, Adesis) in THF (90 mL) at about −78° C. was added n-BuLi (1.6 M solution in hexanes, 10.7 mL, 17.2 mmol) at such a rate that the internal temperature did not exceed about −70° C. After stirring for about 45 min at about −78° C. a solution of 2-ethyl-4-(4-methoxybenzyloxy)cyclopentanecarbaldehyde (3.00 g, 11.4 mmol) in THF (22 mL) was added dropwise and the reaction mixture was stirred at about −78° C. for about 1 h. The reaction was slowly warmed to ambient temperature and stirred for about 0.5 h. The reaction mixture was cooled to about −78° C., saturated aqueous $NH_4Cl$ (40 mL) was added, and the mixture was warmed to rt. Water (10 mL) was added and the layers were separated. The aqueous phase was extracted with EtOAc (3×50 mL). The combined organics were washed with brine (50 mL), dried over anhydrous $MgSO_4$, filtered and concd under reduced pressure. The crude oil was purified by silica gel chromatography eluting with a gradient of 0-40% EtOAc in heptane to give (5-chloro-1-(triisopropylsilyl)-1H-pyrrolo[2,3-b]pyridin-4-yl)-2-ethyl-4-(4-methoxybenzyloxy)cyclopentyl) methanol (4.47 g, 68%, 92% purity) as a yellow oil: LC/MS (Table 1, Method o) $R_t$=2.64 min; MS m/z: 571 $(M+H)^+$.

Step E: (5-chloro-1-(triisopropylsityl)-1H-pyrrolo[2,3-b]pyridin-4-yl)-2-ethyl-4-(4-methoxybenzyloxy) cyclopentyl)methanone

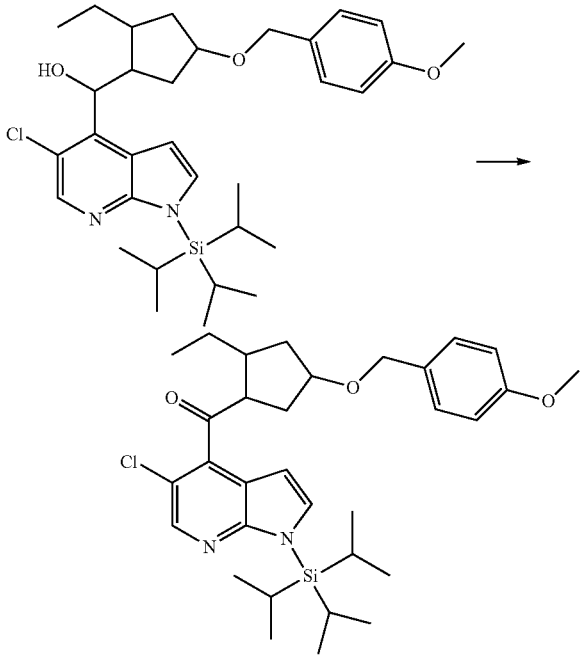

To a solution of (5-chloro-1-(triisopropylsilyl)-1H-pyrrolo[2,3-1)]pyridin-4-yl)-2-ethyl-4-(4-methoxybenzyloxy) cyclopentyl)methanone (4.47 g, 7.20 mmol) in DCM (40 mL) was added Dess-Martin periodinane (4.58 g, 10.8 mmol). The reaction mixture was stirred at ambient temperature for about 90 min. The reaction was diluted with DCM (40 mL), washed with saturated aqueous $NaHCO_3$ (2×60 mL), brine (40 mL), dried over anhydrous $MgSO_4$, filtered, and concd under reduced pressure. The crude material was purified by silica gel chromatography eluting with a gradient of 0-40% EtOAc in heptane to give (5-chloro-1-(triisopropylsilyl)-1H-pyrrolo[2,3-b]pyridin-4-yl)-2-ethyl-4-(4-methoxybenzyloxy)-cyclopentyl)methanone (3.32 g, 81%) as a yellow oil: LC/MS (Table 1, Method o) $R_t$=3.04 min; MS m/z: 569 $(M+H)^+$.

Step F: 5-chloro-4-2-ethyl-4-(4-methoxybenzyloxy) cyclopentyl)-(hydrazono)methyl)-1H-pyrrolo[2,3-b] pyridine

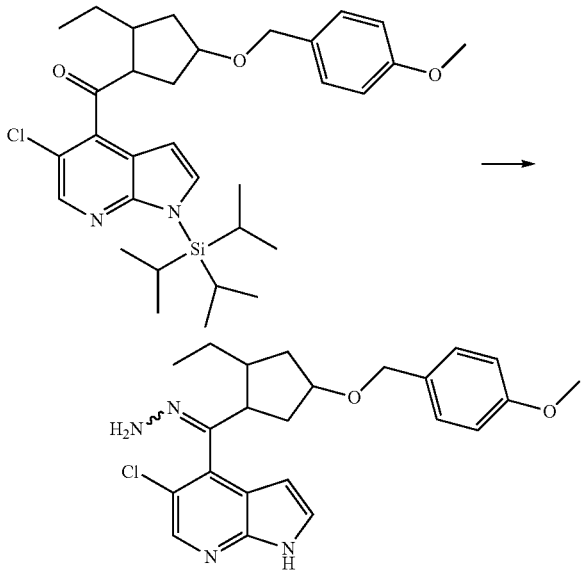

To a solution of (5-chloro-1-(triisopropylsilyl)-1H-pyrrolo[2,3-b]pyridin-4-yl)-2-ethyl-4-(4-methoxybenzyloxy) cyclopentyl)methanone (1.01 g, 1.77 mmol) in EtOH (5.5 mL) were added hydrazine (2.78 mL, 89.0 mmol) and AcOH (0.508 mL, 8.87 mmol). The reaction mixture was heated at about 80° C. for about 18 h. The reaction was cooled to ambient temperature and the solvent was removed under reduced pressure. Water (20 mL) and EtOAc (25 mL) were added and the layers were separated. The organic layer was washed with saturated aqueous $NaHCO_3$ and brine (15 mL each), dried over anhydrous $MgSO_4$, filtered and concd under reduced pressure. The crude oil was purified silica gel chromatography eluting with a gradient of 0-10% MeOH in DCM to give 5-chloro-4-((2-ethyl-4-(4-methoxybenzyloxy) cyclopentyl)-(hydrazono)methyl)-1H-pyrrolo[2,3-b]pyridine (0.354 g, 47%) as a yellow foam: LC/MS (Table 1, Method b) $R_t$=2.40 min, MS m/z: 427 $(M+H)^+$.

Step G: 1-01S,2S,4R)-2-ethyl-4-(4-methoxybenzyloxy)cyclopentyl)-3,6-dihydropyrazolo[4,3-d]pyrrolo [2,3-b]pyridine and 1-((1R,2R,4S)-2-ethyl-4-(4-methoxybenzyloxy)cyclopentyl)-3,6-dihydropyrazolo[4,3-d]pyrrolo[2,3-b]pyridine

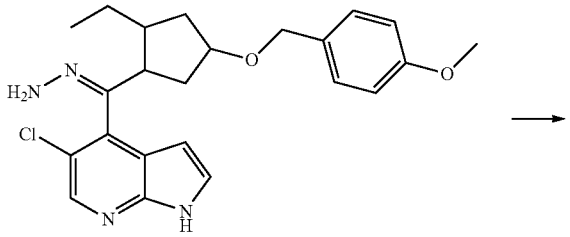

-continued

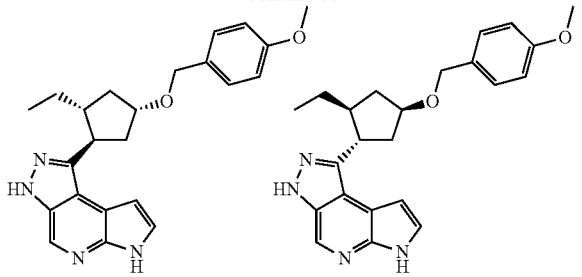

A microwave reaction vial was charged with 5-chloro-4-((2-ethyl-4-(4-methoxybenzyloxy)cyclopentyl)(hydrazono)methyl)-1H-pyrrolo[2,3-b]pyridine (0.900 g, 2.11 mmol) and NMP (14.1 mL). Sodium tert-butoxide (0.506 g, 5.27 mmol), palladium(II) acetate (0.047 g, 0.211 mmol) and ((R)-1-[(S)-2-(dicyclohexylphosphino)ferrocenyl]ethyl-di-tert-butylphosphine (0.117 g, 0.211 mmol) were added sequentially and the mixture was heated in a microwave at about 150° C. for about 1 h (250 psi maximum pressure, 1 min ramp, 150 max watts). EtOAc (20 mL) was added and the mixture was filtered through a pad of Celite® while washing with EtOAc (20 mL). Water (15 mL) was added and the layers were separated. The aqueous layer was extracted with EtOAc (2×10 mL), the combined organics were washed with water (3×10 mL), brine (5×10 mL), dried over anhydrous $MgSO_4$, filtered and concd under reduced pressure. The residue was purified by silica gel chromatography eluting with a gradient of 40-100% EtOAc in heptane followed by purification using General Procedure AA to give 1-((1S,2S,4R)-2-ethyl-4-(4-methoxybenzyloxy)cyclopentyl)-3,6-dihydropyrazolo[4,3-d]pyrrolo[2,3-b]pyridine or 1-((1R,2R,4S)-2-ethyl-4-(4-methoxybenzyloxy)cyclopentyl)-3,6-dihydropyrazolo[4,3-d]pyrrolo[2,3-b]pyridine (0.065 g, 8%, Table 2, Method 35, $R_t$=20.0 min, or =positive) and 1-((1S,2S,4R)-2-ethyl-4-(4-methoxybenzyloxy)cyclopentyl)-3,6-dihydropyrazolo[4,3-d]pyrrolo[2,3-b]pyridine or 1-((1R,2R,4S)-2-ethyl-4-(4-methoxybenzyloxy)cyclopentyl)-3,6-dihydropyrazolo[4,3-d]pyrrolo[2,3-b]pyridine (0.058 g, 7%, Table 2, Method 35, $R_t$=23.4 min, or =negative): LC/MS (Table 1, Method b) $R_t$=2.26 min; MS m/z: 391 $(M+H)^+$.

Example #32

N-cyano-N-((1S,3R,4S)-3-ethyl-4-(6H-pyrrolo[2,3-e][1,2,4]triazolo[4,3-a]pyrazin-1-yl)cyclopentyl)cyclopropanesulfonamide

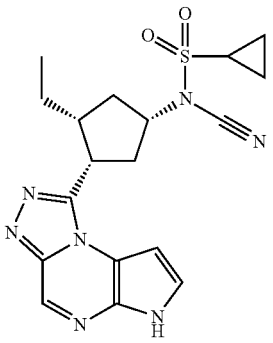

To the solution of N-((1S,3R,4S)-3-ethyl-4-(6H-pyrrolo[2,3-e][1,2,4]triazolo[4,3-a]pyrazin-1-yl)cyclopentyl)cyclopropanesulfonamide (0.05 g, 0.134 mmol, WO2009152133) in DMF (4 mL), KOH (0.022 g, 0.401 mmol) was added and the mixture was stirred at rt for about 5 min. Tosyl cyanide (0.024 g, 0.134 mmol) was added and stirring was continued for about 2 h. The solvent was removed under reduced pressure and the residue purified by preparative HPLC (Table 1, Method q) to yield N-cyano-N-((1S,3R,4S)-3-ethyl-4-(6H-pyrrolo[2,3-e][1,2,4]triazolo[4,3-a]pyrazin-1-yl)cyclopentyl)cyclopropanesulfonamide (0.0025 g, 5%) as an off-white solid: LC/MS (Table 1, Method a) $R_t$=1.84 min; MS m/z: 400 $(M+H)^+$.

Example #33*

N-((1S,3R,4S)-3-ethyl-4-(2,3,4,7-tetrahydro-1H-pyrrolo[2,3-h][1,6]naphthyridin-1-yl)cyclopentyl)cyclopropanesulfonamide

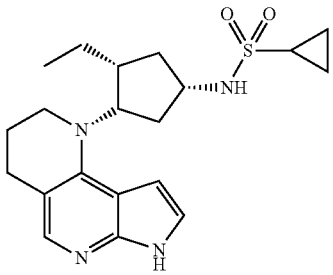

Step A: 4-chloro-1-tosyl-1H-pyrrolo[2,3-b]pyridine-5-carbaldehyde

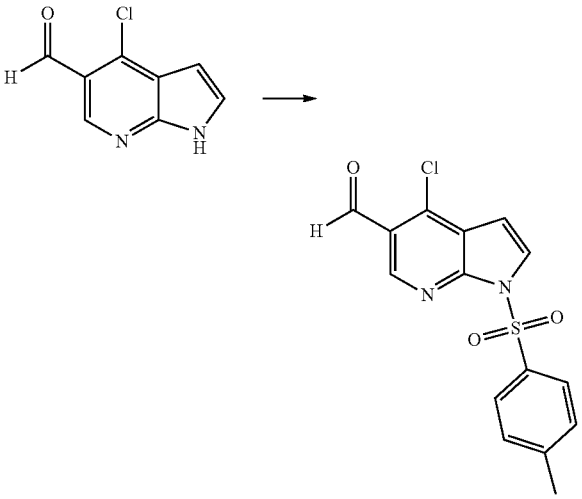

To a suspension of 4-chloro-1H-pyrrolo[2,3-b]pyridine-5-carbaldehyde (2.00 g, 11.1 mmol, Adesis) in DMF (30 mL) was added NaH (60% dispersion in mineral oil, 0.500 g, 12.5 mmol) forming a yellow solution. The reaction mixture was stirred at ambient temperature for about 30 min then 4-methylbenzene-1-sulfonyl chloride (2.40 g, 12.6 mmol) was added. The reaction mixture was stirred at ambient temperature for about 30 min and poured into ice water (about 50 mL). The solid was collected via vacuum filtration, while washing with water (about 15 mL), and dried in a vacuum oven to give 4-chloro-1-tosyl-1H-pyrrolo[2,3-b]pyridine-5-carbaldehyde (3.22 g, 87%) as an off white solid: LC/MS (Table 1, Method b) $R_t$=2.56 min; MS m/z: 335 $(M+H)^+$.

Step B: (E/Z)-5-(2-(1,3-dioxotan-2-yl)vinyl)-4-chloro-1-tosyl-1H-pyrrolo[2,3-b]pyridine

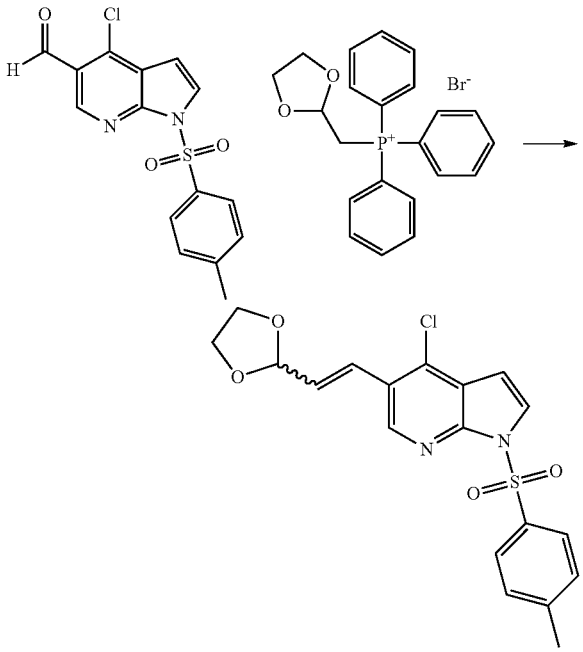

A round bottom flask was charged with ((1,3-dioxolan-2-yl)methyl)triphenylphosphonium bromide (5.29 g, 12.3 mmol) and THF (29.0 mL). The flask was cooled to about 0° C. in an ice bath and potassium tert-butoxide (1.38 g, 12.3 mmol) was added. The mixture was stirred for about 30 min at about 0° C. and a suspension of 4-chloro-1-tosyl-1H-pyrrolo[2,3-b]pyridine-5-carbaldehyde (1.50 g, 4.48 mmol) in THF (8.30 mL) was added dropwise. The reaction was warmed to ambient temperature and stirred for about 16 h. Aqueous sodium hydroxide (2 M, 4.50 mL, 9.00 mmol) was added and the reaction mixture was heated to about 55° C. for about 1 h. Water and ether (10 mL each) were added and the layers were separated. The aqueous phase was extracted with ether (3×10 mL), the combined organics were dried over anhydrous $Na_2SO_4$ and filtered. About 50% of the solvent was removed under reduced pressure and the remaining organic was filtered through silica gel washing with ether (about 15 mL). The filtrate was concentrated under reduced pressure. The residue was purified by silica gel chromatography eluting with a gradient of 0-50% EtOAc in DCM to give a white solid. The solid was dissolved in DMF (12 mL) and NaH (60% dispersion in mineral oil, 0.179 g, 4.49 mmol) was added. The reaction mixture was stirred at ambient temperature for about 30 min then 4-methylbenzene-1-sulfonyl chloride (0.684 g, 3.59 mmol) was added. The reaction was stirred at ambient temperature for about 30 min and poured into ice water (about 30 mL). EtOAc (30 mL) was added and the layers were separated. The aqueous phase was further extracted with EtOAc (2×30 mL) and the combined organics were washed with brine (2×20 mL), dried over anhydrous $MgSO_4$, filtered and concentrated under reduced pressure. The resulting oil was purified by silica gel chromatography eluting with a gradient of 0-50% EtOAc in heptane to give (E/Z)-5-(2-(1,3-dioxolan-2-yl)vinyl)-4-chloro-1-tosyl-1H-pyrrolo[2,3-b]pyridine (0.90 g, 50%) as an off white foam: LC/MS (Table 1, Method b) $R_t$=2.65 min; MS m/z: 405 $(M+H)^+$ and $R_t$=2.70 min; MS m/z: 405 $(M+H)^+$.

Step C: 5-(2-(1,3-dioxolan-2-yl)ethyl)-4-chloro-1-tosyl-1H-pyrrolo[2,3-b]pyridine

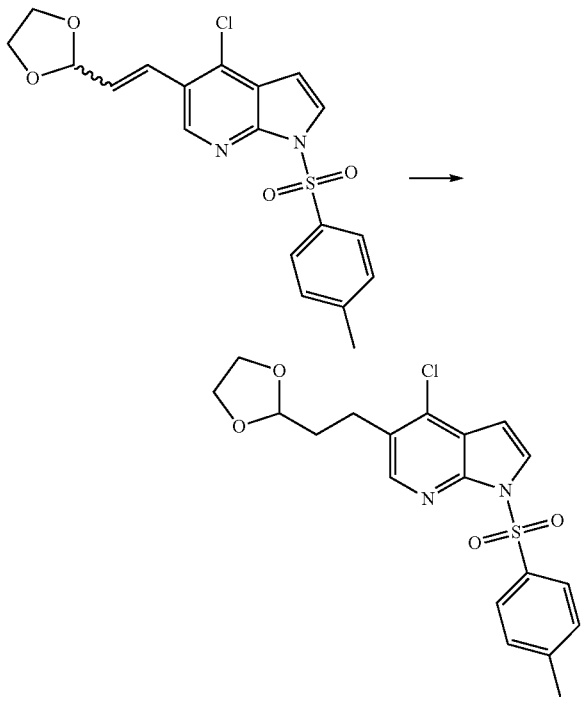

A mixture of (E/Z)-5-(2-(1,3-dioxolan-2-yl)vinyl)-4-chloro-1-tosyl-1-pyrrolo[2,3-b]pyridine (0.900 g, 2.22 mmol) and 10 wt % Pd/C (0.118 g, 0.111 mmol) was purged with $N_2$ and evacuated under vacuum (3×). After the third evacuation EtOAc (23 mL) was added. The flask was purged with $N_2$ and evacuated under vacuum (3×). After the 3rd evacuation the flask was placed under a hydrogen atmosphere for about 1 h. The hydrogen atmosphere was replaced with $N_2$ and the reaction mixture was filtered through a pad of Celite® washing with EtOAc (about 10 mL) and the filtrate was concentrated under reduce pressure to give 5-(2-(1,3-dioxolan-2-yl)ethyl)-4-chloro-1-tosyl-1H-pyrrolo[2,3-b]pyridine (0.530 g, 59%) as a thick oil which solidified upon standing: LC/MS (Table 1, Method b) $R_t$=2.71 min; MS m/z: 407 $(M+H)^+$.

Step D: 3-(4-chloro-1-tosyl-1H-pyrrolo[2,3-b]pyridin-5-yl)propanal

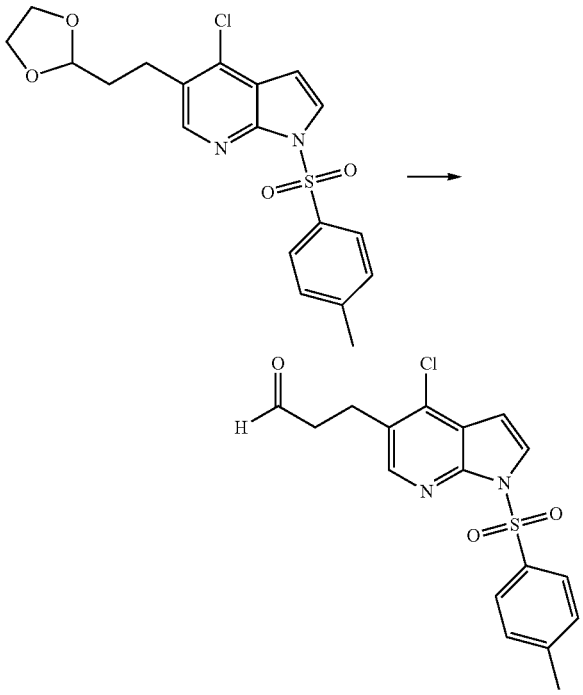

To a solution of 5-(2-(1,3-dioxolan-2-yl)ethyl)-4-chloro-1-tosyl-1H-pyrrolo[2,3-b]pyridine (0.520 g, 1.28 mmol) in THF (4.2 mL) was added aqueous HCl (6 M, 0.639 mL, 3.83 mmol). The reaction mixture was stirred at ambient temperature for about 2 h and was heated to about 50° C. for about 1 h. The reaction was cooled to ambient temperature and water (0.64 mL) was added and the reaction stirred for about 16 h. The pH was adjusted to about 7 with saturated aqueous $NaHCO_3$ and EtOAc (and 10 mL) was added. The layers were separated and the aqueous phase was extracted with EtOAc (10 mL). The combined organics were dried over anhydrous $MgSO_4$, filtered and concentrated under reduced pressure. Acetone (12 mL) and pyridinium p-toluenesulfonate (0.096 g, 0.383 mmol) were added. The reaction was heated at reflux for about 2 h. The reaction was cooled to ambient temperature and concentrated under reduced pressure. The residue was purified by silica gel chromatography eluting with a gradient of 0-50% EtOAc in DCM to give 3-(4-chloro-1-tosyl-1H-pyrrolo[2,3-b]pyridin-5-yl)propanal (0.44 g, 84%, 90% purity) as an off white foam: LC/MS (Table 1, Method b) $R_t$=2.50 min; MS m/z: 363 $(M+H)^+$.

Step E: N-((1S,3S,4R)-3-(3-(4-chloro-1-tosyl-1H-pyrrolo[2,3-b]pyridin-5-yl)propylamino)-4-ethylcyclopentyl)cyclopropanesulfonamide

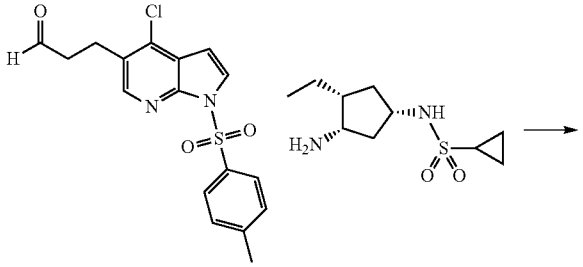

-continued

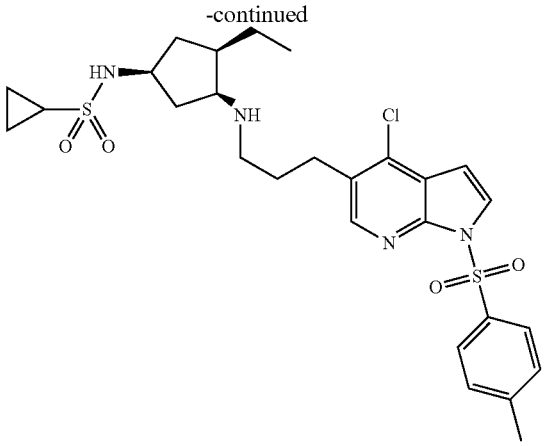

To a mixture of 3-(4-chloro-1-tosyl-1H-pyrrolo[2,3-b]pyridin-5-yl)propanal (0.420 g, 1.04 mmol) and N-((1S,3S,4R)-3-amino-4-ethylcyclopentyl)cyclopropanesulfonamide (0.290 g, 1.25 mmol, prepared using OOO from Example #23 step E with NaOH) in DCE (4.00 mL) was added glacial acetic acid (0.089 mL, 1.6 mmol). The reaction mixture stirred for about 15 min at ambient temperature and sodium triacetoxyborohydride (0.331 g, 1.56 mmol) was added. The reaction was left stirring at ambient temperature for about 72 h. Saturated aqueous $NaHCO_3$ (about 5 mL) was slowly added followed by DCM (5 mL). The layers were separated and the aqueous phase was extracted with DCM (2×5 mL). The combined organics were dried over anhydrous $MgSO_4$, filtered and concentrated under reduced pressure. The remaining yellow oil was purified by silica gel chromatography eluting with a gradient of 0-50% EtOAc in heptane to give N-((1S,3S,4R)-3-(3-(4-chloro-1-tosyl-1H-pyrrolo[2,3-b]pyridin-5-yl)propylamino)-4-ethylcyclopentyl)cyclo-propanesulfonamide (0.330 g, 55%) as a white foam: LC/MS (Table 1, Method b) $R_t$=2.10 min; MS m/z: 579 $(M+H)^+$.

Step F: N-((1S,3R,4S)-3-ethyl-4-(7-tosyl-2,3,4,7-tetrahydro-1H-pyrrolo[2,3-h][1,6]naphthyridin-1-yl)cyclopentyl)cyclopropanesulfonamide

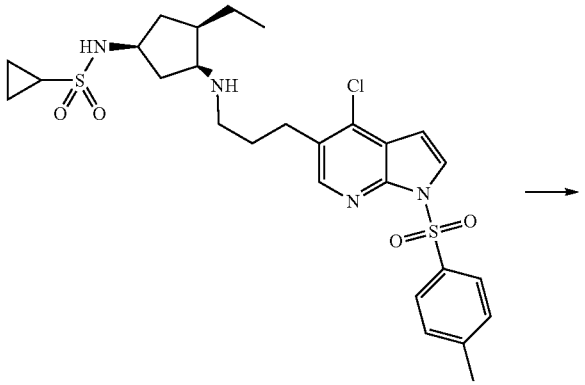

-continued

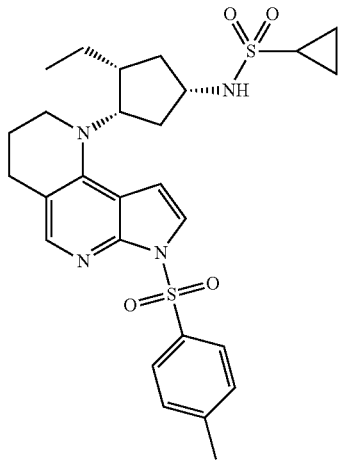

A microwave vial was charged with a solution of N-((1S,3S,4R)-3-(3-(4-chloro-1-tosyl-1H-pyrrolo[2,3-b]pyridin-5-yl)propylamino)-4-ethylcyclopentyl)cyclopropanesulfonamide (0.200 g, 0.345 mmol) in 1-propanol (1.70 mL). DIEA (0.180 mL, 1.04 mmol) and potassium iodide (0.057 g, 0.345 mmol) were added and the reaction mixture was heated in a Biotage® microwave at about 150° C. for about 30 min. The reaction was resubmitted to microwave heating at about 180° C. for about 1 h. The reaction was resubmitted to microwave heating at about 180° C. for about 10 h. The reaction mixture was transferred to a round bottom flask and silica gel (about 1 g) was added. The solvent was removed under reduced pressure and the resulting silica gel mixture was purified by silica gel chromatography eluting with a gradient of 0-10% MeOH in DCM to give N-((1S,3R,4S)-3-ethyl-4-(7-tosyl-2,3,4,7-tetrahydro-1H-pyrrolo[2,3-h][1,6]naphthyridin-1-yl)cyclopentyl)cyclopropanesulfonamide (0.050 g, 27%) as a yellow foam: LC/MS (Table 1, Method b) $R_t$=2.52 min; MS m/z: 543 $(M+H)^+$.

Step G: N-((1S,3R,4S)-3-ethyl-4-(2,3,4,7-tetrahydro-1H-pyrrolo[2,3-h][1,6]naphthyridin-1-yl)cyclopentyl)cyclopropanesulfonamide

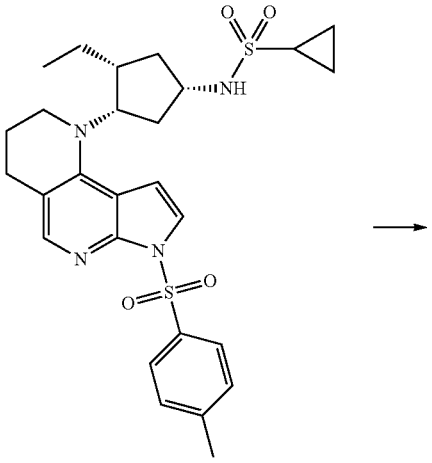

-continued

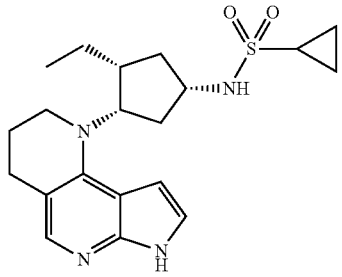

To a solution of N-((1S,3R,4S)-3-ethyl-4-(7-tosyl-2,3,4,7-tetrahydro-1H-pyrrolo[2,3-h][1,6]naphthyridin-1-yl)cyclopentyl)cyclopropanesulfonamide (0.041 g, 0.076 mmol) in 1,4-dioxane was added aqueous NaOH (5 N, 0.106 mL, 0.529 mmol). The reaction was heated to about 80° C. for about 16 h. The reaction mixture was cooled to ambient temperature and water (5 mL) and EtOAc (10 mL) were added. The layers were separated and the aqueous phase was extracted with EtOAc (2×10 mL). The combined organics were dried over anhydrous $MgSO_4$, filtered, and concentrated under reduced pressure. The residue was purified by silica gel chromatography eluting with a gradient of 0-10% MeOH in DCM to give N-((1S,3R,4S)-3-ethyl-4-(2,3,4,7-tetrahydro-1H-pyrrolo[2,3-h][1,6]naphthyridin-1-yl)cyclopentyl)cyclopropane-sulfonamide (0.02 g, 72%) as a white solid: LC/MS (Table 1, Method a) $R_t$=1.48 min; MS m/z: 389 $(M+H)^+$.

Example #34*

N-((1S,3S,4R)-3-(2,3-dihydrodipyrrolo[2,3-b:2',3'-d]pyridin-1(6H)-yl)-4-ethylcyclopentyl)cyclopropane-sulfonamide

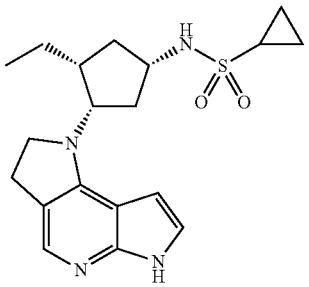

Step A: 4-chloro-1-tosyl-1H-pyrrolo[2,3-b]pyridine-5-carbaldehyde

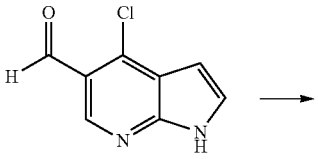

-continued

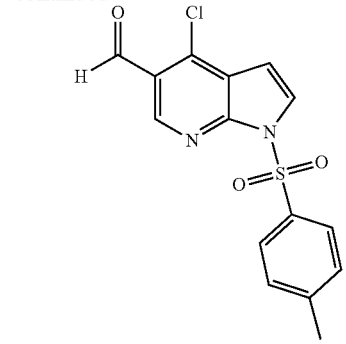

To a suspension of 4-chloro-1H-pyrrolo[2,3-b]pyridine-5-carbaldehyde (2.00 g, 11.1 mmol, Adesis) in DMF (30 mL) was added NaH (60% dispersion in mineral oil, 0.500 g, 12.5 mmol) forming a yellow solution. The reaction mixture was stirred at ambient temperature for about 30 min then 4-methylbenzene-1-sulfonyl chloride (2.40 g, 12.6 mmol) was added. The reaction mixture was stirred at ambient temperature for about 30 min and poured into ice water (about 50 mL). The solid was collected via vacuum filtration, while washing with water (about 15 mL), and dried in a vacuum oven to give 4-chloro-1-tosyl-1H-pyrrolo[2,3-b]pyridine-5-carbaldehyde (3.22 g, 87%) as an off white solid: LC/MS (Table 1, Method b) $R_t$=2.56 min; MS m/z: 335 $(M+H)^+$.

Step B: (E/Z)-4-chloro-5-(2-methoxyvinyl)-1-tosyl-1H-pyrrolo[2,3-b]pyridine

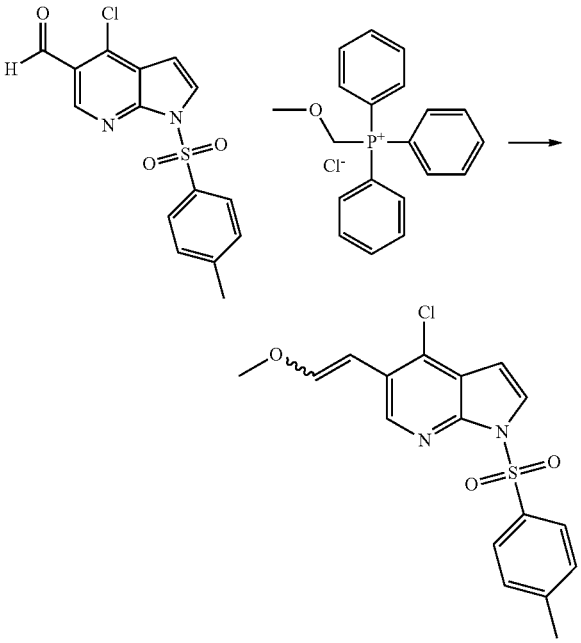

To a suspension of (methoxymethyl)triphenylphosphonium chloride (1.28 g, 3.73 mmol) in THF (14.8 mL) at about 0° C. was added dropwise potassium tert-butoxide (1 M solution in THF, 3.70 mL, 3.70 mmol). The reaction mixture was stirred for about 30 min at about 0° C. and a suspension of 4-chloro-1-tosyl-1H-pyrrolo[2,3-b]pyridine-5-carbaldehyde (1.00 g, 2.99 mmol) in THF (1.80 mL) was added. The reaction mixture was warmed to ambient temperature and stirred for about 4 h. The reaction was neutralized with 1 M aqueous HCl and then EtOAc and water (10 mL each) were added. The layers were separated and the aqueous phase was extracted with EtOAc (2×10 mL). The combined organics were dried over anhydrous $MgSO_4$, filtered and concentrated under reduced pressure. The remaining solid was purified by silica gel chromatography eluting with a gradient of 0-50% EtOAc in heptane to give (E/Z)-4-chloro-5-(2-methoxyvinyl)-1-tosyl-1H-pyrrolo[2,3-b]pyridine (0.96 g, 89%) as an off white solid: LC/MS (Table 1, Method b) $R_t$=2.83 min; MS m/z: 363 $(M+H)^+$ and $R_t$=2.86 min; MS m/z: 363 $(M+H)^+$ Step C: N-((1S,3S,4R)-3-(2-(4-chloro-1-tosyl-1H-pyrrolo[2,3-b]pyridin-5-yl)ethylamino)-4-ethylcyclopentyl)cyclopropanesulfonamide

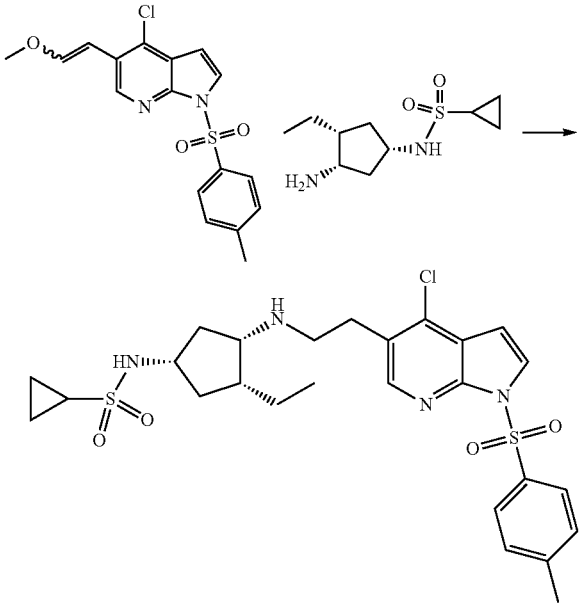

To a mixture of (E/Z)-4-chloro-5-(2-methoxyvinyl)-1-tosyl-1H-pyrrolo[2,3-b]pyridine (0.95 g, 2.62 mmol) in THF (26 mL) was added aqueous HCl (1 M, 6.55 mL, 6.55 mmol). The reaction mixture was heated at reflux for about 16 h. The reaction was cooled to ambient temperature and the pH was adjusted to about 7 with saturated aqueous $NaHCO_3$. DCM (about 30 mL) was added and the layers were separated. The aqueous phase was extracted with DCM (2×20 mL). The combined organics were dried over anhydrous $Na_2SO_4$, filtered, and concentrated under reduced pressure. The residue was taken up in DCE (13 mL) and N-((1S,3S,4R)-3-amino-4-ethylcyclopentyl)cyclopropanesulfonamide (0.608 g, 2.62 mmol, prepared using OOO from Example #23 step E with NaOH) and glacial acetic acid (0.150 mL, 2.62 mmol) were added. Sodium triacetoxyborohydride (0.832 g, 3.93 mmol) was added and the reaction was left stirring at ambient temperature for about 16 h. The reaction was diluted with DCM (20 mL) and saturated aqueous $NaHCO_3$ (20 mL) was added. The layers were separated and the aqueous phase was extracted with DCM (2×10 mL). The combined organics were washed with brine (10 mL), dried over anhydrous $MgSO_4$, filtered and concentrated under reduced pressure. The residue was purified by silica gel chromatography eluting with a gradient of 25-100% EtOAc in heptane to give N-((1S,3S,4R)-3-(2-(4-chloro-1-tosyl-1H-pyrrolo[2,3-b]pyridin-5-yl)ethylamino)-4-ethylcyclopentyl)cyclopropanesulfonamide (0.45 g, 30%) as an off white solid: LC/MS (Table 1, Method a) $R_t$=1.87 min; MS m/z: 565 $(M+H)^+$.

Step D: N-((1S,3S,4R)-3-(2,3-dihydrodipyrrolo[2,3-b:2',3'-d]pyridin-1(6H)-yl)-4-ethylcyclopentyl)cyclopropanesulfonamide

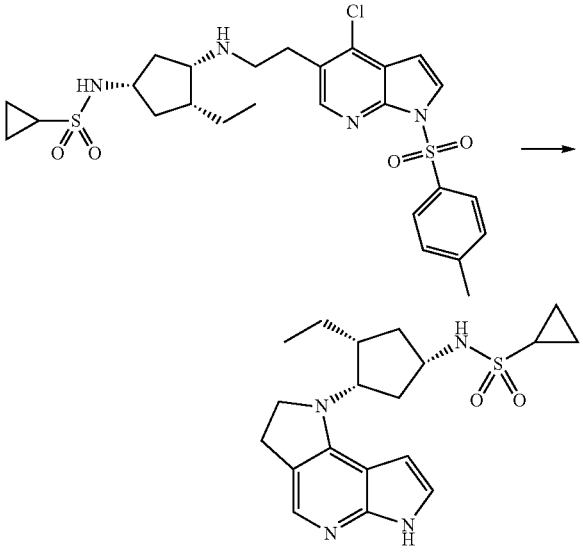

A microwave vial was charged with a solution of N-((1S,3S,4R)-3-(2-(4-chloro-1-tosyl-1H-pyrrolo[2,3-b]pyridin-5-yl)ethylamino)-4-ethylcyclopentyl)cyclopropanesulfonamide (0.350 g, 0.619 mmol) in 1-propanol (3.2 mL). DIPEA (0.324 mL, 1.86 mmol) and potassium iodide (0.154 g, 0.929 mmol) were added and the reaction was heated in a Biotage® microwave for about 10 h at about 180° C. EtOAc and water (10 mL each) were added to the reaction mixture and the layers were separated. The aqueous phase was extracted with EtOAc (2×10 mL). The combined organics were dried over anhydrous $MgSO_4$, filtered and concentrated under reduced pressure. The residue was purified by silica gel chromatography eluting with a gradient of 0-100% DCM/MeOH/Et2NH (950/45/5) in DCM and the solvent was removed under reduced pressure. The solid was further purified by preparative HPLC (Table 1, Method w) to give to give N-((1S,3S,4R)-3-(2,3-dihydrodipyrrolo[2,3-b:2',3'-d]pyridin-1(6H)-yl)-4-ethylcyclopentyl)cyclopropanesulfonamide with 30 mol % ammonium acetate as an excipient (0.099 g, 38%) as a white solid: LC/MS (Table 1, Method a) $R_t$=1.70 min; MS m/z: 375 $(M+H)^+$.

Example #35 and #35.1

1-((1S,2R,4S)-4-(3-cyclopropyl-1H-1,2,4-triazol-1-yl)-2-ethylcyclopentyl)-6H-pyrrolo[2,3-e][1,2,4]triazolo[4,3-a]pyrazine and 1-((1S,2R,4S)-4-(5-cyclopropyl-1H-1,2,4-triazol-1-yl)-2-ethylcyclopentyl)-6H-pyrrolo[2,3-e][1,2,4]triazolo[4,3-a]pyrazine

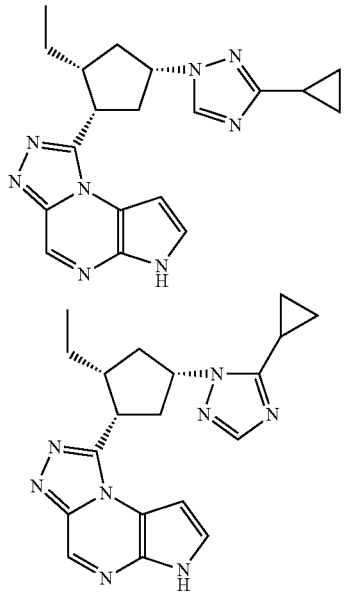

Step A: ethyl 8-ethyl-1,4-dioxaspiro[4.4]nonane-7-carboxylate

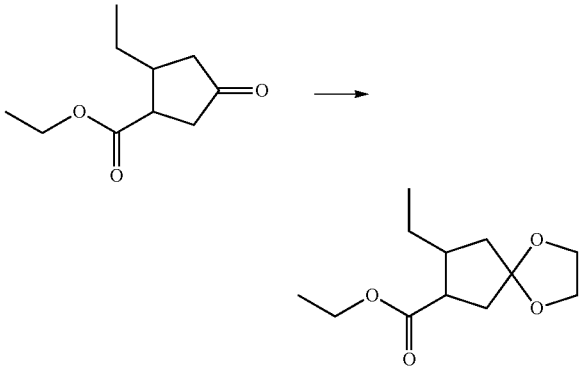

A round bottom flask was charged with ethyl 2-ethyl-4-oxocyclopentanecarboxylate (1.5 g, 8.1 mmol, Example #22, Step B) in DCM (22 mL). To the flask were added ethylene glycol (0.91 mL, 16 mmol), triethylorthoformate (2.0 mL, 12 mmol), and p-toluenesulfonic acid monohydrate (0.31 g, 1.6 mmol). The reaction mixture was stirred at rt for about 24 h. The solution was concd under reduced pressure to give brown oil that was dissolved in EtOAc and purified by silica gel chromatography eluting with a gradient of 0-50% EtOAc in heptane. The product containing fractions were combined and concd to dryness under reduced pressure to give ethyl 8-ethyl-1,4-dioxaspiro[4,4]nonane-7-carboxylate as a light yellow oil (1.6 g, 83%): LC/MS (Table 1, Method c) MS m/z 229 $(M+H)^+$; $^1H$ NMR (CDCl) δ 4.14 (q, 2H), 3.90 (m, 4H), 2.99 (q, 1H), 2.32-2.27 (m, 1H), 2.26-2.11 (m, 1H), 2.05-1.99 (m, 1H), 1.96-1.91 (m, 1H), 1.83-1.78 (m, 1H), 1.46-1.39 (m, 1H), 1.31-1.24 (m, 1H), 1.26 (t, 3H), 0.90 (t, 3H).

Step B: 8-ethyl-1,4-dioxaspiro[4.4]nonane-7-carboxylic acid

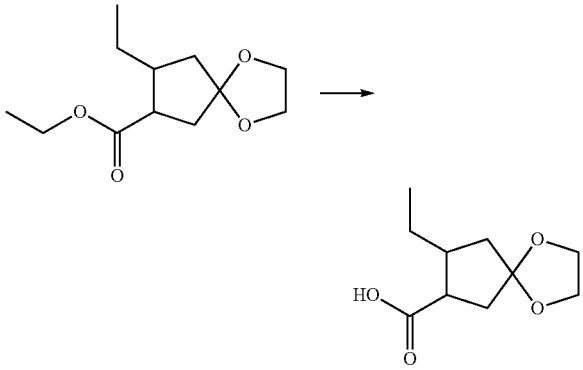

A round bottom flask was charged with ethyl 8-ethyl-1,4-dioxaspiro[4.4]nonane-7-carboxylate (0.32 g, 1.4 mmol) and sodium hydroxide (aqueous 1 N, 14.0 mL, 14.0 mmol). The solution was stirred overnight at rt. To the solution was added DCM (30 mL) followed by the addition of 20% aqueous citric acid (about 20 mL) to reach pH of about 2. The layers were separated and the aqueous solution was extracted with DCM (2×30 mL) and DCM/EtOAc (1:1, 30 mL). The combined extracts were dried over anhydrous $MgSO_4$, filtered, and concd under reduced pressure to give 8-ethyl-1,4-dioxaspiro[4,4]nonane-7-carboxylic acid as a clear, colorless oil (0.27 g, 96%): LC/MS (Table 1, Method c) $R_t$=1.20 min; MS m/z: 201 $(M+H)^+$.

Step C: 8-ethyl-N'-(5-tosyl-5H-pyrrolo[2,3-b]pyrazin-2-yl)-1,4-dioxaspiro[4.4]nonane-7-carbohydrazide

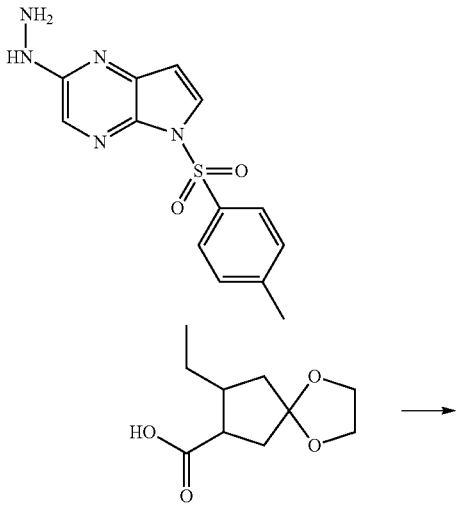

-continued

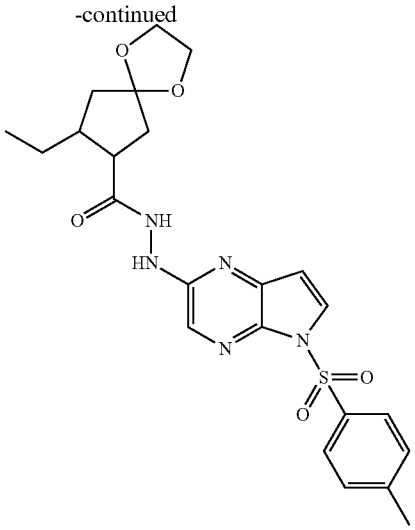

A 50 mL round bottom flask was charged with 2-hydrazinyl-5-tosyl-5H-pyrrolo[2,3-b]pyrazine (0.350 g, 1.16 mmol, Example #1, Step D), 8-ethyl-1,4-dioxaspiro[4.4]nonane-7-carboxylic acid (0.250 g, 1.25 mmol), and DCM (6.0 mL). To the reaction mixture was added HATU (0.483 g, 1.27 mmol) and TEA (0.64 mL, 4.6 mmol) and the resulting yellow suspension was stirred at rt for about 3 h. To the reaction solution was added DCM (25 mL) and the solution was washed with water and brine (20 mL each). The organic layer was dried over anhydrous $MgSO_4$, filtered, and concd under reduced pressure to give a brown oil. The crude product was purified by silica gel chromatography eluting with a gradient of: 0-10% MeOH in DCM. The product containing fractions were concd under reduced pressure to give 8-ethyl-N'-(5-tosyl-5H-pyrrolo[2,3-b]pyrazin-2-yl)-1,4-dioxaspiro[4.4]nonane-7-carbohydrazide as a foam (0.50 g, 89%): LC/MS (Table 1, Method c) $R_t$=1.49 min; MS m/z: 486 $(M+H)^+$.

Step D: 1-(8-ethyl-1,4-dioxaspiro[4.4]nonan-7-yl)-6-tosyl-6H-pyrrolo[2,3-e][1,2,4]triazolo[4,3-a]pyrazine

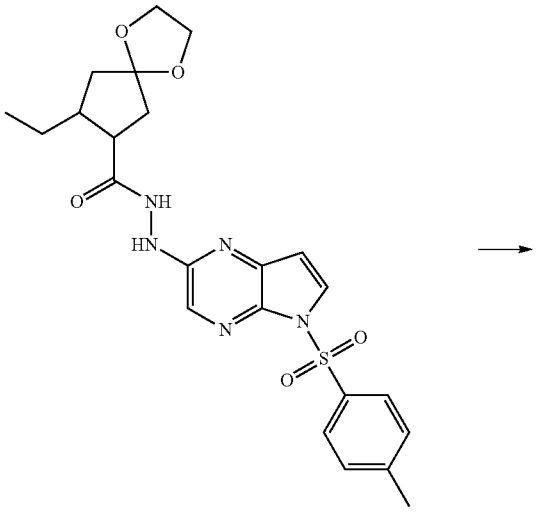

-continued

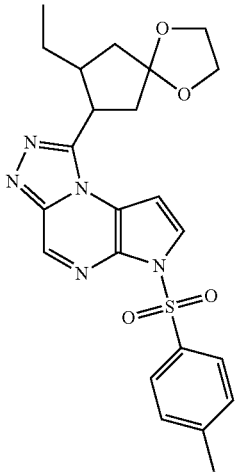

A round bottom flask was charged with 8-ethyl-N-(5-tosyl-5H-pyrrolo[2,3-b]pyrazin-2-yl)-1,4-dioxaspiro[4.4]nonane-7-carbohydrazide (4.90 g, 10.1 mmol) and 1,4-dioxane (50 mL). To the flask was added DIEA (8.81 mL, 50.5 mmol) followed by the addition of thionyl chloride (0.770 mL, 10.6 mmol). The mixture was heated to about 75° C. for about 90 min. Additional thionyl chloride (0.074 mL, 1.0 mmol) was added and heating was continued for about 1 h. The reaction was cooled to rt and stirred overnight. The solution was diluted with DCM (75 mL) and washed with water (50 mL). The layers were separated and the organic layer was dried over anhydrous $MgSO_4$, filtered, and concd under reduced pressure to give a dark brown oil. The crude product was purified via flash silica gel chromatography eluting with a gradient of 0-60% acetone in heptane. The product containing fractions were combined and concd to give material that was loaded onto a second column eluting with a gradient of 0-60% acetone in heptane. The product containing fractions were combined and concd under reduced pressure to give 1-(8-ethyl-1,4-dioxaspiro[4.4]nonan-7-yl)-6-tosyl-6H-pyrrolo[2,3-e][1,2,4]triazolo[4,3-a]pyrazine as a tan powder (3.0 g, 64%): LC/MS (Table 1, Method c) $R_t$=1.44 min; MS m/z: 468 $(M+H)^+$.

Step E: 1-(8-ethyl-1,4-dioxaspiro[4.4]nonan-7-yl)-6H-pyrrolo[2,3-e][1,2,4]triazolo[4,3-a]pyrazine

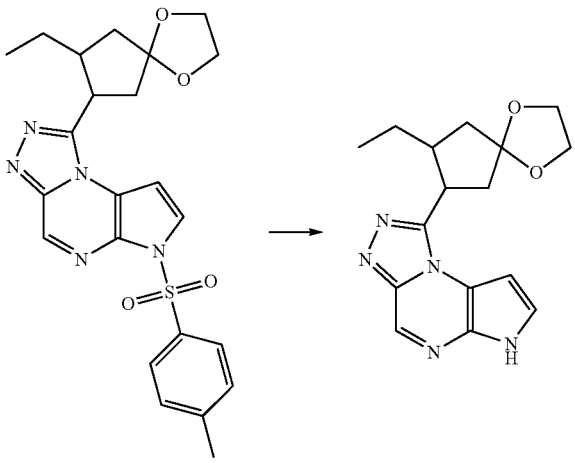

To the solution of 1-(8-ethyl-1,4-dioxaspiro[4.4]nonan-7-yl)-6-tosyl-6H-pyrrolo[2,3-e][1,2,4]triazolo[4,3-a]pyrazine (3.76 g, 8.04 mmol) in 1,4-dioxane (55 mL), aqueous sodium hydroxide solution (2N, 12 mL) was added and the reaction mixture was heated at about 60° C. for about 90 min. The solvent was removed and the residue partitioned between saturated solution of ammonium chloride in water and EtOAc (75 mL each). The aqueous phase was further washed with EtOAc (60 mL); the combined organic extracts were washed with brine (65 mL), dried over anhydrous magnesium sulfate, filtered, and concentrated to yield a brown solid. The solid was triturated in ether (20 mL) and the precipitate was collected by filtration and dried to yield 1-(8-ethyl-1,4-dioxaspiro[4.4]nonan-7-yl)-6H-pyrrolo[2,3-e][1,2,4]triazolo[4,3-a]pyrazine (2.22 g, 88%) as a beige solid. LC/MS (Table 1, Method a) $R_t$=1.71 min; MS m/z: 314 $(M+H)^+$.

Step F: 1-(8-ethyl-1,4-dioxaspiro[4.4]nonan-7-yl)-6-((2-(trimethylsilyl)ethoxy)methyl)-6H-pyrrolo[2,3-e][1,2,4]triazolo[4,3-a]pyrazine

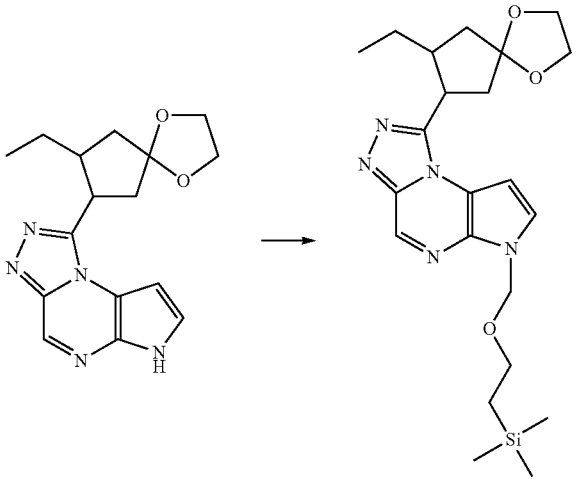

To a suspension of sodium hydride (60% dispersion in mineral oil, 0.355 g, 8.87 mmol) in DMF (45 mL), the solution of 1-(8-ethyl-1,4-dioxaspiro[4.4]nonan-7-yl)-6H-pyrrolo[2,3-e][1,2,4]triazolo[4,3-a]pyrazine (2.78 g, 8.87 mmol) in DMF (45 mL) was added dropwise at about 0° C. and the resulting solution was stirred at this temperature for about 20 min. SEM Cl (1.75 mL, 8.87 mmol) was added dropwise and the resulting mixture was stirred overnight while being gradually warmed up. The solvent was removed under reduced pressure and the residue was partitioned between EtOAc and water (120 mL each). The aqueous phase was further washed with EtOAc (50 mL); the combined organic extracts were washed with brine (100 mL), dried over anhydrous magnesium sulfate, filtered, and concentrated to yield 1-(8-ethyl-1,4-dioxaspiro[4.4]nonan-7-yl)-6-((2-(trimethylsilyl)ethoxy)methyl)-6H -pyrrolo[2,3-e][1,2,4]triazolo[4,3-a]pyrazine (3.87 g, 98%) as a brown amorphous solid. LC/MS (Table 1, Method a) $R_t$=2.49 min; MS m/z: 444 $(M+H)^+$.

Step G: 3-ethyl-4-(6-((2-(trimethylsilyl)ethoxy)methyl)-6H-pyrrolo[2,3-e][1,2,4]triazolo[4,3-a]pyrazin-1-yl)cyclopentanone

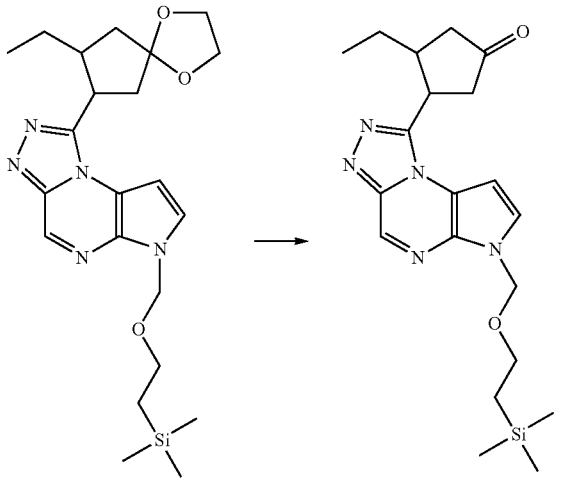

To a solution of 1-(8-ethyl-1,4-dioxaspiro[4.4]nonan-7-yl)-6-((2-(trimethylsilyl)ethoxy)methyl)-6H-pyrrolo[2,3-e][1,2,4]triazolo[4,3-a]pyrazine (3.87 g, 8.72 mmol) in THF (30 mL), was added aqueous HCl (1N, 26.2 mL) at about 0° C. The ice bath was removed and the reaction was stirred at ambient temperature for about 6 h. THF was removed under reduced pressure. The aqueous phase was neutralized by the addition of saturated aqueous $NaHCO_3$ and was extracted with EtOAc (2×50 mL). The combined organic extracts were washed with brine (60 mL), dried over anhydrous $MgSO_4$, filtered, and concentrated. The residue was purified by silica gel column chromatography using 20 to 80% EtOAc in DCM to yield 3-ethyl-4-(6-((2-(trimethylsilyl)ethoxy)methyl)-6H-pyrrolo[2,3-e][1,2,4]triazolo[4,3-a]pyrazin-1-yl)cyclopentanone (2.84 g, 81%) as a yellow amorphous solid. LC/MS (Table 1, Method a) $R_t$=2.44 min; MS m/z: 400 $(M+H)^+$.

Step H: 3-ethyl-4-(6-((2-(trimethylsilyl)ethoxy)methyl)-6H-pyrrolo[2,3-e][1,2,4]triazolo[4,3-a]pyrazin-1-yl)cyclopentanone

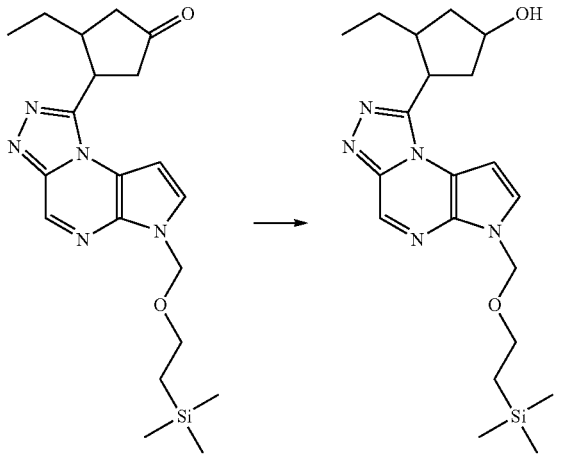

A solution of 3-ethyl-4-((6-((2-(trimethylsilyl)ethoxy)methyl)-6H-pyrrolo[2,3-e][1,2,4]triazolo[4,3-a]pyrazin-1-yl)cyclopentanone (0.296 g, 0.741 mmol) in THF (2.96 mL) was cooled to about 0° C. and to it was added DIBAL-H (1M in cyclohexane, 1.482 mL, 1.482 mmol). The reaction was stirred for about 45 min. The reaction was quenched with MeOH (3 mL). To the reaction mixture was added saturated aqueous $NH_4Cl$ (10 mL) and EtOAc (10 mL). The organic layer was collected and washed with brine (10 mL), dried over anhydrous $MgSO_4$, filtered and concentrated under reduced pressure to provide the crude material. The crude material was purified by silica gel column chromatography using 0-5% MeOH/$CH_2Cl_2$ to provide a scalemic mixture enriched in (1S,3R,4S)-3-ethyl-4-(6-((2-(trimethylsilyl)ethoxy)methyl)-6H-pyrrolo[2,3-e][1,2,4]triazolo[4,3-a]pyrazin-1-yl)cyclopentanol (148 mg, 0.369 mmol, 50%) and a scalemic mixture enriched in (1R,3R,4S)-3-ethyl-4-(6-((2-(trimethylsilyl)ethoxy)methyl)-6H-pyrrolo[2,3-e][1,2,4]triazolo[4,3-a]pyrazin-1-yl)cyclopentanol (60 mg, 0.149 mmol, 20%) both as amorphous solids. LC/MS (Table 1, Method a) $R_t$=2.37 min; MS m/z: 402 $(M+H)^+$ and $R_t$=2.16 min; MS m/z: 402 $(M+H)^+$ respectively.

Step I: 3-ethyl-4-(6-((2-(trimethylsilyl)ethoxy)methyl)-6H-pyrrolo[2,3-e][1,2,4]triazolo[4,3-a]pyrazin-1-yl)cyclopentyl methanesulfonate

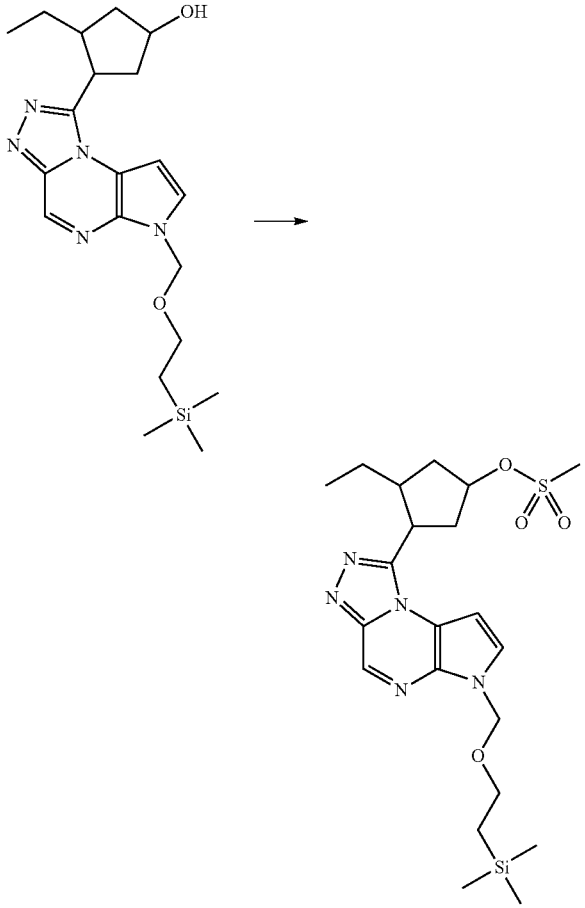

To a solution of the scalemic mixture enriched in (1R,3R,4S)-3-ethyl-4-(6-((2-(trimethylsilyl)ethoxy)methyl)-6H-pyrrolo[2,3-e][1,2,4]triazolo[4,3-a]pyrazin-1-yl)cyclopentanol (0.5 g, 1.245 mmol) and TEA (0.347 mL, 2.49 mmol) in DCM (13 mL) was added MsCl (0.107 mL, 1.37 mmol) dropwise, and the reaction mixture was stirred at room temperature overnight. The solvent was removed under reduced pressure and the residue purified by silica gel column chromatography using 10 to 70% EtOAc in DCM to yield 3-ethyl-4-(6-((2-(trimethylsilyl)ethoxy)methyl)-6H-pyrrolo[2,3-e][1,2,4]triazolo[4,3-a]pyrazin-1-yl)cyclopentyl methanesulfonate (0.48 g, 80%) as a white amorphous solid. LC/MS (Table 1, Method a) $R_t$=2.54 min; MS m/z: 480 $(M+H)^+$ Step J: 1-((1S,2R,4S)-4-(3-cyclopropyl-1H-1,2,4-triazol-1-yl)-2-ethylcyclopentyl)-6H-pyrrolo[2,3-e][1,2,4]triazolo[4,3-a]pyrazine and 1-((1S,2R,4S)-4-(5-cyclopropyl-1H-1,2,4-triazol-1-yl)-2-ethylcyclopentyl)-6H-pyrrolo[2,3-e][1,2,4]triazolo[4,3-a]

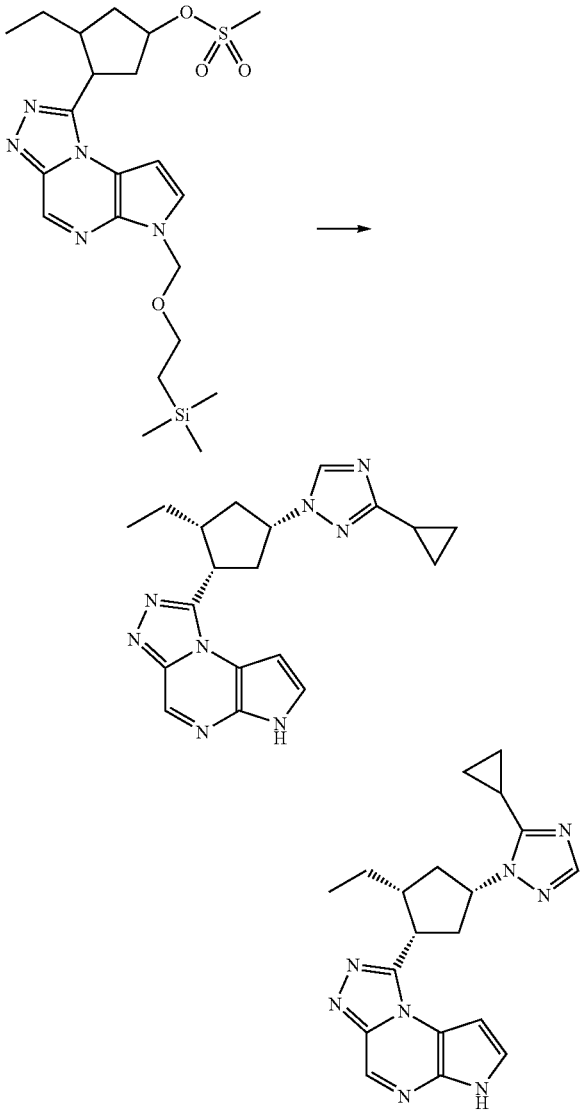

To a solution of 3-cyclopropyl-1H-1,2,4-triazole (0.054 g, 0.494 mmol) in DMF (3 mL), sodium hydride (0.019 g, 0.486 mmol, 60% dispersion in mineral oil) was added at about 0° C. and the reaction mixture was stirred for about 10 min. The temperature was raised to about 50° C. and 3-ethyl-4-(6-((2-(trimethylsilyl)ethoxy)methyl)-6H-pyrrolo[2,3-e][1,2,4]triazolo[4,3-a]pyrazin-1-yl)cyclopentyl methanesulfonate (0.079 g, 0.165 mmol) was added. The reaction mixture was stirred at about 75° C. overnight. The solvent was removed under reduced pressure and the residue partitioned between water and EtOAc (10 mL each). The aqueous phase was further washed with EtOAc (7 mL); the combined extracts were washed with brine (10 mL), dried over anhydrous $MgSO_4$, filtered and concentrated under reduced pressure to yield a mixture of 1-(4-(3-cyclopropyl-1H-1,2,4-triazol-1-yl)-2-ethylcyclopentyl)-6-((2-(trimethylsilyl)ethoxy)methyl)-6H-pyrrolo[2,3-e][1,2,4]triazolo[4,3-a]pyrazine and 1-(4-(5-cyclopropyl-1H-1,2,4-triazol-1-yl)-2-ethylcyclopentyl)-6-((2-(trimethylsilyl)ethoxy)methyl)-6H-pyrrolo[2,3-e][1,2,4]triazolo[4,3-a]pyrazine. This mixture was dissolved in DCM (3 mL) and 2 mL of trifluoroacetic acid was added. The resulting mixture was stirred at ambient temperature for about 2 h. The solvents were removed under reduced pressure. The residue was dissolved in 1,4-dioxane (3 mL); 2 mL of concentrated $NH_4OH$ (4 mL) solution in water was added. The mixture was heated at about 60° C. for about 2 hours. The solvents were removed under reduced pressure and the residue was purified by HPLC (Table 2, Method 32) to yield 1-((1S,2R,4S)-4-(3-cyclopropyl-1H-1,2,4-triazol-1-yl)-2-ethylcyclopentyl)-6H-pyrrolo[2,3-e][1,2,4]triazolo[4,3-a]pyrazine (0.028 g, 25% yield) [Example #35] and 1-((1S,2R,4S)-4-(5-cyclopropyl-1H-1,2,4-triazol-1-yl)-2-ethylcyclopentyl)-6H-pyrrolo[2,3-e][1,2,4]triazolo[4,3-a]pyrazine (0.013 g, 12% yield) [Example #35.1]both as white solids. LC/MS (Table 1, Method a) $R_t$=1.74 min; MS m/z: 363 $(M+H)^+$ and LC/MS (Table 1, Method a) $R_t$=1.73 min; MS m/z: 363 $(M+H)^+$ Examples #36 and #37

(3S,4R)-3-ethyl-4-(6H-pyrrolo[2,3-e][1,2,4]triazolo[4,3-a]pyrazin-1-yl)-N-(2,2,2-trifluoroethyl)pyrrolidine-1-carboxamide and (3R,4S)-3-ethyl-4-(6H-pyrrolo[2,3-e][1,2,4]triazolo[4,3-a]pyrazin-1-yl)-N-(2,2,2-trifluoroethyl)pyrrolidine-1-carboxamide

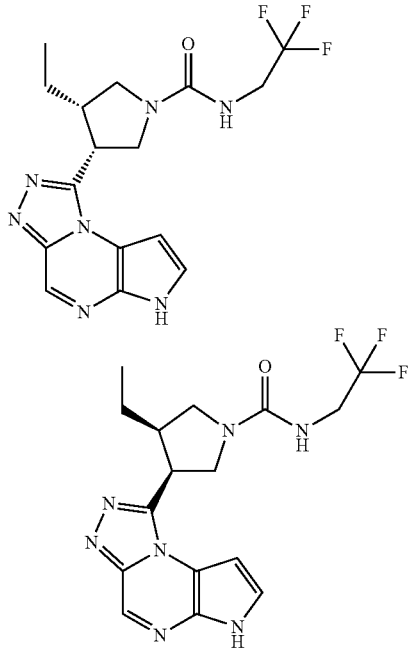

Step A: (Z)-ethyl pent-2-enoate

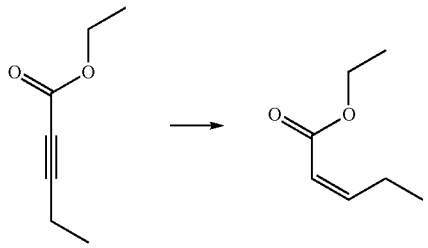

To a slurry of Lindlar catalyst (0.844 g, 0.396 mmol) in THF (100 mL) and pyridine (10.00 mL) was added ethyl pent-2-ynoate (5.22 mL, 39.6 mmol). The reaction mixture was sparged with hydrogen for about 10 min and an atmosphere of hydrogen was maintained via balloon. After about 15 h the reaction mixture was filtered through a pad of Celite®, diluted with $Et_2O$ (30 mL) and washed with saturated aqueous $CuSO_4$ (40 mL), followed by water (40 mL). The organic layer was separated, dried over anhydrous $MgSO_4$, filtered, and concd in vacuo to provide crude (Z)-ethyl pent-2-enoate (5 g, 98%). $^1$H NMR (DMSO-$d_6$) δ 1.05 (t, 3H), 1.28 (t, 3H), 2.65 (m, 2H), 4.18 (q, 2H), 5.72 (m, 1H), 6.21 (m, 1H).

Step B: (cis)-ethyl 1-benzyl-4-ethylpyrrolidine-3-carboxylate

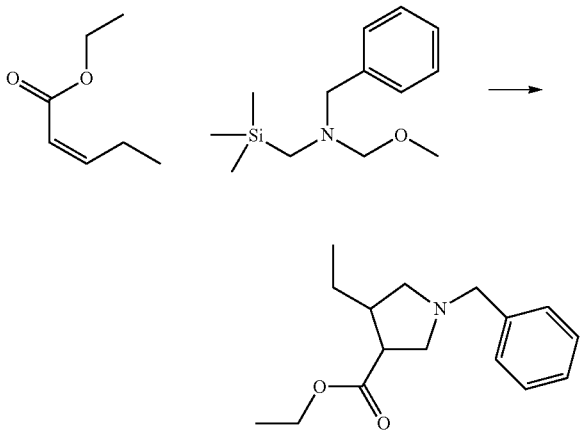

To a solution of N-benzyl-1-methoxy-N-((trimethylsilyl)methyl)methanamine (9.98 mL, 39.0 mmol) and (Z)-ethyl pent-2-enoate (5 g, 39.0 mmol) in DCM (50 mL) was added TFA (0.030 mL, 0.390 mmol) at rt. After about 2 days, the reaction mixture was concd in vacuo to provide crude (cis)-ethyl 1-benzyl-4-ethylpyrrolidine-3-carboxylate (9.8 g, 96%) as an oil. LC/MS (Table 1, Method a) $R_t$=1.62 min; MS m/z: 262 $(M+H)^+$.

Step C: (cis)-ethyl 4-ethylpyrrolidine-3-carboxylate

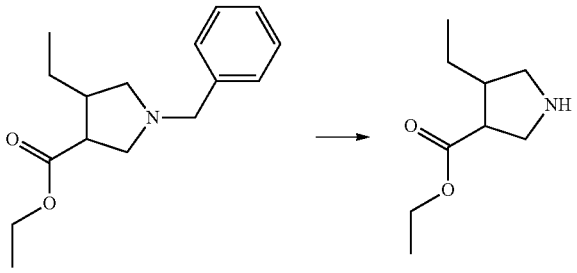

A parr shaker was charged with $PdOH_2$ on carbon (2.243 g, 3.19 mmol) and (cis)-ethyl 1-benzyl-4-ethylpyrrolidine-3-carboxylate (16.7 g, 63.9 mmol) followed by EtOH (100 mL). The reaction mixture was degassed and purged with hydrogen gas and shaken on the parr shaker at 60 psi for about 4 days at ambient temperature. The reaction mixture was degassed and purged with nitrogen. The suspension was filtered through a pad of Celite® washing with EtOH (~900 mL). The solvent was removed under reduced pressure to afford (cis)-ethyl 4-ethylpyrrolidine-3-carboxylate (8.69 g, 79%) as an oil: LC/MS (Table 1, Method a) $R_t$=1.11 min; MS m/z: 172 $(M+H)^+$.

Step D: (cis)-1-(tert-butoxycarbonyl)-4-ethylpyrrolidine-3-carboxylic acid

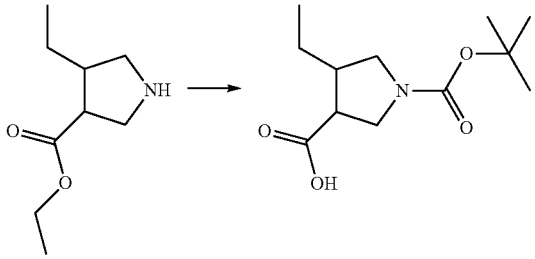

To a flask charged with (cis)-ethyl 4-ethylpyrrolidine-3-carboxylate (8.69 g, 50.7 mmol) was added aqueous HCl (6N, 130 mL, 782 mmol). The solution was heated at about 75° C. for about 12 h. aqueous HCl (6N, 100 mL, 599 mmol) was added and stirred at about 80° C. for about 20 h. Aqueous HCl (6N, 100 mL, 599 mmol) was added and continued stirring at about 80° C. for about 20 h. The reaction mixture was cooled to ambient temperature and the solvent was removed under reduced pressure. 1,4-Dioxane (275 mL) and water (50 mL) were added followed by portionwise addition of $Na_2CO_3$ (13.5 g, 127 mmol). Di-tert-butyl dicarbonate (13.3 g, 60.9 mmol) was added and the reaction mixture was stirred at ambient temperature for about 16 h. The solid was filtered and washed with EtOAc (250 mL). The aqueous layer was acidified with aqueous HCl (1N) to about pH 3-4. The layers were partitioned and the aqueous layer was extracted with EtOAc (3×100 mL). The combined organic layers were dried over anhydrous $Na_2SO_4$, filtered and removed under reduced pressure. As the organic layer was almost fully concentrated (about 10 mL remaining), a solid precipitated. Heptane (30 mL) was added and the solid was filtered washing with heptane to afford (cis)-1-(tert-butoxycarbonyl)-4-ethylpyrrolidine-3-carboxylic acid (3.9 g, 32%) as an off white solid as product: LC/MS (Table 1, Method c) $R_t$=0.57 min; MS m/z: 242 $(M-H)^-$.

Step E: (cis)-tert-butyl 3-ethyl-4-(2-(5-tosyl-5H-pyrrolo[2,3-b]pyrazin-2-yl)hydrazinecarbonyl)pyrrolidine-1-carboxylate

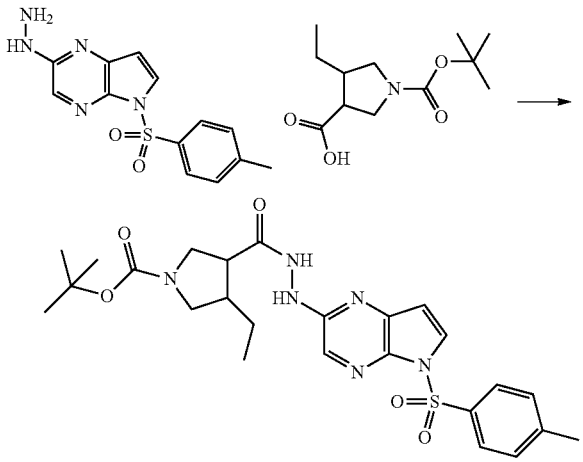

To a suspension of 2-hydrazinyl-5-tosyl-5H-pyrrolo[2,3-b]pyrazine (5.00 g, 16.48 mmol, Example 1, Step D) and (cis)-1-(tert-butoxycarbonyl)-4-ethylpyrrolidine-3-carboxylic acid (4.01 g, 16.48 mmol) in DCM (70 mL) were added TEA (5.75 mL, 41.2 mmol) and HATU (6.90 g, 18.15 mmol, Novabiochem). The resulting suspension was stirred at about 25° C. for about 2 h. The reaction mixture was transferred to a separatory funnel and washed with saturated aqueous $NaHCO_3$ (4×30 mL). The organic layer was dried over anhydrous $MgSO_4$, filtered, and concd in vacuo to give a brown foam. The crude material was purified via flash chromatography on silica gel by dry loading the compound onto the column and eluting with 50-100% EtOAc in DCM/petroleum ether (1:1) to afford (cis)-tert-butyl 3-ethyl-4-(2-(5-tosyl-5H-pyrrolo[2,3-b]pyrazin-2-yl)hydrazinecarbonyl)pyrrolidine-1-carboxylate with EtOAc as an excipient (9.41 g, 100%) as a tan foam: LC/MS (Table 1, Method a) $R_t$=2.45 min; MS m/z: 529 $(M+H)^+$.

Step F: 1-((cis)-4-ethylpyrrolidin-3-yl)-6-tosyl-6H-pyrrolo[2,3-e][1,2,4]triazolo[4,3-a]pyrazine

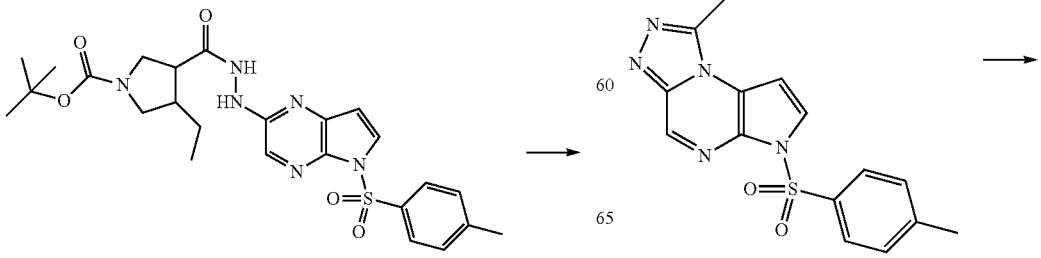

-continued

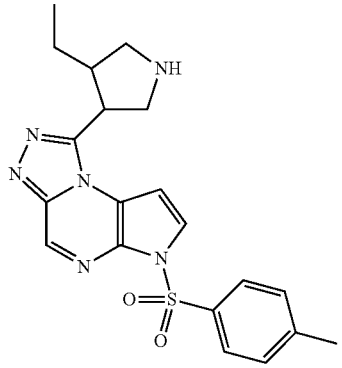

To a solution of (cis)-tert-butyl 3-ethyl-4-(2-(5-tosyl-5H-pyrrolo[2,3-b]pyrazin-2-yl)hydrazinecarbonyl)pyrrolidine-1-carboxylate (9.4 g, 16.41 mmol) in 1,4-dioxane (150 mL), TEA (7.00 mL, 50.2 mmol) and thionyl chloride (1.80 mL, 24.6 mmol) were each added sequentially in one portion to the solution. The reaction was heated at about 70° C. for about 18 h. The solvent was removed under reduced pressure. A solution of HCl (4 M in 1,4-dioxane, 41.0 mL, 164 mmol) was added in one portion and the reaction was stirred for about 3 h. $Et_2O$ (100 mL) was added and the solid was filtered. The solids were combined with the mother liquor and the solvent was removed under reduced pressure. The solid was partially dissolved in EtOAc (650 mL) and washed with aqueous saturated $NaHCO_3$ (150 mL). An emulsion formed and was fitered through Celite® washing with EtOAc. The solid on top of the Celite® layer was product. The solid was scraped off of the Celite® and dissoved in a solution of 10% MeOH in DCM (150 mL). The organic layer was washed with water (2×30 mL). The combined organic layers were washed with saturated aqueous sodium bicarbonate (4×150 mL), dried over $MgSO_4$, filtered, and concentrated under reduced pressure to afford 1-((cis)-4-ethylpyrrolidin-3-yl)-6-tosyl-6H-pyrrolo[2,3-e][1,2,4]triazolo[4,3-a]pyrazine (5.88 g, 80%) as a brown foam: LC/MS (Table 1, Method a) $R_t$=1.55 min; MS m/z: 411 $(M+H)^+$.

Step G: (cis)-3-ethyl-4-(6-tosyl-6H-pyrrolo[2,3-e][1,2,4]triazolo[4,3-a]pyrazin-1-yl)-N-(2,2,2-trifluoroethyl)pyrrolidine-1-carboxamide

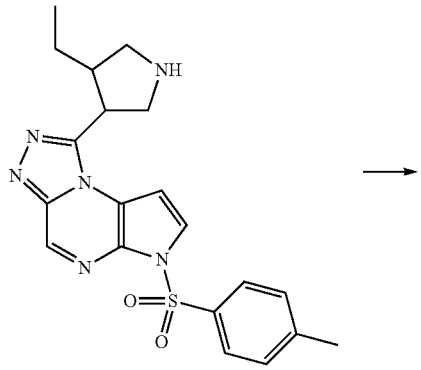

-continued

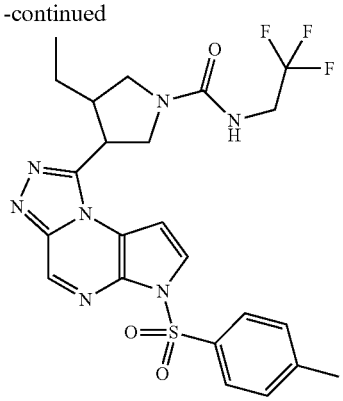

To a solution of 2,2,2-trifluoroethanamine (0.080 g, 0.804 mmol) in DMF (3 mL) was added CDI (0.150 g, 0.926 mmol). The resulting solution was stirred at about 65° C. for about 2 h. 1-((cis)-4-ethylpyrrolidin-3-yl)-6-tosyl-6H-pyrrolo[2,3-e][1,2,4]triazolo[4,3-a]pyrazine (0.250 g, 0.609 mmol) was added and the reaction continued stirring at about 65° C. for about 2 h. The reaction was cooled to about ambient temperature. The solvent was removed under reduced pressure. The crude material was purified by flash chromatography on silica gel eluting with a gradient of 0-10% MeOH in afford (cis)-3-ethyl-4-(6-tosyl-6H-pyrrolo[2,3-e][1,2,4]triazolo[4,3-a]pyrazin-1-yl)-N-(2,2,2-trifluoroethyl)pyrrolidine-1-carboxamide (0.306 g, 94%) as a brown residue: LC/MS (Table 1, Method a) $R_t$=2.19 min; MS m/z: 536 $(M+H)^+$.

Step H: (3S,4R)-3-ethyl-4-(6H-pyrrolo[2,3-e][1,2,4]triazolo[4,3-a]pyrazin-1-yl)-N-(2,2,2-trifluoroethyl)pyrrolidine-1-carboxamide and (3R,4S)-3-ethyl-4-(6H-pyrrolo[2,3-e][1,2,4]triazolo[4,3-a]pyrazin-1-yl)-N-(2,2,2-trifluoroethyl)pyrrolidine-1-carboxamide

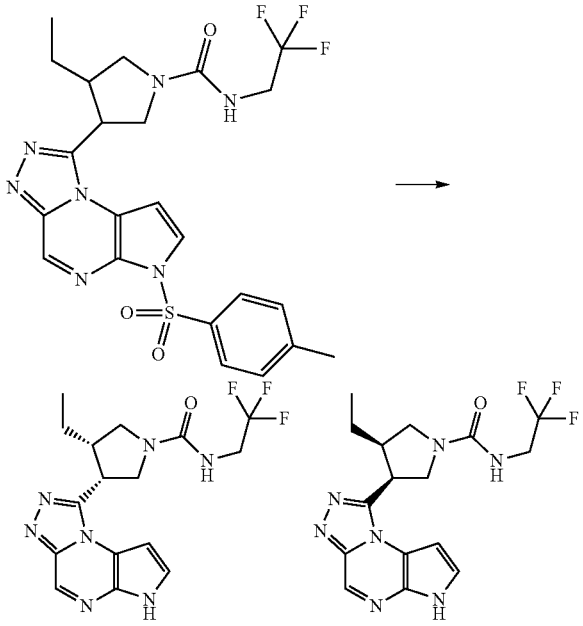

To a solution of (cis)-3-ethyl-4-(6-tosyl-6H-pyrrolo[2,3-e][1,2,4]triazolo[4,3-a]pyrazin-1-yl)-N-(2,2,2-trifluoroethyl)pyrrolidine-1-carboxamide (0.306 g, 0.571 mmol) in 1,4-dioxane (10 mL) was added aqueous NaOH (1 N, 1.50 mL, 1.50 mmol). The reaction was heated at about 50° C. for about 1 h. The layers were partitioned between DCM (25 mL) and water (10 mL). The aqueous layer was acidified with 20% aqueous citric acid to about pH 4 and extracted with DCM (4×25 mL). The combined organic layers were dried over anhydrous $MgSO_4$, filtered, and concd under reduced pressure to give a brown residue. The crude material was purified by flash chromatography on silica gel eluting with a gradient of 0-10% MeOH in DCM to give a racemic mixture of products as a brown residue. The compound was further purified using chiral preparative HPLC (Table 2, Method 55) to afford (3S,4R)-3-ethyl-4-(6H-pyrrolo[2,3-e][1,2,4]triazolo[4,3-a]pyrazin-1-yl)-N-(2,2,2-trifluoroethyl)pyrrolidine-1-carboxamide ($R_t$=14.5 min, or =negative) (0.031 g, 14%)[Example #36]: LC/MS (Table 1, Method a) $R_t$=1.62 min; MS m/z: 382 $(M+H)^1$ and (3R,4S)-3-ethyl-4-(6H-pyrrolo[2,3-e][1,2,4]triazolo[4,3-a]pyrazin-1-yl)-N-(2,2,2-trifluoroethyl)pyrrolidine-1-carboxamide ($R_t$=17.3 min, or =positive) (0.033 g, 15%)[Example #37]: LC/MS (Table 1, Method a) $R_t$=1.62 min; MS m/z: 382 $(M+H)^+$.

Example #38

5-(((1S,3R,4S)-3-ethyl-4-(6H-pyrrolo[2,3-e][1,2,4]triazolo[4,3-a]pyrazin-1-yl)cyclopentyl)methyl)-3-(methoxymethyl)-1,2,4-oxadiazole

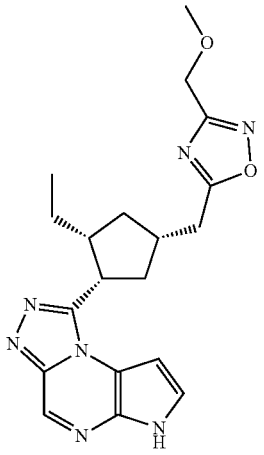

Step A: ethyl 8-ethyl-1,4-dioxaspiro[4.4]nonane-7-carboxylate

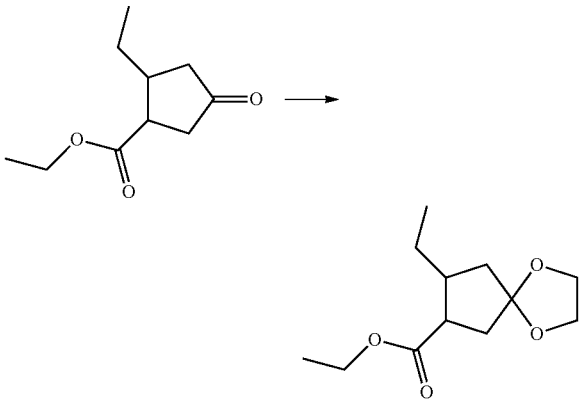

A round bottom flask was charged with ethyl 2-ethyl-4-oxocyclopentanecarboxylate (1.5 g, 8.1 mmol, Example #22, Step B) in DCM (22 mL). To the flask were added ethylene glycol (0.91 mL, 16 mmol), triethylorthoformate (2.0 mL, 12 mmol) and p-toluenesulfonic acid monohydrate (0.31 g, 1.6 mmol). The reaction mixture was stirred at rt for about 24 h. The solution was concd under reduced pressure to give brown oil that was dissolved in EtOAc and purified by silica gel chromatography eluting with a gradient of 0-50% EtOAc in heptane. The product containing fractions were combined and concd to dryness under reduced pressure to give ethyl 8-ethyl-1,4-dioxaspiro[4.4]nonane-7-carboxylate as a light yellow oil (1.6 g, 83%): LC/MS (Table 1, Method c) MS m/z 229 $(M+H)^+$; (CDCl) δ 4.14 (q, 2H), 3.90 (m, 4H), 2.99 (q, 1H), 2.32-2.27 (m, 1H), 2.26-2.11 (m, 1H), 2.05-1.99 (m, 1H), 1.96-1.91 (m, 1H), 1.83-1.78 (m, 1H), 1.46-1.39 (m, 1H), 1.31-1.24 (m, 1H), 1.26 (t, 3H), 0.90 (t, 3H).

Step B: 8-ethyl-1,4-dioxaspiro[4.4]nonane-7-carboxylic acid

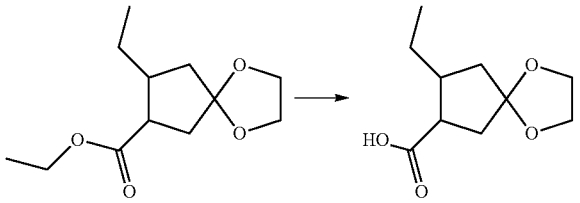

A round bottom flask was charged with ethyl 8-ethyl-1,4-dioxaspiro[4.4]nonane-7-carboxylate (0.32 g, 1.4 mmol) and aqueous sodium hydroxide (1 N, 14.0 mL, 14.0 mmol). The solution was stirred overnight at rt. To the solution was added DCM (30 mL) followed by the addition of 20% aqueous citric acid (about 20 mL) to reach pH of about 2. The layers were separated and the aqueous solution was extracted with DCM (2×30 mL) and DCM/EtOAc (1:1, 30 mL). The combined extracts were dried over anhydrous $MgSO_4$, filtered, and concd under reduced pressure to give 8-ethyl-1,4-dioxaspiro[4.4]nonane-7-carboxylic acid as a clear, colorless oil (0.27 g, 96%): LC/MS (Table 1, Method c) $R_t$=1.20 min; MS m/z: 201 $(M+H)^+$.

Step C: 8-ethyl-N'-(5-tosyl-5H-pyrrolo[2,3-b]pyrazin-2-yl)-1,4-dioxaspiro[4.4]nonane-7-carbohydrazide

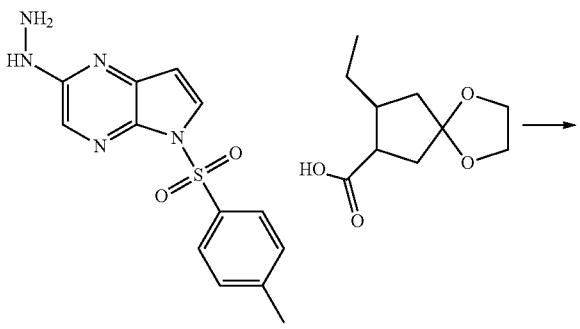

-continued

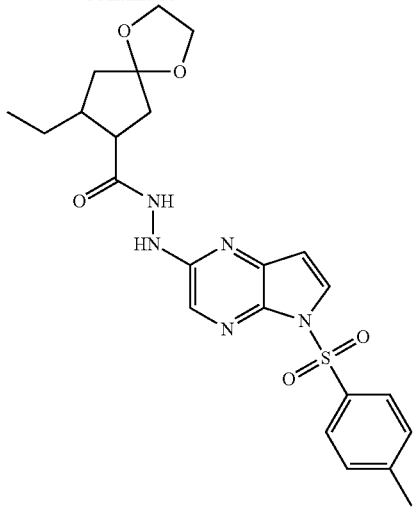

A 50 mL round bottom flask was charged with 2-hydrazinyl-5-tosyl-5H-pyrrolo[2,3-b]pyrazine (0.350 g, 1.16 mmol, Example #1, Step D), 8-ethyl-1,4-dioxaspiro[4.4]nonane-7-carboxylic acid (0.250 g, 1.25 mmol), and DCM (6.0 mL). To the reaction mixture was added HATU (0.483 g, 1.27 mmol) and TEA (0.64 mL, 4.6 mmol) and the resulting yellow suspension was stirred at rt for about 3 h. To the reaction solution was added DCM (25 mL) and the solution was washed with water and brine (20 mL each). The organic layer was dried over anhydrous $MgSO_4$, filtered, and concd under reduced pressure to give a brown oil. The crude product was purified by silica gel chromatography eluting with a gradient of 0-10% MeOH in DCM over 25 min. to give 8-ethyl-N'-(5-tosyl-5H-pyrrolo[2,3-b]pyrazin-2-yl)-1,4-dioxaspiro[4.4]nonane-7-carbohydrazide as a foam (0.50 g, 89%): LC/MS (Table 1, Method c) $R_t$=1.49 min; MS m/z: 486 $(M+H)^+$.

Step D: 1-(8-ethyl-1,4-dioxaspiro[4.4]nonan-7-yl)-6-tosyl-6H-pyrrolo[2,3-e][1,2,4]triazolo[4,3-a]pyrazine

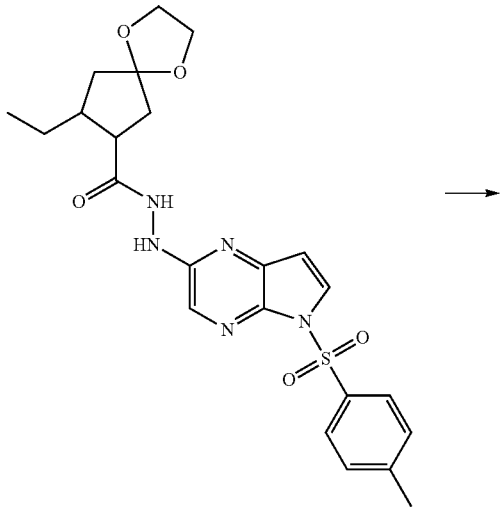

-continued

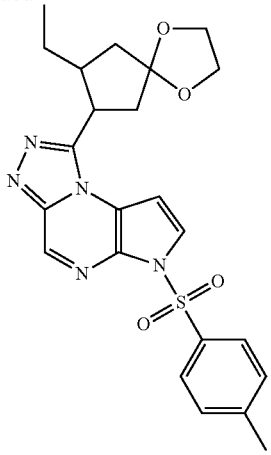

A round bottom flask was charged with 8-ethyl-N'-(5-tosyl-5H-pyrrolo[2,3-b]pyrazin-2-yl)-1,4-dioxaspiro[4.4]nonane-7-carbohydrazide (4.90 g, 10.1 mmol) and 1,4-dioxane (50 mL). To the flask was added DIEA (8.81 mL, 50.5 mmol) followed by the addition of thionyl chloride (0.770 mL, 10.6 mmol). The mixture was heated to about 75° C. for about 90 min. Additional thionyl chloride (0.074 mL, 1.0 mmol) was added and heating was continued for about 1 h. The reaction was cooled to rt and stirred overnight. The solution was diluted with DCM (75 mL) and washed with water (50 mL). The layers were separated and the organic layer was dried over anhydrous $MgSO_4$, filtered, and concd under reduced pressure to give a dark brown oil. The crude product was purified via flash silica gel chromatography eluting with a gradient of 0-60% acetone in heptane. The product containing fractions were combined and concd to give material that was loaded onto a second column eluting with a gradient of 0-60% acetone in heptane. The product containing fractions were combined and concd under reduced pressure to give 1-(8-ethyl-1,4-dioxaspiro[4.4]nonan-7-yl)-6-tosyl-6H-pyrrolo[2,3-e][1,2,4]triazolo[4,3-a]pyrazine as a tan powder (3.0 g, 64%): LC/MS (Table 1, Method c) $R_t$=1.44 min; MS m/z: 468 $(M+H)^+$.

Step E: 3-ethyl-4-(6-tosyl-6H-pyrrolo[2,3-e][1,2,4]triazolo[4,3-a]pyrazin-1-yl)cyclopentanone

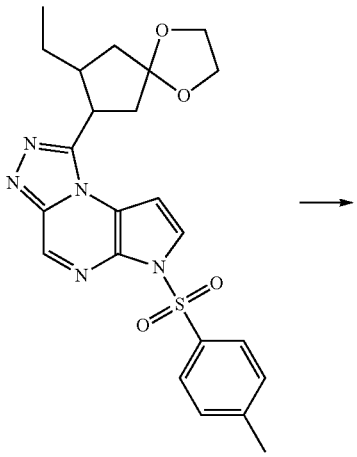

-continued

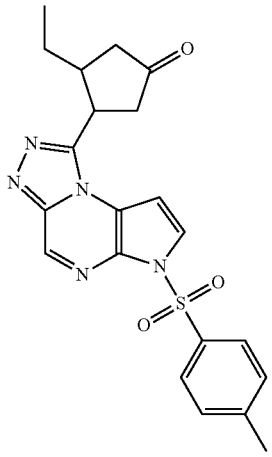

A round bottom flask was charged with 1-47S, 8R)-8-ethyl-1,4-dioxaspiro[4.4]nonan-7-O-6-tosyl-6H-pyrrolo[2,3-e][1,2,4]triazolo[4,3-a]pyrazine (3.56 g, 7.61 mmol) and THF (20 mL). To the solution was added aqueous HCl (6N, 3.81 mL, 22.8 mmol) and the mixture was stirred at rt for about 2 h. The solvent was removed under reduced pressure and DCM (75 mL) and water (50 mL) were added. The layers were separated and the organic solution was dried over anhydrous $MgSO_4$, filtered, and concd under reduced pressure to give 3-ethyl-4-(6-tosyl-6H-pyrrolo[2,3-e][1,2,4]triazolo[4,3-a]pyrazin-1-yl)cyclopentanone as a brown foam (2.99 g, 93%): LC/MS (Table 1, Method c) $R_t$=1.40 min; MS m/z: 424 $(M+H)^+$.

Step F: ethyl 2-((cis)-3-ethyl-4-(6-tosyl-6H-pyrrolo[2,3-e][1,2,4]triazolo[4,3-a]pyrazin-1-yl)cyclopentylidene)acetate

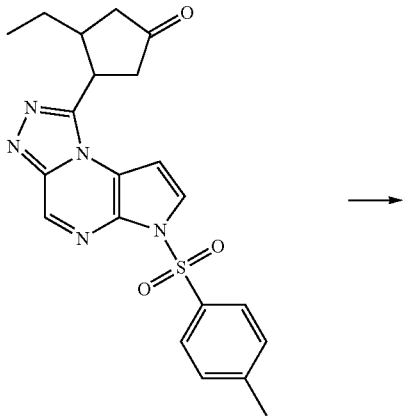

-continued

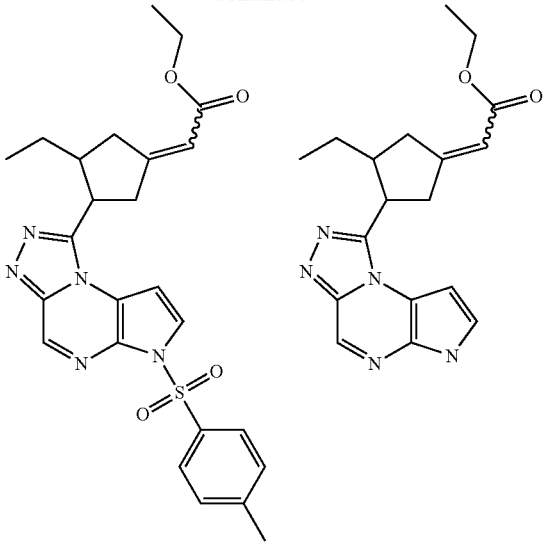

To a slurry of sodium hydride (0.227 g, 5.67 mmol, 60% dispersion in oil) in THF (30 mL) was added ethyl 2-(diethoxyphosphoryl)acetate (1.18 mL, 5.90 mmol). After about 30 min a solution of (cis)-3-ethyl-4-(6-tosyl-6H-pyrrolo[2,3-e][1,2,4]triazolo[4,3-a]pyrazin-1-yl)cyclopentanone (2.00 g, 4.72 mmol) in THF (1.0 mL) was added. After about 4 h EtOAc and sat $NaHCO_3$ were added. The organic layer was separated concd in vacuo and purified by flash chromatography on silica gel eluting with 20-100% EtOAc in DCM to afford ethyl 2-((cis)-3-ethyl-4-(6-tosyl-6H-pyrrolo[2,3-e][1,2,4]triazolo[4,3-a]pyrazin-1-yl)cyclopentylidene)acetate (2.08 g, 89%): LC/MS (Table 1, Method c) $R_t$=2.52-2.56 min; MS m/z: 494 $(M+H)^+$ as a mixture of diastereomers and ethyl 2-((cis)-3-ethyl-4-(6H-pyrrolo[2,3-e][1,2,4]triazolo[4,3-a]pyrazin-1-yl)cyclopentylidene)acetate (0.150 g, 9%), as a mixture of diastereomers: LC/MS (Table 1, Method a) $R_t$=1.85-1.89; MS m/z: 340 $(M+H)^+$.

Step G: ethyl 2-((cis)-3-ethyl-4-(6H-pyrrolo[2,3-e][1,2,4]triazolo[4,3-a]pyrazin-1-yl)cyclopentylidene)acetate

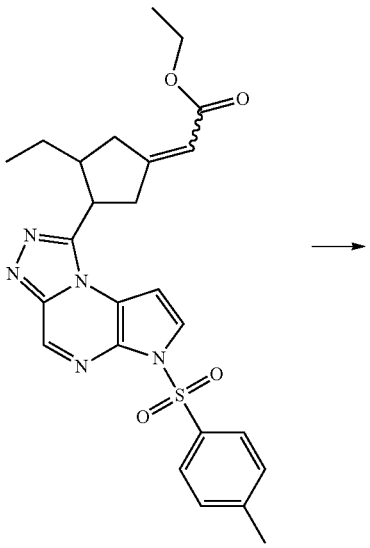

-continued

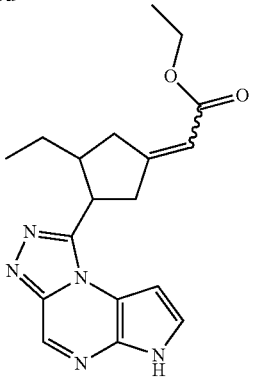

To a solution of ethyl 2-((cis)-3-ethyl-4-(6-tosyl-6H-pyrrolo[2,3-e][1,2,4]triazolo[4,3-a]pyrazin-1-yl)cyclopentylidene)acetate (1.9 g, 3.85 mmol) in THF (30 mL) at 0° C. was added a solution of TBAF (11.55 mL, 11.55 mmol, 1 M in THF). After about 10 min, TBAF (7.70 mL, 7.70 mmol, 1 M in THF) was added. After about 1 h EtOAc and brine were added to the reaction mixture. After about one h the organic layer was separated, concd in vacuo and purified by flash chromatography on silica gel eluting with EtOAc to afford ethyl 2-((cis)-3-ethyl-4-(6H-pyrrolo[2,3-e][1,2,4]triazolo[4,3-a]pyrazin-1-yl)cyclopentylidene)acetate (1.3 g, 100%) as a mixture of diastereomers: LC/MS (Table 1, Method a) $R_t$=1.86-1.90 min; MS m/z: 340 $(M+H)^+$.

Step H: ethyl 2-((1R,3R,4S)-3-ethyl-4-(6H-pyrrolo[2,3-e][1,2,4]triazolo[4,3-a]pyrazin-1-yl)cyclopentyl)acetate and 2-((1S,3R,4S)-3-ethyl-4-(6H-pyrrolo[2,3-e][1,2,4]triazolo[4,3-a]pyrazin-1-yl)cyclopentyl)acetate

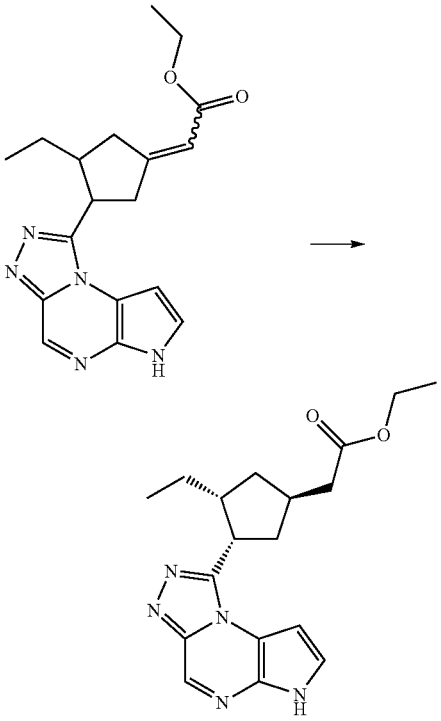

-continued

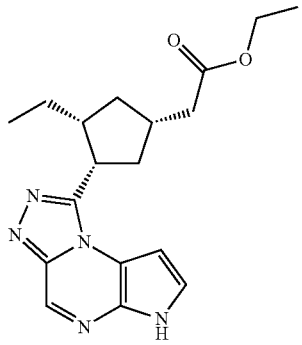

To a slurry of $PdOH_2$ on carbon (0.134 g, 0.192 mmol) in THF (20 mL) was added a solution of ethyl 2-((cis)-3-ethyl-4-(6H-pyrrolo[2,3-e][1,2,4]triazolo[4,3-a]pyrazin-1-yl)cyclopentylidene)acetate (1.3 g, 3.83 mmol) in THF (5 mL). The reaction mixture was sparged with hydrogen and an atmosphere of hydrogen was maintained via balloon. After about 3 days the reaction mixture was filtered through Celite®, concd in vacuo and purified by flash chromatography on silica gel eluting with EtOAc to afford ethyl 2-((cis)-3-ethyl-4-(6H-pyrrolo[2,3-e][1,2,4]triazolo[4,3-a]pyrazin-1-yl)cyclopentyl)acetate (1.3 g, 99% yield) as a dark brown/black solid. The compound was further purified by chiral preparative HPLC (Table 2, method 47) to afford ethyl 2-((1R,3R,4S)-3-ethyl-4-(6H-pyrrolo[2,3-e][1,2,4]triazolo[4,3-a]pyrazin-1-yl)cyclopentyl)acetate ($R_t$=12.0 min, or =negative) (0.400 g, 31%): LC/MS (Table 1, Method a) $R_t$=1.85 min; MS m/z: 342 $(M+H)^+$ and ethyl 2-((1S,3R,4S)-3-ethyl-4-(6H-pyrrolo[2,3-e][1,2,4]triazolo[4,3-a]pyrazin-1-yl)cyclopentyl)acetate ($R_t$=13.7 min, or =negative) (0.420 g, 32%) as a white solid: LC/MS (Table 1, Method a) $R_t$=1.84 min; MS m/z: 342 $(M+H)^+$.

Step I: 5-(((1S,3R,4S)-3-ethyl-4-(6H-pyrrolo[2,3-e][1,2,4]triazolo[4,3-a]pyrazin-1-yl)cyclopentyl)methyl)-3-(methoxymethyl)-1,2,4-oxadiazole

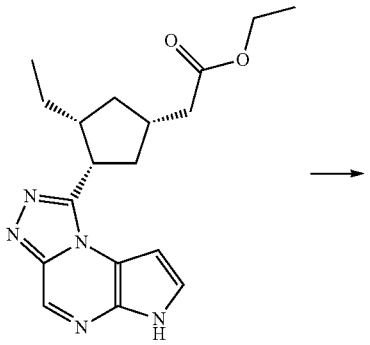

-continued

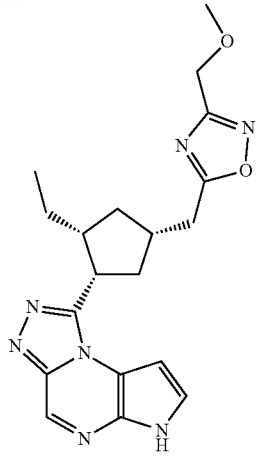

To a solution of ethyl 2-((1S,3R,4S)-3-ethyl-4-(6H-pyrrolo[2,3-e][1,2,4]triazolo[4,3-a]pyrazin-1-yl)cyclopentyl)acetate (0.100 g, 0.293 mmol) in toluene (0.20 mL) and MeOH (0.20 mL) was added (Z)-N'-hydroxy-2-methoxyacetimidamide (0.300 g, 2.89 mmol, Tyger) and $K_2CO_3$ (0.100 g, 0.726 mmol). The solution was heated in a CEM microwave at about 130° C. for about 1 h (250 psi maximum pressure, 1 min ramp, 300 max watts). The solvent was removed under reduced pressure. The residue was diluted with DCM (3 mL) and a small amount of MeOH. The crude material was purified by flash chromatography on silica gel eluting with a gradient of 0-10% MeOH in DCM. The residue was dissolved in EtOAc and heptane was added. The solvent was concd. The solid was dried in a heated vacuum oven (about 70° C.) for about 20 h to afford 5-(((1S,3R,4S)-3-ethyl-4-(6H-pyrrolo[2,3-e][1,2,4]triazolo[4,3-a]pyrazin-1-yl)cyclopentyl)methyl)-3-(methoxymethyl)-1,2,4-oxadiazole (0.062 g, 56%) as a white solid: LC/MS (Table 1, Method a) $R_t$=1.79 min; MS m/z: 382 $(M+H)^+$.

Example #39 cis-4-(3H-imidazo[1,2-a]pyrrolo[2,3-e]pyrazin-8-yl)cyclohexanamine

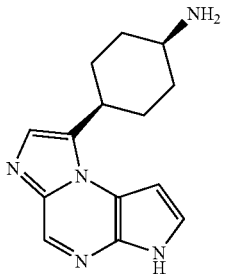

Step A: ethyl 4-(dibenzylamino)cyclohexanecarboxylate

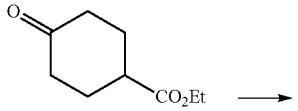

-continued

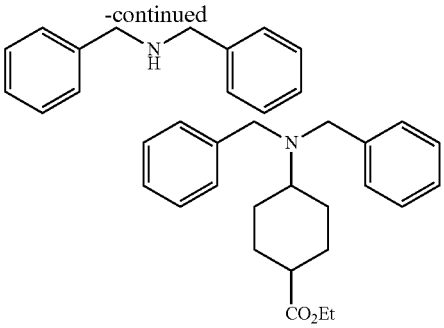

A 250 mL flask was charged with ethyl 4-oxocyclohexanecarboxylate (5 g, 28.5 mmol, Alfa Aesar) and THF (75 mL). The solution was cooled to about 0° C. and AcOH (2.28 mL, 39.9 mmol) and dibenzylamine (6.18 g, 31.3 mmol) (TCI) were added dropwise, resulting in formation of a thick suspension. $Na(OAc)_3BH$ (14.3 g, 64.1 mmol) was added portionwise and the reaction mixture was stirred at ambient temperature for about 72 h. The reaction mixture was cooled to about 10° C. Water (25 mL) was added and the reaction mixture was stirred for about 15 min. Heptanes (50 mL) were added. The layers were separated and the organic layer was washed with 10% aqueous AcOH solution (25 mL) and then with water (10 mL). The organic layer was extracted with 4% HCl solution twice (40 mL and 20 mL). The combined aqueous layer was washed with heptanes (20 mL). To the aqueous layer was slowly added 30% aqueous $K_2CO_3$ solution (30 g) to adjust the pH to 10. The aqueous solution was extracted with heptane twice (75 mL and 15 mL). The combined organic layer was washed with water (30 mL). The organic layer was dried over anhydrous $Na_2SO_4$ and filtered. The filtrate was concd under reduced pressure to give ethyl 4-(dibenzylamino)cyclohexanecarboxylate (7.2 g, 72%) as an oil which solidified upon standing: LC/MS (Table 1, Method a) $R_t$=3.18 and 3.23 min; MS m/z: 352 $(M+H)^+$.

Step B: 4-(dibenzylamino)cyclohexanecarboxylic acid

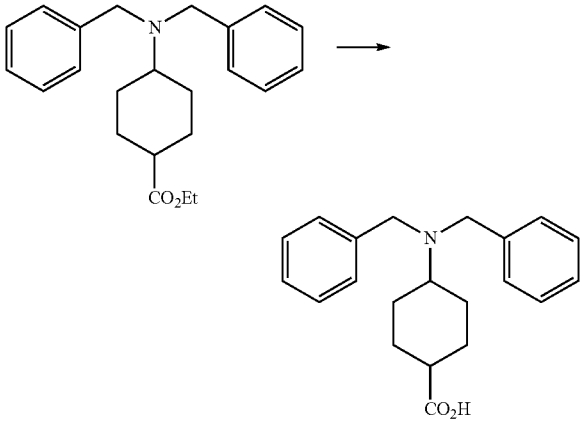

To a 250 mL flask, ethyl 4-(dibenzylamino)cyclohexanecarboxylate (7.2 g, 20.5 mmol) and a solution of conc. $H_2SO_4$ (7.64 mL, 143 mmol) in water (80 mL) were added. The reaction mixture was stirred at about 90° C. for about 18 h, cooled to about 5° C. and the pH was adjusted to about 7 with the addition of 50% aqueous NaOH. The aqueous solution was extracted with ether (300 mL). The organic layer was dried over anhydrous $Na_2SO_4$, filtered and washed with ether. The filtrate was concd under reduced pressure to give 4-(dibenzylamino)cyclohexanecarboxylic acid (5.6 g, 85%) as a solid: LC/MS (Table 1, Method b) $R_t$=1.65 min; MS m/z: 324 $(M+H)^+$.

Step C: sulfoxonium, dimethyl-, 2-(4-(dibenzylamino)cyclohexyl)-2-oxoethylide

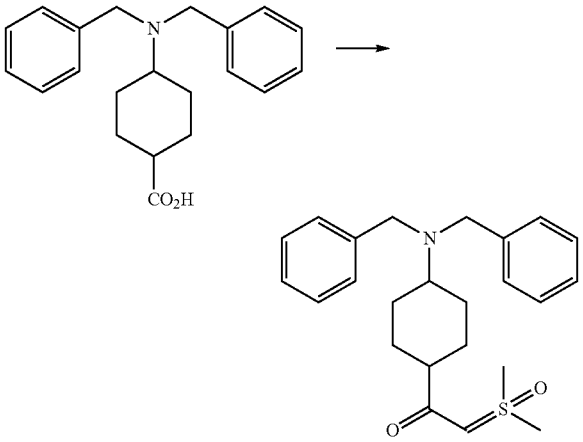

To a 250 mL flask, 4-(dibenzylamino)cyclohexanecarboxylic acid (5.6 g, 17.3 mmol), HATU (6.75 g, 17.4 mmol) and TEA (8.45 mL, 60.6 mmol) in THF (60 mL) were added to give a white suspension. The reaction mixture was stirred at ambient temperature for about 1 h. To a 500 mL flask, trimethylsulfoxonium chloride (6.82 g, 51.9 mmol) and potassium tert-butoxide (6.44 g, 54.5 mmol) in THF (60 mL) were added to give a white suspension. The reaction mixture was stirred at about 65° C. for about 3 h. The reaction mixture was cooled to about 5° C. The above activated ester solution was added dropwise over about 50 min. The reaction mixture was stirred at about 0-5° C. for about 90 min. The reaction mixture was quenched by the addition of water (120 mL) dropwise at about 0-5° C. over about 25 min. The quenched reaction mixture was stirred at about 0-5° C. for about 30 min, then at ambient temperature for about 18 h. THF was removed under reduced pressure to give white suspension. The suspension was partitioned between EtOAc (300 mL) and water (200 mL). The aqueous layer was extracted with EtOAc (2×100 mL). The combined organic layer was washed with water (50 mL) and brine (3×40 mL). The organic layer was dried over anhydrous $Na_2SO_4$ and concd under reduced pressure. The residue was dissolved in hot MeOH (100 mL) and concd under reduced pressure. The oil was dissolved in hot MeOH (60 mL) and concd under reduced pressure to give a white solid. The solid was dissolved in MeOH (36 g) and water (12 g) at about 55° C. The solution was cooled to ambient temperature, then to about 5° C. Additional 3:1 MeOH/water (40 mL) was added to the suspension. The suspension was filtered, washed with 1:1 MeOH/water (20 mL) and heptane (20 mL). The collected wet cake was dried at about 60° C. in a vacuum oven for about 72 h to yield sulfoxonium, dimethyl-, 2-(4-(dibenzylamino)cyclohexyl)-2-oxoethylide (5.44 g, 79%) as white solid: LC/MS (Table 1, Method a) $R_t$=1.42, 1.45 min; MS m/z 398 $(M+H)^+$.

Step D: 1-(4-(dibenzylamino)cyclohexyl)-2-(5-tosyl-5H-pyrrolo[2,3-b]pyrazin-2-ylamino)ethanone

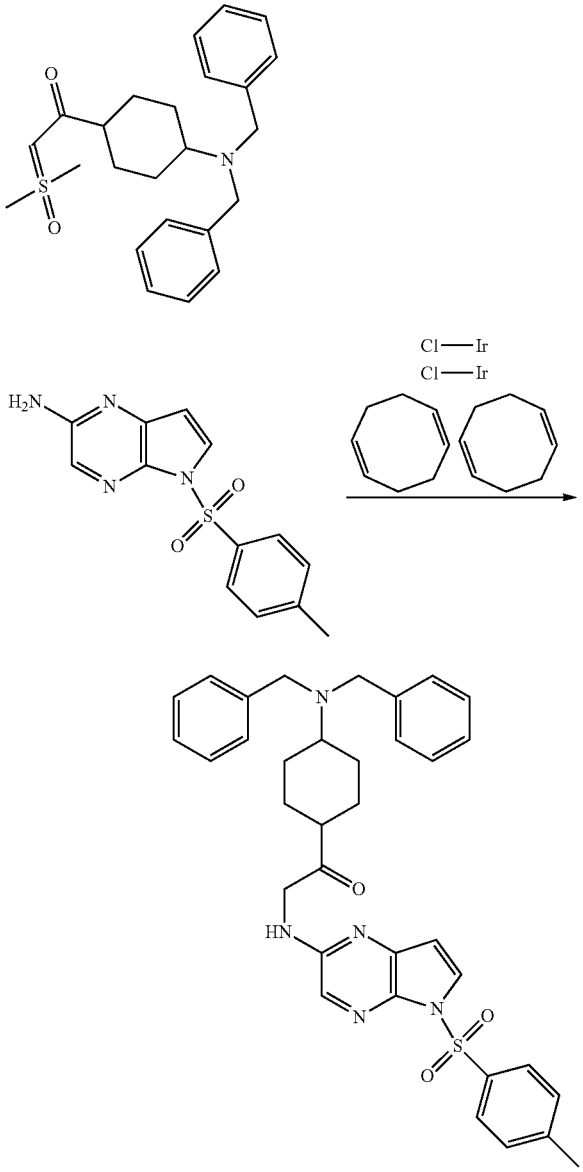

To a 100 mL 2-neck round-bottomed flask, sulfoxonium, dimethyl-, 2-(4-(dibenzylamino)cyclohexyl)-2-oxoethylide (5.4 g, 13.6 mmol), 5-tosyl-5H-pyrrolo[2,3-b]pyrazin-2-amine (4.7 g, 16.3 mmol, Preparation #E.1.1), and $[Ir(COD)Cl]_2$ (0.365 g, 0.543 mmol Alfa Aesar) were added. The reaction vessel was purged with $N_2$ for about 10 min. To the reaction vessel, pre-degassed DCE (25 mL) was added via syringe. The reaction mixture was purged with $N_2$ for about 10 min and stirred under $N_2$ at about 70° C. for about 3 h. The reaction mixture was allowed to cool to ambient temperature and concd under reduced pressure. The residue was purified by silica gel flash chromatography eluting with a gradient of 5-70% EtOAc: heptane to yield 1-(4-(dibenzylamino)cyclohexyl)-2-(5-tosyl-5H-pyrrolo[2,3-b]pyrazin-2-ylamino)ethanone (5.8 g, 65%) as glassy solid: LC/MS (Table 1, Method a) $R_t$=3.24 and 3.26 min; MS m/z 608 $(M+H)^+$.

Step E: N,N-dibenzyl-4-(3-tosyl-3H-imidazo[1,2-a]pyrrolo[2,3-e]pyrazin-8-yl)cyclohexanamine

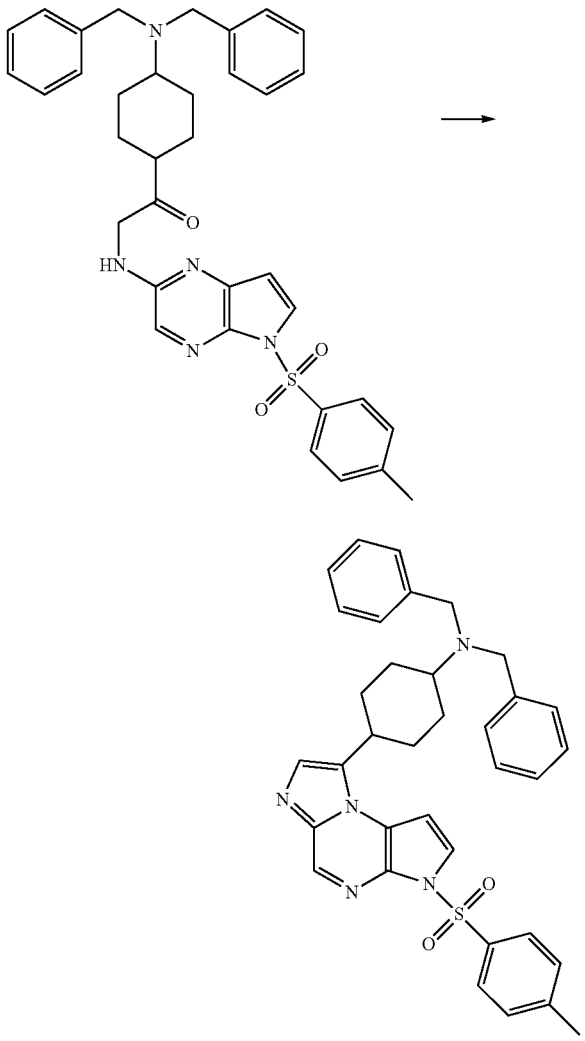

A mixture of 1-(4-(dibenzylamino)cyclohexyl)-2-(5-tosyl-5H-pyrrolo[2,3-b]pyrazin-2-ylamino)ethanone (5.8 g, 9.54 mmol) and PFPAA (23.7 g, 76 mmol) in MeCN (70 mL) was heated at about 50° C. for about 17 h. PFPAA (4.73 g, 15.2 mmol) was added and the reaction mixture was heated at about 60° C. for about 7 h and at ambient temperature for about 72 h. The solvent was removed under reduced pressure to yield N,N-dibenzyl-4-(3-tosyl-3H-imidazo[1,2-a]pyrrolo[2,3-e]pyrazin-8-yl)cyclohexanamine (11.3 g crude, but assumed 5.6 g, 100%) as a foam: LC/MS (Table 1, Method b) $R_t$=3.03 and 3.09 min; MS m/z 590 $(M+H)^+$.

Step F: (cis)-N,N-dibenzyl-4-(3H-imidazo[1,2-a]pyrrolo[2,3-e]pyrazin-8-yl)cyclohexanamine

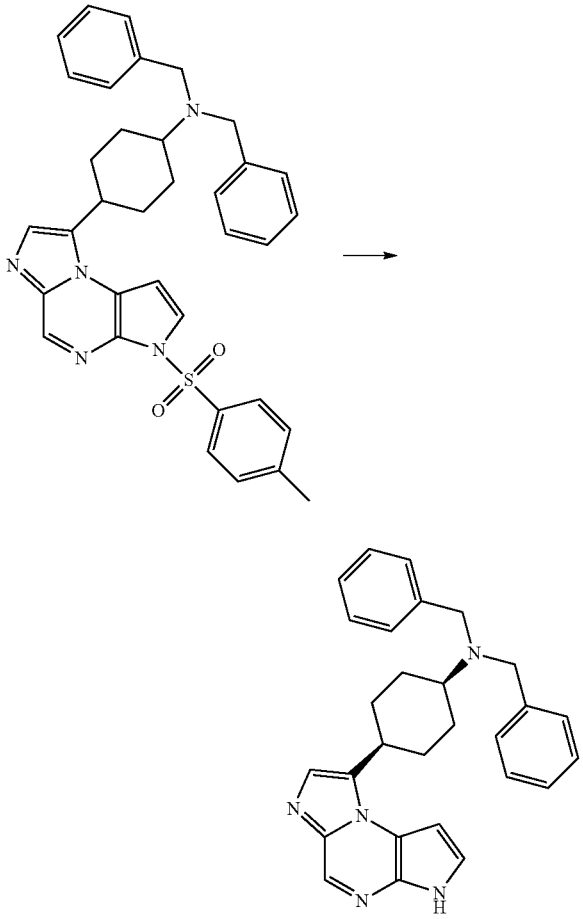

N,N-dibenzyl-4-(3-tosyl-3H-imidazo[1,2-a]pyrrolo[2,3-e]pyrazin-8-yl)cyclohexanamine (5.6 g, 9.5 mmol) was dissolved in 1,4-dioxane (80 mL). Aqueous NaOH (2 N, 47.5 mL, 95 mmol) was added and the reaction mixture was heated at about 60° C. for about 120 min. The organic solvent was removed under reduced pressure and the residue was extracted with 2-methyl tetrahydrofuran (300 mL). The aqueous layer was extracted with 2-methyl tetrahydrofuran (3×50 mL). The combined organic extracts were washed with brine (30 mL), dried over anhydrous $Na_2SO_4$ and concd under reduced pressure. To the residue was added EtOAc (500 mL). The solid was removed by filtration and the filtrate was dried over anhydrous $Na_2SO_4$ and concd under reduced pressure. Purification by silica gel flash chromatography eluting with a gradient of 1-8% MeOH in EtOAc yielded (cis)-N,N-dibenzyl-4-(3H-imidazo[1,2-a]pyrrolo[2,3-e]pyrazin-8-yl)cyclohexanamine (1.0 g, 24%): LC/MS (Table 1, Method a) $R_t$=2.48 min; MS m/z 436 $(M+H)^+$.

Step G: (cis)-4-(3H-imidazo[1,2-a]pyrrolo[2,3-e]pyrazin-8-yl)cyclohexanamine

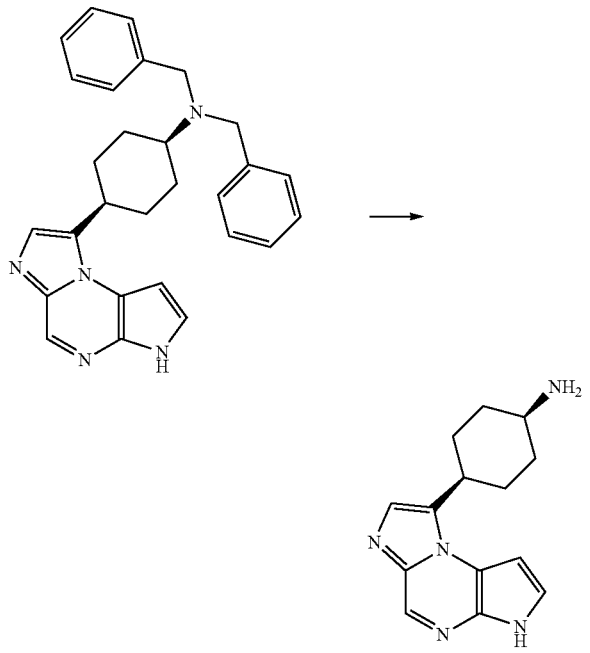

To a mixture of (cis)-N,N-dibenzyl-4-(3H-imidazo[1,2-a]pyrrolo[2,3-e]pyrazin-8-yl)cyclohexanamine (1.0 g, 2.3 mmol) in EtOH (30 mL) was added $Pd(OH)_2$ on carbon (0.64 g, 0.46 mmol) and the resulting mixture was shaken under hydrogen pressure of about 30 psi on a Parr shaker at about 50° C. for about 7 h. The catalyst was filtered off using a pad of Celite® and the filtrate was concd under reduced pressure. The material was purified by chiral chromatography (Table 2, method 34). The collected fractions were combined, concd under reduced pressure and chased with EtOH (20 mL). The resulting solid was dried in a heated vacuum oven at about 60° C. to yield (cis)-4-(3H-imidazo[1,2-a]pyrrolo[2,3-e]pyrazin-8-yl)cyclohexanamine (0.353 g, 60%) as a white solid: LC/MS (Table 1, Method a) $R_t$=0.85 min; MS m/z 256 $(M+H)^+$.

Example #40

4-(6H-pyrrolo[2,3-e][1,2,4]triazolo[4,3-a]pyrazin-8-yl)pyridin-2(1H)-one

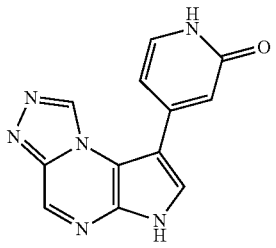

Hydrochloric acid (4 M in 1,4-dioxane, 0.300 mL, 1.20 mmol) was added to a slurry of 8-(2-methoxypyridin-4-yl)-6H-pyrrolo[2,3-e][1,2,4]triazolo[4,3-a]pyrazine (0.016 g, 0.060 mmol, (prepared using D from Preparation #BBBBB.1 and NaOH, GGG.1 with NBS, K.1 with TsCl and NaH, CCCCC with 2-methoxy-4-(tributylstannyl)pyridine [Synthonix], tetrakis(triphenylphosphinepalladium(0), LiCl, CsF, and CuI, D with NaOH) in EtOH (0.500 mL) and water (0.050 mL). The reaction vessel was sealed and the mixture was warmed to about 80° C. After about 15 h, the mixture was warmed to about 90° C. After about 65 h, the solution was allowed to cool to ambient temperature. The volatiles were removed under reduced pressure to afford 4-(6H-pyrrolo[2,3-e][1,2,4]triazolo[4,3-a]pyrazin-8-yl)pyridin-2(1H)-one (0.0153 g, 94%): LC/MS (Table 1, Method a) $R_t$=0.73 min; MS m/z 253 $(M+H)^+$.

Example #41

(1R,3R,4S)-3-ethyl-4-(6H-pyrrolo[2,3-e][1,2,4]triazolo[4,3-a]pyrazin-1-yl)cyclopentyl cyclopropylcarbamate

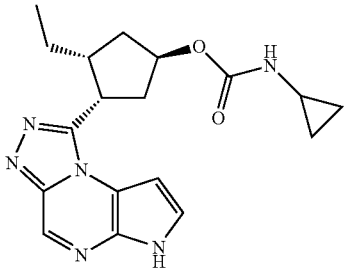

Step A: 5-bromo-3-((trimethylsilyl)ethynyl)pyrazin-2-amine

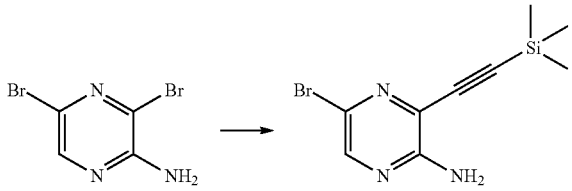

To a solution of 3,5-dibromopyrazin-2-amine (125 g, 494 mmol), TEA (207.0 mL, 1483 mmol), and copper (I) iodide (0.941 g, 4.94 mmol) in THF (1255 mL) was added $PdCl_2(PPh_3)_2$ (3.47 g, 4.94 mmol). The reaction mixture was cooled at about −5-0° C. and a solution of (trimethylsilyl) acetylene (65.0 mL, 470 mmol) in THF (157 mL) was added dropwise over about 15 min. The reaction mixture was stirred at about −5-0° C. for about 1.5 h and then allowed to warm to rt overnight. The reaction mixture was then filtered through a Celite® pad and washed with THF until no further product eluted. The filtrate was concd under reduced pressure to give a brown-orange solid. The solid was triturated and sonicated with warm petroleum ether (b.p. 30-60° C., 400 mL), cooled to rt, collected, washed with petroleum ether (b.p. 30-60° C.; 2×60 mL), and dried to give 5-bromo-3-((trimethylsilyl)ethynyl)pyrazin-2-amine (124 g, 93%, 93% purity) as a brown solid: LC/MS (Table 1, Method b) $R_t$=2.51 min; MS m/z: 270, 272 $(M+H)^+$.

Step B: 2-bromo-5-tosyl-5H-pyrrolo[2,3-b]pyrazine

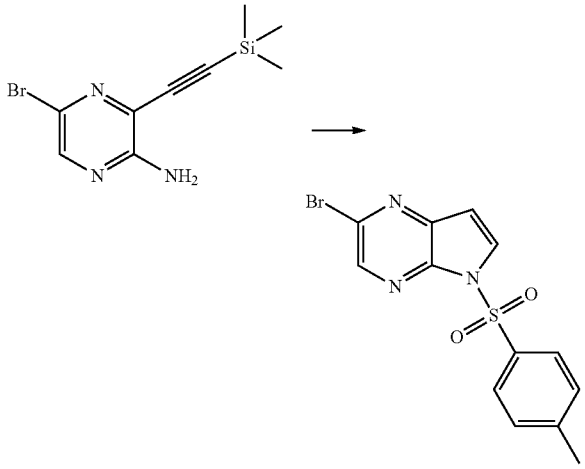

To a solution of 5-bromo-3-((trimethylsilyl)ethynyl) pyrazin-2-amine (3.00 g, 11.1 mmol) in DMF (60 mL) at about 0° C. was added NaH (60% dispersion in mineral oil, 0.577 g, 14.4 mmol) in three portions. After about 15 min, p-toluenesulfonyl chloride (2.75 g, 14.4 mmol) was added and the reaction was allowed to warm slowly to ambient temperature. After about 16 h, the reaction mixture was poured onto ice-cold water (120 mL) and the precipitate was collected by vacuum filtration. The crude solid was dissolved in DCM (15 mL) and purified by silica gel chromatography eluting with DCM to give 2-bromo-5-tosyl-5H-pyrrolo[2,3-b]pyrazine (2.16 g, 52%): LC/MS (Table 1, Method c) $R_t$=1.58 min; MS m/z: 352, 354 $(M+H)^+$.

Step C: tert-butyl 2-(5-tosyl-5H-pyrrolo[2,3-b] pyrazin-2-yl)hydrazinecarboxylate and tert-butyl 1-(5-tosyl-5H-pyrrolo[2,3-b]pyrazin-2-yl)hydrazinecarboxylate

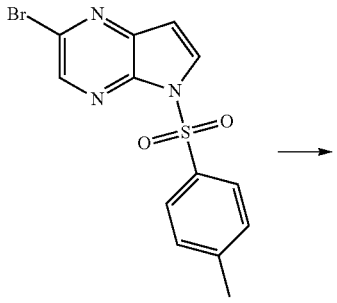

-continued

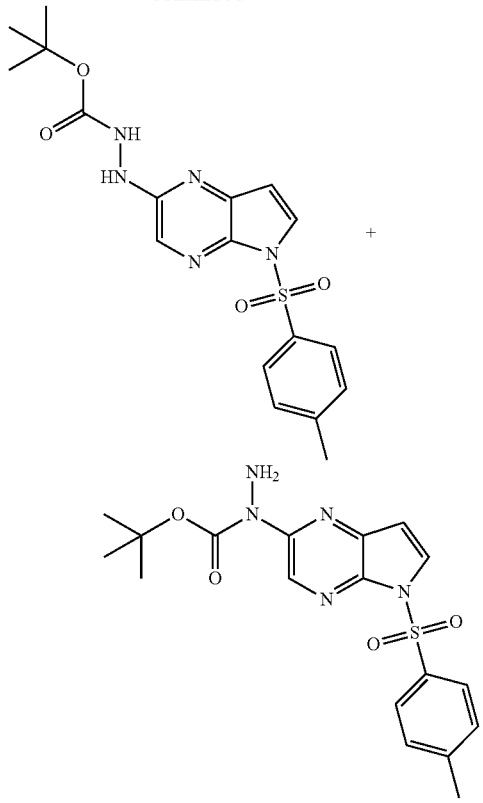

To a flask was added $Pd_2(dba)_3$ (3.90 g, 4.26 mmol), di-tert-butyl-(2',4',6'-triisopropylbiphenyl-2-yl)phosphane (3.62 g, 8.52 mmol), and 1,4-dioxane (453 mL). The catalyst-ligand mixture was degassed via vacuum/nitrogen purge (3 times) and heated at about 80° C. for about 10 min. Then 2-bromo-5-tosyl-5H-pyrrolo[2,3-b]pyrazine (30.0 g, 85 mmol), tert-butyl hydrazinecarboxylate (16.9 g, 128 mmol), and NaOtBu (12.28 g, 128 mmol) were added. After an additional vacuum/nitrogen purge, the reaction was heated at about 80° C. After about 50 min, the reaction mixture was cooled to ambient temperature and filtered through a pad of silica gel (6 cm in height×6 cm in diameter), topped with Celite® (1 cm in height×6 cm in diameter), while washing with EtOAc (3×150 mL). Water (300 mL) was added to the filtrate and the organic layer was separated. The aqueous layer was extracted with additional EtOAc (3×200 mL). The combined organic extracts were washed with saturated aqueous $NH_4Cl$, saturated aqueous $NaHCO_3$, and brine (400 mL each), dried over anhydrous $MgSO_4$, filtered, and concd under reduced pressure to give a dark brown oil (45 g). The brown oil was dissolved in DCM (250 mL), silica gel (200 g) was added, and the mixture was concd under reduced pressure. The resulting silica mixture was purified using silica gel chromatography eluting with a gradient of 25-65% EtOAc in heptane to give a mixture of tert-butyl 2-(5-tosyl-5H-pyrrolo[2,3-b]pyrazin-2-yl)hydrazinecarboxylate [major regioisomer] and tert-butyl 1-(5-tosyl-5H-pyrrolo[2,3-b]pyrazin-2-yl)hydrazinecarboxylate [minor regioisomer] (18.8 g, 50%): LC/MS (Table 1, Method c) $R_t$=1.47 min; MS m/z: 404 $(M+H)^+$.

Step D: 2-hydrazinyl-5-tosyl-5H-pyrrolo[2,3-b]pyrazine

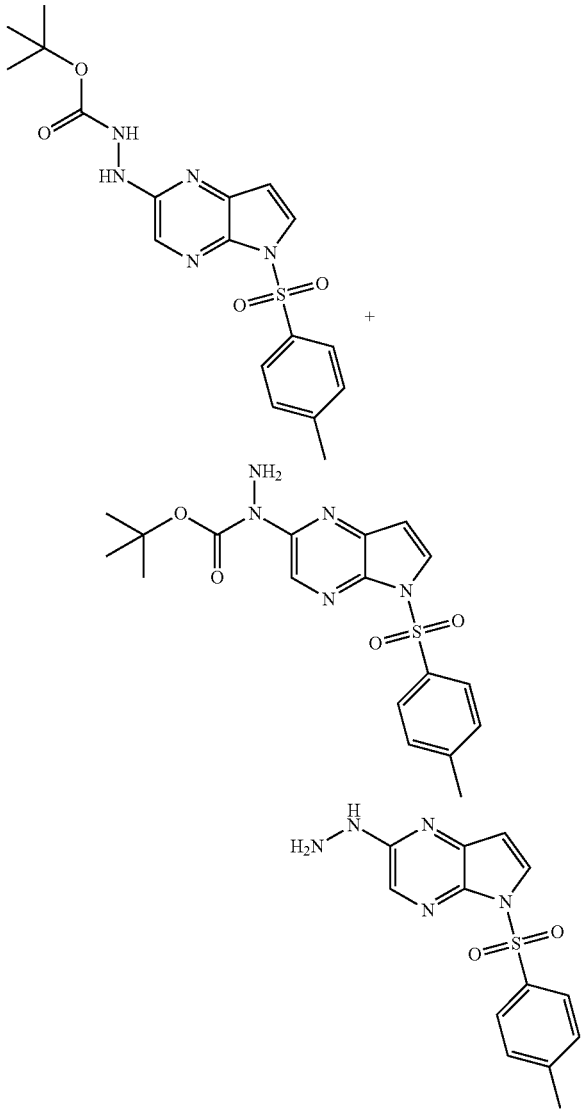

To a mixture of tert-butyl 2-(5-tosyl-5H-pyrrolo[2,3-b]pyrazin-2-yl)hydrazinecarboxylate and tert-butyl 1-(5-tosyl-5H-pyrrolo[2,3-b]pyrazin-2-yl)hydrazinecarboxylate (49.2 g, 122 mmol) in 1,4-dioxane (290 mL) was added HCl (4 M in 1,4-dioxane, 226 mL, 902 mmol). The reaction was heated at about 60° C. for about 2.5 h and then cooled to about 15-20° C. The solid was collected by vacuum filtration, washed with EtOAc (3×50 mL), and then triturated with $Et_2O$ (60 mL), collected by vacuum filtration and dried to a constant weight under vacuum to yield 35.6 g of solid. The solid was stirred with a mixture of saturated aqueous $NaHCO_3$ and EtOAc (1:1, 400 mL). After about 1 h, the solid was collected by vacuum filtration, washed with ice cold water (3×30 mL) and EtOAc (3×30 mL), and dried in a vacuum oven to a constant weight to afford 2-hydrazinyl-5-tosyl-5H-pyrrolo[2,3-b]pyrazine as a tan solid (21.2 g, 57%): LC/MS (Table 1, Method a) $R_t$=1.88 min; MS m/z: 304 $(M+H)^+$.

Step E: sodium 4-(ethoxycarbonyl)-3-ethyl-2-(methoxycarbonyl)cyclopenta-1,3-dienolate

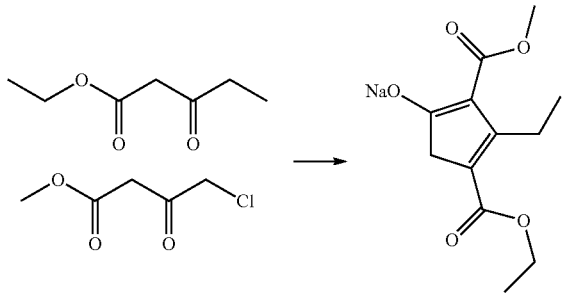

A round bottom flask was charged with THF (1.5 L) followed by the portionwise addition of NaH (60% dispersion in mineral oil, 70.0 g, 1.75 mol). Additional THF (500 mL) was added and the resulting mixture was cooled to about −10° C. and ethyl propionylacetate (250 mL, 1.80 mol) was added dropwise over about 1 h in order to keep the internal temperature below about 10° C. The resulting mixture was stirred at ambient temperature for about 0.5 h to give a clear yellow solution, and methyl 4-chloroacetoacetate (100 mL, 0.88 mol) was added dropwise over about 5 min. The resulting mixture was heated at about 50° C. for about 19 h to give a reddish orange suspension. The reaction mixture was cooled to ambient temperature, concd under reduced pressure and the resulting liquid was transferred to a beaker and diluted with water (350 mL). The mixture was stirred in an ice bath for about 2 h. The solid was collected by vacuum filtration and the filter cake was rinsed with water (150 mL) and dried under vacuum for about 1 h. The solid was suspended in $Et_2O$ (1.5 L), filtered, washed with $Et_2O$ (1.5 L), and dried under vacuum. The resulting solid was azeotroped with toluene (1 L) to give a solid that was re-suspended in $Et_2O$ (1 L) and collected by vacuum filtration. The filter cake was washed with $Et_2O$ (500 mL) and dried under vacuum to give sodium 4-(ethoxycarbonyl)-3-ethyl-2-(methoxycarbonyl)cyclopenta-1,3-dienolate (204.2 g, 89%) as beige solid: $^1$H NMR (DMSO-$d_6$) δ 3.94 (q, J=7.1 Hz, 2H), 3.46 (s, 3H), 3.04 (q, J=7.2 Hz, 2H), 2.66 (s, 2H), 1.13 (t, J=7.1 Hz, 3H), 0.99 (t, J=7.3 Hz, 3H).

Step F: ethyl 2-ethyl-4-oxocyclopent-2-enecarboxylate

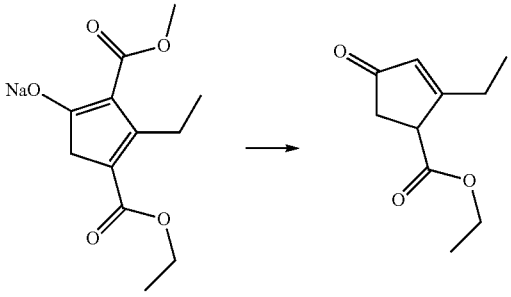

A 5 L round bottom flask was charged with sodium 4-(ethoxycarbonyl)-3-ethyl-2-(methoxycarbonyl)cyclopenta-1,3-dienolate (316 g, 1205 mmol), KCl (126 g, 1687 mmol, JT-Baker), AcOH (241 mL, 4218 mmol, JT-Baker), toluene (1850 mL) and water (130 mL). The reaction was heated at reflux for about 6 h then cooled to ambient temperature and added dropwise to $NaHCO_3$ (8% aqueous, 3.5 L). The resulting biphasic mixture was extracted with MTBE (2×1.5 L). The combined organic layers were washed with brine (1 L), dried over anhydrous $MgSO_4$ and concd under reduced pressure to give 191 g of crude material that was purified by vacuum distillation (97-99° C., 0.600 mm Hg) to give ethyl 2-ethyl-4-oxocyclopent-2-enecarboxylate (160 g, 69%): $^1$H NMR ($CDCl_3$) δ 6.04 (m, 1H), 4.26-4.15 (m, 2H), 3.76-3.69 (m, 1H), 2.75-2.57 (m, 2H), 2.56-2.44 (m, 2H), 1.32-1.26 (m, 3H), 1.23-1.18 (m, 3H).

Step G: ethyl 2-ethyl-4-hydroxycyclopentanecarboxylate

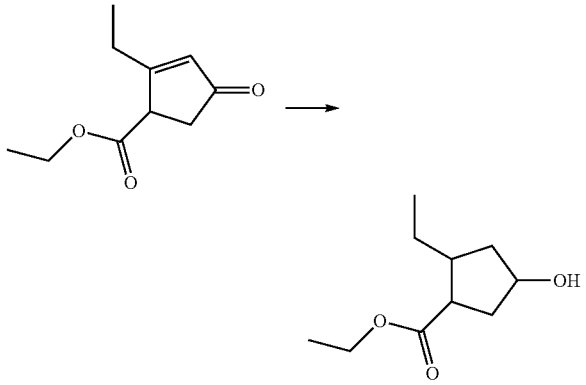

A mixture of copper (I) chloride (0.136 g, 1.37 mmol), (S)-(−)-2,2'-bis(diphenylphosphino)-1,1'-binaphthyl (0.854 g, 1.37 mmol), and NaOt-Bu (0.132 g, 1.37 mmol) in toluene (50 mL) was stirred at ambient temperature for about 15 min then cooled to about 5° C. and polymethylhydrosiloxane (12 mL, 55 mmol) was added. The reaction mixture was stirred for about 40 min at about 5° C. then cooled to about −12° C. A solution of ethyl 2-ethyl-4-oxocyclopent-2-enecarboxylate (5.00 g, 27.4 mmol) and t-BuOH (14 mL, 148 mmol) in toluene (50 mL) was added in one portion and the reaction mixture was stirred for about 16 h at about −12° C. The reaction mixture was quenched by the addition of MeOH (50 mL). The solvents were removed under reduced pressure. The residue was dissolved in MeOH (35 mL) and filtered through a pad of Celite®. The filtrate was concd under reduced pressure and the residue was triturated with EtOAc (100 mL) and filtered. The filtrate was concd under reduced pressure and the residue was purified using silica gel chromatography (280 g) eluting with a gradient of 0-10% EtOAc in heptane to give a scalemic mixture enriched with (1S,2R,4S)-ethyl 2-ethyl-4-hydroxycyclopentanecarboxylate (1.11 g, 22%): $^1$H NMR ($CDCl_3$) δ 4.30 (m, 1H), 4.24-4.08 (m, 2H), 2.88 (td, J=2.1, 7.1 Hz, 1H), 2.40 (dt, J=7.8, 14.0 Hz, 1H), 2.08-1.91 (m, 3H), 1.52-1.31 (m, 3H), 1.29 (t, J=7.1 Hz, 3H), 0.94 (t, J=7.4 Hz, 3H).

Step H: 3-(ethoxycarbonyl)-4-ethylcyclopentyl 4-nitrobenzoate

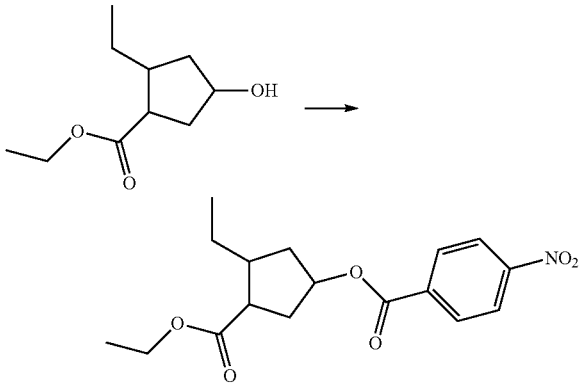

To triphenylphosphine (34.9 g, 133 mmol) in THF (150 mL) at about 0° C. was added a solution of DIAD (26.2 mL, 133 mmol) in THF (20 mL) through an additional funnel. After about 30 min, a solution of 4-nitrobenzoic acid (22.26 g, 133 mmol) in THF (150 mL) was added followed by a solution of a scalemic mixture enriched with (1S,2R,4S)-ethyl 2-ethyl-4-hydroxycyclopentanecarboxylate (16.54 g, 89 mmol) in THF (20 mL) and triethylamine (55.7 mL, 400 mmol). After about 1 h, the ice water bath was removed and the reaction mixture was stirred at ambient temperature for about 16 h. The reaction mixture was diluted with heptane (800 mL), washed with water (200 mL), saturated aqueous $NaHCO_3$ (150 mL) and brine (150 mL), dried over anhydrous $MgSO_4$, filtered, and concd under reduced pressure. After about 300 mL of solvent was removed, the solid was filtered off and washed with heptane (25 mL). The filtrate was concentrated under reduced pressure and the residue was purified using silica gel chromatography eluting with 10-40% EtOAc in heptane to give a scalemic mixture enriched with (1R,3S,4R)-3-(ethoxycarbonyl)-4-ethylcyclopentyl 4-nitrobenzoate (26.77 g, 90%): LC/MS (Table 1, Method b) $R_t$=2.84 min; MS m/z: 394 $(M-H)^-$.

Step I: ethyl 2-ethyl-4-hydroxycyclopentanecarboxylate

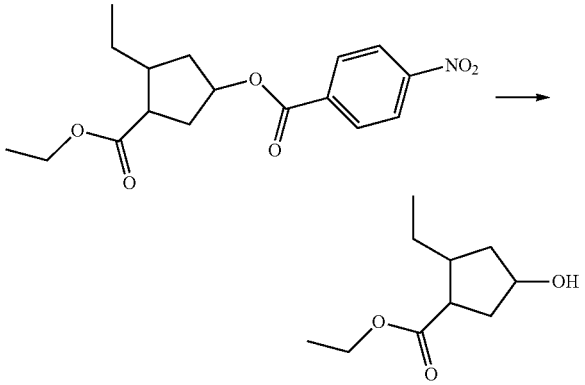

A 2 L flask was charged with freshly ground sodium hydroxide (9.55 g, 239 mmol). Ethanol (500 mL) was added and the mixture was stirred until all solid went into solution. A solution of a scalemic mixture enriched in (1R,3S,4R)-3-(ethoxycarbonyl)-4-ethylcyclopentyl 4-nitrobenzoate (16.02 g, 47.8 mmol) in ethanol (120 mL) was added through an additional funnel. The reaction mixture was stirred at ambient temperature overnight. The solid was filtered off while washing with DCM (100 mL). Saturated aqueous $NaHCO_3$ (800 mL) was added to the filtrate and mixture was stirred for about 30 min. The solid formed was filtered off while washing with DCM (500 mL). The filtrate was washed with saturated aqueous $NaHCO_3$ (2×200 mL) and brine (300 mL). The organic layer was dried over anhydrous $MgSO_4$, filtered and concd under reduced pressure. The residue was purified using silica gel chromatography eluting with 0-60% EtOAc in DCM to give a scalemic mixture enriched in (1S,2R,4R)-ethyl 2-ethyl-4-hydroxycyclopentanecarboxylate (5.49 g, 62%) as a colorless oil: $^1H$ NMR (400 MHz, $CDCl_3$) δ 4.53 (m, 1H), 4.11 (m, 2H), 3.09 (m 1H), 2.40 (m, 1H), 2.28 (m, 1H), 1.80 (m, 1H), 1.68 (m, 1H), 1.44 (m, 2H), 1.26 (t, 3H), 1.18 (m, 1H), 0.92 (t, 3H).

Step J: 2-ethyl-4-hydroxycyclopentanecarboxylic acid

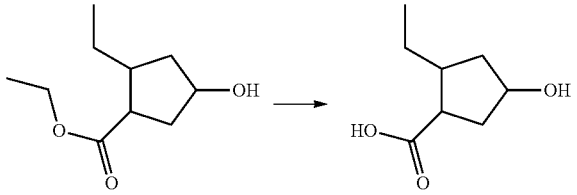

Aqueous sodium hydroxide (1N, 32.4 mL, 32.4 mmol) was added to a scalemic mixture enriched in (1S,2R,4R)-ethyl 2-ethyl-4-hydroxycyclopentanecarboxylate (3.02 g, 16.21 mmol) and the reaction mixture was stirred at ambient temperature overnight. Ether (15 mL) was added and the layers were separated. The aqueous layer was cooled to about 0° C. Aqueous HCl (5N) was slowly added to bring pH to about 1. The aqueous suspension was extracted with EtOAc (4×40 mL). The combined organic layers were washed with brine (50 mL), dried over anhydrous $MgSO_4$, filtered and concd under reduced pressure to give a scalemic mixture enriched in (1S,2R,4R)-2-ethyl-4-hydroxycyclopentanecarboxylic acid (2.56 g, 100%): LC/MS (Table 1, Method b) $R_t$=1.36 min; MS m/z: 157 $(M-H)^-$.

Step K: 4-(tert-butyldimethylsilyloxy)-2-ethylcyclopentanecarboxylic acid

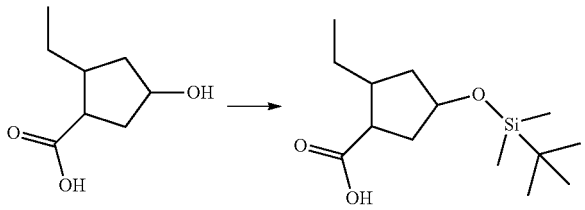

To a scalemic mixture enriched in (1S,2R,4R)-2-ethyl-4-hydroxycyclopentanecarboxylic acid (2.56 g, 16.21 mmol) in DMF (10.81 mL) was added TBDMSCl (2.93 g, 19.45 mmol) and imidazole (2.76 g, 40.5 mmol). The reaction mixture was stirred at ambient temperature for about 2 days then extracted with pentane (3×25 mL). The combined pentane layers were washed with water (25 mL) and brine (25 mL), dried over anhydrous $MgSO_4$, filtered and concd under reduced pressure. The residue was purified using silica gel chromatography eluting with 20-100% EtOAc in heptane give a scalemic mixture enriched in (1S,2R,4R)-4-(tert-butyldimethylsilyloxy)-2-ethylcyclopentanecarboxylic acid (1.13 g, 26%): LC/MS (Table 1, Method b) $R_t$=3.03 min; MS m/z: 273 $(M+H)^+$.

Step L: 4-(tert-butyldimethylsilyloxy)-2-ethyl-N'-(5-tosyl-5H-pyrrolo[2,3-b]pyrazin-2-yl)cyclopentanecarbohydrazide

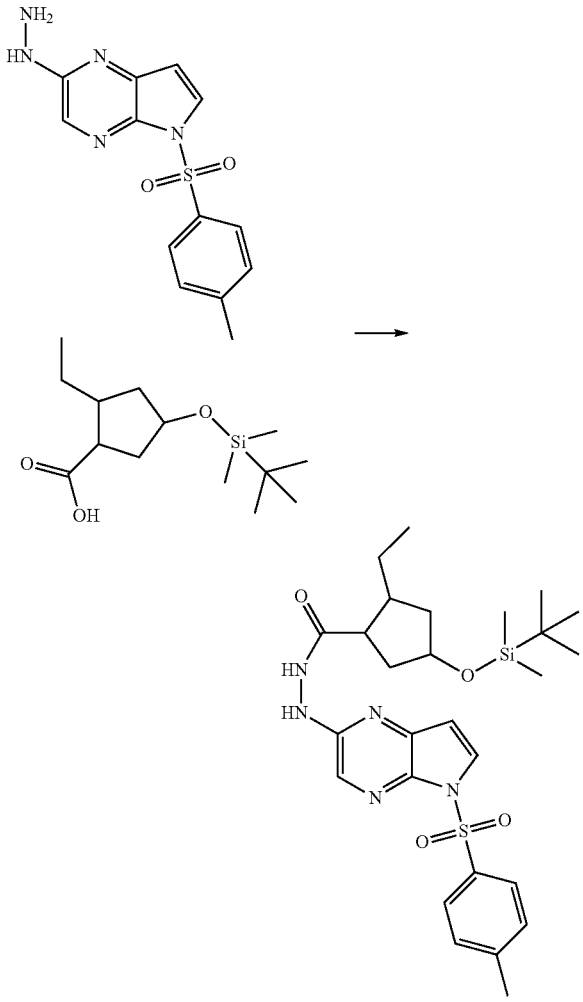

To a scalemic mixture enriched in (1S,2R,4R)-4-(tert-butyldimethylsilyloxy)-2-ethylcyclopentanecarboxylic acid (1.62 g, 5.96 mmol) in DCM (60 mL) was added 2-hydrazinyl-5-tosyl-5H-pyrrolo[2,3-b]pyrazine (Example #1, Step D, 1.86 g, 6.13 mmol), HATU (2.38 g, 6.26 mmol) and TEA (3.32 mL, 23.8 mmol). The reaction mixture was stirred at ambient temperature for about 1 h. The reaction mixture was diluted with DCM (200 mL), washed with water (50 mL) and brine (50 mL), dried over anhydrous $MgSO_4$, filtered, and concd under reduced pressure. The residue was purified using silica gel chromatography eluting with 0-30% EtOAc in DCM to give a scalemic mixture enriched in (1S,2R,4R)-4-(tert-butyldimethylsilyloxy)-2-ethyl-N'-(5-tosyl-5H-pyrrolo[2,3-b]pyrazin-2-yl)cyclopentanecarbohydrazide (2.64 g, 79%) as a brown solid: LC/MS (Table 1, Method b) $R_t$=3.20 min; MS m/z: 558 $(M+H)^+$.

Step M: 4-(tert-butyldimethylsityloxy)-2-ethylcyclopentyl)-6-tosyl-6H-pyrrolo[2,3-e][1,2,4]triazolo[4,3-a]pyrazine

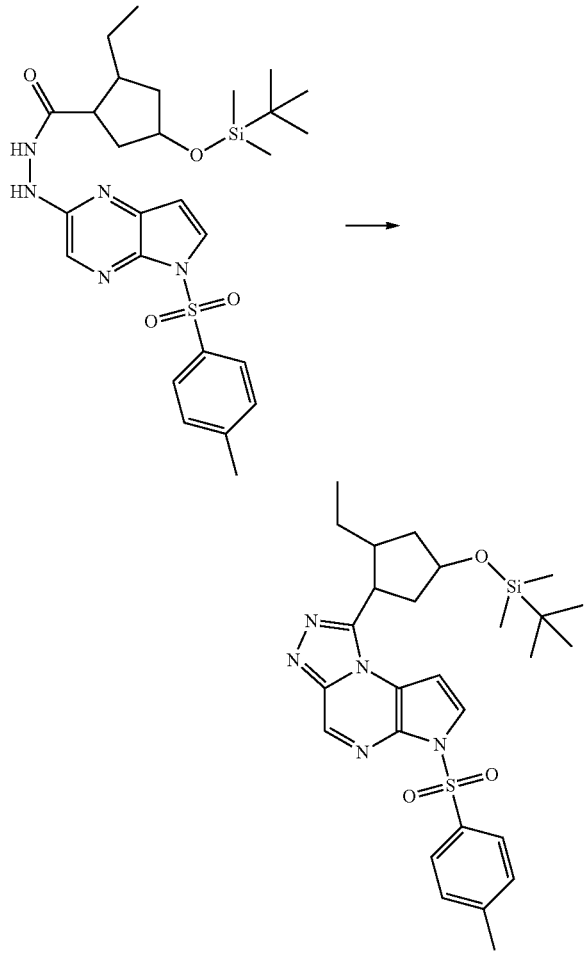

To a scalemic mixture enriched in (1S,2R,4R)-4-(tert-butyldimethylsilyloxy)-2-ethyl -N'-(5-tosyl-5H-pyrrolo[2,3-b]pyrazin-2-yl)cyclopentanecarbohydrazide (2.6 g, 4.66 mmol) in 1,4-dioxane (46.6 mL) was added diisopropylethylamine (3.26 mL, 18.65 mmol) followed by dropwise addition of thionyl chloride (0.680 mL, 9.32 mmol). The reaction mixture was stirred at ambient temperature for about 1 h and then heated at about 70° C. for about 1 h. The reaction mixture was cooled to ambient temperature and EtOAc (300 mL) was added. The mixture was washed with water (80 mL) and brine (80 mL), dried over anhydrous $MgSO_4$, filtered, and concd under reduced pressure. The residue was purified by silica gel chromatography eluting with 0-50% EtOAc in DCM to give a scalemic mixture enriched in 1-((1S,2R,4R)-4-(tert-butyldimethylsilyloxy)-2-ethylcyclopentyl)-6-tosyl-6H-pyrrolo[2,3-e][1,2,4]triazolo[4,3-a]pyrazine (1.56 g, 62%): LC/MS (Table 1, Method b) $R_t$=3.36 min; MS m/z: 540 $(M+H)^+$.

Step N: 3-ethyl-4-(6-tosyl-6H-pyrrolo[2,3-e][1,2,4]triazolo[4,3-a]pyrazin-1-yl)cyclopentanol

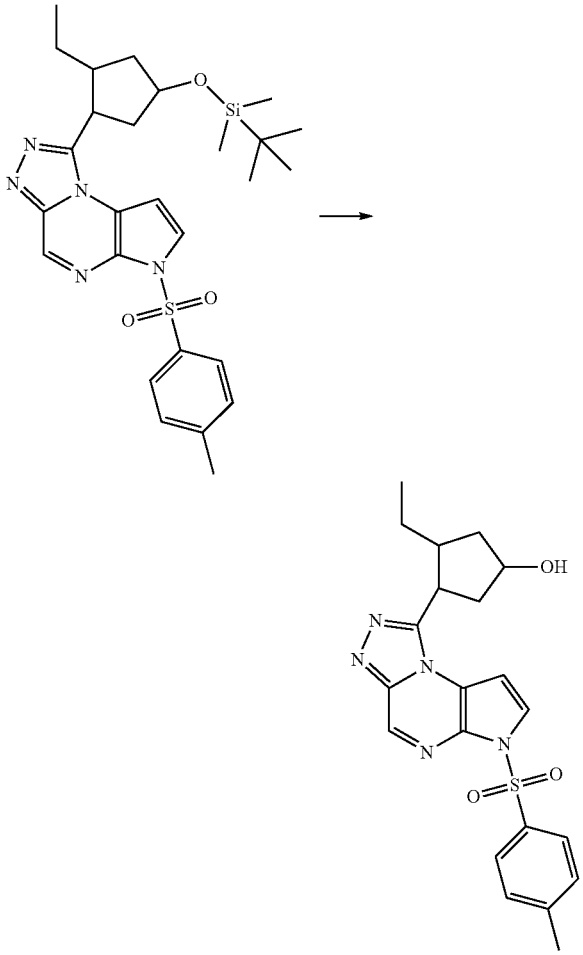

A scalemic mixture enriched in 1-((1S,2R,4R)-4-(tert-butyldimethylsilyloxy)-2-ethylcyclopentyl)-6-tosyl-6H-pyrrolo[2,3-e][1,2,4]triazolo[4,3-a]pyrazine (1.55 g, 2.87 mmol) was suspended in ethanol (30 mL). Concentrated HCl (0.3 mL, 3.65 mmol) was added dropwise. After about 1 h., the suspension was sonicated until all solid went into solution. EtOAc (250 mL) was added and the organics were washed with saturated aqueous $NaHCO_3$ (2×30 mL) and brine (30 mL), dried over anhydrous $MgSO_4$, filtered, and concd under reduce pressure. The residue was purified using silica gel chromatography eluting with 30-80% EtOAc in DCM to give a scalemic mixture enriched in (1R,3R,4S)-3-ethyl-4-(6-tosyl-6H-pyrrolo[2,3-e][1,2,4]triazolo[4,3-a]pyrazin-1-yl)cyclopentanol (1.09 g, 90%): LC/MS (Table 1, Method b) $R_t$=1.99 min; MS m/z: 426 $(M+H)^+$.

Step O: 3-ethyl-4-(6-tosyl-6H-pyrrolo[2,3-e][1,2,4]triazolo[4,3-a]pyrazin-1-yl)cyclopentyl 4-nitrophenyl carbonate

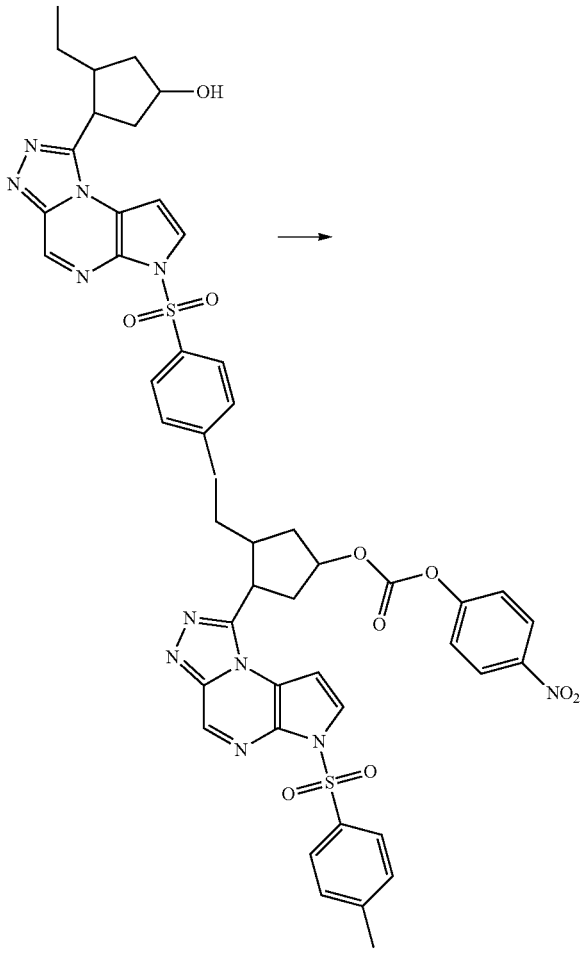

To a scalemic mixture enriched in (1R,3R,4S)-3-ethyl-4-(6-tosyl-6H-pyrrolo[2,3-e][1,2,4]triazolo[4,3-a]pyrazin-1-yl)cyclopentanol (1.20 g, 2.82 mmol) in pyridine (10 mL) was added DMAP (0.103 g, 0.846 mmol) and 4-nitrophenyl carbonochloridate (0.853 g, 4.23 mmol). The resulting mixture was stirred at ambient temperature for about 1 h. The reaction mixture was purified using silica gel chromatography eluting with 0-30% EtOAc in DCM to give a scalemic mixture enriched in (1R,3R,4S)-3-ethyl-4-(6-tosyl-6H-pyrrolo[2,3-e][1,2,4]triazolo[4,3-a]pyrazin-1-yl)cyclopentyl 4-nitrophenyl carbonate (0.72 g. 43%): LC/MS (Table 1, Method b) $R_t$=2.64 min; MS m/z: 591 $(M+H)^+$.

Step P: (1R,3R,4S)-3-ethyl-4-(6H-pyrrolo[2,3-e][1,2,4]triazolo[4,3-a]pyrazin-1-yl)cyclopentyl cyclopropylcarbamate

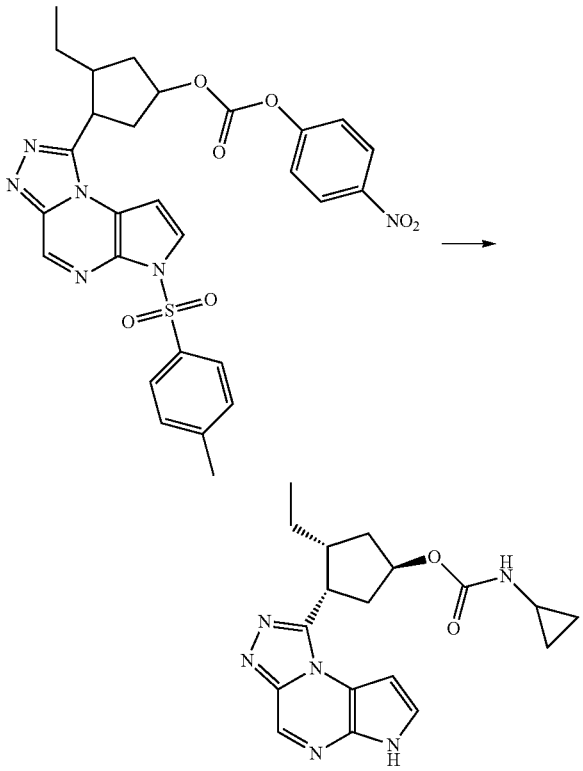

To a scalemic mixture enriched in (1R,3R,4S)-3-ethyl-4-(6-tosyl-6H-pyrrolo[2,3-e][1,2,4]triazolo[4,3-a]pyrazin-1-yl)cyclopentyl 4-nitrophenyl carbonate (0.211 g, 0.357 mmol) in 1,4-dioxane (1.5 mL) was added cyclopropanamine (0.102 g, 1.786 mmol). After about 1 h, aqueous NaOH (1N, 1.5 mL, 1.5 mmol) was added and the reaction mixture was heated at about 60° C. for about 30 min then cooled to ambient temperature. The reaction mixture was extracted with DCM (3×5 mL). The combined organic solvents were concd under reduced pressure. The residue was purified using silica gel chromatography eluting with 0-100% EtOAc:MeOH (9:1) in EtOAc to give (1R,3R,4S)-3-ethyl-4-(6H-pyrrolo[2,3-e][1,2,4]triazolo[4,3-a]pyrazin-1-yl)cyclopentyl cyclopropylcarbamate (0.0847 g, 67%): LC/MS (Table 1, Method b) $R_t$=1.73 min; MS m/z: 355 $(M+H)^+$.

Example #42

(1S,3R,4S)-3-ethyl-4-(6H-pyrrolo[2,3-e][1,2,4]triazolo[4,3-a]pyrazin-1-yl)cyclopentyl cyclobutylcarbamate

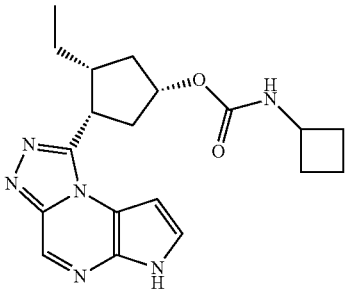

Step A: 5-bromo-3-((trimethylsilyl)ethynyl)pyrazin-2-amine

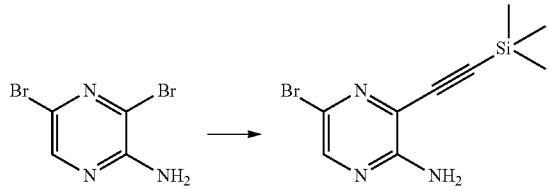

To a solution of 3,5-dibromopyrazin-2-amine (125 g, 494 mmol), TEA (207.0 mL, 1483 mmol), and copper (I) iodide (0.941 g, 4.94 mmol) in THF (1255 mL) was added $PdCl_2(PPh_3)_2$ (3.47 g, 4.94 mmol). The reaction mixture was cooled at about −5-0° C. and a solution of (trimethylsilyl) acetylene (65.0 mL, 470 mmol) in THF (157 mL) was added dropwise over about 15 min. The reaction mixture was stirred at about −5-0° C. for about 1.5 h and then allowed to warm to rt overnight. The reaction mixture was then filtered through a Celite® pad and washed with THF until no further product eluted. The filtrate was concd under reduced pressure to give a brown-orange solid. The solid was triturated and sonicated with warm petroleum ether (b.p. 30-60° C., 400 mL), cooled to rt, collected, washed with petroleum ether (b.p. 30-60° C.; 2×60 mL), and dried to give 5-bromo-3-((trimethylsilyl)ethynyl)pyrazin-2-amine (124 g, 93%, 93% purity) as a brown solid: LC/MS (Table 1, Method b) $R_t$=2.51 min; MS m/z: 270, 272 $(M+H)^+$.

Step B: 2-bromo-5-tosyl-5H-pyrrolo[2,3-b]pyrazine

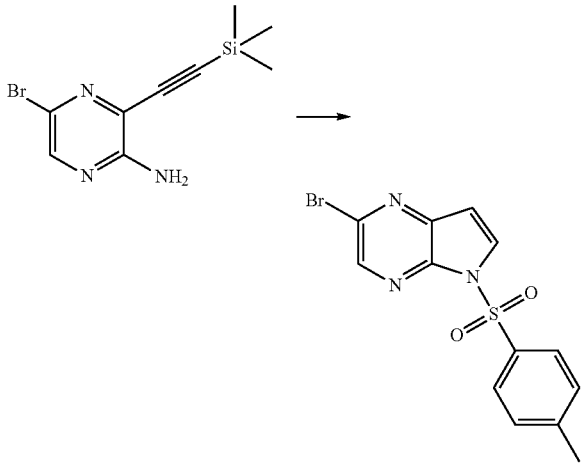

To a solution of 5-bromo-3-((trimethylsilyl)ethynyl) pyrazin-2-amine (3.00 g, 11.1 mmol) in DMF (60 mL) at about 0° C. was added NaH (60% dispersion in mineral oil, 0.577 g, 14.4 mmol) in three portions. After about 15 min, p-toluenesulfonyl chloride (2.75 g, 14.4 mmol) was added and the reaction was allowed to warm slowly to ambient temperature. After about 16 h, the reaction mixture was poured onto ice-cold water (120 mL) and the precipitate was collected by vacuum filtration. The crude solid was dissolved in DCM (15 mL) and purified by silica gel chromatography eluting with DCM to give 2-bromo-5-tosyl-5H-pyrrolo[2,3-b]pyrazine (2.16 g, 52%): LC/MS (Table 1, Method c) $R_t$=1.58 min; MS m/z: 352, 354 $(M+H)^+$.

Step C: tert-butyl 2-(5-tosyl-5H-pyrrolo[2,3-b]pyrazin-2-yl)hydrazinecarboxylate and tert-butyl 1-(5-tosyl-5H-pyrrolo[2,3-b]pyrazin-2-yl)hydrazinecarboxylate

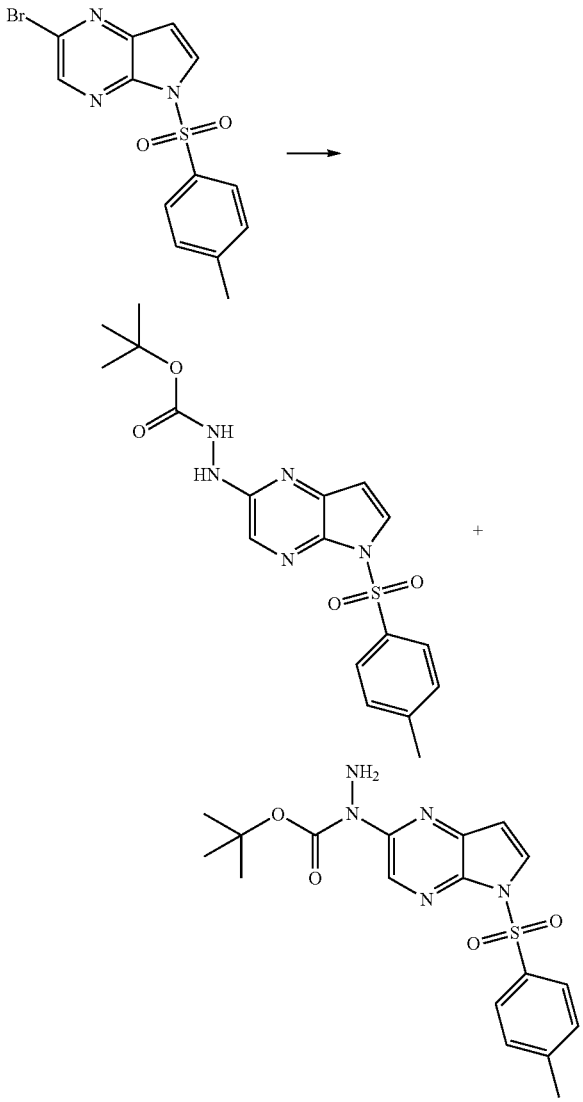

To a flask was added $Pd_2(dba)_3$ (3.90 g, 4.26 mmol), di-tert-butyl-(2',4',6'-triisopropylbiphenyl-2-yl)phosphane (3.62 g, 8.52 mmol), and 1,4-dioxane (453 mL). The catalyst-ligand mixture was degassed via vacuum/nitrogen purge (3 times) and heated at about 80° C. for about 10 min. Then 2-bromo-5-tosyl-5H-pyrrolo[2,3-b]pyrazine (30.0 g, 85 mmol), tert-butyl hydrazinecarboxylate (16.9 g, 128 mmol), and NaOt-Bu (12.28 g, 128 mmol) were added. After an additional vacuum/nitrogen purge, the reaction was heated at about 80° C. After about 50 min, the reaction mixture was cooled to ambient temperature and filtered through a pad of silica gel (6 cm in height×6 cm in diameter), topped with Celite® (1 cm in height×6 cm in diameter), while washing with EtOAc (3×150 mL). Water (300 mL) was added to the filtrate and the organic layer was separated. The aqueous layer was extracted with additional EtOAc (3×200 mL). The combined organic extracts were washed with saturated aqueous $NH_4Cl$, saturated aqueous $NaHCO_3$, and brine (400 mL each), dried over anhydrous $MgSO_4$, filtered, and concd under reduced pressure to give a dark brown oil (45 g). The brown oil was dissolved in DCM (250 mL), silica gel (200 g) was added, and the mixture was concd under reduced pressure. The resulting silica mixture was purified using silica gel chromatography eluting with a gradient of 25-65% EtOAc in heptane to give a mixture of tert-butyl 2-(5-tosyl-5H-pyrrolo[2,3-b]pyrazin-2-yl)hydrazinecarboxylate [major regioisomer] and tert-butyl 1-(5-tosyl-5H-pyrrolo[2,3-b]pyrazin-2-yl)hydrazinecarboxylate [minor regioisomer] (18.8 g, 50%): LC/MS (Table 1, Method c) $R_t$=1.47 min; MS m/z: 404 $(M+H)^+$.

Step D: 2-hydrazinyl-5-tosyl-5H-pyrrolo[2,3-b]pyrazine

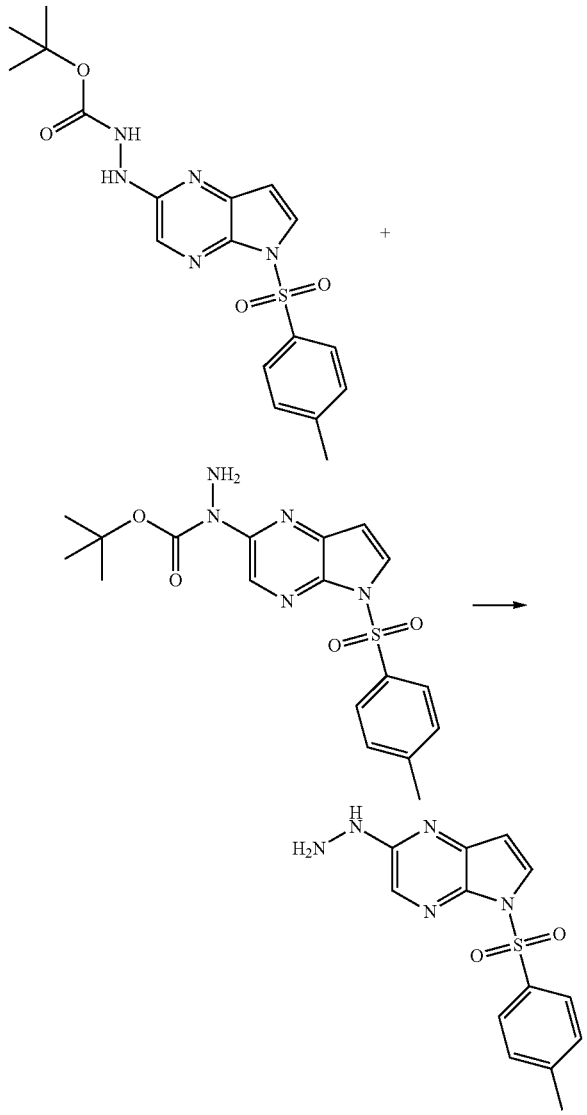

To a mixture of tert-butyl 2-(5-tosyl-5H-pyrrolo[2,3-b]pyrazin-2-yl)hydrazinecarboxylate and tert-butyl 1-(5-tosyl- 5H-pyrrolo[2,3-b]pyrazin-2-yl)hydrazinecarboxylate (49.2 g, 122 mmol) in 1,4-dioxane (290 mL) was added HCl (4 M in 1,4-dioxane, 226 mL, 902 mmol). The reaction was heated at about 60° C. for about 2.5 h and then cooled to about 15-20° C. The solid was collected by vacuum filtration, washed with EtOAc (3×50 mL), and then triturated with Et2O (60 mL), collected by vacuum filtration and dried to a constant weight under vacuum to yield 35.6 g of solid. The solid was stirred with a mixture of saturated aqueous $NaHCO_3$ and EtOAc (1:1, 400 mL). After about 1 h, the solid was collected by vacuum filtration, washed with ice cold water (3×30 mL) and EtOAc (3×30 mL), and dried in a vacuum oven to a constant weight to afford 2-hydrazinyl-5-tosyl-5H-pyrrolo[2,3-b]pyrazine as a tan solid (21.2 g, 57%): LC/MS (Table 1, Method a) $R_t$=1.88 min; MS m/z: 304 $(M+H)^+$.

Step E: sodium 4-(ethoxycarbonyl)-3-ethyl-2-(methoxycarbonyl)cyclopenta-1,3-dienolate

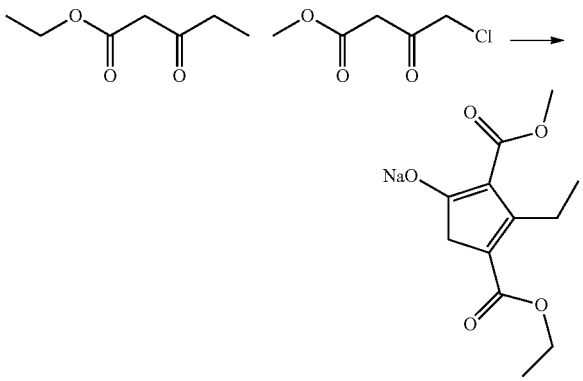

A round bottom flask was charged with THF (1.5 L) followed by the portionwise addition of NaH (60% dispersion in mineral oil, 70.0 g, 1.75 mol). Additional THF (500 mL) was added and the resulting mixture was cooled to about −10° C. and ethyl propionylacetate (250 mL, 1.80 mol) was added dropwise over about 1 h in order to keep the internal temperature below about 10° C. The resulting mixture was stirred at ambient temperature for about 0.5 h to give a clear yellow solution, and methyl 4-chloroacetoacetate (100 mL, 0.88 mol) was added dropwise over about 5 min. The resulting mixture was heated at about 50° C. for about 19 h to give a reddish orange suspension. The reaction mixture was cooled to ambient temperature, concd under reduced pressure and the resulting liquid was transferred to a beaker and diluted with water (350 mL). The mixture was stirred in an ice bath for about 2 h. The solid was collected by vacuum filtration and the filter cake was rinsed with water (150 mL) and dried under vacuum for about 1 h. The solid was suspended in $Et_2O$ (1.5 L), filtered, washed with $Et_2O$ (1.5 L), and dried under vacuum. The resulting solid was azeotroped with toluene (1 L) to give a solid that was re-suspended in $Et_2O$ (1 L) and collected by vacuum filtration. The filter cake was washed with $Et_2O$ (500 mL) and dried under vacuum to give sodium 4-(ethoxycarbonyl)-3-ethyl-2-(methoxycarbonyl)cyclopenta-1,3-dienolate (204.2 g, 89%) as beige solid: $^1$H NMR (DMSO-$d_6$) δ 3.94 (q, J=7.1 Hz, 2H), 3.46 (s, 3H), 3.04 (q, J=7.2 Hz, 2H), 2.66 (s, 2H), 1.13 (t, J=7.1 Hz, 3H), 0.99 (t, J=7.3Hz, 3H).

Step F: ethyl 2-ethyl-4-oxocyclopent-2-enecarboxylate

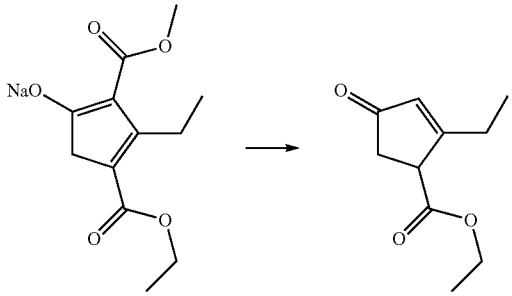

A 5 L round bottom flask was charged with sodium 4-(ethoxycarbonyl)-3-ethyl-2-(methoxycarbonyl)cyclopenta-1,3-dienolate (316 g, 1205 mmol), KCl (126 g, 1687 mmol, JT-Baker), AcOH (241 mL, 4218 mmol, JT-Baker), toluene (1850 mL) and water (130 mL). The reaction was heated at reflux for about 6 h then cooled to ambient temperature and added dropwise to $NaHCO_3$ (8% aqueous, 3.5 L). The resulting biphasic mixture was extracted with MTBE (2×1.5 L). The combined organic layers were washed with brine (1 L), dried over anhydrous $MgSO_4$ and concd under reduced pressure to give 191 g of crude material that was purified by vacuum distillation (97-99° C., 0.600 mm Hg) to give ethyl 2-ethyl-4-oxocyclopent-2-enecarboxylate (160 g, 69%): $^1$H NMR ($CDCl_3$) δ 6.04 (m, 1H), 4.26-4.15 (m, 2H), 3.76-3.69 (m, 1H), 2.75-2.57 (m, 2H), 2.56-2.44 (m, 2H), 1.32-1.26 (m, 3H), 1.23-1.18 (m, 3H).

Step G: ethyl 2-ethyl-4-hydroxycyclopentanecarboxylate

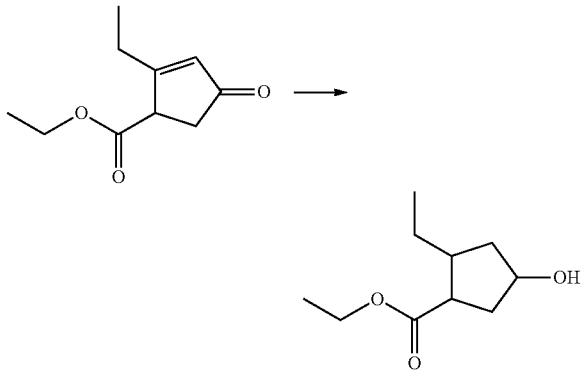

A mixture of copper (I) chloride (0.136 g, 1.37 mmol), (S)-(−)-2,2'-bis(diphenylphosphino)-1,1'-binaphthyl (0.854 g, 1.37 mmol), and NaOt-Bu (0.132 g, 1.37 mmol) in toluene (50 mL) was stirred at ambient temperature for about 15 min then cooled to about 5° C. and polymethylhydrosiloxane (12 mL, 55 mmol) was added. The reaction mixture was stirred for about 40 min at about 5° C. then cooled to about −12° C. A solution of ethyl 2-ethyl-4-oxocyclopent-2-enecarboxylate (5.00 g, 27.4 mmol) and t-BuOH (14 mL, 148 mmol) in toluene (50 mL) was added in one portion and the reaction mixture was stirred for about 16 h at about −12° C. The reaction mixture was quenched by the addition of MeOH (50 mL). The solvents were removed under reduced pressure. The residue was dissolved in MeOH (35 mL) and filtered through a pad of Celite®. The filtrate was concd under reduced pressure and the residue was triturated with EtOAc (100 mL) and filtered. The filtrate was concd under reduced pressure and the residue was purified using silica gel chromatography eluting with a gradient of 0-10% EtOAc in heptane to give a scalemic mixture enriched with (1S,2R,4S)-ethyl 2-ethyl-4-hydroxycyclopentanecarboxylate (1.11 g, 22%): $^1$H NMR ($CDCl_3$) δ 4.30 (m, 1H), 4.24-4.08 (m, 2H), 2.88 (td, J=2.1, 7.1 Hz, 1H), 2.40 (dt, J=7.8, 14.0 Hz, 1H), 2.08-1.91 (m, 3H), 1.52-1.31 (m, 3H), 1.29 (t, J=7.1 Hz, 3H), 0.94 (t, J=7.4 Hz, 3H).

Step H: 2-ethyl-4-hydroxycyclopentanecarboxylic acid

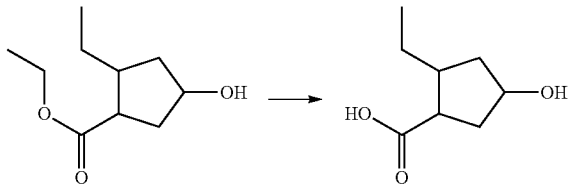

Aqueous NaOH (1 N, 12 mL, 12 mmol) was added to a scalemic mixture enriched in (1S,2R,4S)-ethyl 2-ethyl-4-hydroxycyclopentanecarboxylate (1.11 g, 5.96 mmol). The reaction mixture was stirred at ambient temperature for about 3 days and then extracted with $Et_2O$ (3×25 mL). The $Et_2O$ extracts were discarded and the aqueous portion was cooled to about 0° C. Aqueous HCl (5 N) was slowly added to bring the pH to about 2. The resulting aqueous suspension was extracted with EtOAc (3×40 mL). The combined organic layers were washed with brine (2×80 mL), dried over anhydrous $MgSO_4$, filtered, and concd under reduced pressure to give a scalemic mixture enriched in (1S,2R,4S)-2-ethyl-4-hydroxycyclopentanecarboxylic acid (0.943 g, 100%) as clear oil: $^1$H NMR ($CDCl_3$) δ 4.36 (tdd, J=2.6, 4.9, 7.4, 1H), 2.95 (td, J=2.4, 7.3, 1H), 2.41 (dt, J=7.7, 14.1, 1H), 2.16-1.94 (m, 3H), 1.65-1.49 (m, 1H), 1.49-1.32 (m, 2H), 0.96 (q, J=7.4, 3H).

Step I: 5-ethyl-2-oxabicyclo[2.2.1]heptan-3-one

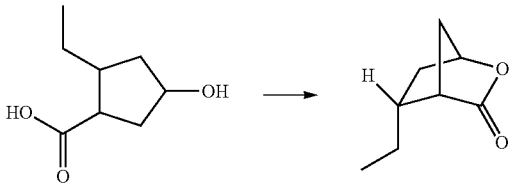

To a scalemic mixture enriched in (1S,2R,4S)-2-ethyl-4-hydroxycyclopentanecarboxylic acid (0.943 g, 5.96 mmol) in DCM (60 mL) was added TEA (2.5 mL, 18 mmol) and BOP-Cl (1.821 g, 7.15 mmol). The reaction mixture was stirred at ambient temperature for about 2 h then poured into $Et_2O$ (350 mL). The solid was removed by filtration while washing with $Et_2O$ (50 mL). The filtrate was concd under reduced pressure to give a yellow oil which was dissolved in DCM (5 mL) and $Et_2O$ was added to give a solid. The supernatant was decanted and the solid was washed with additional $Et_2O$. The combined organic extracts were concd under reduced pressure to give a scalemic mixture enriched in crude (1S,4S,5R)-5-ethyl-2-oxabicyclo[2.2.1]heptan-3-one containing about 15 mol % TEA (0.912 g, 99%): $^1$H NMR ($CDCl_3$) δ 4.85 (s, 1H), 2.88 (s, 1H), 2.19 (m, 2H), 2.08 (m, 1H), 1.69 (m, 1H), 1.41 (m, 3H), 0.97 (t, J=5.4, 3H).

Step J: 2-ethyl-4-hydroxy-N'-(5-tosyl-5H-pyrrolo[2,3-b]pyrazin-2-yl)cyclopentanecarbohydrazide

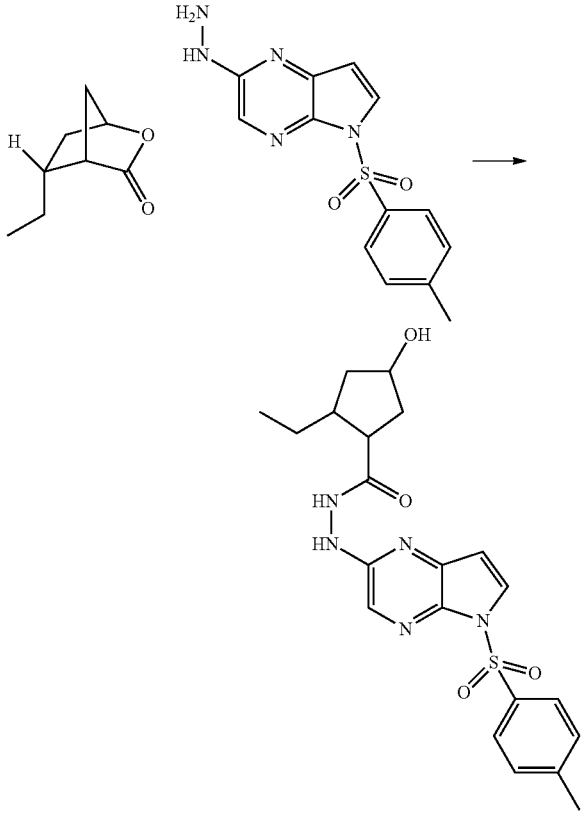

To a scalemic mixture enriched in (1S,4S,5R)-5-ethyl-2-oxabicyclo[2.2.1]heptan-3-one (0.835 g, 5.96 mmol) in 1,4-dioxane (12 mL) was added 2-hydrazinyl-5-tosyl-5H-pyrrolo[2,3-b]pyrazine (step D, 1.810 g, 5.96 mmol). The reaction mixture was heated at about 80° C. for about 16 h then cooled to ambient temperature. 1,4-Dioxane (25 mL) and trimethylaluminum (2 N in toluene, 9 mL, 18 mmol) were added sequentially. The reaction mixture was stirred at ambient temperature for about 30 min then aqueous HCl (1 N, 50 mL) was added dropwise and the reaction mixture was stirred for about 30 min. The layers were separated and the aqueous layer was extracted with EtOAc (2×100 mL). The combined organic extracts were washed with water (10 mL), saturated aqueous $NaHCO_3$ (15 mL), brine (15 mL) and dried over anhydrous $MgSO_4$, filtered, and concd under reduced pressure. The residue was purified using silica gel chromatography eluting with 100% EtOAc to give a scalemic mixture enriched in (1S,2R,4S)-2-ethyl-4-hydroxy-N'-(5-tosyl-5H-pyrrolo[2,3-b]pyrazin-2-yl)cyclopentanecarbo-hydrazide (1.887 g, 71%): LC/MS (Table 1, Method b) $R_t$=2.05 min; MS m/z: 444 $(M+H)^+$.

Step K: 4-(tert-butyldimethylsilyloxy)-2-ethyl-N'-(5-tosyl-5H-pyrrolo[2,3-b]pyrazin-2-yl)cyclopentanecarbohydrazide

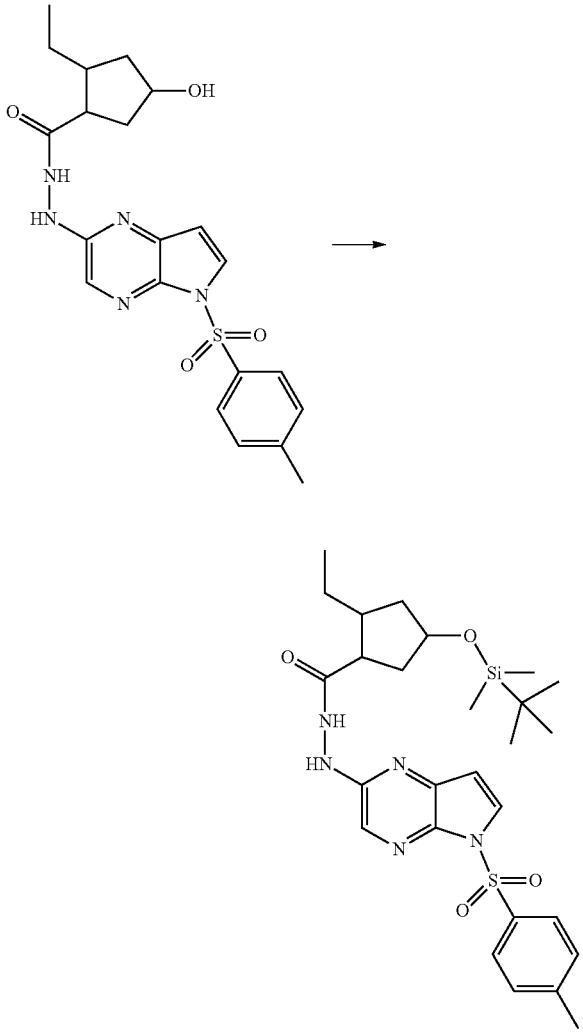

To a scalemic mixture enriched in (1S,2R,4S)-2-ethyl-4-hydroxy-N-(5-tosyl-5H-pyrrolo[2,3-b]pyrazin-2-yl)cyclopentanecarbo-hydrazide (9.06 g, 20.43 mmol) in DMF (40.9 mL) was added TBDMSCl (3.69 g, 24.51 mmol) and imidazole (3.48 g, 51.1 mmol). The reaction mixture was stirred at ambient temperature for about 4 h. The solvent was removed under reduced pressure. The residue was diluted with EtOAc (200 mL), filtered, and washed with EtOAc (20 mL). The filtrate was concd under reduced pressure. The residue was purified using silica gel chromatography eluting with 0-50% EtOAc in DCM to give a scalemic mixture enriched in (1S,2R,4S)-4-(tert-butyldimethylsilyloxy)-2-ethyl-N'-(5-tosyl-5H-pyrrolo[2,3-b]pyrazin-2-yl)cyclopentanecarbohydrazide (11.37 g, 100%) as an orange solid: LC/MS (Table 1, Method b) $R_t$=3.14 min; MS m/z: 558 $(M+H)^+$.

Step L: 4-(tert-butyldimethylsilyloxy)-2-ethylcyclopentyl)-6-tosyl-6H-pyrrolo[2,3-e][1,2,4]triazolo[4,3-a]pyrazine

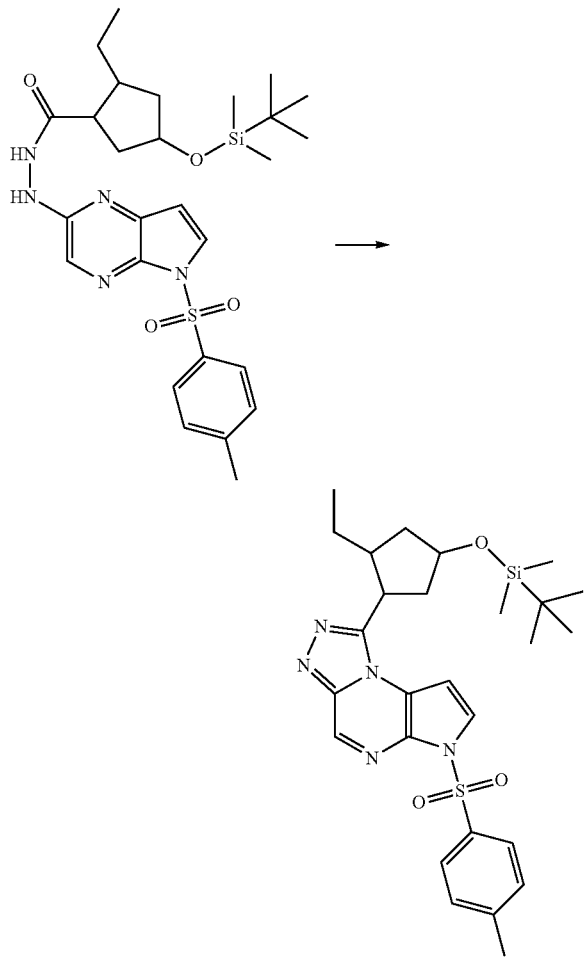

To a scalemic mixture enriched in (1S,2R,4S)-4-(tert-butyldimethylsilyloxy)-2-ethyl-N-(5-tosyl-5H-pyrrolo[2,3-b]pyrazin-2-yl)cyclopentanecarbohydrazide (11.37 g, 20.38 mmol) in 1,4-dioxane (204 mL) was added DIEA (14.24 mL, 82 mmol) followed by thionyl chloride (2.98 mL, 40.8 mmol) dropwise over about 25 min. The reaction mixture was stirred at ambient temperature for about 1 h and heated at about 70° C. for about 1 h. The reaction mixture was cooled to ambient temperature and EtOAc (600 mL) was added. The organic mixture was washed with water (80 mL) and brine (80 mL), dried over anhydrous $MgSO_4$, filtered and concd under reduced pressure. The residue was purified using silica gel chromatography eluting with 0-50% EtOAc in DCM to give a scalemic mixture enriched in 1-((1S,2R,4S)-4-(tert-butyldimethylsilyloxy)-2-ethylcyclopentyl)-6-tosyl-6H-pyrrolo[2,3-e][1,2,4]triazolo[4,3-a]pyrazine (9.58 g, 87%). LC/MS (Table 1, Method b) $R_t$=3.24 min; MS m/z: 540 $(M+H)^+$.

Step M: 3-ethyl-4-(6-tosyl-6H-pyrrolo[2,3-e][1,2,4]triazolo[4,3-a]pyrazin-1-yl)cyclopentanol Step N: 3-ethyl-4-(6-tosyl-6H-pyrrolo[2,3-e][1,2,4]triazolo[4,3-a]pyrazin-1-yl)cyclopentyl 4-nitrophenyl carbonate

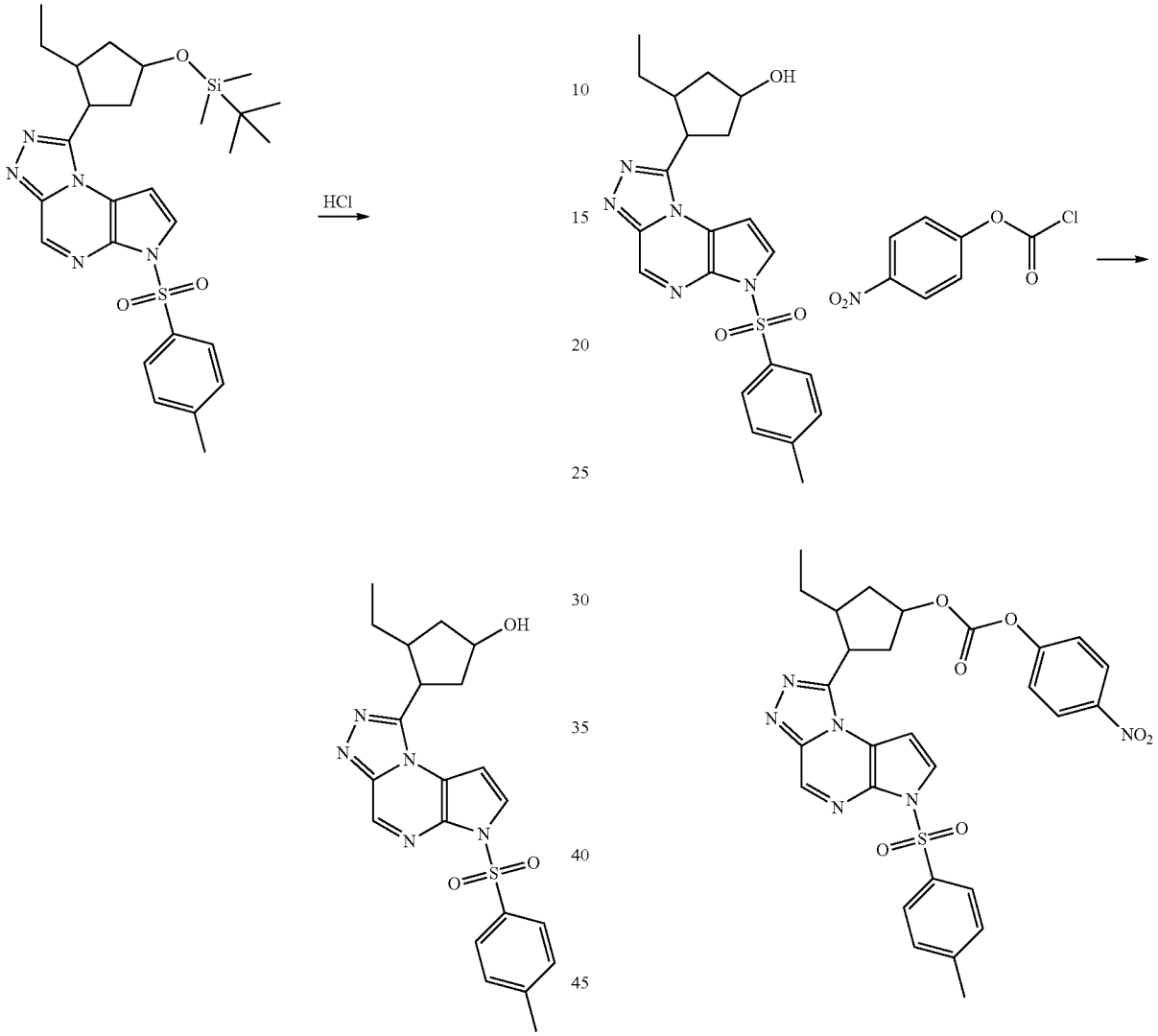

A scalemic mixture enriched in 1-((1S,2R,4S)-4-(tert-butyldimethylsilyloxy)-2-ethylcyclopentyl)-6-tosyl-6H-pyrrolo[2,3-e][1,2,4]triazolo[4,3-a]pyrazine (9.58 g, 17.8 mmol) was dissolved in ethanol (177 mL). Concd HCl (1.75 mL, 21.3 mmol) was added dropwise. After about 1 h, EtOAc (700 mL) was added. The organic mixture was washed with saturated aqueous $NaHCO_3$ (2×120 mL), brine (120 mL), dried over anhydrous $MgSO_4$, filtered and concd under reduced pressure. The residue was purified using silica gel chromatography eluting with 30-100% EtOAc in DCM to give a scalemic mixture enriched in (1S,3R,4S)-3-ethyl-4-(6-tosyl-6H-pyrrolo[2,3-e][1,2,4]triazolo[4,3-a]pyrazin-1-yl)cyclopentanol (6.73 g, 89%): LC/MS (Table 1, Method b) $R_t$=2.11 min; MS m/z: 426 $(M+H)^+$.

To a scalemic mixture enriched in (1S,3R,4S)-3-ethyl-4-(6-tosyl-6H-pyrrolo[2,3-e][1,2,4]triazolo[4,3-a]pyrazin-1-yl)cyclopentanol (6.11 g, 14.4 mmol) in pyridine (100 mL) was added DMAP (1.93 g, 15.8 mmol) and 4-nitrophenyl carbonochloridate (4.34 g, 21.5 mmol). The resulting mixture was stirred at ambient temperature for about 3.5 h and heated at about 33° C. for about 1 h. The solid was filtered off and washed with EtOAc (30 mL). The filtrated was concd under reduced pressure. The residue was purified using silica gel chromatography eluting with 0-30% EtOAc in heptane to give a scalemic mixture enriched in (1S,3R,4S)-3-ethyl-4-(6-tosyl-6H-pyrrolo[2,3-e][1,2,4]triazolo[4,3-a]pyrazin-1-yl)cyclopentyl 4-nitrophenyl carbonate (6.63, 78%). LC/MS (Table 1, Method b) $R_t$=2.65 min; MS m/z: 591 $(M+H)^+$.

Step O: (1S,3R,4S)-3-ethyl-4-(6H-pyrrolo[2,3-e][1,2,4]triazolo[4,3-a]pyrazin-1-yl)cyclopentyl cyclobutylcarbamate

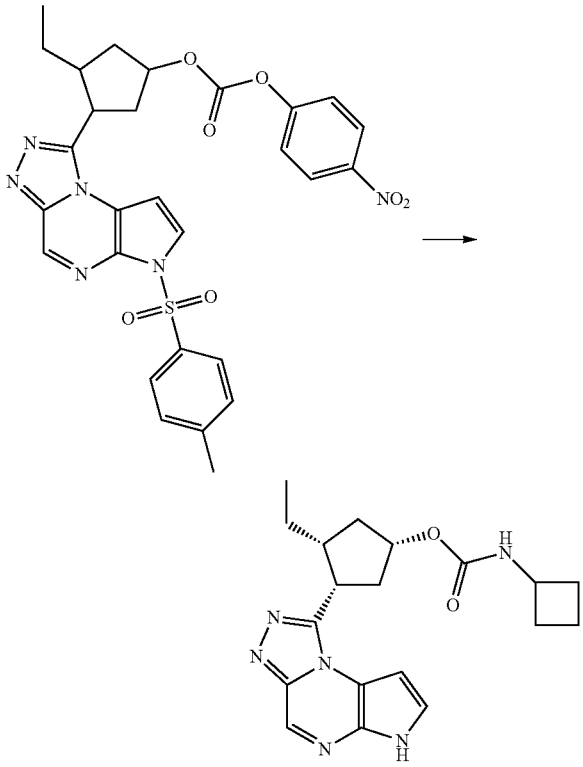

A solution of a scalemic mixture enriched in (1S,3R,4S)-3-ethyl-4-(6-tosyl-6H-pyrrolo[2,3-e][1,2,4]triazolo[4,3-a]pyrazin-1-yl)cyclopentyl 4-nitrophenyl carbonate (0.150 g, 0.254 mmol) in 1,4-dioxane (1 mL) was added to a solution of cyclobutanamine (0.090 g, 1.27 mmol) in 1,4-dioxane (0.2 mL). After about 1 h, aqueous NaOH (1 N, 1.5 mL, 1.50 mmol) was added and the reaction mixture was heated at about 60° C. for about 2 h before cooling to rt. The organic solvent was removed under reduced pressure. The resulting aqueous layer mixture was acidified with AcOH to pH about 5 and extracted with DCM (3×5 mL). The combined organic extracts were concentrated under reduced pressure. The residue was purified by preparative HPLC (Table 1 method d) to give (1S,3R,4S)-3-ethyl-4-(6H-pyrrolo[2,3-e][1,2,4]triazolo[4,3-a]pyrazin-1-yl)cyclopentyl cyclobutylcarbamate (0.0468 g, 50%): LC/MS (Table 1, Method c) $R_t$=1.17 min; MS m/z: 369 $(M+H)^+$.

TABLE 4

Jak3 enzyme data for selected compounds

| Example # | JAK3 enzyme $IC_{50}$ |
|---|---|
| A.1.105 | B |
| A.1.65 | B |
| A.1.78 | A |
| AA.1.10 | B |
| AA.1.100 | C |
| AA.1.101 | A |

TABLE 4-continued

Jak3 enzyme data for selected compounds

| Example # | JAK3 enzyme $IC_{50}$ |
|---|---|
| AA.1.102 | C |
| AA.1.103 | A |
| AA.1.104 | A |
| AA.1.106 | C |
| AA.1.107 | A |
| AA.1.11 | A |
| AA.1.12 | A |
| AA.1.16 | B |
| AA.1.18 | A |
| AA.1.22 | A |
| AA.1.25 | A |
| AA.1.29 | C |
| AA.1.3 | B |
| AA.1.32 | B |
| AA.1.33 | B |
| AA.1.37 | B |
| AA.1.42 | C |
| AA.1.43 | A |
| AA.1.44 | B |
| AA.1.49 | A |
| AA.1.5 | B |
| AA.1.54 | B |
| AA.1.6 | A |
| AA.1.60 | B |
| AA.1.61 | B |
| AA.1.62 | B |
| AA.1.63 | C |
| AA.1.64 | C |
| AA.1.66 | C |
| AA.1.67 | C |
| AA.1.76 | C |
| AA.1.77 | A |
| AA.1.79 | A |
| AA.1.8 | A |
| AA.1.80 | C |
| AA.1.81 | A |
| AA.1.9 | B |
| AA.1.90 | B |
| AA.1.91 | B |
| AA.1.92 | A |
| AA.1.93 | C |
| AA.1.94 | B |
| AA.1.95 | C |
| AA.1.96 | C |
| AA.1.97 | C |
| AA.1.98 | A |
| AA.1.99 | B |
| D.1.10 | B |
| D.1.11 | B |
| D.1.12 | B |
| D.1.13 | B |
| D.1.21 | B |
| D.1.22 | B |
| D.1.24 | B |
| D.1.25 | A |
| D.1.29 | B |
| D.1.30 | B |
| D.1.31 | A |
| D.1.33 | C |
| D.1.35 | A |
| D.1.38 | B |
| D.1.39 | B |
| D.1.45 | A |
| D.1.46 | A |
| D.1.47 | B |
| D.1.49 | B |
| D.1.50 | C |
| D.1.51 | C |
| D.1.52 | B |
| D.1.54 | C |
| D.1.56 | B |
| D.1.58 | B |
| D.1.59 | B |
| D.1.60 | C |

TABLE 4-continued

Jak3 enzyme data for selected compounds

| Example # | JAK3 enzyme $IC_{50}$ |
|---|---|
| D.1.61 | C |
| D.1.62 | C |
| D.1.63 | C |
| D.1.64 | C |
| D.1.65 | C |
| D.1.66 | C |
| D.1.67 | B |
| D.1.69 | C |
| D.1.70 | B |
| D.1.71 | C |
| D.1.72 | B |
| D.1.73 | C |
| D.1.76 | B |
| D.1.77 | B |
| D.1.78 | A |
| D.1.79 | A |
| D.1.80 | A |
| D.1.81 | A |
| D.1.82 | B |
| D.1.83 | A |
| D.1.84 | B |
| D.2.10 | C |
| D.2.11 | B |
| D.2.13 | A |
| D.2.15 | B |
| D.2.19 | B |
| D.2.21 | B |
| D.2.22 | B |
| D.2.23 | C |
| D.2.24 | A |
| D.2.5 | B |
| D.2.6 | C |
| DD.1.1 | A |
| Example # 29 | A |
| Example # 30 | B |
| Example # 31 | B |
| Example #14 | A |
| Example #17 | A |
| Example #18 | B |
| Example #21 | B |
| Example #22 | C |
| Example #23 | A |
| Example #24 | A |
| Example #25 | A |
| Example #26 | B |
| Example #27 | C |
| Example #28 | C |
| Example #3 | A |
| Example #32 | B |
| Example #4 | A |
| Example #5 | B |
| Example #6 | B |
| Example #8 | B |

TABLE 4-continued

Jak3 enzyme data for selected compounds

| Example # | JAK3 enzyme $IC_{50}$ |
|---|---|
| Example #9 | B |
| H.1.1 | A |
| H.1.10 | A |
| H.1.2 | A |
| H.1.21 | A |
| H.1.25 | A |
| H.1.29 | A |
| H.1.6 | A |
| H.3.14 | B |
| H.4.1 | B |
| I.1.1 | A |
| I.1.2 | A |
| I.2.1 | A |
| I.2.2 | A |
| I.3.1 | B |
| J.1.1 | A |
| J.2.1 | A |
| J.2.10 | A |
| J.2.11 | A |
| J.2.12 | A |
| J.2.13 | A |
| J.2.14 | A |
| J.2.15 | A |
| J.2.2 | A |
| J.2.3 | A |
| J.2.5 | A |
| J.2.6 | A |
| J.2.7 | A |
| J.2.8 | A |
| J.2.9 | A |
| J.3.1 | A |
| J.3.10 | A |
| J.3.11 | A |
| J.3.2 | A |
| J.3.4 | A |
| J.3.6 | B |
| J.3.7 | B |
| J.3.8 | B |
| K.3.1 | B |
| K.4.1 | A |
| K.5.1 | A |
| L.1.2 | A |
| L.1.4 | A |
| LL.1.1 | B |
| LL.1.2 | C |
| LL.1.3 | C |
| LL.1.4 | C |
| Preparation #GGG.1 | B |
| QQ.1.4 | A |
| UUU.1.1 | A |
| UUU.1.1 | A |
| YY.1.1 | C |
| YY.1.2 | C |

Key:
A <0.1 μM
B 0.1-1 μM
C >1 μM

What is claimed:

[1. A compound selected from

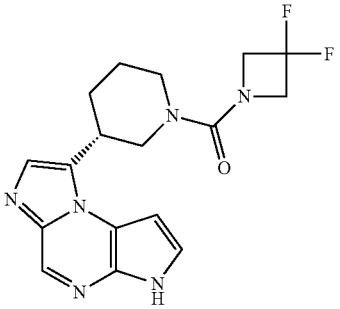

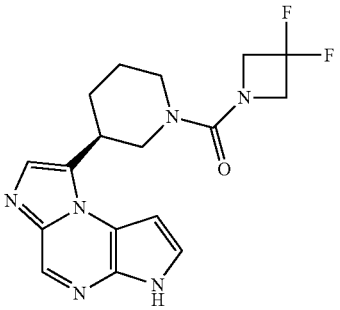

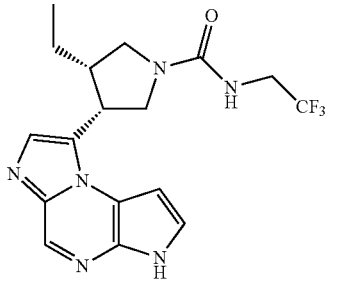

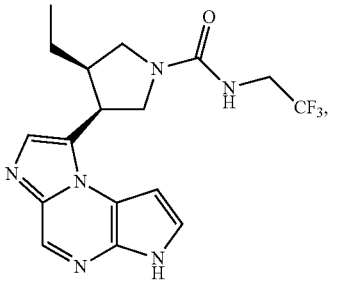

or pharmaceutically acceptable salts, stereoisomers and isomers thereof.]

[2. A compound represented by the following structure:

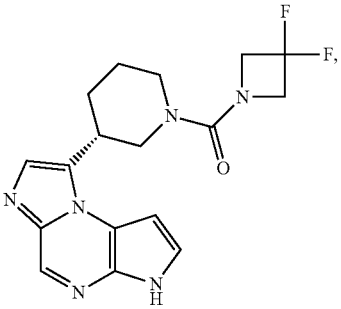

or pharmaceutically acceptable salts, stereoisomers and isomers thereof.]

[3. A compound represented by the following structure:

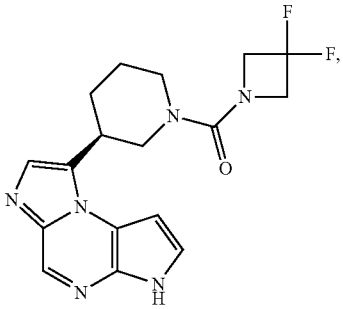

or pharmaceutically acceptable salts, stereoisomers and isomers thereof.]

[4. A compound represented by the following structure:

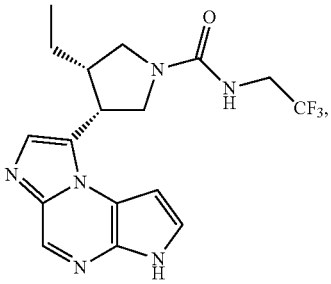

or pharmaceutically acceptable salts, stereoisomers and isomers thereof.]

[5. A compound represented by the following structure:

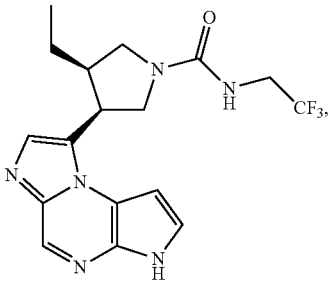

or pharmaceutically acceptable salts, stereoisomers and isomers thereof.]

[6. A compound selected from

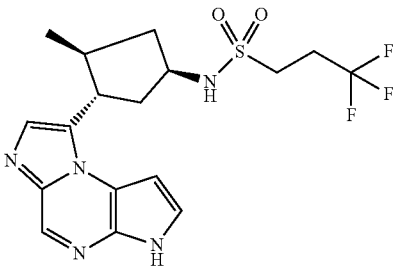

-continued

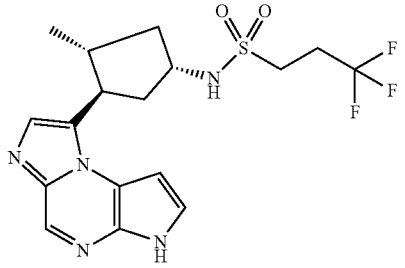

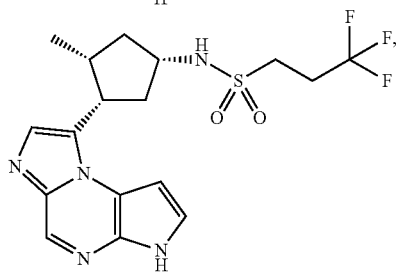

or pharmaceutically acceptable salts, stereoisomers and isomers thereof.]

[7. A compound represented by the following structure:

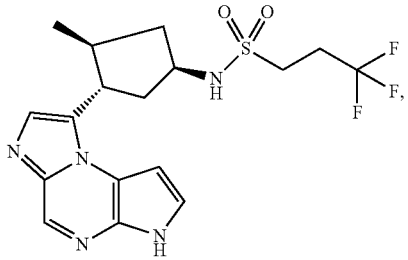

or pharmaceutically acceptable salts, stereoisomers and isomers thereof.]

[8. A compound represented by the following structure:

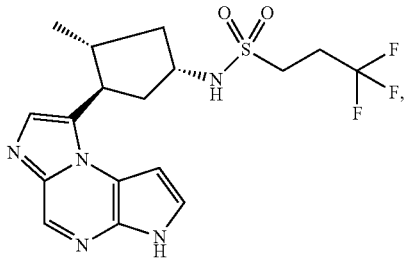

or pharmaceutically acceptable salts, stereoisomers and isomers thereof.]

[9. A compound represented by the following structure:

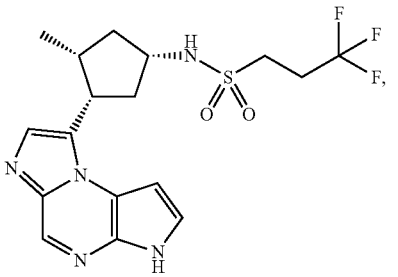

or pharmaceutically acceptable salts, stereoisomers and isomers thereof.]

[10. A compound selected from

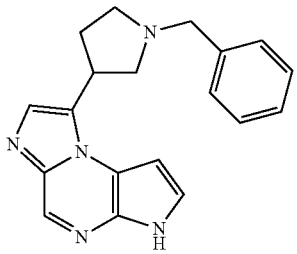

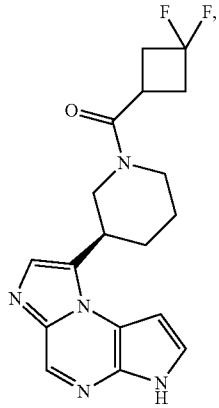

or pharmaceutically acceptable salts, stereoisomers and isomers thereof.]

[11. A compound represented by the following structure:

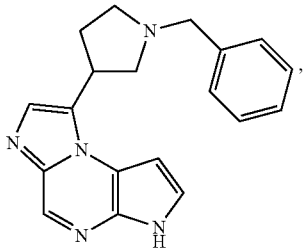

or pharmaceutically acceptable salts, stereoisomers and isomers thereof.]

[12. A compound represented by the following structure:

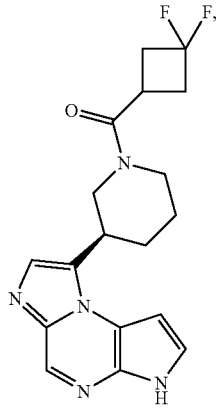

or pharmaceutically acceptable salts, stereoisomers and isomers thereof.]

*13. A compound represented by the following structure:*
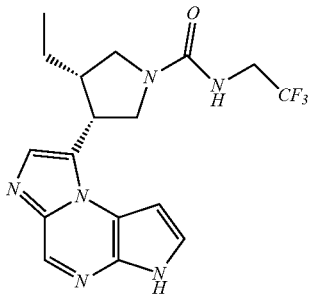
*or a pharmaceutically acceptable salt thereof.*
*14. The compound according to claim 13 represented by the following structure:*
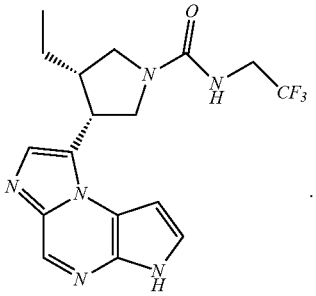
* * * * *